United States Patent
Garner et al.

(10) Patent No.: US 6,472,154 B1
(45) Date of Patent: Oct. 29, 2002

(54) POLYMORPHIC REPEATS IN HUMAN GENES

(75) Inventors: Harold R. Garner, Flower Mound; Jonathan D. Wren, Irving; John D. Minna; John W. Fondon, III, both of Dallas, all of TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 09/475,947

(22) Filed: Dec. 31, 1999

(51) Int. Cl.[7] .......................... C12Q 1/68; C07H 21/04

(52) U.S. Cl. ......................................... 435/6; 536/23.1

(58) Field of Search .............................. 435/6; 536/23.1

(56) References Cited

PUBLICATIONS

Fondon III, J. W. et al., "Computerized polymorphic marker identification: Experimental validatio and a predicted human polymorphism catalog", PNAS USA, vol. 95, pp. 7514–7519 (1998).*

Neri, C. et al., "Survey of CAG/CTG repeats in human cDNAs representing new genes: candidates for inherited neurological disorders", Hum. Mol. Genet., vol. 5, pp. 1001–1009 (1996).*

De Fonzo et al., J. theor. Biol. (1998) 194, 125–42.

* cited by examiner

*Primary Examiner*—Kenneth R. Horlick
*Assistant Examiner*—Teresa Strzelecka
(74) *Attorney, Agent, or Firm*—Richard Aron Osman

(57) ABSTRACT

The invention provides computational methods and compositions for identifying polymorphic repeats in genes. Candidate polymorphic repeats are identified by detecting tandem repeats in a target coding sequence, scoring the repeats for polymorphic probability, and generating a dataset correlating the repeats with polymorphic probability. Actual polymorphic repeat are identified by further detecting the candidate polymorphic repeat in each of a population of different coding sequences, and determining whether the candidate polymorphic repeat is polymorphic in the population. Computationally derived polymorphic repeats are validated with phenotypic variations and these correlates are used to detect the presence or absence of such phenotypic variation in test genes. Variances at polymorphic repeats are identified by detecting in a test gene or coding region the presence or absence of variance at a disclosed unconventional polymorphic repeat.

14 Claims, No Drawings

POLYMORPHIC REPEATS IN HUMAN GENES

The research carried out in the subject application was supported in part by grants from the National Institutes of Health (SPORE Grant No. P50CA70907). The government may have rights in this invention.

INTRODUCTION

FIELD OF THE INVENTION

The field of the invention is computational genetic analysis as applied to identifying and detecting polymorphic repeats in human genes.

BACKGROUND OF THE INVENTION

The exponential rate of accumulation of genomic sequence data in public databases is making it possible to eventually understand, treat and eliminate potentially thousands of genetic diseases, predispositions and adverse drug/treatment reactions. Causes and contributing factors for hundreds of afflictions have been mapped to thousands of specific mutations, some being simple sequence repeat polymorphisms and some single nucleotide polymorphisms (SNPs). Although the now-routine process for identifying these mutations is long and expensive, the medical and commercial value of these discoveries has prompted numerous public and private institutions to apply massive resources to the identification of new potentially causative and correlative genetic variations. These large-scale SNP-centric projects currently underway generally involve the random and therefore low-efficiency re-sequencing of DNAs from several individuals (sometimes panels of patients with a particular affliction of interest) followed by attempts to relate a particular genotype and phenotype. In addition, the inherent sequencing error rate is generally higher than the incidence of most sequence variations, resulting in a very high false-positive rate. This effect is compounded by the well-established population genetic principle that the higher the impact of an allele, the more deleterious it is, the more rare it will be, and hence the less likely it is to be found by these methods. Despite these shortcomings, the value of knowing which variations are present in the population (whatever their frequency) and are linked to phenotypes is such that many companies and institutions are racing in an effort to discover these valuable alleles.

The positional cloning of many disease loci has been facilitated by high-resolution genetic maps. The precise localization of the DNA sequence responsible for a disease usually requires the development of very high density physical and genetic maps. The availability of multiple polymorphic genetic markers is crucial to this effort. Current widely-used methods for the identification of new simple sequence repeat polymorphisms involve PCR based and subcloning strategies, but the large quantities of human genomic sequence being generated by the human genome project are rapidly making these approaches obsolete. The knowledge of the frequency and level of polymorphism of the various types and sizes of microsatellites and variable number tandem repeats (VNTRs) allows one to predict, a priori, which tandem repeats are likely to be highly polymorphic from a single genomic sequence. For microsatellites, the level of heterozygosity has been observed to be directly proportional to the number of repeated units and inversely proportional to the size of the repeated unit.

While there currently exist several software applications for locating some microsatellites or larger tandem repeats, a comprehensive tool for the identification of, and generation of primer sequences for, those repeats correlated with a high probability of polymorphism has been lacking. Because of this need, we wrote software that takes as input human genomic sequence data and will output a list of oligonucleotide sequences that may be used as primers for PCR amplification of those tandem repeat sequences that are predicted to be highly polymorphic based on observations from the literature. A computational system for the prediction of polymorphic loci directly and efficiently from human genomic sequence was developed and verified. A suite of programs, collectively called POMPOUS (POlymorphic Marker Prediction Of Ubiquitous Simple sequences) detects tandem repeats ranging from dinucleotides up to 250-mers, scores them according to predicted level of polymorphism, and designs appropriate flanking prime its for PCR amplification[1].

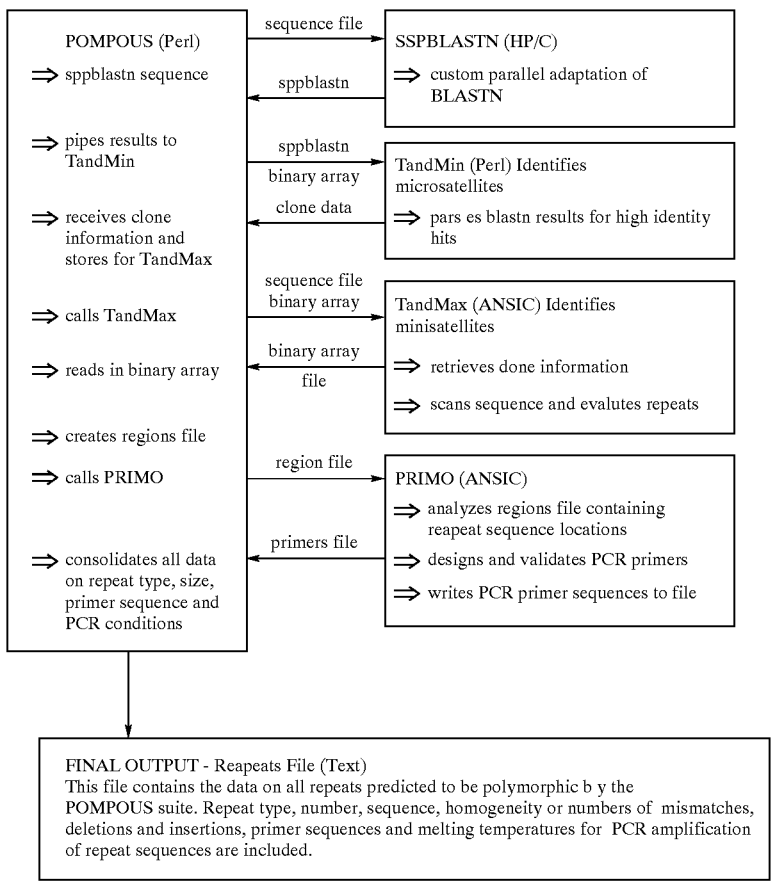

Scheme 1. POMPOUS is a series of programs whose execution is directed by a Perl script. Together, TandMin and TandMax identify di-nucleotide to 250-mer repeats, which are then consolidated by the Perl script, and then oligonucleotide primers are designed using our code PRIMO for those repeats whose characteristics are above thresholds set to select only for those repeats that are highly probable to vary.

An association between certain repeating microsatellite elements and polymorphism has been reported[17], caused by the expansion and contraction of the core repetitive unit by what is believed to be the mechanism of either slipped-strand mispairing[25], uneven recombination or some combination of both[15]. In fact, several inherited neurological disorders have been linked to changes in the copy numbers of certain tri-nucleotide repeats. The repetitive element in some diseases lies directly in the coding sequence, such as Machado-Joseph[8] (CAG repeat), Haw River Syndrome[7] (CAG), Huntington's Disease[3,19] (CAG) and Fragile-X Syndrome[4] (CGG). However, the location of other polymorphic repetitive elements vary with respect to the coding sequence as in Fredreich's Ataxis[5] (GAA, intron), Myotonic Dystrophy[6] (CAG, 3'UTR), and a gene suspected to be linked to Hyperandrogenaemia for which the repeat occurs in the 5' UTR[12]. Triplet repeat expansion diseases (TREDs) also include spinal and bulbar muscular atrophy (SBMA) and fragile X syndrome (FRAXA). Short cytosine-adenine-guanine (CAG) expansions are characteristic for spinal and bulbar muscular atrophy (SBMA), dentatorubral-pallidoluysian atrophy (DRPLA) and spinocerebellar ataxia (SCA) type 1, 2, 3, 6 and 7 (Nilssen O., Tidsskrift for Den Norske Laegeforening. 119(20):3021–7, Aug. 30, 1999). Besides studies of tri-nucleotide repeats associated with neurological disorders[3-8,16,24,36], work on repeats has focused on specific genes of interest containing predominant repeat units having a known association with polymorphism such as CAG or CCG[13].

SUMMARY OF THE INVENTION

The invention provides methods and compositions for identifying polymorphic repeats in genes. In one embodiment, the invention provides methods for identifying a candidate polymorphic repeat within a coding sequence. This embodiment involves scanning a coding sequence for multiple, different candidate polymorphic repeats and generally involves (a) detecting tandem repeats in a target coding sequence; (b) scoring the repeats for polymorphic probability; and (c) generating a dataset correlating the repeats with polymorphic probability. The coding sequence is a transcribed sequence, includes a CDS region and 3' and 5' untranslated regions (UTRs) and may be derived from a single coding sequence, a concatamerized coding sequence, a coding sequence library (e.g. cDNA library), etc. The coding sequence may be derived physically from transcribed polynucleotide or in silico from genomic sequence or other sequence comprising coding sequence. The detecting, scoring and generating steps are preferably implemented by a computer program, preferably wherein the scoring step comprises determining at least the type, number and purity of the repeats. In a particular embodiment the program is the Rep-X algorithm.

In another embodiment, the invention provides methods for identifying an actual polymorphic repeat by validating a computationally identified candidate polymorphic repeat in populations of natural genes. This embodiment generally involves (a) computationally identifying a candidate polymorphic repeat; (b) detecting the candidate polymorphic repeat in each of a population of different coding sequences, each from different individuals; and (c) determining whether the candidate polymorphic repeat is polymorphic in the population.

In yet another embodiment, the invention correlates validated, computationally derived polymorphic repeats with phenotypic variations, which may be manifested or prospective, i.e. present as a predisposition. These correlates are used to detect the presence or absence of such phenotypic variation in test genes.

The invention also provides isolated polynucleotides comprising variants of wild-type, unconventional repeats disclosed herein, polypeptides encoded by such variants, as well as binding agents, such as antibodies, specific thereto. Table 1 provides a dataset of human polymorphic repeats as mined from the Unigene database. The polymorphisms are distributed among known genes in 5' UTR, 3' UTR, border and CDS regions and in uncharacterized genes. The dataset encompasses both otherwise ascertainable conventional repeats and unconventional repeats not previously characterized or suggested. Conventional repeats are readily delineated by computational exclusion.

The invention provides methods for detecting variance at a polymorphic repeat, comprising the step of detecting in a test gene or coding region the presence or absence of variance at an unconventional polymorphic repeat of Table 1, particularly a repeat in an uncharacterized entry. The detecting step may be effected by any convenient means, including specific polynucleotide hybridization and inferentially by determining the amino acid sequence of a polypeptide translate of the coding region.

DETAILED DESCRIPTION OF PARTICULAR EMBODIMENTS OF THE INVENTION

The following descriptions of particular embodiments and examples are offered by way of illustration and not by way of limitation. The invention provides tools for identifying genotypic variation by measuring the polymorphism rate for repeats in genes, correlating this data with other genetic and genomic data, selective testing of this class of genes against genetic panels (e.g. affected/non-affected, families), and/or through association with homologous genes in model organisms which are directly manipulated to reveal phenotype.

In one aspect, the invention provides methods for identifying a candidate polymorphic repeat within a coding sequence, which comprise the steps of (a) detecting tandem repeats in a target coding sequence; (b) scoring the repeats for polymorphic probability; and (c) generating a dataset correlating the repeats with polymorphic probability to identify a candidate polymorphic repeat. The repeats may vary from one to hundreds of nucleotides in length and may be present in from two to dozens of copies. The repeats may be of varying degrees of identity (purity or homogeneity), preferably substantially pure, more preferably pure. The methods are applied to any coding sequence, including a single coding sequence (e.g. a single cDNA sequence), a concatamerized coding sequence and a coding sequence library. The coding sequence may determined physically, e.g. from actual transcribed polynucleotides, or conceptually, e.g. inferred in silico from genomic sequence. The detecting, scoring and/or generating steps may be implemented manually and/or by computer. In a particular embodiment, the steps are effected by a computer program, such as the Rep-X program described below. The scoring step generally comprises determining at least the type and number of the repeats, though measures of repeat purity may also be considered.

Rep-X is an algorithm that works by iteratively comparing each base pair, x, in a given nucleic acid sequence with the ones following it. Upon recognition of two matching base pairs y pairs ahead in the sequence, a one-dimensional array m(s), containing the values of s, a summed amount, increments the value corresponding to that nucleic acid position in the sequence by one plus the number of similar matches that occurred immediately and consecutively before it. Another one-dimensional matrix stores the nucleic acid position at which the match occurred in the sequence. The summed amount represents the amount of consecutive base pair matches for x that have occurred with all prior base pairs, x−1, at that point in the sequence. Upon any mismatch, the summed value is set equal to zero. Once the algorithm has finished running on the sequence, the one-dimensional matrix contains the longest sequence match (besides itself) with respect to that position in the sequence. Values equal to or above 10 in this one-dimensional summary matrix are considered to be significant length matches and the corresponding base pair coordinates of the highest summary value are compared to the x coordinate at which the significant length match occurred, giving a distance value d between the coordinates. If the first d nucleotides of the significant length subunit are equal to the second (2d) nucleotides, the sequence is considered repetitive with the repeating unit length equal to d and the number of repeating units equal to d/s. Note that a repeating unit by this calculation can occur in fractions. For example, the sequence ATGATGATGATA could be considered to have 3 and $\frac{2}{3}$ repeats of the sequence ATG. This part of the algorithm comprises the determination of repetitive sequences, which rules (see Table 2) are used to determine which of these sequences have significant potential for polymorphism. Comparisons are also done to the backwards reverse strand sequence such that comparisons are made with x+1 rather than x−1 and would be equivalent to regions of the sequence able to form hairpin or palindromic structures. Also, the one-dimensional matrix for both the repetitive calculations and the base-pair forming calculations are summed, giving a collective measure of self-similarity or self-complementarity for the sequence when divided by its length. Such measures of self-similarity can be used to determine the likelihood any given sequence has to undergo an uneven recombination. Similarly, the self-complementarity measure can be used to determine the amount of RNA secondary structure formation from transient complementary base pairing.

In another aspect, the invention provides methods for identifying a polymorphic repeat within a coding sequence, comprising the steps of:(a) identifying a candidate polymorphic repeat as described herein; (b) detecting the candidate polymorphic repeat in each of a population of different coding sequences, each from different individuals; and (c) determining whether the candidate polymorphic repeat is polymorphic in the population, wherein polymorphism of the candidate polymorphic repeat within the population indicates a polymorphic repeat.

In another aspect, the invention provides methods for correlating variance at a polymorphic repeat with phenotypic variation, comprising the steps of: (a) identifying a polymorphic repeat as described herein; and (b) correlating variance at the polymorphic repeat with phenotypic variation.

In another aspect, the invention provides methods for detecting variance at a polymorphic repeat by (a) identifying a polymorphic repeat as described herein; and (b) detecting in a test coding region the presence or absence of variance at a polymorphic repeat. While the general method detects a wide variety of variation from the disclosed wild-type polymorphisms, including variation in repeat number and sequence (i.e. purity), in a particular embodiment, the variants differ only in repeat number. Variants are readily localized by flanking sequences, e.g. with flanking sequence-specific primers.

The disclosed methods were used to perform a directed, systematic and exhaustive characterization of simple sequence repeat polymorphism in transcribed (coding) regions of the UniGene database. UniGene, published by NCBI, is a system for automatically partitioning GenBank sequences into a non-redundant set of gene-oriented clusters. Each UniGene cluster contains sequences that represent (are part of) a unique gene, as well as related information such as the tissue types in which the gene has been expressed and map location. Table 1 (appended) discloses polymorphisms found in human genes of the UniGene database. The dataset encompasses both conventional and unconventional repeats. Conventional repeats are known or ascertainable from conventional polymorphic patterns including glutamine-encoding repeats (e.g. CAG) expressed in neurological and brain cells, CA repeats in the untranslated regions, and from genes known to be polymorphic (e.g. apolipoprotein(a), androgen receptor, fibrinogen, PDGFA (platelet derived growth factor A), FLT-1 (kidney disease), DBP, adenosine deaminase (ADA), dopamine D4, POU genes, collagenα2, HCAD, phosphoglycerate kinase, NOS2a, CYP2G1, serotonin transporter gene, plasminogen activator inhibitor-1 (PAI-1), elastin, etc.). Conventional repeats are indexed in Medline and are readily delineated by computational exclusion. Unconventional repeats of Table 1 are not previously characterized or suggested, i.e. have no associated indicia of polymorphism in Medline using a Dec. 31, 1999 publication date cutoff In addition, unconventional repeats are restricted to those found in the disclosed human sequences of Table 1 and do not encompass vector sequences, which are readily ascertainable and computationally excluded by those skilled in the art of computational genomic analysis (e.g. by BLAST analysis against a vector sequence database such as published on Dec. 31, 1999 by NCBI).

While compiled for convenience in a single table, utilization of the unconventional polymorphisms of Table 1 does not require en mass usage. In fact, the polymorphisms may be used in an convenient compilation or as individual probes/targets. Hence, the polymorphic repeats of Table 1 are to be considered as individually disclosed and subject to discrete claims. Useful compilation criteria include any of those of Table 1, including regions, repeat type, length, Unigene identifiers, etc. Particular embodiments include compilations of unconventional repeats having a repeat number of at least N, wherein N is selected from an integer from 2 to 30; unconventional repeats having a unit length of at least M, wherein M is selected from an integer from 2–200; and unconventional repeats having a Table 1-referenced Genbank entry having an unannotated start and stop site or a "/cds=UNKNOWN" indication or the absence of a "/cds=" field.

In another aspect, the invention provides methods for detecting variance at a polymorphic repeat by detecting in a test coding region the presence or absence of variance at an unconventional polymorphic repeat of Table 1, particularly an unconventional repeat in an uncharacterized entry.

The detecting may be effected by any convenient means, including directly by detecting or determining polynucleotide sequence (e.g. by sequencing or by probing arrays of immobilized polymorphism-specific polynucleotides) and inferentially by determining or detecting the amino acid sequence of a polypeptide translate of the coding region (e.g. by sequencing or using sequence-specific binding reagents, such as specific antibodies). Accordingly, the invention also provides isolated polynucleotides comprising and polypeptides encoded by a variant of an unconventional polymorphic repeat of Table 1, particularly a repeat in an uncharacterized entry, as well as binding agents, such as antibodies, specific thereto. Variants are readily and unambiguously identified by flanking sequence of the disclosed wild-type repeat and deviation from the disclosed repeat in terms of repeat number or purity, wherein preferred variants differ only in terms of repeat number. The term antibody is used inclusively to encompass polypeptides comprising antibody complementary determining regions sufficient for specific binding, including specific antibody fragments, hybrids, etc.

Classes of diagnostic repeats of particular interest include those of Table 1 of each of 3' UTR, 5' UTR, border, CDS and unknown regions; frame-shifting mutations, i.e. those not a multiple of three in length (see Table 6, below); those relatively common in genomic DNA but rare in coding regions (See Table 7, below), such as cyclic permutations of AAT, TTA, TTG and TTC.

Individual diagnostic repeats of particular interest include those of the human Sperm Acrosomal Protein-1 repeat, consisting of eight TG repeats at position 875 of gb=AF047437; the human Herpes Viral Entry Protein C repeat, consisting of eight GAG repeats at position 1464 of gb=AF060231; and the human MEK kinase 1 (MEKK 1) repeat, consisting of eight AAC repeats at position 2290 of gb=AF042838.

The subject polynucleotides and fragments thereof may be joined to other components such as labels or other polynucleotide/polypeptide sequences (i.e. they may be part of larger sequences) and are of synthetic/non-natural sequences and/or are isolated, i.e. unaccompanied by at least some of the material with which it is associated in its natural state, preferably constituting at least about 0.5%, preferably at least about 5% by weight of total nucleic acid present in a given fraction, and usually recombinant, meaning they comprise a non-natural sequence or a natural sequence joined to nucleotide(s) other than that which it is joined to on a natural chromosome. Recombinant polynucleotides comprising the subject sequences or fragments thereof, contain such sequence or fragment at a terminus, immediately flanked by (i.e. contiguous with) a sequence other than that which it is joined to on a natural chromosome, or flanked by a native flanking region fewer than 10 kb, preferably fewer than 2 kb, more preferably fewer than 500 bases, most preferably fewer than 100 bases, which is at a terminus or is immediately flanked by a sequence other than that which it is joined to on a natural chromosome. While the nucleic acids are usually RNA or DNA, it is often advantageous to use nucleic acids comprising other bases or nucleotide analogs to provide modified stability, etc.

The subject polypeptides and fragments thereof are isolated or pure: an "isolated" polypeptide is unaccompanied by at least some of the material with which it is associated in its natural state, preferably constituting at least about 0.5%, and more preferably at least about 5% by weight of the total polypeptide in a given sample and a pure polypeptide constitutes at least about 90%, and preferably at least about 99% by weight of the total polypeptide in a given sample. The polypeptides may be synthesized, produced by recombinant technology, or purified from cells. A wide variety of molecular and biochemical methods are available for biochemical synthesis, molecular expression and purification of the subject compositions, see e.g. Molecular Cloning, A Laboratory Manual (Sambrook, et al. Cold Spring Harbor Laboratory), Current Protocols in Molecular Biology (Eds. Ausubel, et al., Greene Publ. Assoc., Wiley-Interscience, NY) or that are otherwise known in the art.

In a particular embodiment, the subject polypeptides provide specific antigens and/or immunogens for making specific antibodies, especially when coupled to carrier proteins. For example, polypeptides are covalently coupled to keyhole limpet antigen (KLH) and the conjugate is emulsified in Freunds complete adjuvant. Laboratory rabbits are immunized according to conventional protocol and bled. The presence of specific antibodies is assayed by solid phase immunosorbant assays using immobilized corresponding polypeptide.

EXAMPLES

This example provides a comparative study of two algorithms, POMPOUS and Rep-X and a statistical analysis of clinical correlates of exemplary polymorphic repeats identified herein. Building upon POMPOUS, we developed a new program, Rep-X, with the intention of improving both the sensitivity of our polymorphism predictions by including repeat units of all sizes and the specificity by requiring greater homogeneity of the repetitive unit. Because POMPOUS allows insertions, deletions and mismatches (up to 10% by sequence length), Rep-X was expected to generate fewer predictions because of the increased stringency even with the allowance for mononucleotide repeats. So POMPOUS was used to generate the initial set so that both the sensitivity and specificity of the two programs could be compared. The criteria by which Rep-X considers a repetitive unit potentially polymorphic is shown in Table 2.

TABLE 2

Sequence requirements for Rep-X to consider a repetitive unit potentially polymorphic

| Repeating unit size (bp) | minimum # of units necessary | Homogeneity |
| --- | --- | --- |
| 1 | 10 | 100% |
| 2 | 6.5 | 100% |
| 3 | 5.5 | 100% |
| 4 | 4.5 | 100% |
| 5–9 | 3.5 | 100% |
| 10+ | 2.5 | 100% |

We applied both of our informatics tools to the Unigene *Homo sapiens* cDNA database and from the set of genes predicted to contain polymorphic repeats, we selected 146 from the POMPOUS program for study based primarily upon the availability of other information of general scientific interest. In addition, we selected a variety of repeat unit types and lengths. We then tested our predictions by designing flanking primers to the predicted regions, amplifying them with PCR using a genomic DNA template and allelotyping them on a panel of individuals for changes in gel mobility.

The Rep-X and POMPOUS programs, were run on a Hewlett Packard Exemplar supercomputer running SPP-UX 5.2. Rep-X was run on the October 1999 version of the UniGene database, downloaded for this analysis. Because UniGene does not give a consensus sequence, we used a subset of each cluster containing the longest sequence with the fewest ambiguous bases. Rep-X works by comparing a sequence to itself and finding the longest similar region for each position in the sequence (besides itself). As similar regions are found, their distance, d, from the original comparison sequence is calculated and if the sequence strings starting at 1 and taking d bp is equal to the same sequence starting at 1+d and taking d bp, then it is considered a repeat. Since it is possible to have fractions of repeating units at the end of the sequence (e.g. CAGCAGCAT is 2.67 CAG repeats), these numbers are rounded to the nearest integer. Mononucleotide A/T repeats near the 3' UTR were excluded from further analysis.

Comparison of peptide repeats with nucleotide repeats was done by translating the UniGene nucleotide sequences into protein sequences using the annotated start and stop sites. For gene fragments without a start site, reading frames uninterrupted by stop codons were chosen. The degeneracy score for the codons used to encode the peptide repeat was computed by comparing each codon with the one immediately following it, summing the number of equalities and then dividing this by the number of peptide repeats and subtracting this number from 1.

For the genes chosen for study by PCR amplification, primers were synthesized using our Mermade oligonucleotide synthesizer[18]. For 64 of the genes in this analysis, genomic DNA was extracted by standard methods from the 30 human EBV immortalized B lymphoblastoid cell lines of lung cancer patients. In addition, for 40 of the genes analyzed, genomic DNA was obtained from the B-cell lines of patients with Hypertrophic Cardiac Myopathy.

Genomic DNA was amplified by polymerase chain reaction using the "touchdown" methodology with an initial denaturation step at 95° C. for 10 min. This was followed by 10 touchdown cycles of 30s at 94° C., 30s at 70° C. (with a decrease in the annealing temperature by 1° C. each cycle), and 30s at 72° C. This was followed by 30 cycles of 30s at 94° C., 30s at 60° C. and 30s at 72° C., with a final extension at 72° C. for 10 min. DNA (~50–100 ng of genomic DNA or ~5–15 ng of cDNA) was amplified in 20 $\mu$l reaction volumes containing: 50 mM KCl, 10 mM Tris (pH 8.3), 1.5 nM $MgCl_2$, 0.001% gelatin, 200 $\mu$M dNTPs, 1 $\mu$M of each primer, and 0.5 U Amplitaq Gold (Perkin Elmer Cetus), and of 2 $\mu$Ci $^{32}$P-dCTP (Amersham). The samples were heat denatured, snap chilled, and run on a 6.8% acrylamide gel (acrylamide/bis acrylamide ratio 19:1) containing 10M urea. The gels were dried and exposed overnight using BioMax film (Kodak).

From the 146 genes chosen for analysis, 104 of them amplified well within 3 rounds of primer design. Of the 104 that amplified, 54 (52%) of them were found to be polymorphic on our panels (polymorphic defined as at least 2 alleles found among a sample size of 60–74 chromosomes). The experimental results are summarized in Table 3 and predictions from the two codes compared.

TABLE 3

Summary of genes tested for polymorphism within gene regions and
comparison of the codes used to predict them
(Rep-X predictions in parentheses)

| Region | Poly-morphic | Non-poly-morphic | % Polymorphic | Avg. Hetero-Zygosity | Avg. # Alleles |
|---|---|---|---|---|---|
| 5' UTR | 6 (6) | 7 (3) | 46% (67%) | 28% ± 30% | 5.33 ± 6.28 |
| CDS | 17 (14) | 27 (12) | 38% (54%) | 22% ± 25% | 2.82 ± 0.95 |
| 3' UTR | 24 (23) | 10 (7) | 70% (77%) | 38% ± 34% | 4.00 ± 2.30 |
| Unknown | 7 (7) | 6 (4) | 53% (64%) | 37% ± 24% | 3.29 ± 1.38 |
| TOTAL | 54 (50) | 50 (26) | 52% (66%) | | |

For both of the untranslated regions, longer average length and higher homogeneity tend to be associated more with a polymorphic locus, but the coding sequence remains approximately the same (Table 4). In addition to known genes, we also analyzed expressed sequence tags (ESTs, see Table 1).

TABLE 4

Average lengths and homogeneities between
polymorphic and non-polymorphic repeats

| | Polymorphic | | Non-polymorphic | |
|---|---|---|---|---|
| Region | Avg. Length | Avg. Homogeneity | Avg. Length | Avg. Homogeneity |
| 5' UTR | 13.0 ± 7.7 | 1.00 | 9.4 ± 4.2 | 0.96 ± 0.03 |
| CDS | 12.3 ± 6.3 | 0.96 ± 0.04 | 11.8 ± 6.3 | 0.94 ± 0.04 |
| 3' UTR | 15.5 ± 5.8 | 0.99 ± 0.01 | 11.4 ± 3.8 | 0.97 ± 0.03 |

As shown in Table 3, POMPOUS predicted 104 to be polymorphic while 54 were (52% accurate) while Rep-X predicted 76 to be polymorphic and 50 were (66% accurate), failing to predict only 4 of the repeats that turned out to be polymorphic. From this we can conclude that, at least for microsatellite repeats, the greater the length and homogeneity of the repeat unit, the more likely it will be highly polymorphic. Given its greater specificity, we used Rep-X to generate predictions of polymorphic regions in the various organisms contained in UniGene (see Table 5). Also, because 3' UTR sequences are more common than 5' UTR sequences[26], we show the relative frequencies of repeats in each of these regions.

We further investigated our new polymorphisms for functional effect, two of which we detail here: Herpes Viral Entry protein C (HVEC) and a sperm acrosomal protein (ACRP). In HVEC, the repeat encodes 8 glutamic acid residues located on the cytoplasmic portion of this transmembrane protein. Although this portion of the protein is not necessary for actual HSV entry into the cell[29], susceptibility to HSV infection is known to exhibit inter-individual variation along with the length, intensity and duration of the lytic cycles that characterize the infectious state[30]. In addition, polyglutamic acid tracts have been associated with microtubule binding[31] and factors promoting DNA conformational changes[32], indicating this region could play a possible role in individual variance in susceptibility and response to HSV infections by either active transport of the viral capsid within the cell or activation of its genetic material in response to signaling. Investigating this possibility using viral entry assays[29], we find these HVEC variants diagnostic of viral susceptibility.

ACRP has a di-nucleotide repeat (TG) at the end of its coding sequence with a stop codon in all 3 frames shortly thereafter, preventing this frame-shifting mutation from varying more than 10 amino acids in allelic variants. This TG repeat (polymorphic CA on the opposite strand) occurs right at the end of the protein with the stop codon being part of the TG repeat (a TGA codon). Any repeat expansion causes a frame shift, but alternating TG will always be Cys-Val. A stop codon follows closely in all frames, the translations being (MCVCV, CVCVCESVNAQVGI and VCVCVRV). The pattern GMCVCV can be subject to myristylation, which can anchor proteins to the cytoplasmic face of membranes. ACRP is a homolog of Fox Sperm Acrosomal protein 1 (FSA-1) where it is found in maturing and elongating spermatid heads[35]. A partial human EST, F26915, has a contraction of the TG repeat to 7 times along with a deletion of a C earlier in the protein (Mao, M. et al, PNAS Jul 7, 1998;95(14):8175–80). Employing sperm penetration assays (Morales P, et al. Andrologia 1999 May;31 (3):131–5), we find these ACRP variants diagnostic of human sperm dysfunction.

Approximately 90% of the tandem repeats we predicted to be polymorphic within the coding sequence of genes had unit lengths a multiple of 3. This we predicted, as any repeat for which an expansion or contraction would lead to a frame shift and nonsense mutation would be selected against. The 5' UTR has a similar bias, although not as pronounced (as shown in Table 6). The 3' UTR regions displayed a broad distribution of repeat unit sizes, but were biased towards

TABLE 5

Number of computationally-derived polymorphic repetitive element predicted in
October 1999 UniGene for listed organisms and where in the cDNA they were found.
Numbers in parentheses represent percentage of the
annotated entries found in the various cDNA regions

| Organism | Total Entries | Annotated | 5'UTR | CDS | 3'UTR | Unknown |
|---|---|---|---|---|---|---|
| H. sapiens | 85,639 | 8,347 | 362(4.3%) | 607(7.3%) | 1,305(15.6%) | 28,258 |
| Frequency of repeats = 1 every | | | 3,453 bp | 23,064 bp | 5,348 bp | 1,284 bp |
| Frequency of ALUs = 1 every | | | 9,842 bp | 823,530 bp | 11,276 bp | 3,239 bp |
| M. musculus | 27,071 | 4,815 | 245(5.0%) | 277(5.7%) | 964(20.0%) | 8,338 |
| Frequency of repeats = 1 every | | | 2,775 bp | 26,714 bp | 2,831 bp | 1,343 bp |
| R. norvegicus | 27,161 | 3,109 | 107(3.4%) | 146(4.7%) | 577(18.6%) | 15,618 |
| Frequency of repeats = 1 every | | | 4,018 bp | 32,191 bp | 3,050 bp | 700 bp |
| D. rerio | 5,614 | 261 | 10(3.8%) | 5(1.9%) | 59(22.6%) | 2,968 | mononucleotide repeats even after the poly-A tails were subtracted from the analysis. Approximately 10% of the repeats in the cds were not multiples of 3—providing the best candidates for major phenotype associated genetic variation.

TABLE 6

Length of repeat units by gene region

| Repeat Length | 5' UTR | CDS | 3' UTR |
|---|---|---|---|
| 1 | 182 | 39 | 1449* |
| 2 | 55 | 16 | 424 |
| 3 | 130 | 406 | 71 |
| 4 | 12 | 1 | 91 |
| 5 | 32 | 9 | 91 |
| 6 | 22 | 70 | 37 |
| 7 | 3 | 0 | 2 |
| 8 | 0 | 0 | 2 |
| 9+ | 14 | 87 | 35 |
| TOTAL | 450 | 628 | 2,202 |
| Divisible By 3 | 155 (34.1%) | 566 (89.2%) | 121 (5.5%) |

*Poly-A tails removed from consideration

TABLE 7

Tri-nucleotide repeats occurring 6 or more times in the genome

| Cyclic permutations | % of repeats in | % of repeats in coding | Amino acids |
|---|---|---|---|
| AAT | 2.27 | 0.00 | NI. |
| TTA | 2.34 | 0.00 | LYI |
| ATC | 0.34 | 0.66 | ISH |
| TAG | 0.05 | 0.00 | .SV |
| AAC | 1.70 | 1.10 | NTQ |
| TTG | 1.71 | 0.00 | LCV |
| ACT | 0.12 | 0.00 | TLY |
| TGA | 0.42 | 3.52 | .DM |
| AAG | 0.62 | 4.19 | KRE |
| TTC | 0.56 | 0.00 | FSL |
| ACC | 0.50 | 8.59 | TPH |
| TGG | 0.28 | 0.66 | WGV |
| ACG | 0.01 | 0.66 | TRD |
| TGC | 0.51 | 11.67 | CAL |
| CCG | 0.50 | 7.49 | PRA |
| GGC | 0.66 | 11.89 | GAR |
| AGG | 0.64 | 14.98 | RGE |
| TCC | 0.56 | 5.51 | SPL |
| CAG | 0.73 | 20.48 | QSA |
| GTC | 0.00 | 0.00 | VSR |
| AAA | 45.34 | 6.61 | K |
| TTT | 40.01 | 1.54 | F |
| CCC | 0.05 | 0.00 | P |
| GGG | 0.06 | 0.44 | G |
| TOTAL | 100% | 100% | |

There is also a bias in the codons used to encode tri-nucleotide repeats. When cyclic permutations and complements of the codon are considered, there are only 10 trinucleotide codon repeat types excluding the monomer based repeats (Table 7). For example, the first three forward strand cyclic permutations of AAC are AAC, ACA and CAA while the reverse strand cyclic permutations are TTG, TGT and GTT. The numbers given under the "Cyclic permutations" column suggest that certain codon repeats are selected against. Indeed, it has been noted that CTG repeats on the lagging strand during DNA synthesis are better able to form stable secondary structures than CAG repeats[16], which could also interfere with transcription, indicating predictive value of criteria beyond length and homogeneity. The bias in repetitive codon usage in Table 7 indicates that other repetitive elements such as TCC, TTC, TGG, ACT and ACG are rarely or never used. These types of repeats, in fact, have been found to be highly polymorphic in intragenic DNA and support slipped-strand mispairing as a source of instability[28].

We analyzed tandem peptide repeats with respect to their codon usage from the annotated UniGene dataset to see if certain amino acid repeats were more or less likely to contain potential polymorphic repeats (Table 8). Whatever role amino acid repeats such as glutamine and histidine serve in the cell, there is more allowance for copy number variance than among amino acid repeats such as proline or glycine. In fact, in the breakdown by quartile for proline, there is considerable selection for diverse codon usage. Some amino acid repeats are used rarely or not at all, some such as tryptophan or tyrosine presumably because their bulkiness could contribute to unstable structures due to steric interference, cysteine possibly because of unstable cross-linking, while others such as isoleucine and valine more likely are rare because they are encoded for by codons containing the fewest number of hydrogen bonds (Table 7). Other amino acid repeats such as glutamic acid are found in relative abundance to other amino acids.

TABLE 8

Occurrence of human tandem peptide repeats and their corresponding codon degeneracy as given by the UniGene database.

| | Polymorphic | | | | | Degeneracy scores | | | | | | | | |
|---|---|---|---|---|---|---|---|---|---|---|---|---|---|---|
| AA | # Reps | # | % | Avg. # of Peptides | Avg. % Position | Avg. Degen. | <.25 | .25–.50 | .51–.75 | >.75 | # of co-dons | Freq.[a] | # aa's counted | % of all aa's used | Freq.[b] | Type of AA |
| G | 147 | 26 | 18% | 7.9 | 38.5 | 0.449 | 30 | 59 | 48 | 10 | 4 | 1.80 | 313929 | 6.7% | 1.68 | Hydrophobic |
| A | 174 | 37 | 21% | 8.1 | 39.3 | 0.448 | 35 | 72 | 47 | 20 | 4 | 2.13 | 327544 | 7.0% | 1.91 | Hydrophobic |
| V | 2 | 0 | 0% | 6.0 | 45.0 | 0.250 | 1 | 1 | 0 | 0 | 4 | 0.02 | 284258 | 6.1% | 0.03 | Hydrophobic |
| L | 123 | 37 | 30% | 7.0 | 18.8 | 0.345 | 45 | 50 | 23 | 5 | 6 | 1.00 | 451805 | 9.6% | 0.98 | Hydrophobic |
| 1 | 0 | 0 | 0% | 0 | 0 | 0 | 0 | 0 | 0 | 0 | 3 | 0 | 208500 | 4.5% | 0 | Hydrophobic |
| P | 213 | 15 | 7% | 7.4 | 52.9 | 0.552 | 24 | 71 | 78 | 40 | 4 | 2.61 | 293628 | 6.3% | 2.60 | Hydrophobic |

TABLE 8-continued

Occurrence of human tandem peptide repeats and their corresponding codon degeneracy as given by the UniGene database.

| | Polymorphic | | | | | Degeneracy scores | | | | | | | | | | |
|---|---|---|---|---|---|---|---|---|---|---|---|---|---|---|---|---|
| AA | # Reps | # | % | Avg. # of Peptides | Avg. % Position | Avg. Degen. | <.25 | .25–.50 | .51–.75 | >.75 | # of codons | Freq.[a] | # aa's counted | % of all aa's used | Freq.[b] | Type of AA |
| M | 1 | 1 | 100% | 7.0 | 0 | 0 | 1 | 0 | 0 | 0 | 1 | 0.05 | 101882 | 2.2% | 0.04 | Hydrophobic Sulfur |
| C | 7 | 5 | 71% | 10.0 | 55.1 | 0.230 | 5 | 1 | 1 | 0 | 2 | 0.17 | 102444 | 2.2% | 0.25 | Hydrophilic Sulfur |
| Q | 109 | 68 | 62% | 11.1 | 54.2 | 0.241 | 53 | 52 | 4 | 0 | 2 | 2.67 | 221732 | 4.7% | 1.76 | Hydrophilic Amide |
| N | 1 | 1 | 100% | 8.0 | 1 | 0 | 1 | 0 | 0 | 0 | 2 | 0.02 | 173598 | 3.7% | 0.02 | Hydrophilic Amide |
| S | 143 | 32 | 22% | 8.1 | 49.4 | 0.443 | 37 | 49 | 41 | 16 | 6 | 1.17 | 378755 | 8.1% | 1.35 | Hydrophilic Hydroxyl |
| T | 19 | 7 | 37% | 7.4 | 48.6 | 0.307 | 7 | 10 | 2 | 0 | 4 | 0.23 | 251010 | 5.4% | 0.27 | Hydrophilic Hydroxyl |
| D | 24 | 13 | 54% | 7.3 | 55.2 | 0.151 | 16 | 7 | 1 | 0 | 2 | 0.59 | 231506 | 4.9% | 0.37 | Acidic |
| E | 240 | 42 | 18% | 8.0 | 52.1 | 0.357 | 53 | 149 | 37 | 1 | 2 | 5.88 | 335522 | 7.2% | 2.57 | Acidic |
| H | 36 | 25 | 69% | 9.1 | 45.8 | 0.200 | 24 | 9 | 3 | 0 | 2 | 0.88 | 118497 | 2.5% | 1.09 | Basic |
| K | 47 | 7 | 15% | 6.7 | 47.3 | 0.444 | 11 | 16 | 20 | 0 | 2 | 1.15 | 272770 | 5.8% | 0.62 | Basic |
| R | 17 | 2 | 12% | 6.5 | 34.1 | 0.409 | 3 | 12 | 1 | 1 | 6 | 0.14 | 261837 | 5.6% | 0.23 | Basic |
| F | 3 | 3 | 100% | 6.7 | 36.3 | 0 | 3 | 0 | 0 | 0 | 2 | 0.07 | 170022 | 3.6% | 0.06 | Aromatic |
| W | 0 | 0 | 0% | 0 | 0 | 0 | 0 | 0 | 0 | 0 | 1 | 0 | 56196 | 1.2% | 0 | Aromatic |
| Y | 0 | 0 | 0% | 0 | 0 | 0 | 0 | 0 | 0 | 0 | 2 | 0 | 128571 | 2.7% | 0 | Aromatic |
| Tot | 1306 | 321 | 25% | | | | 349 | 558 | 306 | 93 | | | 4684006 | | | | freq.[a] = Normalized frequency by codon
freq.[b] = Normalized frequency by codon

References

1) Fondon J W 3rd. Et al. *PNAS.* 95(13):7514–9, Jun. 23, 1998.
2) Chastain P D. et al. *J Mol Biol.* 275(3):405–11, Jan. 23, 1998.
3) The Huntington's Disease Collaborative Research Group, *Cell* Mar. 26, 1993;72(6):971–83
4) Verkerk A J et al. *Cell* May 31, 1991;65(5):905–14
5) Bidichandani S I, et al. *Amer J Human Genetics* 1998 Jan. 62(1):111–21
6) Jansen G, et al. *Amer J Human Genetics.* 54: 575–585, 1994.
7) Goldman A, et al. *J Med Genetics.* 31: 37–40, 1994.
8) Kawaguchi, Y. et al *Nature Genetics.* 8: 221–228, 1994.
12) Gharani N, et al.. *Human Mol Genetics.* 6(3):397–402, 1997 Mar.
13) Kleiderlein J J, et al. *Human Genetics.* 103(6):666–73, 1998 Dec.
15) Jakupciak J P et al. *J Biol Chem,* Vol. 274, Issue 33, 23468–23479, Aug. 13, 1999
16) Wells R D *J Biol Chem* Feb. 9, 1996;271(6):2875–8
17) Weber J L *Curr Opin in Biotech* 1(2):166–71, 1990 Dec.
18) Rayner S et al. *Genome Research.* 8(7):741–7, 1998 Jul.
19) Rubinsztein D C, et al. *Amer J Human Genetics.* 59: 16–22, 1996.
22) Nakamura, Y. et al. *Science* 235: 1616–22, 1987.
23) Sumiyama K. et al. *J Mol Evolution.* 43(3):170–8, 1996 Sept.
24) Ordway J M et al. *Philosophical Transactions of the Royal Society of London—Series B: Biological Sciences.* 54(1386):1083–8, Jun. 29, 1999.
25) Karthikeyan G, et al. *Nucl Acids Res* Oct. 1, 1999;27(19):3851–3858
26) Boguski M S et al. *Nature Genetics* 1995 Aug.;10(4):369–71
28) Gastier J M et al. *Human Molecular Genetics.* 4(10):1829–36, 1995 Oct.
29) Cocchi F, et al. *PNAS* Dec. 22, 1998;95(26):15700–5
30) Garcia-Blanco M A, et al. *Science* Nov. 8, 1991;254(5033):815–20
31) Regnard C et al. *Biochemistry.* 37(23):8395–404, Jun. 9, 1998.
32) Ichiba Y et al. *Biochem Biophys Res Comm.* 242(2):441–5, Jan. 14, 1998.
33) Altschul S F, et al. *Nucleic Acids Research* Sep. 1, 1997;25(17):3389–402
34) Rubinsztein D C et al. *Philosophical Transactions of the Royal Society of London—Series B: Biological Sciences.* 354(1386):1095–9, Jun. 29, 1999.
35) Beaton S, et al. *Reprod Fertil Dev* 1994;6(6):761–70
36) Petruska J et al. *Nucleic Acids Res* Jun. 1, 1996;24(11):1992–8

All publications and patent applications cited in this specification and all references cited therein are herein incorporated by reference as if each individual publication or patent application or reference were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

SEQUENCE LISTING

<160> NUMBER OF SEQ ID NOS: 346

<210> SEQ ID NO 1
<211> LENGTH: 13
<212> TYPE: DNA
<213> ORGANISM: human

<400> SEQUENCE: 1
gattctcaaa gcg                                                          13

<210> SEQ ID NO 2
<211> LENGTH: 10
<212> TYPE: DNA
<213> ORGANISM: human
<220> FEATURE:
<223> OTHER INFORMATION: n signifies a, t, c or g.

<400> SEQUENCE: 2 tttttttnt                                                               10

<210> SEQ ID NO 3
<211> LENGTH: 13
<212> TYPE: DNA
<213> ORGANISM: human

<400> SEQUENCE: 3
aacaaaaaac aac                                                          13

<210> SEQ ID NO 4
<211> LENGTH: 10
<212> TYPE: DNA
<213> ORGANISM: human

<400> SEQUENCE: 4
aatggaatgc                                                              10

<210> SEQ ID NO 5
<211> LENGTH: 10
<212> TYPE: DNA
<213> ORGANISM: human

<400> SEQUENCE: 5
tgggagagac                                                              10

<210> SEQ ID NO 6
<211> LENGTH: 14
<212> TYPE: DNA
<213> ORGANISM: human

<400> SEQUENCE: 6
catgtgtgtg cata                                                         14

<210> SEQ ID NO 7
<211> LENGTH: 123
<212> TYPE: DNA
<213> ORGANISM: human

<400> SEQUENCE: 7
ctcggggaat tccaattcca cattttcaag aaataaggag gcaaaaatgt tcatatatga       60
attggaatta tttgttttct tattaggcct atcctgaagc caaggaaat gagatcggaa       120 ttc                                                                    123

```
<210> SEQ ID NO 8
<211> LENGTH: 10
<212> TYPE: DNA
<213> ORGANISM: human

<400> SEQUENCE: 8
tttttttgta                                                              10

<210> SEQ ID NO 9
<211> LENGTH: 15
<212> TYPE: DNA
<213> ORGANISM: human

<400> SEQUENCE: 9
ggcggcgact tcggc                                                        15

<210> SEQ ID NO 10
<211> LENGTH: 12
<212> TYPE: DNA
<213> ORGANISM: human

<400> SEQUENCE: 10
gcagagggac ac                                                           12

<210> SEQ ID NO 11
<211> LENGTH: 10
<212> TYPE: DNA
<213> ORGANISM: human

<400> SEQUENCE: 11
ctggggtggc                                                              10

<210> SEQ ID NO 12
<211> LENGTH: 19
<212> TYPE: DNA
<213> ORGANISM: human

<400> SEQUENCE: 12
tttctttctt tcttttct                                                     19

<210> SEQ ID NO 13
<211> LENGTH: 10
<212> TYPE: DNA
<213> ORGANISM: human

<400> SEQUENCE: 13
ctttctagcc                                                              10

<210> SEQ ID NO 14
<211> LENGTH: 11
<212> TYPE: DNA
<213> ORGANISM: human

<400> SEQUENCE: 14
tttttttatt t                                                            11

<210> SEQ ID NO 15
<211> LENGTH: 22
<212> TYPE: DNA
<213> ORGANISM: human

<400> SEQUENCE: 15
```

-continued cagtaacgac gttgtgtttt cc                                              22

<210> SEQ ID NO 16
<211> LENGTH: 22
<212> TYPE: DNA
<213> ORGANISM: human

<400> SEQUENCE: 16
acgacgttgt gttttcccag tc                                              22

<210> SEQ ID NO 17
<211> LENGTH: 58
<212> TYPE: DNA
<213> ORGANISM: human

<400> SEQUENCE: 17
gcacagaagc gcagaagcaa agcccaggca gaaccatgct aaccttacag ctcagcct       58

<210> SEQ ID NO 18
<211> LENGTH: 12
<212> TYPE: DNA
<213> ORGANISM: human

<400> SEQUENCE: 18
gaaggaagaa ag                                                         12

<210> SEQ ID NO 19
<211> LENGTH: 12
<212> TYPE: DNA
<213> ORGANISM: human

<400> SEQUENCE: 19
tttttttctt tc                                                         12

<210> SEQ ID NO 20
<211> LENGTH: 18
<212> TYPE: DNA
<213> ORGANISM: human

<400> SEQUENCE: 20
tggtgatggt ggtggtgg                                                   18

<210> SEQ ID NO 21
<211> LENGTH: 18
<212> TYPE: DNA
<213> ORGANISM: human

<400> SEQUENCE: 21
gtcttgatat gtgctgag                                                   18

<210> SEQ ID NO 22
<211> LENGTH: 19
<212> TYPE: DNA
<213> ORGANISM: human

<400> SEQUENCE: 22
tgccgagaga gcatgtagg                                                  19

<210> SEQ ID NO 23
<211> LENGTH: 10
<212> TYPE: DNA
<213> ORGANISM: human

<400> SEQUENCE: 23

```
tgtatgtgta                                                              10

<210> SEQ ID NO 24
<211> LENGTH: 10
<212> TYPE: DNA
<213> ORGANISM: human

<400> SEQUENCE: 24
tgtgtgcatg                                                              10

<210> SEQ ID NO 25
<211> LENGTH: 120
<212> TYPE: DNA
<213> ORGANISM: human

<400> SEQUENCE: 25
ctctcgtcag ccccaaagcc tgtggctgca gccacgcttg tgtcccagca ggctgaagag       60
ggcctcacct taccccagga ctccgctatg acaccgcctc tgcccctaca agacacagat      120

<210> SEQ ID NO 26
<211> LENGTH: 120
<212> TYPE: DNA
<213> ORGANISM: human

<400> SEQUENCE: 26
ttgtgtccca gcaggctgaa gagggcctca ccttacccca ggactccgct atgacaccgc       60
ctctgcccct acaagacaca gatctctcgt cagccccaaa gcctgtggct gcagccacga      120

<210> SEQ ID NO 27
<211> LENGTH: 20
<212> TYPE: DNA
<213> ORGANISM: human

<400> SEQUENCE: 27
ccctcccctc cctcagtcct                                                   20

<210> SEQ ID NO 28
<211> LENGTH: 18
<212> TYPE: DNA
<213> ORGANISM: human

<400> SEQUENCE: 28
acagtgcagt actcagta                                                     18

<210> SEQ ID NO 29
<211> LENGTH: 13
<212> TYPE: DNA
<213> ORGANISM: human

<400> SEQUENCE: 29
caaaaaaaaa aaa                                                          13

<210> SEQ ID NO 30
<211> LENGTH: 36
<212> TYPE: DNA
<213> ORGANISM: human

<400> SEQUENCE: 30
tcatcagctg ggttgattgt gtgggttaga tagagg                                 36

<210> SEQ ID NO 31
```

-continued

```
<211> LENGTH: 12
<212> TYPE: DNA
<213> ORGANISM: human

<400> SEQUENCE: 31
cccacgcgtc cg                                                    12

<210> SEQ ID NO 32
<211> LENGTH: 12
<212> TYPE: DNA
<213> ORGANISM: human

<400> SEQUENCE: 32
cagcagcagc aa                                                    12

<210> SEQ ID NO 33
<211> LENGTH: 10
<212> TYPE: DNA
<213> ORGANISM: human

<400> SEQUENCE: 33
tatatataaa                                                       10

<210> SEQ ID NO 34
<211> LENGTH: 10
<212> TYPE: DNA
<213> ORGANISM: human

<400> SEQUENCE: 34
cccaccctac                                                       10

<210> SEQ ID NO 35
<211> LENGTH: 24
<212> TYPE: DNA
<213> ORGANISM: human

<400> SEQUENCE: 35
cctacacccc ctcccctgcc cctg                                       24

<210> SEQ ID NO 36
<211> LENGTH: 10
<212> TYPE: DNA
<213> ORGANISM: human

<400> SEQUENCE: 36
gggccgggct                                                       10

<210> SEQ ID NO 37
<211> LENGTH: 12
<212> TYPE: DNA
<213> ORGANISM: human

<400> SEQUENCE: 37
cagcagccgc ca                                                    12

<210> SEQ ID NO 38
<211> LENGTH: 43
<212> TYPE: DNA
<213> ORGANISM: human

<400> SEQUENCE: 38
gggtccaggc accggcgccc agccccgtg gggtgtccag ggc                   43
```

-continued

```
<210> SEQ ID NO 39
<211> LENGTH: 16
<212> TYPE: DNA
<213> ORGANISM: human

<400> SEQUENCE: 39
tctccgcgcc ccgagg                                                   16

<210> SEQ ID NO 40
<211> LENGTH: 69
<212> TYPE: DNA
<213> ORGANISM: human

<400> SEQUENCE: 40
gctgaaggct gcagtgggtg agttgccaga gaaatccaag ctgcaggaga tctaccagga   60
gctgacccg                                                           69

<210> SEQ ID NO 41
<211> LENGTH: 12
<212> TYPE: DNA
<213> ORGANISM: human

<400> SEQUENCE: 41
cccccttccc ct                                                       12

<210> SEQ ID NO 42
<211> LENGTH: 12
<212> TYPE: DNA
<213> ORGANISM: human

<400> SEQUENCE: 42
ggagcccacg ga                                                       12

<210> SEQ ID NO 43
<211> LENGTH: 39
<212> TYPE: DNA
<213> ORGANISM: human

<400> SEQUENCE: 43
ccccagagga gcccacctcc ccagctgctg cagtgccca                          39

<210> SEQ ID NO 44
<211> LENGTH: 39
<212> TYPE: DNA
<213> ORGANISM: human

<400> SEQUENCE: 44
cctccccagc tgctgcagtg cccaccccag aggagcccg                          39

<210> SEQ ID NO 45
<211> LENGTH: 39
<212> TYPE: DNA
<213> ORGANISM: human

<400> SEQUENCE: 45
cctccccagc tgctgcagtg cccaccccag aggagccca                          39

<210> SEQ ID NO 46
<211> LENGTH: 18
<212> TYPE: DNA
<213> ORGANISM: human

<400> SEQUENCE: 46
```

-continued

```
tcctgcaggc cagatgac                                              18

<210> SEQ ID NO 47
<211> LENGTH: 10
<212> TYPE: DNA
<213> ORGANISM: human

<400> SEQUENCE: 47
tttttttctt                                                       10

<210> SEQ ID NO 48
<211> LENGTH: 30
<212> TYPE: DNA
<213> ORGANISM: human

<400> SEQUENCE: 48
tccatggact cccagatgtt agcaaccagc                                 30

<210> SEQ ID NO 49
<211> LENGTH: 30
<212> TYPE: DNA
<213> ORGANISM: human

<400> SEQUENCE: 49
ccatggactc ccagatgtta gcaactagct                                 30

<210> SEQ ID NO 50
<211> LENGTH: 24
<212> TYPE: DNA
<213> ORGANISM: human

<400> SEQUENCE: 50
cgctctatga tgtcagccta cgag                                       24

<210> SEQ ID NO 51
<211> LENGTH: 21
<212> TYPE: DNA
<213> ORGANISM: human

<400> SEQUENCE: 51
agccgccgca gccgcacccc c                                          21

<210> SEQ ID NO 52
<211> LENGTH: 59
<212> TYPE: DNA
<213> ORGANISM: human

<400> SEQUENCE: 52
tgattcacac ccagtccctg ccacagaccg tctcagacac gcacagtggg cctgctgca  59

<210> SEQ ID NO 53
<211> LENGTH: 12
<212> TYPE: DNA
<213> ORGANISM: human

<400> SEQUENCE: 53
gacatgcacg ca                                                    12

<210> SEQ ID NO 54
<211> LENGTH: 10
<212> TYPE: DNA
<213> ORGANISM: human

<400> SEQUENCE: 54
```

```
ccgctctcgc                                                          10

<210> SEQ ID NO 55
<211> LENGTH: 25
<212> TYPE: DNA
<213> ORGANISM: human

<400> SEQUENCE: 55
cctgccctgc cctgtcctgt cctgc                                         25

<210> SEQ ID NO 56
<211> LENGTH: 20
<212> TYPE: DNA
<213> ORGANISM: human

<400> SEQUENCE: 56
ccctgccctg tcctgtcctg                                               20

<210> SEQ ID NO 57
<211> LENGTH: 45
<212> TYPE: DNA
<213> ORGANISM: human

<400> SEQUENCE: 57
gggactcctg ccccagctgc tgaagagaca atgaccacca gcccg                   45

<210> SEQ ID NO 58
<211> LENGTH: 18
<212> TYPE: DNA
<213> ORGANISM: human

<400> SEQUENCE: 58
caggctcagg cccaggcg                                                 18

<210> SEQ ID NO 59
<211> LENGTH: 12
<212> TYPE: DNA
<213> ORGANISM: human

<400> SEQUENCE: 59
cagcagcaac aa                                                       12

<210> SEQ ID NO 60
<211> LENGTH: 16
<212> TYPE: DNA
<213> ORGANISM: human

<400> SEQUENCE: 60
ggagagaggc agagag                                                   16

<210> SEQ ID NO 61
<211> LENGTH: 19
<212> TYPE: DNA
<213> ORGANISM: human

<400> SEQUENCE: 61
catatgtatt ttgtatttg                                                19

<210> SEQ ID NO 62
<211> LENGTH: 14
<212> TYPE: DNA
<213> ORGANISM: human
```

```
<400> SEQUENCE: 62
cccggccccg cgcc                                                  14

<210> SEQ ID NO 63
<211> LENGTH: 12
<212> TYPE: DNA
<213> ORGANISM: human

<400> SEQUENCE: 63
cagcagctgc ag                                                    12

<210> SEQ ID NO 64
<211> LENGTH: 21
<212> TYPE: DNA
<213> ORGANISM: human

<400> SEQUENCE: 64
cagaaaaacc caccattccc t                                          21

<210> SEQ ID NO 65
<211> LENGTH: 19
<212> TYPE: DNA
<213> ORGANISM: human

<400> SEQUENCE: 65
tctatctatc tatcatcta                                             19

<210> SEQ ID NO 66
<211> LENGTH: 10
<212> TYPE: DNA
<213> ORGANISM: human

<400> SEQUENCE: 66
aaaaaaaaag                                                       10

<210> SEQ ID NO 67
<211> LENGTH: 48
<212> TYPE: DNA
<213> ORGANISM: human

<400> SEQUENCE: 67
tgtaccaagg tccctgagcc aggctgtacc aaggtccctg agccaggt             48

<210> SEQ ID NO 68
<211> LENGTH: 24
<212> TYPE: DNA
<213> ORGANISM: human

<400> SEQUENCE: 68
gagccaggct gtaccaaggt ccct                                       24

<210> SEQ ID NO 69
<211> LENGTH: 15
<212> TYPE: DNA
<213> ORGANISM: human

<400> SEQUENCE: 69
cctgaggacc aagaa                                                 15

<210> SEQ ID NO 70
<211> LENGTH: 12
<212> TYPE: DNA
<213> ORGANISM: human
```

<400> SEQUENCE: 70
cagcagcagc aa                                                12

<210> SEQ ID NO 71
<211> LENGTH: 18
<212> TYPE: DNA
<213> ORGANISM: human

<400> SEQUENCE: 71
gacagcagtg acagcagc                                          18

<210> SEQ ID NO 72
<211> LENGTH: 18
<212> TYPE: DNA
<213> ORGANISM: human

<400> SEQUENCE: 72
agcagtgaca gcagcgat                                          18

<210> SEQ ID NO 73
<211> LENGTH: 60
<212> TYPE: DNA
<213> ORGANISM: human

<400> SEQUENCE: 73
gagccagccg agagcccatc ggagacccca ggcccccgcc cggcaggacc tgcaggggac    60

<210> SEQ ID NO 74
<211> LENGTH: 21
<212> TYPE: DNA
<213> ORGANISM: human

<400> SEQUENCE: 74
tgaatgaatg agtgaacgga a                                      21

<210> SEQ ID NO 75
<211> LENGTH: 53
<212> TYPE: DNA
<213> ORGANISM: human

<400> SEQUENCE: 75
tggtttcatg agtgtgcgcg tggggtgagt gctcgccgcc gtgacgttcg ggg    53

<210> SEQ ID NO 76
<211> LENGTH: 14
<212> TYPE: DNA
<213> ORGANISM: human

<400> SEQUENCE: 76
tctctctccc cgac                                              14

<210> SEQ ID NO 77
<211> LENGTH: 27
<212> TYPE: DNA
<213> ORGANISM: human

<400> SEQUENCE: 77
aggcaggcag gggaggcagg aggcagg                                27

<210> SEQ ID NO 78
<211> LENGTH: 16
<212> TYPE: DNA

-continued

```
<213> ORGANISM: human

<400> SEQUENCE: 78
gcccagcgag agttgc                                                  16

<210> SEQ ID NO 79
<211> LENGTH: 14
<212> TYPE: DNA
<213> ORGANISM: human

<400> SEQUENCE: 79
ggctgcgggc tccg                                                    14

<210> SEQ ID NO 80
<211> LENGTH: 10
<212> TYPE: DNA
<213> ORGANISM: human

<400> SEQUENCE: 80
tctttctttc                                                         10

<210> SEQ ID NO 81
<211> LENGTH: 12
<212> TYPE: DNA
<213> ORGANISM: human

<400> SEQUENCE: 81
ctctcgctct ct                                                      12

<210> SEQ ID NO 82
<211> LENGTH: 10
<212> TYPE: DNA
<213> ORGANISM: human

<400> SEQUENCE: 82
tagataatag                                                         10

<210> SEQ ID NO 83
<211> LENGTH: 15
<212> TYPE: DNA
<213> ORGANISM: human

<400> SEQUENCE: 83
atatatatat ataaa                                                   15

<210> SEQ ID NO 84
<211> LENGTH: 29
<212> TYPE: DNA
<213> ORGANISM: human

<400> SEQUENCE: 84
tatagaagta tagtattaca tgaaaatag                                    29

<210> SEQ ID NO 85
<211> LENGTH: 12
<212> TYPE: DNA
<213> ORGANISM: human

<400> SEQUENCE: 85
gagacccctg cc                                                      12

<210> SEQ ID NO 86
<211> LENGTH: 42
```

```
<212> TYPE: DNA
<213> ORGANISM: human

<400> SEQUENCE: 86
gggaacacag ccgctcccct ctgctctgca ccccactcgt gg        42

<210> SEQ ID NO 87
<211> LENGTH: 10
<212> TYPE: DNA
<213> ORGANISM: human

<400> SEQUENCE: 87
tatattaata                                            10

<210> SEQ ID NO 88
<211> LENGTH: 10
<212> TYPE: DNA
<213> ORGANISM: human

<400> SEQUENCE: 88
tcactgaagg                                            10

<210> SEQ ID NO 89
<211> LENGTH: 37
<212> TYPE: DNA
<213> ORGANISM: human

<400> SEQUENCE: 89
ccctctggac agcacctggc ccgccactct gccatca              37

<210> SEQ ID NO 90
<211> LENGTH: 10
<212> TYPE: DNA
<213> ORGANISM: human

<400> SEQUENCE: 90
aaaaaaacaa                                            10

<210> SEQ ID NO 91
<211> LENGTH: 11
<212> TYPE: DNA
<213> ORGANISM: human

<400> SEQUENCE: 91
tatacattgt g                                          11

<210> SEQ ID NO 92
<211> LENGTH: 12
<212> TYPE: DNA
<213> ORGANISM: human

<400> SEQUENCE: 92
tatttattta ta                                         12

<210> SEQ ID NO 93
<211> LENGTH: 60
<212> TYPE: DNA
<213> ORGANISM: human

<400> SEQUENCE: 93
acactgtctt tgtctttgca gtttgggcct gttttcgggg cactcctgta aacacagcca  60

<210> SEQ ID NO 94
```

-continued

```
<211> LENGTH: 14
<212> TYPE: DNA
<213> ORGANISM: human

<400> SEQUENCE: 94 ttttttttttt tttc                                                      14

<210> SEQ ID NO 95
<211> LENGTH: 11
<212> TYPE: DNA
<213> ORGANISM: human

<400> SEQUENCE: 95
cctctgcctg c                                                          11

<210> SEQ ID NO 96
<211> LENGTH: 11
<212> TYPE: DNA
<213> ORGANISM: human

<400> SEQUENCE: 96
ggaaaggaaa g                                                          11

<210> SEQ ID NO 97
<211> LENGTH: 12
<212> TYPE: DNA
<213> ORGANISM: human

<400> SEQUENCE: 97
tttttttttt tc                                                         12

<210> SEQ ID NO 98
<211> LENGTH: 10
<212> TYPE: DNA
<213> ORGANISM: human

<400> SEQUENCE: 98
aaaaaaaacc                                                            10

<210> SEQ ID NO 99
<211> LENGTH: 19
<212> TYPE: DNA
<213> ORGANISM: human

<400> SEQUENCE: 99
aggaaggaag gagaaagaa                                                  19

<210> SEQ ID NO 100
<211> LENGTH: 19
<212> TYPE: DNA
<213> ORGANISM: human

<400> SEQUENCE: 100
aggaaggaag gagaaagaa                                                  19

<210> SEQ ID NO 101
<211> LENGTH: 20
<212> TYPE: DNA
<213> ORGANISM: human

<400> SEQUENCE: 101
aatggaatgg aatggaatgc                                                 20
```

-continued

```
<210> SEQ ID NO 102
<211> LENGTH: 16
<212> TYPE: DNA
<213> ORGANISM: human

<400> SEQUENCE: 102
cccccccccc cccct                                                      16

<210> SEQ ID NO 103
<211> LENGTH: 12
<212> TYPE: DNA
<213> ORGANISM: human

<400> SEQUENCE: 103
cggacgcgtg gg                                                         12

<210> SEQ ID NO 104
<211> LENGTH: 18
<212> TYPE: DNA
<213> ORGANISM: human

<400> SEQUENCE: 104
gtatatatat atatatat                                                   18

<210> SEQ ID NO 105
<211> LENGTH: 29
<212> TYPE: DNA
<213> ORGANISM: human

<400> SEQUENCE: 105
tgagtagctg ggattacagg cacgctcct                                       29

<210> SEQ ID NO 106
<211> LENGTH: 10
<212> TYPE: DNA
<213> ORGANISM: human

<400> SEQUENCE: 106
ttttttttct                                                            10

<210> SEQ ID NO 107
<211> LENGTH: 16
<212> TYPE: DNA
<213> ORGANISM: human

<400> SEQUENCE: 107
tttttccttt ccttcc                                                     16

<210> SEQ ID NO 108
<211> LENGTH: 13
<212> TYPE: DNA
<213> ORGANISM: human

<400> SEQUENCE: 108
aaagaaagaa aga                                                        13

<210> SEQ ID NO 109
<211> LENGTH: 17
<212> TYPE: DNA
<213> ORGANISM: human

<400> SEQUENCE: 109
tggaggatga gtccttc                                                    17
```

<210> SEQ ID NO 110
<211> LENGTH: 37
<212> TYPE: DNA
<213> ORGANISM: human

<400> SEQUENCE: 110
cactcacagg tcctgggtgg acatgaattt ccgggga                    37

<210> SEQ ID NO 111
<211> LENGTH: 28
<212> TYPE: DNA
<213> ORGANISM: human

<400> SEQUENCE: 111
agccctgtcc tccaggcgct caatctcc                              28

<210> SEQ ID NO 112
<211> LENGTH: 11
<212> TYPE: DNA
<213> ORGANISM: human

<400> SEQUENCE: 112
aaaaaaaaac c                                                11

<210> SEQ ID NO 113
<211> LENGTH: 48
<212> TYPE: DNA
<213> ORGANISM: human

<400> SEQUENCE: 113
acagaagggc acggaacagt acaatattca acctaaagag acaaaaat        48

<210> SEQ ID NO 114
<211> LENGTH: 22
<212> TYPE: DNA
<213> ORGANISM: human

<400> SEQUENCE: 114
tgccaccatc ttggaagcgg cc                                    22

<210> SEQ ID NO 115
<211> LENGTH: 48
<212> TYPE: DNA
<213> ORGANISM: human

<400> SEQUENCE: 115
ctaacgcagg gctccggcgt gcaggtgtca cggtgtcgct gcttctca         48

<210> SEQ ID NO 116
<211> LENGTH: 10
<212> TYPE: DNA
<213> ORGANISM: human

<400> SEQUENCE: 116
agagagagac                                                  10

<210> SEQ ID NO 117
<211> LENGTH: 19
<212> TYPE: DNA
<213> ORGANISM: human

<400> SEQUENCE: 117
aggaaggaag gagaaagaa                                        19

<210> SEQ ID NO 118
<211> LENGTH: 17
<212> TYPE: DNA
<213> ORGANISM: human

<400> SEQUENCE: 118
tttttttttt tttttcc                                              17

<210> SEQ ID NO 119
<211> LENGTH: 21
<212> TYPE: DNA
<213> ORGANISM: human

<400> SEQUENCE: 119
tttttttttt tatttttttt t                                         21

<210> SEQ ID NO 120
<211> LENGTH: 10
<212> TYPE: DNA
<213> ORGANISM: human

<400> SEQUENCE: 120
aaaaagaaag                                                      10

<210> SEQ ID NO 121
<211> LENGTH: 10
<212> TYPE: DNA
<213> ORGANISM: human

<400> SEQUENCE: 121
agagagagac                                                      10

<210> SEQ ID NO 122
<211> LENGTH: 10
<212> TYPE: DNA
<213> ORGANISM: human

<400> SEQUENCE: 122
ttttttttct                                                      10

<210> SEQ ID NO 123
<211> LENGTH: 10
<212> TYPE: DNA
<213> ORGANISM: human

<400> SEQUENCE: 123
tctctctctg                                                      10

<210> SEQ ID NO 124
<211> LENGTH: 10
<212> TYPE: DNA
<213> ORGANISM: human
<220> FEATURE:
<223> OTHER INFORMATION: n signifies a, t, c or g.

<400> SEQUENCE: 124 tttttnncnn                                                      10

<210> SEQ ID NO 125
<211> LENGTH: 12
<212> TYPE: DNA
<213> ORGANISM: human

-continued

```
<400> SEQUENCE: 125
cccaggtggg gg                                                              12

<210> SEQ ID NO 126
<211> LENGTH: 12
<212> TYPE: DNA
<213> ORGANISM: human

<400> SEQUENCE: 126
ggcccccggg gg                                                              12

<210> SEQ ID NO 127
<211> LENGTH: 10
<212> TYPE: DNA
<213> ORGANISM: human

<400> SEQUENCE: 127
aaaaaaaacc                                                                 10

<210> SEQ ID NO 128
<211> LENGTH: 38
<212> TYPE: DNA
<213> ORGANISM: human

<400> SEQUENCE: 128
gctcaaggct cacgggctga ggtctgtccc cgcgtgga                                  38

<210> SEQ ID NO 129
<211> LENGTH: 41
<212> TYPE: DNA
<213> ORGANISM: human

<400> SEQUENCE: 129
atattacata atattttaaa aagcacttac ataagaagaa t                              41

<210> SEQ ID NO 130
<211> LENGTH: 12
<212> TYPE: DNA
<213> ORGANISM: human

<400> SEQUENCE: 130
tatatatata tt                                                              12

<210> SEQ ID NO 131
<211> LENGTH: 10
<212> TYPE: DNA
<213> ORGANISM: human

<400> SEQUENCE: 131
aagaaagaat                                                                 10

<210> SEQ ID NO 132
<211> LENGTH: 10
<212> TYPE: DNA
<213> ORGANISM: human

<400> SEQUENCE: 132
aaaaaaaacc                                                                 10

<210> SEQ ID NO 133
<211> LENGTH: 11
<212> TYPE: DNA
<213> ORGANISM: human
```

```
<400> SEQUENCE: 133 ttttttttc t                                                          11

<210> SEQ ID NO 134
<211> LENGTH: 24
<212> TYPE: DNA
<213> ORGANISM: human

<400> SEQUENCE: 134
tttttttttt tttttttttt tttc                                           24

<210> SEQ ID NO 135
<211> LENGTH: 10
<212> TYPE: DNA
<213> ORGANISM: human

<400> SEQUENCE: 135
aacagaatag                                                           10

<210> SEQ ID NO 136
<211> LENGTH: 13
<212> TYPE: DNA
<213> ORGANISM: human

<400> SEQUENCE: 136
aaaaaattta aaa                                                       13

<210> SEQ ID NO 137
<211> LENGTH: 59
<212> TYPE: DNA
<213> ORGANISM: human

<400> SEQUENCE: 137
ggcagcctag aaggaattgt gtccagtcca caagtgagca gacctgtcat cctcccccc     59

<210> SEQ ID NO 138
<211> LENGTH: 17
<212> TYPE: DNA
<213> ORGANISM: human

<400> SEQUENCE: 138
caggcaaact aagaaat                                                   17

<210> SEQ ID NO 139
<211> LENGTH: 17
<212> TYPE: DNA
<213> ORGANISM: human

<400> SEQUENCE: 139
aaaaaaaaaa tttttg                                                    17

<210> SEQ ID NO 140
<211> LENGTH: 12
<212> TYPE: DNA
<213> ORGANISM: human

<400> SEQUENCE: 140
ctatgacaat aa                                                        12

<210> SEQ ID NO 141
<211> LENGTH: 22
<212> TYPE: DNA
```

-continued

```
<213> ORGANISM: human

<400> SEQUENCE: 141
atgtatcatt caaactaaat ac                                    22

<210> SEQ ID NO 142
<211> LENGTH: 10
<212> TYPE: DNA
<213> ORGANISM: human

<400> SEQUENCE: 142
agaaagaaag                                                  10

<210> SEQ ID NO 143
<211> LENGTH: 11
<212> TYPE: DNA
<213> ORGANISM: human

<400> SEQUENCE: 143
cacacaccac a                                                11

<210> SEQ ID NO 144
<211> LENGTH: 11
<212> TYPE: DNA
<213> ORGANISM: human

<400> SEQUENCE: 144
tctttctttc t                                                11

<210> SEQ ID NO 145
<211> LENGTH: 46
<212> TYPE: DNA
<213> ORGANISM: human

<400> SEQUENCE: 145
agggagagca gaggggtgc actggagtgc caacggaggg ctagac           46

<210> SEQ ID NO 146
<211> LENGTH: 10
<212> TYPE: DNA
<213> ORGANISM: human

<400> SEQUENCE: 146
cattaggaca                                                  10

<210> SEQ ID NO 147
<211> LENGTH: 12
<212> TYPE: DNA
<213> ORGANISM: human

<400> SEQUENCE: 147
ttaaccagta ta                                               12

<210> SEQ ID NO 148
<211> LENGTH: 14
<212> TYPE: DNA
<213> ORGANISM: human

<400> SEQUENCE: 148
ttttatttat ttat                                             14

<210> SEQ ID NO 149
<211> LENGTH: 12
```

```
<212> TYPE: DNA
<213> ORGANISM: human

<400> SEQUENCE: 149
acacatatat at                                                          12

<210> SEQ ID NO 150
<211> LENGTH: 10
<212> TYPE: DNA
<213> ORGANISM: human

<400> SEQUENCE: 150
aaaaaaaaag                                                             10

<210> SEQ ID NO 151
<211> LENGTH: 20
<212> TYPE: DNA
<213> ORGANISM: human

<400> SEQUENCE: 151
gggctcctgg cctcacatct                                                  20

<210> SEQ ID NO 152
<211> LENGTH: 11
<212> TYPE: DNA
<213> ORGANISM: human

<400> SEQUENCE: 152
agagggagag g                                                           11

<210> SEQ ID NO 153
<211> LENGTH: 27
<212> TYPE: DNA
<213> ORGANISM: human

<400> SEQUENCE: 153
tttttttttt tttttttttt tttattt                                          27

<210> SEQ ID NO 154
<211> LENGTH: 12
<212> TYPE: DNA
<213> ORGANISM: human

<400> SEQUENCE: 154
atatatatag tt                                                          12

<210> SEQ ID NO 155
<211> LENGTH: 10
<212> TYPE: DNA
<213> ORGANISM: human

<400> SEQUENCE: 155
ggaaggttgt                                                             10

<210> SEQ ID NO 156
<211> LENGTH: 10
<212> TYPE: DNA
<213> ORGANISM: human

<400> SEQUENCE: 156
atatatatac                                                             10

<210> SEQ ID NO 157
```

-continued

```
<211> LENGTH: 11
<212> TYPE: DNA
<213> ORGANISM: human

<400> SEQUENCE: 157
ggggggggcc c                                                            11

<210> SEQ ID NO 158
<211> LENGTH: 15
<212> TYPE: DNA
<213> ORGANISM: human
<220> FEATURE:
<223> OTHER INFORMATION: n signifies a, t, c or g.

<400> SEQUENCE: 158
tttttttttt tnttt                                                        15

<210> SEQ ID NO 159
<211> LENGTH: 10
<212> TYPE: DNA
<213> ORGANISM: human

<400> SEQUENCE: 159
gggccgggct                                                              10

<210> SEQ ID NO 160
<211> LENGTH: 12
<212> TYPE: DNA
<213> ORGANISM: human

<400> SEQUENCE: 160
ccccgggggg gg                                                           12

<210> SEQ ID NO 161
<211> LENGTH: 10
<212> TYPE: DNA
<213> ORGANISM: human
<220> FEATURE:
<223> OTHER INFORMATION: n signifies a, t, c or g.

<400> SEQUENCE: 161 tttttttttn                                                              10

<210> SEQ ID NO 162
<211> LENGTH: 10
<212> TYPE: DNA
<213> ORGANISM: human

<400> SEQUENCE: 162
tgtgtgtgta                                                              10

<210> SEQ ID NO 163
<211> LENGTH: 13
<212> TYPE: DNA
<213> ORGANISM: human

<400> SEQUENCE: 163
aaaatgatag aca                                                          13

<210> SEQ ID NO 164
<211> LENGTH: 15
<212> TYPE: DNA
<213> ORGANISM: human

<400> SEQUENCE: 164
``` tttttttttat ttttt                                                    15

<210> SEQ ID NO 165
<211> LENGTH: 25
<212> TYPE: DNA
<213> ORGANISM: human

<400> SEQUENCE: 165
tgtttcttat ttccttgtct agctt                                          25

<210> SEQ ID NO 166
<211> LENGTH: 12
<212> TYPE: DNA
<213> ORGANISM: human

<400> SEQUENCE: 166
ccccgggggg ga                                                        12

<210> SEQ ID NO 167
<211> LENGTH: 11
<212> TYPE: DNA
<213> ORGANISM: human

<400> SEQUENCE: 167
aaaaaaaatt a                                                         11

<210> SEQ ID NO 168
<211> LENGTH: 15
<212> TYPE: DNA
<213> ORGANISM: human

<400> SEQUENCE: 168
gatgatcaaa ggtcg                                                     15

<210> SEQ ID NO 169
<211> LENGTH: 32
<212> TYPE: DNA
<213> ORGANISM: human

<400> SEQUENCE: 169
tctctgggct ctgtgacgtt cctacaggac gc                                  32

<210> SEQ ID NO 170
<211> LENGTH: 11
<212> TYPE: DNA
<213> ORGANISM: human

<400> SEQUENCE: 170
aggcaatggg a                                                         11

<210> SEQ ID NO 171
<211> LENGTH: 25
<212> TYPE: DNA
<213> ORGANISM: human

<400> SEQUENCE: 171
agaacagact aatacaggga ctttg                                          25

<210> SEQ ID NO 172
<211> LENGTH: 15
<212> TYPE: DNA
<213> ORGANISM: human

```
<400> SEQUENCE: 172
gccctccaac cgcca                                              15

<210> SEQ ID NO 173
<211> LENGTH: 15
<212> TYPE: DNA
<213> ORGANISM: human

<400> SEQUENCE: 173
ccaaccgcct gccct                                              15

<210> SEQ ID NO 174
<211> LENGTH: 14
<212> TYPE: DNA
<213> ORGANISM: human

<400> SEQUENCE: 174
gcggggcggg gctc                                               14

<210> SEQ ID NO 175
<211> LENGTH: 22
<212> TYPE: DNA
<213> ORGANISM: human

<400> SEQUENCE: 175
tatatatgta tacatatatg tg                                      22

<210> SEQ ID NO 176
<211> LENGTH: 17
<212> TYPE: DNA
<213> ORGANISM: human

<400> SEQUENCE: 176
gcacatagta catgttc                                            17

<210> SEQ ID NO 177
<211> LENGTH: 18
<212> TYPE: DNA
<213> ORGANISM: human

<400> SEQUENCE: 177
tttcatttct cttaggga                                           18

<210> SEQ ID NO 178
<211> LENGTH: 19
<212> TYPE: DNA
<213> ORGANISM: human

<400> SEQUENCE: 178
ccctccgtgt cccccatgt                                          19

<210> SEQ ID NO 179
<211> LENGTH: 11
<212> TYPE: DNA
<213> ORGANISM: human

<400> SEQUENCE: 179 ttttttttc t                                                   11

<210> SEQ ID NO 180
<211> LENGTH: 15
<212> TYPE: DNA
<213> ORGANISM: human
```

```
<400> SEQUENCE: 180
ctctgtggca tccag                                              15

<210> SEQ ID NO 181
<211> LENGTH: 18
<212> TYPE: DNA
<213> ORGANISM: human

<400> SEQUENCE: 181
aggagcaata caggagaa                                           18

<210> SEQ ID NO 182
<211> LENGTH: 10
<212> TYPE: DNA
<213> ORGANISM: human

<400> SEQUENCE: 182
tgtgtgcgtg                                                    10

<210> SEQ ID NO 183
<211> LENGTH: 11
<212> TYPE: DNA
<213> ORGANISM: human

<400> SEQUENCE: 183
ctgccgtggt c                                                  11

<210> SEQ ID NO 184
<211> LENGTH: 10
<212> TYPE: DNA
<213> ORGANISM: human
<220> FEATURE:
<223> OTHER INFORMATION: n signifies a, t, c or g.

<400> SEQUENCE: 184 tttttttttn                                                    10

<210> SEQ ID NO 185
<211> LENGTH: 11
<212> TYPE: DNA
<213> ORGANISM: human

<400> SEQUENCE: 185
atatatatga t                                                  11

<210> SEQ ID NO 186
<211> LENGTH: 50
<212> TYPE: DNA
<213> ORGANISM: human

<400> SEQUENCE: 186
cctcagtctg cagcctgcta gggacgcacg gccacactcc tgtctttcag         50

<210> SEQ ID NO 187
<211> LENGTH: 10
<212> TYPE: DNA
<213> ORGANISM: human
<220> FEATURE:
<223> OTHER INFORMATION: n signifies a, t, c or g.

<400> SEQUENCE: 187 aaaaaaaaan                                                    10
```

<210> SEQ ID NO 188
<211> LENGTH: 12
<212> TYPE: DNA
<213> ORGANISM: human

<400> SEQUENCE: 188
gagcgagaga ga                                                          12

<210> SEQ ID NO 189
<211> LENGTH: 85
<212> TYPE: DNA
<213> ORGANISM: human

<400> SEQUENCE: 189
gccacacagc aaatgctaat atgctccagt gttagcttag aagccttgtg tcaacaagaa      60
ctggctcctg agtcccaagc ttggt                                            85

<210> SEQ ID NO 190
<211> LENGTH: 10
<212> TYPE: DNA
<213> ORGANISM: human

<400> SEQUENCE: 190
aagaagaact                                                             10

<210> SEQ ID NO 191
<211> LENGTH: 10
<212> TYPE: DNA
<213> ORGANISM: human

<400> SEQUENCE: 191
tttttttttg                                                             10

<210> SEQ ID NO 192
<211> LENGTH: 10
<212> TYPE: DNA
<213> ORGANISM: human

<400> SEQUENCE: 192
aaaaaaaaag                                                             10

<210> SEQ ID NO 193
<211> LENGTH: 32
<212> TYPE: DNA
<213> ORGANISM: human

<400> SEQUENCE: 193
atatgatata taaatgttat atgttatata tg                                    32

<210> SEQ ID NO 194
<211> LENGTH: 32
<212> TYPE: DNA
<213> ORGANISM: human

<400> SEQUENCE: 194
tatgttatat ataatatgat atataaatgt ta                                    32

<210> SEQ ID NO 195
<211> LENGTH: 32
<212> TYPE: DNA
<213> ORGANISM: human

<400> SEQUENCE: 195

-continued tataatatga tatataaatg ttatatgtta tg     32

<210> SEQ ID NO 196
<211> LENGTH: 30
<212> TYPE: DNA
<213> ORGANISM: human

<400> SEQUENCE: 196
ttatatataa tatgatatat aaatgttatg     30

<210> SEQ ID NO 197
<211> LENGTH: 28
<212> TYPE: DNA
<213> ORGANISM: human

<400> SEQUENCE: 197
tcaggaacat gtcagtgtcc cagagcca     28

<210> SEQ ID NO 198
<211> LENGTH: 10
<212> TYPE: DNA
<213> ORGANISM: human

<400> SEQUENCE: 198
aaaaaaaaac     10

<210> SEQ ID NO 199
<211> LENGTH: 21
<212> TYPE: DNA
<213> ORGANISM: human

<400> SEQUENCE: 199
caggagaagg agcggcagaa a     21

<210> SEQ ID NO 200
<211> LENGTH: 27
<212> TYPE: DNA
<213> ORGANISM: human

<400> SEQUENCE: 200
gggacgccgt caagggcatc gctgatc     27

<210> SEQ ID NO 201
<211> LENGTH: 11
<212> TYPE: DNA
<213> ORGANISM: human

<400> SEQUENCE: 201
tttaaataaa t     11

<210> SEQ ID NO 202
<211> LENGTH: 42
<212> TYPE: DNA
<213> ORGANISM: human

<400> SEQUENCE: 202
gaggagaggc tgtgtgaaca ggaggagagg ctacgtgaac ag     42

<210> SEQ ID NO 203
<211> LENGTH: 30
<212> TYPE: DNA
<213> ORGANISM: human

-continued

```
<400> SEQUENCE: 203
tttatttgtg tttctaattt atagtttaaa                                    30

<210> SEQ ID NO 204
<211> LENGTH: 35
<212> TYPE: DNA
<213> ORGANISM: human

<400> SEQUENCE: 204
aggaaaaggc ggcgtggaga gacgggacgc gcggg                              35

<210> SEQ ID NO 205
<211> LENGTH: 38
<212> TYPE: DNA
<213> ORGANISM: human

<400> SEQUENCE: 205
gtggtttggg cccgaccgag ctggtcccgc agtgggcg                           38

<210> SEQ ID NO 206
<211> LENGTH: 22
<212> TYPE: DNA
<213> ORGANISM: human

<400> SEQUENCE: 206
aggcatacag gttgattatt tt                                            22

<210> SEQ ID NO 207
<211> LENGTH: 12
<212> TYPE: DNA
<213> ORGANISM: human

<400> SEQUENCE: 207
gggcggaccc ct                                                       12

<210> SEQ ID NO 208
<211> LENGTH: 36
<212> TYPE: DNA
<213> ORGANISM: human

<400> SEQUENCE: 208
ggggtggcgt attctggtct cctacagtca tatttt                             36

<210> SEQ ID NO 209
<211> LENGTH: 36
<212> TYPE: DNA
<213> ORGANISM: human

<400> SEQUENCE: 209
catattttgg ggtgacgtat tctggtctcc tacagt                             36

<210> SEQ ID NO 210
<211> LENGTH: 11
<212> TYPE: DNA
<213> ORGANISM: human

<400> SEQUENCE: 210 cccccccgggg g                                                       11

<210> SEQ ID NO 211
<211> LENGTH: 18
<212> TYPE: DNA
<213> ORGANISM: human
```

<400> SEQUENCE: 211
attgctcctt tctcctgt                                              18

<210> SEQ ID NO 212
<211> LENGTH: 10
<212> TYPE: DNA
<213> ORGANISM: human

<400> SEQUENCE: 212
aaaaaaaacc                                                        10

<210> SEQ ID NO 213
<211> LENGTH: 12
<212> TYPE: DNA
<213> ORGANISM: human

<400> SEQUENCE: 213 tttttttttgc aa                                                   12

<210> SEQ ID NO 214
<211> LENGTH: 34
<212> TYPE: DNA
<213> ORGANISM: human

<400> SEQUENCE: 214
tccacgttgc actggatgtt ctagccggtt ctga                            34

<210> SEQ ID NO 215
<211> LENGTH: 11
<212> TYPE: DNA
<213> ORGANISM: human
<220> FEATURE:
<223> OTHER INFORMATION: n signifies a, t, c or g.

<400> SEQUENCE: 215
tttttttttn t                                                     11

<210> SEQ ID NO 216
<211> LENGTH: 10
<212> TYPE: DNA
<213> ORGANISM: human
<220> FEATURE:
<223> OTHER INFORMATION: n signifies a, t, c or g.

<400> SEQUENCE: 216 tttttttttn                                                       10

<210> SEQ ID NO 217
<211> LENGTH: 19
<212> TYPE: DNA
<213> ORGANISM: human

<400> SEQUENCE: 217
atatatatat atattatgg                                             19

<210> SEQ ID NO 218
<211> LENGTH: 33
<212> TYPE: DNA
<213> ORGANISM: human

<400> SEQUENCE: 218
tgtgtgtgta atgtgtgttt gtcatcgtga tgt                             33

```
<210> SEQ ID NO 219
<211> LENGTH: 11
<212> TYPE: DNA
<213> ORGANISM: human

<400> SEQUENCE: 219
tttttttttt a                                                              11

<210> SEQ ID NO 220
<211> LENGTH: 10
<212> TYPE: DNA
<213> ORGANISM: human

<400> SEQUENCE: 220
aacatatata                                                                10

<210> SEQ ID NO 221
<211> LENGTH: 20
<212> TYPE: DNA
<213> ORGANISM: human

<400> SEQUENCE: 221
gagaatgggt ccagttaatc                                                     20

<210> SEQ ID NO 222
<211> LENGTH: 12
<212> TYPE: DNA
<213> ORGANISM: human

<400> SEQUENCE: 222
ccccgggggg gg                                                             12

<210> SEQ ID NO 223
<211> LENGTH: 55
<212> TYPE: DNA
<213> ORGANISM: human

<400> SEQUENCE: 223
tggacaccgg agactgttga gacgccgact ggagtcacac acggcagtca acgcg             55

<210> SEQ ID NO 224
<211> LENGTH: 12
<212> TYPE: DNA
<213> ORGANISM: human

<400> SEQUENCE: 224
atatatatac at                                                             12

<210> SEQ ID NO 225
<211> LENGTH: 33
<212> TYPE: DNA
<213> ORGANISM: human

<400> SEQUENCE: 225
cccttccttt agggctggaa agacacgggt cta                                      33

<210> SEQ ID NO 226
<211> LENGTH: 38
<212> TYPE: DNA
<213> ORGANISM: human

<400> SEQUENCE: 226
cagcgaggtc ggcagcggca cagcgaggtc ggcagcgg                                 38
```

```
<210> SEQ ID NO 227
<211> LENGTH: 20
<212> TYPE: DNA
<213> ORGANISM: human

<400> SEQUENCE: 227
cagcggcaca gcgaggtcgg                                          20

<210> SEQ ID NO 228
<211> LENGTH: 10
<212> TYPE: DNA
<213> ORGANISM: human

<400> SEQUENCE: 228
catgaagcag                                                     10

<210> SEQ ID NO 229
<211> LENGTH: 30
<212> TYPE: DNA
<213> ORGANISM: human

<400> SEQUENCE: 229
agccacggtc ccctccgagg tctgagcgtc                               30

<210> SEQ ID NO 230
<211> LENGTH: 11
<212> TYPE: DNA
<213> ORGANISM: human

<400> SEQUENCE: 230
cttttttctt t                                                   11

<210> SEQ ID NO 231
<211> LENGTH: 11
<212> TYPE: DNA
<213> ORGANISM: human

<400> SEQUENCE: 231 ttttttttttg t                                                  11

<210> SEQ ID NO 232
<211> LENGTH: 10
<212> TYPE: DNA
<213> ORGANISM: human

<400> SEQUENCE: 232
ttttttttg                                                      10

<210> SEQ ID NO 233
<211> LENGTH: 16
<212> TYPE: DNA
<213> ORGANISM: human

<400> SEQUENCE: 233
tttctttctt ccttcc                                              16

<210> SEQ ID NO 234
<211> LENGTH: 11
<212> TYPE: DNA
<213> ORGANISM: human

<400> SEQUENCE: 234
```
ggatcttcgg c	11

<210> SEQ ID NO 235
<211> LENGTH: 30
<212> TYPE: DNA
<213> ORGANISM: human

<400> SEQUENCE: 235
cggggtccca ggcgaggcat ggatgatgac	30

<210> SEQ ID NO 236
<211> LENGTH: 130
<212> TYPE: DNA
<213> ORGANISM: human

<400> SEQUENCE: 236
ggtagggttc gtaggtaggg ctagtaggta gggttagtag gtagggctag taggtagggc	60 tagtaggtag ggttagtagg tagggttcgt aggtagggct ggtagtaggg gttagtaggt	120 agggctagta	130

<210> SEQ ID NO 237
<211> LENGTH: 13
<212> TYPE: DNA
<213> ORGANISM: human

<400> SEQUENCE: 237
tagtaggtag ggc	13

<210> SEQ ID NO 238
<211> LENGTH: 13
<212> TYPE: DNA
<213> ORGANISM: human

<400> SEQUENCE: 238
gtaggtaggg ttc	13

<210> SEQ ID NO 239
<211> LENGTH: 13
<212> TYPE: DNA
<213> ORGANISM: human

<400> SEQUENCE: 239
tagtaggtag ggc	13

<210> SEQ ID NO 240
<211> LENGTH: 10
<212> TYPE: DNA
<213> ORGANISM: human

<400> SEQUENCE: 240 cccagcctgc	10

<210> SEQ ID NO 241
<211> LENGTH: 23
<212> TYPE: DNA
<213> ORGANISM: human

<400> SEQUENCE: 241
ttgcagtaac aaactccagt ctg	23

<210> SEQ ID NO 242
<211> LENGTH: 15

```
<212> TYPE: DNA
<213> ORGANISM: human

<400> SEQUENCE: 242
cagcgggaga agctg                                                        15

<210> SEQ ID NO 243
<211> LENGTH: 126
<212> TYPE: DNA
<213> ORGANISM: human

<400> SEQUENCE: 243
cttccaccct cagcggatga taatctcaag acaccttccg agcgtcagct cactcccctt      60
ccaccctcag ctccaccctc agcagatgat aatatcaaga cacctgccga gcgtctgcgg     120
gggccg                                                                126

<210> SEQ ID NO 244
<211> LENGTH: 57
<212> TYPE: DNA
<213> ORGANISM: human

<400> SEQUENCE: 244
tgctcactcc ccttccaccc tcagcggatg ataatctcaa gacacctccc gagtgtg         57

<210> SEQ ID NO 245
<211> LENGTH: 32
<212> TYPE: DNA
<213> ORGANISM: human

<400> SEQUENCE: 245
atatatgtat atatatatgt atgtatatat gt                                    32

<210> SEQ ID NO 246
<211> LENGTH: 60
<212> TYPE: DNA
<213> ORGANISM: human

<400> SEQUENCE: 246
gccccgggct ccaccgcccc cccagcccac ggtgtcacct cggccccgga caccaggccg      60

<210> SEQ ID NO 247
<211> LENGTH: 11
<212> TYPE: DNA
<213> ORGANISM: human

<400> SEQUENCE: 247
cagtccccgc g                                                           11

<210> SEQ ID NO 248
<211> LENGTH: 39
<212> TYPE: DNA
<213> ORGANISM: human

<400> SEQUENCE: 248
aggaggagag gcgcgagcag cagctgaggc gcgagcagg                             39

<210> SEQ ID NO 249
<211> LENGTH: 18
<212> TYPE: DNA
<213> ORGANISM: human

<400> SEQUENCE: 249
```

-continued gaggcgcgag cagcagct                                                18

<210> SEQ ID NO 250
<211> LENGTH: 12
<212> TYPE: DNA
<213> ORGANISM: human

<400> SEQUENCE: 250
gcgggggcat ct                                                      12

<210> SEQ ID NO 251
<211> LENGTH: 33
<212> TYPE: DNA
<213> ORGANISM: human

<400> SEQUENCE: 251
cagcagcagc agcagcagca gcagtagcag cag                               33

<210> SEQ ID NO 252
<211> LENGTH: 69
<212> TYPE: DNA
<213> ORGANISM: human

<400> SEQUENCE: 252
ccaaccacga cacccatcac caccaccact acggtgaccc caaccccaac acccaccggc  60
acacagacc                                                          69

<210> SEQ ID NO 253
<211> LENGTH: 21
<212> TYPE: DNA
<213> ORGANISM: human

<400> SEQUENCE: 253
ccaaccacca ctcccagccc t                                            21

<210> SEQ ID NO 254
<211> LENGTH: 15
<212> TYPE: DNA
<213> ORGANISM: human

<400> SEQUENCE: 254
gaggaggagg aagaa                                                   15

<210> SEQ ID NO 255
<211> LENGTH: 10
<212> TYPE: DNA
<213> ORGANISM: human

<400> SEQUENCE: 255
cacactcaca                                                         10

<210> SEQ ID NO 256
<211> LENGTH: 30
<212> TYPE: DNA
<213> ORGANISM: human

<400> SEQUENCE: 256
gagcagcagg agggcagct ggagctccca                                    30

<210> SEQ ID NO 257
<211> LENGTH: 30
<212> TYPE: DNA
<213> ORGANISM: human

-continued

<400> SEQUENCE: 257
agcagcagga ggggcagctg gagctctctg          30

<210> SEQ ID NO 258
<211> LENGTH: 10
<212> TYPE: DNA
<213> ORGANISM: human

<400> SEQUENCE: 258
aaaaaacaaa          10

<210> SEQ ID NO 259
<211> LENGTH: 18
<212> TYPE: DNA
<213> ORGANISM: human

<400> SEQUENCE: 259
tacctttgtt ggaagacg          18

<210> SEQ ID NO 260
<211> LENGTH: 18
<212> TYPE: DNA
<213> ORGANISM: human

<400> SEQUENCE: 260
ctggaagaca tggatttt          18

<210> SEQ ID NO 261
<211> LENGTH: 57
<212> TYPE: DNA
<213> ORGANISM: human

<400> SEQUENCE: 261
ctgcccctgg agtagaggac atcagcgggc ttccttctgg agaagttcta gagaccg          57

<210> SEQ ID NO 262
<211> LENGTH: 57
<212> TYPE: DNA
<213> ORGANISM: human

<400> SEQUENCE: 262
gggcttcctt ctggagaagt tctagagacc actgcccctg gagtagagga catcagc          57

<210> SEQ ID NO 263
<211> LENGTH: 57
<212> TYPE: DNA
<213> ORGANISM: human

<400> SEQUENCE: 263
gctgcccctg gagtagagga catcagcggg cttccttctg gagaagttct agagact          57

<210> SEQ ID NO 264
<211> LENGTH: 12
<212> TYPE: DNA
<213> ORGANISM: human

<400> SEQUENCE: 264
tagcttcatg aa          12

<210> SEQ ID NO 265
<211> LENGTH: 15
<212> TYPE: DNA

<213> ORGANISM: human

<400> SEQUENCE: 265
ggtggttctg gtggt                                                    15

<210> SEQ ID NO 266
<211> LENGTH: 42
<212> TYPE: DNA
<213> ORGANISM: human

<400> SEQUENCE: 266
ggaggaagag aaaagggcag cagaggagag gcagaggata aa                      42

<210> SEQ ID NO 267
<211> LENGTH: 15
<212> TYPE: DNA
<213> ORGANISM: human

<400> SEQUENCE: 267
tggtggtggt ggctt                                                    15

<210> SEQ ID NO 268
<211> LENGTH: 16
<212> TYPE: DNA
<213> ORGANISM: human

<400> SEQUENCE: 268
tatatatata tctctt                                                   16

<210> SEQ ID NO 269
<211> LENGTH: 10
<212> TYPE: DNA
<213> ORGANISM: human

<400> SEQUENCE: 269
atacatatat                                                          10

<210> SEQ ID NO 270
<211> LENGTH: 24
<212> TYPE: DNA
<213> ORGANISM: human

<400> SEQUENCE: 270
gatatacgta tacagcatat acga                                          24

<210> SEQ ID NO 271
<211> LENGTH: 27
<212> TYPE: DNA
<213> ORGANISM: human

<400> SEQUENCE: 271
aatatatttt attacatata atgtcac                                       27

<210> SEQ ID NO 272
<211> LENGTH: 61
<212> TYPE: DNA
<213> ORGANISM: human

<400> SEQUENCE: 272
atctaacaga taacagtttg tttaaaataa gaataataaa atattttatt attcttattt    60
g                                                                   61

```
<210> SEQ ID NO 273
<211> LENGTH: 10
<212> TYPE: DNA
<213> ORGANISM: human

<400> SEQUENCE: 273
aattttttgg                                                              10

<210> SEQ ID NO 274
<211> LENGTH: 40
<212> TYPE: DNA
<213> ORGANISM: human

<400> SEQUENCE: 274
caaggagagt agttagacaa cacgtcagcc acggagcagg                             40

<210> SEQ ID NO 275
<211> LENGTH: 10
<212> TYPE: DNA
<213> ORGANISM: human

<400> SEQUENCE: 275
taataataat                                                              10

<210> SEQ ID NO 276
<211> LENGTH: 40
<212> TYPE: DNA
<213> ORGANISM: human
<220> FEATURE:
<223> OTHER INFORMATION: n signifies a, t, c or g.

<400> SEQUENCE: 276
ccgggcccct tcacctgggg ntcaggtgag agcaggtttt                              40

<210> SEQ ID NO 277
<211> LENGTH: 10
<212> TYPE: DNA
<213> ORGANISM: human

<400> SEQUENCE: 277
atatatatag                                                              10

<210> SEQ ID NO 278
<211> LENGTH: 14
<212> TYPE: DNA
<213> ORGANISM: human

<400> SEQUENCE: 278
ctgtgctggc actt                                                         14

<210> SEQ ID NO 279
<211> LENGTH: 10
<212> TYPE: DNA
<213> ORGANISM: human

<400> SEQUENCE: 279
gtggatggcc                                                              10

<210> SEQ ID NO 280
<211> LENGTH: 19
<212> TYPE: DNA
<213> ORGANISM: human

<400> SEQUENCE: 280
```

-continued

```
aaatactgta tttataaat                                          19

<210> SEQ ID NO 281
<211> LENGTH: 10
<212> TYPE: DNA
<213> ORGANISM: human

<400> SEQUENCE: 281
gaagaagaaa                                                    10

<210> SEQ ID NO 282
<211> LENGTH: 10
<212> TYPE: DNA
<213> ORGANISM: human

<400> SEQUENCE: 282
gaagaaggaa                                                    10

<210> SEQ ID NO 283
<211> LENGTH: 13
<212> TYPE: DNA
<213> ORGANISM: human

<400> SEQUENCE: 283
tttctttctt tct                                                13

<210> SEQ ID NO 284
<211> LENGTH: 30
<212> TYPE: DNA
<213> ORGANISM: human
<220> FEATURE:
<223> OTHER INFORMATION: n signifies a, t, c or g.

<400> SEQUENCE: 284
gagctggggt atttatgttc cagggtnagg                              30

<210> SEQ ID NO 285
<211> LENGTH: 10
<212> TYPE: DNA
<213> ORGANISM: human

<400> SEQUENCE: 285
atatatataa                                                    10

<210> SEQ ID NO 286
<211> LENGTH: 12
<212> TYPE: DNA
<213> ORGANISM: human

<400> SEQUENCE: 286
gaagaggagg aa                                                 12

<210> SEQ ID NO 287
<211> LENGTH: 41
<212> TYPE: DNA
<213> ORGANISM: human

<400> SEQUENCE: 287
tccaggaagg gaccccgggt tcacgagctg cccacgtcct c                 41

<210> SEQ ID NO 288
<211> LENGTH: 10
<212> TYPE: DNA
<213> ORGANISM: human
```

<400> SEQUENCE: 288
gcagcccggt                                                               10

<210> SEQ ID NO 289
<211> LENGTH: 12
<212> TYPE: DNA
<213> ORGANISM: human

<400> SEQUENCE: 289
cggctccggt cg                                                            12

<210> SEQ ID NO 290
<211> LENGTH: 12
<212> TYPE: DNA
<213> ORGANISM: human

<400> SEQUENCE: 290
cagcagcagc gg                                                            12

<210> SEQ ID NO 291
<211> LENGTH: 16
<212> TYPE: DNA
<213> ORGANISM: human

<400> SEQUENCE: 291
tggggacctc acctgc                                                        16

<210> SEQ ID NO 292
<211> LENGTH: 22
<212> TYPE: DNA
<213> ORGANISM: human

<400> SEQUENCE: 292
gtccagggtg aggagtgagg ga                                                 22

<210> SEQ ID NO 293
<211> LENGTH: 24
<212> TYPE: DNA
<213> ORGANISM: human

<400> SEQUENCE: 293
ggtggtggct gggggcagcc tcat                                               24

<210> SEQ ID NO 294
<211> LENGTH: 10
<212> TYPE: DNA
<213> ORGANISM: human

<400> SEQUENCE: 294
ctcgggacgc                                                               10

<210> SEQ ID NO 295
<211> LENGTH: 10
<212> TYPE: DNA
<213> ORGANISM: human

<400> SEQUENCE: 295
aaaaaaaaac                                                               10

<210> SEQ ID NO 296
<211> LENGTH: 14
<212> TYPE: DNA

-continued

```
<213> ORGANISM: human

<400> SEQUENCE: 296
gtgtgtgagt gtgg                                                    14

<210> SEQ ID NO 297
<211> LENGTH: 24
<212> TYPE: DNA
<213> ORGANISM: human

<400> SEQUENCE: 297
ctcccgacac cacctcccag gagc                                         24

<210> SEQ ID NO 298
<211> LENGTH: 24
<212> TYPE: DNA
<213> ORGANISM: human

<400> SEQUENCE: 298
acaccacctc cccggagtct cccg                                         24

<210> SEQ ID NO 299
<211> LENGTH: 20
<212> TYPE: DNA
<213> ORGANISM: human

<400> SEQUENCE: 299
catgtatggg tgtgtgtacc                                              20

<210> SEQ ID NO 300
<211> LENGTH: 21
<212> TYPE: DNA
<213> ORGANISM: human

<400> SEQUENCE: 300
ctctgtccat ttcaagggtg a                                            21

<210> SEQ ID NO 301
<211> LENGTH: 12
<212> TYPE: DNA
<213> ORGANISM: human

<400> SEQUENCE: 301
ggccacacct gc                                                      12

<210> SEQ ID NO 302
<211> LENGTH: 12
<212> TYPE: DNA
<213> ORGANISM: human

<400> SEQUENCE: 302
tgctgctgct gt                                                      12

<210> SEQ ID NO 303
<211> LENGTH: 24
<212> TYPE: DNA
<213> ORGANISM: human

<400> SEQUENCE: 303
acccctaagg agcctgctcc aact                                         24

<210> SEQ ID NO 304
<211> LENGTH: 15
```

```
<212> TYPE: DNA
<213> ORGANISM: human

<400> SEQUENCE: 304
cagcagcagc agcaa                                                      15

<210> SEQ ID NO 305
<211> LENGTH: 11
<212> TYPE: DNA
<213> ORGANISM: human

<400> SEQUENCE: 305
acaccgccgc c                                                          11

<210> SEQ ID NO 306
<211> LENGTH: 48
<212> TYPE: DNA
<213> ORGANISM: human

<400> SEQUENCE: 306
gtatggaggg tctagcctgg gtgagtatgg aggtctagc ctgggtgt                   48

<210> SEQ ID NO 307
<211> LENGTH: 24
<212> TYPE: DNA
<213> ORGANISM: human

<400> SEQUENCE: 307
gtacggaggg tctagcctgg gtga                                            24

<210> SEQ ID NO 308
<211> LENGTH: 24
<212> TYPE: DNA
<213> ORGANISM: human

<400> SEQUENCE: 308
tctagcctgg gtgagtatgg aggg                                            24

<210> SEQ ID NO 309
<211> LENGTH: 17
<212> TYPE: DNA
<213> ORGANISM: human

<400> SEQUENCE: 309
gggggccctt ccagact                                                    17

<210> SEQ ID NO 310
<211> LENGTH: 14
<212> TYPE: DNA
<213> ORGANISM: human

<400> SEQUENCE: 310
aaaaaaaaaa caaa                                                       14

<210> SEQ ID NO 311
<211> LENGTH: 15
<212> TYPE: DNA
<213> ORGANISM: human

<400> SEQUENCE: 311
gaagaagaag aagag                                                      15

<210> SEQ ID NO 312
```

```
<211> LENGTH: 15
<212> TYPE: DNA
<213> ORGANISM: human

<400> SEQUENCE: 312
gaagaagaag aagag                                              15

<210> SEQ ID NO 313
<211> LENGTH: 12
<212> TYPE: DNA
<213> ORGANISM: human

<400> SEQUENCE: 313
acgcgtccgc cc                                                 12

<210> SEQ ID NO 314
<211> LENGTH: 27
<212> TYPE: DNA
<213> ORGANISM: human

<400> SEQUENCE: 314
cacacagggc acagacccca cgcaccc                                 27

<210> SEQ ID NO 315
<211> LENGTH: 20
<212> TYPE: DNA
<213> ORGANISM: human

<400> SEQUENCE: 315
gttaaacaaa aagttacctt                                         20

<210> SEQ ID NO 316
<211> LENGTH: 43
<212> TYPE: DNA
<213> ORGANISM: human

<400> SEQUENCE: 316
cgttcgatca ggaacgagac gaggacgtgt gctctcacca ccg               43

<210> SEQ ID NO 317
<211> LENGTH: 11
<212> TYPE: DNA
<213> ORGANISM: human

<400> SEQUENCE: 317
ttatttatta t                                                  11

<210> SEQ ID NO 318
<211> LENGTH: 342
<212> TYPE: DNA
<213> ORGANISM: human

<400> SEQUENCE: 318
actacccaaa tgctggcttg atcatgaact actgcaggaa tccagatgct gtggcagctc    60
cttattgtta tacgagggat cccggtgtca ggtgggagta ctgcaacctg acgcaatgct   120
cagacgcaga agggactgcc gtcgcgcctc cgactgttac cccggttcca agcctagagg   180
ctccttccga acaagcaccg actgagcaaa ggcctgggt gcaggagtgc taccatggta    240
atggacagag ttatcgaggc acatactcca ccactgtcac aggaagaacc tgccaagctt   300
ggtcatctat gacaccacac tcgcatagtc ggaccccaga at                     342
```

<210> SEQ ID NO 319
<211> LENGTH: 342
<212> TYPE: DNA
<213> ORGANISM: human

<400> SEQUENCE: 319

```
ggaagaacct gccaagcttg gtcatctatg acaccacact cgcatagtcg gaccccagaa      60
tactacccaa atgctggctt gatcatgaac tactgcagga atccagatgc tgtggcagct     120
ccttattgtt atacgaggga tcccggtgtc aggtgggagt actgcaacct gacgcaatgc     180
tcagacgcag aagggactgc cgtcgcgcct ccgactgtta ccccggttcc aagcctagag     240
gctccttccg aacaagcacc gactgagcag aggcctgggg tgcaggagtg ctaccacggt     300
aatggacaga gttatcgagg cacatactcc accactgtca ct                        342
```

<210> SEQ ID NO 320
<211> LENGTH: 11
<212> TYPE: DNA
<213> ORGANISM: human

<400> SEQUENCE: 320

```
aaaaaaaga a                                                            11
```

<210> SEQ ID NO 321
<211> LENGTH: 63
<212> TYPE: DNA
<213> ORGANISM: human

<400> SEQUENCE: 321

```
tccgggaaag ccagaaggac caccccacaa aggaggaaac cagtcccaag gtcccccacc      60
tcg                                                                    63
```

<210> SEQ ID NO 322
<211> LENGTH: 15
<212> TYPE: DNA
<213> ORGANISM: human

<400> SEQUENCE: 322

```
cggcggcgga agctc                                                       15
```

<210> SEQ ID NO 323
<211> LENGTH: 24
<212> TYPE: DNA
<213> ORGANISM: human

<400> SEQUENCE: 323

```
ttggaggtgg ctatggaggt ggcc                                             24
```

<210> SEQ ID NO 324
<211> LENGTH: 42
<212> TYPE: DNA
<213> ORGANISM: human

<400> SEQUENCE: 324

```
agaagcaaag tccctgaga aggccaagtc cccagtgaag ga                          42
```

<210> SEQ ID NO 325
<211> LENGTH: 42
<212> TYPE: DNA
<213> ORGANISM: human

<400> SEQUENCE: 325

```
aagtccsctg agaaggccaa gtccccagtg aaggcagaag ca                42
```

<210> SEQ ID NO 326
<211> LENGTH: 12
<212> TYPE: DNA
<213> ORGANISM: human

<400> SEQUENCE: 326

```
gagcctgagc cc                                                12
```

<210> SEQ ID NO 327
<211> LENGTH: 12
<212> TYPE: DNA
<213> ORGANISM: human

<400> SEQUENCE: 327

```
ggtatcggga tg                                                12
```

<210> SEQ ID NO 328
<211> LENGTH: 30
<212> TYPE: DNA
<213> ORGANISM: human

<400> SEQUENCE: 328

```
ccagctgctg ccagccaagc tgctgtgaga                             30
```

<210> SEQ ID NO 329
<211> LENGTH: 12
<212> TYPE: DNA
<213> ORGANISM: human

<400> SEQUENCE: 329

```
ctctctctct cc                                                12
```

<210> SEQ ID NO 330
<211> LENGTH: 18
<212> TYPE: DNA
<213> ORGANISM: human

<400> SEQUENCE: 330

```
ggagaggagg atctacct                                          18
```

<210> SEQ ID NO 331
<211> LENGTH: 12
<212> TYPE: DNA
<213> ORGANISM: human

<400> SEQUENCE: 331

```
gcacccgcag ca                                                12
```

<210> SEQ ID NO 332
<211> LENGTH: 30
<212> TYPE: DNA
<213> ORGANISM: human

<400> SEQUENCE: 332

```
ggcggcggcg gcggcggcgg cggcggcgga                             30
```

<210> SEQ ID NO 333
<211> LENGTH: 18
<212> TYPE: DNA
<213> ORGANISM: human

<400> SEQUENCE: 333
ggccccagct ccagcctc                18

<210> SEQ ID NO 334
<211> LENGTH: 10
<212> TYPE: DNA
<213> ORGANISM: human

<400> SEQUENCE: 334
cagagagaga                         10

<210> SEQ ID NO 335
<211> LENGTH: 20
<212> TYPE: DNA
<213> ORGANISM: human

<400> SEQUENCE: 335
cctcgtcact cagccctgga              20

<210> SEQ ID NO 336
<211> LENGTH: 20
<212> TYPE: DNA
<213> ORGANISM: human

<400> SEQUENCE: 336
tcactcagcc ctggacctcc              20

<210> SEQ ID NO 337
<211> LENGTH: 20
<212> TYPE: DNA
<213> ORGANISM: human

<400> SEQUENCE: 337
acacacacac acacacccca              20

<210> SEQ ID NO 338
<211> LENGTH: 21
<212> TYPE: DNA
<213> ORGANISM: human

<400> SEQUENCE: 338
gctgtgggga catgagaggg a            21

<210> SEQ ID NO 339
<211> LENGTH: 20
<212> TYPE: DNA
<213> ORGANISM: human

<400> SEQUENCE: 339
gctgtgggga catgagaggg              20

<210> SEQ ID NO 340
<211> LENGTH: 18
<212> TYPE: DNA
<213> ORGANISM: human

<400> SEQUENCE: 340
gcagcagcag ccccagca                18

<210> SEQ ID NO 341
<211> LENGTH: 15
<212> TYPE: DNA
<213> ORGANISM: human

```
<400> SEQUENCE: 341
gctagaacct ggagg                                                   15

<210> SEQ ID NO 342
<211> LENGTH: 12
<212> TYPE: DNA
<213> ORGANISM: human

<400> SEQUENCE: 342
gatgatgatg gc                                                      12

<210> SEQ ID NO 343
<211> LENGTH: 21
<212> TYPE: DNA
<213> ORGANISM: human

<400> SEQUENCE: 343
gcttggatag aaatgaggag g                                            21

<210> SEQ ID NO 344
<211> LENGTH: 39
<212> TYPE: DNA
<213> ORGANISM: human

<400> SEQUENCE: 344
tcaccagtgg aagagaaagg caagtctcct gtgcccaag                         39

<210> SEQ ID NO 345
<211> LENGTH: 12
<212> TYPE: DNA
<213> ORGANISM: human

<400> SEQUENCE: 345
aagaaggatg ca                                                      12

<210> SEQ ID NO 346
<211> LENGTH: 12
<212> TYPE: DNA
<213> ORGANISM: human

<400> SEQUENCE: 346
gcggcggcgg ca                                                      12
```

TABLE 1

| Genbank # | Region | # reps | Position | Unit sequence |
| --- | --- | --- | --- | --- |
| AA001128 | UNKNOWN | 13 | 0 | T |
| AA001134 | UNKNOWN | 14 | 0 | T |
| AA001367 | UNKNOWN | 16 | 288 | A |
| AA001389 | UNKNOWN | 13 | 0 | T |
| AA001414 | UNKNOWN | 26 | 0 | T |
| AA001423 | UNKNOWN | 7 | 262 | AAT |
| AA001435 | UNKNOWN | 12 | 2 | T |
| AA001498 | UNKNOWN | 23 | 0 | T |
| AA001693 | UNKNOWN | 6.5 | 39 | TG |
| AA001702 | UNKNOWN | 4.5 | 9 | TTAT |
| AA001865 | UNKNOWN | 7.5 | 113 | GA |
| AA001879 | UNKNOWN | 16 | 244 | T |
| AA001924 | UNKNOWN | 13.5 | 313 | TA |
| AA002226 | UNKNOWN | 3.5 | 238 | TCTAAG |
| AA002226 | UNKNOWN | 6.5 | 99 | AT |
| AA004293 | UNKNOWN | 5.66 | 182 | TTG |
| AA005059 | UNKNOWN | 14 | 183 | A |
| AA005136 | UNKNOWN | 12 | 107 | T |

TABLE 1-continued

| Genbank # | Region | # reps | Position | Unit sequence |
|---|---|---|---|---|
| AA005196 | UNKNOWN | 14 | 114 | T |
| AA009476 | UNKNOWN | 7 | 160 | TA |
| AA009699 | UNKNOWN | 12 | 359 | T |
| AA009711 | UNKNOWN | 19 | 0 | T |
| AA010512 | UNKNOWN | 12 | 114 | T |
| AA010973 | UNKNOWN | 15 | 0 | T |
| AA011306 | UNKNOWN | 17 | 0 | T |
| AA011491 | UNKNOWN | 18 | 419 | T |
| AA011543 | UNKNOWN | 16 | 148 | A |
| AA012832 | UNKNOWN | 12 | 0 | T |
| AA012865 | UNKNOWN | 28 | 0 | T |
| AA012894 | UNKNOWN | 12 | 214 | T |
| AA012982 | UNKNOWN | 17 | 0 | T |
| AA013147 | UNKNOWN | 16 | 11 | T |
| AA013162 | UNKNOWN | 13 | 345 | A |
| AA013168 | UNKNOWN | 29 | 18 | T |
| AA013194 | UNKNOWN | 6.25 | 72 | TATT |
| AA013218 | UNKNOWN | 15 | 0 | T |
| AA013247 | UNKNOWN | 10.25 | 4 | TTTA |
| AA013302 | UNKNOWN | 17 | 1 | T |
| AA013418 | UNKNOWN | 15 | 0 | T |
| AA013461 | UNKNOWN | 16 | 5 | T |
| AA015688 | UNKNOWN | 20 | 1 | T |
| AA015742 | UNKNOWN | 12.5 | 138 | TG |
| AA015783 | UNKNOWN | 18 | 0 | T |
| AA015822 | UNKNOWN | 39 | 0 | T |
| AA015946 | UNKNOWN | 22 | 329 | A |
| AA015961 | UNKNOWN | 15 | 0 | T |
| AA016265 | UNKNOWN | 21 | 203 | T |
| AA017066 | UNKNOWN | 25 | 266 | GT |
| AA017093 | UNKNOWN | 5 | 252 | TAAA |
| AA017137 | UNKNOWN | 18 | 0 | T |
| AA017279 | UNKNOWN | 6.5 | 27 | GT |
| AA017332 | UNKNOWN | 16 | 0 | T |
| AA017385 | UNKNOWN | 25 | 0 | T |
| AA017444 | UNKNOWN | 20 | 0 | T |
| AA017494 | UNKNOWN | 12 | 338 | A |
| AA017687 | UNKNOWN | 20 | 198 | A |
| AA018207 | UNKNOWN | 29 | 18 | T |
| AA018217 | UNKNOWN | 15 | 39 | A |
| AA018298 | UNKNOWN | 16 | 0 | T |
| AA018403 | UNKNOWN | 12 | 347 | T |
| AA018406 | UNKNOWN | 15 | 0 | T |
| AA018411 | UNKNOWN | 12 | 0 | T |
| AA018446 | UNKNOWN | 11.5 | 4 | TTAT |
| AA018466 | UNKNOWN | 13 | 0 | T |
| AA018488 | UNKNOWN | 6 | 43 | GTTTT |
| AA018510 | UNKNOWN | 16 | 13 | T |
| AA018554 | UNKNOWN | 25 | 0 | T |
| AA018701 | UNKNOWN | 8.5 | 52 | TG |
| AA018701 | UNKNOWN | 13 | 0 | T |
| AA018769 | UNKNOWN | 13 | 349 | A |
| AA018786 | UNKNOWN | 13 | 361 | A |
| AA019239 | UNKNOWN | 26 | 0 | T |
| AA019257 | UNKNOWN | 37 | 0 | T |
| AA019426 | UNKNOWN | 13 | 0 | T |
| AA019433 | UNKNOWN | 17 | 61 | T |
| AA019522 | UNKNOWN | 13 | 9 | T |
| AA019641 | UNKNOWN | 23.5 | 382 | TG |
| AA019736 | UNKNOWN | 13 | 1 | T |
| AA019826 | UNKNOWN | 13 | 373 | CA |
| AA019826 | UNKNOWN | 6.5 | 338 | TC |
| AA019829 | UNKNOWN | 19 | 0 | T |
| AA019838 | UNKNOWN | 16 | 0 | T |
| AA019973 | UNKNOWN | 29 | 18 | T |
| AA020860 | UNKNOWN | 27 | 0 | T |
| AA020905 | UNKNOWN | 5.66 | 70 | AAC |
| AA020957 | UNKNOWN | 13 | 627 | A |
| AA020977 | UNKNOWN | 5.66 | 290 | TTG |
| AA020977 | UNKNOWN | 12 | 0 | T |
| AA021260 | UNKNOWN | 12.5 | 240 | AC |
| AA021393 | UNKNOWN | 18 | 1 | T |
| AA021454 | UNKNOWN | 13 | 4 | T |
| AA021548 | UNKNOWN | 34 | 0 | T |
| AA021550 | UNKNOWN | 31 | 0 | T |
| AA022589 | UNKNOWN | 12 | 308 | A |
| AA024696 | UNKNOWN | 14 | 318 | T |

TABLE 1-continued

| Genbank # | Region | # reps | Position | Unit sequence |
|---|---|---|---|---|
| AA025061 | UNKNOWN | 17 | 0 | T |
| AA025270 | UNKNOWN | 18 | 0 | T |
| AA025274 | UNKNOWN | 5.5 | 111 | TTAT |
| AA027103 | UNKNOWN | 13 | 261 | T |
| AA027278 | UNKNOWN | 18 | 0 | T |
| AA027784 | UNKNOWN | 23 | 16 | T |
| AA028146 | UNKNOWN | 9 | 87 | AC |
| AA028209 | UNKNOWN | 18 | 437 | A |
| AA028887 | UNKNOWN | 6.5 | 389 | AT |
| AA028926 | UNKNOWN | 18 | 161 | A |
| AA029449 | UNKNOWN | 14 | 0 | T |
| AA029608 | UNKNOWN | 2.76 | 69 | GATTCTCAAAGCG (SEQ ID NO:1) |
| AA029888 | UNKNOWN | 6.5 | 442 | AC |
| AA031354 | UNKNOWN | 15 | 1 | T |
| AA031408 | UNKNOWN | 16 | 0 | T |
| AA031487 | UNKNOWN | 13 | 13 | T |
| AA031958 | UNKNOWN | 18 | 0 | T |
| AA032026 | UNKNOWN | 16 | 69 | A |
| AA033618 | UNKNOWN | 6.5 | 290 | AC |
| AA033784 | UNKNOWN | 12 | 591 | A |
| AA033795 | UNKNOWN | 14 | 47 | T |
| AA034012 | UNKNOWN | 15.5 | 286 | CA |
| AA034111 | UNKNOWN | 12 | 396 | A |
| AA034126 | UNKNOWN | 5.66 | 418 | AAG |
| AA034179 | UNKNOWN | 4.5 | 51 | TAAA |
| AA034412 | UNKNOWN | 19 | 677 | A |
| AA034920 | UNKNOWN | 29 | 0 | T |
| AA035214 | UNKNOWN | 16 | 14 | T |
| AA035214 | UNKNOWN | 13 | 0 | T |
| AA035379 | UNKNOWN | 18 | 107 | T |
| AA035770 | UNKNOWN | 31 | 0 | T |
| AA037399 | UNKNOWN | 9.5 | 185 | AC |
| AA037399 | UNKNOWN | 8 | 165 | AC |
| AA037478 | UNKNOWN | 3.5 | 105 | CCGCTG |
| AA039325 | UNKNOWN | 13 | 0 | T |
| AA041224 | UNKNOWN | 7 | 305 | GAAT |
| AA041255 | UNKNOWN | 7.5 | 376 | TCCA |
| AA041302 | UNKNOWN | 12 | 0 | T |
| AA041303 | UNKNOWN | 13 | 230 | T |
| AA042860 | UNKNOWN | 7.5 | 147 | AC |
| AA043185 | UNKNOWN | 13 | 0 | T |
| AA043242 | UNKNOWN | 12 | 0 | T |
| AA043349 | UNKNOWN | 14 | 139 | T |
| AA043381 | UNKNOWN | 4.5 | 354 | GGAT |
| AA043495 | UNKNOWN | 14 | 549 | A |
| AA044087 | UNKNOWN | 24 | 0 | T |
| AA044184 | UNKNOWN | 4.5 | 519 | AATT |
| AA045020 | UNKNOWN | 19 | 0 | T |
| AA045247 | UNKNOWN | 16 | 60 | A |
| AA045253 | UNKNOWN | 33 | 0 | T |
| AA045369 | UNKNOWN | 12 | 0 | T |
| AA046657 | UNKNOWN | 8.5 | 297 | AC |
| AA046737 | UNKNOWN | 13 | 109 | T |
| AA046849 | UNKNOWN | 3.6 | 377 | ATGAC |
| AA046998 | UNKNOWN | 19 | 52 | A |
| AA047353 | UNKNOWN | 4.5 | 30 | TTAT |
| AA047795 | UNKNOWN | 4.75 | 54 | TTTC |
| AA047795 | UNKNOWN | 7 | 295 | TA |
| AA047795 | UNKNOWN | 6.5 | 251 | TC |
| AA053088 | UNKNOWN | 35 | 0 | T |
| AA053805 | UNKNOWN | 12 | 346 | A |
| AA053853 | UNKNOWN | 13 | 0 | T |
| AA054085 | UNKNOWN | 29 | 18 | T |
| AA054125 | UNKNOWN | 18 | 211 | A |
| AA054137 | UNKNOWN | 3.66 | 63 | TATTGT |
| AA054173 | UNKNOWN | 14 | 347 | T |
| AA054173 | UNKNOWN | 12 | 151 | A |
| AA054276 | UNKNOWN | 13 | 0 | T |
| AA054517 | UNKNOWN | 17 | 258 | A |
| AA054560 | UNKNOWN | 12 | 0 | A |
| AA054639 | UNKNOWN | 13 | 0 | T |
| AA054646 | UNKNOWN | 14 | 208 | A |
| AA055800 | UNKNOWN | 15 | 0 | T |
| AA055901 | UNKNOWN | 15 | 303 | CA |
| AA056112 | UNKNOWN | 16 | 0 | T |
| AA056197 | UNKNOWN | 18 | 312 | A |
| AA056427 | UNKNOWN | 17 | 0 | T |

TABLE 1-continued

| Genbank # | Region | # reps | Position | Unit sequence |
|---|---|---|---|---|
| AA056755 | UNKNOWN | 4.59 | 281 | GGGTG |
| AA057019 | UNKNOWN | 32 | 0 | T |
| AA057428 | UNKNOWN | 6 | 17 | GCT |
| AA057443 | UNKNOWN | 7 | 87 | GCC |
| AA057445 | UNKNOWN | 6.5 | 507 | GT |
| AA057467 | UNKNOWN | 15 | 249 | T |
| AA057585 | UNKNOWN | 13.5 | 385 | TG |
| AA057753 | UNKNOWN | 24 | 68 | A |
| AA057753 | UNKNOWN | 12 | 0 | T |
| AA057782 | UNKNOWN | 18 | 0 | T |
| AA058566 | UNKNOWN | 12 | 0 | T |
| AA058571 | UNKNOWN | 12 | 468 | T |
| AA058773 | UNKNOWN | 12 | 356 | T |
| AA058835 | UNKNOWN | 25 | 0 | T |
| AA058843 | UNKNOWN | 14 | 17 | T |
| AA058853 | UNKNOWN | 6.66 | 75 | AAT |
| AA058884 | UNKNOWN | 16 | 0 | T |
| AA059339 | UNKNOWN | 18 | 4 | T |
| AA059347 | UNKNOWN | 4.75 | 347 | TTTG |
| AA059351 | UNKNOWN | 14 | 594 | A |
| AA059401 | UNKNOWN | 17 | 558 | A |
| AA059411 | UNKNOWN | 17 | 7 | T |
| AA059477 | UNKNOWN | 13 | 194 | GT |
| AA059477 | UNKNOWN | 8.5 | 219 | TA |
| AA059477 | UNKNOWN | 7 | 141 | GT |
| AA059479 | UNKNOWN | 56 | 0 | T |
| AA059479 | UNKNOWN | 22 | 271 | A |
| AA059479 | UNKNOWN | 17 | 198 | C |
| AA059480 | UNKNOWN | 16 | 66 | T |
| AA062548 | UNKNOWN | 7.5 | 404 | CT |
| AA063173 | UNKNOWN | 19 | 192 | A |
| AA063419 | UNKNOWN | 18 | 0 | T |
| AA063434 | UNKNOWN | 12 | 151 | A |
| AA063523 | UNKNOWN | 28 | 0 | T |
| AA063577 | UNKNOWN | 7.75 | 16 | ATTC |
| AA069267 | UNKNOWN | 17 | 132 | A |
| AA069368 | UNKNOWN | 17 | 0 | T |
| AA069391 | UNKNOWN | 12 | 6 | T |
| AA069594 | UNKNOWN | 18 | 84 | T |
| AA069612 | UNKNOWN | 21 | 105 | T |
| AA069619 | UNKNOWN | 16 | 5 | T |
| AA069869 | UNKNOWN | 15 | 0 | T |
| AA071005 | UNKNOWN | 16 | 0 | T |
| AA071012 | UNKNOWN | 16 | 269 | T |
| AA074110 | UNKNOWN | 13 | 210 | A |
| AA074202 | UNKNOWN | 12 | 7 | T |
| AA074212 | UNKNOWN | 26 | 0 | T |
| AA074222 | UNKNOWN | 22 | 0 | T |
| AA074818 | UNKNOWN | 33 | 0 | T |
| AA075407 | UNKNOWN | 16 | 9 | T |
| AA077851 | UNKNOWN | 14 | 201 | A |
| AA078536 | UNKNOWN | 15 | 0 | T |
| AA081007 | UNKNOWN | 13 | 0 | T |
| AA082011 | UNKNOWN | 32 | 0 | T |
| AA082033 | UNKNOWN | 14 | 7 | T |
| AA082045 | UNKNOWN | 16 | 0 | T |
| AA082045 | UNKNOWN | 12 | 39 | A |
| AA082313 | UNKNOWN | 3.6 | 60 | AAACA |
| AA082564 | UNKNOWN | 5 | 347 | CAAAA |
| AA082707 | UNKNOWN | 15 | 27 | T |
| AA082935 | UNKNOWN | 9.5 | 280 | CT |
| AA083213 | UNKNOWN | 16 | 407 | T |
| AA084299 | UNKNOWN | 29 | 0 | T |
| AA084439 | UNKNOWN | 18 | 0 | T |
| AA084725 | UNKNOWN | 12 | 157 | T |
| AA084761 | UNKNOWN | 14 | 0 | T |
| AA085341 | UNKNOWN | 15.5 | 158 | TG |
| AA086020 | UNKNOWN | 24 | 0 | T |
| AA086036 | UNKNOWN | 13 | 14 | T |
| AA086311 | UNKNOWN | 16 | 0 | T |
| AA086368 | UNKNOWN | 15 | 0 | T |
| AA088247 | UNKNOWN | 20 | 0 | T |
| AA088304 | UNKNOWN | 21 | 27 | T |
| AA088304 | UNKNOWN | 18 | 7 | T |
| AA088327 | UNKNOWN | 28 | 12 | T |
| AA088387 | UNKNOWN | 9.25 | 151 | AAAC |
| AA088446 | UNKNOWN | 12 | 523 | A |

TABLE 1-continued

| Genbank # | Region | # reps | Position | Unit sequence |
|---|---|---|---|---|
| AA088549 | UNKNOWN | 30 | 8 | T |
| AA088873 | UNKNOWN | 26 | 0 | T |
| AA088873 | UNKNOWN | 14 | 113 | A |
| AA088900 | UNKNOWN | 12 | 268 | T |
| AA092349 | UNKNOWN | 17 | 195 | A |
| AA093176 | UNKNOWN | 13 | 314 | A |
| AA099412 | UNKNOWN | 15 | 19 | T |
| AA100542 | UNKNOWN | 13 | 0 | T |
| AA100718 | UNKNOWN | 29 | 0 | T |
| AA101113 | UNKNOWN | 6.66 | 311 | TTA |
| AA101229 | UNKNOWN | 15 | 0 | T |
| AA101456 | UNKNOWN | 6.5 | 7 | TA |
| AA101819 | UNKNOWN | 7 | 122 | CT |
| AA101840 | UNKNOWN | 27 | 0 | T |
| AA102046 | UNKNOWN | 27 | 33 | A |
| AA102309 | UNKNOWN | 14 | 0 | A |
| AA102667 | UNKNOWN | 17 | 428 | A |
| AA112409 | UNKNOWN | 13 | 101 | A |
| AA112549 | UNKNOWN | 29 | 0 | T |
| AA112656 | UNKNOWN | 15 | 0 | T |
| AA114099 | UNKNOWN | 17 | 0 | T |
| AA114131 | UNKNOWN | 5.5 | 14 | ATTT |
| AA114180 | UNKNOWN | 27 | 0 | T |
| AA115098 | UNKNOWN | 4.8 | 30 | TTTTG |
| AA115098 | UNKNOWN | 29 | 203 | T |
| AA115202 | UNKNOWN | 16 | 387 | A |
| AA115266 | UNKNOWN | 5.66 | 362 | AAC |
| AA115466 | UNKNOWN | 20 | 0 | T |
| AA115819 | UNKNOWN | 15 | 0 | T |
| AA116106 | UNKNOWN | 14 | 139 | T |
| AA121142 | UNKNOWN | 14 | 0 | T |
| AA121302 | UNKNOWN | 6 | 16 | ATTT |
| AA121338 | UNKNOWN | 21 | 0 | T |
| AA121544 | UNKNOWN | 13 | 512 | T |
| AA121707 | UNKNOWN | 40 | 3 | T |
| AA121810 | UNKNOWN | 21 | 0 | T |
| AA122235 | UNKNOWN | 4.75 | 61 | TTTA |
| AA122265 | UNKNOWN | 13 | 51 | T |
| AA126041 | UNKNOWN | 22.5 | 408 | AC |
| AA126411 | UNKNOWN | 40 | 0 | T |
| AA126450 | UNKNOWN | 27 | 0 | T |
| AA126470 | UNKNOWN | 19 | 0 | T |
| AA126476 | UNKNOWN | 14 | 0 | T |
| AA126510 | UNKNOWN | 17 | 26 | A |
| AA126519 | UNKNOWN | 19 | 4 | T |
| AA126580 | UNKNOWN | 17 | 572 | GT |
| AA126799 | UNKNOWN | 15 | 0 | T |
| AA126811 | UNKNOWN | 15 | 491 | A |
| AA126913 | UNKNOWN | 15 | 0 | T |
| AA127593 | UNKNOWN | 14 | 215 | T |
| AA127595 | UNKNOWN | 11 | 391 | AT |
| AA127682 | UNKNOWN | 4.75 | 47 | TTTC |
| AA127682 | UNKNOWN | 17 | 63 | T |
| AA127741 | UNKNOWN | 37 | 0 | T |
| AA127750 | UNKNOWN | 12 | 177 | T |
| AA127851 | UNKNOWN | 12 | 0 | T |
| AA127916 | UNKNOWN | 6.75 | 6 | TTTA |
| AA128411 | UNKNOWN | 27 | 0 | T |
| AA128592 | UNKNOWN | 24 | 0 | T |
| AA128717 | UNKNOWN | 13 | 341 | A |
| AA129446 | UNKNOWN | 18 | 0 | T |
| AA129561 | UNKNOWN | 29 | 10 | T |
| AA129746 | UNKNOWN | 46 | 0 | T |
| AA130054 | UNKNOWN | 3.6 | 117 | AAAAC |
| AA130158 | UNKNOWN | 15 | 609 | A |
| AA130233 | UNKNOWN | 40 | 6 | T |
| AA130431 | UNKNOWN | 12 | 0 | T |
| AA130457 | UNKNOWN | 12 | 0 | T |
| AA131217 | UNKNOWN | 35 | 0 | T |
| AA131267 | UNKNOWN | 24 | 0 | T |
| AA131315 | UNKNOWN | 22 | 0 | T |
| AA131512 | UNKNOWN | 14 | 0 | T |
| AA131648 | UNKNOWN | 12 | 39 | T |
| AA131648 | UNKNOWN | 12 | 184 | A |
| AA131757 | UNKNOWN | 13 | 198 | A |
| AA131782 | UNKNOWN | 16 | 71 | T |
| AA132509 | UNKNOWN | 16 | 0 | T |

TABLE 1-continued

| Genbank # | Region | # reps | Position | Unit sequence |
|---|---|---|---|---|
| AA132657 | UNKNOWN | 13 | 400 | T |
| AA132739 | UNKNOWN | 31 | 1 | T |
| AA132739 | UNKNOWN | 12 | 55 | A |
| AA132768 | UNKNOWN | 13 | 180 | T |
| AA133203 | UNKNOWN | 12 | 78 | T |
| AA133243 | UNKNOWN | 22 | 734 | A |
| AA133338 | UNKNOWN | 29 | 0 | T |
| AA133395 | UNKNOWN | 27 | 223 | T |
| AA133568 | UNKNOWN | 5.5 | 4 | TTAT |
| AA133679 | UNKNOWN | 5.5 | 2 | TTAT |
| AA133858 | UNKNOWN | 20 | 0 | T |
| AA133872 | UNKNOWN | 22 | 0 | T |
| AA133877 | UNKNOWN | 7.66 | 14 | TTA |
| AA133944 | UNKNOWN | 4.59 | 323 | AAAAT |
| AA133962 | UNKNOWN | 13 | 0 | T |
| AA134589 | UNKNOWN | 6.33 | 64 | TCC |
| AA134771 | UNKNOWN | 12 | 0 | T |
| AA134958 | UNKNOWN | 13 | 0 | T |
| AA135370 | UNKNOWN | 19 | 9 | T |
| AA135523 | UNKNOWN | 25 | 0 | T |
| AA135525 | UNKNOWN | 21 | 336 | AC |
| AA135842 | UNKNOWN | 23 | 0 | T |
| AA136250 | UNKNOWN | 8.5 | 36 | GA |
| AA136575 | UNKNOWN | 34 | 0 | T |
| AA137062 | UNKNOWN | 7 | 372 | GT |
| AA137274 | UNKNOWN | 3.8 | 295 | TTTTG |
| AA142923 | UNKNOWN | 17 | 0 | T |
| AA142939 | UNKNOWN | 7 | 8 | TA |
| AA142978 | UNKNOWN | 21 | 0 | T |
| AA143538 | UNKNOWN | 13 | 0 | T |
| AA143561 | UNKNOWN | 32 | 0 | T |
| AA143593 | UNKNOWN | 32 | 0 | T |
| AA147044 | UNKNOWN | 20 | 0 | T |
| AA147606 | UNKNOWN | 21 | 288 | T |
| AA147606 | UNKNOWN | 16 | 111 | T |
| AA147730 | UNKNOWN | 12 | 661 | A |
| AA147920 | UNKNOWN | 20 | 437 | A |
| AA147933 | UNKNOWN | 23 | 6 | T |
| AA147934 | UNKNOWN | 9 | 16 | TTA |
| AA147981 | UNKNOWN | 4.5 | 208 | AGAT |
| AA148394 | UNKNOWN | 12 | 212 | A |
| AA148541 | UNKNOWN | 6.5 | 98 | GA |
| AA149440 | UNKNOWN | 15 | 82 | GA |
| AA149440 | UNKNOWN | 6.5 | 60 | AG |
| AA149440 | UNKNOWN | 21 | 7 | T |
| AA149526 | UNKNOWN | 43 | 0 | T |
| AA149622 | UNKNOWN | 29 | 0 | T |
| AA149640 | UNKNOWN | 17 | 95 | A |
| AA149652 | UNKNOWN | 14 | 33 | T |
| AA149653 | UNKNOWN | 14 | 0 | T |
| AA149757 | UNKNOWN | 42 | 0 | T |
| AA150194 | UNKNOWN | 26 | 6 | T |
| AA150314 | UNKNOWN | 19 | 1 | T |
| AA150502 | UNKNOWN | 20 | 0 | T |
| AA151126 | UNKNOWN | 13 | 7 | T |
| AA151303 | UNKNOWN | 20 | 3 | T |
| AA151605 | UNKNOWN | 25 | 0 | T |
| AA151723 | UNKNOWN | 13 | 669 | A |
| AA152026 | UNKNOWN | 13 | 666 | A |
| AA152276 | UNKNOWN | 7 | 541 | AG |
| AA155746 | UNKNOWN | 16 | 0 | T |
| AA155754 | UNKNOWN | 10.75 | 278 | AAAT |
| AA155774 | UNKNOWN | 17 | 256 | T |
| AA156214 | UNKNOWN | 12 | 373 | T |
| AA156232 | UNKNOWN | 13 | 6 | T |
| AA156269 | UNKNOWN | 16 | 0 | T |
| AA156638 | UNKNOWN | 6.33 | 24 | GCA |
| AA156657 | UNKNOWN | 13 | 364 | A |
| AA156782 | UNKNOWN | 24 | 0 | T |
| AA156879 | UNKNOWN | 16 | 432 | T |
| AA156902 | UNKNOWN | 8 | 452 | GT |
| AA156997 | UNKNOWN | 12 | 0 | T |
| AA157001 | UNKNOWN | 13 | 0 | T |
| AA157033 | UNKNOWN | 13 | 7 | T |
| AA157881 | UNKNOWN | 8 | 164 | AC |
| AA158566 | UNKNOWN | 15 | 0 | T |
| AA159848 | UNKNOWN | 19 | 343 | AC |

TABLE 1-continued

| Genbank # | Region | # reps | Position | Unit sequence |
|---|---|---|---|---|
| AA159920 | UNKNOWN | 2.7 | 256 | TTTTTTTTNT (SEQ ID NO:2) |
| AA160474 | UNKNOWN | 13 | 352 | A |
| AA160532 | UNKNOWN | 27 | 0 | T |
| AA160939 | UNKNOWN | 15 | 0 | T |
| AA160945 | UNKNOWN | 12 | 0 | T |
| AA160991 | UNKNOWN | 25 | 0 | T |
| AA161476 | UNKNOWN | 4.5 | 51 | AGGC |
| AA161477 | UNKNOWN | 6.5 | 231 | TC |
| AA161477 | UNKNOWN | 16 | 243 | T |
| AA164253 | UNKNOWN | 5.4 | 193 | TCCAT |
| AA164457 | UNKNOWN | 12 | 133 | A |
| AA164546 | UNKNOWN | 19 | 0 | T |
| AA164567 | UNKNOWN | 16 | 0 | T |
| AA164750 | UNKNOWN | 22 | 0 | T |
| AA164958 | UNKNOWN | 13 | 157 | T |
| AA165161 | UNKNOWN | 13 | 129 | A |
| AA165400 | UNKNOWN | 29 | 0 | T |
| AA165597 | UNKNOWN | 18 | 3 | T |
| AA166653 | UNKNOWN | 3.6 | 72 | GGCGA |
| AA166653 | UNKNOWN | 6 | 504 | AAC |
| AA166743 | UNKNOWN | 37 | 0 | T |
| AA166835 | UNKNOWN | 13 | 42 | T |
| AA166917 | UNKNOWN | 6.5 | 281 | TA |
| AA167144 | UNKNOWN | 12.33 | 175 | TTG |
| AA167217 | UNKNOWN | 5.5 | 277 | ATGG |
| AA167284 | UNKNOWN | 15 | 198 | A |
| AA167474 | UNKNOWN | 17 | 0 | T |
| AA167624 | UNKNOWN | 26 | 0 | T |
| AA167626 | UNKNOWN | 19 | 0 | T |
| AA167696 | UNKNOWN | 35 | 0 | T |
| AA167704 | UNKNOWN | 16 | 0 | T |
| AA167714 | UNKNOWN | 13 | 606 | GT |
| AA167715 | UNKNOWN | 37 | 0 | T |
| AA167744 | UNKNOWN | 19 | 186 | T |
| AA169133 | UNKNOWN | 33 | 156 | A |
| AA169255 | UNKNOWN | 15 | 439 | A |
| AA169259 | UNKNOWN | 4.5 | 61 | GATG |
| AA169535 | UNKNOWN | 7.5 | 124 | TTCA |
| AA169635 | UNKNOWN | 30 | 0 | T |
| AA169840 | UNKNOWN | 3.8 | 32 | TTTTG |
| AA170806 | UNKNOWN | 21 | 5 | T |
| AA171478 | UNKNOWN | 14 | 282 | A |
| AA171478 | UNKNOWN | 13 | 134 | T |
| AA171513 | UNKNOWN | 26 | 0 | T |
| AA172046 | UNKNOWN | 13 | 360 | A |
| AA172047 | UNKNOWN | 41 | 0 | T |
| AA173465 | UNKNOWN | 38 | 0 | T |
| AA173763 | UNKNOWN | 18 | 0 | T |
| AA174115 | UNKNOWN | 23 | 0 | T |
| AA174124 | UNKNOWN | 47 | 0 | T |
| AA174149 | UNKNOWN | 14 | 0 | T |
| AA176205 | UNKNOWN | 4 | 201 | AAAGC |
| AA176205 | UNKNOWN | 34 | 0 | T |
| AA176280 | UNKNOWN | 7.5 | 277 | AT |
| AA176528 | UNKNOWN | 10 | 249 | AT |
| AA176629 | UNKNOWN | 12 | 0 | T |
| AA176688 | UNKNOWN | 12 | 96 | AC |
| AA176924 | UNKNOWN | 20 | 145 | TG |
| AA176970 | UNKNOWN | 13 | 0 | T |
| AA176980 | UNKNOWN | 59 | 64 | A |
| AA176980 | UNKNOWN | 28 | 32 | A |
| AA176997 | UNKNOWN | 12 | 394 | T |
| AA177001 | UNKNOWN | 20 | 7 | T |
| AA177037 | UNKNOWN | 13 | 8 | T |
| AA177054 | UNKNOWN | 19 | 3 | T |
| AA177066 | UNKNOWN | 18 | 7 | T |
| AA177072 | UNKNOWN | 18 | 487 | A |
| AA177110 | UNKNOWN | 15 | 332 | A |
| AA177110 | UNKNOWN | 13 | 168 | A |
| AA177115 | UNKNOWN | 30 | 21 | T |
| AA177115 | UNKNOWN | 20 | 0 | T |
| AA177134 | UNKNOWN | 20 | 0 | T |
| AA177138 | UNKNOWN | 12 | 400 | A |
| AA178953 | UNKNOWN | 4.8 | 11 | TTTTA |
| AA179147 | UNKNOWN | 17 | 359 | A |
| AA179161 | UNKNOWN | 13 | 0 | T |
| AA179168 | UNKNOWN | 12 | 16 | T |

TABLE 1-continued

| Genbank # | Region | # reps | Position | Unit sequence |
|---|---|---|---|---|
| AA179274 | UNKNOWN | 19 | 0 | T |
| AA179504 | UNKNOWN | 17 | 0 | T |
| AA180065 | UNKNOWN | 21 | 278 | T |
| AA180065 | UNKNOWN | 13 | 64 | A |
| AA180065 | UNKNOWN | 12 | 0 | T |
| AA180346 | UNKNOWN | 41 | 0 | T |
| AA180775 | UNKNOWN | 19 | 415 | A |
| AA180810 | UNKNOWN | 29 | 0 | T |
| AA180890 | UNKNOWN | 31 | 77 | A |
| AA180967 | UNKNOWN | 7 | 31 | GAA |
| AA181172 | UNKNOWN | 15 | 0 | T |
| AA181657 | UNKNOWN | 12 | 426 | T |
| AA182602 | UNKNOWN | 3.8 | 311 | TTTTG |
| AA182731 | UNKNOWN | 15 | 0 | T |
| AA182909 | UNKNOWN | 12 | 3 | T |
| AA186905 | UNKNOWN | 4.59 | 6 | TTATT |
| AA187207 | UNKNOWN | 22 | 0 | T |
| AA187233 | UNKNOWN | 33 | 0 | T |
| AA187679 | UNKNOWN | 2.84 | 197 | AACAAAAAACAAC (SEQ ID NO:3) |
| AA187679 | UNKNOWN | 3.83 | 182 | AAAAAC |
| AA187979 | UNKNOWN | 17 | 4 | T |
| AA188492 | UNKNOWN | 32 | 0 | T |
| AA188676 | UNKNOWN | 14 | 49 | T |
| AA188763 | UNKNOWN | 12 | 0 | T |
| AA188940 | UNKNOWN | 27 | 0 | T |
| AA188992 | UNKNOWN | 14 | 127 | A |
| AA190757 | UNKNOWN | 15 | 0 | T |
| AA191418 | UNKNOWN | 27 | 0 | T |
| AA191659 | UNKNOWN | 23 | 38 | T |
| AA191670 | UNKNOWN | 4.8 | 132 | TTTTG |
| AA192163 | UNKNOWN | 41 | 0 | T |
| AA192278 | UNKNOWN | 21 | 0 | T |
| AA192415 | UNKNOWN | 40 | 0 | T |
| AA192415 | UNKNOWN | 12 | 142 | A |
| AA192481 | UNKNOWN | 5.25 | 552 | AATT |
| AA192483 | UNKNOWN | 10.5 | 0 | AG |
| AA192747 | UNKNOWN | 17 | 0 | T |
| AA193381 | UNKNOWN | 22 | 0 | T |
| AA193445 | UNKNOWN | 5 | 129 | AAAC |
| AA193515 | UNKNOWN | 12 | 0 | T |
| AA193570 | UNKNOWN | 19 | 0 | T |
| AA194093 | UNKNOWN | 14 | 306 | T |
| AA194633 | UNKNOWN | 17 | 0 | T |
| AA194699 | UNKNOWN | 16 | 9 | T |
| AA194878 | UNKNOWN | 28 | 0 | T |
| AA195038 | UNKNOWN | 17 | 1 | T |
| AA195164 | UNKNOWN | 18 | 63 | A |
| AA195245 | UNKNOWN | 14 | 565 | A |
| AA195351 | UNKNOWN | 16 | 0 | T |
| AA195417 | UNKNOWN | 3.8 | 40 | AAAAC |
| AA195691 | UNKNOWN | 32 | 0 | T |
| AA195963 | UNKNOWN | 5 | 2 | GAAA |
| AA196018 | UNKNOWN | 6.5 | 511 | TG |
| AA196354 | UNKNOWN | 6.5 | 247 | TG |
| AA197185 | UNKNOWN | 13 | 277 | A |
| AA197344 | UNKNOWN | 26 | 0 | T |
| AA203135 | UNKNOWN | 23 | 55 | A |
| AA203136 | UNKNOWN | 13 | 486 | T |
| AA203136 | UNKNOWN | 12 | 209 | A |
| AA203139 | UNKNOWN | 9.5 | 104 | GT |
| AA203155 | UNKNOWN | 14 | 675 | A |
| AA203167 | UNKNOWN | 3.6 | 611 | AGAAA |
| AA203182 | UNKNOWN | 16 | 11 | A |
| AA203219 | UNKNOWN | 14 | 385 | T |
| AA203247 | UNKNOWN | 14 | 0 | T |
| AA203272 | UNKNOWN | 13 | 654 | A |
| AA203285 | UNKNOWN | 17 | 18 | T |
| AA203319 | UNKNOWN | 14 | 194 | A |
| AA203334 | UNKNOWN | 14 | 68 | A |
| AA203350 | UNKNOWN | 9.5 | 1145 | TG |
| AA203361 | UNKNOWN | 13 | 65 | A |
| AA203370 | UNKNOWN | 12 | 584 | A |
| AA203415 | UNKNOWN | 18 | 422 | A |
| AA203448 | UNKNOWN | 15 | 55 | A |
| AA203482 | UNKNOWN | 13 | 19 | A |
| AA203496 | UNKNOWN | 12 | 710 | A |
| AA203502 | UNKNOWN | 13 | 690 | A |

TABLE 1-continued

| Genbank # | Region | # reps | Position | Unit sequence |
|---|---|---|---|---|
| AA203505 | UNKNOWN | 13 | 642 | A |
| AA203507 | UNKNOWN | 4 | 92 | GTTTT |
| AA203507 | UNKNOWN | 13 | 55 | T |
| AA203536 | UNKNOWN | 17 | 375 | TG |
| AA203539 | UNKNOWN | 16 | 545 | A |
| AA203673 | UNKNOWN | 7.5 | 32 | TG |
| AA203680 | UNKNOWN | 12 | 7 | T |
| AA203732 | UNKNOWN | 23 | 606 | A |
| AA205323 | UNKNOWN | 3.8 | 15 | TTTTA |
| AA205323 | UNKNOWN | 17 | 59 | T |
| AA205434 | UNKNOWN | 39 | 0 | T |
| AA205754 | UNKNOWN | 26 | 0 | T |
| AA205873 | UNKNOWN | 19 | 0 | T |
| AA205915 | UNKNOWN | 23 | 90 | T |
| AA206126 | UNKNOWN | 12 | 7 | A |
| AA206693 | UNKNOWN | 6 | 180 | GTTT |
| AA206754 | UNKNOWN | 18 | 0 | T |
| AA206783 | UNKNOWN | 13 | 323 | T |
| AA206801 | UNKNOWN | 6.5 | 271 | TA |
| AA206801 | UNKNOWN | 6.5 | 426 | AC |
| AA206902 | UNKNOWN | 25 | 0 | T |
| AA207072 | UNKNOWN | 21 | 0 | T |
| AA207115 | UNKNOWN | 2.9 | 29 | AATGGAATGC (SEQ ID NO:4) |
| AA207115 | UNKNOWN | 11 | 112 | GGAAT |
| AA207115 | UNKNOWN | 4.4 | 49 | AATGG |
| AA207141 | UNKNOWN | 19 | 515 | A |
| AA209415 | UNKNOWN | 18 | 292 | T |
| AA209423 | UNKNOWN | 15 | 88 | T |
| AA209466 | UNKNOWN | 3.5 | 645 | GGCGAA |
| AA209466 | UNKNOWN | 6.66 | 562 | CTT |
| AA209487 | UNKNOWN | 13 | 266 | T |
| AA210694 | UNKNOWN | 23 | 7 | T |
| AA210711 | UNKNOWN | 18 | 439 | T |
| AA211054 | UNKNOWN | 12 | 0 | T |
| AA211076 | UNKNOWN | 12 | 0 | T |
| AA211078 | UNKNOWN | 13 | 5 | T |
| AA211087 | UNKNOWN | 16 | 377 | A |
| AA211087 | UNKNOWN | 12 | 74 | A |
| AA211371 | UNKNOWN | 40 | 0 | T |
| AA211371 | UNKNOWN | 15 | 262 | A |
| AA211390 | UNKNOWN | 5.25 | 4 | TGTT |
| AA211390 | UNKNOWN | 4.5 | 22 | TTTA |
| AA211615 | UNKNOWN | 22 | 0 | T |
| AA211734 | UNKNOWN | 5 | 360 | TTTA |
| AA211918 | UNKNOWN | 15 | 0 | T |
| AA213626 | UNKNOWN | 16 | 0 | T |
| AA213820 | UNKNOWN | 5.33 | 294 | CATCAC |
| AA213959 | UNKNOWN | 17 | 0 | T |
| AA214530 | UNKNOWN | 34 | 0 | T |
| AA215366 | UNKNOWN | 15 | 0 | T |
| AA215372 | UNKNOWN | 17 | 402 | T |
| AA215374 | UNKNOWN | 17 | 0 | T |
| AA215447 | UNKN9WN | 12 | 128 | A |
| AA215470 | UNKNOWN | 14 | 285 | T |
| AA215634 | UNKNOWN | 28 | 74 | T |
| AA216403 | UNKNOWN | 16 | 0 | T |
| AA216410 | UNKNOWN | 18 | 365 | A |
| AA216419 | UNKNOWN | 16 | 487 | A |
| AA216420 | UNKNOWN | 15 | 329 | A |
| AA218851 | UNKNOWN | 24 | 0 | T |
| AA218943 | UNKNOWN | 26 | 0 | T |
| AA218986 | UNKNOWN | 13 | 14 | T |
| AA219033 | UNKNOWN | 5.66 | 393 | TAT |
| AA219090 | UNKNOWN | 24 | 205 | A |
| AA219315 | UNKNOWN | 13 | 36 | A |
| AA219580 | UNKNOWN | 20 | 0 | T |
| AA223246 | UNKNOWN | 4.4 | 39 | TTTTA |
| AA223508 | UNKNOWN | 15 | 0 | T |
| AA224205 | UNKNOWN | 21 | 0 | T |
| AA224323 | UNKNOWN | 20 | 0 | T |
| AA224594 | UNKNOWN | 15 | 1 | T |
| AA224749 | UNKNOWN | 12 | 0 | T |
| AA224825 | UNKNOWN | 15 | 0 | T |
| AA224952 | UNKNOWN | 20 | 125 | AC |
| AA224952 | UNKNOWN | 10 | 6 | AC |
| AA224952 | UNKNOWN | 17 | 322 | A |
| AA224993 | UNKNOWN | 24 | 113 | A |

TABLE 1-continued

| Genbank # | Region | # reps | Position | Unit sequence |
|---|---|---|---|---|
| AA224993 | UNKNOWN | 16 | 0 | T |
| AA225001 | UNKNOWN | 21 | 8 | T |
| AA225063 | UNKNOWN | 18 | 6 | T |
| AA225237 | UNKNOWN | 6.5 | 27 | AG |
| AA225237 | UNKNOWN | 13 | 327 | A |
| AA225255 | UNKNOWN | 17 | 144 | T |
| AA225291 | UNKNOWN | 7 | 360 | AG |
| AA225291 | UNKNOWN | 12 | 293 | T |
| AA225521 | UNKNOWN | 26 | 290 | T |
| AA225522 | UNKNOWN | 12 | 415 | A |
| AA225546 | UNKNOWN | 15 | 1 | T |
| AA225715 | UNKNOWN | 7 | 155 | AC |
| AA225715 | UNKNOWN | 14 | 282 | A |
| AA225871 | UNKNOWN | 12 | 558 | A |
| AA225906 | UNKNOWN | 34 | 242 | A |
| AA225931 | UNKNOWN | 16 | 7 | T |
| AA225944 | UNKNOWN | 14 | 364 | A |
| AA226017 | UNKNOWN | 14 | 357 | A |
| AA226040 | UNKNOWN | 25 | 279 | T |
| AA226040 | UNKNOWN | 16 | 0 | T |
| AA226152 | UNKNOWN | 13 | 6 | T |
| AA226212 | UNKNOWN | 17 | 358 | A |
| AA226285 | UNKNOWN | 12 | 288 | A |
| AA226352 | UNKNOWN | 13 | 5 | T |
| AA226468 | UNKNOWN | 14 | 2 | T |
| AA226510 | UNKNOWN | 14 | 407 | A |
| AA226538 | UNKNOWN | 17 | 0 | T |
| AA226620 | UNKNOWN | 15 | 0 | T |
| AA226629 | UNKNOWN | 14 | 0 | T |
| AA226639 | UNKNOWN | 15 | 504 | A |
| AA226702 | UNKNOWN | 16 | 448 | A |
| AA226970 | UNKNOWN | 33 | 0 | T |
| AA227469 | UNKNOWN | 19 | 0 | T |
| AA227479 | UNKNOWN | 8.5 | 197 | ATTC |
| AA227479 | UNKNOWN | 26 | 0 | T |
| AA227537 | UNKNOWN | 3.6 | 6 | TTTAT |
| AA227844 | UNKNOWN | 14 | 0 | T |
| AA228425 | UNKNOWN | 3.8 | 370 | AAAAC |
| AA228425 | UNKNOWN | 14 | 391 | A |
| AA228736 | UNKNOWN | 17 | 0 | T |
| AA228834 | UNKNOWN | 14 | 355 | A |
| AA228834 | UNKNOWN | 13 | 154 | A |
| AA228894 | UNKNOWN | 23 | 162 | T |
| AA228894 | UNKNOWN | 15 | 0 | T |
| AA228901 | UNKNOWN | 23 | 332 | A |
| AA228930 | UNKNOWN | 17 | 0 | T |
| AA228981 | UNKNOWN | 16 | 5 | T |
| AA229005 | UNKNOWN | 16 | 287 | A |
| AA229023 | UNKNOWN | 16 | 258 | A |
| AA229496 | UNKNOWN | 16 | 394 | A |
| AA229594 | UNKNOWN | 20 | 200 | A |
| AA229594 | UNKNOWN | 15 | 15 | T |
| AA229594 | UNKNOWN | 12 | 0 | T |
| AA229601 | UNKNOWN | 17 | 0 | T |
| AA229814 | UNKNOWN | 13 | 29 | T |
| AA229851 | UNKNOWN | 14 | 221 | T |
| AA229900 | UNKNOWN | 17 | 292 | A |
| AA229921 | UNKNOWN | 14 | 305 | A |
| AA229932 | UNKNOWN | 15 | 0 | T |
| AA229941 | UNKNOWN | 16 | 5 | T |
| AA230143 | UNKNOWN | 17 | 0 | T |
| AA232854 | UNKNOWN | 22 | 94 | A |
| AA233727 | UNKNOWN | 13 | 17 | A |
| AA234060 | UNKNOWN | 24 | 0 | T |
| AA234121 | UNKNOWN | 6.5 | 167 | TG |
| AA234198 | UNKNOWN | 13 | 416 | A |
| AA234307 | UNKNOWN | 7 | 250 | GT |
| AA234520 | UNKNOWN | 15 | 351 | T |
| AA234524 | UNKNOWN | 14 | 0 | T |
| AA234714 | UNKNOWN | 16 | 18 | A |
| AA234923 | UNKNOWN | 16 | 0 | T |
| AA235975 | UNKNOWN | 40 | 77 | T |
| AA236011 | UNKNOWN | 16 | 0 | T |
| AA236056 | UNKNOWN | 7 | 156 | AC |
| AA236515 | UNKNOWN | 17 | 0 | T |
| AA236903 | UNKNOWN | 24 | 135 | T |
| AA236903 | UNKNOWN | 15 | 319 | A |

TABLE 1-continued

| Genbank # | Region | # reps | Position | Unit sequence |
|---|---|---|---|---|
| AA237005 | UNKNOWN | 14 | 0 | T |
| AA243283 | UNKNOWN | 31 | 0 | T |
| AA243649 | UNKNOWN | 39 | 0 | T |
| AA243724 | UNKNOWN | 13 | 417 | A |
| AA243729 | UNKNOWN | 18 | 0 | T |
| AA243994 | UNKNOWN | 14 | 386 | A |
| AA244012 | UNKNOWN | 15 | 0 | T |
| AA244231 | UNKNOWN | 16 | 0 | T |
| AA244231 | UNKNOWN | 16 | 228 | A |
| AA244425 | UNKNOWN | 17 | 0 | T |
| AA247761 | UNKNOWN | 15 | 122 | A |
| AA249204 | UNKNOWN | 13 | 272 | A |
| AA250763 | UNKNOWN | 18.75 | 322 | TTTC |
| AA250803 | UNKNOWN | 20 | 0 | T |
| AA251146 | UNKNOWN | 23 | 0 | T |
| AA251338 | UNKNOWN | 14 | 0 | T |
| AA251548 | UNKNOWN | 20 | 0 | T |
| AA251806 | UNKNOWN | 29 | 0 | T |
| AA252058 | UNKNOWN | 37 | 0 | T |
| AA252078 | UNKNOWN | 26 | 0 | T |
| AA252323 | UNKNOWN | 14 | 292 | A |
| AA252352 | UNKNOWN | 6 | 0 | ATTT |
| AA252480 | UNKNOWN | 14 | 299 | A |
| AA252652 | UNKNOWN | 12 | 225 | T |
| AA252805 | UNKNOWN | 4.75 | 146 | TTTG |
| AA252937 | UNKNOWN | 18 | 268 | T |
| AA255559 | UNKNOWN | 2.6 | 227 | TGGGAGAGAC (SEQ ID NO:5) |
| AA255651 | UNKNOWN | 14 | 42 | A |
| AA256333 | UNKNOWN | 23 | 0 | T |
| AA256779 | UNKNOWN | 14 | 376 | A |
| AA257108 | UNKNOWN | 21 | 74 | T |
| AA257108 | UNKNOWN | 13 | 228 | A |
| AA257991 | UNKNOWN | 41 | 0 | T |
| AA258168 | UNKNOWN | 7.66 | 135 | TTA |
| AA258238 | UNKNOWN | 8 | 243 | TA |
| AA258323 | UNKNOWN | 3.6 | 216 | AAAAC |
| AA258601 | UNKNOWN | 14 | 0 | T |
| AA258796 | UNKNOWN | 12 | 185 | T |
| AA259247 | UNKNOWN | 18 | 230 | A |
| AA259267 | UNKNOWN | 15 | 0 | T |
| AA261888 | UNKNOWN | 16 | 0 | T |
| AA262029 | UNKNOWN | 15 | 0 | T |
| AA262086 | UNKNOWN | 25 | 0 | T |
| AA262141 | UNKNOWN | 32 | 0 | T |
| AA262338 | UNKNOWN | 9.75 | 215 | TTTA |
| AA262338 | UNKNOWN | 14 | 397 | T |
| AA262456 | UNKNOWN | 26 | 0 | T |
| AA262462 | UNKNOWN | 13 | 378 | A |
| AA262473 | UNKNOWN | 42 | 0 | T |
| AA262529 | UNKNQWN | 17 | 188 | T |
| AA262567 | UNKNOWN | 7.75 | 101 | AAAT |
| AA263043 | UNKNOWN | 12 | 272 | T |
| AA278304 | UNKNOWN | 31 | 0 | T |
| AA278330 | UNKNOWN | 23 | 0 | T |
| AA278594 | UNKNOWN | 22 | 362 | A |
| AA278641 | UNKNOWN | 7.25 | 188 | TATT |
| AA278725 | UNKNOWN | 17 | 0 | T |
| AA278821 | UNKNOWN | 13 | 68 | A |
| AA279013 | UNKNOWN | 18 | 330 | T |
| AA279013 | UNKNOWN | 15 | 421 | A |
| AA279015 | UNKNOWN | 31 | 0 | T |
| AA279018 | UNKNOWN | 13 | 0 | T |
| AA279118 | UNKNOWN | 29 | 0 | T |
| AA279214 | UNKNOWN | 15 | 14 | T |
| AA279328 | UNKNOWN | 16 | 0 | T |
| AA279771 | UNKNOWN | 30 | 0 | T |
| AA279795 | UNKNOWN | 64 | 0 | T |
| AA279795 | UNKNOWN | 16 | 238 | A |
| AA279795 | UNKNOWN | 15 | 183 | G |
| AA279795 | UNKNOWN | 12 | 66 | A |
| AA279977 | UNKNOWN | 11.25 | 279 | GATA |
| AA279977 | UNKNOWN | 7 | 0 | CTTT |
| AA280030 | UNKNOWN | 8.5 | 28 | TATT |
| AA280529 | UNKNOWN | 18 | 0 | T |
| AA280634 | UNKNOWN | 26 | 0 | T |
| AA280634 | UNKNOWN | 13 | 372 | A |
| AA280679 | UNKNOWN | 3.83 | 10 | TTTTTC |

TABLE 1-continued

| Genbank # | Region | # reps | Position | Unit sequence |
|---|---|---|---|---|
| AA280805 | UNKNOWN | 7 | 355 | GT |
| AA280824 | UNKNOWN | 4.75 | 44 | AAAT |
| AA280878 | UNKNOWN | 20 | 0 | T |
| AA280886 | UNKNOWN | 17 | 7 | T |
| AA281062 | UNKNOWN | 23 | 0 | T |
| AA281092 | UNKNOWN | 43 | 0 | T |
| AA281250 | UNKNOWN | 22 | 0 | T |
| AA281793 | UNKNOWN | 5.25 | 256 | AATA |
| AA281925 | UNKNOWN | 5.5 | 2 | TTTA |
| AA282060 | UNKNOWN | 14 | 0 | T |
| AA282243 | UNKNOWN | 43 | 0 | T |
| AA282243 | UNKNOWN | 12 | 109 | A |
| AA282302 | UNKNOWN | 17 | 2 | T |
| AA282536 | UNKNOWN | 13 | 0 | T |
| AA282951 | UNKNOWN | 26 | 1 | T |
| AA283039 | UNKNOWN | 15 | 324 | A |
| AA283365 | UNKNOWN | 18 | 0 | T |
| AA283730 | UNKNOWN | 26 | 185 | T |
| AA283873 | UNKNOWN | 6.5 | 218 | TG |
| AA283912 | UNKNOWN | 18 | 17 | T |
| AA284247 | UNKNOWN | 18 | 434 | A |
| AA284247 | UNKNOWN | 15 | 119 | A |
| AA284259 | UNKNOWN | 13 | 308 | T |
| AA284305 | UNKNOWN | 23 | 454 | A |
| AA284307 | UNKNOWN | 11 | 171 | TG |
| AA284452 | UNKNOWN | 27 | 4 | T |
| AA284463 | UNKNOWN | 6.25 | 303 | TGTT |
| AA285064 | UNKNOWN | 18 | 0 | T |
| AA285066 | UNKNOWN | 18 | 0 | T |
| AA285066 | UNKNOWN | 12 | 199 | A |
| AA285069 | UNKNOWN | 27 | 0 | T |
| AA285171 | UNKNOWN | 19 | 285 | A |
| AA285286 | UNKNOWN | 5.33 | 94 | CCTCAG |
| AA286836 | UNKNOWN | 33 | 0 | T |
| AA286939 | UNKNOWN | 34 | 0 | T |
| AA286942 | UNKNOWN | 13 | 25 | T |
| AA287103 | UNKNOWN | 17 | 0 | T |
| AA287314 | UNKNOWN | 16 | 0 | T |
| AA287656 | UNKNOWN | 20 | 0 | T |
| AA287734 | UNKNOWN | 15.5 | 314 | CA |
| AA287922 | UNKNOWN | 15.5 | 107 | AC |
| AA287940 | UNKNOWN | 12 | 0 | T |
| AA290568 | UNKNOWN | 17 | 77 | A |
| AA290624 | UNKNOWN | 26 | 302 | A |
| AA291066 | UNKNOWN | 12 | 100 | A |
| AA291522 | UNKNOWN | 12 | 0 | T |
| AA291940 | UNKNOWN | 13 | 0 | T |
| AA291948 | UNKNOWN | 15 | 0 | T |
| AA292171 | UNKNOWN | 29 | 1 | T |
| AA292275 | UNKNOWN | 12 | 495 | AC |
| AA292534 | UNKNOWN | 13 | 44 | A |
| AA292540 | UNKNOWN | 16 | 0 | T |
| AA292700 | UNKNOWN | 14 | 144 | A |
| AA292852 | UNKNOWN | 22 | 378 | A |
| AA302674 | UNKNOWN | 5.75 | 167 | TGAA |
| AA302811 | UNKNOWN | 6 | 6 | TATT |
| AA303153 | UNKNOWN | 19 | 133 | T |
| AA309281 | UNKNOWN | 16 | 6 | T |
| AA309379 | UNKNOWN | 14 | 118 | T |
| AA311027 | UNKNOWN | 22 | 331 | GA |
| AA311519 | UNKNOWN | 14 | 51 | A |
| AA316835 | UNKNOWN | 14 | 44 | A |
| AA317734 | UNKNOWN | 22 | 20 | T |
| AA318194 | UNKNOWN | 19 | 22 | T |
| AA321273 | UNKNOWN | 18 | 295 | T |
| AA321977 | UNKNOWN | 17 | 6 | T |
| AA325025 | UNKNOWN | 19 | 24 | T |
| AA325597 | UNKNOWN | 20 | 23 | T |
| AA326709 | UNKNOWN | 8 | 52 | TA |
| AA330569 | UNKNOWN | 12 | 98 | A |
| AA334245 | UNKNOWN | 12 | 240 | T |
| AA334763 | UNKNOWN | 12 | 152 | A |
| AA338601 | UNKNOWN | 7.8 | 15 | TTTTA |
| AA342185 | UNKNOWN | 15 | 250 | A |
| AA342453 | UNKNOWN | 13 | 241 | A |
| AA342616 | UNKNOWN | 4.75 | 0 | ATTT |
| AA342961 | UNKNOWN | 18.5 | 63 | TA |

TABLE 1-continued

| Genbank # | Region | # reps | Position | Unit sequence |
|---|---|---|---|---|
| AA350593 | UNKNOWN | 4.75 | 31 | ATTT |
| AA350773 | UNKNOWN | 4.75 | 341 | TAAA |
| AA350773 | UNKNOWN | 7 | 31 | AT |
| AA350886 | UNKNOWN | 6 | 0 | ATTT |
| AA351003 | UNKNOWN | 4 | 18 | ATTTT |
| AA354066 | UNKNOWN | 14 | 27 | T |
| AA354702 | UNKNOWN | 11 | 261 | AC |
| AA357354 | UNKNOWN | 4.75 | 120 | TTTG |
| AA358502 | UNKNOWN | 12 | 72 | A |
| AA358715 | UNKNOWN | 4 | 154 | TAAAA |
| AA371434 | UNKNOWN | 3.6 | 280 | AAATT |
| AA371616 | UNKNOWN | 6 | 0 | ATTT |
| AA372298 | UNKNOWN | 25 | 61 | A |
| AA380706 | UNKNOWN | 16 | 7 | T |
| AA382973 | UNKNOWN | 9.5 | 35 | AG |
| AA385577 | UNKNOWN | 16 | 173 | A |
| AA393670 | UNKNOWN | 8 | 16 | TC |
| AA393728 | UNKNOWN | 4 | 165 | TTGTGC |
| AA393874 | UNKNOWN | 19 | 0 | T |
| AA394099 | UNKNOWN | 13 | 82 | T |
| AA397442 | UNKNOWN | 6.5 | 178 | TG |
| AA397538 | UNKNOWN | 22 | 214 | A |
| AA397651 | UNKNOWN | 16 | 78 | A |
| AA397763 | UNKNOWN | 22 | 422 | A |
| AA397786 | UNKNOWN | 12 | 10 | T |
| AA397805 | UNKNOWN | 24 | 336 | A |
| AA397879 | UNKNOWN | 19 | 0 | T |
| AA398062 | UNKNOWN | 24 | 2 | T |
| AA398147 | UNKNOWN | 20 | 482 | A |
| AA398239 | UNKNOWN | 23 | 0 | T |
| AA398241 | UNKNOWN | 32 | 0 | T |
| AA398273 | UNKNOWN | 41 | 0 | T |
| AA398274 | UNKNOWN | 35 | 0 | T |
| AA398319 | UNKNOWN | 20 | 359 | T |
| AA398434 | UNKNOWN | 16 | 0 | T |
| AA398482 | UNKNOWN | 24 | 0 | T |
| AA398532 | UNKNOWN | 13 | 15 | T |
| AA398609 | UNKNOWN | 13 | 386 | A |
| AA398696 | UNKNOWN | 12 | 0 | T |
| AA398762 | UNKNOWN | 17 | 441 | T |
| AA398912 | UNKNOWN | 17 | 0 | T |
| AA398936 | UNKNOWN | 3.66 | 51 | TTTTGT |
| AA399028 | UNKNOWN | 13 | 12 | A |
| AA399584 | UNKNOWN | 20 | 0 | T |
| AA399697 | UNKNOWN | 15 | 5 | T |
| AA400013 | UNKNOWN | 6.5 | 284 | TG |
| AA400224 | UNKNOWN | 12 | 101 | C |
| AA400225 | UNKNOWN | 12.5 | 200 | AC |
| AA400298 | UNKNOWN | 13 | 0 | T |
| AA400319 | UNKNOWN | 18 | 0 | T |
| AA400442 | UNKNOWN | 40 | 0 | T |
| AA400458 | UNKNOWN | 10.5 | 360 | TG |
| AA400458 | UNKNOWN | 10 | 301 | AT |
| AA400606 | UNKNOWN | 12 | 28 | A |
| AA401446 | UNKNOWN | 13 | 420 | A |
| AA401488 | UNKNOWN | 13 | 0 | T |
| AA401575 | UNKNOWN | 12 | 468 | A |
| AA402106 | UNKNOWN | 12.5 | 359 | TG |
| AA402185 | UNKNOWN | 20 | 433 | A |
| AA402449 | UNKNOWN | 12.5 | 417 | GT |
| AA402803 | UNKNOWN | 18 | 84 | A |
| AA402934 | UNKNOWN | 6.5 | 73 | AT |
| AA403118 | UNKNOWN | 13 | 0 | T |
| AA404259 | UNKNOWN | 32 | 0 | T |
| AA404290 | UNKNOWN | 13 | 497 | GT |
| AA404293 | UNKNOWN | 18 | 0 | T |
| AA404501 | UNKNOWN | 7.5 | 159 | TA |
| AA404978 | UNKNOWN | 21 | 463 | A |
| AA404993 | UNKNOWN | 29 | 0 | T |
| AA405047 | UNKNOWN | 13 | 400 | T |
| AA405048 | UNKNOWN | 18 | 0 | T |
| AA405424 | UNKNOWN | 14 | 446 | T |
| AA405469 | UNKNOWN | 5.25 | 262 | AAAT |
| AA405673 | UNKNOWN | 23 | 0 | T |
| AA405907 | UNKNOWN | 17 | 154 | T |
| AA406055 | UNKNOWN | 30 | 3 | T |
| AA406078 | UNKNOWN | 21 | 0 | T |

TABLE 1-continued

| Genbank # | Region | # reps | Position | Unit sequence |
|---|---|---|---|---|
| AA406102 | UNKNOWN | 22 | 2 | T |
| AA406208 | UNKNOWN | 14 | 0 | T |
| AA406222 | UNKNOWN | 24 | 0 | T |
| AA406267 | UNKNOWN | 14 | 7 | T |
| AA406400 | UNKNOWN | 5.75 | 313 | AAAC |
| AA406424 | UNKNOWN | 3.6 | 181 | AAAAC |
| AA406454 | UNKNOWN | 20 | 103 | A |
| AA410313 | UNKNOWN | 6.5 | 401 | CA |
| AA410313 | UNKNOWN | 33 | 0 | T |
| AA410431 | UNKNOWN | 15 | 378 | T |
| AA410788 | UNKNOWN | 20 | 83 | T |
| AA411556 | UNKNOWN | 6.5 | 261 | TA |
| AA411618 | UNKNOWN | 14 | 137 | GT |
| AA411849 | UNKNOWN | 15 | 360 | A |
| AA412024 | UNKNOWN | 15 | 0 | T |
| AA412050 | UNKNOWN | 17 | 0 | T |
| AA412103 | UNKNOWN | 16 | 0 | T |
| AA412165 | UNKNOWN | 13 | 460 | A |
| AA412454 | UNKNOWN | 14 | 9 | T |
| AA412531 | UNKNOWN | 28 | 0 | T |
| AA412591 | UNKNOWN | 6.5 | 64 | AC |
| AA416581 | UNKNOWN | 16 | 0 | T |
| AA416829 | UNKNOWN | 20 | 438 | A |
| AA416918 | UNKNOWN | 15 | 0 | T |
| AA417271 | UNKNOWN | 14 | 190 | T |
| AA417349 | UNKNOWN | 5.4 | 148 | TTGTT |
| AA417351 | UNKNOWN | 23 | 0 | T |
| AA417812 | UNKNOWN | 13 | 0 | T |
| AA418230 | UNKNOWN | 16 | 331 | T |
| AA418315 | UNKNOWN | 19 | 0 | T |
| AA418522 | UNKNOWN | 17 | 6 | T |
| AA418623 | UNKNOWN | 18 | 1 | T |
| AA418841 | UNKNOWN | 18 | 0 | T |
| AA419012 | UNKNOWN | 27 | 0 | T |
| AA419145 | UNKNOWN | 27 | 0 | T |
| AA419179 | UNKNOWN | 25 | 260 | T |
| AA419233 | UNKNOWN | 29 | 2 | T |
| AA420548 | UNKNOWN | 16 | 484 | A |
| AA420590 | UNKNOWN | 10 | 451 | CA |
| AA420590 | UNKNOWN | 6.5 | 424 | TA |
| AA420590 | UNKNOWN | 14 | 7 | T |
| AA420723 | UNKNOWN | 17 | 0 | T |
| AA420872 | UNKNOWN | 17 | 351 | A |
| AA421133 | UNKNOWN | 17 | 0 | T |
| AA421137 | UNKNOWN | 3.6 | 186 | TTTGT |
| AA421138 | UNKNOWN | 8 | 443 | TC |
| AA421168 | UNKNOWN | 15 | 0 | T |
| AA421170 | UNKNOWN | 14 | 0 | T |
| AA421334 | UNKNOWN | 16 | 0 | T |
| AA421658 | UNKNOWN | 18 | 0 | T |
| AA421740 | UNKNOWN | 17 | 0 | T |
| AA423830 | UNKNOWN | 6 | 16 | TTTA |
| AA423830 | UNKNOWN | 19 | 0 | T |
| AA423835 | UNKNOWN | 12 | 0 | T |
| AA423869 | UNKNOWN | 9 | 410 | AT |
| AA423911 | UNKNOWN | 16 | 0 | T |
| AA423993 | UNKNOWN | 8 | 21 | ATTTT |
| AA424117 | UNKNOWN | 20 | 172 | A |
| AA424221 | UNKNOWN | 23 | 2 | T |
| AA424249 | UNKNOWN | 25 | 273 | A |
| AA424858 | UNKNOWN | 16 | 0 | T |
| AA425295 | UNKNOWN | 28 | 0 | T |
| AA425380 | UNKNOWN | 82 | 0 | T |
| AA425380 | UNKNOWN | 14 | 102 | A |
| AA425380 | UNKNOWN | 14 | 276 | G |
| AA425380 | UNKNOWN | 12 | 237 | C |
| AA425384 | UNKNOWN | 21 | 0 | T |
| AA425403 | UNKNOWN | 4.87 | 348 | GAAGGAAA |
| AA425403 | UNKNOWN | 9 | 319 | GGAA |
| AA425517 | UNKNOWN | 16 | 395 | A |
| AA425924 | UNKNOWN | 19 | 0 | T |
| AA426038 | UNKNOWN | 22 | 0 | T |
| AA426345 | UNKNOWN | 6.66 | 140 | GGC |
| AA426431 | UNKNOWN | 14 | 0 | T |
| AA427992 | UNKNOWN | 14 | 0 | T |
| AA428167 | UNKNOWN | 19 | 59 | T |
| AA428202 | UNKNOWN | 27 | 0 | T |

TABLE 1-continued

| Genbank # | Region | # reps | Position | Unit sequence |
|---|---|---|---|---|
| AA428202 | UNKNOWN | 12 | 251 | A |
| AA428203 | UNKNOWN | 35 | 0 | T |
| AA428270 | UNKNOWN | 30 | 0 | T |
| AA428559 | UNKNOWN | 18 | 0 | T |
| AA428583 | UNKNOWN | 21 | 0 | T |
| AA428792 | UNKNOWN | 16 | 234 | T |
| AA429215 | UNKNOWN | 33 | 0 | T |
| AA429308 | UNKNOWN | 16 | 64 | T |
| AA429500 | UNKNOWN | 12 | 314 | A |
| AA429522 | UNKNOWN | 15 | 8 | A |
| AA429771 | UNKNOWN | 5.8 | 66 | AAAAC |
| AA429771 | UNKNOWN | 22 | 211 | A |
| AA429916 | UNKNOWN | 2.85 | 290 | CATGTGTGTGCATA (SEQ ID NO:6) |
| AA430137 | UNKNOWN | 16 | 308 | A |
| AA430137 | UNKNOWN | 12 | 0 | T |
| AA430523 | UNKNOWN | 32 | 0 | T |
| AA430571 | UNKNOWN | 17 | 0 | T |
| AA430653 | UNKNOWN | 15 | 24 | A |
| AA431084 | UNKNOWN | 18 | 0 | T |
| AA431085 | UNKNOWN | 13 | 0 | T |
| AA431100 | UNKNOWN | 14 | 0 | T |
| AA431184 | UNKNOWN | 12 | 327 | A |
| AA431260 | UNKNOWN | 14 | 138 | A |
| AA431473 | UNKNOWN | 16 | 0 | T |
| AA431497 | UNKNOWN | 14 | 65 | A |
| AA431733 | UNKNOWN | 37 | 0 | T |
| AA431787 | UNKNOWN | 12 | 0 | T |
| AA431792 | UNKNOWN | 5.25 | 549 | TTTA |
| AA431798 | UNKNOWN | 13 | 208 | A |
| AA431798 | UNKNOWN | 12 | 0 | T |
| AA431903 | UNKNOWN | 12 | 310 | T |
| AA432119 | UNKNOWN | 23 | 0 | T |
| AA432121 | UNKNOWN | 9 | 155 | GT |
| AA432279 | UNKNOWN | 13 | 0 | T |
| AA433894 | UNKNOWN | 23 | 0 | T |
| AA433949 | UNKNOWN | 18 | 0 | T |
| AA434104 | UNKNOWN | 6.25 | 9 | TATT |
| AA434252 | UNKNOWN | 25 | 0 | T |
| AA434540 | UNKNOWN | 13 | 129 | A |
| AA434579 | UNKNOWN | 12 | 153 | T |
| AA434600 | UNKNOWN | 13 | 207 | T |
| AA435509 | UNKNOWN | 6 | 20 | ATTC |
| AA435512 | UNKNOWN | 15 | 290 | T |
| AA435515 | UNKNOWN | 26 | 0 | T |
| AA435530 | UNKNOWN | 12 | 361 | T |
| AA435635 | UNKNOWN | 16 | 0 | T |
| AA435639 | UNKNOWN | 19 | 0 | T |
| AA435646 | UNKNOWN | 17 | 0 | T |
| AA435774 | UNKNOWN | 11.5 | 169 | AG |
| AA435774 | UNKNOWN | 6.5 | 151 | GT |
| AA435936 | UNKNOWN | 6 | 89 | CAA |
| AA435939 | UNKNOWN | 13 | 0 | T |
| AA435997 | UNKNOWN | 22 | 2 | T |
| AA436007 | UNKNOWN | 12 | 0 | T |
| AA436233 | UNKNOWN | 25 | 0 | T |
| AA436250 | UNKNOWN | 5.66 | 360 | TTG |
| AA436280 | UNKNOWN | 28 | 102 | C |
| AA436455 | UNKNOWN | 7.5 | 124 | TA |
| AA436658 | UNKNOWN | 5.75 | 194 | TTTG |
| AA436676 | UNKNOWN | 12 | 0 | T |
| AA436683 | UNKNOWN | 13 | 0 | T |
| AA436872 | UNKNOWN | 16 | 0 | T |
| AA436932 | UNKNOWN | 13 | 176 | T |
| AA437024 | UNKNOWN | 8 | 331 | AC |
| AA437215 | UNKNOWN | 15 | 0 | T |
| AA437259 | UNKNOWN | 14 | 0 | T |
| AA437272 | UNKNOWN | 19 | 0 | T |
| AA437312 | UNKNOWN | 13.5 | 263 | AT |
| AA437312 | UNKNOWN | 15 | 249 | A |
| AA437312 | UNKNOWN | 12 | 0 | T |
| AA437318 | UNKNOWN | 7.5 | 75 | GT |
| AA437324 | UNKNOWN | 21 | 0 | T |
| AA437367 | UNKNOWN | 22 | 0 | T |
| AA441810 | UNKNOWN | 5.66 | 30 | TTG |
| AA442073 | UNKNOWN | 12 | 124 | T |
| AA442216 | UNKNOWN | 19 | 341 | A |
| AA443149 | UNKNOWN | 33 | 0 | T |

TABLE 1-continued

| Genbank # | Region | # reps | Position | Unit sequence |
|---|---|---|---|---|
| AA443149 | UNKNOWN | 12 | 183 | A |
| AA443439 | UNKNOWN | 12 | 372 | T |
| AA443560 | UNKNOWN | 5.5 | 125 | AAAT |
| AA443664 | UNKNOWN | 13 | 134 | T |
| AA443789 | UNKNOWN | 16 | 258 | T |
| AA443842 | UNKNOWN | 22 | 0 | T |
| AA443847 | UNKNOWN | 18 | 0 | T |
| AA443848 | UNKNOWN | 14 | 0 | T |
| AA443927 | UNKNOWN | 20 | 0 | T |
| AA443933 | UNKNOWN | 12 | 12 | A |
| AA443963 | UNKNOWN | 21 | 0 | T |
| AA444100 | UNKNOWN | 15 | 196 | A |
| AA444112 | UNKNOWN | 8.5 | 296 | CA |
| AA445925 | UNKNOWN | 17 | 14 | A |
| AA446008 | UNKNOWN | 12 | 0 | T |
| AA446078 | UNKNOWN | 22 | 307 | A |
| AA446110 | UNKNOWN | 4.8 | 13 | TTTTA |
| AA446141 | UNKNOWN | 14 | 68 | A |
| AA446329 | UNKNOWN | 27 | 0 | T |
| AA446348 | UNKNOWN | 16 | 383 | T |
| AA446385 | UNKNOWN | 21 | 393 | A |
| AA446499 | UNKNOWN | 6.5 | 261 | AG |
| AA446649 | UNKNOWN | 25 | 0 | T |
| AA446860 | UNKNOWN | 5.5 | 196 | TTAT |
| AA446965 | UNKNOWN | 17 | 62 | A |
| AA447209 | UNKNOWN | 15 | 0 | T |
| AA447209 | UNKNOWN | 15 | 53 | A |
| AA447218 | UNKNOWN | 8 | 45 | GT |
| AA447643 | UNKNOWN | 19 | 0 | T |
| AA447648 | UNKNOWN | 12 | 18 | T |
| AA447740 | UNKNOWN | 14 | 0 | T |
| AA447744 | UNKNOWN | 13 | 136 | T |
| AA447749 | UNKNOWN | 14 | 0 | T |
| AA447990 | UNKNOWN | 13 | 30 | T |
| AA448012 | UNKNOWN | 14 | 0 | T |
| AA448254 | UNKNOWN | 12 | 0 | T |
| AA448271 | UNKNOWN | 18 | 0 | T |
| AA448276 | UNKNOWN | 6.5 | 211 | TG |
| AA448328 | UNKNOWN | 20 | 0 | T |
| AA448460 | UNKNOWN | 17 | 0 | T |
| AA448476 | UNKNOWN | 16 | 0 | T |
| AA449090 | UNKNOWN | 13 | 0 | T |
| AA449104 | UNKNOWN | 18 | 179 | T |
| AA449644 | UNKNOWN | 16 | 13 | A |
| AA449768 | UNKNOWN | 83 | 0 | T |
| AA449768 | UNKNOWN | 24 | 179 | A |
| AA449768 | UNKNOWN | 17 | 132 | A |
| AA449768 | UNKNOWN | 13 | 90 | C |
| AA449997 | UNKNOWN | 31 | 0 | T |
| AA450138 | UNKNOWN | 22 | 8 | T |
| AA450211 | UNKNOWN | 12 | 217 | T |
| AA450340 | UNKNOWN | 18 | 0 | T |
| AA451705 | UNKNOWN | 31 | 0 | T |
| AA451932 | UNKNOWN | 13 | 383 | T |
| AA452017 | UNKNOWN | 6.25 | 245 | AAGG |
| AA452017 | UNKNOWN | 4.75 | 100 | AGAA |
| AA452017 | UNKNOWN | 18 | 1 | T |
| AA452106 | UNKNOWN | 20 | 0 | T |
| AA452110 | UNKNOWN | 27 | 0 | T |
| AA452259 | UNKNOWN | 15 | 116 | T |
| AA452409 | UNKNOWN | 20 | 111 | T |
| AA453026 | UNKNOWN | 17 | 0 | T |
| AA453182 | UNKNOWN | 12 | 363 | T |
| AA453274 | UNKNOWN | 3.8 | 131 | TTTTA |
| AA453286 | UNKNOWN | 12 | 204 | T |
| AA453371 | UNKNOWN | 7.5 | 458 | AC |
| AA453462 | UNKNOWN | 21 | 0 | T |
| AA453483 | UNKNOWN | 20 | 0 | T |
| AA453647 | UNKNOWN | 21 | 0 | T |
| AA454038 | UNKNOWN | 22 | 80 | A |
| AA454191 | UNKNOWN | 63 | 510 | A |
| AA454209 | UNKNOWN | 12 | 376 | A |
| AA455041 | UNKNOWN | 5.66 | 11 | TTA |
| AA455041 | UNKNOWN | 13 | 0 | T |
| AA455051 | UNKNOWN | 15 | 0 | T |
| AA455082 | UNKNOWN | 21 | 0 | T |
| AA455639 | UNKNOWN | 22 | 0 | T |

TABLE 1-continued

| Genbank # | Region | # reps | Position | Unit sequence |
|---|---|---|---|---|
| AA455673 | UNKNOWN | 8.5 | 665 | GT |
| AA455939 | UNKNOWN | 17 | 0 | T |
| AA455958 | UNKNOWN | 17 | 0 | T |
| AA456070 | UNKNOWN | 19 | 0 | T |
| AA456107 | UNKNOWN | 27 | 0 | T |
| AA456312 | UNKNOWN | 4.8 | 9 | TTTTA |
| AA456422 | UNKNOWN | 12 | 345 | A |
| AA456454 | UNKNOWN | 11.5 | 307 | TC |
| AA456594 | UNKNOWN | 19 | 0 | T |
| AA457031 | UNKNOWN | 14 | 0 | T |
| AA457249 | UNKNOWN | 21 | 22 | T |
| AA457535 | UNKNOWN | 7 | 117 | GA |
| AA458654 | UNKNOWN | 12 | 0 | T |
| AA458703 | UNKNOWN | 20 | 198 | A |
| AA458705 | UNKNOWN | 6.5 | 94 | AG |
| AA458746 | UNKNOWN | 15 | 9 | T |
| AA458914 | UNKNOWN | 35 | 0 | T |
| AA458945 | UNKNOWN | 27 | 1 | T |
| AA460146 | UNKNOWN | 13 | 0 | T |
| AA460254 | UNKNOWN | 28 | 0 | T |
| AA460371 | UNKNOWN | 24 | 0 | T |
| AA460669 | UNKNOWN | 12 | 255 | T |
| AA460713 | UNKNOWN | 9 | 381 | GTG |
| AA460721 | UNKNOWN | 17 | 526 | GT |
| AA461045 | UNKNOWN | 13 | 0 | T |
| AA461047 | UNKNOWN | 15 | 318 | A |
| AA461106 | UNKNOWN | 11 | 355 | AC |
| AA461206 | UNKNOWN | 15 | 0 | T |
| AA461317 | UNKNOWN | 9.5 | 250 | TG |
| AA461384 | UNKNOWN | 13 | 107 | A |
| AA461617 | UNKNOWN | 12 | 482 | A |
| AA464792 | UNKNOWN | 20 | 10 | T |
| AA464844 | UNKNOWN | 15 | 0 | T |
| AA464948 | UNKNOWN | 12 | 0 | T |
| AA465713 | UNKNOWN | 17 | 81 | T |
| AA467816 | UNKNOWN | 22 | 0 | T |
| AA467820 | UNKNOWN | 17 | 102 | A |
| AA467827 | UNKNOWN | 13 | 329 | A |
| AA467912 | UNKNOWN | 12 | 51 | A |
| AA467987 | UNKNOWN | 7.33 | 109 | TAA |
| AA467987 | UNKNOWN | 16 | 7 | T |
| AA468113 | UNKNOWN | 15 | 7 | T |
| AA468244 | UNKNOWN | 34 | 268 | A |
| AA468244 | UNKNOWN | 12 | 107 | A |
| AA468407 | UNKNOWN | 20 | 0 | T |
| AA468418 | UNKNOWN | 68 | 32 | A |
| AA468784 | UNKNOWN | 4.75 | 72 | TTTA |
| AA468926 | UNKNOWN | 22 | 0 | T |
| AA469140 | UNKNOWN | 17 | 105 | A |
| AA469245 | UNKNOWN | 16 | 0 | T |
| AA469246 | UNKNOWN | 19 | 0 | T |
| AA469295 | UNKNOWN | 18 | 7 | T |
| AA469327 | UNKNOWN | 21 | 0 | T |
| AA469338 | UNKNOWN | 21 | 0 | T |
| AA470012 | UNKNOWN | 15 | 467 | T |
| AA470015 | UNKNOWN | 12 | 338 | A |
| AA470070 | UNKNOWN | 22 | 0 | T |
| AA470160 | UNKNOWN | 13 | 303 | T |
| AA470496 | UNKNOWN | 21 | 0 | T |
| AA470524 | UNKNOWN | 23 | 7 | T |
| AA470532 | UNKNOWN | 15 | 5 | T |
| AA470578 | UNKNOWN | 18 | 0 | T |
| AA470779 | UNKNOWN | 15 | 0 | T |
| AA471079 | UNKNOWN | 15 | 5 | T |
| AA476418 | UNKNOWN | 6 | 55 | ATT |
| AA476740 | UNKNOWN | 12 | 258 | T |
| AA476915 | UNKNOWN | 30 | 0 | T |
| AA477122 | UNKNOWN | 32 | 0 | T |
| AA477503 | UNKNOWN | 10.25 | 19 | TTTA |
| AA477503 | UNKNOWN | 16 | 0 | T |
| AA477547 | UNKNOWN | 18 | 0 | T |
| AA477708 | UNKNOWN | 12 | 4 | T |
| AA478209 | UNKNOWN | 28 | 123 | T |
| AA478549 | UNKNOWN | 6.66 | 2 | TTG |
| AA478980 | UNKNOWN | 5.25 | 274 | TTAT |
| AA479033 | UNKNOWN | 14 | 103 | T |
| AA479091 | UNKNOWN | 19 | 6 | T |

TABLE 1-continued

| Genbank # | Region | # reps | Position | Unit sequence |
|---|---|---|---|---|
| AA479272 | UNKNOWN | 7.66 | 109 | CAT |
| AA479402 | UNKNOWN | 4.5 | 85 | TATC |
| AA479492 | UNKNOWN | 6.5 | 326 | AC |
| AA479835 | UNKNOWN | 19 | 538 | A |
| AA480026 | UNKNOWN | 14 | 190 | A |
| AA480446 | UNKNOWN | 7.5 | 292 | AT |
| AA480446 | UNKNOWN | 19 | 0 | T |
| AA480530 | UNKNOWN | 13 | 259 | A |
| AA480647 | UNKNOWN | 5 | 139 | CAAAA |
| AA480647 | UNKNOWN | 19 | 5 | T |
| AA480791 | UNKNOWN | 13 | 223 | A |
| AA480792 | UNKNOWN | 24 | 270 | A |
| AA480865 | UNKNOWN | 27 | 0 | T |
| AA480877 | UNKNOWN | 24 | 0 | T |
| AA481025 | UNKNOWN | 15 | 0 | T |
| AA481066 | UNKNOWN | 32 | 0 | T |
| AA481164 | UNKNOWN | 32 | 0 | T |
| AA481167 | UNKNOWN | 45 | 0 | T |
| AA481256 | UNKNOWN | 17 | 0 | T |
| AA481274 | UNKNOWN | 17 | 0 | T |
| AA481493 | UNKNOWN | 18 | 210 | A |
| AA481493 | UNKNOWN | 17 | 0 | T |
| AA481524 | UNKNOWN | 26 | 0 | T |
| AA481662 | UNKNOWN | 6.5 | 209 | TG |
| AA481729 | UNKNOWN | 12 | 0 | T |
| AA481788 | UNKNOWN | 22 | 18 | A |
| AA481802 | UNKNOWN | 7.5 | 147 | TG |
| AA481802 | UNKNOWN | 19 | 70 | A |
| AA482027 | UNKNOWN | 12 | 0 | T |
| AA482273 | UNKNOWN | 15 | 0 | T |
| AA482690 | UNKNOWN | 15 | 240 | A |
| AA482710 | UNKNOWN | 16 | 344 | A |
| AA482728 | UNKNOWN | 18 | 178 | A |
| AA482730 | UNKNOWN | 16 | 261 | A |
| AA482730 | UNKNOWN | 12 | 100 | A |
| AA482751 | UNKNOWN | 15 | 377 | A |
| AA482768 | UNKNOWN | 15 | 0 | T |
| AA482775 | UNKNOWN | 18 | 0 | T |
| AA482776 | UNKNOWN | 15 | 399 | A |
| AA482799 | UNKNOWN | 14 | 241 | A |
| AA482810 | UNKNOWN | 17 | 0 | T |
| AA482877 | UNKNOWN | 14 | 268 | A |
| AA483003 | UNKNOWN | 16 | 8 | T |
| AA483087 | UNKNOWN | 13 | 164 | A |
| AA483104 | UNKNOWN | 14 | 347 | A |
| AA483125 | UNKNOWN | 14 | 277 | A |
| AA483135 | UNKNOWN | 13 | 210 | A |
| AA483156 | UNKNOWN | 17 | 217 | A |
| AA483169 | UNKNOWN | 15 | 179 | A |
| AA483217 | UNKNOWN | 14.75 | 114 | AGAA |
| AA483217 | UNKNOWN | 13 | 174 | A |
| AA483218 | UNKNOWN | 20 | 193 | A |
| AA483233 | UNKNOWN | 13 | 134 | A |
| AA483239 | UNKNOWN | 14 | 7 | T |
| AA483240 | UNKNOWN | 15 | 330 | A |
| AA483262 | UNKNOWN | 25 | 137 | A |
| AA483271 | UNKNOWN | 17 | 213 | A |
| AA483387 | UNKNOWN | 14 | 265 | A |
| AA483467 | UNKNOWN | 19 | 372 | A |
| AA483470 | UNKNOWN | 18 | 0 | T |
| AA483478 | UNKNOWN | 16 | 396 | A |
| AA483639 | UNKNOWN | 20 | 0 | T |
| AA483658 | UNKNOWN | 18 | 7 | T |
| AA483687 | UNKNOWN | 16 | 277 | A |
| AA483689 | UNKNOWN | 16 | 385 | A |
| AA483697 | UNKNOWN | 20 | 7 | T |
| AA483719 | UNKNOWN | 28 | 271 | A |
| AA483755 | UNKNOWN | 14 | 265 | A |
| AA483904 | UNKNOWN | 14 | 254 | A |
| AA483917 | UNKNOWN | 18 | 227 | A |
| AA483966 | UNKNOWN | 16 | 0 | T |
| AA484011 | UNKNOWN | 16 | 7 | T |
| AA484140 | UNKNOWN | 21 | 240 | A |
| AA484143 | UNKNOWN | 18 | 284 | A |
| AA484187 | UNKNOWN | 14 | 281 | A |
| AA484197 | UNKNOWN | 17 | 222 | A |
| AA484213 | UNKNOWN | 13 | 232 | A |

TABLE 1-continued

| Genbank # | Region | # reps | Position | Unit sequence |
|---|---|---|---|---|
| AA484225 | UNKNOWN | 15 | 275 | A |
| AA484256 | UNKNOWN | 16 | 291 | A |
| AA484329 | UNKNOWN | 17 | 185 | A |
| AA484329 | UNKNOWN | 13 | 41 | A |
| AA484353 | UNKNOWN | 16 | 150 | A |
| AA484365 | UNKNOWN | 15 | 141 | A |
| AA484366 | UNKNOWN | 23 | 5 | T |
| AA484370 | UNKNOWN | 19 | 271 | A |
| AA484419 | UNKNOWN | 19 | 268 | A |
| AA484428 | UNKNOWN | 19 | 224 | A |
| AA484455 | UNKNOWN | 18 | 5 | T |
| AA484548 | UNKNOWN | 14 | 166 | A |
| AA484785 | UNKNOWN | 15 | 401 | A |
| AA485228 | UNKNOWN | 12 | 0 | T |
| AA485240 | UNKNOWN | 14 | 0 | T |
| AA485328 | UNKNOWN | 13 | 0 | T |
| AA485650 | UNKNOWN | 31 | 0 | T |
| AA485710 | UNKNOWN | 36 | 0 | T |
| AA485720 | UNKNOWN | 15 | 0 | T |
| AA485891 | UNKNOWN | 16 | 364 | A |
| AA486117 | UNKNOWN | 16 | 0 | T |
| AA486412 | UNKNOWN | 12 | 401 | A |
| AA486515 | UNKNOWN | 12 | 0 | T |
| AA487049 | UNKNOWN | 36 | 0 | T |
| AA487085 | UNKNOWN | 16 | 363 | A |
| AA487130 | UNKNOWN | 31 | 0 | T |
| AA487255 | UNKNOWN | 22 | 0 | T |
| AA487272 | UNKNOWN | 26 | 0 | T |
| AA487394 | UNKNOWN | 12 | 321 | T |
| AA487512 | UNKNOWN | 13 | 395 | A |
| AA487605 | UNKNOWN | 12 | 66 | A |
| AA488067 | UNKNOWN | 27 | 0 | T |
| AA488082 | UNKNOWN | 12.75 | 94 | GAAG |
| AA488164 | UNKNOWN | 25 | 0 | T |
| AA488846 | UNKNOWN | 15 | 0 | T |
| AA488867 | UNKNOWN | 17 | 0 | T |
| AA488891 | UNKNOWN | 12 | 0 | T |
| AA488935 | UNKNOWN | 12 | 334 | T |
| AA488988 | UNKNOWN | 18 | 336 | T |
| AA489010 | UNKNOWN | 19 | 0 | T |
| AA489025 | UNKNOWN | 18 | 0 | T |
| AA489029 | UNKNOWN | 14 | 0 | T |
| AA489069 | UNKNOWN | 34 | 0 | T |
| AA489192 | UNKNOWN | 14 | 0 | T |
| AA489212 | UNKNOWN | 18 | 0 | T |
| AA489213 | UNKNOWN | 18 | 172 | T |
| AA489223 | UNKNOWN | 19 | 0 | T |
| AA489227 | UNKNOWN | 7.5 | 500 | CA |
| AA489237 | UNKNOWN | 24 | 0 | T |
| AA489242 | UNKNOWN | 19 | 186 | T |
| AA489247 | UNKNOWN | 6.5 | 352 | AT |
| AA489768 | UNKNOWN | 3.83 | 180 | AAAAAG |
| AA489782 | UNKNOWN | 3.6 | 71 | AAAAC |
| AA489813 | UNKNOWN | 15 | 27 | A |
| AA489988 | UNKNOWN | 20 | 0 | T |
| AA490008 | UNKNOWN | 20 | 66 | A |
| AA490038 | UNKNOWN | 5.66 | 208 | GAG |
| AA490120 | UNKNOWN | 18 | 66 | A |
| AA490586 | UNKNOWN | 6.5 | 312 | AC |
| AA490595 | UNKNOWN | 42 | 0 | T |
| AA490612 | UNKNOWN | 22 | 0 | T |
| AA490619 | UNKNOWN | 18 | 14 | T |
| AA490812 | UNKNOWN | 21 | 0 | T |
| AA490873 | UNKNOWN | 7 | 157 | TA |
| AA490873 | UNKNOWN | 21 | 0 | T |
| AA491117 | UNKNOWN | 13 | 264 | A |
| AA491220 | UNKNOWN | 21 | 0 | T |
| AA491247 | UNKNOWN | 42 | 0 | T |
| AA491550 | UNKNOWN | 18 | 229 | A |
| AA491550 | UNKNOWN | 15 | 208 | A |
| AA491645 | UNKNOWN | 15 | 340 | A |
| AA491755 | UNKNOWN | 13 | 209 | A |
| AA491821 | UNKNOWN | 20 | 331 | A |
| AA491869 | UNKNOWN | 19 | 8 | T |
| AA491877 | UNKNOWN | 13 | 275 | A |
| AA491888 | UNKNOWN | 12 | 155 | T |
| AA491940 | UNKNOWN | 16 | 283 | A |

TABLE 1-continued

| Genbank # | Region | # reps | Position | Unit sequence |
|---|---|---|---|---|
| AA491948 | UNKNOWN | 8 | 142 | GT |
| AA491948 | UNKNOWN | 16 | 0 | T |
| AA491960 | UNKNOWN | 15 | 0 | T |
| AA492008 | UNKNOWN | 15 | 7 | T |
| AA492015 | UNKNOWN | 19 | 7 | T |
| AA492086 | UNKNOWN | 14 | 159 | A |
| AA492138 | UNKNOWN | 16 | 296 | A |
| AA492154 | UNKNOWN | 13 | 252 | A |
| AA492238 | UNKNOWN | 13 | 0 | T |
| AA492293 | UNKNOWN | 18 | 0 | T |
| AA492391 | UNKNOWN | 16 | 323 | A |
| AA492495 | UNKNOWN | 16 | 0 | T |
| AA492507 | UNKNOWN | 17 | 0 | T |
| AA492508 | UNKNOWN | 16 | 0 | T |
| AA493106 | UNKNOWN | 32 | 0 | T |
| AA493225 | UNKNOWN | 16 | 400 | A |
| AA493249 | UNKNOWN | 16 | 1 | T |
| AA493328 | UNKNOWN | 17 | 280 | A |
| AA493420 | UNKNOWN | 14 | 0 | T |
| AA493464 | UNKNOWN | 18 | 339 | A |
| AA493480 | UNKNOWN | 14 | 3 | T |
| AA493593 | UNKNOWN | 17 | 0 | T |
| AA493645 | UNKNOWN | 14 | 7 | T |
| AA493652 | UNKNOWN | 15 | 7 | T |
| AA493653 | UNKNOWN | 12.5 | 404 | AC |
| AA493653 | UNKNOWN | 18 | 7 | T |
| AA493655 | UNKNOWN | 40 | 7 | T |
| AA493655 | UNKNOWN | 19 | 85 | A |
| AA493657 | UNKNOWN | 14 | 11 | T |
| AA493734 | UNKNOWN | 14 | 7 | T |
| AA493771 | UNKNOWN | 15 | 0 | T |
| AA493864 | UNKNOWN | 13 | 112 | A |
| AA493883 | UNKNOWN | 12 | 0 | T |
| AA493884 | UNKNOWN | 13 | 386 | A |
| AA493885 | UNKNOWN | 16 | 7 | T |
| AA493893 | UNKNOWN | 14 | 212 | A |
| AA493901 | UNKNOWN | 17 | 409 | A |
| AA493930 | UNKNOWN | 14 | 0 | T |
| AA493985 | UNKNOWN | 15 | 0 | T |
| AA493990 | UNKNOWN | 17 | 0 | T |
| AA494038 | UNKNOWN | 17 | 331 | A |
| AA494090 | UNKNOWN | 16 | 338 | A |
| AA494225 | UNKNOWN | 15 | 236 | A |
| AA494278 | UNKNOWN | 17 | 0 | T |
| AA494443 | UNKNOWN | 4.75 | 139 | TTTG |
| AA495824 | UNKNOWN | 16 | 343 | T |
| AA495824 | UNKNOWN | 12 | 0 | T |
| AA496028 | UNKNOWN | 21 | 0 | T |
| AA496186 | UNKNOWN | 32 | 212 | G |
| AA496211 | UNKNOWN | 15 | 0 | T |
| AA496369 | UNKNOWN | 15 | 196 | T |
| AA496792 | UNKNOWN | 38 | 0 | T |
| AA496926 | UNKNOWN | 6.5 | 53 | TA |
| AA496941 | UNKNOWN | 20 | 0 | T |
| AA501409 | UNKNOWN | 3.37 | 6 | CTCGGGGAATTCCAATTCCACATTTTCAAGAAATAAGGAGGCAAAAATGTTCATATATGAATTGGAATTATTTGTTTTCTTATTAGGCCTATCCTGAAGCCAAAGGAAATGAGATCGGAATTC (SEQ ID NO:7) |
| AA501461 | UNKNOWN | 16 | 422 | A |
| AA501586 | UNKNOWN | 18 | 155 | A |
| AA501668 | UNKNOWN | 15 | 197 | A |
| AA501698 | UNKNOWN | 21 | 161 | A |
| AA501740 | UNKNOWN | 13 | 93 | A |
| AA501755 | UNKNOWN | 18 | 306 | A |
| AA501777 | UNKNOWN | 18 | 230 | A |
| AA501784 | UNKNOWN | 15 | 328 | A |
| AA501784 | UNKNOWN | 12 | 161 | A |
| AA501785 | UNKNOWN | 16 | 228 | A |
| AA501795 | UNKNOWN | 20 | 0 | T |
| AA501802 | UNKNOWN | 14 | 254 | A |
| AA501866 | UNKNOWN | 17 | 1 | T |
| AA502175 | UNKNOWN | 17 | 376 | A |
| AA502201 | UNKNOWN | 15 | 0 | T |
| AA502220 | UNKNOWN | 19 | 240 | A |
| AA502275 | UNKNOWN | 23 | 0 | T |
| AA502381 | UNKNOWN | 12 | 67 | T |
| AA502440 | UNKNOWN | 15 | 0 | T |

TABLE 1-continued

| Genbank # | Region | # reps | Position | Unit sequence |
|---|---|---|---|---|
| AA502477 | UNKNOWN | 29 | 5 | T |
| AA502516 | UNKNOWN | 13 | 408 | A |
| AA502525 | UNKNOWN | 19 | 0 | T |
| AA502527 | UNKNOWN | 14 | 341 | A |
| AA502538 | UNKNOWN | 22 | 183 | A |
| AA502541 | UNKNOWN | 14 | 174 | A |
| AA502565 | UNKNOWN | 15 | 0 | T |
| AA502664 | UNKNOWN | 18 | 0 | T |
| AA502673 | UNKNOWN | 14 | 0 | T |
| AA502676 | UNKNOWN | 16 | 0 | T |
| AA502698 | UNKNOWN | 15 | 110 | A |
| AA502842 | UNKNOWN | 13 | 354 | A |
| AA502843 | UNKNOWN | 19 | 242 | A |
| AA502939 | UNKNOWN | 26 | 7 | T |
| AA503122 | UNKNOWN | 13 | 7 | T |
| AA503162 | UNKNOWN | 17 | 0 | T |
| AA503172 | UNKNOWN | 16 | 228 | A |
| AA503253 | UNKNOWN | 12 | 0 | T |
| AA503372 | UNKNOWN | 4.5 | 15 | TTAT |
| AA503446 | UNKNOWN | 18 | 8 | T |
| AA503475 | UNKNOWN | 18 | 0 | T |
| AA503673 | UNKNOWN | 14 | 372 | A |
| AA503770 | UNKNOWN | 18 | 235 | A |
| AA503824 | UNKNOWN | 37 | 0 | T |
| AA504131 | UNKNOWN | 35 | 0 | T |
| AA504209 | UNKNOWN | 15 | 0 | T |
| AA504245 | UNKNOWN | 13 | 0 | T |
| AA504253 | UNKNOWN | 29 | 0 | T |
| AA504277 | UNKNOWN | 20 | 0 | T |
| AA504323 | UNKNOWN | 22 | 0 | T |
| AA504454 | UNKNOWN | 14 | 0 | T |
| AA504474 | UNKNOWN | 16 | 0 | T |
| AA504494 | UNKNOWN | 20 | 62 | A |
| AA504626 | UNKNOWN | 31 | 0 | T |
| AA504632 | UNKNOWN | 28 | 0 | T |
| AA504638 | UNKNOWN | 23 | 0 | T |
| AA504646 | UNKNOWN | 6.5 | 245 | AC |
| AA504646 | UNKNOWN | 18 | 0 | T |
| AA504776 | UNKNOWN | 4.59 | 34 | TTTTG |
| AA504777 | UNKNOWN | 30 | 0 | T |
| AA504810 | UNKNOWN | 26 | 0 | T |
| AA505018 | UNKNOWN | 12 | 369 | A |
| AA505100 | UNKNOWN | 12 | 0 | T |
| AA505317 | UNKNOWN | 20 | 0 | T |
| AA506092 | UNKNOWN | 20 | 0 | T |
| AA506375 | UNKNOWN | 5 | 196 | TATT |
| AA506375 | UNKNOWN | 14 | 259 | A |
| AA506436 | UNKNOWN | 36 | 0 | T |
| AA506518 | UNKNOWN | 14 | 70 | T |
| AA506544 | UNKNOWN | 22 | 240 | A |
| AA506621 | UNKNOWN | 13 | 0 | T |
| AA506734 | UNKNOWN | 15 | 358 | A |
| AA506970 | UNKNOWN | 16 | 179 | A |
| AA507036 | UNKNOWN | 12 | 177 | T |
| AA507041 | UNKNOWN | 15 | 0 | T |
| AA507169 | UNKNOWN | 16 | 302 | A |
| AA507342 | UNKNOWN | 16 | 283 | A |
| AA507474 | UNKNOWN | 21 | 0 | T |
| AA507704 | UNKNOWN | 16 | 7 | T |
| AA507853 | UNKNOWN | 14 | 0 | T |
| AA508037 | UNKNOWN | 15 | 151 | A |
| AA508069 | UNKNOWN | 15 | 0 | T |
| AA508082 | UNKNOWN | 12.5 | 157 | TG |
| AA508082 | UNKNOWN | 15 | 0 | T |
| AA508089 | UNKNOWN | 14 | 0 | T |
| AA508091 | UNKNOWN | 5.66 | 111 | GAG |
| AA508104 | UNKNOWN | 15 | 0 | T |
| AA508136 | UNKNOWN | 18 | 0 | T |
| AA508138 | UNKNOWN | 14 | 0 | T |
| AA508139 | UNKNOWN | 16 | 312 | A |
| AA508404 | UNKNOWN | 12 | 0 | T |
| AA508838 | UNKNOWN | 22 | 0 | T |
| AA512999 | UNKNOWN | 18 | 192 | T |
| AA513122 | UNKNOWN | 29 | 0 | T |
| AA513237 | UNKNOWN | 16 | 303 | A |
| AA513327 | UNKNOWN | 16.5 | 148 | AC |
| AA513327 | UNKNOWN | 11.5 | 235 | TG |

TABLE 1-continued

| Genbank # | Region | # reps | Position | Unit sequence |
|---|---|---|---|---|
| AA513327 | UNKNOWN | 9.5 | 257 | TA |
| AA513397 | UNKNOWN | 12 | 366 | T |
| AA513406 | UNKNOWN | 15 | 394 | T |
| AA513538 | UNKNOWN | 22 | 6 | T |
| AA513582 | UNKNOWN | 16 | 0 | T |
| AA513678 | UNKNOWN | 17 | 0 | T |
| AA513863 | UNKNOWN | 13 | 206 | A |
| AA513907 | UNKNOWN | 16 | 232 | A |
| AA513917 | UNKNOWN | 15 | 0 | T |
| AA513922 | UNKNOWN | 18 | 326 | A |
| AA514024 | UNKNOWN | 16 | 374 | A |
| AA514234 | UNKNOWN | 12 | 0 | T |
| AA514328 | UNKNOWN | 12 | 407 | A |
| AA514634 | UNKNOWN | 5.66 | 254 | AAG |
| AA514684 | UNKNOWN | 57 | 0 | T |
| AA514684 | UNKNOWN | 13 | 83 | A |
| AA514694 | UNKNOWN | 15 | 0 | T |
| AA514945 | UNKNOWN | 19 | 0 | T |
| AA515038 | UNKNOWN | 13 | 258 | A |
| AA515047 | UNKNOWN | 19 | 0 | T |
| AA515165 | UNKNOWN | 16 | 243 | A |
| AA515168 | UNKNOWN | 16 | 0 | T |
| AA515176 | UNKNOWN | 15 | 334 | A |
| AA515229 | UNKNOWN | 14 | 305 | A |
| AA515260 | UNKNOWN | 8.5 | 350 | TG |
| AA515321 | UNKNOWN | 19 | 358 | AC |
| AA515321 | UNKNOWN | 15 | 0 | T |
| AA515404 | UNKNOWN | 22 | 164 | T |
| AA515404 | UNKNOWN | 12 | 0 | T |
| AA515439 | UNKNOWN | 8.5 | 81 | TG |
| AA515439 | UNKNOWN | 14 | 7 | T |
| AA515586 | UNKNOWN | 12 | 25 | T |
| AA515705 | UNKNOWN | 18 | 231 | A |
| AA515748 | UNKNOWN | 15 | 7 | T |
| AA515824 | UNKNdWN | 14 | 7 | T |
| AA515844 | UNKNOWN | 14 | 7 | T |
| AA515909 | UNKNOWN | 19 | 0 | T |
| AA516048 | UNKNOWN | 15 | 52 | T |
| AA516148 | UNKNOWN | 15 | 252 | A |
| AA516187 | UNKNOWN | 19 | 0 | T |
| AA516202 | UNKNOWN | 15 | 300 | A |
| AA520980 | UNKNOWN | 13 | 0 | T |
| AA521008 | UNKNOWN | 32 | 0 | T |
| AA521012 | UNKNOWN | 8.5 | 140 | AG |
| AA521017 | UNKNOWN | 18 | 0 | T |
| AA521023 | UNKNOWN | 14.5 | 218 | AT |
| AA521032 | UNKNOWN | 15 | 0 | T |
| AA521035 | UNKNOWN | 13 | 0 | T |
| AA521049 | UNKNOWN | 13 | 0 | T |
| AA521080 | UNKNOWN | 18 | 0 | T |
| AA521088 | UNKNOWN | 16 | 0 | T |
| AA521106 | UNKNOWN | 19 | 0 | T |
| AA521109 | UNKNOWN | 28 | 0 | T |
| AA521145 | UNKNOWN | 17 | 29 | T |
| AA521152 | UNKNOWN | 24 | 0 | T |
| AA521154 | UNKNOWN | 14 | 0 | T |
| AA521168 | UNKNOWN | 2.7 | 74 | TTTTTTTGTA (SEQ ID NO:8) |
| AA521168 | UNKNOWN | 14 | 94 | T |
| AA521196 | UNKNOWN | 30 | 0 | T |
| AA521204 | UNKNOWN | 24 | 0 | T |
| AA521240 | UNKNOWN | 21 | 0 | T |
| AA521246 | UNKNOWN | 21 | 0 | T |
| AA521246 | UNKNOWN | 14 | 564 | A |
| AA521247 | UNKNOWN | 17 | 0 | T |
| AA521247 | UNKNOWN | 12 | 226 | A |
| AA521254 | UNKNOWN | 6.75 | 201 | TTCA |
| AA521262 | UNKNOWN | 12 | 0 | T |
| AA521281 | UNKNOWN | 14 | 0 | T |
| AA521293 | UNKNOWN | 27 | 0 | T |
| AA521299 | UNKNOWN | 65 | 0 | T |
| AA521300 | UNKNOWN | 8 | 291 | AC |
| AA521302 | UNKNOWN | 30 | 0 | T |
| AA521309 | UNKNOWN | 20 | 0 | T |
| AA521311 | UNKNOWN | 9 | 271 | GT |
| AA521370 | UNKNOWN | 7 | 422 | TG |
| AA521387 | UNKNOWN | 22 | 0 | T |
| AA521387 | UNKNOWN | 12 | 469 | A |

TABLE 1-continued

| Genbank # | Region | # reps | Position | Unit sequence |
|---|---|---|---|---|
| AA521399 | UNKNOWN | 26 | 0 | T |
| AA521405 | UNKNOWN | 20 | 0 | T |
| AA521406 | UNKNOWN | 18 | 0 | T |
| AA521416 | UNKNOWN | 32 | 0 | T |
| AA521427 | UNKNOWN | 10 | 62 | AC |
| AA521427 | UNKNOWN | 21 | 0 | T |
| AA521440 | UNKNOWN | 13 | 0 | T |
| AA521445 | UNKNOWN | 23 | 0 | T |
| AA521446 | UNKNOWN | 22 | 0 | T |
| AA521448 | UNKNOWN | 30 | 0 | T |
| AA521452 | UNKNOWN | 17 | 0 | T |
| AA521454 | UNKNOWN | 17 | 0 | T |
| AA521486 | UNKNOWN | 16 | 0 | T |
| AA521489 | UNKNOWN | 21 | 0 | T |
| AA521500 | UNKNOWN | 41 | 0 | T |
| AA521501 | UNKNOWN | 17 | 0 | T |
| AA521503 | UNKNOWN | 16 | 242 | T |
| AA521511 | UNKNOWN | 46 | 0 | T |
| AA522450 | UNKNOWN | 13 | 0 | T |
| AA522457 | UNKNOWN | 18 | 0 | T |
| AA522484 | UNKNOWN | 16 | 154 | A |
| AA522508 | UNKNOWN | 6.66 | 306 | AAC |
| AA522651 | UNKNOWN | 16 | 282 | A |
| AA522653 | UNKNOWN | 15 | 297 | A |
| AA522669 | UNKNOWN | 21 | 255 | A |
| AA522707 | UNKNOWN | 32 | 0 | T |
| AA522736 | UNKNOWN | 15 | 224 | A |
| AA522812 | UNKNOWN | 26 | 0 | T |
| AA522870 | UNKNOWN | 15 | 229 | A |
| AA522986 | UNKNOWN | 15 | 231 | A |
| AA523117 | UNKNOWN | 17 | 103 | A |
| AA523168 | UNKNOWN | 13 | 228 | A |
| AA523242 | UNKNOWN | 17 | 233 | A |
| AA523242 | UNKNOWN | 12 | 63 | A |
| AA523249 | UNKNOWN | 13 | 181 | A |
| AA523300 | UNKNOWN | 37 | 0 | T |
| AA523322 | UNKNOWN | 3.6 | 122 | ATGAG |
| AA523322 | UNKNOWN | 18 | 7 | T |
| AA523326 | UNKNOWN | 15 | 212 | A |
| AA523327 | UNKNOWN | 13 | 393 | A |
| AA523334 | UNKNOWN | 17 | 149 | A |
| AA523409 | UNKNOWN | 27 | 0 | T |
| AA523428 | UNKNOWN | 17 | 0 | T |
| AA523452 | UNKNOWN | 18 | 229 | A |
| AA523583 | UNKNOWN | 13 | 362 | A |
| AA523640 | UNKNOWN | 19 | 218 | A |
| AA523663 | UNKNOWN | 18 | 7 | T |
| AA523680 | UNKNOWN | 16 | 229 | A |
| AA523708 | UNKNOWN | 10.5 | 111 | AC |
| AA523717 | UNKNOWN | 3.8 | 209 | AAACA |
| AA523718 | UNKNOWN | 15 | 0 | T |
| AA523807 | UNKNOWN | 16 | 7 | T |
| AA523821 | UNKNOWN | 17 | 7 | T |
| AA523846 | UNKNOWN | 17 | 133 | A |
| AA523942 | UNKNOWN | 14 | 6 | T |
| AA524012 | UNKNOWN | 7 | 262 | TTA |
| AA524013 | UNKNOWN | 21 | 0 | T |
| AA524020 | UNKNOWN | 20 | 0 | T |
| AA524036 | UNKNOWN | 12 | 5 | T |
| AA524093 | UNKNOWN | 30 | 0 | T |
| AA524095 | UNKNOWN | 20 | 0 | T |
| AA524135 | UNKNOWN | 3.8 | 129 | CCCAC |
| AA524217 | UNKNOWN | 12 | 395 | C |
| AA524291 | UNKNOWN | 25 | 0 | T |
| AA524302 | UNKNOWN | 14 | 16 | T |
| AA524350 | UNKNOWN | 19 | 3 | T |
| AA524447 | UNKNOWN | 3.5 | 20 | TTTATT |
| AA524590 | UNKNOWN | 14 | 329 | A |
| AA524604 | UNKNOWN | 16 | 276 | A |
| AA524616 | UNKNOWN | 17 | 442 | A |
| AA524685 | UNKNOWN | 15 | 0 | T |
| AA524740 | UNKNOWN | 19 | 0 | T |
| AA524766 | UNKNOWN | 13 | 310 | A |
| AA524802 | UNKNOWN | 15 | 0 | T |
| AA524802 | UNKNOWN | 12 | 168 | A |
| AA524804 | UNKNOWN | 15 | 512 | A |
| AA524816 | UNKNOWN | 16 | 7 | T |

TABLE 1-continued

| Genbank # | Region | # reps | Position | Unit sequence |
|---|---|---|---|---|
| AA524817 | UNKNOWN | 17 | 373 | A |
| AA524830 | UNKNOWN | 18 | 0 | T |
| AA524834 | UNKNOWN | 15 | 510 | A |
| AA524835 | UNKNOWN | 17 | 385 | A |
| AA524884 | UNKNOWN | 13 | 8 | T |
| AA524947 | UNKNOWN | 15 | 389 | A |
| AA524951 | UNKNOWN | 6.5 | 351 | TC |
| AA524951 | UNKNOWN | 15 | 493 | A |
| AA524952 | UNKNOWN | 16 | 7 | T |
| AA524953 | UNKNOWN | 12 | 3 | T |
| AA524955 | UNKNOWN | 18 | 448 | A |
| AA524968 | UNKNOWN | 23 | 7 | T |
| AA524980 | UNKNOWN | 17 | 126 | T |
| AA525000 | UNKNOWN | 12 | 304 | A |
| AA525003 | UNKNOWN | 13 | 417 | A |
| AA525014 | UNKNOWN | 14 | 324 | A |
| AA525066 | UNKNOWN | 15 | 0 | T |
| AA525067 | UNKNOWN | 15 | 8 | T |
| AA525067 | UNKNOWN | 12 | 191 | A |
| AA525096 | UNKNOWN | 17 | 439 | A |
| AA525098 | UNKNOWN | 17 | 451 | A |
| AA525126 | UNKNOWN | 6.5 | 70 | TA |
| AA525126 | UNKNOWN | 17 | 226 | A |
| AA525144 | UNKNOWN | 15 | 396 | A |
| AA525172 | UNKNOWN | 15 | 0 | T |
| AA525187 | UNKNOWN | 18 | 35 | T |
| AA525199 | UNKNOWN | 16 | 186 | A |
| AA525253 | UNKNOWN | 17 | 0 | T |
| AA525294 | UNKNOWN | 18 | 204 | A |
| AA525336 | UNKNOWN | 15 | 312 | A |
| AA525348 | UNKNOWN | 13 | 337 | A |
| AA525360 | UNKNOWN | 19 | 118 | A |
| AA525383 | UNKNOWN | 15 | 362 | A |
| AA525400 | UNKNOWN | 14 | 449 | A |
| AA525416 | UNKNOWN | 15 | 415 | A |
| AA525423 | UNKNOWN | 15 | 315 | A |
| AA525448 | UNKNOWN | 25 | 223 | A |
| AA525448 | UNKNOWN | 12 | 52 | A |
| AA525474 | UNKNOWN | 16 | 303 | A |
| AA525758 | UNKNOWN | 10.66 | 37 | AAC |
| AA525805 | UNKNOWN | 16 | 7 | T |
| AA525807 | UNKNOWN | 16 | 7 | T |
| AA525818 | UNKNOWN | 17 | 7 | T |
| AA525823 | UNKNOWN | 16 | 7 | T |
| AA525890 | UNKNOWN | 15 | 338 | A |
| AA525907 | UNKNOWN | 13 | 7 | T |
| AA525928 | UNKNOWN | 17 | 7 | T |
| AA525944 | UNKNOWN | 14 | 7 | T |
| AA525983 | UNKNOWN | 20 | 7 | T |
| AA525986 | UNKNOWN | 13 | 8 | T |
| AA525996 | UNKNOWN | 18 | 7 | T |
| AA525998 | UNKNOWN | 13 | 330 | A |
| AA526041 | UNKNOWN | 13 | 142 | A |
| AA526052 | UNKNOWN | 13 | 305 | A |
| AA526108 | UNKNOWN | 18 | 266 | A |
| AA526230 | UNKNOWN | 12 | 156 | A |
| AA526232 | UNKNOWN | 19 | 8 | T |
| AA526242 | UNKNOWN | 14 | 128 | A |
| AA526253 | UNKNOWN | 21 | 193 | A |
| AA526311 | UNKNOWN | 17 | 218 | A |
| AA526314 | UNKNOWN | 16 | 245 | A |
| AA526316 | UNKNOWN | 15 | 247 | A |
| AA526326 | UNKNOWN | 17 | 0 | T |
| AA526331 | UNKNOWN | 16 | 7 | T |
| AA526340 | UNKNOWN | 16 | 7 | T |
| AA526406 | UNKNOWN | 18 | 160 | A |
| AA526508 | UNKNOWN | 13 | 455 | A |
| AA526533 | UNKNOWN | 13 | 0 | T |
| AA526536 | UNKNOWN | 17 | 215 | A |
| AA526539 | UNKNOWN | 15 | 0 | T |
| AA526595 | UNKNOWN | 36 | 0 | T |
| AA526625 | UNKNOWN | 17 | 0 | T |
| AA526683 | UNKNOWN | 15 | 334 | A |
| AA526796 | UNKNOWN | 21 | 0 | T |
| AA526803 | UNKNOWN | 19 | 232 | A |
| AA526820 | UNKNOWN | 4.13 | 89 | GGCGGCGACTTCGGC (SEQ ID NO: 9) |
| AA526910 | UNKNOWN | 4.5 | 103 | AGGA |

TABLE 1-continued

| Genbank # | Region | # reps | Position | Unit sequence |
|---|---|---|---|---|
| AA526911 | UNKNOWN | 21 | 0 | T |
| AA526962 | UNKNOWN | 4 | 53 | GAGGCT |
| AA527072 | UNKNOWN | 14 | 0 | T |
| AA527138 | UNKNOWN | 16 | 0 | T |
| AA527151 | UNKNOWN | 12 | 0 | T |
| AA527159 | UNKNOWN | 41 | 0 | T |
| AA527161 | UNKNOWN | 9 | 46 | AC |
| AA527161 | UNKNOWN | 6.5 | 32 | AC |
| AA527166 | UNKNOWN | 13 | 71 | A |
| AA527168 | UNKNOWN | 29 | 0 | T |
| AA527172 | UNKNOWN | 35 | 0 | T |
| AA527180 | UNKNOWN | 12 | 0 | T |
| AA527182 | UNKNOWN | 18 | 0 | T |
| AA527274 | UNKNOWN | 6.66 | 83 | GCCCCA |
| AA527277 | UNKNOWN | 16 | 0 | T |
| AA527300 | UNKNOWN | 5.75 | 3 | TTTA |
| AA527400 | UNKNOWN | 6 | 257 | GGT |
| AA527400 | UNKNOWN | 16 | 0 | T |
| AA527419 | UNKNOWN | 12 | 406 | T |
| AA527425 | UNKNOWN | 14 | 102 | A |
| AA527442 | UNKNOWN | 37 | 0 | T |
| AA527445 | UNKNOWN | 15 | 408 | A |
| AA527451 | UNKNOWN | 17 | 418 | T |
| AA527451 | UNKNOWN | 16 | 0 | T |
| AA527560 | UNKNOWN | 27 | 0 | T |
| AA527650 | UNKNOWN | 21 | 322 | A |
| AA527712 | UNKNOWN | 18 | 0 | T |
| AA527716 | UNKNOWN | 18 | 368 | A |
| AA527788 | UNKNOWN | 32 | 348 | T |
| AA527836 | UNKNOWN | 14 | 319 | A |
| AA527929 | UNKNOWN | 16 | 1 | T |
| AA527930 | UNKNOWN | 13 | 1 | T |
| AA527953 | UNKNOWN | 5.75 | 387 | GGAT |
| AA528095 | UNKNOWN | 7.75 | 193 | TTTG |
| AA528095 | UNKNOWN | 25 | 0 | T |
| AA528095 | UNKNOWN | 13 | 378 | A |
| AA528191 | UNKNOWN | 21 | 0 | T |
| AA528243 | UNKNOWN | 19 | 0 | T |
| AA528250 | UNKNOWN | 13 | 258 | A |
| AA528363 | UNKNOWN | 16 | 343 | A |
| AA528401 | UNKNOWN | 14 | 262 | A |
| AA528435 | UNKNOWN | 13 | 237 | A |
| AA528438 | UNKNOWN | 15 | 263 | A |
| AA528462 | UNKNOWN | 17 | 339 | A |
| AA528487 | UNKNOWN | 13 | 276 | A |
| AA528490 | UNKNOWN | 16 | 207 | A |
| AA528503 | UNKNOWN | 17 | 357 | A |
| AA528531 | UNKNOWN | 16 | 263 | A |
| AA528554 | UNKNOWN | 16 | 230 | A |
| AA528559 | UNKNOWN | 26 | 268 | A |
| AA528561 | UNKNOWN | 17 | 143 | A |
| AA528572 | UNKNOWN | 18 | 118 | A |
| AA528597 | UNKNOWN | 18 | 255 | A |
| AA528620 | UNKNOWN | 9.5 | 239 | CA |
| AA528620 | UNKNOWN | 13 | 306 | A |
| AA528629 | UNKNOWN | 16 | 287 | A |
| AA528641 | UNKNOWN | 14 | 247 | A |
| AA528648 | UNKNOWN | 14 | 152 | A |
| AA528666 | UNKNOWN | 19 | 3 | T |
| AA528685 | UNKNOWN | 30 | 3 | T |
| AA528747 | UNKNOWN | 14 | 160 | A |
| AA528767 | UNKNOWN | 13 | 161 | A |
| AA528777 | UNKNOWN | 24 | 196 | A |
| AA528794 | UNKNOWN | 7.66 | 2 | CTA |
| AA528820 | UNKNOWN | 18 | 346 | A |
| AA530867 | UNKNOWN | 12 | 0 | T |
| AA530890 | UNKNOWN | 17 | 0 | T |
| AA530958 | UNKNOWN | 35 | 6 | T |
| AA530994 | UNKNOWN | 18 | 0 | T |
| AA531017 | UNKNOWN | 20 | 162 | T |
| AA531112 | UNKNOWN | 20 | 9 | T |
| AA531128 | UNKNOWN | 23 | 0 | T |
| AA531214 | UNKNOWN | 16 | 5 | T |
| AA531250 | UNKNOWN | 27 | 59 | T |
| AA531305 | UNKNOWN | 15 | 6 | T |
| AA531352 | UNKNOWN | 16 | 5 | T |
| AA531373 | UNKNOWN | 16 | 5 | T |

TABLE 1-continued

| Genbank # | Region | # reps | Position | Unit sequence |
|---|---|---|---|---|
| AA531564 | UNKNOWN | 14 | 5 | T |
| AA532359 | UNKNOWN | 23 | 0 | T |
| AA532444 | UNKNOWN | 30 | 0 | T |
| AA532448 | UNKNOWN | 4 | 0 | ATTTT |
| AA532470 | UNKNOWN | 6.5 | 331 | TG |
| AA532470 | UNKNOWN | 18 | 5 | T |
| AA532505 | UNKNOWN | 18 | 362 | A |
| AA532611 | UNKNOWN | 20 | 5 | T |
| AA532636 | UNKNOWN | 11 | 278 | AT |
| AA532718 | UNKNOWN | 21 | 5 | T |
| AA532745 | UNKNOWN | 20 | 0 | T |
| AA532747 | UNKNOWN | 9.5 | 144 | TATG |
| AA532807 | UNKNOWN | 25 | 0 | T |
| AA532810 | UNKNOWN | 3.8 | 208 | AAAAC |
| AA532810 | UNKNOWN | 22 | 0 | T |
| AA533000 | UNKNOWN | 18 | 1 | T |
| AA533042 | UNKNOWN | 14 | 10 | T |
| AA533088 | UNKNOWN | 26 | 0 | T |
| AA533134 | UNKNOWN | 17 | 5 | T |
| AA533161 | UNKNOWN | 20 | 5 | T |
| AA533253 | UNKNOWN | 15 | 218 | A |
| AA533275 | UNKNOWN | 17 | 5 | T |
| AA533284 | UNKNOWN | 18 | 5 | T |
| AA533300 | UNKNOWN | 18 | 6 | T |
| AA533455 | UNKNOWN | 13 | 494 | A |
| AA533462 | UNKNOWN | 17 | 5 | T |
| AA533463 | UNKNOWN | 20 | 5 | T |
| AA533476 | UNKNOWN | 15 | 5 | T |
| AA533501 | UNKNOWN | 13 | 270 | A |
| AA533505 | UNKNOWN | 16 | 7 | T |
| AA533574 | UNKNOWN | 15 | 333 | T |
| AA533591 | UNKNOWN | 6.5 | 436 | AAAT |
| AA533676 | UNKNOWN | 15 | 343 | A |
| AA533756 | UNKNOWN | 15 | 0 | T |
| AA533775 | UNKNOWN | 17 | 281 | A |
| AA533782 | UNKNOWN | 16 | 271 | A |
| AA533811 | UNKNOWN | 13 | 374 | A |
| AA533816 | UNKNOWN | 29 | 244 | A |
| AA533819 | UNKNOWN | 20 | 299 | A |
| AA533894 | UNKNOWN | 15 | 288 | A |
| AA533916 | UNKNOWN | 18 | 350 | A |
| AA533944 | UNKNOWN | 15 | 303 | A |
| AA533953 | UNKNOWN | 17 | 6 | T |
| AA533963 | UNKNOWN | 17 | 5 | T |
| AA533981 | UNKNOWN | 14 | 165 | A |
| AA534020 | UNKNOWN | 18 | 253 | A |
| AA534022 | UNKNOWN | 20 | 5 | T |
| AA534133 | UNKNOWN | 17 | 258 | A |
| AA534173 | UNKNOWN | 21 | 5 | T |
| AA534189 | UNKNOWN | 13 | 6 | T |
| AA534206 | UNKNOWN | 7.75 | 166 | TTTA |
| AA534206 | UNKNOWN | 16 | 473 | A |
| AA534248 | UNKNOWN | 19 | 302 | A |
| AA534258 | UNKNOWN | 17 | 260 | A |
| AA534286 | UNKNOWN | 15 | 0 | T |
| AA534298 | UNKNOWN | 19 | 3 | T |
| AA534304 | UNKNOWN | 6.33 | 328 | GGC |
| AA534305 | UNKNOWN | 18 | 0 | T |
| AA534313 | UNKNOWN | 12 | 429 | T |
| AA534370 | UNKNOWN | 4 | 12 | TTATTT |
| AA534378 | UNKNOWN | 12 | 25 | T |
| AA534416 | UNKNOWN | 17 | 0 | T |
| AA534427 | UNKNOWN | 6.33 | 97 | CTG |
| AA534457 | UNKNOWN | 19 | 184 | A |
| AA534500 | UNKNOWN | 9.5 | 108 | AC |
| AA534500 | UNKNOWN | 13 | 7 | T |
| AA534526 | UNKNOWN | 12 | 217 | A |
| AA534529 | UNKNOWN | 22 | 0 | T |
| AA534540 | UNKNOWN | 29 | 0 | T |
| AA534565 | UNKNOWN | 15 | 0 | T |
| AA534579 | UNKNOWN | 23 | 0 | T |
| AA534591 | UNKNOWN | 13 | 0 | T |
| AA534674 | UNKNOWN | 26 | 0 | T |
| AA534801 | UNKNOWN | 15 | 0 | T |
| AA535144 | UNKNOWN | 12 | 39 | A |
| AA535494 | UNKNOWN | 16 | 295 | A |
| AA535856 | UNKNOWN | 15 | 347 | A |

TABLE 1-continued

| Genbank # | Region | # reps | Position | Unit sequence |
|---|---|---|---|---|
| AA535917 | UNKNOWN | 12 | 142 | A |
| AA535935 | UNKNOWN | 20 | 5 | T |
| AA535942 | UNKNOWN | 16 | 5 | T |
| AA535978 | UNKNOWN | 11.5 | 317 | TG |
| AA536013 | UNKNOWN | 30 | 0 | T |
| AA536029 | UNKNOWN | 12 | 327 | A |
| AA536040 | UNKNOWN | 18 | 299 | A |
| AA536054 | UNKNOWN | 12 | 0 | T |
| AA536080 | UNKNOWN | 11 | 65 | AC |
| AA536080 | UNKNOWN | 13 | 0 | T |
| AA536086 | UNKNOWN | 26 | 0 | T |
| AA536127 | UNKNOWN | 23 | 10 | T |
| AA536183 | UNKNOWN | 21 | 0 | T |
| AA541301 | UNKNOWN | 13 | 219 | A |
| AA541361 | UNKNOWN | 20 | 231 | A |
| AA541802 | UNKNOWN | 22 | 0 | T |
| AA542823 | UNKNOWN | 17 | 203 | A |
| AA542833 | UNKNOWN | 15 | 85 | A |
| AA542861 | UNKNOWN | 13 | 123 | A |
| AA548301 | UNKNOWN | 14 | 343 | A |
| AA548333 | UNKNOWN | 12 | 2 | T |
| AA548390 | UNKNOWN | 4.4 | 321 | AAAAT |
| AA548390 | UNKNOWN | 3.6 | 0 | TTTAT |
| AA548523 | UNKNOWN | 7 | 99 | AT |
| AA548601 | UNKNOWN | 17 | 227 | A |
| AA548630 | UNKNOWN | 14 | 0 | T |
| AA548677 | UNKNOWN | 14 | 220 | A |
| AA548708 | UNKNOWN | 14 | 78 | A |
| AA548781 | UNKNOWN | 38 | 0 | T |
| AA550710 | UNKNOWN | 15 | 0 | T |
| AA550797 | UNKNOWN | 15 | 103 | T |
| AA550816 | UNKNOWN | 29 | 0 | T |
| AA550817 | UNKNOWN | 15 | 0 | T |
| AA551012 | UNKNOWN | 15 | 206 | A |
| AA551105 | UNKNOWN | 37 | 0 | T |
| AA551154 | UNKNOWN | 18.5 | 582 | TA |
| AA551154 | UNKNOWN | 15 | 0 | T |
| AA551162 | UNKNOWN | 17 | 0 | T |
| AA551250 | UNKNOWN | 14 | 221 | T |
| AA551260 | UNKNOWN | 23 | 0 | T |
| AA551390 | UNKNOWN | 37 | 0 | T |
| AA551437 | UNKNOWN | 14 | 321 | A |
| AA551580 | UNKNOWN | 20 | 450 | A |
| AA551592 | UNKNOWN | 6.5 | 260 | GT |
| AA551592 | UNKNOWN | 12 | 152 | A |
| AA551643 | UNKNOWN | 13 | 213 | A |
| AA551645 | UNKNOWN | 18 | 7 | T |
| AA551975 | UNKNOWN | 7 | 7 | CTA |
| AA551975 | UNKNOWN | 17 | 386 | A |
| AA552060 | UNKNOWN | 3.6 | 33 | GGTGG |
| AA552179 | UNKNOWN | 16 | 304 | A |
| AA552338 | UNKNOWN | 17 | 0 | T |
| AA552467 | UNKNOWN | 17 | 268 | A |
| AA552755 | UNKNOWN | 13 | 271 | A |
| AA552826 | UNKNOWN | 18 | 185 | A |
| AA552843 | UNKNOWN | 16 | 0 | T |
| AA552856 | UNKNOWN | 16 | 0 | T |
| AA552885 | UNKNOWN | 26 | 281 | A |
| AA552969 | UNKNOWN | 11 | 302 | AC |
| AA552986 | UNKNOWN | 27 | 0 | T |
| AA552986 | UNKNOWN | 13 | 244 | A |
| AA553468 | UNKNOWN | 8 | 365 | GT |
| AA553468 | UNKNOWN | 16 | 26 | T |
| AA553481 | UNKNOWN | 18 | 55 | T |
| AA553485 | UNKNOWN | 14 | 0 | T |
| AA553614 | UNKNOWN | 17 | 228 | A |
| AA553614 | UNKNOWN | 15 | 0 | T |
| AA553625 | UNKNOWN | 4.5 | 342 | AATA |
| AA553762 | UNKNOWN | 32 | 0 | T |
| AA553879 | UNKNOWN | 38 | 0 | T |
| AA554156 | UNKNOWN | 14 | 184 | T |
| AA554384 | UNKNOWN | 21 | 0 | T |
| AA554546 | UNKNOWN | 14 | 216 | T |
| AA554694 | UNKNOWN | 42 | 0 | T |
| AA554866 | UNKNOWN | 16 | 332 | A |
| AA555001 | UNKNOWN | 20 | 0 | T |
| AA555023 | UNKNOWN | 9 | 215 | AAC |

TABLE 1-continued

| Genbank # | Region | # reps | Position | Unit sequence |
|---|---|---|---|---|
| AA555086 | UNKNOWN | 5.8 | 102 | AAAAC |
| AA555086 | UNKNOWN | 12 | 0 | T |
| AA555154 | UNKNOWN | 15 | 204 | A |
| AA555166 | UNKNOWN | 42 | 0 | T |
| AA555188 | UNKNOWN | 15 | 0 | T |
| AA555189 | UNKNOWN | 16 | 0 | T |
| AA555259 | UNKNOWN | 14 | 181 | A |
| AA555260 | UNKNOWN | 21 | 342 | A |
| AA555278 | UNKNOWN | 33 | 19 | T |
| AA555306 | UNKNOWN | 21 | 0 | T |
| AA555312 | UNKNOWN | 20 | 484 | A |
| AA555313 | UNKNOWN | 15 | 218 | T |
| AA555313 | UNKNOWN | 13 | 157 | T |
| AA557205 | UNKNOWN | 14 | 0 | T |
| AA557277 | UNKNOWN | 30 | 0 | T |
| AA557314 | UNKNOWN | 26 | 0 | T |
| AA557412 | UNKNOWN | 14 | 287 | A |
| AA557486 | UNKNOWN | 15 | 316 | A |
| AA557486 | UNKNOWN | 12 | 9 | T |
| AA557536 | UNKNOWN | 2.83 | 205 | GCAGAGGGACAC (SEQ ID NO: 10) |
| AA557579 | UNKNOWN | 13 | 264 | A |
| AA557737 | UNKNOWN | 13 | 8 | T |
| AA557903 | UNKNOWN | 14 | 248 | A |
| AA557914 | UNKNOWN | 20 | 317 | A |
| AA557914 | UNKNOWN | 12 | 14 | A |
| AA557940 | UNKNOWN | 16 | 295 | A |
| AA558010 | UNKNOWN | 14 | 114 | A |
| AA558398 | UNKNOWN | 13 | 226 | A |
| AA558434 | UNKNOWN | 16 | 502 | T |
| AA558447 | UNKNOWN | 15 | 234 | A |
| AA558560 | UNKNOWN | 13 | 390 | A |
| AA558966 | UNKNOWN | 8.5 | 134 | TG |
| AA558966 | UNKNOWN | 16 | 150 | T |
| AA558980 | UNKNOWN | 5 | 18 | TAAA |
| AA559185 | UNKNOWN | 7.5 | 353 | AC |
| AA559185 | UNKNOWN | 20 | 8 | T |
| AA563726 | UNKNOWN | 25 | 0 | T |
| AA564203 | UNKNOWN | 21 | 0 | T |
| AA564256 | UNKNOWN | 16 | 383 | A |
| AA564512 | UNKNOWN | 18 | 0 | T |
| AA564584 | UNKNOWN | 35 | 0 | T |
| AA564703 | UNKNOWN | 30 | 0 | T |
| AA564901 | UNKNOWN | 7.5 | 91 | GA |
| AA564910 | UNKNOWN | 14 | 271 | A |
| AA564986 | UNKNOWN | 16 | 381 | A |
| AA565155 | UNKNOWN | 15 | 169 | A |
| AA565230 | UNKNOWN | 14 | 0 | T |
| AA565261 | UNKNOWN | 14 | 244 | A |
| AA565388 | UNKNOWN | 27 | 0 | T |
| AA565528 | UNKNOWN | 11.33 | 181 | AGT |
| AA565528 | UNKNOWN | 8 | 156 | TAG |
| AA565528 | UNKNOWN | 6 | 140 | TTA |
| AA565613 | UNKNOWN | 13 | 361 | A |
| AA565613 | UNKNOWN | 12 | 284 | A |
| AA565723 | UNKNOWN | 25 | 0 | T |
| AA565725 | UNKNOWN | 14 | 312 | T |
| AA565725 | UNKNOWN | 13 | 434 | A |
| AA565980 | UNKNOWN | 17 | 0 | T |
| AA566034 | UNKNOWN | 18 | 14 | TG |
| AA566034 | UNKNOWN | 15 | 0 | T |
| AA568134 | UNKNOWN | 12 | 324 | A |
| AA568247 | UNKNOWN | 30 | 0 | T |
| AA568324 | UNKNOWN | 37 | 0 | T |
| AA568337 | UNKNOWN | 15 | 348 | A |
| AA568397 | UNKNOWN | 16 | 402 | A |
| AA568497 | UNKNOWN | 17 | 0 | T |
| AA568531 | UNKNOWN | 21 | 0 | T |
| AA568751 | UNKNOWN | 15 | 285 | A |
| AA568754 | UNKNOWN | 16 | 0 | T |
| AA568757 | UNKNOWN | 17 | 185 | A |
| AA568758 | UNKNOWN | 15 | 373 | A |
| AA568850 | UNKNOWN | 15 | 7 | T |
| AA568915 | UNKNOWN | 22 | 0 | T |
| AA568953 | UNKNOWN | 14 | 403 | A |
| AA568980 | UNKNOWN | 13 | 10 | T |
| AA569160 | UNKNOWN | 17 | 7 | T |
| AA569215 | UNKNOWN | 15 | 13 | A |

TABLE 1-continued

| Genbank # | Region | # reps | Position | Unit sequence |
|---|---|---|---|---|
| AA569659 | UNKNOWN | 4.2 | 11 | AAACA |
| AA569659 | UNKNOWN | 13 | 316 | A |
| AA569675 | UNKNOWN | 32 | 20 | T |
| AA569763 | UNKNOWN | 17 | 319 | A |
| AA569814 | UNKNOWN | 18 | 0 | T |
| AA569951 | UNKNOWN | 14 | 49 | T |
| AA570178 | UNKNOWN | 29 | 0 | T |
| AA570248 | UNKNOWN | 17 | 249 | A |
| AA570255 | UNKNOWN | 17 | 360 | A |
| AA570348 | UNKNOWN | 16 | 406 | A |
| AA570379 | UNKNOWN | 12 | 120 | T |
| AA570458 | UNKNOWN | 3.5 | 500 | GAAAAA |
| AA570458 | UNKNOWN | 6.5 | 116 | TA |
| AA570496 | UNKNOWN | 15 | 500 | A |
| AA570496 | UNKNOWN | 13 | 362 | A |
| AA570701 | UNKNOWN | 23 | 0 | T |
| AA570710 | UNKNOWN | 17 | 0 | T |
| AA572692 | UNKNOWN | 13 | 426 | A |
| AA572711 | UNKNOWN | 20 | 280 | A |
| AA572713 | UNKNOWN | 12 | 0 | T |
| AA572714 | UNKNOWN | 31 | 388 | A |
| AA572732 | UNKNOWN | 15 | 0 | T |
| AA572763 | UNKNOWN | 13 | 413 | A |
| AA572764 | UNKNOWN | 15 | 384 | A |
| AA572789 | UNKNOWN | 19 | 0 | T |
| AA572813 | UNKNOWN | 16 | 407 | A |
| AA572825 | UNKNOWN | 14 | 0 | T |
| AA572893 | UNKNOWN | 17 | 272 | A |
| AA572949 | UNKNOWN | 13 | 7 | T |
| AA572968 | UNKNOWN | 12 | 7 | A |
| AA572971 | UNKNOWN | 14 | 7 | T |
| AA572974 | UNKNOWN | 14 | 7 | T |
| AA572992 | UNKNOWN | 15 | 307 | A |
| AA572998 | UNKNOWN | 15 | 420 | A |
| AA572999 | UNKNOWN | 20 | 318 | A |
| AA573005 | UNKNOWN | 15 | 260 | A |
| AA573009 | UNKNOWN | 18 | 309 | T |
| AA573009 | UNKNOWN | 15 | 0 | T |
| AA573033 | UNKNOWN | 15 | 0 | T |
| AA573056 | UNKNOWN | 19 | 302 | A |
| AA573068 | UNKNOWN | 15 | 135 | A |
| AA573121 | UNKNOWN | 19 | 0 | T |
| AA573439 | UNKNOWN | 12.5 | 338 | TG |
| AA573572 | UNKNOWN | 16.5 | 61 | CA |
| AA573572 | UNKNOWN | 14 | 250 | A |
| AA573631 | UNKNOWN | 17 | 0 | T |
| AA573644 | UNKNOWN | 20 | 413 | A |
| AA573737 | UNKNOWN | 14 | 0 | T |
| AA573860 | UNKNOWN | 14 | 0 | T |
| AA574000 | UNKNOWN | 19 | 338 | A |
| AA574079 | UNKNOWN | 10.75 | 0 | TTTA |
| AA574098 | UNKNOWN | 31 | 0 | T |
| AA574139 | UNKNOWN | 29 | 0 | T |
| AA574277 | UNKNOWN | 13 | 249 | A |
| AA574385 | UNKNOWN | 15 | 0 | T |
| AA576342 | UNKNOWN | 30 | 0 | T |
| AA576372 | UNKNOWN | 15 | 0 | T |
| AA576961 | UNKNOWN | 14 | 1 | T |
| AA577160 | UNKNOWN | 20 | 0 | T |
| AA577198 | UNKNOWN | 16 | 13 | T |
| AA577198 | UNKNOWN | 12 | 0 | T |
| AA577534 | UNKNOWN | 34 | 0 | T |
| AA577678 | UNKNOWN | 26 | 0 | T |
| AA577701 | UNKNOWN | 15 | 0 | T |
| AA577730 | UNKNOWN | 20 | 509 | T |
| AA577751 | UNKNOWN | 9 | 318 | CA |
| AA577796 | UNKNOWN | 43 | 0 | T |
| AA577799 | UNKNOWN | 35 | 0 | T |
| AA577801 | UNKNOWN | 5.25 | 443 | TAAA |
| AA577852 | UNKNOWN | 21 | 0 | T |
| AA577854 | UNKNOWN | 26 | 26 | T |
| AA577865 | UNKNOWN | 25 | 0 | T |
| AA577874 | UNKNOWN | 34 | 0 | T |
| AA577879 | UNKNOWN | 17 | 0 | T |
| AA577893 | UNKNOWN | 21 | 0 | T |
| AA577911 | UNKNOWN | 20 | 0 | T |
| AA578011 | UNKNOWN | 14 | 300 | A |

TABLE 1-continued

| Genbank # | Region | # reps | Position | Unit sequence |
|---|---|---|---|---|
| AA578115 | UNKNOWN | 14 | 7 | T |
| AA578266 | UNKNOWN | 16 | 250 | A |
| AA578279 | UNKNOWN | 13 | 375 | A |
| AA578285 | UNKNOWN | 16 | 94 | A |
| AA578690 | UNKNOWN | 19 | 0 | T |
| AA578694 | UNKNOWN | 18 | 198 | A |
| AA578695 | UNKNOWN | 22 | 0 | T |
| AA578859 | UNKNOWN | 37 | 0 | T |
| AA578876 | UNKNOWN | 14 | 0 | T |
| AA578897 | UNKNOWN | 20 | 243 | A |
| AA578906 | UNKNOWN | 14 | 7 | T |
| AA578964 | UNKNOWN | 19 | 0 | T |
| AA579064 | UNKNOWN | 17 | 245 | A |
| AA579071 | UNKNOWN | 15 | 0 | T |
| AA579196 | UNKNOWN | 17 | 7 | T |
| AA579197 | UNKNOWN | 15 | 7 | T |
| AA579246 | UNKNOWN | 17 | 344 | A |
| AA579257 | UNKNOWN | 15 | 0 | T |
| AA579427 | UNKNOWN | 15 | 301 | A |
| AA579469 | UNKNOWN | 17 | 0 | T |
| AA579518 | UNKNOWN | 31 | 6 | T |
| AA579541 | UNKNOWN | 13 | 369 | A |
| AA579598 | UNKNOWN | 21 | 0 | T |
| AA579624 | UNKNOWN | 24 | 0 | T |
| AA579726 | UNKNOWN | 15 | 3 | T |
| AA579780 | UNKNOWN | 24 | 0 | T |
| AA579888 | UNKNOWN | 14 | 16 | T |
| AA579969 | UNKNOWN | 11.66 | 313 | TTG |
| AA580019 | UNKNOWN | 15 | 271 | A |
| AA580130 | UNKNOWN | 15 | 0 | T |
| AA580511 | UNKNOWN | 35 | 0 | T |
| AA580630 | UNKNOWN | 21 | 0 | T |
| AA580702 | UNKNOWN | 12 | 0 | T |
| AA580911 | UNKNOWN | 26 | 0 | T |
| AA580941 | UNKNOWN | 18 | 0 | T |
| AA580954 | UNKNOWN | 32 | 0 | T |
| AA581123 | UNKNOWN | 15 | 0 | T |
| AA581248 | UNKNOWN | 31 | 0 | T |
| AA581365 | UNKNOWN | 19 | 0 | T |
| AA581369 | UNKNOWN | 48 | 291 | T |
| AA581369 | UNKNOWN | 20 | 0 | T |
| AA581375 | UNKNOWN | 23 | 0 | T |
| AA581375 | UNKNOWN | 13 | 133 | A |
| AA581385 | UNKNOWN | 17 | 540 | A |
| AA581401 | UNKNOWN | 14 | 15 | T |
| AA581404 | UNKNOWN | 12 | 0 | T |
| AA581409 | UNKNOWN | 12 | 0 | T |
| AA581418 | UNKNOWN | 32 | 0 | T |
| AA581429 | UNKNOWN | 33 | 0 | T |
| AA581429 | UNKNOWN | 27 | 238 | A |
| AA581454 | UNKNOWN | 17 | 0 | T |
| AA581480 | UNKNOWN | 17 | 139 | T |
| AA581483 | UNKNOWN | 30 | 0 | T |
| AA581495 | UNKNOWN | 13 | 440 | A |
| AA581501 | UNKNOWN | 7 | 387 | AT |
| AA581501 | UNKNOWN | 27 | 0 | T |
| AA581594 | UNKNOWN | 15 | 0 | T |
| AA581611 | UNKNOWN | 22 | 0 | T |
| AA581909 | UNKNOWN | 13 | 161 | T |
| AA581913 | UNKNOWN | 24 | 0 | T |
| AA581928 | UNKNOWN | 23 | 319 | T |
| AA581988 | UNKNOWN | 22 | 3 | T |
| AA582043 | UNKNOWN | 14 | 0 | T |
| AA582074 | UNKNOWN | 11.33 | 334 | TGT |
| AA582075 | UNKNOWN | 17 | 0 | T |
| AA582153 | UNKNOWN | 21 | 0 | T |
| AA582497 | UNKNOWN | 40 | 0 | T |
| AA582778 | UNKNOWN | 15 | 0 | T |
| AA582894 | UNKNOWN | 19 | 242 | A |
| AA582901 | UNKNOWN | 6 | 19 | TTA |
| AA582921 | UNKNOWN | 4.5 | 323 | ATCT |
| AA582990 | UNKNOWN | 13 | 0 | T |
| AA583065 | UNKNOWN | 10.25 | 180 | AGAT |
| AA583065 | UNKNOWN | 4.75 | 218 | ATAC |
| AA583245 | UNKNOWN | 20 | 0 | T |
| AA583246 | UNKNOWN | 20 | 0 | T |
| AA583332 | UNKNOWN | 32 | 0 | T |

TABLE 1-continued

| Genbank # | Region | # reps | Position | Unit sequence |
|---|---|---|---|---|
| AA583350 | UNKNOWN | 30 | 0 | T |
| AA583365 | UNKNOWN | 14 | 346 | T |
| AA583372 | UNKNOWN | 20 | 0 | T |
| AA583375 | UNKNOWN | 18 | 51 | CA |
| AA583390 | UNKNOWN | 29 | 0 | T |
| AA583495 | UNKNOWN | 22 | 0 | T |
| AA583496 | UNKNOWN | 15 | 0 | T |
| AA583529 | UNKNOWN | 14 | 383 | A |
| AA583561 | UNKNOWN | 25 | 0 | T |
| AA583568 | UNKNOWN | 17 | 342 | A |
| AA583604 | UNKNOWN | 6.5 | 42 | TG |
| AA583604 | UNKNOWN | 6.5 | 197 | AC |
| AA583860 | UNKNOWN | 37 | 0 | T |
| AA583920 | UNKNOWN | 12 | 0 | T |
| AA584059 | UNKNOWN | 20 | 414 | A |
| AA584067 | UNKNOWN | 13 | 76 | T |
| AA584082 | UNKNOWN | 4.5 | 30 | TTTA |
| AA584115 | UNKNOWN | 8.33 | 392 | GGT |
| AA584120 | UNKNOWN | 15 | 42 | A |
| AA584145 | UNKNOWN | 22 | 0 | T |
| AA584148 | UNKNOWN | 20 | 0 | T |
| AA584195 | UNKNOWN | 29 | 0 | T |
| AA584364 | UNKNOWN | 15 | 0 | T |
| AA584428 | UNKNOWN | 14 | 0 | T |
| AA584449 | UNKNOWN | 4.5 | 24 | CTTT |
| AA584451 | UNKNOWN | 15 | 0 | T |
| AA584511 | UNKNOWN | 13 | 0 | T |
| AA584591 | UNKNOWN | 15 | 0 | T |
| AA584608 | UNKNOWN | 16 | 0 | T |
| AA584654 | UNKNOWN | 12 | 295 | A |
| AA584667 | UNKNOWN | 32 | 0 | T |
| AA584723 | UNKNOWN | 21 | 0 | T |
| AA584733 | UNKNOWN | 26 | 160 | T |
| AA584782 | UNKNOWN | 20 | 249 | T |
| AA584814 | UNKNOWN | 7.5 | 220 | AG |
| AA584814 | UNKNOWN | 39 | 0 | T |
| AA585188 | UNKNOWN | 25 | 24 | T |
| AA585222 | UNKNOWN | 33 | 2 | T |
| AA585230 | UNKNOWN | 16 | 0 | T |
| AA585288 | UNKNOWN | 12 | 0 | T |
| AA585375 | UNKNOWN | 21 | 0 | T |
| AA585416 | UNKNOWN | 16 | 0 | T |
| AA585435 | UNKNOWN | 15 | 0 | T |
| AA585441 | UNKNOWN | 33 | 7 | T |
| AA586354 | UNKNOWN | 12 | 0 | T |
| AA586385 | UNKNOWN | 18 | 205 | A |
| AA586390 | UNKNOWN | 15 | 0 | T |
| AA586401 | UNKNOWN | 12 | 144 | T |
| AA586425 | UNKNOWN | 4.5 | 235 | AAAT |
| AA586425 | UNKNOWN | 15 | 0 | T |
| AA586556 | UNKNOWN | 14 | 0 | T |
| AA586561 | UNKNOWN | 26 | 0 | T |
| AA586577 | UNKNOWN | 25 | 0 | T |
| AA586716 | UNKNOWN | 28 | 0 | T |
| AA586930 | UNKNOWN | 21 | 0 | T |
| AA587245 | UNKNOWN | 13 | 0 | T |
| AA587250 | UNKNOWN | 18 | 307 | T |
| AA587290 | UNKNOWN | 20 | 0 | T |
| AA587351 | UNKNOWN | 40 | 0 | T |
| AA587390 | UNKNOWN | 16 | 0 | T |
| AA587509 | UNKNOWN | 28 | 199 | A |
| AA587552 | UNKNOWN | 20 | 1 | T |
| AA587578 | UNKNOWN | 18 | 197 | A |
| AA587589 | UNKNOWN | 32 | 103 | A |
| AA587590 | UNKNOWN | 57 | 73 | A |
| AA587604 | UNKNOWN | 18 | 0 | T |
| AA587608 | UNKNOWN | 18 | 0 | T |
| AA587807 | UNKNOWN | 15 | 0 | T |
| AA587839 | UNKNOWN | 18 | 323 | A |
| AA587884 | UNKNOWN | 21 | 0 | T |
| AA587908 | UNKNOWN | 32 | 0 | T |
| AA587919 | UNKNOWN | 6 | 7 | ATTT |
| AA587944 | UNKNOWN | 20 | 238 | CA |
| AA588166 | UNKNOWN | 15 | 286 | T |
| AA588186 | UNKNOWN | 16.5 | 301 | TC |
| AA588519 | UNKNOWN | 53 | 1 | T |
| AA588823 | UNKNOWN | 14 | 0 | T |

TABLE 1-continued

| Genbank # | Region | # reps | Position | Unit sequence |
|---|---|---|---|---|
| AA592927 | UNKNOWN | 30 | 0 | T |
| AA593428 | UNKNOWN | 19 | 0 | T |
| AA593529 | UNKNOWN | 13 | 20 | T |
| AA593557 | UNKNOWN | 5.4 | 37 | AAACA |
| AA593768 | UNKNOWN | 45 | 0 | T |
| AA594031 | UNKNOWN | 13 | 25 | A |
| AA594093 | UNKNOWN | 26 | 0 | T |
| AA594128 | UNKNOWN | 14 | 27 | A |
| AA594144 | UNKNOWN | 22 | 0 | T |
| AA594157 | UNKNOWN | 51 | 0 | T |
| AA594161 | UNKNOWN | 14 | 122 | A |
| AA594193 | UNKNOWN | 13 | 70 | A |
| AA594215 | UNKNOWN | 8.66 | 175 | TTA |
| AA594569 | UNKNOWN | 12 | 0 | T |
| AA594746 | UNKNOWN | 15 | 125 | A |
| AA595427 | UNKNOWN | 14 | 0 | T |
| AA595499 | UNKNOWN | 18 | 276 | A |
| AA595507 | UNKNOWN | 19 | 226 | A |
| AA595508 | UNKNOWN | 16 | 278 | A |
| AA595786 | UNKNOWN | 13 | 28 | T |
| AA595988 | UNKNOWN | 4.75 | 5 | TATG |
| AA598432 | UNKNOWN | 15 | 376 | T |
| AA598545 | UNKNOWN | 15 | 0 | T |
| AA598553 | UNKNOWN | 28 | 0 | T |
| AA598645 | UNKNOWN | 19 | 0 | T |
| AA598742 | UNKNOWN | 5.75 | 57 | TTTG |
| AA598742 | UNKNOWN | 55 | 5 | T |
| AA598747 | UNKNOWN | 26 | 0 | T |
| AA598967 | UNKNOWN | 21 | 0 | T |
| AA598973 | UNKNOWN | 13 | 0 | T |
| AA599042 | UNKNOWN | 16 | 2 | T |
| AA599107 | UNKNOWN | 14 | 390 | T |
| AA599141 | UNKNOWN | 21 | 0 | T |
| AA599148 | UNKNOWN | 16 | 0 | T |
| AA599550 | UNKNOWN | 13 | 1 | T |
| AA599659 | UNKNOWN | 43 | 0 | T |
| AA600139 | UNKNOWN | 19 | 0 | T |
| AA600202 | UNKNOWN | 15 | 0 | T |
| AA600215 | UNKNOWN | 20 | 0 | T |
| AA600222 | UNKNOWN | 14 | 133 | T |
| AA600325 | UNKNOWN | 22 | 0 | T |
| AA600373 | UNKNOWN | 20 | 100 | T |
| AA600866 | UNKNOWN | 4 | 211 | GTGGG |
| AA601018 | UNKNOWN | 17 | 0 | T |
| AA601045 | UNKNOWN | 17 | 42 | A |
| AA601106 | UNKNOWN | 24 | 0 | T |
| AA601115 | UNKNOWN | 23 | 0 | T |
| AA601127 | UNKNOWN | 25 | 0 | T |
| AA601149 | UNKNOWN | 27 | 0 | T |
| AA601191 | UNKNOWN | 15 | 16 | T |
| AA601193 | UNKNOWN | 21 | 513 | A |
| AA601193 | UNKNOWN | 20 | 9 | A |
| AA601232 | UNKNOWN | 37 | 0 | T |
| AA601261 | UNKNOWN | 12 | 0 | T |
| AA601268 | UNKNOWN | 19 | 0 | T |
| AA601364 | UNKNOWN | 15 | 198 | A |
| AA601367 | UNKNOWN | 22 | 0 | T |
| AA601275 | UNKNOWN | 12 | 273 | A |
| AA601385 | UNKNOWN | 17 | 559 | A |
| AA601385 | UNKNOWN | 14 | 283 | A |
| AA601394 | UNKNOWN | 17 | 0 | T |
| AA601400 | UNKNOWN | 17 | 0 | T |
| AA601409 | UNKNOWN | 16 | 308 | A |
| AA601409 | UNKNOWN | 12 | 163 | T |
| AA601433 | UNKNOWN | 22 | 216 | A |
| AA601460 | UNKNOWN | 13 | 477 | A |
| AA601487 | UNKNOWN | 24 | 0 | T |
| AA601642 | UNKNOWN | 14 | 0 | T |
| AA601644 | UNKNOWN | 28 | 0 | T |
| AA601646 | UNKNOWN | 21 | 0 | T |
| AA601715 | UNKNOWN | 4.75 | 460 | TTTA |
| AA601902 | UNKNOWN | 14 | 312 | A |
| AA602017 | UNKNOWN | 18 | 0 | T |
| AA602019 | UNKNOWN | 16 | 0 | T |
| AA602019 | UNKNOWN | 13 | 219 | A |
| AA602047 | UNKNOWN | 18 | 284 | A |
| AA602174 | UNKNOWN | 13 | 233 | A |

TABLE 1-continued

| Genbank # | Region | # reps | Position | Unit sequence |
|---|---|---|---|---|
| AA602414 | UNKNOWN | 57 | 0 | T |
| AA602414 | UNKNOWN | 15 | 187 | A |
| AA602414 | UNKNOWN | 14 | 226 | C |
| AA602437 | UNKNOWN | 16 | 271 | A |
| AA602479 | UNKNOWN | 53 | 0 | T |
| AA602769 | UNKNOWN | 40 | 0 | T |
| AA602837 | UNKNOWN | 14 | 0 | T |
| AA602904 | UNKNOWN | 21 | 0 | T |
| AA602918 | UNKNOWN | 17 | 302 | A |
| AA602920 | UNKNOWN | 16 | 289 | A |
| AA602921 | UNKNOWN | 9.5 | 246 | AC |
| AA602942 | UNKNOWN | 13 | 292 | A |
| AA603024 | UNKNOWN | 16 | 0 | T |
| AA603081 | UNKNOWN | 17 | 0 | T |
| AA603110 | UNKNOWN | 14 | 0 | T |
| AA603235 | UNKNOWN | 24 | 8 | T |
| AA603315 | UNKNOWN | 17 | 0 | T |
| AA603319 | UNKNOWN | 16 | 234 | T |
| AA603324 | UNKNOWN | 22 | 0 | T |
| AA603344 | UNKNOWN | 15 | 168 | CTTT |
| AA603466 | UNKNOWN | 8 | 166 | AC |
| AA603478 | UNKNOWN | 27 | 0 | T |
| AA603516 | UNKNOWN | 13 | 422 | A |
| AA603525 | UNKNOWN | 5.25 | 381 | AAAC |
| AA603560 | UNKNOWN | 13 | 332 | A |
| AA603571 | UNKNOWN | 15 | 7 | T |
| AA603709 | UNKNOWN | 71 | 0 | T |
| AA603725 | UNKNOWN | 17 | 0 | T |
| AA603769 | UNKNOWN | 21 | 299 | A |
| AA603785 | UNKNOWN | 7.5 | 164 | AC |
| AA603850 | UNKNOWN | 13 | 353 | A |
| AA603904 | UNKNOWN | 16 | 0 | T |
| AA604138 | UNKNOWN | 8 | 9 | TA |
| AA604138 | UNKNOWN | 16 | 167 | C |
| AA604268 | UNKNOWN | 24 | 0 | T |
| AA604268 | UNKNOWN | 15 | 315 | A |
| AA604289 | UNKNOWN | 15 | 0 | T |
| AA604314 | UNKNOWN | 14 | 340 | T |
| AA604490 | UNKNOWN | 16 | 0 | T |
| AA604601 | UNKNOWN | 15 | 0 | T |
| AA604681 | UNKNOWN | 9.5 | 141 | GT |
| AA604686 | UNKNOWN | 14 | 403 | A |
| AA604700 | UNKNOWN | 24 | 66 | TG |
| AA604777 | UNKNOWN | 27 | 236 | T |
| AA604799 | UNKNOWN | 24 | 0 | T |
| AA604900 | UNKNOWN | 18 | 0 | T |
| AA605020 | UNKNOWN | 12 | 0 | T |
| AA605142 | UNKNOWN | 13 | 2 | T |
| AA608588 | UNKNOWN | 14 | 267 | T |
| AA608601 | UNKNOWN | 38 | 0 | T |
| AA608647 | UNKNOWN | 19 | 0 | T |
| AA608689 | UNKNOWN | 23 | 100 | T |
| AA608710 | UNKNOWN | 14 | 4 | T |
| AA608722 | UNKNOWN | 21 | 368 | T |
| AA608722 | UNKNOWN | 12 | 180 | A |
| AA608747 | UNKNOWN | 19 | 472 | A |
| AA608747 | UNKNOWN | 16 | 133 | T |
| AA608808 | UNKNOWN | 6.33 | 68 | ACA |
| AA608808 | UNKNOWN | 16 | 373 | T |
| AA608808 | UNKNOWN | 12 | 0 | T |
| AA608812 | UNKNOWN | 24 | 0 | T |
| AA608837 | UNKNOWN | 14 | 352 | T |
| AA608958 | UNKNOWN | 14 | 218 | T |
| AA609000 | UNKNOWN | 31 | 0 | T |
| AA609118 | UNKNOWN | 14 | 0 | T |
| AA609170 | UNKNOWN | 5.66 | 26 | TTG |
| AA609238 | UNKNOWN | 35 | 0 | T |
| AA609282 | UNKNOWN | 27 | 0 | T |
| AA609292 | UNKNOWN | 12 | 0 | T |
| AA609361 | UNKNOWN | 5.75 | 195 | TTTG |
| AA609391 | UNKNOWN | 19 | 0 | T |
| AA609422 | UNKNOWN | 14 | 197 | T |
| AA609435 | UNKNOWN | 25 | 0 | T |
| AA609474 | UNKNOWN | 24 | 148 | T |
| AA609483 | UNKNOWN | 36 | 0 | T |
| AA609536 | UNKNOWN | 13 | 0 | T |
| AA609770 | UNKNOWN | 22 | 0 | T |

TABLE 1-continued

| Genbank # | Region | # reps | Position | Unit sequence |
|---|---|---|---|---|
| AA609803 | UNKNOWN | 17 | 0 | T |
| AA609810 | UNKNOWN | 25 | 0 | T |
| AA609857 | UNKNOWN | 12 | 0 | T |
| AA609861 | UNKNOWN | 18 | 0 | T |
| AA609887 | UNKNOWN | 16 | 0 | T |
| AA609914 | UNKNOWN | 22.5 | 170 | AT |
| AA609944 | UNKNOWN | 19 | 0 | T |
| AA609983 | UNKNOWN | 12 | 4 | T |
| AA610019 | UNKNOWN | 15 | 0 | T |
| AA610028 | UNKNOWN | 16 | 0 | T |
| AA610112 | UNKNOWN | 6 | 360 | AAC |
| AA610122 | UNKNOWN | 14 | 0 | T |
| AA610164 | UNKNOWN | 7 | 192 | AAGA |
| AA610164 | UNKNOWN | 4.5 | 173 | AAAG |
| AA610164 | UNKNOWN | 14 | 229 | A |
| AA610243 | UNKNOWN | 17 | 8 | T |
| AA610317 | UNKNOWN | 32 | 0 | T |
| AA610410 | UNKNOWN | 17 | 277 | A |
| AA610416 | UNKNOWN | 16 | 0 | T |
| AA610483 | UNKNOWN | 4.75 | 0 | ATTT |
| AA610522 | UNKNOWN | 16 | 7 | T |
| AA610612 | UNKNOWN | 18 | 7 | T |
| AA610634 | UNKNOWN | 17 | 354 | A |
| AA610700 | UNKNOWN | 14 | 0 | T |
| AA610712 | UNKNOWN | 26 | 7 | T |
| AA610787 | UNKNOWN | 13 | 248 | A |
| AA610788 | UNKNOWN | 16 | 0 | T |
| AA610826 | UNKNOWN | 16 | 0 | T |
| AA610841 | UNKNOWN | 4.4 | 163 | AAAAC |
| AA610841 | UNKNOWN | 14 | 325 | A |
| AA610842 | UNKNOWN | 13 | 3 | A |
| AA612666 | UNKNOWN | 13 | 0 | T |
| AA613203 | UNKNOWN | 23 | 290 | A |
| AA613224 | UNKNOWN | 15 | 75 | A |
| AA613353 | UNKNOWN | 6 | 124 | AAT |
| AA613353 | UNKNOWN | 15 | 0 | T |
| AA613450 | UNKNOWN | 15 | 313 | A |
| AA613460 | UNKNOWN | 14 | 360 | A |
| AA613739 | UNKNOWN | 30 | 0 | T |
| AA614018 | UNKNOWN | 31 | 0 | T |
| AA614078 | UNKNOWN | 16 | 303 | A |
| AA614139 | UNKNOWN | 17 | 0 | T |
| AA614169 | UNKNOWN | 16 | 7 | T |
| AA614251 | UNKNOWN | 16 | 7 | T |
| AA614350 | UNKNOWN | 14 | 265 | A |
| AA614419 | UNKNOWN | 31 | 0 | T |
| AA614439 | UNKNOWN | 12 | 189 | A |
| AA614538 | UNKNOWN | 13 | 416 | T |
| AA614814 | UNKNOWN | 28 | 237 | T |
| AA614819 | UNKNOWN | 43 | 18 | T |
| AA617637 | UNKNOWN | 6 | 179 | AAAC |
| AA617805 | UNKNOWN | 12 | 0 | T |
| AA617929 | UNKNOWN | 6 | 177 | CCA |
| AA618206 | UNKNOWN | 13 | 373 | A |
| AA618252 | UNKNOWN | 15 | 177 | A |
| AA618262 | UNKNOWN | 16 | 203 | A |
| AA618262 | UNKNOWN | 12 | 0 | T |
| AA618263 | UNKNOWN | 17 | 0 | T |
| AA618319 | UNKNOWN | 16 | 8 | T |
| AA618346 | UNKNOWN | 21 | 7 | T |
| AA618403 | UNKNOWN | 16 | 7 | T |
| AA618474 | UNKNOWN | 19 | 0 | T |
| AA620300 | UNKNOWN | 5.66 | 3 | TTA |
| AA620632 | UNKNOWN | 14 | 0 | T |
| AA620632 | UNKNOWN | 12 | 79 | A |
| AA620746 | UNKNOWN | 15 | 0 | T |
| AA620821 | UNKNOWN | 30 | 0 | T |
| AA620836 | UNKNOWN | 17 | 26 | T |
| AA620977 | UNKNOWN | 16 | 0 | T |
| AA621058 | UNKNOWN | 5.5 | 253 | TTCA |
| AA621065 | UNKNOWN | 12 | 0 | T |
| AA621191 | UNKNOWN | 22 | 0 | T |
| AA621192 | UNKNOWN | 14 | 0 | T |
| AA621272 | UNKNOWN | 23 | 0 | T |
| AA621283 | UNKNOWN | 27 | 0 | T |
| AA621370 | UNKNOWN | 14 | 377 | A |
| AA621381 | UNKNOWN | 14 | 53 | T |

TABLE 1-continued

| Genbank # | Region | # reps | Position | Unit sequence |
|---|---|---|---|---|
| AA621529 | UNKNOWN | 4.75 | 256 | AAAT |
| AA621550 | UNKNOWN | 15 | 0 | T |
| AA621597 | UNKNOWN | 16 | 0 | T |
| AA621827 | UNKNOWN | 13 | 0 | T |
| AA621850 | UNKNOWN | 15 | 0 | T |
| AA621893 | UNKNOWN | 13 | 0 | T |
| AA621943 | UNKNOWN | 17 | 1 | T |
| AA622329 | UNKNOWN | 19 | 0 | T |
| AA622522 | UNKNOWN | 34 | 0 | T |
| AA622535 | UNKNOWN | 5.66 | 16 | TTA |
| AA622667 | UNKNOWN | 12 | 0 | T |
| AA622729 | UNKNOWN | 29 | 0 | T |
| AA622801 | UNKNOWN | 14 | 334 | A |
| AA622809 | UNKNOWN | 28 | 0 | T |
| AA625451 | UNKNOWN | 8 | 289 | AT |
| AA625588 | UNKNOWN | 30 | 0 | T |
| AA625656 | UNKNOWN | 18 | 0 | T |
| AA625764 | UNKNOWN | 18 | 0 | T |
| AA625860 | UNKNOWN | 17 | 0 | T |
| AA625882 | UNKNOWN | 12 | 380 | T |
| AA626038 | UNKNOWN | 20 | 0 | T |
| AA626163 | UNKNOWN | 12 | 420 | A |
| AA626180 | UNKNOWN | 20 | 0 | T |
| AA626242 | UNKNOWN | 18 | 296 | T |
| AA626249 | UNKNOWN | 17 | 0 | T |
| AA626325 | UNKNOWN | 41 | 0 | T |
| AA626775 | UNKNOWN | 8.5 | 483 | AG |
| AA627473 | UNKNOWN | 57 | 0 | T |
| AA627473 | UNKNOWN | 13 | 121 | A |
| AA627473 | UNKNOWN | 12 | 168 | C |
| AA627701 | UNKNOWN | 47 | 0 | T |
| AA628093 | UNKNOWN | 38 | 0 | T |
| AA628192 | UNKNOWN | 14 | 0 | T |
| AA628230 | UNKNOWN | 25 | 0 | T |
| AA628419 | UNKNOWN | 16 | 0 | T |
| AA628431 | UNKNOWN | 12 | 0 | T |
| AA628550 | UNKNOWN | 17 | 241 | T |
| AA628831 | UNKNOWN | 11.5 | 102 | TG |
| AA628862 | UNKNOWN | 17 | 243 | T |
| AA628991 | UNKNOWN | 22 | 0 | T |
| AA629004 | UNKNOWN | 16 | 0 | T |
| AA629040 | UNKNOWN | 18 | 0 | T |
| AA629049 | UNKNOWN | 12 | 0 | T |
| AA629254 | UNKNOWN | 13 | 0 | T |
| AA629268 | UNKNOWN | 3.8 | 18 | ATTTT |
| AA629268 | UNKNOWN | 15 | 148 | A |
| AA629532 | UNKNOWN | 31 | 0 | T |
| AA629540 | UNKNOWN | 17 | 0 | T |
| AA629697 | UNKNOWN | 2.8 | 83 | CTGGGGTGGC (SEQ ID NO: 11) |
| AA629757 | UNKNOWN | 18 | 0 | T |
| AA629874 | UNKNOWN | 14 | 292 | T |
| AA629983 | UNKNOWN | 12 | 0 | T |
| AA629992 | UNKNOWN | 24 | 0 | T |
| AA630035 | UNKNOWN | 21 | 0 | T |
| AA630305 | UNKNOWN | 14 | 142 | A |
| AA630451 | UNKNOWN | 13 | 373 | T |
| AA630453 | UNKNOWN | 6.66 | 201 | TTA |
| AA630453 | UNKNOWN | 9.5 | 237 | GT |
| AA630476 | UNKNOWN | 16 | 0 | T |
| AA630672 | UNKNOWN | 25 | 0 | T |
| AA630825 | UNKNOWN | 4.5 | 161 | TTTG |
| AA630825 | UNKNOWN | 17 | 0 | T |
| AA630880 | UNKNOWN | 17 | 7 | T |
| AA630949 | UNKNOWN | 18 | 0 | T |
| AA630950 | UNKNOWN | 16 | 405 | A |
| AA630975 | UNKNOWN | 6.5 | 83 | AT |
| AA631054 | UNKNOWN | 5.66 | 25 | AAC |
| AA631057 | UNKNOWN | 12 | 187 | T |
| AA631078 | UNKNOWN | 13 | 0 | T |
| AA631120 | UNKNOWN | 45 | 0 | T |
| AA631120 | UNKNOWN | 16 | 119 | A |
| AA631392 | UNKNOWN | 23 | 328 | A |
| AA631440 | UNKNOWN | 21 | 363 | A |
| AA631469 | UNKNOWN | 16 | 282 | A |
| AA631480 | UNKNOWN | 23 | 0 | T |
| AA631512 | UNKNOWN | 21 | 0 | T |
| AA631528 | UNKNOWN | 20 | 278 | A |

TABLE 1-continued

| Genbank # | Region | # reps | Position | Unit sequence |
|---|---|---|---|---|
| AA631638 | UNKNOWN | 16 | 0 | T |
| AA631676 | UNKNOWN | 22 | 239 | A |
| AA631722 | UNKNOWN | 17 | 614 | A |
| AA631732 | UNKNOWN | 12 | 0 | T |
| AA631773 | UNKNOWN | 15 | 85 | T |
| AA631782 | UNKNOWN | 18 | 0 | T |
| AA631817 | UNKNOWN | 18 | 409 | A |
| AA631834 | UNKNOWN | 3.83 | 30 | ATATAC |
| AA631910 | UNKNOWN | 15 | 586 | A |
| AA631915 | UNKNOWN | 18 | 0 | T |
| AA631929 | UNKNOWN | 18 | 3 | T |
| AA631997 | UNKNOWN | 12 | 232 | A |
| AA632147 | UNKNOWN | 3.8 | 273 | AAAAC |
| AA632177 | UNKNOWN | 2.57 | 214 | TTTCTTTCTTTCTTTTCT (SEQ ID NO: 12) |
| AA632281 | UNKNOWN | 23 | 280 | T |
| AA632295 | UNKNOWN | 12 | 137 | A |
| AA632424 | UNKNOWN | 4.75 | 307 | TGGC |
| AA632424 | UNKNOWN | 18 | 0 | T |
| AA632473 | UNKNOWN | 14 | 375 | A |
| AA632477 | UNKNOWN | 14 | 340 | A |
| AA632498 | UNKNOWN | 15 | 170 | T |
| AA632498 | UNKNOWN | 14 | 0 | T |
| AA632508 | UNKNOWN | 15 | 7 | A |
| AA632556 | UNKNOWN | 13 | 328 | A |
| AA632622 | UNKNOWN | 15 | 351 | A |
| AA632660 | UNKNOWN | 21 | 0 | T |
| AA632705 | UNKNOWN | 26 | 259 | A |
| AA632718 | UNKNOWN | 15 | 314 | A |
| AA632722 | UNKNOWN | 26 | 227 | A |
| AA632741 | UNKNOWN | 13 | 229 | A |
| AA632744 | UNKNOWN | 17 | 0 | T |
| AA632745 | UNKNOWN | 20 | 3 | T |
| AA632757 | UNKNOWN | 17 | 0 | T |
| AA632834 | UNKNOWN | 17 | 305 | A |
| AA632839 | UNKNOWN | 35 | 0 | T |
| AA632847 | UNKNOWN | 21 | 348 | A |
| AA632976 | UNKNOWN | 17 | 301 | A |
| AA632994 | UNKNOWN | 14 | 346 | A |
| AA633230 | UNKNOWN | 23 | 0 | T |
| AA633232 | UNKNOWN | 16 | 0 | T |
| AA633438 | UNKNOWN | 16 | 7 | T |
| AA633438 | UNKNOWN | 12 | 140 | A |
| AA633703 | UNKNOWN | 39 | 0 | T |
| AA633813 | UNKNOWN | 4.5 | 58 | CTGT |
| AA633813 | UNKNOWN | 6.5 | 8 | TC |
| AA633962 | UNKNOWN | 30 | 0 | T |
| AA634149 | UNKNOWN | 11.5 | 159 | TG |
| AA634265 | UNKNOWN | 27 | 0 | T |
| AA634283 | UNKNOWN | 14 | 0 | T |
| AA634350 | UNKNOWN | 13 | 0 | T |
| AA634351 | UNKNOWN | 13 | 49 | A |
| AA634561 | UNKNOWN | 21 | 0 | T |
| AA634801 | UNKNOWN | 15 | 91 | T |
| AA634801 | UNKNOWN | 12 | 200 | A |
| AA634837 | UNKNOWN | 8 | 48 | AG |
| AA634837 | UNKNOWN | 16 | 381 | A |
| AA634923 | UNKNOWN | 8.5 | 0 | TC |
| AA634923 | UNKNOWN | 6.5 | 16 | TA |
| AA634923 | UNKNOWN | 21 | 28 | T |
| AA635173 | UNKNOWN | 32 | 0 | T |
| AA635181 | UNKNOWN | 13 | 0 | T |
| AA635182 | UNKNOWN | 23 | 0 | T |
| AA635247 | UNKNOWN | 13 | 331 | A |
| AA635284 | UNKNOWN | 15 | 0 | T |
| AA635295 | UNKNOWN | 15 | 0 | T |
| AA635301 | UNKNOWN | 20 | 0 | T |
| AA635310 | UNKNOWN | 21 | 0 | T |
| AA635671 | UNKNOWN | 16 | 251 | A |
| AA635671 | UNKNOWN | 16 | 394 | T |
| AA635974 | UNKNOWN | 15 | 0 | T |
| AA636025 | UNKNOWN | 11.5 | 299 | TC |
| AA639025 | UNKNOWN | 13 | 380 | A |
| AA639289 | UNKNOWN | 19 | 0 | T |
| AA639336 | UNKNOWN | 16 | 360 | A |
| AA639553 | UNKNOWN | 4.5 | 26 | AAGA |
| AA639753 | UNKNOWN | 21 | 479 | A |
| AA639776 | UNKNOWN | 21 | 125 | T |

TABLE 1-continued

| Genbank # | Region | # reps | Position | Unit sequence |
|---|---|---|---|---|
| AA639892 | UNKNOWN | 21 | 8 | T |
| AA639943 | UNKNOWN | 4 | 242 | TTTTA |
| AA639943 | UNKNOWN | 12 | 6 | T |
| AA640256 | UNKNOWN | 15 | 337 | A |
| AA640260 | UNKNOWN | 20 | 0 | T |
| AA640292 | UNKNOWN | 17 | 186 | A |
| AA640416 | UNKNOWN | 14 | 281 | A |
| AA640556 | UNKNOWN | 16 | 7 | T |
| AA640668 | UNKNOWN | 14 | 0 | T |
| AA640668 | UNKNOWN | 12 | 91 | A |
| AA640779 | UNKNOWN | 8 | 7 | CTA |
| AA640779 | UNKNOWN | 103 | 80 | A |
| AA640779 | UNKNOWN | 28 | 49 | A |
| AA641005 | UNKNOWN | 39 | 0 | T |
| AA641023 | UNKNOWN | 17 | 0 | T |
| AA641179 | UNKNOWN | 16 | 8 | T |
| AA641543 | UNKNOWN | 21 | 8 | T |
| AA641545 | UNKNOWN | 12 | 0 | T |
| AA641586 | UNKNOWN | 17 | 7 | T |
| AA641636 | UNKNOWN | 29 | 0 | T |
| AA641651 | UNKNOWN | 20 | 0 | T |
| AA642079 | UNKNOWN | 22 | 139 | A |
| AA642101 | UNKNOWN | 22 | 142 | A |
| AA642129 | UNKNOWN | 16 | 0 | T |
| AA642341 | UNKNOWN | 7.66 | 239 | AAC |
| AA642459 | UNKNOWN | 12 | 0 | T |
| AA642459 | UNKNOWN | 12 | 159 | A |
| AA642476 | UNKNOWN | 12 | 0 | T |
| AA642680 | UNKNOWN | 19 | 0 | T |
| AA642796 | UNKNOWN | 14 | 229 | A |
| AA642863 | UNKNOWN | 13 | 338 | A |
| AA643235 | UNKNOWN | 62 | 0 | T |
| AA643441 | UNKNOWN | 14 | 296 | A |
| AA643542 | UNKNOWN | 13.5 | 114 | AC |
| AA643683 | UNKNOWN | 7 | 230 | GT |
| AA643802 | UNKNOWN | 17 | 303 | A |
| AA643815 | UNKNOWN | 14 | 378 | A |
| AA643961 | UNKNOWN | 14 | 2 | T |
| AA644007 | UNKNOWN | 23 | 0 | T |
| AA644091 | UNKNOWN | 19 | 0 | T |
| AA644123 | UNKNOWN | 38 | 0 | T |
| AA644386 | UNKNOWN | 20 | 0 | T |
| AA644396 | UNKNOWN | 19 | 328 | A |
| AA648038 | UNKNOWN | 5.9 | 1 | CTTTCTAGCC (SEQ ID NO: 13) |
| AA648285 | UNKNOWN | 25 | 0 | T |
| AA648296 | UNKNOWN | 23 | 326 | A |
| AA648312 | UNKNOWN | 25 | 0 | T |
| AA648380 | UNKNOWN | 24 | 0 | T |
| AA648412 | UNKNOWN | 32 | 0 | T |
| AA648413 | UNKNOWN | 13 | 0 | T |
| AA648430 | UNKNOWN | 27 | 2 | T |
| AA648448 | UNKNOWN | 23 | 308 | A |
| AA648468 | UNKNOWN | 31 | 0 | T |
| AA648473 | UNKNOWN | 15 | 57 | T |
| AA648481 | UNKNOWN | 19 | 316 | A |
| AA648481 | UNKNOWN | 14 | 0 | T |
| AA648486 | UNKNOWN | 12 | 0 | T |
| AA648502 | UNKNOWN | 8.5 | 329 | AC |
| AA648502 | UNKNOWN | 14 | 4 | T |
| AA648546 | UNKNOWN | 71 | 0 | T |
| AA648703 | UNKNOWN | 12 | 0 | T |
| AA648848 | UNKNOWN | 33 | 0 | T |
| AA648850 | UNKNOWN | 39 | 0 | T |
| AA648877 | UNKNOWN | 12 | 0 | T |
| AA648957 | UNKNOWN | 22 | 84 | T |
| AA648962 | UNKNOWN | 10.5 | 123 | TG |
| AA648962 | UNKNOWN | 9 | 91 | AT |
| AA648985 | UNKNOWN | 30 | 0 | T |
| AA648990 | UNKNOWN | 24 | 0 | T |
| AA648990 | UNKNOWN | 16 | 459 | A |
| AA649039 | UNKNOWN | 28 | 0 | T |
| AA649051 | UNKNOWN | 12 | 0 | T |
| AA649257 | UNKNOWN | 11.5 | 159 | AC |
| AA649257 | UNKNOWN | 11.5 | 197 | AG |
| AA649282 | UNKNOWN | 13 | 223 | A |
| AA649507 | UNKNOWN | 16 | 327 | A |
| AA649538 | UNKNOWN | 18 | 303 | A |

TABLE 1-continued

| Genbank # | Region | # reps | Position | Unit sequence |
|---|---|---|---|---|
| AA649608 | UNKNOWN | 13 | 294 | A |
| AA649610 | UNKNOWN | 16 | 306 | A |
| AA649629 | UNKNOWN | 15 | 269 | A |
| AA649633 | UNKNOWN | 15 | 0 | T |
| AA649640 | UNKNOWN | 15 | 0 | T |
| AA649641 | UNKNOWN | 5.5 | 352 | TTTC |
| AA649641 | UNKNOWN | 15 | 0 | T |
| AA649774 | UNKNOWN | 17 | 222 | A |
| AA649781 | UNKNOWN | 20 | 0 | T |
| AA649848 | UNKNOWN | 14 | 58 | A |
| AA650148 | UNKNOWN | 14 | 7 | T |
| AA650175 | UNKNOWN | 17 | 0 | T |
| AA650211 | UNKNOWN | 18 | 0 | T |
| AA650221 | UNKNOWN | 14 | 7 | T |
| AA650426 | UNKNOWN | 19 | 395 | A |
| AA651616 | UNKNOWN | 30 | 0 | T |
| AA651639 | UNKNOWN | 24 | 376 | A |
| AA651860 | UNKNOWN | 20 | 0 | T |
| AA651889 | UNKNOWN | 22 | 0 | T |
| AA651907 | UNKNOWN | 15 | 0 | T |
| AA651911 | UNKNOWN | 21.5 | 342 | AC |
| AA651936 | UNKNOWN | 29 | 0 | T |
| AA651939 | UNKNOWN | 13 | 3 | T |
| AA651956 | UNKNOWN | 18 | 0 | T |
| AA651970 | UNKNOWN | 14 | 289 | A |
| AA652052 | UNKNOWN | 17 | 231 | A |
| AA652053 | UNKNOWN | 19 | 53 | A |
| AA652059 | UNKNOWN | 16 | 339 | A |
| AA652086 | UNKNOWN | 15 | 206 | A |
| AA652131 | UNKNOWN | 18 | 315 | A |
| AA652510 | UNKNOWN | 14 | 360 | A |
| AA652675 | UNKNOWN | 15 | 89 | T |
| AA652687 | UNKNOWN | 14 | 0 | T |
| AA653145 | UNKNOWN | 3.8 | 6 | TTTTA |
| AA653154 | UNKNOWN | 22 | 0 | T |
| AA653324 | UNKNOWN | 41 | 0 | T |
| AA653324 | UNKNOWN | 15 | 65 | A |
| AA653431 | UNKNOWN | 18 | 0 | T |
| AA653477 | UNKNOWN | 16 | 0 | T |
| AA653552 | UNKNOWN | 5.75 | 244 | AAAC |
| AA653643 | UNKNOWN | 18 | 0 | T |
| AA653860 | UNKNOWN | 17 | 3 | T |
| AA653955 | UNKNOWN | 14 | 383 | A |
| AA654153 | UNKNOWN | 35 | 0 | T |
| AA654314 | UNKNOWN | 18 | 0 | T |
| AA654664 | UNKNOWN | 13 | 244 | A |
| AA654772 | UNKNOWN | 16 | 7 | T |
| AA655010 | UNKNOWN | 16 | 371 | A |
| AA655011 | UNKNOWN | 15 | 384 | A |
| AA657494 | UNKNOWN | 3.8 | 405 | TTTTG |
| AA657504 | UNKNOWN | 15 | 189 | A |
| AA657523 | UNKNOWN | 15 | 285 | A |
| AA657563 | UNKNOWN | 14 | 210 | A |
| AA657752 | UNKNOWN | 16 | 303 | A |
| AA657826 | UNKNOWN | 16 | 0 | T |
| AA657860 | UNKNOWN | 16 | 0 | T |
| AA657874 | UNKNOWN | 17 | 0 | T |
| AA657881 | UNKNOWN | 15 | 327 | A |
| AA658043 | UNKNOWN | 13 | 309 | A |
| AA658206 | UNKNOWN | 13 | 323 | A |
| AA658327 | UNKNOWN | 19 | 0 | T |
| AA658329 | UNKNOWN | 13 | 324 | A |
| AA658340 | UNKNOWN | 14 | 230 | A |
| AA658365 | UNKNOWN | 22 | 165 | A |
| AA658477 | UNKNOWN | 18 | 0 | T |
| AA658837 | UNKNOWN | 13 | 225 | A |
| AA658852 | UNKNOWN | 14 | 7 | T |
| AA658987 | UNKNOWN | 14 | 61 | A |
| AA659017 | UNKNOWN | 17 | 171 | A |
| AA659238 | UNKNOWN | 13 | 443 | A |
| AA659310 | UNKNOWN | 13 | 0 | T |
| AA659502 | UNKNOWN | 14 | 404 | A |
| AA659502 | UNKNOWN | 13 | 259 | A |
| AA659640 | UNKNOWN | 14 | 150 | A |
| AA659815 | UNKNOWN | 24 | 0 | T |
| AA659832 | UNKNOWN | 17 | 293 | A |
| AA659870 | UNKNOWN | 15 | 91 | A |

TABLE 1-continued

| Genbank # | Region | # reps | Position | Unit sequence |
|---|---|---|---|---|
| AA659923 | UNKNOWN | 32 | 0 | T |
| AA661499 | UNKNOWN | 17 | 278 | A |
| AA661531 | UNKNOWN | 15 | 0 | T |
| AA661596 | UNKNOWN | 14 | 281 | A |
| AA661604 | UNKNOWN | 20 | 223 | A |
| AA661886 | UNKNOWN | 14 | 119 | A |
| AA661924 | UNKNOWN | 18 | 133 | A |
| AA661948 | UNKNOWN | 16 | 0 | T |
| AA661990 | UNKNOWN | 12 | 0 | T |
| AA662046 | UNKNOWN | 15 | 244 | A |
| AA662085 | UNKNOWN | 21 | 0 | T |
| AA662173 | UNKNOWN | 20 | 0 | T |
| AA662212 | UNKNOWN | 26 | 216 | A |
| AA662216 | UNKNOWN | 23 | 81 | A |
| AA662254 | UNKNOWN | 16 | 7 | T |
| AA662326 | UNKNOWN | 18 | 241 | A |
| AA662574 | UNKNOWN | 14 | 0 | T |
| AA662588 | UNKNOWN | 14 | 207 | A |
| AA662593 | UNKNOWN | 19 | 214 | A |
| AA662716 | UNKNOWN | 16 | 0 | T |
| AA662734 | UNKNOWN | 4.8 | 16 | TTTTA |
| AA662815 | UNKNOWN | 18 | 10 | T |
| AA662845 | UNKNOWN | 16 | 663 | A |
| AA663014 | UNKNOWN | 21 | 0 | T |
| AA663093 | UNKNOWN | 21 | 263 | TG |
| AA663093 | UNKNOWN | 16 | 304 | GA |
| AA663237 | UNKNOWN | 13 | 247 | A |
| AA663298 | UNKNOWN | 8.5 | 96 | TC |
| AA663298 | UNKNOWN | 12 | 112 | T |
| AA663597 | UNKNOWN | 7 | 221 | TG |
| AA663638 | UNKNOWN | 3.8 | 368 | TTTTG |
| AA664156 | UNKNOWN | 15 | 375 | AC |
| AA664189 | UNKNOWN | 19 | 5 | T |
| AA664235 | UNKNOWN | 6.5 | 452 | AG |
| AA664265 | UNKNOWN | 15 | 3 | T |
| AA664265 | UNKNOWN | 13 | 236 | A |
| AA664524 | UNKNOWN | 17 | 7 | T |
| AA664548 | UNKNOWN | 16 | 244 | A |
| AA664566 | UNKNOWN | 18 | 221 | A |
| AA664601 | UNKNOWN | 14 | 277 | A |
| AA664641 | UNKNOWN | 13 | 372 | A |
| AA664654 | UNKNOWN | 16 | 335 | A |
| AA664688 | UNKNOWN | 20 | 0 | T |
| AA664690 | UNKNOWN | 14 | 8 | T |
| AA664710 | UNKNOWN | 14 | 145 | A |
| AA664727 | UNKNOWN | 14 | 248 | A |
| AA664791 | UNKNOWN | 17 | 219 | A |
| AA664816 | UNKNOWN | 13 | 133 | A |
| AA664883 | UNKNOWN | 14 | 354 | A |
| AA664942 | UNKNOWN | 19 | 152 | A |
| AA664963 | UNKNOWN | 16 | 0 | T |
| AA664973 | UNKNOWN | 13 | 227 | A |
| AA664982 | UNKNOWN | 15 | 429 | A |
| AA665057 | UNKNOWN | 18 | 234 | A |
| AA665085 | UNKNOWN | 12 | 0 | T |
| AA665096 | UNKNOWN | 18 | 238 | A |
| AA665100 | UNKNOWN | 15 | 366 | A |
| AA665157 | UNKNOWN | 17 | 193 | A |
| AA665185 | UNKNOWN | 17 | 290 | A |
| AA665199 | UNKNOWN | 18 | 296 | A |
| AA665220 | UNKNOWN | 16 | 267 | A |
| AA665330 | UNKNOWN | 23 | 26 | T |
| AA665351 | UNKNOWN | 17 | 144 | A |
| AA665373 | UNKNOWN | 13 | 230 | A |
| AA665374 | UNKNOWN | 16 | 175 | A |
| AA665574 | UNKNOWN | 29 | 0 | T |
| AA665612 | UNKNOWN | 58 | 0 | T |
| AA665612 | UNKNOWN | 18 | 360 | A |
| AA665737 | UNKNOWN | 37 | 0 | T |
| AA665770 | UNKNOWN | 19 | 0 | T |
| AA665837 | UNKNOWN | 17 | 315 | A |
| AA665970 | UNKNOWN | 38 | 0 | T |
| AA666087 | UNKNOWN | 11.33 | 228 | ACA |
| AA666199 | UNKNOWN | 14 | 498 | A |
| AA666341 | UNKNOWN | 15 | 0 | T |
| AA668148 | UNKNOWN | 15 | 282 | A |
| AA668162 | UNKNOWN | 23 | 0 | T |

TABLE 1-continued

| Genbank # | Region | # reps | Position | Unit sequence |
|---|---|---|---|---|
| AA668213 | UNKNOWN | 18 | 0 | T |
| AA668219 | UNKNOWN | 15 | 7 | A |
| AA668228 | UNKNOWN | 6.5 | 358 | CT |
| AA668368 | UNKNOWN | 18 | 65 | A |
| AA668577 | UNKNOWN | 17 | 0 | T |
| AA668587 | UNKNOWN | 17 | 339 | A |
| AA668679 | UNKNOWN | 36 | 288 | T |
| AA668776 | UNKNOWN | 17 | 0 | T |
| AA668789 | UNKNOWN | 6.5 | 113 | TA |
| AA669023 | UNKNOWN | 12 | 30 | A |
| AA669089 | UNKNOWN | 7 | 108 | TG |
| AA669093 | UNKNOWN | 22 | 0 | T |
| AA669097 | UNKNOWN | 12 | 326 | A |
| AA669114 | UNKNOWN | 20 | 0 | T |
| AA669153 | UNKNOWN | 19 | 0 | T |
| AA669320 | UNKNOWN | 34 | 0 | T |
| AA669434 | UNKNOWN | 21 | 0 | T |
| AA669525 | UNKNOWN | 47 | 0 | T |
| AA669647 | UNKNOWN | 15 | 304 | A |
| AA669739 | UNKNOWN | 15 | 0 | T |
| AA669840 | UNKNOWN | 40 | 0 | T |
| AA670270 | UNKNOWN | 15 | 0 | T |
| AA670324 | UNKNOWN | 30 | 0 | T |
| AA670355 | UNKNOWN | 21 | 0 | T |
| AA670392 | UNKNOWN | 15 | 0 | T |
| AA676550 | UNKNOWN | 17 | 290 | T |
| AA676822 | UNKNOWN | 4.59 | 499 | AAACA |
| AA676837 | UNKNOWN | 6.66 | 324 | TTG |
| AA676863 | UNKNOWN | 4.5 | 17 | TTAA |
| AA676864 | UNKNOWN | 12 | 391 | AT |
| AA676980 | UNKNOWN | 12 | 317 | T |
| AA676992 | UNKNOWN | 2.63 | 301 | TTTTTTTATTT (SEQ ID NO: 14) |
| AA676992 | UNKNOWN | 15 | 260 | T |
| AA677018 | UNKNOWN | 13 | 170 | A |
| AA677202 | UNKNOWN | 7.5 | 218 | TC |
| AA677216 | UNKNOWN | 12 | 78 | A |
| AA677358 | UNKNOWN | 8 | 441 | AGC |
| AA677463 | UNKNOWN | 7.33 | 246 | ACA |
| AA677636 | UNKNOWN | 10.66 | 94 | AAT |
| AA677647 | UNKNOWN | 16 | 0 | T |
| AA677677 | UNKNOWN | 7.5 | 458 | AC |
| AA677682 | UNKNOWN | 9.5 | 200 | TG |
| AA677682 | UNKNOWN | 7.5 | 84 | AC |
| AA677682 | UNKNOWN | 7 | 218 | TA |
| AA677923 | UNKNOWN | 16 | 279 | T |
| AA678066 | UNKNOWN | 15 | 72 | A |
| AA678181 | UNKNOWN | 13 | 93 | T |
| AA678459 | UNKNOWN | 13 | 293 | A |
| AA678525 | UNKNOWN | 38 | 0 | T |
| AA678653 | UNKNOWN | 18 | 0 | T |
| AA678832 | UNKNOWN | 17.5 | 348 | AC |
| AA678832 | UNKNOWN | 17 | 0 | T |
| AA678990 | UNKNOWN | 13 | 124 | A |
| AA679101 | UNKNOWN | 15 | 71 | T |
| AA679124 | UNKNOWN | 15 | 5 | T |
| AA679306 | UNKNOWN | 8.5 | 146 | TTAT |
| AA679514 | UNKNOWN | 16 | 0 | T |
| AA679634 | UNKNOWN | 35 | 0 | T |
| AA679670 | UNKNOWN | 15 | 0 | T |
| AA679735 | UNKNOWN | 13 | 215 | A |
| AA679797 | UNKNOWN | 27 | 0 | T |
| AA679863 | UNKNOWN | 24 | 345 | A |
| AA679947 | UNKNOWN | 4.33 | 306 | AAAAAT |
| AA680187 | UNKNOWN | 5.18 | 35 | CAGTAACGACGTTGTGTTTTCC (SEQ ID NO: 15) |
| AA680187 | UNKNOWN | 4.72 | 128 | ACGACGTTGTGTTTTCCCAGTC (SEQ ID NO: 16) |
| AA680250 | UNKNOWN | 25 | 0 | T |
| AA682215 | UNKNOWN | 23 | 0 | T |
| AA682248 | UNKNOWN | 30.5 | 291 | AT |
| AA682280 | UNKNOWN | 12 | 0 | T |
| AA682316 | UNKNOWN | 43 | 0 | T |
| AA682320 | UNKNOWN | 12 | 0 | T |
| AA682323 | UNKNOWN | 4.5 | 131 | TTCT |
| AA682328 | UNKNOWN | 19 | 0 | T |
| AA682344 | UNKNOWN | 15 | 0 | T |
| AA682381 | UNKNOWN | 13 | 0 | T |
| AA682405 | UNKNOWN | 12 | 0 | T |
| AA682406 | UNKNOWN | 12 | 0 | T |

TABLE 1-continued

| Genbank # | Region | # reps | Position | Unit sequence |
|---|---|---|---|---|
| AA682407 | UNKNOWN | 12 | 0 | T |
| AA682412 | UNKNOWN | 13 | 0 | T |
| AA682419 | UNKNOWN | 27 | 0 | T |
| AA682421 | UNKNOWN | 12 | 0 | T |
| AA682425 | UNKNOWN | 13 | 0 | T |
| AA682439 | UNKNOWN | 18 | 0 | T |
| AA682464 | UNKNOWN | 8.5 | 12 | TA |
| AA682512 | UNKNOWN | 14 | 105 | T |
| AA682523 | UNKNOWN | 15 | 69 | A |
| AA682549 | UNKNOWN | 6.5 | 283 | AG |
| AA682599 | UNKNOWN | 14 | 147 | T |
| AA682709 | UNKNOWN | 15 | 0 | T |
| AA682740 | UNKNOWN | 15 | 46 | A |
| AA682745 | UNKNOWN | 34 | 0 | T |
| AA682828 | UNKNOWN | 5.5 | 196 | TATT |
| AA682838 | UNKNOWN | 18 | 122 | A |
| AA683109 | UNKNOWN | 16 | 0 | T |
| AA683411 | UNKNOWN | 13 | 0 | T |
| AA687139 | UNKNOWN | 44 | 0 | T |
| AA687142 | UNKNOWN | 16 | 14 | T |
| AA687163 | UNKNOWN | 29 | 0 | T |
| AA687208 | UNKNOWN | 13 | 251 | A |
| AA687306 | UNKNOWN | 15 | 469 | A |
| AA687314 | UNKNOWN | 12 | 0 | T |
| AA687319 | UNKNOWN | 16 | 0 | T |
| AA687389 | UNKNOWN | 20 | 0 | T |
| AA687494 | UNKNOWN | 17 | 222 | A |
| AA687604 | UNKNOWN | 14 | 0 | T |
| AA687630 | UNKNOWN | 14 | 0 | T |
| AA687730 | UNKNOWN | 18 | 0 | T |
| AA688058 | UNKNOWN | 24 | 0 | T |
| AA688065 | UNKNOWN | 26 | 0 | T |
| AA688140 | UNKNOWN | 30 | 242 | T |
| AA688140 | UNKNOWN | 17 | 328 | A |
| AA688141 | UNKNOWN | 57 | 0 | T |
| AA688152 | UNKNOWN | 30 | 0 | T |
| AA688180 | UNKNOWN | 19 | 0 | T |
| AA688278 | UNKNOWN | 33 | 0 | T |
| AA688285 | UNKNOWN | 17 | 0 | T |
| AA689285 | UNKNOWN | 13 | 208 | A |
| AA689292 | UNKNOWN | 12 | 0 | T |
| AA689293 | UNKNOWN | 16 | 0 | T |
| AA689299 | UNKNOWN | 24 | 0 | T |
| AA693317 | UNKNOWN | 22 | 5 | T |
| AA693370 | UNKNOWN | 33 | 0 | T |
| AA693476 | UNKNOWN | 28 | 0 | T |
| AA693571 | UNKNOWN | 4.75 | 17 | TTTA |
| AA693730 | UNKNOWN | 4.8 | 137 | TTTTA |
| AA693730 | UNKNOWN | 14 | 318 | A |
| AA693816 | UNKNOWN | 3.66 | 266 | TTTGTT |
| AA693816 | UNKNOWN | 29 | 386 | A |
| AA699307 | UNKNOWN | 18 | 277 | A |
| AA699307 | UNKNOWN | 15 | 214 | T |
| AA699342 | UNKNOWN | 12 | 132 | A |
| AA699356 | UNKNOWN | 15 | 0 | T |
| AA699358 | UNKNOWN | 12 | 0 | T |
| AA699437 | UNKNOWN | 3.66 | 7 | TTTTTG |
| AA699437 | UNKNOWN | 12 | 0 | T |
| AA699450 | UNKNOWN | 13 | 0 | T |
| AA699475 | UNKNOWN | 12 | 0 | T |
| AA699492 | UNKNOWN | 3.85 | 14 | TTTTTTG |
| AA699492 | UNKNOWN | 20 | 0 | T |
| AA699497 | UNKNOWN | 12 | 0 | T |
| AA699504 | UNKNOWN | 12 | 0 | T |
| AA699533 | UNKNOWN | 12 | 0 | T |
| AA699557 | UNKNOWN | 5 | 19 | CAAA |
| AA699598 | UNKNOWN | 8 | 40 | AT |
| AA699916 | UNKNOWN | 4.8 | 121 | AAAAC |
| AA700024 | UNKNOWN | 7.5 | 432 | GT |
| AA700098 | UNKNOWN | 15 | 235 | T |
| AA700303 | UNKNOWN | 7.66 | 390 | CAC |
| AA700433 | UNKNOWN | 13 | 298 | A |
| AA700466 | UNKNOWN | 7.5 | 286 | TG |
| AA700554 | UNKNOWN | 13 | 358 | T |
| AA700554 | UNKNOWN | 12 | 0 | T |
| AA700567 | UNKNOWN | 12 | 0 | T |
| AA700573 | UNKNOWN | 12 | 107 | A |

TABLE 1-continued

| Genbank # | Region | # reps | Position | Unit sequence |
|---|---|---|---|---|
| AA700644 | UNKNOWN | 13 | 85 | A |
| AA700843 | UNKNOWN | 4.5 | 330 | AATG |
| AA700846 | UNKNOWN | 10 | 458 | AC |
| AA700906 | UNKNOWN | 3.5 | 9 | TTTTAT |
| AA700932 | UNKNOWN | 27 | 6 | T |
| AA700943 | UNKNOWN | 22 | 0 | T |
| AA700948 | UNKNOWN | 14 | 0 | T |
| AA700958 | UNKNOWN | 12 | 462 | T |
| AA701004 | UNKNOWN | 25 | 44 | T |
| AA701076 | UNKNOWN | 12 | 5 | T |
| AA701099 | UNKNOWN | 20 | 179 | A |
| AA701155 | UNKNOWN | 13 | 375 | A |
| AA701260 | UNKNOWN | 14 | 283 | T |
| AA701260 | UNKNOWN | 13 | 125 | A |
| AA701558 | UNKNOWN | 23 | 0 | T |
| AA701560 | UNKNOWN | 12 | 0 | T |
| AA701597 | UNKNOWN | 9.5 | 228 | TG |
| AA701597 | UNKNOWN | 21 | 7 | T |
| AA701665 | UNKNOWN | 12 | 423 | T |
| AA701909 | UNKNOWN | 11 | 210 | GT |
| AA701994 | UNKNOWN | 19 | 335 | T |
| AA702180 | UNKNOWN | 11 | 129 | GT |
| AA702339 | UNKNOWN | 25 | 46 | T |
| AA702407 | UNKNOWN | 24 | 152 | T |
| AA702463 | UNKNOWN | 16 | 0 | T |
| AA702506 | UNKNOWN | 12 | 93 | T |
| AA702529 | UNKNOWN | 6 | 63 | AAAT |
| AA702674 | UNKNOWN | 15 | 394 | T |
| AA703170 | UNKNOWN | 16 | 381 | A |
| AA703201 | UNKNOWN | 7.5 | 288 | GT |
| AA703247 | UNKNOWN | 3.17 | 318 | GCACAGAAGCGCAGAAGCAAAGCCCAGGCAGAACCATGCTAACCTTACAGCTCAGCCT (SEQ ID NO: 17) |
| AA703400 | UNKNOWN | 2.75 | 237 | GAAGGAAGAAAG (SEQ ID NO: 18) |
| AA703820 | UNKNOWN | 7.25 | 0 | TTTA |
| AA703945 | UNKNOWN | 25 | 0 | T |
| AA704016 | UNKNOWN | 12 | 0 | T |
| AA704166 | UNKNOWN | 13 | 123 | T |
| AA704268 | UNKNOWN | 12 | 101 | A |
| AA704322 | UNKNOWN | 7.5 | 243 | AC |
| AA704340 | UNKNOWN | 18 | 41 | T |
| AA704354 | UNKNOWN | 13 | 2 | T |
| AA704355 | UNKNOWN | 17 | 0 | T |
| AA704379 | UNKNOWN | 10.33 | 23 | TTA |
| AA704465 | UNKNOWN | 5.66 | 141 | TTG |
| AA704585 | UNKNOWN | 8.25 | 0 | ATTT |
| AA704862 | UNKNOWN | 8.5 | 235 | TC |
| AA704969 | UNKNOWN | 4.5 | 59 | AAAT |
| AA704974 | UNKNOWN | 17 | 258 | T |
| AA705059 | UNKNOWN | 5.5 | 117 | TCCT |
| AA705097 | UNKNOWN | 6.5 | 70 | TG |
| AA705201 | UNKNOWN | 6.5 | 417 | CA |
| AA705270 | UNKNOWN | 23 | 18 | A |
| AA705346 | UNKNOWN | 14 | 264 | T |
| AA705540 | UNKNOWN | 5.66 | 24 | AAC |
| AA705920 | UNKNOWN | 23 | 0 | T |
| AA705925 | UNKNOWN | 25 | 0 | T |
| AA706322 | UNKNOWN | 12 | 0 | T |
| AA706398 | UNKNOWN | 16 | 0 | T |
| AA706612 | UNKNOWN | 16 | 0 | T |
| AA706627 | UNKNOWN | 14 | 0 | T |
| AA706751 | UNKNOWN | 12 | 164 | A |
| AA706784 | UNKNOWN | 14 | 65 | A |
| AA707141 | UNKNOWN | 3.6 | 17 | TTTCT |
| AA707256 | UNKNOWN | 12 | 0 | T |
| AA707467 | UNKNOWN | 29 | 0 | T |
| AA707481 | UNKNOWN | 39 | 0 | T |
| AA707680 | UNKNOWN | 7 | 11 | CAAA |
| AA707915 | UNKNOWN | 8 | 101 | AC |
| AA707915 | UNKNOWN | 13 | 0 | T |
| AA708001 | UNKNOWN | 13 | 73 | A |
| AA708114 | UNKNOWN | 12 | 413 | A |
| AA708159 | UNKNOWN | 7.5 | 17 | AG |
| AA708243 | UNKNOWN | 24 | 0 | T |
| AA708322 | UNKNOWN | 16 | 29 | T |
| AA708400 | UNKNOWN | 20 | 0 | T |
| AA708413 | UNKNOWN | 19 | 0 | T |
| AA708658 | UNKNOWN | 21.5 | 282 | TG |

TABLE 1-continued

| Genbank # | Region | # reps | Position | Unit sequence |
|---|---|---|---|---|
| AA708837 | UNKNOWN | 15 | 0 | T |
| AA708883 | UNKNOWN | 12 | 0 | T |
| AA708890 | UNKNOWN | 21 | 0 | T |
| AA708903 | UNKNOWN | 14 | 40 | T |
| AA709270 | UNKNOWN | 26 | 0 | T |
| AA709471 | UNKNOWN | 18 | 38 | T |
| AA713479 | UNKNOWN | 34 | 0 | T |
| AA713486 | UNKNOWN | 13 | 0 | T |
| AA713518 | UNKNOWN | 12 | 0 | T |
| AA713661 | UNKNOWN | 19 | 0 | T |
| AA713671 | UNKNOWN | 13 | 0 | T |
| AA713693 | UNKNOWN | 17 | 372 | A |
| AA713693 | UNKNOWN | 15 | 0 | T |
| AA713796 | UNKNOWN | 15 | 355 | A |
| AA713797 | UNKNOWN | 17 | 0 | T |
| AA713948 | UNKNOWN | 14 | 0 | T |
| AA714023 | UNKNOWN | 37 | 0 | T |
| AA714172 | UNKNOWN | 19 | 0 | T |
| AA714224 | UNKNOWN | 20 | 0 | T |
| AA714338 | UNKNOWN | 44 | 0 | T |
| AA714339 | UNKNOWN | 29 | 0 | T |
| AA714477 | UNKNOWN | 15 | 0 | T |
| AA714487 | UNKNOWN | 28 | 0 | T |
| AA714637 | UNKNOWN | 15 | 263 | TG |
| AA714651 | UNKNOWN | 20 | 97 | T |
| AA714692 | UNKNOWN | 19 | 0 | T |
| AA714694 | UNKNOWN | 16 | 16 | T |
| AA714694 | UNKNOWN | 15 | 0 | T |
| AA714718 | UNKNOWN | 21 | 0 | T |
| AA714777 | UNKNOWN | 17 | 0 | T |
| AA714835 | UNKNOWN | 17 | 687 | T |
| AA714835 | UNKNOWN | 12 | 0 | T |
| AA715101 | UNKNOWN | 16 | 0 | T |
| AA715708 | UNKNOWN | 14 | 0 | T |
| AA718934 | UNKNOWN | 12 | 0 | T |
| AA719019 | UNKNOWN | 6.5 | 226 | CT |
| AA719057 | UNKNOWN | 17 | 0 | T |
| AA719069 | UNKNOWN | 12 | 416 | A |
| AA719160 | UNKNOWN | 3.5 | 67 | AAAACA |
| AA719162 | UNKNOWN | 32 | 0 | T |
| AA719252 | UNKNOWN | 30 | 0 | T |
| AA719376 | UNKNOWN | 25 | 0 | T |
| AA719392 | UNKNOWN | 7.5 | 215 | TC |
| AA720958 | UNKNOWN | 15 | 0 | T |
| AA721020 | UNKNOWN | 27 | 0 | T |
| AA721035 | UNKNOWN | 16 | 0 | T |
| AA721101 | UNKNOWN | 12 | 0 | T |
| AA721185 | UNKNOWN | 22 | 0 | T |
| AA721205 | UNKNOWN | 14 | 0 | T |
| AA721214 | UNKNOWN | 22 | 0 | T |
| AA721248 | UNKNOWN | 17 | 0 | T |
| AA723649 | UNKNOWN | 14 | 173 | T |
| AA723771 | UNKNOWN | 13 | 0 | T |
| AA724157 | UNKNOWN | 17 | 0 | T |
| AA724158 | UNKNOWN | 15.5 | 58 | GT |
| AA724158 | UNKNOWN | 7.5 | 102 | GA |
| AA724164 | UNKNQAN | 35 | 0 | T |
| AA724318 | UNKNOWN | 14 | 339 | T |
| AA724368 | UNKNOWN | 52 | 0 | T |
| AA724373 | UNKNOWN | 18 | 0 | T |
| AA724476 | UNKNOWN | 14 | 0 | T |
| AA724572 | UNKNOWN | 12 | 0 | T |
| AA724610 | UNKNOWN | 20 | 147 | T |
| AA724689 | UNKNOWN | 15 | 180 | A |
| AA724729 | UNKNOWN | 17 | 0 | T |
| AA724775 | UNKNOWN | 13 | 214 | A |
| AA724927 | UNKNOWN | 17 | 0 | T |
| AA724948 | UNKNOWN | 13 | 0 | T |
| AA725023 | UNKNOWN | 14 | 6 | T |
| AA725034 | UNKNOWN | 14 | 0 | T |
| AA725071 | UNKNOWN | 20 | 22 | T |
| AA725071 | UNKNOWN | 15 | 0 | T |
| AA725246 | UNKNOWN | 14 | 284 | T |
| AA725246 | UNKNOWN | 12 | 0 | T |
| AA725270 | UNKNOWN | 17 | 373 | T |
| AA725362 | UNKNOWN | 12 | 0 | T |
| AA725470 | UNKNOWN | 12 | 0 | T |

TABLE 1-continued

| Genbank # | Region | # reps | Position | Unit sequence |
|---|---|---|---|---|
| AA725580 | UNKNOWN | 29 | 0 | T |
| AA725584 | UNKNOWN | 15 | 0 | T |
| AA725644 | UNKNOWN | 23 | 392 | A |
| AA725646 | UNKNOWN | 9.5 | 156 | TG |
| AA725671 | UNKNOWN | 7.5 | 273 | AT |
| AA725725 | UNKNOWN | 16 | 0 | T |
| AA725740 | UNKNOWN | 16 | 0 | T |
| AA725812 | UNKNOWN | 13 | 0 | T |
| AA725844 | UNKNOWN | 13 | 0 | T |
| AA725888 | UNKNOWN | 21 | 0 | T |
| AA728936 | UNKNOWN | 14 | 298 | A |
| AA728946 | UNKNOWN | 14 | 418 | A |
| AA728954 | UNKNOWN | 20 | 294 | A |
| AA728978 | UNKNOWN | 15 | 287 | A |
| AA728999 | UNKNOWN | 16 | 0 | T |
| AA729017 | UNKNOWN | 57 | 0 | T |
| AA729043 | UNKNOWN | 7.5 | 67 | AG |
| AA729232 | UNKNOWN | 13 | 255 | T |
| AA729253 | UNKNOWN | 14 | 273 | A |
| AA729285 | UNKNOWN | 13 | 145 | A |
| AA729300 | UNKNOWN | 15 | 0 | T |
| AA729350 | UNKNOWN | 14 | 298 | A |
| AA729370 | UNKNOWN | 14 | 393 | A |
| AA729396 | UNKNOWN | 5.5 | 206 | TTGT |
| AA729396 | UNKNOWN | 17 | 25 | T |
| AA729474 | UNKNOWN | 14 | 286 | A |
| AA729540 | UNKNOWN | 7.5 | 46 | GT |
| AA729540 | UNKNOWN | 15 | 370 | A |
| AA729630 | UNKNOWN | 15 | 380 | A |
| AA729728 | UNKNOWN | 21 | 275 | A |
| AA730077 | UNKNOWN | 24 | 0 | T |
| AA730310 | UNKNOWN | 16 | 0 | T |
| AA730371 | UNKNOWN | 12 | 390 | A |
| AA730451 | UNKNOWN | 15 | 353 | A |
| AA730474 | UNKNOWN | 16 | 326 | A |
| AA730700 | UNKNOWN | 13 | 348 | A |
| AA730798 | UNKNOWN | 15 | 288 | A |
| AA730872 | UNKNOWN | 15 | 0 | T |
| AA730955 | UNKNOWN | 12 | 0 | T |
| AA731020 | UNKNOWN | 21 | 0 | T |
| AA731313 | UNKNOWN | 20 | 0 | T |
| AA731331 | UNKNOWN | 12 | 0 | T |
| AA731393 | UNKNOWN | 13 | 0 | T |
| AA731426 | UNKNOWN | 13 | 10 | T |
| AA731470 | UNKNOWN | 16 | 422 | T |
| AA731470 | UNKNOWN | 12 | 0 | T |
| AA731470 | UNKNOWN | 12 | 35 | A |
| AA731592 | UNKNOWN | 21 | 0 | T |
| AA731592 | UNKNOWN | 15 | 142 | A |
| AA731679 | UNKNOWN | 13 | 0 | T |
| AA731682 | UNKNOWN | 3.75 | 194 | TTTTTTAT |
| AA731682 | UNKNOWN | 39 | 0 | T |
| AA731703 | UNKNOWN | 34 | 0 | T |
| AA731718 | UNKNOWN | 35 | 0 | T |
| AA731738 | UNKNOWN | 12 | 0 | T |
| AA731833 | UNKNOWN | 29 | 0 | T |
| AA731853 | UNKNOWN | 26 | 0 | T |
| AA731941 | UNKNOWN | 31 | 0 | T |
| AA731990 | UNKNOWN | 35 | 0 | T |
| AA731993 | UNKNOWN | 21 | 0 | T |
| AA731994 | UNKNOWN | 17 | 0 | T |
| AA731998 | UNKNOWN | 31 | 0 | T |
| AA732055 | UNKNOWN | 18 | 172 | T |
| AA732224 | UNKNOWN | 29 | 0 | T |
| AA732242 | UNKNOWN | 17 | 0 | T |
| AA732356 | UNKNOWN | 33 | 0 | T |
| AA732378 | UNKNOWN | 18 | 240 | A |
| AA732385 | UNKNOWN | 20 | 0 | T |
| AA732453 | UNKNOWN | 19 | 160 | A |
| AA732624 | UNKNOWN | 13 | 0 | T |
| AA732628 | UNKNOWN | 15 | 0 | T |
| AA732756 | UNKNOWN | 15 | 0 | T |
| AA732773 | UNKNOWN | 17 | 0 | T |
| AA732814 | UNKNOWN | 18 | 0 | T |
| AA732837 | UNKNOWN | 4.75 | 5 | TTTA |
| AA732921 | UNKNOWN | 8.5 | 244 | TC |
| AA733157 | UNKNOWN | 18 | 0 | T |

TABLE 1-continued

| Genbank # | Region | # reps | Position | Unit sequence |
|---|---|---|---|---|
| AA736477 | UNKNOWN | 19 | 5 | T |
| AA736590 | UNKNOWN | 31 | 0 | T |
| AA736680 | UNKNOWN | 23 | 0 | T |
| AA736878 | UNKNOWN | 7.5 | 284 | TC |
| AA736931 | UNKNOWN | 22 | 0 | T |
| AA737046 | UNKNOWN | 32 | 151 | T |
| AA737046 | UNKNOWN | 20 | 0 | T |
| AA737176 | UNKNOWN | 19 | 0 | T |
| AA737553 | UNKNOWN | 17 | 0 | T |
| AA737804 | UNKNOWN | 31 | 0 | T |
| AA737842 | UNKNOWN | 9.5 | 365 | GT |
| AA738052 | UNKNOWN | 58 | 0 | T |
| AA738052 | UNKNOWN | 15 | 130 | C |
| AA738052 | UNKNOWN | 14 | 337 | A |
| AA738052 | UNKNOWN | 13 | 219 | G |
| AA738052 | UNKNOWN | 12 | 188 | A |
| AA738097 | UNKNOWN | 58 | 0 | T |
| AA738104 | UNKNOWN | 100 | 0 | T |
| AA738104 | UNKNOWN | 17 | 150 | A |
| AA738104 | UNKNOWN | 12 | 351 | C |
| AA738417 | UNKNOWN | 19 | 362 | GT |
| AA740243 | UNKNOWN | 30 | 0 | T |
| AA740246 | UNKNOWN | 17 | 0 | T |
| AA740404 | UNKNOWN | 7 | 293 | CA |
| AA740404 | UNKNOWN | 34 | 0 | T |
| AA740450 | UNKNOWN | 77 | 0 | T |
| AA740450 | UNKNOWN | 18 | 123 | G |
| AA740450 | UNKNOWN | 17 | 162 | C |
| AA740581 | UNKNOWN | 13 | 0 | T |
| AA740612 | UNKNOWN | 26 | 0 | T |
| AA740706 | UNKNOWN | 27 | 0 | T |
| AA740718 | UNKNOWN | 36 | 0 | T |
| AA740729 | UNKNOWN | 33 | 0 | T |
| AA740745 | UNKNOWN | 55 | 16 | T |
| AA740745 | UNKNOWN | 15 | 0 | T |
| AA740745 | UNKNOWN | 14 | 149 | A |
| AA740846 | UNKNOWN | 16 | 0 | T |
| AA740886 | UNKNOWN | 12 | 0 | T |
| AA740902 | UNKNOWN | 8.5 | 116 | TG |
| AA740902 | UNKNOWN | 8.5 | 138 | TA |
| AA740902 | UNKNOWN | 14 | 0 | T |
| AA740990 | UNKNOWN | 23 | 0 | T |
| AA741001 | UNKNOWN | 26 | 0 | T |
| AA741024 | UNKNOWN | 32 | 0 | T |
| AA741051 | UNKNOWN | 9 | 187 | TATC |
| AA741056 | UNKNOWN | 30 | 0 | T |
| AA741061 | UNKNOWN | 13 | 0 | T |
| AA741096 | UNKNOWN | 19 | 0 | T |
| AA741098 | UNKNOWN | 28 | 0 | T |
| AA741105 | UNKNOWN | 27 | 0 | T |
| AA741172 | UNKNOWN | 14 | 321 | A |
| AA741304 | UNKNOWN | 19 | 0 | T |
| AA741565 | UNKNOWN | 12 | 0 | T |
| AA742215 | UNKNOWN | 14 | 0 | T |
| AA742240 | UNKNOWN | 33 | 0 | T |
| AA742274 | UNKNOWN | 14 | 0 | T |
| AA742293 | UNKNOWN | 13 | 0 | T |
| AA742322 | UNKNOWN | 7.33 | 162 | AAT |
| AA742322 | UNKNOWN | 19 | 0 | T |
| AA742331 | UNKNOWN | 14 | 0 | T |
| AA742356 | UNKNOWN | 18 | 0 | T |
| AA742372 | UNKNOWN | 17 | 0 | T |
| AA742386 | UNKNOWN | 19 | 0 | T |
| AA742480 | UNKNOWN | 18 | 0 | T |
| AA742604 | UNKNOWN | 43 | 0 | T |
| AA742635 | UNKNOWN | 12 | 0 | T |
| AA742659 | UNKNOWN | 22 | 0 | T |
| AA742779 | UNKNOWN | 19 | 5 | T |
| AA742988 | UNKNOWN | 31 | 0 | T |
| AA743010 | UNKNOWN | 14 | 0 | T |
| AA743011 | UNKNOWN | 16 | 122 | A |
| AA743090 | UNKNOWN | 22 | 0 | T |
| AA743154 | UNKNOWN | 5 | 21 | ATTT |
| AA743200 | UNKNOWN | 17 | 0 | T |
| AA743213 | UNKNOWN | 7.5 | 261 | AC |
| AA743213 | UNKNOWN | 12 | 0 | T |
| AA743221 | UNKNOWN | 12 | 0 | T |

TABLE 1-continued

| Genbank # | Region | # reps | Position | Unit sequence |
|---|---|---|---|---|
| AA743289 | UNKNOWN | 15 | 0 | T |
| AA743322 | UNKNOWN | 14 | 0 | T |
| AA743397 | UNKNOWN | 13 | 0 | T |
| AA743401 | UNKNOWN | 20 | 316 | T |
| AA743401 | UNKNOWN | 17 | 1 | T |
| AA743413 | UNKNOWN | 17 | 0 | T |
| AA743433 | UNKNOWN | 27 | 0 | T |
| AA743445 | UNKNOWN | 40 | 0 | T |
| AA743474 | UNKNOWN | 44 | 0 | T |
| AA743476 | UNKNOWN | 44 | 0 | T |
| AA743539 | UNKNOWN | 21 | 0 | T |
| AA743546 | UNKNOWN | 12 | 0 | T |
| AA743552 | UNKNOWN | 3.83 | 19 | TTTTTG |
| AA743561 | UNKNOWN | 18 | 0 | T |
| AA743646 | UNKNOWN | 17 | 0 | T |
| AA743726 | UNKNOWN | 41 | 0 | T |
| AA743820 | UNKNOWN | 21 | 0 | T |
| AA743868 | UNKNOWN | 17 | 333 | A |
| AA743933 | UNKNOWN | 12 | 0 | T |
| AA743987 | UNKNOWN | 16 | 295 | A |
| AA743996 | UNKNOWN | 18 | 376 | A |
| AA744018 | UNKNOWN | 14 | 338 | A |
| AA744060 | UNKNOWN | 25 | 255 | A |
| AA744242 | UNKNOWN | 26 | 0 | T |
| AA744287 | UNKNOWN | 13 | 286 | A |
| AA744330 | UNKNOWN | 17 | 359 | A |
| AA744374 | UNKNOWN | 16 | 0 | T |
| AA744519 | UNKNOWN | 33 | 0 | T |
| AA744531 | UNKNOWN | 63 | 0 | T |
| AA744541 | UNKNOWN | 19 | 0 | T |
| AA744550 | UNKNOWN | 17 | 0 | T |
| AA744557 | UNKNOWN | 68 | 0 | T |
| AA744557 | UNKNOWN | 12 | 293 | C |
| AA744636 | UNKNOWN | 15 | 140 | A |
| AA744659 | UNKNOWN | 20 | 0 | T |
| AA744661 | UNKNOWN | 20 | 0 | T |
| AA744730 | UNKNOWN | 6.33 | 163 | TGA |
| AA744730 | UNKNOWN | 26 | 0 | T |
| AA744746 | UNKNOWN | 20 | 0 | T |
| AA744772 | UNKNOWN | 27 | 0 | T |
| AA744837 | UNKNOWN | 14 | 0 | T |
| AA744856 | UNKNOWN | 12 | 0 | T |
| AA744860 | UNKNOWN | 44 | 0 | T |
| AA744862 | UNKNOWN | 12 | 0 | T |
| AA744867 | UNKNOWN | 13 | 321 | A |
| AA744867 | UNKNOWN | 12 | 0 | T |
| AA745092 | UNKNOWN | 16 | 313 | A |
| AA745183 | UNKNOWN | 34 | 0 | T |
| AA745237 | UNKNOWN | 15 | 0 | T |
| AA745258 | UNKNOWN | 21 | 0 | T |
| AA745320 | UNKNOWN | 13 | 307 | A |
| AA745342 | UNKNOWN | 16 | 288 | A |
| AA745458 | UNKNOWN | 15 | 361 | A |
| AA745496 | UNKNOWN | 19 | 0 | T |
| AA745505 | UNKNOWN | 20 | 0 | T |
| AA745606 | UNKNOWN | 12 | 4 | T |
| AA745652 | UNKNOWN | 7 | 468 | TG |
| AA745652 | UNKNOWN | 15 | 0 | T |
| AA745676 | UNKNOWN | 17 | 0 | T |
| AA746175 | UNKNOWN | 35 | 0 | T |
| AA746215 | UNKNOWN | 28 | 0 | T |
| AA746290 | UNKNOWN | 9 | 563 | CA |
| AA746488 | UNKNOWN | 26 | 0 | T |
| AA746506 | UNKNOWN | 16 | 1 | T |
| AA746507 | UNKNOWN | 51 | 0 | T |
| AA746634 | UNKNOWN | 29 | 0 | T |
| AA746671 | UNKNOWN | 19 | 283 | A |
| AA746673 | UNKNOWN | 7.33 | 1 | CTA |
| AA746673 | UNKNOWN | 16 | 319 | A |
| AA746693 | UNKNOWN | 12 | 0 | T |
| AA746911 | UNKNOWN | 16 | 351 | A |
| AA746951 | UNKNOWN | 17 | 271 | A |
| AA746959 | UNKNOWN | 15 | 329 | A |
| AA747000 | UNKNOWN | 19 | 328 | A |
| AA747088 | UNKNOWN | 16 | 179 | A |
| AA747115 | UNKNOWN | 18 | 167 | A |
| AA747309 | UNKNOWN | 12 | 0 | T |

TABLE 1-continued

| Genbank # | Region | # reps | Position | Unit sequence |
|---|---|---|---|---|
| AA747322 | UNKNOWN | 16 | 449 | A |
| AA747514 | UNKNOWN | 14 | 312 | A |
| AA747531 | UNKNOWN | 22 | 0 | T |
| AA747704 | UNKNOWN | 22 | 0 | T |
| AA747713 | UNKNOWN | 12 | 0 | T |
| AA747800 | UNKNOWN | 20 | 0 | T |
| AA747942 | UNKNOWN | 17 | 197 | A |
| AA747957 | UNKNOWN | 14 | 0 | T |
| AA747958 | UNKNOWN | 13 | 0 | T |
| AA748015 | UNKNOWN | 16 | 0 | T |
| AA748045 | UNKNOWN | 19 | 0 | T |
| AA748058 | UNKNOWN | 18 | 505 | A |
| AA748182 | UNKNOWN | 25 | 364 | T |
| AA748182 | UNKNOWN | 15 | 0 | T |
| AA748189 | UNKNOWN | 17 | 0 | T |
| AA748328 | UNKNOWN | 14 | 0 | T |
| AA748343 | UNKNOWN | 67 | 0 | T |
| AA748343 | UNKNOWN | 15 | 83 | A |
| AA748343 | UNKNOWN | 14 | 117 | C |
| AA748343 | UNKNOWN | 13 | 149 | G |
| AA748361 | UNKNOWN | 29 | 0 | T |
| AA748361 | UNKNOWN | 17 | 188 | C |
| AA748387 | UNKNOWN | 19 | 0 | T |
| AA748422 | UNKNOWN | 20 | 0 | T |
| AA748479 | UNKNOWN | 25 | 0 | T |
| AA748494 | UNKNOWN | 14 | 0 | T |
| AA748500 | UNKNOWN | 34 | 0 | T |
| AA748539 | UNKNOWN | 13 | 0 | T |
| AA748556 | UNKNOWN | 16 | 0 | T |
| AA748610 | UNKNOWN | 15 | 0 | T |
| AA748682 | UNKNOWN | 51 | 0 | T |
| AA748722 | UNKNOWN | 3.6 | 39 | TTTTG |
| AA748722 | UNKNOWN | 33 | 0 | T |
| AA748762 | UNKNOWN | 14 | 0 | T |
| AA748779 | UNKNOWN | 19 | 0 | T |
| AA748780 | UNKNOWN | 37 | 0 | T |
| AA748842 | UNKNOWN | 19 | 0 | T |
| AA748897 | UNKNOWN | 12 | 0 | T |
| AA749035 | UNKNOWN | 21 | 0 | T |
| AA749048 | UNKNOWN | 43 | 0 | T |
| AA749058 | UNKNOWN | 23 | 0 | T |
| AA749058 | UNKNOWN | 15 | 37 | A |
| AA749081 | UNKNOWN | 14 | 0 | T |
| AA749123 | UNKNOWN | 36 | 0 | T |
| AA749207 | UNKNOWN | 21 | 0 | T |
| AA749210 | UNKNOWN | 18 | 10 | T |
| AA749217 | UNKNOWN | 35 | 0 | T |
| AA749235 | UNKNOWN | 17 | 0 | T |
| AA749285 | UNKNOWN | 13 | 417 | T |
| AA749338 | UNKNOWN | 13 | 0 | T |
| AA749444 | UNKNOWN | 17 | 0 | T |
| AA757005 | UNKNOWN | 47 | 0 | T |
| AA757106 | UNKNOWN | 14 | 0 | T |
| AA757115 | UNKNOWN | 15 | 0 | T |
| AA757118 | UNKNOWN | 3.8 | 214 | TTTTG |
| AA757196 | UNKNOWN | 19 | 0 | T |
| AA757262 | UNKNOWN | 27 | 0 | T |
| AA757322 | UNKNOWN | 16 | 0 | T |
| AA757343 | UNKNOWN | 18 | 0 | T |
| AA757392 | UNKNOWN | 17 | 0 | T |
| AA757455 | UNKNOWN | 17 | 0 | T |
| AA757484 | UNKNOWN | 4 | 49 | CAAAAA |
| AA757545 | UNKNOWN | 4.75 | 339 | TATG |
| AA757562 | UNKNOWN | 12 | 239 | A |
| AA757661 | UNKNOWN | 36 | 0 | T |
| AA757671 | UNKNOWN | 4.75 | 56 | CTTC |
| AA757710 | UNKNOWN | 13 | 3 | T |
| AA757800 | UNKNOWN | 14 | 5 | T |
| AA757806 | UNKNOWN | 16 | 367 | A |
| AA757812 | UNKNOWN | 28 | 0 | T |
| AA757864 | UNKNOWN | 19 | 125 | A |
| AA757870 | UNKNOWN | 13 | 333 | A |
| AA757900 | UNKNOWN | 15 | 157 | T |
| AA758032 | UNKNOWN | 22 | 0 | T |
| AA758199 | UNKNOWN | 17 | 0 | T |
| AA758211 | UNKNOWN | 17 | 0 | T |
| AA758327 | UNKNOWN | 20 | 0 | T |

TABLE 1-continued

| Genbank # | Region | # reps | Position | Unit sequence |
|---|---|---|---|---|
| AA758385 | UNKNOWN | 33 | 0 | T |
| AA758391 | UNKNOWN | 15 | 0 | T |
| AA758394 | UNKNOWN | 21 | 0 | T |
| AA758396 | UNKNOWN | 12 | 50 | A |
| AA758405 | UNKNOWN | 12 | 0 | T |
| AA758542 | UNKNOWN | 37 | 0 | T |
| AA758546 | UNKNOWN | 13 | 0 | T |
| AA758600 | UNKNOWN | 24 | 0 | T |
| AA758732 | UNKNOWN | 15 | 74 | T |
| AA758751 | UNKNOWN | 8 | 795 | CA |
| AA758751 | UNKNOWN | 43 | 702 | A |
| AA758763 | UNKNOWN | 23 | 0 | T |
| AA758841 | UNKNOWN | 33 | 0 | T |
| AA758920 | UNKNOWN | 39 | 0 | T |
| AA758924 | UNKNOWN | 15 | 0 | T |
| AA759093 | UNKNOWN | 12 | 0 | T |
| AA759190 | UNKNOWN | 12 | 0 | T |
| AA759213 | UNKNOWN | 15 | 24 | T |
| AA759254 | UNKNOWN | 21 | 0 | T |
| AA759269 | UNKNOWN | 20 | 0 | T |
| AA759286 | UNKNOWN | 37 | 0 | T |
| AA760689 | UNKNOWN | 7.5 | 91 | GT |
| AA760689 | UNKNOWN | 31 | 0 | T |
| AA760709 | UNKNOWN | 17 | 0 | T |
| AA760717 | UNKNOWN | 31 | 0 | T |
| AA760777 | UNKNOWN | 12 | 0 | T |
| AA760839 | UNKNOWN | 17 | 0 | T |
| AA760851 | UNKNOWN | 67 | 0 | T |
| AA760852 | UNKNOWN | 21.5 | 499 | GT |
| AA760852 | UNKNOWN | 16 | 11 | T |
| AA760894 | UNKNOWN | 13 | 0 | T |
| AA760899 | UNKNOWN | 12 | 0 | T |
| AA760928 | UNKNOWN | 34 | 0 | T |
| AA760956 | UNKNOWN | 36 | 0 | T |
| AA761040 | UNKNOWN | 15 | 0 | T |
| AA761092 | UNKNOWN | 37 | 0 | T |
| AA761116 | UNKNOWN | 23 | 0 | T |
| AA761158 | UNKNOWN | 25 | 0 | T |
| AA761212 | UNKNOWN | 18 | 0 | T |
| AA761292 | UNKNOWN | 13 | 10 | T |
| AA761300 | UNKNOWN | 34 | 0 | T |
| AA761323 | UNKNOWN | 62 | 0 | T |
| AA761347 | UNKNOWN | 19 | 0 | T |
| AA761369 | UNKNOWN | 29 | 0 | T |
| AA761372 | UNKNOWN | 12 | 115 | T |
| AA761382 | UNKNOWN | 15 | 0 | T |
| AA761387 | UNKNOWN | 22 | 0 | T |
| AA761388 | UNKNOWN | 3.6 | 104 | TTTCT |
| AA761388 | UNKNOWN | 25 | 0 | T |
| AA761399 | UNKNOWN | 7.5 | 75 | AC |
| AA761399 | UNKNOWN | 39 | 0 | T |
| AA761540 | UNKNOWN | 22 | 0 | T |
| AA761541 | UNKNOWN | 17 | 0 | T |
| AA761549 | UNKNOWN | 4 | 325 | TGTTT |
| AA761549 | UNKNOWN | 18 | 0 | T |
| AA761553 | UNKNOWN | 12 | 0 | T |
| AA761556 | UNKNOWN | 16 | 0 | T |
| AA761608 | UNKNOWN | 57 | 0 | T |
| AA761608 | UNKNOWN | 13 | 139 | A |
| AA761619 | UNKNOWN | 25 | 0 | T |
| AA761629 | UNKNOWN | 26 | 0 | T |
| AA761636 | UNKNOWN | 12 | 0 | T |
| AA761748 | UNKNOWN | 28 | 0 | T |
| AA761767 | UNKNOWN | 18 | 0 | T |
| AA761811 | UNKNOWN | 26 | 0 | T |
| AA761944 | UNKNOWN | 17 | 0 | T |
| AA761959 | UNKNOWN | 21 | 0 | T |
| AA764802 | UNKNOWN | 20 | 0 | T |
| AA764875 | UNKNOWN | 12 | 0 | T |
| AA764931 | UNKNOWN | 23 | 0 | T |
| AA764966 | UNKNOWN | 14 | 0 | T |
| AA765014 | UNKNOWN | 34 | 0 | T |
| AA765026 | UNKNOWN | 18 | 0 | T |
| AA765079 | UNKNOWN | 15 | 0 | T |
| AA765095 | UNKNOWN | 18 | 0 | T |
| AA765116 | UNKNOWN | 38 | 0 | T |
| AA765125 | UNKNOWN | 12 | 0 | T |

TABLE 1-continued

| Genbank # | Region | # reps | Position | Unit sequence |
|---|---|---|---|---|
| AA765131 | UNKNOWN | 15 | 0 | T |
| AA765234 | UNKNOWN | 37 | 0 | T |
| AA765305 | UNKNOWN | 14 | 0 | T |
| AA765369 | UNKNOWN | 16 | 0 | T |
| AA765417 | UNKNOWN | 16 | 0 | T |
| AA765439 | UNKNOWN | 18 | 0 | T |
| AA765454 | UNKNOWN | 17 | 325 | A |
| AA765454 | UNKNOWN | 15 | 0 | T |
| AA765580 | UNKNOWN | 21 | 0 | T |
| AA765597 | UNKNOWN | 12 | 5 | T |
| AA765668 | UNKNOWN | 33 | 0 | T |
| AA765672 | UNKNOWN | 4.5 | 32 | TCTT |
| AA765672 | UNKNOWN | 29 | 0 | T |
| AA765695 | UNKNOWN | 22 | 0 | T |
| AA765718 | UNKNOWN | 47 | 0 | T |
| AA765751 | UNKNOWN | 77 | 0 | T |
| AA765751 | UNKNOWN | 18 | 302 | G |
| AA765751 | UNKNOWN | 12 | 192 | G |
| AA765866 | UNKNOWN | 23 | 0 | T |
| AA765917 | UNKNOWN | 13 | 0 | T |
| AA765962 | UNKNOWN | 42 | 0 | T |
| AA766126 | UNKNOWN | 13 | 349 | T |
| AA766144 | UNKNOWN | 7.5 | 330 | AG |
| AA766144 | UNKNOWN | 7 | 317 | CA |
| AA766144 | UNKNOWN | 27 | 0 | T |
| AA766165 | UNKNOWN | 14 | 0 | T |
| AA766174 | UNKNOWN | 16 | 0 | T |
| AA766214 | UNKNOWN | 14 | 109 | A |
| AA766221 | UNKNOWN | 20 | 0 | T |
| AA766269 | UNKNOWN | 25 | 0 | T |
| AA766283 | UNKNOWN | 24 | 0 | T |
| AA766296 | UNKNOWN | 3.6 | 350 | AAAAT |
| AA766300 | UNKNOWN | 16 | 138 | A |
| AA766307 | UNKNOWN | 20 | 0 | T |
| AA766319 | UNKNOWN | 19 | 0 | T |
| AA766374 | UNKNOWN | 17 | 0 | T |
| AA766433 | UNKNOWN | 22 | 0 | T |
| AA766452 | UNKNOWN | 27 | 0 | T |
| AA766497 | UNKNOWN | 19 | 0 | T |
| AA766561 | UNKNOWN | 32 | 0 | T |
| AA766572 | UNKNOWN | 20 | 0 | T |
| AA766584 | UNKNOWN | 16 | 0 | T |
| AA766590 | UNKNOWN | 27 | 0 | T |
| AA766668 | UNKNOWN | 27 | 0 | T |
| AA766752 | UNKNOWN | 18 | 0 | T |
| AA766755 | UNKNOWN | 42 | 0 | T |
| AA766772 | UNKNOWN | 23 | 0 | T |
| AA766776 | UNKNOWN | 30 | 0 | T |
| AA766788 | UNKNOWN | 18 | 0 | T |
| AA766897 | UNKNOWN | 7 | 136 | CA |
| AA766998 | UNKNOWN | 22 | 0 | T |
| AA767009 | UNKNOWN | 41 | 0 | T |
| AA767012 | UNKNOWN | 14 | 98 | T |
| AA767034 | UNKNOWN | 24 | 0 | T |
| AA767039 | UNKNOWN | 52 | 0 | T |
| AA767122 | UNKNOWN | 55 | 0 | T |
| AA767235 | UNKNOWN | 16 | 500 | T |
| AA767368 | UNKNOWN | 19 | 0 | T |
| AA767372 | UNKNOWN | 14 | 0 | T |
| AA767412 | UNKNOWN | 23 | 0 | T |
| AA767416 | UNKNOWN | 22 | 0 | T |
| AA767444 | UNKNOWN | 28 | 0 | T |
| AA767454 | UNKNOWN | 16 | 0 | T |
| AA767459 | UNKNOWN | 19 | 0 | T |
| AA767473 | UNKNOWN | 28 | 0 | T |
| AA767537 | UNKNOWN | 24 | 9 | T |
| AA767643 | UNKNOWN | 14 | 0 | T |
| AA767669 | UNKNOWN | 33 | 0 | T |
| AA767755 | UNKNOWN | 41 | 18 | T |
| AA767755 | UNKNOWN | 17 | 0 | T |
| AA767801 | UNKNOWN | 24 | 0 | T |
| AA767804 | UNKNOWN | 17 | 0 | T |
| AA767881 | UNKNOWN | 14 | 0 | T |
| AA767883 | UNKNOWN | 21 | 0 | T |
| AA767911 | UNKNOWN | 4.75 | 55 | TTTG |
| AA767911 | UNKNOWN | 18 | 2 | T |
| AA767912 | UNKNOWN | 16 | 0 | T |

TABLE 1-continued

| Genbank # | Region | # reps | Position | Unit sequence |
|---|---|---|---|---|
| AA767927 | UNKNOWN | 34 | 0 | T |
| AA767935 | UNKNOWN | 29 | 0 | T |
| AA768041 | UNKNOWN | 13 | 33 | A |
| AA768139 | UNKNOWN | 23 | 0 | T |
| AA768282 | UNKNOWN | 17 | 0 | T |
| AA768284 | UNKNOWN | 15 | 0 | T |
| AA768330 | UNKNOWN | 13 | 0 | T |
| AA768332 | UNKNOWN | 12 | 0 | T |
| AA768633 | UNKNOWN | 31 | 0 | T |
| AA768643 | UNKNOWN | 40 | 0 | T |
| AA768884 | UNKNOWN | 13 | 0 | T |
| AA768895 | UNKNOWN | 22 | 0 | T |
| AA768897 | UNKNOWN | 13 | 0 | T |
| AA769030 | UNKNOWN | 13 | 0 | T |
| AA769053 | UNKNOWN | 12 | 0 | T |
| AA769056 | UNKNOWN | 14 | 0 | T |
| AA769099 | UNKNOWN | 21 | 0 | T |
| AA769219 | UNKNOWN | 19 | 0 | T |
| AA769220 | UNKNOWN | 23 | 0 | T |
| AA769240 | UNKNOWN | 16 | 0 | T |
| AA769310 | UNKNOWN | 21 | 0 | T |
| AA769398 | UNKNOWN | 18 | 0 | T |
| AA769408 | UNKNOWN | 25 | 0 | T |
| AA769428 | UNKNOWN | 29 | 0 | T |
| AA769433 | UNKNOWN | 69 | 0 | T |
| AA769438 | UNKNOWN | 8.5 | 438 | TC |
| AA769516 | UNKNOWN | 15 | 0 | T |
| AA769556 | UNKNOWN | 13 | 0 | T |
| AA769578 | UNKNOWN | 24 | 0 | T |
| AA769601 | UNKNOWN | 60 | 0 | T |
| AA769658 | UNKNOWN | 33 | 0 | T |
| AA769922 | UNKNOWN | 18 | 0 | T |
| AA770008 | UNKNOWN | 33 | 0 | T |
| AA770075 | UNKNOWN | 4 | 121 | TTGTT |
| AA770075 | UNKNOWN | 15 | 51 | A |
| AA770143 | UNKNOWN | 14 | 0 | T |
| AA770165 | UNKNOWN | 31 | 0 | T |
| AA770235 | UNKNOWN | 13 | 204 | A |
| AA770303 | UNKNOWN | 15 | 0 | T |
| AA770315 | UNKNOWN | 21 | 0 | T |
| AA770362 | UNKNOWN | 18 | 0 | T |
| AA770368 | UNKNOWN | 15 | 0 | T |
| AA770375 | UNKNOWN | 12 | 330 | A |
| AA770432 | UNKNOWN | 7 | 38 | TG |
| AA770443 | UNKNOWN | 12 | 0 | T |
| AA771921 | UNKNOWN | 12 | 0 | T |
| AA771925 | UNKNOWN | 15 | 0 | T |
| AA772055 | UNKNOWN | 14 | 231 | T |
| AA772172 | UNKNOWN | 3.66 | 108 | AAAACA |
| AA772242 | UNKNOWN | 5.66 | 184 | GGA |
| AA772259 | UNKNOWN | 24 | 0 | T |
| AA772278 | UNKNOWN | 18 | 204 | A |
| AA772318 | UNKNOWN | 38 | 0 | T |
| AA772318 | UNKNOWN | 12 | 116 | A |
| AA772352 | UNKNOWN | 17 | 0 | T |
| AA772401 | UNKNOWN | 35 | 0 | T |
| AA772405 | UNKNOWN | 12 | 0 | T |
| AA772426 | UNKNOWN | 12 | 0 | T |
| AA772459 | UNKNOWN | 13 | 186 | T |
| AA772493 | UNKNOWN | 12 | 285 | T |
| AA772692 | UNKNOWN | 14 | 0 | T |
| AA772916 | UNKNOWN | 18 | 386 | T |
| AA773098 | UNKNOWN | 3.8 | 371 | AAAAC |
| AA773098 | UNKNOWN | 14 | 38 | A |
| AA773132 | UNKNOWN | 15 | 0 | T |
| AA773319 | UNKNOWN | 26 | 0 | T |
| AA773348 | UNKNOWN | 2.58 | 1 | TTTTTTTCTTTC (SEQ ID NO: 19) |
| AA773348 | UNKNOWN | 22 | 25 | T |
| AA773535 | UNKNOWN | 29 | 0 | T |
| AA773535 | UNKNOWN | 19 | 148 | A |
| AA773601 | UNKNOWN | 31 | 0 | T |
| AA773644 | UNKNOWN | 5.66 | 93 | TTG |
| AA773807 | UNKNOWN | 3.5 | 96 | TGCCCC |
| AA774144 | UNKNOWN | 22 | 154 | T |
| AA774144 | UNKNOWN | 18 | 0 | T |
| AA774306 | UNKNOWN | 14 | 164 | A |
| AA774429 | UNKNOWN | 14 | 198 | T |

TABLE 1-continued

| Genbank # | Region | # reps | Position | Unit sequence |
|---|---|---|---|---|
| AA774452 | UNKNOWN | 3.8 | 78 | TTTTG |
| AA775149 | UNKNOWN | 21 | 0 | T |
| AA775173 | UNKNOWN | 13 | 211 | A |
| AA775179 | UNKNOWN | 15 | 420 | A |
| AA775208 | UNKNOWN | 18 | 0 | T |
| AA775230 | UNKNOWN | 14 | 0 | T |
| AA775240 | UNKNOWN | 24 | 0 | T |
| AA775400 | UNKNOWN | 26 | 248 | T |
| AA775409 | UNKNOWN | 3.8 | 250 | AAAAT |
| AA775409 | UNKNOWN | 12 | 122 | T |
| AA775448 | UNKNOWN | 15 | 0 | T |
| AA775468 | UNKNOWN | 17 | 0 | T |
| AA775574 | UNKNOWN | 16 | 242 | T |
| AA775799 | UNKNOWN | 26 | 0 | T |
| AA775830 | UNKNOWN | 13 | 0 | T |
| AA776076 | UNKNOWN | 6.14 | 64 | AAGAAGA |
| AA776076 | UNKNOWN | 4.14 | 40 | AAGAAGA |
| AA776076 | UNKNOWN | 10 | 115 | AGC |
| AA776076 | UNKNOWN | 6 | 99 | AAG |
| AA776243 | UNKNOWN | 29 | 0 | T |
| AA776289 | UNKNOWN | 6.5 | 235 | TG |
| AA776451 | UNKNOWN | 4.5 | 105 | AAAT |
| AA776478 | UNKNOWN | 4.5 | 165 | AGTC |
| AA776664 | UNKNOWN | 2.94 | 192 | TGGTGATGGTGGTGGTGG (SEQ ID NO: 20) |
| AA776664 | UNKNOWN | 8.66 | 153 | TGG |
| AA776665 | UNKNOWN | 13 | 346 | A |
| AA776694 | UNKNOWN | 16 | 106 | A |
| AA776699 | UNKNOWN | 12 | 53 | A |
| AA776705 | UNKNOWN | 18 | 0 | T |
| AA776731 | UNKNOWN | 12 | 164 | A |
| AA776731 | UNKNOWN | 12 | 357 | T |
| AA776742 | UNKNOWN | 12 | 0 | T |
| AA776881 | UNKNOWN | 16 | 35 | T |
| AA776882 | UNKNOWN | 7 | 42 | CA |
| AA776892 | UNKNOWN | 28 | 0 | T |
| AA777071 | UNKNOWN | 13 | 0 | T |
| AA777084 | UNKNOWN | 5.25 | 81 | AACC |
| AA777084 | UNKNOWN | 20 | 0 | T |
| AA777365 | UNKNOWN | 7 | 231 | GT |
| AA777369 | UNKNOWN | 7 | 484 | AG |
| AA777397 | UNKNOWN | 3.66 | 283 | TTTTCC |
| AA777664 | UNKNOWN | 9.5 | 25 | TA |
| AA777758 | UNKNOWN | 6 | 194 | TTG |
| AA777758 | UNKNOWN | 14 | 224 | T |
| AA777892 | UNKNOWN | 13 | 222 | A |
| AA777892 | UNKNOWN | 12 | 361 | T |
| AA777929 | UNKNOWN | 5.75 | 8 | TTGT |
| AA777933 | UNKNOWN | 35 | 0 | T |
| AA777946 | UNKNOWN | 14 | 0 | T |
| AA778177 | UNKNOWN | 9 | 379 | CA |
| AA778363 | UNKNOWN | 3.6 | 424 | AAATT |
| AA778399 | UNKNOWN | 12 | 178 | A |
| AA778569 | UNKNOWN | 5.66 | 37 | AAT |
| AA778626 | UNKNOWN | 26 | 0 | T |
| AA778636 | UNKNOWN | 19 | 0 | T |
| AA778694 | UNKNOWN | 12 | 265 | A |
| AA778739 | UNKNOWN | 15 | 0 | T |
| AA778758 | UNKNOWN | 12 | 329 | A |
| AA778828 | UNKNOWN | 6.5 | 337 | TA |
| AA778856 | UNKNOWN | 12 | 23 | A |
| AA778906 | UNKNOWN | 11.5 | 119 | CA |
| AA778998 | UNKNOWN | 16 | 258 | T |
| AA779226 | UNKNOWN | 13 | 391 | A |
| AA779441 | UNKNOWN | 20 | 0 | T |
| AA779599 | UNKNOWN | 4.75 | 113 | TTTA |
| AA779609 | UNKNOWN | 4.5 | 121 | TATT |
| AA779733 | UNKNOWN | 15 | 275 | A |
| AA779824 | UNKNOWN | 22 | 119 | T |
| AA779862 | UNKNOWN | 5.8 | 64 | AAAAC |
| AA779895 | UNKNOWN | 12 | 0 | T |
| AA779896 | UNKNOWN | 16 | 0 | T |
| AA779903 | UNKNOWN | 12 | 0 | T |
| AA779907 | UNKNOWN | 13 | 0 | T |
| AA779916 | UNKNOWN | 22 | 0 | T |
| AA779916 | UNKNOWN | 17 | 275 | A |
| AA779918 | UNKNOWN | 12 | 0 | T |
| AA779921 | UNKNOWN | 14 | 0 | T |

TABLE 1-continued

| Genbank # | Region | # reps | Position | Unit sequence |
|---|---|---|---|---|
| AA780014 | UNKNOWN | 21 | 243 | T |
| AA780014 | UNKNOWN | 15 | 0 | T |
| AA780027 | UNKNOWN | 18 | 0 | T |
| AA780033 | UNKNOWN | 13 | 0 | T |
| AA780106 | UNKNOWN | 6.5 | 62 | AC |
| AA780207 | UNKNOWN | 16 | 0 | T |
| AA780218 | UNKNOWN | 12 | 0 | T |
| AA780306 | UNKNOWN | 23 | 0 | T |
| AA780365 | UNKNOWN | 10.5 | 521 | TA |
| AA780912 | UNKNOWN | 15 | 0 | T |
| AA781075 | UNKNOWN | 16 | 0 | T |
| AA781153 | UNKNOWN | 13 | 445 | A |
| AA781156 | UNKNOWN | 15 | 73 | T |
| AA781170 | UNKNOWN | 16 | 0 | T |
| AA781188 | UNKNOWN | 7 | 211 | AC |
| AA781217 | UNKNOWN | 20 | 0 | T |
| AA781263 | UNKNOWN | 12 | 0 | T |
| AA781364 | UNKNOWN | 20 | 0 | TC |
| AA781372 | UNKNOWN | 15 | 0 | T |
| AA781449 | UNKNOWN | 4.59 | 261 | TTTGT |
| AA781810 | UNKNOWN | 21 | 0 | T |
| AA781811 | UNKNOWN | 13 | 159 | T |
| AA781832 | UNKNOWN | 7.75 | 7 | TTTA |
| AA781863 | UNKNOWN | 13 | 0 | T |
| AA781912 | UNKNOWN | 27 | 0 | T |
| AA781941 | UNKNOWN | 20 | 0 | T |
| AA781945 | UNKNOWN | 23 | 184 | T |
| AA782010 | UNKNOWN | 17 | 0 | T |
| AA782012 | UNKNOWN | 15 | 0 | T |
| AA782034 | UNKNOWN | 4.59 | 29 | AAAAC |
| AA782390 | UNKNOWN | 51 | 0 | T |
| AA782526 | UNKNOWN | 13 | 225 | T |
| AA782802 | UNKNOWN | 15 | 0 | T |
| AA782976 | UNKNOWN | 13 | 0 | T |
| AA783003 | UNKNOWN | 15 | 0 | T |
| AA788600 | UNKNOWN | 29 | 0 | T |
| AA788861 | UNKNOWN | 83 | 0 | T |
| AA788861 | UNKNOWN | 14 | 314 | G |
| AA788861 | UNKNOWN | 13 | 294 | A |
| AA788925 | UNKNOWN | 23 | 0 | T |
| AA788998 | UNKNOWN | 15 | 248 | T |
| AA789008 | UNKNOWN | 19 | 0 | T |
| AA789098 | UNKNOWN | 17 | 0 | T |
| AA789105 | UNKNOWN | 13 | 0 | T |
| AA789140 | UNKNOWN | 17 | 0 | T |
| AA789195 | UNKNOWN | 12 | 0 | T |
| AA789212 | UNKNOWN | 15 | 0 | T |
| AA789212 | UNKNOWN | 13 | 84 | A |
| AA789222 | UNKNOWN | 12 | 0 | T |
| AA789226 | UNKNOWN | 42 | 0 | T |
| AA789261 | UNKNOWN | 8.5 | 62 | TC |
| AA789285 | UNKNOWN | 12 | 0 | T |
| AA789298 | UNKNOWN | 17 | 0 | T |
| AA789302 | UNKNOWN | 15 | 512 | T |
| AA789312 | UNKNOWN | 13 | 0 | T |
| AA804177 | UNKNOWN | 23 | 0 | T |
| AA804211 | UNKNOWN | 3.6 | 36 | TTTTG |
| AA804263 | UNKNOWN | 13 | 417 | T |
| AA804267 | UNKNOWN | 12 | 0 | T |
| AA804375 | UNKNOWN | 24 | 0 | T |
| AA804397 | UNKNOWN | 17 | 0 | T |
| AA804482 | UNKNOWN | 17 | 0 | T |
| AA804515 | UNKNOWN | 27 | 0 | T |
| AA804532 | UNKNOWN | 17 | 0 | T |
| AA804538 | UNKNOWN | 20 | 0 | T |
| AA804585 | UNKNOWN | 12 | 0 | T |
| AA804615 | UNKNOWN | 15 | 15 | T |
| AA804615 | UNKNOWN | 13 | 0 | T |
| AA804674 | UNKNOWN | 12 | 0 | T |
| AA804728 | UNKNOWN | 15 | 28 | T |
| AA804743 | UNKNOWN | 28 | 0 | T |
| AA804745 | UNKNOWN | 19 | 0 | T |
| AA804771 | UNKNOWN | 19 | 0 | T |
| AA804776 | UNKNOWN | 43 | 0 | T |
| AA804779 | UNKNOWN | 20 | 0 | T |
| AA804780 | UNKNOWN | 25 | 0 | T |
| AA804804 | UNKNOWN | 21 | 0 | T |

TABLE 1-continued

| Genbank # | Region | # reps | Position | Unit sequence |
|---|---|---|---|---|
| AA804814 | UNKNOWN | 15 | 0 | T |
| AA804860 | UNKNOWN | 55 | 0 | T |
| AA804860 | UNKNOWN | 50 | 226 | A |
| AA804877 | UNKNOWN | 55 | 0 | T |
| AA804877 | UNKNOWN | 50 | 226 | A |
| AA804995 | UNKNOWN | 17 | 274 | A |
| AA805026 | UNKNOWN | 16 | 0 | T |
| AA805044 | UNKNOWN | 17 | 0 | T |
| AA805070 | UNKNOWN | 31 | 0 | T |
| AA805232 | UNKNOWN | 17 | 0 | T |
| AA805239 | UNKNOWN | 18 | 0 | T |
| AA805243 | UNKNOWN | 27 | 0 | T |
| AA805249 | UNKNOWN | 17 | 0 | T |
| AA805263 | UNKNOWN | 26 | 0 | T |
| AA805357 | UNKNOWN | 21 | 0 | T |
| AA805381 | UNKNOWN | 35 | 0 | T |
| AA805434 | UNKNOWN | 90 | 0 | T |
| AA805434 | UNKNOWN | 19 | 360 | A |
| AA805445 | UNKNOWN | 13 | 0 | T |
| AA805479 | UNKNOWN | 15 | 0 | T |
| AA805531 | UNKNOWN | 21 | 0 | T |
| AA805558 | UNKNOWN | 39 | 0 | T |
| AA805618 | UNKNOWN | 31 | 0 | T |
| AA805629 | UNKNOWN | 16 | 0 | T |
| AA805641 | UNKNOWN | 30 | 0 | T |
| AA805681 | UNKNOWN | 24 | 0 | T |
| AA805691 | UNKNOWN | 29 | 0 | T |
| AA805705 | UNKNOWN | 45 | 0 | T |
| AA805717 | UNKNOWN | 13 | 0 | T |
| AA805867 | UNKNOWN | 18 | 217 | A |
| AA805869 | UNKNOWN | 21 | 167 | T |
| AA805869 | UNKNOWN | 17 | 0 | T |
| AA805935 | UNKNOWN | 22 | 0 | T |
| AA805964 | UNKNOWN | 64 | 0 | T |
| AA805964 | UNKNOWN | 19 | 279 | G |
| AA805964 | UNKNOWN | 15 | 146 | A |
| AA805966 | UNKNOWN | 44 | 0 | T |
| AA805997 | UNKNOWN | 22 | 0 | T |
| AA806076 | UNKNOWN | 16 | 0 | T |
| AA806083 | UNKNOWN | 16 | 0 | T |
| AA806114 | UNKNOWN | 19 | 0 | T |
| AA806178 | UNKNOWN | 14 | 0 | T |
| AA806196 | UNKNOWN | 38 | 0 | T |
| AA806254 | UNKNOWN | 13 | 0 | T |
| AA806378 | UNKNOWN | 68 | 0 | T |
| AA806438 | UNKNOWN | 40 | 0 | T |
| AA806538 | UNKNOWN | 31 | 0 | T |
| AA806591 | UNKNOWN | 15 | 176 | T |
| AA806591 | UNKNOWN | 13 | 0 | T |
| AA806605 | UNKNOWN | 55 | 0 | T |
| AA806606 | UNKNOWN | 22 | 332 | A |
| AA806606 | UNKNOWN | 14 | 0 | T |
| AA806617 | UNKNOWN | 26 | 2 | T |
| AA806631 | UNKNOWN | 12 | 24 | T |
| AA806643 | UNKNOWN | 25 | 0 | T |
| AA806650 | UNKNOWN | 32 | 0 | T |
| AA806689 | UNKNOWN | 40 | 0 | T |
| AA806690 | UNKNOWN | 16 | 0 | T |
| AA806690 | UNKNOWN | 12 | 25 | A |
| AA806719 | UNKNOWN | 64 | 0 | T |
| AA806719 | UNKNOWN | 14 | 141 | A |
| AA806720 | UNKNOWN | 95 | 0 | T |
| AA806720 | UNKNOWN | 23 | 182 | C |
| AA806720 | UNKNOWN | 15 | 95 | A |
| AA806720 | UNKNOWN | 15 | 259 | G |
| AA806720 | UNKNOWN | 13 | 159 | G |
| AA806725 | UNKNOWN | 31 | 0 | T |
| AA806757 | UNKNOWN | 58 | 0 | T |
| AA806757 | UNKNOWN | 12 | 264 | G |
| AA806804 | UNKNOWN | 14 | 363 | A |
| AA806809 | UNKNOWN | 12 | 0 | T |
| AA806840 | UNKNOWN | 14 | 0 | T |
| AA806912 | UNKNOWN | 34 | 0 | T |
| AA806965 | UNKNOWN | 15 | 0 | T |
| AA807056 | UNKNOWN | 12 | 0 | T |
| AA807061 | UNKNOWN | 32 | 0 | T |
| AA807088 | UNKNOWN | 72 | 0 | T |

TABLE 1-continued

| Genbank # | Region | # reps | Position | Unit sequence |
|---|---|---|---|---|
| AA807097 | UNKNOWN | 22 | 0 | T |
| AA807133 | UNKNOWN | 13 | 5 | T |
| AA807140 | UNKNOWN | 13 | 0 | T |
| AA807142 | UNKNOWN | 19 | 0 | T |
| AA807154 | UNKNOWN | 17 | 0 | T |
| AA807155 | UNKNOWN | 16 | 0 | T |
| AA807225 | UNKNOWN | 27 | 0 | T |
| AA807269 | UNKNOWN | 38 | 0 | T |
| AA807307 | UNKNOWN | 39 | 0 | T |
| AA807341 | UNKNOWN | 23 | 0 | T |
| AA807352 | UNKNOWN | 82 | 0 | T |
| AA807352 | UNKNOWN | 12 | 254 | A |
| AA807360 | UNKNOWN | 16 | 351 | A |
| AA807360 | UNKNOWN | 15 | 382 | T |
| AA807360 | UNKNOWN | 13 | 291 | A |
| AA807362 | UNKNOWN | 48 | 0 | T |
| AA807362 | UNKNOWN | 21 | 383 | G |
| AA807371 | UNKNOWN | 24 | 0 | T |
| AA807497 | UNKNOWN | 36 | 0 | T |
| AA807544 | UNKNOWN | 31 | 0 | T |
| AA807607 | UNKNOWN | 24 | 0 | T |
| AA807612 | UNKNOWN | 18 | 0 | T |
| AA807676 | UNKNOWN | 7 | 137 | AT |
| AA807676 | UNKNOWN | 6.5 | 82 | AT |
| AA807736 | UNKNOWN | 18 | 0 | T |
| AA807836 | UNKNOWN | 16 | 0 | T |
| AA808002 | UNKNOWN | 14 | 0 | T |
| AA808012 | UNKNOWN | 30 | 0 | T |
| AA808012 | UNKNOWN | 12 | 274 | A |
| AA808060 | UNKNOWN | 95 | 0 | T |
| AA808060 | UNKNOWN | 17 | 129 | G |
| AA808060 | UNKNOWN | 12 | 174 | A |
| AA808153 | UNKNOWN | 4.75 | 50 | TTTA |
| AA808153 | UNKNOWN | 46 | 0 | T |
| AA808176 | UNKNOWN | 15 | 0 | T |
| AA808215 | UNKNOWN | 20 | 0 | T |
| AA808262 | UNKNOWN | 42 | 0 | T |
| AA808263 | UNKNOWN | 17 | 323 | A |
| AA808275 | UNKNOWN | 31 | 0 | T |
| AA808279 | UNKNOWN | 32 | 0 | T |
| AA808639 | UNKNOWN | 37 | 0 | T |
| AA808697 | UNKNOWN | 6.5 | 309 | CA |
| AA808697 | UNKNOWN | 13 | 0 | T |
| AA808788 | UNKNOWN | 14 | 284 | A |
| AA808959 | UNKNOWN | 17 | 0 | T |
| AA808964 | UNKNOWN | 17 | 0 | T |
| AA808991 | UNKNOWN | 13 | 293 | A |
| AA808991 | UNKNOWN | 12 | 144 | T |
| AA809173 | UNKNOWN | 13 | 286 | A |
| AA809265 | UNKNOWN | 18 | 0 | T |
| AA809303 | UNKNOWN | 17 | 0 | T |
| AA809305 | UNKNOWN | 44 | 0 | T |
| AA809314 | UNKNOWN | 15 | 0 | T |
| AA809349 | UNKNOWN | 27 | 0 | T |
| AA809353 | UNKNOWN | 17 | 0 | T |
| AA809405 | UNKNOWN | 18 | 0 | T |
| AA809411 | UNKNOWN | 35 | 0 | T |
| AA809468 | UNKNOWN | 25 | 0 | T |
| AA809469 | UNKNOWN | 32 | 0 | T |
| AA809516 | UNKNOWN | 17 | 185 | A |
| AA809516 | UNKNOWN | 15 | 0 | T |
| AA809647 | UNKNOWN | 27 | 0 | T |
| AA809684 | UNKNOWN | 12 | 0 | T |
| AA809872 | UNKNOWN | 24 | 0 | T |
| AA810089 | UNKNOWN | 16 | 0 | T |
| AA810156 | UNKNOWN | 16 | 186 | A |
| AA810220 | UNKNOWN | 37 | 0 | T |
| AA810267 | UNKNOWN | 16 | 0 | T |
| AA810287 | UNKNOWN | 34 | 0 | T |
| AA810369 | UNKNOWN | 18 | 0 | T |
| AA810404 | UNKNOWN | 12 | 0 | T |
| AA810430 | UNKNOWN | 13 | 0 | T |
| AA810441 | UNKNOWN | 28 | 0 | T |
| AA810474 | UNKNOWN | 28 | 0 | T |
| AA810512 | UNKNOWN | 7 | 103 | ATT |
| AA810512 | UNKNOWN | 15 | 0 | T |
| AA810599 | UNKNOWN | 12 | 0 | T |

TABLE 1-continued

| Genbank # | Region | # reps | Position | Unit sequence |
|---|---|---|---|---|
| AA810600 | UNKNOWN | 25 | 0 | T |
| AA810678 | UNKNOWN | 26 | 0 | T |
| AA810725 | UNKNOWN | 12 | 437 | A |
| AA810728 | UNKNOWN | 22 | 0 | T |
| AA810735 | UNKNOWN | 37 | 0 | T |
| AA810736 | UNKNOWN | 14 | 0 | T |
| AA810740 | UNKNOWN | 24 | 0 | T |
| AA810764 | UNKNOWN | 27 | 0 | T |
| AA810782 | UNKNOWN | 16 | 0 | T |
| AA810831 | UNKNOWN | 20 | 0 | T |
| AA810838 | UNKNOWN | 15 | 0 | T |
| AA810859 | UNKNOWN | 22 | 0 | T |
| AA810907 | UNKNOWN | 18 | 0 | T |
| AA810911 | UNKNOWN | 76 | 0 | T |
| AA810957 | UNKNOWN | 28 | 0 | T |
| AA810969 | UNKNOWN | 44 | 0 | T |
| AA810969 | UNKNOWN | 17 | 52 | A |
| AA811005 | UNKNOWN | 22 | 0 | T |
| AA811133 | UNKNOWN | 15 | 0 | T |
| AA811202 | UNKNOWN | 52 | 0 | T |
| AA811205 | UNKNOWN | 13 | 0 | T |
| AA811211 | UNKNOWN | 14 | 0 | T |
| AA811213 | UNKNOWN | 17 | 0 | T |
| AA811216 | UNKNOWN | 12 | 0 | T |
| AA811230 | UNKNOWN | 12 | 0 | T |
| AA811233 | UNKNOWN | 15 | 317 | T |
| AA811233 | UNKNOWN | 14 | 48 | A |
| AA811280 | UNKNOWN | 13 | 0 | T |
| AA811283 | UNKNOWN | 13 | 0 | T |
| AA811286 | UNKNOWN | 13 | 286 | T |
| AA811297 | UNKNOWN | 24 | 0 | T |
| AA811326 | UNKNOWN | 13 | 0 | T |
| AA811339 | UNKNOWN | 4.16 | 376 | TGGTTT |
| AA811339 | UNKNOWN | 33 | 0 | T |
| AA811341 | UNKNOWN | 17 | 0 | T |
| AA811369 | UNKNOWN | 35 | 0 | T |
| AA811371 | UNKNOWN | 8 | 459 | GA |
| AA811371 | UNKNOWN | 12 | 0 | T |
| AA811373 | UNKNOWN | 14 | 0 | T |
| AA811391 | UNKNOWN | 3.66 | 168 | CTCGTC |
| AA811391 | UNKNOWN | 27 | 0 | T |
| AA811406 | UNKNOWN | 61 | 0 | T |
| AA811465 | UNKNOWN | 15 | 0 | T |
| AA811469 | UNKNOWN | 9.25 | 258 | TCCA |
| AA811478 | UNKNOWN | 14 | 0 | T |
| AA811511 | UNKNOWN | 26 | 0 | T |
| AA811527 | UNKNOWN | 13 | 350 | A |
| AA811539 | UNKNOWN | 22 | 0 | T |
| AA811666 | UNKNOWN | 13 | 166 | A |
| AA811666 | UNKNOWN | 12 | 398 | T |
| AA811673 | UNKNOWN | 28 | 0 | T |
| AA811673 | UNKNOWN | 22 | 241 | A |
| AA811806 | UNKNOWN | 14 | 5 | T |
| AA811835 | UNKNOWN | 13 | 0 | T |
| AA812058 | UNKNOWN | 15 | 0 | T |
| AA812079 | UNKNOWN | 26 | 0 | T |
| AA812150 | UNKNOWN | 28 | 0 | T |
| AA812226 | UNKNOWN | 8 | 155 | TG |
| AA812226 | UNKNOWN | 12 | 0 | T |
| AA812231 | UNKNOWN | 5.75 | 6 | TTTG |
| AA812231 | UNKNOWN | 16 | 125 | A |
| AA812557 | UNKNOWN | 14 | 0 | T |
| AA812580 | UNKNOWN | 18 | 0 | T |
| AA812639 | UNKNOWN | 16 | 0 | T |
| AA812703 | UNKNOWN | 18 | 0 | T |
| AA812721 | UNKNOWN | 13 | 0 | T |
| AA812724 | UNKNOWN | 12 | 0 | T |
| AA812741 | UNKNOWN | 16 | 0 | T |
| AA812754 | UNKNOWN | 12 | 179 | AT |
| AA812848 | UNKNOWN | 22 | 0 | T |
| AA812872 | UNKNOWN | 18 | 0 | T |
| AA812925 | UNKNOWN | 7 | 205 | TA |
| AA813164 | UNKNOWN | 19 | 0 | T |
| AA813204 | UNKNOWN | 5.66 | 114 | TCA |
| AA813214 | UNKNOWN | 22 | 0 | T |
| AA813256 | UNKNOWN | 15 | 0 | T |
| AA813333 | UNKNOWN | 13 | 471 | T |

TABLE 1-continued

| Genbank # | Region | # reps | Position | Unit sequence |
|---|---|---|---|---|
| AA813379 | UNKNOWN | 19 | 0 | T |
| AA813492 | UNKNOWN | 30 | 0 | T |
| AA813496 | UNKNOWN | 4.75 | 217 | TTCA |
| AA813551 | UNKNOWN | 12 | 0 | T |
| AA813589 | UNKNOWN | 2.55 | 131 | GTCTTGATATGTGCTGAG (SEQ ID NO: 21) |
| AA813594 | UNKNOWN | 20 | 0 | T |
| AA813633 | UNKNOWN | 5.5 | 326 | TACC |
| AA813697 | UNKNOWN | 20 | 0 | T |
| AA813774 | UNKNOWN | 13 | 0 | T |
| AA813885 | UNKNOWN | 16 | 0 | T |
| AA813912 | UNKNOWN | 23 | 0 | T |
| AA813998 | UNKNOWN | 37 | 0 | T |
| AA813998 | UNKNOWN | 14 | 647 | A |
| AA814277 | UNKNOWN | 24 | 0 | T |
| AA814293 | UNKNOWN | 13 | 372 | T |
| AA814330 | UNKNOWN | 15 | 0 | T |
| AA814343 | UNKNOWN | 52 | 0 | T |
| AA814349 | UNKNOWN | 37 | 0 | T |
| AA814385 | UNKNOWN | 12 | 0 | T |
| AA814390 | UNKNOWN | 7.5 | 501 | AT |
| AA814390 | UNKNOWN | 26 | 0 | T |
| AA814397 | UNKNOWN | 14 | 0 | T |
| AA814399 | UNKNOWN | 14 | 0 | T |
| AA814407 | UNKNOWN | 99 | 0 | T |
| AA814407 | UNKNOWN | 18 | 207 | A |
| AA814407 | UNKNOWN | 13 | 235 | C |
| AA814409 | UNKNOWN | 35 | 0 | T |
| AA814527 | UNKNOWN | 23 | 267 | T |
| AA814527 | UNKNOWN | 15 | 0 | T |
| AA814583 | UNKNOWN | 32 | 0 | T |
| AA814667 | UNKNOWN | 21 | 0 | T |
| AA814670 | UNKNOWN | 30 | 0 | T |
| AA814693 | UNKNOWN | 30 | 0 | T |
| AA814700 | UNKNOWN | 19 | 0 | T |
| AA814707 | UNKNOWN | 27 | 0 | T |
| AA814807 | UNKNOWN | 28 | 0 | T |
| AA814823 | UNKNOWN | 12 | 237 | A |
| AA814890 | UNKNOWN | 15 | 0 | T |
| AA814914 | UNKNOWN | 37 | 0 | T |
| AA814939 | UNKNOWN | 22 | 0 | T |
| AA814977 | UNKNOWN | 43 | 0 | T |
| AA814986 | UNKNOWN | 26 | 0 | T |
| AA814990 | UNKNOWN | 70 | 0 | T |
| AA814990 | UNKNOWN | 15 | 236 | C |
| AA814994 | UNKNOWN | 15 | 0 | T |
| AA815031 | UNKNOWN | 27 | 0 | T |
| AA815043 | UNKNOWN | 5 | 6 | TTTG |
| AA815045 | UNKNOWN | 36 | 0 | T |
| AA815048 | UNKNOWN | 43 | 0 | T |
| AA815056 | UNKNOWN | 29 | 0 | T |
| AA815146 | UNKNOWN | 20 | 0 | T |
| AA815245 | UNKNOWN | 45 | 0 | T |
| AA815283 | UNKNOWN | 58 | 0 | T |
| AA815283 | UNKNOWN | 21 | 60 | A |
| AA815283 | UNKNOWN | 14 | 211 | G |
| AA815283 | UNKNOWN | 14 | 262 | C |
| AA815354 | UNKNOWN | 6.5 | 324 | AC |
| AA815366 | UNKNOWN | 13 | 0 | T |
| AA824300 | UNKNOWN | 17 | 249 | CA |
| AA824300 | UNKNOWN | 9.5 | 221 | CT |
| AA824316 | UNKNOWN | 13 | 272 | T |
| AA824377 | UNKNOWN | 18 | 0 | T |
| AA824386 | UNKNOWN | 14 | 0 | T |
| AA824393 | UNKNOWN | 14 | 0 | T |
| AA825353 | UNKNOWN | 18 | 30 | A |
| AA825399 | UNKNOWN | 30 | 0 | T |
| AA825503 | UNKNOWN | 18 | 378 | T |
| AA825510 | UNKNOWN | 15 | 0 | T |
| AA825548 | UNKNOWN | 59 | 0 | T |
| AA825556 | UNKNOWN | 19 | 0 | T |
| AA825581 | UNKNOWN | 15 | 0 | T |
| AA825618 | UNKNOWN | 34 | 0 | T |
| AA825638 | UNKNOWN | 27 | 0 | T |
| AA825644 | UNKNOWN | 43 | 0 | T |
| AA825652 | UNKNOWN | 19 | 57 | T |
| AA825664 | UNKNOWN | 24 | 0 | T |
| AA825819 | UNKNOWN | 12 | 0 | T |

TABLE 1-continued

| Genbank # | Region | # reps | Position | Unit sequence |
|---|---|---|---|---|
| AA825840 | UNKNOWN | 26 | 0 | T |
| AA825843 | UNKNOWN | 23 | 0 | T |
| AA825874 | UNKNOWN | 16 | 0 | T |
| AA825881 | UNKNOWN | 21 | 0 | T |
| AA825881 | UNKNOWN | 14 | 147 | A |
| AA825938 | UNKNOWN | 12 | 0 | T |
| AA825971 | UNKNOWN | 44 | 0 | T |
| AA825972 | UNKNOWN | 4.75 | 157 | AAAC |
| AA825972 | UNKNOWN | 21 | 0 | T |
| AA825976 | UNKNOWN | 17 | 0 | T |
| AA826002 | UNKNOWN | 16 | 315 | A |
| AA826020 | UNKNOWN | 16 | 0 | T |
| AA826148 | UNKNOWN | 18 | 0 | T |
| AA826176 | UNKNOWN | 19 | 0 | T |
| AA826186 | UNKNOWN | 68 | 0 | T |
| AA826186 | UNKNOWN | 14 | 192 | C |
| AA826186 | UNKNOWN | 12 | 82 | A |
| AA826300 | UNKNOWN | 16 | 7 | T |
| AA826301 | UNKNOWN | 14 | 0 | T |
| AA826312 | UNKNOWN | 17 | 7 | T |
| AA826316 | UNKNOWN | 16 | 0 | T |
| AA826683 | UNKNOWN | 13 | 0 | T |
| AA826931 | UNKNOWN | 14 | 0 | T |
| AA826933 | UNKNOWN | 15 | 0 | T |
| AA827053 | UNKNOWN | 28 | 0 | T |
| AA827055 | UNKNOWN | 17 | 0 | T |
| AA827080 | UNKNOWN | 15 | 387 | A |
| AA827084 | UNKNOWN | 13 | 436 | T |
| AA827096 | UNKNOWN | 16 | 0 | T |
| AA827118 | UNKNOWN | 20 | 0 | T |
| AA827178 | UNKNOWN | 30 | 0 | T |
| AA827188 | UNKNOWN | 20 | 0 | T |
| AA827203 | UNKNOWN | 34 | 0 | T |
| AA827214 | UNKNOWN | 12 | 0 | T |
| AA827226 | UNKNOWN | 13 | 127 | A |
| AA827293 | UNKNOWN | 22 | 0 | T |
| AA827621 | UNKNOWN | 13 | 0 | T |
| AA827622 | UNKNOWN | 29 | 0 | T |
| AA827623 | UNKNOWN | 13 | 0 | T |
| AA827631 | UNKNOWN | 23 | 0 | T |
| AA827672 | UNKNOWN | 19 | 0 | T |
| AA827674 | UNKNOWN | 13 | 371 | T |
| AA827680 | UNKNOWN | 3.8 | 331 | AAAAC |
| AA827701 | UNKNOWN | 31 | 0 | T |
| AA827722 | UNKNOWN | 24.5 | 226 | TG |
| AA827722 | UNKNOWN | 32 | 0 | T |
| AA827729 | UNKNOWN | 13 | 0 | T |
| AA827779 | UNKNOWN | 17 | 0 | T |
| AA827798 | UNKNOWN | 13 | 0 | T |
| AA827805 | UNKNOWN | 31 | 0 | T |
| AA827805 | UNKNOWN | 12 | 69 | A |
| AA827817 | UNKNOWN | 17 | 415 | A |
| AA827817 | UNKNOWN | 15 | 0 | T |
| AA827856 | UNKNOWN | 24 | 0 | T |
| AA827857 | UNKNOWN | 14 | 0 | T |
| AA827857 | UNKNOWN | 13 | 370 | A |
| AA827863 | UNKNOWN | 30 | 0 | T |
| AA827922 | UNKNOWN | 13 | 0 | T |
| AA828036 | UNKNOWN | 17 | 7 | T |
| AA828062 | UNKNOWN | 18 | 74 | A |
| AA828104 | UNKNOWN | 31 | 0 | T |
| AA828119 | UNKNOWN | 11.5 | 444 | AC |
| AA828119 | UNKNOWN | 29 | 0 | T |
| AA828129 | UNKNOWN | 14 | 0 | T |
| AA828145 | UNKNOWN | 18 | 316 | A |
| AA828268 | UNKNOWN | 16 | 0 | T |
| AA828268 | UNKNOWN | 15 | 387 | A |
| AA828277 | UNKNOWN | 12 | 298 | T |
| AA828293 | UNKNOWN | 28 | 0 | T |
| AA828359 | UNKNOWN | 34 | 0 | T |
| AA828376 | UNKNOWN | 15 | 246 | T |
| AA828395 | UNKNOWN | 35 | 0 | T |
| AA828395 | UNKNOWN | 19 | 380 | A |
| AA828395 | UNKNOWN | 13 | 56 | A |
| AA828419 | UNKNOWN | 16 | 0 | T |
| AA828454 | UNKNOWN | 49 | 0 | T |
| AA828473 | UNKNOWN | 24 | 0 | T |

TABLE 1-continued

| Genbank # | Region | # reps | Position | Unit sequence |
|---|---|---|---|---|
| AA828517 | UNKNOWN | 20 | 0 | T |
| AA828523 | UNKNOWN | 23 | 0 | T |
| AA828614 | UNKNOWN | 15 | 285 | A |
| AA828619 | UNKNOWN | 19 | 363 | A |
| AA828653 | UNKNOWN | 16 | 0 | T |
| AA828710 | UNKNOWN | 16 | 0 | T |
| AA828723 | UNKNOWN | 17 | 318 | A |
| AA828723 | UNKNOWN | 12 | 15 | A |
| AA828726 | UNKNOWN | 15 | 73 | A |
| AA828730 | UNKNOWN | 23 | 287 | A |
| AA828762 | UNKNOWN | 14 | 290 | A |
| AA828767 | UNKNOWN | 15 | 164 | A |
| AA828776 | UNKNOWN | 19 | 249 | A |
| AA828830 | UNKNOWN | 16 | 274 | A |
| AA828832 | UNKNOWN | 16 | 401 | A |
| AA828834 | UNKNOWN | 16 | 368 | A |
| AA828835 | UNKNOWN | 4.2 | 175 | AAAGA |
| AA828835 | UNKNOWN | 16 | 206 | A |
| AA828845 | UNKNOWN | 21 | 246 | A |
| AA828865 | UNKNOWN | 16 | 299 | A |
| AA828933 | UNKNOWN | 13 | 163 | A |
| AA828950 | UNKNOWN | 14 | 337 | A |
| AA829036 | UNKNOWN | 18 | 0 | T |
| AA829044 | UNKNOWN | 16 | 364 | A |
| AA829050 | UNKNOWN | 15 | 152 | A |
| AA829061 | UNKNOWN | 41 | 19 | T |
| AA829061 | UNKNOWN | 18 | 0 | T |
| AA829065 | UNKNOWN | 14 | 403 | A |
| AA829071 | UNKNOWN | 23 | 250 | A |
| AA829073 | UNKNOWN | 16 | 0 | T |
| AA829074 | UNKNOWN | 14 | 284 | A |
| AA829097 | UNKNOWN | 25 | 20 | T |
| AA829140 | UNKNOWN | 14 | 254 | A |
| AA829166 | UNKNOWN | 18 | 276 | A |
| AA829227 | UNKNOWN | 22 | 0 | T |
| AA829233 | UNKNOWN | 15 | 0 | T |
| AA829241 | UNKNOWN | 16 | 0 | T |
| AA829242 | UNKNOWN | 36 | 0 | T |
| AA829265 | UNKNOWN | 17 | 0 | T |
| AA829312 | UNKNOWN | 16 | 0 | T |
| AA829424 | UNKNOWN | 38 | 0 | T |
| AA829430 | UNKNOWN | 16 | 0 | T |
| AA829524 | UNKNOWN | 19 | 0 | T |
| AA829530 | UNKNOWN | 14 | 0 | T |
| AA829564 | UNKNOWN | 14 | 311 | A |
| AA829635 | UNKNOWN | 14 | 10 | T |
| AA829657 | UNKNOWN | 55 | 0 | T |
| AA829657 | UNKNOWN | 14 | 405 | G |
| AA829660 | UNKNOWN | 12 | 0 | T |
| AA829661 | UNKNOWN | 43 | 0 | T |
| AA829670 | UNKNOWN | 19 | 0 | T |
| AA829693 | UNKNOWN | 16 | 347 | A |
| AA829757 | UNKNOWN | 91 | 0 | T |
| AA829757 | UNKNOWN | 21 | 520 | C |
| AA829757 | UNKNOWN | 12 | 123 | A |
| AA829767 | UNKNOWN | 29 | 0 | T |
| AA829775 | UNKNOWN | 46 | 0 | T |
| AA829777 | UNKNOWN | 33 | 0 | T |
| AA829834 | UNKNOWN | 20 | 0 | T |
| AA829847 | UNKNOWN | 22 | 0 | T |
| AA829853 | UNKNOWN | 14 | 0 | T |
| AA829855 | UNKNOWN | 35 | 0 | T |
| AA830083 | UNKNOWN | 12 | 0 | T |
| AA830089 | UNKNOWN | 6.66 | 127 | AAC |
| AA830089 | UNKNOWN | 29 | 0 | T |
| AA830101 | UNKNOWN | 29 | 0 | T |
| AA830144 | UNKNOWN | 19 | 0 | T |
| AA830169 | UNKNOWN | 15 | 0 | T |
| AA830225 | UNKNOWN | 47 | 0 | T |
| AA830240 | UNKNOWN | 41 | 0 | T |
| AA830258 | UNKNOWN | 39 | 0 | T |
| AA830394 | UNKNOWN | 27 | 0 | T |
| AA830396 | UNKNOWN | 60 | 0 | T |
| AA830396 | UNKNOWN | 12 | 322 | A |
| AA830406 | UNKNOWN | 54 | 0 | T |
| AA830409 | UNKNOWN | 27 | 0 | T |
| AA830431 | UNKNOWN | 45 | 0 | T |

TABLE 1-continued

| Genbank # | Region | # reps | Position | Unit sequence |
|---|---|---|---|---|
| AA830455 | UNKNOWN | 22 | 0 | T |
| AA830498 | UNKNOWN | 22 | 28 | C |
| AA830498 | UNKNOWN | 18 | 0 | T |
| AA830498 | UNKNOWN | 17 | 192 | A |
| AA830558 | UNKNOWN | 44 | 0 | T |
| AA830578 | UNKNOWN | 12 | 0 | T |
| AA830590 | UNKNOWN | 12 | 0 | T |
| AA830612 | UNKNOWN | 12 | 0 | T |
| AA830650 | UNKNOWN | 23 | 0 | T |
| AA830668 | UNKNOWN | 20 | 0 | T |
| AA830673 | UNKNOWN | 34 | 0 | T |
| AA830679 | UNKNOWN | 14 | 419 | A |
| AA830701 | UNKNOWN | 12 | 84 | T |
| AA830709 | UNKNOWN | 64 | 0 | T |
| AA830709 | UNKNOWN | 15 | 244 | A |
| AA830709 | UNKNOWN | 12 | 232 | G |
| AA830725 | UNKNOWN | 28 | 0 | T |
| AA830778 | UNKNOWN | 13 | 0 | T |
| AA830821 | UNKNOWN | 76 | 0 | T |
| AA830842 | UNKNOWN | 24 | 0 | T |
| AA830854 | UNKNOWN | 12 | 0 | T |
| AA830881 | UNKNOWN | 29 | 0 | T |
| AA830897 | UNKNOWN | 23 | 0 | T |
| AA830929 | UNKNOWN | 24 | 0 | T |
| AA830958 | UNKNOWN | 44 | 0 | T |
| AA830999 | UNKNOWN | 12 | 0 | T |
| AA831043 | UNKNOWN | 40 | 0 | T |
| AA831152 | UNKNOWN | 3.6 | 150 | TTTTG |
| AA831257 | UNKNOWN | 26 | 0 | T |
| AA831306 | UNKNOWN | 34 | 0 | T |
| AA831323 | UNKNOWN | 12 | 0 | T |
| AA831331 | UNKNOWN | 37 | 0 | T |
| AA831350 | UNKNOWN | 28 | 0 | T |
| AA831350 | UNKNOWN | 22 | 241 | A |
| AA831597 | UNKNOWN | 5.5 | 51 | TTCC |
| AA831597 | UNKNOWN | 41 | 0 | T |
| AA831597 | UNKNOWN | 12 | 237 | A |
| AA831638 | UNKNOWN | 20 | 0 | T |
| AA831682 | UNKNOWN | 14 | 0 | T |
| AA831708 | UNKNOWN | 14 | 0 | T |
| AA831782 | UNKNOWN | 17 | 0 | T |
| AA831830 | UNKNOWN | 17 | 0 | T |
| AA831893 | UNKNOWN | 15 | 0 | T |
| AA832034 | UNKNOWN | 45 | 0 | T |
| AA832050 | UNKNOWN | 24 | 0 | T |
| AA832112 | UNKNOWN | 7 | 328 | CT |
| AA832136 | UNKNOWN | 14 | 200 | A |
| AA832165 | UNKNOWN | 5 | 215 | TAAA |
| AA832165 | UNKNOWN | 15 | 0 | T |
| AA832204 | UNKNOWN | 13 | 0 | T |
| AA832216 | UNKNOWN | 31 | 0 | T |
| AA832278 | UNKNOWN | 10 | 94 | TA |
| AA832336 | UNKNOWN | 14 | 0 | T |
| AA832417 | UNKNOWN | 22 | 0 | T |
| AA832438 | UNKNOWN | 47 | 0 | T |
| AA832466 | UNKNOWN | 15 | 0 | T |
| AA833530 | UNKNOWN | 19 | 0 | T |
| AA833542 | UNKNOWN | 15 | 0 | T |
| AA833633 | UNKNOWN | 16 | 0 | T |
| AA833738 | UNKNOWN | 13 | 0 | T |
| AA834967 | UNKNOWN | 6.33 | 116 | AAT |
| AA834994 | UNKNOWN | 12 | 8 | T |
| AA835006 | UNKNOWN | 7.5 | 52 | TC |
| AA835037 | UNKNOWN | 18 | 0 | T |
| AA835039 | UNKNOWN | 7.5 | 348 | TG |
| AA835070 | UNKNOWN | 14 | 0 | T |
| AA836066 | UNKNOWN | 19 | 206 | AT |
| AA836124 | UNKNOWN | 14 | 0 | T |
| AA836204 | UNKNOWN | 32 | 0 | T |
| AA836240 | UNKNOWN | 15 | 0 | T |
| AA836253 | UNKNOWN | 42 | 0 | T |
| AA836323 | UNKNOWN | 12 | 0 | T |
| AA836366 | UNKNOWN | 29 | 0 | T |
| AA836898 | UNKNOWN | 20 | 337 | T |
| AA837478 | UNKNOWN | 18 | 0 | T |
| AA838753 | UNKNOWN | 15 | 197 | A |
| AA838755 | UNKNOWN | 21 | 118 | A |

TABLE 1-continued

| Genbank # | Region | # reps | Position | Unit sequence |
|---|---|---|---|---|
| AA838755 | UNKNOWN | 15 | 0 | T |
| AA838771 | UNKNOWN | 22 | 0 | T |
| AA838835 | UNKNOWN | 16 | 14 | T |
| AA843120 | UNKNOWN | 22 | 0 | T |
| AA843217 | UNKNOWN | 14 | 0 | T |
| AA843219 | UNKNOWN | 18 | 31 | T |
| AA843242 | UNKNOWN | 15 | 0 | T |
| AA843280 | UNKNOWN | 11 | 205 | TA |
| AA843280 | UNKNOWN | 6.5 | 193 | TG |
| AA843305 | UNKNOWN | 24 | 0 | T |
| AA843417 | UNKNOWN | 26 | 0 | T |
| AA843533 | UNKNOWN | 12 | 0 | T |
| AA843541 | UNKNOWN | 14 | 0 | T |
| AA843545 | UNKNOWN | 12 | 271 | A |
| AA843569 | UNKNOWN | 18 | 15 | T |
| AA843713 | UNKNOWN | 13 | 0 | T |
| AA843728 | UNKNOWN | 13 | 0 | T |
| AA843773 | UNKNOWN | 19 | 0 | T |
| AA843779 | UNKNOWN | 4.75 | 24 | TTTA |
| AA843926 | UNKNOWN | 14 | 0 | T |
| AA843993 | UNKNOWN | 18 | 0 | T |
| AA844106 | UNKNOWN | 12 | 198 | A |
| AA844178 | UNKNOWN | 22 | 0 | T |
| AA844353 | UNKNOWN | 13 | 0 | T |
| AA844688 | UNKNOWN | 23 | 0 | T |
| AA844695 | UNKNOWN | 20 | 0 | T |
| AA844700 | UNKNOWN | 12 | 41 | T |
| AA844706 | UNKNOWN | 13 | 0 | T |
| AA845127 | UNKNOWN | 17 | 0 | T |
| AA845293 | UNKNOWN | 6.66 | 2 | TTA |
| AA845342 | UNKNOWN | 23 | 4 | T |
| AA845372 | UNKNOWN | 18 | 0 | T |
| AA845372 | UNKNOWN | 14 | 185 | A |
| AA845420 | UNKNOWN | 12 | 0 | T |
| AA845462 | UNKNOWN | 31 | 0 | T |
| AA845599 | UNKNOWN | 21 | 0 | T |
| AA846134 | UNKNOWN | 21 | 275 | A |
| AA846134 | UNKNOWN | 13 | 0 | T |
| AA846160 | UNKNOWN | 12 | 0 | T |
| AA846263 | UNKNOWN | 14 | 0 | T |
| AA846338 | UNKNOWN | 3.66 | 508 | TTTTCT |
| AA846343 | UNKNOWN | 34 | 0 | T |
| AA846405 | UNKNOWN | 13 | 0 | T |
| AA846412 | UNKNOWN | 14 | 0 | T |
| AA846790 | UNKNOWN | 7.5 | 286 | AG |
| AA846806 | UNKNOWN | 14 | 0 | T |
| AA846873 | UNKNOWN | 12 | 407 | T |
| AA846894 | UNKNOWN | 13 | 172 | A |
| AA846931 | UNKNOWN | 16 | 162 | A |
| AA846935 | UNKNOWN | 18 | 280 | A |
| AA847038 | UNKNOWN | 16 | 266 | A |
| AA847062 | UNKNOWN | 16 | 0 | T |
| AA847222 | UNKNOWN | 13 | 178 | A |
| AA847316 | UNKNOWN | 14 | 0 | T |
| AA847324 | UNKNOWN | 15 | 0 | T |
| AA847402 | UNKNOWN | 16 | 204 | A |
| AA847405 | UNKNOWN | 14 | 227 | A |
| AA847478 | UNKNOWN | 15 | 365 | A |
| AA847478 | UNKNOWN | 13 | 0 | T |
| AA847815 | UNKNOWN | 26 | 0 | T |
| AA847831 | UNKNOWN | 5.5 | 40 | TTAT |
| AA847831 | UNKNOWN | 25 | 0 | T |
| AA847862 | UNKNOWN | 20 | 0 | T |
| AA847880 | UNKNOWN | 19 | 45 | A |
| AA847880 | UNKNOWN | 18 | 0 | T |
| AA847904 | UNKNOWN | 24 | 0 | T |
| AA847973 | UNKNOWN | 14 | 0 | T |
| AA847976 | UNKNOWN | 14 | 316 | A |
| AA847977 | UNKNOWN | 15 | 292 | A |
| AA847982 | UNKNOWN | 15 | 163 | A |
| AA848010 | UNKNOWN | 32 | 0 | T |
| AA848023 | UNKNOWN | 26 | 0 | T |
| AA848053 | UNKNOWN | 76 | 0 | T |
| AA848053 | UNKNOWN | 16 | 108 | A |
| AA848085 | UNKNOWN | 48 | 0 | T |
| AA848112 | UNKNOWN | 4.75 | 53 | AAAC |
| AA848143 | UNKNOWN | 16 | 0 | T |

TABLE 1-continued

| Genbank # | Region | # reps | Position | Unit sequence |
|---|---|---|---|---|
| AA853944 | UNKNOWN | 7 | 114 | TC |
| AA853944 | UNKNOWN | 27 | 165 | T |
| AA853945 | UNKNOWN | 30 | 0 | T |
| AA853946 | UNKNOWN | 13 | 170 | A |
| AA853948 | UNKNOWN | 20 | 129 | C |
| AA853953 | UNKNOWN | 14 | 140 | G |
| AA853955 | UNKNOWN | 17 | 144 | A |
| AA853955 | UNKNOWN | 15 | 174 | G |
| AA854044 | UNKNOWN | 3.6 | 286 | AAACA |
| AA854150 | UNKNOWN | 14 | 0 | T |
| AA854248 | UNKNOWN | 14 | 0 | T |
| AA854648 | UNKNOWN | 12 | 0 | T |
| AA854756 | UNKNOWN | 13 | 0 | T |
| AA854944 | UNKNOWN | 23 | 0 | T |
| AA854963 | UNKNOWN | 14 | 0 | T |
| AA854993 | UNKNOWN | 5.75 | 30 | TTTA |
| AA855037 | UNKNOWN | 14 | 0 | T |
| AA855039 | UNKNOWN | 18 | 295 | A |
| AA855055 | UNKNOWN | 6.5 | 207 | AG |
| AA855180 | UNKNOWN | 12 | 0 | T |
| AA855182 | UNKNOWN | 16 | 0 | T |
| AA856697 | UNKNOWN | 59 | 0 | T |
| AA856762 | UNKNOWN | 14 | 0 | T |
| AA856841 | UNKNOWN | 25 | 268 | A |
| AA856871 | UNKNOWN | 14 | 304 | A |
| AA856873 | UNKNOWN | 16 | 361 | A |
| AA856946 | UNKNOWN | 14 | 0 | T |
| AA856969 | UNKNOWN | 16 | 0 | T |
| AA857097 | UNKNOWN | 24 | 0 | T |
| AA857306 | UNKNOWN | 86 | 0 | T |
| AA857306 | UNKNOWN | 22 | 226 | G |
| AA857306 | UNKNOWN | 15 | 209 | A |
| AA857306 | UNKNOWN | 13 | 187 | A |
| AA857311 | UNKNOWN | 99 | 0 | T |
| AA857370 | UNKNOWN | 15 | 181 | A |
| AA857380 | UNKNOWN | 18 | 271 | A |
| AA857428 | UNKNOWN | 19 | 0 | T |
| AA857473 | UNKNOWN | 18 | 0 | T |
| AA857486 | UNKNOWN | 17 | 0 | T |
| AA857823 | UNKNOWN | 21 | 288 | T |
| AA857847 | UNKNOWN | 59 | 0 | T |
| AA857847 | UNKNOWN | 34 | 94 | A |
| AA857871 | UNKNOWN | 34 | 0 | T |
| AA858058 | UNKNOWN | 24 | 0 | T |
| AA858289 | UNKNOWN | 23 | 5 | T |
| AA858289 | UNKNOWN | 15 | 184 | A |
| AA858289 | UNKNOWN | 12 | 172 | C |
| AA858297 | UNKNOWN | 7.5 | 39 | TA |
| AA860272 | UNKNOWN | 24 | 0 | T |
| AA860301 | UNKNOWN | 12 | 150 | A |
| AA862350 | UNKNOWN | 5.25 | 173 | AGGG |
| AA862350 | UNKNOWN | 12 | 0 | T |
| AA862485 | UNKNOWN | 48 | 0 | T |
| AA862645 | UNKNOWN | 10 | 44 | GGAA |
| AA862660 | UNKNOWN | 48 | 0 | T |
| AA862662 | UNKNOWN | 12 | 235 | A |
| AA862840 | UNKNOWN | 15 | 0 | T |
| AA863044 | UNKNOWN | 14 | 106 | A |
| AA863371 | UNKNOWN | 15 | 174 | A |
| AA863389 | UNKNOWN | 16 | 0 | T |
| AA863432 | UNKNOWN | 47 | 0 | T |
| AA863432 | UNKNOWN | 14 | 296 | G |
| AA864261 | UNKNOWN | 18 | 299 | A |
| AA864338 | UNKNOWN | 12 | 0 | T |
| AA864642 | UNKNOWN | 33 | 0 | T |
| AA864847 | UNKNOWN | 13 | 0 | T |
| AA865355 | UNKNOWN | 19 | 120 | T |
| AA865574 | UNKNOWN | 12 | 0 | T |
| AA865912 | UNKNOWN | 20 | 0 | T |
| AA865915 | UNKNOWN | 19 | 146 | A |
| AA866600 | UNKNOWN | 17 | 0 | T |
| AA866602 | UNKNOWN | 17 | 5 | T |
| AA868046 | UNKNOWN | 15 | 228 | A |
| AA868189 | UNKNOWN | 13 | 0 | T |
| AA868241 | UNKNOWN | 13 | 0 | T |
| AA868362 | UNKNOWN | 19 | 0 | T |
| AA868368 | UNKNOWN | 16 | 0 | T |

TABLE 1-continued

| Genbank # | Region | # reps | Position | Unit sequence |
|---|---|---|---|---|
| AA868371 | UNKNOWN | 39 | 0 | T |
| AA868391 | UNKNOWN | 22 | 0 | T |
| AA868415 | UNKNOWN | 23 | 0 | T |
| AA868467 | UNKNOWN | 12 | 169 | T |
| AA868469 | UNKNOWN | 4.8 | 0 | TTTTG |
| AA868486 | UNKNOWN | 59 | 0 | T |
| AA868507 | UNKNOWN | 12 | 265 | A |
| AA868555 | UNKNOWN | 15 | 0 | T |
| AA868558 | UNKNOWN | 13 | 0 | T |
| AA868563 | UNKNOWN | 23 | 0 | T |
| AA868575 | UNKNOWN | 15 | 329 | A |
| AA868610 | UNKNOWN | 18 | 201 | T |
| AA868610 | UNKNOWN | 15 | 179 | A |
| AA868623 | UNKNOWN | 13 | 184 | A |
| AA868632 | UNKNOWN | 17 | 0 | T |
| AA868641 | UNKNOWN | 22 | 0 | T |
| AA868714 | UNKNOWN | 16 | 160 | A |
| AA868714 | UNKNOWN | 13 | 0 | T |
| AA868722 | UNKNOWN | 19 | 0 | T |
| AA868726 | UNKNOWN | 6 | 328 | AAAG |
| AA868729 | UNKNOWN | 23 | 2 | T |
| AA868771 | UNKNOWN | 18 | 0 | T |
| AA868961 | UNKNOWN | 42 | 17 | T |
| AA868961 | UNKNOWN | 16 | 0 | T |
| AA868961 | UNKNOWN | 15 | 151 | G |
| AA872047 | UNKNOWN | 44 | 0 | T |
| AA872114 | UNKNOWN | 25 | 0 | T |
| AA872305 | UNKNOWN | 12 | 0 | T |
| AA872394 | UNKNOWN | 22 | 0 | T |
| AA872507 | UNKNOWN | 67 | 0 | T |
| AA872507 | UNKNOWN | 12 | 131 | C |
| AA872528 | UNKNOWN | 16 | 0 | T |
| AA872544 | UNKNOWN | 20 | 0 | T |
| AA872562 | UNKNOWN | 13 | 0 | T |
| AA872573 | UNKNOWN | 21 | 0 | T |
| AA872709 | UNKNOWN | 13 | 0 | T |
| AA872997 | UNKNOWN | 15 | 0 | T |
| AA873008 | UNKNOWN | 23 | 0 | T |
| AA873008 | UNKNOWN | 12 | 203 | A |
| AA873020 | UNKNOWN | 14 | 0 | T |
| AA873032 | UNKNOWN | 12 | 0 | T |
| AA873033 | UNKNOWN | 12 | 521 | T |
| AA873098 | UNKNOWN | 13 | 334 | T |
| AA873182 | UNKNOWN | 12 | 612 | TG |
| AA873479 | UNKNOWN | 24 | 208 | T |
| AA873479 | UNKNOWN | 15 | 0 | T |
| AA873573 | UNKNOWN | 21 | 0 | T |
| AA873632 | UNKNOWN | 13 | 436 | T |
| AA873633 | UNKNOWN | 13 | 0 | T |
| AA873646 | UNKNOWN | 12 | 0 | T |
| AA873650 | UNKNOWN | 17 | 49 | A |
| AA873662 | UNKNOWN | 19 | 0 | T |
| AA873827 | UNKNOWN | 3 | 281 | TGCCGAGAGAGCATGTAGG (SEQ ID NO: 22) |
| AA873876 | UNKNOWN | 21 | 296 | T |
| AA875847 | UNKNOWN | 31 | 0 | T |
| AA875847 | UNKNOWN | 17 | 365 | A |
| AA876002 | UNKNOWN | 18 | 0 | T |
| AA876072 | UNKNOWN | 3.8 | 0 | ATTTT |
| AA876146 | UNKNOWN | 16 | 0 | T |
| AA876183 | UNKNOWN | 43 | 0 | T |
| AA876279 | UNKNOWN | 14 | 0 | T |
| AA876415 | UNKNOWN | 17 | 0 | T |
| AA876490 | UNKNOWN | 17 | 195 | A |
| AA876502 | UNKNOWN | 15 | 108 | A |
| AA876646 | UNKNOWN | 20 | 161 | A |
| AA876676 | UNKNOWN | 15 | 219 | A |
| AA876677 | UNKNOWN | 8 | 1 | CTA |
| AA876677 | UNKNOWN | 17 | 294 | A |
| AA876747 | UNKNOWN | 22 | 274 | A |
| AA876772 | UNKNOWN | 13 | 193 | A |
| AA876957 | UNKNOWN | 8 | 2 | CTA |
| AA876957 | UNKNOWN | 17 | 198 | A |
| AA877064 | UNKNOWN | 18 | 275 | A |
| AA877065 | UNKNOWN | 16 | 0 | T |
| AA877293 | UNKNOWN | 13 | 2 | T |
| AA877413 | UNKNOWN | 22 | 19 | T |
| AA877460 | UNKNOWN | 12 | 35 | T |

TABLE 1-continued

| Genbank # | Region | # reps | Position | Unit sequence |
|---|---|---|---|---|
| AA877712 | UNKNOWN | 4.75 | 138 | TTTG |
| AA877817 | UNKNOWN | 31 | 0 | T |
| AA878055 | UNKNOWN | 14 | 10 | T |
| AA878056 | UNKNOWN | 20 | 0 | T |
| AA878236 | UNKNOWN | 6.5 | 346 | AC |
| AA878309 | UNKNOWN | 13 | 0 | T |
| AA878324 | UNKNOWN | 19 | 3 | T |
| AA878324 | UNKNOWN | 16 | 424 | A |
| AA878532 | UNKNOWN | 44 | 0 | T |
| AA878532 | UNKNOWN | 17 | 103 | A |
| AA878590 | UNKNOWN | 30 | 0 | T |
| AA878590 | UNKNOWN | 17 | 144 | A |
| AA878790 | UNKNOWN | 75 | 0 | T |
| AA878790 | UNKNOWN | 13 | 263 | C |
| AA878790 | UNKNOWN | 12 | 142 | A |
| AA878792 | UNKNOWN | 29 | 22 | T |
| AA878792 | UNKNOWN | 21 | 0 | T |
| AA878795 | UNKNOWN | 54 | 0 | T |
| AA878795 | UNKNOWN | 13 | 399 | C |
| AA878795 | UNKNOWN | 12 | 134 | G |
| AA878801 | UNKNOWN | 24 | 106 | G |
| AA878801 | UNKNOWN | 22 | 0 | T |
| AA878809 | UNKNOWN | 3.8 | 101 | TTTTC |
| AA878809 | UNKNOWN | 16 | 116 | T |
| AA878812 | UNKNOWN | 36 | 0 | T |
| AA878812 | UNKNOWN | 36 | 176 | A |
| AA878817 | UNKNOWN | 22 | 105 | A |
| AA878820 | UNKNOWN | 44 | 0 | T |
| AA878825 | UNKNOWN | 38 | 0 | T |
| AA878825 | UNKNOWN | 15 | 148 | A |
| AA878826 | UNKNOWN | 38 | 0 | T |
| AA878826 | UNKNOWN | 15 | 100 | G |
| AA878827 | UNKNOWN | 15 | 415 | A |
| AA878832 | UNKNOWN | 42 | 0 | T |
| AA878843 | UNKNOWN | 75 | 0 | T |
| AA878843 | UNKNOWN | 17 | 189 | G |
| AA878843 | UNKNOWN | 15 | 248 | C |
| AA878847 | UNKNOWN | 55 | 0 | T |
| AA878847 | UNKNOWN | 14 | 206 | C |
| AA878849 | UNKNOWN | 19 | 0 | T |
| AA878850 | UNKNOWN | 29 | 0 | T |
| AA878850 | UNKNOWN | 14 | 130 | A |
| AA879014 | UNKNOWN | 16 | 211 | A |
| AA879053 | UNKNOWN | 13 | 381 | A |
| AA879097 | UNKNOWN | 20 | 0 | T |
| AA879162 | UNKNOWN | 19 | 191 | A |
| AA879201 | UNKNOWN | 21 | 7 | T |
| AA879209 | UNKNOWN | 20 | 7 | T |
| AA879215 | UNKNOWN | 14 | 161 | A |
| AA879222 | UNKNOWN | 16 | 205 | A |
| AA879280 | UNKNOWN | 17 | 142 | A |
| AA879304 | UNKNOWN | 13 | 193 | A |
| AA879314 | UNKNOWN | 16 | 189 | A |
| AA879455 | UNKNOWN | 18 | 0 | T |
| AA883105 | UNKNOWN | 14 | 73 | T |
| AA883143 | UNKNOWN | 12 | 144 | T |
| AA883188 | UNKNOWN | 16 | 202 | T |
| AA883220 | UNKNOWN | 13 | 187 | T |
| AA883351 | UNKNOWN | 61 | 0 | T |
| AA883351 | UNKNOWN | 18 | 179 | C |
| AA883351 | UNKNOWN | 13 | 133 | A |
| AA883361 | UNKNOWN | 7 | 66 | AT |
| AA883503 | UNKNOWN | 17 | 143 | T |
| AA883533 | UNKNOWN | 3.6 | 171 | TTTTG |
| AA883533 | UNKNOWN | 15 | 0 | T |
| AA883612 | UNKNOWN | 12 | 0 | T |
| AA883644 | UNKNOWN | 23 | 0 | T |
| AA883670 | UNKNOWN | 12 | 0 | T |
| AA883707 | UNKNOWN | 20 | 0 | T |
| AA883884 | UNKNOWN | 12 | 72 | A |
| AA883897 | UNKNOWN | 8.66 | 38 | TTC |
| AA883973 | UNKNOWN | 25 | 0 | T |
| AA884004 | UNKNOWN | 21 | 0 | T |
| AA884030 | UNKNOWN | 13 | 0 | T |
| AA884077 | UNKNOWN | 27 | 0 | T |
| AA884242 | UNKNOWN | 37 | 0 | T |
| AA884242 | UNKNOWN | 20 | 327 | G |

TABLE 1-continued

| Genbank # | Region | # reps | Position | Unit sequence |
|---|---|---|---|---|
| AA884244 | UNKNOWN | 31 | 0 | T |
| AA884275 | UNKNOWN | 26 | 0 | T |
| AA884297 | UNKNOWN | 23 | 0 | T |
| AA884386 | UNKNOWN | 12 | 0 | T |
| AA884465 | UNKNOWN | 7 | 456 | AT |
| AA884465 | UNKNOWN | 7 | 475 | CA |
| AA884465 | UNKNOWN | 15 | 261 | A |
| AA884474 | UNKNOWN | 21 | 0 | T |
| AA884506 | UNKNOWN | 3.6 | 170 | GCCCT |
| AA884512 | UNKNOWN | 13 | 9 | A |
| AA884550 | UNKNOWN | 22 | 0 | T |
| AA884583 | UNKNOWN | 27 | 0 | T |
| AA884618 | UNKNOWN | 19 | 0 | T |
| AA884622 | UNKNOWN | 32 | 0 | T |
| AA884734 | UNKNOWN | 14 | 0 | T |
| AA884735 | UNKNOWN | 8 | 300 | TA |
| AA884826 | UNKNOWN | 14 | 0 | T |
| AA884966 | UNKNOWN | 14 | 0 | T |
| AA885044 | UNKNOWN | 17 | 8 | T |
| AA885197 | UNKNOWN | 38 | 0 | T |
| AA885219 | UNKNOWN | 8.33 | 317 | TGT |
| AA885221 | UNKNOWN | 12 | 0 | T |
| AA885229 | UNKNOWN | 14 | 160 | A |
| AA885409 | UNKNOWN | 15 | 527 | T |
| AA885428 | UNKNOWN | 15 | 330 | T |
| AA885428 | UNKNOWN | 12 | 114 | A |
| AA885440 | UNKNOWN | 21 | 0 | T |
| AA885510 | UNKNOWN | 4.8 | 158 | AAACC |
| AA885567 | UNKNOWN | 17 | 418 | A |
| AA885804 | UNKNOWN | 20 | 2 | T |
| AA885859 | UNKNOWN | 15 | 0 | T |
| AA885900 | UNKNOWN | 19 | 0 | T |
| AA886014 | UNKNOWN | 16 | 0 | T |
| AA886025 | UNKNOWN | 13 | 218 | A |
| AA886052 | UNKNOWN | 18 | 276 | A |
| AA886073 | UNKNOWN | 15 | 142 | A |
| AA886079 | UNKNOWN | 17 | 227 | A |
| AA886080 | UNKNOWN | 14 | 267 | A |
| AA886108 | UNKNOWN | 14.5 | 157 | AC |
| AA886108 | UNKNOWN | 16 | 185 | A |
| AA886136 | UNKNOWN | 13 | 222 | A |
| AA886153 | UNKNOWN | 19 | 414 | A |
| AA886166 | UNKNOWN | 15 | 179 | A |
| AA886546 | UNKNOWN | 13 | 226 | A |
| AA886552 | UNKNOWN | 17 | 211 | A |
| AA886607 | UNKNOWN | 15 | 136 | A |
| AA886753 | UNKNOWN | 5.75 | 23 | TTTA |
| AA886765 | UNKNOWN | 14 | 0 | T |
| AA886815 | UNKNOWN | 16 | 195 | A |
| AA886849 | UNKNOWN | 17 | 133 | A |
| AA886914 | UNKNONN | 12 | 15 | T |
| AA886919 | UNKNOWN | 7 | 500 | GA |
| AA887024 | UNKNOWN | 14 | 258 | A |
| AA887049 | UNKNOWN | 22 | 0 | T |
| AA887054 | UNKNOWN | 16 | 0 | T |
| AA887098 | UNKNOWN | 13 | 0 | T |
| AA887107 | UNKNOWN | 17 | 369 | A |
| AA887130 | UNKNOWN | 20 | 0 | T |
| AA887346 | UNKNOWN | 13 | 7 | T |
| AA887494 | UNKNOWN | 12 | 0 | T |
| AA887581 | UNKNOWN | 4.8 | 178 | TTTTG |
| AA887581 | UNKNOWN | 22 | 160 | T |
| AA887989 | UNKNOWN | 40 | 0 | T |
| AA888155 | UNKNOWN | 15.25 | 0 | TTTC |
| AA888196 | UNKNOWN | 50 | 0 | T |
| AA888196 | UNKNOWN | 12 | 128 | G |
| AA888200 | UNKNOWN | 22 | 104 | A |
| AA888267 | UNKNOWN | 12 | 0 | T |
| AA888281 | UNKNOWN | 14 | 145 | A |
| AA888320 | UNKNOWN | 15 | 325 | A |
| AA888331 | UNKNOWN | 16 | 207 | A |
| AA888369 | UNKNOWN | 16 | 200 | A |
| AA888406 | UNKNOWN | 16 | 239 | A |
| AA888408 | UNKNOWN | 13 | 226 | A |
| AA888419 | UNKNOWN | 13 | 315 | A |
| AA888436 | UNKNOWN | 18 | 225 | A |
| AA888443 | UNKNOWN | 15 | 121 | A |

TABLE 1-continued

| Genbank # | Region | # reps | Position | Unit sequence |
|---|---|---|---|---|
| AA888492 | UNKNOWN | 18 | 334 | A |
| AA888517 | UNKNOWN | 16 | 330 | A |
| AA888539 | UNKNOWN | 15 | 159 | A |
| AA888547 | UNKNOWN | 16 | 167 | A |
| AA888559 | UNKNOWN | 17 | 92 | A |
| AA888569 | UNKNOWN | 15 | 0 | T |
| AA888622 | UNKNOWN | 12 | 217 | T |
| AA888724 | UNKNOWN | 15 | 176 | A |
| AA888735 | UNKNOWN | 15 | 0 | T |
| AA888781 | UNKNOWN | 23 | 0 | T |
| AA888821 | UNKNOWN | 24 | 0 | T |
| AA888887 | UNKNOWN | 46 | 0 | T |
| AA888904 | UNKNOWN | 15 | 162 | T |
| AA888953 | UNKNOWN | 13 | 388 | A |
| AA888985 | UNKNOWN | 7 | 140 | TA |
| AA888985 | UNKNOWN | 12 | 127 | A |
| AA888988 | UNKNOWN | 15 | 0 | T |
| AA889131 | UNKNOWN | 13 | 46 | A |
| AA889423 | UNKNOWN | 17 | 108 | A |
| AA889648 | UNKNOWN | 13 | 5 | T |
| AA889687 | UNKNOWN | 3.66 | 440 | TTTTG |
| AA889687 | UNKNOWN | 14 | 0 | T |
| AA889723 | UNKNOWN | 14 | 0 | T |
| AA889754 | UNKNOWN | 11.5 | 67 | CA |
| AA889854 | UNKNOWN | 14 | 0 | T |
| AA890000 | UNKNOWN | 17 | 0 | T |
| AA890053 | UNKNOWN | 14 | 182 | T |
| AA890198 | UNKNOWN | 39 | 0 | T |
| AA890449 | UNKNOWN | 12 | 0 | T |
| AA890487 | UNKNOWN | 4.75 | 399 | AAAC |
| AA890487 | UNKNOWN | 12 | 415 | A |
| AA890587 | UNKNOWN | 16 | 299 | T |
| AA894392 | UNKNOWN | 32 | 0 | T |
| AA894471 | UNKNOWN | 14 | 179 | A |
| AA894887 | UNKNOWN | 16 | 300 | A |
| AA897338 | UNKNOWN | 20 | 0 | T |
| AA897379 | UNKNOWN | 23 | 0 | T |
| AA897384 | UNKNOWN | 17 | 336 | GT |
| AA897384 | UNKNOWN | 9.5 | 377 | TA |
| AA897461 | UNKNOWN | 7.66 | 73 | TTG |
| AA897501 | UNKNOWN | 3.83 | 341 | TCTTCC |
| AA897597 | UNKNOWN | 3.8 | 103 | TTTTC |
| AA902278 | UNKNOWN | 13 | 0 | T |
| AA902283 | UNKNOWN | 47 | 15 | T |
| AA902283 | UNKNOWN | 15 | 168 | A |
| AA902283 | UNKNOWN | 14 | 0 | T |
| AA902318 | UNKNOWN | 28 | 0 | T |
| AA902368 | UNKNOWN | 12 | 0 | T |
| AA902374 | UNKNOWN | 16 | 199 | A |
| AA902475 | UNKNOWN | 12 | 0 | T |
| AA902661 | UNKNOWN | 29 | 19 | T |
| AA902661 | UNKNOWN | 14 | 0 | T |
| AA902672 | UNKNOWN | 12 | 215 | A |
| AA902730 | UNKNOWN | 14 | 374 | A |
| AA902764 | UNKNOWN | 17 | 0 | T |
| AA902808 | UNKNOWN | 14 | 0 | T |
| AA902912 | UNKNOWN | 12 | 0 | T |
| AA902986 | UNKNOWN | 12 | 0 | T |
| AA903056 | UNKNOWN | 17 | 0 | T |
| AA903067 | UNKNOWN | 56 | 14 | T |
| AA903067 | UNKNOWN | 21 | 379 | G |
| AA903067 | UNKNOWN | 20 | 229 | C |
| AA903067 | UNKNOWN | 19 | 249 | G |
| AA903067 | UNKNOWN | 17 | 164 | A |
| AA903067 | UNKNOWN | 13 | 0 | T |
| AA903067 | UNKNOWN | 12 | 122 | A |
| AA903067 | UNKNOWN | 12 | 181 | C |
| AA903106 | UNKNOWN | 63 | 0 | T |
| AA903109 | UNKNOWN | 16 | 447 | A |
| AA903109 | UNKNOWN | 14 | 0 | T |
| AA903187 | UNKNOWN | 51 | 0 | T |
| AA903187 | UNKNOWN | 15 | 206 | A |
| AA903230 | UNKNOWN | 33 | 0 | T |
| AA903230 | UNKNOWN | 16 | 275 | A |
| AA903243 | UNKNOWN | 33 | 15 | T |
| AA903243 | UNKNOWN | 14 | 0 | T |
| AA903243 | UNKNOWN | 14 | 201 | C |

TABLE 1-continued

| Genbank # | Region | # reps | Position | Unit sequence |
|---|---|---|---|---|
| AA903749 | UNKNOWN | 24 | 0 | T |
| AA903982 | UNKNOWN | 34 | 14 | T |
| AA903982 | UNKNOWN | 12 | 0 | T |
| AA903982 | UNKNOWN | 12 | 157 | G |
| AA904227 | UNKNOWN | 13 | 139 | A |
| AA904275 | UNKNOWN | 17 | 13 | T |
| AA904293 | UNKNOWN | 13 | 301 | A |
| AA904384 | UNKNOWN | 13 | 298 | A |
| AA904423 | UNKNOWN | 13.33 | 15 | TTA |
| AA904461 | UNKNOWN | 13 | 0 | T |
| AA904656 | UNKNOWN | 17 | 0 | T |
| AA904770 | UNKNOWN | 12 | 51 | A |
| AA904793 | UNKNOWN | 20 | 0 | T |
| AA904936 | UNKNOWN | 15 | 0 | T |
| AA904979 | UNKNOWN | 14 | 6 | T |
| AA905059 | UNKNOWN | 17 | 0 | T |
| AA905270 | UNKNOWN | 19 | 0 | T |
| AA905307 | UNKNOWN | 6.5 | 177 | TC |
| AA905375 | UNKNOWN | 15 | 14 | T |
| AA905405 | UNKNOWN | 6 | 32 | TTTG |
| AA905410 | UNKNOWN | 20 | 26 | A |
| AA905449 | UNKNOWN | 14 | 0 | T |
| AA905508 | UNKNOWN | 13 | 0 | T |
| AA905518 | UNKNOWN | 6.5 | 175 | TC |
| AA905942 | UNKNOWN | 14 | 182 | A |
| AA906061 | UNKNOWN | 19 | 0 | T |
| AA906075 | UNKNOWN | 16 | 99 | A |
| AA906248 | UNKNOWN | 12 | 97 | T |
| AA906250 | UNKNOWN | 29 | 0 | T |
| AA906269 | UNKNOWN | 25 | 0 | T |
| AA906378 | UNKNOWN | 13 | 197 | A |
| AA906386 | UNKNOWN | 16 | 0 | T |
| AA907020 | UNKNOWN | 25 | 0 | T |
| AA907022 | UNKNOWN | 16 | 0 | T |
| AA907040 | UNKNOWN | 17 | 54 | T |
| AA907080 | UNKNOWN | 14 | 0 | T |
| AA907660 | UNKNOWN | 17 | 343 | A |
| AA907660 | UNKNOWN | 14 | 309 | T |
| AA907663 | UNKNOWN | 10 | 98 | AT |
| AA907779 | UNKNOWN | 5.66 | 10 | TTG |
| AA907779 | UNKNOWN | 26 | 149 | A |
| AA907779 | UNKNOWN | 12 | 0 | T |
| AA907943 | UNKNOWN | 16 | 0 | T |
| AA908270 | UNKNOWN | 42 | 0 | T |
| AA908270 | UNKNOWN | 12 | 233 | A |
| AA908294 | UNKNOWN | 79 | 0 | T |
| AA908294 | UNKNOWN | 15 | 104 | A |
| AA908351 | UNKNOWN | 3.83 | 51 | AAAACA |
| AA908367 | UNKNOWN | 35 | 0 | T |
| AA908367 | UNKNOWN | 12 | 304 | A |
| AA908496 | UNKNOWN | 34 | 0 | T |
| AA908555 | UNKNOWN | 19.5 | 298 | GT |
| AA908631 | UNKNOWN | 14 | 0 | T |
| AA908687 | UNKNOWN | 21 | 0 | T |
| AA908747 | UNKNOWN | 12 | 0 | T |
| AA908801 | UNKNOWN | 27 | 111 | T |
| AA908801 | UNKNOWN | 12 | 12 | T |
| AA908851 | UNKNOWN | 21 | 3 | T |
| AA908897 | UNKNOWN | 12 | 493 | T |
| AA908979 | UNKNOWN | 45 | 0 | T |
| AA909024 | UNKNOWN | 12 | 0 | T |
| AA909030 | UNKNOWN | 12 | 0 | T |
| AA909064 | UNKNOWN | 15 | 307 | A |
| AA909095 | UNKNOWN | 30 | 0 | T |
| AA909147 | UNKNOWN | 3.6 | 4 | ATTTT |
| AA909317 | UNKNOWN | 13 | 0 | T |
| AA909336 | UNKNOWN | 13 | 0 | T |
| AA909445 | UNKNOWN | 10.66 | 245 | AAT |
| AA909476 | UNKNOWN | 17 | 0 | T |
| AA909501 | UNKNOWN | 16 | 6 | T |
| AA909569 | UNKNOWN | 12 | 264 | A |
| AA909664 | UNKNOWN | 12 | 244 | A |
| AA909694 | UNKNOWN | 12.5 | 82 | CT |
| AA909745 | UNKNOWN | 18 | 0 | T |
| AA909980 | UNKNOWN | 12 | 86 | A |
| AA910186 | UNKNOWN | 18 | 0 | T |
| AA910404 | UNKNOWN | 15 | 87 | A |

TABLE 1-continued

| Genbank # | Region | # reps | Position | Unit sequence |
|---|---|---|---|---|
| AA910523 | UNKNOWN | 5.66 | 187 | GAG |
| AA910680 | UNKNOWN | 18 | 284 | T |
| AA910733 | UNKNOWN | 5.25 | 101 | AGGG |
| AA910846 | UNKNOWN | 14 | 128 | A |
| AA911091 | UNKNOWN | 17 | 0 | T |
| AA911187 | UNKNOWN | 27 | 0 | T |
| AA911214 | UNKNOWN | 16 | 300 | T |
| AA911228 | UNKNOWN | 22 | 344 | A |
| AA911426 | UNKNOWN | 31 | 299 | G |
| AA911426 | UNKNOWN | 27 | 253 | A |
| AA911426 | UNKNOWN | 14 | 226 | C |
| AA911564 | UNKNOWN | 17 | 0 | T |
| AA911569 | UNKNOWN | 31 | 0 | T |
| AA911576 | UNKNOWN | 16 | 0 | T |
| AA911767 | UNKNOWN | 76 | 0 | T |
| AA911767 | UNKNOWN | 19 | 100 | A |
| AA911998 | UNKNOWN | 63 | 0 | T |
| AA912057 | UNKNOWN | 13 | 82 | A |
| AA912127 | UNKNOWN | 12 | 0 | T |
| AA912222 | UNKNOWN | 15 | 0 | T |
| AA912252 | UNKNOWN | 21 | 0 | T |
| AA912445 | UNKNOWN | 16 | 674 | A |
| AA912445 | UNKNOWN | 12 | 690 | G |
| AA912486 | UNKNOWN | 20 | 0 | T |
| AA912664 | UNKNOWN | 8 | 236 | CT |
| AA912703 | UNKNOWN | 19 | 415 | A |
| AA912806 | UNKNOWN | 12 | 0 | T |
| AA912815 | UNKNOWN | 14 | 0 | T |
| AA912925 | UNKNOWN | 17 | 0 | T |
| AA913030 | UNKNOWN | 4.5 | 15 | TTAT |
| AA913293 | UNKNOWN | 22 | 124 | G |
| AA913293 | UNKNOWN | 14 | 7 | T |
| AA913354 | UNKNOWN | 15 | 91 | T |
| AA913354 | UNKNOWN | 12 | 0 | T |
| AA913504 | UNKNOWN | 18 | 409 | A |
| AA913703 | UNKNOWN | 15 | 321 | T |
| AA913720 | UNKNOWN | 13 | 479 | A |
| AA913831 | UNKNOWN | 27 | 0 | T |
| AA913833 | UNKNOWN | 17 | 0 | T |
| AA913839 | UNKNOWN | 16 | 0 | T |
| AA913840 | UNKNOWN | 15 | 0 | T |
| AA913920 | UNKNOWN | 13 | 140 | A |
| AA916033 | UNKNOWN | 50 | 0 | T |
| AA916033 | UNKNOWN | 23 | 130 | A |
| AA916171 | UNKNOWN | 15 | 180 | T |
| AA916357 | UNKNOWN | 3.8 | 74 | TTAAA |
| AA916372 | UNKNOWN | 49 | 0 | T |
| AA916372 | UNKNOWN | 17 | 129 | A |
| AA916543 | UNKNOWN | 17 | 0 | T |
| AA916992 | UNKNOWN | 12 | 100 | A |
| AA917705 | UNKNOWN | 15 | 208 | A |
| AA917834 | UNKNOWN | 5.2 | 3 | TTTTA |
| AA917956 | UNKNOWN | 14 | 0 | T |
| AA918320 | UNKNOWN | 14 | 422 | T |
| AA918571 | UNKNOWN | 16 | 0 | T |
| AA918584 | UNKNOWN | 21 | 0 | T |
| AA918895 | UNKNOWN | 13 | 180 | G |
| AA921805 | UNKNOWN | 12 | 153 | A |
| AA921809 | UNKNOWN | 8 | 184 | CA |
| AA921850 | UNKNOWN | 13 | 0 | T |
| AA921897 | UNKNOWN | 16 | 95 | A |
| AA921942 | UNKNOWN | 25 | 0 | T |
| AA921947 | UNKNOWN | 15 | 0 | T |
| AA921949 | UNKNOWN | 16 | 0 | T |
| AA921956 | UNKNOWN | 4 | 265 | GGTTTT |
| AA921956 | UNKNOWN | 15 | 0 | T |
| AA921960 | UNKNOWN | 23 | 0 | T |
| AA921964 | UNKNOWN | 18 | 0 | T |
| AA922051 | UNKNOWN | 16 | 0 | T |
| AA922192 | UNKNOWN | 12 | 0 | T |
| AA922225 | UNKNOWN | 24 | 0 | T |
| AA922225 | UNKNOWN | 13 | 156 | A |
| AA922330 | UNKNOWN | 14 | 0 | T |
| AA922351 | UNKNOWN | 27 | 0 | T |
| AA923096 | UNKNOWN | 47 | 0 | T |
| AA923730 | UNKNOWN | 23 | 0 | T |
| AA923782 | UNKNOWN | 4.75 | 10 | TTTA |

TABLE 1-continued

| Genbank # | Region | # reps | Position | Unit sequence |
|---|---|---|---|---|
| AA926649 | UNKNOWN | 19 | 0 | T |
| AA926732 | UNKNOWN | 16 | 0 | T |
| AA926736 | UNKNOWN | 12 | 0 | T |
| AA926952 | UNKNOWN | 16 | 0 | T |
| AA926967 | UNKNOWN | 17 | 0 | T |
| AA927133 | UNKNOWN | 14 | 312 | A |
| AA927314 | UNKNOWN | 10.5 | 123 | TG |
| AA927608 | UNKNOWN | 12 | 183 | A |
| AA927732 | UNKNOWN | 20 | 0 | T |
| AA928095 | UNKNOWN | 15 | 0 | T |
| AA928101 | UNKNOWN | 22 | 0 | T |
| AA928546 | UNKNOWN | 44 | 0 | T |
| AA928672 | UNKNOWN | 12 | 0 | T |
| AA928744 | UNKNOWN | 17 | 0 | T |
| AA928780 | UNKNOWN | 23 | 2 | T |
| AA929020 | UNKNOWN | 13 | 0 | T |
| AA931416 | UNKNOWN | 20 | 0 | T |
| AA931528 | UNKNOWN | 15 | 0 | T |
| AA931715 | UNKNOWN | 12 | 0 | T |
| AA931833 | UNKNOWN | 16 | 3 | T |
| AA931957 | UNKNOWN | 23 | 0 | T |
| AA932214 | UNKNOWN | 22 | 133 | A |
| AA932214 | UNKNOWN | 20 | 0 | T |
| AA932638 | UNKNOWN | 3.6 | 95 | TTTCT |
| AA932693 | UNKNOWN | 31 | 0 | T |
| AA932701 | UNKNOWN | 32 | 0 | T |
| AA932742 | UNKNOWN | 12 | 8 | A |
| AA932926 | UNKNOWN | 25 | 5 | T |
| AA933038 | UNKNOWN | 12 | 0 | T |
| AA933710 | UNKNOWN | 24 | 0 | T |
| AA933964 | UNKNOWN | 12 | 0 | T |
| AA934356 | UNKNOWN | 26 | 0 | T |
| AA934358 | UNKNOWN | 14 | 430 | A |
| AA934614 | UNKNOWN | 20 | 0 | T |
| AA934681 | UNKNOWN | 13 | 289 | T |
| AA934735 | UNKNOWN | 13.66 | 20 | TTA |
| AA934803 | UNKNOWN | 20 | 0 | T |
| AA934837 | UNKNOWN | 20 | 304 | A |
| AA934912 | UNKNOWN | 49 | 0 | T |
| AA934912 | UNKNOWN | 13 | 168 | A |
| AA934950 | UNKNOWN | 13 | 178 | A |
| AA935143 | UNKNOWN | 13 | 176 | TG |
| AA935143 | UNKNOWN | 6.5 | 160 | TA |
| AA935143 | UNKNOWN | 14 | 127 | A |
| AA935364 | UNKNOWN | 15 | 329 | A |
| AA935409 | UNKNOWN | 15 | 0 | T |
| AA935432 | UNKNOWN | 13 | 164 | A |
| AA935659 | UNKNOWN | 16 | 123 | A |
| AA935697 | UNKNOWN | 5.66 | 270 | AAC |
| AA935877 | UNKNOWN | 13 | 0 | T |
| AA935964 | UNKNOWN | 16 | 216 | A |
| AA936133 | UNKNOWN | 37 | 0 | T |
| AA936356 | UNKNOWN | 17 | 0 | T |
| AA936412 | UNKNOWN | 5.66 | 236 | AAC |
| AA936421 | UNKNOWN | 6.5 | 249 | TC |
| AA936486 | UNKNOWN | 5.2 | 119 | TGTTT |
| AA936486 | UNKNOWN | 16 | 429 | A |
| AA936524 | UNKNOWN | 25 | 0 | T |
| AA937084 | UNKNOWN | 31 | 0 | T |
| AA937094 | UNKNOWN | 24 | 73 | T |
| AA937094 | UNKNOWN | 16 | 0 | T |
| AA937226 | UNKNOWN | 17 | 0 | T |
| AA937379 | UNKNOWN | 17 | 0 | T |
| AA937393 | UNKNOWN | 16 | 0 | T |
| AA937404 | UNKNOWN | 44 | 17 | T |
| AA937404 | UNKNOWN | 16 | 0 | T |
| AA937407 | UNKNOWN | 12 | 370 | A |
| AA937440 | UNKNOWN | 12 | 0 | T |
| AA937516 | UNKNOWN | 20 | 4 | T |
| AA937558 | UNKNOWN | 47 | 0 | T |
| AA937558 | UNKNOWN | 17 | 135 | A |
| AA937566 | UNKNOWN | 52 | 0 | T |
| AA937566 | UNKNOWN | 14 | 162 | A |
| AA937568 | UNKNOWN | 42 | 0 | T |
| AA937574 | UNKNOWN | 56 | 0 | T |
| AA937574 | UNKNOWN | 15 | 99 | A |
| AA937574 | UNKNOWN | 13 | 346 | G |

TABLE 1-continued

| Genbank # | Region | # reps | Position | Unit sequence |
|---|---|---|---|---|
| AA937626 | UNKNOWN | 13 | 238 | A |
| AA937628 | UNKNOWN | 15 | 210 | A |
| AA937639 | UNKNOWN | 27 | 167 | A |
| AA937754 | UNKNOWN | 28 | 0 | T |
| AA937822 | UNKNOWN | 19 | 204 | A |
| AA937874 | UNKNOWN | 14 | 186 | A |
| AA937874 | UNKNOWN | 12 | 144 | T |
| AA937883 | UNKNOWN | 17 | 190 | A |
| AA937915 | UNKNOWN | 42 | 0 | T |
| AA937915 | UNKNOWN | 22 | 113 | G |
| AA937961 | UNKNOWN | 13 | 0 | T |
| AA938067 | UNKNOWN | 21 | 0 | T |
| AA938067 | UNKNOWN | 18 | 401 | A |
| AA938092 | UNKNOWN | 73 | 0 | T |
| AA938092 | UNKNOWN | 15 | 276 | A |
| AA938155 | UNKNOWN | 43 | 0 | T |
| AA938306 | UNKNOWN | 14 | 0 | T |
| AA938308 | UNKNOWN | 14 | 0 | T |
| AA938328 | UNKNOWN | 5.8 | 195 | TTTTG |
| AA938328 | UNKNOWN | 3.6 | 10 | TTTGT |
| AA938328 | UNKNOWN | 17 | 24 | T |
| AA938388 | UNKNOWN | 15 | 204 | A |
| AA938390 | UNKNOWN | 19 | 369 | A |
| AA938457 | UNKNOWN | 38 | 0 | T |
| AA938593 | UNKNOWN | 19 | 0 | T |
| AA938661 | UNKNOWN | 16 | 16 | T |
| AA938661 | UNKNOWN | 15 | 0 | T |
| AA939043 | UNKNOWN | 13 | 0 | T |
| AA939134 | UNKNOWN | 7.5 | 278 | TA |
| AA939146 | UNKNOWN | 16 | 0 | T |
| AA939199 | UNKNOWN | 53 | 0 | T |
| AA939199 | UNKNOWN | 14 | 85 | C |
| AA939266 | UNKNOWN | 28 | 0 | T |
| AA939334 | UNKNOWN | 6.5 | 148 | TA |
| AA946594 | UNKNOWN | 3.6 | 26 | TTTCT |
| AA946617 | UNKNOWN | 18 | 0 | T |
| AA946675 | UNKNOWN | 25 | 20 | T |
| AA946675 | UNKNOWN | 15 | 0 | T |
| AA946728 | UNKNOWN | 13 | 183 | T |
| AA946741 | UNKNOWN | 84 | 0 | T |
| AA946741 | UNKNOWN | 14 | 228 | C |
| AA947050 | UNKNOWN | 25 | 0 | T |
| AA947194 | UNKNOWN | 21 | 0 | T |
| AA947258 | UNKNOWN | 22 | 251 | A |
| AA947265 | UNKNOWN | 15 | 0 | T |
| AA947305 | UNKNOWN | 17 | 417 | T |
| AA947361 | UNKNOWN | 15 | 0 | T |
| AA947388 | UNKNOWN | 3.6 | 22 | AATGG |
| AA947388 | UNKNOWN | 14 | 0 | T |
| AA947456 | UNKNOWN | 21 | 0 | T |
| AA947534 | UNKNOWN | 17 | 226 | A |
| AA947543 | UNKNOWN | 13 | 215 | A |
| AA947620 | UNKNOWN | 9 | 69 | TG |
| AA947673 | UNKNOWN | 12 | 0 | T |
| AA947802 | UNKNOWN | 16 | 7 | T |
| AA947808 | UNKNOWN | 18 | 7 | T |
| AA947834 | UNKNOWN | 15 | 7 | T |
| AA947991 | UNKNOWN | 18 | 68 | A |
| AA948021 | UNKNOWN | 33 | 0 | T |
| AA948064 | UNKNOWN | 48 | 0 | T |
| AA948318 | UNKNOWN | 53 | 0 | T |
| AA948318 | UNKNOWN | 12 | 181 | G |
| AA948538 | UNKNOWN | 15 | 312 | A |
| AA948560 | UNKNOWN | 6.66 | 48 | TGG |
| AA953480 | UNKNOWN | 13 | 332 | A |
| AA953587 | UNKNOWN | 3.83 | 334 | AAAAAC |
| AA953889 | UNKNOWN | 16 | 14 | T |
| AA954234 | UNKNOWN | 16 | 348 | T |
| AA954400 | UNKNOWN | 5.8 | 83 | AGGAG |
| AA954400 | UNKNOWN | 3.6 | 49 | GAGGG |
| AA954687 | UNKNOWN | 19 | 0 | T |
| AA954782 | UNKNOWN | 20 | 0 | T |
| AA954995 | UNKNOWN | 17 | 183 | T |
| AA960898 | UNKNOWN | 17 | 60 | A |
| AA960997 | UNKNOWN | 13 | 411 | A |
| AA961162 | UNKNOWN | 7 | 258 | AC |
| AA961192 | UNKNOWN | 9 | 59 | CAAA |

TABLE 1-continued

| Genbank # | Region | # reps | Position | Unit sequence |
|---|---|---|---|---|
| AA961420 | UNKNOWN | 11 | 183 | TTA |
| AA961826 | UNKNOWN | 39 | 0 | T |
| AA961826 | UNKNOWN | 22 | 158 | A |
| AA961826 | UNKNOWN | 12 | 64 | A |
| AA961930 | UNKNOWN | 6.5 | 19 | TC |
| AA962601 | UNKNOWN | 14 | 173 | A |
| AA962622 | UNKNOWN | 38 | 16 | T |
| AA962622 | UNKNOWN | 23 | 157 | C |
| AA962622 | UNKNOWN | 17 | 120 | A |
| AA962622 | UNKNOWN | 16 | 137 | C |
| AA962622 | UNKNOWN | 13 | 0 | T |
| AA962622 | UNKNOWN | 13 | 85 | A |
| AA962789 | UNKNOWN | 12 | 487 | A |
| AA968599 | UNKNOWN | 25 | 0 | T |
| AA968611 | UNKNOWN | 6.5 | 219 | AC |
| AA968624 | UNKNOWN | 14 | 69 | A |
| AA969018 | UNKNOWN | 8 | 87 | CATT |
| AA969066 | UNKNOWN | 17 | 0 | T |
| AA969131 | UNKNOWN | 27 | 0 | T |
| AA969259 | UNKNOWN | 8.25 | 285 | ATTC |
| AA969273 | UNKNOWN | 3.8 | 83 | AAAAC |
| AA969314 | UNKNOWN | 5.5 | 94 | CATT |
| AA969341 | UNKNOWN | 18 | 0 | T |
| AA969375 | UNKNOWN | 55 | 0 | T |
| AA969375 | UNKNOWN | 19 | 285 | G |
| AA969375 | UNKNOWN | 16 | 128 | A |
| AA969375 | UNKNOWN | 15 | 352 | C |
| AA969409 | UNKNOWN | 13 | 232 | A |
| AA969766 | UNKNOWN | 13 | 377 | T |
| AA969874 | UNKNOWN | 12 | 0 | T |
| AA970096 | UNKNOWN | 21 | 0 | T |
| AA970098 | UNKNOWN | 16 | 0 | T |
| AA970159 | UNKNOWN | 31 | 0 | T |
| AA970184 | UNKNOWN | 13 | 7 | T |
| AA970334 | UNKNOWN | 26 | 20 | T |
| AA970588 | UNKNOWN | 14 | 130 | A |
| AA970665 | UNKNOWN | 8 | 155 | TG |
| AA970930 | UNKNOWN | 16 | 0 | T |
| AA971049 | UNKNOWN | 4.75 | 20 | TTTG |
| AA971127 | UNKNOWN | 8.5 | 316 | AC |
| AA971243 | UNKNOWN | 13 | 0 | T |
| AA971309 | UNKNOWN | 12 | 0 | T |
| AA971450 | UNKNOWN | 16 | 0 | T |
| AA971476 | UNKNOWN | 22 | 0 | T |
| AA971523 | UNKNOWN | 16 | 134 | T |
| AA971567 | UNKNOWN | 33 | 0 | T |
| AA971574 | UNKNOWN | 31 | 0 | T |
| AA971594 | UNKNOWN | 14 | 351 | T |
| AA971673 | UNKNOWN | 20 | 0 | T |
| AA971794 | UNKNOWN | 21 | 0 | T |
| AA971823 | UNKNOWN | 13 | 1 | T |
| AA971853 | UNKNOWN | 12 | 0 | T |
| AA971890 | UNKNOWN | 14 | 8 | T |
| AA971927 | UNKNOWN | 11 | 78 | AT |
| AA971927 | UNKNOWN | 27 | 105 | T |
| AA971927 | UNKNOWN | 19 | 229 | A |
| AA971975 | UNKNOWN | 6.5 | 111 | AG |
| AA972119 | UNKNOWN | 15 | 0 | T |
| AA972202 | UNKNOWN | 12 | 0 | T |
| AA972252 | UNKNOWN | 39 | 0 | T |
| AA972304 | UNKNOWN | 22 | 7 | T |
| AA972308 | UNKNOWN | 23 | 143 | A |
| AA972684 | UNKNOWN | 15 | 0 | T |
| AA972689 | UNKNOWN | 12 | 90 | A |
| AA972966 | UNKNOWN | 18 | 220 | A |
| AA972966 | UNKNOWN | 14 | 190 | T |
| AA973059 | UNKNOWN | 4.5 | 355 | TTGT |
| AA973059 | UNKNOWN | 18 | 0 | T |
| AA973261 | UNKNOWN | 16 | 387 | A |
| AA973334 | UNKNOWN | 21 | 0 | T |
| AA973345 | UNKNOWN | 4.75 | 18 | TTTA |
| AA973750 | UNKNOWN | 18 | 0 | T |
| AA973904 | UNKNOWN | 20 | 5 | T |
| AA974175 | UNKNOWN | 29 | 0 | T |
| AA974438 | UNKNOWN | 17 | 0 | T |
| AA974476 | UNKNOWN | 28 | 0 | T |
| AA974493 | UNKNOWN | 12 | 0 | T |

TABLE 1-continued

| Genbank # | Region | # reps | Position | Unit sequence |
|---|---|---|---|---|
| AA974494 | UNKNOWN | 9.5 | 256 | GA |
| AA974494 | UNKNOWN | 16 | 0 | T |
| AA974503 | UNKNOWN | 17 | 0 | T |
| AA974597 | UNKNOWN | 6.5 | 120 | AT |
| AA974932 | UNKNOWN | 3.57 | 328 | TTTTGTT |
| AA974932 | UNKNOWN | 21 | 0 | T |
| AA974968 | UNKNOWN | 19 | 1 | T |
| AA975125 | UNKNOWN | 18 | 0 | T |
| AA975140 | UNKNOWN | 14 | 138 | T |
| AA975298 | UNKNOWN | 15 | 0 | T |
| AA975436 | UNKNOWN | 14 | 221 | T |
| AA975588 | UNKNOWN | 61 | 0 | T |
| AA975588 | UNKNOWN | 16 | 334 | C |
| AA975603 | UNKNOWN | 35 | 0 | T |
| AA975952 | UNKNOWN | 73 | 0 | T |
| AA975952 | UNKNOWN | 13 | 175 | A |
| AA975952 | UNKNOWN | 12 | 207 | G |
| AA976046 | UNKNOWN | 41 | 0 | T |
| AA976064 | UNKNOWN | 23 | 0 | T |
| AA976196 | UNKNOWN | 13 | 3 | T |
| AA976314 | UNKNOWN | 20 | 0 | T |
| AA976413 | UNKNOWN | 32 | 0 | T |
| AA976510 | UNKNOWN | 12 | 305 | T |
| AA976599 | UNKNOWN | 17 | 0 | T |
| AA976718 | UNKNOWN | 13 | 314 | A |
| AA976963 | UNKNOWN | 22 | 0 | T |
| AA977137 | UNKNOWN | 15 | 225 | T |
| AA977181 | UNKNOWN | 14 | 44 | A |
| AA977190 | UNKNOWN | 14 | 410 | T |
| AA977896 | UNKNOWN | 24 | 0 | T |
| AA978128 | UNKNOWN | 5.66 | 238 | GGT |
| AA978223 | UNKNOWN | 13 | 240 | A |
| AA983199 | UNKNOWN | 18 | 0 | T |
| AA983199 | UNKNOWN | 16 | 200 | A |
| AA983754 | UNKNOWN | 16 | 0 | T |
| AA983800 | UNKNOWN | 20 | 143 | TA |
| AA983883 | UNKNOWN | 73 | 0 | T |
| AA983907 | UNKNOWN | 16 | 0 | T |
| AA983922 | UNKNOWN | 15 | 0 | T |
| AA983940 | UNKNOWN | 23 | 0 | T |
| AA984077 | UNKNOWN | 33 | 46 | A |
| AA984114 | UNKNOWN | 3.6 | 158 | TTTGT |
| AA984192 | UNKNOWN | 14 | 240 | A |
| AA984283 | UNKNOWN | 22 | 100 | T |
| AA984384 | UNKNOWN | 35 | 0 | T |
| AA984465 | UNKNOWN | 4.75 | 13 | TTTG |
| AA984678 | UNKNOWN | 6.5 | 397 | CA |
| AA984699 | UNKNOWN | 5.75 | 77 | AAAT |
| AA984995 | UNKNOWN | 2.5 | 406 | TGTATGTGTA (SEQ ID NO: 23) |
| AA984995 | UNKNOWN | 11 | 428 | TA |
| AA985061 | UNKNOWN | 19.5 | 92 | TG |
| AA985125 | UNKNOWN | 14 | 199 | AT |
| AA987242 | UNKNOWN | 3.8 | 16 | TTTTA |
| AA987815 | UNKNOWN | 15 | 0 | T |
| AA987927 | UNKNOWN | 14 | 437 | A |
| AA987982 | UNKNOWN | 14 | 165 | A |
| AA988020 | UNKNOWN | 14 | 0 | T |
| AA988241 | UNKNOWN | 13 | 103 | G |
| AA988301 | UNKNOWN | 17 | 372 | T |
| AA988655 | UNKNOWN | 12 | 164 | T |
| AA988769 | UNKNOWN | 10 | 52 | ATT |
| AA989035 | UNKNOWN | 55 | 0 | T |
| AA989335 | UNKNOWN | 5.75 | 3 | TTTA |
| AA989420 | UNKNOWN | 14 | 378 | A |
| AA991577 | UNKNOWN | 16 | 3 | T |
| AA991685 | UNKNOWN | 12 | 45 | A |
| AA991933 | UNKNOWN | 26 | 1 | T |
| AA992015 | UNKNOWN | 12 | 303 | A |
| AA992028 | UNKNOWN | 25 | 0 | T |
| AA992065 | UNKNOWN | 16 | 0 | T |
| AA992108 | UNKNOWN | 36 | 0 | T |
| AA992108 | UNKNOWN | 12 | 177 | A |
| AA992121 | UNKNOWN | 24 | 0 | T |
| AA992185 | UNKNOWN | 4 | 316 | AATAA |
| AA992240 | UNKNOWN | 15 | 58 | A |
| AA992240 | UNKNOWN | 12 | 0 | T |
| AA992347 | UNKNOWN | 44 | 0 | T |

TABLE 1-continued

| Genbank # | Region | # reps | Position | Unit sequence |
|---|---|---|---|---|
| AA992380 | UNKNOWN | 6.5 | 287 | TC |
| AA992428 | UNKNOWN | 14 | 0 | T |
| AA992540 | UNKNOWN | 20 | 7 | T |
| AA992547 | UNKNOWN | 19 | 0 | T |
| AA992617 | UNKNOWN | 15 | 0 | T |
| AA992649 | UNKNOWN | 51 | 0 | T |
| AA992649 | UNKNOWN | 19 | 426 | A |
| AA992649 | UNKNOWN | 15 | 143 | C |
| AA992691 | UNKNOWN | 12 | 0 | T |
| AA992742 | UNKNOWN | 17 | 325 | T |
| AA993056 | UNKNOWN | 16 | 0 | T |
| AA993105 | UNKNOWN | 17 | 9 | T |
| AA993256 | UNKNOWN | 12 | 0 | T |
| AA993289 | UNKNOWN | 15 | 140 | T |
| AA993310 | UNKNOWN | 14 | 0 | T |
| AA993361 | UNKNOWN | 11.5 | 141 | GT |
| AA993475 | UNKNOWN | 23 | 0 | T |
| AA993524 | UNKNOWN | 18 | 0 | T |
| AA993703 | UNKNOWN | 16 | 0 | T |
| AA993717 | UNKNOWN | 18 | 0 | T |
| AA993736 | UNKNOWN | 13 | 378 | GT |
| AA993736 | UNKNOWN | 9 | 411 | TA |
| AA993841 | UNKNOWN | 22 | 2 | T |
| AA993895 | UNKNOWN | 16 | 97 | A |
| AA993924 | UNKNOWN | 16.5 | 249 | AC |
| AA993924 | UNKNOWN | 10.5 | 281 | AG |
| AA993924 | UNKNOWN | 9.5 | 229 | AC |
| AA994000 | UNKNOWN | 18 | 0 | T |
| AA994013 | UNKNOWN | 12 | 0 | T |
| AA994419 | UNKNOWN | 21 | 0 | T |
| AA994451 | UNKNOWN | 3.8 | 220 | AAAAC |
| AA994958 | UNKNOWN | 15 | 0 | T |
| AA994979 | UNKNOWN | 17 | 0 | T |
| AA995139 | UNKNOWN | 4.2 | 356 | AAAAC |
| AA995496 | UNKNOWN | 3.66 | 0 | TTTTAT |
| AA995908 | UNKNOWN | 6.5 | 51 | TG |
| AA996290 | UNKNOWN | 12 | 0 | T |
| AA999790 | UNKNOWN | 17 | 0 | T |
| AA999906 | UNKNOWN | 63 | 0 | T |
| AB000714 | 5'UTR | 5.75 | 81 | GTCC |
| AB000714 | 3'UTR | 7 | 881 | CCA |
| AB000732 | CDS | 8.33 | 59 | CAA |
| AB000732 | CDS | 8.33 | 2079 | GCC |
| AB001325 | 3'UTR | 2.8 | 1225 | TGTGTGCATG (SEQ ID NO: 24) |
| AB001325 | 3'UTR | 7 | 1209 | TG |
| AB001451 | CDS | 5.66 | 227 | CGC |
| AB001835 | CDS | 8 | 807 | CAC |
| AB001835 | CDS | 7 | 308 | CGC |
| AB001835 | CDS | 6.66 | 102 | GGC |
| AB001895 | CDS | 8 | 3115 | GCA |
| AB001914 | CDS | 3.66 | 388 | GGGCGCGGG |
| AB002097 | CDS | 6 | 52 | GCT |
| AB002293 | CDS | 6 | 2806 | CAC |
| AB002293 | 3'UTR | 7 | 6426 | TA |
| AB002295 | CDS | 6.66 | 974 | GAA |
| AB002295 | 3'UTR | 4.8 | 4589 | CACCA |
| AB002295 | 3'UTR | 4.2 | 4553 | GCACC |
| AB002296 | 5'UTR | 26 | 1122 | T |
| AB002306 | CDS | 5.66 | 1799 | TCC |
| AB002306 | 3'UTR | 14 | 5871 | A |
| AB002307 | 3'UTR | 16 | 5350 | T |
| AB002311 | 3'UTR | 3.57 | 5559 | TTTTGTT |
| AB002312 | CDS | 3.66 | 1710 | TCAGCT |
| AB002312 | 3'UTR | 19.5 | 4667 | TG |
| AB002316 | 3'UTR | 13 | 3435 | A |
| AB002316 | 3'UTR | 12 | 4402 | T |
| AB002317 | 5'UTR | 9 | 267 | GT |
| AB002317 | 3'UTR | 12 | 5355 | T |
| AB002318 | 3'UTR | 11 | 4206 | CT |
| AB002325 | 5'UTR | 10.5 | 711 | GT |
| AB002325 | 5'UTR | 14 | 1162 | T |
| AB002325 | 3'UTR | 20.5 | 5388 | TG |
| AB002326 | 3'UTR | 12 | 6006 | A |
| AB002328 | CDS | 3.5 | 4502 | GCCCCC |
| AB002329 | 5'UTR | 16 | 110 | T |
| AB002329 | 5'UTR | 12 | 93 | T |
| AB002329 | 3'UTR | 9 | 5219 | AC |

TABLE 1-continued

| Genbank # | Region | # reps | Position | Unit sequence |
|---|---|---|---|---|
| AB002332 | CDS | 6.33 | 2512 | GCA |
| AB002336 | 3'UTR | 14 | 4237 | T |
| AB002337 | CDS | 5.66 | 3811 | TCC |
| AB002338 | 3'UTR | 19.5 | 6197 | AC |
| AB002342 | 5'UTR | 14 | 427 | T |
| AB002343 | 3'UTR | 13 | 4811 | T |
| AB002344 | CDS | 15 | 550 | ACC |
| AB002344 | 3'UTR | 15 | 5013 | T |
| AB002345 | 3'UTR | 27 | 5193 | T |
| AB002347 | 3'UTR | 12 | 4448 | T |
| AB002349 | 3'UTR | 8.5 | 2430 | GT |
| AB002353 | 3'UTR | 5.75 | 4065 | GCCT |
| AB002353 | 3'UTR | 5.5 | 5795 | TATG |
| AB002357 | 5'UTR | 12.66 | 43 | CCG |
| AB002359 | 3'UTR | 17 | 4733 | T |
| AB002361 | CDS | 3.3 | 1838 | CTCTCGTCAGCCCCAAAGCCTGTGGCTGCAGCCACGCTTGTGTCCCAGCAGGCTGAAGAGGGCCTCACCTTACCCCAGGACTCCGCTATGACACCGCCTCTGCCCCTACAAGACACAGAT (SEQ ID NO: 25) |
| AB002361 | CDS | 2.99 | 2115 | TTGTGTCCCAGCAGGCTGAAGAGGGCCTCACCTTACCCCAGGACTCCGCTATGACACCGCCTCTGCCCCTACAAGACACAGATCTCTCGTCAGCCCCAAAGCCTGTGGCTGCAGCCACGA (SEQ ID NO: 26) |
| AB002363 | 3'UTR | 12 | 4028 | T |
| AB002364 | 3'UTR | 6.5 | 4515 | TG |
| AB002369 | 3'UTR | 14 | 4091 | T |
| AB002370 | 3'UTR | 12 | 5179 | A |
| AB002373 | 3'UTR | 5 | 5272 | TATT |
| AB002375 | 3'UTR | 8 | 5307 | AT |
| AB002376 | 3'UTR | 14 | 3461 | T |
| AB002378 | 5'UTR | 3.8 | 500 | TTTTC |
| AB002378 | 5'UTR | 12 | 42 | T |
| AB002380 | 3'UTR | 6 | 5237 | GTT |
| AB002381 | CDS | 8 | 1630 | GAA |
| AB002381 | CDS | 5.66 | 2404 | GAG |
| AB002381 | 3'UTR | 13 | 4695 | A |
| AB002384 | 3'UTR | 12 | 4347 | A |
| AB002389 | 3'UTR | 15 | 3860 | A |
| AB002390 | 3'UTR | 16 | 2062 | A |
| AB002390 | 3'UTR | 12 | 2404 | T |
| AB002454 | 3'UTR | 10.19 | 3501 | AAAAC |
| AB002454 | 3'UTR | 3.6 | 4526 | AAAGA |
| AB002454 | 3'UTR | 17 | 2949 | T |
| AB002454 | 3'UTR | 17 | 4499 | A |
| AB002533 | 3'UTR | 9 | 1638 | TA |
| AB002533 | 3'UTR | 8 | 1613 | AT |
| AB002533 | 3'UTR | 34 | 1683 | A |
| AB002803 | 3'UTR | 14.5 | 4130 | TG |
| AB003103 | 3'UTR | 22 | 2143 | T |
| AB003103 | 3'UTR | 16 | 1986 | T |
| AB004066 | 3'UTR | 15 | 1572 | GT |
| AB005060 | CDS | 3.83 | 2202 | CCCGGG |
| AB005060 | CDS | 9 | 321 | AGC |
| AB005060 | CDS | 6.33 | 296 | CAG |
| AB005216 | CDS | 8.33 | 167 | AGC |
| AB005297 | CDS | 6 | 237 | CTG |
| AB005754 | CDS | 7 | 1709 | AC |
| AB006537 | 3'UTR | 8.5 | 3272 | AT |
| AB006621 | 3'UTR | 12 | 4473 | A |
| AB006625 | CDS | 3.5 | 420 | TGAACG |
| AB006625 | CDS | 5.66 | 2698 | GAA |
| AB006625 | 3'UTR | 17 | 4242 | T |
| AB006625 | 3'UTR | 14 | 3859 | T |
| AB006625 | 3'UTR | 13 | 4646 | A |
| AB006626 | 5'UTR | 3.83 | 43 | GCCCGA |
| AB006626 | 5'UTR | 6.33 | 78 | CGC |
| AB006626 | 3'UTR | 4.59 | 8113 | TTTTG |
| AB006626 | 3'UTR | 8 | 5281 | TA |
| AB006627 | 3'UTR | 7 | 6495 | AC |
| AB006630 | CDS | 5.66 | 4574 | AGC |
| AB006630 | 3'UTR | 3.8 | 5276 | GCCCC |
| AB006630 | 3'UTR | 6.5 | 5487 | AT |
| AB006630 | 3'UTR | 12 | 5902 | T |
| AB006631 | CDS | 5.66 | 1847 | TCC |
| AB006631 | 3'UTR | 6.5 | 6001 | AC |
| AB006780 | 3'UTR | 13 | 823 | A |
| AB007191 | 3'UTR | 7 | 877 | TG |

TABLE 1-continued

| Genbank # | Region | # reps | Position | Unit sequence |
|---|---|---|---|---|
| AB007855 | 3'UTR | 8 | 3373 | TA |
| AB007855 | 3'UTR | 16 | 6256 | A |
| AB007856 | 3'UTR | 12 | 5154 | T |
| AB007859 | 3'UTR | 6.5 | 2384 | CA |
| AB007860 | 3'UTR | 14 | 4771 | T |
| AB007861 | 3'UTR | 13 | 4949 | T |
| AB007863 | 3'UTR | 4.75 | 2971 | AAAC |
| AB007863 | 3'UTR | 12 | 6051 | T |
| AB007865 | 5'UTR | 13 | 905 | A |
| AB007865 | 3'UTR | 11.5 | 7185 | AC |
| AB007865 | 3'UTR | 6.5 | 4915 | CT |
| AB007866 | 3'UTR | 9 | 7178 | CA |
| AB007866 | 3'UTR | 16 | 5130 | T |
| AB007866 | 3'UTR | 12 | 3075 | T |
| AB007868 | 3'UTR | 3.6 | 4810 | AAAAC |
| AB007868 | 3'UTR | 12.5 | 5488 | TG |
| AB007869 | CDS | 5.66 | 216 | GAG |
| AB007869 | 3'UTR | 21 | 3630 | T |
| AB007870 | 3'UTR | 8.5 | 3140 | TG |
| AB007870 | 3'UTR | 12 | 5991 | A |
| AB007871 | 3'UTR | 7.5 | 2364 | TA |
| AB007871 | 3'UTR | 14 | 4617 | T |
| AB007872 | 3'UTR | 6.5 | 3232 | TG |
| AB007872 | 3'UTR | 22 | 5157 | T |
| AB007872 | 3'UTR | 12 | 4236 | T |
| AB007874 | 5'UTR | 18 | 580 | A |
| AB007874 | 5'UTR | 12 | 418 | A |
| AB007874 | 3'UTR | 7 | 4337 | AT |
| AB007876 | 3'UTR | 16.5 | 2900 | CA |
| AB007879 | 3'UTR | 20 | 4522 | A |
| AB007884 | 5'UTR | 12 | 693 | A |
| AB007884 | 3'UTR | 17.5 | 2498 | AC |
| AB007884 | 3'UTR | 8.5 | 2444 | AC |
| AB007886 | 3'UTR | 4 | 3590 | CAAAA |
| AB007888 | 3'UTR | 4.4 | 3787 | TTTTG |
| AB007888 | 3'UTR | 15 | 3300 | T |
| AB007891 | 3'UTR | 18 | 4659 | AC |
| AB007891 | 3'UTR | 16 | 3972 | A |
| AB007891 | 3'UTR | 14 | 3812 | T |
| AB007892 | 3'UTR | 19 | 5402 | T |
| AB007895 | 5'UTR | 12 | 653 | T |
| AB007899 | 3'UTR | 15 | 3434 | T |
| AB007902 | CDS | 4 | 1315 | CAGCAC |
| AB007902 | CDS | 8.66 | 3114 | CCA |
| AB007902 | 3'UTR | 20 | 5011 | A |
| AB007903 | 3'UTR | 7.5 | 5132 | TA |
| AB007913 | 3'UTR | 7 | 6206 | GT |
| AB007915 | 5'UTR | 12 | 2251 | T |
| AB007915 | 3'UTR | 22.5 | 5207 | TG |
| AB007917 | 3'UTR | 7 | 4299 | AT |
| AB007919 | 5'UTR | 2.8 | 2237 | CCCTCCCCTCCCTCAGTCCT (SEQ ID NO: 27) |
| AB007920 | 5'UTR | 10 | 559 | AAT |
| AB007922 | 3'UTR | 14 | 4859 | TG |
| AB007922 | 3'UTR | 6.5 | 4886 | GC |
| AB007924 | 5'UTR | 9.5 | 2436 | CA |
| AB007925 | 3'UTR | 15.5 | 3768 | AC |
| AB007925 | 3'UTR | 6.5 | 3751 | AC |
| AB007925 | 3'UTR | 13 | 5018 | T |
| AB007926 | 3'UTR | 3.05 | 3628 | ACAGTGCAGTACTCAGTA (SEQ ID NO: 28) |
| AB007927 | CDS | 3.66 | 2812 | GGAGAA |
| AB007928 | 3'UTR | 21 | 4104 | T |
| AB007930 | 3'UTR | 13 | 4326 | T |
| AB007933 | CDS | 6 | 1287 | CAG |
| AB007935 | CDS | 9 | 1555 | GGA |
| AB007935 | CDS | 6 | 1580 | GAC |
| AB007937 | 3'UTR | 3.66 | 6296 | TTTTGT |
| AB007937 | 3'UTR | 4.75 | 6324 | TTTG |
| AB007938 | CDS | 3.6 | 812 | CGCCG |
| AB007938 | 3'UTR | 13 | 2451 | T |
| AB007940 | 5'UTR | 12.5 | 34 | CA |
| AB007940 | 3'UTR | 20 | 3300 | T |
| AB007941 | 3'UTR | 2.53 | 3107 | CAAAAAAAAAAAA (SEQ ID NO: 29) |
| AB007941 | 3'UTR | 15 | 1770 | A |
| AB007942 | 3'UTR | 4.5 | 4468 | TTTG |
| AB007942 | 3'UTR | 20.5 | 5323 | AC |
| AB007943 | 3'UTR | 12.25 | 1739 | CCAT |
| AB007944 | 3'UTR | 13 | 4612 | A |

TABLE 1-continued

| Genbank # | Region | # reps | Position | Unit sequence |
|---|---|---|---|---|
| AB007945 | CDS | 17 | 2917 | CAG |
| AB007946 | 5'UTR | 6 | 608 | GCC |
| AB007947 | 3'UTR | 15 | 4165 | T |
| AB007948 | 3'UTR | 3.8 | 2145 | AAAAC |
| AB007948 | 3'UTR | 8.33 | 1784 | AGC |
| AB007948 | 3'UTR | 26 | 3933 | AC |
| AB007948 | 3'UTR | 7.5 | 1717 | CA |
| AB007953 | UNKNOWN | 25 | 351 | T |
| AB007954 | UNKNOWN | 20 | 1952 | AC |
| AB007954 | UNKNOWN | 23 | 2310 | T |
| AB007954 | UNKNOWN | 13 | 2384 | A |
| AB007955 | UNKNOWN | 8.5 | 530 | TG |
| AB007955 | UNKNOWN | 25 | 1520 | T |
| AB007955 | UNKNOWN | 17 | 431 | T |
| AB007956 | UNKNOWN | 17 | 2066 | T |
| AB007956 | UNKNOWN | 13 | 764 | T |
| AB007957 | UNKNOWN | 3.87 | 2455 | GAAAGAAC |
| AB007957 | UNKNOWN | 9 | 2479 | GAAA |
| AB007957 | UNKNOWN | 6 | 2438 | AGAA |
| AB007957 | UNKNOWN | 26 | 3540 | A |
| AB007957 | UNKNOWN | 19 | 2314 | A |
| AB007958 | UNKNOWN | 4.59 | 2294 | AAACA |
| AB007959 | UNKNOWN | 20 | 2896 | T |
| AB007961 | UNKNOWN | 26 | 4562 | T |
| AB007961 | UNKNOWN | 15 | 2221 | T |
| AB007961 | UNKNOWN | 12 | 868 | A |
| AB007963 | 3'UTR | 3.5 | 4958 | TTTGGT |
| AB007964 | UNKNOWN | 4.55 | 2864 | TCATCAGCTGGGTTGATTGTGTGGGTTAGATAGAGG (SEQ ID NO: 30) |
| AB007970 | UNKNOWN | 4.75 | 3118 | CTCC |
| AB007970 | UNKNOWN | 12 | 175 | T |
| AB007973 | UNKNOWN | 9.5 | 5050 | GT |
| AB007975 | UNKNOWN | 17 | 3007 | A |
| AB007976 | UNKNOWN | 10.5 | 3885 | AC |
| AB007976 | UNKNOWN | 18 | 504 | A |
| AB007978 | UNKNOWN | 21 | 1622 | T |
| AB007978 | UNKNOWN | 16 | 3909 | A |
| AB007979 | UNKNOWN | 3.83 | 1589 | TTTTTC |
| AB007979 | UNKNOWN | 16 | 4948 | CA |
| AB008109 | 3'UTR | 16 | 1713 | A |
| AB008112 | 5'UTR | 3.08 | 5 | CCCACGCGTCCG (SEQ ID NO: 31) |
| AB008226 | 3'UTR | 12 | 6787 | A |
| AB008822 | 3'UTR | 12 | 1543 | A |
| AB009426 | 5'UTR | 3.8 | 109 | AAAAC |
| AB009462 | 5'UTR | 3.66 | 92 | AGCCCG |
| AB009973 | 3'UTR | 7 | 1580 | AC |
| AB009973 | 3'UTR | 6.5 | 1593 | CG |
| AB010414 | 3'UTR | 3.66 | 331 | TCTCTG |
| AB010414 | 3'UTR | 7.5 | 301 | TC |
| AB010894 | CDS | 2.91 | 1451 | CAGCAGCAGCAA (SEQ ID NO: 32) |
| AB010894 | CDS | 10 | 1475 | CAG |
| AB010894 | CDS | 6.33 | 1443 | AGC |
| AB010894 | CDS | 7 | 2696 | GA |
| AB011085 | 5'UTR | 5.5 | 45 | TTGA |
| AB011085 | 3'UTR | 4.75 | 4153 | TTTG |
| AB011085 | 3'UTR | 18 | 5480 | T |
| AB011089 | 3'UTR | 10 | 3532 | TA |
| AB011089 | 3'UTR | 13 | 6370 | T |
| AB011090 | 3'UTR | 20 | 3975 | T |
| AB011091 | 5'UTR | 7.66 | 4 | GGC |
| AB011094 | CDS | 7.66 | 3915 | CAC |
| AB011098 | 3'UTR | 12 | 3670 | A |
| AB011099 | 3'UTR | 3.6 | 3248 | TTTAT |
| AB011102 | 3'UTR | 3.8 | 5660 | TTTTG |
| AB011103 | 3'UTR | 21 | 4687 | GT |
| AB011107 | 3'UTR | 11.5 | 5050 | AC |
| AB011109 | 5'UTR | 7.33 | 816 | GCC |
| AB011109 | 3'UTR | 5.6 | 4853 | AAACA |
| AB011110 | 3'UTR | 4.75 | 5855 | AAAC |
| AB011110 | 3'UTR | 9.66 | 2562 | TTG |
| AB011110 | 3'UTR | 26 | 4948 | T |
| AB011110 | 3'UTR | 21 | 5405 | A |
| AB011116 | 3'UTR | 5.75 | 5680 | TTTG |
| AB011116 | 3'UTR | 26 | 3033 | AC |
| AB012116 | 3'UTR | 15 | 5244 | T |
| AB011117 | 3'UTR | 13 | 4576 | AT |
| AB011117 | 3'UTR | 18 | 5184 | T |

TABLE 1-continued

| Genbank # | Region | # reps | Position | Unit sequence |
|---|---|---|---|---|
| AB011118 | 3'UTR | 6.66 | 3856 | TTG |
| AB011118 | 3'UTR | 11.5 | 3530 | TA |
| AB011118 | 3'UTR | 17 | 3552 | T |
| AB011119 | 3'UTR | 16 | 4463 | A |
| AB011119 | 3'UTR | 12 | 4065 | A |
| AB011121 | 3'UTR | 12 | 4060 | T |
| AB011124 | 5'UTR | 8.4 | 1099 | GCTGA |
| AB011124 | 5'UTR | 3.8 | 195 | CCCCT |
| AB011124 | 3'UTR | 2.7 | 5163 | TATATATAAA (SEQ ID NO: 33) |
| AB011127 | CDS | 6.5 | 1947 | AG |
| AB011127 | 3'UTR | 16 | 4877 | T |
| AB011129 | 3'UTR | 31 | 3045 | A |
| AB011131 | 3'UTR | 12 | 4010 | A |
| AB011133 | 3'UTR | 18 | 4189 | T |
| AB011134 | 3'UTR | 3.66 | 5057 | TTTTTG |
| AB011134 | 3'UTR | 7.5 | 4898 | AT |
| AB011134 | 3'UTR | 14 | 4668 | A |
| AB011135 | 5'UTR | 2.6 | 1557 | CCCACCCTAC (SEQ ID NO: 34) |
| AB011135 | 5'UTR | 4 | 562 | ATTTT |
| AB011142 | CDS | 6.66 | 2324 | CAC |
| AB011145 | 3'UTR | 13 | 1540 | A |
| AB011147 | 3'UTR | 7 | 3966 | GTTTT |
| AB011147 | 3'UTR | 12 | 4792 | T |
| AB011150 | 3'UTR | 14.5 | 5326 | CA |
| AB011151 | CDS | 7.33 | 1212 | ACC |
| AB011154 | 3'UTR | 14 | 2266 | A |
| AB011155 | 3'UTR | 13 | 4929 | T |
| AB011156 | 3'UTR | 12 | 2770 | A |
| AB011158 | 5'UTR | 4.75 | 131 | AAAT |
| AB011159 | 5'UTR | 8.33 | 416 | CGC |
| AB011163 | 3'UTR | 16.5 | 4265 | AC |
| AB011165 | 3'UTR | 6.5 | 4076 | GT |
| AB011166 | 3'UTR | 5.75 | 4534 | TTTG |
| AB011170 | 3'UTR | 7 | 4057 | GT |
| AB011171 | 3'UTR | 19 | 3162 | T |
| AB011178 | 3'UTR | 6.8 | 2994 | TTTTG |
| AB011179 | 3'UTR | 28.5 | 3162 | CA |
| AB011399 | CDS | 6.66 | 5151 | GAG |
| AB011420 | 3'UTR | 11 | 2273 | AG |
| AB012043 | CDS | 5.66 | 1513 | CAC |
| AB012851 | 5'UTR | 9 | 8 | CGC |
| AB012851 | 3'UTR | 22 | 1606 | T |
| AB012922 | 5'UTR | 7.66 | 4283 | AAC |
| AB012922 | 5'UTR | 18 | 1807 | T |
| AB012922 | 5'UTR | 13 | 1126 | T |
| AB012922 | 3'UTR | 27 | 9646 | T |
| AB012955 | 3'UTR | 12 | 960 | A |
| AB014511 | 3'UTR | 20.5 | 3104 | TG |
| AB014512 | CDS | 6.66 | 3434 | GAG |
| AB014513 | CDS | 2.54 | 1303 | CCTACACCCCCTCCCCTGCCCCTG (SEQ ID NO: 35) |
| AB014516 | 3'UTR | 14 | 3981 | T |
| AB014517 | 5'UTR | 8 | 130 | GCC |
| AB014519 | 5'UTR | 2.9 | 245 | GGGCCGGGCT (SEQ ID NO: 36) |
| AB014519 | 5'UTR | 3.8 | 235 | GGGCC |
| AB014519 | 3'UTR | 3.83 | 6026 | TTTTG |
| AB014519 | 3'UTR | 8.5 | 5086 | AT |
| AB014522 | 3'UTR | 18.5 | 5561 | GT |
| AB014523 | 3'UTR | 13 | 4376 | T |
| AB014525 | 3'UTR | 12 | 2797 | A |
| AB014528 | 3'UTR | 12 | 5111 | T |
| AB014529 | 3'UTR | 26 | 2523 | GT |
| AB014529 | 3'UTR | 12 | 2889 | T |
| AB014530 | 3'UTR | 14 | 5197 | T |
| AB014531 | 3'UTR | 13 | 2976 | A |
| AB014531 | 3'UTR | 13 | 5075 | T |
| AB014534 | CDS | 6.33 | 745 | GCT |
| AB014534 | CDS | 5.66 | 392 | GCC |
| AB014535 | 3'UTR | 17 | 4871 | GT |
| AB014535 | 3'UTR | 12 | 4471 | A |
| AB014540 | 3'UTR | 6 | 2182 | CAAAA |
| AB014541 | CDS | 6 | 3384 | GGA |
| AB014542 | CDS | 2.66 | 2953 | CAGCAGCCGCCA (SEQ ID NO: 37) |
| AB014542 | CDS | 6 | 2037 | GCA |
| AB014545 | 3'UTR | 7.75 | 4907 | TTTG |
| AB014546 | 3'UTR | 3.66 | 2459 | TTTAA |
| AB014547 | 3'UTR | 3.83 | 4286 | TTTTTG |
| AB014550 | 3'UTR | 10 | 3195 | TA |

TABLE 1-continued

| Genbank # | Region | # reps | Position | Unit sequence |
|---|---|---|---|---|
| AB014550 | 3'UTR | 9.5 | 3177 | TG |
| AB014553 | CDS | 2.62 | 1383 | GGGTCCAGGCACCGGCGCCCAGCCCCCGTGGGGTGTCCAGGGC (SEQ ID NO: 38) |
| AB014553 | CDS | 2.5 | 66 | TCTCCGCGCCCCGAGG (SEQ ID NO: 39) |
| AB014558 | 3'UTR | 7 | 1881 | TG |
| AB014560 | 3'UTR | 9.5 | 3682 | AT |
| AB014560 | 3'UTR | 12 | 3507 | T |
| AB014562 | 3'UTR | 6.5 | 3756 | TC |
| AB014565 | 3'UTR | 8 | 4064 | AT |
| AB014566 | 3'UTR | 5.75 | 3635 | AAAC |
| AB014569 | 3'UTR | 14 | 4296 | T |
| AB014570 | CDS | 6.66 | 637 | GAG |
| AB014570 | CDS | 7 | 3685 | GA |
| AB014577 | 3'UTR | 5.75 | 3732 | GTGC |
| AB014577 | 3'UTR | 8 | 3719 | TG |
| AB014580 | 3'UTR | 13 | 3041 | A |
| AB014581 | 3'UTR | 11 | 3102 | TG |
| AB014581 | 3'UTR | 7 | 3086 | TG |
| AB014582 | 3'UTR | 7 | 3767 | TCAT |
| AB014585 | 3'UTR | 3.6 | 3235 | TTTAA |
| AB014588 | 3'UTR | 3.6 | 3691 | TTTTG |
| AB014588 | 3'UTR | 4.75 | 3513 | TTTC |
| AB014588 | 3'UTR | 8.5 | 3366 | GT |
| AB014588 | 3'UTR | 13 | 3503 | T |
| AB014589 | CDS | 4.66 | 425 | CTGGCC |
| AB014590 | CDS | 7 | 2923 | GAG |
| AB014591 | 5'UTR | 17 | 1038 | AC |
| AB014593 | 3'UTR | 6.5 | 2908 | AAAT |
| AB014602 | CDS | 6.66 | 4061 | GAG |
| AB014603 | 5'UTR | 20 | 383 | T |
| AB014606 | 3'UTR | 4.75 | 5305 | CAAG |
| AB014606 | 3'UTR | 4.5 | 4066 | GTCT |
| AB015019 | 3'UTR | 19 | 2032 | A |
| AB015051 | CDS | 5.66 | 1450 | GAG |
| AB015132 | 5'UTR | 3.6 | 192 | AAACA |
| AB015132 | 3'UTR | 11.5 | 1360 | AC |
| AB015629 | CDS | 3.95 | 293 | GCTGAAGGCTGCAGTGGGTGAGTTGCCAGAGAAATCCAAGCTGCAGGAGATCTACCAGGAGCTGACCCG (SEQ ID NO: 40) |
| AB015718 | 5'UTR | 4.66 | 1 | AGCCCG |
| AB015982 | 3'UTR | 10 | 3541 | TA |
| AB015982 | 3'UTR | 12 | 4789 | A |
| AB016092 | CDS | 7.66 | 8079 | TCC |
| AB016243 | 3'UTR | 2.58 | 1531 | CCCCCTTCCCCT (SEQ ID NO: 41) |
| AB016243 | 3'UTR | 9.5 | 1347 | AG |
| AB016789 | 5'UTR | 2.58 | 11 | GGAGCCCACGGA (SEQ ID NO: 42) |
| AB016811 | 3'UTR | 5.5 | 615 | TGGA |
| AB017546 | 3'UTR | 4.66 | 1335 | CCAGCC |
| AB017563 | CDS | 11.33 | 1026 | ACC |
| AB017642 | 5'UTR | 6.66 | 240 | GCG |
| AB017642 | 3'UTR | 12 | 3753 | T |
| AB018249 | 3'UTR | 6 | 1390 | AGA |
| AB018249 | 3'UTR | 7.5 | 1378 | AG |
| AB018249 | 3'UTR | 14 | 1365 | A |
| AB018263 | CDS | 8.66 | 1716 | GAG |
| AB018263 | 3'UTR | 15 | 3345 | T |
| AB018269 | 3'UTR | 4.33 | 3785 | GGCTGG |
| AB018269 | 3'UTR | 10 | 4192 | TG |
| AB018280 | CDS | 6 | 1316 | GCT |
| AB018280 | 3'UTR | 12 | 2811 | T |
| AB018284 | CDS | 5.66 | 1746 | GAG |
| AB018286 | 3'UTR | 7.5 | 3832 | AC |
| AB018289 | 3'UTR | 17.5 | 3912 | TG |
| AB018291 | 5'UTR | 3.5 | 91 | TTTCTT |
| AB018291 | 3'UTR | 12 | 2810 | A |
| AB018295 | 3'UTR | 16 | 1441 | A |
| AB018297 | CDS | 6.35 | 925 | CCCCAGAGGAGCCCACCTCCCCAGCTGCTGCAGTGCCCA (SEQ ID NO: 43) |
| AB018297 | CDS | 2.94 | 1135 | CCTCCCCAGCTGCTGCAGTGCCCACCCCAGAGGAGCCCG (SEQ ID NO: 44) |
| AB018297 | CDS | 2.58 | 823 | CCTCCCCAGCTGCTGCAGTGCCCACCCCAGAGGAGCCCA (SEQ ID NO: 45) |
| AB018297 | 3'UTR | 8 | 3065 | TA |
| AB018297 | 3'UTR | 18 | 3082 | T |
| AB018297 | 3'UTR | 12 | 2891 | T |
| AB018299 | 3'UTR | 4.2 | 3969 | AGGCC |
| AB018301 | 3'UTR | 6.75 | 3357 | GAAG |

TABLE 1-continued

| Genbank # | Region | # reps | Position | Unit sequence |
|---|---|---|---|---|
| AB018304 | 3'UTR | 15 | 2820 | T |
| AB018304 | 3'UTR | 14 | 2082 | T |
| AB018307 | 3'UTR | 6 | 2899 | ATTT |
| AB018308 | CDS | 3.83 | 1468 | GGCCCC |
| AB018309 | 3'UTR | 15 | 2734 | T |
| AB018310 | 3'UTR | 4.66 | 1750 | TTTTCT |
| AB018310 | 3'UTR | 13 | 1773 | T |
| AB018311 | 3'UTR | 13 | 2757 | T |
| AB018311 | 3'UTR | 12 | 3350 | A |
| AB018312 | 3'UTR | 16 | 3605 | T |
| AB018315 | 3'UTR | 16 | 2620 | T |
| AB018318 | 3'UTR | 3.8 | 3323 | GAGGA |
| AB018320 | CDS | 6.33 | 2442 | CAC |
| AB018322 | CDS | 6.33 | 692 | GCA |
| AB018322 | 3'UTR | 17 | 2147 | T |
| AB018322 | 3'UTR | 13 | 3008 | A |
| AB018324 | 3'UTR | 15 | 2239 | A |
| AB018330 | CDS | 13 | 1583 | A |
| AB018332 | 3'UTR | 8.66 | 2342 | TGA |
| AB018335 | CDS | 6.33 | 2556 | GCA |
| AB018337 | 3'UTR | 3.8 | 3987 | TTTTA |
| AB018341 | 3'UTR | 22 | 3438 | A |
| AB018343 | 5'UTR | 7 | 5 | TG |
| AB018351 | 5'UTR | 16 | 46 | T |
| AB018359 | CDS | 6.33 | 1308 | AGC |
| AB018551 | 5'UTR | 7.5 | 22 | CT |
| AB019494 | CDS | 4.5 | 6609 | AGATTC |
| AB019565 | UNKNOWN | 115 | 136 | A |
| AB020316 | 3'UTR | 12 | 1948 | T |
| AB020628 | 5'UTR | 17 | 0 | T |
| AB020630 | 3'UTR | 9.5 | 1575 | AC |
| AB020631 | CDS | 3.83 | 1355 | AAATCG |
| AB020631 | 3'UTR | 8.5 | 5490 | AT |
| AB020633 | 3'UTR | 15 | 5046 | A |
| AB020635 | 3'UTR | 8 | 4835 | AT |
| AB020637 | 3'UTR | 13 | 2317 | T |
| AB020638 | 3'UTR | 12 | 3578 | T |
| AB020640 | 3'UTR | 5.75 | 4623 | TTTG |
| AB020640 | 3'UTR | 6.5 | 4164 | CA |
| AB020641 | 3'UTR | 7.5 | 3757 | TC |
| AB020644 | CDS | 4.8 | 33 | GGCCG |
| AB020645 | 5'UTR | 16 | 38 | GCA |
| AB020645 | 3'UTR | 12 | 3177 | T |
| AB020648 | 3'UTR | 4.75 | 3383 | TTTC |
| AB020648 | 3'UTR | 20 | 3035 | T |
| AB020653 | 3'UTR | 5 | 2802 | TTGTT |
| AB020654 | 3'UTR | 12 | 2617 | T |
| AB020655 | 3'UTR | 21 | 3688 | AC |
| AB020655 | 3'UTR | 7 | 3995 | TA |
| AB020666 | 3'UTR | 12 | 2223 | T |
| AB020667 | 3'UTR | 19 | 2931 | T |
| AB020668 | 3'UTR | 6 | 3830 | ATTT |
| AB020669 | 3'UTR | 13 | 3513 | T |
| AB020670 | CDS | 2.5 | 1531 | TCCTGCAGGCCAGATGAC (SEQ ID NO: 46) |
| AB020670 | 3'UTR | 15 | 3588 | A |
| AB020671 | 3'UTR | 6.66 | 3741 | TTA |
| AB020672 | CDS | 4 | 2278 | CCGCCC |
| AB020672 | 3'UTR | 9 | 3290 | GT |
| AB020674 | 3'UTR | 7 | 3818 | GT |
| AB020676 | 3'UTR | 7.5 | 2855 | AC |
| AB020678 | 5'UTR | 6.5 | 479 | GT |
| AB020678 | 5'UTR | 14 | 379 | T |
| AB020679 | 3'UTR | 9 | 3646 | TA |
| AB020679 | 3'UTR | 8.5 | 3602 | TA |
| AB020680 | 3'UTR | 12 | 2208 | A |
| AB020682 | 3'UTR | 15 | 2871 | A |
| AB020683 | CDS | 6 | 423 | GAG |
| AB020683 | 3'UTR | 3.6 | 2904 | AAAAC |
| AB020684 | 3'UTR | 6.5 | 2409 | TC |
| AB020685 | 3'UTR | 12 | 2481 | A |
| AB020688 | CDS | 6.66 | 1540 | GAG |
| AB020690 | 3'UTR | 4 | 1430 | CTCTC |
| AB020690 | 3'UTR | 5.5 | 1376 | CCTT |
| AB020694 | 3'UTR | 6 | 1435 | TAT |
| AB020694 | 3'UTR | 6.5 | 1897 | TA |
| AB020694 | 3'UTR | 12 | 1406 | A |
| AB020696 | 5'UTR | 14 | 92 | A |

TABLE 1-continued

| Genbank # | Region | # reps | Position | Unit sequence |
|---|---|---|---|---|
| AB020696 | 3'UTR | 10.75 | 1975 | TCTG |
| AB020696 | 3'UTR | 6.25 | 2015 | TCTA |
| AB020696 | 3'UTR | 13 | 2338 | T |
| AB020701 | 3'UTR | 6 | 2468 | GTTT |
| AB020701 | 3'UTR | 6.5 | 3696 | AG |
| AB020701 | 3'UTR | 13 | 2522 | T |
| AB020707 | 3'UTR | 7.5 | 3232 | TC |
| AB020707 | 3'UTR | 16 | 3246 | T |
| AB020709 | CDS | 7.66 | 3089 | GAG |
| AB020709 | 5'UTR | 12.66 | 153 | GCA |
| AB020709 | 5'UTR | 6 | 189 | GCC |
| AB020714 | CDS | 4.66 | 1352 | CCCCAG |
| AB020714 | 3'UTR | 2.6 | 2959 | TTTTTTTCTT (SEQ ID NO: 47) |
| AB020714 | 3'UTR | 8 | 2486 | GA |
| AB020715 | 3'UTR | 12 | 3221 | A |
| AB020718 | CDS | 4 | 3574 | GAGGAA |
| AB020718 | 5'UTR | 6.33 | 645 | CGG |
| AB020721 | 3'UTR | 7 | 2579 | CA |
| AB020725 | CDS | 5.66 | 2400 | GCA |
| AB020735 | 5'UTR | 6.5 | 835 | TG |
| AB020735 | 5'UTR | 17 | 339 | A |
| AB020735 | 5'UTR | 12 | 870 | T |
| AB021179 | CDS | 3.5 | 1657 | GGAGCT |
| AB021227 | CDS | 3.5 | 192 | GCGGTG |
| AB021227 | CDS | 8.33 | 38 | GCC |
| AB021227 | CDS | 6.66 | 104 | GCT |
| AB021227 | CDS | 6.66 | 155 | GGC |
| AB021742 | 5'UTR | 8 | 624 | GT |
| AB021742 | 5'UTR | 18 | 1687 | T |
| AB021742 | 3'UTR | 31 | 4981 | A |
| AB022698 | 5'UTR | 3.83 | 185 | GGCAGC |
| AB023061 | 3'UTR | 15 | 2391 | T |
| AB023137 | CDS | 6.33 | 1737 | CAG |
| AB023137 | 3'UTR | 9.5 | 4759 | TG |
| AB023138 | 3'UTR | 3.6 | 4889 | GGGTG |
| AB023141 | 3'UTR | 7 | 5120 | AT |
| AB023141 | 3'UTR | 27 | 4587 | T |
| AB023143 | CDS | 6.5 | 1185 | AG |
| AB023144 | 3'UTR | 19 | 5107 | T |
| AB023148 | 3'UTR | 12 | 2478 | T |
| AB023149 | 3'UTR | 3.8 | 2819 | TTTTG |
| AB023152 | 3'UTR | 19 | 2776 | T |
| AB023154 | 3'UTR | 13.5 | 3564 | TA |
| AB023155 | 3'UTR | 16 | 4035 | T |
| AB023157 | 3'UTR | 6.66 | 2277 | TTA |
| AB023157 | 3'UTR | 12 | 4275 | T |
| AB023158 | 3'UTR | 16 | 3794 | T |
| AB023158 | 3'UTR | 12 | 3517 | T |
| AB023159 | 3'UTR | 12 | 1341 | A |
| AB023160 | 3'UTR | 4.75 | 1817 | TTTG |
| AB023160 | 3'UTR | 6 | 5239 | GCT |
| AB023165 | 3'UTR | 9.5 | 3133 | TG |
| AB023166 | 3'UTR | 18 | 3241 | T |
| AB023167 | 3'UTR | 3.6 | 1162 | CCCAG |
| AB023168 | 3'UTR | 6.5 | 3254 | AC |
| AB023170 | 3'UTR | 18 | 3357 | T |
| AB023172 | 3'UTR | 22 | 4310 | T |
| AB023172 | 3'UTR | 12 | 2084 | T |
| AB023176 | 3'UTR | 13 | 4335 | A |
| AB023178 | 3'UTR | 19 | 3910 | T |
| AB023179 | 3'UTR | 19 | 3348 | T |
| AB023179 | 3'UTR | 15 | 4730 | A |
| AB023181 | 3'UTR | 6.5 | 4016 | CA |
| AB023185 | 3'UTR | 4.5 | 4419 | AATA |
| AB023185 | 3'UTR | 6.66 | 4404 | AAT |
| AB023185 | 3'UTR | 18 | 2529 | T |
| AB023185 | 3'UTR | 12 | 3164 | A |
| AB023186 | 3'UTR | 22.5 | 4202 | AG |
| AB023186 | 3'UTR | 6.5 | 4184 | AG |
| AB023188 | 3'UTR | 7.5 | 2643 | AC |
| AB023192 | 3'UTR | 4.83 | 4931 | TGTTGC |
| AB023193 | 3'UTR | 5.4 | 3644 | TGTTT |
| AB023196 | 3'UTR | 19 | 4298 | T |
| AB023198 | 3'UTR | 14 | 4832 | T |
| AB023199 | 3'UTR | 10.5 | 3980 | GT |
| AB023202 | 5'UTR | 33 | 17 | GA |
| AB023202 | 3'UTR | 15 | 2779 | AC |

TABLE 1-continued

| Genbank # | Region | # reps | Position | Unit sequence |
|---|---|---|---|---|
| AB023203 | CDS | 11 | 4327 | TGA |
| AB023207 | 5'UTR | 9.66 | 442 | GCG |
| AB023207 | 3'UTR | 13 | 3312 | T |
| AB023210 | 3'UTR | 8.5 | 2454 | AT |
| AB023211 | 3'UTR | 7.5 | 3837 | TG |
| AB023211 | 3'UTR | 19 | 3883 | T |
| AB023212 | CDS | 6.66 | 404 | CGG |
| AB023212 | 3'UTR | 6.25 | 3732 | AAAC |
| AB023218 | 3'UTR | 6.5 | 3616 | TG |
| AB023218 | 3'UTR | 12 | 4001 | A |
| AB023219 | CDS | 6.66 | 1610 | CAG |
| AB023219 | 3'UTR | 23 | 3571 | T |
| AB023221 | CDS | 6.66 | 580 | GAG |
| AB023221 | 3'UTR | 4.5 | 2647 | GGAG |
| AB023231 | CDS | 6.66 | 1884 | CCT |
| AB023233 | CDS | 7 | 274 | CCA |
| AB024334 | 3'UTR | 12 | 3271 | T |
| AB024718 | 5'UTR | 6.5 | 112 | AG |
| AB025904 | 5'UTR | 9.5 | 208 | CT |
| AB025905 | CDS | 4.5 | 174 | GGCTAT |
| AB026493 | 3'UTR | 23 | 1543 | T |
| AB026542 | CDS | 5.66 | 1182 | CCT |
| AB026908 | 3'UTR | 12 | 1015 | T |
| AB027013 | CDS | 8.66 | 995 | GAG |
| AB027464 | 3'UTR | 14 | 1846 | T |
| AB027567 | 3'UTR | 7 | 6577 | AC |
| AB028449 | 3'UTR | 13 | 6270 | T |
| AB028942 | CDS | 4 | 1090 | TCCATGGACTCCCAGATGTTAGCAACCAGC (SEQ ID NO: 48) |
| AB028942 | CDS | 2.96 | 971 | CCATGGACTCCCAGATGTTAGCAACTAGCT (SEQ ID NO: 49) |
| AB028942 | CDS | 2.58 | 1783 | CGCTCTATGATGTCAGCCTACGAG (SEQ ID NO: 50) |
| AB028942 | CDS | 4.38 | 4552 | AGCCGCCGCAGCCGCACCCCC (SEQ ID NO: 51) |
| AB028942 | 3'UTR | 7 | 6055 | AT |
| AB028943 | 3'UTR | 7 | 2707 | GT |
| AB028944 | 3'UTR | 3.03 | 5263 | TGATTCACACCCAGTCCCTGCCACAGACCGTCTCAGACACGCACAGTGGGCCTGCTGCA (SEQ ID NO: 52) |
| AB028945 | 3'UTR | 12 | 4988 | T |
| AB028946 | 3'UTR | 6.6 | 2607 | GGCTG |
| AB028949 | 3'UTR | 3.5 | 5171 | TTTGTT |
| AB028951 | 3'UTR | 12 | 3865 | T |
| AB028952 | CDS | 5.66 | 2863 | CCGCCC |
| AB028952 | 3'UTR | 24.5 | 3553 | CA |
| AB028952 | 3'UTR | 9 | 3536 | TC |
| AB028957 | 3'UTR | 16 | 3971 | T |
| AB028957 | 3'UTR | 12 | 3014 | A |
| AB028958 | 3'UTR | 7 | 3237 | GT |
| AB028961 | 3'UTR | 20 | 1928 | T |
| AB028962 | 3'UTR | 21 | 2757 | T |
| AB028963 | 3'UTR | 16 | 4029 | T |
| AB028964 | 3'UTR | 8 | 4117 | GT |
| AB028968 | 3'UTR | 15 | 4905 | T |
| AB028969 | 3'UTR | 27 | 2736 | C |
| AB028971 | CDS | 6.66 | 1980 | CAG |
| AB028971 | 5'UTR | 31 | 308 | A |
| AB028971 | 3'UTR | 14 | 3191 | T |
| AB028973 | CDS | 3.83 | 9 | GAGGAA |
| AB028973 | 3'UTR | 21 | 4614 | T |
| AB028975 | 5'UTR | 17 | 192 | T |
| AB028976 | 3'UTR | 18 | 3257 | TG |
| AB028976 | 3'UTR | 14 | 5290 | T |
| AB028977 | 3'UTR | 15 | 1874 | T |
| AB028986 | 3'UTR | 23 | 3754 | T |
| AB028987 | CDS | 2.58 | 1114 | GACATGCACGCA (SEQ ID NO: 53) |
| AB028987 | 3'UTR | 22 | 4713 | T |
| AB028994 | CDS | 7 | 1051 | CTG |
| AB028995 | CDS | 6.33 | 226 | GAACCC |
| AB028997 | CDS | 6.33 | 1869 | GAT |
| AB029002 | CDS | 6.33 | 322 | GCT |
| AB029003 | 3'UTR | 33.5 | 1710 | TG |
| AB029006 | 3'UTR | 15 | 3521 | T |
| AB029007 | 3'UTR | 12 | 2938 | A |
| AB029009 | 3'UTR | 7.75 | 3765 | AAAC |
| AB029010 | CDS | 5.66 | 2208 | GAG |
| AB029016 | CDS | 8.33 | 2071 | GCA |
| AB029021 | 3'UTR | 24 | 3377 | T |
| AB029025 | CDS | 6.5 | 632 | GA |

TABLE 1-continued

| Genbank # | Region | # reps | Position | Unit sequence |
|---|---|---|---|---|
| AB029025 | 3'UTR | 16 | 2726 | T |
| AB029028 | 3'UTR | 4.5 | 4214 | CTAA |
| AB029028 | 3'UTR | 20 | 3394 | T |
| AB029030 | CDS | 5.66 | 450 | CAG |
| AB029033 | 3'UTR | 4.75 | 5190 | GCCT |
| AB029033 | 3'UTR | 9 | 3811 | TG |
| AB029034 | 3'UTR | 4.16 | 4075 | GTGGCT |
| AB029290 | 3'UTR | 12 | 16620 | A |
| AB030905 | 3'UTR | 13.5 | 896 | TG |
| AB030905 | 3'UTR | 6.5 | 550 | TA |
| AB031038 | CDS | 7.66 | 357 | GCC |
| AC002086 | CDS | 6.66 | 563 | TGA |
| AC002310 | CDS | 6 | 3548 | GCT |
| AC004079 | CDS | 6 | 333 | GCC |
| AC004080 | CDS | 6.66 | 378 | GCC |
| AC004221 | CDS | 7.33 | 13 | CCA |
| AC004381 | 3'UTR | 13 | 1960 | A |
| AC004382 | 3'UTR | 5.83 | 1485 | GGTGGG |
| AC004528 | CDS | 3.66 | 143 | CGCCCG |
| AC004770 | 5'UTR | 14 | 1626 | T |
| AC005175 | CDS | 3.66 | 1229 | GAGGGC |
| AC005255 | 5'UTR | 7.5 | 190 | TC |
| AC005559 | 5'UTR | 6.33 | 70 | CGG |
| AC005759 | 5'UTR | 3.6 | 750 | GGGCG |
| AC005943 | CDS | 7 | 844 | GAG |
| AC005952 | 5'UTR | 13 | 741 | A |
| AC006276 | CDS | 4.2 | 23 | GGGTG |
| AC006293 | 5'UTR | 13 | 30 | A |
| AC006538 | 3'UTR | 16 | 1840 | T |
| AC007059 | CDS | 9.66 | 1452 | GAG |
| AD001528 | 3'UTR | 3.5 | 1496 | TTTTGT |
| AD001530 | 5'UTR | 9.33 | 43 | CCG |
| AF000152 | 5'UTR | 3.6 | 235 | CCCAG |
| AF000561 | BORDER | 4 | 1773 | AGGACG |
| AF000652 | 3'UTR | 7.5 | 1499 | TG |
| AF000982 | 3'UTR | 13 | 5026 | T |
| AF000991 | 3'UTR | 6.5 | 1045 | TG |
| AF001548 | 3'UTR | 7 | 5955 | ACC |
| AF001549 | 5'UTR | 15 | 93 | A |
| AF001549 | 3'UTR | 12 | 772 | T |
| AF002246 | 3'UTR | 13 | 4635 | T |
| AF002715 | CDS | 10 | 3707 | CTG |
| AF002999 | 3'UTR | 16 | 1709 | T |
| AF003738 | UNKNOWN | 46 | 1356 | A |
| AF003837 | 5'UTR | 12 | 73 | T |
| AF004230 | CDS | 7 | 1586 | CTC |
| AF004231 | CDS | 7 | 1621 | CTC |
| AF004231 | 3'UTR | 15 | 2798 | TG |
| AF004715 | 3'UTR | 18 | 2434 | T |
| AF005046 | CDS | 6 | 933 | TCC |
| AF005046 | 3'UTR | 7 | 2367 | TG |
| AF006199 | UNKNOWN | 22 | 1165 | A |
| AF006199 | UNKNOWN | 21 | 871 | A |
| AF006484 | 5'UTR | 6.33 | 456 | CGC |
| AF006514 | 5'UTR | 9 | 19 | TC |
| AF006514 | 5'UTR | 13 | 38 | T |
| AF007111 | 3'UTR | 15 | 2037 | T |
| AF007128 | UNKNOWN | 9 | 679 | TA |
| AF007128 | UNKNOWN | 24 | 1540 | A |
| AF007128 | UNKNOWN | 14 | 1525 | A |
| AF007131 | UNKNOWN | 22 | 1971 | A |
| AF007132 | UNKNOWN | 22 | 292 | A |
| AF007136 | UNKNOWN | 7.25 | 786 | ATAG |
| AF007136 | UNKNOWN | 18 | 1587 | A |
| AF007138 | UNKNOWN | 12.5 | 1842 | TG |
| AF007138 | UNKNOWN | 18 | 2083 | A |
| AF007143 | UNKNOWN | 21 | 1783 | A |
| AF007146 | UNKNOWN | 24 | 1991 | A |
| AF007147 | UNKNOWN | 25 | 1838 | A |
| AF007147 | UNKNOWN | 15 | 1748 | T |
| AF007149 | UNKNOWN | 18 | 2301 | A |
| AF007150 | UNKNOWN | 21 | 1444 | A |
| AF007152 | CDS | 2.6 | 22 | CCGCTCTCGC (SEQ ID NO: 54) |
| AF007153 | UNKNOWN | 31 | 1794 | A |
| AF007748 | 3'UTR | 6 | 2967 | CAC |
| AF007872 | 3'UTR | 7 | 1554 | TG |
| AF007876 | 3'UTR | 3.83 | 2889 | AAAAAC |

TABLE 1-continued

| Genbank # | Region | # reps | Position | Unit sequence |
|---|---|---|---|---|
| AF007876 | 3'UTR | 7 | 1773 | CA |
| AF007876 | 3'UTR | 18 | 2336 | T |
| AF008192 | CDS | 9 | 1203 | GA |
| AF008192 | 3'UTR | 15 | 1462 | A |
| AF008216 | CDS | 5.66 | 561 | GAG |
| AF008915 | 3'UTR | 6.75 | 6627 | TTTG |
| AF008915 | 3'UTR | 12.5 | 2531 | TA |
| AF008915 | 3'UTR | 15 | 6555 | A |
| AF009314 | UNKNOWN | 21 | 1463 | A |
| AF009314 | UNKNOWN | 20 | 517 | T |
| AF009424 | 3'UTR | 9.33 | 5983 | TGC |
| AF009772 | UNKNOWN | 13 | 723 | T |
| AF010233 | 5'UTR | 3.83 | 198 | GCGGCA |
| AF010233 | 5'UTR | 7 | 63 | GGC |
| AF010238 | 3'UTR | 4.4 | 1634 | TTGTT |
| AF010242 | UNKNOWN | 4.8 | 320 | CCAGC |
| AF010309 | 5'UTR | 2.6 | 449 | CCTGCCCTGCCCTGTCCTGTCCTGC (SEQ ID NO: 55) |
| AF010309 | 5'UTR | 2.5 | 433 | CCCTGCCCTGTCCTGTCCTG (SEQ ID NO: 56) |
| AF010312 | 3'UTR | 13 | 1172 | T |
| AF010313 | 3'UTR | 26 | 1698 | A |
| AF010316 | 3'UTR | 23.5 | 1621 | TG |
| AF010400 | 5'UTR | 6 | 14 | CGC |
| AF011374 | 5'UTR | 3.66 | 5 | AGCGGG |
| AF012072 | 3'UTR | 14 | 5315 | A |
| AF012072 | 3'UTR | 13 | 5525 | T |
| AF012108 | CDS | 4.83 | 3974 | CAGCAA |
| AF012108 | CDS | 9.66 | 3950 | CAG |
| AF012108 | CDS | 7 | 3928 | GCA |
| AF012108 | 3'UTR | 9.5 | 5909 | TG |
| AF012108 | 3'UTR | 7.5 | 5893 | TG |
| AF013168 | CDS | 6.66 | 3330 | GCA |
| AF013168 | 3'UTR | 22 | 5234 | T |
| AF013759 | 3'UTR | 14 | 2415 | A |
| AF013956 | CDS | 11 | 1327 | CAC |
| AF014459 | 3'UTR | 13 | 822 | T |
| AF014643 | CDS | 7 | 472 | GAG |
| AF015287 | 3'UTR | 13 | 1344 | GT |
| AF016052 | 3'UTR | 12 | 1279 | A |
| AF016267 | CDS | 3.26 | 748 | GGGACTCCTGCCCCAGCTGCTGAAGAGACAATGACCACCAGCCCG (SEQ ID NO: 57) |
| AF016898 | 5'UTR | 7 | 2 | AG |
| AF017257 | 3'UTR | 4.75 | 2432 | TTTG |
| AF017307 | 5'UTR | 10 | 0 | GA |
| AF017789 | CDS | 2.94 | 549 | CAGGCTCAGGCCCAGGCG (SEQ ID NO: 58) |
| AF017789 | CDS | 6.33 | 627 | CAGGCC |
| AF017789 | 3'UTR | 12 | 3701 | T |
| AF018080 | 3'UTR | 18 | 2837 | T |
| AF019085 | CDS | 7 | 2024 | AGC |
| AF019612 | CDS | 6 | 115 | TGG |
| AF020202 | 3'UTR | 7 | 5938 | TC |
| AF020544 | UNKNOWN | 6.5 | 2805 | TC |
| AF020762 | CDS | 5 | 407 | TTTTG |
| AF022152 | 3'UTR | 7 | 3356 | TC |
| AF022375 | 3'UTR | 8.5 | 2858 | TA |
| AF022375 | 3'UTR | 7.5 | 1635 | TA |
| AF022654 | 5'UTR | 7 | 99 | GT |
| AF022654 | 3'UTR | 3.5 | 2495 | TTTTGT |
| AF022654 | 3'UTR | 25 | 1864 | AT |
| AF023142 | CDS | 7.33 | 2907 | CAG |
| AF023259 | CDS | 2.58 | 278 | CAGCAGCAACAA (SEQ ID NO: 59) |
| AF023450 | 5'UTR | 6.33 | 315 | GCG |
| AF023614 | 3'UTR | 3 | 1121 | GGAGAGAGGCAGAGAG (SEQ ID NO: 60) |
| AF024578 | 3'UTR | 8 | 3964 | CA |
| AF025771 | 5'UTR | 3.83 | 1251 | TTTTTA |
| AF026029 | CDS | 7 | 1284 | GGC |
| AF026029 | 3'UTR | 14 | 2266 | A |
| AF026029 | 3'UTR | 12 | 2911 | T |
| AF026547 | CDS | 5.66 | 3847 | CAC |
| AF026547 | 3'UTR | 8.5 | 5026 | AC |
| AF026941 | UNKNOWN | 32 | 3163 | A |
| AF026941 | UNKNOWN | 14 | 2369 | T |
| AF027153 | 3'UTR | 17 | 8621 | A |
| AF027208 | 3'UTR | 6.5 | 3343 | AG |
| AF027299 | CDS | 5.66 | 2264 | AGC |
| AF028706 | CDS | 9 | 653 | CGC |
| AF028828 | 3'UTR | 5.25 | 1111 | TTCA |

TABLE 1-continued

| Genbank # | Region | # reps | Position | Unit sequence |
|---|---|---|---|---|
| AF029729 | 3'UTR | 7.5 | 2844 | TG |
| AF029750 | 3'UTR | 15 | 1557 | T |
| AF029750 | 3'UTR | 12 | 1515 | T |
| AF029778 | 5'UTR | 6.33 | 262 | CGC |
| AF030111 | 5'UTR | 4.59 | 249 | TTTAT |
| AF030339 | 5'UTR | 5.66 | 158 | CCG |
| AF030354 | UNKNOWN | 13 | 240 | A |
| AF030555 | 3'UTR | 7.5 | 3766 | TG |
| AF030880 | 3'UTR | 25 | 4486 | A |
| AF031469 | 3'UTR | 15.66 | 1837 | AAT |
| AF031815 | CDS | 14.33 | 484 | CAG |
| AF031815 | CDS | 8.33 | 371 | AGC |
| AF032111 | UNKNOWN | 16 | 4986 | A |
| AF032387 | 3'UTR | 12 | 5013 | G |
| AF032456 | 3'UTR | 12 | 677 | T |
| AF032906 | 5'UTR | 13 | 30 | A |
| AF032986 | 3'UTR | 3.5 | 2174 | CCCAGC |
| AF033199 | UNKNOWN | 17 | 2613 | A |
| AF034176 | UNKNOWN | 20 | 4943 | T |
| AF034176 | UNKNOWN | 14 | 3632 | T |
| AF034184 | UNKNOWN | 18 | 231 | A |
| AF034374 | UNKNOWN | 3.8 | 2461 | CCTGT |
| AF034374 | UNKNOWN | 4.75 | 2847 | ATCA |
| AF034374 | UNKNOWN | 34 | 2979 | A |
| AF034960 | UNKNOWN | 24 | 1759 | A |
| AF035278 | UNKNOWN | 17 | 1329 | A |
| AF035281 | UNKNOWN | 19 | 1401 | A |
| AF035282 | UNKNOWN | 27 | 1733 | A |
| AF035284 | UNKNOWN | 23 | 85 | A |
| AF035287 | 3'UTR | 9 | 1007 | AT |
| AF035288 | UNKNOWN | 20 | 760 | T |
| AF035288 | UNKNOWN | 18 | 2349 | A |
| AF035290 | UNKNOWN | 21 | 905 | T |
| AF035290 | UNKNOWN | 18 | 1605 | A |
| AF035291 | UNKNOWN | 20 | 1600 | A |
| AF035296 | UNKNOWN | 26 | 1494 | A |
| AF035296 | UNKNOWN | 13 | 766 | T |
| AF035306 | UNKNOWN | 20 | 2086 | A |
| AF035308 | UNKNOWN | 24 | 2518 | A |
| AF035313 | UNKNOWN | 18 | 1369 | A |
| AF035314 | UNKNOWN | 10.5 | 174 | GT |
| AF035314 | UNKNOWN | 9.5 | 156 | GA |
| AF035314 | UNKNOWN | 19 | 2047 | A |
| AF035314 | UNKNOWN | 15 | 37 | T |
| AF035315 | UNKNOWN | 23 | 1331 | A |
| AF035317 | UNKNOWN | 18 | 1730 | A |
| AF035318 | UNKNOWN | 18 | 1654 | A |
| AF035582 | 3'UTR | 13 | 3237 | T |
| AF035587 | 3'UTR | 15 | 1142 | T |
| AF035594 | UNKNOWN | 12 | 1158 | A |
| AF036329 | CDS | 3.6 | 377 | GCCCC |
| AF037204 | 3'UTR | 13 | 1554 | A |
| AF037219 | UNKNOWN | 18 | 4565 | A |
| AF037219 | UNKNOWN | 16 | 2766 | T |
| AF037219 | UNKNOWN | 12 | 2383 | A |
| AF037332 | 5'UTR | 18 | 5 | T |
| AF037448 | 5'UTR | 4.8 | 287 | AGGGA |
| AF037448 | 5'UTR | 5.66 | 199 | GTG |
| AF038170 | UNKNOWN | 27 | 1390 | A |
| AF038171 | UNKNOWN | 18 | 1350 | A |
| AF038172 | UNKNOWN | 21 | 1567 | A |
| AF038174 | UNKNOWN | 19 | 1209 | A |
| AF038176 | UNKNOWN | 34 | 1242 | A |
| AF038177 | UNKNOWN | 20 | 1091 | A |
| AF038181 | UNKNOWN | 17 | 1196 | A |
| AF038182 | UNKNOWN | 19 | 1508 | A |
| AF038184 | UNKNOWN | 26 | 1293 | A |
| AF038185 | UNKNOWN | 8.5 | 1301 | TA |
| AF038185 | UNKNOWN | 19 | 1540 | A |
| AF038186 | UNKNOWN | 22 | 1406 | A |
| AF038187 | UNKNOWN | 18 | 1642 | A |
| AF038187 | UNKNOWN | 17 | 1138 | T |
| AF038188 | UNKNOWN | 28 | 1450 | A |
| AF038189 | UNKNOWN | 20 | 1984 | A |
| AF038190 | UNKNOWN | 6.4 | 164 | ATTTC |
| AF038190 | UNKNOWN | 40 | 1887 | A |
| AF038192 | UNKNOWN | 18 | 1187 | A |

TABLE 1-continued

| Genbank # | Region | # reps | Position | Unit sequence |
|---|---|---|---|---|
| AF038193 | UNKNOWN | 18 | 1567 | A |
| AF038194 | UNKNOWN | 37 | 1353 | A |
| AF038196 | UNKNOWN | 22 | 1401 | A |
| AF038198 | UNKNOWN | 19 | 1521 | A |
| AF038199 | UNKNOWN | 24 | 1112 | A |
| AF038199 | UNKNOWN | 17 | 183 | A |
| AF038201 | UNKNOWN | 21 | 1371 | A |
| AF038202 | UNKNOWN | 19 | 1742 | A |
| AF038203 | UNKNOWN | 28 | 1473 | A |
| AF038204 | UNKNOWN | 28 | 1656 | A |
| AF038658 | UNKNOWN | 16 | 570 | T |
| AF038660 | CDS | 7.33 | 223 | AGC |
| AF038844 | 5'UTR | 3.6 | 35 | CCGCG |
| AF039081 | 3'UTR | 6.4 | 2301 | TCTAG |
| AF039185 | UNKNOWN | 3.8 | 78 | TTTTA |
| AF039185 | UNKNOWN | 14 | 1523 | A |
| AF039307 | CDS | 5.66 | 528 | GCG |
| AF039555 | 3'UTR | 25 | 829 | CA |
| AF039571 | CDS | 6.66 | 3992 | GAG |
| AF039656 | 3'UTR | 12 | 780 | CT |
| AF040709 | 5'UTR | 7.66 | 116 | CCG |
| AF040709 | 3'UTR | 12.5 | 4792 | AC |
| AF040709 | 3'UTR | 6.5 | 5012 | GT |
| AF041037 | 3'UTR | 3.6 | 474 | TTTTG |
| AF041081 | UNKNOWN | 16 | 6290 | A |
| AF041210 | 3'UTR | 20 | 3136 | A |
| AF041240 | CDS | 7.33 | 132 | CTG |
| AF041245 | 5'UTR | 13 | 32 | G |
| AF041259 | 3'UTR | 13 | 3942 | T |
| AF041339 | CDS | 5.66 | 726 | GCC |
| AF042357 | UNKNOWN | 15 | 1577 | A |
| AF042385 | 5'UTR | 12 | 32 | G |
| AF042498 | CDS | 5.66 | 1138 | GAG |
| AF042800 | CDS | 4.66 | 1658 | AGCCGC |
| AF042800 | CDS | 3.83 | 1364 | TCCCGC |
| AF042800 | CDS | 3.66 | 1028 | TCCCGC |
| AF042800 | CDS | 8 | 1225 | CTC |
| AF042832 | CDS | 4 | 2988 | CCGCAC |
| AF042838 | CDS | 8.66 | 2770 | CAA |
| AF043250 | 3'UTR | 3.5 | 1205 | TCCACC |
| AF043324 | 3'UTR | 6.5 | 1821 | TA |
| AF043325 | 3'UTR | 16 | 2533 | A |
| AF043978 | 3'UTR | 2.63 | 1915 | CATATGTATTTTGTATTTG (SEQ ID NO: 61) |
| AF043978 | 3'UTR | 9 | 1734 | CA |
| AF044209 | 5'UTR | 5.66 | 34 | GCG |
| AF045458 | 5'UTR | 2.57 | 148 | CCCGGCCCCGCGCC (SEQ ID NO: 62) |
| AF046001 | 5'UTR | 32 | 0 | AG |
| AF047002 | 3'UTR | 14 | 859 | T |
| AF047002 | 3'UTR | 12 | 846 | T |
| AF047347 | 5'UTR | 7 | 16 | GGC |
| AF047347 | 3'UTR | 11 | 3517 | CA |
| AF047347 | 3'UTR | 19 | 2918 | T |
| AF047348 | 3'UTR | 5.5 | 2980 | TGAT |
| AF047419 | 5'UTR | 9 | 221 | TC |
| AF047432 | 3'UTR | 19 | 784 | T |
| AF047437 | CDS | 8 | 875 | TG |
| AF047442 | 3'UTR | 22 | 1124 | T |
| AF048693 | CDS | 8 | 1337 | CGG |
| AF048730 | CDS | 5.66 | 1590 | ATC |
| AF049105 | CDS | 3.66 | 4192 | CCAGGC |
| AF049910 | 3'UTR | 17 | 5490 | A |
| AF049910 | 3'UTR | 15 | 3677 | T |
| AF049910 | 3'UTR | 12 | 2836 | A |
| AF050199 | 3'UTR | 16 | 1120 | T |
| AF050640 | 3'UTR | 17.5 | 1474 | TG |
| AF051160 | 3'UTR | 15 | 1762 | T |
| AF051782 | 3'UTR | 8 | 5508 | AG |
| AF051941 | 3'UTR | 18 | 1153 | A |
| AF052087 | UNKNOWN | 27 | 1082 | A |
| AF052090 | UNKNOWN | 19 | 1242 | A |
| AF052091 | UNKNOWN | 7.33 | 584 | TGG |
| AF052091 | UNKNOWN | 20 | 1333 | A |
| AF052093 | UNKNOWN | 24 | 1352 | A |
| AF052094 | UNKNOWN | 22 | 1242 | A |
| AF052095 | UNKNOWN | 25 | 1641 | A |
| AF052097 | UNKNOWN | 22 | 1476 | A |
| AF052099 | UNKNOWN | 8.66 | 1238 | TTG |

TABLE 1-continued

| Genbank # | Region | # reps | Position | Unit sequence |
|---|---|---|---|---|
| AF052099 | UNKNOWN | 18 | 1737 | A |
| AF052099 | UNKNOWN | 13 | 426 | T |
| AF052100 | UNKNOWN | 23 | 1531 | A |
| AF052102 | UNKNOWN | 31 | 1884 | A |
| AF052103 | UNKNOWN | 18 | 1311 | A |
| AF052105 | UNKNOWN | 7 | 452 | CA |
| AF052105 | UNKNOWN | 17 | 1542 | A |
| AF052106 | UNKNOWN | 18 | 1851 | A |
| AF052107 | UNKNOWN | 20 | 1556 | A |
| AF052108 | UNKNOWN | 22 | 1684 | A |
| AF052109 | UNKNOWN | 5.83 | 1275 | TTTTG |
| AF052109 | UNKNOWN | 5.8 | 155 | TTTTG |
| AF052109 | UNKNOWN | 18 | 2477 | A |
| AF052111 | UNKNOWN | 18 | 1285 | A |
| AF052113 | UNKNOWN | 18 | 1652 | A |
| AF052114 | UNKNOWN | 17 | 2416 | A |
| AF052115 | UNKNOWN | 23 | 1643 | A |
| AF052116 | UNKNOWN | 31 | 1519 | A |
| AF052117 | UNKNOWN | 30 | 1592 | A |
| AF052117 | UNKNOWN | 13 | 657 | T |
| AF052119 | UNKNOWN | 19 | 2382 | A |
| AF052120 | UNKNOWN | 23 | 1671 | A |
| AF052121 | UNKNOWN | 23 | 1549 | A |
| AF052122 | UNKNOWN | 35 | 1036 | A |
| AF052123 | UNKNOWN | 22 | 1772 | A |
| AF052130 | UNKNOWN | 12 | 1215 | T |
| AF052134 | UNKNOWN | 22 | 1157 | A |
| AF052137 | UNKNOWN | 22 | 1273 | A |
| AF052138 | UNKNOWN | 18 | 1204 | A |
| AF052140 | UNKNOWN | 18 | 1480 | A |
| AF052141 | UNKNOWN | 19 | 1578 | A |
| AF052142 | UNKNOWN | 22 | 1486 | A |
| AF052143 | UNKNOWN | 3.6 | 242 | AAACA |
| AF052143 | UNKNOWN | 21.5 | 1135 | TA |
| AF052143 | UNKNOWN | 7 | 704 | AC |
| AF052143 | UNKNOWN | 31 | 1459 | A |
| AF052143 | UNKNOWN | 12 | 1268 | T |
| AF052145 | UNKNOWN | 19 | 1415 | A |
| AF052146 | UNKNOWN | 18 | 1584 | A |
| AF052148 | UNKNOWN | 31 | 1442 | A |
| AF052148 | UNKNOWN | 20 | 627 | A |
| AF052149 | UNKNOWN | 31 | 1633 | A |
| AF052150 | UNKNOWN | 4.66 | 1741 | AAAACA |
| AF052150 | UNKNOWN | 14 | 167 | A |
| AF052151 | UNKNOWN | 18 | 1337 | A |
| AF052152 | UNKNOWN | 18 | 1568 | A |
| AF052155 | UNKNOWN | 19 | 1465 | A |
| AF052159 | UNKNOWN | 39 | 1277 | A |
| AF052160 | UNKNOWN | 25 | 1401 | A |
| AF052162 | UNKNOWN | 36 | 1344 | A |
| AF052167 | UNKNOWN | 3.6 | 343 | CCCTG |
| AF052167 | UNKNOWN | 27 | 1496 | A |
| AF052169 | UNKNOWN | 19 | 1385 | A |
| AF052172 | UNKNOWN | 20 | 1308 | A |
| AF052174 | UNKNOWN | 19 | 1439 | A |
| AF052176 | UNKNOWN | 18 | 1307 | A |
| AF052177 | UNKNOWN | 20 | 1272 | A |
| AF052178 | UNKNOWN | 24 | 1464 | A |
| AF052181 | UNKNOWN | 20 | 1383 | A |
| AF052182 | UNKNOWN | 28 | 1298 | A |
| AF052183 | UNKNOWN | 22 | 1331 | A |
| AF052185 | UNKNOWN | 22 | 1298 | A |
| AF052186 | UNKNOWN | 24 | 1180 | A |
| AF052187 | UNKNOWN | 21 | 1502 | A |
| AF052224 | CDS | 2.66 | 7480 | CAGCAGCTGCAG (SEQ ID NO: 63) |
| AF052224 | CDS | 3.5 | 190 | GGCCCC |
| AF052224 | 3'UTR | 11 | 15564 | GT |
| AF052288 | 3'UTR | 15 | 5433 | A |
| AF052288 | 3'UTR | 12 | 3633 | T |
| AF052493 | UNKNOWN | 16 | 498 | A |
| AF052496 | UNKNOWN | 33 | 1323 | A |
| AF052496 | UNKNOWN | 14 | 1140 | T |
| AF052497 | UNKNOWN | 6.66 | 2209 | TGA |
| AF052497 | UNKNOWN | 18 | 3288 | A |
| AF053356 | CDS | 2.8 | 1713 | CAGAAAAACCCACCATTCCCT (SEQ ID NO: 64) |
| AF053356 | CDS | 6.33 | 1675 | CAG |
| AF053356 | CDS | 6 | 578 | AGG |

TABLE 1-continued

| Genbank # | Region | # reps | Position | Unit sequence |
|---|---|---|---|---|
| AF053712 | 3'UTR | 13 | 2079 | T |
| AF054172 | UNKNOWN | 15 | 427 | A |
| AF054589 | UNKNOWN | 12 | 2040 | TAAA |
| AF054589 | UNKNOWN | 6.66 | 430 | GAG |
| AF054994 | UNKNOWN | 20 | 1665 | A |
| AF054995 | UNKNOWN | 19 | 2482 | A |
| AF054996 | UNKNOWN | 39 | 1555 | A |
| AF054998 | UNKNOWN | 18 | 1862 | A |
| AF055007 | UNKNOWN | 9 | 1287 | AT |
| AF055007 | UNKNOWN | 20 | 1709 | A |
| AF055009 | UNKNOWN | 4 | 160 | CAAAA |
| AF055009 | UNKNOWN | 21 | 1800 | A |
| AF055011 | UNKNOWN | 7 | 1313 | CT |
| AF055011 | UNKNOWN | 23 | 1701 | A |
| AF055011 | UUKNOWN | 15 | 1053 | A |
| AF055012 | UNKNOWN | 4.75 | 628 | TTTG |
| AF055012 | UNKNOWN | 31 | 1757 | A |
| AF055018 | UNKNOWN | 18 | 1784 | A |
| AF055019 | UNKNOWN | 18 | 1649 | A |
| AF055019 | UNKNOWN | 13 | 223 | T |
| AF055023 | UNKNOWN | 21 | 1220 | T |
| AF055023 | UNKNOWN | 19 | 1834 | A |
| AF055024 | UNKNOWN | 3.6 | 1047 | TGCCC |
| AF055024 | UNKNOWN | 28 | 1830 | A |
| AF055027 | UNKNOWN | 18 | 2142 | A |
| AF055029 | UNKNOWN | 19 | 1816 | A |
| AF055030 | UNKNOWN | 19 | 1706 | A |
| AF055033 | 5'UTR | 3.83 | 171 | TTTTTG |
| AF055033 | 5'UTR | 3.66 | 643 | AAAACA |
| AF055376 | CDS | 8.66 | 1482 | GGC |
| AF055376 | CDS | 6.66 | 1348 | ACC |
| AF055376 | 5'UTR | 7.66 | 778 | GCG |
| AF055376 | 3'UTR | 15.5 | 2099 | CA |
| AF055376 | 3'UTR | 7.5 | 2409 | TG |
| AF055376 | 3'UTR | 18 | 2240 | T |
| AF055581 | 3'UTR | 12 | 3714 | T |
| AF055584 | 3'UTR | 19 | 1601 | T |
| AF055917 | 3'UTR | 5 | 1798 | AATT |
| AF055917 | 3'UTR | 15 | 4277 | T |
| AF056032 | 3'UTR | 2.73 | 2076 | TCTATCTATCTATCATCTA (SEQ ID NO. 65) |
| AF056032 | 3'UTR | 13 | 2109 | ATCT |
| AF056085 | CDS | 6 | 489 | GCC |
| AF056085 | 3'UTR | 18 | 4214 | T |
| AF056085 | 3'UTR | 16 | 3572 | A |
| AF056322 | 3'UTR | 12 | 3051 | A |
| AF057036 | 5'UTR | 8 | 6 | CA |
| AF057164 | 3'UTR | 17 | 2833 | T |
| AF057280 | 3'UTR | 42 | 1181 | T |
| AF058291 | 3'UTR | 3.6 | 1998 | CCTTT |
| AF058291 | 3'UTR | 6.66 | 4952 | AAT |
| AF058291 | 3'UTR | 12 | 3002 | A |
| AF059195 | 3'UTR | 2.8 | 1587 | AAAAAAAAAG (SEQ ID NO: 66) |
| AF059198 | CDS | 6.66 | 1562 | GCA |
| AF059293 | 3'UTR | 8.5 | 1578 | GT |
| AF059611 | 3'UTR | 4.5 | 3351 | TTTA |
| AF060231 | CDS | 8.33 | 1464 | GAG |
| AF060877 | 3'UTR | 5.25 | 1256 | GTAT |
| AF061016 | 3'UTR | 15 | 1585 | T |
| AF061034 | UNKNOWN | 23 | 2116 | A |
| AF061326 | 3'UTR | 13 | 3625 | A |
| AF061736 | 3'UTR | 7 | 639 | TG |
| AF062529 | 3'UTR | 12 | 1039 | T |
| AF062717 | UNKNOWN | 15 | 8 | T |
| AF062719 | UNKNOWN | 35 | 3 | T |
| AF062726 | UNKNOWN | 86 | 5 | T |
| AF063936 | 3'UTR | 12 | 1236 | A |
| AF064019 | 3'UTR | 3.8 | 1332 | TTGTT |
| AF064839 | UNKNOWN | 7.66 | 512 | CCG |
| AF064839 | UNKNOWN | 5.66 | 382 | GGA |
| AF064843 | UNKNOWN | 4.2 | 1111 | TCGCC |
| AF064843 | UNKNOWN | 10 | 478 | GGC |
| AF064845 | UNKNOWN | 5.66 | 463 | GGC |
| AF064854 | UNKNOWN | 7.66 | 2181 | GCG |
| AF064854 | UNKNOWN | 15 | 46 | T |
| AF065482 | 3'UTR | 17 | 1717 | AC |
| AF065854 | CDS | 14 | 453 | T |
| AF067008 | CDS | 7.66 | 1551 | AAG |

TABLE 1-continued

| Genbank # | Region | # reps | Position | Unit sequence |
|---|---|---|---|---|
| AF067223 | 3'UTR | 13 | 1928 | A |
| AF068006 | 3'UTR | 10.5 | 1010 | TA |
| AF068006 | 3'UTR | 20 | 1030 | T |
| AF068179 | 3'UTR | 13 | 779 | A |
| AF068227 | 5'UTR | 15 | 0 | T |
| AF068846 | 3'UTR | 14 | 2964 | T |
| AF068864 | CDS | 5.66 | 531 | GAA |
| AF069250 | 3'UTR | 6 | 1833 | TTA |
| AF069250 | 3'UTR | 13 | 502 | T |
| AF069747 | 3'UTR | 4.75 | 4244 | TTTG |
| AF069747 | 3'UTR | 17 | 3824 | A |
| AF070523 | 5'UTR | 6 | 63 | GCC |
| AF070524 | UNKNOWN | 21 | 1578 | A |
| AF070525 | UNKNOWN | 26 | 1924 | A |
| AF070526 | UNKNOWN | 20 | 1942 | A |
| AF070528 | UNKNOWN | 27 | 1568 | A |
| AF070529 | UNKNOWN | 19 | 273 | A |
| AF070530 | CDS | 8 | 191 | CCT |
| AF070535 | UNKNOWN | 30 | 1464 | A |
| AF070536 | UNKNOWN | 19 | 1433 | A |
| AF070537 | UNKNOWN | 21 | 1407 | A |
| AF070538 | UNKNOWN | 18 | 1551 | A |
| AF070541 | UNKNOWN | 19 | 1557 | A |
| AF070541 | UNKNOWN | 12 | 900 | T |
| AF070543 | UNKNOWN | 22 | 1566 | A |
| AF070543 | UNKNOWN | 14 | 108 | A |
| AF070546 | UNKNOWN | 28 | 1449 | A |
| AF070547 | UNKNOWN | 3.8 | 360 | AAAAC |
| AF070547 | UNKNOWN | 24 | 2322 | A |
| AF070549 | UNKNOWN | 19 | 1352 | A |
| AF070549 | UNKNOWN | 17 | 1279 | T |
| AF070551 | UNKNOWN | 27 | 1628 | A |
| AF070552 | UNKNOWN | 27 | 1465 | A |
| AF070554 | UNKNOWN | 18 | 1433 | A |
| AF070557 | UNKNOWN | 18 | 1615 | A |
| AF076559 | UNKNOWN | 24 | 1684 | A |
| AF070564 | UNKNOWN | 19 | 1468 | A |
| AF070565 | UNKNOWN | 20 | 1430 | A |
| AF070568 | UNKNOWN | 18 | 1359 | A |
| AF070569 | UNKNOWN | 20 | 2221 | A |
| AF070570 | UNKNOWN | 28 | 1775 | A |
| AF070570 | UNKNOWN | 14 | 692 | T |
| AF070570 | UNKNOWN | 13 | 221 | A |
| AF070571 | UNKNOWN | 19 | 2639 | A |
| AF070574 | UNKNOWN | 30 | 1569 | A |
| AF070575 | UNKNOWN | 5.75 | 963 | TTTG |
| AF070575 | UNKNOWN | 16 | 1763 | A |
| AF070577 | UNKNOWN | 19 | 1521 | A |
| AF070578 | UNKNOWN | 20 | 1688 | A |
| AF070579 | UNKNOWN | 18 | 1565 | A |
| AF070580 | UNKNOWN | 20 | 1668 | A |
| AF070581 | UNKNOWN | 4.5 | 1647 | TTGT |
| AF070581 | UNKNOWN | 18 | 1730 | A |
| AF070582 | UNKNOWN | 28 | 1744 | A |
| AF070584 | UNKNOWN | 18 | 1737 | A |
| AF070585 | UNKNOWN | 23 | 2114 | A |
| AF070586 | UNKNOWN | 18 | 1824 | A |
| AF070587 | UNKNOWN | 27 | 1633 | A |
| AF070590 | UNKNOWN | 22 | 1835 | A |
| AF070592 | UNKNOWN | 18 | 1876 | A |
| AF070595 | UNKNOWN | 19 | 1895 | A |
| AF070596 | UNKNOWN | 17 | 1576 | A |
| AF070599 | UNKNOWN | 19 | 1719 | A |
| AF070602 | UNKNOWN | 18 | 1693 | A |
| AF070606 | UNKNOWN | 19 | 1828 | A |
| AF070610 | UNKNOWN | 18 | 1603 | A |
| AF070611 | UNKNOWN | 19 | 1856 | A |
| AF070617 | UNKNOWN | 21 | 1305 | A |
| AF070617 | UNKNOWN | 12 | 1223 | A |
| AF070618 | UNKNOWN | 32 | 1179 | A |
| AF070620 | UNKNOWN | 19 | 1589 | A |
| AF070620 | UNKNOWN | 15 | 638 | T |
| AF070621 | UNKNOWN | 19 | 1675 | A |
| AF070623 | UNKNOWN | 23 | 1226 | A |
| AF070625 | UNKNOWN | 18 | 1710 | A |
| AF070628 | UNKNOWN | 18 | 1469 | A |
| AF070632 | UNKNOWN | 48 | 1398 | A |

TABLE 1-continued

| Genbank # | Region | # reps | Position | Unit sequence |
|---|---|---|---|---|
| AF070632 | UNKNOWN | 12 | 1250 | A |
| AF070633 | UNKNOWN | 22 | 1459 | A |
| AF070640 | UNKNOWN | 26 | 1583 | A |
| AF070641 | UNKNOWN | 19 | 1410 | A |
| AF070642 | UNKNOWN | 8.5 | 983 | AC |
| AF070642 | UNKNOWN | 18 | 1103 | A |
| AF070643 | UNKNOWN | 42 | 1485 | A |
| AF070644 | UNKNOWN | 27 | 1355 | A |
| AF070647 | UNKNOWN | 14 | 136 | A |
| AF070648 | UNKNOWN | 19 | 1313 | A |
| AF070649 | UNKNOWN | 18 | 1474 | A |
| AF071058 | UNKNOWN | 7.5 | 212 | TG |
| AF071058 | UNKNOWN | 15 | 414 | A |
| AF071309 | CDS | 7 | 6216 | CAG |
| AF071787 | CDS | 14 | 1865 | A |
| AF073931 | CDS | 6 | 1814 | CAC |
| AF073931 | 5'UTR | 3.66 | 102 | GGGGCC |
| AF074675 | UNKNOWN | 97 | 5 | T |
| AF075292 | 5'UTR | 9.33 | 433 | GCG |
| AF075347 | UNKNOWN | 45 | 4 | T |
| AF075348 | UNKNOWN | 20 | 2 | T |
| AF077346 | 3'UTR | 6.5 | 2352 | TG |
| AF077374 | CDS | 2.52 | 343 | TGTACCAAGGTCCCTGAGCCAGGCTGTACCAAGGTCCCT GAGCCAGGT (SEQ ID NO: 67) |
| AF077374 | CDS | 3.33 | 310 | GAGCCAGGCTGTACCAAGGTCCCT (SEQ ID NO: 68) |
| AF077599 | 3'UTR | 12 | 2115 | T |
| AF077754 | 3'UTR | 13 | 2060 | T |
| AF077820 | CDS | 9.33 | 120 | GCT |
| AF079167 | 3'UTR | 5 | 1433 | GACA |
| AF079167 | 3'UTR | 16.5 | 1450 | AC |
| AF079167 | 3'UTR | 13 | 1961 | T |
| AF079221 | CDS | 5.66 | 119 | ACA |
| AF079529 | 3'UTR | 12 | 2465 | A |
| AF080237 | 3'UTR | 3.88 | 821 | CCCCTGCTG |
| AF080237 | 3'UTR | 5.66 | 1111 | CTG |
| AF081195 | 3'UTR | 15 | 4643 | A |
| AF081195 | 3'UTR | 13 | 3788 | A |
| AF081281 | 3'UTR | 12 | 1380 | A |
| AF081287 | CDS | 7 | 1422 | GGA |
| AF082889 | CDS | 6 | 138 | GCT |
| AF086904 | CDS | 2.53 | 222 | CCTGAGGACCAAGAA (SEQ ID NO: 69) |
| AF087020 | 5'UTR | 6 | 97 | GCG |
| AF087142 | CDS | 7 | 100 | CTG |
| AF087481 | 3'UTR | 3.6 | 5450 | AAAAC |
| AF088219 | 3'UTR | 23 | 768 | A |
| AF089744 | 3'UTR | 3.8 | 4165 | TTTTG |
| AF089816 | 5'UTR | 11.33 | 18 | GCG |
| AF089824 | CDS | 3.16 | 4093 | CAGCAGCAGCAA (SEQ ID NO: 70) |
| AF089824 | CDS | 6.66 | 2977 | CAG |
| AF089841 | 3'UTR | 11.5 | 8280 | AC |
| AF089854 | 3'UTR | 27 | 2210 | A |
| AF089854 | 3'UTR | 12 | 2237 | T |
| AF090099 | UNKNOWN | 20 | 22 | T |
| AF090100 | UNKNOWN | 20 | 0 | T |
| AF090101 | UNKNOWN | 17 | 19 | T |
| AF090318 | 3'UTR | 14 | 2339 | T |
| AF090693 | 3'UTR | 5.25 | 6516 | TTGA |
| AF090693 | 3'UTR | 14 | 3824 | A |
| AF090988 | 3'UTR | 15 | 1390 | T |
| AF091095 | CDS | 10 | 838 | TGA |
| AF091242 | 5'UTR | 6.33 | 5 | GCC |
| AF091395 | CDS | 6 | 6765 | GGC |
| AF092047 | CDS | 7 | 568 | GGC |
| AF092047 | 5'UTR | 3.83 | 86 | CTCTCC |
| AF092047 | 5'UTR | 7.5 | 180 | GT |
| AF093239 | 5'UTR | 5.6 | 117 | GCCCC |
| AF093774 | 3'UTR | 4.75 | 2155 | ACAT |
| AF093774 | 3'UTR | 21 | 4890 | T |
| AF094508 | CDS | 3.88 | 2085 | GACAGCAGTGACAGCAGC (SEQ ID NO: 71) |
| AF094508 | CDS | 3.77 | 1683 | AGCAGTGACAGCAGCAT (SEQ ID NO: 72) |
| AF094508 | CDS | 3.83 | 2307 | AGTGAC |
| AF095448 | 3'UTR | 13 | 1379 | T |
| AF096870 | 3'UTR | 12 | 2114 | T |
| AF098162 | CDS | 5.66 | 2149 | GAG |
| AF098462 | 3'UTR | 10 | 2321 | AG |
| AF098462 | 3'UTR | 13 | 1861 | A |
| AF098485 | UNKNOWN | 18 | 1335 | A |

TABLE 1-continued

| Genbank # | Region | # reps | Position | Unit sequence |
|---|---|---|---|---|
| AF099989 | CDS | 5.66 | 294 | CGGCCC |
| AF099989 | 5'UTR | 10 | 34 | CGG |
| AF100143 | 3'UTR | 4.59 | 1343 | AAACA |
| AF100143 | 3'UTR | 13 | 1628 | T |
| AF100907 | CDS | 10.66 | 122 | GCG |
| AF104902 | CDS | 9.66 | 692 | CCA |
| AF104902 | CDS | 5.66 | 75 | GCG |
| AF104913 | CDS | 5.66 | 1263 | GAA |
| AF104942 | 3'UTR | 8 | 5481 | TC |
| AF106861 | CDS | 6.33 | 249 | GCG |
| AF107044 | CDS | 6.66 | 477 | GCC |
| AF107735 | CDS | 6 | 140 | GAG |
| AF109134 | CDS | 2.6 | 1804 | GAGCCAGCCGAGAGCCCATCGGAGACCCCAGGCCCCGC CCGGCAGGACCTGCAGGGGAC (SEQ ID NO: 73) |
| AF110146 | CDS | 7.33 | 110 | GCT |
| AF110146 | 3'UTR | 6.5 | 3718 | AT |
| AF111173 | CDS | 6 | 2175 | GAG |
| AF112219 | 3'UTR | 14 | 1099 | A |
| AF114095 | UNKNOWN | 19 | 350 | A |
| AF114095 | UNKNOWN | 12 | 49 | A |
| AF114821 | CDS | 7.33 | 47 | GCT |
| AF116846 | CDS | 8.66 | 175 | CAG |
| AF116846 | 3'UTR | 8.5 | 3583 | AC |
| AF117815 | UNKNOWN | 20 | 1315 | A |
| AF119043 | CDS | 6 | 212 | GGA |
| AF121141 | 3'UTR | 10.5 | 6864 | TA |
| AF131740 | UNKNOWN | 20 | 1574 | A |
| AF131741 | UNKNOWN | 16 | 1468 | A |
| AF131745 | UNKNOWN | 22 | 2090 | A |
| AF131752 | UNKNOWN | 5.75 | 567 | TTTG |
| AF131752 | UNKNOWN | 19 | 1457 | A |
| AF131753 | UNKNOWN | 18 | 1858 | A |
| AF131756 | UNKNOWN | 18 | 1578 | A |
| AF131758 | 3'UTR | 5.66 | 1054 | AAC |
| AF131762 | UNKNOWN | 19.5 | 1945 | AC |
| AF131762 | UNKNOWN | 27 | 2495 | A |
| AF131763 | UNKNOWN | 21 | 2027 | A |
| AF131764 | UNKNOWN | 24 | 1774 | A |
| AF131767 | UNKNOWN | 18 | 1365 | A |
| AF131768 | UNKNOWN | 20 | 1946 | A |
| AF131769 | UNKNOWN | 25 | 1285 | A |
| AF131769 | UNKNOWN | 15 | 0 | T |
| AF131770 | UNKNOWN | 4.5 | 548 | ATAA |
| AF131770 | UNKNOWN | 18 | 1736 | A |
| AF131772 | UNKNOWN | 18 | 1505 | A |
| AF131773 | UNKNOWN | 50 | 1286 | A |
| AF131773 | UNKNOWN | 19 | 138 | A |
| AF131774 | UNKNOWN | 21 | 1155 | A |
| AF131776 | UNKNOWN | 13 | 38 | A |
| AF131777 | UNKNOWN | 25 | 1970 | A |
| AF131779 | UNKNOWN | 18 | 1228 | A |
| AF131782 | UNKNOWN | 17 | 1926 | A |
| AF131783 | UNKNOWN | 19 | 1518 | A |
| AF131784 | UNKNOWN | 21 | 2565 | A |
| AF131787 | UNKNOWN | 21 | 1481 | A |
| AF131788 | UNKNOWN | 18 | 2167 | A |
| AF131789 | UNKNOWN | 9 | 1829 | TG |
| AF131789 | UNKNOWN | 33 | 1975 | A |
| AF131789 | UNKNOWN | 13 | 1798 | T |
| AF131791 | UNKNOWN | 20 | 1402 | A |
| AF131793 | UNKNOWN | 28 | 2187 | A |
| AF131795 | UNKNOWN | 7.5 | 1417 | AC |
| AF131795 | UNKNOWN | 18 | 1500 | A |
| AF131796 | UNKNOWN | 24.5 | 1211 | CA |
| AF131796 | UNKNOWN | 25 | 1508 | A |
| AF131796 | UNKNOWN | 16 | 889 | A |
| AF131798 | UNKNOWN | 23 | 1151 | A |
| AF131799 | UNKNOWN | 18 | 1316 | A |
| AF131803 | UNKNOWN | 26 | 1231 | A |
| AF131804 | UNKNOWN | 30 | 1638 | A |
| AF131805 | UNKNOWN | 24.5 | 1107 | TC |
| AF131805 | UNKNOWN | 12 | 1155 | TA |
| AF131805 | UNKNOWN | 26 | 1676 | A |
| AF131805 | UNKNOWN | 12 | 1187 | T |
| AF131806 | UNKNOWN | 23 | 1818 | A |
| AF131808 | UNKNOWN | 25 | 1769 | A |
| AF131811 | UNKNOWN | 18 | 1752 | A |

TABLE 1-continued

| Genbank # | Region | # reps | Position | Unit sequence |
|---|---|---|---|---|
| AF131812 | UNKNOWN | 18 | 2058 | A |
| AF131813 | UNKNOWN | 22 | 1835 | A |
| AF131814 | UNKNOWN | 47 | 1278 | A |
| AF131814 | UNKNOWN | 16 | 306 | T |
| AF131814 | UNKNOWN | 12 | 1204 | A |
| AF131815 | UNKNOWN | 7 | 258 | GTT |
| AF131815 | UNKNOWN | 19 | 1615 | A |
| AF131817 | UNKNOWN | 27 | 1439 | A |
| AF131817 | UNKNOWN | 16 | 960 | T |
| AF131818 | UNKNOWN | 18 | 2490 | A |
| AF131819 | UNKNOWN | 18 | 1954 | A |
| AF131821 | UNKNOWN | 50 | 1793 | A |
| AF131822 | UNKNOWN | 27 | 1807 | A |
| AF131823 | UNKNOWN | 18 | 1497 | A |
| AF131825 | UNKNOWN | 19 | 1486 | A |
| AF131828 | UNKNOWN | 6.5 | 485 | TG |
| AF131828 | UNKNOWN | 20 | 1784 | A |
| AF131829 | UNKNOWN | 19 | 1458 | A |
| AF131830 | UNKNOWN | 19 | 1274 | A |
| AF131831 | UNKNOWN | 19 | 2048 | A |
| AF131831 | UNKNOWN | 15 | 1211 | T |
| AF131832 | UNKNOWN | 20 | 1680 | A |
| AF131834 | UNKNOWN | 43 | 1941 | A |
| AF131835 | UNKNOWN | 13.33 | 658 | TAA |
| AF131835 | UNKNOWN | 18 | 1784 | A |
| AF131837 | UNKNOWN | 9.5 | 441 | AC |
| AF131837 | UNKNOWN | 19 | 1730 | A |
| AF131838 | UNKNOWN | 18 | 444 | A |
| AF131839 | 3'UTR | 3.66 | 1748 | CCCACC |
| AF131839 | 3'UTR | 6.5 | 1685 | TC |
| AF131840 | UNKNOWN | 18 | 1344 | A |
| AF131841 | UNKNOWN | 20 | 1722 | A |
| AF131842 | 3'UTR | 6.5 | 1049 | TC |
| AF131842 | 3'UTR | 17 | 1061 | T |
| AF131843 | UNKNOWN | 19 | 1511 | A |
| AF131844 | UNKNOWN | 23 | 1546 | A |
| AF131846 | UNKNOWN | 8 | 555 | TC |
| AF131846 | UNKNOWN | 18 | 1676 | A |
| AF131846 | UNKNOWN | 15 | 655 | T |
| AF131851 | 3'UTR | 6.33 | 805 | GAG |
| AF131853 | UNKNOWN | 20 | 2119 | A |
| AF131854 | UNKNOWN | 21 | 1664 | A |
| AF131855 | UNKNOWN | 31 | 1633 | A |
| AF131856 | 3'UTR | 6.5 | 887 | TG |
| AF131857 | UNKNOWN | 21 | 1317 | A |
| AF131858 | UNKNOWN | 18 | 1399 | A |
| AF131859 | UNKNOWN | 5.5 | 1405 | AAAC |
| AF131859 | UNKNOWN | 19 | 1786 | A |
| AF147771 | UNKNOWN | 14 | 98 | A |
| AF147773 | UNKNOWN | 19 | 2 | T |
| AF147777 | UNKNOWN | 14 | 290 | T |
| AF150122 | UNKNOWN | 30 | 408 | A |
| AF150127 | UNKNOWN | 13 | 27 | T |
| AF150136 | UNKNOWN | 15 | 529 | A |
| AF150138 | UNKNOWN | 27 | 325 | A |
| AF150189 | UNKNOWN | 29 | 502 | A |
| AF150191 | UNKNOWN | 25 | 141 | A |
| AF150196 | UNKNOWN | 2.52 | 43 | TGAATGAATGAGTGAACGGAA (SEQ ID NO: 74) |
| AF150220 | UNKNOWN | 14 | 355 | A |
| AF150232 | UNKNOWN | 12 | 1263 | GT |
| AF150251 | UNKNOWN | 12 | 152 | A |
| AF150262 | UNKNOWN | 16 | 73 | T |
| AF150262 | UNKNOWN | 16 | 734 | A |
| AF150275 | UNKNOWN | 13 | 1277 | A |
| AF150287 | UNKNOWN | 13 | 267 | A |
| AF150289 | UNKNOWN | 30 | 724 | A |
| AF150295 | UNKNOWN | 28 | 264 | A |
| AF150310 | UNKNOWN | 25 | 489 | A |
| AF150317 | UNKNOWN | 3.6 | 341 | TAGTG |
| AF150329 | UNKNOWN | 29 | 471 | A |
| AF150335 | UNKNOWN | 29 | 1066 | A |
| AF150335 | UNKNOWN | 21 | 8 | T |
| AF150335 | UNKNOWN | 17 | 81 | A |
| AF150342 | UNKNOWN | 29 | 385 | A |
| AF150368 | UNKNOWN | 29 | 754 | A |
| AF150373 | UNKNOWN | 26 | 308 | A |
| AF150374 | UNKNOWN | 31 | 281 | A |

TABLE 1-continued

| Genbank # | Region | # reps | Position | Unit sequence |
|---|---|---|---|---|
| AF150398 | UNKNOWN | 29 | 526 | A |
| AF150402 | UNKNOWN | 30 | 662 | A |
| AF150433 | UNKNOWN | 12 | 439 | T |
| AF156571 | UNKNOWN | 21 | 2436 | A |
| AI000341 | UNKNOWN | 14 | 18 | A |
| AI000485 | UNKNOWN | 25 | 0 | T |
| AI002003 | UNKNOWN | 14 | 0 | T |
| AI002006 | UNKNOWN | 13 | 0 | T |
| AI002238 | UNKNOWN | 14 | 0 | T |
| AI002390 | UNKNOWN | 18 | 0 | T |
| AI002510 | UNKNOWN | 27 | 0 | T |
| AI002637 | UNKNOWN | 10.5 | 188 | TC |
| AI002637 | UNKNOWN | 8.5 | 146 | TC |
| AI002637 | UNKNOWN | 19 | 402 | A |
| AI002666 | UNKNOWN | 12 | 0 | T |
| AI002941 | UNKNOWN | 18 | 0 | T |
| AI003088 | UNKNOWN | 61 | 24 | T |
| AI003088 | UNKNOWN | 23 | 0 | T |
| AI003088 | UNKNOWN | 15 | 170 | C |
| AI003088 | UNKNOWN | 13 | 403 | G |
| AI003088 | UNKNOWN | 12 | 240 | A |
| AI003503 | UNKNOWN | 6.25 | 215 | TATT |
| AI003543 | UNKNOWN | 20 | 0 | T |
| AI003576 | UNKNOWN | 19 | 0 | T |
| AI003611 | UNKNOWN | 24 | 0 | T |
| AI003521 | UNKNOWN | 18 | 0 | T |
| AI003712 | UNKNOWN | 17 | 0 | T |
| AI003750 | UNKNOWN | 23 | 118 | T |
| AI003750 | UNKNOWN | 15 | 6 | T |
| AI003755 | UNKNOWN | 10.5 | 59 | TG |
| AI003794 | UNKNOWN | 8 | 56 | AC |
| AI003907 | UNKNOWN | 26 | 0 | T |
| AI003963 | UNKNOWN | 12 | 364 | T |
| AI004234 | UNKNOWN | 6.5 | 343 | AT |
| AI004234 | UNKNOWN | 14 | 0 | T |
| AI004235 | UNKNOWN | 8 | 474 | CA |
| AI004402 | UNKNOWN | 4.8 | 144 | TTTTG |
| AI004402 | UNKNOWN | 13 | 248 | A |
| AI004572 | UNKNOWN | 14 | 55 | A |
| AI004605 | UNKNOWN | 10 | 406 | AC |
| AI004605 | UNKNOWN | 7 | 435 | CT |
| AI004606 | UNKNOWN | 5.5 | 5 | TTTA |
| AI004606 | UNKNOWN | 23 | 84 | A |
| AI004614 | UNKNOWN | 14 | 0 | T |
| AI004631 | UNKNOWN | 15 | 0 | T |
| AI004643 | UNKNOWN | 12 | 372 | T |
| AI004662 | UNKNOWN | 22 | 4 | T |
| AI004666 | UNKNOWN | 19 | 4 | T |
| AI004671 | UNKNOWN | 19 | 0 | T |
| AI004674 | UNKNOWN | 19 | 4 | T |
| AI004765 | UNKNOWN | 20 | 0 | T |
| AI004911 | UNKNOWN | 5 | 129 | CAAAA |
| AI004911 | UNKNOWN | 56 | 0 | T |
| AI004995 | UNKNOWN | 14 | 0 | T |
| AI004992 | UNKNOWN | 16 | 0 | T |
| AI005043 | UNKNOWN | 20 | 0 | T |
| AI005051 | UNKNOWN | 44 | 0 | T |
| AI005102 | UNKNOWN | 33 | 0 | T |
| AI005104 | UNKNOWN | 12.5 | 405 | TG |
| AI005104 | UNKNOWN | 8.5 | 429 | TA |
| AI005106 | UNKNOWN | 12 | 0 | T |
| AI005135 | UNKNOWN | 7 | 48 | CT |
| AI005270 | UNKNOWN | 13 | 0 | T |
| AI005283 | UNKNOWN | 16 | 276 | A |
| AI005286 | UNKNOWN | 12 | 0 | T |
| AI005310 | UNKNOWN | 20 | 0 | T |
| AI005336 | UNKNOWN | 27 | 0 | T |
| AI005338 | UNKNOWN | 12 | 0 | T |
| AI005383 | UNKNOWN | 12 | 0 | T |
| AI005406 | UNKNOWN | 20 | 0 | T |
| AI005416 | UNKNOWN | 13 | 0 | T |
| AI005473 | UNKNOWN | 17 | 0 | T |
| AI005474 | UNKNOWN | 16 | 49 | A |
| AI005479 | UNKNOWN | 13 | 153 | T |
| AI005479 | UNKNOWN | 12 | 0 | T |
| AI005591 | UNKNOWN | 23 | 210 | T |
| AI005642 | UNKNOWN | 14 | 0 | T |

TABLE 1-continued

| Genbank # | Region | # reps | Position | Unit sequence |
|---|---|---|---|---|
| AI005651 | UNKNOWN | 16 | 0 | T |
| AI014424 | UNKNOWN | 17 | 284 | T |
| AI014521 | UNKNOWN | 12.5 | 305 | CA |
| AI014545 | UNKNOWN | 14 | 0 | T |
| AI014568 | UNKNOWN | 3.6 | 32 | TCGCC |
| AI014568 | UNKNOWN | 7.5 | 295 | TG |
| AI014569 | UNKNOWN | 15 | 0 | T |
| AI014615 | UNKNOWN | 6.5 | 190 | TG |
| AI014680 | UNKNOWN | 23 | 0 | T |
| AI014683 | UNKNOWN | 16 | 0 | T |
| AI014688 | UNKNOWN | 15 | 0 | T |
| AI014697 | UNKNOWN | 12 | 0 | T |
| AI014702 | UNKNOWN | 15 | 0 | T |
| AI014709 | UNKNOWN | 14 | 0 | T |
| AI014712 | UNKNOWN | 19 | 0 | T |
| AI014714 | UNKNOWN | 15 | 0 | T |
| AI014867 | UNKNOWN | 14 | 0 | T |
| AI014936 | UNKNOWN | 12 | 40 | T |
| AI014971 | UNKNOWN | 6.33 | 42 | TAT |
| AI014971 | UNKNOWN | 32 | 0 | T |
| AI015076 | UNKNOWN | 13 | G | T |
| AI015084 | UNKNOWN | 18 | 0 | T |
| AI015110 | UNKNOWN | 14 | 0 | T |
| AI015210 | UNKNOWN | 21 | 190 | T |
| AI015248 | UNKNOWN | 19 | 0 | T |
| AI015255 | UNKNOWN | 23 | 419 | A |
| AI015333 | UNKNOWN | 12 | 219 | T |
| AI015357 | UNKNOWN | 6 | 12 | ATTT |
| AI015393 | UNKNOWN | 8 | 290 | CA |
| AI015430 | UNKNOWN | 5 | 183 | TCTT |
| AI015529 | UNKNOWN | 14 | 0 | T |
| AI015547 | UNKNOWN | 6 | 476 | AGC |
| AI015583 | UNKNOWN | 18 | 4 | T |
| AI015591 | UNKNOWN | 16 | 0 | T |
| AI015599 | UNKNOWN | 7 | 383 | GT |
| AI015772 | UNKNOWN | 4.75 | 152 | AAAT |
| AI015776 | UNKNOWN | 14 | 0 | T |
| AI015813 | UNKNOWN | 7.5 | 274 | AC |
| AI015954 | UNKNOWN | 16 | 432 | T |
| AI015955 | UNKNOWN | 9.5 | 127 | GT |
| AI015982 | UNKNOWN | 14 | 0 | T |
| AI016120 | UNKNOWN | 12 | 76 | A |
| AI016204 | UNKNOWN | 24 | 102 | AC |
| AI016238 | UNKNOWN | 13 | 0 | T |
| AI016271 | UNKNOWN | 13 | 0 | T |
| AI016289 | UNKNOWN | 12 | 0 | T |
| AI016305 | UNKNOWN | 10.66 | 104 | TAA |
| AI016316 | UNKNOWN | 12 | 351 | A |
| AI016538 | UNKNOWN | 18 | 0 | T |
| AI016542 | UNKNOWN | 14 | 80 | T |
| AI016561 | UNKNOWN | 15 | 0 | T |
| AI016577 | UNKOWN | 7.5 | 254 | TC |
| AI016577 | UNKNOWN | 12 | 423 | T |
| AI016586 | UNKNOWN | 8.5 | 330 | AAAC |
| AI016586 | UNKNOWN | 6.75 | 11 | TTTA |
| AI016586 | UNKNOWN | 14 | 0 | T |
| AI016604 | UNKNOWN | 20 | 293 | A |
| AI016634 | UNKNOWN | 12 | 118 | TG |
| AI016660 | UNKNOWN | 18 | 0 | T |
| AI016704 | UNKNOWN | 28 | 162 | T |
| AI016704 | UNKNOWN | 12 | 0 | T |
| AI016729 | UNKNOWN | 33 | 0 | T |
| AI016744 | UNKNOWN | 12 | 184 | A |
| AI016781 | UNKNOWN | 2 | 0 | T |
| AI016815 | UNKNOWN | 27 | 0 | T |
| AI016822 | UNKNOWN | 30 | 0 | T |
| AI016855 | UNKNOWN | 12 | 6 | T |
| AI017170 | UNKNOWN | 6.6 | 26 | AAACA |
| AI017214 | UNKNOWN | 12 | 0 | T |
| AI017415 | UNKNOWN | 4.8 | 19 | TTTTA |
| AI017427 | UNKNOWN | 44 | 0 | T |
| AI017577 | UNKNOWN | 17 | 0 | T |
| AI017603 | UNKNOWN | 7.66 | 102 | GCA |
| AI017615 | UNKNOWN | 12 | 4 | A |
| AI017718 | UNKNOWN | 26 | 0 | T |
| AI017760 | UNKNOWN | 33 | 0 | T |
| AI017792 | UNKNOWN | 22 | 0 | T |

TABLE 1-continued

| Genbank # | Region | # reps | Position | Unit sequence |
|---|---|---|---|---|
| AI017875 | UNKNOWN | 18 | 0 | T |
| AI017881 | UNKNOWN | 7 | 399 | TG |
| AI017881 | UNKNOWN | 12 | 0 | T |
| AI017883 | UNKNOWN | 15 | 0 | T |
| AI018001 | UNKNOWN | 13 | 0 | T |
| AI018036 | UNKNOWN | 8 | 407 | AC |
| AI018074 | UNKNOWN | 12 | 0 | T |
| AI018192 | UNKNOWN | 19 | 0 | T |
| AI018215 | UNKNOWN | 14 | 0 | T |
| AI018283 | UNKNOWN | 6 | 80 | AAC |
| AI018330 | UNKNOWN | 12 | 0 | T |
| AI018331 | UNKNOWN | 5.75 | 33 | TCCC |
| AI018343 | UNKNOWN | 14 | 0 | T |
| AI018439 | UNKNOWN | 16 | 0 | T |
| AI018507 | UNKNOWN | 21 | 0 | T |
| AI018561 | UNKNOWN | 4.5 | 22 | TTAT |
| AI018605 | UNKNOWN | 18 | 0 | T |
| AI018686 | UNKNOWN | 58 | 0 | T |
| AI018686 | UNKNOWN | 23 | 208 | A |
| AI018686 | UNKNOWN | 20 | 160 | C |
| AI018686 | UNKNOWN | 17 | 121 | C |
| AI018686 | UNKNOWN | 12 | 60 | G |
| AI018758 | UNKNOWN | 13 | 485 | T |
| AI018784 | UNKNOWN | 12 | 0 | T |
| AI018796 | UNKNOWN | 14 | 0 | T |
| AI021899 | UNKNOWN | 21 | 0 | T |
| AI021899 | UNKNOWN | 13 | 113 | C |
| AI021899 | UNKNOWN | 12 | 275 | A |
| AI021984 | UNKNOWN | 25 | 0 | T |
| AI021989 | UNKNOWN | 12 | 0 | T |
| AI021992 | UNKNOWN | 16 | 473 | T |
| AI021996 | UNKNOWN | 7 | 46 | CT |
| AI022072 | UNKNOWN | 14 | 244 | T |
| AI022100 | UNKNOWN | 16 | 0 | T |
| AI022177 | UNKNOWN | 6.5 | 170 | AG |
| AI022208 | UNKNOWN | 4.75 | 381 | TTTC |
| AI022208 | UNKNOWN | 13 | 397 | T |
| AI022236 | UNKNOWN | 13 | 0 | T |
| AI022240 | UNKNOWN | 13 | 348 | A |
| AI022303 | UNKNOWN | 8.5 | 0 | CT |
| AI022606 | UNKNOWN | 12 | 183 | T |
| AI022648 | UNKNOWN | 12 | 0 | T |
| AI022821 | UNKNOWN | 13 | 0 | T |
| AI022831 | UNKNOWN | 29 | 0 | T |
| AI022877 | UNKNOWN | 16 | 0 | T |
| AI022906 | UNKNOWN | 4.75 | 350 | TTTG |
| AI022928 | UNKNOWN | 5.75 | 369 | AAAC |
| AI023115 | UNKNOWN | 9 | 4 | TTA |
| AI023295 | UNKNOWN | 12 | 213 | A |
| AI023318 | UNKNOWN | 12 | 372 | T |
| AI023327 | UNKNOWN | 6 | 486 | TCTG |
| AI023333 | UNKNOWN | 13 | 394 | T |
| AI023438 | UNKNOWN | 12 | 308 | G |
| AI023558 | UNKNOWN | 13 | 284 | T |
| AI023637 | UNKNOWN | 4.75 | 73 | AAAC |
| AI023637 | UNKNOWN | 18 | 0 | T |
| AI023688 | UNKNOWN | 4.98 | 98 | TGGTTTCATGAGTGTGCGCGTGGGGTGAGTGCTCGCCGC CGTGACGTTCGGGG (SEQ ID NO: 75) |
| AI023698 | UNKNOWN | 7 | 264 | TCAA |
| AI023763 | UNKNOWN | 22 | 0 | T |
| AI023810 | UNKNOWN | 23 | 0 | T |
| AI023820 | UNKNOWN | 14 | 0 | T |
| AI023895 | UNKNOWN | 13.5 | 376 | GT |
| AI024205 | UNKNOWN | 17 | 0 | T |
| AI024207 | UNKNOWN | 18 | 168 | A |
| AI024215 | UNKNOWN | 25 | 0 | T |
| AI024323 | UNKNOWN | 27 | 0 | T |
| AI024336 | UNKNOWN | 22 | 0 | T |
| AI024432 | UNKNOWN | 4.8 | 367 | CACAG |
| AI024432 | UNKNOWN | 13 | 0 | T |
| AI024536 | UNKNOWN | 15 | 0 | T |
| AI024544 | UNKNOWN | 15 | 0 | T |
| AI024554 | UNKNOWN | 12 | 0 | T |
| AI024559 | UNKNOWN | 16 | 0 | T |
| AI024564 | UNKNOWN | 15 | 0 | T |
| AI024567 | UNKNOWN | 16 | 0 | T |
| AI024592 | UNKNOWN | 18 | 0 | T |

TABLE 1-continued

| Genbank # | Region | # reps | Position | Unit sequence |
|---|---|---|---|---|
| AI024616 | UNKNOWN | 15 | 0 | T |
| AI024618 | UNKNOWN | 16 | 0 | T |
| AI024620 | UNKNOWN | 17 | 0 | T |
| AI024639 | UNKNOWN | 14 | 0 | T |
| AI024643 | UNKNOWN | 35 | 0 | T |
| AI024698 | UNKNOWN | 7.5 | 240 | AC |
| AI024868 | UNKNOWN | 46 | 0 | T |
| AI024868 | UNKNOWN | 16 | 123 | A |
| AI024877 | UNKNOWN | 19 | 0 | T |
| AI024971 | UNKNOWN | 21 | 0 | T |
| AI024984 | UNKNOWN | 27 | 0 | T |
| AI025031 | UNKNOWN | 33 | 0 | T |
| AI025043 | UNKNOWN | 16 | 0 | T |
| AI025C99 | UNKNOWN | 15 | 0 | T |
| AI025103 | UNKNOWN | 12 | 0 | T |
| AI025143 | UNKNOWN | 11 | 21 | TTA |
| AI025161 | UNKNOWN | 24 | 0 | T |
| AI025223 | UNKNOWN | 6.5 | 38 | CA |
| AI025333 | UNKNOWN | 6.5 | 352 | AT |
| AI025415 | UNKNOWN | 20 | 463 | A |
| AI025427 | UNKNOWN | 37 | 0 | T |
| AI025482 | UNKNOWN | 17 | 0 | T |
| AI025522 | UNKNOWN | 12 | 0 | T |
| AI025571 | UNKNOWN | 12 | 54 | A |
| AI025588 | UNKNOWN | 15 | 64 | T |
| AI025648 | UNKNOWN | 12 | 0 | T |
| AI025757 | UNKNOWN | 12 | 0 | T |
| AI025762 | UNKNOWN | 14.5 | 470 | AT |
| AI025808 | UNKNOWN | 19 | 0 | T |
| AI025811 | UNKNOWN | 7.66 | 18 | TTA |
| AI025822 | UNKNOWN | 21 | 0 | T |
| AI025850 | UNKNOWN | 6.75 | 26 | TTTA |
| AI025850 | UNKNOWN | 17 | 0 | T |
| AI025942 | UNKNOWN | 13 | 0 | T |
| AI025943 | UNKNOWN | 14 | 0 | T |
| AI025974 | UNKNOWN | 13 | 0 | T |
| AI025975 | UNKNOWN | 15 | 0 | T |
| AI025999 | UNKNOWN | 13 | 0 | T |
| AI026623 | UNKNOWN | 12 | 0 | T |
| AI026670 | UNKNOWN | 15 | 0 | T |
| AI026706 | UNKNOWN | 13 | 0 | T |
| AI026735 | UNKNOWN | 16 | 0 | T |
| AI026735 | UNKNOWN | 12 | 191 | A |
| AI026789 | UNKNOWN | 25 | 0 | T |
| AI026791 | UNKNOWN | 35 | 0 | T |
| AI026816 | UNKNOWN | 19 | 0 | T |
| AI026818 | UNKNOWN | 37 | 0 | T |
| AI026820 | UNKNOWN | 15.5 | 165 | TC |
| AI026820 | UNKNOWN | 26 | 15 | T |
| AI026829 | UNKNOWN | 15 | 0 | T |
| AI026830 | UNKNOWN | 15 | 0 | T |
| AI026836 | UNKNOWN | 15 | 0 | T |
| AI026870 | UNKNOWN | 17 | 0 | T |
| AI027087 | UNKNOWN | 3.66 | 235 | CAGATA |
| AI027120 | UNKNOWN | 16 | 0 | T |
| AI027175 | UNKNOWN | 3.8 | 19 | TTTTA |
| AI027175 | UNKNOWN | 26 | 63 | T |
| AI027215 | UNKNOWN | 15 | 0 | T |
| AI027216 | UNKNOWN | 15 | 0 | T |
| AI027236 | UNKNOWN | 18 | 0 | T |
| AI027240 | UNKNOWN | 16 | 0 | T |
| AI027265 | UNKNOWN | 20 | 0 | T |
| AI027271 | UNKNOWN | 19 | 0 | T |
| AI027273 | UNKNOWN | 19 | 0 | T |
| AI027294 | UNKNOWN | 18 | 0 | T |
| AI027300 | UNKNOWN | 14 | 0 | T |
| AI027304 | UNKNOWN | 12 | 0 | T |
| AI027321 | UNKNOWN | 13 | 326 | A |
| AI027342 | UNKNOWN | 15 | 0 | T |
| AI027434 | UNKNOWN | 13 | 0 | T |
| AI027498 | UNKNOWN | 13 | 0 | T |
| AI027602 | UNKNOWN | 12.5 | 52 | AAAT |
| AI027602 | UNKNOWN | 15 | 0 | T |
| AI027607 | UNKNOWN | 17 | 0 | T |
| AI027609 | UNKNOWN | 17 | 0 | T |
| AI027730 | UNKNOWN | 4.75 | 278 | TTTA |
| AI027733 | UNKNOWN | 21 | 0 | T |

TABLE 1-continued

| Genbank # | Region | # reps | Position | Unit sequence |
|---|---|---|---|---|
| AI027773 | UNKNOWN | 15 | 0 | T |
| AI027893 | UNKNOWN | 14 | 353 | T |
| AI028146 | UNKNOWN | 14 | 0 | T |
| AI028148 | UNKNOWN | 19 | 0 | T |
| AI028154 | UNKNOWN | 30 | 0 | T |
| AI028167 | UNKNOWN | 12 | 201 | G |
| AI028177 | UNKNOWN | 14 | 0 | T |
| AI028225 | UNKNOWN | 17 | 0 | T |
| AI028273 | UNKNOWN | 15 | 0 | T |
| AI028276 | UNKNOWN | 15 | 0 | T |
| AI028282 | UNKNOWN | 16 | 0 | T |
| AI028302 | UNKNOWN | 14 | 0 | T |
| AI028308 | UNKNOWN | 16 | 0 | T |
| AI028309 | UNKNOWN | 26 | 0 | T |
| AI028310 | UNKNOWN | 18 | 0 | T |
| AI028311 | UNKNOWN | 15 | 0 | T |
| AI028364 | UNKNOWN | 13 | 0 | T |
| AI028383 | UNKNOWN | 22 | 0 | T |
| AI028558 | UNKNOWN | 15 | 0 | T |
| AI028612 | UNKNOWN | 16 | 369 | T |
| AI028663 | UNKNOWN | 20 | 0 | T |
| AI028665 | UNKNOWN | 15 | 0 | T |
| AI028738 | UNKNOWN | 7 | 320 | TC |
| AI031527 | UNKNOWN | 46 | 0 | T |
| AI031552 | UNKNOWN | 13 | 0 | T |
| AI031560 | UNKNOWN | 19 | 0 | T |
| AI031666 | UNKNOWN | 16 | 0 | T |
| AI031674 | UNKNOWN | 21 | 0 | T |
| AI031686 | UNKNOWN | 18 | 0 | T |
| AI031813 | UNKNOWN | 16 | 0 | T |
| AI031816 | UNKNOWN | 14 | 0 | T |
| AI031874 | UNKNOWN | 17 | 0 | T |
| AI031973 | UNKNOWN | 25 | 0 | T |
| AI032071 | UNKNOWN | 6 | 170 | AAAT |
| AI032071 | UNKNOWN | 12 | 161 | A |
| AI032094 | UNKNOWN | 4.75 | 194 | AAAT |
| AI032107 | UNKNOWN | 13 | 63 | T |
| AI032142 | UNKNOWN | 30.5 | 346 | TG |
| AI032142 | UNKNOWN | 15 | 0 | T |
| AI032730 | UNKNOWN | 11 | 214 | GT |
| AI032786 | UNKNOWN | 7.5 | 388 | AC |
| AI032819 | UNKNOWN | 2.78 | 175 | TCTCTCTCCCCGAC (SEQ ID NO: 76) |
| AI032870 | UNKNOWN | 16 | 0 | T |
| AI032872 | UNKNOWN | 18 | 0 | T |
| AI032875 | UNKNOWN | 16 | 0 | T |
| AI032876 | UNKNOWN | 18 | 0 | T |
| AI032886 | UNKNOWN | 29 | 0 | T |
| AI032980 | UNKNOWN | 3.7 | 96 | AGGCAGGCAGGGGAGGCAGGAGGCAGG (SEQ ID NO: 77) |
| AI033061 | UNKNOWN | 4.5 | 6 | TTAT |
| AI033109 | UNKNOWN | 23 | 49 | AC |
| AI033119 | UNKNOWN | 7.5 | 95 | TC |
| AI033119 | UNKNOWN | 14 | 82 | T |
| AI033125 | UNKNOWN | 15 | 345 | A |
| AI033175 | UNKNOWN | 16 | 390 | A |
| AI033361 | UNKNOWN | 12 | 139 | T |
| AI033498 | UNKNOWN | 5.66 | 283 | TTG |
| AI033512 | UNKNOWN | 34 | 0 | T |
| AI033578 | UNKNOWN | 4.75 | 18 | TTTA |
| AI033662 | UNKNOWN | 20 | 0 | T |
| AI033683 | UNKNOWN | 13 | 39 | A |
| AI033789 | UNKNOWN | 12 | 192 | A |
| AI033790 | UNKNOWN | 7 | 168 | AT |
| AI033816 | UNKNOWN | 10.5 | 103 | CA |
| AI033857 | UNKNOWN | 16 | 100 | A |
| AI034073 | UNKNOWN | 9 | 341 | AC |
| AI034241 | UNKNOWN | 3.6 | 339 | TTTTG |
| AI034351 | UNKNOWN | 12 | 0 | T |
| AI034353 | UNKNOWN | 18 | 4 | T |
| AI034360 | UNKNOWN | 18 | 0 | T |
| AI034386 | UNKNOWN | 15 | 0 | T |
| AI034390 | UNKNOWN | 14 | 0 | T |
| AI038092 | UNKNOWN | 20 | 0 | T |
| AI038149 | UNKNOWN | 4.59 | 307 | TTTGT |
| AI038299 | UNKNOWN | 39 | 0 | T |
| AI038316 | UNKNOWN | 23 | 0 | T |
| AI039433 | UNKNOWN | 15 | 0 | T |

TABLE 1-continued

| Genbank # | Region | # reps | Position | Unit sequence |
|---|---|---|---|---|
| AI035552 | UNKNOWN | 15 | 374 | AG |
| AI038552 | UNKNOWN | 11 | 403 | GT |
| AI039552 | UNKNOWN | 14 | 146 | A |
| AI038595 | UNKNOWN | 29 | 0 | T |
| AI038615 | UNKNOWN | 9.5 | 329 | TA |
| AI038846 | UNKNOWN | 39 | 0 | T |
| AI038682 | UNKNOWN | 46 | 0 | T |
| AI038682 | UNKNOWN | 14 | 338 | C |
| AI038724 | UNKNOWN | 17 | 0 | T |
| AI038976 | UNKNOWN | 12 | 407 | T |
| AI039054 | UNKNOWN | 4.5 | 106 | TTGT |
| AI039054 | UNKNOWN | 6.66 | 301 | TTG |
| AI039083 | UNKNOWN | 48 | 0 | T |
| AI039083 | UNKNOWN | 14 | 266 | C |
| AI039119 | UNKNOWN | 24 | 0 | T |
| AI039141 | UNKNOWN | 6 | 223 | TTTG |
| AI039141 | UNKNOWN | 43 | 0 | T |
| AI039161 | UNKNOWN | 21 | 0 | T |
| AI039233 | UNKNOWN | 19 | 0 | T |
| AI039276 | UNKNOWN | 32 | 0 | T |
| AI039291 | UNKNOWN | 27 | 0 | T |
| AI039375 | UNKNOWN | 20 | 324 | A |
| AI039375 | UNKNOWN | 19 | 0 | T |
| AI039375 | UNKNOWN | 12 | 144 | A |
| AI039416 | UNKNOWN | 12 | 0 | T |
| AI039463 | UNKNOWN | 28 | 0 | T |
| AI039472 | UNKNOWN | 21 | 0 | T |
| AI039565 | UNKNOWN | 13 | 308 | T |
| AI039683 | UNKNOWN | 17 | 0 | T |
| AI039738 | UNKNOWN | 14 | 0 | T |
| AI039847 | UNKNOWN | 12 | 0 | T |
| AI040033 | UNKNOWN | 14 | 0 | T |
| AI040189 | UNKNOWN | 27 | 0 | T |
| AI040319 | UNKNOWN | 17 | 0 | T |
| AI040342 | UNKNOWN | 15 | 401 | T |
| AI040581 | UNKNOWN | 12 | 14 | T |
| AI040638 | UNKNOWN | 14 | 284 | A |
| AI040743 | UNKNOWN | 12 | 0 | T |
| AI040811 | UNKNOWN | 20 | 0 | T |
| AI040888 | UNKNOWN | 29 | 0 | T |
| AI040955 | UNKNOWN | 22 | 0 | T |
| AI040984 | UNKNOWN | 21 | 428 | A |
| AI040984 | UNKNOWN | 14 | 138 | T |
| AI041011 | UNKNOWN | 77 | 0 | T |
| AI041011 | UNKNOWN | 13 | 94 | A |
| AI041011 | UNKNOWN | 12 | 196 | C |
| AI041037 | UNKNOWN | 34 | 0 | T |
| AI041038 | UNKNOWN | 14 | 0 | T |
| AI041166 | UNKNOWN | 19 | 0 | T |
| AI041218 | UNKNOWN | 16 | 0 | T |
| AI041287 | UNKNOWN | 6 | 164 | CAT |
| AI041291 | UNKNOWN | 15 | 58 | A |
| AI041434 | UNKNOWN | 12 | 0 | T |
| AI041443 | UNKNOWN | 14 | 383 | A |
| AI041452 | UNKNOWN | 12 | 0 | T |
| AI041482 | UNKNOWN | 28 | 0 | T |
| AI041540 | UNKNOWN | 20.5 | 151 | TG |
| AI041544 | UNKNOWN | 15 | 0 | T |
| AI041816 | UNKNOWN | 25 | 0 | T |
| AI041842 | UNKNOWN | 14 | 0 | T |
| AI041959 | UNKNOWN | 15 | 0 | T |
| AI042011 | UNKNOWN | 26 | 0 | T |
| AI042019 | UNKNOWN | 15 | 0 | T |
| AI042140 | UNKNOWN | 36 | 21 | T |
| AI042140 | UNKNOWN | 20 | 0 | T |
| AI042140 | UNKNOWN | 12 | 327 | C |
| AI042164 | UNKNOWN | 17 | 0 | T |
| AI042180 | UNKNOWN | 22 | 0 | T |
| AI042323 | UNKNOWN | 18 | 0 | T |
| AI042326 | UNKNOWN | 14 | 0 | T |
| AI042339 | UNKNOWN | 16 | 0 | T |
| AI042341 | UNKNOWN | 13 | 0 | T |
| AI042343 | UNKNOWN | 16 | 0 | T |
| AI042344 | UNKNOWN | 15 | 272 | T |
| AI042353 | UNKNOWN | 22 | 0 | T |
| AI042600 | UNKNOWN | 16 | 307 | AT |
| AI042600 | UNKNOWN | 15 | 342 | T |

TABLE 1-continued

| Genbank # | Region | # reps | Position | Unit sequence |
| --- | --- | --- | --- | --- |
| AI042633 | UNKNOWN | 20 | 0 | T |
| AI042647 | UNKNOWN | 40 | 0 | T |
| AI049575 | UNKNOWN | 46 | 0 | T |
| AI049643 | UNKNOWN | 31 | 0 | T |
| AI049669 | UNKNOWN | 61 | 0 | T |
| AI049671 | UNKNOWN | 14 | 0 | T |
| AI049703 | UNKNOWN | 39 | 10 | T |
| AI049707 | UNKNOWN | 4.75 | 92 | AAAT |
| AI049733 | UNKNOWN | 52 | 0 | T |
| AI049733 | UNKNOWN | 15 | 163 | C |
| AI049769 | UNKNOWN | 32 | 0 | T |
| AI049787 | UNKNOWN | 80 | 0 | T |
| AI049787 | UNKNOWN | 5 | 302 | C |
| AI049817 | UNKNOWN | 24 | 0 | T |
| AI049817 | UNKNOWN | 14 | 551 | C |
| AI049817 | UNKNOWN | 13 | 510 | G |
| AI049870 | UNKNOWN | 15 | 0 | T |
| AI049923 | UNKNOWN | 55 | 0 | T |
| AI049951 | UNKNOWN | 33 | 0 | T |
| AI049975 | UNKNOWN | 22 | 9 | T |
| AI049978 | UNKNOWN | 27 | 0 | T |
| AI050081 | UNKNOWN | 39 | 0 | T |
| AI050812 | UNKNOWN | 3 | 356 | GCCCAGCGAGAGTTGC (SEQ ID NO: 78) |
| AI050855 | UNKNOWN | 38 | 0 | T |
| AI050877 | UNKNOWN | 40 | 0 | T |
| AI050881 | UNKNOWN | 89 | 0 | T |
| AI050881 | UNKNOWN | 14 | 144 | G |
| AI051082 | UNKNOWN | 20 | 0 | T |
| AI051235 | UNKNOWN | 13 | 0 | T |
| AI051236 | UNKNOWN | 12 | 0 | T |
| AI051244 | UNKNOWN | 12 | 0 | T |
| AI051290 | UNKNOWN | 8.66 | 239 | ACC |
| AI051295 | UNKNOWN | 26 | 0 | T |
| AI051390 | UNKNOWN | 13 | 0 | T |
| AI051428 | UNKNOWN | 15 | 329 | T |
| AI051591 | UNKNOWN | 12 | 0 | T |
| AI051612 | UNKNOWN | 20 | 0 | T |
| AI051621 | UNKNOWN | 16 | 0 | T |
| AI051664 | UNKNOWN | 28 | 0 | T |
| AI051709 | UNKNOWN | 51 | 0 | T |
| AI051799 | UNKNOWN | 13 | 76 | G |
| AI051839 | UNKNOWN | 30 | 0 | T |
| AI051857 | UNKNOWN | 17 | 0 | T |
| AI051912 | UNKNOWN | 20 | 0 | T |
| AI051923 | UNKNOWN | 13 | 0 | T |
| AI051933 | UNKNOWN | 28 | 0 | T |
| AI051936 | UNKNOWN | 12 | 450 | A |
| AI051961 | UNKNOWN | 5 | 111 | AATC |
| AI052020 | UNKNOWN | 6.66 | 419 | AAC |
| AI052026 | UNKNOWN | 41 | 0 | T |
| AI052039 | UNKNOWN | 14 | 0 | T |
| AI052041 | UNKNOWN | 15 | 185 | T |
| AI052121 | UNKNOWN | 20 | 0 | T |
| AI052127 | UNKNOWN | 15 | 0 | T |
| AI052139 | UNKNOWN | 11.5 | 140 | AC |
| AI052139 | UNKNOWN | 19 | 0 | T |
| AI052238 | UNKNOWN | 31 | 325 | T |
| AI052238 | UNKNOWN | 21 | 0 | T |
| AI052238 | UNKNOWN | 16 | 153 | A |
| AI052253 | UNKNOWN | 2.57 | 396 | GGCTGCGGGCTCCG (SEQ ID NO: 79) |
| AI052293 | UNKNOWN | 35 | 0 | T |
| AI052298 | UNKNOWN | 32 | 0 | T |
| AI052298 | UNKNOWN | 14 | 140 | A |
| AI052350 | UNKNOWN | 5.5 | 259 | TTAT |
| AI052358 | UNKNOWN | 12 | 33 | T |
| AI052506 | UNKNOWN | 14 | 0 | T |
| AI052508 | UNKNOWN | 15 | 0 | T |
| AI052511 | UNKNOWN | 13 | 0 | T |
| AI052521 | UNKNOWN | 18 | 0 | T |
| AI052524 | UNKNOWN | 21 | 0 | T |
| AI052528 | UNKNOWN | 13 | 0 | T |
| AI052530 | UNKNOWN | 12 | 318 | T |
| AI052543 | UNKNOWN | 29 | 0 | T |
| AI052571 | UNKNOWN | 12 | 298 | G |
| AI052583 | UNKNOWN | 15 | 0 | T |
| AI052586 | UNKNOWN | 12 | 307 | G |
| AI052684 | UNKNOWN | 13 | 0 | T |

TABLE 1-continued

| Genbank # | Region | # reps | Position | Unit sequence |
|---|---|---|---|---|
| AI052706 | UNKNOWN | 17 | 0 | T |
| AI052718 | UNKNOWN | 17 | 0 | T |
| AI052754 | UNKNOWN | 12 | 0 | T |
| AI053398 | UNKNOWN | 25 | 0 | T |
| AI053419 | UNKNOWN | 19 | 0 | T |
| AI053445 | UNKNOWN | 21 | 0 | T |
| AI053458 | UNKNOWN | 20 | 0 | T |
| AI053463 | UNKNOWN | 20 | 0 | T |
| AI053472 | UNKNOWN | 18 | 0 | T |
| AI053482 | UNKNOWN | 16 | 0 | T |
| AI053492 | UNKNOWN | 16 | 0 | T |
| AI053509 | UNKNOWN | 20 | 0 | T |
| AI053513 | UNKNOWN | 18 | 0 | T |
| AI053562 | UNKNOWN | 13 | 3 | T |
| AI053582 | UNKNOWN | 16 | 0 | T |
| AI053583 | UNKNOWN | 19 | 0 | T |
| AI053589 | UNKNOWN | 19 | 0 | T |
| AI053606 | UNKNOWN | 15 | 0 | T |
| AI053619 | UNKNOWN | 17 | 0 | T |
| AI053625 | UNKNOWN | 19 | 0 | T |
| AI053644 | UNKNOWN | 14 | 0 | T |
| AI053663 | UNKNOWN | 18 | 0 | T |
| AI053671 | UNKNOWN | 19 | 0 | T |
| AI053671 | UNKNOWN | 19 | 43 | A |
| AI053684 | UNKNOWN | 17 | 0 | T |
| AI053696 | UNKNOWN | 19 | 0 | T |
| AI053697 | UNKNOWN | 32 | 0 | T |
| AI053711 | UNKNOWN | 18 | 17 | CTTT |
| AI053711 | UNKNOWN | 6.5 | 90 | TC |
| AI053738 | UNKNOWN | 16 | 0 | T |
| AI053748 | UNKNOWN | 17 | 0 | T |
| AI053779 | UNKNOWN | 19 | 0 | T |
| AI053784 | UNKNOWN | 18 | 0 | T |
| AI053786 | UNKNOWN | 19 | 0 | T |
| AI053789 | UNKNOWN | 21 | 0 | T |
| AI053799 | UNKNOWN | 14 | 0 | T |
| AI053800 | UNKNOWN | 15 | 0 | T |
| AI053820 | UNKNOWN | 23 | 0 | T |
| AI053822 | UNKNOWN | 17 | 0 | T |
| AI053848 | UNKNOWN | 17 | 0 | T |
| AI053851 | UNKNOWN | 16 | 0 | T |
| AI053862 | UNKNOWN | 3.1 | 58 | TCTTTCTTTC (SEQ ID NO: 80) |
| AI053862 | UNKNOWN | 5.75 | 46 | TCTT |
| AI053862 | UNKNOWN | 18 | 138 | TC |
| AI053862 | UNKNOWN | 31 | 0 | T |
| AI053884 | UNKNOWN | 21 | 0 | T |
| AI053889 | UNKNOWN | 18 | 0 | T |
| AI053911 | UNKNOWN | 17 | 0 | T |
| AI053936 | UNKNOWN | 18 | 0 | T |
| AI053956 | UNKNOWN | 19 | 0 | T |
| AI053963 | UNKNOWN | 3.5 | 96 | TCTTTC |
| AI053963 | UNKNOWN | 9 | 16 | TTTC |
| AI053963 | UNKNOWN | 13 | 112 | TC |
| AI053963 | UNKNOWN | 19 | 0 | T |
| AI053994 | UNKNOWN | 15 | 0 | T |
| AI054056 | UNKNOWN | 22 | 0 | T |
| AI054107 | UNKNOWN | 18 | 0 | T |
| AI054127 | UNKNOWN | 17 | 0 | T |
| AI054133 | UNKNOWN | 19 | 0 | T |
| AI054151 | UNKNOWN | 17 | 0 | T |
| AI054157 | UNKNOWN | 19 | 0 | T |
| AI054183 | UNKNOWN | 22 | 0 | T |
| AI054193 | UNKNOWN | 20 | 0 | T |
| AI054216 | UNKNOWN | 19 | 0 | T |
| AI054258 | UNKNOWN | 15 | 0 | T |
| AI054269 | UNKNOWN | 22 | 0 | T |
| AI054296 | UNKNOWN | 20 | 0 | T |
| AI054298 | UNKNOWN | 12 | 0 | T |
| AI054343 | UNKNOWN | 14 | 357 | C |
| AI054352 | UNKNOWN | 24 | 0 | T |
| AI054353 | UNKNOWN | 21 | 0 | T |
| AI054353 | UNKNOWN | 14 | 249 | A |
| AI054354 | UNKNOWN | 15 | 0 | T |
| AI054354 | UNKNOWN | 13 | 316 | G |
| AI054354 | UNKNOWN | 13 | 330 | C |
| AI054355 | UNKNOWN | 22 | 117 | C |
| AI054355 | UNKNOWN | 18 | 35 | A |

TABLE 1-continued

| Genbank # | Region | # reps | Position | Unit sequence |
|---|---|---|---|---|
| AI054355 | UNKNOWN | 14 | 96 | T |
| AI054355 | UNKNOWN | 12 | 53 | C |
| AI054359 | UNKNOWN | 20 | 142 | A |
| AI054368 | UNKNOWN | 19 | 89 | T |
| AI054368 | UNKNOWN | 14 | 121 | A |
| AI054371 | UNKNOWN | 17 | 92 | A |
| AI054371 | UNKNOWN | 14 | 109 | T |
| AI054378 | UNKNOWN | 15 | 1 | T |
| AI054378 | UNKNOWN | 13 | 322 | G |
| AI054378 | UNKNOWN | 13 | 349 | C |
| AI054381 | UNKNOWN | 14 | 0 | T |
| AI054383 | UNKNOWN | 18 | 0 | T |
| AI054383 | UNKNOWN | 15 | 360 | A |
| AI054383 | UNKNOWN | 13 | 283 | A |
| AI054388 | UNKNOWN | 19 | 0 | T |
| AI054397 | UNKNOWN | 19 | 0 | T |
| AI054411 | UNKNOWN | 19 | 0 | T |
| AI054418 | UNKNOWN | 23 | 0 | T |
| AI054422 | UNKNOWN | 18 | 0 | T |
| AI055799 | UNKNOWN | 15 | 0 | T |
| AI055850 | UNKNOWN | 8.5 | 332 | TG |
| AI055850 | UNKNOWN | 27 | 0 | T |
| AI055952 | UNKNOWN | 14 | 0 | T |
| AI056122 | UNKNOWN | 4.75 | 382 | TTTG |
| AI056124 | UNKNOWN | 27 | 0 | T |
| AI056181 | UNKNOWN | 16 | 0 | T |
| AI056225 | UNKNOWN | 12 | 0 | T |
| AI056238 | UNKNOWN | 13 | 0 | T |
| AI056255 | UNKNOWN | 18 | 0 | T |
| AI056268 | UNKNOWN | 12 | 0 | T |
| AI056270 | UNKNOWN | 14 | 0 | T |
| AI056272 | UNKNOWN | 20 | 0 | T |
| AI056273 | UNKNOWN | 14 | 0 | T |
| AI056279 | UNKNOWN | 12 | 0 | T |
| AI056284 | UNKNOWN | 12 | 0 | T |
| AI056292 | UNKNOWN | 16 | 0 | T |
| AI056318 | UNKNOWN | 17 | 0 | T |
| AI056322 | UNKNOWN | 21 | 0 | T |
| AI056322 | UNKNOWN | 12 | 453 | A |
| AI056338 | UNKNOWN | 21 | 0 | T |
| AI056364 | UNKNOWN | 13 | 0 | T |
| AI056367 | UNKNOWN | 19 | 0 | T |
| AI056392 | UNKNOWN | 7 | 7 | TC |
| AI056404 | UNKNOWN | 27 | 0 | T |
| AI056414 | UNKNOWN | 4 | 0 | T |
| AI056438 | UNKNOWN | 19 | 0 | T |
| AI056506 | UNKNOWN | 3.6 | 55 | TTTGT |
| AI056506 | UNKNOWN | 10.5 | 224 | TG |
| AI056599 | UNKNOWN | 15 | 0 | T |
| AI056666 | UNKNOWN | 15 | 0 | T |
| AI056671 | UNKNOWN | 12 | 0 | T |
| AI056689 | UNKNOWN | 15 | 0 | T |
| AI056692 | UNKNOWN | 13 | 532 | T |
| AI056694 | UNKNOWN | 67 | 0 | T |
| AI056694 | UNKNOWN | 13 | 186 | C |
| AI056813 | UNKNOWN | 6.5 | 235 | AG |
| AI056825 | UNKNOWN | 15 | 201 | T |
| AI056863 | UNKNOWN | 17 | 0 | T |
| AI056866 | UNKNOWN | 12 | 0 | T |
| AI056868 | UNKNOWN | 12 | 0 | T |
| AI056871 | UNKNOWN | 12 | 0 | T |
| AI056872 | UNKNOWN | 15 | 0 | T |
| AI056873 | UNKNOWN | 13 | 0 | T |
| AI056874 | UNKNOWN | 21 | 0 | T |
| AI056877 | UNKNOWN | 13 | 0 | T |
| AI056882 | UNKNOWN | 12 | 0 | T |
| AI056883 | UNKNOWN | 12 | 0 | T |
| AI056890 | UNKNOWN | 12 | 0 | T |
| AI056890 | UNKNOWN | 12 | 62 | A |
| AI056891 | UNKNOWN | 14 | 0 | T |
| AI056893 | UNKNOWN | 18 | 0 | T |
| AI056903 | UNKNOWN | 15 | 0 | T |
| AI056904 | UNKNOWN | 12 | 0 | T |
| AI056913 | UNKNOWN | 4.75 | 54 | TTTA |
| AI056913 | UNKNOWN | 29 | 0 | T |
| AI056913 | UNKNOWN | 26 | 203 | A |
| AI056982 | UNKNOWN | 26 | 389 | T |

TABLE 1-continued

| Genbank # | Region | # reps | Position | Unit sequence |
|---|---|---|---|---|
| AI056982 | UNKNOWN | 20 | 0 | T |
| AI056998 | UNKNOWN | 14 | 0 | T |
| AI057035 | UNKNOWN | 21 | 0 | T |
| AI057267 | UNKNOWN | 37 | 0 | T |
| AI057329 | UNKNOWN | 17 | 0 | T |
| AI057353 | UNKNOWN | 15 | 0 | T |
| AI057363 | UNKNOWN | 14 | 0 | T |
| AI057444 | UNKNOWN | 13 | 223 | A |
| AI057469 | UNKNOWN | 14 | 346 | A |
| AI057469 | UNKNOWN | 12 | 0 | T |
| AI057599 | UNKNOWN | 18 | 0 | T |
| AI057629 | UNKNOWN | 13 | 0 | T |
| AI061104 | UNKNOWN | 15 | 0 | T |
| AI061271 | UNKNOWN | 14 | 0 | T |
| AI061304 | UNKNOWN | 30 | 0 | T |
| AI061394 | UNKNOWN | 33 | 0 | T |
| AI061405 | UNKNOWN | 48 | 0 | T |
| AI061577 | UNKNOWN | 19 | 182 | T |
| AI061584 | UNKNOWN | 13 | 536 | T |
| AI061599 | UNKNOWN | 18 | 5 | T |
| AI061620 | UNKNOWN | 15 | 2 | T |
| AI061641 | UNKNOWN | 22 | 5 | T |
| AI064690 | UNKNOWN | 22 | 469 | A |
| AI064743 | UNKNOWN | 18 | 3 | T |
| AI064743 | UNKNOWN | 14 | 556 | A |
| AI064744 | UNKNOWN | 6.5 | 95 | TN |
| AI064744 | UNKNOWN | 76 | 5 | T |
| AI064759 | UNKNOWN | 35 | 261 | A |
| AI064832 | UNKNOWN | 21 | 2 | T |
| AI064862 | UNKNOWN | 16 | 738 | A |
| AI064906 | UNKNOWN | 17 | 3 | T |
| AI064964 | UNKNOWN | 15 | 4 | T |
| AI064991 | UNKNOWN | 20 | 747 | A |
| AI065027 | UNKNOWN | 91 | 5 | T |
| AI065030 | UNKNOWN | 15 | 212 | A |
| AI065059 | UNKNOWN | 15 | 2 | T |
| AI065104 | UNKNOWN | 21 | 672 | A |
| AI065106 | UNKNOWN | 20 | 4 | T |
| AI065118 | UNKNOWN | 22 | 724 | A |
| AI065119 | UNKNOWN | 5.66 | 98 | TTG |
| AI065119 | UNKNOWN | 15 | 1 | T |
| AI065120 | UNKNOWN | 108 | 0 | T |
| AI065120 | UNKNOWN | 12 | 214 | C |
| AI065131 | UNKNOWN | 37 | 2 | T |
| AI065151 | UNKNOWN | 22 | 439 | A |
| AI065165 | UNKNOWN | 16 | 657 | A |
| AI066408 | UNKNOWN | 5.75 | 368 | TTTG |
| AI066477 | UNKNOWN | 17 | 0 | T |
| AI066497 | UNKNOWN | 50 | 0 | T |
| AI066497 | UNKNOWN | 14 | 162 | G |
| AI066504 | UNKNOWN | 31 | 0 | T |
| AI066520 | UNKNOWN | 14 | 0 | T |
| AI066532 | UNKNOWN | 14 | 0 | T |
| AI066545 | UNKNOWN | 26 | 0 | T |
| AI066574 | UNKNOWN | 16 | 0 | T |
| AI066656 | UNKNOWN | 16 | 0 | T |
| AI066680 | UNKNOWN | 20 | 0 | T |
| AI066769 | UNKNOWN | 16 | 0 | T |
| AI066778 | UNKNOWN | 24 | 0 | T |
| AI073373 | UNKNOWN | 3.83 | 106 | TTTTTG |
| AI073383 | UNKNOWN | 65 | 0 | T |
| AI073383 | UNKNOWN | 13 | 103 | A |
| AI073403 | UNKNOWN | 5.66 | 144 | TTG |
| AI073412 | UNKNOWN | 17 | 0 | T |
| AI073504 | UNKNOWN | 2.75 | 90 | CTCTCGCTCTCT (SEQ ID NO: 81) |
| AI073504 | UNKNOWN | 27 | 0 | T |
| AI073507 | UNKNOWN | 20 | 438 | A |
| AI073507 | UNKNOWN | 14 | 0 | T |
| AI073533 | UNKNOWN | 14 | 253 | T |
| AI073740 | UNKNOWN | 4.75 | 357 | AAAC |
| AI073805 | UNKNOWN | 15 | 0 | T |
| AI073847 | UNKNOWN | 19 | 0 | T |
| AI073952 | UNKNOWN | 77 | 0 | T |
| AI073952 | UNKNOWN | 14 | 161 | G |
| AI073952 | UNKNOWN | 12 | 107 | A |
| AI073984 | UNKNOWN | 14 | 0 | T |
| AI074141 | UNKNOWN | 20 | 0 | T |

TABLE 1-continued

| Genbank # | Region | # reps | Position | Unit sequence |
|---|---|---|---|---|
| AI074447 | UNKNOWN | 13 | 0 | T |
| AI074460 | UNKNOWN | 13 | 0 | T |
| AI074465 | UNKNOWN | 7 | 127 | AC |
| AI074524 | UNKNOWN | 16 | 0 | T |
| AI074534 | UNKNOWN | 7.5 | 0 | TATT |
| AI074559 | UNKNOWN | 43 | 0 | T |
| AI074578 | UNKNOWN | 14 | 50 | A |
| AI074580 | UNKNOWN | 5.75 | 46 | AAAC |
| AI074593 | UNKNOWN | 8.5 | 529 | CA |
| AI074723 | UNKNOWN | 12 | 0 | T |
| AI075041 | UNKNOWN | 18 | 0 | T |
| AI075153 | UNKNOWN | 26 | 335 | T |
| AI075158 | UNKNOWN | 17 | 0 | T |
| AI075261 | UNKNOWN | 7.5 | 166 | TC |
| AI075288 | UNKNOWN | 6 | 7 | TTG |
| AI075312 | UNKNOWN | 4.59 | 122 | TTTGT |
| AI075329 | UNKNOWN | 29 | 0 | T |
| AI075345 | UNKNOWN | 16 | 172 | T |
| AI075658 | UNKNOWN | 54 | 0 | T |
| AI075658 | UNKNOWN | 17 | 201 | G |
| AI075658 | UNKNOWN | 16 | 225 | C |
| AI075708 | UNKNOWN | 13 | 0 | T |
| AI075726 | UNKNOWN | 33 | 0 | T |
| AI075726 | UNKNOWN | 13 | 141 | G |
| AI075727 | UNKNOWN | 50 | 0 | T |
| AI075727 | UNKNOWN | 19 | 105 | G |
| AI075727 | UNKNOWN | 13 | 293 | C |
| AI075761 | UNKNOWN | 16 | 0 | T |
| AI075834 | UNKNOWN | 13 | 0 | T |
| AI075877 | UNKNOWN | 13 | 0 | T |
| AI075885 | UNKNOWN | 48 | 0 | T |
| AI075885 | UNKNOWN | 12 | 48 | A |
| AI075904 | UNKNOWN | 12 | 0 | T |
| AI075911 | UNKNOWN | 12 | 0 | T |
| AI075923 | UNKNOWN | 39 | 0 | T |
| AI075949 | UNKNOWN | 29 | 0 | T |
| AI075971 | UNKNOWN | 7.33 | 191 | ACA |
| AI075995 | UNKNOWN | 10.5 | 105 | AC |
| AI075995 | UNKNOWN | 21 | 0 | T |
| AI076005 | UNKNOWN | 23 | 0 | T |
| AI076030 | UNKNOWN | 14 | 380 | A |
| AI076030 | UNKNOWN | 12 | 0 | T |
| AI076062 | UNKNOWN | 24 | 0 | T |
| AI076068 | UNKNOWN | 44 | 0 | T |
| AI076096 | UNKNOWN | 5.75 | 18 | TTTG |
| AI076132 | UNKNOWN | 2.6 | 84 | TAGATAATAG (SEQ ID NO: 82) |
| AI076132 | UNKNOWN | 10.5 | 116 | TAGA |
| AI076132 | UNKNOWN | 20 | 0 | T |
| AI076157 | UNKNOWN | 45 | 0 | T |
| AI076157 | UNKNOWN | 13 | 283 | G |
| AI076157 | UNKNOWN | 12 | 130 | G |
| AI076167 | UNKNOWN | 26 | 10 | T |
| AI076772 | UNKNOWN | 14 | 0 | T |
| AI076180 | UNKNOWN | 13 | 0 | T |
| AI076182 | UNKNOWN | 13 | 0 | T |
| AI076195 | UNKNOWN | 26 | 0 | T |
| AI076198 | UNKNOWN | 7 | 85 | CA |
| AI076204 | UNKNOWN | 19 | 0 | T |
| AI076319 | UNKNOWN | 13 | 0 | T |
| AI076335 | UNKNOWN | 13 | 0 | T |
| AI076338 | UNKNOWN | 12 | 0 | T |
| AI076344 | UNKNOWN | 76 | 0 | T |
| AI076344 | UNKNOWN | 14 | 131 | A |
| AI076344 | UNKNOWN | 13 | 320 | C |
| AI076356 | UNKNOWN | 16 | 0 | T |
| AI076542 | UNKNOWN | 13 | 396 | A |
| AI076623 | UNKNOWN | 29 | 0 | T |
| AI076661 | UNKNOWN | 13 | 0 | T |
| AI076689 | UNKNOWN | 15 | 223 | A |
| AI076735 | UNKNOWN | 54 | 0 | T |
| AI076735 | UNKNOWN | 14 | 389 | G |
| AI076749 | UNKNOWN | 14 | 0 | T |
| AI076761 | UNKNOWN | 65 | 0 | T |
| AI076761 | UNKNOWN | 12 | 218 | G |
| AI076774 | UNKNOWN | 47 | 0 | T |
| AI076774 | UNKNOWN | 33 | 78 | G |
| AI076822 | UNKNOWN | 21 | 201 | T |

TABLE 1-continued

| Genbank # | Region | # reps | Position | Unit sequence |
|---|---|---|---|---|
| AI076826 | UNKNOWN | 8.5 | 437 | CT |
| AI076826 | UNKNOWN | 8 | 453 | CA |
| AI076834 | UNKNOWN | 5.5 | 245 | CAAT |
| AI076834 | UNKNOWN | 12 | 0 | T |
| AI076928 | UNKNOWN | 23 | 0 | T |
| AI077340 | UNKNOWN | 17 | 0 | T |
| AI077352 | UNKNOWN | 12 | 0 | T |
| AI077396 | UNKNOWN | 23 | 0 | T |
| AI077458 | UNKNOWN | 9 | 286 | AC |
| AI077540 | UNKNOWN | 16 | 0 | T |
| AI077554 | UNKNOWN | 33 | 0 | T |
| AI077573 | UNKNOWN | 4 | 0 | T |
| AI077580 | UNKNOWN | 12 | 0 | T |
| AI077773 | UNKNOWN | 21 | 0 | T |
| AI077773 | UNKNOWN | 13 | 203 | A |
| AI077781 | UNKNOWN | 9 | 87 | CA |
| AI078038 | UNKNOWN | 6.5 | 325 | AC |
| AI078101 | UNKNOWN | 32 | 0 | T |
| AI078101 | UNKNOWN | 13 | 133 | A |
| AI078141 | UNKNOWN | 25 | 0 | T |
| AI078177 | UNKNOWN | 3.6 | 418 | AAAAG |
| AI078296 | UNKNOWN | 5 | 0 | ATTT |
| AI078318 | UNKNOWN | 12 | 60 | A |
| AI078320 | UNKNOWN | 6.66 | 194 | AAC |
| AI078364 | UNKNOWN | 31 | 0 | T |
| AI078364 | UNKNOWN | 13 | 119 | A |
| AI078411 | UNKNOWN | 18 | 367 | A |
| AI078452 | UNKNOWN | 21 | 280 | A |
| AI078452 | UNKNOWN | 17 | 171 | T |
| AI078473 | UNKNOWN | 12 | 0 | T |
| AI078475 | UNKNOWN | 31 | 0 | T |
| AI078510 | UNKNOWN | 65 | 0 | T |
| AI078510 | UNKNOWN | 18 | 160 | C |
| AI078510 | UNKNOWN | 18 | 354 | G |
| AI078511 | UNKNOWN | 29 | 0 | T |
| AI078518 | UNKNOWN | 12 | 66 | T |
| AI078534 | UNKNOWN | 20 | 0 | T |
| AI078552 | UNKNOWN | 5.8 | 258 | AAACA |
| AI075552 | UNKNOWN | 34 | 0 | T |
| AI078818 | UNKNOWN | 41 | 0 | T |
| AI079092 | UNKNOWN | 40 | 0 | T |
| AI079122 | UNKNOWN | 3.8 | 185 | TTTTG |
| AI079148 | UNKNOWN | 12 | 102 | T |
| AI079340 | UNKNOWN | 16 | 89 | A |
| AI079397 | UNKNOWN | 19 | 0 | T |
| AI079511 | UNKNOWN | 19 | 0 | T |
| AI079534 | UNKNOWN | 13 | 0 | T |
| AI079540 | UNKNOWN | 6.33 | 199 | CAG |
| AI079542 | UNKNOWN | 8 | 108 | CA |
| AI079544 | UNKNOWN | 12 | 0 | T |
| AI079545 | UNKNOWN | 19 | 0 | T |
| AI079558 | UNKNOWN | 13 | 0 | T |
| AI079632 | UNKNOWN | 12 | 0 | T |
| AI079723 | UNKNOWN | 30 | 0 | T |
| AI079736 | UNKNOWN | 66 | 0 | T |
| AI079736 | UNKNOWN | 15 | 211 | C |
| AI079736 | UNKNOWN | 12 | 127 | G |
| AI079780 | UNKNOWN | 16 | 0 | T |
| AI079787 | UNKNOWN | 12 | 0 | T |
| AI079814 | UNKNOWN | 12 | 419 | T |
| AI079924 | UNKNOWN | 15 | 0 | T |
| AI080106 | UNKNOWN | 20 | 0 | T |
| AI080150 | UNKNOWN | 3.5 | 35 | TTTCAT |
| AI080150 | UNKNOWN | 7.5 | 396 | TC |
| AI080150 | UNKNOWN | 17 | 261 | A |
| AI080164 | UNKNOWN | 5 | 404 | AAAT |
| AI080256 | UNKNOWN | 53 | 0 | T |
| AI080256 | UNKNOWN | 20 | 243 | G |
| AI080321 | UNKNOWN | 40 | 0 | T |
| AI080618 | UNKNOWN | 21 | 442 | T |
| AI080633 | UNKNOWN | 14 | 0 | T |
| AI080634 | UNKNOWN | 15 | 0 | T |
| AI080743 | UNKNOWN | 17 | 0 | T |
| AI081099 | UNKNOWN | 13 | 0 | T |
| AI081118 | UNKNOWN | 18 | 390 | T |
| AI081275 | UNKNOWN | 29 | 0 | T |
| AI081275 | UNKNOWN | 13 | 281 | A |

TABLE 1-continued

| Genbank # | Region | # reps | Position | Unit sequence |
|---|---|---|---|---|
| AI081297 | UNKNOWN | 32 | 0 | T |
| AI081345 | UNKNOWN | 16 | 162 | T |
| AI081380 | UNKNOWN | 12 | 0 | T |
| AI081523 | UNKNOWN | 16 | 0 | T |
| AI081565 | UNKNOWN | 4.75 | 62 | TTTG |
| AI081593 | UNKNOWN | 27 | 0 | T |
| AI081740 | UNKNOWN | 73 | 0 | T |
| AI081740 | UNKNOWN | 14 | 272 | C |
| AI081773 | UNKNOWN | 5.25 | 43 | ACCA |
| AI081821 | UNKNOWN | 8 | 243 | GT |
| AI081821 | UNKNOWN | 14 | 9 | T |
| AI081980 | UNKNOWN | 3.85 | 93 | GGGCGCG |
| AI082062 | UNKNOWN | 15 | 0 | T |
| AI082134 | UNKNOWN | 19 | 0 | T |
| AI082160 | UNKNOWN | 15 | 0 | T |
| AI082160 | UNKNOWN | 12 | 392 | A |
| AI082172 | UNKNOWN | 14 | 0 | T |
| AI082244 | UNKNOWN | 16.5 | 241 | AC |
| AI082244 | UNKNOWN | 6.5 | 227 | AC |
| AI082290 | UNKNOWN | 12 | 90 | T |
| AI082431 | UNKNOWN | 22 | 0 | T |
| AI082470 | UNKNOWN | 19 | 0 | T |
| AI082612 | UNKNOWN | 15 | 0 | T |
| AI082711 | UNKNOWN | 25 | 0 | T |
| AI082754 | UNKNOWN | 12 | 237 | A |
| AI083327 | UNKNOWN | 42 | 0 | T |
| AI083527 | UNKNOWN | 13 | 283 | A |
| AI083799 | UNKNOWN | 16 | 0 | T |
| AI083899 | UNKNOWN | 6.66 | 175 | GCG |
| AI084001 | UNKNOWN | 22 | 0 | T |
| AI084024 | UNKNOWN | 4.86 | 276 | ATATATATATATAAA (SEQ ID NO: 83) |
| AI084024 | UNKNOWN | 8.5 | 336 | AT |
| AI084024 | UNKNOWN | 7 | 275 | TA |
| AI084220 | UNKNOWN | 30 | 0 | T |
| AI084224 | UNKNOWN | 13 | 0 | T |
| AI084738 | UNKNOWN | 22 | 0 | T |
| AI085018 | UNKNOWN | 32 | 0 | T |
| AI085018 | UNKNOWN | 14 | 277 | A |
| AI085242 | UNKNOWN | 43 | 0 | T |
| AI065338 | UNKNOWN | 17 | 45 | A |
| AI085387 | UNKNOWN | 18 | 0 | T |
| AI085588 | UNKNOWN | 32 | 0 | T |
| AI085588 | UNKNOWN | 19 | 124 | G |
| AI085606 | UNKNOWN | 13 | 319 | T |
| AI085608 | UNKNOWN | 15 | 0 | T |
| AI055567 | UNKNOWN | 19 | 0 | T |
| AI085943 | UNKNOWN | 13 | 222 | T |
| AI086032 | UNKNOWN | 12 | 0 | T |
| AI086049 | UNKNOWN | 12 | 0 | T |
| AI086058 | UNKNOWN | 14 | 0 | T |
| AI086101 | UNKNOWN | 6.5 | 101 | AC |
| AI086126 | UNKNOWN | 27 | 0 | T |
| AI086259 | UNKNOWN | 14 | 216 | A |
| AI086338 | UNKNOWN | 22 | 5 | T |
| AI086422 | UNKNOWN | 16 | 0 | T |
| AI086545 | UNKNOWN | 22 | 0 | T |
| AI056583 | UNKNOWN | 30 | 0 | T |
| AI086592 | UNKNOWN | 7 | 306 | ATT |
| AI086684 | UNKNOWN | 14 | 0 | T |
| AI086646 | UNKNOWN | 6.5 | 176 | TA |
| AI086646 | UNKNOWN | 19 | 0 | T |
| AI086685 | UNKNOWN | 5.75 | 2 | TTTA |
| AI086727 | UNKNOWN | 6.5 | 34 | TA |
| AI086727 | UNKNOWN | 12 | 0 | T |
| AI086783 | UNKNOWN | 48 | 0 | T |
| AI086912 | UNKNOWN | 21 | 0 | T |
| AI087055 | UNKNOWN | 20 | 8 | T |
| AI087235 | UNKNOWN | 13 | 0 | T |
| AI087277 | UNKNOWN | 46 | 0 | T |
| AI087225 | UNKNOWN | 27 | 0 | T |
| AI087843 | UNKNOWN | 18 | 24 | T |
| AI087910 | UNKNOWN | 19 | 0 | T |
| AI087910 | UNKNOWN | 18 | 115 | A |
| AI087971 | UNKNOWN | 28 | 0 | T |
| AI087972 | UNKNOWN | 17 | 0 | T |
| AI097975 | UNKNOWN | 12 | 234 | A |
| AI088801 | UNKNOWN | 12 | 0 | T |

TABLE 1-continued

| Genbank # | Region | # reps | Position | Unit sequence |
|---|---|---|---|---|
| AI088840 | UNKNOWN | 22 | 0 | T |
| AI088139 | UNKNOWN | 14 | 137 | A |
| AI088139 | UNKNOWN | 12 | 92 | A |
| AI088183 | UNKNOWN | 23 | 0 | T |
| AI068192 | UNKNOWN | 22 | 0 | T |
| AI088327 | UNKNOWN | 12 | 0 | T |
| AI088370 | UNKNOWN | 45 | 0 | T |
| AI088375 | UNKNOWN | 45 | 0 | T |
| AI088524 | UNKNOWN | 15 | 479 | A |
| AI088613 | UNKNOWN | 3.8 | 325 | AAAAC |
| AI088613 | UNKNOWN | 17 | 270 | T |
| AI088689 | UNKNOWN | 25 | 0 | T |
| AI088789 | UNKNOWN | 56 | 8 | T |
| AI088929 | UNKNOWN | 46 | 0 | T |
| AI088945 | UNKNOWN | 11.5 | 133 | CATA |
| AI089146 | UNKNOWN | 4 | 11 | ATTTT |
| AI089187 | UNKNOWN | 3.8 | 83 | AAAAT |
| AI089396 | UNKNOWN | 5.66 | 92 | GGC |
| AI089421 | UNKNOWN | 13 | 0 | T |
| AI089443 | UNKNOWN | 21 | 0 | T |
| AI089469 | UNKNOWN | 51 | 0 | T |
| AI089479 | UNKNOWN | 45 | 0 | T |
| AI089525 | UNKNOWN | 19 | 0 | T |
| AI089560 | UNKNOWN | 4.5 | 314 | TGTT |
| AI089585 | UNKNOWN | 16 | 4 | T |
| AI089622 | UNKNOWN | 13 | 0 | T |
| AI089632 | UNKNOWN | 16 | 27 | T |
| AI089641 | UNKNOWN | 12 | 322 | A |
| AI089748 | UNKNOWN | 86 | 0 | T |
| AI089748 | UNKNOWN | 25 | 203 | G |
| AI089748 | UNKNOWN | 22 | 342 | C |
| AI089748 | UNKNOWN | 14 | 173 | A |
| AI089774 | UNKNOWN | 14 | 0 | T |
| AI089782 | UNKNOWN | 85 | 0 | T |
| AI089782 | UNKNOWN | 15 | 256 | A |
| AI089782 | UNKNOWN | 13 | 193 | A |
| AI089783 | UNKNOWN | 23 | 13 | T |
| AI089811 | UNKNOWN | 44 | 0 | T |
| AI089920 | UNKNOWN | 12 | 0 | T |
| AI089956 | UNKNOWN | 41 | 0 | T |
| AI089958 | UNKNOWN | 23 | 0 | T |
| AI089970 | UNKNOWN | 79 | 0 | T |
| AI089970 | UNKNOWN | 33 | 103 | A |
| AI089570 | UNKNOWN | 19 | 262 | C |
| AI090052 | UNKNOWN | 16 | 2 | T |
| AI090305 | UNKNOWN | 7 | 201 | TA |
| AI090305 | UNKNOWN | 21 | 0 | T |
| AI090346 | UNKNOWN | 49 | 0 | T |
| AI090346 | UNKNOWN | 16 | 250 | G |
| AI090475 | UNKNOWN | 20 | 0 | T |
| AI090487 | UNKNOWN | 13 | 1 | T |
| AI090525 | UNKNOWN | 15 | 264 | A |
| AI090533 | UNKNOWN | 18 | 0 | T |
| AI090537 | UNKNOWN | 6.5 | 289 | CA |
| AI090576 | UNKNOWN | 11.5 | 379 | AC |
| AI090708 | UNKNOWN | 13 | 122 | A |
| AI090740 | UNKNOWN | 14 | 340 | A |
| AI090818 | UNKNOWN | 12 | 0 | T |
| AI090875 | UNKNOWN | 12 | 273 | T |
| AI091210 | UNKNOWN | 26 | 0 | T |
| AI091370 | UNKNOWN | 14 | 0 | T |
| AI091387 | UNKNOWN | 13 | 0 | T |
| AI091400 | UNKNOWN | 17 | 0 | T |
| AI091468 | UNKNOWN | 77 | 18 | T |
| AI091468 | UNKNOWN | 31 | 167 | G |
| AI091468 | UNKNOWN | 17 | 239 | C |
| AI091468 | UNKNOWN | 16 | 0 | T |
| AI091468 | UNKNOWN | 16 | 138 | C |
| AI091469 | UNKNOWN | 23 | 0 | T |
| AI091641 | UNKNOWN | 15 | 0 | T |
| AI091648 | UNKNOWN | 17 | 64 | A |
| AI091648 | UNKNOWN | 14 | 0 | T |
| AI091653 | UNKNOWN | 13 | 64 | A |
| AI091654 | UNKNOWN | 15 | 0 | T |
| AI091671 | UNKNOWN | 15 | 0 | T |
| AI091777 | UNKNOWN | 12 | 247 | A |
| AI092008 | UNKNOWN | 12 | 0 | T |

TABLE 1-continued

| Genbank # | Region | # reps | Position | Unit sequence |
|---|---|---|---|---|
| AI092027 | UNKNOWN | 87 | 0 | T |
| AI092027 | UNKNOWN | 20 | 149 | G |
| AI092027 | UNKNOWN | 18 | 118 | A |
| AI092274 | UNKNOWN | 6.33 | 216 | TGT |
| AI092274 | UNKNOWN | 15 | 0 | T |
| AI092429 | UNKNOWN | 24 | 0 | T |
| AI092441 | UNKNOWN | 27 | 23 | T |
| AI092441 | UNKNOWN | 21 | 0 | T |
| AI092548 | UNKNOWN | 13 | 0 | T |
| AI092552 | UNKNOWN | 15 | 0 | T |
| AI092576 | UNKNOWN | 18 | 0 | T |
| AI092623 | UNKNOWN | 32 | 0 | T |
| AI092624 | UNKNOWN | 5.25 | 11 | TATT |
| AI092824 | UNKNOWN | 7 | 42 | AC |
| AI092855 | UNKNOWN | 18 | 0 | T |
| AI092883 | UNKNOWN | 3.5 | 456 | AGCGCG |
| AI092883 | UNKNOWN | 20 | 0 | T |
| AI092963 | UNKNOWN | 8.33 | 167 | CCG |
| AI093016 | UNKNOWN | 18 | 0 | T |
| AI093171 | UNKNOWN | 5.2 | 307 | AAAAT |
| AI083171 | UNKNOWN | 13 | 0 | T |
| AI093188 | UNKNOWN | 16 | 0 | T |
| AI093221 | UNKNOWN | 13 | 0 | T |
| AI093325 | UNKNOWN | 37 | 0 | T |
| AI093359 | UNKNOWN | 35 | 0 | T |
| AI093397 | UNKNOWN | 12 | 114 | A |
| AI093526 | UNKNOWN | 40 | 0 | T |
| AI093531 | UNKNOWN | 39 | 0 | T |
| AI093876 | UNKNOWN | 12 | 0 | T |
| AI093928 | UNKNOWN | 12 | 0 | T |
| AI093982 | UNKNOWN | 20 | 0 | T |
| AI094092 | UNKNOWN | 45 | 0 | T |
| AI054276 | UNKNOWN | 13 | 0 | T |
| AI094299 | UNKNOWN | 12 | 0 | T |
| AI094489 | UNKNOWN | 62 | 0 | T |
| AI094489 | UNKNOWN | 14 | 203 | G |
| AI094489 | UNKNOWN | 13 | 146 | G |
| AI094489 | UNKNOWN | 13 | 256 | C |
| AI094610 | UNKNOWN | 12 | 428 | T |
| AI094611 | UNKNOWN | 23 | 0 | T |
| AI094626 | UNKNOWN | 34 | 0 | T |
| AI094639 | UNKNOWN | 43 | 0 | T |
| AI094647 | UNKNOWN | 35 | 0 | T |
| AI094726 | UNKNOWN | 38 | 0 | T |
| AI094749 | UNKNOWN | 57 | 0 | T |
| AI094787 | UNKNOWN | 21 | 0 | T |
| AI094550 | UNKNOWN | 47 | 0 | T |
| AI094893 | UNKNOWN | 31 | 0 | T |
| AI094893 | UNKNOWN | 19 | 134 | G |
| AI094910 | UNKNOWN | 63 | 0 | T |
| AI094933 | UNKNOWN | 24 | 0 | T |
| AI094933 | UNKNOWN | 16 | 174 | A |
| AI094942 | UNKNOWN | 50 | 0 | T |
| AI095003 | UNKNOWN | 62 | 0 | T |
| AI095003 | UNKNOWN | 13 | 147 | A |
| AI095024 | UNKNOWN | 50 | 0 | T |
| AI095070 | UNKNOWN | 26 | 17 | T |
| AI095085 | UNKNOWN | 44 | 0 | T |
| AI095098 | UNKNOWN | 27 | 0 | T |
| AI095098 | UNKNOWN | 25 | 199 | A |
| AI095103 | UNKNOWN | 8.5 | 8 | TTTA |
| AI095113 | UNKNOWN | 63 | 0 | T |
| AI095113 | UNKNOWN | 13 | 259 | G |
| AI095119 | UNKNOWN | 77 | 0 | T |
| AI095119 | UNKNOWN | 23 | 165 | A |
| AI095119 | UNKNOWN | 18 | 95 | A |
| AI095130 | UNKNOWN | 43 | 0 | T |
| AI095416 | UNKNOWN | 13 | 0 | T |
| AI095494 | UNKNOWN | 16 | 196 | A |
| AI095569 | UNKNOWN | 36 | 0 | T |
| AI095668 | UNKNOWN | 23 | 0 | T |
| AI095530 | UNKNOWN | 5.5 | 118 | CTTT |
| AI095830 | UNKNOWN | 7.5 | 67 | TC |
| AI095849 | UNKNOWN | 12 | 0 | T |
| AI095850 | UNKNOWN | 15 | 171 | T |
| AI056357 | UNKNOWN | 12 | 84 | A |
| AI096364 | UNKNOWN | 13 | 0 | T |

TABLE 1-continued

| Genbank # | Region | # reps | Position | Unit sequence |
|---|---|---|---|---|
| AI096408 | UNKNOWN | 5.5 | 113 | TGGA |
| AI096408 | UNKNOWN | 24 | 233 | TA |
| AI096432 | UNKNOWN | 51 | 0 | T |
| AI096443 | UNKNOWN | 37 | 0 | T |
| AI096468 | UNKNOWN | 16 | 0 | T |
| AI056481 | UNKNOWN | 65 | 0 | T |
| AI096481 | UNKNOWN | 12 | 174 | C |
| AI096494 | UNKNOWN | 34 | 0 | T |
| AI096534 | UNKNOWN | 72 | 0 | T |
| AI056534 | UNKNOWN | 14 | 199 | G |
| AI096543 | UNKNOWN | 44 | 0 | T |
| AI096613 | UNKNOWN | 65 | 0 | T |
| AI096613 | UNKNOWN | 13 | 297 | G |
| AI096692 | UNKNOWN | 12 | 0 | T |
| AI096782 | UNKNOWN | 23 | 0 | T |
| AI096786 | UNKNOWN | 14 | 0 | T |
| AI096881 | UNKNOWN | 57 | 0 | T |
| AI096902 | UNKNOWN | 16 | 0 | T |
| AI096953 | UNKNOWN | 48 | 0 | T |
| AI097026 | UNKNOWN | 15 | 0 | T |
| AI097094 | UNKNOWN | 51 | 0 | T |
| AI097091 | UNKNOWN | 19 | 0 | T |
| AI097137 | UNKNOWN | 64 | 0 | T |
| AI097137 | UNKNOWN | 15 | 145 | A |
| AI097137 | UNKNOWN | 12 | 90 | A |
| AI097143 | UNKNOWN | 43 | 0 | T |
| AI097202 | UNKNOWN | 39 | 0 | T |
| AI097202 | UNKNOWN | 24 | 137 | A |
| AI097245 | UNKNOWN | 55 | 0 | T |
| AI097245 | UNKNOWN | 14 | 182 | A |
| AI097248 | UNKNOWN | 91 | 23 | T |
| AI097248 | UNKNOWN | 22 | 0 | T |
| AI097248 | UNKNOWN | 18 | 217 | A |
| AI097252 | UNKNOWN | 58 | 0 | T |
| AI097253 | UNKNOWN | 48 | 0 | T |
| AI097253 | UNKNOWN | 19 | 183 | A |
| AI097264 | UNKNOWN | 60 | 0 | T |
| AI097264 | UNKNOWN | 14 | 117 | A |
| AI097290 | UNKNOWN | 12 | 0 | T |
| AI097399 | UNKNOWN | 16 | 65 | T |
| AI097399 | UNKNOWN | 14 | 0 | T |
| AI097410 | UNKNOWN | 94 | 0 | T |
| AI097410 | UNKNOWN | 20 | 159 | C |
| AI097410 | UNKNOWN | 13 | 179 | G |
| AI097410 | UNKNOWN | 13 | 238 | A |
| AI097429 | UNKNOWN | 12 | 166 | T |
| AI097570 | UNKNOWN | 13 | 0 | T |
| AI097617 | UNKNOWN | 50 | 0 | T |
| AI097617 | UNKNOWN | 13 | 81 | G |
| AI097628 | UNKNOWN | 37 | 0 | T |
| AI097628 | UNKNOWN | 15 | 159 | A |
| AI097641 | UNKNOWN | 17 | 334 | T |
| AI097643 | UNKNOWN | 75 | 0 | T |
| AI097643 | UNKNOWN | 15 | 138 | C |
| AI110585 | UNKNOWN | 17 | 646 | A |
| AI110591 | UNKNOWN | 118 | 5 | T |
| AI110591 | UNKNOWN | 16 | 497 | C |
| AI110591 | UNKNOWN | 15 | 177 | C |
| AI110591 | UNKNOWN | 13 | 164 | A |
| AI110618 | UNKNOWN | 86 | 5 | T |
| AI110689 | UNKNOWN | 15 | 5 | T |
| AI110708 | UNKNOWN | 38 | 2 | T |
| AI110732 | UNKNOWN | 50 | 5 | T |
| AI110737 | UNKNOWN | 61 | 147 | A |
| AI110746 | UNKNOWN | 13 | 634 | T |
| AI110768 | UNKNOWN | 97 | 5 | T |
| AI110819 | UNKNOWN | 16 | 746 | A |
| AI110831 | UNKNOWN | 36 | 67 | A |
| AI110844 | UNKNOWN | 33 | 2 | T |
| AI110849 | UNKNOWN | 45 | 4 | T |
| AI110865 | UNKNOWN | 11 | 340 | AC |
| AI110867 | UNKNOWN | 15 | 560 | A |
| AI110875 | UNKNOWN | 16 | 560 | A |
| AI114440 | UNKNOWN | 13 | 595 | A |
| AI114450 | UNKNOWN | 22 | 653 | A |
| AI114454 | UNKNOWN | 15 | 579 | A |
| AI114454 | UNKNOWN | 12 | 130 | T |

TABLE 1-continued

| Genbank # | Region | # reps | Position | Unit sequence |
|---|---|---|---|---|
| AI114461 | UNKNOWN | 59 | 6 | T |
| AI114477 | UNKNOWN | 17 | 705 | A |
| AI114452 | UNKNOWN | 18 | 802 | A |
| AI114494 | UNKNOWN | 19 | 100 | T |
| AI114494 | UNKNOWN | 17 | 6 | T |
| AI114502 | UNKNOWN | 22 | 0 | T |
| AI114508 | UNKNOWN | 15 | 700 | A |
| AI114527 | UNKNOWN | 16 | 682 | A |
| AI114534 | UNKNOWN | 21 | 609 | A |
| AI114540 | UNKNOWN | 96 | 3 | T |
| AI114543 | UNKNOWN | 15 | 516 | A |
| AI114543 | UNKNOWN | 13 | 34 | A |
| AI114574 | UNKNOWN | 21 | 3 | T |
| AI114628 | UNKNOWN | 15 | 613 | A |
| AI114645 | UNKNOWN | 20 | 654 | A |
| AI114645 | UNKNOWN | 14 | 63 | T |
| AI114650 | UNKNOWN | 21 | 616 | A |
| AI114650 | UNKNOWN | 15 | 3 | T |
| AI114652 | UNKNOWN | 34 | 0 | T |
| AI114655 | UNKNOWN | 15 | 2 | T |
| AI114683 | UNKNOWN | 13 | 549 | T |
| AI114686 | UNKNOWN | 15 | 500 | A |
| AI114708 | UNKNOWN | 16 | 579 | A |
| AI114731 | UNKNOWN | 14 | 603 | A |
| AI114733 | UNKNOWN | 18 | 232 | T |
| AI114733 | UNKNOWN | 16 | 6 | T |
| AI114751 | UNKNOWN | 14 | 9 | T |
| AI114755 | UNKNOWN | 22 | 2 | T |
| AI114765 | UNKNOWN | 15 | 649 | A |
| AI114752 | UNKNOWN | 3.8 | 90 | TTTGT |
| AI114782 | UNKNOWN | 19 | 43 | AC |
| AI114782 | UNKNOWN | 15 | 3 | T |
| AI114788 | UNKNOWN | 14 | 600 | A |
| AI114815 | UNKNOWN | 15 | 345 | A |
| AI114817 | UNKNOWN | 20 | 675 | A |
| AI114551 | UNKNOWN | 19 | 371 | T |
| AI114861 | UNKNOWN | 8.5 | 456 | TC |
| AI122689 | UNKNOWN | 27 | 0 | T |
| AI122715 | UNKNOWN | 14 | 0 | T |
| AI122720 | UNKNOWN | 43 | 0 | T |
| AI122722 | UNKNOWN | 12 | 0 | T |
| AI122735 | UNKNOWN | 14 | 0 | T |
| AI122757 | UNKNOWN | 12 | 36 | A |
| AI122800 | UNKNOWN | 29 | 0 | T |
| AI122808 | UNKNOWN | 16 | 0 | T |
| AI122831 | UNKNOWN | 14 | 0 | T |
| AI123130 | UNKNOWN | 15 | 173 | T |
| AI123249 | UNKNOWN | 45 | 0 | T |
| AI123255 | UNKNOWN | 16 | 0 | T |
| AI123289 | UNKNOWN | 17 | 191 | TG |
| AI123257 | UNKNOWN | 19 | 0 | T |
| AI123303 | UNKNOWN | 17 | 0 | T |
| AI123320 | UNKNOWN | 16 | 199 | A |
| AI123352 | UNKNOWN | 19 | 0 | T |
| AI123396 | UNKNOWN | 18 | 105 | T |
| AI123398 | UNKNOWN | 14 | 0 | T |
| AI123402 | UNKNOWN | 22 | 0 | T |
| AI123470 | UNKNOWN | 21 | 0 | T |
| AI123512 | UNKNOWN | 17 | 0 | T |
| AI123569 | UNKNOWN | 21 | 0 | T |
| AI123586 | UNKNOWN | 3.44 | 19 | TATAGAAGTATAGTATTACATGAAAATAG (SEQ ID NO: 84) |
| AI123601 | UNKNOWN | 18 | 0 | T |
| AI123603 | UNKNOWN | 17 | 0 | T |
| AI123745 | UNKNOWN | 31 | 0 | T |
| AI123752 | UNKNOWN | 22 | 0 | T |
| AI123790 | UNKNOWN | 19 | 0 | T |
| AI123812 | UNKNOWN | 13 | 129 | A |
| AI123826 | UNKNOWN | 14 | 0 | T |
| AI123908 | UNKNOWN | 17 | 0 | T |
| AI124588 | UNKNOWN | 17 | 431 | A |
| AI124671 | UNKNOWN | 2.91 | 139 | GAGACCCCTGCC (SEQ ID NO: 85) |
| AI124773 | UNKNOWN | 5.25 | 127 | GGCA |
| AI125003 | UNKNOWN | 12 | 180 | T |
| AI125031 | UNKNOWN | 16 | 0 | T |
| AI125085 | UNKNOWN | 74 | 0 | T |
| AI125035 | UNKNOWN | 14 | 236 | A |

TABLE 1-continued

| Genbank # | Region | # reps | Position | Unit sequence |
|---|---|---|---|---|
| AI125237 | UNKNOWN | 15 | 309 | T |
| AI125239 | UNKNOWN | 14 | 0 | T |
| AI125256 | UNKNOWN | 24 | 163 | T |
| AI125261 | UNKNOWN | 25 | 0 | T |
| AI125266 | UNKNOWN | 12 | 0 | T |
| AI125270 | UNKNOWN | 26 | 0 | T |
| AI125323 | UNKNOWN | 26 | 0 | T |
| AI125329 | UNKNOWN | 15 | 0 | T |
| AI125332 | UNKNOWN | 15 | 0 | T |
| AI125335 | UNKNOWN | 15 | 0 | T |
| AI125338 | UNKNOWN | 15 | 0 | T |
| AI125340 | UNKNOWN | 17 | 0 | T |
| AI125420 | UNKNOWN | 13 | 0 | T |
| AI125430 | UNKNOWN | 17 | 0 | T |
| AI125433 | UNKNOWN | 15 | 0 | T |
| AI125452 | UNKNOWN | 17 | 0 | T |
| AI125465 | UNKNOWN | 25 | 0 | T |
| AI125472 | UNKNOWN | 15 | 0 | T |
| AI125490 | UNKNOWN | 12 | 0 | T |
| AI125494 | UNKNOWN | 15 | 0 | T |
| AI125512 | UNKNOWN | 23 | 2 | T |
| AI125519 | UNKNOWN | 22 | 2 | T |
| AI125520 | UNKNOWN | 23 | 2 | T |
| AI125561 | UNKNOWN | 16 | 0 | T |
| AI125564 | UNKNOWN | 18 | 517 | T |
| AI125565 | UNKNOWN | 14 | 0 | T |
| AI125592 | UNKNOWN | 16 | 0 | T |
| AI125606 | UNKNOWN | 17 | 0 | T |
| AI125608 | UNKNOWN | 22 | 0 | T |
| AI125641 | UNKNOWN | 12 | 0 | T |
| AI125645 | UNKNOWN | 4.75 | 12 | TTTC |
| AI125645 | UNKNOWN | 18 | 28 | T |
| AI125651 | UNKNOWN | 26 | 0 | T |
| AI125721 | UNKNOWN | 15 | 0 | T |
| AI125751 | UNKNOWN | 17 | 0 | T |
| AI125757 | UNKNOWN | 15 | 0 | T |
| AI125785 | UNKNOWN | 19 | 0 | T |
| AI125829 | UNKNOWN | 17 | 0 | T |
| AI125845 | UNKNOWN | 48 | 0 | T |
| AI125848 | UNKNOWN | 15 | 0 | T |
| AI125852 | UNKNOWN | 16 | 0 | T |
| AI125854 | UNKNOWN | 15 | 0 | T |
| AI125856 | UNKNOWN | 16 | 0 | T |
| AI125859 | UNKNOWN | 19 | 0 | T |
| AI125861 | UNKNOWN | 23 | 11 | T |
| AI125854 | UNKNOWN | 15 | 0 | T |
| AI125876 | UNKNOWN | 23 | 2 | T |
| AI125884 | UNKNOWN | 71 | 0 | T |
| AI125884 | UNKNOWN | 12 | 71 | A |
| AI125902 | UNKNOWN | 21 | 0 | T |
| AI126036 | UNKNOWN | 55 | 0 | T |
| AI126036 | UNKNOWN | 15 | 172 | A |
| AI126055 | UNKNOWN | 7.5 | 449 | AC |
| AI126055 | UNKNOWN | 6.5 | 471 | TA |
| AI126075 | UNKNOWN | 13 | 356 | T |
| AI126133 | UNKNOWN | 15 | 0 | T |
| AI126178 | UNKNOWN | 16 | 0 | T |
| AI126184 | UNKNOWN | 7 | 381 | GT |
| AI126206 | UNKNOWN | 14 | 0 | T |
| AI126213 | UNKNOWN | 15 | 0 | T |
| AI126222 | UNKNOWN | 16 | 140 | T |
| AI126257 | UNKNOWN | 26 | 0 | T |
| AI126313 | UNKNOWN | 7 | 80 | ATT |
| AI126320 | UNKNOWN | 19 | 0 | T |
| AI126327 | UNKNOWN | 19 | 0 | T |
| AI126340 | UNKNOWN | 23 | 0 | T |
| AI126363 | UNKNOWN | 4.2 | 12 | TATTT |
| AI126372 | UNKNOWN | 55 | 0 | T |
| AI126372 | UNKNOWN | 13 | 244 | A |
| AI126447 | UNKNOWN | 21 | 0 | T |
| AI126508 | UNKNOWN | 16 | 0 | T |
| AI126510 | UNKNOWN | 38 | 0 | T |
| AI126520 | UNKNOWN | 11 | 2 | TTAT |
| AI126576 | UNKNOWN | 53 | 0 | T |
| AI126576 | UNKNOWN | 14 | 162 | G |
| AI126576 | UNKNOWN | 12 | 280 | A |
| AI126592 | UNKNOWN | 18 | 0 | T |

TABLE 1-continued

| Genbank # | Region | # reps | Position | Unit sequence |
|---|---|---|---|---|
| AI126594 | UNKNOWN | 6.5 | 12 | TTTA |
| AI126620 | UNKNOWN | 19 | 0 | T |
| AI126688 | UNKNOWN | 17 | 0 | T |
| AI126727 | UNKNOWN | 13 | 0 | T |
| AI126759 | UNKNOWN | 27 | 0 | T |
| AI126802 | UNKNOWN | 12 | 0 | T |
| AI126831 | UNKNOWN | 13 | 0 | T |
| AI126846 | UNKNOWN | 18 | 442 | A |
| AI126877 | UNKNOWN | 30 | 0 | T |
| AI126917 | UNKNOWN | 14 | 0 | T |
| AI126920 | UNKNOWN | 43 | 0 | T |
| AI126930 | UNKNOWN | 56 | 0 | T |
| AI127030 | UNKNOWN | 6 | 10 | TTTA |
| AI127067 | UNKNOWN | 20 | 0 | T |
| AI127295 | UNKNOWN | 4.26 | 129 | GGGAACACAGCCGCTCCCCTCTGCTCTGCACCCCACTCGTGG (SEQ ID NO: 86) |
| AI127306 | UNKNOWN | 28 | 0 | T |
| AI127586 | UNKNOWN | 50 | 0 | T |
| AI127586 | UNKNOWN | 14 | 241 | G |
| AI127590 | UNKNOWN | 18 | 0 | T |
| AI127611 | UNKNOWN | 2.7 | 316 | TATATTAATA (SEQ ID NO: 87) |
| AI127624 | UNKNOWN | 11.5 | 412 | TG |
| AI127624 | UNKNOWN | 16 | 311 | T |
| AI127658 | UNKNOWN | 24 | 0 | T |
| AI127666 | UNKNOWN | 22 | 0 | T |
| AI127666 | UNKNOWN | 12 | 334 | A |
| AI127712 | UNKNOWN | 13 | 336 | T |
| AI127859 | UNKNOWN | 41 | 0 | T |
| AI127871 | UNKNOWN | 26 | 0 | T |
| AI128032 | UNKNOWN | 34 | 0 | T |
| AI128130 | UNKNOWN | 6 | 228 | CAA |
| AI128149 | UNKNOWN | 19 | 129 | T |
| AI128203 | UNKNOWN | 21 | 0 | T |
| AI128225 | UNKNOWN | 6.5 | 196 | GA |
| AI128239 | UNKNOWN | 51 | 0 | T |
| AI128239 | UNKNOWN | 17 | 230 | A |
| AI128263 | UNKNOWN | 23 | 0 | T |
| AI128267 | UNKNOWN | 18 | 0 | T |
| AI128372 | UNKNOWN | 33 | 0 | T |
| AI128661 | UNKNOWN | 19 | 0 | T |
| AI128899 | UNKNOWN | 13 | 0 | T |
| AI128934 | UNKNOWN | 21 | 0 | T |
| AI129107 | UNKNOWN | 33 | 0 | T |
| AI129148 | UNKNOWN | 6.75 | 104 | TTTA |
| AI129156 | UNKNOWN | 13 | 0 | T |
| AI129373 | UNKNOWN | 17 | 0 | T |
| AI129405 | UNKNOWN | 31 | 0 | T |
| AI129455 | UNKNOWN | 16 | 0 | T |
| AI129455 | UNKNOWN | 14 | 177 | A |
| AI129540 | UNKNOWN | 33 | 0 | T |
| AI129592 | UNKNOWN | 11 | 337 | GT |
| AI129719 | UNKNOWN | 47 | 0 | T |
| AI129719 | UNKNOWN | 17 | 106 | G |
| AI129782 | UNKNOWN | 14 | 4 | T |
| AI129881 | UNKNOWN | 39 | 0 | T |
| AI129960 | UNKNOWN | 22 | 0 | T |
| AI129979 | UNKNOWN | 18 | 0 | T |
| AI129979 | UNKNOWN | 12 | 200 | G |
| AI130006 | UNKNOWN | 12 | 0 | T |
| AI130697 | UNKNOWN | 13 | 303 | A |
| AI130701 | UNKNOWN | 43 | 0 | T |
| AI130701 | UNKNOWN | 15 | 154 | G |
| AI130780 | UNKNOWN | 22 | 421 | T |
| AI130888 | UNKNOWN | 19 | 0 | T |
| AI131026 | UNKNOWN | 14 | 0 | T |
| AI131046 | UNKNOWN | 15 | 0 | T |
| AI131054 | UNKNOWN | 4 | 271 | GTTTT |
| AI131206 | UNKNOWN | 35 | 0 | T |
| AI131308 | UNKNOWN | 8 | 405 | GT |
| AI131315 | UNKNOWN | 13 | 0 | T |
| AI131555 | UNKNOWN | 15 | 0 | T |
| AI132934 | UNKNOWN | 15 | 3 | T |
| AI132935 | UNKNOWN | 4.2 | 88 | AATAA |
| AI132955 | UNKNOWN | 16 | 86 | A |
| AI132994 | UNKNOWN | 22 | 3 | T |
| AI132995 | UNKNOWN | 18 | 624 | A |
| AI133007 | UNKNOWN | 15 | 526 | A |

TABLE 1-continued

| Genbank # | Region | # reps | Position | Unit sequence |
|---|---|---|---|---|
| AI133029 | UNKNOWN | 48 | 3 | T |
| AI133031 | UNKNOWN | 26.5 | 396 | AC |
| AI133032 | UNKNOWN | 14.5 | 390 | AC |
| AI133032 | UNKNOWN | 14 | 2 | T |
| AI133044 | UNKNOWN | 16 | 226 | GT |
| AI133044 | UNKNOWN | 24 | 4 | T |
| AI133045 | UNKNOWN | 15 | 2 | T |
| AI133083 | UNKNOWN | 7.5 | 0 | GA |
| AI133083 | UNKNOWN | 15 | 390 | A |
| AI133084 | UNKNOWN | 18 | 712 | A |
| AI133093 | UNKNOWN | 15 | 2 | T |
| AI133111 | UNKNOWN | 15 | 722 | A |
| AI133149 | UNKNOWN | 17 | 309 | T |
| AI133163 | UNKNOWN | 15 | 769 | A |
| AI133165 | UNKNOWN | 20 | 742 | A |
| AI133191 | UNKNOWN | 18 | 511 | A |
| AI133194 | UNKNOWN | 15 | 229 | A |
| AI133138 | UNKNOWN | 14 | 668 | A |
| AI133198 | UNKNOWN | 13 | 212 | A |
| AI133200 | UNKNOWN | 17 | 0 | T |
| AI133203 | UNKNOWN | 17 | 717 | A |
| AI133215 | UNKNOWN | 8 | 18 | TG |
| AI433215 | UNKNOWN | 25 | 781 | A |
| AI133215 | UNKNOWN | 12 | 622 | A |
| AI133217 | UNKNOWN | 22 | 464 | A |
| AI133240 | UNKNOWN | 13 | 557 | A |
| AI133250 | UNKNOWN | 15 | 3 | T |
| AI133256 | UNKNOWN | 6.25 | 329 | ATAC |
| AI133256 | UNKNOWN | 14 | 51 | T |
| AI133270 | UNKNOWN | 15 | 0 | T |
| AI133285 | UNKNOWN | 27 | 740 | A |
| AI133287 | UNKNOWN | 16 | 0 | T |
| AI133292 | UNKNOWN | 12 | 802 | A |
| AI133296 | UNKNOWN | 26 | 3 | T |
| AI133322 | UNKNOWN | 16 | 3 | T |
| AI133362 | UNKNOWN | 15 | 4 | T |
| AI133376 | UNKNOWN | 6.75 | 52 | AAAT |
| AI133376 | UNKNOWN | 16 | 678 | A |
| AI133383 | UNKNOWN | 21 | 657 | A |
| AI133383 | UNKNOWN | 15 | 3 | T |
| AI133397 | UNKNOWN | 18 | 807 | A |
| AI133397 | UNKNOWN | 16 | 5 | T |
| AI133455 | UNKNOWN | 15 | 725 | A |
| AI133483 | UNKNOWN | 15 | 4 | T |
| AI133501 | UNKNOWN | 17 | 763 | A |
| AI133509 | UNKNOWN | 15 | 2 | T |
| AI133519 | UNKNOWN | 15 | 3 | T |
| AI133522 | UNKNOWN | 15 | 364 | A |
| AI133523 | UNKNOWN | 37 | 5 | T |
| AI133524 | UNKNOWN | 15 | 619 | A |
| AI133530 | UNKNOWN | 18 | 0 | T |
| AI133549 | UNKNOWN | 14 | 0 | T |
| AI133564 | UNKNOWN | 15 | 378 | A |
| AI133566 | UNKNOWN | 20 | 621 | A |
| AI133568 | UNKNOWN | 15 | 571 | A |
| AI133573 | UNKNOWN | 18 | 378 | A |
| AI133600 | UNKNOWN | 12 | 5 | T |
| AI133629 | UNKNOWN | 20 | 631 | A |
| AI133655 | UNKNOWN | 15 | 3 | T |
| AI133664 | UNKNOWN | 28 | 7 | T |
| AI133686 | UNKNOWN | 14 | 622 | A |
| AI133695 | UNKNOWN | 25 | 699 | A |
| AI133709 | UNKNOWN | 19 | 731 | A |
| AI133727 | UNKNOWN | 23 | 2025 | A |
| AI133727 | UNKNOWN | 22 | 609 | T |
| AI138213 | UNKNOWN | 16 | 0 | T |
| AI138216 | UNKNOWN | 6.25 | 307 | GGAT |
| AI138221 | UNKNOWN | 59 | 0 | T |
| AI138221 | UNKNOWN | 17 | 209 | G |
| AI138243 | UNKNOWN | 12 | 0 | T |
| AI138266 | UNKNOWN | 30 | 0 | T |
| AI138281 | UNKNOWN | 25 | 0 | T |
| AI138306 | UNKNOWN | 15 | 0 | T |
| AI138342 | UNKNOWN | 3.8 | 47 | TTTTA |
| AI138342 | UNKNOWN | 28 | 0 | T |
| AI138437 | UNKNOWN | 57 | 0 | T |
| AI138437 | UNKNOWN | 25 | 298 | C |

TABLE 1-continued

| Genbank # | Region | # reps | Position | Unit sequence |
|---|---|---|---|---|
| AI138437 | UNKNOWN | 13 | 243 | G |
| AI138452 | UNKNOWN | 52 | 0 | T |
| AI138452 | UNKNOWN | 15 | 149 | G |
| AI138480 | UNKNOWN | 78 | 0 | T |
| AI138480 | UNKNOWN | 23 | 371 | G |
| AI138480 | UNKNOWN | 13 | 129 | A |
| AI138480 | UNKNOWN | 13 | 146 | G |
| AI138482 | UNKNOWN | 23 | 0 | T |
| AI138486 | UNKNOWN | 9.25 | 189 | TAGA |
| AI138486 | UNKNOWN | 16 | 0 | T |
| AI138492 | UNKNOWN | 51 | 0 | T |
| AI138492 | UNKNOWN | 13 | 170 | A |
| AI138518 | UNKNOWN | 14 | 0 | T |
| AI138521 | UNKNOWN | 14 | 0 | T |
| AI138554 | UNKNOWN | 15 | 213 | T |
| AI138567 | UNKNOWN | 14 | 0 | T |
| AI138644 | UNKNOWN | 38 | 0 | T |
| AI138720 | UNKNOWN | 18 | 0 | T |
| AI138727 | UNKNOWN | 12 | 0 | T |
| AI138765 | UNKNOWN | 13 | 0 | T |
| AI138766 | UNKNOWN | 22 | 2 | T |
| AI138775 | UNKNOWN | 22 | 2 | T |
| AI138781 | UNKNOWN | 19 | 0 | T |
| AI138783 | UNKNOWN | 19 | 0 | T |
| AI138784 | UNKNOWN | 7.5 | 147 | AC |
| AI138784 | UNKNOWN | 22 | 2 | T |
| AI138787 | UNKNOWN | 2.5 | 128 | TCACTGAAGG (SEQ ID NO: 88) |
| AI138787 | UNKNOWN | 23 | 2 | T |
| AI138818 | UNKNOWN | 16 | 0 | T |
| AI138842 | UNKNOWN | 13 | 407 | A |
| AI138848 | UNKNOWN | 16 | 0 | T |
| AI138865 | UNKNOWN | 15 | 0 | T |
| AI138877 | UNKNOWN | 26 | 0 | T |
| AI138886 | UNKNOWN | 18 | 4 | T |
| AI138911 | UNKNOWN | 12 | 0 | T |
| AI138923 | UNKNOWN | 20 | 0 | T |
| AI138923 | UNKNOWN | 13 | 20 | G |
| AI138988 | UNKNOWN | 20 | 0 | T |
| AI139025 | UNKNOWN | 28 | 0 | T |
| AI139106 | UNKNOWN | 25 | 0 | T |
| AI139114 | UNKNOWN | 27 | 58 | A |
| AI139532 | UNKNOWN | 13.5 | 121 | AC |
| AI139548 | UNKNOWN | 14 | 396 | T |
| AI139568 | UNKNOWN | 34 | 0 | T |
| AI139568 | UNKNOWN | 17 | 196 | A |
| AI139574 | UNKNOWN | 38 | 0 | T |
| AI139591 | UNKNOWN | 26 | 0 | T |
| AI139734 | UNKNOWN | 26 | 0 | T |
| AI139757 | UNKNOWN | 22 | 11 | T |
| AI139759 | UNKNOWN | 25 | 0 | T |
| AI139763 | UNKNOWN | 16 | 0 | T |
| AI139771 | UNKNOWN | 18 | 0 | T |
| AI139781 | UNKNOWN | 24 | 11 | T |
| AI139785 | UNKNOWN | 24 | 11 | T |
| AI139786 | UNKNOWN | 15 | 0 | T |
| AI139813 | UNKNOWN | 22 | 2 | T |
| AI139813 | UNKNOWN | 12 | 61 | A |
| AI139815 | UNKNOWN | 15 | 0 | T |
| AI139817 | UNKNOWN | 15 | 0 | T |
| AI139819 | UNKNOWN | 22 | 2 | T |
| AI139856 | UNKNOWN | 15 | 0 | T |
| AI139861 | UNKNOWN | 24 | 11 | T |
| AI140134 | UNKNOWN | 54 | 0 | T |
| AI140180 | UNKNOWN | 37 | 0 | T |
| AI140221 | UNKNOWN | 26 | 0 | T |
| AI140281 | UNKNOWN | 20 | 225 | T |
| AI140281 | UNKNOWN | 12 | 0 | T |
| AI140423 | UNKNOWN | 44 | 0 | T |
| AI140423 | UNKNOWN | 14 | 387 | A |
| AI140462 | UNKNOWN | 17 | 0 | T |
| AI140593 | UNKNOWN | 15 | 0 | T |
| AI140599 | UNKNOWN | 5 | 0 | T |
| AI140602 | UNKNOWN | 15 | 0 | T |
| AI140607 | UNKNOWN | 18 | 0 | T |
| AI140608 | UNKNOWN | 15 | 0 | T |
| AI140609 | UNKNOWN | 15 | 0 | T |
| AI140624 | UNKNOWN | 15 | 0 | T |

TABLE 1-continued

| Genbank # | Region | # reps | Position | Unit sequence |
|---|---|---|---|---|
| AI140626 | UNKNOWN | 15 | 0 | T |
| AI140628 | UNKNOWN | 15 | 0 | T |
| AI140686 | UNKNOWN | 17 | 0 | T |
| AI140687 | UNKNOWN | 3.56 | 178 | CCCTCTGGACAGCACCTGGCCCGCCACTCTGCCATCA (SEQ ID NO: 89) |
| AI140753 | UNKNOWN | 16 | 0 | T |
| AI140764 | UNKNOWN | 15 | 0 | T |
| AI140766 | UNKNOWN | 12 | 0 | T |
| AI140810 | UNKNOWN | 20 | 0 | T |
| AI141004 | UNKNOWN | 42 | 0 | T |
| AI141004 | UNKNOWN | 13 | 335 | G |
| AI141202 | UNKNOWN | 25 | 136 | T |
| AI141288 | UNKNOWN | 53 | 5 | T |
| AI141288 | UNKNOWN | 20 | 217 | G |
| AI141288 | UNKNOWN | 18 | 107 | C |
| AI141288 | UNKNOWN | 15 | 164 | G |
| AI141288 | UNKNOWN | 14 | 82 | A |
| AI141294 | UNKNOWN | 17 | 352 | A |
| AI141294 | UNKNOWN | 14 | 286 | T |
| AI141294 | UNKNOWN | 13 | 109 | A |
| AI141399 | UNKNOWN | 57 | 0 | T |
| AI141400 | UNKNOWN | 51 | 0 | T |
| AI141400 | UNKNOWN | 12 | 272 | C |
| AI141535 | UNKNOWN | 8 | 299 | TA |
| AI141551 | UNKNOWN | 3.5 | 298 | TTTTTG |
| AI141551 | UNKNOWN | 16 | 478 | T |
| AI141556 | UNKNOWN | 12 | 0 | T |
| AI141567 | UNKNOWN | 37 | 0 | T |
| AI141579 | UNKNOWN | 13 | 0 | T |
| AI141684 | UNKNOWN | 15 | 0 | T |
| AI141700 | UNKNOWN | 27 | 0 | T |
| AI141725 | UNKNOWN | 102 | 0 | T |
| AI141725 | UNKNOWN | 18 | 353 | A |
| AI141725 | UNKNOWN | 16 | 305 | G |
| AI141725 | UNKNOWN | 15 | 136 | A |
| AI141734 | UNKNOWN | 18 | 4 | T |
| AI141742 | UNKNOWN | 62 | 0 | T |
| AI141764 | UNKNOWN | 8.5 | 42 | GT |
| AI141783 | UNKNOWN | 15 | 170 | T |
| AI141902 | UNKNOWN | 29 | 132 | T |
| AI141502 | UNKNOWN | 15 | 0 | T |
| AI141931 | UNKNOWN | 12 | 12 | A |
| AI141975 | UNKNOWN | 14 | 0 | T |
| AI142037 | UNKNOWN | 19 | 0 | T |
| AI142094 | UNKNOWN | 28 | 0 | T |
| AI142101 | UNKNOWN | 53 | 23 | T |
| AI142101 | UNKNOWN | 22 | 0 | T |
| AI142101 | UNKNOWN | 17 | 108 | A |
| AI142101 | UNKNOWN | 13 | 76 | A |
| AI142101 | UNKNOWN | 12 | 227 | G |
| AI142118 | UNKNOWN | 3.57 | 247 | TTTTGTT |
| AI142121 | UNKNOWN | 3.57 | 456 | GTTGAAA |
| AI142327 | UNKNOWN | 3.6 | 382 | GCCAG |
| AI142434 | UNKNOWN | 12 | 0 | T |
| AI142552 | UNKNOWN | 17 | 0 | T |
| AI142739 | UNKNOWN | 5.66 | 267 | TTG |
| AI142740 | UNKNOWN | 27 | 0 | T |
| AI142769 | UNKNOWN | 25 | 2 | T |
| AI142832 | UNKNOWN | 6.5 | 528 | TG |
| AI142862 | UNKNOWN | 21 | 0 | T |
| AI142877 | UNKNOWN | 5.5 | 484 | TTAT |
| AI142960 | UNKNOWN | 20 | 0 | T |
| AI143013 | UNKNOWN | 65 | 0 | T |
| AI143013 | UNKNOWN | 14 | 274 | A |
| AI143013 | UNKNOWN | 13 | 125 | A |
| AI143013 | UNKNOWN | 12 | 170 | C |
| AI143069 | UNKNOWN | 4 | 95 | GTTTTTT |
| AI143074 | UNKNOWN | 12 | 140 | T |
| AI143106 | UNKNOWN | 37 | 0 | T |
| AI143204 | UNKNOWN | 24 | 0 | T |
| AI143296 | UNKNOWN | 17 | 0 | T |
| AI143430 | UNKNOWN | 2.5 | 266 | AAAAAAACAA (SEQ ID NO: 90) |
| AI143456 | UNKNOWN | 13 | 212 | T |
| AI143476 | UNKNOWN | 19 | 0 | T |
| AI143587 | UNKNOWN | 70 | 25 | T |
| AI143587 | UNKNOWN | 23 | 0 | T |
| AI143587 | UNKNOWN | 20 | 184 | C |

TABLE 1-continued

| Genbank # | Region | # reps | Position | Unit sequence |
|---|---|---|---|---|
| AI143587 | UNKNOWN | 17 | 270 | G |
| AI143587 | UNKNOWN | 15 | 101 | A |
| AI143587 | UNKNOWN | 15 | 119 | G |
| AI143597 | UNKNOWN | 51 | 0 | T |
| AI143597 | UNKNOWN | 15 | 152 | A |
| AI143641 | UNKNOWN | 18 | 0 | T |
| AI143864 | UNKNOWN | 16 | 273 | T |
| AI143892 | UNKNOWN | 13 | 0 | T |
| AI143927 | UNKNOWN | 23 | 0 | T |
| AI144001 | UNKNOWN | 42 | 0 | T |
| AI144025 | UNKNOWN | 17 | 325 | A |
| AI144926 | UNKNOWN | 28 | 312 | A |
| AI144036 | UNKNOWN | 22 | 343 | A |
| AI144043 | UNKNOWN | 27 | 90 | A |
| AI144047 | UNKNOWN | 38 | 139 | A |
| AI144052 | UNKNOWN | 29 | 109 | A |
| AI144055 | UNKNOWN | 23 | 341 | A |
| AI144058 | UNKNOWN | 17 | 200 | A |
| AI144079 | UNKNOWN | 29 | 74 | A |
| AI144083 | UNKNOWN | 6.25 | 222 | AGAA |
| AI144083 | UNKNOWN | 10 | 47 | GA |
| AI144083 | UNKNOWN | 22 | 266 | A |
| AI144091 | UNKNOWN | 6.5 | 107 | AG |
| AI144091 | UNKNOWN | 29 | 125 | A |
| AI144105 | UNKNOWN | 17 | 82 | A |
| AI144116 | UNKNOWN | 56 | 0 | T |
| AI144266 | UNKNOWN | 78 | 0 | T |
| AI144266 | UNKNOWN | 17 | 119 | A |
| AI144266 | UNKNOWN | 17 | 136 | G |
| AI144308 | UNKNOWN | 24 | 0 | T |
| AI144310 | UNKNOWN | 47 | 0 | T |
| AI144412 | UNKNOWN | 39 | 3 | T |
| AI146354 | UNKNOWN | 37 | 0 | T |
| AI146372 | UNKNOWN | 12 | 0 | T |
| AI146553 | UNKNOWN | 38 | 0 | T |
| AI146556 | UNKNOWN | 42 | 0 | T |
| AI146568 | UNKNOWN | 55 | 0 | T |
| AI146746 | UNKNOWN | 12 | 0 | T |
| AI146787 | UNKNOWN | 32 | 0 | T |
| AI146863 | UNKNOWN | 53 | 0 | T |
| AI146863 | UNKNOWN | 17 | 255 | G |
| AI146863 | UNKNOWN | 12 | 218 | G |
| AI146956 | UNKNOWN | 20 | 0 | T |
| AI147061 | UNKNOWN | 18 | 0 | T |
| AI147284 | UNKNOWN | 20 | 0 | T |
| AI147288 | UNKNOWN | 54 | 0 | T |
| AI147291 | UNKNOWN | 28 | 0 | T |
| AI147292 | UNKNOWN | 57 | 0 | T |
| AI147292 | UNKNOWN | 16 | 244 | G |
| AI147310 | UNKNOWN | 30 | 0 | T |
| AI147314 | UNKNOWN | 59 | 0 | T |
| AI147314 | UNKNOWN | 15 | 102 | A |
| AI147416 | UNKNOWN | 13 | 0 | T |
| AI147425 | UNKNOWN | 27 | 264 | A |
| AI147500 | UNKNOWN | 54 | 0 | T |
| AI147547 | UNKNOWN | 15 | 144 | T |
| AI147686 | UNKNOWN | 72 | 0 | T |
| AI147686 | UNKNOWN | 12 | 231 | C |
| AI147705 | UNKNOWN | 34 | 0 | T |
| AI147725 | UNKNOWN | 72 | 0 | T |
| AI147725 | UNKNOWN | 14 | 371 | G |
| AI147725 | UNKNOWN | 12 | 135 | G |
| AI147875 | UNKNOWN | 4.8 | 396 | AAAAC |
| AI147875 | UNKNOWN | 12 | 0 | T |
| AI147877 | UNKNOWN | 46 | 0 | T |
| AI147915 | UNKNOWN | 19 | 0 | T |
| AI147928 | UNKNOWN | 6.5 | 333 | GT |
| AI148005 | UNKNOWN | 14 | 0 | T |
| AI148022 | UNKNOWN | 15 | 0 | T |
| AI148113 | UNKNOWN | 56 | 0 | T |
| AI148113 | UNKNOWN | 12 | 178 | C |
| AI148165 | UNKNOWN | 13 | 0 | T |
| AI148181 | UNKNOWN | 52 | 0 | T |
| AI148181 | UNKNOWN | 13 | 212 | A |
| AI148256 | UNKNOWN | 47 | 0 | T |
| AI148272 | UNKNOWN | 78 | 0 | T |
| AI148272 | UNKNOWN | 18 | 147 | A |

TABLE 1-continued

| Genbank # | Region | # reps | Position | Unit sequence |
|---|---|---|---|---|
| AI148272 | UNKNOWN | 16 | 113 | C |
| AI148272 | UNKNOWN | 12 | 358 | G |
| AI148286 | UNKNOWN | 20 | 0 | T |
| AI148288 | UNKNOWN | 13 | 7 | T |
| AI148382 | UNKNOWN | 17 | 0 | T |
| AI148403 | UNKNOWN | 16 | 0 | T |
| AI148415 | UNKNOWN | 18 | 259 | T |
| AI148415 | UNKNOWN | 16 | 0 | T |
| AI148441 | UNKNOWN | 15 | 0 | T |
| AI148443 | UNKNOWN | 17 | 0 | T |
| AI148452 | UNKNOWN | 28 | 0 | T |
| AI148670 | UNKNOWN | 24 | 299 | T |
| AI148708 | UNKNOWN | 20 | 0 | T |
| AI148863 | UNKNOWN | 21 | 0 | T |
| AI148953 | UNKNOWN | 42 | 0 | T |
| AI148953 | UNKNOWN | 13 | 113 | G |
| AI148973 | UNKNOWN | 3.09 | 137 | TATACATTGTG (SEQ ID NO: 91) |
| AI148977 | UNKNOWN | 12 | 0 | T |
| AI149009 | UNKNOWN | 17 | 0 | T |
| AI149015 | UNKNOWN | 12 | 0 | T |
| AI149177 | UNKNOWN | 17 | 0 | T |
| AI149303 | UNKNOWN | 17 | 0 | T |
| AI149508 | UNKNOWN | 16 | 456 | A |
| AI149537 | UNKNOWN | 13 | 0 | T |
| AI149610 | UNKNOWN | 39 | 0 | T |
| AI149716 | UNKNOWN | 22 | 0 | T |
| AI149719 | UNKNOWN | 16 | 0 | T |
| AI149723 | UNKNOWN | 26 | 0 | T |
| AI149741 | UNKNOWN | 21 | 0 | T |
| AI149746 | UNKNOWN | 27 | 0 | T |
| AI149748 | UNKNOWN | 15 | 0 | T |
| AI149810 | UNKNOWN | 17 | 0 | T |
| AI149824 | UNKNOWN | 20 | 0 | T |
| AI149831 | UNKNOWN | 12 | 0 | T |
| AI149838 | UNKNOWN | 7.5 | 385 | GT |
| AI149838 | UNKNOWN | 15 | 0 | T |
| AI149842 | UNKNOWN | 18 | 0 | T |
| AI149844 | UNKNOWN | 16 | 0 | T |
| AI149833 | UNKNOWN | 15 | 0 | T |
| AI149857 | UNKNOWN | 15 | 0 | T |
| AI149858 | UNKNOWN | 15 | 0 | T |
| AI149880 | UNKNOWN | 18 | 9 | T |
| AI149955 | UNKNOWN | 17 | 0 | T |
| AI149965 | UNKNOWN | 17 | 0 | T |
| AI149987 | UNKNOWN | 2.91 | 24 | TATTTATTTATA (SEQ ID NO: 92) |
| AI150032 | UNKNOWN | 16 | 0 | T |
| AI150084 | UNKNOWN | 16 | 0 | T |
| AI150104 | UNKNOWN | 21 | 0 | T |
| AI150161 | UNKNOWN | 18 | 0 | T |
| AI150192 | UNKNOWN | 14 | 0 | T |
| AI150199 | UNKNOWN | 20 | 0 | T |
| AI150207 | UNKNOWN | 13 | 133 | T |
| AI150207 | UNKNOWN | 13 | 466 | A |
| AI150285 | UNKNOWN | 13 | 72 | A |
| AI150318 | UNKNOWN | 16 | 0 | T |
| AI150327 | UNKNOWN | 37 | 325 | C |
| AI150327 | UNKNOWN | 25 | 0 | T |
| AI150327 | UNKNOWN | 21 | 262 | C |
| AI150327 | UNKNOWN | 16 | 214 | C |
| AI150327 | UNKNOWN | 13 | 184 | C |
| AI150331 | UNKNOWN | 13 | 0 | T |
| AI150837 | UNKNOWN | 17 | 0 | T |
| AI150403 | UNKNOWN | 7.5 | 230 | CA |
| AI150418 | UNKNOWN | 18 | 0 | T |
| AI150424 | UNKNOWN | 20 | 0 | T |
| AI150432 | UNKNOWN | 15 | 0 | T |
| AI150443 | UNKNOWN | 18 | 0 | T |
| AI150548 | UNKNOWN | 24 | 471 | A |
| AI150577 | UNKNOWN | 13 | 0 | T |
| AI150610 | UNKNOWN | 15 | 0 | T |
| AI150693 | UNKNOWN | 23 | 304 | T |
| AI150693 | UNKNOWN | 13 | 138 | T |
| AI150747 | UNKNOWN | 45 | 0 | T |
| AI150983 | UNKNOWN | 20 | 0 | T |
| AI150993 | UNKNOWN | 73 | 7 | T |
| AI150993 | UNKNOWN | 13 | 281 | G |
| AI150993 | UNKNOWN | 12 | 295 | C |

TABLE 1-continued

| Genbank # | Region | # reps | Position | Unit sequence |
|---|---|---|---|---|
| AI151016 | UNKNOWN | 83 | 1 | T |
| AI151016 | UNKNOWN | 18 | 146 | C |
| AI151035 | UNKNOWN | 47 | 0 | T |
| AI151035 | UNKNOWN | 17 | 244 | G |
| AI151035 | UNKNOWN | 13 | 229 | C |
| AI151044 | UNKNOWN | 30 | 0 | T |
| AI151101 | UNKNOWN | 60 | 0 | T |
| AI151105 | UNKNOWN | 47 | 0 | T |
| AI151136 | UNKNOWN | 60 | 0 | T |
| AI151136 | UNKNOWN | 15 | 60 | A |
| AI151136 | UNKNOWN | 13 | 151 | C |
| AI151136 | UNKNOWN | 13 | 215 | G |
| AI151254 | UNKNOWN | 25 | 0 | T |
| AI151221 | UNKNOWN | 12 | 0 | T |
| AI151359 | UNKNOWN | 14 | 305 | T |
| AI159837 | UNKNOWN | 81 | 0 | T |
| AI159837 | UNKNOWN | 21 | 231 | A |
| AI159837 | UNKNOWN | 15 | 216 | G |
| AI169083 | UNKNOWN | 13 | 0 | T |
| AI160121 | UNKNOWN | 16 | 263 | A |
| AI160135 | UNKNOWN | 31 | 0 | T |
| AI160157 | UNKNOWN | 42 | 0 | T |
| AI160226 | UNKNOWN | 30 | 0 | T |
| AI160319 | UNKNOWN | 25 | 354 | T |
| AI160324 | UNKNOWN | 7.5 | 46 | TC |
| AI160368 | UNKNOWN | 20 | 0 | T |
| AI160713 | UNKNOWN | 53 | 0 | T |
| AI160717 | UNKNOWN | 17 | 0 | T |
| AI160786 | UNKNOWN | 5 | 14 | TTTA |
| AI160786 | UNKNOWN | 18 | 370 | A |
| AI160795 | UNKNOWN | 19 | 104 | A |
| AI160820 | UNKNOWN | 13 | 0 | T |
| AI160835 | UNKNOWN | 37 | 0 | T |
| AI160835 | UNKNOWN | 15 | 190 | C |
| AI160954 | UNKNOWN | 115 | 0 | T |
| AI160954 | UNKNOWN | 18 | 33 | G |
| AI160954 | UNKNOWN | 15 | 160 | A |
| AI160954 | UNKNOWN | 14 | 338 | C |
| AI160954 | UNKNOWN | 12 | 294 | C |
| AI160982 | UNKNOWN | 17 | 423 | A |
| AI160982 | UNKNOWN | 16 | 159 | T |
| AI161015 | UNKNOWN | 18 | 452 | A |
| AI161016 | UNKNOWN | 54 | 0 | T |
| AI161016 | UNKNOWN | 13 | 58 | A |
| AI161027 | UNKNOWN | 3.8 | 200 | AAAAC |
| AI161027 | UNKNOWN | 12 | 187 | A |
| AI161043 | UNKNOWN | 31 | 0 | T |
| AI161198 | UNKNOWN | 31 | 0 | T |
| AI161198 | UNKNOWN | 12 | 204 | A |
| AI161278 | UNKNOWN | 61 | 0 | T |
| AI161278 | UNKNOWN | 18 | 91 | A |
| AI161278 | UNKNOWN | 18 | 312 | G |
| AI161279 | UNKNOWN | 3.5 | 305 | AAAACC |
| AI161279 | UNKNOWN | 71 | 0 | T |
| AI161279 | UNKNOWN | 12 | 102 | A |
| AI161314 | UNKNOWN | 16 | 0 | T |
| AI161358 | UNKNOWN | 16 | 0 | T |
| AI161380 | UNKNOWN | 14 | 395 | T |
| AI161409 | UNKNOWN | 15 | 0 | T |
| AI167231 | UNKNOWN | 45 | 0 | T |
| AI167232 | UNKNOWN | 20 | 0 | T |
| AI167255 | UNKNOWN | 9.5 | 65 | TC |
| AI167353 | UNKNOWN | 60 | 0 | T |
| AI167353 | UNKNOWN | 22 | 161 | A |
| AI167356 | UNKNOWN | 3.8 | 20 | TTTTA |
| AI167356 | UNKNOWN | 12 | 35 | T |
| AI167460 | UNKNOWN | 12 | 53 | T |
| AI167594 | UNKNOWN | 43 | 0 | T |
| AI167628 | UNKNOWN | 18 | 0 | T |
| AI167815 | UNKNOWN | 24 | 0 | T |
| AI167912 | UNKNOWN | 32 | 0 | T |
| AI167563 | UNKNOWN | 4.8 | 78 | AAAAC |
| AI167953 | UNKNOWN | 18 | 0 | T |
| AI168031 | UNKNOWN | 24 | 0 | T |
| AI168209 | UNKNOWN | 16 | 0 | T |
| AI168210 | UNKNOWN | 13 | 0 | T |
| AI168233 | UNKNOWN | 19 | 0 | T |

TABLE 1-continued

| Genbank # | Region | # reps | Position | Unit sequence |
|---|---|---|---|---|
| AI168596 | UNKNOWN | 22 | 0 | T |
| AI168605 | UNKNOWN | 21 | 383 | T |
| AI168605 | UNKNOWN | 16 | 129 | A |
| AI168760 | UNKNOWN | 17 | 0 | T |
| AI174341 | UNKNOWN | 36 | 0 | T |
| AI174341 | UNKNOWN | 12 | 101 | A |
| AI174394 | UNKNOWN | 93 | 0 | T |
| AI174394 | UNKNOWN | 14 | 167 | A |
| AI174404 | UNKNOWN | 42 | 0 | T |
| AI174446 | UNKNOWN | 71 | 0 | T |
| AI174446 | UNKNOWN | 18 | 230 | C |
| AI174446 | UNKNOWN | 15 | 119 | G |
| AI174446 | UNKNOWN | 13 | 185 | C |
| AI174446 | UNKNOWN | 12 | 198 | A |
| AI174591 | UNKNOWN | 91 | 0 | T |
| AI174591 | UNKNOWN | 13 | 144 | C |
| AI174671 | UNKNOWN | 15 | 768 | A |
| AI174698 | UNKNOWN | 15 | 2 | T |
| AI174755 | UNKNOWN | 22 | 131 | A |
| AI174766 | UNKNOWN | 27 | 190 | A |
| AI174766 | UNKNOWN | 17 | 8 | T |
| AI174779 | UNKNOWN | 18 | 671 | A |
| AI174796 | UNKNOWN | 23 | 708 | A |
| AI174827 | UNKNOWN | 22 | 38 | A |
| AI174861 | UNKNOWN | 16 | 8 | T |
| AI174861 | UNKNOWN | 15 | 635 | A |
| AI174871 | UNKNOWN | 13 | 738 | A |
| AI174876 | UNKNOWN | 29 | 553 | A |
| AI174893 | UNKNOWN | 15 | 3 | T |
| AI174900 | UNKNOWN | 16 | 627 | A |
| AI174977 | UNKNOWN | 15 | 445 | A |
| AI174978 | UNKNOWN | 20 | 653 | A |
| AI174979 | UNKNOWN | 18 | 777 | A |
| AI174987 | UNKNOWN | 16 | 693 | A |
| AI174988 | UNKNOWN | 22 | 6 | T |
| AI183416 | UNKNOWN | 24 | 0 | T |
| AI183446 | UNKNOWN | 36 | 0 | T |
| AI183446 | UNKNOWN | 13 | 275 | G |
| AI183463 | UNKNOWN | 15 | 388 | T |
| AI183517 | UNKNOWN | 19 | 0 | T |
| AI183519 | UNKNOWN | 22 | 0 | T |
| AI183554 | UNKNOWN | 26 | 0 | T |
| AI183561 | UNKNOWN | 15 | 0 | T |
| AI183661 | UNKNOWN | 12 | 0 | T |
| AI183685 | UNKNOWN | 12 | 482 | G |
| AI183720 | UNKNOWN | 12 | 0 | T |
| AI183927 | UNKNOWN | 12 | 0 | T |
| AI183942 | UNKNOWN | 7 | 283 | TG |
| AI183969 | UNKNOWN | 30 | 0 | T |
| AI183970 | UNKNOWN | 16 | 0 | T |
| AI183975 | UNKNOWN | 15 | 0 | T |
| AI183992 | UNKNOWN | 13 | 0 | T |
| AI184052 | UNKNOWN | 16 | 14 | T |
| AI184206 | UNKNOWN | 13 | 0 | T |
| AI184207 | UNKNOWN | 19 | 0 | T |
| AI184220 | UNKNOWN | 24 | 0 | T |
| AI184299 | UNKNOWN | 40 | 0 | T |
| AI184506 | UNKNOWN | 6.5 | 194 | AT |
| AI184306 | UNKNOWN | 2 | 86 | T |
| AI184541 | UNKNOWN | 14 | 0 | T |
| AI184548 | UNKNOWN | 17 | 0 | T |
| AI184553 | UNKNOWN | 16 | 331 | A |
| AI184553 | UNKNOWN | 14 | 0 | T |
| AI184580 | UNKNOWN | 18 | 0 | T |
| AI184581 | UNKNOWN | 9.5 | 144 | CT |
| AI184615 | UNKNOWN | 47 | 0 | T |
| AI184810 | UNKNOWN | 13 | 0 | T |
| AI184903 | UNKNOWN | 83 | 0 | T |
| AI184903 | UNKNOWN | 16 | 270 | C |
| AI184903 | UNKNOWN | 15 | 286 | G |
| AI184903 | UNKNOWN | 14 | 135 | A |
| AI184903 | UNKNOWN | 13 | 117 | A |
| AI184903 | UNKNOWN | 13 | 216 | G |
| AI184903 | UNKNOWN | 12 | 200 | G |
| AI184568 | UNKNOWN | 13 | 53 | A |
| AI185116 | UNKNOWN | 29 | 0 | T |
| AI185399 | UNKNOWN | 55 | 0 | T |

TABLE 1-continued

| Genbank # | Region | # reps | Position | Unit sequence |
|---|---|---|---|---|
| AI185399 | UNKNOWN | 24 | 210 | G |
| AI185399 | UNKNOWN | 18 | 120 | A |
| AI185399 | UNKNOWN | 14 | 192 | G |
| AI185535 | UNKNOWN | 60 | 0 | T |
| AI185612 | UNKNOWN | 17 | 0 | T |
| AI185634 | UNKNOWN | 19 | 110 | T |
| AI185665 | UNKNOWN | 40 | 0 | T |
| AI185665 | UNKNOWN | 12 | 85 | A |
| AI186169 | UNKNOWN | 26 | 221 | A |
| AI186220 | UNKNOWN | 25 | 0 | T |
| AI186221 | UNKNOWN | 6.5 | 88 | AT |
| AI186292 | UNKNOWN | 15 | 0 | T |
| AI186297 | UNKNOWN | 14 | 0 | T |
| AI186437 | UNKNOWN | 25 | 0 | T |
| AI186476 | UNKNOWN | 28 | 0 | T |
| AI186499 | UNKNOWN | 6.66 | 178 | CGC |
| AI186673 | UNKNOWN | 33 | 0 | T |
| AI186846 | UNKNOWN | 13 | 0 | T |
| AI186854 | UNKNOWN | 4.2 | 189 | AAAAT |
| AI186854 | UNKNOWN | 20 | 354 | A |
| AI186854 | UNKNOWN | 18 | 0 | T |
| AI187194 | UNKNOWN | 15 | 0 | T |
| AI187214 | UNKNOWN | 16 | 0 | T |
| AI187389 | UNKNOWN | 6.5 | 66 | GT |
| AI187390 | UNKNOWN | 17 | 0 | T |
| AI187426 | UNKNOWN | 15 | 0 | T |
| AI187732 | UNKNOWN | 12 | 173 | A |
| AI187772 | UNKNOWN | 32 | 0 | T |
| AI187776 | UNKNOWN | 15 | 0 | T |
| AI187782 | UNKNOWN | 14 | 264 | A |
| AI187821 | UNKNOWN | 13 | 0 | T |
| AI187912 | UNKNOWN | 15 | 0 | T |
| AI187917 | UNKNOWN | 22 | 0 | T |
| AI188092 | UNKNOWN | 13 | 0 | T |
| AI188092 | UNKNOWN | 12 | 17 | A |
| AI188107 | UNKNOWN | 15 | 0 | T |
| AI188108 | UNKNOWN | 15 | 0 | T |
| AI188191 | UNKNOWN | 12 | 812 | T |
| AI188205 | UNKNOWN | 8.5 | 134 | TG |
| AI188210 | UNKNOWN | 12 | 0 | T |
| AI188218 | UNKNOWN | 15 | 0 | T |
| AI188226 | UNKNOWN | 4.75 | 255 | AAAG |
| AI188248 | UNKNOWN | 18 | 361 | A |
| AI188412 | UNKNOWN | 4.59 | 244 | TTTATT |
| AI188412 | UNKNOWN | 15 | 82 | T |
| AI188436 | UNKNOWN | 20 | 1 | T |
| AI188445 | UNKNOWN | 12 | 0 | T |
| AI188503 | UNKNOWN | 19 | 1 | T |
| AI188522 | UNKNOWN | 22 | 1 | T |
| AI188527 | UNKNOWN | 12 | 7 | T |
| AI188576 | UNKNOWN | 19 | 1 | T |
| AI188613 | UNKNOWN | 18 | 0 | T |
| AI188653 | UNKNOWN | 13 | 0 | T |
| AI188739 | UNKNOWN | 14 | 0 | T |
| AI188749 | UNKNOWN | 13 | 0 | T |
| AI188762 | UNKNOWN | 19 | 0 | T |
| AI188792 | UNKNOWN | 31 | 0 | T |
| AI189109 | UNKNOWN | 7 | 92 | GAA |
| AI189109 | UNKNOWN | 13 | 78 | A |
| AI189109 | UNKNOWN | 12 | 6 | T |
| AI189132 | UNKNOWN | 20 | 0 | T |
| AI189255 | UNKNOWN | 9.5 | 321 | AG |
| AI189255 | UNKNOWN | 8.5 | 257 | TG |
| AI189255 | UNKNOWN | 6.5 | 309 | AT |
| AI189297 | UNKNOWN | 18 | 0 | T |
| AI189312 | UNKNOWN | 15 | 0 | T |
| AI189378 | UNKNOWN | 13 | 0 | T |
| AI189385 | UNKNOWN | 18 | 9 | T |
| AI189435 | UNKNOWN | 24 | 0 | T |
| AI189551 | UNKNOWN | 8 | 427 | CA |
| AI189551 | UNKNOWN | 14 | 0 | T |
| AI189552 | UNKNOWN | 22 | 0 | T |
| AI189579 | UNKNOWN | 14 | 0 | T |
| AI189587 | UNKNOWN | 18 | 0 | T |
| AI189665 | UNKNOWN | 17 | 0 | T |
| AI189680 | UNKNOWN | 15 | 0 | T |
| AI189702 | UNKNOWN | 14 | 80 | A |

TABLE 1-continued

| Genbank # | Region | # reps | Position | Unit sequence |
|---|---|---|---|---|
| AI189778 | UNKNOWN | 43 | 0 | T |
| AI190209 | UNKNOWN | 15 | 0 | T |
| AI190306 | UNKNOWN | 21 | 321 | T |
| AI190325 | UNKNOWN | 15 | 0 | T |
| AI190467 | UNKNOWN | 18 | 456 | A |
| AI190492 | UNKNOWN | 17 | 206 | A |
| AI190525 | UNKNOWN | 20 | 5 | T |
| AI190572 | UNKNOWN | 12 | 0 | T |
| AI190589 | UNKNOWN | 31 | 0 | T |
| AI190598 | UNKNOWN | 15 | 0 | T |
| AI190602 | UNKNOWN | 15 | 0 | T |
| AI190608 | UNKNOWN | 26 | 0 | T |
| AI190616 | UNKNOWN | 14 | 0 | T |
| AI190712 | UNKNOWN | 21 | 0 | T |
| AI190715 | UNKNOWN | 12 | 0 | T |
| AI190744 | UNKNOWN | 16 | 0 | T |
| AI190745 | UNKNOWN | 16 | 0 | T |
| AI190760 | UNKNOWN | 19 | 0 | T |
| AI190768 | UNKNOWN | 12 | 0 | T |
| AI190774 | UNKNOWN | 15 | 0 | T |
| AI190890 | UNKNOWN | 17 | 0 | T |
| AI190903 | UNKNOWN | 13 | 0 | T |
| AI190905 | UNKNOWN | 20 | 0 | T |
| AI190914 | UNKNOWN | 19 | 0 | T |
| AI190916 | UNKNOWN | 15 | 0 | T |
| AI190924 | UNKNOWN | 28 | 0 | T |
| AI190927 | UNKNOWN | 15 | 208 | A |
| AI190946 | UNKNOWN | 4 | 372 | AAAAG |
| AI191127 | UNKNOWN | 3.5 | 88 | GGAAGA |
| AI191265 | UNKNOWN | 42 | 0 | T |
| AI191318 | UNKNOWN | 17 | 0 | T |
| AI191562 | UNKNOWN | 17 | 278 | T |
| AI191562 | UNKNOWN | 14 | 385 | A |
| AI191591 | UNKNOWN | 13 | 295 | T |
| AI191614 | UNKNOWN | 15 | 0 | T |
| AI191625 | UNKNOWN | 14 | 0 | T |
| AI191771 | UNKNOWN | 21 | 497 | A |
| AI191804 | UNKNOWN | 15 | 0 | T |
| AI191883 | UNKNOWN | 20 | 0 | T |
| AI191894 | UNKNOWN | 4.2 | 0 | TTTAT |
| AI191894 | UNKNOWN | 7.33 | 30 | TTA |
| AI191917 | UNKNOWN | 17 | 0 | T |
| AI191918 | UNKNOWN | 15 | 0 | T |
| AI191940 | UNKNOWN | 17 | 0 | T |
| AI191943 | UNKNOWN | 15 | 0 | T |
| AI192061 | UNKNOWN | 28 | 0 | T |
| AI192067 | UNKNOWN | 15 | 0 | T |
| AI192078 | UNKNOWN | 14 | 0 | T |
| AI192302 | UNKNOWN | 15 | 42 | T |
| AI192365 | UNKNOWN | 28 | 0 | T |
| AI192631 | UNKNOWN | 16 | 0 | T |
| AI192850 | UNKNOWN | 7 | 124 | AG |
| AI192889 | UNKNOWN | 26 | 0 | T |
| AI192958 | UNKNOWN | 17 | 201 | T |
| AI193207 | UNKNOWN | 19 | 0 | T |
| AI193235 | UNKNOWN | 16 | 1 | T |
| AI193837 | UNKNOWN | 17.5 | 249 | GT |
| AI193928 | UNKNOWN | 12 | 0 | T |
| AI193993 | UNKNOWN | 16 | 0 | T |
| AI194091 | UNKNOWN | 17 | 0 | T |
| AI198059 | UNKNOWN | 31 | 0 | T |
| AI198145 | UNKNOWN | 31 | 0 | T |
| AI198211 | UNKNOWN | 16 | 32 | T |
| AI198264 | UNKNOWN | 18 | 0 | T |
| AI198310 | UNKNOWN | 14 | 0 | T |
| AI198340 | UNKNOWN | 15 | 0 | T |
| AI198436 | UNKNOWN | 21 | 0 | T |
| AI198503 | UNKNOWN | 20 | 0 | T |
| AI198533 | UNKNOWN | 14 | 0 | T |
| AI198536 | UNKNOWN | 15 | 0 | T |
| AI198538 | UNKNOWN | 30 | 0 | T |
| AI198541 | UNKNOWN | 16 | 0 | T |
| AI198543 | UNKNOWN | 18 | 0 | T |
| AI198562 | UNKNOWN | 15 | 0 | T |
| AI198602 | UNKNOWN | 22 | 3 | T |
| AI198623 | UNKNOWN | 23 | 2 | T |
| AI198628 | UNKNOWN | 22 | 2 | T |

TABLE 1-continued

| Genbank # | Region | # reps | Position | Unit sequence |
|---|---|---|---|---|
| AI198633 | UNKNOWN | 19 | 0 | T |
| AI198641 | UNKNOWN | 18 | 0 | T |
| AI198650 | UNKNOWN | 18 | 0 | T |
| AI198820 | UNKNOWN | 15 | 0 | T |
| AI198829 | UNKNOWN | 18 | 0 | T |
| AI198841 | UNKNOWN | 15 | 0 | T |
| AI198847 | UNKNOWN | 16 | 0 | T |
| AI198850 | UNKNOWN | 23 | 2 | T |
| AI198851 | UNKNOWN | 16 | 0 | T |
| AI198854 | UNKNOWN | 16 | 0 | T |
| AI198855 | UNKNOWN | 12 | 0 | T |
| AI198857 | UNKNOWN | 15 | 0 | T |
| AI198868 | UNKNOWN | 26 | 0 | T |
| AI198870 | UNKNOWN | 16 | 0 | T |
| AI198873 | UNKNOWN | 15 | 0 | T |
| AI198876 | UNKNOWN | 15 | 0 | T |
| AI198876 | UNKNOWN | 13 | 282 | A |
| AI198877 | UNKNOWN | 19 | 0 | T |
| AI198880 | UNKNOWN | 15 | 0 | T |
| AI198890 | UNKNOWN | 15 | 0 | T |
| AI198908 | UNKNOWN | 28 | 0 | T |
| AI198917 | UNKNOWN | 12 | 236 | T |
| AI198928 | UNKNOWN | 2.83 | 220 | ACACTGTCTTTGTCTTTGCAGTTTGGGCCTGTTTTCGGG GCACTCCTGTAAACACAGCCA (SEQ ID NO: 93) |
| AI198932 | UNKNOWN | 16 | 0 | T |
| AI199025 | UNKNOWN | 22 | 0 | T |
| AI199030 | UNKNOWN | 37 | 0 | T |
| AI199030 | UNKNOWN | 21 | 199 | A |
| AI199289 | UNKNOWN | 32 | 0 | T |
| AI199189 | UNKNOWN | 14 | 314 | C |
| AI199189 | UNKNOWN | 12 | 217 | C |
| AI199388 | UNKNOWN | 44 | 0 | T |
| AI199418 | UNKNOWN | 18 | 4 | T |
| AI199420 | UNKNOWN | 18 | 0 | T |
| AI199453 | UNKNOWN | 20 | 1 | T |
| AI199453 | UNKNOWN | 12 | 99 | A |
| AI199562 | UNKNOWN | 21 | 0 | T |
| AI199575 | UNKNOWN | 7 | 372 | GA |
| AI199829 | UNKNOWN | 21 | 0 | T |
| AI199997 | UNKNOWN | 39 | 0 | T |
| AI199997 | UNKNOWN | 16 | 112 | A |
| AI200292 | UNKNOWN | 12 | 9 | T |
| AI200678 | UNKNOWN | 34 | 0 | T |
| AI200788 | UNKNOWN | 16 | 0 | T |
| AI200793 | UNKNOWN | 22 | 2 | T |
| AI200796 | UNKNOWN | 23 | 2 | T |
| AI200809 | UNKNOWN | 15 | 0 | T |
| AI200816 | UNKNOWN | 15 | 0 | T |
| AI200818 | UNKNOWN | 15 | 0 | T |
| AI200821 | UNKNOWN | 23 | 3 | T |
| AI200826 | UNKNOWN | 15 | 0 | T |
| AI200831 | UNKNOWN | 15 | 0 | T |
| AI200834 | UNKNOWN | 22 | 2 | T |
| AI200836 | UNKNOWN | 22 | 2 | T |
| AI200844 | UNKNOWN | 23 | 2 | T |
| AI200853 | UNKNOWN | 15 | 0 | T |
| AI200854 | UNKNOWN | 15 | 0 | T |
| AI200855 | UNKNOWN | 16 | 0 | T |
| AI200856 | UNKNOWN | 15 | 0 | T |
| AI200857 | UNKNOWN | 17 | 0 | T |
| AI200858 | UNKNOWN | 30 | 0 | T |
| AI200860 | UNKNOWN | 23 | 11 | T |
| AI200874 | UNKNOWN | 21 | 0 | T |
| AI200877 | UNKNOWN | 22 | 0 | T |
| AI200882 | UNKNOWN | 15 | 0 | T |
| AI200883 | UNKNOWN | 15 | 0 | T |
| AI200885 | UNKNOWN | 16 | 0 | T |
| AI200890 | UNKNOWN | 15 | 0 | |
| AI200904 | UNKNOWN | 15 | 0 | T |
| AI200906 | UNKNOWN | 15 | 0 | T |
| AI200915 | UNKNOWN | 24 | 0 | T |
| AI200919 | UNKNOWN | 15 | 0 | T |
| AI200920 | UNKNOWN | 12 | 0 | T |
| AI200954 | UNKNOWN | 15 | 0 | T |
| AI200964 | UNKNOWN | 16 | 0 | T |
| AI200976 | UNKNOWN | 16 | 0 | T |
| AI200990 | UNKNOWN | 15 | 0 | T |

TABLE 1-continued

| Genbank # | Region | # reps | Position | Unit sequence |
|---|---|---|---|---|
| AI201001 | UNKNOWN | 16 | 0 | T |
| AI201003 | UNKNOWN | 15 | 0 | T |
| AI201057 | UNKNOWN | 14 | 0 | T |
| AI201082 | UNKNOWN | 13 | 0 | T |
| AI201093 | UNKNOWN | 15 | 0 | T |
| AI201094 | UNKNOWN | 22 | 3 | T |
| AI201097 | UNKNOWN | 24 | 2 | T |
| AI201099 | UNKNOWN | 24 | 2 | T |
| AI201101 | UNKNOWN | 22 | 2 | T |
| AI201103 | UNKNOWN | 15 | 0 | T |
| AI201104 | UNKNOWN | 15 | 0 | T |
| AI201109 | UNKNOWN | 17 | 0 | T |
| AI201111 | UNKNOWN | 22 | 2 | T |
| AI201156 | UNKNOWN | 15 | 0 | T |
| AI201187 | UNKNOWN | 28 | 0 | T |
| AI201175 | UNKNOWN | 16 | 0 | T |
| AI201183 | UNKNOWN | 17 | 0 | T |
| AI201185 | UNKNOWN | 20 | 0 | T |
| AI201186 | UNKNOWN | 17 | 0 | T |
| AI201197 | UNKNOWN | 16 | 0 | T |
| AI201213 | UNKNOWN | 41 | 0 | T |
| AI201229 | UNKNOWN | 15 | 0 | T |
| AI201248 | UNKNOWN | 22 | 2 | T |
| AI201252 | UNKNOWN | 26 | 0 | T |
| AI201264 | UNKNOWN | 17 | 0 | T |
| AI201272 | UNKNOWN | 2.71 | 41 | TTTTTTTTTTTTC (SEQ ID NO: 94) |
| AI201272 | UNKNOWN | 54 | 0 | T |
| AI201272 | UNKNOWN | 29 | 219 | C |
| AI201272 | UNKNOWN | 16 | 158 | C |
| AI201272 | UNKNOWN | 13 | 188 | G |
| AI201273 | UNKNOWN | 16 | 0 | T |
| AI201277 | UNKNOWN | 17 | 0 | T |
| AI201300 | UNKNOWN | 20 | 0 | T |
| AI201301 | UNKNOWN | 13 | 0 | T |
| AI201303 | UNKNOWN | 16 | 0 | T |
| AI201304 | UNKNOWN | 19 | 0 | T |
| AI201305 | UNKNOWN | 20 | 0 | T |
| AI202312 | UNKNOWN | 16 | 0 | T |
| AI201374 | UNKNOWN | 15 | 0 | T |
| AI201398 | UNKNOWN | 20 | 0 | T |
| AI201576 | UNKNOWN | 15 | 0 | T |
| AI201652 | UNKNOWN | 44 | 0 | T |
| AI201728 | UNKNOWN | 12 | 0 | T |
| AI201830 | UNKNOWN | 44 | 0 | T |
| AI201851 | UNKNOWN | 19 | 0 | T |
| AI201900 | UNKNOWN | 28 | 0 | T |
| AI201958 | UNKNOWN | 14 | 0 | T |
| AI202065 | UNKNOWN | 4.75 | 150 | AATA |
| AI202154 | UNKNOWN | 21 | 122 | T |
| AI202203 | UNKNOWN | 66 | 0 | T |
| AI202280 | UNKNOWN | 27 | 0 | T |
| AI202316 | UNKNOWN | 20 | 0 | T |
| AI202325 | UNKNOWN | 26 | 0 | T |
| AI202351 | UNKNOWN | 15 | 157 | T |
| AI202441 | UNKNOWN | 31 | 244 | T |
| AI202441 | UNKNOWN | 17 | 0 | T |
| AI202590 | UNKNOWN | 16 | 0 | T |
| AI202738 | UNKNOWN | 19 | 0 | T |
| AI202739 | UNKNOWN | 12 | 0 | T |
| AI202875 | UNKNOWN | 25 | 0 | T |
| AI202908 | UNKNOWN | 14 | 0 | T |
| AI202994 | UNKNOWN | 4.75 | 327 | AAAG |
| AI203036 | UNKNOWN | 17 | 0 | T |
| AI203081 | UNKNOWN | 24 | 0 | T |
| AI203107 | UNKNOWN | 29 | 0 | T |
| AI203220 | UNKNOWN | 15 | 0 | T |
| AI203226 | UNKNOWN | 14 | 425 | A |
| AI203272 | UNKNOWN | 18 | 0 | T |
| AI203299 | UNKNOWN | 7.5 | 271 | TAGA |
| AI203476 | UNKNOWN | 20 | 0 | T |
| AI203529 | UNKNOWN | 49 | 0 | T |
| AI203683 | UNKNOWN | 15 | 758 | T |
| AI203683 | UNKNOWN | 13 | 730 | G |
| AI203701 | UNKNOWN | 12 | 0 | T |
| AI203705 | UNKNOWN | 13 | 0 | T |
| AI203903 | UNKNOWN | 50 | 0 | T |
| AI203925 | UNKNOWN | 6.66 | 22 | TTA |

TABLE 1-continued

| Genbank # | Region | # reps | Position | Unit sequence |
|---|---|---|---|---|
| AI203955 | UNKNOWN | 31 | 0 | T |
| AI204075 | UNKNOWN | 21 | 0 | T |
| AI204098 | UNKNOWN | 13 | 89 | A |
| AI204202 | UNKNOWN | 15 | 0 | T |
| AI204289 | UNKNOWN | 14 | 0 | T |
| AI204310 | UNKNOWN | 7.5 | 98 | TA |
| AI204310 | UNKNOWN | 15 | 327 | A |
| AI204341 | UNKNOWN | 6.5 | 79 | TA |
| AI204389 | UNKNOWN | 31 | 0 | T |
| AI204443 | UNKNOWN | 26 | 0 | T |
| AI204483 | UNKNOWN | 19 | 0 | T |
| AI204506 | UNKNOWN | 15 | 0 | T |
| AI204528 | UNKNOWN | 13.5 | 92 | AC |
| AI204593 | UNKNOWN | 25 | 0 | T |
| AI204599 | UNKNOWN | 14 | 0 | T |
| AI204601 | UNKNOWN | 13 | 0 | T |
| AI204624 | UNKNOWN | 25 | 0 | T |
| AI204957 | UNKNOWN | 17 | 0 | T |
| AI205181 | UNKNOWN | 10.75 | 0 | TTTA |
| AI205578 | UNKNOWN | 23 | 0 | T |
| AI205600 | UNKNOWN | 19 | 0 | T |
| AI205811 | UNKNOWN | 18 | 0 | T |
| AI205869 | UNKNOWN | 46 | 0 | T |
| AI205869 | UNKNOWN | 13 | 127 | A |
| AI205693 | UNKNOWN | 10 | 51 | AT |
| AI205931 | UNKNOWN | 22 | 0 | T |
| AI205959 | UNKNOWN | 5.66 | 11 | TTC |
| AI206025 | UNKNOWN | 6.25 | 12 | TTAT |
| AI206082 | UNKNOWN | 14 | 0 | T |
| AI206101 | UNKNOWN | 15 | 182 | T |
| AI206119 | UNKNOWN | 7.25 | 394 | AATA |
| AI206119 | UNKNOWN | 15 | 161 | T |
| AI206129 | UNKNOWN | 15 | 0 | T |
| AI206175 | UNKNOWN | 17 | 0 | T |
| AI206253 | UNKNOWN | 15 | 0 | T |
| AI206262 | UNKNOWN | 3.83 | 20 | TTTTTG |
| AI206269 | UNKNOWN | 5.75 | 36 | AAAT |
| AI206269 | UNKNOWN | 21.5 | 89 | CA |
| AI206275 | UNKNOWN | 23 | 0 | T |
| AI206296 | UNKNOWN | 35 | 0 | T |
| AI206560 | UNKNOWN | 14 | 371 | G |
| AI206568 | UNKNOWN | 23 | 0 | T |
| AI206965 | UNKNOWN | 2.54 | 694 | CCTCTGCCTGC (SEQ ID NO. 95) |
| AI206970 | UNKNOWN | 8 | 206 | AC |
| AI207056 | UNKNOWN | 58 | 0 | T |
| AI207056 | UNKNOWN | 14 | 194 | G |
| AI207056 | UNKNOWN | 12 | 160 | A |
| AI207091 | UNKNOWN | 20 | 0 | T |
| AI297120 | UNKNOWN | 19 | 0 | T |
| AI207410 | UNKNOWN | 16 | 728 | A |
| AI207415 | UNKNOWN | 5.25 | 397 | ATAG |
| AI207415 | UNKNOWN | 5.66 | 14 | TTG |
| AI207415 | UNKNOWN | 6.5 | 352 | TG |
| AI207415 | UNKNOWN | 14 | 795 | A |
| AI207527 | UNKNOWN | 15 | 562 | A |
| AI207544 | UNKNOWN | 13 | 809 | A |
| AI207547 | UNKNOWN | 20 | 4 | T |
| AI207548 | UNKNOWN | 12 | 742 | A |
| AI207555 | UNKNOWN | 15 | 694 | A |
| AI207562 | UNKNOWN | 14 | 5 | T |
| AI207564 | UNKNOWN | 13 | 721 | A |
| AI207593 | UNKNOWN | 21 | 0 | T |
| AI207007 | UNKNOWN | 5 | 561 | A |
| AI207648 | UNKNOWN | 16 | 802 | A |
| AI207684 | UNKNOWN | 19 | 5 | T |
| AI207718 | UNKNOWN | 15 | 5 | T |
| AI207720 | UNKNOWN | 12 | 577 | A |
| AI207722 | UNKNOWN | 17 | 730 | A |
| AI207728 | UNKNOWN | 40 | 649 | A |
| AI207891 | UNKNOWN | 3.8 | 153 | AAAAC |
| AI207977 | UNKNOWN | 12 | 216 | T |
| AI208035 | UNKNOWN | 16 | 306 | T |
| AI208117 | UNKNOWN | 19 | 0 | T |
| AI208140 | UNKNOWN | 12 | 0 | T |
| AI208142 | UNKNOWN | 19 | 0 | T |
| AI208158 | UNKNOWN | 24 | 0 | T |
| AI208176 | UNKNOWN | 16 | 0 | T |

TABLE 1-continued

| Genbank # | Region | # reps | Position | Unit sequence |
|---|---|---|---|---|
| AI208184 | UNKNOWN | 16 | 6 | T |
| AI208255 | UNKNOWN | 16 | 0 | T |
| AI205281 | UNKNOWN | 26 | 0 | T |
| AI208328 | UNKNOWN | 37 | 0 | T |
| AI208371 | UNKNOWN | 12 | 149 | A |
| AI208426 | UNKNOWN | 28 | 0 | T |
| AI208468 | UNKNOWN | 15 | 0 | T |
| AI208528 | UNKNOWN | 19 | 0 | T |
| AI208770 | UNKNOWN | 21 | 0 | T |
| AI208840 | UNKNOWN | 13 | 0 | T |
| AI208808 | UNKNOWN | 17 | 0 | T |
| AI208948 | UNKNOWN | 20 | 243 | T |
| AI209085 | UNKNOWN | 12 | 0 | T |
| AI209093 | UNKNOWN | 15 | 0 | T |
| AI209204 | UNKNOWN | 18 | 0 | T |
| AI209215 | UNKNOWN | 12 | 0 | T |
| AI214603 | UNKNOWN | 19 | 44 | A |
| AI214727 | UNKNOWN | 16 | 0 | T |
| AI214757 | UNKNOWN | 32 | 10 | T |
| AI214758 | UNKNOWN | 42 | 0 | T |
| AI714913 | UNKNOWN | 20 | 0 | T |
| AI214985 | UNKNOWN | 36 | 0 | T |
| AI215052 | UNKNOWN | 18 | 0 | T |
| AI215090 | UNKNOWN | 13 | 0 | T |
| AI215424 | UNKNOWN | 46 | 0 | T |
| AI215487 | UNKNOWN | 17 | 0 | T |
| AI215523 | UNKNOWN | 12 | 0 | T |
| AI215571 | UNKNOWN | 15 | 524 | G |
| AI215610 | UNKNOWN | 12 | 251 | TG |
| AI215610 | UNKNOWN | 14 | 106 | T |
| AI215667 | UNKNOWN | 21 | 0 | T |
| AI215674 | UNKNOWN | 13 | 396 | T |
| AI215698 | UNKNOWN | 6.5 | 41 | AC |
| AI215788 | UNKNOWN | 16 | 329 | GT |
| AI215936 | UNKNOWN | 4.75 | 28 | TTTA |
| AI215936 | UNKNOWN | 31 | 0 | T |
| AI216134 | UNKNOWN | 12 | 0 | T |
| AI216235 | UNKNOWN | 18 | 3 | T |
| AI216418 | UNKNOWN | 29 | 0 | T |
| AI216449 | UNKNOWN | 13 | 0 | T |
| AI216576 | UNKNOWN | 8.5 | 309 | TA |
| AI216879 | UNKNOWN | 14 | 0 | T |
| AI216990 | UNKNOWN | 23 | 21 | T |
| AI217038 | UNKNOWN | 25 | 23 | T |
| AI217063 | UNKNOWN | 15 | 147 | T |
| AI217106 | UNKNOWN | 13 | 0 | T |
| AI217121 | UNKNOWN | 4.75 | 293 | AAAC |
| AI217121 | UNKNOWN | 14 | 252 | T |
| AI217123 | UNKNOWN | 6.75 | 11 | TTAT |
| AI217128 | UNKNOWN | 15 | 0 | T |
| AI217131 | UNKNOWN | 15 | 0 | T |
| AI217164 | UNKNOWN | 14 | 0 | T |
| AI217175 | UNKNOWN | 17 | 0 | T |
| AI217278 | UNKNOWN | 13 | 0 | T |
| AI217303 | UNKNOWN | 13.33 | 313 | ATC |
| AI217382 | UNKNOWN | 12 | 73 | T |
| AI217385 | UNKNOWN | 16 | 275 | AC |
| AI217490 | UNKNOWN | 23 | 0 | T |
| AI217586 | UNKNOWN | 17 | 0 | T |
| AI217586 | UNKNOWN | 12 | 126 | G |
| AI217639 | UNKNOWN | 8 | 450 | ATT |
| AI217650 | UNKNOWN | 17 | 0 | T |
| AI217760 | UNKNOWN | 17 | 0 | T |
| AI217810 | UNKNOWN | 8.75 | 0 | TTTA |
| AI217897 | UNKNOWN | 15 | 0 | T |
| AI217898 | UNKNOWN | 17 | 0 | T |
| AI217906 | UNKNOWN | 18 | 0 | T |
| AI217921 | UNKNOWN | 17 | 0 | T |
| AI217922 | UNKNOWN | 15 | 0 | T |
| AI217928 | UNKNOWN | 15 | 0 | T |
| AI217932 | UNKNOWN | 22 | 2 | T |
| AI217978 | UNKNOWN | 22 | 2 | T |
| AI217986 | UNKNOWN | 22 | 2 | T |
| AI217990 | UNKNOWN | 22 | 2 | T |
| AI217996 | UNKNOWN | 22 | 3 | T |
| AI218019 | UNKNOWN | 27 | 0 | T |
| AI218038 | UNKNOWN | 18 | 250 | T |

TABLE 1-continued

| Genbank # | Region | # reps | Position | Unit sequence |
|---|---|---|---|---|
| AI218124 | UNKNOWN | 22 | 0 | T |
| AI218156 | UNKNOWN | 51 | 0 | T |
| AI219187 | UNKNOWN | 4 | 97 | TGGGG |
| AI218190 | UNKNOWN | 14 | 41 | T |
| AI218315 | UNKNOWN | 12 | 0 | T |
| AI218450 | UNKNOWN | 13 | 0 | T |
| AI218491 | UNKNOWN | 15 | 0 | T |
| AI218506 | UNKNOWN | 4.75 | 141 | TTGT |
| AI218507 | UNKNOWN | 4.75 | 141 | TTGT |
| AI216523 | UNKNOWN | 15 | 34 | A |
| AI218609 | UNKNOWN | 23 | 2 | T |
| AI218611 | UNKNOWN | 22 | 3 | T |
| AI218612 | UNKNOWN | 22 | 2 | T |
| AI218614 | UNKNOWN | 22 | 2 | T |
| AI218617 | UNKNOWN | 19 | 8 | T |
| AI218620 | UNKNOWN | 22 | 0 | T |
| AI218628 | UNKNOWN | 22 | 11 | T |
| AI218671 | UNKNOWN | 27 | 0 | T |
| AI218683 | UNKNOWN | 22 | 2 | T |
| AI218684 | UNKNOWN | 22 | 2 | T |
| AI218876 | UNKNOWN | 20 | 0 | T |
| AI218924 | UNKNOWN | 12 | 27 | A |
| AI218934 | UNKNOWN | 27 | 0 | T |
| AI218954 | UNKNOWN | 16 | 0 | T |
| AI216967 | UNKNOWN | 13 | 0 | T |
| AI219120 | UNKNOWN | 23 | 0 | T |
| AI219291 | UNKNOWN | 24 | 0 | T |
| AI219353 | UNKNOWN | 12 | 0 | T |
| AI219444 | UNKNOWN | 28 | 0 | T |
| AI219563 | UNKNOWN | 21 | 1 | T |
| AI219564 | UNKNOWN | 7.5 | 376 | AC |
| AI219564 | UNKNOWN | 19 | 1 | T |
| AI219584 | UNKNOWN | 19 | 0 | T |
| AI219707 | UNKNOWN | 14 | 217 | T |
| AI219734 | UNKNOWN | 24 | 166 | T |
| AI219775 | UNKNOWN | 19 | 0 | T |
| AI219911 | UNKNOWN | 13 | 146 | T |
| AI219930 | UNKNOWN | 20 | 0 | T |
| AI219978 | UNKNOWN | 12 | 0 | T |
| AI220231 | UNKNOWN | 20 | 0 | T |
| AI220328 | UNKNOWN | 13 | 331 | A |
| AI220420 | UNKNOWN | 19 | 229 | A |
| AI220420 | UNKNOWN | 14 | 111 | T |
| AI220517 | UNKNOWN | 17 | 0 | T |
| AI220532 | UNKNOWN | 19 | 0 | T |
| AI220558 | UNKNOWN | 12 | 0 | T |
| AI220561 | UNKNOWN | 31 | 0 | T |
| AI220642 | UNKNOWN | 28 | 0 | T |
| AI220726 | UNKNOWN | 12 | 0 | T |
| AI220731 | UNKNOWN | 19 | 0 | T |
| AI220784 | UNKNOWN | 39 | 0 | T |
| AI220784 | UNKNOWN | 12 | 225 | A |
| AI220828 | UNKNOWN | 44 | 0 | T |
| AI220941 | UNKNOWN | 38 | 17 | T |
| AI220941 | UNKNOWN | 16 | 0 | T |
| AI221087 | UNKNOWN | 12 | 11 | T |
| AI221136 | UNKNOWN | 17 | 0 | T |
| AI221176 | UNKNOWN | 26 | 0 | T |
| AI221196 | UNKNOWN | 10.5 | 154 | GA |
| AI221196 | UNKNOWN | 15 | 0 | T |
| AI221316 | UNKNOWN | 12 | 33 | A |
| AI221398 | UNKNOWN | 19 | 0 | T |
| AI221408 | UNKNOWN | 14 | 306 | A |
| AI221546 | UNKNOWN | 14 | 163 | T |
| AI221606 | UNKNOWN | 30 | 0 | T |
| AI221633 | UNKNOWN | 19 | 0 | T |
| AI221669 | UNKNOWN | 19 | 4 | T |
| AI221782 | UNKNOWN | 3.83 | 85 | CAAAAA |
| AI221782 | UNKNOWN | 3.8 | 8 | TTTTC |
| AI221762 | UNKNOWN | 15 | 23 | T |
| AI221933 | UNKNOWN | 17 | 340 | A |
| AI221994 | UNKNOWN | 23 | 2 | T |
| AI222069 | UNKNOWN | 6.33 | 301 | GCT |
| AI222153 | UNKNOWN | 3.6 | 260 | AGAGG |
| AI222198 | UNKNOWN | 13 | 358 | A |
| AI222413 | UNKNOWN | 32 | 4 | T |
| AI222415 | UNKNOWN | 15 | 0 | T |

TABLE 1-continued

| Genbank # | Region | # reps | Position | Unit sequence |
|---|---|---|---|---|
| AI222416 | UNKNOWN | 17 | 248 | T |
| AI222420 | UNKNOWN | 15 | 0 | T |
| AI222424 | UNKNOWN | 21 | 0 | T |
| AI222440 | UNKNOWN | 15 | 0 | T |
| AI222444 | UNKNOWN | 15 | 0 | T |
| AI222461 | UNKNOWN | 8.5 | 169 | GA |
| AI222520 | UNKNOWN | 40 | 0 | T |
| AI222592 | UNKNOWN | 14 | 0 | T |
| AI222663 | UNKNOWN | 45 | 0 | T |
| AI222713 | UNKNOWN | 18 | 0 | T |
| AI222742 | UNKNOWN | 29 | 286 | T |
| AI222742 | UNKNOWN | 13 | 272 | T |
| AI222805 | UNKNOWN | 14 | 432 | A |
| AI223116 | UNKNOWN | 18 | 2 | T |
| AI223158 | UNKNOWN | 19 | 0 | T |
| AI223261 | UNKNOWN | 12 | 0 | T |
| AI223322 | UNKNOWN | 8.5 | 208 | AT |
| AI223385 | UNKNOWN | 12 | 0 | T |
| AI223423 | UNKNOWN | 12 | 0 | T |
| AI223445 | UNKNOWN | 21 | 0 | T |
| AI223487 | UNKNOWN | 28 | 95 | A |
| AI223518 | UNKNOWN | 22 | 152 | A |
| AI223529 | UNKNOWN | 27 | 67 | A |
| AI223555 | UNKNOWN | 24 | 197 | A |
| AI223567 | UNKNOWN | 29 | 73 | A |
| AI223568 | UNKNOWN | 28 | 90 | A |
| AI223590 | UNKNOWN | 23 | 290 | A |
| AI223600 | UNKNOWN | 27 | 177 | A |
| AI223604 | UNKNOWN | 26 | 110 | A |
| AI223633 | UNKNOWN | 27 | 76 | A |
| AI223636 | UNKNOWN | 27 | 109 | A |
| AI223647 | UNKNOWN | 26 | 134 | A |
| AI223678 | UNKNOWN | 24 | 302 | A |
| AI223684 | UNKNOWN | 19 | 111 | A |
| AI223700 | UNKNOWN | 20 | 343 | A |
| AI223700 | UNKNOWN | 14 | 283 | A |
| AI223735 | UNKNOWN | 29 | 172 | A |
| AI223756 | UNKNOWN | 24 | 187 | A |
| AI223817 | UNKNOWN | 17 | 0 | T |
| AI223857 | UNKNOWN | 12 | 356 | A |
| AI223917 | UNKNOWN | 28 | 76 | A |
| AI223955 | UNKNOWN | 19 | 0 | T |
| AI223980 | UNKNOWN | 5.25 | 180 | GGCG |
| AI223980 | UNKNOWN | 51 | 0 | T |
| AI223980 | UNKNOWN | 17 | 81 | G |
| AI223996 | UNKNOWN | 42 | 0 | T |
| AI224020 | UNKNOWN | 14 | 165 | A |
| AI224027 | UNKNOWN | 99 | 0 | T |
| AI224027 | UNKNOWN | 23 | 294 | G |
| AI224027 | UNKNOWN | 13 | 160 | C |
| AI224027 | UNKNOWN | 12 | 103 | A |
| AI224027 | UNKNOWN | 12 | 121 | C |
| AI224091 | UNKNOWN | 14 | 0 | T |
| AI224092 | UNKNOWN | 18 | 243 | A |
| AI224092 | UNKNOWN | 15 | 120 | A |
| AI224092 | UNKNOWN | 14 | 72 | G |
| AI224092 | UNKNOWN | 12 | 44 | T |
| AI224092 | UNKNOWN | 12 | 214 | C |
| AI224119 | UNKNOWN | 19 | 0 | T |
| AI224126 | UNKNOWN | 18 | 292 | T |
| AI224184 | UNKNOWN | 30 | 150 | A |
| AI224206 | UNKNOWN | 20 | 111 | A |
| AI224250 | UNKNOWN | 28 | 92 | A |
| AI224299 | UNKNOWN | 24 | 110 | A |
| AI224303 | UNKNOWN | 26 | 111 | A |
| AI224307 | UNKNOWN | 27 | 110 | A |
| AI224334 | UNKNOWN | 28 | 118 | A |
| AI224403 | UNKNOWN | 34 | 0 | T |
| AI224403 | UNKNOWN | 16 | 125 | A |
| AI224403 | UNKNOWN | 14 | 279 | G |
| AI224403 | UNKNOWN | 53 | 0 | T |
| AI224463 | UNKNOWN | 14 | 226 | A |
| AI224463 | UNKNOWN | 12 | 189 | C |
| AI224492 | UNKNOWN | 31 | 0 | T |
| AI224599 | UNKNOWN | 19 | 0 | T |
| AI224626 | UNKNOWN | 13 | 151 | A |
| AI224653 | UNKNOWN | 13 | 392 | A |

TABLE 1-continued

| Genbank # | Region | # reps | Position | Unit sequence |
|---|---|---|---|---|
| AI224676 | UNKNOWN | 21 | 116 | A |
| AI224690 | UNKNOWN | 29 | 85 | A |
| AI224709 | UNKNOWN | 27 | 109 | A |
| AI224731 | UNKNOWN | 21 | 107 | A |
| AI224765 | UNKNOWN | 27 | 204 | A |
| AI224765 | UNKNOWN | 14 | 94 | T |
| AI224788 | UNKNOWN | 20 | 191 | A |
| AI224790 | UNKNOWN | 29 | 90 | A |
| AI224806 | UNKNOWN | 30 | 71 | A |
| AI224981 | UNKNOWN | 41 | 0 | T |
| AI224992 | UNKNOWN | 120 | 0 | T |
| AI225000 | UNKNOWN | 53 | 0 | T |
| AI225004 | UNKNOWN | 65 | 0 | T |
| AI225004 | UNKNOWN | 13 | 180 | G |
| AI225007 | UNKNOWN | 7 | 322 | ATT |
| AI225011 | UNKNOWN | 68 | 0 | T |
| AI225011 | UNKNOWN | 22 | 131 | G |
| AI225023 | UNKNOWN | 80 | 0 | T |
| AI225023 | UNKNOWN | 15 | 244 | A |
| AI225023 | UNKNOWN | 14 | 144 | A |
| AI225023 | UNKNOWN | 13 | 101 | G |
| AI225023 | UNKNOWN | 12 | 117 | C |
| AI225037 | UNKNOWN | 19 | 0 | T |
| AI225047 | UNKNOWN | 90 | 0 | T |
| AI225047 | UNKNOWN | 14 | 233 | C |
| AI225084 | UNKNOWN | 4.2 | 144 | TATTT |
| AI225105 | UNKNOWN | 13 | 0 | T |
| AI225129 | UNKNOWN | 49 | 0 | T |
| AI225129 | UNKNOWN | 15 | 408 | A |
| AI225185 | UNKNOWN | 28 | 163 | A |
| AI225187 | UNKNOWN | 25 | 74 | A |
| AI225216 | UNKNOWN | 47 | 0 | T |
| AI225283 | UNKNOWN | 26 | 207 | A |
| AI239415 | UNKNOWN | 14 | 383 | A |
| AI239437 | UNKNOWN | 26 | 0 | T |
| AI239473 | UNKNOWN | 9.5 | 96 | TG |
| AI239492 | UNKNOWN | 12 | 80 | A |
| AI239497 | UNKNOWN | 24 | 0 | T |
| AI239568 | UNKNOWN | 18 | 301 | T |
| AI239570 | UNKNOWN | 13 | 0 | T |
| AI239701 | UNKNOWN | 42 | 0 | T |
| AI239729 | UNKNOWN | 17 | 0 | T |
| AI239754 | UNKNOWN | 19 | 0 | T |
| AI239760 | UNKNOWN | 17 | 0 | T |
| AI239769 | UNKNOWN | 12 | 390 | T |
| AI239791 | UNKNOWN | 14 | 6 | T |
| AI239803 | UNKNOWN | 38 | 0 | T |
| AI239803 | UNKNOWN | 16 | 279 | A |
| AI239865 | UNKNOWN | 12 | 259 | GT |
| AI239857 | UNKNOWN | 13 | 0 | T |
| AI239919 | UNKNOWN | 22 | 0 | T |
| AI240135 | UNKNOWN | 35 | 33 | T |
| AI240135 | UNKNOWN | 32 | 0 | T |
| AI240135 | UNKNOWN | 12 | 278 | G |
| AI240168 | UNKNOWN | 3.8 | 6 | TTTTA |
| AI240194 | UNKNOWN | 18 | 384 | A |
| AI240199 | UNKNOWN | 13 | 22 | T |
| AI240275 | UNKNOWN | 14.5 | 91 | AI |
| AI240275 | UNKNOWN | 14.5 | 119 | AC |
| AI240275 | UNKNOWN | 7.5 | 67 | AI |
| AI240278 | UNKNOWN | 27 | 0 | T |
| AI240378 | UNKNOWN | 37 | 0 | T |
| AI240438 | UNKNOWN | 38 | 0 | T |
| AI240573 | UNKNOWN | 22 | 0 | T |
| AI240602 | UNKNOWN | 64 | 0 | T |
| AI240602 | UNKNOWN | 15 | 267 | G |
| AI240682 | UNKNOWN | 6.33 | 578 | AAG |
| AI240707 | UNKNOWN | 8.5 | 213 | TG |
| AI240707 | UNKNOWN | 8 | 243 | TA |
| AI240707 | UNKNOWN | 6.5 | 229 | TA |
| AI240803 | UNKNOWN | 16 | 154 | A |
| AI240822 | UNKNOWN | 20 | 0 | T |
| AI240939 | UNKNOWN | 17 | 0 | T |
| AI240978 | UNKNOWN | 59 | 0 | T |
| AI240978 | UNKNOWN | 12 | 238 | G |
| AI241030 | UNKNOWN | 10 | 261 | AT |
| AI241058 | UNKNOWN | 6.25 | 8 | TTAT |

TABLE 1-continued

| Genbank # | Region | # reps | Position | Unit sequence |
|---|---|---|---|---|
| AI241058 | UNKNOWN | 7 | 256 | CT |
| AI241058 | UNKNOWN | 14 | 269 | T |
| AI241072 | UNKNOWN | 40 | 0 | T |
| AI241143 | UNKNOWN | 51 | 0 | T |
| AI241246 | UNKNOWN | 19 | 0 | T |
| AI241330 | UNKNOWN | 16 | 0 | T |
| AI241359 | UNKNOWN | 13 | 128 | A |
| AI241399 | UNKNOWN | 30 | 0 | T |
| AI241457 | UNKNOWN | 17 | 0 | T |
| AI241507 | UNKNOWN | 23 | 0 | T |
| AI241564 | UNKNOWN | 13 | 1 | T |
| AI241598 | UNKNOWN | 20 | 412 | G |
| AI241657 | UNKNOWN | 22 | 25 | T |
| AI241663 | UNKNOWN | 12 | 289 | T |
| AI241675 | UNKNOWN | 55 | 0 | T |
| AI241675 | UNKNOWN | 16 | 336 | G |
| AI241678 | UNKNOWN | 54 | 0 | T |
| AI241686 | UNKNOWN | 3.6 | 3 | TTTAT |
| AI241694 | UNKNOWN | 34 | 44 | T |
| AI241694 | UNKNOWN | 15 | 0 | T |
| AI241741 | UNKNOWN | 58 | 0 | T |
| AI241741 | UNKNOWN | 17 | 235 | G |
| AI241741 | UNKNOWN | 12 | 137 | C |
| AI241743 | UNKNOWN | 32 | 0 | T |
| AI241744 | UNKNOWN | 85 | 0 | T |
| AI241744 | UNKNOWN | 23 | 259 | G |
| AI241744 | UNKNOWN | 20 | 87 | A |
| AI241744 | UNKNOWN | 13 | 200 | C |
| AI241763 | UNKNOWN | 75 | 0 | T |
| AI241792 | UNKNOWN | 69 | 0 | T |
| AI241795 | UNKNOWN | 37 | 0 | T |
| AI241800 | UNKNOWN | 47 | 0 | T |
| AI241812 | UNKNOWN | 46 | 0 | T |
| AI241812 | UNKNOWN | 18 | 396 | A |
| AI241819 | UNKNOWN | 92 | 0 | T |
| AI241819 | UNKNOWN | 17 | 111 | A |
| AI241819 | UNKNOWN | 15 | 156 | G |
| AI241821 | UNKNOWN | 16 | 0 | T |
| AI241901 | UNKNOWN | 57 | 0 | T |
| AI241923 | UNKNOWN | 74 | 0 | T |
| AI241939 | UNKNOWN | 62 | 0 | T |
| AI241939 | UNKNOWN | 13 | 295 | C |
| AI241974 | UNKNOWN | 29 | 76 | A |
| AI241982 | UNKNOWN | 28 | 104 | A |
| AI241993 | UNKNOWN | 18 | 134 | A |
| AI242000 | UNKNOWN | 23 | 170 | A |
| AI242003 | UNKNOWN | 2.63 | 30 | GGAAAGGAAAG (SEQ ID NO: 96) |
| AI242003 | UNKNOWN | 4.16 | 46 | GGAAAG |
| AI242003 | UNKNOWN | 25 | 108 | A |
| AI242006 | UNKNOWN | 18 | 443 | A |
| AI242009 | UNKNOWN | 31 | 108 | A |
| AI242010 | UNKNOWN | 29 | 61 | A |
| AI242011 | UNKNOWN | 29 | 288 | A |
| AI242031 | UNKNOWN | 14 | 0 | T |
| AI242062 | UNKNOWN | 7.5 | 150 | TG |
| AI242067 | UNKNOWN | 20 | 0 | T |
| AI242072 | UNKNOWN | 35 | 0 | T |
| AI242096 | UNKNOWN | 12 | 0 | T |
| AI242157 | UNKNOWN | 42 | 0 | T |
| AI242205 | UNKNOWN | 14 | 144 | A |
| AI242227 | UNKNOWN | 17.5 | 159 | AT |
| AI242227 | UNKNOWN | 36 | 0 | T |
| AI242246 | UNKNOWN | 63 | 0 | T |
| AI242246 | UNKNOWN | 17 | 136 | G |
| AI242246 | UNKNOWN | 16 | 192 | C |
| AI242246 | UNKNOWN | 12 | 114 | C |
| AI242248 | UNKNOWN | 69 | 0 | T |
| AI242249 | UNKNOWN | 117 | 0 | T |
| AI242249 | UNKNOWN | 15 | 247 | C |
| AI242249 | UNKNOWN | 13 | 156 | C |
| AI242251 | UNKNOWN | 88 | 0 | T |
| AI242251 | UNKNOWN | 13 | 122 | G |
| AI242255 | UNKNOWN | 35 | 0 | T |
| AI242269 | UNKNOWN | 2.91 | 8 | TTTTTTTTTTC (SEQ ID NO: 97) |
| AI242269 | UNKNOWN | 23 | 32 | T |
| AI242269 | UNKNOWN | 19 | 0 | T |
| AI242269 | UNKNOWN | 19 | 226 | G |

TABLE 1-continued

| Genbank # | Region | # reps | Position | Unit sequence |
|---|---|---|---|---|
| AI242269 | UNKNOWN | 18 | 125 | A |
| AI242337 | UNKNOWN | 49 | 0 | T |
| AI242337 | UNKNOWN | 17 | 144 | C |
| AI242467 | UNKNOWN | 20 | 0 | T |
| AI242505 | UNKNOWN | 46 | 0 | T |
| AI242646 | UNKNOWN | 99 | 0 | T |
| AI242646 | UNKNOWN | 14 | 355 | G |
| AI242646 | UNKNOWN | 13 | 369 | A |
| AI242646 | UNKNOWN | 12 | 263 | A |
| AI242695 | UNKNOWN | 39 | 0 | T |
| AI242726 | UNKNOWN | 15 | 11 | T |
| AI242803 | UNKNOWN | 7 | 281 | TG |
| AI242826 | UNKNOWN | 17 | 0 | T |
| AI242931 | UNKNOWN | 79 | 0 | T |
| AI242931 | UNKNOWN | 17 | 253 | G |
| AI243093 | UNKNOWN | 13 | 0 | T |
| AI243115 | UNKNOWN | 16 | 0 | T |
| AI243123 | UNKNOWN | 16 | 0 | T |
| AI243124 | UNKNOWN | 16 | 0 | T |
| AI243177 | UNKNOWN | 4.75 | 300 | TTTC |
| AI243177 | UNKNOWN | 15 | 0 | T |
| AI243199 | UNKNOWN | 25 | 0 | T |
| AI243307 | UNKNOWN | 36 | 0 | T |
| AI243325 | UNKNOWN | 14 | 277 | A |
| AI243352 | UNKNOWN | 3.6 | 233 | TTTTA |
| AI243352 | UNKNOWN | 5.75 | 244 | TTTA |
| AI243406 | UNKNOWN | 15 | 444 | A |
| AI243493 | UNKNOWN | 15 | 0 | T |
| AI243504 | UNKNOWN | 16 | 0 | T |
| AI243597 | UNKNOWN | 15 | 0 | T |
| AI243701 | UNKNOWN | 32 | 0 | T |
| AI243731 | UNKNOWN | 12 | 215 | A |
| AI243779 | UNKNOWN | 11.66 | 175 | TTG |
| AI243814 | UNKNOWN | 12 | 0 | T |
| AI243860 | UNKNOWN | 26 | 316 | T |
| AI243910 | UNKNOWN | 3.83 | 77 | AAAAAT |
| AI243910 | UNKNOWN | 4.75 | 31 | TTTA |
| AI243910 | UNKNOWN | 15 | 47 | T |
| AI243988 | UNKNOWN | 3.8 | 150 | TTTTG |
| AI243988 | UNKNOWN | 15 | 0 | T |
| AI244127 | UNKNOWN | 19 | 0 | T |
| AI244136 | UNKNOWN | 85 | 0 | T |
| AI244136 | UNKNOWN | 14 | 176 | G |
| AI244136 | UNKNOWN | 14 | 191 | A |
| AI244148 | UNKNOWN | 82 | 0 | T |
| AI244208 | UNKNOWN | 6.5 | 189 | AT |
| AI244249 | UNKNOWN | 65 | 0 | T |
| AI244329 | UNKNOWN | 54 | 0 | T |
| AI244329 | UNKNOWN | 20 | 197 | A |
| AI244343 | UNKNOWN | 56 | 0 | T |
| AI244343 | UNKNOWN | 13 | 88 | G |
| AI244360 | UNKNOWN | 44 | 0 | T |
| AI244360 | UNKNOWN | 21 | 129 | G |
| AI244380 | UNKNOWN | 68 | 0 | T |
| AI244380 | UNKNOWN | 17 | 95 | G |
| AI244436 | UNKNOWN | 30 | 0 | T |
| AI244483 | UNKNOWN | 36 | 0 | T |
| AI244540 | UNKNOWN | 30 | 0 | T |
| AI244690 | UNKNOWN | 31 | 0 | T |
| AI244704 | UNKNOWN | 44 | 0 | T |
| AI244704 | UNKNOWN | 13 | 146 | A |
| AI244764 | UNKNOWN | 26 | 0 | T |
| AI244901 | UNKNOWN | 5.66 | 92 | GGC |
| AI244908 | UNKNOWN | 5.16 | 335 | ACAAAA |
| AI244957 | UNKNOWN | 17.5 | 299 | AC |
| AI244995 | UNKNOWN | 16 | 0 | T |
| AI245308 | UNKNOWN | 67 | 0 | T |
| AI245173 | UNKNOWN | 14 | 26 | A |
| AI245197 | UNKNOWN | 59 | 0 | T |
| AI245201 | UNKNOWN | 19.5 | 280 | AC |
| AI245238 | UNKNOWN | 13 | 342 | A |
| AI245240 | UNKNOWN | 29 | 0 | T |
| AI245279 | UNKNOWN | 55 | 0 | T |
| AI245304 | UNKNOWN | 70 | 0 | T |
| AI245304 | UNKNOWN | 16 | 184 | C |
| AI245322 | UNKNOWN | 27 | 0 | T |
| AI245332 | UNKNOWN | 2.8 | 110 | AAAAAACC (SEQ ID NO: 98) |

TABLE 1-continued

| Genbank # | Region | # reps | Position | Unit sequence |
|---|---|---|---|---|
| AI245332 | UNKNOWN | 47 | 0 | T |
| AI245334 | UNKNOWN | 13 | 0 | T |
| AI245391 | UNKNOWN | 23 | 0 | T |
| AI245455 | UNKNOWN | 15 | 0 | T |
| AI245540 | UNKNOWN | 30 | 0 | T |
| AI245613 | UNKNOWN | 36 | 0 | T |
| AI245589 | UNKNOWN | 32 | 0 | T |
| AI245690 | UNKNOWN | 3.8 | 221 | AAAAC |
| AI245739 | UNKNOWN | 12 | 0 | T |
| AI245748 | UNKNOWN | 54 | 0 | T |
| AI245748 | UNKNOWN | 14 | 164 | A |
| AI245748 | UNKNOWN | 12 | 112 | A |
| AI245838 | UNKNOWN | 43 | 0 | T |
| AI245839 | UNKNOWN | 19 | 0 | T |
| AI245570 | UNKNOWN | 14 | 0 | T |
| AI245894 | UNKNOWN | 41 | 0 | T |
| AI245973 | UNKNOWN | 42 | 0 | T |
| AI246067 | UNKNOWN | 20 | 100 | A |
| AI246073 | UNKNOWN | 20 | 75 | A |
| AI246074 | UNKNOWN | 28 | 86 | A |
| AI246319 | UNKNOWN | 88 | 0 | T |
| AI246319 | UNKNOWN | 15 | 286 | C |
| AI246319 | UNKNOWN | 15 | 320 | A |
| AI246319 | UNKNOWN | 12 | 267 | A |
| AI246554 | UNKNOWN | 16 | 0 | T |
| AI246590 | UNKNOWN | 18 | 0 | T |
| AI246594 | UNKNOWN | 18 | 0 | T |
| AI246696 | UNKNOWN | 26 | 0 | T |
| AI246845 | UNKNOWN | 29 | 83 | A |
| AI246889 | UNKNOWN | 14 | 97 | T |
| AI246905 | UNKNOWN | 69 | 0 | T |
| AI246905 | UNKNOWN | 12 | 189 | A |
| AI246966 | UNKNOWN | 26 | 68 | A |
| AI247005 | UNKNOWN | 74 | 0 | T |
| AI247005 | UNKNOWN | 20 | 84 | A |
| AI247005 | UNKNOWN | 19 | 227 | C |
| AI247082 | UNKNOWN | 62 | 0 | T |
| AI247082 | UNKNOWN | 22 | 274 | C |
| AI247082 | UNKNOWN | 12 | 183 | A |
| AI247101 | UNKNOWN | 16 | 0 | T |
| AI247132 | UNKNOWN | 39 | 0 | T |
| AI247182 | UNKNOWN | 20 | 293 | A |
| AI247182 | UNKNOWN | 16 | 193 | A |
| AI247182 | UNKNOWN | 15 | 132 | A |
| AI247182 | UNKNOWN | 13 | 0 | T |
| AI247187 | UNKNOWN | 43 | 0 | T |
| AI247153 | UNKNOWN | 96 | 0 | T |
| AI247193 | UNKNOWN | 18 | 123 | A |
| AI247194 | UNKNOWN | 41 | 0 | T |
| AI247218 | UNKNOWN | 12 | 0 | T |
| AI247293 | UNKNOWN | 99 | 0 | T |
| AI247293 | UNKNOWN | 23 | 196 | A |
| AI247293 | UNKNOWN | 15 | 99 | A |
| AI247293 | UNKNOWN | 14 | 142 | G |
| AI247293 | UNKNOWN | 13 | 225 | C |
| AI247336 | UNKNOWN | 42 | 13 | T |
| AI247336 | UNKNOWN | 13 | 120 | A |
| AI247336 | UNKNOWN | 12 | 0 | T |
| AI247345 | UNKNOWN | 16 | 0 | T |
| AI247365 | UNKNOWN | 13 | 0 | T |
| AI247405 | UNKNOWN | 12 | 54 | AT |
| AI247440 | UNKNOWN | 35 | 0 | T |
| AI247440 | UNKNOWN | 13 | 110 | A |
| AI247518 | UNKNOWN | 13 | 0 | T |
| AI247560 | UNKNOWN | 12 | 23 | T |
| AI247614 | UNKNOWN | 26 | 0 | T |
| AI247819 | UNKNOWN | 17 | 0 | T |
| AI247837 | UNKNOWN | 12 | 216 | T |
| AI247871 | UNKNOWN | 32 | 0 | T |
| AI247945 | UNKNOWN | 5.75 | 82 | AAAC |
| AI247951 | UNKNOWN | 24 | 0 | T |
| AI248013 | UNKNOWN | 13 | 366 | G |
| AI248050 | UNKNOWN | 25 | 0 | T |
| AI248068 | UNKNOWN | 16 | 0 | T |
| AI248073 | UNKNOWN | 12 | 0 | T |
| AI248198 | UNKNOWN | 20 | 0 | T |
| AI248198 | UNKNOWN | 14 | 176 | A |

TABLE 1-continued

| Genbank # | Region | # reps | Position | Unit sequence |
|---|---|---|---|---|
| AI248214 | UNKNOWN | 25 | 0 | T |
| AI248261 | UNKNOWN | 3.6 | 104 | ACTAC |
| AI248261 | UNKNOWN | 9 | 421 | TG |
| AI248265 | UNKNOWN | 33 | 0 | T |
| AI248265 | UNKNOWN | 16 | 104 | A |
| AI248282 | UNKNOWN | 23 | 0 | T |
| AI248306 | UNKNOWN | 13 | 0 | T |
| AI248319 | UNKNOWN | 17 | 8 | T |
| AI248344 | UNKNOWN | 4.75 | 20 | AAAC |
| AI248347 | UNKNOWN | 14 | 9 | T |
| AI248491 | UNKNOWN | 34 | 0 | T |
| AI248806 | UNKNOWN | 13 | 508 | T |
| AI248815 | UNKNOWN | 6 | 73 | CAA |
| AI248833 | UNKNOWN | 21 | 0 | T |
| AI248841 | UNKNOWN | 17 | 0 | T |
| AI248894 | UNKNOWN | 36 | 0 | T |
| AI248908 | UNKNOWN | 12 | 0 | T |
| AI248941 | UNKNOWN | 23 | 0 | T |
| AI249019 | UNKNOWN | 13 | 245 | T |
| AI249029 | UNKNOWN | 13 | 7 | T |
| AI249150 | UNKNOWN | 18 | 139 | T |
| AI249253 | UNKNOWN | 69 | 0 | T |
| AI249253 | UNKNOWN | 18 | 204 | G |
| AI249257 | UNKNOWN | 122 | 0 | T |
| AI249257 | UNKNOWN | 14 | 146 | G |
| AI249257 | UNKNOWN | 14 | 160 | C |
| AI249257 | UNKNOWN | 13 | 260 | A |
| AI249274 | UNKNOWN | 52 | 0 | T |
| AI249279 | UNKNOWN | 28 | 180 | A |
| AI249317 | UNKNOWN | 24 | 223 | A |
| AI249323 | UNKNOWN | 107 | 0 | T |
| AI249337 | UNKNOWN | 53 | 0 | T |
| AI249348 | UNKNOWN | 51 | 0 | T |
| AI249365 | UNKNOWN | 15 | 0 | T |
| AI249389 | UNKNOWN | 57 | 0 | T |
| AI249426 | UNKNOWN | 27 | 111 | A |
| AI249436 | UNKNOWN | 46 | 0 | T |
| AI249436 | UNKNOWN | 15 | 89 | A |
| AI249447 | UNKNOWN | 22 | 16 | T |
| AI249447 | UNKNOWN | 15 | 0 | T |
| AI249468 | UNKNOWN | 27 | 0 | T |
| AI249474 | UNKNOWN | 27 | 0 | T |
| AI249523 | UNKNOWN | 44 | 0 | T |
| AI249524 | UNKNOWN | 17 | 0 | T |
| AI249526 | UNKNOWN | 15 | 18 | T |
| AI249576 | UNKNOWN | 22 | 226 | A |
| AI249647 | UNKNOWN | 25 | 124 | A |
| AI249703 | UNKNOWN | 52 | 0 | T |
| AI249734 | UNKNOWN | 36 | 0 | T |
| AI249759 | UNKNOWN | 43 | 0 | T |
| AI249500 | UNKNOWN | 93 | 0 | T |
| AI249800 | UNKNOWN | 15 | 325 | G |
| AI249802 | UNKNOWN | 18 | 0 | T |
| AI249823 | UNKNOWN | 23 | 2 | T |
| AI249862 | UNKNOWN | 32 | 144 | A |
| AI249877 | UNKNOWN | 84 | 0 | T |
| AI249877 | UNKNOWN | 19 | 91 | A |
| AI249877 | UNKNOWN | 18 | 110 | G |
| AI249880 | UNKNOWN | 40 | 0 | T |
| AI249923 | UNKNOWN | 26 | 0 | T |
| AI249939 | UNKNOWN | 16 | 0 | T |
| AI249962 | UNKNOWN | 88 | 0 | T |
| AI249962 | UNKNOWN | 20 | 169 | A |
| AI249962 | UNKNOWN | 13 | 92 | A |
| AI249993 | UNKNOWN | 18 | 327 | A |
| AI249995 | UNKNOWN | 17 | 194 | A |
| AI249996 | UNKNOWN | 24 | 90 | A |
| AI250038 | UNKNOWN | 39 | 0 | T |
| AI250059 | UNKNOWN | 16 | 0 | T |
| AI250101 | UNKNOWN | 20 | 134 | A |
| AI250159 | UNKNOWN | 45 | 5 | T |
| AI250168 | UNKNOWN | 34 | 19 | T |
| AI250168 | UNKNOWN | 18 | 0 | T |
| AI250168 | UNKNOWN | 17 | 289 | A |
| AI250186 | UNKNOWN | 37 | 0 | T |
| AI250260 | UNKNOWN | 16 | 0 | T |
| AI250262 | UNKNOWN | 22 | 0 | T |

TABLE 1-continued

| Genbank # | Region | # reps | Position | Unit sequence |
|---|---|---|---|---|
| AI250270 | UNKNOWN | 33 | 0 | T |
| AI250282 | UNKNOWN | 46 | 0 | T |
| AI250282 | UNKNOWN | 15 | 121 | A |
| AI250296 | UNKNOWN | 55 | 0 | T |
| AI250292 | UNKNOWN | 15 | 0 | T |
| AI250293 | UNKNOWN | 125 | 0 | T |
| AI250293 | UNKNOWN | 18 | 149 | G |
| AI250293 | UNKNOWN | 17 | 190 | C |
| AI250841 | UNKNOWN | 52 | 0 | T |
| AI250842 | UNKNOWN | 36 | 0 | T |
| AI250858 | UNKNOWN | 29 | 0 | T |
| AI250869 | UNKNOWN | 89 | 0 | T |
| AI250869 | UNKNOWN | 14 | 166 | C |
| AI250869 | UNKNOWN | 13 | 186 | G |
| AI250409 | UNKNOWN | 35 | 0 | T |
| AI250433 | UNKNOWN | 20 | 80 | A |
| AI250454 | UNKNOWN | 26 | 111 | A |
| AI250470 | UNKNOWN | 27 | 91 | A |
| AI250472 | UNKNOWN | 27 | 108 | A |
| AI250505 | UNKNOWN | 19 | 111 | A |
| AI250508 | UNKNOWN | 25 | 131 | A |
| AI250545 | UNKNOWN | 28 | 110 | A |
| AI250550 | UNKNOWN | 17 | 186 | A |
| AI250556 | UNKNOWN | 30 | 82 | A |
| AI250577 | UNKNOWN | 25 | 143 | A |
| AI250584 | UNKNOWN | 25 | 121 | A |
| AI250584 | UNKNOWN | 12 | 58 | T |
| AI250625 | UNKNOWN | 40 | 0 | T |
| AI250627 | UNKNOWN | 61 | 0 | T |
| AI250634 | UNKNOWN | 33 | 0 | T |
| AI250663 | UNKNOWN | 97 | 0 | T |
| AI250663 | UNKNOWN | 13 | 178 | G |
| AI250663 | UNKNOWN | 13 | 191 | C |
| AI250673 | UNKNOWN | 35 | 0 | T |
| AI250684 | UNKNOWN | 21 | 0 | T |
| AI250716 | UNKNOWN | 27 | 77 | A |
| AI250724 | UNKNOWN | 27 | 67 | A |
| AI250725 | UNKNOWN | 29 | 78 | A |
| AI250738 | UNKNOWN | 28 | 135 | A |
| AI250742 | UNKNOWN | 27 | 141 | A |
| AI250747 | UNKNOWN | 29 | 195 | A |
| AI250748 | UNKNOWN | 22 | 364 | A |
| AI250773 | UNKNOWN | 6.8 | 90 | AAAAT |
| AI250783 | UNKNOWN | 16 | 0 | T |
| AI250786 | UNKNOWN | 23 | 0 | T |
| AI250819 | UNKNOWN | 84 | 0 | T |
| AI250819 | UNKNOWN | 15 | 248 | C |
| AI250819 | UNKNOWN | 13 | 106 | C |
| AI250821 | UNKNOWN | 48 | 0 | T |
| AI250825 | UNKNOWN | 32 | 222 | C |
| AI250825 | UNKNOWN | 22 | 192 | C |
| AI250831 | UNKNOWN | 20 | 0 | T |
| AI250847 | UNKNOWN | 23 | 0 | T |
| AI250848 | UNKNOWN | 84 | 0 | T |
| AI250848 | UNKNOWN | 16 | 260 | G |
| AI250848 | UNKNOWN | 14 | 124 | C |
| AI250848 | UNKNOWN | 12 | 243 | A |
| AI250852 | UNKNOWN | 83 | 0 | T |
| AI250852 | UNKNOWN | 16 | 147 | C |
| AI250552 | UNKNOWN | 12 | 208 | G |
| AI250856 | UNKNOWN | 65 | 0 | T |
| AI250856 | UNKNOWN | 19 | 171 | G |
| AI250871 | UNKNOWN | 66 | 0 | T |
| AI251066 | UNKNOWN | 26 | 170 | A |
| AI251118 | UNKNOWN | 6.5 | 216 | AT |
| AI251190 | UNKNOWN | 19 | 71 | A |
| AI251234 | UNKNOWN | 31 | 121 | A |
| AI251256 | UNKNOWN | 21 | 164 | A |
| AI251269 | UNKNOWN | 27 | 64 | A |
| AI251292 | UNKNOWN | 21 | 85 | A |
| AI251302 | UNKNOWN | 30 | 82 | A |
| AI251307 | UNKNOWN | 8.19 | 80 | ACAAA |
| AI251307 | UNKNOWN | 27 | 160 | A |
| AI251308 | UNKNOWN | 29 | 87 | A |
| AI251311 | UNKNOWN | 19 | 291 | A |
| AI251313 | UNKNOWN | 26 | 164 | A |
| AI251322 | UNKNOWN | 26 | 150 | A |

TABLE 1-continued

| Genbank # | Region | # reps | Position | Unit sequence |
|---|---|---|---|---|
| AI251327 | UNKNOWN | 22 | 121 | A |
| AI251328 | UNKNOWN | 14 | 149 | A |
| AI251329 | UNKNOWN | 24 | 361 | A |
| AI251329 | UNKNOWN | 13 | 212 | A |
| AI251332 | UNKNOWN | 2.63 | 37 | AGGAAGGAAGGAGAAAGAA (SEQ ID NO: 99) |
| AI251332 | UNKNOWN | 33 | 110 | A |
| AI251339 | UNKNOWN | 17 | 241 | A |
| AI251355 | UNKNOWN | 26 | 330 | A |
| AI251359 | UNKNOWN | 28 | 228 | A |
| AI251360 | UNKNOWN | 21 | 100 | A |
| AI251363 | UNKNOWN | 30 | 85 | A |
| AI251369 | UNKNOWN | 28 | 149 | A |
| AI251379 | UNKNOWN | 28 | 102 | A |
| AI251385 | UNKNOWN | 3.5 | 30 | AGAGAA |
| AI251385 | UNKNOWN | 13.25 | 86 | AGAA |
| AI251385 | UNKNOWN | 9 | 17 | GA |
| AI251385 | UNKNOWN | 21 | 136 | A |
| AI251391 | UNKNOWN | 19 | 101 | A |
| AI251395 | UNKNOWN | 25 | 196 | A |
| AI251418 | UNKNOWN | 29 | 70 | A |
| AI251434 | UNKNOWN | 88 | 0 | T |
| AI251434 | UNKNOWN | 27 | 186 | G |
| AI251434 | UNKNOWN | 15 | 88 | C |
| AI251434 | UNKNOWN | 12 | 103 | A |
| AI251458 | UNKNOWN | 59 | 0 | T |
| AI251458 | UNKNOWN | 14 | 182 | G |
| AI251460 | UNKNOWN | 24 | 78 | T |
| AI251495 | UNKNOWN | 25 | 177 | A |
| AI251503 | UNKNOWN | 29 | 89 | A |
| AI251503 | UNKNOWN | 28 | 32 | T |
| AI251572 | UNKNOWN | 31 | 146 | A |
| AI251584 | UNKNOWN | 15 | 290 | A |
| AI251591 | UNKNOWN | 24 | 327 | A |
| AI251599 | UNKNOWN | 29 | 107 | A |
| AI251601 | UNKNOWN | 22 | 163 | A |
| AI251605 | UNKNOWN | 24 | 96 | A |
| AI251610 | UNKNOWN | 20 | 107 | A |
| AI251613 | UNKNOWN | 23 | 295 | A |
| AI251618 | UNKNOWN | 26 | 99 | A |
| AI251639 | UNKNOWN | 28 | 172 | A |
| AI251642 | UNKNOWN | 27 | 184 | A |
| AI251690 | UNKNOWN | 27 | 239 | A |
| AI251696 | UNKNOWN | 23 | 375 | A |
| AI251699 | UNKNOWN | 30 | 79 | A |
| AI251700 | UNKNOWN | 3.5 | 79 | AGAAAG |
| AI251700 | UNKNOWN | 8.75 | 103 | AGAA |
| AI251700 | UNKNOWN | 25 | 149 | A |
| AI251702 | UNKNOWN | 19 | 100 | A |
| AI251715 | UNKNOWN | 20 | 129 | A |
| AI251722 | UNKNOWN | 13 | 160 | A |
| AI251773 | UNKNOWN | 39 | 0 | T |
| AI251812 | UNKNOWN | 12 | 306 | A |
| AI251830 | UNKNOWN | 101 | 0 | T |
| AI251830 | UNKNOWN | 26 | 141 | C |
| AI251830 | UNKNOWN | 13 | 105 | G |
| AI251830 | UNKNOWN | 13 | 128 | A |
| AI251870 | UNKNOWN | 3.6 | 13 | TTTTG |
| AI251876 | UNKNOWN | 97 | 0 | T |
| AI251876 | UNKNOWN | 19 | 139 | A |
| AI251876 | UNKNOWN | 17 | 295 | C |
| AI251876 | UNKNOWN | 14 | 220 | G |
| AI251906 | UNKNOWN | 49 | 0 | T |
| AI251906 | UNKNOWN | 26 | 176 | C |
| AI251911 | UNKNOWN | 45 | 10 | T |
| AI251911 | UNKNOWN | 19 | 262 | G |
| AI251911 | UNKNOWN | 13 | 84 | C |
| AI251924 | UNKNOWN | 41 | 0 | T |
| AI251941 | UNKNOWN | 28 | 73 | T |
| AI251941 | UNKNOWN | 24 | 217 | C |
| AI251941 | UNKNOWN | 15 | 191 | G |
| AI251941 | UNKNOWN | 12 | 12 | T |
| AI251947 | UNKNOWN | 24 | 134 | A |
| AI251952 | UNKNOWN | 19 | 205 | A |
| AI251957 | UNKNOWN | 18 | 164 | A |
| AI251960 | UNKNOWN | 22 | 58 | A |
| AI251966 | UNKNOWN | 26 | 163 | A |
| AI251970 | UNKNOWN | 30 | 108 | A |

TABLE 1-continued

| Genbank # | Region | # reps | Position | Unit sequence |
|---|---|---|---|---|
| AI251972 | UNKNOWN | 29 | 104 | A |
| AI251988 | UNKNOWN | 14 | 191 | A |
| AI251993 | UNKNOWN | 25 | 178 | A |
| AI252005 | UNKNOWN | 22 | 299 | A |
| AI252017 | UNKNOWN | 8 | 27 | TG |
| AI252017 | UNKNOWN | 29 | 102 | A |
| AI252065 | UNKNOWN | 30 | 157 | A |
| AI252080 | UNKNOWN | 17 | 282 | A |
| AI252097 | UNKNOWN | 18 | 208 | A |
| AI252097 | UNKNOWN | 12 | 194 | A |
| AI252106 | UNKNOWN | 23 | 164 | A |
| AI252113 | UNKNOWN | 27 | 134 | A |
| AI252122 | UNKNOWN | 24 | 265 | A |
| AI252125 | UNKNOWN | 16 | 106 | A |
| AI252129 | UNKNOWN | 27 | 145 | A |
| AI252139 | UNKNOWN | 29 | 174 | A |
| AI252161 | UNKNOWN | 30 | 79 | A |
| AI252176 | UNKNOWN | 25 | 299 | A |
| AI252182 | UNKNOWN | 29 | 164 | A |
| AI252183 | UNKNOWN | 21 | 201 | A |
| AI252189 | UNKNOWN | 18 | 79 | A |
| AI252194 | UNKNOWN | 26 | 106 | A |
| AI252199 | UNKNOWN | 6.25 | 184 | AGAA |
| AI252199 | UNKNOWN | 17 | 17 | GA |
| AI252199 | UNKNOWN | 18 | 228 | A |
| AI252200 | UNKNOWN | 17 | 117 | A |
| AI252215 | UNKNOWN | 18 | 0 | T |
| AI252246 | UNKNOWN | 29 | 74 | A |
| AI252382 | UNKNOWN | 5.5 | 100 | AAGG |
| AI252382 | UNKNOWN | 29 | 206 | A |
| AI252384 | UNKNOWN | 26 | 70 | A |
| AI252413 | UNKNOWN | 24 | 117 | A |
| AI252422 | UNKNOWN | 32 | 168 | A |
| AI252435 | UNKNOWN | 40 | 52 | A |
| AI252456 | UNKNOWN | 29 | 119 | A |
| AI252471 | UNKNOWN | 26 | 108 | A |
| AI252472 | UNKNOWN | 26 | 199 | A |
| AI252489 | UNKNOWN | 31 | 107 | A |
| AI252506 | UNKNOWN | 19 | 295 | A |
| AI252517 | UNKNOWN | 26 | 107 | A |
| AI252563 | UNKNOWN | 31 | 114 | A |
| AI252586 | UNKNOWN | 29 | 226 | A |
| AI252643 | UNKNOWN | 77 | 0 | T |
| AI252643 | UNKNOWN | 17 | 204 | C |
| AI252697 | UNKNOWN | 27 | 63 | A |
| AI252709 | UNKNOWN | 31 | 111 | A |
| AI252712 | UNKNOWN | 13.25 | 69 | AGAA |
| AI252712 | UNKNOWN | 18.5 | 35 | AG |
| AI252712 | UNKNOWN | 32 | 137 | A |
| AI252760 | UNKNOWN | 41 | 0 | T |
| AI252760 | UNKNOWN | 14 | 123 | A |
| AI252782 | UNKNOWN | 20 | 0 | T |
| AI252789 | UNKNOWN | 64 | 0 | T |
| AI252813 | UNKNOWN | 101 | 0 | T |
| AI252813 | UNKNOWN | 26 | 231 | G |
| AI252827 | UNKNOWN | 35 | 160 | A |
| AI252833 | UNKNOWN | 5.25 | 40 | AAGG |
| AI252833 | UNKNOWN | 31 | 62 | A |
| AI252841 | UNKNOWN | 16 | 435 | A |
| AI252858 | UNKNOWN | 12.25 | 231 | AGAA |
| AI252858 | UNKNOWN | 13 | 30 | GA |
| AI252858 | UNKNOWN | 20 | 277 | A |
| AI252869 | UNKNOWN | 32 | 328 | A |
| AI252870 | UNKNOWN | 30 | 105 | A |
| AI252878 | UNKNOWN | 30 | 160 | A |
| AI252890 | UNKNOWN | 20 | 251 | A |
| AI252899 | UNKNOWN | 17 | 114 | A |
| AI252907 | UNKNOWN | 25 | 105 | A |
| AI252919 | UNKNOWN | 27 | 275 | A |
| AI252937 | UNKNOWN | 26 | 138 | A |
| AI252940 | UNKNOWN | 23 | 131 | A |
| AI252941 | UNKNOWN | 23 | 110 | A |
| AI252955 | UNKNOWN | 2.63 | 45 | AGGAAGGAAGGAGAAAGAA (SEQ ID NO: 100) |
| AI252955 | UNKNOWN | 27 | 109 | A |
| AI252960 | UNKNOWN | 21 | 131 | A |
| AI252974 | UNKNOWN | 29 | 99 | A |
| AI252978 | UNKNOWN | 27 | 313 | A |

TABLE 1-continued

| Genbank # | Region | # reps | Position | Unit sequence |
|---|---|---|---|---|
| AI252985 | UNKNOWN | 29 | 130 | A |
| AI252988 | UNKNOWN | 3.5 | 60 | TTTTC |
| AI252988 | UNKNOWN | 31 | 111 | A |
| AI253008 | UNKNOWN | 30 | 77 | A |
| AI253144 | UNKNOWN | 16 | 0 | T |
| AI253157 | UNKNOWN | 14 | 0 | T |
| AI253196 | UNKNOWN | 12 | 0 | T |
| AI253287 | UNKNOWN | 29 | 23 | T |
| AI253326 | UNKNOWN | 26 | 21 | T |
| AI253386 | UNKNOWN | 23 | 23 | T |
| AI253407 | UNKNOWN | 20 | 22 | T |
| AI253423 | UNKNOWN | 25 | 23 | T |
| AI253446 | UNKNOWN | 26 | 23 | T |
| AI254003 | UNKNOWN | 31 | 61 | A |
| AI254029 | UNKNOWN | 28 | 131 | A |
| AI254030 | UNKNOWN | 26 | 116 | A |
| AI254039 | UNKNOWN | 21 | 237 | A |
| AI254054 | UNKNOWN | 28 | 246 | A |
| AI254063 | UNKNOWN | 18 | 329 | A |
| AI254078 | UNKNOWN | 24 | 161 | A |
| AI254083 | UNKNOWN | 5.25 | 251 | AGAA |
| AI254083 | UNKNOWN | 13 | 18 | GA |
| AI254090 | UNKNOWN | 18 | 134 | A |
| AI254094 | UNKNOWN | 16 | 89 | A |
| AI254110 | UNKNOWN | 25 | 112 | A |
| AI254121 | UNKNOWN | 23 | 307 | A |
| AI254151 | UNKNOWN | 23 | 286 | A |
| AI254155 | UNKNOWN | 21 | 240 | A |
| AI254174 | UNKNOWN | 28 | 111 | A |
| AI254190 | UNKNOWN | 20 | 270 | A |
| AI254192 | UNKNOWN | 20 | 299 | A |
| AI254201 | UNKNOWN | 36 | 0 | T |
| AI254216 | UNKNOWN | 76 | 0 | T |
| AI254226 | UNKNOWN | 19 | 116 | G |
| AI254249 | UNKNOWN | 51 | 0 | T |
| AI254263 | UNKNOWN | 30 | 71 | A |
| AI254303 | UNKNOWN | 4.5 | 41 | GAAA |
| AI254303 | UNKNOWN | 28 | 131 | A |
| AI254307 | UNKNOWN | 12 | 354 | A |
| AI254312 | UNKNOWN | 25 | 200 | A |
| AI254326 | UNKNOWN | 21 | 154 | A |
| AI254330 | UNKNOWN | 30 | 64 | A |
| AI254362 | UNKNOWN | 30 | 61 | A |
| AI254371 | UNKNOWN | 26 | 150 | A |
| AI254378 | UNKNOWN | 31 | 61 | A |
| AI254417 | UNKNOWN | 23 | 108 | A |
| AI254447 | UNKNOWN | 20 | 106 | A |
| AI254449 | UNKNOWN | 27 | 142 | A |
| AI254472 | UNKNOWN | 27 | 260 | A |
| AI254506 | UNKNOWN | 29 | 133 | A |
| AI254529 | UNKNOWN | 7.25 | 139 | AGAA |
| AI254529 | UNKNOWN | 9 | 40 | GA |
| AI254529 | UNKNOWN | 17 | 187 | A |
| AI254531 | UNKNOWN | 20 | 132 | A |
| AI254549 | UNKNOWN | 30 | 68 | A |
| AI254557 | UNKNOWN | 30 | 71 | A |
| AI254575 | UNKNOWN | 26 | 140 | A |
| AI254588 | UNKNOWN | 28 | 161 | A |
| AI254606 | UNKNOWN | 20 | 334 | A |
| AI254615 | UNKNOWN | 19 | 344 | A |
| AI254618 | UNKNOWN | 31 | 253 | A |
| AI254620 | UNKNOWN | 33 | 89 | A |
| AI254627 | UNKNOWN | 10.25 | 220 | AGAA |
| AI254627 | UNKNOWN | 13 | 17 | GA |
| AI254627 | UNKNOWN | 24 | 258 | A |
| AI254644 | UNKNOWN | 25 | 128 | A |
| AI254655 | UNKNOWN | 30 | 61 | A |
| AI254657 | UNKNOWN | 24 | 190 | A |
| AI254666 | UNKNOWN | 8 | 67 | TG |
| AI254666 | UNKNOWN | 23 | 84 | A |
| AI254674 | UNKNOWN | 26 | 126 | A |
| AI254674 | UNKNOWN | 22 | 44 | A |
| AI254684 | UNKNOWN | 11.25 | 220 | AGAA |
| AI254684 | UNKNOWN | 13 | 17 | GA |
| AI254684 | UNKNOWN | 20 | 262 | A |
| AI254655 | UNKNOWN | 26 | 83 | A |
| AI254656 | UNKNOWN | 25 | 122 | A |

TABLE 1-continued

| Genbank # | Region | # reps | Position | Unit sequence |
|---|---|---|---|---|
| AI254727 | UNKNOWN | 76 | 0 | T |
| AI254727 | UNKNOWN | 12 | 125 | C |
| AI254731 | UNKNOWN | 103 | 0 | T |
| AI254731 | UNKNOWN | 18 | 188 | C |
| AI254731 | UNKNOWN | 13 | 103 | A |
| AI254731 | UNKNOWN | 13 | 259 | G |
| AI254754 | UNKNOWN | 52 | 0 | T |
| AI254756 | UNKNOWN | 30 | 60 | A |
| AI254759 | UNKNOWN | 22 | 164 | A |
| AI254769 | UNKNOWN | 28 | 64 | A |
| AI254776 | UNKNOWN | 26 | 90 | A |
| AI254779 | UNKNOWN | 17 | 332 | A |
| AI254789 | UNKNOWN | 28 | 75 | A |
| AI254829 | UNKNOWN | 28 | 177 | A |
| AI254843 | UNKNOWN | 30 | 63 | A |
| AI254850 | UNKNOWN | 30 | 61 | A |
| AI254907 | UNKNOWN | 22 | 352 | A |
| AI254913 | UNKNOWN | 26 | 288 | A |
| AI254934 | UNKNOWN | 27 | 87 | A |
| AI254958 | UNKNOWN | 16 | 153 | A |
| AI254959 | UNKNOWN | 28 | 308 | A |
| AI254961 | UNKNOWN | 22 | 144 | A |
| AI254963 | UNKNOWN | 27 | 260 | A |
| AI254964 | UNKNOWN | 14 | 149 | A |
| AI254967 | UNKNOWN | 23 | 164 | A |
| AI254980 | UNKNOWN | 17 | 118 | A |
| AI254981 | UNKNOWN | 27 | 137 | A |
| AI255027 | UNKNOWN | 27 | 86 | A |
| AI255029 | UNKNOWN | 27 | 153 | A |
| AI255037 | UNKNOWN | 27 | 161 | A |
| AI255045 | UNKNOWN | 23 | 97 | A |
| AI255054 | UNKNOWN | 15 | 109 | A |
| AI255058 | UNKNOWN | 3.8 | 55 | AAAAG |
| AI255058 | UNKNOWN | 29 | 168 | A |
| AI255076 | UNKNOWN | 14 | 235 | A |
| AI255095 | UNKNOWN | 19 | 345 | A |
| AI255108 | UNKNOWN | 29 | 255 | A |
| AI255115 | UNKNOWN | 29 | 259 | A |
| AI255116 | UNKNOWN | 27 | 142 | A |
| AI255117 | UNKNOWN | 27 | 94 | A |
| AI255118 | UNKNOWN | 17 | 309 | A |
| AI255140 | UNKNOWN | 28 | 65 | A |
| AI261207 | UNKNOWN | 34 | 0 | T |
| AI261344 | UNKNOWN | 88 | 0 | T |
| AI261344 | UNKNOWN | 15 | 142 | A |
| AI261344 | UNKNOWN | 14 | 184 | G |
| AI261344 | UNKNOWN | 13 | 117 | C |
| AI261358 | UNKNOWN | 15 | 177 | T |
| AI261439 | UNKNOWN | 45 | 0 | T |
| AI261589 | UNKNOWN | 55 | 0 | T |
| AI261627 | UNKNOWN | 9.5 | 35 | CAGT |
| AI261662 | UNKNOWN | 61 | 0 | T |
| AI261694 | UNKNOWN | 47 | 0 | T |
| AI261704 | UNKNOWN | 36 | 0 | T |
| AI261708 | UNKNOWN | 12 | 0 | T |
| AI261815 | UNKNOWN | 3.5 | 256 | CCTGGG |
| AI261815 | UNKNOWN | 47 | 0 | T |
| AI261815 | UNKNOWN | 17 | 113 | G |
| AI261844 | UNKNOWN | 24 | 0 | T |
| AI261913 | UNKNOWN | 5 | 0 | ATTT |
| AI261993 | UNKNOWN | 21 | 4 | T |
| AI262090 | UNKNOWN | 18 | 4 | T |
| AI262092 | UNKNOWN | 18 | 4 | T |
| AI262104 | UNKNOWN | 45 | 4 | T |
| AI262186 | UNKNOWN | 59 | 0 | T |
| AI262504 | UNKNOWN | 13 | 284 | T |
| AI262592 | UNKNOWN | 40 | 0 | T |
| AI262660 | UNKNOWN | 17 | 0 | T |
| AI262863 | UNKNOWN | 30 | 0 | T |
| AI262931 | UNKNOWN | 13 | 0 | T |
| AI263008 | UNKNOWN | 7.33 | 45 | CAT |
| AI263023 | UNKNOWN | 44 | 0 | T |
| AI263046 | UNKNOWN | 16 | 39 | A |
| AI263142 | UNKNOWN | 55 | 0 | T |
| AI263142 | UNKNOWN | 19 | 121 | A |
| AI263166 | UNKNOWN | 13 | 0 | T |
| AI263222 | UNKNOWN | 6.5 | 184 | TC |

TABLE 1-continued

| Genbank # | Region | # reps | Position | Unit sequence |
|---|---|---|---|---|
| AI263307 | UNKNOWN | 16 | 0 | T |
| AI263312 | UNKNOWN | 69 | 0 | T |
| AI263312 | UNKNOWN | 16 | 92 | A |
| AI263312 | UNKNOWN | 16 | 176 | C |
| AI263331 | UNKNOWN | 69 | 0 | T |
| AI263331 | UNKNOWN | 13 | 138 | A |
| AI263331 | UNKNOWN | 12 | 113 | C |
| AI263376 | UNKNOWN | 18 | 70 | A |
| AI263475 | UNKNOWN | 13 | 411 | A |
| AI263527 | UNKNOWN | 14 | 0 | T |
| AI263541 | UNKNOWN | 13 | 44 | T |
| AI263584 | UNKNOWN | 57 | 0 | T |
| AI263585 | UNKNOWN | 14 | 48 | T |
| AI263616 | UNKNOWN | 23 | 0 | T |
| AI263625 | UNKNOWN | 4.4 | 175 | TTCTT |
| AI263641 | UNKNOWN | 25 | 60 | A |
| AI263653 | UNKNOWN | 26 | 106 | A |
| AI263692 | UNKNOWN | 12 | 0 | T |
| AI263834 | UNKNOWN | 15 | 106 | T |
| AI264099 | UNKNOWN | 34 | 0 | T |
| AI264121 | UNKNOWN | 15 | 7 | T |
| AI264296 | UNKNOWN | 8.5 | 306 | TGTT |
| AI264299 | UNKNOWN | 50 | 0 | T |
| AI264611 | UNKNOWN | 15 | 0 | T |
| AI264626 | UNKNOWN | 11.5 | 450 | TA |
| AI264701 | UNKNOWN | 18 | 0 | T |
| AI264741 | UNKNOWN | 102 | 0 | T |
| AI264741 | UNKNOWN | 15 | 255 | C |
| AI264741 | UNKNOWN | 13 | 102 | G |
| AI264774 | UNKNOWN | 15 | 0 | T |
| AI264800 | UNKNOWN | 18 | 347 | A |
| AI264830 | UNKNOWN | 26 | 0 | T |
| AI264876 | UNKNOWN | 40 | 0 | T |
| AI264894 | UNKNOWN | 16.5 | 232 | CA |
| AI264894 | UNKNOWN | 10 | 213 | TC |
| AI264954 | UNKNOWN | 27 | 0 | T |
| AI265772 | UNKNOWN | 71 | 0 | T |
| AI265773 | UNKNOWN | 17 | 0 | T |
| AI265784 | UNKNOWN | 13 | 0 | T |
| AI265788 | UNKNOWN | 22 | 0 | T |
| AI265824 | UNKNOWN | 18 | 0 | T |
| AI265879 | UNKNOWN | 32 | 0 | T |
| AI265927 | UNKNOWN | 15 | 0 | T |
| AI265958 | UNKNOWN | 14 | 0 | T |
| AI265991 | UNKNOWN | 27 | 0 | T |
| AI266000 | UNKNOWN | 17 | 188 | T |
| AI266255 | UNKNOWN | 15 | 0 | T |
| AI266302 | UNKNOWN | 17 | 102 | A |
| AI266303 | UNKNOWN | 23 | 244 | A |
| AI266426 | UNKNOWN | 21 | 0 | T |
| AI266436 | UNKNOWN | 74 | 0 | T |
| AI266439 | UNKNOWN | 17 | 0 | T |
| AI266474 | UNKNOWN | 23 | 393 | T |
| AI266474 | UNKNOWN | 14 | 148 | T |
| AI266501 | UNKNOWN | 47 | 0 | T |
| AI266501 | UNKNOWN | 20 | 200 | A |
| AI266501 | UNKNOWN | 12 | 53 | G |
| AI266512 | UNKNOWN | 19 | 0 | T |
| AI266558 | UNKNOWN | 60 | 0 | T |
| AI266558 | UNKNOWN | 14 | 163 | G |
| AI266643 | UNKNOWN | 60 | 0 | T |
| AI266643 | UNKNOWN | 14 | 60 | A |
| AI266652 | UNKNOWN | 50 | 0 | T |
| AI266668 | UNKNOWN | 24 | 80 | A |
| AI266688 | UNKNOWN | 22 | 0 | T |
| AI266711 | UNKNOWN | 26 | 0 | T |
| AI266719 | UNKNOWN | 63 | 0 | T |
| AI266719 | UNKNOWN | 12 | 63 | G |
| AI266766 | UNKNOWN | 31 | 115 | A |
| AI267148 | UNKNOWN | 31 | 23 | T |
| AI267269 | UNKNOWN | 31 | 21 | T |
| AI267282 | UNKNOWN | 47 | 21 | T |
| AI267320 | UNKNOWN | 24 | 22 | T |
| AI267323 | UNKNOWN | 26 | 22 | T |
| AI267328 | UNKNOWN | 26 | 25 | T |
| AI267335 | UNKNOWN | 23 | 297 | A |
| AI267337 | UNKNOWN | 26 | 21 | T |

TABLE 1-continued

| Genbank # | Region | # reps | Position | Unit sequence |
|---|---|---|---|---|
| AI267339 | UNKNOWN | 21 | 22 | T |
| AI267349 | UNKNOWN | 21 | 21 | T |
| AI267356 | UNKNOWN | 28 | 24 | T |
| AI267375 | UNKNOWN | 23 | 23 | T |
| AI267389 | UNKNOWN | 24 | 21 | T |
| AI267417 | UNKNOWN | 20 | 24 | T |
| AI267443 | UNKNOWN | 28 | 23 | T |
| AI267478 | UNKNOWN | 20 | 21 | T |
| AI267489 | UNKNOWN | 21 | 26 | T |
| AI267491 | UNKNOWN | 17 | 26 | T |
| AI267507 | UNKNOWN | 25 | 24 | T |
| AI267573 | UNKNOWN | 23 | 23 | T |
| AI267607 | UNKNOWN | 28 | 25 | T |
| AI267656 | UNKNOWN | 21 | 23 | T |
| AI267659 | UNKNOWN | 22 | 21 | T |
| AI267807 | UNKNOWN | 23 | 26 | T |
| AI267808 | UNKNOWN | 2.95 | 333 | AATGGAATGGAATGGAATGC (SEQ ID NO: 101) |
| AI267808 | UNKNOWN | 9.6 | 418 | AATGG |
| AI267808 | UNKNOWN | 8 | 146 | GGAAT |
| AI267808 | UNKNOWN | 4.59 | 62 | GAATG |
| AI267814 | UNKNOWN | 25 | 22 | T |
| AI267818 | UNKNOWN | 23 | 26 | T |
| AI267820 | UNKNOWN | 23 | 23 | T |
| AI267823 | UNKNOWN | 27 | 21 | T |
| AI267845 | UNKNOWN | 28 | 26 | T |
| AI267850 | UNKNOWN | 20 | 26 | T |
| AI267973 | UNKNOWN | 23 | 0 | T |
| AI268003 | UNKNOWN | 51 | 0 | T |
| AI268150 | UNKNOWN | 33 | 0 | T |
| AI268194 | UNKNOWN | 26 | 0 | T |
| AI268310 | UNKNOWN | 21 | 218 | A |
| AI268313 | UNKNOWN | 36 | 0 | T |
| AI268320 | UNKNOWN | 69 | 0 | T |
| AI268320 | UNKNOWN | 16 | 242 | A |
| AI268320 | UNKNOWN | 15 | 203 | G |
| AI268320 | UNKNOWN | 12 | 105 | A |
| AI268331 | UNKNOWN | 12 | 0 | T |
| AI268348 | UNKNOWN | 31 | 0 | T |
| AI268584 | UNKNOWN | 14 | 333 | T |
| AI268717 | UNKNOWN | 17 | 412 | A |
| AI269019 | UNKNOWN | 12 | 0 | T |
| AI269054 | UNKNOWN | 12.5 | 175 | AG |
| AI269086 | UNKNOWN | 18 | 0 | T |
| AI269098 | UNKNOWN | 44 | 0 | T |
| AI269107 | UNKNOWN | 13 | 0 | T |
| AI269188 | UNKNOWN | 36 | 0 | T |
| AI269205 | UNKNOWN | 107 | 0 | T |
| AI269205 | UNKNOWN | 17 | 131 | A |
| AI269205 | UNKNOWN | 13 | 200 | G |
| AI269245 | UNKNOWN | 24 | 0 | T |
| AI269270 | UNKNOWN | 37 | 0 | T |
| AI269275 | UNKNOWN | 21 | 0 | T |
| AI269275 | UNKNOWN | 16 | 59 | A |
| AI269317 | UNKNOWN | 3.6 | 28 | TTTAT |
| AI269323 | UNKNOWN | 68 | 0 | T |
| AI269331 | UNKNOWN | 21 | 0 | T |
| AI269345 | UNKNOWN | 38 | 0 | T |
| AI269367 | UNKNOWN | 13 | 0 | T |
| AI269374 | UNKNOWN | 30 | 0 | T |
| AI269374 | UNKNOWN | 13 | 168 | A |
| AI269411 | UNKNOWN | 11.5 | 13 | TTAT |
| AI269449 | UNKNOWN | 14 | 0 | T |
| AI269469 | UNKNOWN | 61 | 0 | T |
| AI269469 | UNKNOWN | 12 | 134 | A |
| AI269504 | UNKNOWN | 12 | 205 | T |
| AI269563 | UNKNOWN | 47 | 0 | T |
| AI269563 | UNKNOWN | 12 | 98 | A |
| AI269580 | UNKNOWN | 66 | 0 | T |
| AI269580 | UNKNOWN | 17 | 125 | A |
| AI269592 | UNKNOWN | 18 | 0 | T |
| AI269602 | UNKNOWN | 16 | 0 | T |
| AI269615 | UNKNOWN | 13 | 25 | C |
| AI269620 | UNKNOWN | 3.6 | 211 | AAACC |
| AI269636 | UNKNOWN | 81 | 0 | T |
| AI269640 | UNKNOWN | 40 | 0 | T |
| AI269642 | UNKNOWN | 40 | 0 | T |
| AI269659 | UNKNOWN | 22 | 0 | T |

TABLE 1-continued

| Genbank # | Region | # reps | Position | Unit sequence |
|---|---|---|---|---|
| AI269696 | UNKNOWN | 118 | 0 | T |
| AI269696 | UNKNOWN | 25 | 177 | C |
| AI269696 | UNKNOWN | 15 | 141 | G |
| AI269721 | UNKNOWN | 14 | 0 | T |
| AI269726 | UNKNOWN | 18 | 0 | T |
| AI269758 | UNKNOWN | 27 | 0 | T |
| AI269879 | UNKNOWN | 23 | 510 | T |
| AI269909 | UNKNOWN | 61 | 0 | T |
| AI269909 | UNKNOWN | 18 | 275 | A |
| AI269909 | UNKNOWN | 16 | 359 | G |
| AI269909 | UNKNOWN | 13 | 300 | G |
| AI269935 | UNKNOWN | 5.75 | 169 | TATT |
| AI269935 | UNKNOWN | 14 | 578 | T |
| AI269988 | UNKNOWN | 70 | 0 | T |
| AI269988 | UNKNOWN | 21 | 127 | G |
| AI270019 | UNKNOWN | 24 | 0 | T |
| AI270048 | UNKNOWN | 41 | 73 | T |
| AI270048 | UNKNOWN | 19 | 126 | A |
| AI270048 | UNKNOWN | 17 | 257 | G |
| AI270048 | UNKNOWN | 16 | 56 | T |
| AI270048 | UNKNOWN | 12 | 36 | T |
| AI270051 | UNKNOWN | 67 | 0 | T |
| AI270055 | UNKNOWN | 120 | 0 | T |
| AI270055 | UNKNOWN | 17 | 179 | G |
| AI270055 | UNKNOWN | 15 | 196 | A |
| AI270084 | UNKNOWN | 18 | 136 | G |
| AI270096 | UNKNOWN | 17 | 0 | T |
| AI270098 | UNKNOWN | 27 | 0 | T |
| AI270099 | UNKNOWN | 95 | 0 | T |
| AI270099 | UNKNOWN | 17 | 141 | G |
| AI270099 | UNKNOWN | 12 | 324 | C |
| AI270143 | UNKNOWN | 29 | 121 | A |
| AI270153 | UNKNOWN | 31 | 61 | A |
| AI270163 | UNKNOWN | 27 | 189 | A |
| AI270183 | UNKNOWN | 87 | 0 | T |
| AI270183 | UNKNOWN | 24 | 186 | C |
| AI270183 | UNKNOWN | 20 | 210 | A |
| AI270183 | UNKNOWN | 13 | 146 | C |
| AI270193 | UNKNOWN | 20 | 0 | T |
| AI270205 | UNKNOWN | 94 | 0 | T |
| AI270205 | UNKNOWN | 19 | 281 | G |
| AI270205 | UNKNOWN | 16 | 201 | G |
| AI270205 | UNKNOWN | 13 | 168 | A |
| AI270205 | UNKNOWN | 12 | 225 | C |
| AI270280 | UNKNOWN | 29 | 0 | T |
| AI270295 | UNKNOWN | 65 | 0 | T |
| AI270328 | UNKNOWN | 44 | 0 | T |
| AI270350 | UNKNOWN | 2.93 | 182 | CCCCCCCCCCCCCCCT (SEQ ID NO: 102) |
| AI270350 | UNKNOWN | 74 | 0 | T |
| AI270350 | UNKNOWN | 23 | 214 | C |
| AI270350 | UNKNOWN | 21 | 129 | C |
| AI270399 | UNKNOWN | 33 | 0 | T |
| AI270429 | UNKNOWN | 81 | 0 | T |
| AI270429 | UNKNOWN | 13 | 188 | C |
| AI270439 | UNKNOWN | 39 | 0 | T |
| AI270447 | UNKNOWN | 76 | 0 | T |
| AI270474 | UNKNOWN | 49 | 0 | T |
| AI270561 | UNKNOWN | 101 | 0 | T |
| AI270561 | UNKNOWN | 26 | 371 | C |
| AI270566 | UNKNOWN | 28 | 0 | T |
| AI270572 | UNKNOWN | 39 | 0 | T |
| AI270615 | UNKNOWN | 17 | 0 | T |
| AI270632 | UNKNOWN | 65 | 0 | T |
| AI270657 | UNKNOWN | 79 | 0 | T |
| AI270676 | UNKNOWN | 3 | 394 | CGGACGCGTGGG (SEQ ID NO: 103) |
| AI270706 | UNKNOWN | 81 | 0 | T |
| AI270706 | UNKNOWN | 13 | 81 | A |
| AI270707 | UNKNOWN | 107 | 0 | T |
| AI270707 | UNKNOWN | 15 | 118 | C |
| AI270707 | UNKNOWN | 12 | 144 | A |
| AI270707 | UNKNOWN | 12 | 232 | G |
| AI270748 | UNKNOWN | 38 | 0 | T |
| AI270864 | UNKNOWN | 23 | 141 | A |
| AI270867 | UNKNOWN | 28 | 76 | A |
| AI270896 | UNKNOWN | 27 | 68 | A |
| AI270899 | UNKNOWN | 25 | 158 | A |
| AI270960 | UNKNOWN | 30 | 110 | A |

TABLE 1-continued

| Genbank # | Region | # reps | Position | Unit sequence |
| --- | --- | --- | --- | --- |
| AI270998 | UNKNOWN | 35 | 67 | A |
| AI271016 | UNKNOWN | 20 | 157 | A |
| AI271021 | UNKNOWN | 26 | 87 | A |
| AI271089 | UNKNOWN | 24 | 107 | A |
| AI271096 | UNKNOWN | 20 | 128 | A |
| AI271180 | UNKNOWN | 32 | 107 | A |
| AI271217 | UNKNOWN | 27 | 216 | A |
| AI271227 | UNKNOWN | 28 | 140 | A |
| AI271234 | UNKNOWN | 61 | 25 | A |
| AI271243 | UNKNOWN | 28 | 182 | A |
| AI271269 | UNKNOWN | 34 | 25 | A |
| AI271318 | UNKNOWN | 22 | 122 | A |
| AI271333 | UNKNOWN | 27 | 0 | T |
| AI271339 | UNKNOWN | 12 | 425 | T |
| AI271348 | UNKNOWN | 21 | 2 | T |
| AI271353 | UNKNOWN | 18 | 35 | T |
| AI271488 | UNKNOWN | 24 | 189 | A |
| AI271495 | UNKNOWN | 24 | 127 | A |
| AI271502 | UNKNOWN | 15 | 198 | A |
| AI271590 | UNKNOWN | 23 | 94 | A |
| AI271596 | UNKNOWN | 28 | 148 | A |
| AI271614 | UNKNOWN | 28 | 0 | T |
| AI271623 | UNKNOWN | 15 | 5 | T |
| AI271654 | UNKNOWN | 16 | 258 | T |
| AI271757 | UNKNOWN | 14 | 0 | T |
| AI271767 | UNKNOWN | 39 | 0 | T |
| AI271786 | UNKNOWN | 119 | 0 | T |
| AI271786 | UNKNOWN | 21 | 155 | A |
| AI271786 | UNKNOWN | 16 | 244 | G |
| AI271786 | UNKNOWN | 15 | 176 | C |
| AI271796 | UNKNOWN | 87 | 0 | T |
| AI271796 | UNKNOWN | 16 | 337 | C |
| AI271846 | UNKNOWN | 19 | 0 | T |
| AI271869 | UNKNOWN | 4.2 | 242 | TGTTT |
| AI271878 | UNKNOWN | 20 | 0 | T |
| AI271917 | UNKNOWN | 40 | 0 | T |
| AI271923 | UNKNOWN | 33 | 0 | T |
| AI272020 | UNKNOWN | 16.5 | 222 | TG |
| AI272038 | UNKNOWN | 54 | 23 | T |
| AI272038 | UNKNOWN | 21 | 0 | T |
| AI272052 | UNKNOWN | 28 | 0 | T |
| AI272058 | UNKNOWN | 46 | 0 | T |
| AI272065 | UNKNOWN | 69 | 0 | T |
| AI272065 | UNKNOWN | 14 | 169 | C |
| AI272080 | UNKNOWN | 38 | 0 | T |
| AI272091 | UNKNOWN | 36 | 0 | T |
| AI272116 | UNKNOWN | 97 | 0 | T |
| AI272116 | UNKNOWN | 20 | 268 | G |
| AI272116 | UNKNOWN | 15 | 222 | G |
| AI272116 | UNKNOWN | 15 | 249 | A |
| AI272116 | UNKNOWN | 13 | 167 | G |
| AI272116 | UNKNOWN | 12 | 147 | A |
| AI272116 | UNKNOWN | 12 | 237 | C |
| AI272125 | UNKNOWN | 17 | 0 | T |
| AI272238 | UNKNOWN | 31 | 0 | T |
| AI272364 | UNKNOWN | 30 | 31 | T |
| AI272368 | UNKNOWN | 26 | 0 | T |
| AI272804 | UNKNOWN | 19 | 0 | T |
| AI272875 | UNKNOWN | 15 | 282 | T |
| AI272959 | UNKNOWN | 18 | 0 | T |
| AI272973 | UNKNOWN | 56 | 0 | T |
| AI272994 | UNKNOWN | 47 | 0 | T |
| AI273003 | UNKNOWN | 71 | 0 | T |
| AI273003 | UNKNOWN | 13 | 168 | A |
| AI273030 | UNKNOWN | 27 | 0 | T |
| AI273030 | UNKNOWN | 25 | 328 | G |
| AI273030 | UNKNOWN | 12 | 261 | C |
| AI273034 | UNKNOWN | 49 | 0 | T |
| AI273048 | UNKNOWN | 106 | 0 | T |
| AI273048 | UNKNOWN | 14 | 153 | A |
| AI273085 | UNKNOWN | 74 | 0 | T |
| AI273085 | UNKNOWN | 19 | 135 | A |
| AI273085 | UNKNOWN | 15 | 187 | C |
| AI273085 | UNKNOWN | 12 | 165 | G |
| AI273094 | UNKNOWN | 90 | 15 | T |
| AI273094 | UNKNOWN | 14 | 0 | T |
| AI273094 | UNKNOWN | 13 | 289 | G |

TABLE 1-continued

| Genbank # | Region | # reps | Position | Unit sequence |
|---|---|---|---|---|
| AI273094 | UNKNOWN | 12 | 263 | C |
| AI273106 | UNKNOWN | 73 | 0 | T |
| AI273106 | UNKNOWN | 16 | 187 | G |
| AI273112 | UNKNOWN | 72 | 0 | T |
| AI273112 | UNKNOWN | 15 | 289 | G |
| AI273112 | UNKNOWN | 15 | 304 | A |
| AI273112 | UNKNOWN | 14 | 232 | A |
| AI273112 | UNKNOWN | 13 | 195 | G |
| AI273114 | UNKNOWN | 23 | 0 | T |
| AI273116 | UNKNOWN | 44 | 0 | T |
| AI273142 | UNKNOWN | 2.14 | 0 | T |
| AI273142 | UNKNOWN | 18 | 174 | C |
| AI273142 | UNKNOWN | 18 | 225 | G |
| AI273142 | UNKNOWN | 25 | 137 | A |
| AI273183 | UNKNOWN | 45 | 14 | T |
| AI273183 | UNKNOWN | 13 | 0 | T |
| AI273189 | UNKNOWN | 61 | 0 | T |
| AI273189 | UNKNOWN | 16 | 82 | C |
| AI273189 | UNKNOWN | 13 | 115 | A |
| AI273197 | UNKNOWN | 62 | 0 | T |
| AI273197 | UNKNOWN | 21 | 387 | A |
| AI273197 | UNKNOWN | 15 | 169 | G |
| AI273507 | UNKNOWN | 16 | 214 | T |
| AI273546 | UNKNOWN | 25 | 243 | A |
| AI273546 | UNKNOWN | 17 | 0 | T |
| AI273555 | UNKNOWN | 46 | 0 | T |
| AI273640 | UNKNOWN | 19 | 0 | T |
| AI273649 | UNKNOWN | 14 | 431 | A |
| AI273670 | UNKNOWN | 49 | 0 | T |
| AI273681 | UNKNOWN | 17 | 0 | T |
| AI273703 | UNKNOWN | 3.8 | 21 | TTTTG |
| AI273784 | UNKNOWN | 14 | 289 | A |
| AI273791 | UNKNOWN | 70 | 0 | T |
| AI273791 | UNKNOWN | 12 | 108 | A |
| AI273805 | UNKNOWN | 22 | 0 | T |
| AI273821 | UNKNOWN | 43 | 0 | T |
| AI273837 | UNKNOWN | 15 | 0 | T |
| AI273839 | UNKNOWN | 46 | 0 | T |
| AI273839 | UNKNOWN | 12 | 167 | A |
| AI273843 | UNKNOWN | 101 | 0 | T |
| AI273843 | UNKNOWN | 13 | 317 | G |
| AI273856 | UNKNOWN | 50 | 0 | T |
| AI273856 | UNKNOWN | 18 | 81 | A |
| AI273880 | UNKNOWN | 31 | 0 | T |
| AI273899 | UNKNOWN | 59 | 0 | T |
| AI273901 | UNKNOWN | 88 | 0 | T |
| AI273901 | UNKNOWN | 12 | 330 | G |
| AI273964 | UNKNOWN | 80 | 0 | T |
| AI273964 | UNKNOWN | 16 | 173 | G |
| AI273964 | UNKNOWN | 16 | 215 | C |
| AI273970 | UNKNOWN | 35 | 0 | T |
| AI273987 | UNKNOWN | 53 | 0 | T |
| AI273987 | UNKNOWN | 12 | 225 | G |
| AI274013 | UNKNOWN | 101 | 0 | T |
| AI274013 | UNKNOWN | 21 | 184 | A |
| AI274013 | UNKNOWN | 15 | 155 | C |
| AI274013 | UNKNOWN | 13 | 141 | A |
| AI274013 | UNKNOWN | 12 | 210 | G |
| AI274301 | UNKNOWN | 4.75 | 227 | TTTA |
| AI274301 | UNKNOWN | 13 | 0 | T |
| AI274429 | UNKNOWN | 18 | 25 | T |
| AI274438 | UNKNOWN | 45 | 0 | T |
| AI274446 | UNKNOWN | 39 | 0 | T |
| AI274452 | UNKNOWN | 51 | 0 | T |
| AI274495 | UNKNOWN | 61 | 0 | T |
| AI274500 | UNKNOWN | 59 | 0 | T |
| AI274507 | UNKNOWN | 88 | 0 | T |
| AI274507 | UNKNOWN | 15 | 209 | G |
| AI274507 | UNKNOWN | 14 | 133 | A |
| AI274507 | UNKNOWN | 13 | 259 | C |
| AI274508 | UNKNOWN | 105 | 0 | T |
| AI274508 | UNKNOWN | 20 | 225 | G |
| AI274508 | UNKNOWN | 15 | 210 | A |
| AI274515 | UNKNOWN | 55 | 0 | T |
| AI274541 | UNKNOWN | 115 | 0 | T |
| AI274541 | UNKNOWN | 23 | 234 | C |
| AI274541 | UNKNOWN | 14 | 174 | C |

TABLE 1-continued

| Genbank # | Region | # reps | Position | Unit sequence |
|---|---|---|---|---|
| AI274541 | UNKNOWN | 13 | 257 | A |
| AI274541 | UNKNOWN | 12 | 153 | C |
| AI274614 | UNKNOWN | 53 | 0 | T |
| AI274626 | UNKNOWN | 33 | 15 | T |
| AI274626 | UNKNOWN | 14 | 0 | T |
| AI274629 | UNKNOWN | 25 | 0 | T |
| AI274631 | UNKNOWN | 12 | 307 | A |
| AI274633 | UNKNOWN | 84 | 0 | T |
| AI274633 | UNKNOWN | 15 | 231 | A |
| AI274633 | UNKNOWN | 14 | 91 | C |
| AI274647 | UNKNOWN | 81 | 0 | T |
| AI274647 | UNKNOWN | 14 | 226 | G |
| AI274647 | UNKNOWN | 12 | 101 | A |
| AI274655 | UNKNOWN | 62 | 0 | T |
| AI274655 | UNKNOWN | 15 | 107 | G |
| AI274692 | UNKNOWN | 22 | 137 | T |
| AI274696 | UNKNOWN | 39 | 0 | T |
| AI274728 | UNKNOWN | 56 | 0 | T |
| AI274728 | UNKNOWN | 16 | 195 | G |
| AI274745 | UNKNOWN | 79 | 0 | T |
| AI274745 | UNKNOWN | 14 | 182 | A |
| AI274745 | UNKNOWN | 12 | 110 | A |
| AI274750 | UNKNOWN | 23 | 0 | T |
| AI274768 | UNKNOWN | 58 | 0 | T |
| AI274769 | UNKNOWN | 91 | 0 | T |
| AI274773 | UNKNOWN | 21 | 0 | T |
| AI274785 | UNKNOWN | 91 | 0 | T |
| AI274785 | UNKNOWN | 16 | 100 | A |
| AI274785 | UNKNOWN | 16 | 207 | G |
| AI274785 | UNKNOWN | 15 | 388 | C |
| AI274798 | UNKNOWN | 27 | 0 | T |
| AI274811 | UNKNOWN | 61 | 0 | T |
| AI274811 | UNKNOWN | 14 | 237 | A |
| AI275009 | UNKNOWN | 18 | 0 | T |
| AI275047 | UNKNOWN | 36 | 0 | T |
| AI275068 | UNKNOWN | 21 | 0 | T |
| AI275092 | UNKNOWN | 20 | 0 | T |
| AI275163 | UNKNOWN | 91 | 0 | T |
| AI275163 | UNKNOWN | 14 | 99 | A |
| AI275305 | UNKNOWN | 25 | 102 | A |
| AI275328 | UNKNOWN | 32 | 142 | A |
| AI275350 | UNKNOWN | 20 | 74 | A |
| AI275355 | UNKNOWN | 19 | 243 | A |
| AI275358 | UNKNOWN | 19 | 80 | A |
| AI275403 | UNKNOWN | 26 | 0 | T |
| AI275419 | UNKNOWN | 13 | 4 | T |
| AI275458 | UNKNOWN | 15 | 0 | T |
| AI275510 | UNKNOWN | 44 | 0 | T |
| AI275512 | UNKNOWN | 12 | 0 | T |
| AI275524 | UNKNOWN | 31 | 0 | T |
| AI275550 | UNKNOWN | 13 | 0 | T |
| AI275609 | UNKNOWN | 61 | 0 | T |
| AI275609 | UNKNOWN | 13 | 65 | A |
| AI275610 | UNKNOWN | 13 | 0 | T |
| AI275631 | UNKNOWN | 15 | 0 | T |
| AI275635 | UNKNOWN | 15 | 0 | T |
| AI275640 | UNKNOWN | 81 | 0 | T |
| AI275640 | UNKNOWN | 15 | 120 | A |
| AI275651 | UNKNOWN | 32 | 0 | T |
| AI275710 | UNKNOWN | 30 | 58 | T |
| AI275755 | UNKNOWN | 23 | 0 | T |
| AI275766 | UNKNOWN | 28 | 0 | T |
| AI275830 | UNKNOWN | 42 | 0 | T |
| AI275921 | UNKNOWN | 45 | 0 | T |
| AI275936 | UNKNOWN | 26 | 0 | T |
| AI275956 | UNKNOWN | 48 | 0 | T |
| AI275961 | UNKNOWN | 27 | 0 | T |
| AI275996 | UNKNOWN | 12 | 145 | T |
| AI276014 | UNKNOWN | 52 | 0 | T |
| AI276180 | UNKNOWN | 33 | 0 | T |
| AI276214 | UNKNOWN | 17 | 0 | T |
| AI276234 | UNKNOWN | 24 | 0 | T |
| AI276310 | UNKNOWN | 51 | 0 | T |
| AI276358 | UNKNOWN | 56 | 0 | T |
| AI276416 | UNKNOWN | 34 | 0 | T |
| AI276500 | UNKNOWN | 22 | 0 | T |
| AI276642 | UNKNOWN | 10 | 414 | AT |

TABLE 1-continued

| Genbank # | Region | # reps | Position | Unit sequence |
|---|---|---|---|---|
| AI276650 | UNKNOWN | 43 | 0 | T |
| AI276650 | UNKNOWN | 13 | 225 | A |
| AI276680 | UNKNOWN | 19 | 202 | T |
| AI276770 | UNKNOWN | 29 | 0 | T |
| AI276808 | UNKNOWN | 27 | 0 | T |
| AI276882 | UNKNOWN | 37 | 0 | T |
| AI276891 | UNKNOWN | 53 | 0 | T |
| AI276891 | UNKNOWN | 18 | 165 | C |
| AI276891 | UNKNOWN | 14 | 143 | G |
| AI276956 | UNKNOWN | 16 | 280 | T |
| AI276969 | UNKNOWN | 30 | 0 | T |
| AI276985 | UNKNOWN | 19 | 317 | T |
| AI277008 | UNKNOWN | 64 | 0 | T |
| AI277008 | UNKNOWN | 13 | 111 | A |
| AI277025 | UNKNOWN | 13 | 10 | T |
| AI277034 | UNKNOWN | 21 | 133 | T |
| AI277089 | UNKNOWN | 23 | 0 | T |
| AI277106 | UNKNOWN | 2.66 | 88 | GTATATATATATATATAT (SEQ ID NO: 104) |
| AI277106 | UNKNOWN | 13 | 137 | TA |
| AI277106 | UNKNOWN | 11 | 65 | TA |
| AI277153 | UNKNOWN | 21 | 0 | T |
| AI277255 | UNKNOWN | 87 | 0 | T |
| AI277255 | UNKNOWN | 21 | 251 | C |
| AI277255 | UNKNOWN | 5 | 160 | A |
| AI277255 | UNKNOWN | 12 | 146 | G |
| AI277325 | UNKNOWN | 66 | 0 | T |
| AI277325 | UNKNOWN | 15 | 165 | A |
| AI277330 | UNKNOWN | 3.66 | 17 | TTTTA |
| AI277347 | UNKNOWN | 3.6 | 26 | TTTAT |
| AI277348 | UNKNOWN | 21 | 0 | T |
| AI277368 | UNKNOWN | 34 | 0 | T |
| AI277368 | UNKNOWN | 15 | 167 | A |
| AI277451 | UNKNOWN | 15 | 0 | T |
| AI277540 | UNKNOWN | 14 | 154 | T |
| AI277603 | UNKNOWN | 14 | 0 | T |
| AI277621 | UNKNOWN | 23 | 0 | T |
| AI277625 | UNKNOWN | 23 | 0 | T |
| AI277650 | UNKNOWN | 37 | 30 | T |
| AI277650 | UNKNOWN | 29 | 0 | T |
| AI277650 | UNKNOWN | 13 | 285 | C |
| AI277650 | UNKNOWN | 13 | 298 | G |
| AI277650 | UNKNOWN | 1.2 | 109 | G |
| AI277650 | UNKNOWN | 12 | 142 | A |
| AI277652 | UNKNOWN | 15 | 0 | T |
| AI277665 | UNKNOWN | 16 | 0 | T |
| AI277736 | UNKNOWN | 33 | 0 | T |
| AI277760 | UNKNOWN | 25 | 0 | T |
| AI277761 | UNKNOWN | 36 | 0 | T |
| AI277784 | UNKNOWN | 18 | 0 | T |
| AI277872 | UNKNOWN | 46 | 0 | T |
| AI277938 | UNKNOWN | 51 | 0 | T |
| AI277938 | UNKNOWN | 13 | 383 | A |
| AI277938 | UNKNOWN | 12 | 217 | G |
| AI277938 | UNKNOWN | 12 | 371 | C |
| AI277946 | UNKNOWN | 21 | 102 | A |
| AI278006 | UNKNOWN | 30 | 0 | T |
| AI278055 | UNKNOWN | 21 | 0 | T |
| AI278071 | UNKNOWN | 16 | 0 | T |
| AI278263 | UNKNOWN | 12 | 203 | T |
| AI278325 | UNKNOWN | 17 | 0 | T |
| AI278379 | UNKNOWN | 27 | 0 | T |
| AI278380 | UNKNOWN | 15 | 137 | A |
| AI278400 | UNKNOWN | 63 | 0 | T |
| AI278400 | UNKNOWN | 7 | 143 | A |
| AI278400 | UNKNOWN | 15 | 275 | C |
| AI278445 | UNKNOWN | 17 | 420 | T |
| AI278485 | UNKNOWN | 43 | 0 | T |
| AI278808 | UNKNOWN | 30 | 0 | T |
| AI278937 | UNKNOWN | 15 | 422 | A |
| AI278978 | UNKNOWN | 4 | 421 | AAATA |
| AI279036 | UNKNOWN | 60 | 0 | T |
| AI279036 | UNKNOWN | 12 | 358 | G |
| AI279062 | UNKNOWN | 12 | 120 | A |
| AI279102 | UNKNOWN | 8 | 197 | AC |
| AI279192 | UNKNOWN | 27 | 0 | T |
| AI279276 | UNKNOWN | 18 | 0 | T |
| AI279333 | UNKNOWN | 12 | 100 | A |

TABLE 1-continued

| Genbank # | Region | # reps | Position | Unit sequence |
|---|---|---|---|---|
| AI279399 | UNKNOWN | 14 | 0 | T |
| AI279417 | UNKNOWN | 32 | 0 | T |
| AI279449 | UNKNOWN | 21 | 0 | T |
| AI279511 | UNKNOWN | 13 | 0 | T |
| AI279677 | UNKNOWN | 47 | 0 | T |
| AI279721 | UNKNOWN | 38 | 0 | T |
| AI279798 | UNKNOWN | 5 | 0 | T |
| AI279812 | UNKNOWN | 40 | 0 | T |
| AI279890 | UNKNOWN | 40 | 0 | T |
| AI279901 | UNKNOWN | 19 | 0 | T |
| AI279925 | UNKNOWN | 67 | 0 | T |
| AI279925 | UNKNOWN | 14 | 110 | C |
| AI279984 | UNKNOWN | 112 | 0 | T |
| AI279984 | UNKNOWN | 18 | 293 | G |
| AI279984 | UNKNOWN | 1.2 | 179 | C |
| AI279984 | UNKNOWN | 12 | 231 | G |
| AI280028 | UNKNOWN | 13 | 107 | A |
| AI280093 | UNKNOWN | 6.75 | 328 | TTTG |
| AI280097 | UNKNOWN | 14 | 0 | T |
| AI280127 | UNKNOWN | 12 | 298 | T |
| AI280194 | UNKNOWN | 12 | 10 | T |
| AI280225 | UNKNOWN | 39 | 25 | T |
| AI280225 | UNKNOWN | 23 | 0 | T |
| AI280269 | UNKNOWN | 35 | 0 | T |
| AI280411 | UNKNOWN | 32 | 0 | T |
| AI280430 | UNKNOWN | 34 | 0 | T |
| AI280439 | UNKNOWN | 37 | 0 | T |
| AI280446 | UNKNOWN | 12 | 490 | C |
| AI280508 | UNKNOWN | 17 | 0 | T |
| AI280509 | UNKNOWN | 12 | 0 | T |
| AI280517 | UNKNOWN | 54 | 0 | T |
| AI280517 | UNKNOWN | 14 | 157 | A |
| AI280521 | UNKNOWN | 101 | 0 | T |
| AI280521 | UNKNOWN | 13 | 160 | G |
| AI280521 | UNKNOWN | 12 | 142 | A |
| AI280561 | UNKNOWN | 65 | 0 | T |
| AI280607 | UNKNOWN | 73 | 0 | T |
| AI280608 | UNKNOWN | 17 | 0 | T |
| AI280628 | UNKNOWN | 24 | 0 | T |
| AI280637 | UNKNOWN | 95 | 0 | T |
| AI280637 | UNKNOWN | 16 | 227 | A |
| AI280637 | UNKNOWN | 12 | 95 | A |
| AI280639 | UNKNOWN | 15 | 0 | T |
| AI280655 | UNKNOWN | 78 | 0 | T |
| AI280655 | UNKNOWN | 21 | 237 | C |
| AI280655 | UNKNOWN | 16 | 258 | A |
| AI280661 | UNKNOWN | 95 | 0 | T |
| AI280661 | UNKNOWN | 23 | 156 | C |
| AI280661 | UNKNOWN | 12 | 121 | A |
| AI280670 | UNKNOWN | 83 | 0 | T |
| AI280674 | UNKNOWN | 6.5 | 27 | TC |
| AI280678 | UNKNOWN | 21 | 0 | T |
| AI280689 | UNKNOWN | 75 | 18 | T |
| AI280689 | UNKNOWN | 16 | 0 | T |
| AI280689 | UNKNOWN | 16 | 155 | G |
| AI280689 | UNKNOWN | 12 | 102 | A |
| AI280732 | UNKNOWN | 84 | 0 | T |
| AI280732 | UNKNOWN | 14 | 130 | G |
| AI280732 | UNKNOWN | 14 | 157 | C |
| AI280747 | UNKNOWN | 97 | 0 | T |
| AI280747 | UNKNOWN | 20 | 129 | A |
| AI280751 | UNKNOWN | 94 | 0 | T |
| AI280751 | UNKNOWN | 7 | 212 | C |
| AI280751 | UNKNOWN | 12 | 184 | C |
| AI280763 | UNKNOWN | 23 | 22 | T |
| AI280997 | UNKNOWN | 12 | 0 | T |
| AI281057 | UNKNOWN | 19 | 4 | T |
| AI281068 | UNKNOWN | 12 | 224 | T |
| AI281098 | UNKNOWN | 12 | 0 | T |
| AI281115 | UNKNOWN | 39 | 0 | T |
| AI281115 | UNKNOWN | 16 | 62 | A |
| AI281152 | UNKNOWN | 43 | 0 | T |
| AI281244 | UNKNOWN | 39 | 0 | T |
| AI281256 | UNKNOWN | 46 | 1 | T |
| AI281256 | UNKNOWN | 23 | 311 | C |
| AI281306 | UNKNOWN | 23 | 0 | T |
| AI281326 | UNKNOWN | 39 | 0 | T |

TABLE 1-continued

| Genbank # | Region | # reps | Position | Unit sequence |
|---|---|---|---|---|
| AI281412 | UNKNOWN | 67 | 0 | T |
| AI281412 | UNKNOWN | 17 | 173 | A |
| AI281566 | UNKNOWN | 4.5 | 0 | TTCT |
| AI281589 | UNKNOWN | 17 | 0 | T |
| AI281653 | UNKNOWN | 72 | 2 | T |
| AI281659 | UNKNOWN | 75 | 4 | T |
| AI281659 | UNKNOWN | 21 | 143 | A |
| AI281659 | UNKNOWN | 13 | 251 | G |
| AI281660 | UNKNOWN | 91 | 0 | T |
| AI281660 | UNKNOWN | 23 | 137 | G |
| AI281660 | UNKNOWN | 12 | 252 | C |
| AI281673 | UNKNOWN | 63 | 0 | T |
| AI281673 | UNKNOWN | 12 | 106 | A |
| AI281687 | UNKNOWN | 64 | 0 | T |
| AI281687 | UNKNOWN | 16 | 185 | A |
| AI281687 | UNKNOWN | 13 | 115 | C |
| AI281712 | UNKNOWN | 14 | 0 | T |
| AI281757 | UNKNOWN | 69 | 0 | T |
| AI281762 | UNKNOWN | 118 | 0 | T |
| AI281762 | UNKNOWN | 19 | 159 | A |
| AI281762 | UNKNOWN | 13 | 224 | C |
| AI281772 | UNKNOWN | 97 | 0 | T |
| AI281772 | UNKNOWN | 15 | 213 | G |
| AI281772 | UNKNOWN | 14 | 180 | C |
| AI281773 | UNKNOWN | 84 | 5 | T |
| AI281774 | UNKNOWN | 22 | 0 | T |
| AI281779 | UNKNOWN | 126 | 0 | T |
| AI281779 | UNKNOWN | 18 | 152 | C |
| AI281779 | UNKNOWN | 15 | 246 | G |
| AI281779 | UNKNOWN | 13 | 139 | A |
| AI281782 | UNKNOWN | 88 | 0 | T |
| AI281800 | UNKNOWN | 82 | 0 | T |
| AI281800 | UNKNOWN | 16 | 268 | C |
| AI281800 | UNKNOWN | 15 | 195 | G |
| AI281800 | UNKNOWN | 13 | 161 | C |
| AI281815 | UNKNOWN | 39 | 0 | T |
| AI281815 | UNKNOWN | 12 | 153 | G |
| AI281837 | UNKNOWN | 112 | 0 | T |
| AI281837 | UNKNOWN | 18 | 207 | C |
| AI281837 | UNKNOWN | 16 | 235 | G |
| AI281837 | UNKNOWN | 12 | 144 | G |
| AI281865 | UNKNOWN | 33 | 0 | T |
| AI281867 | UNKNOWN | 73 | 0 | T |
| AI281867 | UNKNOWN | 14 | 151 | A |
| AI281867 | UNKNOWN | 12 | 121 | G |
| AI281880 | UNKNOWN | 49 | 0 | T |
| AI281899 | UNKNOWN | 43 | 0 | T |
| AI281913 | UNKNOWN | 38 | 0 | T |
| AI281954 | UNKNOWN | 19 | 16 | T |
| AI281976 | UNKNOWN | 12 | 151 | T |
| AI281981 | UNKNOWN | 13 | 164 | A |
| AI282040 | UNKNOWN | 26 | 163 | T |
| AI282040 | UNKNOWN | 12 | 346 | A |
| AI282043 | UNKNOWN | 18 | 0 | T |
| AI282063 | UNKNOWN | 45 | 0 | T |
| AI282281 | UNKNOWN | 117 | 0 | T |
| AI282281 | UNKNOWN | 12 | 135 | A |
| AI282307 | UNKNOWN | 71 | 0 | T |
| AI282307 | UNKNOWN | 14 | 81 | A |
| AI282317 | UNKNOWN | 42 | 0 | T |
| AI282319 | UNKNOWN | 72 | 0 | T |
| AI282319 | UNKNOWN | 14 | 127 | G |
| AI282319 | UNKNOWN | 12 | 167 | C |
| AI282326 | UNKNOWN | 102 | 0 | T |
| AI282326 | UNKNOWN | 12 | 172 | G |
| AI282346 | UNKNOWN | 55 | 0 | T |
| AI282346 | UNKNOWN | 13 | 74 | A |
| AI282349 | UNKNOWN | 12 | 0 | T |
| AI282355 | UNKNOWN | 76 | 0 | T |
| AI282355 | UNKNOWN | 28 | 136 | A |
| AI282376 | UNKNOWN | 73 | 0 | T |
| AI282376 | UNKNOWN | 18 | 131 | A |
| AI282376 | UNKNOWN | 14 | 189 | G |
| AI282376 | UNKNOWN | 13 | 105 | G |
| AI282376 | UNKNOWN | 13 | 203 | C |
| AI282376 | UNKNOWN | 12 | 93 | C |
| AI282409 | UNKNOWN | 21 | 0 | T |

TABLE 1-continued

| Genbank # | Region | # reps | Position | Unit sequence |
|---|---|---|---|---|
| AI282422 | UNKNOWN | 45 | 0 | T |
| AI282479 | UNKNOWN | 13 | 8 | T |
| AI232504 | UNKNOWN | 107 | 0 | T |
| AI282504 | UNKNOWN | 23 | 249 | A |
| AI282504 | UNKNOWN | 20 | 285 | G |
| AI282508 | UNKNOWN | 71 | 0 | T |
| AI282508 | UNKNOWN | 18 | 297 | A |
| AI282572 | UNKNOWN | 62 | 0 | T |
| AI282572 | UNKNOWN | 20 | 161 | G |
| AI282572 | UNKNOWN | 12 | 196 | C |
| AI282602 | UNKNOWN | 80 | 0 | T |
| AI282602 | UNKNOWN | 14 | 135 | G |
| AI282641 | UNKNOWN | 33 | 0 | T |
| AI282651 | UNKNOWN | 88 | 0 | T |
| AI282651 | UNKNOWN | 12 | 125 | A |
| AI282651 | UNKNOWN | 12 | 213 | G |
| AI282652 | UNKNOWN | 58 | 0 | T |
| AI282655 | UNKNOWN | 85 | 0 | T |
| AI282655 | UNKNOWN | 22 | 198 | G |
| AI282655 | UNKNOWN | 19 | 129 | C |
| AI282673 | UNKNOWN | 48 | 0 | T |
| AI282679 | UNKNOWN | 82 | 0 | T |
| AI282679 | UNKNOWN | 16 | 158 | G |
| AI282688 | UNKNOWN | 63 | 0 | T |
| AI282688 | UNKNOWN | 15 | 83 | A |
| AI282695 | UNKNOWN | 79 | 0 | T |
| AI282710 | UNKNOWN | 19 | 0 | T |
| AI282743 | UNKNOWN | 65 | 0 | T |
| AI282889 | UNKNOWN | 15 | 0 | T |
| AI282903 | UNKNOWN | 120 | 0 | T |
| AI282903 | UNKNOWN | 21 | 220 | A |
| AI282903 | UNKNOWN | 17 | 182 | A |
| AI282903 | UNKNOWN | 15 | 167 | G |
| AI282927 | UNKNOWN | 42 | 0 | T |
| AI282930 | UNKNOWN | 69 | 0 | T |
| AI282967 | UNKNOWN | 57 | 0 | T |
| AI282967 | UNKNOWN | 12 | 138 | G |
| AI282992 | UNKNOWN | 51 | 0 | T |
| AI283008 | UNKNOWN | 12 | 0 | T |
| AI283016 | UNKNOWN | 19 | 4 | T |
| AI283032 | UNKNOWN | 43 | 0 | T |
| AI283032 | UNKNOWN | 13 | 137 | G |
| AI283047 | UNKNOWN | 29 | 0 | T |
| AI283068 | UNKNOWN | 36 | 0 | T |
| AI283093 | UNKNOWN | 3.8 | 157 | TTTTC |
| AI283093 | UNKNOWN | 18 | 0 | T |
| AI283105 | UNKNOWN | 37 | 0 | T |
| AI283105 | UNKNOWN | 14 | 335 | A |
| AI283112 | UNKNOWN | 15 | 69 | T |
| AI283118 | UNKNOWN | 47 | 0 | T |
| AI283143 | UNKNOWN | 86 | 0 | T |
| AI283143 | UNKNOWN | 13 | 218 | G |
| AI283143 | UNKNOWN | 12 | 141 | G |
| AI283143 | UNKNOWN | 12 | 231 | C |
| AI283175 | UNKNOWN | 11 | 26 | GT |
| AI283290 | UNKNOWN | 14 | 8 | T |
| AI283290 | UNKNOWN | 12 | 218 | A |
| AI283322 | UNKNOWN | 48 | 0 | T |
| AI283336 | UNKNOWN | 86 | 121 | TGAGTAGCTGGGATTACAGGCACGCTCCT (SEQ ID NO: 105) |
| AI283548 | UNKNOWN | 17 | 273 | T |
| AI283571 | UNKNOWN | 13 | 0 | T |
| AI283628 | UNKNOWN | 32 | 0 | T |
| AI283635 | UNKNOWN | 7 | 270 | AT |
| AI283729 | UNKNOWN | 17 | 209 | A |
| AI283748 | UNKNOWN | 13 | 452 | A |
| AI283748 | UNKNOWN | 12 | 0 | T |
| AI283760 | UNKNOWN | 96 | 0 | T |
| AI283760 | UNKNOWN | 25 | 282 | G |
| AI283760 | UNKNOWN | 16 | 266 | A |
| AI283760 | UNKNOWN | 15 | 165 | A |
| AI283760 | UNKNOWN | 14 | 193 | G |
| AI283760 | UNKNOWN | 12 | 238 | C |
| AI283914 | UNKNOWN | 95 | 0 | T |
| AI283914 | UNKNOWN | 13 | 122 | A |
| AI283914 | UNKNOWN | 13 | 135 | C |
| AI283919 | UNKNOWN | 19 | 143 | G |

TABLE 1-continued

| Genbank # | Region | # reps | Position | Unit sequence |
|---|---|---|---|---|
| AI283919 | UNKNOWN | 15 | 0 | T |
| AI283941 | UNKNOWN | 92 | 0 | T |
| AI283941 | UNKNOWN | 14 | 217 | G |
| AI283941 | UNKNOWN | 13 | 200 | C |
| AI283941 | UNKNOWN | 12 | 162 | A |
| AI283953 | UNKNOWN | 21 | 5 | T |
| AI283969 | UNKNOWN | 25 | 0 | T |
| AI283990 | UNKNOWN | 42 | 0 | T |
| AI284000 | UNKNOWN | 37 | 0 | T |
| AI284015 | UNKNOWN | 62 | 0 | T |
| AI284020 | UNKNOWN | 111 | 0 | T |
| AI284020 | UNKNOWN | 19 | 131 | A |
| AI284020 | UNKNOWN | 14 | 264 | C |
| AI284034 | UNKNOWN | 72 | 0 | T |
| AI284034 | UNKNOWN | 13 | 225 | C |
| AI284035 | UNKNOWN | 78 | 0 | T |
| AI284035 | UNKNOWN | 19 | 224 | C |
| AI284060 | UNKNOWN | 56 | 0 | T |
| AI284060 | UNKNOWN | 12 | 149 | A |
| AI284084 | UNKNOWN | 102 | 0 | T |
| AI284084 | UNKNOWN | 14 | 196 | C |
| AI284084 | UNKNOWN | 14 | 223 | G |
| AI284084 | UNKNOWN | 12 | 146 | C |
| AI284103 | UNKNOWN | 58 | 0 | T |
| AI284111 | UNKNOWN | 5.75 | 325 | TTTG |
| AI284131 | UNKNOWN | 101 | 0 | T |
| AI284131 | UNKNOWN | 12 | 189 | G |
| AI284170 | UNKNOWN | 31 | 0 | T |
| AI284202 | UNKNOWN | 13 | 0 | T |
| AI284368 | UNKNOWN | 8 | 51 | GT |
| AI284425 | UNKNOWN | 2.8 | 148 | TTTTTTTCT (SEQ ID NO: 106) |
| AI284425 | UNKNOWN | 16 | 167 | T |
| AI284467 | UNKNOWN | 17 | 0 | T |
| AI284468 | UNKNOWN | 40 | 0 | T |
| AI284478 | UNKNOWN | 3.5 | 12 | TTTTTA |
| AI284484 | UNKNOWN | 109 | 0 | T |
| AI284484 | UNKNOWN | 13 | 182 | G |
| AI284484 | UNKNOWN | 12 | 136 | C |
| AI284486 | UNKNOWN | 37 | 0 | T |
| AI284518 | UNKNOWN | 15 | 11 | T |
| AI284625 | UNKNOWN | 30 | 60 | A |
| AI284627 | UNKNOWN | 27 | 187 | A |
| AI284700 | UNKNOWN | 19 | 137 | A |
| AI284704 | UNKNOWN | 20 | 247 | A |
| AI284718 | UNKNOWN | 12 | 0 | T |
| AI284728 | UNKNOWN | 26 | 0 | T |
| AI284770 | UNKNOWN | 27 | 155 | A |
| AI284781 | UNKNOWN | 54 | 0 | T |
| AI284783 | UNKNOWN | 31 | 0 | T |
| AI284786 | UNKNOWN | 27 | 0 | T |
| AI284881 | UNKNOWN | 27 | 142 | A |
| AI285165 | UNKNOWN | 42 | 0 | T |
| AI285242 | UNKNOWN | 27 | 0 | T |
| AI285384 | UNKNOWN | 46 | 0 | T |
| AI285407 | UNKNOWN | 38 | 0 | T |
| AI285411 | UNKNOWN | 6.5 | 211 | AT |
| AI285411 | UNKNOWN | 19 | 0 | T |
| AI285431 | UNKNOWN | 74 | 33 | T |
| AI285431 | UNKNOWN | 32 | 0 | T |
| AI285431 | UNKNOWN | 16 | 173 | C |
| AI285431 | UNKNOWN | 13 | 219 | G |
| AI285438 | UNKNOWN | 70 | 0 | T |
| AI285438 | UNKNOWN | 27 | 307 | C |
| AI285448 | UNKNOWN | 94 | 0 | T |
| AI285448 | UNKNOWN | 22 | 196 | C |
| AI285448 | UNKNOWN | 18 | 158 | A |
| AI285448 | UNKNOWN | 16 | 176 | C |
| AI285448 | UNKNOWN | 15 | 123 | A |
| AI285464 | UNKNOWN | 82 | 0 | T |
| AI285464 | UNKNOWN | 12 | 185 | A |
| AI285574 | UNKNOWN | 6.8 | 217 | AAATA |
| AI285574 | UNKNOWN | 22 | 33 | A |
| AI285574 | UNKNOWN | 15 | 0 | T |
| AI285584 | UNKNOWN | 30 | 0 | T |
| AI285588 | UNKNOWN | 12 | 135 | T |
| AI285713 | UNKNOWN | 22 | 0 | T |
| AI285721 | UNKNOWN | 41 | 0 | T |

TABLE 1-continued

| Genbank # | Region | # reps | Position | Unit sequence |
|---|---|---|---|---|
| AI285723 | UNKNOWN | 14 | 0 | T |
| AI285732 | UNKNOWN | 78 | 0 | T |
| AI285732 | UNKNOWN | 19 | 172 | G |
| AI285735 | UNKNOWN | 129 | 0 | T |
| AI285735 | UNKNOWN | 17 | 265 | A |
| AI285735 | UNKNOWN | 16 | 239 | C |
| AI285736 | UNKNOWN | 20 | 0 | T |
| AI285753 | UNKNOWN | 26 | 296 | A |
| AI285777 | UNKNOWN | 55 | 0 | T |
| AI285787 | UNKNOWN | 30 | 0 | T |
| AI285826 | UNKNOWN | 97 | 11 | T |
| AI285964 | UNKNOWN | 13 | 0 | T |
| AI285989 | UNKNOWN | 9 | 366 | TA |
| AI285989 | UNKNOWN | 7 | 335 | AT |
| AI285989 | UNKNOWN | 15 | 0 | T |
| AI285989 | UNKNOWN | 13 | 247 | A |
| AI285994 | UNKNOWN | 14 | 0 | T |
| AI285998 | UNKNOWN | 17 | 0 | T |
| AI286027 | UNKNOWN | 8.5 | 156 | AG |
| AI286033 | UNKNOWN | 4.8 | 113 | AAAAC |
| AI286039 | UNKNOWN | 34 | 0 | T |
| AI286040 | UNKNOWN | 30 | 0 | T |
| AI286088 | UNKNOWN | 6.5 | 65 | AG |
| AI286105 | UNKNOWN | 17 | 0 | T |
| AI286142 | UNKNOWN | 13 | 373 | T |
| AI286206 | UNKNOWN | 27 | 296 | T |
| AI286218 | UNKNOWN | 22 | 0 | T |
| AI286226 | UNKNOWN | 15 | 0 | T |
| AI286230 | UNKNOWN | 16 | 0 | T |
| AI286256 | UNKNOWN | 96 | 0 | T |
| AI286256 | UNKNOWN | 19 | 277 | G |
| AI286256 | UNKNOWN | 17 | 110 | A |
| AI286256 | UNKNOWN | 17 | 236 | G |
| AI286256 | UNKNOWN | 14 | 127 | G |
| AI286256 | UNKNOWN | 14 | 152 | C |
| AI286310 | UNKNOWN | 31 | 0 | T |
| AI286322 | UNKNOWN | 22 | 0 | T |
| AI286335 | UNKNOWN | 27 | 0 | T |
| AI287233 | UNKNOWN | 68 | 0 | T |
| AI287235 | UNKNOWN | 44 | 0 | T |
| AI287252 | UNKNOWN | 49 | 0 | T |
| AI287301 | UNKNOWN | 41 | 0 | T |
| AI287326 | UNKNOWN | 95 | 0 | T |
| AI287326 | UNKNOWN | 21 | 153 | G |
| AI287326 | UNKNOWN | 18 | 130 | A |
| AI287326 | UNKNOWN | 12 | 118 | C |
| AI287343 | UNKNOWN | 52 | 0 | T |
| AI287343 | UNKNOWN | 13 | 298 | G |
| AI287357 | UNKNOWN | 16 | 50 | T |
| AI287386 | UNKNOWN | 43 | 0 | T |
| AI287391 | UNKNOWN | 66 | 0 | T |
| AI287391 | UNKNOWN | 16 | 141 | A |
| AI287391 | UNKNOWN | 13 | 279 | G |
| AI287391 | UNKNOWN | 12 | 267 | C |
| AI287427 | UNKNOWN | 26 | 80 | A |
| AI287442 | UNKNOWN | 46 | 0 | T |
| AI287446 | UNKNOWN | 69 | 0 | T |
| AI287449 | UNKNOWN | 76 | 0 | T |
| AI287449 | UNKNOWN | 15 | 124 | G |
| AI287449 | UNKNOWN | 14 | 240 | A |
| AI287449 | UNKNOWN | 12 | 141 | A |
| AI287449 | UNKNOWN | 12 | 204 | C |
| AI287476 | UNKNOWN | 51 | 0 | T |
| AI287479 | UNKNOWN | 27 | 0 | T |
| AI287489 | UNKNOWN | 106 | 0 | T |
| AI287489 | UNKNOWN | 20 | 263 | G |
| AI287489 | UNKNOWN | 14 | 123 | A |
| AI287489 | UNKNOWN | 14 | 228 | C |
| AI287489 | UNKNOWN | 12 | 178 | G |
| AI287496 | UNKNOWN | 47 | 0 | T |
| AI287498 | UNKNOWN | 50 | 0 | T |
| AI287498 | UNKNOWN | 12 | 172 | A |
| AI287511 | UNKNOWN | 36 | 0 | T |
| AI287526 | UNKNOWN | 15 | 0 | T |
| AI287586 | UNKNOWN | 6.5 | 187 | AT |
| AI287622 | UNKNOWN | 4 | 66 | AAATA |
| AI287622 | UNKNOWN | 5.25 | 38 | AAAT |

TABLE 1-continued

| Genbank # | Region | # reps | Position | Unit sequence |
|---|---|---|---|---|
| AI287635 | UNKNOWN | 33 | 0 | T |
| AI287637 | UNKNOWN | 39 | 0 | T |
| AI287704 | UNKNOWN | 84 | 0 | T |
| AI287704 | UNKNOWN | 14 | 215 | C |
| AI287729 | UNKNOWN | 20 | 239 | A |
| AI287766 | UNKNOWN | 19 | 403 | A |
| AI287777 | UNKNOWN | 45 | 0 | T |
| AI287785 | UNKNOWN | 42 | 0 | T |
| AI287793 | UNKNOWN | 52 | 0 | T |
| AI287809 | UNKNOWN | 43 | 0 | T |
| AI287823 | UNKNOWN | 19 | 159 | T |
| AI287823 | UNKNOWN | 17 | 219 | A |
| AI287823 | UNKNOWN | 14 | 1 | T |
| AI287824 | UNKNOWN | 44 | 0 | T |
| AI287824 | UNKNOWN | 12 | 214 | A |
| AI287827 | UNKNOWN | 48 | 0 | T |
| AI287831 | UNKNOWN | 40 | 0 | T |
| AI287862 | UNKNOWN | 57 | 0 | T |
| AI287862 | UNKNOWN | 16 | 80 | A |
| AI287886 | UNKNOWN | 12 | 84 | A |
| AI287898 | UNKNOWN | 3.6 | 14 | ATTTT |
| AI288005 | UNKNOWN | 13 | 326 | A |
| AI288050 | UNKNOWN | 73 | 0 | T |
| AI288050 | UNKNOWN | 12 | 174 | A |
| AI288083 | UNKNOWN | 41 | 0 | T |
| AI288089 | UNKNOWN | 26 | 0 | T |
| AI288106 | UNKNOWN | 32 | 0 | T |
| AI288116 | UNKNOWN | 81 | 0 | T |
| AI288116 | UNKNOWN | 13 | 167 | G |
| AI288149 | UNKNOWN | 59 | 0 | T |
| AI288149 | UNKNOWN | 15 | 225 | C |
| AI288149 | UNKNOWN | 14 | 131 | A |
| AI288152 | UNKNOWN | 66 | 0 | T |
| AI288162 | UNKNOWN | 18 | 0 | T |
| AI288242 | UNKNOWN | 15 | 370 | T |
| AI288285 | UNKNOWN | 88 | 0 | T |
| AI288285 | UNKNOWN | 14 | 122 | C |
| AI288305 | UNKNOWN | 88 | 0 | T |
| AI288305 | UNKNOWN | 12 | 176 | G |
| AI288326 | UNKNOWN | 41 | 6 | T |
| AI288328 | UNKNOWN | 58 | 0 | T |
| AI288335 | UNKNOWN | 57 | 0 | T |
| AI288337 | UNKNOWN | 19 | 7 | T |
| AI288416 | UNKNOWN | 15 | 0 | T |
| AI288420 | UNKNOWN | 15 | 0 | T |
| AI288735 | UNKNOWN | 17 | 0 | T |
| AI288738 | UNKNOWN | 20 | 0 | T |
| AI288838 | UNKNOWN | 14 | 0 | T |
| AI288843 | UNKNOWN | 60 | 0 | T |
| AI288949 | UNKNOWN | 18 | 0 | T |
| AI289077 | UNKNOWN | 51 | 0 | T |
| AI289098 | UNKNOWN | 36 | 0 | T |
| AI289134 | UNKNOWN | 47 | 0 | T |
| AI289134 | UNKNOWN | 14 | 197 | A |
| AI289160 | UNKNOWN | 32 | 0 | T |
| AI289171 | UNKNOWN | 12 | 0 | T |
| AI289185 | UNKNOWN | 27 | 0 | T |
| AI289218 | UNKNOWN | 13 | 0 | T |
| AI289276 | UNKNOWN | 16 | 0 | T |
| AI289291 | UNKNOWN | 22 | 0 | T |
| AI289310 | UNKNOWN | 63 | 0 | T |
| AI289310 | UNKNOWN | 22 | 131 | G |
| AI289335 | UNKNOWN | 28 | 0 | T |
| AI289337 | UNKNOWN | 89 | 0 | T |
| AI289337 | UNKNOWN | 14 | 164 | A |
| AI289337 | UNKNOWN | 12 | 203 | C |
| AI289372 | UNKNOWN | 27 | 205 | A |
| AI289387 | UNKNOWN | 27 | 11 | T |
| AI289400 | UNKNOWN | 52 | 0 | T |
| AI289405 | UNKNOWN | 36 | 0 | T |
| AI289410 | UNKNOWN | 41 | 0 | T |
| AI289436 | UNKNOWN | 49 | 0 | T |
| AI289440 | UNKNOWN | 17 | 0 | T |
| AI289471 | UNKNOWN | 3.8 | 185 | AAAAC |
| AI289471 | UNKNOWN | 43 | 0 | T |
| AI289471 | UNKNOWN | 20 | 69 | A |
| AI289472 | UNKNOWN | 40 | 0 | T |

TABLE 1-continued

| Genbank # | Region | # reps | Position | Unit sequence |
|---|---|---|---|---|
| AI289472 | UNKNOWN | 12 | 342 | G |
| AI289483 | UNKNOWN | 46 | 0 | T |
| AI289503 | UNKNOWN | 38 | 0 | T |
| AI289597 | UNKNOWN | 18 | 0 | T |
| AI289608 | UNKNOWN | 58 | 0 | T |
| AI289608 | UNKNOWN | 18 | 97 | A |
| AI289629 | UNKNOWN | 91 | 0 | T |
| AI289629 | UNKNOWN | 17 | 192 | C |
| AI289629 | UNKNOWN | 12 | 155 | G |
| AI289632 | UNKNOWN | 12 | 0 | T |
| AI289659 | UNKNOWN | 43 | 0 | T |
| AI289680 | UNKNOWN | 27 | 116 | A |
| AI289746 | UNKNOWN | 33 | 0 | T |
| AI289775 | UNKNOWN | 46 | 0 | T |
| AI289817 | UNKNOWN | 54 | 0 | T |
| AI289817 | UNKNOWN | 12 | 151 | G |
| AI289852 | UNKNOWN | 52 | 0 | T |
| AI289863 | UNKNOWN | 61 | 0 | T |
| AI289863 | UNKNOWN | 23 | 146 | A |
| AI289892 | UNKNOWN | 42 | 0 | T |
| AI289937 | UNKNOWN | 105 | 0 | T |
| AI289937 | UNKNOWN | 22 | 225 | G |
| AI289937 | UNKNOWN | 15 | 210 | A |
| AI289993 | UNKNOWN | 35 | 0 | T |
| AI290069 | UNKNOWN | 13 | 0 | T |
| AI290071 | UNKNOWN | 63 | 0 | T |
| AI290107 | UNKNOWN | 18 | 0 | T |
| AI290128 | UNKNOWN | 60 | 0 | T |
| AI290132 | UNKNOWN | 16 | 0 | T |
| AI290140 | UNKNOWN | 15 | 203 | T |
| AI290147 | UNKNOWN | 59 | 0 | T |
| AI290153 | UNKNOWN | 65 | 0 | T |
| AI290154 | UNKNOWN | 115 | 0 | T |
| AI290154 | UNKNOWN | 21 | 140 | C |
| AI290154 | UNKNOWN | 21 | 213 | G |
| AI290157 | UNKNOWN | 4.75 | 89 | TTTC |
| AI290203 | UNKNOWN | 64 | 0 | T |
| AI290203 | UNKNOWN | 14 | 144 | C |
| AI290203 | UNKNOWN | 13 | 105 | A |
| AI290203 | UNKNOWN | 13 | 280 | G |
| AI290230 | UNKNOWN | 12 | 388 | A |
| AI290405 | UNKNOWN | 4.75 | 16 | TTTA |
| AI290474 | UNKNOWN | 17 | 0 | T |
| AI290482 | UNKNOWN | 18 | 0 | T |
| AI290489 | UNKNOWN | 16 | 0 | T |
| AI290504 | UNKNOWN | 7.5 | 190 | AT |
| AI290504 | UNKNOWN | 7 | 174 | AT |
| AI290556 | UNKNOWN | 14 | 435 | T |
| AI290596 | UNKNOWN | 8.5 | 139 | TA |
| AI290626 | UNKNOWN | 16 | 0 | T |
| AI290760 | UNKNOWN | 4.75 | 452 | AAAT |
| AI290820 | UNKNOWN | 24 | 0 | T |
| AI290919 | UNKNOWN | 7.66 | 413 | AAT |
| AI290919 | UNKNOWN | 6 | 394 | TAA |
| AI290947 | UNKNOWN | 17 | 13 | T |
| AI290960 | UNKNOWN | 12 | 242 | A |
| AI291037 | UNKNOWN | 12 | 0 | T |
| AI291041 | UNKNOWN | 14 | 0 | T |
| AI291049 | UNKNOWN | 17 | 0 | T |
| AI291174 | UNKNOWN | 34 | 0 | T |
| AI291189 | UNKNOWN | 3.8 | 427 | TTTTC |
| AI291189 | UNKNOWN | 16 | 0 | T |
| AI291214 | UNKNOWN | 55 | 0 | T |
| AI291214 | UNKNOWN | 13 | 434 | G |
| AI291274 | UNKNOWN | 18 | 398 | A |
| AI291365 | UNKNOWN | 23 | 0 | T |
| AI291445 | UNKNOWN | 11 | 8 | AT |
| AI291450 | UNKNOWN | 12 | 0 | T |
| AI291480 | UNKNOWN | 10 | 58 | CA |
| AI291524 | UNKNOWN | 18 | 435 | A |
| AI291563 | UNKNOWN | 14 | 0 | T |
| AI291601 | UNKNOWN | 67 | 0 | T |
| AI291601 | UNKNOWN | 17 | 82 | A |
| AI291606 | UNKNOWN | 15 | 0 | T |
| AI291618 | UNKNOWN | 52 | 0 | T |
| AI291705 | UNKNOWN | 3.6 | 162 | TTTAT |
| AI291705 | UNKNOWN | 13 | 232 | A |

TABLE 1-continued

| Genbank # | Region | # reps | Position | Unit sequence |
|---|---|---|---|---|
| AI291714 | UNKNOWN | 16 | 0 | T |
| AI291857 | UNKNOWN | 13 | 40 | A |
| AI291896 | UNKNOWN | 26 | 0 | T |
| AI291973 | UNKNOWN | 32 | 29 | T |
| AI291973 | UNKNOWN | 28 | 0 | T |
| AI291979 | UNKNOWN | 41 | 0 | T |
| AI291981 | UNKNOWN | 38 | 0 | T |
| AI291981 | UNKNOWN | 21 | 216 | T |
| AI292032 | UNKNOWN | 26 | 0 | T |
| AI292034 | UNKNOWN | 41 | 0 | T |
| AI292034 | UNKNOWN | 14 | 291 | G |
| AI292193 | UNKNOWN | 90 | 0 | T |
| AI292193 | UNKNOWN | 17 | 263 | A |
| AI292193 | UNKNOWN | 13 | 145 | G |
| AI292193 | UNKNOWN | 13 | 383 | C |
| AI292249 | UNKNOWN | 60 | 0 | T |
| AI292254 | UNKNOWN | 13 | 282 | T |
| AI292257 | UNKNOWN | 31 | 0 | T |
| AI292317 | UNKNOWN | 5 | 43 | TTTA |
| AI292340 | UNKNOWN | 49 | 0 | T |
| AI292340 | UNKNOWN | 12 | 277 | A |
| AI298006 | UNKNOWN | 12 | 348 | A |
| AI298006 | UNKNOWN | 12 | 415 | T |
| AI298026 | UNKNOWN | 51 | 0 | T |
| AI298072 | UNKNOWN | 20 | 0 | T |
| AI298076 | UNKNOWN | 26 | 0 | T |
| AI298134 | UNKNOWN | 43 | 0 | T |
| AI298279 | UNKNOWN | 22 | 338 | T |
| AI298318 | UNKNOWN | 41 | 0 | T |
| AI298321 | UNKNOWN | 48 | 0 | T |
| AI298321 | UNKNOWN | 13 | 48 | A |
| AI298344 | UNKNOWN | 44 | 0 | T |
| AI298368 | UNKNOWN | 12 | 0 | T |
| AI298495 | UNKNOWN | 5.66 | 1 | TTG |
| AI298528 | UNKNOWN | 16 | 251 | T |
| AI298556 | UNKNOWN | 21 | 0 | T |
| AI298567 | UNKNOWN | 25 | 0 | T |
| AI298798 | UNKNOWN | 20 | 0 | T |
| AI298826 | UNKNOWN | 19 | 0 | T |
| AI298923 | UNKNOWN | 17 | 0 | T |
| AI299035 | UNKNOWN | 45 | 0 | T |
| AI299040 | UNKNOWN | 13 | 368 | A |
| AI299182 | UNKNOWN | 62 | 0 | T |
| AI299182 | UNKNOWN | 18 | 232 | G |
| AI299182 | UNKNOWN | 13 | 161 | C |
| AI299303 | UNKNOWN | 65 | 0 | T |
| AI299303 | UNKNOWN | 14 | 76 | A |
| AI299303 | UNKNOWN | 12 | 216 | G |
| AI299356 | UNKNOWN | 18 | 319 | T |
| AI299404 | UNKNOWN | 17 | 163 | A |
| AI299432 | UNKNOWN | 13 | 151 | T |
| AI299445 | UNKNOWN | 14 | 37 | T |
| AI299461 | UNKNOWN | 31 | 0 | T |
| AI299478 | UNKNOWN | 16 | 0 | T |
| AI299509 | UNKNOWN | 24 | 0 | T |
| AI299650 | UNKNOWN | 83 | 0 | T |
| AI299650 | UNKNOWN | 14 | 252 | A |
| AI299650 | UNKNOWN | 13 | 232 | C |
| AI299677 | UNKNOWN | 61 | 0 | T |
| AI299694 | UNKNOWN | 17 | 149 | T |
| AI299705 | UNKNOWN | 49 | 0 | T |
| AI299705 | UNKNOWN | 13 | 69 | A |
| AI299746 | UNKNOWN | 38 | 0 | T |
| AI299746 | UNKNOWN | 12 | 193 | A |
| AI299854 | UNKNOWN | 26 | 0 | T |
| AI299877 | UNKNOWN | 29 | 0 | T |
| AI299903 | UNKNOWN | 51 | 0 | T |
| AI299903 | UNKNOWN | 12 | 120 | C |
| AI299952 | UNKNOWN | 12 | 0 | T |
| AI299953 | UNKNOWN | 58 | 0 | T |
| AI299953 | UNKNOWN | 17 | 107 | A |
| AI299961 | UNKNOWN | 33 | 2 | T |
| AI300008 | UNKNOWN | 17 | 409 | A |
| AI300055 | UNKNOWN | 20 | 0 | T |
| AI300077 | UNKNOWN | 15 | 0 | T |
| AI300116 | UNKNOWN | 27 | 0 | T |
| AI300116 | UNKNOWN | 13 | 514 | A |

TABLE 1-continued

| Genbank # | Region | # reps | Position | Unit sequence |
|---|---|---|---|---|
| AI300123 | UNKNOWN | 53 | 0 | T |
| AI300123 | UNKNOWN | 14 | 221 | G |
| AI300168 | UNKNOWN | 13 | 0 | T |
| AI300190 | UNKNOWN | 14 | 305 | T |
| AI300220 | UNKNOWN | 24 | 0 | T |
| AI300233 | UNKNOWN | 47 | 0 | T |
| AI300248 | UNKNOWN | 36 | 20 | T |
| AI300248 | UNKNOWN | 19 | 0 | T |
| AI300248 | UNKNOWN | 13 | 89 | A |
| AI300294 | UNKNOWN | 73 | 0 | T |
| AI300294 | UNKNOWN | 22 | 110 | G |
| AI300354 | UNKNOWN | 66 | 0 | T |
| AI300354 | UNKNOWN | 18 | 263 | G |
| AI300354 | UNKNOWN | 13 | 382 | C |
| AI300362 | UNKNOWN | 16 | 0 | T |
| AI300425 | UNKNOWN | 15 | 0 | T |
| AI300504 | UNKNOWN | 14 | 46 | A |
| AI300542 | UNKNOWN | 15 | 0 | T |
| AI300557 | UNKNOWN | 16 | 0 | T |
| AI300564 | UNKNOWN | 48 | 0 | T |
| AI300572 | UNKNOWN | 12 | 0 | T |
| AI300574 | UNKNOWN | 12 | 0 | T |
| AI300575 | UNKNOWN | 45 | 0 | T |
| AI300660 | UNKNOWN | 49 | 0 | T |
| AI300730 | UNKNOWN | 53 | 0 | T |
| AI300808 | UNKNOWN | 54 | 0 | T |
| AI300808 | UNKNOWN | 13 | 207 | A |
| AI300832 | UNKNOWN | 30 | 0 | T |
| AI300834 | UNKNOWN | 28 | 0 | T |
| AI300913 | UNKNOWN | 19 | 0 | T |
| AI301046 | UNKNOWN | 59 | 0 | T |
| AI301123 | UNKNOWN | 28 | 0 | T |
| AI301203 | UNKNOWN | 25 | 0 | T |
| AI301227 | UNKNOWN | 12 | 0 | T |
| AI301241 | UNKNOWN | 12 | 0 | T |
| AI301319 | UNKNOWN | 29 | 0 | T |
| AI301335 | UNKNOWN | 16 | 0 | T |
| AI301449 | UNKNOWN | 47 | 0 | T |
| AI301451 | UNKNOWN | 25 | 0 | T |
| AI301507 | UNKNOWN | 84 | 0 | T |
| AI301507 | UNKNOWN | 15 | 371 | G |
| AI301507 | UNKNOWN | 14 | 299 | G |
| AI301512 | UNKNOWN | 3.85 | 12 | GGTGTCC |
| AI301513 | UNKNOWN | 22 | 0 | T |
| AI301625 | UNKNOWN | 14 | 0 | T |
| AI301670 | UNKNOWN | 18 | 0 | T |
| AI301734 | UNKNOWN | 25 | 0 | T |
| AI301973 | UNKNOWN | 27 | 0 | T |
| AI302188 | UNKNOWN | 12 | 175 | A |
| AI302216 | UNKNOWN | 31 | 0 | T |
| AI302499 | UNKNOWN | 31 | 21 | T |
| AI302499 | UNKNOWN | 20 | 0 | T |
| AI302499 | UNKNOWN | 13 | 92 | G |
| AI302500 | UNKNOWN | 29 | 0 | T |
| AI302557 | UNKNOWN | 19 | 0 | T |
| AI302559 | UNKNOWN | 73 | 0 | T |
| AI302560 | UNKNOWN | 27 | 0 | T |
| AI302590 | UNKNOWN | 56 | 0 | T |
| AI302637 | UNKNOWN | 47 | 32 | T |
| AI302637 | UNKNOWN | 30 | 0 | T |
| AI302637 | UNKNOWN | 16 | 222 | G |
| AI302707 | UNKNOWN | 13 | 214 | T |
| AI302775 | UNKNOWN | 43 | 0 | T |
| AI302822 | UNKNOWN | 12 | 100 | T |
| AI302868 | UNKNOWN | 22 | 0 | T |
| AI302868 | UNKNOWN | 16 | 248 | C |
| AI302868 | UNKNOWN | 12 | 172 | A |
| AI302910 | UNKNOWN | 91 | 0 | T |
| AI302910 | UNKNOWN | 15 | 226 | A |
| AI304392 | UNKNOWN | 12 | 663 | T |
| AI304663 | UNKNOWN | 42 | 0 | T |
| AI304787 | UNKNOWN | 21 | 0 | T |
| AI304861 | UNKNOWN | 25 | 0 | T |
| AI304876 | UNKNOWN | 13 | 0 | T |
| AI305114 | UNKNOWN | 18 | 828 | A |
| AI305189 | UNKNOWN | 41 | 32 | T |
| AI305189 | UNKNOWN | 29 | 0 | T |

TABLE 1-continued

| Genbank # | Region | # reps | Position | Unit sequence |
|---|---|---|---|---|
| AI305189 | UNKNOWN | 17 | 340 | C |
| AI305189 | UNKNOWN | 12 | 158 | A |
| AI305202 | UNKNOWN | 13 | 0 | T |
| AI305227 | UNKNOWN | 27 | 322 | T |
| AI305293 | UNKNOWN | 27 | 71 | A |
| AI305310 | UNKNOWN | 20 | 120 | A |
| AI305318 | UNKNOWN | 25 | 83 | A |
| AI305327 | UNKNOWN | 30 | 106 | A |
| AI305430 | UNKNOWN | 24 | 127 | A |
| AI305547 | UNKNOWN | 20 | 331 | A |
| AI305578 | UNKNOWN | 20 | 118 | A |
| AI305650 | UNKNOWN | 29 | 76 | A |
| AI305745 | UNKNOWN | 40 | 62 | A |
| AI305747 | UNKNOWN | 30 | 106 | A |
| AI305806 | UNKNOWN | 62 | 0 | T |
| AI305806 | UNKNOWN | 13 | 113 | G |
| AI306037 | UNKNOWN | 29 | 139 | A |
| AI306208 | UNKNOWN | 25 | 109 | A |
| AI306287 | UNKNOWN | 28 | 116 | A |
| AI306363 | UNKNOWN | 23 | 218 | A |
| AI306378 | UNKNOWN | 19 | 207 | A |
| AI306542 | UNKNOWN | 15 | 373 | T |
| AI306562 | UNKNOWN | 60 | 0 | T |
| AI306562 | UNKNOWN | 14 | 312 | C |
| AI306590 | UNKNOWN | 44 | 0 | T |
| AI306610 | UNKNOWN | 60 | 0 | T |
| AI306613 | UNKNOWN | 93 | 0 | T |
| AI306685 | UNKNOWN | 51 | 0 | T |
| AI306685 | UNKNOWN | 12 | 74 | A |
| AI306705 | UNKNOWN | 87 | 0 | T |
| AI306705 | UNKNOWN | 13 | 118 | G |
| AI306705 | UNKNOWN | 12 | 174 | A |
| AI306706 | UNKNOWN | 76 | 0 | T |
| AI306706 | UNKNOWN | 13 | 126 | C |
| AI306740 | UNKNOWN | 15 | 0 | T |
| AI306789 | UNKNOWN | 29 | 145 | A |
| AI306803 | UNKNOWN | 28 | 84 | A |
| AI306831 | UNKNOWN | 23 | 83 | A |
| AI306853 | UNKNOWN | 30 | 68 | A |
| AI306958 | UNKNOWN | 23 | 84 | A |
| AI306964 | UNKNOWN | 27 | 108 | A |
| AI306966 | UNKNOWN | 23 | 146 | A |
| AI306979 | UNKNOWN | 27 | 157 | A |
| AI307022 | UNKNOWN | 14 | 110 | A |
| AI307056 | UNKNOWN | 18 | 134 | A |
| AI307086 | UNKNOWN | 31 | 210 | A |
| AI307097 | UNKNOWN | 12 | 110 | A |
| AI307210 | UNKNOWN | 85 | 21 | A |
| AI307247 | UNKNOWN | 18 | 0 | T |
| AI307285 | UNKNOWN | 73 | 0 | T |
| AI307456 | UNKNOWN | 55 | 20 | A |
| AI307459 | UNKNOWN | 67 | 20 | A |
| AI307477 | UNKNOWN | 29 | 57 | A |
| AI307477 | UNKNOWN | 7 | 19 | A |
| AI307479 | UNKNOWN | 28 | 331 | A |
| AI307480 | UNKNOWN | 27 | 149 | A |
| AI307483 | UNKNOWN | 26 | 122 | A |
| AI307490 | UNKNOWN | 29 | 107 | A |
| AI307505 | UNKNOWN | 52 | 5 | A |
| AI307513 | UNKNOWN | 43 | 19 | A |
| AI307514 | UNKNOWN | 31 | 154 | A |
| AI307514 | UNKNOWN | 14 | 139 | A |
| AI307515 | UNKNOWN | 45 | 19 | A |
| AI307529 | UNKNOWN | 26 | 112 | A |
| AI307538 | UNKNOWN | 42 | 20 | A |
| AI307565 | UNKNOWN | 27 | 267 | A |
| AI307572 | UNKNOWN | 24 | 249 | A |
| AI307578 | UNKNOWN | 73 | 19 | A |
| AI307579 | UNKNOWN | 25 | 29 | A |
| AI307588 | UNKNOWN | 28 | 324 | A |
| AI307608 | UNKNOWN | 13 | 354 | A |
| AI307615 | UNKNOWN | 13 | 0 | T |
| AI307632 | UNKNOWN | 17 | 0 | T |
| AI307716 | UNKNOWN | 27 | 329 | A |
| AI307719 | UNKNOWN | 31 | 65 | A |
| AI307728 | UNKNOWN | 30 | 259 | A |
| AI307738 | UNKNOWN | 29 | 84 | A |

TABLE 1-continued

| Genbank # | Region | # reps | Position | Unit sequence |
|---|---|---|---|---|
| AI307769 | UNKNOWN | 33 | 0 | T |
| AI307795 | UNKNOWN | 35 | 0 | T |
| AI307797 | UNKNOWN | 15 | 0 | T |
| AI307912 | UNKNOWN | 23 | 101 | A |
| AI308026 | UNKNOWN | 32 | 57 | A |
| AI308165 | UNKNOWN | 12.5 | 239 | TCTA |
| AI308165 | UNKNOWN | 6 | 0 | T |
| AI308193 | UNKNOWN | 10.5 | 100 | AT |
| AI308196 | UNKNOWN | 2.5 | 55 | TTTTTTCCTTCCTTCC (SEQ ID NO: 107) |
| AI308196 | UNKNOWN | 5 | 96 | TCCT |
| AI308196 | UNKNOWN | 34 | 0 | T |
| AI308196 | UNKNOWN | 16 | 391 | A |
| AI308270 | UNKNOWN | 19 | 131 | A |
| AI308383 | UNKNOWN | 17 | 80 | A |
| AI308340 | UNKNOWN | 31 | 86 | A |
| AI308342 | UNKNOWN | 24 | 106 | A |
| AI308429 | UNKNOWN | 26 | 179 | A |
| AI308446 | UNKNOWN | 21 | 122 | A |
| AI308461 | UNKNOWN | 21 | 93 | A |
| AI308507 | UNKNOWN | 19 | 114 | A |
| AI308518 | UNKNOWN | 10.25 | 53 | AGAA |
| AI308518 | UNKNOWN | 10.5 | 35 | AG |
| AI308518 | UNKNOWN | 21 | 103 | A |
| AI308543 | UNKNOWN | 22 | 85 | A |
| AI308590 | UNKNOWN | 16 | 107 | A |
| AI308592 | UNKNOWN | 18 | 122 | A |
| AI308602 | UNKNOWN | 16 | 291 | A |
| AI308612 | UNKNOWN | 23 | 98 | A |
| AI308617 | UNKNOWN | 24 | 110 | A |
| AI308785 | UNKNOWN | 0 | 0 | T |
| AI308790 | UNKNOWN | 34 | 0 | T |
| AI308790 | UNKNOWN | 14 | 116 | C |
| AI308798 | UNKNOWN | 31 | 0 | T |
| AI308885 | UNKNOWN | 26 | 53 | A |
| AI309016 | UNKNOWN | 8.5 | 379 | AG |
| AI309016 | UNKNOWN | 15 | 0 | T |
| AI309037 | UNKNOWN | 21 | 0 | T |
| AI309045 | UNKNOWN | 16 | 393 | T |
| AI309075 | UNKNOWN | 4.75 | 51 | AAGA |
| AI309075 | UNKNOWN | 4.75 | 103 | AAGG |
| AI309075 | UNKNOWN | 28 | 123 | A |
| AI309080 | UNKNOWN | 28 | 229 | A |
| AI309187 | UNKNOWN | 51 | 0 | T |
| AI309235 | UNKNOWN | 33 | 0 | T |
| AI309244 | UNKNOWN | 72 | 0 | T |
| AI309244 | UNKNOWN | 16 | 299 | G |
| AI309244 | UNKNOWN | 15 | 182 | A |
| AI309244 | UNKNOWN | 14 | 264 | C |
| AI309272 | UNKNOWN | 26 | 0 | T |
| AI309306 | UNKNOWN | 66 | 0 | T |
| AI309306 | UNKNOWN | 17 | 88 | A |
| AI309313 | UNKNOWN | 15 | 0 | T |
| AI309321 | UNKNOWN | 16 | 0 | T |
| AI309322 | UNKNOWN | 13.5 | 160 | TA |
| AI309322 | UNKNOWN | 15 | 0 | T |
| AI309330 | UNKNOWN | 15 | 0 | T |
| AI309334 | UNKNOWN | 16 | 0 | T |
| AI309351 | UNKNOWN | 20 | 84 | A |
| AI309371 | UNKNOWN | 25 | 174 | A |
| AI309384 | UNKNOWN | 1.4 | 363 | A |
| AI309395 | UNKNOWN | 30 | 244 | A |
| AI309398 | UNKNOWN | 29 | 276 | A |
| AI309404 | UNKNOWN | 27 | 338 | A |
| AI309405 | UNKNOWN | 27 | 200 | A |
| AI309407 | UNKNOWN | 30 | 122 | A |
| AI309441 | UNKNOWN | 29 | 61 | A |
| AI309441 | UNKNOWN | 16 | 19 | A |
| AI309443 | UNKNOWN | 77 | 19 | A |
| AI309448 | UNKNOWN | 16 | 108 | T |
| AI309515 | UNKNOWN | 24 | 87 | A |
| AI309523 | UNKNOWN | 16 | 120 | A |
| AI309589 | UNKNOWN | 53 | 0 | T |
| AI309589 | UNKNOWN | 21 | 157 | A |
| AI309644 | UNKNOWN | 46 | 0 | T |
| AI309677 | UNKNOWN | 15 | 136 | A |
| AI309701 | UNKNOWN | 23 | 97 | A |
| AI309769 | UNKNOWN | 68 | 0 | T |

TABLE 1-continued

| Genbank # | Region | # reps | Position | Unit sequence |
|---|---|---|---|---|
| AI309851 | UNKNOWN | 19 | 0 | T |
| AI309877 | UNKNOWN | 25 | 99 | A |
| AI309889 | UNKNOWN | 24 | 163 | A |
| AI309989 | UNKNOWN | 31 | 0 | T |
| AI309993 | UNKNOWN | 39 | 0 | T |
| AI309993 | UNKNOWN | 16 | 131 | G |
| AI310035 | UNKNOWN | 23 | 106 | A |
| AI310134 | UNKNOWN | 19 | 0 | T |
| AI310135 | UNKNOWN | 15 | 0 | T |
| AI310139 | UNKNOWN | 14 | 0 | T |
| AI310146 | UNKNOWN | 15 | 0 | T |
| AI310151 | UNKNOWN | 15 | 0 | T |
| AI310155 | UNKNOWN | 79 | 0 | T |
| AI310155 | UNKNOWN | 17 | 177 | C |
| AI310155 | UNKNOWN | 16 | 209 | G |
| AI310180 | UNKNOWN | 16 | 139 | A |
| AI310332 | UNKNOWN | 86 | 0 | T |
| AI310332 | UNKNOWN | 23 | 185 | C |
| AI310332 | UNKNOWN | 14 | 121 | A |
| AI310332 | UNKNOWN | 13 | 108 | G |
| AI310460 | UNKNOWN | 48 | 0 | T |
| AI310500 | UNKNOWN | 79 | 0 | T |
| AI310500 | UNKNOWN | 18 | 339 | G |
| AI310500 | UNKNOWN | 15 | 103 | G |
| AI310500 | UNKNOWN | 15 | 420 | A |
| AI310500 | UNKNOWN | 12 | 162 | C |
| AI310500 | UNKNOWN | 12 | 383 | A |
| AI310504 | UNKNOWN | 79 | 0 | T |
| AI310504 | UNKNOWN | 15 | 103 | G |
| AI310504 | UNKNOWN | 15 | 420 | A |
| AI310504 | UNKNOWN | 13 | 162 | C |
| AI310504 | UNKNOWN | 12 | 383 | A |
| AI310519 | UNKNOWN | 32 | 0 | T |
| AI310519 | UNKNOWN | 13 | 81 | G |
| AI310535 | UNKNOWN | 29 | 62 | A |
| AI310577 | UNKNOWN | 7 | 135 | GA |
| AI310577 | UNKNOWN | 22 | 112 | A |
| AI310589 | UNKNOWN | 28 | 111 | A |
| AI310592 | UNKNOWN | 70 | 19 | A |
| AI310606 | UNKNOWN | 57 | 23 | A |
| AI310626 | UNKNOWN | 13 | 93 | A |
| AI310655 | UNKNOWN | 28 | 146 | A |
| AI310663 | UNKNOWN | 16 | 346 | A |
| AI310669 | UNKNOWN | 27 | 218 | A |
| AI310680 | UNKNOWN | 31 | 286 | A |
| AI310709 | UNKNOWN | 73 | 0 | T |
| AI310709 | UNKNOWN | 15 | 225 | G |
| AI310709 | UNKNOWN | 14 | 305 | A |
| AI310783 | UNKNOWN | 30 | 233 | A |
| AI310787 | UNKNOWN | 29 | 300 | A |
| AI310844 | UNKNOWN | 31 | 68 | A |
| AI310844 | UNKNOWN | 15 | 45 | A |
| AI310855 | UNKNOWN | 26 | 181 | A |
| AI310858 | UNKNOWN | 27 | 204 | A |
| AI310865 | UNKNOWN | 30 | 65 | A |
| AI310879 | UNKNOWN | 3.15 | 88 | AAAGAAAGAAAGA (SEQ ID NO: 108) |
| AI310879 | UNKNOWN | 6 | 136 | AAAG |
| AI310879 | UNKNOWN | 5.25 | 82 | AGAA |
| AI310879 | UNKNOWN | 5 | 42 | AGGA |
| AI310879 | UNKNOWN | 29 | 174 | A |
| AI310927 | UNKNOWN | 73 | 19 | A |
| AI310940 | UNKNOWN | 42 | 25 | A |
| AI310949 | UNKNOWN | 29 | 89 | A |
| AI310951 | UNKNOWN | 44 | 43 | A |
| AI310992 | UNKNOWN | 16 | 303 | A |
| AI311047 | UNKNOWN | 31 | 83 | A |
| AI311050 | UNKNOWN | 4.75 | 35 | AAGA |
| AI311050 | UNKNOWN | 28 | 86 | A |
| AI311058 | UNKNOWN | 24 | 97 | A |
| AI311070 | UNKNOWN | 43 | 0 | T |
| AI311091 | UNKNOWN | 43 | 0 | T |
| AI311094 | UNKNOWN | 38 | 0 | T |
| AI311146 | UNKNOWN | 28 | 333 | A |
| AI311185 | UNKNOWN | 28 | 62 | A |
| AI311186 | UNKNOWN | 29 | 107 | A |
| AI311226 | UNKNOWN | 18 | 350 | A |
| AI311234 | UNKNOWN | 27 | 204 | A |

TABLE 1-continued

| Genbank # | Region | # reps | Position | Unit sequence |
|---|---|---|---|---|
| AI311241 | UNKNOWN | 41 | 19 | A |
| AI311250 | UNKNOWN | 24 | 160 | A |
| AI311284 | UNKNOWN | 24 | 153 | A |
| AI311289 | UNKNOWN | 25 | 395 | A |
| AI311290 | UNKNOWN | 31 | 122 | A |
| AI311304 | UNKNOWN | 47 | 0 | T |
| AI311317 | UNKNOWN | 18 | 0 | T |
| AI311321 | UNKNOWN | 12 | 0 | T |
| AI311332 | UNKNOWN | 29 | 155 | A |
| AI311365 | UNKNOWN | 30 | 321 | A |
| AI311472 | UNKNOWN | 56 | 0 | T |
| AI311509 | UNKNOWN | 28 | 124 | A |
| AI311511 | UNKNOWN | 29 | 92 | A |
| AI311534 | UNKNOWN | 34 | 0 | T |
| AI311557 | UNKNOWN | 12 | 0 | T |
| AI311558 | UNKNOWN | 45 | 0 | T |
| AI311599 | UNKNOWN | 31 | 75 | A |
| AI311618 | UNKNOWN | 21 | 100 | A |
| AI311626 | UNKNOWN | 3.5 | 62 | AGAGAA |
| AI311626 | UNKNOWN | 9 | 118 | AGAA |
| AI311626 | UNKNOWN | 7 | 53 | GA |
| AI311626 | UNKNOWN | 28 | 156 | A |
| AI311636 | UNKNOWN | 28 | 134 | A |
| AI311753 | UNKNOWN | 12.75 | 94 | AGAA |
| AI311753 | UNKNOWN | 28 | 152 | A |
| AI311779 | UNKNOWN | 23 | 352 | A |
| AI311870 | UNKNOWN | 30 | 191 | A |
| AI311876 | UNKNOWN | 28 | 165 | A |
| AI311883 | UNKNOWN | 27 | 119 | A |
| AI311901 | UNKNOWN | 28 | 92 | A |
| AI311924 | UNKNOWN | 9 | 173 | GA |
| AI311924 | UNKNOWN | 7.5 | 149 | GA |
| AI311926 | UNKNOWN | 95 | 0 | T |
| AI311926 | UNKNOWN | 21 | 105 | A |
| AI311926 | UNKNOWN | 12 | 173 | G |
| AI311943 | UNKNOWN | 28 | 163 | A |
| AI311986 | UNKNOWN | 14 | 100 | A |
| AI312040 | UNKNOWN | 50 | 0 | T |
| AI312131 | UNKNOWN | 21 | 269 | A |
| AI312137 | UNKNOWN | 28 | 149 | A |
| AI312143 | UNKNOWN | 82 | 19 | A |
| AI312146 | UNKNOWN | 95 | 20 | A |
| AI312164 | UNKNOWN | 28 | 296 | A |
| AI312165 | UNKNOWN | 52 | 21 | A |
| AI312168 | UNKNOWN | 49 | 19 | A |
| AI312188 | UNKNOWN | 20 | 78 | A |
| AI312234 | UNKNOWN | 30 | 73 | A |
| AI312281 | UNKNOWN | 15 | 278 | A |
| AI312295 | UNKNOWN | 26 | 89 | A |
| AI312298 | UNKNOWN | 27 | 68 | A |
| AI312298 | UNKNOWN | 13 | 38 | A |
| AI312325 | UNKNOWN | 89 | 19 | A |
| AI312326 | UNKNOWN | 29 | 24 | A |
| AI312339 | UNKNOWN | 94 | 20 | A |
| AI312351 | UNKNOWN | 22 | 122 | A |
| AI312353 | UNKNOWN | 43 | 22 | A |
| AI312358 | UNKNOWN | 27 | 106 | A |
| AI312397 | UNKNOWN | 29 | 46 | A |
| AI312397 | UNKNOWN | 25 | 19 | A |
| AI312399 | UNKNOWN | 70 | 45 | A |
| AI312428 | UNKNOWN | 105 | 51 | A |
| AI312438 | UNKNOWN | 27 | 206 | A |
| AI312445 | UNKNOWN | 28 | 260 | A |
| AI312454 | UNKNOWN | 31 | 133 | A |
| AI312481 | UNKNOWN | 28 | 124 | A |
| AI312542 | UNKNOWN | 94 | 29 | T |
| AI312542 | UNKNOWN | 27 | 200 | A |
| AI312542 | UNKNOWN | 21 | 0 | T |
| AI312542 | UNKNOWN | 21 | 310 | C |
| AI312542 | UNKNOWN | 16 | 141 | A |
| AI312542 | UNKNOWN | 14 | 256 | C |
| AI312542 | UNKNOWN | 12 | 177 | C |
| AI312596 | UNKNOWN | 17 | 0 | T |
| AI312766 | UNKNOWN | 29 | 0 | T |
| AI312829 | UNKNOWN | 47 | 0 | T |
| AI312955 | UNKNOWN | 27 | 181 | A |
| AI312963 | UNKNOWN | 49 | 33 | A |

TABLE 1-continued

| Genbank # | Region | # reps | Position | Unit sequence |
|---|---|---|---|---|
| AI312963 | UNKNOWN | 13 | 19 | A |
| AI312965 | UNKNOWN | 29 | 224 | A |
| AI312980 | UNKNOWN | 28 | 66 | A |
| AI313043 | UNKNOWN | 16 | 128 | A |
| AI313068 | UNKNOWN | 27 | 128 | A |
| AI313085 | UNKNOWN | 14 | 106 | A |
| AI313160 | UNKNOWN | 6 | 67 | GAG |
| AI313306 | UNKNOWN | 22 | 88 | A |
| AI313322 | UNKNOWN | 30 | 127 | A |
| AI313323 | UNKNOWN | 30 | 174 | A |
| AI313333 | UNKNOWN | 31 | 104 | A |
| AI313352 | UNKNOWN | 77 | 20 | A |
| AI313464 | UNKNOWN | 46 | 0 | T |
| AI318044 | UNKNOWN | 28 | 0 | T |
| AI318069 | UNKNONN | 30 | 0 | T |
| AI318089 | UNKNOWN | 36 | 0 | T |
| AI318089 | UNKNOWN | 12 | 263 | A |
| AI318173 | UNKNOWN | 16 | 287 | A |
| AI318283 | UNKNOWN | 7.5 | 38 | AG |
| AI318283 | UNKNOWN | 26 | 72 | A |
| AI332373 | UNKNOWN | 22 | 0 | T |
| AI332432 | UNKNOWN | 34 | 0 | T |
| AI332437 | UNKNOWN | 16 | 0 | T |
| AI332476 | UNKNOWN | 12 | 3 | T |
| AI332676 | UNKNOWN | 17 | 135 | A |
| AI332682 | UNKNOWN | 6 | 127 | ATAA |
| AI332710 | UNKNOWN | 10 | 226 | AAAC |
| AI332710 | UNKNOWN | 21 | 141 | T |
| AI332712 | UNKNOWN | 37 | 0 | T |
| AI332957 | UNKNOWN | 47 | 0 | T |
| AI332957 | UNKNOWN | 21 | 181 | A |
| AI332957 | UNKNOWN | 14 | 252 | C |
| AI332957 | UNKNOWN | 12 | 47 | A |
| AI332963 | UNKNOWN | 40 | 0 | T |
| AI332981 | UNKNOWN | 13 | 0 | T |
| AI333006 | UNKNOWN | 9 | 275 | TA |
| AI333006 | UNKNOWN | 17 | 0 | T |
| AI333104 | UNKNOWN | 56 | 0 | T |
| AI333104 | UNKNOWN | 16 | 103 | A |
| AI333104 | UNKNOWN | 12 | 129 | G |
| AI333122 | UNKNOWN | 44 | 0 | T |
| AI333125 | UNKNOWN | 35 | 33 | T |
| AI333125 | UNKNOWN | 32 | 0 | T |
| AI333125 | UNKNOWN | 20 | 372 | C |
| AI333125 | UNKNOWN | 15 | 102 | A |
| AI333125 | UNKNOWN | 13 | 85 | A |
| AI333287 | UNKNOWN | 6.5 | 122 | TG |
| AI333298 | UNKNOWN | 10.5 | 293 | TG |
| AI333299 | UNKNOWN | 4.5 | 206 | AAGG |
| AI333299 | UNKNOWN | 7.5 | 179 | AG |
| AI333299 | UNKNOWN | 18 | 0 | T |
| AI333397 | UNKNOWN | 12 | 0 | T |
| AI333552 | UNKNOWN | 53 | 0 | T |
| AI333600 | UNKNOWN | 12 | 401 | T |
| AI333638 | UNKNOWN | 83 | 0 | T |
| AI333638 | UNKNOWN | 17 | 144 | C |
| AI333638 | UNKNOWN | 15 | 106 | A |
| AI333643 | UNKNOWN | 17 | 0 | T |
| AI333659 | UNKNOWN | 14 | 141 | A |
| AI334040 | UNKNOWN | 19 | 0 | T |
| AI334248 | UNKNOWN | 15 | 119 | T |
| AI334253 | UNKNOWN | 39 | 0 | T |
| AI334354 | UNKNOWN | 25 | 154 | T |
| AI334424 | UNKNOWN | 19 | 0 | T |
| AI334435 | UNKNOWN | 29 | 313 | A |
| AI334439 | UNKNOWN | 23 | 88 | A |
| AI334443 | UNKNOWN | 41 | 366 | A |
| AI334451 | UNKNOWN | 16 | 197 | A |
| AI334452 | UNKNOWN | 71 | 20 | A |
| AI334455 | UNKNOWN | 26 | 111 | A |
| AI334527 | UNKNOWN | 20 | 152 | A |
| AI334574 | UNKNOWN | 14 | 200 | A |
| AI334621 | UNKNOWN | 54 | 0 | T |
| AI334714 | UNKNOWN | 67 | 0 | T |
| AI334731 | UNKNOWN | 33 | 0 | T |
| AI334731 | UNKNOWN | 23 | 205 | A |
| AI334735 | UNKNOWN | 12 | 102 | A |

TABLE 1-continued

| Genbank # | Region | # reps | Position | Unit sequence |
|---|---|---|---|---|
| AI334777 | UNKNOWN | 65 | 0 | T |
| AI334777 | UNKNOWN | 19 | 243 | G |
| AI334788 | UNKNOWN | 33 | 0 | T |
| AI334797 | UNKNOWN | 6.5 | 85 | GT |
| AI334808 | UNKNOWN | 15 | 0 | T |
| AI334820 | UNKNOWN | 71 | 0 | T |
| AI334918 | UNKNOWN | 30 | 85 | A |
| AI335038 | UNKNOWN | 27 | 182 | A |
| AI335048 | UNKNOWN | 24 | 88 | A |
| AI335065 | UNKNOWN | 29 | 139 | A |
| AI335082 | UNKNOWN | 13 | 0 | T |
| AI335100 | UNKNOWN | 13.66 | 149 | TTA |
| AI335118 | UNKNOWN | 18 | 144 | A |
| AI335154 | UNKNOWN | 18 | 169 | A |
| AI335155 | UNKNOWN | 28 | 153 | A |
| AI335227 | UNKNOWN | 29 | 274 | A |
| AI335235 | UNKNOWN | 58 | 22 | A |
| AI335255 | UNKNOWN | 34 | 0 | T |
| AI335277 | UNKNOWN | 2.58 | 228 | TGGAGGATGAGTCCTTC (SEQ ID NO:109) |
| AI335290 | UNKNOWN | 32 | 104 | A |
| AI335290 | UNKNOWN | 13 | 84 | A |
| AI335296 | UNKNOWN | 28 | 215 | A |
| AI335304 | UNKNOWN | 29 | 101 | A |
| AI335308 | UNKNOWN | 27 | 102 | A |
| AI335338 | UNKNOWN | 77 | 0 | T |
| AI335362 | UNKNOWN | 30 | 172 | A |
| AI335375 | UNKNOWN | 24 | 341 | A |
| AI335375 | UNKNOWN | 22 | 38 | A |
| AI335380 | UNKNOWN | 33 | 63 | A |
| AI335380 | UNKNOWN | 22 | 40 | A |
| AI335380 | UNKNOWN | 20 | 19 | A |
| AI335387 | UNKNOWN | 25 | 375 | A |
| AI335393 | UNKNOWN | 27 | 124 | A |
| AI335438 | UNKNOWN | 29 | 142 | A |
| AI335441 | UNKNOWN | 30 | 240 | A |
| AI335458 | UNKNOWN | 12 | 307 | A |
| AI335470 | UNKNOWN | 29 | 137 | A |
| AI335486 | UNKNOWN | 27 | 116 | A |
| AI335508 | UNKNOWN | 27 | 70 | A |
| AI335517 | UNKNOWN | 32 | 81 | A |
| AI335538 | UNKNOWN | 43 | 0 | T |
| AI335547 | UNKNOWN | 41 | 0 | T |
| AI335611 | UNKNOWN | 30 | 0 | T |
| AI335817 | UNKNOWN | 41 | 0 | T |
| AI335919 | UNKNOWN | 9 | 249 | GA |
| AI335919 | UNKNOWN | 8 | 234 | TG |
| AI335995 | UNKNOWN | 12 | 317 | A |
| AI336013 | UNKNOWN | 24 | 0 | T |
| AI336109 | UNKNOWN | 28 | 0 | T |
| AI336204 | UNKNOWN | 13 | 0 | T |
| AI336278 | UNKNOWN | 35 | 0 | T |
| AI336330 | UNKNOWN | 40 | 0 | T |
| AI336403 | UNKNOWN | 46 | 0 | T |
| AI336483 | UNKNOWN | 27 | 262 | A |
| AI336483 | UNKNOWN | 14 | 93 | A |
| AI336507 | UNKNOWN | 6 | 100 | TTG |
| AI336507 | UNKNOWN | 19 | 320 | A |
| AI336514 | UNKNOWN | 3.6 | 191 | AAAAC |
| AI336514 | UNKNOWN | 28 | 369 | A |
| AI336585 | UNKNOWN | 59 | 20 | A |
| AI336591 | UNKNOWN | 15 | 398 | A |
| AI336633 | UNKNOWN | 56 | 58 | A |
| AI336645 | UNKNOWN | 26 | 205 | A |
| AI336662 | UNKNOWN | 65 | 48 | A |
| AI336728 | UNKNOWN | 27 | 162 | A |
| AI336753 | UNKNOWN | 54 | 0 | T |
| AI336754 | UNKNOWN | 61 | 0 | T |
| AI336754 | UNKNOWN | 15 | 219 | A |
| AI336754 | UNKNOWN | 12 | 137 | A |
| AI336759 | UNKNOWN | 30 | 0 | T |
| AI336833 | UNKNOWN | 28 | 0 | T |
| AI336860 | UNKNOWN | 13 | 0 | T |
| AI336885 | UNKNOWN | 17 | 0 | T |
| AI336904 | UNKNOWN | 44 | 0 | T |
| AI336979 | UNKNOWN | 35 | 0 | T |
| AI337028 | UNKNOWN | 16 | 0 | T |
| AI337077 | UNKNOWN | 15 | 0 | T |

TABLE 1-continued

| Genbank # | Region | # reps | Position | Unit sequence |
|---|---|---|---|---|
| AI337079 | UNKNOWN | 14 | 115 | A |
| AI337108 | UNKNOWN | 16 | 0 | T |
| AI337124 | UNKNOWN | 32 | 0 | T |
| AI337124 | UNKNOWN | 12 | 257 | A |
| AI337149 | UNKNOWN | 16 | 284 | T |
| AI337167 | UNKNOWN | 13 | 469 | T |
| AI337186 | UNKNOWN | 54 | 0 | T |
| AI337186 | UNKNOWN | 19 | 191 | A |
| AI337314 | UNKNOWN | 52 | 0 | T |
| AI337314 | UNKNOWN | 14 | 335 | A |
| AI337314 | UNKNOWN | 12 | 196 | A |
| AI337413 | UNKNOWN | 33 | 0 | T |
| AI337588 | UNKNOWN | 28 | 0 | T |
| AI337740 | UNKNOWN | 40 | 0 | T |
| AI337874 | UNKNOWN | 34 | 0 | T |
| AI337876 | UNKNOWN | 28 | 0 | T |
| AI338023 | UNKNOWN | 37 | 0 | T |
| AI338023 | UNKNOWN | 12 | 373 | A |
| AI338060 | UNKNOWN | 57 | 0 | T |
| AI338060 | UNKNOWN | 18 | 231 | C |
| AI338060 | UNKNOWN | 12 | 336 | A |
| AI338159 | UNKNOWN | 56 | 0 | T |
| AI338212 | UNKNOWN | 72 | 0 | T |
| AI338212 | UNKNOWN | 14 | 216 | C |
| AI338236 | UNKNOWN | 15 | 211 | A |
| AI338427 | UNKNOWN | 55 | 0 | T |
| AI338427 | UNKNOWN | 18 | 254 | A |
| AI338427 | UNKNOWN | 14 | 360 | C |
| AI338427 | UNKNOWN | 12 | 181 | G |
| AI338538 | UNKNOWN | 5 | 260 | GAGG |
| AI338592 | UNKNOWN | 15 | 0 | T |
| AI338601 | UNKNOWN | 15 | 0 | T |
| AI338725 | UNKNOWN | 37 | 0 | T |
| AI338876 | UNKNOWN | 57 | 0 | T |
| AI338876 | UNKNOWN | 20 | 57 | A |
| AI338876 | UNKNOWN | 20 | 280 | G |
| AI338884 | UNKNOWN | 3.6 | 9 | TTTGT |
| AI338884 | UNKNOWN | 12 | 177 | T |
| AI338892 | UNKNOWN | 32 | 0 | T |
| AI338892 | UNKNOWN | 13 | 145 | A |
| AI338915 | UNKNOWN | 12 | 0 | T |
| AI339001 | UNKNOWN | 31 | 0 | T |
| AI339001 | UNKNOWN | 14 | 53 | A |
| AI339041 | UNKNOWN | 26 | 0 | T |
| AI339115 | UNKNOWN | 55 | 0 | T |
| AI339115 | UNKNOWN | 15 | 212 | G |
| AI339219 | UNKNOWN | 26 | 0 | T |
| AI339230 | UNKNOWN | 78 | 0 | T |
| AI339253 | UNKNOWN | 32 | 0 | T |
| AI339311 | UNKNOWN | 17 | 158 | A |
| AI339388 | UNKNOWN | 82 | 0 | T |
| AI339388 | UNKNOWN | 18 | 327 | C |
| AI339388 | UNKNOWN | 12 | 158 | A |
| AI339393 | UNKNOWN | 49 | 0 | T |
| AI339410 | UNKNOWN | 12 | 0 | T |
| AI339435 | UNKNOWN | 89 | 0 | T |
| AI339435 | UNKNOWN | 13 | 154 | G |
| AI339496 | UNKNOWN | 28 | 0 | T |
| AI339507 | UNKNOWN | 15 | 0 | T |
| AI339544 | UNKNOWN | 43 | 0 | T |
| AI339667 | UNKNOWN | 15 | 357 | T |
| AI339738 | UNKNOWN | 13 | 0 | T |
| AI339746 | UNKNOWN | 45 | 0 | T |
| AI339748 | UNKNOWN | 17 | 18 | T |
| AI339787 | UNKNOWN | 23 | 0 | T |
| AI339851 | UNKNOWN | 37 | 0 | T |
| AI339851 | UNKNOWN | 22 | 223 | G |
| AI339865 | UNKNOWN | 6.66 | 275 | AGC |
| AI340042 | UNKNOWN | 6.5 | 76 | AC |
| AI340092 | UNKNOWN | 32 | 0 | T |
| AI340101 | UNKNOWN | 2.86 | 64 | CACTCACAGGTCCTGGGTGGACATGAATTTCCGGGGA (SEQ ID NO:110) |
| AI340107 | UNKNOWN | 22 | 0 | T |
| AI340148 | UNKNOWN | 17 | 0 | T |
| AI340203 | UNKNOWN | 30 | 0 | T |
| AI340229 | UNKNOWN | 18 | 0 | T |
| AI340242 | UNKNOWN | 4.75 | 124 | TTTG |

TABLE 1-continued

| Genbank # | Region | # reps | Position | Unit sequence |
|---|---|---|---|---|
| AI340312 | UNKNOWN | 16 | 346 | A |
| AI340316 | UNKNOWN | 37 | 0 | T |
| AI340348 | UNKNOWN | 15 | 0 | T |
| AI340398 | UNKNOWN | 24 | 206 | A |
| AI340416 | UNKNOWN | 25 | 130 | A |
| AI340490 | UNKNOWN | 4.5 | 20 | GAAG |
| AI340490 | UNKNOWN | 28 | 77 | A |
| AI340510 | UNKNOWN | 42 | 20 | A |
| AI340511 | UNKNOWN | 78 | 22 | A |
| AI340512 | UNKNOWN | 30 | 191 | A |
| AI340518 | UNKNOWN | 29 | 233 | A |
| AI340533 | UNKNOWN | 86 | 22 | A |
| AI340537 | UNKNOWN | 67 | 20 | A |
| AI340552 | UNKNOWN | 49 | 23 | A |
| AI340556 | UNKNOWN | 19 | 382 | A |
| AI340581 | UNKNOWN | 28 | 239 | A |
| AI340593 | UNKNOWN | 49 | 23 | A |
| AI340600 | UNKNOWN | 34 | 26 | A |
| AI340603 | UNKNOWN | 95 | 52 | A |
| AI340603 | UNKNOWN | 20 | 29 | A |
| AI340604 | UNKNOWN | 46 | 18 | A |
| AI340606 | UNKNOWN | 16 | 420 | A |
| AI340610 | UNKNOWN | 48 | 20 | A |
| AI340612 | UNKNOWN | 28 | 67 | A |
| AI340618 | UNKNOWN | 25 | 139 | A |
| AI340620 | UNKNOWN | 23 | 311 | A |
| AI340627 | UNKNOWN | 103 | 22 | A |
| AI340629 | UNKNOWN | 27 | 92 | A |
| AI340638 | UNKNOWN | 25 | 91 | A |
| AI340639 | UNKNOWN | 47 | 20 | A |
| AI340641 | UNKNOWN | 24 | 484 | A |
| AI340645 | UNKNOWN | 26 | 172 | A |
| AI340653 | UNKNOWN | 51 | 21 | A |
| AI340659 | UNKNOWN | 80 | 19 | A |
| AI340726 | UNKNOWN | 30 | 88 | A |
| AI340726 | UNKNOWN | 22 | 64 | A |
| AI340731 | UNKNOWN | 30 | 74 | A |
| AI340789 | UNKNOWN | 25 | 74 | A |
| AI340798 | UNKNOWN | 15 | 159 | A |
| AI340819 | UNKNOWN | 25 | 79 | A |
| AI340941 | UNKNOWN | 13.66 | 13 | TTA |
| AI340982 | UNKNOWN | 72 | 22 | T |
| AI340982 | UNKNOWN | 21 | 0 | T |
| AI340982 | UNKNOWN | 17 | 97 | A |
| AI340982 | UNKNOWN | 16 | 253 | C |
| AI340982 | UNKNOWN | 13 | 239 | G |
| AI341029 | UNKNOWN | 25 | 107 | A |
| AI341046 | UNKNOWN | 34 | 119 | A |
| AI341092 | UNKNOWN | 18 | 0 | T |
| AI341167 | UNKNOWN | 3.8 | 0 | TTTCT |
| AI341189 | UNKNOWN | 33 | 0 | T |
| AI341203 | UNKNOWN | 43 | 0 | T |
| AI341233 | UNKNOWN | 6.75 | 124 | AAAC |
| AI341300 | UNKNOWN | 15 | 353 | T |
| AI341423 | UNKNOWN | 9.5 | 287 | CA |
| AI341432 | UNKNOWN | 4.75 | 208 | AAAT |
| AI341432 | UNKNOWN | 18 | 0 | T |
| AI341455 | UNKNOWN | 36 | 0 | T |
| AI341468 | UNKNOWN | 16 | 0 | T |
| AI341491 | UNKNOWN | 13 | 0 | T |
| AI341532 | UNKNOWN | 19 | 0 | T |
| AI341539 | UNKNOWN | 62 | 0 | T |
| AI341543 | UNKNOWN | 16 | 0 | T |
| AI341563 | UNKNOWN | 14 | 275 | A |
| AI341566 | UNKNOWN | 37 | 0 | T |
| AI341571 | UNKNOWN | 17 | 247 | T |
| AI341571 | UNKNOWN | 14 | 0 | T |
| AI341581 | UNKNOWN | 15 | 183 | A |
| AI341602 | UNKNOWN | 7.33 | 263 | CAG |
| AI341603 | UNKNOWN | 48 | 0 | T |
| AI341637 | UNKNOWN | 29 | 0 | T |
| AI341653 | UNKNOWN | 4.75 | 48 | TTTA |
| AI341653 | UNKNOWN | 16 | 101 | T |
| AI341655 | UNKNOWN | 28 | 0 | T |
| AI341669 | UNKNOWN | 52 | 0 | T |
| AI341690 | UNKNOWN | 62 | 0 | T |
| AI341690 | UNKNOWN | 18 | 285 | A |

TABLE 1-continued

| Genbank # | Region | # reps | Position | Unit sequence |
|---|---|---|---|---|
| AI341690 | UNKNOWN | 13 | 101 | C |
| AI341690 | UNKNOWN | 12 | 367 | G |
| AI341730 | UNKNOWN | 15 | 0 | T |
| AI341769 | UNKNOWN | 14 | 0 | T |
| AI341796 | UNKNOWN | 6 | 325 | TTC |
| AI341806 | UNKNOWN | 13 | 190 | A |
| AI341838 | UNKNOWN | 72 | 0 | T |
| AI341838 | UNKNOWN | 15 | 209 | C |
| AI341934 | UNKNOWN | 13 | 0 | T |
| AI342023 | UNKNOWN | 49 | 0 | T |
| AI342037 | UNKNOWN | 21 | 0 | T |
| AI342147 | UNKNOWN | 15 | 0 | T |
| AI342169 | UNKNOWN | 21 | 0 | T |
| AI342210 | UNKNOWN | 53 | 0 | T |
| AI342210 | UNKNOWN | 13 | 164 | G |
| AI342627 | UNKNOWN | 33 | 0 | T |
| AI342642 | UNKNOWN | 12 | 85 | A |
| AI342710 | UNKNOWN | 47 | 0 | T |
| AI342710 | UNKNOWN | 20 | 304 | G |
| AI342710 | UNKNOWN | 12 | 184 | G |
| AI343023 | UNKNOWN | 16 | 406 | A |
| AI343029 | UNKNOWN | 26 | 161 | A |
| AI343030 | UNKNOWN | 56 | 65 | A |
| AI343030 | UNKNOWN | 44 | 20 | A |
| AI343059 | UNKNOWN | 104 | 21 | A |
| AI343076 | UNKNOWN | 31 | 118 | A |
| AI343081 | UNKNOWN | 29 | 82 | A |
| AI343091 | UNKNOWN | 78 | 21 | A |
| AI343112 | UNKNOWN | 116 | 20 | A |
| AI343117 | UNKNOWN | 24 | 381 | A |
| AI343123 | UNKNOWN | 24 | 301 | A |
| AI343135 | UNKNOWN | 29 | 157 | A |
| AI343136 | UNKNOWN | 23 | 150 | A |
| AI343143 | UNKNOWN | 17 | 357 | A |
| AI343144 | UNKNOWN | 30 | 401 | A |
| AI343170 | UNKNOWN | 27 | 59 | A |
| AI343173 | UNKNOWN | 16 | 341 | A |
| AI343173 | UNKNOWN | 12 | 326 | A |
| AI343178 | UNKNOWN | 23 | 306 | A |
| AI343188 | UNKNOWN | 24 | 223 | A |
| AI343190 | UNKNOWN | 29 | 131 | A |
| AI343194 | UNKNOWN | 27 | 154 | A |
| AI343204 | UNKNOWN | 26 | 135 | A |
| AI343210 | UNKNOWN | 29 | 64 | A |
| AI343238 | UNKNOWN | 29 | 103 | A |
| AI343238 | UNKNOWN | 15 | 83 | A |
| AI343263 | UNKNOWN | 18 | 0 | T |
| AI343310 | UNKNOWN | 32 | 106 | A |
| AI343325 | UNKNOWN | 55 | 0 | T |
| AI343349 | UNKNOWN | 13 | 241 | A |
| AI343353 | UNKNOWN | 18 | 142 | GT |
| AI343368 | UNKNOWN | 37 | 0 | T |
| AI343381 | UNKNOWN | 4 | 245 | CAGCA |
| AI343381 | UNKNOWN | 16 | 0 | T |
| AI343391 | UNKNOWN | 7.5 | 300 | TC |
| AI343427 | UNKNOWN | 29 | 0 | T |
| AI343431 | UNKNOWN | 12 | 0 | T |
| AI343447 | UNKNOWN | 27 | 0 | T |
| AI343489 | UNKNOWN | 39 | 0 | T |
| AI343501 | UNKNOWN | 12 | 0 | T |
| AI343564 | UNKNOWN | 12 | 354 | T |
| AI343582 | UNKNOWN | 80 | 0 | T |
| AI343726 | UNKNOWN | 40 | 0 | T |
| AI343726 | UNKNOWN | 12 | 390 | A |
| AI343745 | UNKNOWN | 18 | 0 | T |
| AI343748 | UNKNOWN | 44 | 0 | T |
| AI343815 | UNKNOWN | 12 | 0 | T |
| AI343952 | UNKNOWN | 17 | 0 | T |
| AI343994 | UNKNOWN | 28 | 133 | A |
| AI343995 | UNKNOWN | 44 | 20 | A |
| AI344014 | UNKNOWN | 31 | 109 | A |
| AI344049 | UNKNOWN | 8 | 12 | ATTT |
| AI344049 | UNKNOWN | 17 | 166 | T |
| AI344063 | UNKNOWN | 25 | 101 | A |
| AI344086 | UNKNOWN | 29 | 64 | A |
| AI344095 | UNKNOWN | 25 | 136 | A |
| AI344105 | UNKNOWN | 17 | 0 | T |

TABLE 1-continued

| Genbank # | Region | # reps | Position | Unit sequence |
|---|---|---|---|---|
| AI344124 | UNKNOWN | 5.25 | 473 | AGTT |
| AI344141 | UNKNOWN | 8.07 | 97 | AGCCCTGTCCTCCAGGCGCTCAATCTCC (SEQ ID NO:111) |
| AI344141 | UNKNOWN | 12 | 0 | T |
| AI344146 | UNKNOWN | 25 | 149 | A |
| AI344149 | UNKNOWN | 18 | 369 | A |
| AI344151 | UNKNOWN | 27 | 202 | A |
| AI344161 | UNKNOWN | 23 | 88 | A |
| AI344165 | UNKNOWN | 30 | 108 | A |
| AI344179 | UNKNOWN | 13 | 106 | A |
| AI344185 | UNKNOWN | 30 | 62 | A |
| AI344185 | UNKNOWN | 12 | 30 | A |
| AI344204 | UNKNOWN | 16 | 0 | T |
| AI344217 | UNKNOWN | 18 | 0 | T |
| AI344226 | UNKNOWN | 35 | 0 | T |
| AI344226 | UNKNOWN | 14 | 471 | G |
| AI344234 | UNKNOWN | 28 | 284 | A |
| AI344236 | UNKNOWN | 21 | 18 | GA |
| AI344236 | UNKNOWN | 29 | 194 | A |
| AI344251 | UNKNOWN | 23 | 151 | A |
| AI344261 | UNKNOWN | 27 | 314 | A |
| AI344266 | UNKNOWN | 25 | 137 | A |
| AI344277 | UNKNOWN | 12 | 0 | T |
| AI344288 | UNKNOWN | 12 | 0 | T |
| AI344289 | UNKNOWN | 15 | 0 | T |
| AI344325 | UNKNOWN | 32 | 0 | T |
| AI344328 | UNKNOWN | 14 | 305 | A |
| AI344371 | UNKNOWN | 18 | 0 | T |
| AI344419 | UNKNOWN | 42 | 0 | T |
| AI344435 | UNKNOWN | 14 | 350 | T |
| AI344512 | UNKNOWN | 31 | 0 | T |
| AI344562 | UNKNOWN | 51 | 0 | T |
| AI344616 | UNKNOWN | 38 | 0 | T |
| AI344649 | UNKNOWN | 19 | 0 | T |
| AI344698 | UNKNOWN | 16.5 | 125 | GT |
| AI344779 | UNKNOWN | 45 | 19 | A |
| AI344784 | UNKNOWN | 28 | 343 | A |
| AI344809 | UNKNOWN | 20 | 81 | A |
| AI344819 | UNKNOWN | 7 | 7 | CTA |
| AI344819 | UNKNOWN | 45 | 58 | A |
| AI344825 | UNKNOWN | 6.66 | 2 | CTA |
| AI344825 | UNKNOWN | 22 | 163 | A |
| AI344826 | UNKNOWN | 40 | 42 | A |
| AI344828 | UNKNOWN | 22 | 216 | A |
| AI344834 | UNKNOWN | 28 | 140 | A |
| AI344876 | UNKNOWN | 13 | 95 | A |
| AI344906 | UNKNOWN | 22 | 334 | A |
| AI344935 | UNKNOWN | 70 | 34 | A |
| AI344938 | UNKNOWN | 65 | 21 | A |
| AI344948 | UNKNOWN | 14 | 309 | A |
| AI344954 | UNKNOWN | 30 | 238 | A |
| AI344968 | UNKNOWN | 26 | 142 | A |
| AI344972 | UNKNOWN | 20 | 303 | A |
| AI344982 | UNKNOWN | 15 | 122 | A |
| AI344994 | UNKNOWN | 24 | 134 | A |
| AI344995 | UNKNOWN | 30 | 263 | A |
| AI345005 | UNKNOWN | 78 | 27 | A |
| AI345012 | UNKNOWN | 32 | 353 | A |
| AI345021 | UNKNOWN | 17 | 211 | A |
| AI345025 | UNKNOWN | 30 | 320 | A |
| AI345026 | UNKNOWN | 58 | 33 | A |
| AI345030 | UNKNOWN | 15 | 124 | A |
| AI345068 | UNKNOWN | 15 | 157 | A |
| AI345081 | UNKNOWN | 19 | 244 | A |
| AI345093 | UNKNOWN | 18 | 112 | A |
| AI345102 | UNKNOWN | 10.25 | 54 | AGAA |
| AI345102 | UNKNOWN | 10.5 | 36 | AG |
| AI345102 | UNKNOWN | 23 | 104 | A |
| AI345108 | UNKNOWN | 24 | 389 | A |
| AI345121 | UNKNOWN | 28 | 266 | A |
| AI345123 | UNKNOWN | 25 | 321 | A |
| AI345123 | UNKNOWN | 20 | 153 | A |
| AI345125 | UNKNOWN | 30 | 200 | A |
| AI345158 | UNKNOWN | 19 | 182 | A |
| AI345165 | UNKNOWN | 23 | 100 | A |
| AI345178 | UNKNOWN | 22 | 138 | A |
| AI345198 | UNKNOWN | 26 | 87 | A |

TABLE 1-continued

| Genbank # | Region | # reps | Position | Unit sequence |
|---|---|---|---|---|
| AI345212 | UNKNOWN | 28 | 137 | A |
| AI345236 | UNKNOWN | 29 | 256 | A |
| AI345253 | UNKNOWN | 82 | 23 | A |
| AI345254 | UNKNOWN | 7.5 | 32 | AG |
| AI345254 | UNKNOWN | 13 | 410 | A |
| AI345255 | UNKNOWN | 23 | 237 | A |
| AI345258 | UNKNOWN | 92 | 20 | A |
| AI345264 | UNKNOWN | 28 | 68 | A |
| AI345297 | UNKNOWN | 29 | 169 | A |
| AI345308 | UNKNOWN | 26 | 78 | A |
| AI345312 | UNKNOWN | 28 | 79 | A |
| AI345326 | UNKNOWN | 28 | 197 | A |
| AI345334 | UNKNOWN | 23 | 396 | A |
| AI345336 | UNKNOWN | 25 | 179 | A |
| AI345345 | UNKNOWN | 16 | 251 | A |
| AI345346 | UNKNOWN | 20 | 139 | A |
| AI345370 | UNKNOWN | 70 | 22 | A |
| AI345384 | UNKNOWN | 30 | 91 | A |
| AI345394 | UNKNOWN | 19 | 354 | A |
| AI345414 | UNKNOWN | 25 | 455 | A |
| AI345416 | UNKNOWN | 67 | 78 | A |
| AI345418 | UNKNOWN | 19 | 417 | A |
| AI345442 | UNKNOWN | 28 | 62 | A |
| AI345471 | UNKNOWN | 88 | 23 | A |
| AI345489 | UNKNOWN | 20 | 370 | A |
| AI345497 | UNKNOWN | 24 | 361 | A |
| AI345527 | UNKNOWN | 50 | 23 | A |
| AI345536 | UNKNOWN | 23 | 86 | T |
| AI345536 | UNKNOWN | 23 | 137 | A |
| AI345541 | UNKNOWN | 27 | 122 | A |
| AI345555 | UNKNOWN | 29 | 372 | A |
| AI345559 | UNKNOWN | 27 | 94 | A |
| AI345567 | UNKNOWN | 46 | 62 | A |
| AI345568 | UNKNOWN | 26 | 88 | A |
| AI345590 | UNKNOWN | 25 | 219 | A |
| AI345606 | UNKNOWN | 27 | 211 | A |
| AI345611 | UNKNOWN | 6 | 2 | CTA |
| AI345611 | UNKNOWN | 30 | 224 | A |
| AI345619 | UNKNOWN | 32 | 188 | A |
| AI345629 | UNKNOWN | 23 | 166 | A |
| AI345643 | UNKNOWN | 18 | 246 | A |
| AI345674 | UNKNOWN | 66 | 19 | A |
| AI345681 | UNKNOWN | 21 | 349 | A |
| AI345688 | UNKNOWN | 68 | 68 | A |
| AI345695 | UNKNOWN | 20 | 308 | A |
| AI345703 | UNKNOWN | 32 | 176 | A |
| AI345704 | UNKNOWN | 28 | 139 | A |
| AI345705 | UNKNOWN | 28 | 258 | A |
| AI345709 | UNKNOWN | 28 | 189 | A |
| AI345711 | UNKNOWN | 28 | 240 | A |
| AI345718 | UNKNOWN | 30 | 135 | A |
| AI345721 | UNKNOWN | 24 | 360 | A |
| AI345726 | UNKNOWN | 18 | 393 | A |
| AI345727 | UNKNOWN | 17 | 344 | A |
| AI345735 | UNKNOWN | 126 | 31 | A |
| AI345739 | UNKNOWN | 80 | 20 | A |
| AI345783 | UNKNOWN | 28 | 374 | A |
| AI345794 | UNKNOWN | 28 | 140 | A |
| AI345797 | UNKNOWN | 37 | 259 | A |
| AI345801 | UNKNOWN | 17 | 158 | A |
| AI345804 | UNKNOWN | 14 | 253 | A |
| AI345827 | UNKNOWN | 24 | 337 | A |
| AI345836 | UNKNOWN | 30 | 118 | A |
| AI345842 | UNKNOWN | 27 | 257 | A |
| AI345857 | UNKNOWN | 25 | 156 | A |
| AI345875 | UNKNOWN | 26 | 156 | A |
| AI345896 | UNKNOWN | 13 | 172 | A |
| AI345900 | UNKNOWN | 28 | 142 | A |
| AI346100 | UNKNOWN | 10 | 403 | AC |
| AI346100 | UNKNOWN | 6.5 | 365 | AC |
| AI346149 | UNKNOWN | 33 | 0 | T |
| AI346149 | UNKNOWN | 12 | 61 | A |
| AI346507 | UNKNOWN | 23 | 0 | T |
| AI346561 | UNKNOWN | 14 | 0 | T |
| AI346600 | UNKNOWN | 6 | 315 | CCT |
| AI346656 | UNKNOWN | 16 | 24 | A |
| AI346765 | UNKNOWN | 14 | 330 | T |

TABLE 1-continued

| Genbank # | Region | # reps | Position | Unit sequence |
|---|---|---|---|---|
| AI346858 | UNKNOWN | 36 | 0 | T |
| AI346858 | UNKNOWN | 17 | 240 | A |
| AI346897 | UNKNOWN | 26 | 0 | T |
| AI346910 | UNKNOWN | 3.6 | 345 | AAACA |
| AI347067 | UNKNOWN | 9.5 | 595 | AC |
| AI347067 | UNKNOWN | 7.5 | 581 | AT |
| AI347194 | UNKNOWN | 26 | 0 | T |
| AI347215 | UNKNOWN | 15 | 0 | T |
| AI347333 | UNKNOWN | 5.66 | 187 | GGC |
| AI347334 | UNKNOWN | 32 | 0 | T |
| AI347347 | UNKNOWN | 32 | 0 | T |
| AI347361 | UNKNOWN | 17 | 419 | T |
| AI347396 | UNKNOWN | 40 | 0 | T |
| AI347396 | UNKNOWN | 12 | 103 | A |
| AI347424 | UNKNOWN | 29 | 0 | T |
| AI347569 | UNKNOWN | 81 | 0 | T |
| AI347569 | UNKNOWN | 20 | 121 | A |
| AI347569 | UNKNOWN | 12 | 386 | C |
| AI347694 | UNKNOWN | 14 | 0 | T |
| AI347701 | UNKNOWN | 88 | 0 | T |
| AI347701 | UNKNOWN | 13 | 104 | A |
| AI347706 | UNKNOWN | 16 | 0 | T |
| AI347885 | UNKNOWN | 31 | 0 | T |
| AI348086 | UNKNOWN | 16 | 0 | T |
| AI348378 | UNKNOWN | 22 | 0 | T |
| AI348403 | UNKNOWN | 53 | 0 | T |
| AI348420 | UNKNOWN | 8 | 141 | TA |
| AI348597 | UNKNOWN | 19 | 0 | T |
| AI348731 | UNKNOWN | 19 | 246 | A |
| AI348773 | UNKNOWN | 29 | 99 | A |
| AI348775 | UNKNOWN | 15 | 113 | A |
| AI348780 | UNKNOWN | 29 | 351 | A |
| AI348854 | UNKNOWN | 90 | 22 | A |
| AI348867 | UNKNOWN | 13 | 360 | A |
| AI348870 | UNKNOWN | 49 | 37 | A |
| AI348881 | UNKNOWN | 26 | 211 | A |
| AI348883 | UNKNOWN | 28 | 38 | T |
| AI348883 | UNKNOWN | 27 | 350 | A |
| AI348892 | UNKNOWN | 30 | 323 | A |
| AI348902 | UNKNOWN | 29 | 300 | A |
| AI348911 | UNKNOWN | 33 | 57 | A |
| AI348913 | UNKNOWN | 29 | 175 | A |
| AI348917 | UNKNOWN | 68 | 59 | A |
| AI348954 | UNKNOWN | 16 | 109 | A |
| AI348969 | UNKNOWN | 60 | 24 | A |
| AI348996 | UNKNOWN | 26 | 219 | A |
| AI348996 | UNKNOWN | 19 | 105 | T |
| AI349018 | UNKNOWN | 28 | 267 | A |
| AI349021 | UNKNOWN | 7 | 8 | CTA |
| AI349022 | UNKNOWN | 12 | 398 | A |
| AI349049 | UNKNOWN | 15 | 143 | A |
| AI349119 | UNKNOWN | 32 | 72 | A |
| AI349121 | UNKNOWN | 19 | 237 | A |
| AI349129 | UNKNOWN | 28 | 227 | A |
| AI349130 | UNKNOWN | 18 | 300 | A |
| AI349134 | UNKNOWN | 23 | 72 | A |
| AI349146 | UNKNOWN | 27 | 215 | A |
| AI349151 | UNKNOWN | 40 | 20 | A |
| AI349186 | UNKNOWN | 60 | 23 | A |
| AI349207 | UNKNOWN | 44 | 50 | A |
| AI349211 | UNKNOWN | 37 | 20 | A |
| AI349226 | UNKNOWN | 51 | 36 | A |
| AI349237 | UNKNOWN | 29 | 135 | A |
| AI349246 | UNKNOWN | 59 | 37 | A |
| AI349246 | UNKNOWN | 16 | 20 | A |
| AI349266 | UNKNOWN | 73 | 20 | A |
| AI349276 | UNKNOWN | 34 | 32 | A |
| AI349301 | UNKNOWN | 51 | 0 | T |
| AI349532 | UNKNOWN | 25 | 0 | T |
| AI349598 | UNKNOWN | 116 | 20 | A |
| AI349604 | UNKNOWN | 28 | 277 | A |
| AI349614 | UNKNOWN | 122 | 19 | A |
| AI349622 | UNKNOWN | 73 | 21 | A |
| AI349628 | UNKNOWN | 51 | 20 | A |
| AI349644 | UNKNOWN | 41 | 19 | A |
| AI349645 | UNKNOWN | 127 | 21 | A |
| AI349691 | UNKNOWN | 22 | 174 | A |

TABLE 1-continued

| Genbank # | Region | # reps | Position | Unit sequence |
|---|---|---|---|---|
| AI349697 | UNKNOWN | 19 | 122 | A |
| AI349718 | UNKNOWN | 12 | 105 | A |
| AI349729 | UNKNOWN | 38 | 31 | A |
| AI349733 | UNKNOWN | 23 | 303 | A |
| AI349738 | UNKNOWN | 53 | 19 | A |
| AI349742 | UNKNOWN | 31 | 66 | A |
| AI349742 | UNKNOWN | 27 | 19 | A |
| AI349744 | UNKNOWN | 32 | 316 | A |
| AI349750 | UNKNOWN | 27 | 156 | A |
| AI349773 | UNKNOWN | 26 | 167 | A |
| AI349774 | UNKNOWN | 11.33 | 65 | AGA |
| AI349774 | UNKNOWN | 29 | 97 | A |
| AI349782 | UNKNOWN | 30 | 111 | A |
| AI349787 | UNKNOWN | 70 | 20 | A |
| AI349800 | UNKNOWN | 20 | 259 | A |
| AI349805 | UNKNOWN | 61 | 20 | A |
| AI349817 | UNKNOWN | 29 | 314 | A |
| AI349818 | UNKNOWN | 28 | 199 | A |
| AI349826 | UNKNOWN | 8 | 268 | TG |
| AI349826 | UNKNOWN | 26 | 385 | A |
| AI349840 | UNKNOWN | 20 | 404 | A |
| AI349879 | UNKNOWN | 20 | 88 | A |
| AI349921 | UNKNOWN | 22 | 114 | A |
| AI349922 | UNKNOWN | 22 | 104 | A |
| AI349933 | UNKNOWN | 131 | 21 | A |
| AI349937 | UNKNOWN | 129 | 19 | A |
| AI349954 | UNKNOWN | 13 | 371 | A |
| AI349955 | UNKNOWN | 81 | 19 | A |
| AI349958 | UNKNOWN | 2.81 | 90 | AAAAAAAACC (SEQ ID NO:112) |
| AI349958 | UNKNOWN | 54 | 45 | A |
| AI349963 | UNKNOWN | 16 | 299 | A |
| AI349971 | UNKNOWN | 57 | 21 | A |
| AI349972 | UNKNOWN | 8 | 8 | CTA |
| AI349972 | UNKNOWN | 21 | 94 | A |
| AI350006 | UNKNOWN | 5.91 | 9 | ACAGAAGGGCACGGAACAGTACAATATTCAACCTAAAGAGACAAAAAT (SEQ ID NO:113) |
| AI350006 | UNKNOWN | 17 | 339 | A |
| AI350020 | UNKNOWN | 23 | 118 | A |
| AI350045 | UNKNOWN | 16 | 92 | A |
| AI350093 | UNKNOWN | 49 | 0 | T |
| AI350093 | UNKNOWN | 12 | 411 | G |
| AI350182 | UNKNOWN | 6.33 | 260 | TAT |
| AI350413 | UNKNOWN | 19 | 3 | C |
| AI350489 | UNKNOWN | 51 | 0 | T |
| AI350664 | UNKNOWN | 19 | 34 | T |
| AI350749 | UNKNOWN | 23 | 0 | T |
| AI350851 | UNKNOWN | 25 | 0 | T |
| AI350880 | UNKNOWN | 57 | 0 | T |
| AI351056 | UNKNOWN | 31 | 0 | T |
| AI351062 | UNKNOWN | 5.66 | 289 | CAC |
| AI351063 | UNKNOWN | 63 | 0 | T |
| AI351191 | UNKNOWN | 13.5 | 254 | TG |
| AI351244 | UNKNOWN | 44 | 0 | T |
| AI351333 | UNKNOWN | 20 | 243 | A |
| AI351333 | UNKNOWN | 18 | 0 | T |
| AI351344 | UNKNOWN | 31 | 0 | T |
| AI351344 | UNKNOWN | 12 | 170 | A |
| AI351368 | UNKNOWN | 31 | 0 | T |
| AI351368 | UNKNOWN | 23 | 88 | A |
| AI351412 | UNKNOWN | 19 | 0 | T |
| AI351597 | UNKNOWN | 8 | 387 | AG |
| AI351607 | UNKNOWN | 20 | 0 | T |
| AI351677 | UNNMOKN | 17 | 0 | T |
| AI351689 | UNKNOWN | 30 | 0 | T |
| AI351693 | UNKNOWN | 7.5 | 42 | ATTT |
| AI351693 | UNKNOWN | 34 | 0 | T |
| AI351737 | UNKNOWN | 47 | 0 | T |
| AI351743 | UNKNOWN | 38 | 0 | T |
| AI351753 | UNKNOWN | 6.5 | 168 | AG |
| AI351753 | UNKNOWN | 14 | 198 | T |
| AI351800 | UNKNOWN | 15 | 0 | T |
| AI351807 | UNKNOWN | 37 | 0 | T |
| AI351831 | UNKNOWN | 12 | 0 | T |
| AI351831 | UNKNOWN | 12 | 191 | C |
| AI351835 | UNKNOWN | 22 | 0 | T |
| AI351913 | UNKNOWN | 12 | 254 | A |
| AI351959 | UNKNOWN | 61 | 0 | T |

TABLE 1-continued

| Genbank # | Region | # reps | Position | Unit sequence |
|---|---|---|---|---|
| AI351975 | UNKNOWN | 24 | 0 | T |
| AI352077 | UNKNOWN | 42 | 0 | T |
| AI352084 | UNKNOWN | 16 | 0 | T |
| AI352089 | UNKNOWN | 6.5 | 41 | TG |
| AI352131 | UNKNOWN | 38 | 0 | T |
| AI352131 | UNKNOWN | 16 | 220 | A |
| AI352131 | UNKNOWN | 12 | 88 | A |
| AI352165 | UNKNOWN | 27 | 0 | T |
| AI352165 | UNKNOWN | 13 | 466 | G |
| AI352184 | UNKNOWN | 67 | 0 | T |
| AI352184 | UNKNOWN | 24 | 123 | A |
| AI352184 | UNKNOWN | 14 | 153 | C |
| AI352188 | UNKNOWN | 9 | 105 | GAT |
| AI352188 | UNKNOWN | 6 | 130 | ATA |
| AI352188 | UNKNOWN | 22 | 0 | T |
| AI352235 | UNKNOWN | 46 | 0 | T |
| AI352267 | UNKNOWN | 37 | 0 | T |
| AI352267 | UNKNOWN | 16 | 194 | A |
| AI352274 | UNKNOWN | 70 | 0 | T |
| AI352274 | UNKNOWN | 14 | 121 | C |
| AI352290 | UNKNOWN | 68 | 0 | T |
| AI352290 | UNKNOWN | 16 | 191 | G |
| AI352290 | UNKNOWN | 14 | 108 | A |
| AI352290 | UNKNOWN | 14 | 169 | C |
| AI352320 | UNKNOWN | 45 | 0 | T |
| AI352330 | UNKNOWN | 12 | 30 | A |
| AI352369 | UNKNOWN | 34 | 0 | T |
| AI352376 | UNKNOWN | 82 | 0 | T |
| AI352376 | UNKNOWN | 13 | 94 | A |
| AI352385 | UNKNOWN | 16 | 0 | T |
| AI352411 | UNKNOWN | 15 | 0 | T |
| AI352430 | UNKNOWN | 26 | 0 | T |
| AI352437 | UNKNOWN | 16 | 0 | T |
| AI352441 | UNKNOWN | 23 | 0 | T |
| AI352495 | UNKNOWN | 61 | 0 | T |
| AI352495 | UNKNOWN | 12 | 196 | G |
| AI352497 | UNKNOWN | 83 | 0 | T |
| AI352497 | UNKNOWN | 13 | 84 | A |
| AI352497 | UNKNOWN | 13 | 182 | C |
| AI352507 | UNKNOWN | 4 | 237 | TTTTG |
| AI352512 | UNKNOWN | 13 | 0 | T |
| AI352523 | UNKNOWN | 24 | 0 | T |
| AI352535 | UNKNOWN | 61 | 0 | T |
| AI352535 | UNKNOWN | 15 | 296 | A |
| AI352571 | UNKNOWN | 2.95 | 228 | TGCCACCATCTTGGAAGCGGCC (SEQ ID NO:114) |
| AI352573 | UNKNOWN | 71 | 0 | T |
| AI352573 | UNKNOWN | 13 | 98 | A |
| AI352577 | UNKNOWN | 14 | 57 | A |
| AI352595 | UNKNOWN | 23 | 0 | T |
| AI352639 | UNKNOWN | 21 | 0 | T |
| AI352648 | UNKNOWN | 40 | 0 | T |
| AI352701 | UNKNOWN | 42 | 0 | T |
| AI354231 | UNKNOWN | 37 | 0 | T |
| AI354269 | UNKNOWN | 58 | 0 | T |
| AI354272 | UNKNOWN | 47 | 0 | T |
| AI354272 | UNKNOWN | 12 | 232 | G |
| AI354283 | UNKNOWN | 96 | 0 | T |
| AI354283 | UNKNOWN | 14 | 362 | G |
| AI354283 | UNKNOWN | 12 | 185 | A |
| AI354283 | UNKNOWN | 12 | 241 | C |
| AI354392 | UNKNOWN | 46 | 0 | T |
| AI354431 | UNKNOWN | 42 | 11 | T |
| AI354453 | UNKNOWN | 35 | 0 | T |
| AI354508 | UNKNOWN | 39 | 0 | T |
| AI354523 | UNKNOWN | 51 | 0 | T |
| AI354523 | UNKNOWN | 15 | 332 | A |
| AI354545 | UNKNOWN | 14 | 0 | T |
| AI354560 | UNKNOWN | 57 | 0 | T |
| AI354595 | UNKNOWN | 41 | 0 | T |
| AI354595 | UNKNOWN | 15 | 216 | A |
| AI354598 | UNKNOWN | 23 | 0 | T |
| AI354627 | UNKNOWN | 88 | 0 | T |
| AI354627 | UNKNOWN | 16 | 93 | A |
| AI354627 | UNKNOWN | 14 | 173 | C |
| AI354627 | UNKNOWN | 13 | 120 | C |
| AI354630 | UNKNOWN | 79 | 0 | T |
| AI354630 | UNKNOWN | 15 | 214 | G |

TABLE 1-continued

| Genbank # | Region | # reps | Position | Unit sequence |
|---|---|---|---|---|
| AI354630 | UNKNOWN | 14 | 245 | A |
| AI354631 | UNKNOWN | 49 | 0 | T |
| AI354643 | UNKNOWN | 68 | 0 | T |
| AI354643 | UNKNOWN | 12 | 68 | A |
| AI354643 | UNKNOWN | 12 | 133 | G |
| AI354651 | UNKNOWN | 34 | 0 | T |
| AI354806 | UNKNOWN | 15 | 199 | A |
| AI354889 | UNKNOWN | 17 | 0 | T |
| AI354897 | UNKNOWN | 12 | 170 | T |
| AI354981 | UNKNOWN | 51 | 11 | T |
| AI355070 | UNKNOWN | 4 | 0 | ATTTTT |
| AI355104 | UNKNOWN | 45 | 0 | T |
| AI355105 | UNKNOWN | 25 | 255 | C |
| AI355105 | UNKNOWN | 20 | 226 | C |
| AI355120 | UNKNOWN | 15 | 11 | T |
| AI355147 | UNKNOWN | 49 | 0 | T |
| AI355237 | UNKNOWN | 46 | 0 | T |
| AI355246 | UNKNOWN | 16 | 2 | T |
| AI355249 | UNKNOWN | 35 | 0 | T |
| AI355252 | UNKNOWN | 15 | 0 | T |
| AI355277 | UNKNOWN | 60 | 0 | T |
| AI355286 | UNKNOWN | 54 | 0 | T |
| AI355286 | UNKNOWN | 15 | 206 | A |
| AI355343 | UNKNOWN | 37 | 0 | T |
| AI355546 | UNKNOWN | 43 | 0 | T |
| AI355551 | UNKNOWN | 21 | 0 | T |
| AI355613 | UNKNOWN | 61 | 0 | T |
| AI355613 | UNKNOWN | 16 | 139 | G |
| AI355613 | UNKNOWN | 13 | 249 | A |
| AI355675 | UNKNOWN | 52 | 0 | T |
| AI355675 | UNKNOWN | 12 | 246 | G |
| AI355807 | UNKNOWN | 4.75 | 272 | TTTG |
| AI355827 | UNKNOWN | 94 | 0 | T |
| AI355827 | UNKNOWN | 26 | 190 | C |
| AI355827 | UNKNOWN | 14 | 94 | A |
| AI355849 | UNKNOWN | 67 | 0 | T |
| AI355849 | UNKNOWN | 31 | 161 | A |
| AI355976 | UNKNOWN | 24 | 0 | T |
| AI355990 | UNKNOWN | 50 | 0 | T |
| AI355990 | UNKNOWN | 12 | 156 | A |
| AI356004 | UNKNOWN | 39 | 0 | T |
| AI356027 | UNKNOWN | 43 | 0 | T |
| AI356065 | UNKNOWN | 49 | 0 | T |
| AI356106 | UNKNOWN | 38 | 0 | T |
| AI356139 | UNKNOWN | 64 | 0 | T |
| AI356142 | UNKNOWN | 30 | 0 | T |
| AI356291 | UNKNOWN | 23 | 0 | T |
| AI356388 | UNKNOWN | 18 | 0 | T |
| AI356402 | UNKNOWN | 12 | 351 | T |
| AI356405 | UNKNOWN | 12 | 0 | T |
| AI356414 | UNKNOWN | 17 | 0 | T |
| AI356470 | UNKNOWN | 48 | 0 | T |
| AI356505 | UNKNOWN | 55 | 0 | T |
| AI356699 | UNKNOWN | 44 | 0 | T |
| AI356821 | UNKNOWN | 50 | 0 | T |
| AI356821 | UNKNOWN | 19 | 104 | C |
| AI356821 | UNKNOWN | 12 | 306 | G |
| AI356868 | UNKNOWN | 52 | 0 | T |
| AI356868 | UNKNOWN | 12 | 116 | G |
| AI356965 | UNKNOWN | 19 | 0 | T |
| AI356982 | UNKNOWN | 55 | 0 | T |
| AI356996 | UNKNOWN | 27 | 0 | T |
| AI357000 | UNKNOWN | 48 | 0 | T |
| AI357049 | UNKNOWN | 57 | 0 | T |
| AI357061 | UNKNOWN | 22 | 0 | T |
| AI357075 | UNKNOWN | 70 | 0 | T |
| AI357075 | UNKNOWN | 14 | 277 | G |
| AI357075 | UNKNOWN | 13 | 245 | A |
| AI357115 | UNKNOWN | 70 | 0 | T |
| AI357147 | UNKNOWN | 21 | 291 | A |
| AI357147 | UNKNOWN | 12 | 97 | C |
| AI357189 | UNKNOWN | 66 | 0 | T |
| AI357191 | UNKNOWN | 57 | 0 | T |
| AI357191 | UNKNOWN | 14 | 120 | C |
| AI357194 | UNKNOWN | 41 | 0 | T |
| AI357199 | UNKNOWN | 20 | 186 | T |
| AI357218 | UNKNOWN | 41 | 0 | T |

TABLE 1-continued

| Genbank # | Region | # reps | Position | Unit sequence |
|---|---|---|---|---|
| AI357222 | UNKNOWN | 38 | 0 | T |
| AI357229 | UNKNOWN | 39 | 0 | T |
| AI357229 | UNKNOWN | 13 | 65 | A |
| AI357273 | UNKNOWN | 64 | 0 | T |
| AI357273 | UNKNOWN | 16 | 237 | A |
| AI357273 | UNKNOWN | 14 | 64 | A |
| AI357283 | UNKNOWN | 55 | 0 | T |
| AI357290 | UNKNOWN | 38 | 0 | T |
| AI357316 | UNKNOWN | 95 | 0 | T |
| AI357316 | UNKNOWN | 22 | 206 | A |
| AI357316 | UNKNOWN | 21 | 249 | C |
| AI357316 | UNKNOWN | 12 | 98 | C |
| AI357326 | UNKNOWN | 54 | 0 | T |
| AI357331 | UNKNOWN | 34 | 0 | T |
| AI357414 | UNKNOWN | 35 | 0 | T |
| AI357464 | UNKNOWN | 23 | 0 | T |
| AI357470 | UNKNOWN | 15 | 0 | T |
| AI357599 | UNKNOWN | 63 | 0 | T |
| AI357599 | UNKNOWN | 15 | 79 | A |
| AI357616 | UNKNOWN | 39 | 0 | T |
| AI357626 | UNKNOWN | 39 | 0 | T |
| AI357639 | UNKNOWN | 8.5 | 192 | CA |
| AI357658 | UNKNOWN | 29 | 0 | T |
| AI357697 | UNKNOWN | 17 | 0 | T |
| AI357718 | UNKNOWN | 32 | 0 | T |
| AI357738 | UNKNOWN | 60 | 0 | T |
| AI357741 | UNKNOWN | 32 | 0 | T |
| AI357752 | UNKNOWN | 49 | 0 | T |
| AI357752 | UNKNOWN | 18 | 176 | A |
| AI357775 | UNKNOWN | 23 | 0 | T |
| AI357789 | UNKNOWN | 3.8 | 175 | CCAAC |
| AI357789 | UNKNOWN | 61 | 0 | T |
| AI357789 | UNKNOWN | 12 | 291 | A |
| AI357809 | UNKNOWN | 18 | 24 | A |
| AI357830 | UNKNOWN | 47 | 0 | T |
| AI357845 | UNKNOWN | 44 | 0 | T |
| AI357899 | UNKNOWN | 31 | 0 | T |
| AI357901 | UNKNOWN | 38 | 0 | T |
| AI357902 | UNKNOWN | 51 | 0 | T |
| AI357903 | UNKNOWN | 45 | 0 | T |
| AI357924 | UNKNOWN | 18 | 0 | T |
| AI357937 | UNKNOWN | 67 | 0 | T |
| AI357937 | UNKNOWN | 14 | 203 | C |
| AI357940 | UNKNOWN | 79 | 0 | T |
| AI357940 | UNKNOWN | 20 | 79 | A |
| AI357960 | UNKNOWN | 23 | 0 | T |
| AI357982 | UNKNOWN | 43 | 0 | T |
| AI357989 | UNKNOWN | 41 | 1 | T |
| AI357996 | UNKNOWN | 62 | 0 | T |
| AI357996 | UNKNOWN | 15 | 67 | A |
| AI358005 | UNKNOWN | 35 | 0 | T |
| AI358007 | UNKNOWN | 38 | 0 | T |
| AI358022 | UNKNOWN | 33 | 0 | T |
| AI358042 | UNKNOWN | 65 | 0 | T |
| AI358042 | UNKNOWN | 17 | 175 | G |
| AI358096 | UNKNOWN | 25 | 0 | T |
| AI358101 | UNKNOWN | 48 | 0 | T |
| AI358107 | UNKNOWN | 94 | 0 | T |
| AI358107 | UNKNOWN | 22 | 289 | A |
| AI358107 | UNKNOWN | 18 | 195 | G |
| AI358107 | UNKNOWN | 12 | 94 | A |
| AI358116 | UNKNOWN | 38 | 0 | T |
| AI358120 | UNKNOWN | 44 | 0 | T |
| AI358138 | UNKNOWN | 40 | 0 | T |
| AI358172 | UNKNOWN | 37 | 0 | T |
| AI358183 | UNKNOWN | 35 | 0 | T |
| AI358183 | UNKNOWN | 12 | 68 | G |
| AI358184 | UNKNOWN | 61 | 0 | T |
| AI358190 | UNKNOWN | 51 | 0 | T |
| AI358190 | UNKNOWN | 13 | 115 | C |
| AI358200 | UNKNOWN | 47 | 0 | T |
| AI358200 | UNKNOWN | 14 | 97 | A |
| AI358200 | UNKNOWN | 12 | 52 | A |
| AI358209 | UNKNOWN | 74 | 0 | T |
| AI358209 | UNKNOWN | 13 | 177 | C |
| AI358213 | UNKNOWN | 78 | 0 | T |
| AI358213 | UNKNOWN | 12 | 208 | A |

TABLE 1-continued

| Genbank # | Region | # reps | Position | Unit sequence |
|---|---|---|---|---|
| AI358288 | UNKNOWN | 22 | 0 | T |
| AI358301 | UNKNOWN | 36 | 0 | T |
| AI358314 | UNKNOWN | 14 | 275 | A |
| AI358314 | UNKNOWN | 12 | 101 | A |
| AI358333 | UNKNOWN | 29 | 0 | T |
| AI358384 | UNKNOWN | 22 | 0 | T |
| AI358386 | UNKNOWN | 11.5 | 388 | AT |
| AI358386 | UNKNOWN | 24 | 0 | T |
| AI358400 | UNKNOWN | 43 | 0 | T |
| AI358455 | UNKNOWN | 91 | 0 | T |
| AI358455 | UNKNOWN | 22 | 145 | A |
| AI358455 | UNKNOWN | 15 | 273 | C |
| AI358455 | UNKNOWN | 14 | 128 | G |
| AI358456 | UNKNOWN | 77 | 0 | T |
| AI358456 | UNKNOWN | 12 | 281 | A |
| AI358462 | UNKNOWN | 43 | 0 | T |
| AI358462 | UNKNOWN | 16 | 388 | A |
| AI358462 | UNKNOWN | 13 | 230 | A |
| AI358464 | UNKNOWN | 56 | 0 | T |
| AI358465 | UNKNOWN | 52 | 0 | T |
| AI358465 | UNKNOWN | 13 | 190 | C |
| AI358466 | UNKNOWN | 9 | 285 | AC |
| AI358466 | UNKNOWN | 7.5 | 315 | TC |
| AI358534 | UNKNOWN | 6.5 | 149 | TC |
| AI358534 | UNKNOWN | 15 | 120 | T |
| AI358543 | UNKNOWN | 34 | 0 | T |
| AI358585 | UNKNOWN | 17 | 0 | T |
| AI358585 | UNKNOWN | 17 | 186 | C |
| AI358590 | UNKNOWN | 55 | 0 | T |
| AI358640 | UNKNOWN | 41 | 0 | T |
| AI358684 | UNKNOWN | 32 | 0 | T |
| AI358685 | UNKNOWN | 48 | 0 | T |
| AI358685 | UNKNOWN | 12 | 117 | A |
| AI358702 | UNKNOWN | 20 | 0 | T |
| AI358704 | UNKNOWN | 23 | 0 | T |
| AI358712 | UNKNOWN | 33 | 0 | T |
| AI358725 | UNKNOWN | 66 | 0 | T |
| AI358725 | UNKNOWN | 13 | 105 | A |
| AI358751 | UNKNOWN | 16 | 0 | T |
| AI358751 | UNKNOWN | 13 | 38 | A |
| AI358790 | UNKNOWN | 45 | 0 | T |
| AI358792 | UNKNOWN | 20 | 0 | T |
| AI358884 | UNKNOWN | 31 | 0 | T |
| AI358968 | UNKNOWN | 15 | 0 | T |
| AI359076 | UNKNOWN | 14 | 426 | C |
| AI359076 | UNKNOWN | 14 | 456 | G |
| AI359076 | UNKNOWN | 13 | 443 | T |
| AI359106 | UNKNOWN | 28 | 0 | T |
| AI359144 | UNKNOWN | 3.66 | 54 | AAAACA |
| AI359144 | UNKNOWN | 22 | 0 | T |
| AI359163 | UNKNOWN | 75 | 0 | T |
| AI359163 | UNKNOWN | 12 | 208 | C |
| AI359212 | UNKNOWN | 41 | 0 | T |
| AI359212 | UNKNOWN | 12 | 44 | A |
| AI359267 | UNKNOWN | 13 | 366 | A |
| AI359279 | UNKNOWN | 47 | 0 | T |
| AI359279 | UNKNOWN | 15 | 252 | G |
| AI359400 | UNKNOWN | 40 | 0 | T |
| AI359400 | UNKNOWN | 12 | 57 | A |
| AI359412 | UNKNOWN | 37 | 0 | T |
| AI359412 | UNKNOWN | 15 | 181 | A |
| AI359412 | UNKNOWN | 14 | 83 | A |
| AI359465 | UNKNOWN | 18 | 0 | T |
| AI359467 | UNKNOWN | 32 | 0 | T |
| AI359470 | UNKNOWN | 47 | 0 | T |
| AI359470 | UNKNOWN | 16 | 224 | G |
| AI359489 | UNKNOWN | 12 | 0 | T |
| AI359497 | UNKNOWN | 81 | 0 | T |
| AI359515 | UNKNOWN | 13 | 0 | T |
| AI359521 | UNKNOWN | 26 | 0 | T |
| AI359536 | UNKNOWN | 14 | 0 | T |
| AI359551 | UNKNOWN | 6.5 | 329 | AC |
| AI359586 | UNKNOWN | 59 | 0 | T |
| AI359586 | UNKNOWN | 13 | 166 | C |
| AI359590 | UNKNOWN | 70 | 0 | T |
| AI359599 | UNKNOWN | 36 | 0 | T |
| AI359600 | UNKNOWN | 60 | 0 | T |

TABLE 1-continued

| Genbank # | Region | # reps | Position | Unit sequence |
|---|---|---|---|---|
| AI359600 | UNKNOWN | 14 | 192 | G |
| AI359600 | UNKNOWN | 14 | 206 | C |
| AI359606 | UNKNOWN | 18 | 0 | T |
| AI359635 | UNKNOWN | 42 | 0 | T |
| AI359725 | UNKNOWN | 53 | 0 | T |
| AI359787 | UNKNOWN | 61 | 0 | T |
| AI359787 | UNKNOWN | 18 | 337 | A |
| AI359787 | UNKNOWN | 12 | 89 | A |
| AI359821 | UNKNOWN | 39 | 0 | T |
| AI359821 | UNKNOWN | 13 | 363 | A |
| AI359850 | UNKNOWN | 41 | 0 | T |
| AI359850 | UNKNOWN | 15 | 299 | C |
| AI359850 | UNKNOWN | 14 | 322 | A |
| AI359852 | UNKNOWN | 51 | 0 | T |
| AI359852 | UNKNOWN | 12 | 244 | A |
| AI359858 | UNKNOWN | 22 | 0 | T |
| AI359858 | UNKNOWN | 20 | 346 | A |
| AI359876 | UNKNOWN | 21 | 0 | T |
| AI359898 | UNKNOWN | 42 | 0 | T |
| AI359898 | UNKNOWN | 13 | 364 | G |
| AI359924 | UNKNOWN | 36 | 0 | T |
| AI359924 | UNKNOWN | 12 | 56 | A |
| AI360088 | UNKNOWN | 18 | 6 | T |
| AI360127 | UNKNOWN | 34 | 0 | T |
| AI360185 | UNKNOWN | 48 | 0 | T |
| AI360281 | UNKNOWN | 25 | 0 | T |
| AI360361 | UNKNOWN | 40 | 76 | T |
| AI360377 | UNKNOWN | 48 | 0 | T |
| AI360409 | UNKNOWN | 12 | 0 | T |
| AI360426 | UNKNOWN | 20 | 428 | T |
| AI360437 | UNKNOWN | 24 | 0 | T |
| AI360461 | UNKNOWN | 17 | 0 | T |
| AI360509 | UNKNOWN | 11 | 248 | AGGA |
| AI360509 | UNKNOWN | 4.5 | 361 | GAAA |
| AI360521 | UNKNOWN | 16 | 0 | T |
| AI360529 | UNKNOWN | 46 | 0 | T |
| AI360530 | UNKNOWN | 82 | 0 | T |
| AI360530 | UNKNOWN | 15 | 394 | c |
| AI360562 | UNKNOWN | 38 | 0 | T |
| AI360562 | UNKNOWN | 16 | 262 | G |
| AI360575 | UNKNOWN | 19 | 0 | T |
| AI360600 | UNKNOWN | 34 | 0 | T |
| AI360628 | UNKNOWN | 40 | 0 | T |
| AI360663 | UNKNOWN | 35 | 0 | T |
| AI360679 | UNKNOWN | 14 | 0 | T |
| AI360736 | UNKNOWN | 36 | 0 | T |
| AI360751 | UNKNOWN | 38 | 0 | T |
| AI360751 | UNKNOWN | 13 | 250 | C |
| AI360810 | UNKNOWN | 49 | 0 | T |
| AI360816 | UNKNOWN | 49 | 0 | T |
| AI360830 | UNKNOWN | 57 | 0 | T |
| AI360867 | UNKNOWN | 45 | 0 | T |
| AI360880 | UNKNOWN | 46 | 0 | T |
| AI360880 | UNKNOWN | 12 | 172 | G |
| AI360920 | UNKNOWN | 12 | 71 | G |
| AI360963 | UNKNOWN | 13 | 0 | T |
| AI361009 | UNKNOWN | 40 | 0 | T |
| AI361035 | UNKNOWN | 13 | 21 | T |
| AI361045 | UNKNOWN | 31 | 0 | T |
| AI361045 | UNKNOWN | 12 | 164 | C |
| AI361047 | UNKNOWN | 35 | 0 | T |
| AI361069 | UNKNOWN | 43 | 0 | T |
| AI361069 | UNKNOWN | 17 | 80 | A |
| AI361069 | UNKNOWN | 16 | 127 | G |
| AI361069 | UNKNOWN | 15 | 247 | C |
| AI361090 | UNKNOWN | 19 | 38 | T |
| AI361291 | UNKNOWN | 54 | 0 | T |
| AI361291 | UNKNOWN | 16 | 211 | G |
| AI361291 | UNKNOWN | 12 | 158 | G |
| AI361291 | UNKNOWN | 12 | 184 | A |
| AI361294 | UNKNOWN | 31 | 0 | T |
| AI361317 | UNKNOWN | 52 | 0 | T |
| AI361317 | UNKNOWN | 16 | 138 | G |
| AI361319 | UNKNOWN | 55 | 0 | T |
| AI361319 | UNKNOWN | 16 | 151 | C |
| AI361319 | UNKNOWN | 12 | 172 | G |
| AI361339 | UNKNOWN | 42 | 0 | T |

TABLE 1-continued

| Genbank # | Region | # reps | Position | Unit sequence |
|---|---|---|---|---|
| AI361339 | UNKNOWN | 18 | 386 | C |
| AI361339 | UNKNOWN | 12 | 74 | A |
| AI361339 | UNKNOWN | 12 | 292 | C |
| AI361344 | UNKNOWN | 25 | 0 | T |
| AI361375 | UNKNOWN | 36 | 0 | T |
| AI361406 | UNKNOWN | 20 | 0 | T |
| AI361586 | UNKNOWN | 60 | 0 | T |
| AI361586 | UNKNOWN | 13 | 91 | A |
| AI361653 | UNKNOWN | 35 | 0 | T |
| AI361701 | UNKNOWN | 64 | 0 | T |
| AI361715 | UNKNOWN | 20 | 0 | T |
| AI361729 | UNKNOWN | 4.5 | 22 | TTTA |
| AI361733 | UNKNOWN | 50 | 0 | T |
| AI361739 | UNKNOWN | 82 | 0 | T |
| AI361739 | UNKNOWN | 13 | 363 | G |
| AI361767 | UNKNOWN | 17 | 0 | T |
| AI361833 | UNKNOWN | 3.5 | 128 | AAAATA |
| AI361849 | UNKNOWN | 25 | 0 | T |
| AI361866 | UNKNOWN | 30 | 0 | T |
| AI361890 | UNKNOWN | 4.75 | 7 | TTTA |
| AI361900 | UNKNOWN | 6.25 | 0 | TATT |
| AI361948 | UNKNOWN | 13 | 0 | T |
| AI361961 | UNKNOWN | 24 | 0 | T |
| AI361968 | UNKNOWN | 41 | 0 | T |
| AI362002 | UNKNOWN | 22 | 0 | T |
| AI362042 | UNKNOWN | 17 | 75 | TA |
| AI362042 | UNKNOWN | 25 | 0 | T |
| AI362042 | UNKNOWN | 13 | 309 | A |
| AI362052 | UNKNOWN | 72 | 0 | T |
| AI362052 | UNKNOWN | 17 | 154 | A |
| AI362052 | UNKNOWN | 15 | 180 | G |
| AI362081 | UNKNOWN | 96 | 0 | T |
| AI362081 | UNKNOWN | 24 | 279 | G |
| AI362081 | UNKNOWN | 23 | 256 | A |
| AI362081 | UNKNOWN | 16 | 151 | G |
| AI362189 | UNKNOWN | 19 | 0 | T |
| AI362239 | UNKNOWN | 70 | 0 | T |
| AI362239 | UNKNGKN | 12 | 244 | A |
| AI362248 | UNKNOWN | 67 | 0 | T |
| AI362248 | UNKNOWN | 26 | 67 | A |
| AI362248 | UNKNOWN | 23 | 213 | C |
| AI362248 | UNKNOWN | 22 | 133 | C |
| AI362248 | UNKNOWN | 12 | 93 | c |
| AI362248 | UNKNOWN | 12 | 267 | G |
| AI362280 | UNKNGKN | 44 | 0 | T |
| AI362307 | UNKNOWN | 12 | 36 | A |
| AI362332 | UNKNOWN | 47 | 2 | T |
| AI362347 | UNKNOWN | 96 | 0 | T |
| AI362360 | UNKNOWN | 19 | 0 | T |
| AI362374 | UNKNOWN | 20 | 0 | T |
| AI362401 | UNKNOWN | 38 | 0 | T |
| AI362428 | UNKNOWN | 39 | 0 | T |
| AI362428 | UNKNOWN | 17 | 306 | A |
| AI362444 | UNKNOWN | 14 | 0 | T |
| AI362449 | UNKNOWN | 44 | 0 | T |
| AI362462 | UNKNOWN | 30 | 0 | T |
| AI362465 | UNKNOWN | 33 | 0 | T |
| AI362502 | UNKNOWN | 28 | 0 | T |
| AI362513 | UNKNOWN | 35 | 0 | T |
| AI362522 | UNKNOWN | 87 | 0 | T |
| AI362522 | UNKNOWN | 15 | 178 | G |
| AI362522 | UNKNOWN | 13 | 226 | C |
| AI362525 | UNKNOWN | 47 | 0 | T |
| AI362525 | UNKNOWN | 13 | 140 | A |
| AI362536 | UNKNOWN | 15 | 42 | T |
| AI362537 | UNKNOWN | 55 | 0 | T |
| AI362537 | UNKNOWN | 19 | 251 | A |
| AI362537 | UNKNOWN | 14 | 155 | A |
| AI362575 | UNKNOWN | 21 | 0 | T |
| AI362579 | UNKNOWN | 20 | 221 | A |
| AI362579 | UNKNOWN | 13 | 149 | G |
| AI362580 | UNKNOWN | 84 | 0 | T |
| AI362580 | UNKNOWN | 15 | 111 | A |
| AI362587 | UNKNOWN | 19 | 185 | T |
| AI362600 | UNKNOWN | 49 | 0 | T |
| AI362611 | UNKNOWN | 26 | 0 | T |
| AI362637 | UNKNOWN | 104 | 0 | T |

TABLE 1-continued

| Genbank # | Region | # reps | Position | Unit sequence |
|---|---|---|---|---|
| AI362637 | UNKNOWN | 20 | 227 | C |
| AI362637 | UNKNOWN | 15 | 172 | C |
| AI362637 | UNKNOWN | 12 | 210 | A |
| AI362657 | UNKNOWN | 30 | 0 | T |
| AI362666 | UNKNOWN | 19 | 0 | T |
| AI362687 | UNKNOWN | 24 | 0 | T |
| AI362694 | UNKNOWN | 25 | 0 | T |
| AI362713 | UNKNOWN | 57 | 0 | T |
| AI362713 | UNKNOWN | 13 | 290 | G |
| AI362809 | UNKNOWN | 37 | 0 | T |
| AI362842 | UNKNOWN | 23 | 7 | T |
| AI362919 | UNKNOWN | 30 | 0 | T |
| AI362941 | UNKNOWN | 19 | 166 | T |
| AI362941 | UNKNOWN | 12 | 0 | T |
| AI362994 | UNKNOWN | 38 | 0 | T |
| AI363064 | UNKNOWN | 47 | 0 | T |
| AI363138 | UNKNOWN | 63 | 0 | T |
| AI363138 | UNKNOWN | 12 | 353 | A |
| AI363164 | UNKNOWN | 25 | 0 | T |
| AI363164 | UNKNOWN | 20 | 55 | A |
| AI363203 | UNKNOWN | 29 | 0 | T |
| AI363206 | UNKNOWN | 30 | 0 | T |
| AI363330 | UNKNOWN | 44 | 0 | T |
| AI363346 | UNKNOWN | 22 | 0 | T |
| AI363443 | UNKNOWN | 40 | 0 | T |
| AI363443 | UNKNOWN | 12 | 77 | G |
| AI363451 | UNKNOWN | 52 | 0 | T |
| AI363461 | UNKNOWN | 16 | 0 | T |
| AI363486 | UNKNOWN | 18 | 0 | T |
| AI363743 | UNKNOWN | 39 | 0 | T |
| AI363743 | UNKNOWN | 12 | 169 | A |
| AI363756 | UNKNOWN | 13 | 76 | T |
| AI363782 | UNKNOWN | 4 | 0 | ATTTT |
| AI363782 | UNKNOWN | 5.25 | 63 | AAAT |
| AI363935 | UNKNOWN | 23 | 0 | T |
| AI363953 | UNKNOWN | 22 | 0 | T |
| AI363957 | UNKNOWN | 69 | 0 | T |
| AI363957 | UNKNOWN | 15 | 152 | C |
| AI363957 | UNKNOWN | 15 | 172 | G |
| AI363979 | UNKNOWN | 18 | 0 | T |
| AI364034 | UNKNOWN | 54 | 0 | T |
| AI364046 | UNKNOWN | 31 | 0 | T |
| AI364075 | UNKNOWN | 37 | 0 | T |
| AI364135 | UNKNOWN | 53 | 0 | T |
| AI364206 | UNKNOWN | 24 | 0 | T |
| AI364238 | UNKNOWN | 23 | 0 | T |
| AI364335 | UNKNOWN | 31 | 0 | T |
| AI364529 | UNKNOWN | 5.66 | 181 | GCG |
| AI364539 | UNKNOWN | 22 | 0 | T |
| AI364614 | UNKNOWN | 22 | 0 | T |
| AI364639 | UNKNOWN | 69 | 0 | T |
| AI364761 | UNKNOWN | 9 | 310 | AATA |
| AI364777 | UNKNOWN | 28 | 0 | T |
| AI364781 | UNKNOWN | 25 | 0 | T |
| AI364801 | UNKNOWN | 6 | 267 | AAAC |
| AI364895 | UNKNOWN | 41 | 0 | T |
| AI364926 | UNKNOWN | 50 | 0 | T |
| AI364931 | UNKNOWN | 44 | 0 | T |
| AI364944 | UNKNOWN | 15 | 265 | A |
| AI365041 | UNKNOWN | 33 | 0 | T |
| AI365099 | UNKNOWN | 14 | 0 | T |
| AI365135 | UNKNOWN | 40 | 0 | T |
| AI365233 | UNKNOWN | 21 | 0 | T |
| AI365256 | UNKNOWN | 83 | 0 | T |
| AI365256 | UNKNOWN | 19 | 108 | A |
| AI365306 | UNKNOWN | 20 | 0 | T |
| AI365343 | UNKNOWN | 8 | 182 | AAAC |
| AI365343 | UNKNOWN | 15 | 0 | T |
| AI365449 | UNKNOWN | 21 | 0 | T |
| AI365473 | UNKNOWN | 22 | 0 | T |
| AI365491 | UNKNOWN | 35 | 5 | T |
| AI365550 | UNKNOWN | 6.75 | 171 | AAAT |
| AI365708 | UNKNOWN | 11.5 | 301 | TG |
| AI365708 | UNKNOWN | 6.5 | 289 | TA |
| AI365915 | UNKNOWN | 42 | 0 | T |
| AI366382 | UNKNOWN | 19 | 26 | T |
| AI366549 | UNKNOWN | 102 | 49 | T |

TABLE 1-continued

| Genbank # | Region | # reps | Position | Unit sequence |
|---|---|---|---|---|
| AI366549 | UNKNOWN | 25 | 22 | T |
| AI366555 | UNKNOWN | 30 | 22 | T |
| AI366564 | UNKNOWN | 57 | 0 | T |
| AI366796 | UNKNOWN | 62 | 0 | T |
| AI366796 | UNKNOWN | 19 | 146 | G |
| AI366864 | UNKNOWN | 42 | 0 | T |
| AI366873 | UNKNOWN | 42 | 0 | T |
| AI366875 | UNKNOWN | 62 | 0 | T |
| AI366887 | UNKNOWN | 8.5 | 444 | TA |
| AI366888 | UNKNOWN | 61 | 22 | T |
| AI366888 | UNKNOWN | 19 | 0 | T |
| AI366888 | UNKNOWN | 13 | 116 | C |
| AI366888 | UNKNOWN | 13 | 164 | A |
| AI366895 | UNKNOWN | 45 | 0 | T |
| AI366895 | UNKNOWN | 23 | 245 | A |
| AI366905 | UNKNOWN | 72 | 0 | T |
| AI366910 | UNKNOWN | 59 | 11 | T |
| AI366921 | UNKNOWN | 16 | 156 | T |
| AI366922 | UNKNOWN | 65 | 0 | T |
| AI366959 | UNKNOWN | 57 | 48 | A |
| AI366965 | UNKNOWN | 20 | 270 | A |
| AI366982 | UNKNOWN | 25 | 315 | A |
| AI366991 | UNKNOWN | 90 | 90 | A |
| AI366991 | UNKNOWN | 41 | 48 | A |
| AI366991 | UNKNOWN | 16 | 200 | T |
| AI366991 | UNKNOWN | 13 | 181 | T |
| AI366992 | UNKNOWN | 88 | 21 | A |
| AI366993 | UNKNOWN | 27 | 324 | A |
| AI367034 | UNKNOWN | 20 | 251 | T |
| AI367203 | UNKNOWN | 51 | 0 | T |
| AI367203 | UNKNOWN | 25 | 144 | A |
| AI367210 | UNKNOWN | 73 | 0 | T |
| AI367233 | UNKNOWN | 42 | 0 | T |
| AI367233 | UNKNOWN | 15 | 431 | A |
| AI367328 | UNKNOWN | 55 | 0 | T |
| AI367356 | UNKNOWN | 45 | 0 | T |
| AI367364 | UNKNOWN | 53 | 0 | T |
| AI367364 | UNKNOWN | 12 | 200 | C |
| AI367371 | UNKNOWN | 4.75 | 182 | TTTG |
| AI367373 | UNKNOWN | 3.8 | 332 | AAAAC |
| AI367414 | UNKNOWN | 45 | 0 | T |
| AI367428 | UNKNOWN | 76 | 0 | T |
| AI367428 | UNKNOWN | 12 | 129 | A |
| AI367468 | UNKNOWN | 6.66 | 9 | TTA |
| AI367533 | UNKNOWN | 36 | 0 | T |
| AI367539 | UNKNOWN | 49 | 0 | T |
| AI367562 | UNKNOWN | 35 | 0 | T |
| AI367580 | UNKNOWN | 13 | 86 | A |
| AI367680 | UNKNOWN | 83 | 0 | T |
| AI367680 | UNKNOWN | 22 | 171 | A |
| AI367680 | UNKNOWN | 22 | 300 | G |
| AI367680 | UNKNOWN | 19 | 281 | C |
| AI367680 | UNKNOWN | 15 | 83 | A |
| AI367691 | UNKNOWN | 40 | 0 | T |
| AI367705 | UNKNOWN | 70 | 0 | T |
| AI367705 | UNKNOWN | 17 | 281 | G |
| AI367712 | UNKNOWN | 15.5 | 200 | CA |
| AI367712 | UNKNOWN | 14 | 11 | T |
| AI367754 | UNKNOWN | 23.5 | 347 | AC |
| AI367817 | UNKNOWN | 15 | 0 | T |
| AI367932 | UNKNOWN | 48 | 0 | T |
| AI367945 | UNKNOWN | 38 | 0 | T |
| AI368035 | UNKNOWN | 17 | 0 | T |
| AI368043 | UNKNOWN | 54 | 0 | T |
| AI368122 | UNKNOWN | 27 | 0 | T |
| AI368214 | UNKNOWN | 20 | 0 | T |
| AI368250 | UNKNOWN | 24 | 0 | T |
| AI368256 | UNKNOWN | 18 | 0 | T |
| AI368262 | UNKNOWN | 44 | 0 | T |
| AI368262 | UNKNOWN | 19 | 290 | A |
| AI368359 | UNKNOWN | 35 | 0 | T |
| AI368382 | UNKNOWN | 30 | 0 | T |
| AI368415 | UNKNOWN | 16 | 37 | AT |
| AI368418 | UNKNOWN | 35 | 0 | T |
| AI368579 | UNKNOWN | 55 | 0 | T |
| AI368579 | UNKNOWN | 18 | 164 | A |
| AI368646 | UNKNOWN | 26 | 0 | T |

TABLE 1-continued

| Genbank # | Region | # reps | Position | Unit sequence |
|---|---|---|---|---|
| AI368667 | UNKNOWN | 23 | 0 | T |
| AI368691 | UNKNOWN | 50 | 0 | T |
| AI368708 | UNKNOWN | 44 | 0 | T |
| AI368726 | UNKNOWN | 34 | 0 | T |
| AI368816 | UNKNOWN | 87 | 0 | T |
| AI368816 | UNKNOWN | 14 | 338 | C |
| AI368816 | UNKNOWN | 13 | 137 | A |
| AI368816 | UNKNOWN | 13 | 185 | C |
| AI368850 | UNKNOWN | 40 | 0 | T |
| AI368853 | UNKNOWN | 40 | 0 | T |
| AI368868 | UNKNOWN | 80 | 0 | T |
| AI368868 | UNKNOWN | 26 | 230 | G |
| AI368868 | UNKNOWN | 13 | 208 | C |
| AI368908 | UNKNOWN | 36 | 0 | T |
| AI368942 | UNKNOWN | 33 | 0 | T |
| AI368943 | UNKNOWN | 82 | 0 | T |
| AI368943 | UNKNOWN | 13 | 112 | G |
| AI368943 | UNKNOWN | 12 | 82 | A |
| AI368976 | UNKNOWN | 16 | 0 | T |
| AI368976 | UNKNOWN | 15 | 285 | C |
| AI368988 | UNKNOWN | 15 | 152 | T |
| AI369004 | UNKNOWN | 15 | 0 | T |
| AI369029 | UNKNOWN | 41 | 0 | T |
| AI369064 | UNKNOWN | 38 | 0 | T |
| AI369064 | UNKNOWN | 15 | 76 | A |
| AI369193 | UNKNOWN | 12 | 69 | T |
| AI369220 | UNKNOWN | 38 | 0 | T |
| AI369242 | UNKNOWN | 40 | 0 | T |
| Ar369242 | UNKNOWN | 16 | 183 | A |
| AI369242 | UNKNOWN | 15 | 163 | C |
| AI369261 | UNKNOWN | 21 | 147 | T |
| AI369261 | UNKNOWN | 14 | 223 | A |
| AI369334 | UNKNOWN | 42 | 0 | T |
| AI369457 | UNKNOWN | 18 | 0 | T |
| AI369521 | UNKNOWN | 35 | 31 | T |
| AI369521 | UNKNOWN | 24 | 5 | T |
| AI369577 | UNKNOWN | 55 | 0 | T |
| AI369580 | UNKNOWN | 34 | 33 | T |
| AI369581 | UNKNOWN | 20 | 0 | T |
| AI369582 | UNKNOWN | 21 | 0 | T |
| AI369586 | UNKNOWN | 16 | 0 | T |
| AI369604 | UNKNOWN | 15 | 34 | A |
| AI369614 | UNKNOWN | 38 | 0 | T |
| AI369707 | UNKNOWN | 36 | 0 | T |
| AI369734 | UNKNOWN | 33 | 0 | T |
| AI369935 | UNKNOWN | 12 | 381 | G |
| AI369953 | UNKNOWN | 15 | 0 | T |
| AI369995 | UNKNOWN | 31 | 0 | T |
| AI370037 | UNKNOWN | 70 | 0 | T |
| AI370040 | UNKNOWN | 14 | 0 | T |
| AI370041 | UNKNOWN | 17 | 0 | T |
| AI370074 | UNKNOWN | 13 | 346 | A |
| AI370082 | UNKNOWN | 25 | 331 | A |
| AI370089 | UNKNOWN | 23 | 163 | A |
| AI370181 | UNKNOWN | 59 | 0 | T |
| AI370234 | UNKNOWN | 33 | 0 | T |
| AI370356 | UNKNOWN | 14 | 68 | GAT |
| AI370390 | UNKNOWN | 87 | 0 | T |
| AI370392 | UNKNOWN | 34 | 26 | T |
| AI370392 | UNKNOWN | 25 | 0 | T |
| AI370414 | UNKNOWN | 35 | 0 | T |
| AI370425 | UNKNOWN | 17 | 0 | T |
| AI370502 | UNKNOWN | 17 | 0 | T |
| AI370522 | UNKNOWN | 30 | 0 | T |
| AI370564 | UNKNOWN | 51 | 0 | T |
| AI370675 | UNKNOWN | 39 | 0 | T |
| AI370717 | UNKNOWN | 27 | 0 | T |
| AI370746 | UNKNOWN | 29 | 0 | T |
| AI370812 | UNKNOWN | 62 | 0 | T |
| AI370812 | UNKNOWN | 17 | 325 | A |
| AI370812 | UNKNOWN | 14 | 303 | C |
| AI370820 | UNKNOWN | 20 | 0 | T |
| AI370877 | UNKNOWN | 7 | 4 | TTAT |
| AI370890 | UNKNOWN | 70 | 0 | T |
| AI370890 | UNKNOWN | 17 | 165 | G |
| AI370890 | UNKNOWN | 13 | 226 | C |
| AI370935 | UNKNOWN | 40 | 24 | T |

TABLE 1-continued

| Genbank # | Region | # reps | Position | Unit sequence |
|---|---|---|---|---|
| AI370935 | UNKNOWN | 22 | 0 | T |
| AI370935 | UNKNOWN | 14 | 162 | A |
| AI370938 | UNKNOWN | 15 | 0 | T |
| AI370938 | UNKNOWN | 13 | 115 | A |
| AI370943 | UNKNOWN | 40 | 0 | T |
| AI370945 | UNKNOWN | 38 | 28 | T |
| AI370945 | UNKNOWN | 27 | 0 | T |
| AI370945 | UNKNOWN | 15 | 122 | G |
| AI370945 | UNKNOWN | 12 | 97 | C |
| AI370965 | UNKNOWN | 49 | 0 | T |
| AI371009 | UNKNOWN | 80 | 0 | T |
| AI371009 | UNKNOWN | 14 | 178 | C |
| AI371010 | UNKNOWN | 47 | 0 | T |
| AI371010 | UNKNOWN | 13 | 266 | C |
| AI371265 | UNKNOWN | 78 | 11 | T |
| AI371265 | UNKNOWN | 13 | 189 | A |
| AI371265 | UNKNOWN | 13 | 238 | C |
| AI371278 | UNKNOWN | 12 | 310 | G |
| AI371300 | UNKNOWN | 21 | 272 | T |
| AI371376 | UNKNOWN | 17 | 0 | T |
| AI371473 | UNKNOWN | 5 | 125 | TATT |
| AI371559 | UNKNOWN | 7.25 | 55 | AGAA |
| AI371559 | UNKNOWN | 11.5 | 35 | AG |
| AI371559 | UNKNOWN | 24 | 115 | A |
| AI371570 | UNKNOWN | 26 | 154 | A |
| AI371576 | UNKNOWN | 30 | 92 | A |
| AI371577 | UNKNOWN | 20 | 149 | A |
| AI371578 | UNKNOWN | 20 | 295 | A |
| AI371603 | UNKNOWN | 14 | 123 | A |
| AI371603 | UNKNOWN | 12 | 76 | G |
| AI371607 | UNKNOWN | 20 | 106 | A |
| AI371611 | UNKNOWN | 21 | 83 | A |
| AI371644 | UNKNOWN | 29 | 172 | A |
| AI371676 | UNKNOWN | 31 | 0 | T |
| AI371676 | UNKNOWN | 13 | 34 | A |
| AI371750 | UNKNOWN | 18 | 0 | T |
| AI371786 | UNKNOWN | 76 | 0 | T |
| AI371786 | UNKNOWN | 12 | 141 | G |
| AI371799 | UNKNOWN | 19 | 0 | T |
| AI371801 | UNKNOWN | 21 | 0 | T |
| AI371819 | UNKNOWN | 4.2 | 132 | CGCCG |
| AI371875 | UNKNOWN | 48 | 0 | T |
| AI371886 | UNKNOWN | 65 | 0 | T |
| AI371886 | UNKNOWN | 14 | 288 | C |
| AI371963 | UNKNOWN | 30 | 149 | A |
| AI371978 | UNKNOWN | 45 | 0 | T |
| AI371984 | UNKNOWN | 59 | 0 | T |
| AI371984 | UNKNOWN | 14 | 252 | A |
| AI371985 | UNKNOWN | 58 | 0 | T |
| AI372009 | UNKNOWN | 63 | 0 | T |
| AI372009 | UNKNOWN | 14 | 82 | A |
| AI372027 | UNKNOWN | 32 | 0 | T |
| AI372041 | UNKNOWN | 57 | 0 | T |
| AI372096 | UNKNOWN | 54 | 0 | T |
| AI372096 | UNKNOWN | 13 | 152 | C |
| AI372967 | UNKNOWN | 19 | 0 | T |
| AI372969 | UNKNOWN | 40 | 0 | T |
| AI373019 | UNKNOWN | 15 | 99 | A |
| AI373019 | UNKNOWN | 12 | 289 | T |
| AI373039 | UNKNOWN | 23 | 0 | T |
| AI373057 | UNKNOWN | 43 | 0 | T |
| AI373071 | UNKNOWN | 15 | 0 | T |
| AI373077 | UNKNOWN | 43 | 0 | T |
| AI373169 | UNKNOWN | 21 | 0 | T |
| AI373306 | UNKNOWN | 4.75 | 278 | AAAT |
| AI373341 | UNKNOWN | 25 | 0 | T |
| AI373357 | UNKNOWN | 31 | 0 | T |
| AI373487 | UNKNOWN | 43 | 0 | T |
| AI373488 | UNKNOWN | 30 | 0 | T |
| AI373503 | UNKNOWN | 12 | 0 | T |
| AI373512 | UNKNOWN | 15 | 0 | T |
| AI373535 | UNKNOWN | 35 | 0 | T |
| AI373617 | UNKNOWN | 78 | 0 | T |
| AI373617 | UNKNOWN | 14 | 117 | C |
| AI373619 | UNKNOWN | 20 | 0 | T |
| AI373622 | UNKNOWN | 57 | 0 | T |
| AI373628 | UNKNOWN | 23 | 0 | T |

TABLE 1-continued

| Genbank # | Region | # reps | Position | Unit sequence |
|---|---|---|---|---|
| AI373784 | UNKNOWN | 6.5 | 7 | GC |
| AI373818 | UNKNOWN | 13 | 351 | A |
| AI373858 | UNKNOWN | 17 | 1 | T |
| AI373888 | UNKNOWN | 51 | 0 | T |
| AI373914 | UNKNOWN | 73 | 0 | T |
| AI374594 | UNKNOWN | 28 | 0 | T |
| AI374633 | UNKNOWN | 12 | 0 | T |
| AI374679 | UNKNOWN | 43 | 0 | T |
| AI374722 | UNKNOWN | 18 | 86 | A |
| AI374722 | UNKNOWN | 12 | 0 | T |
| AI374775 | UNKNOWN | 13 | 0 | T |
| AI374796 | UNKNOWN | 12 | 144 | T |
| AI374827 | UNKNOWN | 57 | 0 | T |
| AI374857 | UNKNOWN | 55 | 0 | T |
| AI374864 | UNKNOWN | 20 | 0 | T |
| AI374871 | UNKNOWN | 5.75 | 84 | AAAC |
| AI374878 | UNKNOWN | 55 | 0 | T |
| AI374878 | UNKNOWN | 13 | 201 | G |
| AI374878 | UNKNOWN | 12 | 82 | A |
| AI374878 | UNKNOWN | 12 | 187 | C |
| AI374987 | UNKNOWN | 56 | 0 | T |
| AI374987 | UNKNOWN | 14 | 56 | A |
| AI374993 | UNKNOWN | 18 | 0 | T |
| AI375025 | UNKNOWN | 18 | 0 | T |
| AI375037 | UNKNOWN | 14 | 0 | T |
| AI375058 | UNKNOWN | 14 | 0 | T |
| AI375067 | UNKNOWN | 8.25 | 413 | TATT |
| AI375094 | UNKNOWN | 14 | 83 | A |
| AI375142 | UNKNOWN | 7 | 174 | TA |
| AI375148 | UNKNOWN | 25 | 0 | T |
| AI375167 | UNKNOWN | 19 | 0 | T |
| AI375230 | UNKNOWN | 27 | 0 | T |
| AI375298 | UNKNOWN | 29 | 0 | T |
| AI375303 | UNKNOWN | 72 | 0 | T |
| AI375303 | UNKNOWN | 15 | 143 | G |
| AI375303 | UNKNOWN | 15 | 269 | C |
| AI375310 | UNKNOWN | 45 | 0 | T |
| AI375331 | UNKNOWN | 40 | 0 | T |
| AI375331 | UNKNOWN | 17 | 140 | C |
| AI375420 | UNKNOWN | 65 | 0 | T |
| AI375420 | UNKNOWN | 17 | 237 | C |
| AI375420 | UNKNOWN | 13 | 321 | G |
| AI375420 | UNKNOWN | 12 | 152 | C |
| AI375487 | UNKNOWN | 25 | 0 | T |
| AI375530 | UNKNOWN | 30 | 0 | T |
| AI375530 | UNKNOWN | 18 | 230 | A |
| AI375534 | UNKNOWN | 12 | 0 | T |
| AI375615 | UNKNOWN | 57 | 0 | T |
| AI375615 | UNKNOWN | 18 | 279 | G |
| AI375657 | UNKNOWN | 17 | 45 | A |
| AI375659 | UNKNOWN | 33 | 0 | T |
| AI375702 | UNKNOWN | 36 | 30 | T |
| AI375702 | UNKNOWN | 29 | 0 | T |
| AI375702 | UNKNOWN | 15 | 107 | A |
| AI375730 | UNKNOWN | 78 | 0 | T |
| AI375730 | UNKNOWN | 17 | 113 | A |
| AI375730 | UNKNOWN | 17 | 203 | C |
| AI375730 | UNKNOWN | 14 | 78 | G |
| AI375817 | UNKNOWN | 22 | 0 | T |
| AI375988 | UNKNOWN | 22 | 0 | T |
| AI376086 | UNKNOWN | 39 | 0 | T |
| AI376095 | UNKNOWN | 33 | 0 | T |
| AI376134 | UNKNOWN | 18 | 0 | T |
| AI376180 | UNKNOWN | 84 | 0 | T |
| AI376180 | UNKNOWN | 19 | 389 | C |
| AI376180 | UNKNOWN | 15 | 166 | C |
| AI376194 | UNKNOWN | 19 | 0 | T |
| AI376213 | UNKNOWN | 13 | 0 | T |
| AI376228 | UNKNOWN | 41 | 0 | T |
| AI376376 | UNKNOWN | 64 | 0 | T |
| AI376376 | UNKNOWN | 13 | 159 | C |
| AI376400 | UNKNOWN | 26 | 0 | T |
| AI376425 | UNKNOWN | 68 | 0 | T |
| AI376425 | UNKNOWN | 18 | 135 | C |
| AI376425 | UNKNOWN | 15 | 353 | A |
| AI376425 | UNKNOWN | 14 | 68 | A |
| AI376468 | UNKNOWN | 46 | 0 | T |

TABLE 1-continued

| Genbank # | Region | # reps | Position | Unit sequence |
|---|---|---|---|---|
| AI376468 | UNKNOWN | 21 | 231 | G |
| AI376468 | UNKNOWN | 13 | 186 | A |
| AI376523 | UNKNOWN | 17 | 0 | T |
| AI376526 | UNKNOWN | 8.5 | 278 | TG |
| AI376590 | UNKNOWN | 16 | 0 | T |
| AI376608 | UNKNOWN | 13 | 10 | T |
| AI376665 | UNKNOWN | 13 | 0 | T |
| AI376680 | UNKNOWN | 27 | 0 | T |
| AI376685 | UNKNOWN | 14 | 0 | T |
| AI376692 | UNKNOWN | 30 | 27 | T |
| AI376692 | UNKNOWN | 26 | 0 | T |
| AI376692 | UNKNOWN | 19 | 261 | C |
| AI376692 | UNKNOWN | 14 | 239 | G |
| AI376692 | UNKNOWN | 12 | 206 | G |
| AI376701 | UNKNOWN | 12 | 0 | T |
| AI376739 | UNKNOWN | 6.5 | 294 | TA |
| AI376748 | UNKNOWN | 61 | 0 | T |
| AI376748 | UNKNOWN | 18 | 145 | A |
| AI376748 | UNKNOWN | 17 | 390 | G |
| AI376748 | UNKNOWN | 13 | 132 | C |
| AI376816 | UNKNOWN | 18 | 0 | T |
| AI376826 | UNKNOWN | 19 | 0 | T |
| AI376831 | UNKNOWN | 18 | 0 | T |
| AI376846 | UNKNOWN | 23 | 0 | T |
| AI376872 | UNKNOWN | 71 | 0 | T |
| AI376872 | UNKNOWN | 22 | 108 | G |
| AI376884 | UNKNOWN | 29 | 0 | T |
| AI376904 | UNKNOWN | 21 | 0 | T |
| AI376922 | UNKNOWN | 32 | 0 | T |
| AI376971 | UNKNOWN | 32 | 0 | T |
| AI376973 | UNKNOWN | 69 | 0 | T |
| AI376973 | UNKNOWN | 25 | 109 | A |
| AI376973 | UNKNOWN | 13 | 332 | G |
| AI376973 | UNKNOWN | 12 | 74 | c |
| AI377000 | UNKNOWN | 46 | 0 | T |
| AI377001 | UNKNOWN | 64 | 0 | T |
| AI377007 | UNKNOWN | 15 | 43 | A |
| AI377119 | UNKNOWN | 17 | 0 | T |
| AI377147 | UNKNOWN | 11.5 | 62 | AG |
| AI377147 | UNKNOWN | 29 | 84 | A |
| AI377148 | UNKNOWN | 29 | 183 | A |
| AI377157 | UNKNOWN | 31 | 97 | A |
| AI377165 | UNKNOWN | 26 | 221 | A |
| AI377250 | UNKNOWN | 13 | 171 | A |
| AI377314 | UNKNOWN | 34 | 0 | T |
| AI377367 | UNKNOWN | 17 | 0 | T |
| AI377373 | UNKNOWN | 15 | 0 | T |
| AI377379 | UNKNOWN | 15 | 0 | T |
| AI377417 | UNKNOWN | 46 | 28 | T |
| AI377417 | UNKNOWN | 26 | 0 | T |
| AI377417 | UNKNOWN | 18 | 164 | G |
| AI377417 | UNKNOWN | 13 | 183 | C |
| AI377553 | UNKNOWN | 14 | 0 | T |
| AI377597 | UNKNOWN | 26 | 214 | A |
| AI377618 | UNKNOWN | 25 | 106 | A |
| AI377628 | UNKNOWN | 27 | 65 | A |
| AI377636 | UNKNOWN | 5.75 | 79 | AAAG |
| AI377636 | UNKNOWN | 27 | 126 | A |
| AI377652 | UNKNOWN | 41 | 0 | T |
| AI377652 | UNKNOWN | 16 | 285 | A |
| AI377672 | UNKNOWN | 13 | 0 | T |
| AI377755 | UNKNOWN | 6.5 | 203 | TC |
| AI377755 | UNKNOWN | 20 | 0 | T |
| AI377764 | UNKNOWN | 19 | 114 | A |
| AI377785 | UNKNOWN | 19 | 0 | T |
| AI377860 | UNKNOWN | 14 | 0 | T |
| AI377887 | UNKNOWN | 30 | 0 | T |
| AI377891 | UNKNOWN | 12.5 | 143 | TA |
| AI377915 | UNKNOWN | 31 | 21 | T |
| AI377915 | UNKNOWN | 20 | 0 | T |
| AI377939 | UNKNOWN | 19 | 0 | T |
| AI377947 | UNKNOWN | 17 | 0 | T |
| AI377964 | UNKNOWN | 6.5 | 293 | TG |
| AI377999 | UNKNOWN | 23 | 0 | T |
| AI378000 | UNKNOWN | 12 | 0 | T |
| AI378019 | UNKNOWN | 15 | 0 | T |
| AI378021 | UNKNOWN | 7 | 280 | GA |

TABLE 1-continued

| Genbank # | Region | # reps | Position | Unit sequence |
|---|---|---|---|---|
| AI378044 | UNKNOWN | 14 | 440 | T |
| AI378046 | UNKNOWN | 15 | 0 | T |
| AI378055 | UNKNOWN | 14 | 0 | T |
| AI378080 | UNKNOWN | 73 | 0 | T |
| AI378080 | UNKNOWN | 20 | 111 | A |
| AI378095 | UNKNOWN | 35 | 0 | T |
| AI378113 | UNKNOWN | 14 | 0 | T |
| AI378123 | UNKNOWN | 63 | 0 | T |
| AI378196 | UNKNOWN | 4.83 | 49 | AAAAC |
| AI378266 | UNKNOWN | 28 | 0 | T |
| AI378339 | UNKNOWN | 19 | 0 | T |
| AI378346 | UNKNOWN | 7.5 | 55 | TA |
| AI378346 | UNKNOWN | 43 | 0 | T |
| AI378394 | UNKNOWN | 12 | 0 | T |
| AI378425 | UNKNOWN | 26 | 0 | T |
| AI378457 | UNKNOWN | 25 | 0 | T |
| AI378519 | UNKNOWN | 12 | 155 | T |
| AI378556 | UNKNOWN | 3.8 | 150 | CGGGG |
| AI378570 | UNKNOWN | 4.59 | 62 | AAACA |
| AI378571 | UNKNOWN | 46 | 0 | T |
| AI378624 | UNKNOWN | 48 | 0 | T |
| AI378629 | UNKNOWN | 12 | 0 | T |
| AI378689 | UNKNOWN | 30 | 112 | A |
| AI378730 | UNKNOWN | 30 | 207 | A |
| AI378730 | UNKNOWN | 24 | 29 | A |
| AI378776 | UNKNOWN | 4.75 | 20 | TTTA |
| AI378808 | UNKNOWN | 22 | 0 | T |
| AI378833 | UNKNOWN | 29 | 0 | T |
| AI378915 | UNKNOWN | 7 | 136 | TC |
| AI378928 | UNKNOWN | 17 | 70 | TC |
| AI378928 | UNKNOWN | 8 | 103 | CA |
| AI378928 | UNKNOWN | 13 | 0 | T |
| AI378951 | UNKNOWN | 43 | 0 | T |
| AI378968 | UNKNOWN | 17 | 221 | T |
| AI378970 | UNKNOWN | 4.5 | 208 | TTAT |
| AI378983 | UNKNOWN | 15 | 0 | T |
| AI379007 | UNKNOWN | 13 | 0 | T |
| AI379045 | UNKNOWN | 16 | 168 | T |
| AI379160 | UNKNOWN | 21 | 0 | T |
| AI379228 | UNKNOWN | 16 | 0 | T |
| AI379234 | UNKNOWN | 48 | 0 | T |
| AI379234 | UNKNOWN | 22 | 378 | A |
| AI379363 | UNKNOWN | 19 | 78 | A |
| AI379474 | UNKNOWN | 6.5 | 400 | AC |
| AI379581 | UNKNOWN | 17 | 0 | T |
| AI379600 | UNKNOWN | 14 | 4 | T |
| AI379624 | UNKNOWN | 6.5 | 460 | AC |
| AI379624 | UNKNOWN | 12 | 0 | T |
| AI379723 | UNKNOWN | 15 | 0 | T |
| AI379751 | UNKNOWN | 13 | 53 | A |
| AI379793 | UNKNOWN | 14 | 245 | A |
| AI379797 | UNKNOWN | 15 | 140 | A |
| AI379877 | UNKNOWN | 37 | 0 | T |
| AI379935 | UNKNOWN | 16 | 11 | T |
| AI380031 | UNKNOWN | 12 | 0 | T |
| AI380058 | UNKNOWN | 38 | 0 | T |
| AI380061 | UNKNOWN | 3.83 | 315 | TAGATA |
| AI380064 | UNKNOWN | 29 | 0 | T |
| AI380107 | UNKNOWN | 17 | 0 | T |
| AI380117 | UNKNOWN | 46 | 0 | T |
| AI380163 | UNKNOWN | 71 | 0 | T |
| AI380163 | UNKNOWN | 26 | 266 | C |
| AI380163 | UNKNOWN | 21 | 121 | G |
| AI380163 | UNKNOWN | 13 | 217 | A |
| AI380163 | UNKNOWN | 12 | 91 | A |
| AI380163 | UNKNOWN | 12 | 179 | C |
| AI380173 | UNKNOWN | 58 | 0 | T |
| AI380173 | UNKNOWN | 12 | 162 | C |
| AI380176 | UNKNOWN | 76 | 0 | T |
| AI380176 | UNKNOWN | 17 | 122 | C |
| AI380176 | UNKNOWN | 12 | 243 | G |
| AI380190 | UNKNOWN | 44 | 0 | T |
| AI380197 | UNKNOWN | 28 | 0 | T |
| AI380207 | UNKNOWN | 22 | 0 | T |
| AI380220 | UNKNOWN | 21 | 0 | T |
| AI380252 | UNKNOWN | 19 | 0 | T |
| AI380272 | UNKNOWN | 20 | 0 | T |

TABLE 1-continued

| Genbank # | Region | # reps | Position | Unit sequence |
|---|---|---|---|---|
| AI380277 | UNKNOWN | 19 | 0 | T |
| AI380278 | UNKNOWN | 14 | 0 | T |
| AI380283 | UNKNOWN | 38 | 0 | T |
| AI380304 | UNKNOWN | 13 | 0 | T |
| AI380323 | UNKNOWN | 13 | 0 | T |
| AI380329 | UNKNOWN | 54 | 0 | T |
| AI380381 | UNKNOWN | 23 | 0 | T |
| AI380429 | UNKNOWN | 23 | 6 | T |
| AI380441 | UNKNOWN | 17 | 0 | T |
| AI380449 | UNKNOWN | 26 | 0 | T |
| AI380529 | UNKNOWN | 16 | 0 | T |
| AI380549 | UNKNOWN | 21 | 0 | T |
| AI380555 | UNKNOWN | 6.5 | 91 | TTCC |
| AI380594 | UNKNOWN | 39 | 0 | T |
| AI380594 | UNKNOWN | 13 | 266 | G |
| AI380609 | UNKNOWN | 35 | 0 | T |
| AI380642 | UNKNOWN | 20 | 0 | T |
| AI380642 | UNKNOWN | 14 | 303 | A |
| AI380687 | UNKNOWN | 21 | 0 | T |
| AI380713 | UNKNOWN | 13 | 0 | T |
| AI380719 | UNKNOWN | 54 | 9 | T |
| AI380736 | UNKNOWN | 35 | 0 | T |
| AI380805 | UNKNOWN | 12 | 0 | T |
| AI380874 | UNKNOWN | 26 | 0 | T |
| AI380932 | UNKNOWN | 14 | 455 | A |
| AI380942 | UNKNOWN | 15 | 0 | T |
| AI380955 | UNKNOWN | 42 | 0 | T |
| AI381037 | UNKNOWN | 42 | 0 | T |
| AI381037 | UNKNOWN | 12 | 93 | A |
| AI381298 | UNKNOWN | 38 | 0 | T |
| AI381298 | UNKNOWN | 16 | 300 | C |
| AI381369 | UNKNOWN | 4.75 | 30 | TTTA |
| AI381369 | UNKNOWN | 18 | 0 | T |
| AI381382 | UNKNOWN | 217 | 0 | T |
| AI381524 | UNKNOWN | 12 | 446 | A |
| AI381533 | UNKNOWN | 6.5 | 145 | AC |
| AI381553 | UNKNOWN | 15 | 0 | T |
| AI381568 | UNKNOWN | 15 | 232 | T |
| AI381574 | UNKNOWN | 13 | 0 | T |
| AI381575 | UNKNOWN | 15 | 0 | T |
| AI381601 | UNKNOWN | 56 | 0 | T |
| AI381623 | UNKNOWN | 22 | 0 | T |
| AI381635 | UNKNOWN | 33 | 0 | T |
| AI381635 | UNKNOWN | 15 | 219 | A |
| AI381635 | UNKNOWN | 12 | 64 | A |
| AI381665 | UNKNOWN | 4.5 | 21 | TTAT |
| AI381669 | UNKNOWN | 29 | 0 | T |
| AI381676 | UNKNOWN | 47 | 0 | T |
| AI381704 | UNKNOWN | 35 | 0 | T |
| AI381735 | UNKNOWN | 19 | 0 | T |
| AI381920 | UNKNOWN | 23 | 0 | T |
| AI381930 | UNKNOWN | 12 | 146 | A |
| AI381934 | UNKNOWN | 16 | 0 | T |
| AI381977 | UNKNOWN | 30 | 0 | T |
| AI381977 | UNKNOWN | 12 | 169 | A |
| AI382001 | UNKNOWN | 15 | 463 | T |
| AI382003 | UNKNOWN | 39 | 0 | T |
| AI382181 | UNKNOWN | 20 | 480 | T |
| AI382181 | UNKNOWN | 18 | 0 | T |
| AI382201 | UNKNOWN | 71 | 0 | T |
| AI382201 | UNKNOWN | 14 | 220 | G |
| AI382201 | UNKNOWN | 12 | 153 | C |
| AI382313 | UNKNOWN | 56 | 0 | T |
| AI382313 | UNKNOWN | 13 | 228 | A |
| AI382329 | UNKNOWN | 42 | 0 | T |
| AI382378 | UNKNOWN | 13 | 0 | T |
| AI382423 | UNKNOWN | 35 | 0 | T |
| AI382434 | UNKNOWN | 15 | 0 | T |
| AI382569 | UNKNOWN | 20 | 0 | T |
| AI382624 | UNKNOWN | 33 | 0 | T |
| AI382670 | UNKNOWN | 76 | 0 | T |
| AI382717 | UNKNOWN | 41 | 0 | T |
| AI382806 | UNKNOWN | 40 | 0 | T |
| AI382806 | UNKNOWN | 13 | 128 | A |
| AI383043 | UNKNOWN | 14 | 75 | A |
| AI383133 | UNKNOWN | 17 | 302 | A |
| AI383170 | UNKNOWN | 6.5 | 167 | AC |

TABLE 1-continued

| Genbank # | Region | # reps | Position | Unit sequence |
|---|---|---|---|---|
| AI383340 | UNKNOWN | 8.66 | 198 | TAT |
| AI383340 | UNKNOWN | 13 | 0 | T |
| AI383359 | UNKNOWN | 23 | 0 | T |
| AI383442 | UNKNOWN | 16 | 0 | T |
| AI383482 | UNKNGWN | 16 | 0 | T |
| AI383510 | UNKNOWN | 65 | 0 | T |
| AI383510 | UNKNOWN | 12 | 332 | A |
| AI383717 | UNKNOWN | 4.75 | 45 | TTTA |
| AI383717 | UNKNOWN | 16 | 98 | T |
| AI383735 | UNKNOWN | 19 | 0 | T |
| AI383784 | UNKNOWN | 5.2 | 2 | TTATT |
| AI383804 | UNKNOWN | 56 | 0 | T |
| AI383919 | UNKNOWN | 96 | 2 | T |
| AI383919 | UNKNOWN | 14 | 200 | G |
| AI383968 | UNKNOWN | 12 | 1 | T |
| AI384035 | UNKNOWN | 4.4 | 10 | TTTAT |
| AI384035 | UNKNOWN | 4.5 | 25 | TTTA |
| AI384117 | UNKNOWN | 45 | 0 | T |
| AI384117 | UNKNOWN | 14 | 239 | A |
| AI391446 | UNKNOWN | 17 | 0 | T |
| AI391451 | UNKNOWN | 27 | 0 | T |
| AI391500 | UNKNOWN | 18 | 0 | T |
| AI391585 | UNKNOWN | 7.5 | 441 | TA |
| AI391605 | UNKNOWN | 28 | 0 | T |
| AI391660 | UNKNOWN | 22 | 0 | T |
| AI391662 | UNKNOWN | 17 | 0 | T |
| AI392609 | UNKNOWN | 12 | 0 | T |
| AI392659 | UNKNOWN | 36 | 0 | T |
| AI392660 | UNKNOWN | 8.5 | 158 | GT |
| AI392660 | UNKNOWN | 7 | 145 | AG |
| AI392661 | UNKNOWN | 21 | 0 | T |
| AI392793 | UNKNOWN | 41 | 0 | T |
| AI392814 | UNKNOWN | 14 | 0 | T |
| AI392837 | UNKNOWN | 18 | 0 | T |
| AI392953 | UNKNOWN | 16 | 0 | T |
| AI392964 | UNKNOWN | 16 | 0 | T |
| AI392990 | UNKNOWN | 54 | 0 | T |
| AI392999 | UNKNOWN | 47 | 0 | T |
| AI393006 | UNKNOWN | 57 | 0 | T |
| AI393017 | UNKNOWN | 3.6 | 253 | AAACC |
| AI393017 | UNKNOWN | 30 | 0 | T |
| AI393038 | UNKNOWN | 42 | 0 | T |
| AI393150 | UNKNOWN | 30 | 0 | T |
| AI393155 | UNKNOWN | 37 | 0 | T |
| AI393169 | UNKNOWN | 29 | 0 | T |
| AI393216 | UNKNOWN | 13 | 372 | A |
| AI393218 | UNKNOWN | 56 | 0 | T |
| AI393240 | UNKNOWN | 18 | 4 | T |
| AI393356 | UNKNOWN | 16 | 0 | T |
| AI393446 | UNKNOWN | 21 | 0 | T |
| AI393456 | UNKNOWN | 19 | 0 | T |
| AI393467 | UNKNOWN | 20 | 0 | T |
| AI393478 | UNKNOWN | 20 | 0 | T |
| AI393514 | UNKNOWN | 12 | 0 | T |
| AI393541 | UNKNOWN | 23 | 0 | T |
| AI393621 | UNKNOWN | 23 | 0 | T |
| AI393733 | UNKNOWN | 44 | 0 | T |
| AI393844 | UNKNOWN | 5 | 0 | TTTG |
| AI393908 | UNKNOWN | 14 | 0 | T |
| AI393930 | UNKNOWN | 13 | 0 | T |
| AI393962 | UNKNOWN | 12 | 23 | A |
| AI393981 | UNKNOWN | 18 | 0 | T |
| AI393982 | UNKNOWN | 17 | 0 | T |
| AI394009 | UNKNOWN | 12 | 0 | T |
| AI394010 | UNKNOWN | 15 | 7 | T |
| AI394164 | UNKNOWN | 4.8 | 39 | AAAAT |
| AI394182 | UNKNOWN | 4.75 | 193 | AAAC |
| AI394182 | UNKNOWN | 20 | 0 | T |
| AI394303 | UNKNOWN | 16 | 6 | T |
| AI394476 | UNKNOWN | 59 | 0 | T |
| AI394476 | UNKNOWN | 13 | 182 | G |
| AI394476 | UNKNOWN | 13 | 269 | A |
| AI394489 | UNKNOWN | 13 | 0 | T |
| AI394513 | UNKNOWN | 23 | 9 | T |
| AI394539 | UNKNOWN | 53 | 0 | T |
| AI394560 | UNKNOWN | 20 | 4 | T |
| AI394574 | UNKNOWN | 16 | 0 | T |

TABLE 1-continued

| Genbank # | Region | # reps | Position | Unit sequence |
|---|---|---|---|---|
| AI394637 | UNKNOWN | 20 | 0 | T |
| AI394679 | UNKNOWN | 15 | 0 | T |
| AI394690 | UNKNOWN | 42 | 0 | T |
| AI394725 | UNKNOWN | 19 | 0 | T |
| AI394730 | UNKNOWN | 49 | 0 | T |
| AI399664 | UNKNOWN | 13 | 0 | T |
| AI399759 | UNKNOWN | 44 | 0 | T |
| AI399759 | UNKNOWN | 16 | 247 | A |
| AI399977 | UNKNOWN | 49 | 0 | T |
| AI399982 | UNKNOWN | 15 | 2 | T |
| AI399982 | UNKNOWN | 15 | 377 | A |
| AI400114 | UNKNOWN | 30 | 0 | T |
| AI400203 | UNKNOWN | 5 | 226 | GCCCC |
| AI400289 | UNKNOWN | 3.04 | 259 | CTAACGCAGGGCTCCGGCGTGCAGGTGTCACGGTGTCGCTGCTTCTCA (SEQ ID NO:115) |
| AI400356 | UNKNOWN | 18 | 0 | T |
| AI400387 | UNKNOWN | 14 | 0 | T |
| AI400513 | UNKNOWN | 13 | 357 | T |
| AI400533 | UNKNOWN | 59 | 0 | T |
| AI400533 | UNKNOWN | 12 | 113 | A |
| AI400638 | UNKNOWN | 13 | 121 | A |
| AI400725 | UNKNOWN | 80 | 0 | T |
| AI400725 | UNKNOWN | 15 | 173 | C |
| AI400725 | UNKNOWN | 13 | 149 | C |
| AI400796 | UNKNOWN | 14 | 0 | T |
| AI400802 | UNKNOWN | 8.5 | 475 | AC |
| AI400802 | UNKNOWN | 7.5 | 447 | AC |
| AI400802 | UNKNOWN | 6.5 | 152 | TG |
| AI400826 | UNKNOWN | 41 | 0 | T |
| AI400839 | UNKNOWN | 21 | 4 | T |
| AI400846 | UNKNOWN | 18 | 0 | T |
| AI400854 | UNKNOWN | 64 | 0 | T |
| AI400854 | UNKNOWN | 12 | 150 | A |
| AI400888 | UNKNOWN | 12 | 0 | T |
| AI401001 | UNKNOWN | 15 | 176 | T |
| AI401056 | UNKNOWN | 12 | 129 | T |
| AI401095 | UNKNOWN | 14 | 0 | T |
| AI401109 | UNKNOWN | 24 | 0 | T |
| AI401179 | UNKNOWN | 30 | 0 | T |
| AI401193 | UNKNOWN | 49 | 0 | T |
| AI401193 | UNKNOWN | 16 | 105 | C |
| AI401299 | UNKNOWN | 22 | 43 | A |
| AI401303 | UNKNOWN | 53 | 0 | T |
| AI401413 | UNKNOWN | 13 | 0 | T |
| AI401577 | UNKNOWN | 20 | 0 | T |
| AI401672 | UNKNOWN | 35 | 0 | T |
| AI401697 | UNKNOWN | 57 | 0 | T |
| AI401697 | UNKNOWN | 14 | 113 | A |
| AI401699 | UNKNOWN | 50 | 0 | T |
| AI401699 | UNKNOWN | 13 | 81 | G |
| AI401799 | UNKNOWN | 19 | 24 | T |
| AI401799 | UNKNOWN | 18 | 0 | T |
| AI417000 | UNKNOWN | 39 | 0 | T |
| AI417049 | UNKNOWN | 33 | 0 | T |
| AI417074 | UNKNOWN | 21 | 6 | A |
| AI417084 | UNKNOWN | 12 | 0 | T |
| AI417090 | UNKNOWN | 15 | 2 | T |
| AI417098 | UNKNOWN | 15 | 2 | T |
| AI417160 | UNKNOWN | 15 | 0 | T |
| AI417193 | UNKNOWN | 17 | 0 | T |
| AI417267 | UNKNOWN | 13 | 622 | T |
| AI417312 | UNKNOWN | 45 | 0 | T |
| AI417354 | UNKNOWN | 24 | 323 | A |
| AI417378 | UNKNOWN | 41 | 0 | T |
| AI417401 | UNKNOWN | 7.5 | 79 | AC |
| AI417470 | UNKNOWN | 14 | 223 | T |
| AI417502 | UNKNOWN | 38 | 0 | T |
| AI417526 | UNKNOWN | 16 | 154 | T |
| AI417554 | UNKNOWN | 12 | 11 | T |
| AI417678 | UNKNOWN | 14 | 302 | T |
| AI417686 | UNKNOWN | 21 | 0 | T |
| AI417699 | UNKNOWN | 9 | 269 | GT |
| AI417699 | UNKNOWN | 9 | 289 | GA |
| AI417754 | UNKNOWN | 41 | 0 | T |
| AI417755 | UNKNOWN | 20 | 4 | T |
| AI417766 | UNKNOWN | 43 | 0 | T |
| AI417790 | UNKNOWN | 70 | 0 | T |

TABLE 1-continued

| Genbank # | Region | # reps | Position | Unit sequence |
|---|---|---|---|---|
| AI417790 | UNKNOWN | 13 | 123 | A |
| AI417905 | UNKNOWN | 21 | 0 | T |
| AI417952 | UNKNOWN | 24 | 0 | T |
| AI417957 | UNKNOWN | 44 | 0 | T |
| AI417986 | UNKNOWN | 25 | 0 | T |
| AI417996 | UNKNOWN | 9.5 | 151 | CA |
| AI418024 | UNKNOWN | 57 | 15 | T |
| AI418024 | UNKNOWN | 12 | 0 | T |
| AI418128 | UNKNOWN | 66 | 0 | T |
| AI418128 | UNKNOWN | 14 | 128 | G |
| AI418234 | UNKNOWN | 50 | 0 | T |
| AI418254 | UNKNOWN | 57 | 0 | T |
| AI418254 | UNKNOWN | 16 | 97 | A |
| AI418254 | UNKNOWN | 16 | 113 | G |
| AI418261 | UNKNOWN | 17 | 0 | T |
| AI418289 | UNKNOWN | 16 | 367 | T |
| AI418293 | UNKNOWN | 26 | 0 | T |
| AI418335 | UNKNOWN | 19 | 0 | T |
| AI418393 | UNKNOWN | 49 | 0 | T |
| AI418422 | UNKNOWN | 13 | 0 | T |
| AI418432 | UNKNOWN | 23 | 0 | T |
| AI418436 | UNKNOWN | 44 | 0 | T |
| AI418436 | UNKNOWN | 12 | 60 | A |
| AI418438 | UNKNOWN | 5.75 | 4 | TTTA |
| AI418468 | UNKNOWN | 17 | 0 | T |
| AI418470 | UNKNOWN | 13 | 0 | T |
| AI418478 | UNKNOWN | 17 | 0 | T |
| AI418481 | UNKNOWN | 14 | 0 | T |
| AI418485 | UNKNOWN | 15 | 0 | T |
| AI418520 | UNKNOWN | 15 | 0 | T |
| AI418533 | UNKNOWN | 23 | 0 | T |
| AI418572 | UNKNOWN | 39 | 0 | T |
| AI418589 | UNKNOWN | 14 | 0 | T |
| AI418591 | UNKNOWN | 13 | 0 | T |
| AI418597 | UNKNOWN | 27 | 0 | T |
| AI418598 | UNKNOWN | 34 | 0 | T |
| AI418635 | UNKNOWN | 17 | 0 | T |
| AI418635 | UNKNOWN | 12 | 194 | G |
| AI418681 | UNKNOWN | 63 | 0 | T |
| AI418841 | UNKNOWN | 24 | 0 | T |
| AI418873 | UNKNOWN | 23 | 0 | T |
| AI418885 | UNKNOWN | 47 | 0 | T |
| AI418963 | UNKNOWN | 7 | 117 | GGC |
| AI418970 | UNKNOWN | 85 | 0 | T |
| AI418970 | UNKNOWN | 14 | 126 | C |
| AI419054 | UNKNOWN | 19 | 0 | T |
| AI419060 | UNKNOWN | 7 | 423 | AG |
| AI419160 | UNKNOWN | 34 | 0 | T |
| AI419212 | UNKNOWN | 48 | 21 | T |
| AI419212 | UNKNOWN | 17 | 0 | T |
| AI419212 | UNKNOWN | 15 | 268 | A |
| AI419273 | UNKNOWN | 40 | 0 | T |
| AI419311 | UNKNOWN | 73 | 0 | T |
| AI419311 | UNKNOWN | 12 | 184 | C |
| AI419337 | UNKNOWN | 19 | 38 | T |
| AI419374 | UNKNOWN | 60 | 0 | T |
| AI419374 | UNKNOWN | 13 | 179 | C |
| AI419374 | UNKNOWN | 13 | 256 | G |
| AI419374 | UNKNOWN | 12 | 109 | G |
| AI419417 | UNKNOWN | 79 | 0 | T |
| AI419417 | UNKNOWN | 19 | 195 | C |
| AI419417 | UNKNOWN | 16 | 175 | A |
| AI419417 | UNKNOWN | 14 | 90 | A |
| AI419440 | UNKNOWN | 56 | 0 | T |
| AI419440 | UNKNOWN | 18 | 136 | A |
| AI419455 | UNKNOWN | 55 | 0 | T |
| AI419455 | UNKNOWN | 13 | 202 | C |
| AI419455 | UNKNOWN | 12 | 159 | C |
| AI419480 | UNKNOWN | 44 | 0 | T |
| AI419480 | UNKNOWN | 16 | 145 | C |
| AI419650 | UNKNOWN | 72 | 0 | T |
| AI419756 | UNKNOWN | 46 | 0 | T |
| AI419811 | UNKNOWN | 18 | 128 | A |
| AI419840 | UNKNOWN | 23 | 0 | T |
| AI419882 | UNKNOWN | 14 | 0 | T |
| AI419893 | UNKNOWN | 17 | 0 | T |
| AI419899 | UNKNOWN | 8.5 | 282 | TA |

TABLE 1-continued

| Genbank # | Region | # reps | Position | Unit sequence |
|---|---|---|---|---|
| AI419901 | UNKNOWN | 18 | 148 | T |
| AI419937 | UNKNOWN | 12 | 0 | T |
| AI420069 | UNKNOWN | 12 | 0 | T |
| AI420113 | UNKNOWN | 23 | 0 | T |
| AI420213 | UNKNOWN | 20 | 333 | T |
| AI420256 | UNKNOWN | 15 | 0 | T |
| AI420319 | UNKNOWN | 16 | 0 | T |
| AI420336 | UNKNOWN | 13 | 0 | T |
| AI420349 | UNKNOWN | 26 | 0 | T |
| AI420419 | UNKNOWN | 24 | 0 | T |
| AI420473 | UNKNOWN | 13 | 0 | T |
| AI420521 | UNKNOWN | 99 | 0 | T |
| AI420521 | UNKNOWN | 18 | 118 | A |
| AI420521 | UNKNOWN | 16 | 148 | G |
| AI420523 | UNKNOWN | 3.83 | 0 | TTTTA |
| AI420572 | UNKNOWN | 4.75 | 26 | TTTA |
| AI420611 | UNKNOWN | 3.8 | 256 | TTTTC |
| AI420611 | UNKNOWN | 15 | 271 | T |
| AI420692 | UNKNOWN | 29 | 0 | T |
| AI420698 | UNKNOWN | 41 | 0 | T |
| AI420796 | UNKNOWN | 59 | 0 | T |
| AI420817 | UNKNOWN | 15 | 0 | T |
| AI420865 | UNKNOWN | 7.5 | 361 | TA |
| AI420865 | UNKNOWN | 7 | 312 | TG |
| AI420897 | UNKNOWN | 38 | 0 | T |
| AI421013 | UNKNOWN | 13 | 258 | T |
| AI421079 | UNKNOWN | 4.59 | 0 | TTTGT |
| AI421085 | UNKNOWN | 75 | 0 | T |
| AI421087 | UNKNOWN | 59 | 0 | T |
| AI421087 | UNKNOWN | 17 | 95 | A |
| AI421087 | UNKNOWN | 14 | 261 | C |
| AI421087 | UNKNOWN | 12 | 332 | G |
| AI421091 | UNKNOWN | 68 | 0 | T |
| AI421104 | UNKNOWN | 43 | 0 | T |
| AI421104 | UNKNOWN | 15 | 110 | A |
| AI421149 | UNKNOWN | 51 | 0 | T |
| AI421149 | UNKNOWN | 14 | 155 | G |
| AI421149 | UNKNOWN | 12 | 192 | A |
| AI421197 | UNKNOWN | 48 | 0 | T |
| AI421220 | UNKNOWN | 12.2 | 12 | TTTAT |
| AI421222 | UNKNOWN | 51 | 0 | T |
| AI421222 | UNKNOWN | 16 | 65 | A |
| AI421222 | UNKNOWN | 12 | 100 | G |
| AI421252 | UNKNOWN | 53 | 0 | T |
| AI421307 | UNKNOWN | 27 | 0 | T |
| AI421317 | UNKNOWN | 48 | 0 | T |
| AI421318 | UNKNOWN | 41 | 0 | T |
| AI421328 | UNKNOWN | 54 | 0 | T |
| AI421442 | UNKNOWN | 43 | 0 | T |
| AI421470 | UNKNOWN | 55 | 0 | T |
| AI421470 | UNKNOWN | 12 | 147 | A |
| AI421523 | UNKNOWN | 56 | 0 | T |
| AI421523 | UNKNOWN | 19 | 271 | G |
| AI421523 | UNKNOWN | 18 | 149 | G |
| AI421523 | UNKNOWN | 15 | 381 | C |
| AI421524 | UNKNOWN | 29 | 0 | T |
| AI421526 | UNKNOWN | 54 | 0 | T |
| AI421526 | UNKNOWN | 15 | 361 | G |
| AI421526 | UNKNOWN | 12 | 317 | G |
| AI421578 | UNKNOWN | 41 | 0 | T |
| AI421578 | UNKNOWN | 12 | 210 | C |
| AI421585 | UNKNOWN | 41 | 0 | T |
| AI421585 | UNKNOWN | 17 | 101 | G |
| AI421585 | UNKNOWN | 14 | 139 | C |
| AI421585 | UNKNOWN | 12 | 89 | A |
| AI421663 | UNKNOWN | 27 | 0 | T |
| AI421755 | UNKNOWN | 13 | 0 | T |
| AI421798 | UNKNOWN | 66 | 0 | T |
| AI421798 | UNKNOWN | 12 | 90 | C |
| AI421903 | UNKNOWN | 73 | 16 | T |
| AI421903 | UNKNOWN | 24 | 139 | A |
| AI421903 | UNKNOWN | 15 | 0 | T |
| AI421903 | UNKNOWN | 14 | 275 | G |
| AI421903 | UNKNOWN | 13 | 243 | C |
| AI422002 | UNKNOWN | 42 | 0 | T |
| AI422008 | UNKNOWN | 3.8 | 464 | TTTA |
| AI422023 | UNKNOWN | 12 | 0 | T |

TABLE 1-continued

| Genbank # | Region | # reps | Position | Unit sequence |
|---|---|---|---|---|
| AI422024 | UNKNOWN | 41 | 0 | T |
| AI422034 | UNKNOWN | 33 | 0 | T |
| AI422050 | UNKNOWN | 39 | 0 | T |
| AI422050 | UNKNOWN | 12 | 133 | G |
| AI422077 | UNKNOWN | 44 | 0 | T |
| AI422077 | UNKNOWN | 17 | 102 | G |
| AI422077 | UNKNOWN | 16 | 86 | A |
| AI422080 | UNKNOWN | 51 | 23 | T |
| AI422080 | UNKNOWN | 21 | 0 | T |
| AI422080 | UNKNOWN | 16 | 328 | C |
| AI422096 | UNKNOWN | 12 | 270 | T |
| AI422220 | UNKNOWN | 34 | 0 | T |
| AI422384 | UNKNOWN | 25 | 0 | T |
| AI422387 | UNKNOWN | 6 | 329 | AGA |
| AI422414 | UNKNOWN | 16 | 378 | T |
| AI422453 | UNKNOWN | 18 | 0 | T |
| AI422458 | UNKNOWN | 13 | 37 | T |
| AI422498 | UNKNOWN | 41 | 0 | T |
| AI422521 | UNKNOWN | 52 | 0 | T |
| AI422523 | UNKNOWN | 39 | 0 | T |
| AI422688 | UNKNOWN | 67 | 13 | T |
| AI422688 | UNKNOWN | 12 | 0 | T |
| AI422714 | UNKNOWN | 46 | 0 | T |
| AI422773 | UNKNOWN | 51 | 0 | T |
| AI422773 | UNKNOWN | 24 | 120 | C |
| AI422773 | UNKNOWN | 19 | 101 | G |
| AI422773 | UNKNOWN | 12 | 80 | C |
| AI422843 | UNKNOWN | 42 | 0 | T |
| AI422850 | UNKNOWN | 5.75 | 500 | TTTC |
| AI422853 | UNKNOWN | 24 | 0 | T |
| AI422855 | UNKNOWN | 52 | 0 | T |
| AI422958 | UNKNOWN | 31 | 0 | T |
| AI422958 | UNKNOWN | 19 | 119 | G |
| AI422958 | UNKNOWN | 14 | 93 | C |
| AI422975 | UNKNOWN | 31 | 0 | T |
| AI422985 | UNKNOWN | 71 | 0 | T |
| AI422985 | UNKNOWN | 22 | 224 | A |
| AI422985 | UNKNOWN | 19 | 256 | C |
| AI422985 | UNKNOWN | 12 | 188 | A |
| AI423012 | UNKNOWN | 45 | 0 | T |
| AI423012 | UNKNOWN | 25 | 145 | C |
| AI423018 | UNKNOWN | 19 | 320 | T |
| AI423043 | UNKNOWN | 30 | 93 | T |
| AI423043 | UNKNOWN | 14 | 9 | T |
| AI423056 | UNKNOWN | 7 | 191 | CA |
| AI423105 | UNKNOWN | 68 | 6 | T |
| AI423105 | UNKNOWN | 19 | 132 | G |
| AI423105 | UNKNOWN | 17 | 158 | A |
| AI423112 | UNKNOWN | 48 | 0 | T |
| AI423121 | UNKNOWN | 63 | 0 | T |
| AI423126 | UNKNOWN | 15 | 0 | T |
| AI423192 | UNKNOWN | 39 | 0 | T |
| AI423198 | UNKNOWN | 49 | 9 | T |
| AI423201 | UNKNOWN | 17 | 59 | A |
| AI423247 | UNKNOWN | 50 | 0 | T |
| AI423326 | UNKNOWN | 65 | 0 | T |
| AI423326 | UNKNOWN | 16 | 107 | G |
| AI423479 | UNKNOWN | 42 | 0 | T |
| AI423511 | UNKNOWN | 19 | 25 | A |
| AI423518 | UNKNOWN | 50 | 0 | T |
| AI423556 | UNKNOWN | 40 | 0 | T |
| AI423570 | UNKNOWN | 24 | 0 | T |
| AI423570 | UNKNOWN | 17 | 289 | G |
| AI423571 | UNKNOWN | 26 | 0 | T |
| AI423585 | UNKNOWN | 52 | 0 | T |
| AI423585 | UNKNOWN | 14 | 225 | G |
| AI423585 | UNKNOWN | 13 | 114 | G |
| AI423631 | UNKNOWN | 49 | 0 | T |
| AI423733 | UNKNOWN | 43 | 0 | T |
| AI423780 | UNKNOWN | 27 | 0 | T |
| AI423780 | UNKNOWN | 13 | 192 | G |
| AI423786 | UNKNOWN | 12 | 0 | T |
| AI423786 | UNKNOWN | 12 | 170 | G |
| AI423802 | UNKNOWN | 46 | 0 | T |
| AI423802 | UNKNOWN | 13 | 250 | C |
| AI423802 | UNKNOWN | 12 | 65 | A |
| AI423876 | UNKNOWN | 24 | 0 | T |

TABLE 1-continued

| Genbank # | Region | # reps | Position | Unit sequence |
|---|---|---|---|---|
| AI423982 | UNKNOWN | 52 | 0 | T |
| AI423982 | UNKoWN | 19 | 59 | A |
| AI423982 | UNKNOWN | 15 | 381 | C |
| AI423998 | UNKNOWN | 25 | 0 | T |
| AI424152 | UNKNOWN | 31 | 0 | T |
| AI424192 | UNKNOWN | 44 | 0 | T |
| AI424192 | UNKNOWN | 19 | 205 | C |
| AI424262 | UNKNOWN | 7 | 101 | CA |
| AI424278 | UNKNOWN | 14 | 0 | T |
| AI424326 | UNKNOWN | 27 | 0 | T |
| AI424494 | UNKNOWN | 39 | 0 | T |
| AI424494 | UNKNOWN | 14 | 39 | A |
| AI424538 | UNKNOWN | 20 | 0 | T |
| AI424880 | UNKNOWN | 17 | 0 | T |
| AI424902 | UNKNOWN | 15 | 240 | A |
| AI424999 | UNKNOWN | 18 | 1 | T |
| AI425028 | UNKNOWN | 3.6 | 276 | AAACA |
| AI425073 | UNKNOWN | 12 | 441 | A |
| AI431291 | UNKNOWN | 66 | 0 | T |
| AI431291 | UNKNOWN | 17 | 115 | A |
| AI431300 | UNKNOWN | 65 | 0 | T |
| AI431300 | UNKNOWN | 13 | 229 | C |
| AI431300 | UNKNOWN | 12 | 113 | A |
| AI431304 | UNKNOWN | 15 | 30 | T |
| AI431304 | UNKNOWN | 14 | 241 | A |
| AI431324 | UNKNOWN | 15 | 90 | A |
| AI431326 | UNKNOWN | 16 | 30 | T |
| AI431327 | UNKNOWN | 110 | 0 | T |
| AI431327 | UNKNOWN | 19 | 221 | C |
| AI431327 | UNKNOWN | 15 | 179 | C |
| AI431327 | UNKNOWN | 13 | 110 | A |
| AI431327 | UNKNOWN | 12 | 156 | C |
| AI431327 | UNKNOWN | 12 | 194 | G |
| AI431408 | UNKNOWN | 95 | 0 | T |
| AI431408 | UNKNOWN | 15 | 456 | C |
| AI431415 | UNKNOWN | 51 | 0 | T |
| AI431422 | UNKNOWN | 20 | 0 | T |
| AI431424 | UNKNOWN | 100 | 0 | T |
| AI431424 | UNKNOWN | 14 | 108 | G |
| AI431424 | UNKNOWN | 12 | 147 | A |
| AI431431 | UNKNOWN | 29 | 0 | T |
| AI431431 | UNKNOWN | 23 | 172 | A |
| AI431431 | UNKNOWN | 15 | 249 | C |
| AI431431 | UNKNOWN | 13 | 145 | C |
| AI431433 | UNKNOWN | 42 | 0 | T |
| AI431448 | UNKNOWN | 15 | 50 | T |
| AI431454 | UNKNOWN | 29 | 0 | T |
| AI431589 | UNKNOWN | 7 | 272 | CA |
| AI431785 | UNKNOWN | 71 | 0 | T |
| AI431786 | UNKNOWN | 16 | 0 | T |
| AI431811 | UNKNOWN | 38 | 0 | T |
| AI431897 | UNKNOWN | 43 | 0 | T |
| AI431909 | UNKNOWN | 88 | 0 | T |
| AI431909 | UNKNOWN | 24 | 178 | G |
| AI431909 | UNKNOWN | 12 | 124 | A |
| AI431932 | UNKNOWN | 13 | 133 | AC |
| AI431962 | UNKNOWN | 76 | 0 | T |
| AI431973 | UNKNOWN | 26 | 0 | T |
| AI431975 | UNKNOWN | 102 | 0 | T |
| AI431975 | UNKNOWN | 12 | 197 | A |
| AI431979 | UNKNOWN | 74 | 0 | T |
| AI432030 | UNKNOWN | 79 | 0 | T |
| AI432030 | UNKNOWN | 20 | 184 | C |
| AI432030 | UNKNOWN | 17 | 157 | G |
| AI432030 | UNKNOWN | 13 | 79 | A |
| AI432040 | UNKNOWN | 83 | 0 | T |
| AI432040 | UNKNOWN | 15 | 105 | A |
| AI432047 | UNKNOWN | 33 | 0 | T |
| AI432047 | UNKNOWN | 19 | 81 | A |
| AI432053 | UNKNOWN | 54 | 0 | T |
| AI432085 | UNKNOWN | 98 | 0 | T |
| AI432085 | UNKNOWN | 22 | 195 | G |
| AI432085 | UNKNOWN | 13 | 138 | A |
| AI432085 | UNKNOWN | 13 | 172 | C |
| AI432085 | UNKNOWN | 12 | 157 | G |
| AI432163 | UNKNOWN | 21 | 381 | T |
| AI432218 | UNKNOWN | 90 | 0 | T |

TABLE 1-continued

| Genbank # | Region | # reps | Position | Unit sequence |
|---|---|---|---|---|
| AI432218 | UNKNOWN | 13 | 129 | A |
| AI432218 | UNKNOWN | 12 | 177 | G |
| AI432229 | UNKNOWN | 121 | 0 | T |
| AI432229 | UNKNOWN | 17 | 271 | C |
| AI432229 | UNKNOWN | 14 | 176 | G |
| AI432229 | UNKNOWN | 12 | 240 | A |
| AI432237 | UNKNOWN | 87 | 0 | T |
| AI432237 | UNKNOWN | 14 | 290 | C |
| AI432237 | UNKNOWN | 12 | 112 | A |
| AI432334 | UNKNOWN | 5.66 | 426 | GAA |
| AI432335 | UNKNOWN | 40 | 0 | T |
| AI432352 | UNKNOWN | 17 | 0 | T |
| AI432357 | UNKNOWN | 18 | 0 | T |
| AI432380 | UNKNOWN | 16 | 0 | T |
| AI432444 | UNKNOWN | 16 | 0 | T |
| AI432507 | UNKNOWN | 57 | 0 | T |
| AI432513 | UNKNOWN | 42 | 0 | T |
| AI432532 | UNKNOWN | 57 | 0 | T |
| AI432570 | UNKNOWN | 57 | 3 | T |
| AI432603 | UNKNOWN | 4.75 | 17 | TTTA |
| AI432656 | UNKNOWN | 115 | 16 | T |
| AI432656 | UNKNOWN | 22 | 174 | A |
| AI432656 | UNKNOWN | 15 | 420 | G |
| AI432656 | UNKNOWN | 13 | 157 | G |
| AI432671 | UNKNOWN | 12 | 0 | T |
| AI432693 | UNKNOWN | 42 | 0 | T |
| AI432736 | UNKNOWN | 80 | 0 | T |
| AI432736 | UNKNOWN | 12 | 132 | G |
| AI432790 | UNKNOWN | 83 | 0 | T |
| AI432790 | UNKNOWN | 16 | 216 | A |
| AI432790 | UNKNOWN | 13 | 145 | C |
| AI432805 | UNKNOWN | 7.5 | 63 | AG |
| AI432813 | UNKNOWN | 107 | 0 | T |
| AI432813 | UNKNOWN | 19 | 154 | A |
| AI432813 | UNKNOWN | 13 | 325 | C |
| AI432813 | UNKNOWN | 12 | 173 | C |
| AI432813 | UNKNOWN | 12 | 191 | G |
| AI432817 | UNKNOWN | 72 | 0 | T |
| AI432829 | UNKNOWN | 16 | 191 | A |
| AI432851 | UNKNOWN | 20 | 253 | A |
| AI432935 | UNKNOWN | 39 | 0 | T |
| AI432942 | UNKNOWN | 58 | 0 | T |
| AI432942 | UNKNOWN | 12 | 124 | A |
| AI432943 | UNKNOWN | 14 | 0 | T |
| AI432963 | UNKNOWN | 23 | 0 | T |
| AI432969 | UNKNOWN | 116 | 0 | T |
| AI432969 | UNKNOWN | 18 | 187 | A |
| AI432969 | UNKNOWN | 13 | 174 | C |
| AI432972 | UNKNOWN | 35 | 0 | T |
| AI433011 | UNKNOWN | 51 | 0 | T |
| AI433011 | UNKNOWN | 25 | 108 | G |
| AI433021 | UNKNOWN | 85 | 0 | T |
| AI433021 | UNKNOWN | 13 | 196 | C |
| AI433023 | UNKNOWN | 97 | 0 | T |
| AI433023 | UNKNOWN | 13 | 197 | C |
| AI433023 | UNKNOWN | 12 | 176 | A |
| AI433023 | UNKNOWN | 12 | 267 | G |
| AI433034 | UNKNOWN | 76 | 0 | T |
| AI433034 | UNKNOWN | 18 | 168 | G |
| AI433035 | UNKNOWN | 48 | 0 | T |
| AI433037 | UNKNOWN | 101 | 11 | T |
| AI433055 | UNKNOWN | 46 | 0 | T |
| AI433157 | UNKNOWN | 136 | 11 | T |
| AI433157 | UNKNOWN | 18 | 147 | A |
| AI433163 | UNKNOWN | 15 | 11 | T |
| AI433198 | UNKNOWN | 43 | 0 | T |
| AI433206 | UNKNOWN | 79 | 0 | T |
| AI433206 | UNKNOWN | 15 | 97 | A |
| AI433206 | UNKNOWN | 15 | 262 | G |
| AI433230 | UNKNOWN | 34 | 0 | T |
| AI433234 | UNKNOWN | 4.59 | 411 | AAAC |
| AI433293 | UNKNOWN | 20 | 0 | T |
| AI433375 | UNKNOWN | 16 | 6 | T |
| AI433384 | UNKNOWN | 99 | 0 | T |
| AI433384 | UNKNOWN | 15 | 165 | G |
| AI433384 | UNKNOWN | 14 | 106 | C |
| AI433384 | UNKNOWN | 13 | 120 | G |

TABLE 1-continued

| Genbank # | Region | # reps | Position | Unit sequence |
|---|---|---|---|---|
| AI433579 | UNKNOWN | 14 | 0 | T |
| AI433590 | UNKNOWN | 77 | 0 | T |
| AI433590 | UNKNOWN | 21 | 290 | A |
| AI433590 | UNKNOWN | 15 | 122 | A |
| AI433590 | UNKNOWN | 12 | 110 | G |
| AI433600 | UNKNOWN | 77 | 0 | T |
| AI433600 | UNKNOWN | 13 | 134 | G |
| AI433614 | UNKNOWN | 15 | 4 | T |
| AI433647 | UNKNOWN | 63 | 0 | T |
| AI433647 | UNKNOWN | 13 | 135 | G |
| AI433684 | UNKNOWN | 17 | 0 | T |
| AI433706 | UNKNOWN | 6.5 | 538 | AC |
| AI433709 | UNKNOWN | 33 | 0 | T |
| AI433787 | UNKNOWN | 6.5 | 421 | TGTT |
| AI433819 | UNKNOWN | 17 | 0 | T |
| AI433875 | UNKNOWN | 21 | 0 | T |
| AI433912 | UNKNOWN | 44 | 0 | T |
| AI433922 | UNKNOWN | 94 | 0 | T |
| AI433922 | UNKNOWN | 16 | 266 | A |
| AI433922 | UNKNOWN | 15 | 152 | G |
| AI433922 | UNKNOWN | 14 | 167 | A |
| AI433922 | UNKNOWN | 12 | 140 | C |
| AI433974 | UNKNOWN | 15 | 11 | T |
| AI433976 | UNKNOWN | 137 | 10 | T |
| AI433976 | UNKNOWN | 16 | 170 | C |
| AI433994 | UNKNOWN | 53 | 0 | T |
| AI434020 | UNKNOWN | 92 | 0 | T |
| AI434020 | UNKNOWN | 12 | 111 | G |
| AI434038 | UNKNOWN | 76 | 0 | T |
| AI434038 | UNKNOWN | 14 | 118 | A |
| AI434038 | UNKNOWN | 12 | 81 | A |
| AI434080 | UNKNOWN | 43 | 0 | T |
| AI434109 | UNKNOWN | 43 | 0 | T |
| AI434123 | UNKNOWN | 53 | 0 | T |
| AI434126 | UNKNOWN | 8.66 | 166 | AAC |
| AI434126 | UNKNOWN | 7 | 339 | AT |
| AI434130 | UNKNOWN | 14 | 362 | TG |
| AI434130 | UNKNOWN | 16 | 187 | T |
| AI434134 | UNKNOWN | 75 | 0 | T |
| AI434134 | UNKNOWN | 12 | 176 | C |
| AI434223 | UNKNOWN | 103 | 11 | T |
| AI434229 | UNKNOWN | 47 | 11 | T |
| AI434249 | UNKNOWN | 59 | 0 | T |
| AI434253 | UNKOWN | 33 | 11 | T |
| AI434274 | UNKNOWN | 71 | 0 | T |
| AI434274 | UNKNOWN | 18 | 346 | C |
| AI434279 | UNKNOWN | 64 | 0 | T |
| AI434279 | UNKNOWN | 12 | 190 | C |
| AI434281 | UNKNOWN | 122 | 0 | T |
| AI434281 | UNKNOWN | 18 | 152 | G |
| AI434281 | UNKNOWN | 13 | 139 | C |
| AI434413 | UNKNOWN | 16 | 0 | T |
| AI434414 | UNKNOWN | 24 | 0 | T |
| AI434426 | UNKNOWN | 15 | 0 | T |
| AI434432 | UNKNOWN | 55 | 0 | T |
| AI434443 | UNKNOWN | 12 | 0 | T |
| AI434453 | UNKNOWN | 73 | 0 | T |
| AI434453 | UNKNOWN | 15 | 185 | G |
| AI434453 | UNKNOWN | 12 | 170 | C |
| AI434464 | UNKNOWN | 80 | 0 | T |
| AI434464 | UNKNOWN | 16 | 306 | A |
| AI434464 | UNKNOWN | 13 | 461 | C |
| AI434468 | UNKNOWN | 94 | 0 | T |
| AI434468 | UNKNOWN | 23 | 148 | A |
| AI434472 | UNKNOWN | 63 | 0 | T |
| AI434482 | UNKNOWN | 26 | 0 | T |
| AI434550 | UNKNOWN | 74 | 0 | T |
| AI434550 | UNKNOWN | 13 | 176 | G |
| AI434589 | UNKNOWN | 7 | 341 | AC |
| AI434594 | UNKNOWN | 13 | 0 | T |
| AI434612 | UNKNOWN | 42 | 0 | T |
| AI434656 | UNKNOWN | 61 | 0 | T |
| AI434673 | UNKNOWN | 8 | 121 | GA |
| AI434686 | UNKNOWN | 12 | 66 | T |
| AI434693 | UNKNOWN | 54 | 0 | T |
| AI434731 | UNKNOWN | 60 | 0 | T |
| AI434741 | UNKNOWN | 79 | 0 | T |

TABLE 1-continued

| Genbank # | Region | # reps | Position | Unit sequence |
|---|---|---|---|---|
| AI434780 | UNKNOWN | 48 | 0 | T |
| AI434805 | UNKNOWN | 41 | 0 | T |
| AI434805 | UNKNOWN | 16 | 189 | A |
| AI434833 | UNKNOWN | 80 | 0 | T |
| AI434833 | UNKNOWN | 16 | 246 | G |
| AI434863 | UNKNOWN | 7 | 4 | TA |
| AI434872 | UNKNOWN | 23 | 0 | T |
| AI434932 | UNKNOWN | 37 | 0 | T |
| AI434965 | UNKNOWN | 28 | 0 | T |
| AI434969 | UNKNOWN | 58 | 0 | T |
| AI434969 | UNKNOWN | 15 | 214 | A |
| AI434991 | UNKNOWN | 4 | 150 | CAAAA |
| AI434991 | UNKNOWN | 41 | 0 | T |
| AI435086 | UNKNOWN | 12 | 0 | T |
| AI435087 | UNKNOWN | 45 | 0 | T |
| AI435091 | UNKNOWN | 18 | 0 | T |
| AI435091 | UNKNOWN | 13 | 145 | A |
| AI435100 | UNKNOWN | 15 | 0 | T |
| AI435192 | UNKNOWN | 43 | 0 | T |
| AI435225 | UNKNOWN | 15 | 0 | T |
| AI435248 | UNKNOWN | 18 | 163 | T |
| AI435253 | UNKNOWN | 67 | 0 | T |
| AI435268 | UNKNOWN | 82 | 0 | T |
| AI435268 | UNKNOWN | 15 | 128 | G |
| AI435303 | UNKNOWN | 39 | 0 | T |
| AI435363 | UNKNOWN | 64 | 0 | T |
| AI435363 | UNKNOWN | 21 | 314 | A |
| AI435363 | UNKNOWN | 18 | 146 | G |
| AI435366 | UNKNOWN | 3.8 | 244 | TTTTC |
| AI435366 | UNKNOWN | 16 | 259 | T |
| AI435405 | UNKNOWN | 48 | 0 | T |
| AI435421 | UNKNOWN | 12 | 0 | T |
| AI435422 | UNKNOWN | 16 | 202 | A |
| AI435437 | UNKNOWN | 12 | 28 | A |
| AI435503 | UNKNOWN | 34 | 0 | T |
| AI435503 | UNKNOWN | 18 | 211 | A |
| AI435510 | UNKNOWN | 43 | 0 | T |
| AI435510 | UNKNOWN | 12 | 178 | A |
| AI435529 | UNKNOWN | 15 | 186 | T |
| AI435529 | UNKNOWN | 12 | 249 | A |
| AI435566 | UNKNOWN | 23 | 0 | T |
| AI435591 | UNKNOWN | 15 | 383 | A |
| AI435631 | UNKNOWN | 85 | 0 | T |
| AI435631 | UNKNOWN | 20 | 149 | G |
| AI435631 | UNKNOWN | 18 | 126 | A |
| AI435631 | UNKNOWN | 12 | 114 | C |
| AI435641 | UNKNOWN | 97 | 0 | T |
| AI435641 | UNKNOWN | 15 | 154 | A |
| AI435641 | UNKNOWN | 13 | 97 | A |
| AI435641 | UNKNOWN | 13 | 179 | C |
| AI435641 | UNKNOWN | 12 | 202 | G |
| AI435688 | UNKNOWN | 2.7 | 79 | AGAGAGAGAC (SEQ ID NO:116) |
| AI435688 | UNKNOWN | 27 | 34 | GA |
| AI435999 | UNKNOWN | 71 | 0 | T |
| AI435999 | UNKNOWN | 14 | 92 | A |
| AI435999 | UNKNOWN | 12 | 179 | G |
| AI436109 | UNKNOWN | 12 | 0 | T |
| AI436196 | UNKNOWN | 29 | 0 | T |
| AI436256 | UNKNOWN | 13 | 0 | T |
| AI436259 | UNKNOWN | 11 | 134 | CA |
| AI436316 | UNKNOWN | 33 | 0 | T |
| AI436379 | UNKNOWN | 28 | 178 | T |
| AI436406 | UNKNOWN | 14 | 519 | A |
| AI436418 | UNKNOWN | 12 | 51 | T |
| AI436449 | UNKNOWN | 83 | 0 | T |
| AI436449 | UNKNOWN | 17 | 174 | C |
| AI436449 | UNKNOWN | 16 | 158 | A |
| AI436449 | UNKNOWN | 12 | 193 | G |
| AI436454 | UNKNOWN | 18 | 11 | T |
| AI436456 | UNKNOWN | 141 | 11 | T |
| AI436456 | UNKNOWN | 24 | 195 | G |
| AI436456 | UNKNOWN | 17 | 253 | C |
| AI436456 | UNKNOWN | 14 | 225 | C |
| AI436456 | UNKNOWN | 14 | 239 | A |
| AI436478 | UNKNOWN | 2.63 | 37 | AGGAAGGAAGGAGAAAGAA (SEQ ID NO:117) |
| AI436478 | UNKNOWN | 28 | 108 | A |
| AI436545 | UNKNOWN | 18 | 72 | A |

TABLE 1-continued

| Genbank # | Region | # reps | Position | Unit sequence |
|---|---|---|---|---|
| AI436576 | UNKNOWN | 98 | 0 | T |
| AI436576 | UNKNOWN | 23 | 214 | C |
| AI436576 | UNKNOWN | 16 | 135 | C |
| AI436576 | UNKNOWN | 12 | 363 | G |
| AI436601 | UNKNOWN | 21 | 13 | T |
| AI436610 | UNKNOWN | 23 | 0 | T |
| AI436644 | UNKNOWN | 108 | 0 | T |
| AI436644 | UNKNOWN | 19 | 183 | A |
| AI436644 | UNKNOWN | 16 | 137 | A |
| AI436644 | UNKNOWN | 16 | 238 | G |
| AI436644 | UNKNOWN | 15 | 154 | C |
| AI436644 | UNKNOWN | 13 | 215 | G |
| AI436672 | UNKNOWN | 22 | 0 | T |
| AI436736 | UNKNOWN | 24 | 0 | T |
| AI436759 | UNKNOWN | 21.5 | 154 | AC |
| AI436784 | UNKNOWN | 17 | 248 | A |
| AI438975 | UNKNOWN | 26 | 0 | T |
| AI438980 | UNKNOWN | 16 | 0 | T |
| AI439020 | UNKNOWN | 57 | 0 | T |
| AI439044 | UNKNOWN | 56 | 0 | T |
| AI439044 | UNKNOWN | 17 | 257 | C |
| AI439060 | UNKNOWN | 15 | 0 | T |
| AI439062 | UNKNOWN | 44 | 0 | T |
| AI439073 | UNKNOWN | 35 | 0 | T |
| AI439087 | UNKNOWN | 124 | 0 | T |
| AI439087 | UNKNOWN | 23 | 262 | G |
| AI439087 | UNKNOWN | 13 | 133 | A |
| AI439089 | UNKNOWN | 105 | 0 | T |
| AI439089 | UNKNOWN | 20 | 300 | A |
| AI439089 | UNKNOWN | 14 | 105 | C |
| AI439089 | UNKNOWN | 13 | 142 | A |
| AI439089 | UNKNOWN | 12 | 209 | G |
| AI439097 | UNKNOWN | 45 | 0 | T |
| AI439109 | UNKNOWN | 4.4 | 336 | AACAA |
| AI439122 | UNKNOWN | 21 | 152 | A |
| AI439149 | UNKNOWN | 41 | 0 | T |
| AI439169 | UNKNOWN | 24 | 0 | T |
| AI439170 | UNKNOWN | 7.5 | 319 | TA |
| AI439170 | UNKNOWN | 6.5 | 307 | TG |
| AI439172 | UNKNOWN | 35 | 0 | T |
| AI439180 | UNKNOWN | 16 | 0 | T |
| AI439197 | UNKNOWN | 25 | 0 | T |
| AI439230 | UNKNOWN | 15 | 0 | T |
| AI439256 | UNKNOWN | 96 | 0 | T |
| AI439256 | UNKNOWN | 21 | 203 | C |
| AI439256 | UNKNOWN | 13 | 177 | G |
| AI439290 | UNKNOWN | 55 | 0 | T |
| AI439310 | UNKNOWN | 16 | 0 | T |
| AI439324 | UNKNOWN | 51 | 0 | T |
| AI439342 | UNKNOWN | 49 | 0 | T |
| AI439344 | UNKNOWN | 34 | 0 | T |
| AI439344 | UNKNOWN | 14 | 329 | A |
| AI439350 | UNKNOWN | 98 | 0 | T |
| AI439350 | UNKNOWN | 18 | 220 | G |
| AI439372 | UNKNOWN | 3.6 | 336 | AAAC |
| AI439385 | UNKNOWN | 61 | 0 | T |
| AI439385 | UNKNOWN | 12 | 272 | G |
| AI439406 | UNKNOWN | 15 | 0 | T |
| AI439412 | UNKNOWN | 38 | 0 | T |
| AI439443 | UNKNOWN | 93 | 0 | T |
| AI439443 | UNKNOWN | 20 | 135 | G |
| AI439443 | UNKNOWN | 17 | 203 | C |
| AI439443 | UNKNOWN | 14 | 121 | C |
| AI439452 | UNKNOWN | 84 | 0 | T |
| AI439452 | UNKNOWN | 20 | 292 | C |
| AI439452 | UNKNOWN | 18 | 107 | A |
| AI439452 | UNKNOWN | 17 | 164 | C |
| AI439478 | UNKNOWN | 102 | 0 | T |
| AI439478 | UNKNOWN | 15 | 140 | G |
| AI439478 | UNKNOWN | 13 | 242 | C |
| AI439527 | UNKNOWN | 72 | 0 | T |
| AI439527 | UNKNOWN | 15 | 201 | C |
| AI439601 | UNKNOWN | 87 | 0 | T |
| AI439601 | UNKNOWN | 13 | 140 | G |
| AI439675 | UNKNOWN | 78 | 0 | T |
| AI439675 | UNKNOWN | 13 | 307 | G |
| AI439717 | UNKNOWN | 103 | 0 | T |

TABLE 1-continued

| Genbank # | Region | # reps | Position | Unit sequence |
|---|---|---|---|---|
| AI439717 | UNKNOWN | 14 | 145 | A |
| AI439736 | UNKNOWN | 47 | 0 | T |
| AI439739 | UNKNOWN | 6.33 | 179 | ACA |
| AI439745 | UNKNOWN | 69 | 52 | T |
| AI439745 | UNKNOWN | 40 | 11 | T |
| AI439745 | UNKNOWN | 22 | 177 | G |
| AI439745 | UNKNOWN | 16 | 158 | A |
| AI439745 | UNKNOWN | 13 | 145 | C |
| AI439762 | UNKNOWN | 108 | 0 | T |
| AI439762 | UNKNOWN | 30 | 236 | A |
| AI439762 | UNKNOWN | 12 | 343 | C |
| AI439773 | UNKNOWN | 21 | 0 | T |
| AI439777 | UNKNOWN | 25 | 0 | T |
| AI439789 | UNKNOWN | 15 | 0 | T |
| AI439793 | UNKNOWN | 41 | 0 | T |
| AI439799 | UNKNOWN | 46 | 0 | T |
| AI439801 | UNKNOWN | 69 | 0 | T |
| AI439814 | UNKNOWN | 38 | 0 | T |
| AI439896 | UNKNOWN | 42 | 0 | T |
| AI439896 | UNKNOWN | 23 | 164 | G |
| AI439896 | UNKNOWN | 23 | 199 | C |
| AI439903 | UNKNOWN | 48 | 0 | T |
| AI439920 | UNKNOWN | 95 | 14 | T |
| AI439920 | UNKNOWN | 22 | 123 | A |
| AI439920 | UNKNOWN | 20 | 350 | C |
| AI439920 | UNKNOWN | 14 | 257 | C |
| AI439920 | UNKNOWN | 13 | 0 | T |
| AI439962 | UNKNOWN | 70 | 0 | T |
| AI439962 | UNKNOWN | 19 | 194 | G |
| AI440028 | UNKNOWN | 40 | 0 | T |
| AI440037 | UNKNOWN | 27 | 0 | T |
| AI440037 | UNKNOWN | 17 | 331 | A |
| AI440042 | UNKNOWN | 44 | 0 | T |
| AI440061 | UNKNOWN | 43 | 0 | T |
| AI440088 | UNKNOWN | 48 | 0 | T |
| AI440091 | UNKNOWN | 62 | 12 | T |
| AI440097 | UNKNOWN | 39 | 0 | T |
| AI440117 | UNKNOWN | 37 | 8 | T |
| AI440126 | UNKNOWN | 48 | 0 | T |
| AI440133 | UNKNOWN | 47 | 0 | T |
| AI440133 | UNKNOWN | 16 | 366 | A |
| AI440153 | UNKNOWN | 13 | 0 | T |
| AI440174 | UNKNOWN | 40 | 0 | T |
| AI440192 | UNKNOWN | 23 | 0 | T |
| AI440200 | UNKNOWN | 19 | 0 | T |
| AI440200 | UNKNOWN | 19 | 142 | C |
| AI440210 | UNKNOWN | 61 | 0 | T |
| AI440210 | UNKNOWN | 13 | 80 | A |
| AI440212 | UNKNOWN | 38 | 0 | T |
| AI440212 | UNKNOWN | 21 | 123 | A |
| AI440233 | UNKNOWN | 39 | 0 | T |
| AI440233 | UNKNOWN | 13 | 214 | A |
| AI440239 | UNKNOWN | 120 | 11 | T |
| AI440239 | UNKNOWN | 19 | 290 | C |
| AI440239 | UNKNOWN | 14 | 131 | A |
| AI440239 | UNKNOWN | 12 | 208 | C |
| AI440269 | UNKNOWN | 48 | 0 | T |
| AI440274 | UNKNOWN | 89 | 0 | T |
| AI440274 | UNKNOWN | 15 | 120 | C |
| AI440274 | UNKNOWN | 12 | 225 | G |
| AI440284 | UNKNOWN | 74 | 0 | T |
| AI440294 | UNKNOWN | 59 | 0 | T |
| AI440294 | UNKNOWN | 21 | 102 | A |
| AI440422 | UNKNOWN | 78 | 0 | T |
| AI440422 | UNKNOWN | 12 | 78 | A |
| AI440426 | UNKNOWN | 129 | 0 | T |
| AI440426 | UNKNOWN | 20 | 275 | C |
| AI440426 | UNKNOWN | 15 | 260 | G |
| AI440448 | UNKNOWN | 94 | 0 | T |
| AI440448 | UNKNOWN | 17 | 261 | A |
| AI440448 | UNKNOWN | 13 | 153 | C |
| AI440448 | UNKNOWN | 12 | 94 | A |
| AI440457 | UNKNOWN | 58 | 0 | T |
| AI444972 | UNKNOWN | 17 | 0 | T |
| AI444992 | UNKNOWN | 46 | 0 | T |
| AI445025 | UNKNOWN | 117 | 0 | T |
| AI445025 | UNKNOWN | 18 | 117 | A |

TABLE 1-continued

| Genbank # | Region | # reps | Position | Unit sequence |
|---|---|---|---|---|
| AI445025 | UNKNOWN | 14 | 166 | C |
| AI445025 | UNKNOWN | 13 | 227 | G |
| AI445039 | UNKNOWN | 34 | 0 | T |
| AI445069 | UNKNOWN | 80 | 0 | T |
| AI445115 | UNKNOWN | 88 | 0 | T |
| AI445115 | UNKNOWN | 17 | 328 | C |
| AI445115 | UNKNOWN | 15 | 169 | A |
| AI445115 | UNKNOWN | 15 | 353 | G |
| AI445115 | UNKNOWN | 14 | 230 | C |
| AI445115 | UNKNOWN | 12 | 189 | C |
| AI445131 | UNKNOWN | 97 | 0 | T |
| AI445131 | UNKNOWN | 15 | 316 | C |
| AI445131 | UNKNOWN | 13 | 228 | C |
| AI445131 | UNKNOWN | 12 | 122 | A |
| AI445165 | UNKNOWN | 112 | 0 | T |
| AI445165 | UNKNOWN | 12 | 146 | G |
| AI445168 | UNKNOWN | 50 | 0 | T |
| AI445233 | UNKNOWN | 49 | 0 | T |
| AI445256 | UNKNOWN | 59 | 0 | T |
| AI445256 | UNKNOWN | 13 | 287 | G |
| AI445303 | UNKNOWN | 78 | 0 | T |
| AI445303 | UNKNOWN | 17 | 86 | C |
| AI445303 | UNKNOWN | 12 | 221 | A |
| AI445342 | UNKNOWN | 23 | 0 | T |
| AI445368 | UNKNOWN | 84 | 0 | T |
| AI445368 | UNKNOWN | 12 | 229 | G |
| AI445398 | UNKNOWN | 83 | 0 | T |
| AI445414 | UNKNOWN | 109 | 0 | T |
| AI445414 | UNKNOWN | 23 | 370 | A |
| AI445414 | UNKNOWN | 21 | 207 | C |
| AI445414 | UNKNOWN | 13 | 228 | G |
| AI445414 | UNKNOWN | 12 | 142 | A |
| AI445414 | UNKNOWN | 12 | 172 | C |
| AI445430 | UNKNOWN | 67 | 0 | T |
| AI445430 | UNKNOWN | 12 | 156 | A |
| AI445432 | UNKNOWN | 123 | 0 | T |
| AI445432 | UNKNOWN | 26 | 276 | C |
| AI445432 | UNKNOWN | 19 | 187 | C |
| AI445432 | UNKNOWN | 17 | 140 | C |
| AI445432 | UNKNOWN | 15 | 157 | G |
| AI445432 | UNKNOWN | 12 | 123 | A |
| AI445439 | UNKNOWN | 40 | 0 | T |
| AI445445 | UNKNOWN | 14 | 0 | T |
| AI445448 | UNKNOWN | 13 | 0 | T |
| AI445448 | UNKNOWN | 12 | 317 | A |
| AI445487 | UNKNOWN | 49 | 0 | T |
| AI445487 | UNKNOWN | 12 | 170 | C |
| AI445492 | UNKNOWN | 13 | 0 | T |
| AI445505 | UNKNOWN | 51 | 0 | T |
| AI445521 | UNKNOWN | 37 | 0 | T |
| AI445523 | UNKNOWN | 19 | 0 | T |
| AI445535 | UNKNOWN | 16 | 0 | T |
| AI445566 | UNKNOWN | 13 | 0 | T |
| AI445571 | UNKNOWN | 63 | 0 | T |
| AI445588 | UNKNOWN | 66 | 0 | T |
| AI445611 | UNKNOWN | 63 | 0 | T |
| AI445611 | UNKNOWN | 22 | 193 | G |
| AI445620 | UNKNOWN | 59 | 0 | T |
| AI445663 | UNKNOWN | 75 | 0 | T |
| AI445663 | UNKNOWN | 16 | 316 | A |
| AI445663 | UNKNOWN | 15 | 181 | A |
| AI445663 | UNKNOWN | 14 | 82 | A |
| AI445671 | UNKNOWN | 24 | 0 | T |
| AI445701 | UNKNOWN | 24 | 0 | T |
| AI445712 | UNKNOWN | 53 | 0 | T |
| AI445718 | UNKNOWN | 48 | 0 | T |
| AI445720 | UNKNOWN | 37 | 0 | T |
| AI445720 | UNKNOWN | 20 | 203 | A |
| AI445743 | UNKNOWN | 42 | 0 | T |
| AI445792 | UNKNOWN | 13 | 167 | A |
| AI445801 | UNKNOWN | 23 | 28 | T |
| AI445829 | UNKNOWN | 77 | 0 | T |
| AI445829 | UNKNOWN | 15 | 78 | A |
| AI445831 | UNKNOWN | 45 | 0 | T |
| AI445836 | UNKNOWN | 49 | 0 | T |
| AI445864 | UNKNOWN | 80 | 0 | T |
| AI445864 | UNKNOWN | 21 | 347 | A |

TABLE 1-continued

| Genbank # | Region | # reps | Position | Unit sequence |
|---|---|---|---|---|
| AI445877 | UNKNOWN | 63 | 0 | T |
| AI445965 | UNKNOWN | 76 | 0 | T |
| AI445965 | UNKNOWN | 15 | 154 | A |
| AI445975 | UNKNOWN | 84 | 0 | T |
| AI445975 | UNKNOWN | 14 | 116 | G |
| AI445975 | UNKNOWN | 12 | 130 | A |
| AI445976 | UNKNOWN | 82 | 0 | T |
| AI445976 | UNKNOWN | 13 | 118 | A |
| AI445976 | UNKNOWN | 13 | 192 | G |
| AI445990 | UNKNOWN | 83 | 0 | T |
| AI445990 | UNKNOWN | 22 | 152 | C |
| AI445992 | UNKNOWN | 87 | 0 | T |
| AI445992 | UNKNOWN | 23 | 144 | C |
| AI445992 | UNKNOWN | 18 | 126 | A |
| AI446003 | UNKNOWN | 90 | 0 | T |
| AI446003 | UNKNOWN | 12 | 90 | G |
| AI446023 | UNKNOWN | 69 | 0 | T |
| AI446046 | UNKNOWN | 68 | 5 | T |
| AI446046 | UNKNOWN | 19 | 116 | C |
| AI446046 | UNKNOWN | 16 | 91 | G |
| AI446092 | UNKNOWN | 99 | 0 | T |
| AI446092 | UNKNOWN | 22 | 190 | C |
| AI446092 | UNKNOWN | 14 | 150 | G |
| AI446110 | UNKNOWN | 47 | 0 | T |
| AI446120 | UNKNOWN | 49 | 0 | T |
| AI446139 | UNKNOWN | 51 | 0 | T |
| AI446148 | UNKNOWN | 64 | 0 | T |
| AI446148 | UNKNOWN | 19 | 164 | C |
| AI446166 | UNKNOWN | 16 | 0 | T |
| AI446248 | UNKNOWN | 83 | 0 | T |
| AI446248 | UNKNOWN | 14 | 117 | A |
| AI446248 | UNKNOWN | 14 | 199 | G |
| AI446269 | UNKNOWN | 4.5 | 119 | AAGG |
| AI446269 | UNKNOWN | 54 | 0 | T |
| AI446269 | UNKNOWN | 14 | 251 | G |
| AI446301 | UNKNOWN | 57 | 0 | T |
| AI446373 | UNKNOWN | 97 | 0 | T |
| AI446374 | UNKNOWN | 2.88 | 35 | TTTTTTTTTTTTTTCC (SEQ ID NO.118) |
| AI446374 | UNKNOWN | 33 | 17 | T |
| AI446384 | UNKNOWN | 47 | 0 | T |
| AI446405 | UNKNOWN | 66 | 0 | T |
| AI446405 | UNKNOWN | 15 | 92 | A |
| AI446434 | UNKNOWN | 33 | 0 | T |
| AI446499 | UNKNOWN | 30 | 11 | T |
| AI446500 | UNKNOWN | 20 | 11 | T |
| AI446511 | UNKNOWN | 58 | 0 | T |
| AI446511 | UNKNOWN | 13 | 323 | A |
| AI446515 | UNKNOWN | 48 | 0 | T |
| AI446553 | UNKNOWN | 16 | 0 | T |
| AI446579 | UNKNOWN | 50 | 0 | T |
| AI446579 | UNKNOWN | 19 | 299 | C |
| AI446597 | UNKNOWN | 55 | 0 | T |
| AI446605 | UNKNOWN | 103 | 0 | T |
| AI446605 | UNKNOWN | 16 | 232 | C |
| AI446606 | UNKNOWN | 98 | 0 | T |
| AI446606 | UNKNOWN | 20 | 180 | C |
| AI446606 | UNKNOWN | 19 | 200 | G |
| AI446606 | UNKNOWN | 17 | 144 | A |
| AI446607 | UNKNOWN | 45 | 0 | T |
| AI446611 | UNKNOWN | 57 | 0 | T |
| AI446611 | UNKNOWN | 15 | 122 | C |
| AI446628 | UNKNOWN | 108 | 0 | T |
| AI446637 | UNKNOWN | 22 | 0 | T |
| AI446646 | UNKNOWN | 52 | 0 | T |
| AI446647 | UNKNOWN | 41 | 0 | T |
| AI446684 | UNKNOWN | 103 | 0 | T |
| AI446684 | UNKNOWN | 18 | 348 | C |
| AI446684 | UNKNOWN | 15 | 170 | C |
| AI446701 | UNKNOWN | 21 | 0 | T |
| AI446704 | UNKNOWN | 61 | 0 | T |
| AI446704 | UNKNOWN | 15 | 218 | G |
| AI446704 | UNKNOWN | 14 | 435 | A |
| AI446708 | UNKNOWN | 14 | 0 | T |
| AI446721 | UNKNOWN | 66 | 0 | T |
| AI446775 | UNKNOWN | 55 | 0 | T |
| AI446775 | UNKNOWN | 13 | 122 | G |
| AI446785 | UNKNOWN | 70 | 0 | T |

TABLE 1-continued

| Genbank # | Region | # reps | Position | Unit sequence |
|---|---|---|---|---|
| AI446785 | UNKNOWN | 14 | 105 | A |
| AI446787 | UNKNOWN | 47 | 0 | T |
| AI446795 | UNKNOWN | 104 | 0 | T |
| AI446795 | UNKNOWN | 17 | 170 | G |
| AI446795 | UNKNOWN | 13 | 269 | A |
| AI446802 | UNKNOWN | 93 | 0 | T |
| AI446802 | UNKNOWN | 16 | 217 | A |
| AI446802 | UNKNOWN | 13 | 163 | G |
| AI446809 | UNKNOWN | 64 | 0 | T |
| AI446809 | UNKNOWN | 15 | 108 | A |
| AI446815 | UNKNOWN | 38 | 0 | T |
| AI446820 | UNKNOWN | 15 | 0 | T |
| AI446821 | UNKNOWN | 17 | 0 | T |
| AI446823 | UNKNOWN | 58 | 0 | T |
| AI446829 | UNKNOWN | 80 | 0 | T |
| AI452389 | UNKNOWN | 34 | 0 | T |
| AI452469 | UNKNOWN | 12 | 196 | A |
| AI452477 | UNKNOWN | 12 | 0 | T |
| AI452512 | UNKNOWN | 13 | 0 | T |
| AI452552 | UNKNOWN | 17 | 374 | T |
| AI452556 | UNKNOWN | 64 | 0 | T |
| AI452560 | UNKNOWN | 85 | 0 | T |
| AI452560 | UNKNOWN | 14 | 192 | C |
| AI452560 | UNKNOWN | 12 | 85 | A |
| AI452560 | UNKNOWN | 12 | 144 | C |
| AI452591 | UNKNOWN | 26 | 0 | T |
| AI452659 | UNKNOWN | 16 | 0 | T |
| AI452664 | UNKNOWN | 13 | 123 | T |
| AI452667 | UNKNOWN | 16 | 0 | T |
| AI452707 | UNKNOWN | 83 | 0 | T |
| AI452707 | UNKNOWN | 18 | 145 | C |
| AI452707 | UNKNOWN | 13 | 132 | A |
| AI452738 | UNKNOWN | 21 | 0 | T |
| AI452783 | UNKNOWN | 22 | 0 | T |
| AI452866 | UNKNOWN | 28 | 0 | T |
| AI452875 | UNKNOWN | 35 | 0 | T |
| AI452876 | UNKNOWN | 94 | 0 | T |
| AI452876 | UNKNOWN | 21 | 224 | G |
| AI452876 | UNKNOWN | 17 | 155 | G |
| AI452876 | UNKNOWN | 16 | 266 | C |
| AI452876 | UNKNOWN | 13 | 210 | C |
| AI452930 | UNKNOWN | 35 | 0 | T |
| AI452959 | UNKNOWN | 34 | 0 | T |
| AI452961 | UNKNOWN | 12 | 0 | T |
| AI452969 | UNKNOWN | 20 | 0 | T |
| AI452993 | UNKNOWN | 76 | 0 | T |
| AI453118 | UNKNOWN | 4.4 | 355 | AGAAC |
| AI453130 | UNKNOWN | 18 | 0 | T |
| AI453130 | UNKNOWN | 12 | 470 | A |
| AI453199 | UNKNOWN | 64 | 0 | T |
| AI453199 | UNKNOWN | 12 | 95 | A |
| AI453215 | UNKNOWN | 58 | 0 | T |
| AI453248 | UNKNOWN | 58 | 0 | T |
| AI453297 | UNKNOWN | 41 | 0 | T |
| AI453322 | UNKNOWN | 102 | 0 | T |
| AI453322 | UNKNOWN | 22 | 169 | A |
| AI453339 | UNKNOWN | 67 | 19 | T |
| AI453339 | UNKNOWN | 17 | 0 | T |
| AI453382 | UNKNOWN | 80 | 5 | T |
| AI453382 | UNKNOWN | 20 | 331 | A |
| AI453410 | UNKNOWN | 3.83 | 13 | TTTTTG |
| AI453410 | UNKNOWN | 18 | 0 | T |
| AI453413 | UNKNOWN | 81 | 0 | T |
| AI453413 | UNKNOWN | 12 | 205 | G |
| AI453444 | UNKNOWN | 22 | 0 | T |
| AI453456 | UNKNOWN | 43 | 0 | T |
| AI453482 | UNKNOWN | 53 | 0 | T |
| AI453482 | UNKNOWN | 12 | 210 | A |
| AI453487 | UNKNOWN | 69 | 0 | T |
| AI453487 | UNKNOWN | 12 | 322 | G |
| AI453512 | UNKNOWN | 19 | 0 | T |
| AI453545 | UNKNOWN | 16 | 0 | T |
| AI453548 | UNKNOWN | 17 | 0 | T |
| AI453615 | UNKNOWN | 69 | 0 | T |
| AI453615 | UNKNOWN | 18 | 117 | G |
| AI453615 | UNKNOWN | 12 | 143 | C |
| AI453651 | UNKNOWN | 14 | 202 | A |

TABLE 1-continued

| Genbank # | Region | # reps | Position | Unit sequence |
|---|---|---|---|---|
| AI453667 | UNKNOWN | 35 | 0 | T |
| AI453709 | UNKNOWN | 28 | 0 | T |
| AI453709 | UNKNOWN | 14 | 241 | A |
| AI453714 | UNKNOWN | 17 | 154 | T |
| AI453716 | UNKNOWN | 44 | 0 | T |
| AI453729 | UNKNOWN | 40 | 0 | T |
| AI453753 | UNKNOWN | 17 | 0 | T |
| AI453761 | UNKNOWN | 32 | 0 | T |
| AI453767 | UNKNOWN | 68 | 0 | T |
| AI453767 | UNKNOWN | 17 | 112 | A |
| AI453779 | UNKNOWN | 35 | 0 | T |
| AI453795 | UNKNOWN | 17 | 36 | A |
| AI453795 | UNKNOWN | 15 | 0 | T |
| AI453804 | UNKNOWN | 64 | 0 | T |
| AI453804 | UNKNOWN | 16 | 238 | A |
| AI453824 | UNKNOWN | 69 | 0 | T |
| AI457113 | UNKNOWN | 69 | 0 | T |
| AI457135 | UNKNOWN | 110 | 0 | T |
| AI457135 | UNKNOWN | 15 | 193 | G |
| AI457135 | UNKNOWN | 13 | 213 | C |
| AI457165 | UNKNOWN | 53 | 0 | T |
| AI457188 | UNKNOWN | 87 | 0 | T |
| AI457210 | UNKNOWN | 84 | 0 | T |
| AI457210 | UNKNOWN | 19 | 109 | G |
| AI457210 | UNKNOWN | 12 | 236 | C |
| AI457278 | UNKNOWN | 15 | 211 | A |
| AI457343 | UNKNOWN | 47 | 0 | T |
| AI457369 | UNKNOWN | 95 | 0 | T |
| AI457369 | UNKNOWN | 15 | 223 | A |
| AI457369 | UNKNOWN | 14 | 195 | C |
| AI457369 | UNKNOWN | 12 | 183 | A |
| AI457375 | UNKNOWN | 17 | 304 | T |
| AI457375 | UNKNOWN | 14 | 14 | A |
| AI457389 | UNKNOWN | 6.5 | 36 | TA |
| AI457475 | UNKNOWN | 6.5 | 236 | AC |
| AI457490 | UNKNOWN | 57 | 0 | T |
| AI457492 | UNKNOWN | 39 | 19 | T |
| AI457492 | UNKNOWN | 18 | 0 | T |
| AI457506 | UNKNOWN | 48 | 0 | T |
| AI457542 | UNKNOWN | 42 | 0 | T |
| AI457589 | UNKNOWN | 67 | 0 | T |
| AI457589 | UNKNOWN | 16 | 131 | C |
| AI457597 | UNKNOWN | 14 | 472 | A |
| AI457643 | UNKNOWN | 39 | 0 | T |
| AI457656 | UNKNOWN | 45 | 0 | T |
| AI457656 | UNKNOWN | 12 | 206 | A |
| AI457660 | UNKNOWN | 18 | 1 | T |
| AI457697 | UNKNOWN | 7.5 | 207 | CT |
| AI457965 | UNKNOWN | 12 | 0 | T |
| AI457968 | UNKNOWN | 56 | 0 | T |
| AI457997 | UNKNOWN | 14 | 0 | T |
| AI458003 | UNKNOWN | 12 | 0 | T |
| AI458016 | UNKNOWN | 20 | 0 | T |
| AI458030 | UNKNOWN | 23 | 0 | T |
| AI458086 | UNKNOWN | 16 | 0 | T |
| AI458089 | UNKNOWN | 35 | 0 | T |
| AI458094 | UNKNOWN | 14 | 0 | T |
| AI458122 | UNKNOWN | 32 | 0 | T |
| AI458122 | UNKNOWN | 12 | 57 | G |
| AI458136 | UNKNOWN | 16 | 0 | T |
| AI458140 | UNKNOWN | 15 | 0 | T |
| AI458237 | UNKNOWN | 78 | 0 | T |
| AI458237 | UNKNOWN | 23 | 134 | A |
| AI458237 | UNKNOWN | 14 | 225 | G |
| AI458237 | UNKNOWN | 13 | 157 | C |
| AI458237 | UNKNOWN | 12 | 113 | A |
| AI458239 | UNKNOWN | 26 | 0 | T |
| AI458266 | UNKNOWN | 12 | 0 | T |
| AI458410 | UNKNOWN | 25 | 0 | T |
| AI458410 | UNKNOWN | 12 | 404 | A |
| AI458418 | UNKNOWN | 17 | 0 | T |
| AI458420 | UNKNOWN | 21 | 0 | T |
| AI458420 | UNKNOWN | 13 | 104 | G |
| AI458429 | UNKNOWN | 18 | 0 | T |
| AI458434 | UNKNOWN | 21 | 0 | T |
| AI458439 | UNKNOWN | 22 | 0 | T |
| AI458443 | UNKNOWN | 64 | 0 | T |

TABLE 1-continued

| Genbank # | Region | # reps | Position | Unit sequence |
|---|---|---|---|---|
| AI458453 | UNKNOWN | 17 | 393 | T |
| AI458481 | UNKNOWN | 23 | 0 | T |
| AI458521 | UNKNOWN | 20 | 7 | T |
| AI458588 | UNKNOWN | 59 | 0 | T |
| AI458588 | UNKNOWN | 15 | 249 | G |
| AI458657 | UNKNOWN | 6.5 | 171 | AC |
| AI458715 | UNKNOWN | 57 | 0 | T |
| AI458715 | UNKNOWN | 12 | 156 | A |
| AI458874 | UNKNOWN | 15 | 0 | T |
| AI458940 | UNKNOWN | 19 | 0 | T |
| AI458949 | UNKNOWN | 15 | 158 | A |
| AI458954 | UNKNOWN | 12 | 240 | GT |
| AI458955 | UNKNOWN | 7.75 | 37 | AAAC |
| AI459061 | UNKNOWN | 14 | 0 | T |
| AI459092 | UNKNOWN | 17 | 314 | T |
| AI459092 | UNKNOWN | 15 | 227 | T |
| AI459114 | UNKNOWN | 5.66 | 149 | GCC |
| AI459136 | UNKNOWN | 17 | 374 | T |
| AI459174 | UNKNOWN | 21 | 0 | T |
| AI459239 | UNKNOWN | 4 | 550 | GTTTT |
| AI459239 | UNKNOWN | 14 | 187 | A |
| AI459244 | UNKNOWN | 7 | 212 | CGAA |
| AI459244 | UNKNOWN | 12 | 0 | T |
| AI459283 | UNKNOWN | 6.66 | 161 | CGG |
| AI459283 | UNKNOWN | 7.5 | 10 | TG |
| AI459283 | UNKNOWN | 13 | 415 | T |
| AI459463 | UNKNOWN | 12 | 157 | A |
| AI459503 | UNKNOWN | 5.66 | 227 | GCA |
| AI460032 | UNKNOWN | 22 | 46 | T |
| AI460119 | UNKNOWN | 26 | 0 | T |
| AI460304 | UNKNOWN | 14 | 0 | T |
| AI467796 | UNKNOWN | 22 | 2 | T |
| AI467854 | UNKNOWN | 15 | 0 | T |
| AI467860 | UNKNOWN | 15 | 0 | T |
| AI467915 | UNKNOWN | 27 | 0 | T |
| AI467918 | UNKNOWN | 17 | 0 | T |
| AI467935 | UNKNOWN | 18 | 0 | T |
| AI467941 | UNKNOWN | 19 | 0 | T |
| AI468014 | UNKNOWN | 11.5 | 234 | TC |
| AI468022 | UNKNOWN | 13 | 0 | T |
| AI468048 | UNKNOWN | 29 | 0 | T |
| AI468184 | UNKNOWN | 12 | 204 | T |
| AI468251 | UNKNOWN | 22 | 0 | T |
| AI466340 | UNKNOWN | 6.5 | 86 | AC |
| AI468416 | UNKNOWN | 17 | 0 | T |
| AI468416 | UNKNOWN | 17 | 173 | G |
| AI468416 | UNKNOWN | 13 | 131 | A |
| AI468668 | UNKNOWN | 5.5 | 94 | AACC |
| AI468668 | UNKNOWN | 17 | 42 | T |
| AI468829 | UNKNOWN | 18 | 0 | T |
| AI468872 | UNKNOWN | 101 | 0 | T |
| AI468872 | UNKNOWN | 14 | 127 | C |
| AI468873 | UNKNOWN | 51 | 0 | T |
| AI468930 | UNKNOWN | 62 | 0 | T |
| AI468930 | UNKNOWN | 17 | 159 | A |
| AI468930 | UNKNOWN | 17 | 225 | C |
| AI468930 | UNKNOWN | 16 | 294 | G |
| AI466956 | UNKNOWN | 44 | 0 | T |
| AI468956 | UNKNOWN | 13 | 118 | A |
| AI468992 | UNKNOWN | 18 | 11 | T |
| AI468992 | UNKNOWN | 13 | 114 | A |
| AI469014 | UNKNOWN | 66 | 0 | T |
| AI469062 | UNKNOWN | 31 | 0 | T |
| AI469071 | UNKNOWN | 13 | 0 | T |
| AI469075 | UNKNOWN | 35 | 0 | T |
| AI469079 | UNKNOWN | 36 | 0 | T |
| AI469081 | UNKNOWN | 52 | 0 | T |
| AI469112 | UNKNOWN | 91 | 0 | T |
| AI469112 | UNKNOWN | 21 | 91 | A |
| AI469112 | UNKNOWN | 14 | 339 | C |
| AI469117 | UNKNOWN | 37 | 0 | T |
| AI469119 | UNKNOWN | 112 | 0 | T |
| AI469119 | UNKNOWN | 16 | 130 | C |
| AI469153 | UNKNOWN | 23 | 0 | T |
| AI469157 | UNKNOWN | 51 | 0 | T |
| AI469157 | UNKNOWN | 16 | 129 | G |
| AI469157 | UNKNOWN | 12 | 74 | A |

TABLE 1-continued

| Genbank # | Region | # reps | Position | Unit sequence |
|---|---|---|---|---|
| AI469183 | UNKNOWN | 15 | 0 | T |
| AI469194 | UNKNOWN | 18 | 4 | T |
| AI469198 | UNKNOWN | 12 | 0 | T |
| AI469250 | UNKNOWN | 33 | 0 | T |
| AI469270 | UNKNOWN | 70 | 0 | T |
| AI469290 | UNKNOWN | 47 | 0 | T |
| AI469301 | UNKNOWN | 3.8 | 330 | CAAAA |
| AI469310 | UNKNOWN | 30 | 0 | T |
| AI469377 | UNKNOWN | 15 | 0 | T |
| AI469384 | UNKNOWN | 15 | 102 | T |
| AI469385 | UNKNOWN | 36 | 0 | T |
| AI469412 | UNKNOWN | 7.25 | 3 | TATT |
| AI469425 | UNKNOWN | 53 | 0 | T |
| AI469436 | UNKNOWN | 33 | 0 | T |
| AI469470 | UNKNOWN | 52 | 0 | T |
| AI469470 | UNKNOWN | 21 | 228 | C |
| AI469504 | UNKNOWN | 37 | 0 | T |
| AI469516 | UNKNOWN | 55 | 0 | T |
| AI469516 | UNKNOWN | 16 | 110 | G |
| AI469532 | UNKNOWN | 135 | 0 | T |
| AI469532 | UNKNOWN | 23 | 135 | A |
| AI469573 | UNKNOWN | 55 | 0 | T |
| AI469573 | UNKNOWN | 15 | 186 | A |
| AI469674 | UNKNOWN | 72 | 0 | T |
| AI469681 | UNKNOWN | 50 | 0 | T |
| AI469738 | UNKNOWN | 78 | 0 | T |
| AI469753 | UNKNOWN | 15 | 4 | T |
| AI469781 | UNKNOWN | 15 | 11 | T |
| AI469801 | UNKNOWN | 62 | 0 | T |
| AI469801 | UNKNOWN | 13 | 325 | G |
| AI469801 | UNKNOWN | 12 | 304 | C |
| AI469805 | UNKNOWN | 73 | 0 | T |
| AI469805 | UNKNOWN | 15 | 111 | A |
| AI469805 | UNKNOWN | 12 | 410 | G |
| AI469811 | UNKNOWN | 118 | 0 | T |
| AI469811 | UNKNOWN | 18 | 228 | C |
| AI469811 | UNKNOWN | 12 | 118 | G |
| AI469811 | UNKNOWN | 12 | 135 | A |
| AI469824 | UNKNOWN | 17 | 269 | T |
| AI469919 | UNKNOWN | 53 | 0 | T |
| AI469961 | UNKNOWN | 46 | 0 | T |
| AI469997 | UNKNOWN | 16 | 504 | T |
| AI470169 | UNKNOWN | 45 | 0 | T |
| AI470177 | UNKNOWN | 16 | 0 | T |
| AI470235 | UNKNOWN | 5.5 | 8 | TTAT |
| AI470258 | UNKNOWN | 45 | 0 | T |
| AI470284 | UNKNOWN | 4 | 119 | CGGGGG |
| AI470284 | UNKNOWN | 74 | 0 | T |
| AI470284 | UNKNOWN | 12 | 98 | A |
| AI470293 | UNKNOWN | 76 | 0 | T |
| AI470293 | UNKNOWN | 16 | 126 | A |
| AI470295 | UNKNOWN | 18 | 0 | T |
| AI470299 | UNKNOWN | 46 | 0 | T |
| AI470299 | UNKNOWN | 18 | 209 | A |
| AI470454 | UNKNOWN | 20 | 0 | T |
| AI470477 | UNKNOWN | 46 | 0 | T |
| AI470477 | UNKNOWN | 13 | 148 | A |
| AI470579 | UNKNOWN | 39 | 4 | T |
| AI470648 | UNKNOWN | 81 | 0 | T |
| AI470648 | UNKNOWN | 13 | 162 | A |
| AI470649 | UNKNOWN | 12 | 101 | T |
| AI470651 | UNKNOWN | 78 | 0 | T |
| AI470651 | UNKNOWN | 17 | 176 | C |
| AI470662 | UNKNOWN | 14 | 14 | T |
| AI470674 | UNKNOWN | 78 | 0 | T |
| AI470695 | UNKNOWN | 49 | 0 | T |
| AI470701 | UNKNOWN | 90 | 0 | T |
| AI470701 | UNKNOWN | 14 | 173 | A |
| AI470798 | UNKNOWN | 16 | 0 | T |
| AI470798 | UNKNOWN | 15 | 204 | A |
| AI470814 | UNKNOWN | 68 | 0 | T |
| AI470814 | UNKNOWN | 12 | 292 | A |
| AI470863 | UNKNOWN | 24 | 0 | T |
| AI470885 | UNKNOWN | 27 | 0 | T |
| AI470916 | UNKNOWN | 13 | 135 | T |
| AI471007 | UNKNOWN | 36 | 0 | T |
| AI471007 | UNKNOWN | 14 | 221 | G |

TABLE 1-continued

| Genbank # | Region | # reps | Position | Unit sequence |
|---|---|---|---|---|
| AI471007 | UNKNOWN | 12 | 69 | A |
| AI471054 | UNKNOWN | 32 | 0 | T |
| AI471184 | UNKNOWN | 21 | 230 | T |
| AI471227 | UNKNOWN | 71 | 0 | T |
| AI471227 | UNKNOWN | 12 | 195 | A |
| AI471278 | UNKNOWN | 39 | 0 | T |
| AI471305 | UNKNOWN | 38 | 0 | T |
| AI471311 | UNKNOWN | 29 | 0 | T |
| AI471325 | UNKNOWN | 51 | 0 | T |
| AI471361 | UNKNOWN | 84 | 0 | T |
| AI471361 | UNKNOWN | 14 | 133 | C |
| AI471388 | UNKNOWN | 24 | 0 | T |
| AI471398 | UNKNOWN | 15 | 2 | T |
| AI471438 | UNKNOWN | 4.66 | 253 | CCTTGG |
| AI471438 | UNKNOWN | 43 | 0 | T |
| AI471438 | UNKNOWN | 15 | 114 | G |
| AI471468 | UNKNOWN | 15 | 0 | T |
| AI471503 | UNKNOWN | 59 | 0 | T |
| AI471503 | UNKNOWN | 14 | 180 | G |
| AI471527 | UNKNOWN | 99 | 0 | T |
| AI471527 | UNKNOWN | 18 | 144 | G |
| AI471527 | UNKNOWN | 13 | 347 | C |
| AI471527 | UNKNOWN | 12 | 162 | A |
| AI471539 | UNKNOWN | 84 | 0 | T |
| AI471539 | UNKNOWN | 21 | 338 | A |
| AI471539 | UNKNOWN | 14 | 89 | G |
| AI471539 | UNKNOWN | 14 | 225 | C |
| AI471539 | UNKNOWN | 13 | 197 | A |
| AI471540 | UNKNOWN | 57 | 0 | T |
| AI471540 | UNKNOWN | 13 | 99 | A |
| AI471548 | UNKNOWN | 81 | 7 | T |
| AI471548 | UNKNOWN | 17 | 213 | C |
| AI471562 | UNKNOWN | 52 | 0 | T |
| AI471568 | UNKNOWN | 64 | 0 | T |
| AI471583 | UNKNOWN | 13 | 268 | A |
| AI471662 | UNKNOWN | 77 | 0 | T |
| AI471699 | UNKNOWN | 17 | 0 | T |
| AI471704 | UNKNOWN | 72 | 0 | T |
| AI471712 | UNKNOWN | 115 | 6 | T |
| AI471712 | UNKNOWN | 20 | 202 | A |
| AI471712 | UNKNOWN | 18 | 294 | C |
| AI471712 | UNKNOWN | 15 | 355 | G |
| AI471712 | UNKNOWN | 12 | 132 | C |
| AI471760 | UNKNOWN | 12 | 0 | T |
| AI471775 | UNKNOWN | 15 | 0 | T |
| AI471862 | UNKNOWN | 31 | 0 | T |
| AI471898 | UNKNOWN | 57 | 0 | T |
| AI471905 | UNKNOWN | 24 | 27 | T |
| AI471909 | UNKNOWN | 56 | 0 | T |
| AI471910 | UNKNOWN | 65 | 7 | T |
| AI471933 | UNKNOWN | 18 | 0 | T |
| AI472063 | UNKNOWN | 20 | 0 | T |
| AI472071 | UNKNOWN | 16 | 456 | T |
| AI472075 | UNKNOWN | 5 | 30 | TATT |
| AI472119 | UNKNOWN | 24 | 0 | T |
| AI472126 | UNKNOWN | 43 | 0 | T |
| AI472126 | UNKNOWN | 12 | 71 | A |
| AI472133 | UNKNOWN | 13 | 0 | T |
| AI472135 | UNKNOWN | 20 | 0 | T |
| AI472136 | UNKNOWN | 17 | 0 | T |
| AI472142 | UNKNOWN | 14 | 0 | T |
| AI472143 | UNKNOWN | 33 | 0 | T |
| AI472145 | UNKNOWN | 17 | 0 | T |
| AI472201 | UNKNOWN | 12 | 0 | T |
| AI472255 | UNKNOWN | 10 | 201 | GT |
| AI472255 | UNKNOWN | 17 | 0 | T |
| AI472257 | UNKNOWN | 13 | 0 | T |
| AI472273 | UNKNOWN | 34 | 0 | T |
| AI472305 | UNKNOWN | 14 | 0 | T |
| AI472318 | UNKNOWN | 21 | 0 | T |
| AI472331 | UNKNOWN | 13 | 0 | T |
| AI472422 | UNKNOWN | 96 | 0 | T |
| AI472459 | UNKNOWN | 6.5 | 196 | AG |
| AI472459 | UNKNOWN | 13 | 0 | T |
| AI472476 | UNKNOWN | 48 | 0 | T |
| AI472476 | UNKNOWN | 14 | 157 | A |
| AI472487 | UNKNOWN | 53 | 0 | T |

TABLE 1-continued

| Genbank # | Region | # reps | Position | Unit sequence |
|---|---|---|---|---|
| AI472536 | UNKNOWN | 68 | 0 | T |
| AI472543 | UNKNOWN | 29 | 0 | T |
| AI472566 | UNKNOWN | 61 | 0 | T |
| AI472566 | UNKNOWN | 18 | 68 | A |
| AI472566 | UNKNOWN | 12 | 132 | G |
| AI472705 | UNKNOWN | 12 | 154 | A |
| AI472767 | UNKNOWN | 62 | 0 | T |
| AI472767 | UNKNOWN | 15 | 118 | G |
| AI472773 | UNKNOWN | 20 | 4 | T |
| AI472823 | UNKNOWN | 33 | 0 | T |
| AI472901 | UNKNOWN | 6.75 | 157 | AAAC |
| AI472976 | UNKNOWN | 24 | 163 | A |
| AI473085 | UNKNOWN | 20 | 17 | GA |
| AI473085 | UNKNOWN | 21 | 86 | A |
| AI473141 | UNKNOWN | 16 | 0 | T |
| AI473150 | UNKNOWN | 61 | 0 | T |
| AI473190 | UNKNOWN | 10 | 27 | TG |
| AI473190 | UNKNOWN | 29 | 103 | A |
| AI473199 | UNKNOWN | 18 | 4 | T |
| AI473240 | UNKNOWN | 50 | 0 | T |
| AI473412 | UNKNOWN | 15 | 0 | T |
| AI473447 | UNKNOWN | 49 | 0 | T |
| AI473450 | UNKNOWN | 27 | 0 | T |
| AI473451 | UNKNOWN | 75 | 0 | T |
| AI473451 | UNKNOWN | 18 | 108 | A |
| AI473471 | UNKNOWN | 50 | 0 | T |
| AI473475 | UNKNOWN | 18 | 25 | T |
| AI473482 | UNKNOWN | 66 | 0 | T |
| AI473517 | UNKNOWN | 40 | 0 | T |
| AI473528 | UNKNOWN | 63 | 0 | T |
| AI473528 | UNKNOWN | 12 | 128 | A |
| AI473537 | UNKNOWN | 15 | 0 | T |
| AI473547 | UNKNOWN | 60 | 0 | T |
| AI473554 | UNKNOWN | 95 | 0 | T |
| AI473554 | UNKNOWN | 15 | 110 | A |
| AI473572 | UNKNOWN | 36 | 0 | T |
| AI473592 | UNKNOWN | 77 | 0 | T |
| AI473592 | UNKNOWN | 15 | 312 | C |
| AI473592 | UNKNOWN | 12 | 161 | G |
| AI473598 | UNKNOWN | 75 | 0 | T |
| AI473601 | UNKNOWN | 12 | 0 | T |
| AI473616 | UNKNOWN | 36 | 0 | T |
| AI473639 | UNKNOWN | 53 | 0 | T |
| AI473652 | UNKNOWN | 63 | 0 | T |
| AI473652 | UNKNOWN | 22 | 125 | G |
| AI473673 | UNKNOWN | 37 | 0 | T |
| AI473783 | UNKNOWN | 14.5 | 464 | AC |
| AI473799 | UNKNOWN | 81 | 0 | T |
| AI473799 | UNKNOWN | 22 | 290 | C |
| AI473799 | UNKNOWN | 13 | 82 | A |
| AI473808 | UNKNOWN | 46 | 0 | T |
| AI473845 | UNKNOWN | 49 | 0 | T |
| AI473858 | UNKNOWN | 31 | 0 | T |
| AI473878 | UNKNOWN | 9 | 257 | AG |
| AI473878 | UNKNOWN | 19 | 143 | A |
| AI473903 | UNKNOWN | 13 | 442 | A |
| AI473934 | UNKNOWN | 41 | 0 | T |
| AI473954 | UNKNOWN | 8 | 265 | TA |
| AI473954 | UNKNOWN | 29 | 0 | T |
| AI474059 | UNKNOWN | 44 | 0 | T |
| AI474076 | UNKNOWN | 99 | 0 | T |
| AI474076 | UNKNOWN | 15 | 221 | C |
| AI474076 | UNKNOWN | 12 | 99 | G |
| AI474107 | UNKNOWN | 106 | 0 | T |
| AI474107 | UNKNOWN | 19 | 139 | A |
| AI474107 | UNKNOWN | 18 | 311 | G |
| AI474107 | UNKNOWN | 15 | 213 | G |
| AI474107 | UNKNOWN | 12 | 170 | G |
| AI474137 | UNKNOWN | 67 | 0 | T |
| AI474137 | UNKNOWN | 13 | 103 | G |
| AI474137 | UNKNOWN | 12 | 67 | A |
| AI474138 | UNKNOWN | 49 | 0 | T |
| AI474146 | UNKNOWN | 80 | 0 | T |
| AI474339 | UNKNOWN | 21 | 308 | T |
| AI474535 | UNKNOWN | 15 | 0 | T |
| AI474556 | UNKNOWN | 37 | 0 | T |
| AI474646 | UNKNOWN | 2.52 | 1 | TTTTTTTTTTTATTTTTTTT (SEQ ID NO:119) |

TABLE 1-continued

| Genbank # | Region | # reps | Position | Unit sequence |
|---|---|---|---|---|
| AI474646 | UNKNOWN | 34 | 34 | T |
| AI474646 | UNKNOWN | 20 | 13 | T |
| AI474646 | UNKNOWN | 15 | 129 | A |
| AI474665 | UNKNOWN | 17 | 0 | T |
| AI474845 | UNKNOWN | 20 | 0 | T |
| AI475114 | UNKNOWN | 8.5 | 264 | TAAA |
| AI475114 | UNKNOWN | 17 | 5 | T |
| AI475129 | UNKNOWN | 47 | 0 | T |
| AI475134 | UNKNOWN | 124 | 0 | T |
| AI475134 | UNKNOWN | 22 | 274 | A |
| AI475134 | UNKNOWN | 19 | 138 | A |
| AI475134 | UNKNOWN | 15 | 242 | C |
| AI475139 | UNKNOWN | 84 | 0 | T |
| AI475139 | UNKNOWN | 14 | 86 | A |
| AI475139 | UNKNOWN | 12 | 263 | C |
| AI475148 | UNKNOWN | 70 | 0 | T |
| AI475149 | UNKNOWN | 39 | 0 | T |
| AI475151 | UNKNOWN | 109 | 0 | T |
| AI475175 | UNKNOWN | 69 | 0 | T |
| AI475175 | UNKNOWN | 13 | 319 | G |
| AI475224 | UNKNOWN | 30 | 0 | T |
| AI475227 | UNKNOWN | 13 | 212 | G |
| AI475234 | UNKNOWN | 45 | 0 | T |
| AI475241 | UNKNOWN | 41 | 0 | T |
| AI475267 | UNKNOWN | 67 | 0 | T |
| AI475270 | UNKNOWN | 64 | 0 | T |
| AI475285 | UNKNOWN | 32 | 11 | T |
| AI475308 | UNKNOWN | 22 | 0 | T |
| AI475330 | UNKNOWN | 54 | 0 | T |
| AI475331 | UNKNOWN | 48 | 0 | T |
| AI475339 | UNKNOWN | 51 | 0 | T |
| AI475351 | UNKNOWN | 19 | 19 | T |
| AI475351 | UNKNOWN | 18 | 180 | A |
| AI475351 | UNKNOWN | 12 | 0 | T |
| AI475371 | UNKNOWN | 127 | 0 | T |
| AI475371 | UNKNOWN | 23 | 306 | G |
| AI475371 | UNKNOWN | 15 | 169 | G |
| AI475371 | UNKNOWN | 15 | 247 | C |
| AI475371 | UNKNOWN | 13 | 234 | A |
| AI475372 | UNKNOWN | 12 | 307 | A |
| AI475373 | UNKNOWN | 2.5 | 230 | AAAAAGAAAG (SEQ ID NO:120) |
| AI475373 | UNKNOWN | 32 | 0 | T |
| AI475377 | UNKNOWN | 82 | 0 | T |
| AI475377 | UNKNOWN | 18 | 122 | G |
| AI475394 | UNKNOWN | 97 | 0 | T |
| AI475394 | UNKNOWN | 16 | 130 | C |
| AI475394 | UNKNOWN | 15 | 209 | A |
| AI475394 | UNKNOWN | 13 | 242 | G |
| AI475408 | UNKNOWN | 78 | 0 | T |
| AI475408 | UNKNOWN | 15 | 252 | G |
| AI475408 | UNKNOWN | 14 | 152 | G |
| AI475410 | UNKNOWN | 58 | 0 | T |
| AI475430 | UNKNOWN | 95 | 0 | T |
| AI475430 | UNKNOWN | 16 | 142 | A |
| AI475430 | UNKNOWN | 16 | 158 | C |
| AI475451 | UNKNOWN | 113 | 0 | T |
| AI475451 | UNKNOWN | 17 | 226 | A |
| AI475451 | UNKNOWN | 14 | 121 | A |
| AI475453 | UNKNOWN | 22 | 0 | T |
| AI475454 | UNKNOWN | 74 | 0 | T |
| AI475454 | UNKNOWN | 19 | 107 | G |
| AI475455 | UNKNOWN | 118 | 0 | T |
| AI475455 | UNKNOWN | 20 | 129 | A |
| AI475455 | UNKNOWN | 14 | 243 | G |
| AI475455 | UNKNOWN | 12 | 152 | G |
| AI475473 | UNKNOWN | 12 | 0 | T |
| AI475495 | UNKNOWN | 16 | 0 | T |
| AI475495 | UNKNOWN | 12 | 325 | A |
| AI475536 | UNKNOWN | 22 | 0 | T |
| AI475577 | UNKNOWN | 20 | 1 | T |
| AI475653 | UNKNOWN | 21 | 0 | T |
| AI475680 | UNKNOWN | 14 | 157 | A |
| AI475688 | UNKNOWN | 51 | 0 | T |
| AI475690 | UNKNOWN | 5.66 | 262 | CCG |
| AI475787 | UNKNOWN | 10.5 | 59 | CA |
| AI475787 | UNKNOWN | 22 | 0 | T |
| AI475798 | UNKNOWN | 16 | 0 | T |

TABLE 1-continued

| Genbank # | Region | # reps | Position | Unit sequence |
|---|---|---|---|---|
| AI475806 | UNKNOWN | 83 | 0 | T |
| AI475806 | UNKNOWN | 13 | 411 | C |
| AI475806 | UNKNOWN | 12 | 84 | A |
| AI475815 | UNKNOWN | 49 | 0 | T |
| AI475815 | UNKNOWN | 13 | 390 | G |
| AI475817 | UNKNOWN | 113 | 0 | T |
| AI475817 | UNKNOWN | 22 | 210 | G |
| AI475817 | UNKNOWN | 14 | 162 | A |
| AI475817 | UNKNOWN | 14 | 311 | C |
| AI475827 | UNKNOWN | 13.5 | 362 | GT |
| AI475827 | UNKNOWN | 10 | 340 | GT |
| AI475833 | UNKNOWN | 41 | 0 | T |
| AI475884 | UNKNOWN | 24 | 0 | T |
| AI475885 | UNKNOWN | 6.5 | 161 | AACA |
| AI475909 | UNKNOWN | 63 | 0 | T |
| AI475909 | UNKNOWN | 16 | 155 | G |
| AI475909 | UNKNOWN | 14 | 204 | C |
| AI475947 | UNKNOWN | 113 | 0 | T |
| AI475947 | UNKNOWN | 15 | 164 | C |
| AI476019 | UNKNOWN | 22 | 30 | T |
| AI476019 | UNKNOWN | 13 | 0 | T |
| AI476021 | UNKNOWN | 51 | 0 | T |
| AI476021 | UNKNOWN | 18 | 98 | A |
| AI476029 | UNKNOWN | 41 | 0 | T |
| AI476038 | UNKNOWN | 17 | 12 | T |
| AI476046 | UNKNOWN | 99 | 0 | T |
| AI476046 | UNKNOWN | 25 | 138 | A |
| AI476046 | UNKNOWN | 13 | 163 | C |
| AI476046 | UNKNOWN | 12 | 110 | A |
| AI476076 | UNKNOWN | 62 | 0 | T |
| AI476077 | UNKNOWN | 71 | 0 | T |
| AI476077 | UNKNOWN | 15 | 133 | C |
| AI476077 | UNKNOWN | 13 | 148 | A |
| AI476088 | UNKNOWN | 37 | 0 | T |
| AI476109 | UNKNOWN | 98 | 0 | T |
| AI476109 | UNKNOWN | 16 | 207 | G |
| AI476228 | UNKNOWN | 7 | 250 | CT |
| AI476228 | UNKNOWN | 14 | 0 | T |
| AI476318 | UNKNOWN | 24 | 313 | A |
| AI476340 | UNKNOWN | 27 | 0 | T |
| AI476344 | UNKNOWN | 17 | 0 | T |
| AI476365 | UNKNOWN | 64 | 0 | T |
| AI476365 | UNKNOWN | 18 | 149 | C |
| AI476365 | UNKNOWN | 13 | 335 | G |
| AI476365 | UNKNOWN | 12 | 64 | A |
| AI476371 | UNKNOWN | 65 | 0 | T |
| AI476371 | UNKNOWN | 14 | 183 | A |
| AI476376 | UNKNOWN | 91 | 0 | T |
| AI476459 | UNKNOWN | 19 | 0 | T |
| AI476478 | UNKNOWN | 94 | 0 | T |
| AI476478 | UNKNOWN | 19 | 96 | A |
| AI476480 | UNKNOWN | 63 | 0 | T |
| AI476480 | UNKNOWN | 12 | 261 | G |
| AI476527 | UNKNOWN | 78 | 0 | T |
| AI476527 | UNKNOWN | 15 | 136 | C |
| AI476581 | UNKNOWN | 13 | 413 | T |
| AI476592 | UNKNOWN | 12 | 72 | A |
| AI476620 | UNKNOWN | 61 | 0 | T |
| AI476721 | UNKNOWN | 15 | 323 | G |
| AI476721 | UNKNOWN | 12 | 352 | T |
| AI476747 | UNKNOWN | 16 | 0 | T |
| AI476789 | UNKNOWN | 18 | 0 | T |
| AI476791 | UNKNOWN | 17 | 0 | T |
| AI478114 | UNKNOWN | 18 | 0 | T |
| AI478123 | UNKNOWN | 85 | 0 | T |
| AI478138 | UNKNOWN | 12 | 0 | T |
| AI478200 | UNKNOWN | 13 | 0 | T |
| AI478230 | UNKNOWN | 44 | 0 | T |
| AI478269 | UNKNOWN | 14 | 0 | T |
| AI478282 | UNKNOWN | 62 | 0 | T |
| AI478349 | UNKNOWN | 15 | 0 | T |
| AI478355 | UNKNOWN | 52 | 0 | T |
| AI478355 | UNKNOWN | 16 | 132 | G |
| AI478416 | UNKNOWN | 12 | 188 | T |
| AI478437 | UNKNOWN | 15 | 0 | T |
| AI478488 | UNKNOWN | 3.6 | 104 | GCCCC |
| AI478489 | UNKNOWN | 6.5 | 283 | AC |

TABLE 1-continued

| Genbank # | Region | # reps | Position | Unit sequence |
|---|---|---|---|---|
| AI478489 | UNKNOWN | 6.5 | 301 | AG |
| AI478533 | UNKNOWN | 52 | 0 | T |
| AI478571 | UNKNOWN | 65 | 0 | T |
| AI478619 | UNKNOWN | 21 | 0 | T |
| AI478639 | UNKNOWN | 77 | 0 | T |
| AI478639 | UNKNOWN | 16 | 158 | G |
| AI478639 | UNKNOWN | 14 | 133 | C |
| AI478714 | UNKNOWN | 48 | 0 | T |
| AI478723 | UNKNOWN | 58 | 0 | T |
| AI478727 | UNKNOWN | 34 | 0 | T |
| AI478741 | UNKNOWN | 16 | 0 | T |
| AI478776 | UNKNOWN | 15 | 341 | A |
| AI478776 | UNKNOWN | 14 | 25 | T |
| AI478793 | UNKNOWN | 22 | 0 | T |
| AI478821 | UNKNOWN | 12 | 104 | A |
| AI478898 | UNKNOWN | 12 | 313 | A |
| AI478902 | UNKNOWN | 56 | 0 | T |
| AI478902 | UNKNOWN | 19 | 320 | C |
| AI478902 | UNKNOWN | 15 | 210 | G |
| AI478966 | UNKNOWN | 4.16 | 249 | GTGGCA |
| AI478977 | UNKNOWN | 22 | 0 | T |
| AI479011 | UNKNOWN | 16 | 8 | T |
| AI479022 | UNKNOWN | 15 | 184 | T |
| AI479023 | UNKNOWN | 3.71 | 160 | AAAAACA |
| AI779029 | UNKNOWN | 18 | 0 | T |
| AI479049 | UNKNOWN | 19 | 377 | T |
| AI479075 | UNKNOWN | 15 | 0 | T |
| AI479126 | UNKNOWN | 79 | 0 | T |
| AI479165 | UNKNOWN | 63 | 0 | T |
| AI479245 | UNKNOWN | 13 | 87 | A |
| AI479292 | UNKNOWN | 57 | 0 | T |
| AI479320 | UNKNOWN | 17 | 0 | T |
| AI479324 | UNKNOWN | 15 | 0 | T |
| AI479334 | UNKNOWN | 27 | 0 | T |
| AI479346 | UNKNOWN | 18 | 0 | T |
| AI479346 | UNKNOWN | 13 | 251 | A |
| AI479351 | UNKNOWN | 12 | 649 | T |
| AI479358 | UNKNOWN | 14 | 0 | T |
| AI479377 | UNKNOWN | 16 | 0 | T |
| AI479380 | UNKNOWN | 14 | 0 | T |
| AI479419 | UNKNOWN | 15 | 0 | T |
| AI479439 | UNKNOWN | 12 | 28 | A |
| AI479461 | UNKNOWN | 21 | 0 | T |
| AI479465 | UNKNOWN | 45 | 0 | T |
| AI479524 | UNKNOWN | 6.5 | 242 | AT |
| AI479524 | UNKNOWN | 30 | 0 | T |
| AI479562 | UNKNOWN | 12 | 0 | T |
| AI479577 | UNKNOWN | 66 | 0 | T |
| AI479577 | UNKNOWN | 12 | 226 | C |
| AI479596 | UNKNOWN | 20 | 0 | T |
| AI479610 | UNKNOWN | 14 | 0 | T |
| AI479878 | UNKNOWN | 18 | 457 | A |
| AI479885 | UNKNOWN | 19 | 0 | T |
| AI479886 | UNKNOWN | 8.5 | 153 | AC |
| AI479903 | UNKNOWN | 45 | 0 | T |
| AI479935 | UNKNOWN | 9 | 98 | GT |
| AI479944 | UNKNOWN | 4.59 | 8 | TTTTC |
| AI479944 | UNKNOWN | 23 | 32 | T |
| AI479944 | UNKNOWN | 12 | 0 | T |
| AI480030 | UNKNOWN | 34 | 0 | T |
| AI480050 | UNKNOWN | 41 | 0 | T |
| AI480091 | UNKNOWN | 12 | 252 | T |
| AI480104 | UNKNOWN | 55 | 0 | T |
| AI480110 | UNKNOWN | 28 | 1 | T |
| AI480118 | UNKNOWN | 106 | 0 | T |
| AI480118 | UNKNOWN | 22 | 123 | A |
| AI480118 | UNKNOWN | 14 | 277 | C |
| AI480118 | UNKNOWN | 12 | 108 | G |
| AI480118 | UNKNOWN | 12 | 221 | C |
| AI480121 | UNKNOWN | 20 | 0 | T |
| AI480161 | UNKNOWN | 3.6 | 108 | AATAA |
| AI480182 | UNKNOWN | 19 | 0 | T |
| AI480187 | UNKNOWN | 5.5 | 178 | TTCC |
| AI480189 | UNKNOWN | 12 | 0 | T |
| AI480198 | UNKNOWN | 13 | 122 | A |
| AI480198 | UNKNOWN | 12 | 0 | T |
| AI480204 | UNKNOWN | 21 | 0 | T |

TABLE 1-continued

| Genbank # | Region | # reps | Position | Unit sequence |
|---|---|---|---|---|
| AI480240 | UNKNOWN | 13 | 187 | A |
| AI480289 | UNKNOWN | 11.5 | 154 | GT |
| AI480292 | UNKNOWN | 17 | 0 | T |
| AI480305 | UNKNOWN | 21 | 357 | A |
| AI480329 | UNKNOWN | 55 | 0 | T |
| AI480329 | UNKNOWN | 12 | 156 | G |
| AI480329 | UNKNOWN | 12 | 303 | A |
| AI480380 | UNKNOWN | 17 | 0 | T |
| AI480387 | UNKNOWN | 16 | 111 | T |
| AI491750 | UNKNOWN | 28 | 0 | T |
| AI491769 | UNKNOWN | 44 | 0 | T |
| AI491776 | UNKNOWN | 107 | 11 | T |
| AI491783 | UNKNOWN | 91 | 0 | T |
| AI491783 | UNKNOWN | 20 | 295 | G |
| AI491783 | UNKNOWN | 14 | 199 | G |
| AI491785 | UNKNOWN | 42 | 0 | T |
| AI491798 | UNKNOWN | 88 | 0 | T |
| AI491798 | UNKNOWN | 15 | 208 | C |
| AI491805 | UNKNOWN | 77 | 0 | T |
| AI491805 | UNKNOWN | 17 | 129 | A |
| AI491832 | UNKNOWN | 35 | 0 | T |
| AI491839 | UNKNOWN | 57 | 0 | T |
| AI491855 | UNKNOWN | 15 | 0 | T |
| AI491856 | UNKNOWN | 50 | 0 | T |
| AI491856 | UNKNOWN | 12 | 103 | G |
| AI491856 | UNKNOWN | 12 | 177 | C |
| AI491890 | UNKNOWN | 14 | 0 | T |
| AI491897 | UNKNOWN | 102 | 0 | T |
| AI491897 | UNKNOWN | 12 | 108 | G |
| AI491904 | UNKNOWN | 55 | 0 | T |
| AI491916 | UNKNOWN | 63 | 0 | T |
| AI491942 | UNKNOWN | 16 | 0 | T |
| AI492034 | UNKNOWN | 18 | 4 | T |
| AI492066 | UNKNOWN | 17 | 0 | T |
| AI492127 | UNKNOWN | 49 | 0 | T |
| AI492127 | UNKNOWN | 18 | 88 | A |
| AI492127 | UNKNOWN | 13 | 179 | G |
| AI492162 | UNKNOWN | 3.5 | 427 | CTCGCT |
| AI492162 | UNKNOWN | 8 | 406 | TC |
| AI492164 | UNKNOWN | 15 | 0 | T |
| AI492173 | UNKNOWN | 15 | 0 | T |
| AI492256 | UNKNOWN | 14 | 186 | T |
| AI492273 | UNKNOWN | 20 | 248 | T |
| AI492388 | UNKNOWN | 14 | 243 | T |
| AI492398 | UNKNOWN | 12 | 483 | TA |
| AI492422 | UNKNOWN | 24 | 0 | T |
| AI492435 | UNKNOWN | 9 | 480 | AG |
| AI492500 | UNKNOWN | 15 | 596 | T |
| AI492500 | UNKNOWN | 13 | 0 | T |
| AI492527 | UNKNOWN | 39 | 0 | T |
| AI492528 | UNKNOWN | 115 | 0 | T |
| AI492528 | UNKNOWN | 16 | 152 | G |
| AI492528 | UNKNOWN | 16 | 239 | C |
| AI492528 | UNKNOWN | 15 | 120 | A |
| AI492562 | UNKNOWN | 40 | 0 | T |
| AI492570 | UNKNOWN | 32 | 0 | T |
| AI492588 | UNKNOWN | 18 | 0 | T |
| AI492593 | UNKNOWN | 44 | 0 | T |
| AI492597 | UNKNOWN | 21 | 0 | T |
| AI492643 | UNKNOWN | 18 | 0 | T |
| AI492648 | UNKNOWN | 46 | 0 | T |
| AI492651 | UNKNOWN | 9 | 140 | AG |
| AI492651 | UNKNOWN | 13 | 0 | T |
| AI492653 | UNKNOWN | 27 | 0 | T |
| AI492752 | UNKNOWN | 63 | 0 | T |
| AI492752 | UNKNOWN | 17 | 269 | A |
| AI492752 | UNKNOWN | 14 | 164 | A |
| AI492777 | UNKNOWN | 2.7 | 75 | AGAGAGAGAC (SEQ ID NO:121) |
| AI492777 | UNKNOWN | 24 | 36 | GA |
| AI492790 | UNKNOWN | 21 | 120 | A |
| AI492839 | UNKNOWN | 2.8 | 374 | TTTTTTTCT (SEQ ID NO:122) |
| AI492839 | UNKNOWN | 17 | 393 | T |
| AI492886 | UNKNOWN | 16 | 113 | A |
| AI492916 | UNKNOWN | 3.8 | 305 | CGGGC |
| AI493054 | UNKNOWN | 14 | 0 | T |
| AI493077 | UNKNOWN | 26 | 0 | T |
| AI493126 | UNKNOWN | 12 | 0 | T |

TABLE 1-continued

| Genbank # | Region | # reps | Position | Unit sequence |
|---|---|---|---|---|
| AI493128 | UNKNOWN | 15 | 0 | T |
| AI493146 | UNKNOWN | 12 | 0 | T |
| AI493243 | UNKNOWN | 36 | 0 | T |
| AI493248 | UNKNOWN | 123 | 0 | T |
| AI493248 | UNKNOWN | 22 | 206 | G |
| AI493248 | UNKNOWN | 20 | 319 | C |
| AI493248 | UNKNOWN | 16 | 181 | A |
| AI493248 | UNKNOWN | 12 | 167 | G |
| AI493289 | UNKNOWN | 14 | 0 | T |
| AI493385 | UNKNOWN | 30 | 0 | T |
| AI493385 | UNKNOWN | 15 | 198 | G |
| AI493426 | UNKNOWN | 70 | 0 | T |
| AI493426 | UNKNOWN | 14 | 395 | G |
| AI493426 | UNKNOWN | 13 | 214 | A |
| AI493426 | UNKNOWN | 12 | 179 | G |
| AI493543 | UNKNOWN | 57 | 0 | T |
| AI493543 | UNKNOWN | 15 | 346 | A |
| AI493567 | UNKNOWN | 92 | 0 | T |
| AI493567 | UNKNOWN | 26 | 149 | C |
| AI493567 | UNKNOWN | 17 | 113 | A |
| AI493567 | UNKNOWN | 13 | 136 | G |
| AI493571 | UNKNOWN | 18 | 0 | T |
| AI493576 | UNKNOWN | 90 | 0 | T |
| AI493576 | UNKNOWN | 12 | 201 | C |
| AI493576 | UNKNOWN | 12 | 260 | G |
| AI493588 | UNKNOWN | 43 | 0 | T |
| AI493593 | UNKNOWN | 51 | 0 | T |
| AI493601 | UNKNOWN | 77 | 0 | T |
| AI493601 | UNKNOWN | 18 | 313 | C |
| AI493676 | UNKNOWN | 14 | 0 | T |
| AI493706 | UNKNOWN | 43 | 0 | T |
| AI493711 | UNKNOWN | 18 | 0 | T |
| AI493740 | UNKNOWN | 52 | 0 | T |
| AI493846 | UNKNOWN | 24 | 386 | T |
| AI493849 | UNKNOWN | 3.83 | 245 | CTTCTC |
| AI493849 | UNKNOWN | 18.5 | 49 | AC |
| AI493858 | UNKNOWN | 47 | 0 | T |
| AI494102 | UNKNOWN | 23 | 79 | A |
| AI494102 | UNKNOWN | 16 | 0 | T |
| AI494153 | UNKNOWN | 45 | 0 | T |
| AI494198 | UNKNOWN | 49 | 0 | T |
| AI494215 | UNKNOWN | 13 | 438 | A |
| AI494290 | UNKNOWN | 20 | 0 | T |
| AI494327 | UNKNOWN | 38 | 0 | T |
| AI494343 | UNKNOWN | 90 | 0 | T |
| AI494343 | UNKNOWN | 16 | 186 | A |
| AI494343 | UNKNOWN | 15 | 101 | A |
| AI494449 | UNKNOWN | 52 | 0 | T |
| AI494453 | UNKNOWN | 13 | 15 | T |
| AI494463 | UNKNOWN | 6 | 19 | TTTA |
| AI494463 | UNKNOWN | 22 | 0 | T |
| AI494463 | UNKNOWN | 14 | 434 | A |
| AI494473 | UNKNOWN | 7.5 | 485 | TA |
| AI494500 | UNKNOWN | 12 | 0 | T |
| AI494568 | UNKNOWN | 35 | 0 | T |
| AI494612 | UNKNOWN | 19 | 0 | T |
| AI497590 | UNKNOWN | 46 | 0 | T |
| AI497599 | UNKNOWN | 49 | 0 | T |
| AI497617 | UNKNOWN | 27 | 0 | T |
| AI497725 | UNKNOWN | 43 | 0 | T |
| AI497725 | UNKNOWN | 14 | 140 | A |
| AI497733 | UNKNOWN | 92 | 0 | T |
| AI497733 | UNKNOWN | 15 | 169 | C |
| AI497733 | UNKNOWN | 14 | 184 | G |
| AI497955 | UNKNOWN | 18 | 0 | T |
| AI498011 | UNKNOWN | 28 | 0 | T |
| AI498067 | UNKNOWN | 97 | 0 | T |
| AI498067 | UNKNOWN | 19 | 184 | C |
| AI498092 | UNKNOWN | 36 | 0 | T |
| AI498092 | UNKNOWN | 16 | 179 | A |
| AI498161 | UNKNOWN | 13 | 0 | T |
| AI498204 | UNKNOWN | 17 | 77 | TA |
| AI498288 | UNKNOWN | 48 | 0 | T |
| AI498317 | UNKNOWN | 18 | 4 | T |
| AI498323 | UNKNOWN | 43 | 0 | T |
| AI498360 | UNKNOWN | 27 | 0 | T |
| AI498414 | UNKNOWN | 36 | 0 | T |

TABLE 1-continued

| Genbank # | Region | # reps | Position | Unit sequence |
|---|---|---|---|---|
| AI498431 | UNKNOWN | 34 | 0 | T |
| AI498431 | UNKNOWN | 12 | 195 | A |
| AI498454 | UNKNOWN | 19 | 0 | T |
| AI498454 | UNKNOWN | 17 | 423 | A |
| AI498491 | UNKNOWN | 26 | 0 | T |
| AI498544 | UNKNOWN | 24 | 0 | T |
| AI498579 | UNKNOWN | 123 | 0 | T |
| AI498579 | UNKNOWN | 17 | 137 | C |
| AI498579 | UNKNOWN | 14 | 154 | G |
| AI498582 | UNKNOWN | 50 | 0 | T |
| AI498646 | UNKNOWN | 32 | 0 | T |
| AI498656 | UNKNOWN | 12 | 0 | T |
| AI498658 | UNKNOWN | 15 | 0 | T |
| AI498664 | UNKNOWN | 8 | 212 | CA |
| AI498714 | UNKNOWN | 58 | 0 | T |
| AI498716 | UNKNOWN | 47 | 0 | T |
| AI498740 | UNKNOWN | 12 | 0 | T |
| AI498894 | UNKNOWN | 40 | 0 | T |
| AI498957 | UNKNOWN | 14 | 0 | T |
| AI498979 | UNKNOWN | 14 | 0 | T |
| AI499056 | UNKNOWN | 13 | 298 | A |
| AI499057 | UNKNOWN | 48 | 0 | T |
| AI499111 | UNKNOWN | 49 | 0 | T |
| AI499127 | UNKNOWN | 19 | 10 | T |
| AI499131 | UNKNOWN | 120 | 0 | T |
| AI499131 | UNKNOWN | 22 | 123 | A |
| AI499131 | UNKNOWN | 18 | 236 | G |
| AI499138 | UNKNOWN | 21 | 0 | T |
| AI499139 | UNKNOWN | 12 | 13 | T |
| AI499146 | UNKNOWN | 113 | 0 | T |
| AI499146 | UNKNOWN | 20 | 169 | C |
| AI499146 | UNKNOWN | 16 | 153 | A |
| AI499147 | UNKNOWN | 35 | 0 | T |
| AI499161 | UNKNOWN | 59 | 9 | T |
| AI499178 | UNKNOWN | 46 | 0 | T |
| AI499224 | UNKNOWN | 38 | 0 | T |
| AI499229 | UNKNOWN | 30 | 0 | T |
| AI499240 | UNKNOWN | 60 | 0 | T |
| AI499263 | UNKNOWN | 96 | 0 | T |
| AI499263 | UNKNOWN | 13 | 153 | G |
| AI499282 | UNKNOWN | 36 | 0 | T |
| AI499285 | UNKNOWN | 97 | 0 | T |
| AI499285 | UNKNOWN | 22 | 161 | C |
| AI499285 | UNKNOWN | 16 | 183 | A |
| AI499285 | UNKNOWN | 14 | 142 | G |
| AI499285 | UNKNOWN | 12 | 130 | A |
| AI499298 | UNKNOWN | 29 | 11 | T |
| AI499306 | UNKNOWN | 12 | 0 | T |
| AI499323 | UNKNOWN | 12 | 0 | T |
| AI499381 | UNKNOWN | 100 | 0 | T |
| AI499381 | UNKNOWN | 21 | 194 | A |
| AI499391 | UNKNOWN | 64 | 0 | T |
| AI499391 | UNKNOWN | 15 | 298 | G |
| AI499393 | UNKNOWN | 130 | 0 | T |
| AI499393 | UNKNOWN | 20 | 215 | A |
| AI499393 | UNKNOWN | 14 | 137 | A |
| AI499393 | UNKNOWN | 12 | 151 | G |
| AI499393 | UNKNOWN | 12 | 186 | C |
| AI499420 | UNKNOWN | 57 | 0 | T |
| AI499463 | UNKNOWN | 121 | 11 | T |
| AI499463 | UNKNOWN | 15 | 167 | G |
| AI499463 | UNKNOWN | 13 | 197 | A |
| AI499490 | UNKNOWN | 15 | 11 | T |
| AI499573 | UNKNOWN | 56 | 0 | T |
| AI499581 | UNKNOWN | 65 | 11 | T |
| AI499588 | UNKNOWN | 32 | 11 | T |
| AI499621 | UNKNOWN | 72 | 0 | T |
| AI499623 | UNKNOWN | 60 | 0 | T |
| AI499652 | UNKNOWN | 89 | 0 | T |
| AI499652 | UNKNOWN | 14 | 200 | A |
| AI499697 | UNKNOWN | 39 | 0 | T |
| AI499697 | UNKNOWN | 12 | 142 | G |
| AI499814 | UNKNOWN | 16 | 11 | T |
| AI499814 | UNKNOWN | 14 | 339 | C |
| AI499823 | UNKNOWN | 23 | 0 | T |
| AI499863 | UNKNOWN | 13 | 188 | T |
| AI499877 | UNKNOWN | 18 | 0 | T |

TABLE 1-continued

| Genbank # | Region | # reps | Position | Unit sequence |
|---|---|---|---|---|
| AI499890 | UNKNOWN | 77 | 0 | T |
| AI499890 | UNKNOWN | 12 | 77 | A |
| AI499913 | UNKNOWN | 60 | 0 | T |
| AI499920 | UNKNOWN | 103 | 0 | T |
| AI499920 | UNKNOWN | 19 | 128 | A |
| AI499920 | UNKNOWN | 13 | 166 | G |
| AI499920 | UNKNOWN | 13 | 420 | C |
| AI499947 | UNKNOWN | 64 | 0 | T |
| AI499947 | UNKNOWN | 23 | 70 | A |
| AI499947 | UNKNOWN | 22 | 132 | G |
| AI499947 | UNKNOWN | 12 | 154 | C |
| AI499960 | UNKNOWN | 87 | 0 | T |
| AI499960 | UNKNOWN | 17 | 272 | C |
| AI499963 | UNKNOWN | 77 | 0 | T |
| AI499963 | UNKNOWN | 13 | 178 | G |
| AI499963 | UNKNOWN | 12 | 77 | A |
| AI499963 | UNKNOWN | 12 | 191 | C |
| AI499974 | UNKNOWN | 64 | 0 | T |
| AI499977 | UNKNOWN | 52 | 0 | T |
| AI499977 | UNKNOWN | 12 | 135 | G |
| AI499986 | UNKNOWN | 91 | 0 | T |
| AI500039 | UNKNOWN | 102 | 0 | T |
| AI500061 | UNKNOWN | 87 | 0 | T |
| AI500061 | UNKNOWN | 12 | 125 | G |
| AI500077 | UNKNOWN | 134 | 0 | T |
| AI500077 | UNKNOWN | 13 | 177 | G |
| AI500077 | UNKNOWN | 12 | 205 | A |
| AI500099 | UNKNOWN | 40 | 0 | T |
| AI500104 | UNKNOWN | 37 | 0 | T |
| AI500146 | UNKNOWN | 103 | 0 | T |
| AI500146 | UNKNOWN | 19 | 132 | G |
| AI500146 | UNKNOWN | 12 | 246 | A |
| AI500301 | UNKNOWN | 43 | 0 | T |
| AI500301 | UNKNOWN | 17 | 179 | A |
| AI500319 | UNKNOWN | 41 | 0 | T |
| AI500319 | UNKNOWN | 14 | 153 | G |
| AI500430 | UNKNOWN | 34 | 0 | T |
| AI500433 | UNKNOWN | 15 | 11 | T |
| AI500447 | UNKNOWN | 29 | 0 | T |
| AI500456 | UNKNOWN | 12 | 5 | T |
| AI500463 | UNKNOWN | 69 | 0 | T |
| AI500480 | UNKNOWN | 19 | 0 | T |
| AI500483 | UNKNOWN | 43 | 0 | T |
| AI500484 | UNKNOWN | 62 | 0 | T |
| AI500504 | UNKNOWN | 83 | 0 | T |
| AI500504 | UNKNOWN | 12 | 155 | A |
| AI500523 | UNKNOWN | 111 | 11 | T |
| AI500553 | UNKNOWN | 144 | 0 | T |
| AI500553 | UNKNOWN | 22 | 188 | A |
| AI500553 | UNKNOWN | 19 | 212 | C |
| AI500553 | UNKNOWN | 15 | 252 | G |
| AI500553 | UNKNOWN | 12 | 163 | C |
| AI500562 | UNKNOWN | 23 | 0 | T |
| AI500588 | UNKNOWN | 89 | 0 | T |
| AI500588 | UNKNOWN | 17 | 164 | G |
| AI500588 | UNKNOWN | 15 | 318 | A |
| AI500595 | UNKNOWN | 75 | 0 | T |
| AI500622 | UNKNOWN | 36 | 0 | T |
| AI500650 | UNKNOWN | 17 | 298 | A |
| AI500650 | UNKNOWN | 15 | 11 | T |
| AI500659 | UNKNOWN | 119 | 11 | T |
| AI500661 | UNKNOWN | 22 | 0 | T |
| AI500688 | UNKNOWN | 53 | 0 | T |
| AI500719 | UNKNOWN | 40 | 0 | T |
| AI500719 | UNKNOWN | 15 | 130 | A |
| AI510703 | UNKNOWN | 33 | 0 | T |
| AI520662 | UNKNOWN | 39 | 0 | T |
| AI520702 | UNKNOWN | 86 | 0 | T |
| AI520702 | UNKNOWN | 16 | 107 | A |
| AI520702 | UNKNOWN | 13 | 223 | C |
| AI520702 | UNKNOWN | 12 | 145 | C |
| AI520785 | UNKNOWN | 103 | 0 | T |
| AI520785 | UNKNOWN | 17 | 140 | G |
| AI520785 | UNKNOWN | 15 | 108 | A |
| AI520793 | UNKNOWN | 106 | 0 | T |
| AI520793 | UNKNOWN | 21 | 162 | A |
| AI520793 | UNKNOWN | 12 | 250 | G |

TABLE 1-continued

| Genbank # | Region | # reps | Position | Unit sequence |
|---|---|---|---|---|
| AI520809 | UNKNOWN | 84 | 0 | T |
| AI520809 | UNKNOWN | 21 | 142 | G |
| AI520809 | UNKNOWN | 15 | 122 | A |
| AI520810 | UNKNOWN | 76 | 0 | T |
| AI520859 | UNKNOWN | 70 | 0 | T |
| AI520862 | UNKNOWN | 95 | 15 | T |
| AI520862 | UNKNOWN | 20 | 114 | A |
| AI520862 | UNKNOWN | 14 | 0 | T |
| AI520862 | UNKNOWN | 14 | 198 | G |
| AI520862 | UNKNOWN | 14 | 255 | C |
| AI520868 | UNKNOWN | 47 | 0 | T |
| AI520881 | UNKNOWN | 68 | 17 | T |
| AI520881 | UNKNOWN | 16 | 0 | T |
| AI520881 | UNKNOWN | 16 | 136 | A |
| AI520881 | UNKNOWN | 13 | 121 | G |
| AI520931 | UNKNOWN | 115 | 0 | T |
| AI520931 | UNKNOWN | 18 | 246 | C |
| AI520931 | UNKNOWN | 16 | 321 | A |
| AI520931 | UNKNOWN | 12 | 282 | A |
| AI520946 | UNKNOWN | 66 | 0 | T |
| AI520946 | UNKNOWN | 13 | 185 | G |
| AI520946 | UNKNOWN | 12 | 101 | C |
| AI520964 | UNKNOWN | 50 | 0 | T |
| AI521013 | UNKNOWN | 8.19 | 0 | ATTTT |
| AI521027 | UNKNOWN | 56 | 0 | T |
| AI521027 | UNKNOWN | 17 | 215 | C |
| AI521040 | UNKNOWN | 108 | 0 | T |
| AI521040 | UNKNOWN | 17 | 202 | C |
| AI521040 | UNKNOWN | 13 | 181 | C |
| AI521040 | UNKNOWN | 12 | 136 | C |
| AI521080 | UNKNOWN | 61 | 0 | T |
| AI521080 | UNKNOWN | 14 | 171 | G |
| AI521095 | UNKNOWN | 79 | 0 | T |
| AI521095 | UNKNOWN | 16 | 172 | G |
| AI521095 | UNKNOWN | 13 | 130 | A |
| AI521095 | UNKNOWN | 13 | 258 | C |
| AI521100 | UNKNOWN | 65 | 51 | T |
| AI521100 | UNKNOWN | 33 | 15 | T |
| AI521100 | UNKNOWN | 17 | 213 | G |
| AI521100 | UNKNOWN | 14 | 0 | T |
| AI521100 | UNKNOWN | 12 | 201 | C |
| AI521103 | UNKNOWN | 88 | 0 | T |
| AI521103 | UNKNOWN | 18 | 241 | A |
| AI521103 | UNKNOWN | 15 | 163 | C |
| AI521103 | UNKNOWN | 13 | 145 | G |
| AI521106 | UNKNOWN | 20 | 0 | T |
| AI521108 | UNKNOWN | 62 | 0 | T |
| AI521108 | UNKNOWN | 13 | 197 | A |
| AI521128 | UNKNOWN | 60 | 0 | T |
| AI521136 | UNKNOWN | 47 | 0 | T |
| AI521184 | UNKNOWN | 19 | 0 | T |
| AI521187 | UNKNOWN | 26 | 0 | T |
| AI521244 | UNKNOWN | 110 | 0 | T |
| AI521244 | UNKNOWN | 14 | 246 | C |
| AI521246 | UNKNOWN | 7 | 619 | CA |
| AI521350 | UNKNOWN | 26 | 0 | T |
| AI521351 | UNKNOWN | 41 | 0 | T |
| AI521382 | UNKNOWN | 65 | 0 | T |
| AI521382 | UNKNOWN | 22 | 127 | G |
| AI521385 | UNKNOWN | 47 | 0 | T |
| AI521386 | UNKNOWN | 83 | 0 | T |
| AI521386 | UNKNOWN | 15 | 141 | C |
| AI521386 | UNKNOWN | 15 | 156 | A |
| AI521398 | UNKNOWN | 20 | 0 | T |
| AI521402 | UNKNOWN | 8.33 | 18 | TTA |
| AI521445 | UNKNOWN | 13 | 415 | T |
| AI521452 | UNKNOWN | 15 | 131 | T |
| AI521476 | UNKNOWN | 100 | 0 | T |
| AI521476 | UNKNOWN | 18 | 148 | C |
| AI521476 | UNKNOWN | 12 | 200 | A |
| AI521494 | UNKNOWN | 18 | 0 | T |
| AI521545 | UNKNOWN | 23 | 11 | T |
| AI521594 | UNKNOWN | 87 | 11 | T |
| AI521597 | UNKNOWN | 2.6 | 120 | TCTCTCTCTG (SEQ ID NO:123) |
| AI521597 | UNKNOWN | 10 | 147 | CT |
| AI521597 | UNKNOWN | 6.5 | 116 | TC |
| AI521628 | UNKNOWN | 64 | 0 | T |

TABLE 1-continued

| Genbank # | Region | # reps | Position | Unit sequence |
|---|---|---|---|---|
| AI521728 | UNKNOWN | 12 | 194 | A |
| AI521749 | UNKNOWN | 12 | 0 | T |
| AI521775 | UNKNOWN | 13 | 119 | A |
| AI521777 | UNKNOWN | 43 | 0 | T |
| AI521799 | UNKNOWN | 56 | 0 | T |
| AI521799 | UNKNOWN | 19 | 118 | A |
| AI521805 | UNKNOWN | 16 | 1 | T |
| AI521904 | UNKNOWN | 4.5 | 349 | AGGG |
| AI521951 | UNKNOWN | 12 | 302 | T |
| AI522004 | UNKNOWN | 35 | 0 | T |
| AI522008 | UNKNOWN | 8 | 84 | TA |
| AI522030 | UNKNOWN | 37 | 0 | T |
| AI522052 | UNKNOWN | 81 | 0 | T |
| AI522052 | UNKNOWN | 16 | 107 | A |
| AI522052 | UNKNOWN | 15 | 208 | C |
| AI522152 | UNKNOWN | 18 | 4 | T |
| AI522216 | UNKNOWN | 15 | 0 | T |
| AI522224 | UNKNOWN | 44 | 0 | T |
| AI522224 | UNKNOWN | 18 | 109 | A |
| AI522256 | UNKNOWN | 45 | 0 | T |
| AI522264 | UNKNOWN | 12 | 988 | G |
| AI522312 | UNKNOWN | 51 | 0 | T |
| AI522328 | UNKNOWN | 3.6 | 52 | TTTCT |
| AI523094 | UNKNOWN | 29 | 19 | T |
| AI523114 | UNKNOWN | 16 | 0 | T |
| AI523205 | UNKNOWN | 29 | 0 | T |
| AI523241 | UNKNOWN | 13 | 0 | T |
| AI523283 | UNKNOWN | 15 | 290 | T |
| AI523317 | UNKNOWN | 13.75 | 233 | TTTC |
| AI523317 | UNKNOWN | 11.5 | 312 | TC |
| AI523342 | UNKNOWN | 23 | 267 | T |
| AI523400 | UNKNOWN | 3.5 | 9 | TTTAAT |
| AI523423 | UNKNOWN | 24 | 5 | T |
| AI523423 | UNKNOWN | 12 | 94 | C |
| AI523521 | UNKNOWN | 62 | 0 | T |
| AI523574 | UNKNOWN | 43 | 0 | T |
| AI523577 | UNKNOWN | 7 | 112 | TCC |
| AI523609 | UNKNOWN | 5.66 | 430 | TTG |
| AI523617 | UNKNOWN | 60 | 0 | T |
| AI523629 | UNKNOWN | 25 | 0 | T |
| AI523678 | UNKNOWN | 16 | 0 | T |
| AI523710 | UNKNOWN | 47 | 0 | T |
| AI523759 | UNKNOWN | 4 | 536 | CTCTC |
| AI523806 | UNKNOWN | 86 | 0 | T |
| AI523806 | UNKNOWN | 19 | 151 | C |
| AI523806 | UNKNOWN | 16 | 183 | G |
| AI523827 | UNKNOWN | 88 | 0 | T |
| AI523857 | UNKNOWN | 6.66 | 116 | GCC |
| AI523941 | UNKNOWN | 12 | 0 | T |
| AI523959 | UNKNOWN | 12 | 1 | T |
| AI523964 | UNKNOWN | 64 | 0 | T |
| AI523973 | UNKNOWN | 50 | 0 | T |
| AI523973 | UNKNOWN | 21 | 181 | G |
| AI524004 | UNKNOWN | 57 | 0 | T |
| AI524013 | UNKNOWN | 38 | 0 | T |
| AI524022 | UNKNOWN | 22 | 151 | T |
| AI524095 | UNKNOWN | 6.75 | 11 | TTTA |
| AI524139 | UNKNOWN | 53 | 0 | T |
| AI524179 | UNKNOWN | 60 | 0 | T |
| AI524179 | UNKNOWN | 23 | 84 | A |
| AI524212 | UNKNOWN | 14 | 128 | T |
| AI524233 | UNKNOWN | 56 | 0 | T |
| AI524233 | UNKNOWN | 14 | 222 | C |
| AI524266 | UNKNOWN | 45 | 0 | T |
| AI524427 | UNKNOWN | 66 | 0 | T |
| AI524427 | UNKNOWN | 13 | 235 | A |
| AI524482 | UNKNOWN | 77 | 0 | T |
| AI524482 | UNKNOWN | 16 | 251 | A |
| AI524482 | UNKNOWN | 12 | 209 | A |
| AI524484 | UNKNOWN | 12 | 0 | T |
| AI524489 | UNKNOWN | 13 | 0 | T |
| AI524515 | UNKNOWN | 4.5 | 2 | TTAT |
| AI524526 | UNKNOWN | 102 | 0 | T |
| AI524526 | UNKNOWN | 17 | 252 | C |
| AI524526 | UNKNOWN | 14 | 221 | A |
| AI524530 | UNKNOWN | 14 | 0 | T |
| AI524534 | UNKNOWN | 26 | 0 | T |

TABLE 1-continued

| Genbank # | Region | # reps | Position | Unit sequence |
|---|---|---|---|---|
| AI524601 | UNKNOWN | 18 | 0 | T |
| AI524601 | UNKNOWN | 15 | 220 | A |
| AI524605 | UNKNOWN | 37 | 0 | T |
| AI524607 | UNKNOWN | 95 | 0 | T |
| AI524608 | UNKNOWN | 52 | 0 | T |
| AI524608 | UNKNOWN | 15 | 137 | G |
| AI524609 | UNKNOWN | 34 | 0 | T |
| AI524610 | UNKNOWN | 13 | 0 | T |
| AI524626 | UNKNOWN | 48 | 0 | T |
| AI524626 | UNKNOWN | 12 | 304 | G |
| AI524652 | UNKNOWN | 66 | 0 | T |
| AI524652 | UNKNOWN | 12 | 321 | C |
| AI524663 | UNKNOWN | 70 | 0 | T |
| AI524663 | UNKNOWN | 23 | 127 | G |
| AI524663 | UNKNOWN | 12 | 96 | C |
| AI524671 | UNKNOWN | 114 | 0 | T |
| AI524671 | UNKNOWN | 14 | 157 | G |
| AI524671 | UNKNOWN | 12 | 135 | A |
| AI524677 | UNKNOWN | 88 | 0 | T |
| AI524677 | UNKNOWN | 12 | 195 | G |
| AI524677 | UNKNOWN | 12 | 207 | A |
| AI524677 | UNKNOWN | 12 | 239 | C |
| AI524698 | UNKNOWN | 14 | 145 | A |
| AI524700 | UNKNOWN | 66 | 0 | T |
| AI524700 | UNKNOWN | 12 | 72 | A |
| AI524724 | UNKNOWN | 65 | 0 | T |
| AI524759 | UNKNOWN | 46 | 0 | T |
| AI524780 | UNKNOWN | 78 | 0 | T |
| AI524780 | UNKNOWN | 19 | 119 | A |
| AI524810 | UNKNOWN | 17 | 4 | T |
| AI524900 | UNKNOWN | 7 | 358 | TTA |
| AI525023 | UNKNOWN | 13 | 666 | T |
| AI525176 | UNKNOWN | 4 | 28 | CAAAA |
| AI525274 | UNKNOWN | 13 | 624 | A |
| AI525522 | UNKNOWN | 25 | 1 | T |
| AI525532 | UNKNOWN | 5.75 | 24 | TTTA |
| AI525622 | UNKNOWN | 12 | 736 | G |
| AI525627 | UNKNOWN | 16 | 616 | A |
| AI525877 | UNKNOWN | 18 | 35 | T |
| AI525879 | UNKNOWN | 12 | 663 | A |
| AI525946 | UNKNOWN | 7.5 | 575 | AN |
| AI525946 | UNKNOWN | 16 | 657 | A |
| AI525946 | UNKNOWN | 12 | 390 | A |
| AI535663 | UNKNOWN | 16 | 42 | T |
| AI535732 | UNKNOWN | 15 | 0 | T |
| AI535733 | UNKNOWN | 14 | 0 | T |
| AI535736 | UNKNOWN | 18 | 0 | T |
| AI535738 | UNKNOWN | 28 | 0 | T |
| AI535740 | UNKNOWN | 24 | 0 | T |
| AI535740 | UNKNOWN | 14 | 508 | C |
| AI535885 | UNKNOWN | 56 | 0 | T |
| AI535895 | UNKNOWN | 17 | 0 | T |
| AI535919 | UNKNOWN | 18 | 0 | T |
| AI535930 | UNKNOWN | 18 | 0 | T |
| AI535932 | UNKNOWN | 18 | 0 | T |
| AI535963 | UNKNOWN | 61 | 0 | T |
| AI535967 | UNKNOWN | 17 | 0 | T |
| AI535978 | UNKNOWN | 28 | 0 | T |
| AI535980 | UNKNOWN | 24 | 0 | T |
| AI535980 | UNKNOWN | 14 | 508 | C |
| AI536060 | UNKNOWN | 30 | 0 | T |
| AI536062 | UNKNOWN | 56 | 0 | T |
| AI536064 | UNKNOWN | 16 | 0 | T |
| AI536099 | UNKNOWN | 12 | 227 | A |
| AI536557 | UNKNOWN | 103 | 0 | T |
| AI536557 | UNKNOWN | 20 | 115 | C |
| AI536558 | UNKNOWN | 30 | 0 | T |
| AI536563 | UNKNOWN | 55 | 0 | T |
| AI536563 | UNKNOWN | 12 | 87 | A |
| AI536563 | UNKNOWN | 12 | 145 | G |
| AI536574 | UNKNOWN | 80 | 0 | T |
| AI536574 | UNKNOWN | 18 | 323 | G |
| AI536574 | UNKNOWN | 16 | 302 | A |
| AI536574 | UNKNOWN | 13 | 130 | G |
| AI536601 | UNKNOWN | 67 | 0 | T |
| AI536601 | UNKNOWN | 14 | 226 | G |
| AI536603 | UNKNOWN | 14 | 394 | T |

TABLE 1-continued

| Genbank # | Region | # reps | Position | Unit sequence |
|---|---|---|---|---|
| AI536616 | UNKNOWN | 27 | 0 | T |
| AI536623 | UNKNOWN | 38 | 0 | T |
| AI536638 | UNKNOWN | 111 | 0 | T |
| AI536638 | UNKNOWN | 24 | 250 | A |
| AI536638 | UNKNOWN | 14 | 111 | A |
| AI536638 | UNKNOWN | 13 | 160 | G |
| AI536664 | UNKNOWN | 69 | 0 | T |
| AI536685 | UNKNOWN | 121 | 0 | T |
| AI536685 | UNKNOWN | 23 | 217 | C |
| AI536685 | UNKNOWN | 22 | 240 | A |
| AI536685 | UNKNOWN | 16 | 279 | G |
| AI536685 | UNKNOWN | 15 | 137 | A |
| AI536685 | UNKNOWN | 13 | 177 | C |
| AI536698 | UNKNOWN | 25 | 0 | T |
| AI536702 | UNKNOWN | 30 | 0 | T |
| AI536738 | UNKNOWN | 81 | 0 | T |
| AI536746 | UNKNOWN | 24 | 210 | T |
| AI536755 | UNKNOWN | 30 | 0 | T |
| AI536761 | UNKNOWN | 47 | 0 | T |
| AI536761 | UNKNOWN | 12 | 196 | A |
| AI536790 | UNKNOWN | 19 | 249 | T |
| AI536836 | UNKNOWN | 72 | 0 | T |
| AI536836 | UNKNOWN | 22 | 138 | C |
| AI536836 | UNKNOWN | 14 | 119 | G |
| AI536910 | UNKNOWN | 96 | 0 | T |
| AI536923 | UNKNOWN | 53 | 0 | T |
| AI536923 | UNKNOWN | 15 | 83 | A |
| AI536981 | UNKNOWN | 48 | 0 | T |
| AI537011 | UNKNOWN | 67 | 0 | T |
| AI537011 | UNKNOWN | 12 | 266 | G |
| AI537024 | UNKNOWN | 98 | 0 | T |
| AI537024 | UNKNOWN | 19 | 216 | G |
| AI537024 | UNKNOWN | 16 | 165 | C |
| AI537045 | UNKNOWN | 51 | 0 | T |
| AI537045 | UNKNOWN | 25 | 167 | A |
| AI537074 | UNKNOWN | 81 | 0 | T |
| AI537074 | UNKNOWN | 22 | 99 | A |
| AI537075 | UNKNOWN | 112 | 0 | T |
| AI537075 | UNKNOWN | 26 | 174 | C |
| AI537075 | UNKNOWN | 22 | 269 | G |
| AI537075 | UNKNOWN | 18 | 200 | A |
| AI537075 | UNKNOWN | 15 | 159 | G |
| AI537076 | UNKNOWN | 98 | 0 | T |
| AI537076 | UNKNOWN | 22 | 182 | G |
| AI537078 | UNKNOWN | 40 | 0 | T |
| AI537081 | UNKNOWN | 59 | 0 | T |
| AI537107 | UNKNOWN | 32 | 0 | T |
| AI537107 | UNKNOWN | 25 | 370 | A |
| AI537116 | UNKNOWN | 16 | 0 | T |
| AI537123 | UNKNOWN | 32 | 44 | T |
| AI537123 | UNKNOWN | 24 | 17 | T |
| AI537123 | UNKNOWN | 21 | 136 | G |
| AI537123 | UNKNOWN | 15 | 92 | A |
| AI537123 | UNKNOWN | 13 | 207 | C |
| AI537171 | UNKNOWN | 19 | 0 | T |
| AI537182 | UNKNOWN | 24 | 11 | T |
| AI537190 | UNKNOWN | 59 | 0 | T |
| AI537261 | UNKNOWN | 78 | 0 | T |
| AI537261 | UNKNOWN | 18 | 154 | C |
| AI537261 | UNKNOWN | 14 | 134 | A |
| AI537270 | UNKNOWN | 16 | 0 | T |
| AI537273 | UNKNOWN | 94 | 11 | T |
| AI537273 | UNKNOWN | 13 | 174 | A |
| AI537274 | UNKNOWN | 59 | 0 | T |
| AI537303 | UNKNOWN | 117 | 0 | T |
| AI537303 | UNKNOWN | 36 | 142 | A |
| AI537303 | UNKNOWN | 14 | 315 | G |
| AI537303 | UNKNOWN | 12 | 281 | C |
| AI537307 | UNKNOWN | 70 | 0 | T |
| AI537307 | UNKNOWN | 22 | 206 | A |
| AI537307 | UNKNOWN | 15 | 262 | C |
| AI537400 | UNKNOWN | 38 | 0 | T |
| AI537408 | UNKNOWN | 62 | 0 | T |
| AI537408 | UNKNOWN | 12 | 125 | A |
| AI537439 | UNKNOWN | 48 | 0 | T |
| AI537509 | UNKNOWN | 95 | 0 | T |
| AI537509 | UNKNOWN | 16 | 265 | A |

TABLE 1-continued

| Genbank # | Region | # reps | Position | Unit sequence |
|---|---|---|---|---|
| AI537509 | UNKNOWN | 14 | 161 | C |
| AI537509 | UNKNOWN | 12 | 252 | G |
| AI537510 | UNKNOWN | 49 | 0 | T |
| AI537516 | UNKNOWN | 54 | 0 | T |
| AI537617 | UNKNOWN | 93 | 0 | T |
| AI537617 | UNKNOWN | 23 | 154 | C |
| AI537617 | UNKNOWN | 12 | 119 | A |
| AI537643 | UNKNOWN | 58 | 0 | T |
| AI537643 | UNKNOWN | 12 | 111 | A |
| AI537677 | UNKNOWN | 109 | 11 | T |
| AI537730 | UNKNOWN | 50 | 0 | T |
| AI537743 | UNKNOWN | 27 | 0 | T |
| AI537804 | UNKNOWN | 27 | 0 | T |
| AI537809 | UNKNOWN | 47 | 30 | T |
| AI537809 | UNKNOWN | 21 | 208 | C |
| AI537809 | UNKNOWN | 20 | 0 | T |
| AI537809 | UNKNOWN | 19 | 167 | G |
| AI537809 | UNKNOWN | 12 | 192 | C |
| AI537817 | UNKNOWN | 3.8 | 12 | TTTTC |
| AI537837 | UNKNOWN | 69 | 0 | T |
| AI537863 | UNKNOWN | 59 | 0 | T |
| AI537863 | UNKNOWN | 15 | 146 | C |
| AI537883 | UNKNOWN | 50 | 0 | T |
| AI537889 | UNKNOWN | 3.8 | 320 | CTTTT |
| AI537889 | UNKNOWN | 58 | 0 | T |
| AI537889 | UNKNOWN | 15 | 164 | A |
| AI537941 | UNKNOWN | 79 | 0 | T |
| AI537959 | UNKNOWN | 44 | 0 | T |
| AI537960 | UNKNOWN | 84 | 0 | T |
| AI537960 | UNKNOWN | 16 | 147 | G |
| AI537967 | UNKNOWN | 60 | 0 | T |
| AI537989 | UNKNOWN | 81 | 0 | T |
| AI537989 | UNKNOWN | 19 | 304 | G |
| AI537989 | UNKNOWN | 12 | 102 | A |
| AI537991 | UNKNOWN | 88 | 0 | T |
| AI537991 | UNKNOWN | 12 | 167 | G |
| AI538008 | UNKNOWN | 75 | 0 | T |
| AI538008 | UNKNOWN | 13 | 292 | A |
| AI538055 | UNKNOWN | 73 | 0 | T |
| AI538055 | UNKNOWN | 19 | 136 | A |
| AI538070 | UNKNOWN | 3.6 | 107 | AAACA |
| AI538070 | UNKNOWN | 27 | 0 | T |
| AI538073 | UNKNOWN | 46 | 0 | T |
| AI538073 | UNKNOWN | 20 | 154 | A |
| AI538085 | UNKNOWN | 99 | 0 | T |
| AI538085 | UNKNOWN | 21 | 157 | G |
| AI538085 | UNKNOWN | 17 | 135 | A |
| AI538116 | UNKNOWN | 94 | 0 | T |
| AI538116 | UNKNOWN | 14 | 168 | G |
| AI538116 | UNKNOWN | 14 | 188 | C |
| AI538124 | UNKNOWN | 22 | 0 | T |
| AI538183 | UNKNOWN | 21 | 205 | A |
| AI538203 | UNKNOWN | 45 | 0 | T |
| AI538218 | UNKNOWN | 98 | 0 | T |
| AI538218 | UNKNOWN | 15 | 165 | C |
| AI538218 | UNKNOWN | 15 | 250 | G |
| AI538247 | UNKNOWN | 63 | 0 | T |
| AI538259 | UNKNOWN | 109 | 0 | T |
| AI538259 | UNKNOWN | 15 | 287 | G |
| AI538259 | UNKNOWN | 14 | 172 | G |
| AI538259 | UNKNOWN | 13 | 200 | C |
| AI538259 | UNKNOWN | 12 | 109 | A |
| AI538270 | UNKNOWN | 77 | 0 | T |
| AI538270 | UNKNOWN | 13 | 147 | A |
| AI538270 | UNKNOWN | 12 | 205 | G |
| AI538272 | UNKNOWN | 13 | 0 | T |
| AI538289 | UNKNOWN | 50 | 0 | T |
| AI538298 | UNKNOWN | 47 | 0 | T |
| AI538307 | UNKNOWN | 15 | 4 | T |
| AI538336 | UNKNOWN | 27 | 0 | T |
| AI538342 | UNKNOWN | 84 | 0 | T |
| AI538374 | UNKNOWN | 40 | 0 | T |
| AI538386 | UNKNOWN | 24 | 90 | T |
| AI538386 | UNKNOWN | 15 | 224 | C |
| AI538386 | UNKNOWN | 14 | 120 | A |
| AI538408 | UNKNOWN | 49 | 0 | T |
| AI538420 | UNKNOWN | 41 | 0 | T |

TABLE 1-continued

| Genbank # | Region | # reps | Position | Unit sequence |
|---|---|---|---|---|
| AI538444 | UNKNOWN | 13 | 166 | A |
| AI538507 | UNKNOWN | 7.33 | 204 | GGC |
| AI538575 | UNKNOWN | 68 | 1 | T |
| AI538575 | UNKNOWN | 12 | 105 | A |
| AI538612 | UNKNOWN | 35 | 17 | T |
| AI538612 | UNKNOWN | 14 | 205 | A |
| AI538612 | UNKNOWN | 12 | 65 | A |
| AI538637 | UNKNOWN | 62 | 0 | T |
| AI538647 | UNKNOWN | 68 | 0 | T |
| AI538647 | UNKNOWN | 12 | 152 | C |
| AI538657 | UNKNOWN | 24 | 0 | T |
| AI538657 | UNKNOWN | 17 | 47 | A |
| AI538686 | UNKNOWN | 62 | 0 | T |
| AI538686 | UNKNOWN | 17 | 391 | G |
| AI538716 | UNKNOWN | 130 | 0 | T |
| AI538716 | UNKNOWN | 28 | 157 | A |
| AI538716 | UNKNOWN | 13 | 247 | C |
| AI538733 | UNKNOWN | 51 | 0 | T |
| AI538764 | UNKNOWN | 77 | 0 | T |
| AI538769 | UNKNOWN | 43 | 0 | T |
| AI538790 | UNKNOWN | 112 | 0 | T |
| AI538790 | UNKNOWN | 19 | 198 | G |
| AI538790 | UNKNOWN | 16 | 180 | A |
| AI538790 | UNKNOWN | 13 | 244 | C |
| AI538790 | UNKNOWN | 12 | 139 | A |
| AI538805 | UNKNOWN | 52 | 0 | T |
| AI538817 | UNKNOWN | 88 | 0 | T |
| AI538817 | UNKNOWN | 12 | 418 | G |
| AI538829 | UNKNOWN | 111 | 0 | T |
| AI538829 | UNKNOWN | 16 | 194 | C |
| AI538829 | UNKNOWN | 14 | 180 | G |
| AI538829 | UNKNOWN | 13 | 239 | A |
| AI538829 | UNKNOWN | 12 | 139 | G |
| AI538870 | UNKNOWN | 36 | 11 | T |
| AI538895 | UNKNOWN | 28 | 0 | T |
| AI538908 | UNKNOWN | 52 | 0 | T |
| AI538908 | UNKNOWN | 18 | 326 | A |
| AI538924 | UNKNOWN | 37 | 0 | T |
| AI538938 | UNKNOWN | 92 | 0 | T |
| AI538938 | UNKNOWN | 14 | 216 | G |
| AI538980 | UNKNOWN | 72 | 0 | T |
| AI539013 | UNKNOWN | 56 | 0 | T |
| AI539013 | UNKNOWN | 12 | 202 | A |
| AI539028 | UNKNOWN | 88 | 0 | T |
| AI539028 | UNKNOWN | 12 | 210 | G |
| AI539029 | UNKNOWN | 28 | 0 | T |
| AI539035 | UNKNOWN | 12 | 0 | T |
| AI539042 | UNKNOWN | 67 | 0 | T |
| AI539068 | UNKNOWN | 42 | 0 | T |
| AI539071 | UNKNOWN | 79 | 0 | T |
| AI539080 | UNKNOWN | 55 | 0 | T |
| AI539080 | UNKNOWN | 15 | 145 | G |
| AI539089 | UNKNOWN | 64 | 0 | T |
| AI539098 | UNKNOWN | 46 | 0 | T |
| AI539106 | UNKNOWN | 74 | 0 | T |
| AI539106 | UNKNOWN | 12 | 96 | A |
| AI539111 | UNKNOWN | 70 | 0 | T |
| AI539153 | UNKNOWN | 115 | 0 | T |
| AI539153 | UNKNOWN | 14 | 133 | A |
| AI539170 | UNKNOWN | 42 | 0 | T |
| AI539188 | UNKNOWN | 16 | 188 | T |
| AI539219 | UNKNOWN | 51 | 0 | T |
| AI539227 | UNKNOWN | 21.5 | 395 | CA |
| AI539227 | UNKNOWN | 11 | 374 | TC |
| AI539227 | UNKNOWN | 22 | 0 | T |
| AI539238 | UNKNOWN | 102 | 0 | T |
| AI539238 | UNKNOWN | 18 | 125 | C |
| AI539238 | UNKNOWN | 16 | 230 | G |
| AI539238 | UNKNOWN | 13 | 164 | A |
| AI539362 | UNKNOWN | 16 | 0 | T |
| AI539417 | UNKNOWN | 6.5 | 64 | AC |
| AI539417 | UNKNOWN | 12 | 0 | T |
| AI539426 | UNKNOWN | 15 | 68 | A |
| AI539442 | UNKNOWN | 26 | 0 | T |
| AI539443 | UNKNOWN | 18.5 | 73 | GT |
| AI539444 | UNKNOWN | 13 | 196 | T |
| AI539462 | UNKNOWN | 58 | 0 | T |

TABLE 1-continued

| Genbank # | Region | # reps | Position | Unit sequence |
|---|---|---|---|---|
| AI539462 | UNKNOWN | 16 | 286 | G |
| AI539474 | UNKNOWN | 46 | 0 | T |
| AI539531 | UNKNOWN | 23 | 0 | T |
| AI539541 | UNKNOWN | 49 | 0 | T |
| AI539545 | UNKNOWN | 51 | 0 | T |
| AI539560 | UNKNOWN | 63 | 0 | T |
| AI539562 | UNKNOWN | 97 | 0 | T |
| AI539562 | UNKNOWN | 15 | 161 | C |
| AI539562 | UNKNOWN | 12 | 305 | G |
| AI539578 | UNKNOWN | 65 | 0 | T |
| AI539578 | UNKNOWN | 18 | 103 | A |
| AI539578 | UNKNOWN | 12 | 87 | A |
| AI539589 | UNKNOWN | 62 | 0 | T |
| AI539632 | UNKNOWN | 88 | 11 | T |
| AI539654 | UNKNOWN | 57 | 0 | T |
| AI539661 | UNKNOWN | 52 | 0 | T |
| AI539667 | UNKNOWN | 66 | 0 | T |
| AI539667 | UNKNOWN | 20 | 261 | C |
| AI539667 | UNKNOWN | 17 | 146 | C |
| AI539667 | UNKNOWN | 12 | 249 | A |
| AI539687 | UNKNOWN | 97 | 0 | T |
| AI539687 | UNKNOWN | 15 | 216 | G |
| AI539687 | UNKNOWN | 14 | 165 | C |
| AI539687 | UNKNOWN | 13 | 255 | A |
| AI539687 | UNKNOWN | 12 | 107 | A |
| AI539709 | UNKNOWN | 16 | 11 | T |
| AI539711 | UNKNOWN | 105 | 0 | T |
| AI539711 | UNKNOWN | 20 | 183 | A |
| AI539711 | UNKNOWN | 16 | 167 | C |
| Ar539723 | UNKNOWN | 57 | 0 | T |
| AI539766 | UNKNOWN | 66 | 0 | T |
| AI539771 | UNKNOWN | 118 | 11 | T |
| AI539780 | UNKNOWN | 118 | 0 | T |
| AI539780 | UNKNOWN | 13 | 176 | G |
| AI539780 | UNKNOWN | 12 | 118 | A |
| AI539780 | UNKNOWN | 12 | 150 | G |
| AI539780 | UNKNOWN | 12 | 196 | C |
| AI539783 | UNKNOWN | 15 | 11 | T |
| AI539788 | UNKNOWN | 45 | 0 | T |
| AI539808 | UNKNOWN | 98 | 0 | T |
| AI539808 | UNKNOWN | 23 | 156 | A |
| AI539808 | UNKNOWN | 13 | 142 | G |
| AI539829 | UNKNOWN | 85 | 0 | T |
| AI539829 | UNKNOWN | 13 | 163 | G |
| AI539849 | UNKNOWN | 44 | 11 | T |
| AI540178 | UNKNOWN | 70 | 0 | T |
| AI540178 | UNKNOWN | 13 | 281 | A |
| AI540178 | UNKNOWN | 12 | 294 | C |
| AI540193 | UNKNOWN | 15 | 31 | T |
| AI540199 | UNKNOWN | 19 | 0 | T |
| AI540204 | UNKNOWN | 13 | 52 | A |
| AI540238 | UNKNOWN | 21 | 0 | T |
| AI540239 | UNKNOWN | 29 | 0 | T |
| AI540321 | UNKNOWN | 20 | 0 | T |
| AI540321 | UNKNOWN | 13 | 334 | A |
| AI540350 | UNKNOWN | 50 | 0 | T |
| AI540350 | UNKNOWN | 20 | 218 | A |
| AI540354 | UNKNOWN | 47 | 0 | T |
| AI540382 | UNKNOWN | 79 | 0 | T |
| AI540382 | UNKNOWN | 22 | 228 | A |
| AI540382 | UNKNOWN | 16 | 251 | C |
| AI540382 | UNKNOWN | 15 | 103 | G |
| AI540400 | UNKNOWN | 26 | 0 | T |
| AI540474 | UNKNOWN | 66 | 0 | T |
| AI540474 | UNKNOWN | 15 | 305 | G |
| AI540555 | UNKNOWN | 18 | 0 | T |
| AI540587 | UNKNOWN | 42 | 0 | T |
| AI540597 | UNKNOWN | 16 | 0 | T |
| AI540606 | UNKNOWN | 66 | 0 | T |
| AI540608 | UNKNOWN | 13 | 0 | T |
| AI540633 | UNKNOWN | 95 | 0 | T |
| AI540633 | UNKNOWN | 12 | 168 | G |
| AI540633 | UNKNOWN | 12 | 226 | A |
| AI540654 | UNKNOWN | 12 | 0 | T |
| AI540674 | UNKNOWN | 67 | 0 | T |
| AI540676 | UNKNOWN | 65 | 0 | T |
| AI540676 | UNKNOWN | 17 | 141 | C |

TABLE 1-continued

| Genbank # | Region | # reps | Position | Unit sequence |
|---|---|---|---|---|
| AI540752 | UNKNOWN | 44 | 0 | T |
| AI540754 | UNKNOWN | 72 | 0 | T |
| AI540754 | UNKNOWN | 21 | 129 | G |
| AI540759 | UNKNOWN | 66 | 0 | T |
| AI540761 | UNKNOWN | 16 | 0 | T |
| AI540784 | UNKNOWN | 61 | 0 | T |
| AI540784 | UNKNOWN | 15 | 189 | A |
| AI540789 | UNKNOWN | 74 | 0 | T |
| AI540823 | UNKNOWN | 82 | 0 | T |
| AI540823 | UNKNOWN | 12 | 214 | A |
| AI540831 | UNKNOWN | 48 | 0 | T |
| AI540832 | UNKNOWN | 122 | 0 | T |
| AI540832 | UNKNOWN | 24 | 222 | G |
| AI540832 | UNKNOWN | 17 | 148 | C |
| AI540832 | UNKNOWN | 14 | 283 | A |
| AI540832 | UNKNOWN | 12 | 246 | A |
| AI540845 | UNKNOWN | 61 | 0 | T |
| AI540845 | UNKNOWN | 28 | 135 | G |
| AI540845 | UNKNOWN | 13 | 180 | C |
| AI540850 | UNKNOWN | 89 | 0 | T |
| AI540850 | UNKNOWN | 18 | 302 | C |
| AI540850 | UNKNOWN | 14 | 221 | C |
| AI540850 | UNKNOWN | 12 | 154 | C |
| AI540921 | UNKNOWN | 12 | 9 | T |
| AI541250 | UNKNOWN | 46 | 26 | T |
| AI541429 | UNKNOWN | 19 | 28 | T |
| AI546877 | UNKNOWN | 13 | 466 | A |
| AI546908 | UNKNOWN | 12 | 500 | A |
| AI547017 | UNKNOWN | 12 | 84 | A |
| AI547110 | UNKNOWN | 19 | 1 | T |
| AI547137 | UNKNOWN | 18 | 183 | A |
| AI553645 | UNKNOWN | 68 | 0 | T |
| AI553645 | UNKNOWN | 12 | 107 | A |
| AI553724 | UNKNOWN | 5.75 | 402 | TTTC |
| AI553724 | UNKNOWN | 18 | 1 | T |
| AI553743 | UNKNOWN | 21 | 4 | T |
| AI553754 | UNKNOWN | 16 | 257 | A |
| AI553757 | UNKNOWN | 17 | 1 | T |
| AI553805 | UNKNOWN | 21 | 0 | T |
| AI553825 | UNKNOWN | 24 | 0 | T |
| AI553847 | UNKNOWN | 45 | 0 | T |
| AI553868 | UNKNOWN | 31 | 0 | T |
| AI553868 | UNKNOWN | 12 | 135 | G |
| AI553880 | UNKNOWN | 3.8 | 265 | TTTTC |
| AI553880 | UNKNOWN | 25 | 0 | T |
| AI553926 | UNKNOWN | 52 | 0 | T |
| AI553926 | UNKNOWN | 12 | 222 | A |
| AI553955 | UNKNOWN | 12 | 580 | T |
| AI554000 | UNKNOWN | 16 | 0 | T |
| AI554003 | UNKNOWN | 23 | 0 | T |
| AI554050 | UNKNOWN | 22 | 0 | T |
| AI554060 | UNKNOWN | 22 | 0 | T |
| AI554072 | UNKNOWN | 26 | 0 | T |
| AI554086 | UNKNOWN | 14 | 0 | T |
| AI554094 | UNKNOWN | 14 | 0 | T |
| AI554154 | UNKNOWN | 16 | 0 | T |
| AI554169 | UNKNOWN | 14 | 336 | T |
| AI554177 | UNKNOWN | 13 | 330 | A |
| AI554186 | UNKNOWN | 101 | 0 | T |
| AI554186 | UNKNOWN | 21 | 132 | C |
| AI554186 | UNKNOWN | 16 | 352 | A |
| AI554218 | UNKNOWN | 91 | 0 | T |
| AI554218 | UNKNOWN | 14 | 128 | A |
| AI554218 | UNKNOWN | 13 | 91 | G |
| AI554240 | UNKNOWN | 42 | 0 | T |
| AI554249 | UNKNOWN | 44 | 0 | T |
| AI554283 | UNKNOWN | 51 | 0 | T |
| AI554283 | UNKNOWN | 15 | 273 | A |
| AI554286 | UNKNOWN | 64 | 0 | T |
| AI554286 | UNKNOWN | 23 | 175 | G |
| AI554301 | UNKNOWN | 45 | 0 | T |
| AI554320 | UNKNOWN | 31 | 0 | T |
| AI554329 | UNKNOWN | 38 | 0 | T |
| AI554335 | UNKNOWN | 66 | 0 | T |
| AI554335 | UNKNOWN | 18 | 218 | G |
| AI554343 | UNKNOWN | 71 | 0 | T |
| AI554344 | UNKNOWN | 95 | 0 | T |

TABLE 1-continued

| Genbank # | Region | # reps | Position | Unit sequence |
|---|---|---|---|---|
| AI554344 | UNKNOWN | 13 | 151 | A |
| AI554375 | UNKNOWN | 13 | 0 | T |
| AI554386 | UNKNOWN | 41 | 0 | T |
| AI554402 | UNKNOWN | 48 | 0 | T |
| AI554404 | UNKNOWN | 14 | 234 | A |
| AI554411 | UNKNOWN | 58 | 0 | T |
| AI554417 | UNKNOWN | 38 | 0 | T |
| AI554417 | UNKNOWN | 12 | 236 | G |
| AI554425 | UNKNOWN | 90 | 0 | T |
| AI554427 | UNKNOWN | 109 | 1 | T |
| AI554427 | UNKNOWN | 13 | 229 | A |
| AI554428 | UNKNOWN | 49 | 0 | T |
| AI554439 | UNKNOWN | 34 | 0 | T |
| AI554444 | UNKNOWN | 58 | 0 | T |
| AI554459 | UNKNOWN | 26 | 0 | T |
| AI554484 | UNKNOWN | 113 | 0 | T |
| AI554484 | UNKNOWN | 18 | 161 | G |
| AI554485 | UNKNOWN | 91 | 0 | T |
| AI554485 | UNKNOWN | 19 | 133 | G |
| AI554485 | UNKNOWN | 14 | 333 | C |
| AI554486 | UNKNOWN | 51 | 0 | T |
| AI554486 | UNKNOWN | 14 | 183 | A |
| AI554487 | UNKNOWN | 71 | 0 | T |
| AI554500 | UNKNOWN | 15 | 0 | T |
| AI554513 | UNKNOWN | 29 | 0 | T |
| AI554516 | UNKNOWN | 64 | 0 | T |
| AI554537 | UNKNOWN | 24 | 0 | T |
| AI554537 | UNKNOWN | 12 | 229 | A |
| AI554544 | UNKNOWN | 71 | 0 | T |
| AI554544 | UNKNOWN | 14 | 157 | G |
| AI554660 | UNKNOWN | 12 | 151 | T |
| AI554670 | UNKNOWN | 41 | 0 | T |
| AI554726 | UNKNOWN | 22 | 376 | T |
| AI554733 | UNKNOWN | 12 | 0 | T |
| AI554738 | UNKNOWN | 19 | 0 | T |
| AI554758 | UNKNOWN | 23 | 129 | T |
| AI554758 | UNKNOWN | 15 | 280 | A |
| AI554765 | UNKNOWN | 28 | 0 | T |
| AI554809 | UNKNOWN | 21 | 0 | T |
| AI554818 | UNKNOWN | 112 | 0 | T |
| AI554818 | UNKNOWN | 12 | 337 | A |
| AI554821 | UNKNOWN | 88 | 10 | T |
| AI554821 | UNKNOWN | 22 | 131 | A |
| AI554849 | UNKNOWN | 38 | 0 | T |
| AI554849 | UNKNOWN | 14 | 200 | G |
| AI554902 | UNKNOWN | 13 | 0 | T |
| AI554915 | UNKNOWN | 19 | 75 | A |
| AI554926 | UNKNOWN | 6.5 | 212 | TG |
| AI556963 | UNKNOWN | 2.5 | 840 | TTTTTNNCNN (SEQ ID NO:124) |
| AI557056 | UNKNOWN | 14 | 732 | A |
| AI557066 | UNKNOWN | 18 | 27 | T |
| AI557082 | UNKNOWN | 25 | 354 | A |
| AI557082 | UNKNOWN | 20 | 333 | A |
| AI557083 | UNKNOWN | 22 | 2 | T |
| AI557104 | UNKNOWN | 65 | 7 | T |
| AI557106 | UNKNOWN | 13 | 501 | A |
| AI557114 | UNKNOWN | 14 | 1 | T |
| AI557212 | UNKNOWN | 12 | 645 | A |
| AI557215 | UNKNOWN | 12 | 571 | A |
| AI557218 | UNKNOWN | 22 | 629 | A |
| AI557250 | UNKNOWN | 12 | 621 | A |
| AI557285 | UNKNOWN | 21 | 619 | A |
| AI557290 | UNKNOWN | 12 | 549 | A |
| AI557306 | UNKNOWN | 2.5 | 734 | CCCAGGTGGGGG (SEQ ID NO:125) |
| AI557311 | UNKNOWN | 14 | 759 | A |
| AI557395 | UNKNOWN | 15 | 43 | T |
| AI557431 | UNKNOWN | 18 | 11 | T |
| AI557431 | UNKNOWN | 14 | 183 | A |
| AI557533 | UNKNOWN | 28 | 382 | A |
| AI557564 | UNKNOWN | 20 | 559 | A |
| AI557569 | UNKNOWN | 18 | 13 | T |
| AI557570 | UNKNOWN | 14 | 525 | A |
| AI557572 | UNKNOWN | 13 | 715 | A |
| AI557583 | UNKNOWN | 17 | 209 | A |
| AI557584 | UNKNOWN | 17 | 666 | A |
| AI557622 | UNKNOWN | 47 | 2 | T |
| AI557691 | UNKNOWN | 19 | 43 | T |

TABLE 1-continued

| Genbank # | Region | # reps | Position | Unit sequence |
|---|---|---|---|---|
| AI557691 | UNKNOWN | 12 | 30 | T |
| AI559096 | UNKNOWN | 15 | 0 | T |
| AI559149 | UNKNOWN | 44 | 0 | T |
| AI559149 | UNKNOWN | 16 | 124 | A |
| AI559152 | UNKNOWN | 28 | 0 | T |
| AI559162 | UNKNOWN | 46 | 0 | T |
| AI559177 | UNKNOWN | 15 | 0 | T |
| AI559179 | UNKNOWN | 13 | 0 | T |
| AI559218 | UNKNOWN | 15 | 295 | T |
| AI559252 | UNKNOWN | 15 | 4 | T |
| AI559287 | UNKNOWN | 75 | 0 | T |
| AI559296 | UNKNOWN | 103 | 0 | T |
| AI559296 | UNKNOWN | 18 | 140 | G |
| AI559296 | UNKNOWN | 14 | 103 | A |
| AI559296 | UNKNOWN | 12 | 170 | C |
| AI559312 | UNKNOWN | 102 | 0 | T |
| AI559312 | UNKNOWN | 22 | 203 | G |
| AI559312 | UNKNOWN | 17 | 181 | A |
| AI559312 | UNKNOWN | 13 | 162 | C |
| AI559317 | UNKNOWN | 61 | 0 | T |
| AI559317 | UNKNOWN | 20 | 351 | G |
| AI559412 | UNKNOWN | 43 | 0 | T |
| AI559479 | UNKNOWN | 55 | 0 | T |
| AI559479 | UNKNOWN | 17 | 223 | A |
| AI559479 | UNKNOWN | 12 | 115 | A |
| AI559484 | UNKNOWN | 74 | 0 | T |
| AI559484 | UNKNOWN | 13 | 99 | A |
| AI559524 | UNKNOWN | 65 | 0 | T |
| AI559524 | UNKNOWN | 16 | 82 | A |
| AI559531 | UNKNOWN | 74 | 0 | T |
| AI559531 | UNKNOWN | 22 | 200 | G |
| AI559531 | UNKNOWN | 12 | 118 | G |
| AI559555 | UNKNOWN | 75 | 0 | T |
| AI559555 | UNKNOWN | 20 | 272 | A |
| AI559555 | UNKNOWN | 15 | 323 | G |
| AI559555 | UNKNOWN | 14 | 309 | C |
| AI559555 | UNKNOWN | 12 | 141 | C |
| AI559569 | UNKNOWN | 49 | 0 | T |
| AI559596 | UNKNOWN | 62 | 0 | T |
| AI559596 | UNKNOWN | 14 | 151 | C |
| AI559599 | UNKNOWN | 74 | 0 | T |
| AI559599 | UNKNOWN | 12 | 98 | C |
| AI559611 | UNKNOWN | 68 | 0 | T |
| AI559619 | UNKNOWN | 75 | 0 | T |
| AI559619 | UNKNOWN | 14 | 78 | A |
| AI559619 | UNKNOWN | 13 | 176 | G |
| AI559624 | UNKNOWN | 42 | 0 | T |
| AI559625 | UNKNOWN | 14 | 391 | A |
| AI559632 | UNKNOWN | 82 | 0 | T |
| AI559632 | UNKNOWN | 18 | 168 | A |
| AI559632 | UNKNOWN | 14 | 104 | A |
| AI559667 | UNKNOWN | 51 | 0 | T |
| AI559667 | UNKNOWN | 13 | 85 | C |
| AI559718 | UNKNOWN | 18 | 0 | T |
| AI559737 | UNKNOWN | 93 | 0 | T |
| AI559737 | UNKNOWN | 24 | 304 | A |
| AI559737 | UNKNOWN | 15 | 266 | C |
| AI559737 | UNKNOWN | 12 | 219 | C |
| AI559752 | UNKNOWN | 60 | 0 | T |
| AI559763 | UNKNOWN | 23 | 0 | T |
| AI559782 | UNKNOWN | 54 | 0 | T |
| AI559782 | UNKNOWN | 12 | 183 | A |
| AI559793 | UNKNOWN | 29 | 0 | T |
| AI559852 | UNKNOWN | 21 | 0 | T |
| AI559859 | UNKNOWN | 12 | 217 | A |
| AI559903 | UNKNOWN | 22 | 64 | T |
| AI559903 | UNKNOWN | 21 | 0 | T |
| AI559996 | UNKNOWN | 6.5 | 45 | AG |
| AI560006 | UNKNOWN | 36 | 0 | T |
| AI560006 | UNKNOWN | 24 | 162 | A |
| AI560010 | UNKNOWN | 83 | 0 | T |
| AI560011 | UNKNOWN | 60 | 0 | T |
| AI560011 | UNKNOWN | 16 | 276 | G |
| AI560030 | UNKNOWN | 90 | 0 | T |
| AI560030 | UNKNOWN | 16 | 148 | A |
| AI560030 | UNKNOWN | 15 | 133 | G |
| AI560052 | UNKNOWN | 76 | 0 | T |

TABLE 1-continued

| Genbank # | Region | # reps | Position | Unit sequence |
|---|---|---|---|---|
| AI560052 | UNKNOWN | 14 | 132 | A |
| AI560064 | UNKNOWN | 13 | 456 | T |
| AI560096 | UNKNOWN | 72 | 0 | T |
| AI560099 | UNKNOWN | 108 | 0 | T |
| AI560099 | UNKNOWN | 17 | 121 | A |
| AI560099 | UNKNOWN | 13 | 216 | C |
| AI560110 | UNKNOWN | 21 | 9 | T |
| AI560147 | UNKNOWN | 14 | 0 | T |
| AI560159 | UNKNOWN | 12 | 555 | A |
| AI560160 | UNKNOWN | 12 | 0 | T |
| AI560171 | UNKNOWN | 39 | 0 | T |
| AI560171 | UNKNOWN | 13 | 124 | A |
| AI560183 | UNKNOWN | 41 | 0 | T |
| AI560184 | UNKNOWN | 80 | 0 | T |
| AI560184 | UNKNOWN | 12 | 230 | G |
| AI560184 | UNKNOWN | 12 | 242 | A |
| AI560191 | UNKNOWN | 15 | 0 | T |
| AI560193 | UNKNOWN | 28 | 0 | T |
| AI560227 | UNKNOWN | 60 | 0 | T |
| AI560242 | UNKNOWN | 16 | 0 | T |
| AI560298 | UNKNOWN | 46 | 0 | T |
| AI560391 | UNKNOWN | 4 | 325 | AGGCCG |
| AI560491 | UNKNOWN | 28 | 0 | T |
| AI560495 | UNKNOWN | 15 | 0 | T |
| AI560514 | UNKNOWN | 43 | 0 | T |
| AI560536 | UNKNOWN | 50 | 0 | T |
| AI560545 | UNKNOWN | 60 | 0 | T |
| AI560545 | UNKNOWN | 12 | 87 | A |
| AI560547 | UNKNOWN | 28 | 121 | A |
| AI560547 | UNKNOWN | 21 | 93 | T |
| AI560547 | UNKNOWN | 17 | 164 | C |
| AI560625 | UNKNOWN | 85 | 0 | T |
| AI560625 | UNKNOWN | 14 | 311 | G |
| AI560625 | UNKNOWN | 12 | 140 | C |
| AI560651 | UNKNOWN | 41 | 0 | T |
| AI560655 | UNKNOWN | 36 | 0 | T |
| AI560656 | UNKNOWN | 24 | 0 | T |
| AI560679 | UNKNOWN | 57 | 0 | T |
| AI560683 | UNKNOWN | 77 | 0 | T |
| AI560683 | UNKNOWN | 18 | 118 | A |
| AI560683 | UNKNOWN | 12 | 183 | C |
| AI560712 | UNKNOWN | 45 | 0 | T |
| AI560722 | UNKNOWN | 55 | 0 | T |
| AI560777 | UNKNOWN | 58 | 0 | T |
| AI560806 | UNKNOWN | 56 | 0 | T |
| AI560826 | UNKNOWN | 15 | 0 | T |
| AI560833 | UNKNOWN | 55 | 0 | T |
| AI560844 | UNKNOWN | 73 | 0 | T |
| AI560844 | UNKNOWN | 17 | 274 | G |
| AI560845 | UNKNOWN | 27 | 0 | T |
| AI560845 | UNKNOWN | 15 | 226 | C |
| AI560845 | UNKNOWN | 12 | 180 | A |
| AI560854 | UNKNOWN | 12 | 0 | T |
| AI560866 | UNKNOWN | 12 | 0 | T |
| AI560873 | UNKNOWN | 55 | 0 | T |
| AI560873 | UNKNOWN | 13 | 110 | A |
| AI560954 | UNKNOWN | 48 | 0 | T |
| AI560954 | UNKNOWN | 12 | 124 | A |
| AI560968 | UNKNOWN | 13 | 0 | T |
| AI561032 | UNKNOWN | 12 | 0 | T |
| AI561038 | UNKNOWN | 78 | 0 | T |
| AI561038 | UNKNOWN | 18 | 225 | C |
| AI561038 | UNKNOWN | 13 | 157 | A |
| AI561038 | UNKNOWN | 12 | 345 | G |
| AI561052 | UNKNOWN | 47 | 0 | T |
| AI561056 | UNKNOWN | 14 | 0 | T |
| AI561070 | UNKNOWN | 19 | 141 | T |
| AI561087 | UNKNOWN | 63 | 0 | T |
| AI561119 | UNKNOWN | 22 | 0 | T |
| AI561132 | UNKNOWN | 84 | 0 | T |
| AI561132 | UNKNOWN | 14 | 198 | G |
| AI561147 | UNKNOWN | 40 | 11 | T |
| AI561149 | UNKNOWN | 18 | 0 | T |
| AI561153 | UNKNOWN | 21 | 11 | T |
| AI561167 | UNKNOWN | 32 | 11 | T |
| AI561192 | UNKNOWN | 16 | 11 | T |
| AI561197 | UNKNOWN | 31 | 0 | T |

TABLE 1-continued

| Genbank # | Region | # reps | Position | Unit sequence |
|---|---|---|---|---|
| AI561197 | UNKNOWN | 12 | 93 | A |
| AI561199 | UNKNOWN | 61 | 0 | T |
| AI561228 | UNKNOWN | 62 | 0 | T |
| AI561231 | UNKNOWN | 84 | 0 | T |
| AI561231 | UNKNOWN | 15 | 225 | G |
| AI561290 | UNKNOWN | 14 | 0 | T |
| AI561297 | UNKNOWN | 40 | 0 | T |
| AI561299 | UNKNOWN | 104 | 0 | T |
| AI561356 | UNKNOWN | 63 | 0 | T |
| AI561356 | UNKNOWN | 21 | 132 | A |
| AI563905 | UNKNOWN | 5 | 10 | GCCTGAGT |
| AI564022 | UNKNOWN | 21 | 33 | T |
| AI564022 | UNKNOWN | 12 | 3 | T |
| AI564075 | UNKNOWN | 14 | 181 | T |
| AI564132 | UNKNOWN | 21 | 0 | T |
| AI564135 | UNKNOWN | 20 | 0 | T |
| AI564138 | UNKNOWN | 25 | 0 | T |
| AI564144 | UNKNOWN | 9 | 101 | AC |
| AI564144 | UNKNOWN | 54 | 0 | T |
| AI564144 | UNKNOWN | 18 | 218 | A |
| AI564160 | UNKNOWN | 48 | 0 | T |
| AI564166 | UNKNOWN | 74 | 0 | T |
| AI564166 | UNKNOWN | 15 | 161 | G |
| AI564166 | UNKNOWN | 13 | 122 | G |
| AI564170 | UNKNOWN | 108 | 0 | T |
| AI564170 | UNKNOWN | 21 | 198 | A |
| AI564170 | UNKNOWN | 14 | 351 | C |
| AI564170 | UNKNOWN | 13 | 181 | G |
| AI564171 | UNKNOWN | 53 | 0 | T |
| AI564174 | UNKNOWN | 27 | 0 | T |
| AI564186 | UNKNOWN | 66 | 0 | T |
| AI564192 | UNKNOWN | 31 | 0 | T |
| AI564204 | UNKNOWN | 27 | 23 | T |
| AI564204 | UNKNOWN | 22 | 0 | T |
| AI564234 | UNKNOWN | 71 | 0 | T |
| AI564234 | UNKNOWN | 13 | 334 | G |
| AI564245 | UNKNOWN | 47 | 0 | T |
| AI564245 | UNKNOWN | 12 | 262 | A |
| AI564247 | UNKNOWN | 102 | 0 | T |
| AI564247 | UNKNOWN | 12 | 170 | C |
| AI564258 | UNKNOWN | 32 | 0 | T |
| AI564258 | UNKNOWN | 18 | 195 | A |
| AI564290 | UNKNOWN | 55 | 29 | T |
| AI564290 | UNKNOWN | 28 | 0 | T |
| AI564290 | UNKNOWN | 15 | 117 | A |
| AI564306 | UNKNOWN | 71 | 0 | T |
| AI564306 | UNKNOWN | 18 | 295 | G |
| AI564306 | UNKNOWN | 13 | 257 | C |
| AI564306 | UNKNOWN | 12 | 339 | A |
| AI564311 | UNKNOWN | 69 | 0 | T |
| AI564311 | UNKNOWN | 18 | 280 | G |
| AI564311 | UNKNOWN | 13 | 221 | C |
| AI564311 | UNKNOWN | 12 | 126 | C |
| AI564326 | UNKNOWN | 32 | 0 | T |
| AI564384 | UNKNOWN | 27 | 6 | T |
| AI564389 | UNKNOWN | 41 | 0 | T |
| AI564391 | UNKNOWN | 39 | 0 | T |
| AI564407 | UNKNOWN | 33 | 0 | T |
| AI564418 | UNKNOWN | 25 | 0 | T |
| AI564426 | UNKNOWN | 79 | 0 | T |
| AI564426 | UNKNOWN | 16 | 101 | A |
| AI564432 | UNKNOWN | 55 | 0 | T |
| AI564454 | UNKNOWN | 13 | 0 | T |
| AI564459 | UNKNOWN | 57 | 0 | T |
| AI564500 | UNKNOWN | 46 | 0 | T |
| AI564515 | UNKNOWN | 102 | 0 | T |
| AI564515 | UNKNOWN | 39 | 161 | G |
| AI564515 | UNKNOWN | 17 | 102 | C |
| AI564574 | UNKNOWN | 30 | 0 | T |
| AI564593 | UNKNOWN | 14 | 0 | T |
| AI564602 | UNKNOWN | 86 | 0 | T |
| AI564649 | UNKNOWN | 18 | 433 | T |
| AI564716 | UNKNOWN | 51 | 0 | T |
| AI564719 | UNKNOWN | 124 | 0 | T |
| AI564719 | UNKNOWN | 21 | 124 | A |
| AI564719 | UNKNOWN | 15 | 206 | C |
| AI564723 | UNKNOWN | 93 | 0 | T |

TABLE 1-continued

| Genbank # | Region | # reps | Position | Unit sequence |
|---|---|---|---|---|
| AI564723 | UNKNOWN | 18 | 99 | A |
| AI564723 | UNKNOWN | 16 | 156 | C |
| AI564723 | UNKNOWN | 14 | 181 | G |
| AI564736 | UNKNOWN | 104 | 2 | T |
| AI564736 | UNKNOWN | 17 | 151 | A |
| AI564736 | UNKNOWN | 17 | 290 | G |
| AI564736 | UNKNOWN | 13 | 117 | C |
| AI564749 | UNKNOWN | 78 | 0 | T |
| AI564749 | UNKNOWN | 22 | 135 | G |
| AI564749 | UNKNOWN | 15 | 101 | C |
| AI564759 | UNKNOWN | 47 | 0 | T |
| AI564765 | UNKNOWN | 79 | 0 | T |
| AI564765 | UNKNOWN | 12 | 161 | A |
| AI564783 | UNKNOWN | 5 | 443 | ATTT |
| AI564992 | UNKNOWN | 113 | 0 | T |
| AI564992 | UNKNOWN | 20 | 157 | G |
| AI564992 | UNKNOWN | 18 | 251 | A |
| AI564992 | UNKNOWN | 16 | 113 | C |
| AI564992 | UNKNOWN | 15 | 177 | A |
| AI565001 | UNKNOWN | 14 | 0 | T |
| AI565031 | UNKNOWN | 66 | 0 | T |
| AI565031 | UNKNOWN | 13 | 97 | A |
| AI565038 | UNKNOWN | 44 | 0 | T |
| AI565048 | UNKNOWN | 59 | 0 | T |
| AI565062 | UNKNOWN | 100 | 0 | T |
| AI565062 | UNKNOWN | 13 | 130 | A |
| AI565069 | UNKNOWN | 60 | 0 | T |
| AI565069 | UNKNOWN | 13 | 274 | G |
| AI565085 | UNKNOWN | 20 | 0 | T |
| AI565105 | UNKNOWN | 23 | 0 | T |
| AI565128 | UNKNOWN | 80 | 0 | T |
| AI565128 | UNKNOWN | 29 | 130 | C |
| AI565128 | UNKNOWN | 21 | 381 | G |
| AI565128 | UNKNOWN | 14 | 264 | A |
| AI565130 | UNKNOWN | 38 | 0 | T |
| AI565145 | UNKNOWN | 41 | 0 | T |
| AI565147 | UNKNOWN | 48 | 0 | T |
| AI565161 | UNKNOWN | 32 | 0 | T |
| AI565170 | UNKNOWN | 16 | 0 | T |
| AI565172 | UNKNOWN | 64 | 0 | T |
| AI565366 | UNKNOWN | 16 | 0 | T |
| AI565382 | UNKNOWN | 41 | 0 | T |
| AI565426 | UNKNOWN | 12 | 0 | T |
| AI565496 | UNKNOWN | 35 | 0 | T |
| AI565514 | UNKNOWN | 19 | 1 | T |
| AI565598 | UNKNOWN | 43 | 0 | T |
| AI565773 | UNKNOWN | 12 | 527 | T |
| AI565820 | UNKNOWN | 3.8 | 83 | AAAAC |
| AI565820 | UNKNOWN | 4.75 | 101 | AAAC |
| AI565895 | UNKNOWN | 43 | 13 | T |
| AI565947 | UNKNOWN | 3.8 | 26 | CCAGC |
| AI565970 | UNKNOWN | 67 | 0 | T |
| AI565970 | UNKNOWN | 15 | 130 | G |
| AI566003 | UNKNOWN | 90 | 0 | T |
| AI566003 | UNKNOWN | 25 | 310 | A |
| AI566003 | UNKNOWN | 13 | 107 | A |
| AI566028 | UNKNOWN | 14 | 0 | T |
| AI566032 | UNKNOWN | 23 | 0 | T |
| AI566042 | UNKNOWN | 65 | 0 | T |
| AI566049 | UNKNOWN | 32 | 0 | T |
| AI566076 | UNKNOWN | 6.5 | 0 | CTTT |
| AI566080 | UNKNOWN | 15 | 0 | T |
| AI566121 | UNKNOWN | 32 | 0 | T |
| AI566233 | UNKNOWN | 20 | 0 | T |
| AI566386 | UNKNOWN | 66 | 0 | T |
| AI566386 | UNKNOWN | 22 | 347 | G |
| AI566386 | UNKNOWN | 19 | 101 | G |
| AI566399 | UNKNOWN | 70 | 0 | T |
| AI566430 | UNKNOWN | 55 | 0 | T |
| AI566430 | UNKNOWN | 12 | 323 | A |
| AI566450 | UNKNOWN | 43 | 0 | T |
| AI566452 | UNKNOWN | 102 | 0 | T |
| AI566452 | UNKNOWN | 13 | 183 | A |
| AI566452 | UNKNOWN | 12 | 267 | G |
| AI566455 | UNKNOWN | 47 | 0 | T |
| AI566455 | UNKNOWN | 12 | 155 | G |
| AI566465 | UNKNOWN | 44 | 0 | T |

TABLE 1-continued

| Genbank # | Region | # reps | Position | Unit sequence |
|---|---|---|---|---|
| AI566479 | UNKNOWN | 101 | 0 | T |
| AI566479 | UNKNOWN | 16 | 125 | A |
| AI566479 | UNKNOWN | 13 | 258 | C |
| AI566483 | UNKNOWN | 12 | 0 | T |
| AI566499 | UNKNOWN | 43 | 0 | T |
| AI566507 | UNKNOWN | 91 | 19 | T |
| AI566507 | UNKNOWN | 18 | 0 | T |
| AI566507 | UNKNOWN | 13 | 110 | G |
| AI566507 | UNKNOWN | 12 | 140 | C |
| AI566526 | UNKNOWN | 16 | 0 | T |
| AI566527 | UNKNOWN | 13 | 0 | T |
| AI566613 | UNKNOWN | 48 | 0 | T |
| AI566613 | UNKNOWN | 13 | 122 | A |
| AI566614 | UNKNOWN | 29 | 0 | T |
| AI566614 | UNKNOWN | 18 | 137 | A |
| AI566630 | UNKNOWN | 80 | 0 | T |
| AI566630 | UNKNOWN | 13 | 80 | G |
| AI566662 | UNKNOWN | 27 | 0 | T |
| AI566670 | UNKNOWN | 107 | 0 | T |
| AI566670 | UNKNOWN | 16 | 156 | G |
| AI566670 | UNKNOWN | 16 | 270 | A |
| AI566670 | UNKNOWN | 13 | 172 | A |
| AI566670 | UNKNOWN | 13 | 236 | C |
| AI566670 | UNKNOWN | 12 | 129 | G |
| AI566670 | UNKNOWN | 12 | 144 | C |
| AI566675 | UNKNOWN | 13 | 57 | T |
| AI566718 | UNKNOWN | 13 | 247 | A |
| AI566724 | UNKNOWN | 65 | 14 | T |
| AI566724 | UNKNOWN | 13 | 0 | T |
| AI566752 | UNKNOWN | 16 | 0 | T |
| AI566819 | UNKNOWN | 5.66 | 4 | TTG |
| AI566839 | UNKNOWN | 38 | 0 | T |
| AI566848 | UNKNOWN | 17 | 176 | T |
| AI566876 | UNKNOWN | 43 | 0 | T |
| AI566876 | UNKNOWN | 17 | 238 | G |
| AI566902 | UNKNOWN | 18 | 1 | T |
| AI567077 | UNKNOWN | 18 | 0 | T |
| AI567114 | UNKNOWN | 37 | 0 | T |
| AI567115 | UNKNOWN | 57 | 0 | T |
| AI567128 | UNKNOWN | 112 | 2 | T |
| AI567128 | UNKNOWN | 18 | 114 | A |
| AI567128 | UNKNOWN | 14 | 133 | C |
| AI567128 | UNKNOWN | 13 | 160 | G |
| AI567190 | UNKNOWN | 50 | 0 | T |
| AI567190 | UNKNOWN | 15 | 242 | G |
| AI567206 | UNKNOWN | 38 | 0 | T |
| AI567207 | UNKNOWN | 13 | 0 | T |
| AI567218 | UNKNOWN | 22 | 1 | T |
| AI567230 | UNKNOWN | 6 | 0 | TATT |
| AI567238 | UNKNOWN | 79 | 0 | T |
| AI567238 | UNKNOWN | 13 | 271 | G |
| AI567243 | UNKNOWN | 76 | 0 | T |
| AI567245 | UNKNOWN | 18 | 0 | T |
| AI567264 | UNKNOWN | 28 | 0 | T |
| AI567269 | UNKNOWN | 26 | 0 | T |
| AI567287 | UNKNOWN | 26 | 0 | T |
| AI567290 | UNKNOWN | 48 | 0 | T |
| AI567290 | UNKNOWN | 15 | 274 | A |
| AI567293 | UNKNOWN | 44 | 0 | T |
| AI567299 | UNKNOWN | 44 | 0 | T |
| AI567302 | UNKNOWN | 71 | 0 | T |
| AI567302 | UNKNOWN | 15 | 185 | C |
| AI567305 | UNKNOWN | 50 | 0 | T |
| AI567351 | UNKNOWN | 132 | 0 | T |
| AI567351 | UNKNOWN | 20 | 154 | A |
| AI567360 | UNKNOWN | 98 | 0 | T |
| AI567360 | UNKNOWN | 14 | 233 | G |
| AI567373 | UNKNOWN | 70 | 0 | T |
| AI567373 | UNKNOWN | 17 | 220 | C |
| AI567373 | UNKNOWN | 17 | 309 | G |
| AI567373 | UNKNOWN | 15 | 155 | A |
| AI567452 | UNKNOWN | 4.75 | 165 | AAAC |
| AI567452 | UNKNOWN | 15 | 190 | A |
| AI567501 | UNKNOWN | 96 | 0 | T |
| AI567501 | UNKNOWN | 17 | 324 | G |
| AI567501 | UNKNOWN | 13 | 282 | G |
| AI567501 | UNKNOWN | 12 | 112 | A |

TABLE 1-continued

| Genbank # | Region | # reps | Position | Unit sequence |
|---|---|---|---|---|
| AI567501 | UNKNOWN | 12 | 216 | G |
| AI567513 | UNKNOWN | 62 | 0 | T |
| AI567513 | UNKNOWN | 14 | 62 | A |
| AI567525 | UNKNOWN | 37 | 17 | T |
| AI567540 | UNKNOWN | 59 | 1 | T |
| AI567540 | UNKNOWN | 16 | 205 | G |
| AI567541 | UNKNOWN | 36 | 0 | T |
| AI567571 | UNKNOWN | 41 | 0 | T |
| AI567582 | UNKNOWN | 80 | 0 | T |
| AI567582 | UNKNOWN | 16 | 115 | C |
| AI567582 | UNKNOWN | 15 | 131 | A |
| AI567598 | UNKNOWN | 27 | 0 | T |
| AI567612 | UNKNOWN | 110 | 0 | T |
| AI567612 | UNKNOWN | 13 | 156 | G |
| AI567612 | UNKNOWN | 12 | 131 | C |
| AI567625 | UNKNOWN | 47 | 0 | T |
| AI567625 | UNKNOWN | 12 | 100 | A |
| AI567637 | UNKNOWN | 66 | 0 | T |
| AI567680 | UNKNOWN | 39 | 0 | T |
| AI567710 | UNKNOWN | 46 | 0 | T |
| AI567758 | UNKNOWN | 32 | 0 | T |
| AI567769 | UNKNOWN | 90 | 0 | T |
| AI567769 | UNKNOWN | 13 | 115 | C |
| AI567769 | UNKNOWN | 12 | 90 | A |
| AI567769 | UNKNOWN | 12 | 340 | G |
| AI567807 | UNKNOWN | 43 | 44 | T |
| AI567807 | UNKNOWN | 15 | 94 | G |
| AI567807 | UNKNOWN | 13 | 12 | T |
| AI567807 | UNKNOWN | 13 | 134 | A |
| AI567814 | UNKNOWN | 91 | 0 | T |
| AI567814 | UNKNOWN | 1B | 124 | A |
| AI567823 | UNKNOWN | 2.58 | 179 | GGCCCCCGGGGG (SEQ ID NO:126) |
| AI567823 | UNKNOWN | 42 | 3 | T |
| AI567823 | UNKNOWN | 15 | 343 | C |
| AI567826 | UNKNOWN | 32 | 0 | T |
| AI567832 | UNKNOWN | 35 | 0 | T |
| AI567834 | UNKNOWN | 62 | 0 | T |
| AI567834 | UNKNOWN | 18 | 123 | A |
| AI567834 | UNKNOWN | 13 | 175 | C |
| AI567866 | UNKNOWN | 72 | 0 | T |
| AI567866 | UNKNOWN | 19 | 280 | G |
| AI567871 | UNKNOWN | 63 | 0 | T |
| AI567883 | UNKNOWN | 53 | 0 | T |
| AI567902 | UNKNOWN | 17 | 0 | T |
| AI567902 | UNKNOWN | 15 | 632 | A |
| AI567940 | UNKNOWN | 107 | 11 | T |
| AI567940 | UNKNOWN | 18 | 326 | A |
| AI567941 | UNKNOWN | 15 | 11 | T |
| AI567967 | UNKNOWN | 28 | 11 | T |
| AI567976 | UNKNOWN | 9 | 204 | AC |
| AI567976 | UNKNOWN | 28 | 11 | T |
| AI567978 | UNKNOWN | 110 | 0 | T |
| AI567978 | UNKNOWN | 27 | 367 | C |
| AI567986 | UNKNOWN | 15 | 11 | T |
| AI567993 | UNKNOWN | 101 | 9 | T |
| AI567993 | UNKNOWN | 21 | 341 | A |
| AI567993 | UNKNOWN | 17 | 287 | G |
| AI568038 | UNKNOWN | 57 | 0 | T |
| AI568038 | UNKNOWN | 12 | 186 | C |
| AI568060 | UNKNOWN | 66 | 0 | T |
| AI568099 | UNKNOWN | 16 | 0 | T |
| AI568114 | UNKNOWN | 69 | 0 | T |
| AI568132 | UNKNOWN | 68 | 0 | T |
| AI568132 | UNKNOWN | 14 | 130 | C |
| AI568137 | UNKNOWN | 12 | 165 | T |
| AI568138 | UNKWOWN | 74 | 0 | T |
| AI568138 | UNKNOWN | 13 | 144 | A |
| AI568207 | UNKNOWN | 13 | 352 | A |
| AI568296 | UNKNOWN | 101 | 0 | T |
| AI568296 | UNKNOWN | 21 | 136 | G |
| AI568296 | UNKNOWN | 12 | 108 | A |
| AI568338 | UNKNOWN | 69 | 0 | T |
| AI568374 | UNKNOWN | 78 | 0 | T |
| AI568375 | UNKNOWN | 30 | 0 | T |
| AI568424 | UNKNOWN | 20 | 195 | T |
| AI568452 | UNKNOWN | 6.5 | 25 | TTAT |
| AI568452 | UNKNOWN | 11.66 | 106 | ATC |

TABLE 1-continued

| Genbank # | Region | # reps | Position | Unit sequence |
|---|---|---|---|---|
| AI568452 | UNKNOWN | 20 | 0 | T |
| AI568463 | UNKNOWN | 39 | 0 | T |
| AI568552 | UNKNOWN | 23 | 0 | T |
| AI568552 | UNKNOWN | 12 | 128 | A |
| AI568561 | UNKNOWN | 13 | 0 | T |
| AI568590 | UNKNOWN | 21 | 330 | T |
| AI568592 | UNKNOWN | 57 | 26 | T |
| AI568592 | UNKNOWN | 25 | 0 | T |
| AI568592 | UNKNOWN | 15 | 139 | C |
| AI568604 | UNKNOWN | 24 | 415 | T |
| AI568636 | UNKNOWN | 42 | 0 | T |
| AI568695 | UNKNOWN | 47 | 0 | T |
| AI568702 | UNKNOWN | 12 | 334 | A |
| AI568751 | UNKNOWN | 3.6 | 388 | TTGTT |
| AI568751 | UNKNOWN | 17 | 630 | A |
| AI568753 | UNKNOWN | 36 | 0 | T |
| AI568765 | UNKNOWN | 94 | 0 | T |
| AI568765 | UNKNOWN | 17 | 198 | G |
| AI568765 | UNKNOWN | 12 | 239 | C |
| AI568771 | UNKNOWN | 53 | 0 | T |
| AI568773 | UNKNOWN | 52 | 0 | T |
| AI568774 | UNKNOWN | 14 | 0 | T |
| AI568779 | UNKNOWN | 12 | 0 | T |
| AI568788 | UNKNOWN | 13 | 0 | T |
| AI568820 | UNKNOWN | 4.75 | 44 | TTTC |
| AI568820 | UNKNOWN | 12 | 60 | T |
| AI568830 | UNKNOWN | 19 | 198 | T |
| AI568852 | UNKNOWN | 46 | 0 | T |
| AI568854 | UNKNOWN | 127 | 0 | T |
| AI568854 | UNKNOWN | 19 | 293 | A |
| AI568854 | UNKNOWN | 12 | 184 | G |
| AI568854 | UNKNOWN | 12 | 253 | A |
| AI568855 | UNKNOWN | 112 | 0 | T |
| AI568855 | UNKNOWN | 16 | 144 | A |
| AI568855 | UNKNOWN | 14 | 269 | C |
| AI568865 | UNKNOWN | 82 | 0 | T |
| AI568870 | UNKNOWN | 131 | 0 | T |
| AI568870 | UNKNOWN | 15 | 270 | G |
| AI568870 | UNKNOWN | 12 | 131 | G |
| AI568880 | UNKNOWN | 17 | 0 | T |
| AI568886 | UNKNOWN | 74 | 0 | T |
| AI568886 | UNKNOWN | 14 | 299 | A |
| AI568886 | UNKNOWN | 13 | 263 | C |
| AI568900 | UNKNOWN | 107 | 0 | T |
| AI568900 | UNKNOWN | 18 | 136 | G |
| AI568900 | UNKNOWN | 18 | 310 | A |
| AI568900 | UNKNOWN | 14 | 122 | A |
| AI568913 | UNKNOWN | 64 | 0 | T |
| AI568913 | UNKNOWN | 12 | 88 | C |
| AI568916 | UNKNOWN | 13 | 0 | T |
| AI568960 | UNKNOWN | 52 | 0 | T |
| AI568967 | UNKNOWN | 47 | 0 | T |
| AI569051 | UNKNOWN | 15 | 3 | T |
| AI569294 | UNKNOWN | 63 | 0 | T |
| AI569309 | UNKNOWN | 86 | 0 | T |
| AI569328 | UNKNOWN | 68 | 25 | T |
| AI569328 | UNKNOWN | 29 | 124 | A |
| AI569328 | UNKNOWN | 24 | 0 | T |
| AI569367 | UNKNOWN | 67 | 0 | T |
| AI569518 | UNKNOWN | 30 | 0 | T |
| AI569518 | UNKNOWN | 18 | 71 | A |
| AI569521 | UNKNOWN | 100 | 7 | T |
| AI569521 | UNKNOWN | 13 | 213 | C |
| AI569521 | UNKNOWN | 12 | 180 | G |
| AI569523 | UNKNOWN | 96 | 0 | T |
| AI569523 | UNKNOWN | 24 | 145 | G |
| AI569523 | UNKNOWN | 15 | 169 | C |
| AI569523 | UNKNOWN | 13 | 96 | G |
| AI569524 | UNKNOWN | 44 | 0 | T |
| AI569565 | UNKNOWN | 19 | 0 | T |
| AI569579 | UNKNOWN | 61 | 0 | T |
| AI569579 | UNkNOWN | 12 | 147 | G |
| AI569579 | UNKNOWN | 12 | 201 | C |
| AI569583 | UNKNOWN | 107 | 8 | T |
| AI569583 | UNKNOWN | 20 | 161 | A |
| AI569583 | UNKNOWN | 13 | 181 | G |
| AI569583 | UNkNOWN | 12 | 137 | C |

TABLE 1-continued

| Genbank # | Region | # reps | Position | Unit sequence |
|---|---|---|---|---|
| AI569589 | UNKNOWN | 60 | 0 | T |
| AI569589 | UNKNOWN | 12 | 142 | G |
| AI569616 | UNKNOWN | 111 | 8 | T |
| AI569616 | UNKNOWN | 14 | 218 | C |
| AI569632 | UNKNOWN | 2.8 | 152 | AAAAAAAACC (SEQ ID NO:127) |
| AI569632 | UNKNOWN | 88 | 0 | T |
| AI569637 | UNKNOWN | 90 | 0 | T |
| AI569637 | UNKNOWN | 14 | 118 | C |
| AI569684 | UNKNOWN | 18 | 14 | T |
| AI569808 | UNKNOWN | 22 | 0 | T |
| AI569845 | UNKNOWN | 14 | 0 | T |
| AI569879 | UNKNOWN | 15 | 200 | T |
| AI569937 | UNKNOWN | 35 | 0 | T |
| AI569943 | UNKNOWN | 43 | 0 | T |
| AI569945 | UNKNOWN | 90 | 0 | T |
| AI569945 | UNKNOWN | 22 | 103 | A |
| AI569945 | UNKNOWN | 21 | 208 | G |
| AI569945 | UNKNOWN | 20 | 151 | G |
| AI569945 | UNKNOWN | 19 | 242 | C |
| AI569975 | UNKNOWN | 80 | 0 | T |
| AI569975 | UNKNOWN | 29 | 131 | A |
| AI569975 | UNKNOWN | 22 | 249 | G |
| AI570009 | UNKNOWN | 111 | 4 | T |
| AI570009 | UNKNOWN | 22 | 207 | C |
| AI570009 | UNKNOWN | 20 | 187 | G |
| AI570009 | UNKNOWN | 13 | 174 | A |
| AI570027 | UNKNOWN | 22 | 0 | T |
| AI570140 | UNKNOWN | 65 | 0 | T |
| AI570140 | UNKNOWN | 18 | 284 | G |
| AI570142 | UNKNOWN | 80 | 0 | T |
| AI570152 | UNKNOWN | 53 | 0 | T |
| AI570164 | UNKNOWN | 4.59 | 35 | TTTAT |
| AI570164 | UNKNOWN | 19 | 0 | T |
| AI570169 | UNKNOWN | 96 | 0 | T |
| AI570169 | UNKNOWN | 23 | 169 | G |
| AI570169 | UNKNOWN | 20 | 198 | A |
| AI570169 | UNKNOWN | 13 | 156 | C |
| AI570182 | UNKNOWN | 15 | 136 | T |
| AI570216 | UNKNOWN | 18 | 245 | TA |
| AI570216 | UNKNOWN | 10.5 | 169 | AT |
| AI570220 | UNKNOWN | 36 | 0 | T |
| AI570220 | UNKNOWN | 14 | 183 | G |
| AI570247 | UNKNOWN | 15 | 4 | T |
| AI570257 | UNKNOWN | 55 | 0 | T |
| AI570334 | UNKNOWN | 51 | 0 | T |
| AI570334 | UNKNOWN | 13 | 100 | G |
| AI570375 | UNkNOWN | 55 | 0 | T |
| AI570375 | UNKNOWN | 14 | 142 | G |
| AI570384 | UNKNOWN | 117 | 0 | T |
| AI570384 | UNKNOWN | 13 | 140 | C |
| AI570389 | UNKNOWN | 56 | 4 | T |
| AI570455 | UNKNOWN | 15 | 361 | A |
| AI570475 | UNKNOWN | 14 | 299 | T |
| AI570497 | UNKNOWN | 5 | 47 | TTTTG |
| AI570497 | UNKNOWN | 16 | 84 | A |
| AI570497 | UNKNOWN | 13 | 17 | T |
| AI570506 | UNKNOWN | 30 | 0 | T |
| AI570506 | UNKNOWN | 18 | 79 | G |
| AI570526 | UNKNOWN | 12 | 0 | T |
| AI570557 | UNKNOWN | 23 | 0 | T |
| AI570557 | UNKNOWN | 14 | 139 | A |
| AI570569 | UNKNOWN | 32 | 0 | T |
| AI570588 | UNKNOWN | 42 | 0 | T |
| AI570639 | UNKNOWN | 40 | 0 | T |
| AI570654 | UNKNOWN | 30 | 0 | T |
| AI570654 | UNKNOWN | 15 | 119 | G |
| AI570774 | UNKNOWN | 52 | 0 | T |
| AI570774 | UNKNOWN | 17 | 142 | G |
| AI570781 | UNKNOWN | 94 | 0 | T |
| AI570781 | UNKNOWN | 14 | 204 | G |
| AI570781 | UNKNOWN | 12 | 128 | C |
| AI570786 | UNKNOWN | 88 | 0 | T |
| AI570800 | UNKNOWN | 51 | 0 | T |
| AI570807 | UNKNOWN | 89 | 0 | T |
| AI570807 | UNKNOWN | 13 | 89 | A |
| AI570857 | UNKNOWN | 53 | 0 | T |
| AI570861 | UNKNOWN | 90 | 0 | T |

TABLE 1-continued

| Genbank # | Region | # reps | Position | Unit sequence |
|---|---|---|---|---|
| AI570861 | UNKNOWN | 14 | 147 | C |
| AI570861 | UNKNOWN | 12 | 161 | A |
| AI570872 | UNKNOWN | 73 | 0 | T |
| AI570872 | UNKNOWN | 15 | 96 | G |
| AI570872 | UNKNOWN | 12 | 300 | A |
| AI570884 | UNKNOWN | 97 | 0 | T |
| AI570884 | UNKNOWN | 18 | 279 | G |
| AI570884 | UNKNOWN | 15 | 151 | A |
| AI570884 | UNKNOWN | 14 | 229 | G |
| AI570909 | UNKNOWN | 110 | 0 | T |
| AI570909 | UNKNOWN | 21 | 167 | G |
| AI570909 | UNKNOWN | 12 | 134 | C |
| AI570912 | UNKNOWN | 78 | 0 | T |
| AI570912 | UNKNOWN | 20 | 147 | A |
| AI570912 | UNKNOWN | 13 | 120 | G |
| AI570923 | UNKNOWN | 12 | 438 | T |
| AI570961 | UNKNOWN | 12 | 319 | T |
| AI570966 | UNKNOWN | 71 | 0 | T |
| AI570972 | UNKNOWN | 28 | 0 | T |
| AI570989 | UNKNOWN | 100 | 0 | T |
| AI570989 | UNKNOWN | 18 | 147 | A |
| AI570989 | UNKNOWN | 13 | 107 | A |
| AI570997 | UNKNOWN | 78 | 0 | T |
| AI570997 | UNKNOWN | 13 | 130 | A |
| AI570997 | UNKNOWN | 13 | 317 | G |
| AI571007 | UNKNOWN | 43 | 0 | T |
| AI571046 | UNKNOWN | 82 | 0 | T |
| AI571049 | UNKNOWN | 76 | 0 | T |
| AI571110 | UNKNOWN | 99 | 0 | T |
| AI571110 | UNKNOWN | 16 | 263 | C |
| AI571133 | UNKNOWN | 115 | 6 | T |
| AI571133 | UNKNOWN | 18 | 221 | G |
| AI571133 | UNKNOWN | 17 | 282 | A |
| AI571149 | UNKNOWN | 29 | 177 | C |
| AI571149 | UNKNOWN | 27 | 10 | T |
| AI571160 | UNKNOWN | 14 | 106 | A |
| AI571202 | UNKNOWN | 15 | 0 | T |
| AI571203 | UNKNOWN | 20 | 26 | T |
| AI571203 | UNKNOWN | 15 | 0 | T |
| AI571306 | UNKNOWN | 15 | 183 | T |
| AI571356 | UNKNOWN | 22 | 0 | T |
| AI571356 | UNKNOWN | 16 | 282 | A |
| AI571367 | UNKNOWN | 56 | 0 | T |
| AI571391 | UNKNOWN | 31 | 0 | T |
| AI571424 | UNKNOWN | 24 | 0 | T |
| AI571439 | UNKNOWN | 86 | 0 | T |
| AI571439 | UNKNOWN | 17 | 181 | A |
| AI571439 | UNKNOWN | 15 | 86 | A |
| AI571439 | UNKNOWN | 15 | 130 | G |
| AI571442 | UNKNOWN | 49 | 0 | T |
| AI571511 | UNKNOWN | 68 | 4 | T |
| AI571511 | UNKNOWN | 16 | 209 | G |
| AI571511 | UNKNOWN | 12 | 197 | A |
| AI571527 | UNKNOWN | 48 | 0 | T |
| AI571529 | UNKNOWN | 69 | 0 | T |
| AI571536 | UNKNOWN | 16 | 0 | T |
| AI571551 | UNKNOWN | 108 | 0 | T |
| AI571551 | UNKNOWN | 15 | 209 | A |
| AI571551 | UNKNOWN | 13 | 154 | C |
| AI571551 | UNKNOWN | 13 | 181 | G |
| AI571570 | UNKNOWN | 21 | 160 | A |
| AI571570 | UNKNOWN | 15 | 190 | G |
| AI571575 | UNKNOWN | 62 | 0 | T |
| AI571575 | UNKNOWN | 24 | 95 | A |
| AI571575 | UNKNOWN | 13 | 189 | G |
| AI571583 | UNKNOWN | 31 | 0 | T |
| AI571650 | UNKNOWN | 15 | 0 | T |
| AI571678 | UNKNOWN | 25 | 0 | T |
| AI571786 | UNKNOWN | 12 | 24 | A |
| AI571861 | UNKNOWN | 105 | 0 | T |
| AI571861 | UNKNOWN | 16 | 172 | G |
| AI571861 | UNKNOWN | 15 | 125 | A |
| AI571861 | UNKNOWN | 14 | 188 | C |
| AI571867 | UNKNOWN | 90 | 0 | T |
| AI571867 | UNKNOWN | 13 | 165 | G |
| AI571868 | UNKNOWN | 82 | 0 | T |
| AI571868 | UNKNOWN | 18 | 238 | C |

TABLE 1-continued

| Genbank # | Region | # reps | Position | Unit sequence |
|---|---|---|---|---|
| AI571873 | UNKNOWN | 68 | 0 | T |
| AI571888 | UNKNOWN | 21 | 0 | T |
| AI571909 | UNKNOWN | 107 | 0 | T |
| AI571909 | UNKNOWN | 19 | 190 | G |
| AI571932 | UNKNOWN | 36 | 0 | T |
| AI571945 | UNKNOWN | 62 | 0 | T |
| AI571966 | UNKNOWN | 51 | 0 | T |
| AI571976 | UNKNOWN | 14 | 254 | AC |
| AI572021 | UNKNOWN | 89 | 0 | T |
| AI572021 | UNKNOWN | 14 | 124 | C |
| AI572096 | UNKNOWN | 76 | 0 | T |
| AI572096 | UNKNOWN | 12 | 153 | G |
| AI572226 | UNKNOWN | 17 | 477 | T |
| AI572391 | UNKNOWN | 65 | 0 | T |
| AI572391 | UNKNOWN | 18 | 250 | A |
| AI572391 | UNKNOWN | 12 | 166 | A |
| AI572418 | UNKNOWN | 48 | 0 | T |
| AI572499 | UNKNOWN | 13 | 61 | A |
| AI572546 | UNKNOWN | 12 | 56 | A |
| AI572569 | UNKNOWN | 114 | 0 | T |
| AI572569 | UNKNOWN | 16 | 227 | C |
| AI572569 | UNKNOWN | 14 | 122 | G |
| AI572569 | UNKNOWN | 14 | 365 | A |
| AI572569 | UNKNOWN | 13 | 311 | A |
| AI572569 | UNKNOWN | 12 | 161 | A |
| AI572574 | UNKNOWN | 49 | 0 | T |
| AI572574 | UNKNOWN | 12 | 161 | A |
| AI572629 | UNKNOWN | 25 | 0 | T |
| AI572676 | UNKNOWN | 57 | 8 | T |
| AI572676 | UNKNOWN | 17 | 251 | G |
| AI572676 | UNKNOWN | 16 | 149 | C |
| AI572676 | UNKNOWN | 15 | 166 | A |
| AI572676 | UNKNOWN | 14 | 191 | G |
| AI572693 | UNKNOWN | 16 | 194 | A |
| AI572717 | UNKNOWN | 73 | 0 | T |
| AI572717 | UNKNOWN | 13 | 123 | C |
| AI572719 | UNKNOWN | 58 | 0 | T |
| AI572730 | UNKNOWN | 50 | 0 | T |
| AI572778 | UNKNOWN | 45 | 0 | T |
| AI572778 | UNKNOWN | 21 | 116 | A |
| AI572787 | UNKNOWN | 113 | 0 | T |
| AI572787 | UNKNOWN | 22 | 127 | A |
| AI572787 | UNKNOWN | 20 | 149 | G |
| AI572892 | UNKNOWN | 87 | 0 | T |
| AI573026 | UNKNOWN | 76 | 0 | T |
| AI573032 | UNKNOWN | 116 | 0 | T |
| AI573032 | UNKNOWN | 24 | 121 | A |
| AI573032 | UNKNOWN | 16 | 182 | G |
| AI573032 | UNKNOWN | 14 | 145 | C |
| AI573038 | UNKNOWN | 97 | 0 | T |
| AI573038 | UNKNOWN | 16 | 149 | A |
| AI573046 | UNKNOWN | 30 | 0 | T |
| AI573060 | UNKNOWN | 92 | 0 | T |
| AI573060 | UNKNOWN | 19 | 115 | G |
| AI573060 | UNKNOWN | 12 | 92 | A |
| AI573085 | UNKNOWN | 73 | 0 | T |
| AI573085 | UNKNOWN | 17 | 171 | A |
| AI573093 | UNKNOWN | 72 | 0 | T |
| AI573108 | UNKNOWN | 50 | 0 | T |
| AI573148 | UNKNOWN | 41 | 0 | T |
| AI573149 | UNKNOWN | 48 | 0 | T |
| AI573149 | UNNNOWN | 13 | 167 | A |
| AI573164 | UNKNOWN | 46 | 0 | T |
| AI573164 | UNKNOWN | 14 | 111 | C |
| AI573167 | UNKNOWN | 69 | 0 | T |
| AI573168 | UNKNOWN | 12 | 140 | A |
| AI573171 | UNKNOWN | 78 | 0 | T |
| AI573171 | UNKNOWN | 13 | 169 | G |
| AI573171 | UNKNOWN | 12 | 422 | A |
| AI573200 | UNKNOWN | 56 | 0 | T |
| AI573241 | UNKNOWN | 16 | 99 | A |
| AI579901 | UNKNOWN | 83 | 0 | T |
| AI579901 | UNKNOWN | 17 | 83 | A |
| AI579901 | UNKNOWN | 13 | 250 | C |
| AI579907 | UNKNOWN | 46 | 0 | T |
| AI579962 | UNKNOWN | 19 | 165 | A |
| AI579979 | UNKNOWN | 48 | 0 | T |

TABLE 1-continued

| Genbank # | Region | # reps | Position | Unit sequence |
|---|---|---|---|---|
| AI579990 | UNKNOWN | 32 | 0 | T |
| AI579991 | UNKNOWN | 74 | 0 | T |
| AI579991 | UNKNOWN | 13 | 294 | A |
| AI579991 | UNKNOWN | 12 | 247 | A |
| AI580007 | UNKNOWN | 47 | 0 | T |
| AI580027 | UNKNOWN | 53 | 0 | T |
| AI580043 | UNKNOWN | 18 | 0 | T |
| AI580072 | UNKNOWN | 12 | 0 | T |
| AI580097 | UNKNOWN | 24 | 0 | T |
| AI580141 | UNKNOWN | 13 | 0 | T |
| AI580143 | UNKNOWN | 15 | 0 | T |
| AI580150 | UNKNOWN | 15 | 0 | T |
| AI580163 | UNKNOWN | 14 | 278 | A |
| AI580183 | UNKNOWN | 14 | 373 | T |
| AI580190 | UNKNOWN | 145 | 0 | T |
| AI580190 | UNKNOWN | 24 | 280 | C |
| AI580190 | UNKNOWN | 20 | 250 | G |
| AI580190 | UNKNOWN | 15 | 145 | A |
| a1580190 | UNKNOWN | 14 | 185 | C |
| AI580198 | UNKNOWN | 104 | 0 | T |
| AI580198 | UNKNOWN | 14 | 376 | G |
| AI580198 | UNKNOWN | 13 | 363 | A |
| AI580198 | UNKNOWN | 12 | 246 | C |
| AI580207 | UNKNOWN | 49 | 0 | T |
| AI580207 | UNKNOWN | 18 | 128 | A |
| AI580207 | UNKNOWN | 13 | 191 | G |
| AI580208 | UNKNOWN | 56 | 0 | T |
| AI580214 | UNKNOWN | 70 | 0 | T |
| AI580214 | UNKNOWN | 16 | 136 | C |
| AI580240 | UNKNOWN | 118 | 0 | T |
| AI580240 | UNKNOWN | 16 | 165 | A |
| AI580240 | UNKNOWN | 16 | 212 | C |
| AI580240 | UNKNOWN | 15 | 150 | G |
| AI580240 | UNKNOWN | 12 | 185 | C |
| AI580254 | UNKNOWN | 70 | 0 | T |
| AI580254 | UNKNOWN | 12 | 109 | A |
| AI580255 | UNKNOWN | 43 | 0 | T |
| AI580270 | UNKNOWN | 25 | 0 | T |
| AI580278 | UNKNOWN | 5 | 13 | CCCAG |
| AI580294 | UNKNOWN | 15.5 | 268 | AT |
| AI580296 | UNKNOWN | 18 | 0 | T |
| AI580353 | UNKnOWN | 25 | 136 | T |
| AI580353 | UNKNOWN | 13 | 323 | C |
| AI580434 | UNKNOWN | 16 | 0 | T |
| AI580435 | UNKNOWN | 98 | 0 | T |
| AI580435 | UNKNOWN | 33 | 219 | C |
| AI580435 | UNKNOWN | 18 | 274 | A |
| AI580435 | UNKNOWN | 13 | 121 | C |
| AI580435 | UNKNOWN | 12 | 315 | G |
| AI580436 | UNKNOWN | 78 | 0 | T |
| AI580436 | UNKNOWN | 12 | 326 | G |
| AI580451 | UNKNOWN | 66 | 0 | T |
| AI580451 | UNKNOWN | 13 | 141 | C |
| AI580464 | UNKNOWN | 12 | 0 | T |
| AI580510 | UNKNOWN | 26 | 0 | T |
| AI580513 | UNKNOWN | 30 | 0 | T |
| AI580514 | UNKNOWN | 15 | 0 | T |
| AI580601 | UNKNOWN | 29 | 194 | A |
| AI580605 | UNKNOWN | 24 | 67 | A |
| AI580669 | UNKNOWN | 5.5 | 3 | TTAT |
| AI580674 | UNKNOWN | 73 | 0 | T |
| AI580674 | UNKNOWN | 22 | 131 | G |
| AI580674 | UNKNOWN | 16 | 96 | C |
| AI580694 | UNKNOWN | 76 | 0 | T |
| AI580694 | UNKNOWN | 13 | 172 | C |
| AI580721 | UNKNOWN | 25 | 0 | T |
| AI580721 | UNKNOWN | 14 | 104 | A |
| AI580927 | UNKNOWN | 110 | 0 | T |
| AI580927 | UNKNOWN | 23 | 110 | C |
| AI580927 | UNKNOWN | 14 | 329 | A |
| AI580927 | UNKNOWN | 12 | 315 | G |
| AI580957 | UNKNOWN | 69 | 0 | T |
| AI580957 | UNKNOWN | 18 | 236 | A |
| AI580957 | UNKNOWN | 12 | 69 | A |
| AI580957 | UNKNOWN | 12 | 128 | C |
| AI580959 | UNKNOWN | 56 | 0 | T |
| AI580959 | UNKNOWN | 14 | 176 | G |

TABLE 1-continued

| Genbank # | Region | # reps | Position | Unit sequence |
|---|---|---|---|---|
| AI580984 | UNKNOWN | 118 | 0 | T |
| AI580984 | UNKNOWN | 19 | 164 | G |
| AI580984 | UNKNOWN | 19 | 203 | A |
| AI580984 | UNKNOWN | 12 | 150 | C |
| AI581003 | UNKNOWN | 30 | 0 | T |
| AI581031 | UNKNOWN | 54 | 0 | T |
| AI581031 | UNKNOWN | 13 | 136 | G |
| AI581048 | UNKNOWN | 98 | 0 | T |
| AI581048 | UNKNOWN | 14 | 98 | C |
| AI581048 | UNKNOWN | 13 | 135 | A |
| AI581053 | UNKNOWN | 46 | 0 | T |
| AI581061 | UNKNOWN | 41 | 0 | T |
| AI581100 | UNKNOWN | 77 | 0 | T |
| AI581100 | UNKNOWN | 14 | 297 | G |
| AI581121 | UNKNOWN | 19 | 0 | T |
| AI581124 | UNKNOWN | 15 | 0 | T |
| AI581139 | UNKNOWN | 63 | 0 | T |
| AI581139 | UNKNOWN | 16 | 96 | A |
| AI581142 | UNKNOWN | 15 | 0 | T |
| AI581223 | UNKNOWN | 18 | 191 | A |
| AI581228 | UNNNOWN | 19 | 128 | A |
| AI581285 | UNKNOWN | 16 | 0 | T |
| AI581362 | UNKNOWN | 63 | 0 | T |
| AI581362 | UNKNOWN | 14 | 103 | A |
| AI581362 | UNKNOWN | 14 | 358 | G |
| AI581362 | UNKNOWN | 12 | 151 | C |
| AI581369 | UNKNOWN | 39 | 0 | T |
| AI581387 | UNKNOWN | 49 | 0 | T |
| AI581413 | UNKNOWN | 80 | 0 | T |
| AI581413 | UNKNOWN | 15 | 186 | A |
| AI581413 | UNKNOWN | 12 | 91 | A |
| AI581732 | UNKNOWN | 34 | 0 | T |
| AI581857 | UNKNOWN | 34 | 0 | T |
| AI581880 | UNKNOWN | 35 | 0 | T |
| AI581880 | UNKNOWN | 13 | 226 | G |
| AI582203 | UNKNOWN | 46 | 0 | T |
| AI582233 | UNKNOWN | 14 | 77 | A |
| AI582240 | UNKNOWN | 56 | 0 | T |
| AI582391 | UNKNOWN | 50 | 0 | T |
| AI582391 | UNKNOWN | 17 | 146 | G |
| AI582391 | UNKNOWN | 15 | 219 | C |
| AI582391 | UNKNOWN | 12 | 96 | A |
| AI582396 | UNKNOWN | 50 | 0 | T |
| AI582396 | UNKNOWN | 20 | 143 | G |
| AI582413 | UNKNOWN | 72 | 0 | T |
| AI582413 | UNKNOWN | 17 | 239 | A |
| AI582413 | UNKNOWN | 12 | 72 | A |
| AI582413 | UNKNOWN | 12 | 131 | C |
| AI582417 | UNKNOWN | 46 | 0 | T |
| AI582428 | UNKNOWN | 26 | 0 | T |
| AI582434 | UNKNOWN | 47 | 0 | T |
| AI582455 | UNKNOWN | 46 | 0 | T |
| AI582461 | UNKNOWN | 46 | 0 | T |
| AI582483 | UNKNOWN | 76 | 0 | T |
| AI582483 | UNKNOWN | 13 | 185 | G |
| AI582483 | UNKNOWN | 12 | 108 | C |
| AI582499 | UNKNOWN | 14 | 207 | G |
| AI582499 | UNKNOWN | 12 | 139 | A |
| AI582516 | UNKNOWN | 58 | 0 | T |
| AI582516 | UNKNOWN | 12 | 134 | A |
| AI582522 | UNKNOWN | 49 | 0 | T |
| AI582544 | UNKNOWN | 22 | 244 | C |
| AI582544 | UNKNOWN | 21 | 266 | A |
| AI582544 | UNKNOWN | 17 | 7 | T |
| AI582544 | UNKNOWN | 17 | 161 | A |
| AI582544 | UNKNOWN | 16 | 304 | G |
| AI582544 | UNKNOWN | 13 | 203 | C |
| AI582544 | UNKNOWN | 12 | 145 | A |
| AI582547 | UNKNOWN | 68 | 0 | T |
| AI582547 | UNKNOWN | 18 | 304 | A |
| AI582547 | UNKNOWN | 16 | 249 | A |
| AI582547 | UNKNOWN | 12 | 74 | A |
| AI582551 | UNKNOWN | 47 | 0 | T |
| AI582557 | UNKNOWN | 25 | 11 | T |
| AI582558 | UNKNOWN | 97 | 0 | T |
| AI582558 | UNKNOWN | 20 | 142 | C |
| AI582558 | UNKNOWN | 19 | 199 | G |

TABLE 1-continued

| Genbank # | Region | # reps | Position | Unit sequence |
|---|---|---|---|---|
| AI582558 | UNKNOWN | 13 | 121 | A |
| AI582611 | UNKNOWN | 12 | 56 | A |
| AI582632 | UNKNOWN | 14 | 0 | T |
| AI582635 | UNKNOWN | 15 | 136 | T |
| AI582635 | UNKNOWN | 15 | 265 | A |
| AI582778 | UNKNOWN | 24 | 0 | T |
| AI582817 | UNKNOWN | 18 | 342 | A |
| AI582818 | UNKNOWN | 17 | 342 | AC |
| AI582818 | UNKNOWN | 8 | 107 | GA |
| AI582822 | UNKNOWN | 45 | 0 | T |
| AI582822 | UNNNOWN | 18 | 104 | G |
| AI582871 | UNKNOWN | 68 | 0 | T |
| AI582871 | UNKNOWN | 24 | 98 | A |
| AI582900 | UNKNOWN | 57 | 0 | T |
| AI582928 | UNKNOWN | 21 | 11 | T |
| AI582928 | UNKNOWN | 14 | 89 | A |
| AI582941 | UNKNOWN | 20 | 0 | T |
| AI582966 | UNKNOWN | 60 | 0 | T |
| AI583022 | UNKNOWN | 40 | 0 | T |
| AI583032 | UNKNOWN | 59 | 0 | T |
| AI583054 | UNKNOWN | 80 | 0 | T |
| AI583054 | UNKNOWN | 14 | 139 | G |
| AI583064 | UNKNOWN | 21 | 0 | T |
| AI583065 | UNKNOWN | 105 | 0 | T |
| AI583065 | UNKNOWN | 26 | 269 | A |
| AI583065 | UNKNOWN | 21 | 107 | A |
| AI583067 | UNKNOWN | 39 | 0 | T |
| AI583085 | UNKNOWN | 79 | 0 | T |
| AI583085 | UNKNOWN | 20 | 84 | A |
| AI583085 | UNKNOWN | 16 | 283 | C |
| AI583085 | UNKNOWN | 12 | 125 | G |
| AI583164 | UNKNOWN | 45 | 0 | T |
| AI583167 | UNKNOWN | 22 | 46 | T |
| AI583167 | UNKNOWN | 16 | 0 | T |
| AI583167 | UNKNOWN | 15 | 111 | G |
| AI583167 | UNKNOWN | 14 | 215 | C |
| AI583167 | UNKNOWN | 13 | 150 | A |
| AI583168 | UNKNOWN | 26 | 0 | T |
| AI583205 | UNKNOWN | 19 | 0 | T |
| AI583255 | UNKNOWN | 17 | 163 | A |
| AI583265 | UNKNOWN | 28 | 72 | A |
| AI583266 | UNKNOWN | 29 | 137 | A |
| AI583300 | UNKNOWN | 15 | 109 | A |
| AI583308 | UNKNOWN | 94 | 0 | T |
| AI583308 | UNKNOWN | 16 | 105 | A |
| AI583308 | UNKNOWN | 14 | 243 | G |
| AI583316 | UNKNOWN | 130 | 0 | T |
| AI583316 | UNKNOWN | 20 | 182 | G |
| AI583316 | UNKNOWN | 15 | 152 | A |
| AI583353 | UNKNOWN | 18 | 252 | A |
| AI583374 | UNKNOWN | 28 | 107 | A |
| AI583375 | UNKNOWN | 32 | 140 | A |
| AI583399 | UNKNOWN | 40 | 0 | T |
| AI583423 | UNKNOWN | 75 | 0 | T |
| AI583425 | UNKNOWN | 21 | 0 | T |
| AI583442 | UNKNOWN | 19 | 203 | A |
| AI583448 | UNKNOWN | 24 | 379 | A |
| AI583533 | UNKNOWN | 78 | 0 | T |
| AI583533 | UNKNOWN | 12 | 78 | A |
| AI583533 | UNKNOWN | 12 | 183 | G |
| AI583558 | UNKNOWN | 64 | 0 | T |
| AI583558 | UNKNOWN | 14 | 148 | A |
| AI583567 | UNKNOWN | 57 | 0 | T |
| AI583578 | UNKNOWN | 59 | 0 | T |
| AI583600 | UNKNOWN | 21 | 38 | T |
| AI583600 | UNKNOWN | 19 | 12 | T |
| AI583600 | UNKNOWN | 18 | 283 | A |
| AI583600 | UNKNOWN | 15 | 268 | C |
| AI583607 | UNKNOWN | 23 | 0 | T |
| AI583611 | UNKNOWN | 63 | 7 | T |
| AI583611 | UNKNOWN | 18 | 385 | G |
| AI583626 | UNKNOWN | 30 | 114 | A |
| AI583632 | UNKNOWN | 30 | 176 | A |
| AI583637 | UNKNOWN | 8 | 8 | CTA |
| AI583637 | UNKNOWN | 13 | 372 | A |
| AI583647 | UNKNOWN | 29 | 212 | A |
| AI583662 | UNKNOWN | 28 | 296 | A |

TABLE 1-continued

| Genbank # | Region | # reps | Position | Unit sequence |
|---|---|---|---|---|
| AI583750 | UNKNOWN | 12 | 104 | TG |
| AI583750 | UNKNOWN | 29 | 375 | A |
| AI583763 | UNKNOWN | 30 | 144 | A |
| AI583778 | UNKNOWN | 23 | 130 | A |
| AI583801 | UNKNOWN | 22 | 154 | A |
| AI583811 | UNKNOWN | 30 | 232 | A |
| AI583850 | UNKNOWN | 22 | 120 | A |
| AI583858 | UNKNOWN | 23 | 372 | A |
| AI583874 | UNKNOWN | 27 | 132 | A |
| AI583890 | UNKNOWN | 28 | 383 | A |
| AI583916 | UNKNOWN | 17 | 404 | A |
| AI583936 | UNKNOWN | 38 | 164 | T |
| AI583947 | UNKNOWN | 43 | 0 | T |
| AI583961 | UNKNOWN | 80 | 0 | T |
| AI583966 | UNKNOWN | 44 | 0 | T |
| AI583982 | UNKNOWN | 61 | 0 | T |
| AI583982 | UNKNOWN | 12 | 101 | G |
| AI584014 | UNKNOWN | 20 | 0 | T |
| AI584066 | UNKNOWN | 51 | 0 | T |
| AI584118 | UNKNOWN | 52 | 0 | T |
| AI584128 | UNKNOWN | 63 | 0 | T |
| AI584128 | UNKNOWN | 13 | 233 | C |
| AI584140 | UNKNOWN | 96 | 0 | T |
| AI584140 | UNKNOWN | 12 | 154 | C |
| AI584153 | UNKNOWN | 69 | 0 | T |
| AI584159 | UNKNOWN | 61 | 0 | T |
| AI586931 | UNKNOWN | 59 | 0 | T |
| AI586937 | UNKNOWN | 15 | 0 | T |
| AI586938 | UNKNOWN | 26 | 0 | T |
| AI586945 | UNKNOWN | 21 | 0 | T |
| AI586955 | UNKNOWN | 12 | 187 | T |
| AI586984 | UNKNOWN | 92 | 0 | T |
| AI586984 | UNKNOWN | 20 | 212 | A |
| AI586984 | UNKNOWN | 15 | 292 | C |
| AI587000 | UNKNOWN | 55 | 0 | T |
| AI587001 | UNKNOWN | 30 | 0 | T |
| AI587001 | UNKNOWN | 13 | 78 | A |
| AI587006 | UNKNOWN | 16 | 0 | T |
| AI587032 | UNKNOWN | 16 | 0 | T |
| AI587040 | UNKNOWN | 15 | 0 | T |
| AI587049 | UNKNOWN | 55 | 0 | T |
| AI587056 | UNKNOWN | 94 | 0 | T |
| AI587056 | UNKNOWN | 13 | 119 | A |
| AI587114 | UNKNOWN | 116 | 0 | T |
| AI587114 | UNKNOWN | 20 | 116 | A |
| AI587114 | UNKNOWN | 14 | 174 | G |
| AI587114 | UNKNOWN | 13 | 268 | C |
| AI587114 | UNKNOWN | 12 | 212 | C |
| AI587117 | UNKNOWN | 50 | 0 | T |
| AI587121 | UNKNOWN | 67 | 0 | T |
| AI587143 | UNKNOWN | 97 | 0 | T |
| AI587143 | UNKNOWN | 29 | 234 | G |
| AI587143 | UNKNOWN | 17 | 133 | G |
| AI587143 | UNKNOWN | 15 | 219 | A |
| AI587143 | UNKNOWN | 12 | 102 | A |
| AI587153 | UNJJNOWN | 75 | 20 | T |
| AI587153 | UNKNOWN | 14 | 121 | A |
| AI587153 | UNKNOWN | 14 | 282 | C |
| AI587156 | UNKNOWN | 80 | 0 | T |
| AI587156 | UNKNOWN | 13 | 227 | G |
| AI587209 | UNKNOWN | 56 | 0 | T |
| AI587209 | UNKNOWN | 12 | 104 | A |
| AI587233 | UNKNOWN | 21 | 0 | T |
| AI587279 | UNKNOWN | 77 | 0 | T |
| AI587279 | UNKNOWN | 17 | 250 | A |
| AI587288 | UNKNOWN | 104 | 0 | T |
| AI587288 | UNKNOWN | 14 | 167 | C |
| AI587289 | UNKNOWN | 79 | 0 | T |
| AI587289 | UNKNOWN | 19 | 191 | G |
| AI587289 | UNKNOWN | 15 | 125 | A |
| AI587289 | UNKNOWN | 15 | 327 | C |
| AI587292 | UNKNOWN | 17 | 50 | A |
| AI587292 | UNKNOWN | 12 | 0 | T |
| AI587301 | UNKNOWN | 54 | 0 | T |
| AI587302 | UNKNOWN | 63 | 0 | T |
| AI587302 | UNKNOWN | 21 | 110 | A |
| AI587326 | UNKNOWN | 44 | 0 | T |

TABLE 1-continued

| Genbank # | Region | # reps | Position | Unit sequence |
|---|---|---|---|---|
| AI587394 | UNKNOWN | 14 | 16 | A |
| AI587441 | UNKNOWN | 57 | 0 | T |
| AI587466 | UNKNOWN | 68 | 0 | T |
| AI587489 | UNKNOWN | 61 | 0 | T |
| AI587499 | UNKNOWN | 17 | 0 | T |
| AI587510 | UNKNOWN | 14 | 0 | T |
| AI587606 | UNKNOWN | 84 | 0 | T |
| AI587606 | UNKNOWN | 12 | 129 | G |
| AI587619 | UNKNOWN | 55 | 0 | T |
| AI587664 | UNKNOWN | 78 | 0 | T |
| AI588839 | UNKNOWN | 39 | 0 | T |
| AI588850 | UNKNOWN | 50 | 0 | T |
| AI588891 | UNKNOWN | 57 | 0 | T |
| AI588892 | UNKNOWN | 70 | 0 | T |
| AI588892 | UNKNOWN | 21 | 149 | C |
| AI588892 | UNKNOWN | 13 | 129 | A |
| AI588926 | UNKNOWN | 18 | 0 | T |
| AI588928 | UNKNOWN | 14 | 145 | A |
| AI588977 | UNKNOWN | 5.75 | 406 | AAAC |
| AI589004 | UNKNOWN | 66 | 0 | T |
| AI589004 | UNKNOWN | 18 | 159 | G |
| AI589081 | UNKNOWN | 58 | 0 | T |
| AI589081 | UNKNOWN | 14 | 80 | C |
| AI589081 | UNKNOWN | 13 | 108 | G |
| AI589091 | UNKNOWN | 50 | 0 | T |
| AI589097 | UNKNOWN | 33 | 0 | T |
| AI589127 | UNKNOWN | 20 | 0 | T |
| AI589134 | UNKNOWN | 64 | 0 | T |
| AI589134 | UNKNOWN | 18 | 158 | G |
| AI589140 | UNKNOWN | 56 | 0 | T |
| AI589196 | UNKNOWN | 48 | 0 | T |
| AI589212 | UNKNOWN | 17 | 417 | A |
| AI589218 | UNKNOWN | 85 | 0 | T |
| AI589218 | UNKNOWN | 13 | 324 | G |
| AI589261 | UNKNOWN | 89 | 1 | T |
| AI589261 | UNKNOWN | 14 | 270 | A |
| AI589267 | UNKNOWN | 92 | 0 | T |
| AI589267 | UNKNOWN | 14 | 99 | G |
| AI589267 | UNKNOWN | 13 | 138 | A |
| AI589273 | UNKNOWN | 85 | 0 | T |
| AI589273 | UNKNOWN | 17 | 12B | A |
| AI589273 | UNKNOWN | 15 | 210 | G |
| AI589273 | UNKNOWN | 12 | 145 | C |
| AI589295 | UNKNOWN | 3.6 | 177 | GGGGC |
| AI589295 | UNKNOWN | 12 | 111 | A |
| AI589329 | UNKNOWN | 42 | 0 | T |
| AI589365 | UNKNOWN | 30 | 0 | T |
| AI589370 | UNKNOWN | 5 | 151 | CAAAA |
| AI589370 | UNKNOWN | 16 | 0 | T |
| AI589378 | UNKNOWN | 28 | 0 | T |
| AI589380 | UNKNOWN | 35 | 0 | T |
| AI589389 | UNKNOWN | 78 | 0 | T |
| AI589389 | UNKNOWN | 14 | 172 | A |
| AI589389 | UNKNOWN | 13 | 140 | A |
| AI589391 | UNKNOWN | 75 | 0 | T |
| AI589391 | UNKNOWN | 15 | 149 | C |
| AI589427 | UNKNOWN | 44 | 0 | T |
| AI589450 | UNKNOWN | 26.5 | 185 | AT |
| AI589450 | UNKNOWN | 45 | 0 | T |
| AI589450 | UNKNOWN | 15 | 171 | A |
| AI589535 | UNKNOWN | 19 | 0 | T |
| AI589535 | UNKNOWN | 19 | 90 | A |
| AI589567 | UNKNOWN | 44 | 0 | T |
| AI589570 | UNKNOWN | 21 | 335 | T |
| AI589658 | UNKNOWN | 12 | 2 | A |
| AI589668 | UNKNOWN | 68 | 0 | T |
| AI589668 | UNKNOWN | 12 | 171 | G |
| AI589803 | UNKNOWN | 29 | 0 | T |
| AI589851 | UNKNOWN | 5 | 157 | GCTCAAGGCTCACGGGCTGAGGTCTGTCCCCGCGTGGA (SEQ ID NO:128) |
| AI589867 | UNKNOWN | 19 | 0 | T |
| AI589889 | UNKNOWN | 45 | 0 | T |
| AI589947 | UNKNOWN | 77 | 0 | T |
| AI589998 | UNKNOWN | 114 | 0 | T |
| AI589998 | UNKNOWN | 20 | 141 | G |
| AI589998 | UNKNOWN | 14 | 168 | C |
| AI590020 | UNKNOWN | 65 | 0 | T |

TABLE 1-continued

| Genbank # | Region | # reps | Position | Unit sequence |
|---|---|---|---|---|
| AI590020 | UNKNOWN | 14 | 225 | G |
| AI590021 | UNKNOWN | 108 | 0 | T |
| AI590021 | UNKNOWN | 34 | 112 | A |
| AI590021 | UNKNOWN | 12 | 316 | C |
| AI590024 | UNKNOWN | 45 | 0 | T |
| AI590048 | UNKNOWN | 50 | 0 | T |
| AI590053 | UNKNOWN | 12 | 0 | T |
| AI590118 | UNKNOWN | 101 | 0 | T |
| AI590118 | UNKNOWN | 21 | 146 | C |
| AI590118 | UNKNOWN | 19 | 203 | G |
| AI590118 | UNKNOWN | 13 | 126 | A |
| AI590120 | UNKNOWN | 108 | 0 | T |
| AI590120 | UNKNOWN | 21 | 176 | G |
| AI590128 | UNKNOWN | 124 | 0 | T |
| AI590128 | UNKNOWN | 20 | 250 | G |
| AI590128 | UNKNOWN | 17 | 199 | C |
| AI590128 | UNKNOWN | 13 | 133 | A |
| AI590128 | UNKNOWN | 13 | 219 | G |
| AI590134 | UNKNOWN | 82 | 0 | T |
| AI590227 | UNKNOWN | 108 | 0 | T |
| AI590227 | UNKNOWN | 21 | 167 | A |
| AI590227 | UNKNOWN | 17 | 130 | G |
| AI590247 | UNKNOWN | 31 | 162 | A |
| AI590255 | UNKNOWN | 24 | 358 | A |
| AI590337 | UNKNOWN | 12 | 0 | T |
| AI590376 | UNKNOWN | 50 | 0 | T |
| AI590385 | UNKNOWN | 47 | 0 | T |
| AI590401 | UNKNOWN | 19 | 0 | T |
| AI590403 | UNKNOWN | 38 | 0 | T |
| AI590415 | UNKNOWN | 109 | 0 | T |
| AI590415 | UNKNOWN | 17 | 324 | A |
| AI590415 | UNKNOWN | 16 | 154 | C |
| AI590415 | UNKNOWN | 12 | 341 | G |
| AI590423 | UNKNOWN | 88 | 0 | T |
| AI590442 | UNKNOWN | 24 | 342 | A |
| AI590459 | UNKNOWN | 20 | 309 | A |
| AI590459 | UNKNOWN | 16 | 133 | A |
| AI590465 | UNKNOWN | 28 | 211 | A |
| AI590471 | UNKNOWN | 22 | 291 | A |
| AI590476 | UNKNOWN | 30 | 352 | A |
| AI590479 | UNKNOWN | 21 | 319 | A |
| AI590485 | UNKNOWN | 29 | 335 | A |
| AI590499 | UNKNOWN | 24 | 389 | A |
| AI590522 | UNKNOWN | 33 | 318 | A |
| AI590522 | UNKNOWN | 16 | 154 | A |
| AI590530 | UNKNOWN | 102 | 0 | T |
| AI590530 | UNKNOWN | 13 | 110 | A |
| AI590533 | UNKNOWN | 36 | 0 | T |
| AI590549 | UNKNOWN | 44 | 0 | T |
| AI590575 | UNKNOWN | 62 | 0 | T |
| AI590575 | UNKNOWN | 17 | 81 | A |
| AI590600 | UNKNOWN | 38 | 0 | T |
| AI590600 | UNKNOWN | 15 | 53 | A |
| AI590601 | UNKNOWN | 99 | 0 | T |
| AI590601 | UNKNOWN | 18 | 152 | G |
| AI590603 | UNKNOWN | 107 | 0 | T |
| AI590603 | UNKNOWN | 15 | 182 | A |
| AI590603 | UNKNOWN | 12 | 123 | C |
| AI590615 | UNKNOWN | 18 | 308 | GT |
| AI590616 | UNKNOWN | 41 | 0 | T |
| AI590624 | UNKNOWN | 81 | 1 | T |
| AI590630 | UNKNOWN | 80 | 0 | T |
| AI590630 | UNKNOWN | 14 | 123 | C |
| AI590632 | UNKNOWN | 99 | 0 | T |
| AI590632 | UNKNOWN | 19 | 287 | C |
| AI590632 | UNKNOWN | 15 | 161 | A |
| AI590635 | UNKNOWN | 103 | 0 | T |
| AI590635 | UNKNOWN | 16 | 377 | c |
| AI590635 | UNKNOWN | 12 | 237 | C |
| AI590635 | UNKNOWN | 12 | 264 | G |
| AI590645 | UNKNOWN | 109 | 0 | T |
| AI590645 | UNKNOWN | 15 | 380 | C |
| AI590686 | UNKNOWN | 79 | 0 | T |
| AI590686 | UNNNOWN | 23 | 162 | G |
| AI590702 | UNKNOWN | 65 | 0 | T |
| AI590737 | UNKNOWN | 24 | 0 | T |
| AI590738 | UNKNOWN | 51 | 0 | T |

TABLE 1-continued

| Genbank # | Region | # reps | Position | Unit sequence |
|---|---|---|---|---|
| AI590761 | UNKNOWN | 110 | 0 | T |
| AI590761 | UNKNOWN | 26 | 370 | C |
| AI590761 | UNNNOWN | 15 | 240 | C |
| AI590764 | UNKNOWN | 84 | 0 | T |
| AI590764 | UNKNOWN | 13 | 361 | C |
| AI590764 | UNKNOWN | 12 | 289 | G |
| AI590781 | UNKNOWN | 70 | 0 | T |
| AI590785 | UNNNOWN | 100 | 0 | T |
| AI590785 | UNKNOWN | 20 | 323 | C |
| AI590785 | UNKNOWN | 18 | 148 | A |
| AI590785 | UNKNOWN | 12 | 582 | G |
| AI590787 | UNKNOWN | 84 | 0 | T |
| AI590787 | UNKNOWN | 25 | 377 | C |
| AI590787 | UNKNOWN | 12 | 247 | C |
| AI590830 | UNKNOWN | 89 | 0 | T |
| AI590830 | UNKNOWN | 15 | 173 | G |
| AI590860 | UNKNOWN | 51 | 0 | T |
| AI590864 | UNKNOWN | 49 | 0 | T |
| AI590878 | UNKNOWN | 11 | 428 | CA |
| AI590879 | UNKNOWN | 13 | 0 | T |
| AI590906 | UNKNOWN | 16 | 300 | A |
| AI590914 | UNKNOWN | 4.5 | 163 | ACAA |
| AI590918 | UNKNOWN | 43 | 0 | T |
| AI590943 | UNKNOWN | 65 | 0 | T |
| AI590954 | UNKNOWN | 40 | 0 | T |
| AI590979 | UNKNOWN | 21 | 0 | T |
| AI590982 | UNKNOWN | 22 | 44 | AC |
| AI590997 | UNKNOWN | 63 | 0 | T |
| AI590997 | UNKNOWN | 19 | 205 | C |
| AI590997 | UNKNOWN | 14 | 369 | G |
| AI590999 | UNKNOWN | 105 | 0 | T |
| AI590999 | UNKNOWN | 18 | 211 | G |
| AI590999 | UNKNOWN | 12 | 191 | G |
| AI591025 | UNKNOWN | 79 | 0 | T |
| AI591025 | UNKNOWN | 16 | 161 | C |
| AI591046 | UNKNOWN | 51 | 0 | T |
| AI591049 | UNKNOWN | 15 | 0 | T |
| AI591050 | UNKNOWN | 25 | 0 | T |
| AI591053 | UNKNOWN | 48 | 0 | T |
| AI591056 | UNKNOWN | 30 | 0 | T |
| AI591057 | UNKNOWN | 82 | 0 | T |
| AI591057 | UNKNOWN | 16 | 351 | C |
| AI591070 | UNKNOWN | 36 | 0 | T |
| AI591073 | UNKNOWN | 118 | 0 | T |
| AI591073 | UNKNOWN | 13 | 118 | C |
| AI591073 | UNKNOWN | 12 | 331 | G |
| AI591074 | UNKNOWN | 112 | 0 | T |
| AI591074 | UNKNOWN | 16 | 241 | C |
| AI591075 | UNKNOWN | 99 | 0 | T |
| AI591075 | UNKNOWN | 16 | 99 | A |
| AI591075 | UNKNOWN | 14 | 306 | G |
| AI591076 | UNKNOWN | 57 | 29 | T |
| AI591076 | UNKNOWN | 26 | 0 | T |
| AI591076 | UNKNOWN | 12 | 286 | G |
| AI591101 | UNKNOWN | 66 | 0 | T |
| AI591110 | UNKNOWN | 19 | 0 | T |
| AI591129 | UNKNOWN | 26 | 26 | A |
| AI591182 | UNKNOWN | 12 | 0 | T |
| AI591201 | UNKNOWN | 73 | 0 | T |
| AI591201 | UNKNOWN | 14 | 142 | A |
| AI591201 | UNKNOWN | 12 | 97 | G |
| AI591201 | UNKNOWN | 12 | 156 | C |
| AI591203 | UNKNOWN | 4.75 | 163 | TTTG |
| AI591213 | UNKNOWN | 24 | 0 | T |
| AI591216 | UNKNOWN | 19 | 0 | T |
| AI591221 | UNKNOWN | 22 | 0 | T |
| AI591228 | UNKNOWN | 91 | 0 | T |
| AI591228 | UNKNOWN | 14 | 178 | G |
| AI591251 | UNKNOWN | 31 | 169 | A |
| AI591256 | UNKNOWN | 16 | 244 | A |
| AI591310 | UNKNOWN | 77 | 1 | T |
| AI591311 | UNKNOWN | 121 | 2 | T |
| AI591311 | UNKNOWN | 18 | 210 | C |
| AI591311 | UNKNOWN | 12 | 160 | G |
| AI591316 | UNKNOWN | 105 | 2 | T |
| AI591318 | UNKNOWN | 15 | 0 | T |
| AI591319 | UNKNOWN | 15 | 0 | T |

TABLE 1-continued

| Genbank # | Region | # reps | Position | Unit sequence |
|---|---|---|---|---|
| AI591387 | UNKNOWN | 73 | 0 | T |
| AI591387 | UNKNOWN | 16 | 73 | A |
| AI591387 | UNKNOWN | 12 | 192 | G |
| AI591407 | UNKNOWN | 87 | 0 | T |
| AI591407 | UNKNOWN | 15 | 169 | A |
| AI591420 | UNKNOWN | 89 | 0 | T |
| AI591420 | UNKNOWN | 14 | 174 | G |
| AI591420 | UNKNOWN | 14 | 209 | C |
| AI591420 | UNKNOWN | 13 | 112 | A |
| AI597604 | UNKNOWN | 39 | 0 | T |
| AI597604 | UNKNOWN | 16 | 405 | A |
| AI597645 | UNKNOWN | 27 | 20 | T |
| AI597645 | UNKNOWN | 18 | 135 | A |
| AI597651 | UNKNOWN | 15 | 159 | A |
| AI597685 | UNKNOWN | 7.5 | 239 | AC |
| AI597707 | UNKNOWN | 42 | 0 | T |
| AI597731 | UNKNOWN | 85 | 0 | T |
| AI597731 | UNKNOWN | 14 | 256 | A |
| AI597731 | UNKNOWN | 14 | 287 | C |
| AI597738 | UNKNOWN | 90 | 0 | T |
| AI597738 | UNKNOWN | 16 | 137 | G |
| AI597738 | UNKNOWN | 15 | 318 | C |
| AI597738 | UNKNOWN | 12 | 185 | C |
| AI597748 | UNKNOWN | 58 | 0 | T |
| AI597748 | UNKNOWN | 12 | 384 | C |
| AI597750 | UNKNOWN | 122 | 0 | T |
| AI597750 | UNKNOWN | 17 | 260 | G |
| AI597750 | UNKNOWN | 13 | 277 | C |
| AI597805 | UNKNOWN | 67 | 0 | T |
| AI597810 | UNKNOWN | 2.87 | 151 | ATATTACATAATATTTTAAAAAGCACTTACATAAGAAGAAT (SEQ ID NO:129) |
| AI597860 | UNKNOWN | 14 | 0 | T |
| AI597866 | UNKNOWN | 28 | 0 | T |
| AI597894 | UNKNOWN | 18 | 0 | T |
| AI597918 | UNKNOWN | 128 | 0 | T |
| AI597918 | UNKNOWN | 29 | 336 | A |
| AI597918 | UNKNOWN | 18 | 388 | C |
| AI597918 | UNKNOWN | 15 | 181 | G |
| AI597918 | UNKNOWN | 14 | 196 | C |
| AI597931 | UNKNOWN | 5.8 | 298 | AAAAC |
| AI597931 | UNKNOWN | 22 | 349 | A |
| AI597931 | UNKNOWN | 14 | 150 | T |
| AI597952 | UNKNOWN | 37 | 0 | T |
| AI597953 | UNKNOWN | 81 | 0 | T |
| AI597953 | UNKNOWN | 13 | 106 | C |
| AI598001 | UNKNOWN | 17 | 11 | T |
| AI598010 | UNKNOWN | 23 | 0 | T |
| AI598017 | UNKNOWN | 49 | 0 | T |
| AI598017 | UNKNOWN | 12 | 54 | A |
| AI598026 | UNKNOWN | 25 | 0 | T |
| AI598058 | UNKNOWN | 57 | 0 | T |
| AI598058 | UNKNOWN | 17 | 116 | G |
| AI598061 | UNKNOWN | 104 | 0 | T |
| AI598061 | UNKNOWN | 15 | 192 | G |
| AI598067 | UNKNOWN | 46 | 0 | T |
| AI598113 | UNKNOWN | 73 | 0 | T |
| AI598113 | UNKNOWN | 12 | 80 | G |
| AI598209 | UNKNOWN | 54 | 0 | T |
| AI598218 | UNKNOWN | 36 | 0 | T |
| AI598222 | UNKNOWN | 19 | 0 | T |
| AI598222 | UNKNOWN | 12 | 20 | A |
| AI598253 | UNKNOWN | 28 | 0 | T |
| AI608655 | UNKNOWN | 39 | 0 | T |
| AI608655 | UNKNOWN | 12 | 76 | A |
| AI608667 | UNKNOWN | 132 | 0 | T |
| AI608667 | UNKNOWN | 17 | 149 | G |
| AI608667 | UNKNOWN | 12 | 137 | A |
| AI608667 | UNKNOWN | 12 | 195 | C |
| AI608676 | UNKNOWN | 90 | 0 | T |
| AI608676 | UNKNOWN | 12 | 192 | C |
| AI608678 | UNKNOWN | 28 | 0 | T |
| AI608711 | UNKNOWN | 54 | 0 | T |
| AI608743 | UNKNOWN | 57 | 0 | T |
| AI608781 | UNKNOWN | 16 | 0 | T |
| AI608807 | UNKNOWN | 52 | 0 | T |
| AI608813 | UNKNOWN | 87 | 0 | T |
| AI608813 | UNKNOWN | 12 | 140 | G |

TABLE 1-continued

| Genbank # | Region | # reps | Position | Unit sequence |
|---|---|---|---|---|
| AI608858 | UNKNOWN | 18 | 0 | T |
| AI608882 | UNKNOWN | 48 | 0 | T |
| AI608917 | UNKNOWN | 44 | 0 | T |
| AI608917 | UNKNOWN | 12 | 146 | G |
| AI608932 | UNKNOWN | 81 | 0 | T |
| AI608932 | UNKNOWN | 19 | 301 | A |
| AI608932 | UNKNOWN | 17 | 181 | C |
| AI608936 | UNKNOWN | 102 | 0 | T |
| AI608950 | UNKNOWN | 7 | 228 | TA |
| AI608950 | UNKNOWN | 64 | 0 | T |
| AI608950 | UNKNOWN | 15 | 164 | A |
| AI608970 | UNKNOWN | 70 | 0 | T |
| AI609047 | UNKNOWN | 39 | 0 | T |
| AI609047 | UNKNOWN | 18 | 208 | G |
| AI609059 | UNKNOWN | 100 | 1 | T |
| AI609059 | UNKNOWN | 15 | 371 | C |
| AI609063 | UNKNOWN | 47 | 0 | T |
| AI609069 | UNKNOWN | 77 | 0 | T |
| AI609070 | UNKNOWN | 36 | 0 | T |
| AI609076 | UNKNOWN | 18 | 0 | T |
| AI609127 | UNKNOWN | 91 | 0 | T |
| AI609127 | UNKNOWN | 15 | 179 | A |
| AI609127 | UNKNOWN | 15 | 200 | G |
| AI609128 | UNKNOWN | 79 | 0 | T |
| AI609128 | UNKNOWN | 14 | 345 | A |
| AI609128 | UNKNQWN | 13 | 143 | C |
| AI609140 | UNKNOWN | 29 | 0 | T |
| AI609143 | UNKNOWN | 10.5 | 118 | TA |
| AI609143 | UNKNOWN | 21 | 0 | T |
| AI609179 | UNKNOWN | 48 | 0 | T |
| AI609181 | UNKNOWN | 62 | 0 | T |
| AI609181 | UNKNOWN | 15 | 116 | A |
| AI609181 | UNKNOWN | 12 | 138 | C |
| AI609190 | UNKNOWN | 111 | 0 | T |
| AI609190 | UNKNOWN | 15 | 124 | G |
| AI609190 | UNKNOWN | 13 | 111 | C |
| AI609195 | UNKNOWN | 50 | 0 | T |
| AI609196 | UNKNOWN | 79 | 0 | T |
| AI609196 | UNKNOWN | 22 | 225 | A |
| AI609196 | UNKNOWN | 17 | 205 | C |
| AI609199 | UNKNOWN | 108 | 0 | T |
| AI609199 | UNKNOWN | 15 | 157 | C |
| AI609211 | UNKNOWN | 43 | 0 | T |
| AI609236 | UNKNOWN | 76 | 0 | T |
| AI609254 | UNKNOWN | 20 | 0 | T |
| AI609254 | UNKNOWN | 12 | 90 | A |
| AI609285 | UNKNOWN | 27 | 193 | T |
| AI609307 | UNKNOWN | 50 | 0 | T |
| AI609326 | UNKNOWN | 52 | 0 | T |
| AI609331 | UNKNOWN | 70 | 0 | T |
| AI609331 | UNKNOWN | 17 | 252 | G |
| AI609331 | UNKNOWN | 16 | 218 | C |
| AI609331 | UNKNOWN | 14 | 153 | A |
| AI609342 | UNKNOWN | 14 | 0 | T |
| AI609360 | UNKNOWN | 84 | 0 | T |
| AI609365 | UNKNOWN | 81 | 0 | T |
| AI609367 | UNKNOWN | 3.8 | 164 | AAAAC |
| AI609367 | UNKNOWN | 10.5 | 42 | TG |
| AI609374 | UNKNOWN | 3.83 | 8 | ATTTTA |
| AI609375 | UNKNOWN | 97 | 0 | T |
| AI609375 | UNKNOWN | 18 | 198 | C |
| AI609375 | UNKNOWN | 17 | 97 | A |
| AI609375 | UNKNOWN | 12 | 227 | G |
| AI609409 | UNKNOWN | 89 | 0 | T |
| AI609409 | UNKNOWN | 19 | 117 | A |
| AI609409 | UNKNOWN | 16 | 212 | G |
| AI609409 | UNKNOWN | 12 | 230 | C |
| AI609433 | UNKNOWN | 25 | 161 | A |
| AI609455 | UNKNOWN | 24 | 52 | A |
| AI609470 | UNKNOWN | 29 | 67 | A |
| AI609506 | UNKNOWN | 22 | 0 | T |
| AI609556 | UNKNOWN | 88 | 0 | T |
| AI609559 | UNKNOWN | 33 | 0 | T |
| AI609572 | UNKNOWN | 26 | 0 | T |
| AI609580 | UNKNOWN | 109 | 0 | T |
| AI609580 | UNKNOWN | 20 | 179 | C |
| AI609580 | UNKNOWN | 15 | 129 | A |

TABLE 1-continued

| Genbank # | Region | # reps | Position | Unit sequence |
|---|---|---|---|---|
| AI609580 | UNKNOWN | 12 | 303 | G |
| AI609589 | UNKNOWN | 111 | 1 | T |
| AI609589 | UNKNOWN | 19 | 302 | C |
| AI609589 | UNKNOWN | 17 | 165 | A |
| AI609591 | UNKNOWN | 18 | 0 | T |
| AI609592 | UNKNOWN | 131 | 1 | T |
| AI609592 | UNKNOWN | 27 | 239 | C |
| AI609592 | UNKNOWN | 24 | 189 | A |
| AI609592 | UNKNOWN | 23 | 214 | G |
| AI609593 | UNKNOWN | 110 | 0 | T |
| AI609593 | UNKNOWN | 15 | 112 | G |
| AI609594 | UNKNOWN | 101 | 0 | T |
| AI609594 | UNKNOWN | 16 | 131 | C |
| AI609594 | UNKNOWN | 14 | 117 | A |
| AI609594 | UNKNOWN | 13 | 281 | G |
| AI609677 | UNKNOWN | 97 | 0 | T |
| AI609677 | UNKNOWN | 15 | 367 | C |
| AI609684 | UNKNOWN | 104 | 1 | T |
| AI609684 | UNKNOWN | 14 | 302 | C |
| AI609689 | UNKNOWN | 44 | 0 | T |
| AI609696 | UNKNOWN | 18 | 0 | T |
| AI609716 | UNKNOWN | 22 | 358 | T |
| AI609716 | UNKNOWN | 13 | 33 | T |
| AI609760 | UNKNOWN | 67 | 0 | T |
| AI609773 | UNKNOWN | 42 | 0 | T |
| AI609791 | UNKNOWN | 13 | 374 | A |
| AI609793 | UNKNOWN | 24 | 13 | T |
| AI609793 | UNKNOWN | 24 | 356 | A |
| AI609793 | UNKNOWN | 12 | 0 | T |
| AI609824 | UNKNOWN | 49 | 0 | T |
| AI609824 | UNKNOWN | 14 | 200 | G |
| AI609876 | UNKNOWN | 27 | 333 | A |
| AI609880 | UNKNOWN | 26 | 170 | A |
| AI609901 | UNKNOWN | 17 | 182 | A |
| AI609911 | UNKNOWN | 43 | 65 | A |
| AI609970 | UNKNOWN | 19 | 220 | A |
| AI609972 | UNKNOWN | 27 | 378 | A |
| AI609984 | UNKNOWN | 26 | 395 | A |
| AI609992 | UNKNOWN | 27 | 420 | A |
| AI610003 | UNKNOWN | 20 | 538 | A |
| AI610022 | UNKNOWN | 30 | 82 | A |
| AI610058 | UNKNOWN | 26 | 212 | A |
| AI610079 | UNKNOWN | 16 | 0 | T |
| AI610086 | UNKNOWN | 97 | 0 | T |
| AI610086 | UNKNOWN | 20 | 119 | A |
| AI610086 | UNKNOWN | 15 | 171 | G |
| AI610089 | UNKNOWN | 4.75 | 22 | TTTA |
| AI610093 | UNKNOWN | 83 | 0 | T |
| AI610093 | UNKNOWN | 12 | 206 | A |
| AI610096 | UNKNOWN | 40 | 0 | T |
| AI610097 | UNKNOWN | 62 | 0 | T |
| AI610097 | UNKNOWN | 21 | 202 | A |
| AI610108 | UNKNOWN | 15 | 0 | T |
| AI610110 | UNKNOWN | 3.6 | 185 | CAGAA |
| AI610114 | UNKNOWN | 83 | 0 | T |
| AI610114 | UNKNOWN | 17 | 196 | A |
| AI610114 | UNKNOWN | 17 | 386 | G |
| AI610114 | UNKNOWN | 15 | 213 | C |
| AI610114 | UNKNOWN | 13 | 157 | G |
| AI610115 | UNKNOWN | 85 | 0 | T |
| AI610115 | UNKNOWN | 18 | 213 | C |
| AI610115 | UNKNOWN | 14 | 90 | A |
| AI610132 | UNKNOWN | 20 | 0 | T |
| AI610186 | UNKNOWN | 13 | 0 | T |
| AI610203 | UNKNOWN | 14 | 0 | T |
| AI610206 | UNKNOWN | 25 | 0 | T |
| AI610255 | UNKNOWN | 26 | 28 | T |
| AI610255 | UNKNOWN | 21 | 0 | T |
| AI610293 | UNKNOWN | 66 | 0 | T |
| AI610293 | UNKNOWN | 14 | 292 | A |
| AI610293 | UNKNOWN | 12 | 134 | A |
| AI610307 | UNKNOWN | 125 | 0 | T |
| AI610307 | UNKNOWN | 17 | 271 | G |
| AI610307 | UNKNOWN | 14 | 288 | C |
| AI610307 | UNKNOWN | 13 | 178 | C |
| AI610307 | UNKNOWN | 13 | 258 | A |
| AI610307 | UNKNOWN | 12 | 164 | A |

TABLE 1-continued

| Genbank # | Region | # reps | Position | Unit sequence |
|---|---|---|---|---|
| AI610332 | UNKNOWN | 41 | 17 | T |
| AI610332 | UNKNOWN | 17 | 224 | C |
| AI610332 | UNKNOWN | 16 | 0 | T |
| AI610332 | UNKNOWN | 12 | 123 | A |
| AI610362 | UNKNOWN | 95 | 11 | T |
| AI610362 | UNKNOWN | 13 | 232 | A |
| AI610399 | UNKNOWN | 62 | 0 | T |
| AI610399 | UNKNOWN | 16 | 156 | C |
| AI610399 | UNKNOWN | 12 | 100 | C |
| AI610402 | UNKNOWN | 106 | 10 | T |
| AI610402 | UNKNOWN | 12 | 172 | G |
| AI610435 | UNKNOWN | 17 | 0 | T |
| AI610446 | UNKNOWN | 68 | 0 | T |
| AI610468 | UNKNOWN | 22 | 0 | T |
| AI610468 | UNKNOWN | 15 | 405 | A |
| AI610488 | UNKNOWN | 18 | 8 | T |
| AI610494 | UNKNOWN | 33 | 0 | T |
| AI610498 | UNKNOWN | 71 | 0 | T |
| AI610616 | UNKNOWN | 51 | 0 | T |
| AI610616 | UNKNOWN | 12 | 154 | A |
| AI610643 | UNKNOWN | 2.91 | 143 | TATATATATATT (SEQ ID NO:130) |
| AI610643 | UNKNOWN | 7 | 167 | TA |
| AI610643 | UNKNOWN | 6.5 | 141 | TA |
| AI610645 | UNKNOWN | 118 | 0 | T |
| AI610645 | UNKNOWN | 18 | 171 | G |
| AI610654 | UNKNOWN | 28 | 0 | T |
| AI610667 | UNKNOWN | 69 | 0 | T |
| AI610671 | UNKNOWN | 67 | 0 | T |
| AI610690 | UNKNOWN | 108 | 0 | T |
| AI610690 | UNKNOWN | 21 | 108 | A |
| AI610690 | UNKNOWN | 19 | 284 | C |
| AI610690 | UNKNOWN | 12 | 163 | G |
| AI610707 | UNKNOWN | 90 | 0 | T |
| AI610751 | UNKNOWN | 20 | 273 | T |
| AI610756 | UNKNOWN | 114 | 0 | T |
| AI610756 | UNKNOWN | 18 | 242 | C |
| AI610756 | UNKNOWN | 12 | 222 | G |
| AI610768 | UNKNOWN | 78 | 0 | T |
| AI610770 | UNKNOWN | 79 | 0 | T |
| AI610770 | UNKNOWN | 17 | 169 | G |
| AI610770 | UNKNOWN | 12 | 103 | G |
| AI610770 | UNKNOWN | 12 | 122 | A |
| AI610799 | UNKNOWN | 103 | 0 | T |
| AI610799 | UNKNOWN | 16 | 298 | C |
| AI610799 | UNKNOWN | 15 | 220 | A |
| AI610799 | UNKNOWN | 13 | 143 | G |
| AI610809 | UNKNOWN | 55 | 0 | T |
| AI610822 | UNKNOWN | 88 | 0 | T |
| AI610822 | UNKNOWN | 20 | 99 | A |
| AI610837 | UNKNOWN | 35 | 0 | T |
| AI610882 | UNKNOWN | 58 | 0 | T |
| AI610895 | UNKNOWN | 87 | 26 | T |
| AI610895 | UNKNOWN | 20 | 0 | T |
| AI610895 | UNKNOWN | 18 | 227 | G |
| AI610895 | UNKNOWN | 13 | 197 | C |
| AI610895 | UNKNOWN | 12 | 180 | G |
| AI610910 | UNKNOWN | 27 | 87 | A |
| AI610931 | UNKNOWN | 13 | 170 | A |
| AI611034 | UNKNOWN | 17 | 0 | T |
| AI611084 | UNKNOWN | 6 | 176 | AGG |
| AI611107 | UNKNOWN | 15 | 0 | T |
| AI611186 | UNKNOWN | 47 | 0 | T |
| AI611267 | UNKNOWN | 20 | 0 | T |
| AI611348 | UNKNOWN | 92 | 0 | T |
| AI611354 | UNKNOWN | 64 | 0 | T |
| AI611354 | UNKNOWN | 13 | 149 | A |
| AI611354 | UNKNOWN | 13 | 245 | C |
| AI611354 | UNKNOWN | 12 | 300 | G |
| AI611424 | UNKNOWN | 24 | 518 | A |
| AI611475 | UNKNOWN | 10.25 | 54 | AAAG |
| AI611475 | UNKNOWN | 7.5 | 92 | AG |
| AI611475 | UNKNOWN | 26 | 106 | A |
| AI611490 | UNKNOWN | 26 | 170 | A |
| AI611494 | UNKNOWN | 29 | 213 | A |
| AI611522 | UNKNOWN | 16 | 100 | A |
| AI611533 | UNKNOWN | 31 | 311 | A |
| AI611550 | UNKNOWN | 7.5 | 140 | AG |

TABLE 1-continued

| Genbank # | Region | # reps | Position | Unit sequence |
|---|---|---|---|---|
| AI611550 | UNKNOWN | 6.5 | 24 | AG |
| AI611550 | UNKNOWN | 17 | 277 | A |
| AI611564 | UNKNOWN | 9.66 | 226 | GAA |
| AI611564 | UNKNOWN | 9 | 70 | AAG |
| AI611600 | UNKNOWN | 23 | 354 | A |
| AI611613 | UNKNOWN | 6.25 | 220 | AGAA |
| AI611613 | UNKNOWN | 17 | 49 | GA |
| AI611613 | UNKNOWN | 28 | 266 | A |
| AI611617 | UNKNOWN | 22 | 76 | A |
| AI611627 | UNKNOWN | 12 | 209 | A |
| AI611686 | UNKNOWN | 54 | 0 | T |
| AI611686 | UNKNOWN | 15 | 129 | G |
| AI611717 | UNKNOWN | 56 | 19 | T |
| AI611717 | UNKNOWN | 21 | 365 | C |
| AI611717 | UNKNOWN | 18 | 0 | T |
| AI611717 | UNKNOWN | 13 | 232 | C |
| AI611728 | UNKNOWN | 50 | 18 | T |
| AI611728 | UNKNOWN | 17 | 0 | T |
| AI611738 | UNKNOWN | 96 | 0 | T |
| AI611738 | UNKNOWN | 16 | 142 | G |
| AI611743 | UNKNOWN | 92 | 0 | T |
| AI611743 | UNKNOWN | 17 | 127 | G |
| AI611743 | UNKNOWN | 12 | 100 | A |
| AI611795 | UNKNOWN | 20 | 0 | T |
| AI611803 | UNKNOWN | 38 | 16 | T |
| AI611803 | UNKNOWN | 18 | 335 | A |
| AI611803 | UNKNOWN | 16 | 160 | G |
| AI611803 | UNKNOWN | 15 | 0 | T |
| AI611803 | UNKNOWN | 13 | 315 | C |
| AI611810 | UNKNOWN | 76 | 0 | T |
| AI611810 | UNKNOWN | 14 | 123 | A |
| AI611816 | UNKNOWN | 56 | 0 | T |
| AI611879 | UNKNOWN | 18 | 133 | A |
| AI611895 | UNKNOWN | 24 | 119 | A |
| AI611954 | UNKNOWN | 25 | 275 | A |
| AI611960 | UNKNOWN | 18 | 163 | A |
| AI611961 | UNKNOWN | 27 | 202 | A |
| AI611990 | UNKNOWN | 25 | 328 | A |
| AI612000 | UNKNOWN | 27 | 264 | A |
| AI612020 | UNKNOWN | 21 | 182 | A |
| AI612022 | UNKNOWN | 7 | 8 | CTA |
| AI612022 | UNKNOWN | 29 | 74 | A |
| AI612031 | UNKNOWN | 22 | 80 | A |
| AI612032 | UNKNOWN | 5 | 72 | AAGA |
| AI612032 | UNKNOWN | 15 | 234 | A |
| AI612053 | UNKNOWN | 16 | 162 | A |
| AI612071 | UNKNOWN | 2.5 | 77 | AAGAAAGAAT (SEQ ID NO:131) |
| AI612071 | UNKNOWN | 17 | 126 | A |
| AI612073 | UNKNOWN | 27 | 70 | A |
| AI612085 | UNKNOWN | 25 | 195 | A |
| AI612111 | UNKNOWN | 5.25 | 355 | AAAC |
| AI612118 | UNKNOWN | 14 | 416 | A |
| AI612126 | UNKNOWN | 28 | 300 | A |
| AI612150 | UNKNOWN | 17 | 368 | A |
| AI612680 | UNKNOWN | 27 | 217 | A |
| AI612701 | UNKNOWN | 21 | 231 | A |
| AI612721 | UNKNOWN | 105 | 0 | T |
| AI612721 | UNKNOWN | 16 | 145 | C |
| AI612721 | UNKNOWN | 16 | 185 | G |
| AI612723 | UNKNOWN | 58 | 0 | T |
| AI612738 | UNKNOWN | 54 | 0 | T |
| AI612747 | UNKNOWN | 59 | 0 | T |
| AI612750 | UNKNOWN | 73 | 0 | T |
| AI612750 | UNKNOWN | 17 | 127 | C |
| AI612750 | UNKNOWN | 16 | 109 | G |
| AI612750 | UNKNOWN | 13 | 146 | A |
| AI612759 | UNKNOWN | 106 | 0 | T |
| AI612759 | UNKNOWN | 25 | 167 | C |
| AI612759 | UNKNOWN | 13 | 132 | A |
| AI612775 | UNKNOWN | 21 | 0 | T |
| AI612780 | UNKNOWN | 46 | 0 | T |
| AI612797 | UNKNOWN | 14 | 0 | T |
| AI612813 | UNKNOWN | 70 | 0 | T |
| AI612815 | UNKNOWN | 50 | 0 | T |
| AI612825 | UNKNOWN | 30 | 0 | T |
| AI612832 | UNKNOWN | 109 | 10 | T |
| AI612832 | UNKNOWN | 19 | 259 | G |

TABLE 1-continued

| Genbank # | Region | # reps | Position | Unit sequence |
|---|---|---|---|---|
| AI612832 | UNKNOWN | 16 | 241 | C |
| AI612832 | UNKNOWN | 15 | 214 | C |
| AI612832 | UNKNOWN | 13 | 152 | A |
| AI612840 | UNKNOWN | 40 | 0 | T |
| AI612843 | UNKNOWN | 106 | 0 | T |
| AI612844 | UNKNOWN | 30 | 0 | T |
| AI612852 | UNKNOWN | 85 | 0 | T |
| AI612852 | UNKNOWN | 12 | 123 | C |
| AI612852 | UNKNOWN | 12 | 154 | G |
| AI612875 | UNKNOWN | 60 | 0 | T |
| AI612885 | UNKNOWN | 103 | 16 | T |
| AI612898 | UNKNOWN | 83 | 0 | T |
| AI612898 | UNKNOWN | 13 | 153 | G |
| AI612898 | UNKNOWN | 12 | 195 | C |
| AI612901 | UNKNOWN | 12 | 0 | T |
| AI612913 | UNKNOWN | 120 | 11 | T |
| AI612913 | UNKNOWN | 13 | 238 | C |
| AI612920 | UNKNOWN | 110 | 0 | T |
| AI612954 | UNKNOWN | 27 | 0 | T |
| AI613012 | UNKNOWN | 38 | 0 | T |
| AI613012 | UNKNOWN | 19 | 204 | A |
| AI613017 | UNKNOWN | 122 | 0 | T |
| AI613017 | UNKNOWN | 24 | 139 | A |
| AI613038 | UNKNOWN | 78 | 0 | T |
| AI613038 | UNKNOWN | 15 | 143 | G |
| AI613038 | UNKNOWN | 13 | 79 | A |
| AI613183 | UNKNOWN | 19 | 26 | T |
| AI613201 | UNKNOWN | 62 | 0 | T |
| AI613206 | UNKNOWN | 61 | 0 | T |
| AI613206 | UNKNOWN | 15 | 130 | C |
| AI613213 | UNKNOWN | 83 | 0 | T |
| AI613213 | UNKNOWN | 13 | 153 | G |
| AI613214 | UNKNOWN | 44 | 0 | T |
| AI613231 | UNKNOWN | 4 | 246 | AAAC |
| AI613231 | UNKNOWN | 28 | 0 | T |
| AI613270 | UNKNOWN | 101 | 0 | T |
| AI613270 | UNKNOWN | 15 | 140 | A |
| AI613270 | UNKNOWN | 13 | 271 | G |
| AI613297 | UNKNOWN | 46 | 0 | T |
| AI613297 | UNKNOWN | 12 | 63 | A |
| AI613314 | UNKNOWN | 4.5 | 80 | TTAA |
| AI613314 | UNKNOWN | 53 | 9 | T |
| AI613314 | UNKNOWN | 14 | 171 | G |
| AI613366 | UNKNOWN | 28 | 121 | A |
| AI613398 | UNKNOWN | 19 | 111 | A |
| AI613422 | UNKNOWN | 61 | 7 | T |
| AI613436 | UNKNOWN | 86 | 0 | T |
| AI613436 | UNKNOWN | 14 | 309 | A |
| AI613436 | UNKNOWN | 13 | 251 | A |
| AI613448 | UNKNOWN | 15 | 11 | T |
| AI613449 | UNKNOWN | 70 | 0 | T |
| AI613453 | UNKNOWN | 2.8 | 128 | AAAAAAAACC (SEQ ID NO:132) |
| AI613453 | UNKNOWN | 63 | 2 | T |
| AI613453 | UNKNOWN | 12 | 277 | G |
| AI613471 | UNKNOWN | 82 | 0 | T |
| AI613471 | UNKNOWN | 14 | 221 | G |
| AI613480 | UNKNOWN | 23 | 0 | T |
| AI613492 | UNKNOWN | 80 | 0 | T |
| AI613492 | UNKNOWN | 14 | 222 | C |
| AI613493 | UNKNOWN | 57 | 0 | T |
| AI613505 | UNKNOWN | 39 | 0 | T |
| AI613521 | UNKNOWN | 26 | 0 | T |
| AI613523 | UNKNOWN | 68 | 0 | T |
| AI613532 | UNKNOWN | 66 | 0 | T |
| AI613532 | UNKNOWN | 14 | 136 | C |
| AI613532 | UNKNOWN | 13 | 303 | A |
| AI613534 | UNKNOWN | 43 | 0 | T |
| AI613534 | UNKNOWN | 17 | 233 | A |
| AI613541 | UNKNOWN | 30 | 65 | A |
| AI619426 | UNKNOWN | 85 | 0 | T |
| AI619426 | UNKNOWN | 16 | 211 | C |
| AI619426 | UNKNOWN | 13 | 238 | G |
| AI619426 | UNKNOWN | 13 | 280 | A |
| AI619485 | UNKNOWN | 65 | 0 | T |
| AI619485 | UNKNOWN | 14 | 106 | C |
| AI619485 | UNKNOWN | 12 | 221 | G |
| AI619485 | UNKNOWN | 12 | 268 | A |

TABLE 1-continued

| Genbank # | Region | # reps | Position | Unit sequence |
|---|---|---|---|---|
| AI619500 | UNKNOWN | 20 | 0 | T |
| AI619502 | UNKNOWN | 116 | 0 | T |
| AI619502 | UNKNOWN | 24 | 178 | A |
| AI619502 | UNKNOWN | 16 | 116 | A |
| AI619502 | UNKNOWN | 14 | 164 | C |
| AI619513 | UNKNOWN | 62 | 0 | T |
| AI619513 | UNKNOWN | 22 | 119 | G |
| AI619525 | UNKNOWN | 48 | 0 | T |
| AI619525 | UNKNOWN | 13 | 123 | A |
| AI619529 | UNKNOWN | 6.75 | 189 | TTTA |
| AI619574 | UNKNOWN | 44 | 0 | T |
| AI619581 | UNKNOWN | 75 | 0 | T |
| AI619581 | UNKNOWN | 16 | 300 | C |
| AI619581 | UNKNOWN | 12 | 160 | C |
| AI619587 | UNKNOWN | 81 | 0 | T |
| AI619587 | UNKNOWN | 12 | 122 | A |
| AI619607 | UNKNOWN | 92 | 0 | T |
| AI619607 | UNKNOWN | 21 | 229 | G |
| AI619607 | UNKNOWN | 17 | 135 | A |
| AI619607 | UNKNOWN | 15 | 206 | A |
| AI619607 | UNKNOWN | 13 | 108 | A |
| AI619607 | UNKNOWN | 12 | 122 | G |
| AI619662 | UNKNOWN | 64 | 0 | T |
| AI619662 | UNKNOWN | 15 | 66 | A |
| AI619664 | UNKNOWN | 20 | 0 | T |
| AI619665 | UNKNOWN | 64 | 0 | T |
| AI619691 | UNKNOWN | 77 | 0 | T |
| AI619716 | UNKNOWN | 91 | 0 | T |
| AI619716 | UNKNOWN | 17 | 118 | A |
| AI619737 | UNKNOWN | 86 | 0 | T |
| AI619741 | UNKNOWN | 29 | 0 | T |
| AI619743 | UNKNOWN | 41 | 0 | T |
| AI619748 | UNKNOWN | 106 | 0 | T |
| AI619748 | UNKNOWN | 16 | 271 | C |
| AI619748 | UNKNOWN | 14 | 241 | G |
| AI619749 | UNKNOWN | 102 | 0 | T |
| AI619749 | UNKNOWN | 16 | 237 | G |
| AI619749 | UNKNOWN | 12 | 110 | A |
| AI619751 | UNKNOWN | 85 | 0 | T |
| AI619751 | UNKNOWN | 25 | 286 | G |
| AI619751 | UNKNOWN | 15 | 98 | A |
| AI619754 | UNKNOWN | 105 | 0 | T |
| AI619754 | UNKNOWN | 24 | 135 | G |
| AI619754 | UNKNOWN | 22 | 159 | C |
| AI619754 | UNKNOWN | 14 | 121 | A |
| AI619770 | UNKNOWN | 35 | 0 | T |
| AI619777 | UNKNOWN | 88 | 0 | T |
| AI619777 | UNKNOWN | 19 | 211 | A |
| AI619777 | UNKNOWN | 16 | 164 | A |
| AI619777 | UNKNOWN | 13 | 301 | G |
| AI619777 | UNKNOWN | 12 | 289 | C |
| AI619781 | UNKNOWN | 89 | 0 | T |
| AI619781 | UNKNOWN | 17 | 95 | G |
| AI619781 | UNKNOWN | 13 | 336 | C |
| AI619813 | UNKNOWN | 74 | 0 | T |
| AI619813 | UNKNOWN | 12 | 97 | A |
| AI619817 | UNKNOWN | 87 | 0 | T |
| AI619817 | UNKNOWN | 17 | 134 | G |
| AI619817 | UNKNOWN | 15 | 92 | A |
| AI619817 | UNKNOWN | 13 | 151 | C |
| AI619844 | UNKNOWN | 36 | 0 | T |
| AI619914 | UNKNOWN | 15 | 0 | T |
| AI619989 | UNKNOWN | 25 | 0 | T |
| AI619990 | UNKNOWN | 56 | 0 | T |
| AI619992 | UNKNOWN | 77 | 0 | T |
| AI619992 | UNKNOWN | 14 | 102 | G |
| AI620003 | UNKNOWN | 96 | 0 | T |
| AI620003 | UNKNOWN | 15 | 114 | G |
| AI620003 | UNKNOWN | 14 | 147 | C |
| AI620003 | UNKNOWN | 12 | 129 | A |
| AI620007 | UNKNOWN | 94 | 0 | T |
| AI620007 | UNKNOWN | 21 | 150 | A |
| AI620007 | UNKNOWN | 13 | 113 | A |
| AI620015 | UNKNOWN | 93 | 0 | T |
| AI620015 | UNKNOWN | 17 | 189 | G |
| AI620015 | UNKNOWN | 14 | 114 | A |
| AI620022 | UNKNOWN | 53 | 0 | T |

TABLE 1-continued

| Genbank # | Region | # reps | Position | Unit sequence |
|---|---|---|---|---|
| AI620024 | UNKNOWN | 39 | 0 | T |
| AI620056 | UNKNOWN | 56 | 0 | T |
| AI620056 | UNKNOWN | 14 | 134 | A |
| AI620063 | UNKNOWN | 14 | 0 | T |
| AI620075 | UNKNOWN | 77 | 0 | T |
| AI620075 | UNKNOWN | 22 | 134 | G |
| AI620089 | UNKNOWN | 82 | 0 | T |
| AI620089 | UNKNOWN | 19 | 148 | C |
| AI620091 | UNKNOWN | 118 | 0 | T |
| AI620091 | UNKNOWN | 14 | 162 | A |
| AI620091 | UNKNOWN | 13 | 182 | G |
| AI620091 | UNKNOWN | 13 | 275 | C |
| AI620093 | UNKNOWN | 74 | 0 | T |
| AI620097 | UNKNOWN | 48 | 0 | T |
| AI620097 | UNKNOWN | 28 | 322 | G |
| AI620097 | UNKNOWN | 18 | 208 | C |
| AI620097 | UNKNOWN | 16 | 184 | A |
| AI620097 | UNKNOWN | 13 | 162 | C |
| AI620097 | UNKNOWN | 12 | 274 | G |
| AI620150 | UNKNOWN | 2.81 | 188 | TTTTTTTTCT (SEQ ID NO:133) |
| AI620150 | UNKNOWN | 14 | 209 | T |
| AI620183 | UNKNOWN | 60 | 0 | T |
| AI620183 | UNKNOWN | 15 | 187 | C |
| AI620183 | UNKNOWN | 12 | 122 | C |
| AI620188 | UNKNOWN | 40 | 0 | T |
| AI620266 | UNKNOWN | 14 | 0 | T |
| AI620287 | UNKNOWN | 98 | 0 | T |
| AI620287 | UNKNOWN | 15 | 238 | G |
| AI620287 | UNKNOWN | 13 | 181 | A |
| AI620300 | UNKNOWN | 44 | 0 | T |
| AI620302 | UNKNOWN | 72 | 0 | T |
| AI620302 | UNKNOWN | 16 | 181 | G |
| AI620314 | UNKNOWN | 89 | 0 | T |
| AI620314 | UNKNOWN | 12 | 293 | A |
| AI620354 | UNKNOWN | 14 | 0 | T |
| AI620374 | UNKNOWN | 27 | 0 | T |
| AI620400 | UNKNOWN | 26 | 0 | T |
| AI620433 | UNKNOWN | 15 | 0 | T |
| AI620480 | UNKNOWN | 43 | | T |
| AI620485 | UNKNOWN | 14 | 0 | T |
| AI620517 | UNKNOWN | 80 | 0 | T |
| AI620517 | UNKNOWN | 18 | 248 | C |
| AI620517 | UNKNOWN | 15 | 209 | A |
| AI620517 | UNKNOWN | 15 | 224 | G |
| AI620517 | UNKNOWN | 13 | 135 | A |
| AI620517 | UNKNOWN | 12 | 164 | C |
| AI620639 | UNKNOWN | 58 | 49 | T |
| AI620639 | UNKNOWN | 29 | 0 | T |
| AI620645 | UNKNOWN | 4.8 | 363 | CAAAA |
| AI620645 | UNKNOWN | 44 | 0 | T |
| AI620650 | UNKNOWN | 42 | 0 | T |
| AI620671 | UNKNOWN | 51 | 0 | T |
| AI620693 | UNKNOWN | 47 | 0 | T |
| AI620714 | UNKNOWN | 64 | 0 | T |
| AI620714 | UNKNOWN | 15 | 265 | C |
| AI620726 | UNKNOWN | 12 | 261 | A |
| AI620807 | UNKNOWN | 32 | 0 | T |
| AI620808 | UNKNOWN | 16 | 0 | T |
| AI620841 | UNKNOWN | 52 | 0 | T |
| AI620859 | UNKNOWN | 72 | 0 | T |
| AI620859 | UNKNOWN | 20 | 217 | G |
| AI620859 | UNKNOWN | 14 | 82 | A |
| AI620859 | UNKNOWN | 13 | 248 | C |
| AI620864 | UNKNOWN | 51 | 0 | T |
| AI620865 | UNKNOWN | 45 | 0 | T |
| AI620866 | UNKNOWN | 98 | 0 | T |
| AI620866 | UNKNOWN | 17 | 339 | C |
| AI620866 | UNKNOWN | 15 | 363 | G |
| AI620866 | UNKNOWN | 13 | 144 | G |
| AI620866 | UNKNOWN | 13 | 179 | A |
| AI620866 | UNKNOWN | 13 | 198 | C |
| AI620868 | UNKNOWN | 120 | 0 | T |
| AI620868 | UNKNOWN | 16 | 328 | G |
| AI620868 | UNKNOWN | 13 | 173 | A |
| AI620911 | UNKNOWN | 12 | 395 | T |
| AI620944 | UNKNOWN | 50 | 0 | T |
| AI620948 | UNKNOWN | 12 | 336 | T |

TABLE 1-continued

| Genbank # | Region | # reps | Position | Unit sequence |
|---|---|---|---|---|
| AI620970 | UNKNOWN | 48 | 0 | T |
| AI621106 | UNKNOWN | 45 | 0 | T |
| AI621119 | UNKNOWN | 17 | 0 | T |
| AI621170 | UNKNOWN | 17 | 0 | T |
| AI621171 | UNKNOWN | 62 | 3 | T |
| AI621177 | UNKNOWN | 13 | 26 | T |
| AI621179 | UNKNOWN | 90 | 0 | T |
| AI621196 | UNKNOWN | 13 | 425 | A |
| AI621209 | UNKNOWN | 98 | 10 | T |
| AI621209 | UNKNOWN | 12 | 108 | C |
| AI621224 | UNKNOWN | 13 | 23 | A |
| AI621244 | UNKNOWN | 41 | 0 | T |
| AI621263 | UNKNOWN | 16 | 0 | T |
| AI621285 | UNKNOWN | 5.25 | 138 | TCTA |
| AI621290 | UNKNOWN | 15 | 0 | T |
| AI621341 | UNKNOWN | 65 | 0 | T |
| AI621345 | UNKNOWN | 24 | 0 | T |
| AI621362 | UNKNOWN | 89 | 0 | T |
| AI621362 | UNKNOWN | 15 | 100 | A |
| AI621364 | UNKNOWN | 19 | 53 | T |
| AI621364 | UNKNOWN | 19 | 290 | G |
| AI623133 | UNKNOWN | 89 | 0 | T |
| AI623133 | UNKNOWN | 15 | 348 | C |
| AI623133 | UNKNOWN | 13 | 171 | G |
| AI623154 | UNKNOWN | 46 | 0 | T |
| AI623162 | UNKNOWN | 13 | 157 | C |
| AI623206 | UNKNOWN | 12 | 0 | T |
| AI623295 | UNKNOWN | 16 | 235 | A |
| AI623295 | UNKNOWN | 14 | 0 | T |
| AI623305 | UNKNOWN | 22 | 0 | T |
| AI623306 | UNKNOWN | 12 | 372 | T |
| AI623311 | UNKNOWN | 12 | 0 | T |
| AI623315 | UNKNOWN | 14 | 12 | T |
| AI623316 | UNKNOWN | 41 | 0 | T |
| AI623337 | UNKNOWN | 50 | 0 | T |
| AI623363 | UNKNOWN | 72 | 0 | T |
| AI623363 | UNKNOWN | 15 | 134 | C |
| AI623392 | UNKNOWN | 43 | 0 | T |
| AI623396 | UNKNOWN | 100 | 0 | T |
| AI623396 | UNKNOWN | 21 | 191 | A |
| AI623396 | UNKNOWN | 12 | 179 | G |
| AI623507 | UNKNOWN | 45 | 0 | T |
| AI623512 | UNKNOWN | 40 | 0 | T |
| AI623514 | UNKNOWN | 29 | 24 | T |
| AI623517 | UNKNOWN | 30 | 0 | T |
| AI623547 | UNKNOWN | 42 | 0 | T |
| AI623591 | UNKNOWN | 41 | 0 | T |
| AI623596 | UNKNOWN | 44 | 0 | T |
| AI623596 | UNKNOWN | 18 | 82 | A |
| AI623622 | UNKNOWN | 65 | 0 | T |
| AI623622 | UNKNOWN | 17 | 142 | C |
| AI623648 | UNKNOWN | 67 | 0 | T |
| AI623648 | UNKNOWN | 15 | 199 | A |
| AI623648 | UNKNOWN | 14 | 238 | C |
| AI623650 | UNKNOWN | 21 | 65 | T |
| AI623650 | UNKNOWN | 15 | 91 | G |
| AI623654 | UNKNOWN | 50 | 0 | T |
| AI623662 | UNKNOWN | 58 | 0 | T |
| AI623662 | UNKNOWN | 16 | 119 | A |
| AI623662 | UNKNOWN | 13 | 135 | C |
| AI623682 | UNKNOWN | 53 | 0 | T |
| AI623682 | UNKNOWN | 14 | 109 | G |
| AI623698 | UNKNOWN | 22 | 0 | T |
| AI623719 | UNKNOWN | 2.7 | 27 | TTTTTTTTTTTTTTTTTTTTTTTTC (SEQ ID NO: 134) |
| AI623719 | UNKNOWN | 50 | 0 | T |
| AI623719 | UNKNOWN | 20 | 240 | G |
| AI623739 | UNKNOWN | 17 | 0 | T |
| AI623746 | UNKNOWN | 85 | 0 | T |
| AI623746 | UNKNOWN | 15 | 246 | G |
| AI623746 | UNKNOWN | 13 | 282 | A |
| AI623777 | UNKNOWN | 93 | 3 | T |
| AI623778 | UNKNOWN | 14 | 437 | T |
| AI623778 | UNKNOWN | 13 | 361 | A |
| AI623796 | UNKNOWN | 91 | 0 | T |
| AI623796 | UNKNOWN | 16 | 332 | C |
| AI623797 | UNKNOWN | 57 | 0 | T |

TABLE 1-continued

| Genbank # | Region | # reps | Position | Unit sequence |
|---|---|---|---|---|
| AI623797 | UNKNOWN | 15 | 118 | C |
| AI623800 | UNKNOWN | 45 | 0 | T |
| AI623810 | UNKNOWN | 98 | 0 | T |
| AI623810 | UNKNOWN | 15 | 219 | C |
| AI623810 | UNKNOWN | 13 | 302 | A |
| AI623810 | UNKNOWN | 12 | 151 | A |
| AI623810 | UNKNOWN | 12 | 204 | G |
| AI623823 | UNKNOWN | 51 | 0 | T |
| AI623823 | UNKNOWN | 14 | 119 | A |
| AI623826 | UNKNOWN | 18 | 215 | AC |
| AI623834 | UNKNOWN | 55 | 0 | T |
| AI623835 | UNKNOWN | 56 | 0 | T |
| AI623835 | UNKNOWN | 16 | 136 | A |
| AI623839 | UNKNOWN | 15 | 382 | A |
| AI623853 | UNKNOWN | 22 | 0 | T |
| AI623905 | UNKNOWN | 74 | 0 | T |
| AI623905 | UNKNOWN | 12 | 167 | G |
| AI623941 | UNKNOWN | 76 | 0 | T |
| AI623941 | UNKNOWN | 12 | 115 | A |
| AI623971 | UNKNOWN | 34 | 0 | T |
| AI623971 | UNKNOWN | 19 | 232 | C |
| AI624021 | UNKNOWN | 70 | 0 | T |
| AI624021 | UNKNOWN | 13 | 212 | C |
| AI624028 | UNKNOWN | 33 | 0 | T |
| AI624030 | UNKNOWN | 43 | 0 | T |
| AI624052 | UNKNOWN | 66 | 0 | T |
| AI624052 | UNKNOWN | 14 | 135 | G |
| AI624056 | UNKNOWN | 100 | 0 | T |
| AI624056 | UNKNOWN | 15 | 189 | C |
| AI624056 | UNKNOWN | 14 | 130 | G |
| AI624056 | UNKNOWN | 13 | 114 | A |
| AI624057 | UNKNOWN | 45 | 0 | T |
| AI624057 | UNKNOWN | 16 | 334 | G |
| AI624084 | UNKNOWN | 106 | 0 | T |
| AI624120 | UNKNOWN | 83 | 0 | T |
| AI624120 | UNKNOWN | 13 | 116 | G |
| AI624129 | UNKNOWN | 16 | 0 | T |
| AI624154 | UNKNOWN | 98 | 0 | T |
| AI624154 | UNKNOWN | 12 | 270 | G |
| AI624157 | UNKNOWN | 62 | 0 | T |
| AI624157 | UNKNOWN | 12 | 127 | A |
| AI624206 | UNKNOWN | 108 | 0 | T |
| AI624206 | UNKNOWN | 14 | 116 | C |
| AI624206 | UNKNOWN | 13 | 135 | G |
| AI624239 | UNKNOWN | 53 | 0 | T |
| AI624241 | UNKNOWN | 24 | 0 | T |
| AI624244 | UNKNOWN | 12 | 64 | T |
| AI624245 | UNKNOWN | 57 | 0 | T |
| AI624247 | UNKNOWN | 65 | 0 | T |
| AI624262 | UNKNOWN | 51 | 9 | T |
| AI624262 | UNKNOWN | 14 | 365 | A |
| AI624274 | UNKNOWN | 12 | 0 | T |
| AI624279 | UNKNOWN | 59 | 36 | T |
| AI624279 | UNKNOWN | 13 | 210 | G |
| AI624289 | UNKNOWN | 12 | 0 | T |
| AI624293 | UNKNOWN | 76 | 0 | T |
| AI624293 | UNKNOWN | 16 | 151 | A |
| AI624355 | UNKNOWN | 40 | 0 | T |
| AI624418 | UNKNOWN | 67 | 0 | T |
| AI624454 | UNKNOWN | 24 | 0 | T |
| AI624514 | UNKNOWN | 50 | 0 | T |
| AI624516 | UNKNOWN | 46 | 0 | T |
| AI624540 | UNKNOWN | 100 | 0 | T |
| AI624540 | UNKNOWN | 13 | 287 | C |
| AI624540 | UNKNOWN | 12 | 150 | A |
| AI624545 | UNKNOWN | 78 | 0 | T |
| AI624545 | UNKNOWN | 13 | 121 | A |
| AI624548 | UNKNOWN | 87 | 0 | T |
| AI624548 | UNKNOWN | 24 | 127 | A |
| AI624579 | UNKNOWN | 17 | 0 | T |
| AI624604 | UNKNOWN | 93 | 0 | T |
| AI624604 | UNKNOWN | 22 | 151 | G |
| AI624604 | UNKNOWN | 16 | 130 | A |
| AI624604 | UNKNOWN | 13 | 117 | C |
| AI624641 | UNKNOWN | 61 | 0 | T |
| AI624641 | UNKNOWN | 13 | 329 | C |
| AI624655 | UNKNOWN | 15 | 26 | A |

TABLE 1-continued

| Genbank # | Region | # reps | Position | Unit sequence |
|---|---|---|---|---|
| AI624668 | UNKNOWN | 117 | 0 | T |
| AI624668 | UNKNOWN | 21 | 191 | C |
| AI624668 | UNKNOWN | 19 | 117 | G |
| AI624668 | UNKNOWN | 13 | 178 | A |
| AI624671 | UNKNOWN | 80 | 0 | T |
| AI624671 | UNKNOWN | 22 | 146 | G |
| AI624671 | UNKNOWN | 15 | 217 | C |
| AI624689 | UNKNOWN | 12 | 113 | C |
| AI624693 | UNKNOWN | 85 | 0 | T |
| AI624693 | UNKNOWN | 18 | 152 | A |
| AI624693 | UNKNOWN | 14 | 109 | A |
| AI624693 | UNKNOWN | 12 | 88 | A |
| AI624755 | UNKNOWN | 19 | 0 | T |
| AI624776 | UNKNOWN | 25 | 0 | T |
| AI624847 | UNKNOWN | 14 | 0 | T |
| AI624851 | UNKNOWN | 25 | 0 | T |
| AI624855 | UNKNOWN | 41 | 0 | T |
| AI624865 | UNKNOWN | 29 | 0 | T |
| AI624935 | UNKNOWN | 75 | 0 | T |
| AI624938 | UNKNOWN | 68 | 0 | T |
| AI624938 | UNKNOWN | 13 | 178 | A |
| AI624943 | UNKNOWN | 72 | 0 | T |
| AI624943 | UNKNOWN | 13 | 197 | A |
| AI624950 | UNKNOWN | 77 | 0 | T |
| AI624950 | UNKNOWN | 30 | 223 | G |
| AI624950 | UNKNOWN | 25 | 156 | A |
| AI624950 | UNKNOWN | 18 | 181 | G |
| AI624950 | UNKNOWN | 14 | 209 | C |
| AI624963 | UNKNOWN | 71 | 0 | T |
| AI624963 | UNKNOWN | 12 | 197 | A |
| AI624982 | UNKNOWN | 48 | 0 | T |
| AI624993 | UNKNOWN | 77 | 0 | T |
| AI625046 | UNKNOWN | 40 | 0 | T |
| AI625063 | UNKNOWN | 46 | 0 | T |
| AI625079 | UNKNOWN | 123 | 0 | T |
| AI625079 | UNKNOWN | 16 | 123 | A |
| AI625081 | UNKNOWN | 39 | 0 | T |
| AI625083 | UNKNOWN | 16 | 130 | A |
| AI625116 | UNKNOWN | 36 | 0 | T |
| AI625130 | UNKNOWN | 34 | 0 | T |
| AI625149 | UNKNOWN | 25 | 0 | T |
| AI625152 | UNKNOWN | 52 | 0 | T |
| AI625154 | UNKNOWN | 42 | 0 | T |
| AI625158 | UNKNOWN | 16 | 0 | T |
| AI625187 | UNKNOWN | 18 | 0 | T |
| AI625194 | UNKNOWN | 13 | 381 | G |
| AI625209 | UNKNOWN | 74 | 0 | T |
| AI625209 | UNKNOWN | 14 | 111 | A |
| AI625222 | UNKNOWN | 35 | 0 | T |
| AI625226 | UNKNOWN | 65 | 0 | T |
| AI625226 | UNKNOWN | 15 | 538 | G |
| AI625237 | UNKNOWN | 81 | 0 | T |
| AI625237 | UNKNOWN | 15 | 274 | A |
| AI625237 | UNKNOWN | 14 | 134 | C |
| AI625237 | UNKNOWN | 12 | 254 | G |
| AI625293 | UNKNOWN | 52 | 0 | T |
| AI625293 | UNKNOWN | 21 | 218 | G |
| AI625316 | UNKNOWN | 98 | 7 | T |
| AI625316 | UNKNOWN | 15 | 139 | A |
| AI625329 | UNKNOWN | 87 | 0 | T |
| AI625329 | UNKNOWN | 12 | 202 | A |
| AI625342 | UNKNOWN | 22 | 1 | T |
| AI625342 | UNKNOWN | 16 | 49 | A |
| AI625368 | UNKNOWN | 41 | 7 | T |
| AI625384 | UNKNOWN | 94 | 0 | T |
| AI625384 | UNKNOWN | 13 | 214 | C |
| AI625384 | UNKNOWN | 13 | 294 | G |
| AI625384 | UNKNOWN | 12 | 99 | A |
| AI625396 | UNKNOWN | 36 | 54 | T |
| AI625396 | UNKNOWN | 35 | 17 | T |
| AI625396 | UNKNOWN | 16 | 0 | T |
| AI625396 | UNKNOWN | 12 | 116 | C |
| AI625396 | UNKNOWN | 12 | 234 | G |
| AI625422 | UNKNOWN | 42 | 0 | T |
| AI625431 | UNKNOWN | 14 | 0 | T |
| AI625456 | UNKNOWN | 67 | 0 | T |
| AI625464 | UNKNOWN | 67 | 0 | T |

TABLE 1-continued

| Genbank # | Region | # reps | Position | Unit sequence |
|---|---|---|---|---|
| AI625464 | UNKNOWN | 13 | 142 | A |
| AI625467 | UNKNOWN | 87 | 0 | T |
| AI625467 | UNKNOWN | 15 | 273 | G |
| AI625467 | UNKNOWN | 13 | 137 | A |
| AI625516 | UNKNOWN | 59 | 0 | T |
| AI625531 | UNKNOWN | 26 | 0 | T |
| AI625531 | UNKNOWN | 18 | 300 | A |
| AI625535 | UNKNOWN | 14 | 0 | T |
| AI625538 | UNKNOWN | 20 | 0 | T |
| AI625589 | UNKNOWN | 91 | 0 | T |
| AI625589 | UNKNOWN | 15 | 150 | C |
| AI625595 | UNKNOWN | 93 | 0 | T |
| AI625595 | UNKNOWN | 19 | 329 | A |
| AI625595 | UNKNOWN | 12 | 315 | C |
| AI625604 | UNKNOWN | 24 | 0 | T |
| AI625701 | UNKNOWN | 98 | 0 | T |
| AI625701 | UNKNOWN | 18 | 316 | A |
| AI625701 | UNKNOWN | 16 | 247 | G |
| AI625719 | UNKNOWN | 44 | 0 | T |
| AI625719 | UNKNOWN | 15 | 170 | A |
| AI625740 | UNKNOWN | 18 | 4 | T |
| AI625823 | UNKNOWN | 3.8 | 237 | TTTTG |
| AI625827 | UNKNOWN | 16 | 281 | A |
| AI625880 | UNKNOWN | 6.5 | 65 | GT |
| AI625880 | UNKNOWN | 18 | 0 | T |
| AI625926 | UNKNOWN | 63 | 0 | T |
| AI625926 | UNKNOWN | 20 | 200 | G |
| AI625926 | UNKNOWN | 15 | 114 | A |
| AI625926 | UNKNOWN | 12 | 366 | C |
| AI625950 | UNKNOWN | 42 | 0 | T |
| AI625950 | UNKNOWN | 17 | 246 | A |
| AI625971 | UNKNOWN | 5.75 | 16 | TTTA |
| AI625997 | UNKNOWN | 20 | 242 | A |
| AI625997 | UNKNOWN | 12 | 0 | T |
| AI627181 | UNKNOWN | 38 | 0 | T |
| AI627201 | UNKNOWN | 87 | 0 | T |
| AI627201 | UNKNOWN | 13 | 290 | A |
| AI627336 | UNKNOWN | 23 | 342 | T |
| AI627357 | UNKNOWN | 32 | 0 | T |
| AI627358 | UNKNOWN | 20 | 0 | T |
| AI627360 | UNKNOWN | 106 | 1 | T |
| AI627360 | UNKNOWN | 17 | 209 | G |
| AI627360 | UNKNOWN | 16 | 165 | A |
| AI627378 | UNKNOWN | 40 | 5 | T |
| AI627390 | UNKNOWN | 60 | 0 | T |
| AI627445 | UNKNOWN | 23 | 0 | T |
| AI627528 | UNKNOWN | 56 | 0 | T |
| AI627533 | UNKNOWN | 55 | 0 | T |
| AI627534 | UNKNOWN | 12 | 0 | T |
| AI627560 | UNKNOWN | 56 | 0 | T |
| AI627560 | UNKNOWN | 12 | 138 | G |
| AI627569 | UNKNOWN | 37 | 0 | T |
| AI627575 | UNKNOWN | 35 | 0 | T |
| AI627600 | UNKNOWN | 56 | 0 | T |
| AI627604 | UNKNOWN | 79 | 0 | T |
| AI627639 | UNKNOWN | 39 | 0 | T |
| AI627650 | UNKNOWN | 15 | 0 | T |
| AI627702 | UNKNOWN | 33 | 0 | T |
| AI627714 | UNKNOWN | 56 | 0 | T |
| AI627714 | UNKNOWN | 22 | 111 | G |
| AI627738 | UNKNOWN | 5 | 312 | TTCC |
| AI627738 | UNKNOWN | 41 | 0 | T |
| AI627745 | UNKNOWN | 72 | 0 | T |
| AI627745 | UNKNOWN | 22 | 229 | C |
| AI627745 | UNKNOWN | 19 | 333 | G |
| AI627745 | UNKNOWN | 18 | 315 | A |
| AI627745 | UNKNOWN | 12 | 151 | A |
| AI627748 | UNKNOWN | 77 | 0 | T |
| AI627748 | UNKNOWN | 15 | 258 | C |
| AI627774 | UNKNOWN | 13 | 3 | T |
| AI627806 | UNKNOWN | 5.66 | 90 | GCA |
| AI627814 | UNKNOWN | 26 | 0 | T |
| AI627827 | UNKNOWN | 4.5 | 10 | TTAT |
| AI627840 | UNKNOWN | 12 | 0 | T |
| AI627853 | UNKNOWN | 22 | 0 | T |
| AI627866 | UNKNOWN | 67 | 0 | T |
| AI627866 | UNKNOWN | 16 | 261 | A |

TABLE 1-continued

| Genbank # | Region | # reps | Position | Unit sequence |
|---|---|---|---|---|
| AI627874 | UNKNOWN | 49 | 0 | T |
| AI627874 | UNKNOWN | 13 | 216 | G |
| AI627879 | UNKNOWN | 36 | 0 | T |
| AI627880 | UNKNOWN | 84 | 0 | T |
| AI627893 | UNKNOWN | 91 | 0 | T |
| AI627893 | UNKNOWN | 13 | 203 | C |
| AI627896 | UNKNOWN | 79 | 0 | T |
| AI627896 | UNKNOWN | 17 | 186 | A |
| AI627909 | UNKNOWN | 113 | 0 | T |
| AI627909 | UNKNOWN | 17 | 237 | C |
| AI627909 | UNKNOWN | 13 | 188 | A |
| AI627909 | UNKNOWN | 12 | 201 | C |
| AI627909 | UNKNOWN | 12 | 213 | G |
| AI627954 | UNKNOWN | 42 | 0 | T |
| AI627985 | UNKNOWN | 49 | 37 | T |
| AI627985 | UNKNOWN | 36 | 0 | T |
| AI627985 | UNKNOWN | 19 | 256 | G |
| AI627985 | UNKNOWN | 14 | 279 | C |
| AI627988 | UNKNOWN | 91 | 0 | T |
| AI628015 | UNKNOWN | 70 | 0 | T |
| AI628015 | UNKNOWN | 25 | 246 | G |
| AI628015 | UNKNOWN | 15 | 117 | A |
| AI628120 | UNKNOWN | 36 | 0 | T |
| AI628165 | UNKNOWN | 43 | 0 | T |
| AI62B182 | UNKNOWN | 27 | 0 | T |
| AI628188 | UNKNOWN | 52 | 0 | T |
| AI628205 | UNKNOWN | 124 | 0 | T |
| AI628205 | UNKNOWN | 19 | 172 | A |
| AI628205 | UNKNOWN | 18 | 196 | C |
| AI628207 | UNKNOWN | 52 | 0 | T |
| AI628217 | UNKNOWN | 81 | 0 | T |
| AI628217 | UNKNOWN | 22 | 139 | G |
| AI628217 | UNKNOWN | 12 | 105 | C |
| AI628219 | UNKNOWN | 12 | 0 | T |
| AI628243 | UNKNOWN | 29 | 0 | T |
| AI628254 | UNKNOWN | 87 | 0 | T |
| AI628254 | UNKNOWN | 18 | 360 | A |
| AI628273 | UNKNOWN | 50 | 0 | T |
| AI628273 | UNKNOWN | 13 | 51 | G |
| AI628279 | UNKNOWN | 41 | 0 | T |
| AI628284 | UNKNOWN | 68 | 0 | T |
| AI628292 | UNKNOWN | 108 | 3 | T |
| AI628292 | UNKNOWN | 16 | 254 | C |
| AI628292 | UNKNOWN | 14 | 111 | G |
| AI628292 | UNKNOWN | 14 | 166 | A |
| AI628296 | UNKNOWN | 83 | 0 | T |
| AI628316 | UNKNOWN | 86 | 0 | T |
| AI628316 | UNKNOWN | 20 | 229 | A |
| AI628316 | UNKNOWN | 18 | 201 | C |
| AI628316 | UNKNOWN | 17 | 138 | A |
| AI628324 | UNKNOWN | 91 | 0 | T |
| AI628324 | UNKNOWN | 21 | 200 | G |
| AI628324 | UNKNOWN | 14 | 114 | A |
| AI628324 | UNKNOWN | 13 | 155 | C |
| AI628331 | UNKNOWN | 91 | 0 | T |
| AI628331 | UNKNOWN | 15 | 91 | A |
| AI628331 | UNKNOWN | 14 | 202 | C |
| AI628331 | UNKNOWN | 13 | 187 | G |
| AI628337 | UNKNOWN | 71 | 0 | T |
| AI628344 | UNKNOWN | 58 | 0 | T |
| AI628344 | UNKNOWN | 12 | 85 | A |
| AI628371 | UNKNOWN | 17 | 0 | T |
| AI628371 | UNKNOWN | 13 | 296 | A |
| AI628379 | UNKNOWN | 26 | 0 | T |
| AI628380 | UNKNOWN | 18 | 0 | T |
| AI628395 | UNKNOWN | 19 | 322 | A |
| AI628444 | UNKNOWN | 38 | 0 | T |
| AI628457 | UNKNOWN | 13 | 354 | T |
| AI628486 | UNKNOWN | 15 | 0 | T |
| AI628541 | UNKNOWN | 6.5 | 9 | TC |
| AI628541 | UNKNOWN | 21 | 167 | T |
| AI628612 | UNKNOWN | 26 | 0 | T |
| AI628638 | UNKNOWN | 13 | 167 | A |
| AI628643 | UNKNOWN | 15 | 0 | T |
| AI628651 | UNKNOWN | 42 | 0 | T |
| AI628688 | UNKNOWN | 26 | 11 | T |
| AI628711 | UNKNOWN | 63 | 0 | T |

TABLE 1-continued

| Genbank # | Region | # reps | Position | Unit sequence |
|---|---|---|---|---|
| AI628711 | UNKNOWN | 15 | 133 | A |
| AI628833 | UNKNOWN | 77 | 0 | T |
| AI628834 | UNKNOWN | 46 | 0 | T |
| AI628834 | UNKNOWN | 20 | 103 | A |
| AI628851 | UNKNOWN | 53 | 0 | T |
| AI628866 | UNKNOWN | 34 | 0 | T |
| AI628875 | UNKNOWN | 53 | 0 | T |
| AI628917 | UNKNOWN | 3.85 | 112 | GAGATGG |
| AI629022 | UNKNOWN | 7 | 180 | AC |
| AI629041 | UNKNOWN | 16 | 0 | T |
| AI630156 | UNKNOWN | 26 | 292 | A |
| AI630176 | UNKNOWN | 23 | 2 | T |
| AI630733 | UNKNOWN | 47 | 0 | T |
| AI630733 | UNKNOWN | 12 | 193 | G |
| AI630747 | UNKNOWN | 96 | 0 | T |
| AI630749 | UNKNOWN | 101 | 0 | T |
| AI630749 | UNKNOWN | 17 | 235 | A |
| AI630749 | UNKNOWN | 14 | 131 | A |
| AI630749 | UNKNOWN | 13 | 220 | C |
| AI630749 | UNKNOWN | 12 | 145 | C |
| AI630772 | UNKNOWN | 26 | 0 | T |
| AI630793 | UNKNOWN | 14.5 | 330 | AT |
| AI630876 | UNKNOWN | 77 | 0 | T |
| AI630876 | UNKNOWN | 14 | 341 | G |
| AI630876 | UNKNOWN | 12 | 321 | C |
| AI630877 | UNKNOWN | 71 | 0 | T |
| AI630877 | UNKNOWN | 16 | 147 | G |
| AI630877 | UNKNOWN | 13 | 123 | C |
| AI630898 | UNKNOWN | 47 | 0 | T |
| AI630910 | UNKNOWN | 16 | 0 | T |
| AI630910 | UNKNOWN | 12 | 181 | A |
| AI630919 | UNKNOWN | 30 | 0 | T |
| AI630928 | UNKNOWN | 109 | 0 | T |
| AI630928 | UNKNOWN | 23 | 149 | A |
| AI630928 | UNKNOWN | 14 | 135 | C |
| AI630931 | UNKNOWN | 75 | 24 | T |
| AI630931 | UNKNOWN | 21 | 0 | T |
| AI630931 | UNKNOWN | 19 | 281 | G |
| AI630931 | UNKNOWN | 12 | 104 | A |
| AI630940 | UNKNOWN | 52 | 0 | T |
| AI630940 | UNKNOWN | 13 | 178 | A |
| AI630947 | UNKNOWN | 49 | 0 | T |
| AI630952 | UNKNOWN | 38 | 0 | T |
| AI630997 | UNKNOWN | 13 | 219 | A |
| AI631057 | UNKNOWN | 113 | 0 | T |
| AI631057 | UNKNOWN | 24 | 346 | G |
| AI631057 | UNKNOWN | 21 | 118 | G |
| AI631057 | UNKNOWN | 14 | 278 | C |
| AI631057 | UNKNOWN | 13 | 149 | C |
| AI631064 | UNKNOWN | 31 | 0 | T |
| AI631072 | UNKNOWN | 13 | 52 | T |
| AI631076 | UNKNOWN | 55 | 0 | T |
| AI631082 | UNKNOWN | 55 | 0 | T |
| AI631083 | UNKNOWN | 46 | 0 | T |
| AI631091 | UNKNOWN | 21 | 0 | T |
| AI631095 | UNKNOWN | 74 | 0 | T |
| AI631095 | UNKNOWN | 15 | 362 | C |
| AI631107 | UNKNOWN | 129 | 0 | T |
| AI631107 | UNKNOWN | 29 | 169 | G |
| AI631107 | UNKNOWN | 14 | 134 | C |
| AI631109 | UNKNOWN | 45 | 0 | T |
| AI631112 | UNKNOWN | 73 | 0 | T |
| AI631116 | UNKNOWN | 26 | 0 | T |
| AI631135 | UNKNOWN | 13 | 398 | T |
| AI631201 | UNKNOWN | 14 | 0 | T |
| AI631212 | UNKNOWN | 72 | 0 | T |
| AI631212 | UNKNOWN | 13 | 160 | C |
| AI631212 | UNKNOWN | 13 | 197 | A |
| AI631216 | UNKNOWN | 65 | 0 | T |
| AI631240 | UNKNOWN | 49 | 0 | T |
| AI631264 | UNKNOWN | 90 | 0 | T |
| AI631264 | UNKNOWN | 16 | 290 | C |
| AI631264 | UNKNOWN | 14 | 160 | A |
| AI631264 | UNKNOWN | 13 | 130 | C |
| AI631269 | UNKNOWN | 81 | 0 | T |
| AI631269 | UNKNOWN | 15 | 87 | A |
| AI631269 | UNKNOWN | 13 | 147 | G |

TABLE 1-continued

| Genbank # | Region | # reps | Position | Unit sequence |
|---|---|---|---|---|
| AI631273 | UNKNOWN | 114 | 0 | T |
| AI631273 | UNKNOWN | 18 | 263 | G |
| AI631273 | UNKNOWN | 17 | 350 | A |
| AI631273 | UNKNOWN | 16 | 310 | C |
| AI631273 | UNKNOWN | 13 | 159 | G |
| AI631305 | UNKNOWN | 50 | 0 | T |
| AI631307 | UNKNOWN | 40 | 0 | T |
| AI631336 | UNKNOWN | 54 | 0 | T |
| AI631390 | UNKNOWN | 84 | 0 | T |
| AI631390 | UNKNOWN | 12 | 130 | A |
| AI631390 | UNKNOWN | 12 | 368 | G |
| AI631482 | UNKNOWN | 21 | 0 | T |
| AI631526 | UNKNOWN | 17 | 0 | T |
| AI631527 | UNKNOWN | 28 | 0 | T |
| AI631594 | UNKNOWN | 17 | 0 | T |
| AI631655 | UNKNOWN | 25 | 0 | T |
| AI631683 | UNKNOWN | 28 | 0 | T |
| AI631693 | UNKNOWN | 19 | 6 | T |
| AI631719 | UNKNOWN | 30 | 0 | T |
| AI631725 | UNKNOWN | 13 | 0 | T |
| AI631741 | UNKNOWN | 12 | 0 | T |
| AI631744 | UNKNOWN | 12 | 0 | T |
| AI631758 | UNKNOWN | 13 | 0 | T |
| AI631796 | UNKNOWN | 46 | 0 | T |
| AI631797 | UNKNOWN | 12 | 0 | T |
| AI631833 | UNKNOWN | 14 | 82 | A |
| AI631833 | UNKNOWN | 13 | 0 | T |
| AI631842 | UNKNOWN | 20 | 0 | T |
| AI631871 | UNKNOWN | 5.66 | 48 | AAC |
| AI631876 | UNKNOWN | 41 | 0 | T |
| AI631876 | UNKNOWN | 19 | 155 | A |
| AI631977 | UNKNOWN | 59 | 0 | T |
| AI631989 | UNKNOWN | 3.8 | 177 | TTTTC |
| AI632001 | UNKNOWN | 15 | 309 | T |
| AI632012 | UNKNOWN | 33 | 0 | T |
| AI632015 | UNKNOWN | 15 | 0 | T |
| AI632033 | UNKNOWN | 103 | 0 | T |
| AI632033 | UNKNOWN | 16 | 170 | A |
| AI632033 | UNKNOWN | 12 | 130 | A |
| AI632036 | UNKNOWN | 51 | 0 | T |
| AI632096 | UNKNOWN | 44 | 0 | T |
| AI632143 | UNKNOWN | 16 | 0 | T |
| AI632162 | UNKNOWN | 27 | 22 | T |
| AI632162 | UNKNOWN | 20 | 0 | T |
| AI632200 | UNKNOWN | 12 | 8 | T |
| AI632240 | UNKNOWN | 16 | 0 | T |
| AI632257 | UNKNOWN | 21 | 369 | A |
| AI632257 | UNKNOWN | 13 | 404 | T |
| AI632259 | UNKNOWN | 3.6 | 441 | AAAAC |
| AI632259 | UNKNOWN | 4.75 | 452 | AAAC |
| AI632259 | UNKNOWN | 18 | 241 | T |
| AI632272 | UNKNOWN | 60 | 0 | T |
| AI632303 | UNKNOWN | 60 | 0 | T |
| AI632314 | UNKNOWN | 13 | 0 | T |
| AI632322 | UNKNOWN | 4.8 | 103 | AAAAC |
| AI632341 | UNKNOWN | 47 | 0 | T |
| AI632365 | UNKNOWN | 61 | 0 | T |
| AI632391 | UNKNOWN | 67 | 0 | T |
| AI632408 | UNKNOWN | 97 | 0 | T |
| AI632408 | UNKNOWN | 18 | 125 | C |
| AI632408 | UNKNOWN | 13 | 195 | G |
| AI632445 | UNKNOWN | 16 | 243 | T |
| AI632623 | UNKNOWN | 35 | 0 | T |
| AI632676 | UNKNOWN | 18 | 0 | T |
| AI632678 | UNKNOWN | 24 | 0 | T |
| AI632701 | UNKNOWN | 36 | 0 | T |
| AI632711 | UNKNOWN | 2.7 | 441 | AACAGAATAG (SEQ ID NO:135) |
| AI632711 | UNKNOWN | 8.6 | 479 | AGAAT |
| AI632713 | UNKNOWN | 14 | 148 | T |
| AI632744 | UNKNOWN | 25 | 0 | T |
| AI632789 | UNKNOWN | 15 | 0 | T |
| AI632808 | UNKNOWN | 54 | 0 | T |
| AI632808 | UNKNOWN | 17 | 289 | A |
| AI632808 | UNKNOWN | 14 | 94 | A |
| AI632819 | UNKNOWN | 59 | 0 | T |
| AI632819 | UNKNOWN | 22 | 241 | A |
| AI632819 | UNKNOWN | 17 | 263 | C |

TABLE 1-continued

| Genbank # | Region | # reps | Position | Unit sequence |
|---|---|---|---|---|
| AI632830 | UNKNOWN | 30 | 0 | T |
| AI632839 | UNKNOWN | 30 | 0 | T |
| AI632850 | UNKNOWN | 61 | 0 | T |
| AI632851 | UNKNOWN | 76 | 0 | T |
| AI632851 | UNKNOWN | 15 | 303 | G |
| AI632851 | UNKNOWN | 13 | 96 | A |
| AI632854 | UNKNOWN | 55 | 0 | T |
| AI632899 | UNKNOWN | 16 | 0 | T |
| AI632903 | UNKNOWN | 26 | 0 | T |
| AI632911 | UNKNOWN | 12 | 135 | T |
| AI632924 | UNKNOWN | 4 | 267 | AAAAC |
| AI632997 | UNKNOWN | 102 | 0 | T |
| AI632997 | UNKNOWN | 20 | 368 | G |
| AI632997 | UNKNOWN | 19 | 347 | A |
| AI632997 | UNKNOWN | 15 | 133 | A |
| AI632997 | UNKNOWN | 12 | 181 | C |
| AI633000 | UNKNOWN | 77 | 0 | T |
| AI633000 | UNKNOWN | 20 | 77 | A |
| AI633000 | UNKNOWN | 16 | 306 | G |
| AI633042 | UNKNOWN | 69 | 0 | T |
| AI633061 | UNKNOWN | 58 | 0 | T |
| AI633061 | UNKNOWN | 14 | 92 | A |
| AI633062 | UNKNOWN | 79 | 0 | T |
| AI633062 | UNKNOWN | 14 | 152 | G |
| AI633066 | UNKNOWN | 44 | 0 | T |
| AI633073 | UNKNOWN | 111 | 0 | T |
| AI633073 | UNKNOWN | 17 | 164 | A |
| AI633073 | UNKNOWN | 16 | 147 | G |
| AI633073 | UNKNOWN | 12 | 181 | C |
| AI633157 | UNKNOWN | 17 | 48 | A |
| AI633165 | UNKNOWN | 45 | 0 | T |
| AI633183 | UNKNOWN | 24 | 0 | T |
| AI633196 | UNKNOWN | 70 | 0 | T |
| AI633198 | UNKNOWN | 70 | 0 | T |
| AI633198 | UNKNOWN | 17 | 117 | G |
| AI633216 | UNKNOWN | 32 | 0 | T |
| AI633225 | UNKNOWN | 51 | 0 | T |
| AI633228 | UNKNOWN | 16 | 0 | T |
| AI633246 | UNKNOWN | 11.5 | 223 | TG |
| AI633253 | UNKNOWN | 42 | 0 | T |
| AI633288 | UNKNOWN | 34 | 0 | T |
| AI633297 | UNKNOWN | 107 | 0 | T |
| AI633297 | UNKNOWN | 16 | 296 | C |
| AI633297 | UNKNOWN | 16 | 312 | G |
| AI633297 | UNKNOWN | 12 | 192 | C |
| AI633300 | UNKNOWN | 57 | 0 | T |
| AI633305 | UNKNOWN | 45 | 0 | T |
| AI633305 | UNKNOWN | 13 | 154 | A |
| AI633305 | UNKNOWN | 12 | 191 | C |
| AI633306 | UNKNOWN | 97 | 0 | T |
| AI633306 | UNKNOWN | 12 | 97 | G |
| AI633308 | UNKNOWN | 105 | 0 | T |
| AI633308 | UNKNOWN | 14 | 215 | C |
| AI633308 | UNKNOWN | 13 | 307 | G |
| AI633308 | UNKNOWN | 12 | 114 | A |
| AI633314 | UNKNOWN | 85 | 0 | T |
| AI633314 | UNKNOWN | 18 | 124 | A |
| AI633314 | UNKNOWN | 16 | 172 | C |
| AI633314 | UNKNOWN | 12 | 216 | G |
| AI633321 | UNKNOWN | 59 | 0 | T |
| AI633321 | UNKNOWN | 14 | 81 | C |
| AI633325 | UNKNOWN | 20 | 0 | T |
| AI633330 | UNKNOWN | 102 | 0 | T |
| AI633330 | UNKNOWN | 26 | 130 | C |
| AI633330 | UNKNOWN | 20 | 159 | G |
| AI633351 | UNKNOWN | 13 | 0 | T |
| AI633397 | UNKNOWN | 3.5 | 117 | AAAACC |
| AI633397 | UNKNOWN | 4.5 | 91 | AACC |
| AI633397 | UNKNOWN | 33 | 0 | T |
| AI633397 | UNKNOWN | 14 | 107 | A |
| AI633402 | UNKNOWN | 74 | 0 | T |
| AI633402 | UNKNOWN | 19 | 153 | C |
| AI633402 | UNKNOWN | 16 | 187 | G |
| AI633419 | UNKNOWN | 121 | 0 | T |
| AI633419 | UNKNOWN | 17 | 194 | G |
| AI633477 | UNKNOWN | 74 | 0 | T |
| AI633500 | UNKNOWN | 15 | 11 | T |

TABLE 1-continued

| Genbank # | Region | # reps | Position | Unit sequence |
|---|---|---|---|---|
| AI633523 | UNKNOWN | 5 | 106 | AAACA |
| AI633574 | UNKNOWN | 14 | 0 | T |
| AI633690 | UNKNOWN | 17 | 0 | T |
| AI633743 | UNKNOWN | 19 | 0 | T |
| AI633810 | UNKNOWN | 30 | 0 | T |
| AI633885 | UNKNOWN | 27 | 0 | T |
| AI633983 | UNKNOWN | 19 | 0 | T |
| AI633993 | UNKNOWN | 6 | 51 | GAG |
| AI634016 | UNKNOWN | 10.5 | 9 | TA |
| AI634110 | UNKNOWN | 12 | 415 | A |
| AI634219 | UNKNOWN | 93 | 0 | T |
| AI634219 | UNKNOWN | 13 | 223 | A |
| AI634219 | UNKNOWN | 12 | 94 | G |
| AI634221 | UNKNOWN | 69 | 0 | T |
| AI634221 | UNKNOWN | 12 | 92 | A |
| AI634223 | UNKNOWN | 76 | 0 | T |
| AI634223 | UNKNOWN | 16 | 362 | C |
| AI634224 | UNKNOWN | 103 | 0 | T |
| AI634224 | UNKNOWN | 18 | 218 | A |
| AI634224 | UNKNOWN | 13 | 169 | A |
| AI634235 | UNKNOWN | 42 | 0 | T |
| AI634249 | UNKNOWN | 56 | 0 | T |
| AI634251 | UNKNOWN | 90 | 0 | T |
| AI634274 | UNKNOWN | 37 | 0 | T |
| AI634305 | UNKNOWN | 68 | 0 | T |
| AI634305 | UNKNOWN | 22 | 124 | G |
| AI634305 | UNKNOWN | 12 | 94 | C |
| AI634326 | UNKNOWN | 14.5 | 109 | AT |
| AI634326 | UNKNOWN | 14 | 0 | T |
| AI634345 | UNKNOWN | 110 | 0 | T |
| AI634345 | UNKNOWN | 20 | 186 | A |
| AI634345 | UNKNOWN | 16 | 349 | G |
| AI634345 | UNKNOWN | 14 | 110 | A |
| AI634345 | UNKNOWN | 13 | 213 | G |
| AI634345 | UNKNOWN | 13 | 323 | C |
| AI634347 | UNKNOWN | 14 | 0 | T |
| AI634350 | UNKNOWN | 50 | 0 | T |
| AI634350 | UNKNOWN | 12 | 116 | A |
| AI634371 | UNKNOWN | 21 | 377 | A |
| AI634375 | UNKNOWN | 28 | 66 | T |
| AI634400 | UNKNOWN | 48 | 0 | T |
| AI634436 | UNKNOWN | 5.75 | 59 | AAAC |
| AI634457 | UNKNOWN | 53 | 0 | T |
| AI634467 | UNKNOWN | 72 | 0 | T |
| AI634467 | UNKNOWN | 16 | 250 | A |
| AI634527 | UNKNOWN | 36 | 0 | T |
| AI634548 | UNKNOWN | 16 | 0 | T |
| AI634565 | UNKNOWN | 13 | 438 | T |
| AI634592 | UNKNOWN | 27 | 0 | T |
| AI634595 | UNKNOWN | 43 | 0 | T |
| AI634626 | UNKNOWN | 55 | 0 | T |
| AI634626 | UNKNOWN | 13 | 300 | A |
| AI634634 | UNKNOWN | 72 | 0 | T |
| AI634646 | UNKNOWN | 14 | 0 | T |
| AI634678 | UNKNOWN | 18 | 0 | T |
| Ar634682 | UNKNOWN | 81 | 0 | T |
| AI634682 | UNKNOWN | 12 | 95 | A |
| AI634682 | UNKNOWN | 12 | 172 | C |
| AI634683 | UNKNOWN | 29 | 0 | T |
| AI634707 | UNKNOWN | 93 | 0 | T |
| AI634707 | UNKNOWN | 18 | 113 | A |
| AI634707 | UNKNOWN | 17 | 290 | C |
| AI634707 | UNKNOWN | 13 | 207 | G |
| AI634719 | UNKNOWN | 69 | 0 | T |
| AI634719 | UNKNOWN | 20 | 138 | C |
| AI634719 | UNKNOWN | 15 | 123 | A |
| AI634723 | UNKNOWN | 47 | 0 | T |
| AI634731 | UNKNOWN | 61 | 0 | T |
| AI634731 | UNKNOWN | 16 | 167 | G |
| AI634731 | UNKNOWN | 14 | 124 | C |
| AI634736 | UNKNOWN | 60 | 0 | T |
| AI634737 | UNKNOWN | 96 | 17 | T |
| AI634737 | UNKNOWN | 18 | 247 | C |
| AI634737 | UNKNOWN | 17 | 230 | G |
| AI634737 | UNKNOWN | 16 | 0 | T |
| AI634737 | UNKNOWN | 14 | 176 | A |
| AI634751 | UNKNOWN | 104 | 0 | T |

TABLE 1-continued

| Genbank # | Region | # reps | Position | Unit sequence |
|---|---|---|---|---|
| AI634805 | UNKNOWN | 2.53 | 125 | AAAAAATTTAAAA (SEQ ID NO:136) |
| AI634805 | UNKNOWN | 61 | 0 | T |
| AI634863 | UNKNOWN | 3.83 | 415 | AGCAGA |
| AI634919 | UNKNOWN | 69 | 0 | T |
| AI634919 | UNKNOWN | 15 | 166 | C |
| AI634930 | UNKNOWN | 48 | 0 | T |
| AI634930 | UNKNOWN | 12 | 206 | A |
| AI635013 | UNKNOWN | 57 | 0 | T |
| AI635013 | UNKNOWN | 14 | 116 | C |
| AI635016 | UNKNOWN | 84 | 0 | T |
| AI635016 | UNKNOWN | 16 | 284 | G |
| AI635016 | UNKNOWN | 15 | 84 | A |
| AI635032 | UNKNOWN | 78 | 0 | T |
| AI635032 | UNKNOWN | 16 | 109 | A |
| AI635032 | UNKNOWN | 15 | 127 | G |
| AI635038 | UNKNOWN | 69 | 0 | T |
| AI635038 | UNKNOWN | 21 | 367 | C |
| AI635038 | UNKNOWN | 17 | 143 | G |
| AI635038 | UNKNOWN | 15 | 190 | A |
| AI635038 | UNKNOWN | 12 | 224 | C |
| AI635045 | UNKNOWN | 89 | 0 | T |
| AI635045 | UNKNOWN | 15 | 98 | A |
| AI635066 | UNKNOWN | 3.8 | 271 | TTTTG |
| AI635067 | UNKNOWN | 85 | 0 | T |
| AI635067 | UNKNOWN | 14 | 175 | G |
| AI635079 | UNKNOWN | 51 | 0 | T |
| AI635079 | UNKNOWN | 13 | 196 | A |
| AI635082 | UNKNOWN | 50 | 0 | T |
| AI635111 | UNKNOWN | 72 | 0 | T |
| AI635132 | UNKNOWN | 60 | 0 | T |
| AI635132 | UNKNOWN | 16 | 212 | G |
| AI635132 | UNKNOWN | 14 | 231 | A |
| AI635154 | UNKNOWN | 58 | 0 | T |
| AI635154 | UNKNOWN | 17 | 225 | A |
| AI635154 | UNKNOWN | 12 | 58 | A |
| AI635158 | UNKNOWN | 53 | 0 | T |
| AI635164 | UNKNOWN | 71 | 0 | T |
| AI635164 | UNKNOWN | 20 | 217 | G |
| AI635216 | UNKNOWN | 73 | 0 | T |
| AI635216 | UNKNOWN | 15 | 339 | A |
| AI635216 | UNKNOWN | 14 | 121 | A |
| AI635216 | UNKNOWN | 12 | 295 | C |
| AI635217 | UNKNOWN | 17 | 30 | T |
| AI635224 | UNKNOWN | 44 | 0 | T |
| AI635226 | UNKNOWN | 36 | 0 | T |
| AI635247 | UNKNOWN | 19 | 0 | T |
| AI635287 | UNKNOWN | 76 | 0 | T |
| AI635287 | UNKNOWN | 14 | 76 | A |
| AI635287 | UNKNOWN | 13 | 127 | G |
| AI635299 | UNKNOWN | 75 | 0 | T |
| AI635299 | UNKNOWN | 17 | 150 | A |
| AI635351 | UNKNOWN | 17 | 0 | T |
| AI635367 | UNKNOWN | 73 | 0 | T |
| AI635367 | UNKNOWN | 17 | 145 | A |
| AI635367 | UNKNOWN | 16 | 162 | C |
| AI635398 | UNKNOWN | 5.75 | 315 | ATAA |
| AI635457 | UNKNOWN | 73 | 0 | T |
| AI635457 | UNKNOWN | 27 | 346 | C |
| AI635457 | UNKNOWN | 16 | 217 | C |
| AI635457 | UNKNOWN | 12 | 383 | G |
| AI635461 | UNKNOWN | 124 | 0 | T |
| AI635461 | UNKNOWN | 20 | 257 | C |
| AI635461 | UNKNOWN | 14 | 124 | A |
| AI635461 | UNKNOWN | 12 | 172 | G |
| AI635464 | UNKNOWN | 85 | 0 | T |
| AI635464 | UNKNOWN | 12 | 147 | C |
| AI635464 | UNKNOWN | 12 | 164 | A |
| AI635466 | UNKNOWN | 23 | 0 | T |
| AI635467 | UNKNOWN | 99 | 0 | T |
| AI635467 | UNKNOWN | 23 | 252 | G |
| AI635467 | UNKNOWN | 13 | 155 | C |
| AI635467 | UNKNOWN | 12 | 99 | A |
| AI635467 | UNKNOWN | 12 | 143 | G |
| AI635478 | UNKNOWN | 91 | 0 | T |
| AI635478 | UNKNOWN | 28 | 101 | A |
| AI635478 | UNKNOWN | 16 | 256 | G |
| AI635478 | UNKNOWN | 15 | 174 | G |

TABLE 1-continued

| Genbank # | Region | # reps | Position | Unit sequence |
|---|---|---|---|---|
| AI635492 | UNKNOWN | 86 | 0 | T |
| AI635492 | UNKNOWN | 26 | 179 | C |
| AI635492 | UNKNOWN | 14 | 211 | G |
| AI635492 | UNKNOWN | 14 | 270 | A |
| AI635498 | UNKNOWN | 23 | 0 | T |
| AI635513 | UNKNOWN | 17 | 0 | T |
| AI635522 | UNKNOWN | 19 | 336 | A |
| AI635634 | UNKNOWN | 51 | 0 | T |
| AI635634 | UNKNOWN | 13 | 112 | A |
| AI635634 | UNKNOWN | 12 | 95 | A |
| AI635639 | UNKNOWN | 63 | 0 | T |
| AI635639 | UNKNOWN | 12 | 83 | A |
| AI635639 | UNKNOWN | 12 | 115 | C |
| AI635659 | UNKNOWN | 10.5 | 127 | AC |
| AI635684 | UNKNOWN | 12 | 0 | T |
| AI635702 | UNKNOWN | 56 | 0 | T |
| AI635702 | UNKNOWN | 17 | 163 | A |
| AI635729 | UNKNOWN | 21 | 0 | T |
| AI635787 | UNKNOWN | 18 | 0 | T |
| AI635794 | UNKNOWN | 49 | 0 | T |
| AI635794 | UNKNOWN | 13 | 49 | A |
| AI635813 | UNKNOWN | 55 | 0 | T |
| AI635825 | UNKNOWN | 22 | 0 | T |
| AI635851 | UNKNOWN | 60 | 0 | T |
| AI635851 | UNKNOWN | 17 | 265 | A |
| AI635851 | UNKNOWN | 14 | 60 | A |
| AI635861 | UNKNOWN | 69 | 0 | T |
| AI635861 | UNKNOWN | 13 | 132 | A |
| AI635871 | UNKNOWN | 26 | 147 | T |
| AI635897 | UNKNOWN | 69 | 0 | T |
| AI635925 | UNKNOWN | 64 | 0 | T |
| AI635925 | UNKNOWN | 13 | 178 | G |
| AI635926 | UNKNOWN | 76 | 0 | T |
| AI635926 | UNKNOWN | 13 | 325 | A |
| AI635926 | UNKNOWN | 12 | 121 | A |
| AI635950 | UNKNOWN | 52 | 0 | T |
| AI635955 | UNKNOWN | 52 | 0 | T |
| AI635958 | UNKNOWN | 55 | 0 | T |
| AI635958 | UNKNOWN | 14 | 217 | G |
| AI635982 | UNKNOWN | 65 | 0 | T |
| AI635982 | UNKNOWN | 19 | 115 | A |
| AI635987 | UNKNOWN | 3.5 | 8 | TTTATT |
| AI636016 | UNKNOWN | 13 | 0 | T |
| AI636035 | UNKNOWN | 20 | 2 | T |
| AI636067 | UNKNOWN | 6.5 | 259 | TA |
| AI636102 | UNKNOWN | 21 | 285 | T |
| AI636137 | UNKNOWN | 70 | 0 | T |
| AI636137 | UNKNOWN | 12 | 237 | G |
| AI636138 | UNKNOWN | 35 | 0 | T |
| AI636148 | UNKNOWN | 34 | 0 | T |
| AI636149 | UNKNOWN | 61 | 0 | T |
| AI636169 | UNKNOWN | 13 | 400 | A |
| AI636170 | UNKNOWN | 72 | 0 | T |
| AI636183 | UNKNOWN | 108 | 0 | T |
| AI636183 | UNKNOWN | 22 | 313 | G |
| AI636183 | UNKNOWN | 16 | 240 | C |
| AI636183 | UNKNOWN | 15 | 151 | A |
| AI636183 | UNKNOWN | 12 | 197 | G |
| AI636187 | UNKNOWN | 49 | 0 | T |
| AI636197 | UNKNOWN | 63 | 0 | T |
| AI636197 | UNKNOWN | 12 | 243 | G |
| AI636218 | UNKNOWN | 13 | 0 | T |
| AI636233 | UNKNOWN | 26 | 0 | T |
| AI636242 | UNKNOWN | 15 | 304 | A |
| AI636245 | UNKNOWN | 12 | 198 | A |
| AI636250 | UNKNOWN | 12 | 85 | T |
| AI636268 | UNKNOWN | 80 | 0 | T |
| AI636268 | UNKNOWN | 14 | 198 | G |
| AI636268 | UNKNOWN | 12 | 185 | C |
| AI636273 | UNKNOWN | 18 | 253 | A |
| AI636309 | UNKNOWN | 66 | 0 | T |
| AI636346 | UNKNOWN | 52 | 0 | T |
| AI636348 | UNKNOWN | 15 | 348 | A |
| AI636362 | UNKNOWN | 55 | 0 | T |
| AI636372 | UNKNOWN | 93 | 0 | T |
| AI636372 | UNKNOWN | 18 | 164 | A |
| AI636386 | UNKNOWN | 63 | 0 | T |

TABLE 1-continued

| Genbank # | Region | # reps | Position | Unit sequence |
|---|---|---|---|---|
| AI636399 | UNKNOWN | 67 | 0 | T |
| AI636399 | UNKNOWN | 15 | 83 | G |
| AI636410 | UNKNOWN | 48 | 0 | T |
| AI636410 | UNKNOWN | 15 | 132 | A |
| AI636445 | UNKNOWN | 116 | 0 | T |
| AI636456 | UNKNOWN | 100 | 0 | T |
| AI636456 | UNKNOWN | 18 | 166 | G |
| AI636456 | UNKNOWN | 15 | 238 | A |
| AI636456 | UNKNOWN | 15 | 263 | C |
| AI636457 | UNKNOWN | 68 | 0 | T |
| AI636457 | UNKNOWN | 25 | 215 | A |
| AI636457 | UNKNOWN | 18 | 240 | C |
| AI636457 | UNKNOWN | 13 | 121 | A |
| AI636457 | UNKNOWN | 12 | 68 | C |
| AI636457 | UNKNOWN | 12 | 83 | A |
| AI636467 | UNKNOWN | 61 | 0 | T |
| AI636467 | UNKNOWN | 17 | 102 | A |
| AI636474 | UNKNOWN | 24 | 0 | T |
| AI636474 | UNKNOWN | 13 | 107 | A |
| AI636482 | UNKNOWN | 59 | 0 | T |
| AI636482 | UNKNOWN | 16 | 225 | G |
| AI636485 | UNKNOWN | 97 | 0 | T |
| AI636485 | UNKNOWN | 25 | 340 | C |
| AI636485 | UNKNOWN | 12 | 281 | G |
| AI636550 | UNKNOWN | 24 | 0 | T |
| AI636570 | UNKNOWN | 17 | 0 | T |
| AI636571 | UNKNOWN | 12 | 0 | T |
| AI636583 | UNKNOWN | 14 | 2 | G |
| AI636585 | UNKNOWN | 112 | 0 | T |
| AI636585 | UNKNOWN | 15 | 310 | C |
| AI636585 | UNKNOWN | 13 | 264 | G |
| AI636585 | UNKNOWN | 12 | 160 | G |
| AI636591 | UNKNOWN | 43 | 0 | T |
| AI636595 | UNKNOWN | 90 | 0 | T |
| AI636595 | UNKNOWN | 13 | 209 | C |
| AI636595 | UNKNOWN | 12 | 131 | A |
| AI636619 | UNKNOWN | 79 | 0 | T |
| AI636627 | UNKNOWN | 3.83 | 363 | AAAAC |
| AI636627 | UNKNOWN | 15 | 0 | T |
| AI636648 | UNKNOWN | 6.75 | 1 | TTTA |
| AI636648 | UNKNOWN | 12 | 360 | A |
| AI636650 | UNKNOWN | 44 | 0 | T |
| AI636650 | UNKNOWN | 15 | 173 | A |
| AI636672 | UNKNOWN | 8.5 | 263 | TG |
| AI636677 | UNKNOWN | 27 | 0 | T |
| AI636707 | UNKNOWN | 12 | 0 | T |
| AI636719 | UNKNOWN | 110 | 0 | T |
| AI636719 | UNKNOWN | 23 | 129 | A |
| AI636727 | UNKNOWN | 45 | 0 | T |
| AI636735 | UNKNOWN | 57 | 0 | T |
| AI636790 | UNKNOWN | 39 | 0 | T |
| AI636865 | UNKNOWN | 37 | 0 | T |
| AI636919 | UNKNOWN | 14 | 0 | T |
| AI636948 | UNKNOWN | 23 | 176 | A |
| AI637509 | UNKNOWN | 35 | 0 | T |
| AI637521 | UNKNOWN | 61 | 0 | T |
| AI637553 | UNKNOWN | 19 | 77 | T |
| AI637553 | UNKNOWN | 17 | 135 | G |
| AI637553 | UNKNOWN | 15 | 96 | A |
| AI637563 | UNKNOWN | 37 | 0 | T |
| AI637584 | UNKNOWN | 111 | 0 | T |
| AI637584 | UNKNOWN | 33 | 183 | C |
| AI637584 | UNKNOWN | 18 | 133 | A |
| AI637584 | UNKNOWN | 15 | 111 | A |
| AI637584 | UNKNOWN | 15 | 218 | G |
| AI637584 | UNKNOWN | 13 | 170 | G |
| AI637584 | UNKNOWN | 12 | 151 | C |
| AI637613 | UNKNOWN | 14 | 0 | T |
| AI637661 | UNKNOWN | 16 | 0 | T |
| AI637664 | UNKNOWN | 18 | 0 | T |
| AI637665 | UNKNOWN | 50 | 0 | T |
| AI637665 | UNKNOWN | 13 | 296 | A |
| AI637665 | UNKNOWN | 12 | 278 | C |
| AI637667 | UNKNOWN | 15 | 2 | T |
| AI637682 | UNKNOWN | 30 | 83 | T |
| AI637733 | UNKNOWN | 12 | 232 | A |
| AI637735 | UNKNOWN | 22 | 0 | T |

TABLE 1-continued

| Genbank # | Region | # reps | Position | Unit sequence |
|---|---|---|---|---|
| AI637748 | UNKNOWN | 79 | 0 | T |
| AI637748 | UNKNOWN | 18 | 185 | G |
| AI637784 | UNKNOWN | 7 | 210 | CAAA |
| AI637833 | UNKNOWN | 65 | 0 | T |
| AI637841 | UNKNOWN | 12 | 0 | T |
| AI637873 | UNKNOWN | 18 | 278 | T |
| AI637876 | UNKNOWN | 3.5 | 202 | AAACAA |
| AI637896 | UNKNOWN | 34 | 0 | T |
| AI637914 | UNKNOWN | 61 | 362 | C |
| AI637914 | UNKNOWN | 40 | 266 | C |
| AI637914 | UNKNOWN | 15 | 250 | C |
| AI637930 | UNKNOWN | 41 | 0 | T |
| AI637955 | UNKNOWN | 12 | 0 | T |
| AI637977 | UNKNOWN | 15 | 0 | T |
| AI638034 | UNKNOWN | 19 | 0 | T |
| AI638058 | UNKNOWN | 25 | 0 | T |
| AI638077 | UNKNOWN | 18 | 0 | T |
| AI638120 | UNKNOWN | 14 | 2 | T |
| AI638166 | UNKNOWN | 15 | 0 | T |
| AI638184 | UNKNOWN | 28 | 0 | T |
| AI638190 | UNKNOWN | 4.75 | 369 | AAGA |
| AI638295 | UNKNOWN | 20 | 0 | T |
| AI638299 | UNKNOWN | 7 | 30 | GCT |
| AI638403 | UNKNOWN | 12 | 0 | T |
| AI638412 | UNKNOWN | 7.5 | 120 | GA |
| AI638435 | UNKNOWN | 33 | 0 | T |
| AI638468 | UNKNOWN | 13 | 0 | T |
| AI638497 | UNKNOWN | 20 | 0 | T |
| AI638532 | UNKNOWN | 14.66 | 49 | AAC |
| AI638581 | UNKNOWN | 47 | 0 | T |
| AI638581 | UNKNOWN | 12 | 99 | A |
| AI638582 | UNKNOWN | 46 | 0 | T |
| AI638593 | UNKNOWN | 12 | 0 | T |
| AI638623 | UNKNOWN | 15 | 0 | T |
| AI638633 | UNKNOWN | 12 | 0 | T |
| AI638641 | UNKNOWN | 26 | 0 | T |
| AI638641 | UNKNOWN | 13 | 322 | A |
| AI638678 | UNKNOWN | 17 | 0 | T |
| AI638691 | UNKNOWN | 9.66 | 180 | TTA |
| AI638721 | UNKNOWN | 7 | 261 | CT |
| AI638772 | UNKNOWN | 3.8 | 145 | AAAAT |
| AI638798 | UNKNOWN | 77 | 0 | T |
| AI638831 | UNKNOWN | 12 | 0 | T |
| AI638850 | UNKNOWN | 35 | 0 | T |
| AI638852 | UNKNOWN | 18 | 203 | T |
| AI638881 | UNKNOWN | 17 | 0 | T |
| AI640133 | UNKNOWN | 4 | 316 | CAATAC |
| AI640147 | UNKNOWN | 12 | 175 | T |
| AI640153 | UNKNOWN | 19 | 55 | A |
| AI640174 | UNKNOWN | 14 | 317 | A |
| AI640262 | UNKNOWN | 16 | 0 | T |
| AI640280 | UNKNOWN | 19 | 0 | T |
| AI640290 | UNKNOWN | 26 | 0 | T |
| AI640309 | UNKNOWN | 30 | 0 | T |
| AI640355 | UNKNOWN | 13 | 0 | T |
| AI640360 | UNKNOWN | 14 | 20 | T |
| AI640365 | UNKNOWN | 13 | 0 | T |
| AI640375 | UNKNOWN | 52 | 0 | T |
| AI640379 | UNKNOWN | 110 | 0 | T |
| AI640379 | UNKNOWN | 21 | 187 | A |
| AI640379 | UNKNOWN | 15 | 172 | C |
| AI640392 | UNKNOWN | 65 | 0 | T |
| AI640415 | UNKNOWN | 18 | 0 | T |
| AI640446 | UNKNOWN | 31 | 0 | T |
| AI640483 | UNKNOWN | 16 | 164 | A |
| AI640555 | UNKNOWN | 8.5 | 420 | CA |
| AI640555 | UNKNOWN | 7 | 407 | GC |
| AI640616 | UNKNOWN | 17 | 108 | A |
| AI640624 | UNKNOWN | 15 | 0 | T |
| AI640634 | UNKNOWN | 15 | 386 | T |
| AI640635 | UNKNOWN | 24 | 0 | T |
| AI640646 | UNKNOWN | 38 | 0 | T |
| AI640663 | UNKNOWN | 13 | 0 | T |
| AI640700 | UNKNOWN | 79 | 0 | T |
| AI640700 | UNKNOWN | 16 | 136 | C |
| AI640700 | UNKNOWN | 15 | 152 | A |
| AI640704 | UNKNOWN | 92 | 17 | T |

TABLE 1-continued

| Genbank # | Region | # reps | Position | Unit sequence |
|---|---|---|---|---|
| AI640704 | UNKNOWN | 15 | 176 | C |
| AI640704 | UNKNOWN | 12 | 109 | A |
| AI640704 | UNKNOWN | 12 | 222 | G |
| AI640729 | UNKNOWN | 84 | 0 | T |
| AI640729 | UNKNOWN | 14 | 253 | G |
| AI640729 | UNKNOWN | 14 | 277 | C |
| AI640737 | UNKNOWN | 49 | 0 | T |
| AI640781 | UNKNOWN | 21 | 0 | T |
| AI640783 | UNKNOWN | 33 | 0 | T |
| AI640799 | UNKNOWN | 82 | 0 | T |
| AI640799 | UNKNOWN | 14 | 289 | G |
| AI640799 | UNKNOWN | 12 | 245 | G |
| AI640873 | UNKNOWN | 63 | 0 | T |
| AI640873 | UNKNOWN | 17 | 156 | A |
| AI640873 | UNKNOWN | 13 | 113 | A |
| AI640873 | UNKNOWN | 12 | 173 | C |
| AI648402 | UNKNOWN | 35 | 0 | T |
| AI648408 | UNKNOWN | 72 | 0 | T |
| AI648408 | UNKNOWN | 14 | 148 | G |
| AI648408 | UNKNOWN | 12 | 133 | A |
| AI648433 | UNKNOWN | 32 | 0 | T |
| AI648454 | UNKNOWN | 71 | 0 | T |
| AI648454 | UNKNOWN | 16 | 96 | A |
| AI648458 | UNKNOWN | 80 | 0 | T |
| AI648458 | UNKNOWN | 12 | 121 | A |
| AI648473 | UNKNOWN | 80 | 0 | T |
| AI648473 | UNKNOWN | 12 | 263 | A |
| AI648481 | UNKNOWN | 16 | 0 | T |
| AI648502 | UNKNOWN | 84 | 0 | T |
| AI648502 | UNKNOWN | 12 | 193 | A |
| AI648508 | UNKNOWN | 69 | 0 | T |
| AI648509 | UNKNOWN | 102 | 0 | T |
| AI648509 | UNKNOWN | 15 | 102 | T |
| AI648509 | UNKNOWN | 15 | 259 | C |
| AI648584 | UNKNOWN | 27 | 0 | T |
| AI648585 | UNKNOWN | 21 | 0 | T |
| AI648663 | UNKNOWN | 101 | 0 | T |
| AI648663 | UNKNOWN | 16 | 199 | A |
| AI648663 | UNKNOWN | 15 | 123 | C |
| AI648684 | UNKNOWN | 111 | 0 | T |
| AI648684 | UNKNOWN | 14 | 157 | G |
| AI648684 | UNKNOWN | 13 | 130 | A |
| AI650251 | UNKNOWN | 14 | 0 | T |
| AI650256 | UNKNOWN | 4,8 | 20 | TTTTG |
| AI650291 | UNKNOWN | 14 | 0 | T |
| AI650305 | UNKNOWN | 27 | 0 | T |
| AI650310 | UNKNOWN | 59 | 0 | T |
| AI650310 | UNKNOWN | 12 | 248 | C |
| AI650341 | UNKNOWN | 30 | 380 | T |
| AI650343 | UNKNOWN | 16 | 405 | A |
| AI650404 | UNKNOWN | 15 | 0 | T |
| AI650442 | UNKNOWN | 19 | 4 | T |
| AI650477 | UNKNOWN | 18 | 52 | T |
| AI650492 | UNKNOWN | 17 | 0 | T |
| AI650525 | UNKNOWN | 37 | 0 | T |
| AI650525 | UNKNOWN | 15 | 139 | A |
| AI650545 | UNKNOWN | 15 | 538 | AC |
| AI650645 | UNKNOWN | 31 | 0 | T |
| AI650658 | UNKNOWN | 16 | 0 | T |
| AI650678 | UNKNOWN | 21 | 0 | T |
| AI650711 | UNKNOWN | 38 | 0 | T |
| AI650763 | UNKNOWN | 12 | 0 | T |
| AI650787 | UNKNOWN | 75 | 0 | T |
| AI650787 | UNKNOWN | 15 | 239 | G |
| AI650851 | UNKNOWN | 12 | 52 | A |
| AI650872 | UNKNOWN | 5.66 | 71 | GCT |
| AI650883 | UNKNOWN | 31 | 0 | T |
| AI650985 | UNKNOWN | 17 | 65 | A |
| AI650994 | UNKNOWN | 27 | 0 | T |
| AI651039 | UNKNOWN | 18 | 0 | T |
| AI651043 | UNKNOWN | 15 | 129 | T |
| AI651045 | UNKNOWN | 83 | 0 | T |
| AI651045 | UNKNOWN | 13 | 109 | G |
| AI651118 | UNKNOWN | 32 | 0 | T |
| AI651127 | UNKNOWN | 22 | 0 | T |
| AI651263 | UNKNOWN | 12 | 20 | T |
| AI651314 | UNKNOWN | 13 | 0 | T |

TABLE 1-continued

| Genbank # | Region | # reps | Position | Unit sequence |
|---|---|---|---|---|
| AI651322 | UNKNOWN | 29 | 0 | T |
| AI651329 | UNKNOWN | 6.66 | 331 | GTA |
| AI651384 | UNKNOWN | 13 | 0 | T |
| AI651478 | UNKNOWN | 7 | 44 | AT |
| AI651482 | UNKNOWN | 6.75 | 478 | AAAC |
| AI651484 | UNKNOWN | 12 | 384 | A |
| AI651510 | UNKNOWN | 12 | 0 | T |
| AI651527 | UNKNOWN | 4.33 | 211 | TTTGTT |
| AI651558 | UNKNOWN | 12 | 0 | T |
| AI651609 | UNKNOWN | 36 | 0 | T |
| AI651610 | UNKNOWN | 12 | 0 | T |
| AI651641 | UNKNOWN | 3.6 | 136 | TTTGG |
| AI651641 | UNKNOWN | 16 | 174 | A |
| AI651641 | UNKNOWN | 15 | 0 | T |
| AI651666 | UNKNOWN | 6 | 29 | GCC |
| AI651712 | UNKNOWN | 15 | 326 | T |
| AI651732 | UNKNOWN | 15 | 0 | T |
| AI651811 | UNKNOWN | 23 | 0 | T |
| AI651840 | UNKNOWN | 77 | 0 | T |
| AI651840 | UNKNOWN | 13 | 127 | G |
| AI651848 | UNKNOWN | 14 | 0 | T |
| AI651866 | UNKNOWN | 19 | 0 | T |
| AI651903 | UNKNOWN | 18 | 4 | T |
| AI651922 | UNKNOWN | 14 | 0 | T |
| AI651930 | UNKNOWN | 24 | 13 | T |
| AI651938 | UNKNOWN | 22 | 4 | T |
| AI651942 | UNKNOWN | 17 | 0 | T |
| AI651964 | UNKNOWN | 15 | 0 | T |
| AI651965 | UNKNOWN | 12 | 922 | T |
| AI651967 | UNKNOWN | 16 | 0 | T |
| AI652028 | UNKNOWN | 56 | 0 | T |
| AI652028 | UNKNOWN | 17 | 84 | A |
| AI652028 | UNKNOWN | 15 | 151 | G |
| AI652030 | UNKNOWN | 12 | 0 | T |
| AI652068 | UNKNOWN | 23 | 0 | T |
| AI652072 | UNKNOWN | 18 | 0 | T |
| AI652085 | UNKNOWN | 13 | 0 | T |
| AI652087 | UNKNOWN | 14 | 0 | T |
| AI652128 | UNKNOWN | 18 | 52 | A |
| AI652174 | UNKNOWN | 13 | 0 | T |
| AI652277 | UNKNOWN | 12 | 0 | T |
| AI652331 | UNKNOWN | 12 | 0 | T |
| AI652336 | UNKNOWN | 58 | 0 | T |
| AI652367 | UNKNOWN | 14 | 0 | T |
| AI652384 | UNKNOWN | 8.5 | 235 | TA |
| AI652384 | UNKNOWN | 14 | 0 | T |
| AI652450 | UNKNOWN | 3.6 | 429 | AACCA |
| AI652450 | UNKNOWN | 22 | 0 | T |
| AI652451 | UNKNOWN | 31 | 0 | T |
| AI652471 | UNKNOWN | 18 | 0 | T |
| AI652516 | UNKNOWN | 5.75 | 346 | TTTG |
| AI652516 | UNKNOWN | 13 | 155 | A |
| AI652523 | UNKNOWN | 8 | 354 | CAAT |
| AI652534 | UNKNOWN | 16 | 9 | T |
| AI652539 | UNKNOWN | 20 | 1 | T |
| AI652568 | UNKNOWN | 17 | 99 | A |
| AI652568 | UNKNOWN | 14 | 0 | T |
| AI652640 | UNKNOWN | 26 | 0 | T |
| AI652654 | UNKNOWN | 28 | 0 | T |
| AI652654 | UNKNOWN | 19 | 188 | A |
| AI652677 | UNKNOWN | 30 | 0 | T |
| AI652703 | UNKNOWN | 18 | 0 | T |
| AI652703 | UNKNOWN | 12 | 514 | A |
| AI652822 | UNKNOWN | 14 | 0 | T |
| AI652837 | UNKNOWN | 41 | 0 | T |
| AI652843 | UNKNOWN | 36 | 0 | T |
| AI652843 | UNKNOWN | 13 | 206 | A |
| AI652855 | UNKNOWN | 13 | 0 | T |
| AI652868 | UNKNOWN | 17 | 0 | T |
| AI652899 | UNKNOWN | 12 | 0 | T |
| AI652919 | UNKNOWN | 17 | 479 | T |
| AI652930 | UNKNOWN | 27 | 0 | T |
| AI652961 | UNKNOWN | 30 | 0 | T |
| AI653029 | UNKNOWN | 32 | 0 | T |
| AI653152 | UNKNOWN | 23 | 0 | T |
| AI653154 | UNKNOWN | 16 | 0 | T |
| AI653174 | UNKNOWN | 13 | 256 | A |

TABLE 1-continued

| Genbank # | Region | # reps | Position | Unit sequence |
|---|---|---|---|---|
| AI653181 | UNKNOWN | 32 | 0 | T |
| AI653231 | UNKNOWN | 38 | 0 | T |
| AI653251 | UNKNOWN | 6.66 | 301 | TCC |
| AI653269 | UNKNOWN | 16 | 0 | T |
| AI653280 | UNKNOWN | 20 | 0 | T |
| AI653303 | UNKNOWN | 43 | 0 | T |
| AI653306 | UNKNOWN | 29 | 0 | T |
| AI653350 | UNKNOWN | 21 | 0 | T |
| AI653368 | UNKNOWN | 12 | 103 | T |
| AI653409 | UNKNOWN | 19 | 0 | T |
| AI653415 | UNKNOWN | 26 | 0 | T |
| AI653430 | UNKNOWN | 38 | 0 | T |
| AI653430 | UNKNOWN | 20 | 358 | A |
| AI653443 | UNKNOWN | 83 | 0 | T |
| AI653443 | UNKNOWN | 13 | 188 | A |
| AI653446 | UNKNOWN | 46 | 0 | T |
| AI653464 | UNKNOWN | 48 | 0 | T |
| AI653487 | UNKNOWN | 20 | 0 | T |
| AI653527 | UNKNOWN | 44 | 0 | T |
| AI653537 | UNKNOWN | 100 | 0 | T |
| AI653537 | UNKNOWN | 16 | 192 | A |
| AT653537 | UNKNOWN | 15 | 159 | A |
| AI653537 | UNKNOWN | 15 | 177 | G |
| AI653537 | UNKNOWN | 13 | 146 | C |
| AI653541 | UNKNOWN | 119 | 0 | T |
| AI653541 | UNKNOWN | 21 | 246 | C |
| AI653541 | UNKNOWN | 18 | 132 | A |
| AI653541 | UNKNOWN | 18 | 150 | C |
| AI653541 | UNKNOWN | 13 | 307 | G |
| AI653541 | UNKNOWN | 12 | 267 | G |
| AI653576 | UNKNOWN | 43 | 0 | T |
| AI653578 | UNKNOWN | 60 | 0 | T |
| AI653636 | UNKNOWN | 13 | 28 | T |
| AI653669 | UNKNOWN | 21 | 0 | T |
| AI653763 | UNKNOWN | 45 | 0 | T |
| AI653766 | UNKNOWN | 46 | 0 | T |
| AI653769 | UNKNOWN | 61 | 0 | T |
| AI653771 | UNKNOWN | 44 | 0 | T |
| AI653777 | UNKNOWN | 41 | 0 | T |
| AI653782 | UNKNOWN | 50 | 0 | T |
| AI653829 | UNKNOWN | 61 | 0 | T |
| AI653829 | UNKNOWN | 12 | 239 | G |
| AI653836 | UNKNOWN | 108 | 0 | T |
| AI653840 | UNKNOWN | 96 | 0 | T |
| AI653840 | UNKNOWN | 18 | 261 | G |
| AI653840 | UNKNOWN | 13 | 209 | C |
| AI653923 | UNKNOWN | 69 | 0 | T |
| AI653973 | UNKNOWN | 82 | 0 | T |
| AI653973 | UNKNOWN | 18 | 94 | A |
| AI653973 | UNKNOWN | 14 | 315 | G |
| AI653977 | UNKNOWN | 24 | 40 | T |
| AI653979 | UNKNOWN | 89 | 0 | T |
| AI653979 | UNKNOWN | 16 | 126 | G |
| AI653979 | UNKNOWN | 15 | 93 | A |
| AI653989 | UNKNOWN | 55 | 0 | T |
| AI653999 | UNKNOWN | 20 | 125 | T |
| AI654015 | UNKNOWN | 73 | 0 | T |
| AI654016 | UNKNOWN | 12 | 0 | T |
| AI654051 | UNKNOWN | 19 | 0 | T |
| AI654054 | UNKNOWN | 15 | 0 | T |
| AI654073 | UNKNOWN | 7 | 261 | AC |
| AI654105 | UNKNOWN | 42 | 0 | T |
| AI654108 | UNKNOWN | 22 | 0 | T |
| AI654110 | UNKNOWN | 38 | 0 | T |
| AI654110 | UNKNOWN | 13 | 392 | A |
| AI654132 | UNKNOWN | 12 | 456 | A |
| AI654135 | UNKNOWN | 55 | 0 | T |
| AI654137 | UNKNOWN | 46 | 0 | T |
| AI654155 | UNKNOWN | 13 | 61 | A |
| AI654185 | UNKNOWN | 14 | 0 | T |
| AI654216 | UNKNOWN | 19 | 0 | T |
| AI654222 | UNKNOWN | 16 | 9 | T |
| AI654229 | UNKNOWN | 20 | 10 | T |
| AI654230 | UNKNOWN | 24 | 0 | T |
| AI654258 | UNKNOWN | 52 | 0 | T |
| AI654258 | UNKNOWN | 12 | 126 | A |
| AI654261 | UNKNOWN | 13 | 0 | T |

TABLE 1-continued

| Genbank # | Region | # reps | Position | Unit sequence |
|---|---|---|---|---|
| AI654270 | UNKNOWN | 90 | 0 | T |
| AI654270 | UNKNOWN | 12 | 124 | A |
| AI654270 | UNKNOWN | 12 | 212 | G |
| AI654276 | UNKNOWN | 100 | 20 | T |
| AI654276 | UNKNOWN | 17 | 212 | C |
| AI654276 | UNKNOWN | 16 | 425 | A |
| AI654276 | UNKNOWN | 15 | 245 | G |
| AI654305 | UNKNOWN | 35 | 0 | T |
| AI654370 | UNKNOWN | 12 | 149 | A |
| AI654389 | UNKNOWN | 91 | 0 | T |
| AI654389 | UNKNOWN | 16 | 176 | A |
| AI654389 | UNKNOWN | 16 | 437 | G |
| AI654389 | UNKNOWN | 15 | 264 | C |
| AI654389 | UNKNOWN | 13 | 133 | G |
| AI654453 | UNKNOWN | 63 | 0 | T |
| AI654453 | UNKNOWN | 12 | 149 | A |
| AI654601 | UNKNOWN | 87 | 0 | T |
| AI654601 | UNKNOWN | 14 | 169 | G |
| AI654601 | UNKNOWN | 14 | 325 | C |
| AI654601 | UNKNOWN | 13 | 196 | A |
| AI654622 | UNKNOWN | 30 | 0 | T |
| AI654636 | UNKNOWN | 12 | 0 | T |
| AI654637 | UNKNOWN | 24 | 0 | T |
| AI654658 | UNKNOWN | 22 | 0 | T |
| AI654672 | UNKNOWN | 94 | 0 | T |
| AI654672 | UNKNOWN | 23 | 137 | C |
| AI654672 | UNKNOWN | 15 | 207 | G |
| AI654672 | UNKNOWN | 14 | 123 | A |
| Ar654674 | UNKNOWN | 30 | 0 | T |
| AI654675 | UNKNOWN | 25 | 0 | T |
| AI654675 | UNKNOWN | 14 | 349 | A |
| AI654750 | UNKNOWN | 119 | 0 | T |
| AI654750 | UNKNOWN | 25 | 271 | G |
| AI654750 | UNKNOWN | 24 | 123 | A |
| AI654750 | UNKNOWN | 13 | 538 | C |
| AI654756 | UNKNOWN | 47 | 0 | T |
| AI654857 | UNKNOWN | 24 | 0 | T |
| AI654867 | UNKNOWN | 14 | 0 | T |
| AI654885 | UNKNOWN | 22 | 0 | T |
| AI655057 | UNKNOWN | 18 | 4 | T |
| AI655064 | UNKNOWN | 6.5 | 265 | AG |
| AI655070 | UNKNOWN | 7.5 | 369 | AG |
| AI655165 | UNKNOWN | 23 | 0 | T |
| AI655172 | UNKNOWN | 14 | 0 | T |
| AI655323 | UNKNOWN | 65 | 0 | T |
| AI655372 | UNKNOWN | 35 | 0 | T |
| AI655376 | UNKNOWN | 19 | 0 | T |
| AI655410 | UNKNOWN | 5.16 | 238 | GTGGCA |
| AI655413 | UNKNOWN | 18 | 0 | T |
| AI655491 | UNKNOWN | 12 | 0 | T |
| AI655494 | UNKNOWN | 3.57 | 281 | TTTTTA |
| AI655499 | UNKNOWN | 16 | 315 | A |
| AI655524 | UNKNOWN | 6.5 | 520 | AG |
| AI655573 | UNKNOWN | 2.98 | 129 | GGCAGCCTAGAAGGAATTGTGTCCAGTCCACAAGTGAGC AGACCTGTCATCCTCCCCCC (SEQ ID NO:137) |
| AI655617 | UNKNOWN | 6.33 | 189 | CCG |
| AI655658 | UNKNOWN | 17 | 0 | T |
| AI655665 | UNKNOWN | 14 | 0 | T |
| AI655716 | UNKNOWN | 21 | 338 | T |
| AI655778 | UNKNOWN | 29 | 176 | A |
| AI655778 | UNKNOWN | 15 | 0 | T |
| AI655824 | UNKNOWN | 19 | 0 | T |
| AI655841 | UNKNOWN | 74 | 0 | T |
| AI655841 | UNKNOWN | 16 | 214 | G |
| AI655846 | UNKNOWN | 15 | 0 | T |
| AI655932 | UNKNOWN | 88 | 6 | T |
| AI655932 | UNKNOWN | 14 | 252 | A |
| AI655932 | UNKNOWN | 12 | 119 | A |
| AI655983 | UNKNOWN | 21 | 0 | T |
| AI656012 | UNKNOWN | 19 | 4 | T |
| AI656013 | UNKNOWN | 19 | 4 | T |
| AI656036 | UNKNOWN | 3.83 | 314 | AAAACA |
| AI656036 | UNKNOWN | 17 | 237 | T |
| AI656040 | UNKNOWN | 2.94 | 49 | CAGGCAAACTAAGAAAT (SEQ ID NO:138) |
| AI656047 | UNKNOWN | 5.66 | 371 | TCT |
| AI656051 | UNKNOWN | 17 | 67 | T |
| AI656091 | UNKNOWN | 30 | 0 | T |

TABLE 1-continued

| Genbank # | Region | # reps | Position | Unit sequence |
|---|---|---|---|---|
| AI656094 | UNKNOWN | 16 | 0 | T |
| AI656100 | UNKNOWN | 27 | 0 | T |
| AI656116 | UNKNOWN | 12 | 0 | T |
| AI656128 | UNKNOWN | 30 | 0 | T |
| AI656293 | UNKNOWN | 29 | 0 | T |
| AI656361 | UNKNOWN | 16 | 0 | T |
| AI656385 | UNKNOWN | 15 | 0 | T |
| AI656504 | UNKNOWN | 14 | 0 | T |
| AI656522 | UNKNOWN | 54 | 0 | T |
| AI656522 | UNKNOWN | 15 | 129 | A |
| AI656524 | UNKNOWN | 17 | 0 | T |
| AI656534 | UNKNOWN | 7.75 | 75 | AAAT |
| AI656534 | UNKNOWN | 47 | 0 | T |
| AI656619 | UNKNOWN | 26 | 0 | T |
| AI656630 | UNKNOWN | 14 | 0 | T |
| AI656632 | UNKNOWN | 35 | 0 | T |
| A1656634 | UNKNOWN | 20 | 0 | T |
| AI656658 | UNKNOWN | 5.75 | 35 | AAAG |
| AI656658 | UNKNOWN | 19 | 405 | T |
| AI656693 | UNKNOWN | 19 | 0 | T |
| AI656741 | UNKNOWN | 56 | 0 | T |
| AI656741 | UNKNOWN | 13 | 383 | A |
| AI656741 | UNKNOWN | 12 | 107 | C |
| AI656743 | UNKNOWN | 30 | 0 | T |
| AI656759 | UNKNOWN | 15 | 0 | T |
| AI656821 | UNKNOWN | 41 | 0 | T |
| AI656836 | UNKNOWN | 15 | 197 | C |
| AI656836 | UNKNOWN | 12 | 169 | A |
| AI656840 | UNKNOWN | 7 | 55 | ATT |
| AI656892 | UNKNOWN | 30 | 0 | T |
| AI656897 | UNKNOWN | 17 | 0 | T |
| AI657019 | UNKNOWN | 12 | 165 | A |
| AI657032 | UNKNOWN | 21 | 0 | T |
| AI657063 | UNKNOWN | 17 | 0 | T |
| AI657096 | UNKNOWN | 52 | 0 | T |
| AI657485 | UNKNOWN | 18 | 1271 | A |
| AI657485 | UNKNOWN | 14 | 1162 | T |
| AI658485 | UNKNOWN | 13 | 0 | T |
| AI658522 | UNKNOWN | 18 | 0 | T |
| AI658560 | UNKNOWN | 64 | 0 | T |
| AI658560 | UNKNOWN | 19 | 134 | C |
| AI658560 | UNKNOWN | 13 | 108 | G |
| AI658623 | UNKNOWN | 7 | 132 | AC |
| AI658684 | UNKNOWN | 41 | 0 | T |
| AI658704 | UNKNOWN | 18 | 0 | T |
| AI658784 | UNKNOWN | 14 | 29 | T |
| AI658828 | UNKNOWN | 19 | 0 | T |
| AI658835 | UNKNOWN | 3.8 | 2 | TTTTC |
| AI658835 | UNKNOWN | 12 | 17 | T |
| AI658924 | UNKNOWN | 15 | 0 | T |
| AI658928 | UNKNOWN | 6.5 | 377 | AC |
| AI658939 | UNKNOWN | 15 | 0 | T |
| AI658955 | UNKNOWN | 24 | 74 | T |
| AI658963 | UNKNOWN | 12 | 0 | T |
| AI659006 | UNKNOWN | 14 | 0 | T |
| AI659041 | UNKNOWN | 49 | 0 | T |
| AI659043 | UNKNOWN | 51 | 0 | T |
| AI659043 | UNKNOWN | 12 | 144 | A |
| AI659074 | UNKNOWN | 35 | 0 | T |
| AI659074 | UNKNOWN | 19 | 88 | A |
| AI659084 | UNKNOWN | 14 | 43 | T |
| AI659099 | UNKNOWN | 39 | 0 | T |
| AI659131 | UNKNOWN | 19 | 0 | T |
| AI659195 | UNKNOWN | 12 | 69 | T |
| AI659217 | UNKNOWN | 23 | 0 | T |
| AI659251 | UNKNOWN | 17 | 97 | T |
| AI659273 | UNKNOWN | 4.66 | 145 | TTTTTG |
| AI659297 | UNKNOWN | 43 | 0 | T |
| AI659334 | UNKNOWN | 77 | 0 | T |
| AI659334 | UNKNOWN | 22 | 125 | C |
| AI659334 | UNKNOWN | 15 | 82 | A |
| AI659359 | UNKNOWN | 37 | 0 | T |
| AI659377 | UNKNOWN | 13 | 0 | T |
| AI659398 | UNKNOWN | 36 | 0 | T |
| AI659462 | UNKNOWN | 10.5 | 368 | TG |
| AI659475 | UNKNOWN | 68 | 0 | T |
| AI659475 | UNKNOWN | 15 | 219 | C |

TABLE 1-continued

| Genbank # | Region | # reps | Position | Unit sequence |
|---|---|---|---|---|
| AI659475 | UNKNOWN | 12 | 365 | G |
| AI659477 | UNKNOWN | 25 | 0 | T |
| AI659491 | UNKNOWN | 38 | 0 | T |
| AI659498 | UNKNOWN | 18 | 4 | T |
| AI659518 | UNKNOWN | 76 | 0 | T |
| AI659518 | UNKNOWN | 17 | 195 | G |
| AI659518 | UNKNOWN | 14 | 139 | C |
| AI659552 | UNKNOWN | 39 | 0 | T |
| AI659555 | UNKNOWN | 74 | 0 | T |
| AI659575 | UNKNOWN | 35 | 0 | T |
| AI659585 | UNKNOWN | 64 | 0 | T |
| AI659585 | UNKNOWN | 22 | 405 | A |
| AI659585 | UNKNOWN | 21 | 239 | A |
| AI659585 | UNKNOWN | 17 | 117 | C |
| AI659585 | UNKNOWN | 14 | 64 | A |
| AI659587 | UNKNOWN | 17 | 248 | T |
| AI659641 | UNKNOWN | 12 | 157 | T |
| AI659681 | UNKNOWN | 18 | 0 | T |
| AI659753 | UNKNOWN | 19 | 0 | T |
| AI659788 | UNKNOWN | 16 | 0 | T |
| AI659790 | UNKNOWN | 24 | 0 | T |
| AI659794 | UNKNOWN | 45 | 0 | T |
| AI659795 | UNKNOWN | 78 | 0 | T |
| AI659795 | UNKNOWN | 23 | 186 | C |
| AI659795 | UNKNOWN | 20 | 139 | C |
| AI659834 | UNKNOWN | 12 | 396 | T |
| AI659900 | UNKNOWN | 40 | 0 | T |
| AI659927 | UNKNOWN | 14 | 233 | A |
| AI659939 | UNKNOWN | 12 | 0 | T |
| AI659989 | UNKNOWN | 47 | 0 | T |
| AI660153 | UNKNOWN | 43 | 0 | T |
| AI660174 | UNKNOWN | 37 | 0 | T |
| AI660245 | UNKNOWN | 36 | 0 | T |
| AI660247 | UNKNOWN | 22 | 0 | T |
| AI660377 | UNKNOWN | 24 | 0 | T |
| AI660432 | UNKNOWN | 65 | 0 | T |
| AI660432 | UNKNOWN | 12 | 286 | G |
| AI660468 | UNKNOWN | 13 | 0 | T |
| AI660538 | UNKNOWN | 45 | 0 | T |
| AI660538 | UNKNOWN | 15 | 82 | G |
| AI660652 | UNKNOWN | 21 | 0 | T |
| AI660898 | UNKNOWN | 35 | 0 | T |
| AI668557 | UNKNOWN | 13 | 384 | T |
| AI668574 | UNKNOWN | 5.75 | 158 | CATC |
| AI668574 | UNKNOWN | 22 | 429 | A |
| AI668607 | UNKNOWN | 9.5 | 426 | AT |
| AI668607 | UNKNOWN | 17 | 410 | A |
| AI668612 | UNKNOWN | 14 | 172 | T |
| AI668632 | UNKNOWN | 12 | 0 | T |
| AI668639 | UNKNOWN | 12 | 191 | A |
| AI668641 | UNKNOWN | 16 | 0 | T |
| AI668659 | UNKNOWN | 12 | 131 | T |
| AI668694 | UNKNOWN | 4.5 | 113 | CTCC |
| AI668694 | UNKNOWN | 7.66 | 173 | CTC |
| AI668694 | UNKNOWN | 5.66 | 132 | TCC |
| AI668694 | UNKNOWN | 6.5 | 202 | TC |
| AI668697 | UNKNOWN | 15 | 286 | A |
| AI668780 | UNKNOWN | 15 | 0 | T |
| AI668893 | UNKNOWN | 110 | 0 | T |
| AI668893 | UNKNOWN | 19 | 247 | C |
| AI668893 | UNKNOWN | 16 | 127 | C |
| AI668893 | UNKNOWN | 14 | 233 | A |
| AI668893 | UNKNOWN | 12 | 359 | G |
| AI668927 | UNKNOWN | 34 | 0 | T |
| AI668935 | UNKNOWN | 18 | 4 | T |
| AI668935 | UNKNOWN | 14 | 347 | A |
| AI668959 | UNKNOWN | 20 | 20 | T |
| AI668959 | UNKNOWN | 14 | 5 | T |
| AI668990 | UNKNOWN | 6 | 25 | TATT |
| AI668994 | UNKNOWN | 8 | 372 | AC |
| AI668996 | UNKNOWN | 24 | 0 | T |
| AI668996 | UNKNOWN | 19 | 118 | A |
| AI669000 | UNKNOWN | 37 | 0 | T |
| AI669004 | UNKNOWN | 14 | 4 | T |
| AI669006 | UNKNOWN | 15 | 0 | T |
| AI669131 | UNKNOWN | 21 | 0 | T |
| AI669202 | UNKNOWN | 27 | 0 | T |

TABLE 1-continued

| Genbank # | Region | # reps | Position | Unit sequence |
|---|---|---|---|---|
| AI669212 | UNKNOWN | 6 | 174 | CCA |
| AI669234 | UNKNOWN | 41 | 0 | T |
| AI669244 | UNKNOWN | 49 | 0 | T |
| AI669244 | UNKNOWN | 17 | 141 | A |
| AI669321 | UNKNOWN | 74 | 0 | T |
| AI669321 | UNKNOWN | 19 | 162 | C |
| AI669321 | UNKNOWN | 13 | 301 | A |
| AI669321 | UNKNOWN | 12 | 192 | G |
| AI669330 | UNKNOWN | 16 | 0 | T |
| AI669359 | UNKNOWN | 16 | 228 | T |
| AI669380 | UNKNOWN | 34 | 0 | T |
| AI669389 | UNKNOWN | 27 | 0 | T |
| AI669410 | UNKNOWN | 36 | 0 | T |
| AI669459 | UNKNOWN | 93 | 0 | T |
| AI669459 | UNKNOWN | 17 | 103 | A |
| AI669459 | UNKNOWN | 15 | 324 | C |
| AI669465 | UNKNOWN | 82 | 0 | T |
| AI669465 | UNKNOWN | 13 | 371 | G |
| AI669465 | UNKNOWN | 12 | 297 | G |
| AI669465 | UNKNOWN | 12 | 349 | c |
| AI669469 | UNKNOWN | 34 | 0 | T |
| AI669493 | UNKNOWN | 22 | 0 | T |
| AI669587 | UNKNOWN | 35 | 0 | T |
| AI669589 | UNKNOWN | 19 | 9 | T |
| AI669591 | UNKNOWN | 18 | 293 | A |
| AI669603 | UNKNOWN | 64 | 0 | T |
| AI669609 | UNKNOWN | 120 | 0 | T |
| AI669609 | UNKNOWN | 17 | 142 | A |
| AI669609 | UNKNOWN | 17 | 197 | G |
| AI669609 | UNKNOWN | 15 | 120 | C |
| AI669612 | UNKNOWN | 77 | 0 | T |
| AI669616 | UNKNOWN | 84 | 0 | T |
| AI669616 | UNKNOWN | 22 | 96 | A |
| AI669637 | UNKNOWN | 17 | 0 | T |
| AI669639 | UNKNOWN | 63 | 0 | T |
| AI669639 | UNKNOWN | 16 | 84 | A |
| AI669693 | UNKNOWN | 22 | 0 | T |
| AI669704 | UNKNOWN | 12 | 0 | T |
| AI669751 | UNKNOWN | 19 | 0 | T |
| AI669760 | UNKNOWN | 50 | 0 | T |
| AI669835 | UNKNOWN | 56 | 0 | T |
| AI669835 | UNKNOWN | 21 | 123 | G |
| AI669849 | UNKNOWN | 46 | 0 | T |
| AI669849 | UNKNOWN | 12 | 297 | G |
| AI669879 | UNKNOWN | 24 | 0 | T |
| AI669897 | UNKNOWN | 50 | 0 | T |
| AI669928 | UNKNOWN | 13 | 0 | T |
| AI669962 | UNKNOWN | 29 | 0 | T |
| AI670002 | UNKNOWN | 91 | 0 | T |
| AI670002 | UNKNOWN | 22 | 220 | G |
| AI670002 | UNKNOWN | 18 | 127 | A |
| AI670002 | UNKNOWN | 15 | 91 | A |
| AI670009 | UNKNOWN | 91 | 0 | T |
| AI670009 | UNKNOWN | 19 | 152 | C |
| AI670009 | UNKNOWN | 16 | 92 | A |
| AI670016 | UNKNOWN | 18 | 0 | T |
| AI670051 | UNKNOWN | 72 | 0 | T |
| AI670051 | UNKNOWN | 14 | 220 | C |
| AI670124 | UNKNOWN | 19 | 155 | T |
| AI670698 | UNKNOWN | 62 | 0 | T |
| AI670698 | UNKNOWN | 14 | 253 | G |
| AI670753 | UNKNOWN | 13 | 0 | T |
| AI670767 | UNKNOWN | 73 | 0 | T |
| AI670767 | UNKNOWN | 16 | 96 | C |
| AI670767 | UNKNOWN | 16 | 120 | A |
| AI670776 | UNKNOWN | 6.5 | 116 | CT |
| AI670782 | UNKNOWN | 102 | 0 | T |
| AI670782 | UNKNOWN | 17 | 154 | G |
| AI670790 | UNKNOWN | 70 | 0 | T |
| AI670790 | UNKNOWN | 26 | 92 | C |
| AI670790 | UNKNOWN | 12 | 73 | C |
| AI670801 | UNKNOWN | 50 | 1 | T |
| AI670843 | UNKNOWN | 14 | 17 | T |
| AI670846 | UNKNOWN | 14 | 494 | A |
| AI670849 | UNKNOWN | 59 | 19 | T |
| AI670849 | UNKNOWN | 12 | 2 | T |
| AI670883 | UNKNOWN | 27 | 0 | T |

TABLE 1-continued

| Genbank # | Region | # reps | Position | Unit sequence |
|---|---|---|---|---|
| AI670895 | UNKNOWN | 60 | 0 | T |
| AI670895 | UNKNOWN | 16 | 150 | C |
| AI670984 | UNKNOWN | 46 | 0 | T |
| AI670997 | UNKNOWN | 17 | 13 | T |
| AI671080 | UNKNOWN | 33 | 0 | T |
| AI671101 | UNKNOWN | 19 | 0 | T |
| AI671122 | UNKNOWN | 14 | 0 | T |
| AI671275 | UNKNOWN | 13 | 0 | T |
| AI671278 | UNKNOWN | 34 | 0 | T |
| AI671284 | UNKNOWN | 48 | 0 | T |
| AI671319 | UNKNOWN | 16 | 312 | A |
| AI671361 | UNKNOWN | 44 | 0 | T |
| AI671385 | UNKNOWN | 20 | 0 | T |
| AI671408 | UNKNOWN | 19 | 0 | T |
| AI671429 | UNKNOWN | 47 | 0 | T |
| AI671429 | UNKNOWN | 13 | 216 | G |
| AI671439 | UNKNOWN | 5.75 | 37 | TTTC |
| AI671439 | UNKNOWN | 14 | 74 | TC |
| AI671439 | UNKNOWN | 12.5 | 101 | CA |
| AI671464 | UNKNOWN | 13 | 0 | T |
| AI671477 | UNKNOWN | 42 | 0 | T |
| AI671488 | UNKNOWN | 24 | 276 | T |
| AI671564 | UNKNOWN | 33 | 0 | T |
| AI671566 | UNKNOWN | 15 | 0 | T |
| AI671582 | UNKNOWN | 18 | 11 | T |
| AI671590 | UNKNOWN | 25 | 0 | T |
| AI671638 | UNKNOWN | 43 | 0 | T |
| AI671651 | UNKNOWN | 74 | 0 | T |
| AI671661 | UNKNOWN | 64 | 0 | T |
| AI671661 | UNKNOWN | 12 | 434 | G |
| AI671663 | UNKNOWN | 81 | 0 | T |
| AI671669 | UNKNOWN | 74 | 0 | T |
| AI671673 | UNKNOWN | 60 | 0 | T |
| AI671679 | UNKNOWN | 105 | 24 | T |
| AI671679 | UNKNOWN | 26 | 312 | A |
| AI671679 | UNKNOWN | 23 | 0 | T |
| AI671679 | UNKNOWN | 19 | 258 | A |
| AI671679 | UNKNOWN | 19 | 344 | C |
| AI671679 | UNKNOWN | 12 | 145 | A |
| AI671679 | UNKNOWN | 12 | 172 | G |
| AI671722 | UNKNOWN | 13 | 0 | T |
| AI671726 | UNKNOWN | 40 | 0 | T |
| AI671766 | UNKNOWN | 26 | 0 | T |
| AI671819 | UNKNOWN | 6.25 | 391 | TTTA |
| AI671834 | UNKNOWN | 3.6 | 50 | AAAAT |
| AI671836 | UNKNOWN | 16 | 0 | T |
| AI671897 | UNKNOWN | 12 | 10 | T |
| AI671910 | UNKNOWN | 33 | 0 | T |
| AI671931 | UNKNOWN | 77 | 0 | T |
| AI671956 | UNKNOWN | 16 | 0 | T |
| AI672059 | UNKNOWN | 12 | 0 | T |
| AI672072 | UNKNOWN | 6.5 | 104 | AT |
| AI672102 | UNKNOWN | 27 | 0 | T |
| AI672130 | UNKNOWN | 79 | 0 | T |
| AI672141 | UNKNOWN | 16 | 0 | T |
| AI672231 | UNKNOWN | 48 | 0 | T |
| AI672324 | UNKNOWN | 17 | 0 | T |
| AI672382 | UNKNOWN | 7.5 | 130 | AC |
| AI672384 | UNKNOWN | 66 | 0 | T |
| AI672384 | UNKNOWN | 18 | 86 | A |
| AI672386 | UNKNOWN | 12 | 445 | T |
| AI672389 | UNKNOWN | 8.5 | 323 | AC |
| AI672389 | UNKNOWN | 13 | 309 | A |
| AI672396 | UNKNOWN | 17 | 6 | T |
| AI672404 | UNKNOWN | 15 | 151 | A |
| AI672426 | UNKNOWN | 15 | 0 | T |
| AI672461 | UNKNOWN | 14 | 480 | T |
| AI672468 | UNKNOWN | 18 | 71 | T |
| AI672509 | UNKNOWN | 24 | 0 | T |
| AI672725 | UNKNOWN | 27 | 8 | T |
| AI672764 | UNKNOWN | 62 | 0 | T |
| AI672764 | UNKNOWN | 13 | 209 | G |
| AI672765 | UNKNOWN | 13.5 | 401 | TC |
| AI672794 | UNKNOWN | 46 | 0 | T |
| AI672794 | UNKNOWN | 12 | 106 | G |
| AI672847 | UNKNOWN | 45 | 0 | T |
| AI672860 | UNKNOWN | 18 | 146 | T |

TABLE 1-continued

| Genbank # | Region | # reps | Position | Unit sequence |
|---|---|---|---|---|
| AI672860 | UNKNOWN | 17 | 0 | T |
| AI672873 | UNKNOWN | 13 | 0 | T |
| AI672939 | UNKNOWN | 22 | 3 | T |
| AI673028 | UNKNOWN | 29 | 0 | T |
| AI673048 | UNKNOWN | 43 | 0 | T |
| AI673069 | UNKNOWN | 43 | 0 | T |
| AI673094 | UNKNOWN | 13 | 228 | T |
| AI673244 | UNKNOWN | 9 | 550 | ATT |
| AI673251 | UNKNOWN | 70 | 0 | T |
| AI673256 | UNKNOWN | 132 | 0 | T |
| AI673256 | UNKNOWN | 21 | 197 | G |
| AI673256 | UNKNOWN | 20 | 166 | A |
| AI673256 | UNKNOWN | 12 | 308 | C |
| AI673267 | UNKNOWN | 61 | 0 | T |
| AI673267 | UNKNOWN | 14 | 227 | A |
| AI673278 | UNKNOWN | 62 | 0 | T |
| AI673278 | UNKNOWN | 16 | 87 | A |
| AI673281 | UNKNOWN | 13 | 0 | T |
| AI673286 | UNKNOWN | 22 | 0 | T |
| AI673287 | UNKNOWN | 43 | 0 | T |
| AI673297 | UNKNOWN | 118 | 0 | T |
| AI673297 | UNKNOWN | 18 | 152 | G |
| AI673301 | UNKNOWN | 51 | 0 | T |
| AI673301 | UNKNOWN | 16 | 112 | G |
| AI673317 | UNKNOWN | 21 | 0 | T |
| AI673352 | UNKNOWN | 49 | 0 | T |
| AI673360 | UNKNOWN | 29 | 15 | T |
| AI673360 | UNKNOWN | 14 | 0 | T |
| AI673363 | UNKNOWN | 84 | 0 | T |
| AI673363 | UNKNOWN | 19 | 146 | G |
| AI673363 | UNKNOWN | 17 | 317 | A |
| AI673363 | UNKNOWN | 14 | 84 | A |
| AI673382 | UNKNOWN | 19 | 0 | T |
| AI673395 | UNKNOWN | 45 | 0 | T |
| AI673602 | UNKNOWN | 23 | 0 | T |
| AI673710 | UNKNOWN | 112 | 0 | T |
| AI673710 | UNKNOWN | 18 | 230 | C |
| AI673710 | UNKNOWN | 16 | 127 | A |
| AI673710 | UNKNOWN | 13 | 151 | G |
| AI673745 | UNKNOWN | 35 | 0 | T |
| AI673785 | UNKNOWN | 99 | 0 | T |
| AI673785 | UNKNOWN | 14 | 166 | C |
| AI674120 | UNKNOWN | 35 | 0 | T |
| AI674134 | UNKNOWN | 4.8 | 506 | CAAAC |
| AI674168 | UNKNOWN | 28 | 0 | T |
| AI674177 | UNKNOWN | 41 | 0 | T |
| AI674190 | UNKNOWN | 17 | 0 | T |
| AI674205 | UNKNOWN | 39 | 0 | T |
| AI674234 | UNKNOWN | 52 | 0 | T |
| AI674305 | UNKNOWN | 38 | 0 | T |
| AI674337 | UNKNOWN | 27 | 0 | T |
| AI674423 | UNKNOWN | 43 | 0 | T |
| AI674471 | UNKNOWN | 19 | 0 | T |
| AI674472 | UNKNOWN | 18 | 4 | T |
| AI674479 | UNKNOWN | 12 | 0 | T |
| AI674482 | UNKNOWN | 12 | 0 | T |
| AI674615 | UNKNOWN | 45 | 0 | T |
| AI674627 | UNKNOWN | 49 | 0 | T |
| AI674627 | UNKNOWN | 12 | 413 | G |
| AI674636 | UNKNOWN | 13 | 0 | T |
| AI674755 | UNKNOWN | 17 | 0 | T |
| AI674757 | UNKNOWN | 14 | 1 | T |
| AI674772 | UNKNOWN | 11.5 | 409 | TG |
| AI674786 | UNKNOWN | 15 | 0 | T |
| AI674810 | UNKNOWN | 18 | 3 | T |
| AI674811 | UNKNOWN | 19 | 0 | T |
| AI674812 | UNKNOWN | 12 | 0 | T |
| AI674838 | UNKNOWN | 95 | 0 | T |
| AI674838 | UNKNOWN | 18 | 97 | G |
| AI674838 | UNKNOWN | 12 | 322 | A |
| AI674856 | UNKNOWN | 27 | 0 | T |
| AI674862 | UNKNOWN | 52 | 0 | T |
| AI674872 | UNKNOWN | 41 | 0 | T |
| AI674872 | UNKNOWN | 14 | 170 | A |
| AI674880 | UNKNOWN | 47 | 0 | T |
| AI674912 | UNKNOWN | 93 | 0 | T |
| AI674912 | UNKNOWN | 15 | 93 | G |

TABLE 1-continued

| Genbank # | Region | # reps | Position | Unit sequence |
|---|---|---|---|---|
| AI674912 | UNKNOWN | 12 | 244 | A |
| AI674989 | UNKNOWN | 7 | 129 | GA |
| AI674995 | UNKNOWN | 23 | 0 | T |
| AI675004 | UNKNOWN | 33 | 0 | T |
| AI675052 | UNKNOWN | 83 | 0 | T |
| AI675052 | UNKNOWN | 12 | 304 | A |
| AI675128 | UNKNOWN | 55 | 0 | T |
| AI675158 | UNKNOWN | 22 | 0 | T |
| AI675240 | UNKNOWN | 11.5 | 159 | GT |
| AI675252 | UNKNOWN | 45 | 0 | T |
| AI675297 | UNKNOWN | 14 | 0 | T |
| AI675308 | UNKNOWN | 30 | 0 | T |
| AI675419 | UNKNOWN | 20 | 0 | T |
| AI675425 | UNKNOWN | 6.5 | 77 | TC |
| AI675476 | UNKNOWN | 32 | 451 | T |
| AI675648 | UNKNOWN | 17 | 0 | T |
| AI675679 | UNKNOWN | 35 | 25 | T |
| AI675703 | UNKNOWN | 13 | 0 | T |
| AI675773 | UNKNOWN | 16 | 0 | T |
| AI675824 | UNKNOWN | 29 | 0 | T |
| AI675836 | UNKNOWN | 13 | 141 | T |
| AI675849 | UNKNOWN | 3.6 | 64 | TTTGT |
| AI675849 | UNKNOWN | 12 | 47 | T |
| AI675881 | UNKNOWN | 7 | 512 | AT |
| AI675881 | UNKNOWN | 16 | 0 | T |
| AI675897 | UNKNOWN | 14 | 0 | T |
| AI675949 | UNKNOWN | 21 | 4 | T |
| AI676028 | UNKNOWN | 13 | 0 | T |
| AI676048 | UNKNOWN | 38 | 0 | T |
| AI676070 | UNKNOWN | 20 | 0 | T |
| AI676172 | UNKNOWN | 22 | 17 | T |
| AI676173 | UNKNOWN | 18 | 4 | T |
| AI676236 | UNKNOWN | 16 | 417 | CA |
| AI676251 | UNKNOWN | 49 | 0 | T |
| AI677636 | UNKNOWN | 52 | 0 | T |
| AI677646 | UNKNOWN | 80 | 0 | T |
| AI677646 | UNKNOWN | 12 | 203 | C |
| AI677762 | UNKNOWN | 26 | 17 | T |
| AI677762 | UNKNOWN | 15 | 0 | T |
| AI677777 | UNKNOWN | 81 | 0 | T |
| AI677796 | UNKNOWN | 103 | 0 | T |
| AI677796 | UNKNOWN | 22 | 103 | A |
| AI677796 | UNKNOWN | 15 | 185 | C |
| AI677797 | UNKNOWN | 74 | 0 | T |
| AI677815 | UNKNOWN | 78 | 0 | T |
| AI677815 | UNKNOWN | 12 | 294 | G |
| AI677824 | UNKNOWN | 71 | 0 | T |
| AI677824 | UNKNOWN | 15 | 92 | A |
| AI677842 | UNKNOWN | 19 | 0 | T |
| AI677850 | UNKNOWN | 21 | 2 | T |
| AI677858 | UNKNOWN | 5.25 | 7 | TCTT |
| AI677894 | UNKNOWN | 16 | 0 | T |
| AI677910 | UNKNOWN | 13 | 0 | T |
| AI677926 | UNKNOWN | 38 | 0 | T |
| AI677926 | UNKNOWN | 21 | 364 | A |
| AI677926 | UNKNOWN | 12 | 38 | A |
| AI677971 | UNKNOWN | 37 | 0 | T |
| AI677983 | UNKNOWN | 67 | 0 | T |
| AI678021 | UNKNOWN | 70 | 0 | T |
| AI678032 | UNKNOWN | 22 | 0 | T |
| AI678033 | UNKNOWN | 13 | 0 | T |
| AI678052 | UNKNOWN | 12 | 53 | A |
| AI678061 | UNKNOWN | 16 | 0 | T |
| AI678086 | UNKNOWN | 15 | 0 | T |
| AI678095 | UNKNOWN | 16 | 0 | T |
| AI678101 | UNKNOWN | 13 | 306 | T |
| AI678113 | UNKNOWN | 15 | 0 | T |
| AI678116 | UNKNOWN | 16 | 0 | T |
| AI678137 | UNKNOWN | 15 | 93 | T |
| AI678184 | UNKNOWN | 22 | 322 | T |
| AI678184 | UNKNOWN | 16 | 9 | T |
| AI678185 | UNKNOWN | 61 | 0 | T |
| AI678185 | UNKNOWN | 13 | 321 | C |
| AI678193 | UNKNOWN | 26 | 0 | T |
| AI678239 | UNKNOWN | 17 | 0 | T |
| AI678274 | UNKNOWN | 21 | 0 | T |
| AI678284 | UNKNOWN | 67 | 0 | T |

TABLE 1-continued

| Genbank # | Region | # reps | Position | Unit sequence |
|---|---|---|---|---|
| AI678284 | UNKNOWN | 18 | 125 | C |
| AI678284 | UNKNOWN | 18 | 145 | G |
| AI678293 | UNKNOWN | 40 | 0 | T |
| AI678302 | UNKNOWN | 125 | 0 | T |
| AI678302 | UNKNOWN | 19 | 158 | C |
| AI678310 | UNKNOWN | 25 | 0 | T |
| AI678324 | UNKNOWN | 44 | 0 | T |
| AI678324 | UNKNOWN | 21 | 94 | A |
| AI678355 | UNKNOWN | 88 | 0 | T |
| AI678355 | UNKNOWN | 15 | 223 | C |
| AI678357 | UNKNOWN | 89 | 0 | T |
| AI678357 | UNKNOWN | 19 | 200 | G |
| AI678409 | UNKNOWN | 57 | 0 | T |
| AI678411 | UNKNOWN | 76 | 0 | T |
| AI678411 | UNKNOWN | 12 | 92 | A |
| AI678428 | UNKNOWN | 87 | 0 | T |
| AI678443 | UNKNOWN | 97 | 0 | T |
| AI678443 | UNKNOWN | 14 | 97 | G |
| AI678480 | UNKNOWN | 70 | 0 | T |
| AI678493 | UNKNOWN | 34 | 0 | T |
| AI678496 | UNKNOWN | 49 | 0 | T |
| AI678496 | UNKNOWN | 13 | 163 | A |
| AI678541 | UNKNOWN | 12 | 0 | T |
| AI678544 | UNKNOWN | 6.33 | 196 | AAT |
| AI678599 | UNKNOWN | 95 | 0 | T |
| AI678599 | UNKNOWN | 14 | 98 | G |
| AI678599 | UNKNOWN | 13 | 245 | C |
| AI678602 | UNKNOWN | 77 | 0 | T |
| AI678602 | UNKNOWN | 17 | 365 | A |
| AI678602 | UNKNOWN | 14 | 351 | C |
| AI678602 | UNKNOWN | 12 | 143 | C |
| AI678602 | UNKNOWN | 12 | 219 | A |
| AI678613 | UNKNOWN | 15 | 11 | T |
| AI678637 | UNKNOWN | 50 | 0 | T |
| AI678675 | UNKNOWN | 27 | 0 | T |
| AI678676 | UNKNOWN | 6 | 149 | TATT |
| AI678688 | UNKNOWN | 74 | 0 | T |
| AI678688 | UNKNOWN | 12 | 232 | A |
| AI678721 | UNKNOWN | 14 | 0 | T |
| AI678745 | UNKNOWN | 4.5 | 0 | ATTT |
| AI678749 | UNKNOWN | 7.66 | 618 | CAG |
| AI678749 | UNKNOWN | 6.66 | 39 | CGC |
| AI678762 | UNKNOWN | 110 | 0 | T |
| AI678762 | UNKNOWN | 17 | 378 | G |
| AI678762 | UNKNOWN | 14 | 133 | G |
| AI678762 | UNKNOWN | 12 | 287 | C |
| AI678777 | UNKNOWN | 49 | 0 | T |
| AI678778 | UNKNOWN | 59 | 0 | T |
| AI678778 | UNKNOWN | 15 | 275 | G |
| AI678791 | UNKNOWN | 39 | 0 | T |
| AI678807 | UNKNOWN | 55 | 0 | T |
| AI678814 | UNKNOWN | 27 | 0 | T |
| AI678833 | UNKNOWN | 48 | 0 | T |
| AI678850 | UNKNOWN | 91 | 0 | T |
| AI678850 | UNKNOWN | 14 | 116 | A |
| AI678850 | UNKNOWN | 13 | 228 | G |
| AI678857 | UNKNOWN | 55 | 0 | T |
| AI678875 | UNKNOWN | 70 | 0 | T |
| AI678875 | UNKNOWN | 12 | 92 | G |
| AI678956 | UNKNOWN | 21 | 7 | T |
| AI678989 | UNKNOWN | 75 | 0 | T |
| AI678989 | UNKNOWN | 24 | 265 | A |
| AI678989 | UNKNOWN | 18 | 154 | C |
| AI678989 | UNKNOWN | 14 | 203 | A |
| AI679043 | UNKNOWN | 50 | 0 | T |
| AI679095 | UNKNOWN | 57 | 0 | T |
| AI679098 | UNKNOWN | 77 | 0 | T |
| AI679098 | UNKNOWN | 22 | 84 | A |
| AI679098 | UNKNOWN | 16 | 149 | C |
| AI679098 | UNKNOWN | 15 | 235 | G |
| AI679117 | UNKNOWN | 66 | 0 | T |
| AI679117 | UNKNOWN | 12 | 342 | C |
| AI679125 | UNKNOWN | 62 | 0 | T |
| AI679149 | UNKNOWN | 26 | 0 | T |
| AI679152 | UNKNOWN | 39 | 0 | T |
| AI679164 | UNKNOWN | 56 | 0 | T |
| AI679164 | UNKNOWN | 12 | 88 | A |

TABLE 1-continued

| Genbank # | Region | # reps | Position | Unit sequence |
|---|---|---|---|---|
| AI679174 | UNKNOWN | 101 | 0 | T |
| AI679174 | UNKNOWN | 12 | 163 | C |
| AI679179 | UNKNOWN | 87 | 0 | T |
| AI679179 | UNKNOWN | 20 | 171 | G |
| AI679179 | UNKNOWN | 16 | 251 | A |
| AI679179 | UNKNOWN | 12 | 296 | C |
| AI679183 | UNKNOWN | 35 | 0 | T |
| AI679196 | UNKNOWN | 56 | 0 | T |
| AI679201 | UNKNOWN | 14 | 0 | T |
| AI679201 | UNKNOWN | 13 | 120 | A |
| AI679204 | UNKNOWN | 17 | 0 | T |
| AI679207 | UNKNOWN | 60 | 0 | T |
| AI679207 | UNKNOWN | 23 | 348 | G |
| AI679207 | UNKNOWN | 13 | 216 | C |
| AI679207 | UNKNOWN | 12 | 260 | G |
| AI679209 | UNKNOWN | 70 | 0 | T |
| AI679209 | UNKNOWN | 12 | 104 | A |
| AI679211 | UNKNOWN | 75 | 0 | T |
| AI679211 | UNKNOWN | 13 | 184 | C |
| AI679247 | UNKNOWN | 69 | 0 | T |
| AI679248 | UNKNOWN | 38 | 0 | T |
| AI679248 | UNKNOWN | 12 | 241 | A |
| AI679264 | UNKNOWN | 43 | 0 | T |
| AI679264 | UNKNOWN | 19 | 202 | A |
| AI679266 | UNKNOWN | 77 | 0 | T |
| AI679275 | UNKNOWN | 29 | 0 | T |
| AI679282 | UNKNOWN | 10 | 118 | GTAT |
| AI679282 | UNKNOWN | 10 | 155 | TATC |
| AI679312 | UNKNOWN | 57 | 0 | T |
| AI679321 | UNKNOWN | 105 | 0 | T |
| AI679321 | UNKNOWN | 22 | 161 | A |
| AI679321 | UNKNOWN | 15 | 302 | C |
| AI679321 | UNKNOWN | 14 | 221 | C |
| AI679357 | UNKNOWN | 40 | 0 | T |
| AI679362 | UNKNOWN | 48 | 0 | T |
| AI679366 | UNKNOWN | 20 | 65 | T |
| AI679366 | UNKNOWN | 13 | 178 | G |
| AI679366 | UNKNOWN | 12 | 52 | T |
| AI679382 | UNKNOWN | 74 | 0 | T |
| AI679388 | UNKNOWN | 44 | 0 | T |
| AI679423 | UNKNOWN | 18 | 0 | T |
| AI679472 | UNKNOWN | 52 | 0 | T |
| AI679472 | UNKNOWN | 16 | 187 | A |
| AI679487 | UNKNOWN | 56 | 0 | T |
| AI679504 | UNKNOWN | 103 | 0 | T |
| AI679504 | UNKNOWN | 19 | 160 | G |
| AI679504 | UNKNOWN | 13 | 237 | C |
| AI679506 | UNKNOWN | 78 | 0 | T |
| AI679506 | UNKNOWN | 21 | 143 | G |
| AI679526 | UNKNOWN | 29 | 0 | T |
| AI679529 | UNKNOWN | 63 | 0 | T |
| AI679529 | UNKNOWN | 16 | 283 | A |
| AI679550 | UNKNOWN | 63 | 0 | T |
| AI679563 | UNKNOWN | 33 | 0 | T |
| AI679573 | UNKNOWN | 14 | 158 | T |
| AI679589 | UNKNOWN | 12 | 208 | T |
| AI679620 | UNKNOWN | 93 | 0 | T |
| AI679620 | UNKNOWN | 20 | 254 | A |
| AI679631 | UNKNOWN | 75 | 0 | T |
| AI679631 | UNKNOWN | 14 | 343 | A |
| AI679658 | UNKNOWN | 7 | 52 | TA |
| AI679658 | UNKNOWN | 31 | 0 | T |
| AI679658 | UNKNOWN | 13 | 308 | A |
| AI679667 | UNKNOWN | 40 | 15 | T |
| AI679670 | UNKNOWN | 50 | 0 | T |
| AI679672 | UNKNOWN | 77 | 0 | T |
| AI679672 | UNKNOWN | 16 | 149 | C |
| AI679672 | UNKNOWN | 15 | 235 | G |
| AI679672 | UNKNOWN | 13 | 294 | A |
| AI679672 | UNKNOWN | 12 | 207 | A |
| AI679724 | UNKNOWN | 96 | 0 | T |
| AI679724 | UNKNOWN | 18 | 268 | C |
| AI679724 | UNKNOWN | 17 | 286 | A |
| AI679724 | UNKNOWN | 13 | 154 | A |
| AI679724 | UNKNOWN | 12 | 135 | G |
| AI679728 | UNKNOWN | 85 | 0 | T |
| AI679728 | UNKNOWN | 18 | 221 | C |

TABLE 1-continued

| Genbank # | Region | # reps | Position | Unit sequence |
|---|---|---|---|---|
| AI679728 | UNKNOWN | 14 | 143 | C |
| AI679728 | UNKNOWN | 14 | 284 | A |
| AI679758 | UNKNOWN | 100 | 0 | T |
| AI679758 | UNKNOWN | 16 | 212 | C |
| AI679758 | UNKNOWN | 14 | 105 | G |
| AI679758 | UNKNOWN | 12 | 145 | A |
| AI679759 | UNKNOWN | 9.5 | 434 | TC |
| AI679759 | UNKNOWN | 15 | 0 | T |
| AI679764 | UNKNOWN | 121 | 0 | T |
| AI679764 | UNKNOWN | 15 | 190 | G |
| AI679764 | UNKNOWN | 13 | 229 | C |
| AI679764 | UNKNOWN | 12 | 299 | A |
| AI679771 | UNKNOWN | 59 | 0 | T |
| AI679778 | UNKNOWN | 51 | 0 | T |
| AI679792 | UNKNOWN | 58 | 0 | T |
| AI679796 | UNKNOWN | 52 | 0 | T |
| AI679800 | UNKNOWN | 74 | 0 | T |
| AI679800 | UNKNOWN | 12 | 242 | C |
| AI679824 | UNKNOWN | 39 | 0 | T |
| AI679824 | UNKNOWN | 12 | 241 | A |
| AI679836 | UNKNOWN | 54 | 0 | T |
| AI679836 | UNKNOWN | 12 | 177 | G |
| AI679839 | UNKNOWN | 43 | 0 | T |
| AI679839 | UNKNOWN | 19 | 201 | A |
| AI679888 | UNKNOWN | 7.5 | 360 | CT |
| AI679902 | UNKNOWN | 3.6 | 2 | TTTTA |
| AI679916 | UNKNOWN | 94 | 0 | T |
| AI679916 | UNKNOWN | 20 | 120 | A |
| AI679916 | UNKNOWN | 16 | 193 | C |
| AI679916 | UNKNOWN | 12 | 209 | G |
| AI679949 | UNKNOWN | 22 | 347 | C |
| AI679949 | UNKNOWN | 15 | 63 | T |
| AI679949 | UNKNOWN | 15 | 208 | C |
| AI679949 | UNKNOWN | 15 | 372 | G |
| AI679949 | UNKNOWN | 12 | 163 | A |
| AI679949 | UNKNOWN | 12 | 237 | G |
| AI679952 | UNKNOWN | 4.75 | 321 | TTTG |
| AI679988 | UNKNOWN | 26 | 0 | T |
| AI679990 | UNKNOWN | 98 | 0 | T |
| AI679990 | UNKNOWN | 12 | 123 | C |
| AI679990 | UNKNOWN | 12 | 249 | G |
| AI679990 | UNKNOWN | 12 | 261 | A |
| AI680066 | UNKNOWN | 70 | 0 | T |
| AI680066 | UNKNOWN | 13 | 264 | A |
| AI680066 | UNKNOWN | 13 | 308 | C |
| AI680082 | UNKNOWN | 20 | 0 | T |
| AI680095 | UNKNOWN | 5.75 | 5 | TTTA |
| AI680113 | UNKNOWN | 125 | 0 | T |
| AI680113 | UNKNOWN | 15 | 200 | C |
| AI680113 | UNKNOWN | 14 | 132 | G |
| AI680113 | UNKNOWN | 14 | 375 | A |
| AI680113 | UNKNOWN | 13 | 171 | A |
| AI680119 | UNKNOWN | 78 | 0 | T |
| AI680119 | UNKNOWN | 12 | 321 | C |
| AI680138 | UNKNOWN | 97 | 0 | T |
| AI680138 | UNKNOWN | 24 | 154 | C |
| AI680138 | UNKNOWN | 19 | 135 | A |
| AI680138 | UNKNOWN | 12 | 227 | G |
| AI680139 | UNKNOWN | 79 | 0 | T |
| AI680139 | UNKNOWN | 14 | 362 | C |
| AI680162 | UNKNOWN | 89 | 0 | T |
| AI680162 | UNKNOWN | 13 | 194 | G |
| AI680165 | UNKNOWN | 110 | 0 | T |
| AI680165 | UNKNOWN | 14 | 260 | C |
| AI680165 | UNKNOWN | 13 | 204 | C |
| AI680194 | UNKNOWN | 94 | 0 | T |
| AI680194 | UNKNOWN | 19 | 167 | G |
| AI680194 | UNKNOWN | 12 | 122 | A |
| AI680221 | UNKNOWN | 63 | 0 | T |
| AI680221 | UNKNOWN | 23 | 207 | A |
| AI680221 | UNKNOWN | 15 | 145 | A |
| AI680221 | UNKNOWN | 12 | 101 | A |
| AI680225 | UNKNOWN | 63 | 0 | T |
| AI680225 | UNKNOWN | 13 | 141 | A |
| AI680226 | UNKNOWN | 98 | 0 | T |
| AI680226 | UNKNOWN | 16 | 150 | A |
| AI680235 | UNKNOWN | 100 | 0 | T |

TABLE 1-continued

| Genbank # | Region | # reps | Position | Unit sequence |
|---|---|---|---|---|
| AI680235 | UNKNOWN | 16 | 281 | C |
| AI680235 | UNKNOWN | 15 | 141 | C |
| AI680235 | UNKNOWN | 13 | 268 | A |
| AI680243 | UNKNOWN | 29 | 0 | T |
| AI680259 | UNKNOWN | 14 | 22 | T |
| AI680280 | UNKNOWN | 105 | 0 | T |
| AI680280 | UNKNOWN | 18 | 130 | G |
| AI680289 | UNKNOWN | 44 | 0 | T |
| AI680326 | UNKNOWN | 67 | 0 | T |
| AI680377 | UNKNOWN | 76 | 0 | T |
| AI680377 | UNKNOWN | 15 | 166 | A |
| AI680388 | UNKNOWN | 102 | 0 | T |
| AI680388 | UNKNOWN | 16 | 170 | C |
| AI680389 | UNKNOWN | 84 | 0 | T |
| AI680389 | UNKNOWN | 18 | 329 | G |
| AI680420 | UNKNOWN | 71 | 0 | T |
| AI680420 | UNKNOWN | 16 | 136 | A |
| AI680435 | UNKNOWN | 100 | 0 | T |
| AI680435 | UNKNOWN | 26 | 110 | A |
| AI680435 | UNKNOWN | 20 | 136 | C |
| AI680435 | UNKNOWN | 19 | 200 | G |
| AI680442 | UNKNOWN | 52 | 0 | T |
| AI680447 | UNKNOWN | 66 | 0 | T |
| AI680457 | UNKNOWN | 78 | 0 | T |
| AI680457 | UNKNOWN | 12 | 82 | G |
| AI680459 | UNKNOWN | 3.66 | 209 | AAAATT |
| AI680459 | UNKNOWN | 36 | 0 | T |
| AI680463 | UNKNOWN | 86 | 0 | T |
| AI680463 | UNKNOWN | 18 | 132 | C |
| AI680463 | UNKNOWN | 12 | 208 | A |
| AI680467 | UNKNOWN | 56 | 0 | T |
| AI680498 | UNKNOWN | 99 | 0 | T |
| AI680498 | UNKNOWN | 22 | 135 | A |
| AI680498 | UNKNOWN | 16 | 162 | G |
| AI680500 | UNKNOWN | 31 | 0 | T |
| AI680501 | UNKNOWN | 45 | 0 | T |
| AI680501 | UNKNOWN | 15 | 210 | G |
| AI680539 | UNKNOWN | 78 | 0 | T |
| AI680539 | UNKNOWN | 18 | 78 | G |
| AI680613 | UNKNOWN | 46 | 0 | T |
| AI680613 | UNKNOWN | 14 | 80 | A |
| AI680689 | UNKNOWN | 23 | 0 | T |
| AI680729 | UNKNOWN | 15 | 94 | A |
| AI680792 | UNKNOWN | 45 | 0 | T |
| AI680822 | UNKNOWN | 15 | 38 | T |
| AI680842 | UNKNOWN | 22 | 0 | T |
| AI680851 | UNKNOWN | 23 | 0 | T |
| AI680898 | UNKNOWN | 21 | 6 | T |
| AI681040 | UNKNOWN | 29 | 0 | T |
| AI681235 | UNKNOWN | 13 | 4 | A |
| AI681260 | UNKNOWN | 7 | 49 | CA |
| AI681260 | UNKNOWN | 13 | 0 | T |
| AI681288 | UNKNOWN | 17 | 0 | T |
| AI681302 | UNKNOWN | 15 | 0 | T |
| AI681438 | UNKNOWN | 21 | 0 | T |
| AI681447 | UNKNOWN | 13 | 155 | T |
| AI681524 | UNKNOWN | 18 | 18 | T |
| AI681541 | UNKNOWN | 31 | 0 | T |
| AI681557 | UNKNOWN | 11 | 372 | GT |
| AI681557 | UNKNOWN | 7.5 | 352 | GA |
| AI681562 | UNKNOWN | 14 | 499 | T |
| AI681664 | UNKNOWN | 12 | 296 | T |
| AI681668 | UNKNOWN | 5 | 109 | GTTT |
| AI681680 | UNKNOWN | 10.5 | 341 | AT |
| AI681680 | UNKNOWN | 9.5 | 361 | AC |
| AI681711 | UNKNOWN | 22 | 0 | T |
| AI681749 | UNKNOWN | 18 | 0 | T |
| AI681807 | UNKNOWN | 8 | 398 | GCC |
| AI681811 | UNKNOWN | 15 | 0 | T |
| AI681868 | UNKNOWN | 15 | 24 | A |
| AI681900 | UNKNOWN | 22 | 0 | T |
| AI681917 | UNKNOWN | 12 | 0 | T |
| AI681918 | UNKNOWN | 18 | 0 | T |
| AI681927 | UNKNOWN | 6.5 | 112 | AC |
| AI681952 | UNKNOWN | 85 | 5 | T |
| AI681952 | UNKNOWN | 12 | 92 | C |
| AI681952 | UNKNOWN | 12 | 217 | G |

TABLE 1-continued

| Genbank # | Region | # reps | Position | Unit sequence |
|---|---|---|---|---|
| AI681952 | UNKNOWN | 12 | 418 | A |
| AI681968 | UNKNOWN | 53 | 0 | T |
| AI681982 | UNKNOWN | 14 | 19 | T |
| AI681985 | UNKNOWN | 90 | 0 | T |
| AI681985 | UNKNOWN | 18 | 173 | A |
| AI681985 | UNKNOWN | 17 | 149 | G |
| AI681987 | UNKNOWN | 18 | 365 | A |
| AI681987 | UNKNOWN | 12 | 124 | T |
| AI682000 | UNKNOWN | 14 | 363 | A |
| AI682012 | UNKNOWN | 41 | 0 | T |
| AI682015 | UNKNOWN | 18 | 0 | T |
| AI682018 | UNKNOWN | 31 | 0 | T |
| AI682018 | UNKNOWN | 13 | 199 | A |
| AI682068 | UNKNOWN | 18 | 0 | T |
| AI682075 | UNKNOWN | 80 | 7 | T |
| AI682075 | UNKNOWN | 16 | 268 | C |
| AI682075 | UNKNOWN | 14 | 150 | C |
| AI682121 | UNKNOWN | 58 | 0 | T |
| AI682228 | UNKNOWN | 5.75 | 7 | TTTA |
| AI682372 | UNKNOWN | 46 | 0 | T |
| AI682372 | UNKNOWN | 13 | 89 | A |
| AI682424 | UNKNOWN | 19 | 0 | T |
| AI682464 | UNKNOWN | 33 | 0 | T |
| AI682473 | UNKNOWN | 42 | 0 | T |
| AI682478 | UNKNOWN | 28 | 0 | T |
| AI682593 | UNKNOWN | 31 | 0 | T |
| AI682593 | UNKNOWN | 12 | 161 | C |
| AI682594 | UNKNOWN | 15 | 0 | T |
| AI682639 | UNKNOWN | 7 | 303 | TA |
| AI682640 | UNKNOWN | 54 | 0 | T |
| AI682652 | UNKNOWN | 73 | 0 | T |
| AI682652 | UNKNOWN | 12 | 203 | A |
| AI682667 | UNKNOWN | 49 | 0 | T |
| AI682707 | UNKNOWN | 42 | 0 | T |
| AI682720 | UNKNOWN | 111 | 0 | T |
| AI682720 | UNKNOWN | 18 | 289 | G |
| AI682720 | UNKNOWN | 16 | 164 | C |
| AI682725 | UNKNOWN | 90 | 0 | T |
| AI682725 | UNKNOWN | 13 | 96 | A |
| AI682743 | UNKNOWN | 115 | 0 | T |
| AI682743 | UNKNOWN | 20 | 173 | G |
| AI682743 | UNKNOWN | 14 | 250 | C |
| AI682745 | UNKNOWN | 22 | 0 | T |
| AI682749 | UNKNOWN | 65 | 0 | T |
| AI682779 | UNKNOWN | 75 | 0 | T |
| AI682783 | UNKNOWN | 23 | 0 | T |
| AI682798 | UNKNOWN | 91 | 0 | T |
| AI682798 | UNKNOWN | 13 | 143 | G |
| AI682832 | UNKNOWN | 41 | 0 | T |
| AI682837 | UNKNOWN | 93 | 0 | T |
| AI682837 | UNKNOWN | 15 | 111 | A |
| AI682837 | UNKNOWN | 15 | 158 | C |
| AI682841 | UNKNOWN | 119 | 0 | T |
| AI682841 | UNKNOWN | 24 | 163 | C |
| AI682861 | UNKNOWN | 57 | 0 | T |
| AI682891 | UNKNOWN | 71 | 0 | T |
| AI682891 | UNKNOWN | 12 | 205 | A |
| AI682903 | UNKNOWN | 77 | 0 | T |
| AI682903 | UNKNOWN | 28 | 278 | A |
| AI682926 | UNKNOWN | 48 | 0 | T |
| AI682928 | UNKNOWN | 37 | 0 | T |
| AI682934 | UNKNOWN | 58 | 0 | T |
| AI682934 | UNKNOWN | 18 | 274 | G |
| AI682934 | UNKNOWN | 12 | 299 | A |
| AI682958 | UNKNOWN | 70 | 0 | T |
| AI682968 | UNKNOWN | 64 | 0 | T |
| AI682970 | UNKNOWN | 25 | 21 | T |
| AI682970 | UNKNOWN | 16 | 249 | A |
| AI682971 | UNKNOWN | 117 | 0 | T |
| AI682971 | UNKNOWN | 18 | 241 | A |
| AI682971 | UNKNOWN | 15 | 117 | A |
| AI682971 | UNKNOWN | 14 | 367 | G |
| AI682971 | UNKNOWN | 13 | 215 | G |
| AI682971 | UNKNOWN | 13 | 228 | C |
| AI682973 | UNKNOWN | 44 | 0 | T |
| AI683057 | UNKNOWN | 36 | 0 | T |
| AI683072 | UNKNOWN | 83 | 0 | T |

TABLE 1-continued

| Genbank # | Region | # reps | Position | Unit sequence |
|---|---|---|---|---|
| AI683072 | UNKNOWN | 13 | 275 | G |
| AI683072 | UNKNOWN | 12 | 309 | A |
| AI683084 | UNKNOWN | 42 | 0 | T |
| AI683099 | UNKNOWN | 92 | 0 | T |
| AI683099 | UNKNOWN | 14 | 357 | G |
| AI683099 | UNKNOWN | 12 | 192 | C |
| AI683104 | UNKNOWN | 114 | 0 | T |
| AI683104 | UNKNOWN | 14 | 378 | G |
| AI683104 | UNKNOWN | 13 | 233 | A |
| AI683104 | UNKNOWN | 12 | 295 | G |
| AI683106 | UNKNOWN | 54 | 0 | T |
| AI683173 | UNKNOWN | 81 | 0 | T |
| AI683173 | UNKNOWN | 13 | 164 | A |
| AI683198 | UNKNOWN | 40 | 0 | T |
| AI683209 | UNKNOWN | 66 | 0 | T |
| AI683223 | UNKNOWN | 47 | 0 | T |
| AI683241 | UNKNOWN | 62 | 0 | T |
| AI683255 | UNKNOWN | 86 | 0 | T |
| AI683255 | UNKNOWN | 13 | 153 | C |
| AI683270 | UNKNOWN | 53 | 0 | T |
| AI683292 | UNKNOWN | 3.8 | 342 | AAAC |
| AI683292 | UNKNOWN | 58 | 0 | T |
| AI683292 | UNKNOWN | 15 | 326 | C |
| AI683340 | UNKNOWN | 111 | 0 | T |
| AI683340 | UNKNOWN | 15 | 159 | C |
| AI683340 | UNKNOWN | 14 | 117 | G |
| AI683341 | UNKNOWN | 19 | 0 | T |
| AI683345 | UNKNOWN | 32 | 0 | T |
| AI683396 | UNKNOWN | 35 | 0 | T |
| AI683430 | UNKNOWN | 60 | 0 | T |
| AI683463 | UNKNOWN | 95 | 0 | T |
| AI683463 | UNKNOWN | 13 | 206 | A |
| AI683463 | UNKNOWN | 12 | 102 | C |
| AI683475 | UNKNOWN | 104 | 0 | T |
| AI683475 | UNKNOWN | 15 | 284 | G |
| AI683483 | UNKNOWN | 49 | 7 | T |
| AI683486 | UNKNOWN | 76 | 0 | T |
| AI683492 | UNKNOWN | 86 | 0 | T |
| AI683497 | UNKNOWN | 60 | 0 | T |
| AI683497 | UNKNOWN | 13 | 187 | A |
| AI683498 | UNKNOWN | 36 | 0 | T |
| AI683513 | UNKNOWN | 58 | 0 | T |
| AI683528 | UNKNOWN | 42 | 0 | T |
| AI683542 | UNKNOWN | 21 | 0 | T |
| AI683547 | UNKNOWN | 5.25 | 3 | ATTT |
| AI683555 | UNKNOWN | 43 | 283 | A |
| AI683555 | UNKNOWN | 32 | 8 | T |
| AI683574 | UNKNOWN | 35 | 0 | T |
| AI683580 | UNKNOWN | 36 | 0 | T |
| AI683580 | UNKNOWN | 14 | 70 | A |
| AI683585 | UNKNOWN | 112 | 0 | T |
| AI683585 | UNKNOWN | 17 | 183 | G |
| AI683585 | UNKNOWN | 15 | 283 | C |
| AI683585 | UNKNOWN | 12 | 138 | G |
| AI683586 | UNKNOWN | 14 | 0 | T |
| AI683590 | UNKNOWN | 63 | 0 | T |
| AI683590 | UNKNOWN | 19 | 93 | A |
| AI683606 | UNKNOWN | 61 | 0 | T |
| AI683606 | UNKNOWN | 19 | 275 | G |
| AI683606 | UNKNOWN | 14 | 61 | A |
| AI683616 | UNKNOWN | 28 | 0 | T |
| AI683617 | UNKNOWN | 88 | 0 | T |
| AI683617 | UNKNOWN | 12 | 255 | G |
| AI683621 | UNKNOWN | 14 | 0 | T |
| AI683634 | UNKNOWN | 59 | 0 | T |
| AI683637 | UNKNOWN | 28 | 0 | T |
| AI683668 | UNKNOWN | 51 | 0 | T |
| AI683672 | UNKNOWN | 37 | 0 | T |
| AI683684 | UNKNOWN | 99 | 0 | T |
| AI683684 | UNKNOWN | 14 | 187 | A |
| AI683684 | UNKNOWN | 13 | 130 | G |
| AI683691 | UNKNOWN | 27 | 0 | T |
| AI683707 | UNKNOWN | 53 | 29 | T |
| AI683707 | UNKNOWN | 28 | 0 | T |
| AI683707 | UNKNOWN | 20 | 130 | A |
| AI683707 | UNKNOWN | 12 | 277 | C |
| AI683714 | UNKNOWN | 94 | 0 | T |

TABLE 1-continued

| Genbank # | Region | # reps | Position | Unit sequence |
|---|---|---|---|---|
| AI683714 | UNKNOWN | 22 | 289 | A |
| AI683714 | UNKNOWN | 17 | 370 | G |
| AI683714 | UNKNOWN | 15 | 216 | A |
| AI683714 | UNKNOWN | 14 | 231 | C |
| AI683714 | UNKNOWN | 13 | 335 | G |
| AI683744 | UNKNOWN | 17 | 0 | T |
| AI683747 | UNKNOWN | 50 | 0 | T |
| AI683752 | UNKNOWN | 17 | 391 | A |
| AI683765 | UNKNOWN | 21 | 0 | T |
| AI683776 | UNKNOWN | 39 | 0 | T |
| AI683810 | UNKNOWN | 42 | 0 | T |
| AI683824 | UNKNOWN | 51 | 0 | T |
| AI683824 | UNKNOWN | 17 | 114 | G |
| AI683860 | UNKNOWN | 86 | 0 | T |
| AI683860 | UNKNOWN | 15 | 123 | G |
| AI683860 | UNKNOWN | 15 | 162 | C |
| AI683860 | UNKNOWN | 15 | 251 | A |
| AI683867 | UNKNOWN | 21 | 0 | T |
| AI683871 | UNKNOWN | 45 | 0 | T |
| AI683894 | UNKNOWN | 47 | 0 | T |
| AI683939 | UNKNOWN | 60 | 0 | T |
| AI683940 | UNKNOWN | 56 | 0 | T |
| AI683940 | UNKNOWN | 13 | 295 | A |
| AI683979 | UNKNOWN | 55 | 0 | T |
| AI683979 | UNKNOWN | 15 | 116 | A |
| AI683997 | UNKNOWN | 36 | 0 | T |
| AI684013 | UNKNOWN | 60 | 0 | T |
| AI684013 | UNKNOWN | 13 | 143 | A |
| AI684021 | UNKNOWN | 84 | 0 | T |
| AI684036 | UNKNOWN | 89 | 0 | T |
| AI684036 | UNKNOWN | 14 | 234 | A |
| AI684036 | UNKNOWN | 13 | 92 | C |
| AI684053 | UNKNOWN | 82 | 0 | T |
| AI684053 | UNKNOWN | 12 | 85 | C |
| AI684069 | UNKNOWN | 60 | 0 | T |
| AI684098 | UNKNOWN | 26 | 0 | T |
| AI684111 | UNKNOWN | 12 | 243 | A |
| AI684116 | UNKNOWN | 57 | 0 | T |
| AI684119 | UNKNOWN | 12 | 0 | T |
| AI684127 | UNKNOWN | 64 | 0 | T |
| AI684127 | UNKNOWN | 18 | 132 | A |
| AI684127 | UNKNOWN | 15 | 291 | C |
| AI684129 | UNKNOWN | 70 | 0 | T |
| AI684145 | UNKNOWN | 70 | 0 | T |
| AI684164 | UNKNOWN | 52 | 0 | T |
| AI684192 | UNKNOWN | 39 | 0 | T |
| AI684230 | UNKNOWN | 36 | 0 | T |
| AI684234 | UNKNOWN | 96 | 0 | T |
| AI684240 | UNKNOWN | 67 | 0 | T |
| AI684240 | UNKNOWN | 15 | 415 | A |
| AI684240 | UNKNOWN | 12 | 233 | G |
| AI684244 | UNKNOWN | 61 | 0 | T |
| AI684250 | UNKNOWN | 20 | 0 | T |
| AI684265 | UNKNOWN | 120 | 0 | T |
| AI684265 | UNKNOWN | 17 | 294 | C |
| AI684265 | UNKNOWN | 12 | 208 | C |
| AI684279 | UNKNOWN | 105 | 0 | T |
| AI684288 | UNKNOWN | 64 | 0 | T |
| AI684288 | UNKNOWN | 19 | 228 | A |
| AI684300 | UNKNOWN | 50 | 0 | T |
| AI684305 | UNKNOWN | 79 | 0 | T |
| AI684305 | UNKNOWN | 13 | 175 | G |
| AI684369 | UNKNOWN | 66 | 0 | T |
| AI684369 | UNKNOWN | 12 | 67 | A |
| AI684424 | UNKNOWN | 8 | 12 | AT |
| AI684451 | UNKNOWN | 12 | 238 | A |
| AI684462 | UNKNOWN | 53 | 0 | T |
| AI684486 | UNKNOWN | 13 | 0 | T |
| AI684496 | UNKNOWN | 5.25 | 7 | TTTA |
| AI684508 | UNKNOWN | 13 | 0 | T |
| AI684509 | UNKNOWN | 45 | 0 | T |
| AI684658 | UNKNOWN | 12 | 0 | T |
| AI684664 | UNKNOWN | 13 | 0 | T |
| AI684673 | UNKNOWN | 14 | 0 | T |
| AI684816 | UNKNOWN | 20 | 0 | T |
| AI684824 | UNKNOWN | 13 | 146 | A |
| AI684886 | UNKNOWN | 22 | 0 | T |

TABLE 1-continued

| Genbank # | Region | # reps | Position | Unit sequence |
|---|---|---|---|---|
| AI684912 | UNKNOWN | 23 | 0 | T |
| AI684928 | UNKNOWN | 14 | 129 | T |
| AI684964 | UNKNOWN | 42 | 0 | T |
| AI685005 | UNKNOWN | 66 | 0 | T |
| AI685005 | UNKNOWN | 19 | 222 | A |
| AI685074 | UNKNOWN | 11 | 184 | GT |
| AI685080 | UNKNOWN | 70 | 0 | T |
| AI685080 | UNKNOWN | 14 | 148 | A |
| AI685094 | UNKNOWN | 104 | 0 | T |
| AI685094 | UNKNOWN | 21 | 181 | A |
| AI685094 | UNKNOWN | 16 | 165 | C |
| AI685106 | UNKNOWN | 76 | 0 | T |
| AI685106 | UNKNOWN | 19 | 212 | G |
| AI685106 | UNKNOWN | 15 | 231 | A |
| AI685106 | UNKNOWN | 12 | 126 | C |
| AI685109 | UNKNOWN | 35 | 0 | T |
| AI685116 | UNKNOWN | 3.8 | 19 | TTTTA |
| AI685145 | UNKNOWN | 4.4 | 255 | AAGGG |
| AI685146 | UNKNOWN | 41 | 0 | T |
| AI685186 | UNKNOWN | 60 | 0 | T |
| AI685186 | UNKNOWN | 21 | 317 | C |
| AI685186 | UNKNOWN | 15 | 114 | G |
| AI685186 | UNKNOWN | 14 | 222 | C |
| AI685186 | UNKNOWN | 13 | 154 | A |
| AI685195 | UNKNOWN | 50 | 0 | T |
| AI685211 | UNKNOWN | 74 | 0 | T |
| AI685211 | UNKNOWN | 17 | 193 | G |
| AI685211 | UNKNOWN | 14 | 210 | C |
| AI685314 | UNKNOWN | 20 | 0 | T |
| AI685333 | UNKNOWN | 5.25 | 110 | AAAT |
| AI685341 | UNKNOWN | 3.8 | 124 | TTTTA |
| AI685375 | UNKNOWN | 14 | 0 | T |
| AI685450 | UNKNOWN | 29 | 0 | T |
| AI685469 | UNKNOWN | 25 | 0 | T |
| AI685498 | UNKNOWN | 5.66 | 225 | TCC |
| AI685517 | UNKNOWN | 45 | 0 | T |
| AI685525 | UNKNOWN | 44 | 0 | T |
| AI685558 | UNKNOWN | 10 | 491 | AC |
| AI685558 | UNKNOWN | 14 | 0 | T |
| AI685661 | UNKNOWN | 27 | 0 | T |
| AI685724 | UNKNOWN | 48 | 0 | T |
| AI685771 | UNKNOWN | 41 | 0 | T |
| AI685798 | UNKNOWN | 68 | 0 | T |
| AI685798 | UNKNOWN | 23 | 152 | C |
| AI685811 | UNKNOWN | 13 | 8 | T |
| AI685814 | UNKNOWN | 4.59 | 248 | AACAA |
| AI685814 | UNKNOWN | 4.75 | 43 | TTTA |
| AI685814 | UNKNOWN | 35 | 0 | T |
| AI685822 | UNKNOWN | 48 | 0 | T |
| AI685839 | UNKNOWN | 16 | 4 | T |
| AI685857 | UNKNOWN | 25 | 0 | T |
| AI685902 | UNKNOWN | 37 | 0 | T |
| AI685917 | UNKNOWN | 13 | 0 | T |
| AI685960 | UNKNOWN | 49 | 0 | T |
| AI685979 | UNKNOWN | 24 | 105 | T |
| AI686013 | UNKNOWN | 12 | 0 | T |
| AI686036 | UNKNOWN | 22 | 0 | T |
| AI686073 | UNKNOWN | 80 | 0 | T |
| AI686073 | UNKNOWN | 14 | 151 | C |
| AI686081 | UNKNOWN | 49 | 0 | T |
| AI686149 | UNKNOWN | 13 | 303 | A |
| AI686152 | UNKNOWN | 13 | 0 | T |
| AI686154 | UNKNOWN | 17 | 0 | T |
| AI686161 | UNKNOWN | 13 | 0 | T |
| AI686179 | UNKNOWN | 8 | 152 | TA |
| AI686179 | UNKNOWN | 26 | 0 | T |
| AI686226 | UNKNOWN | 12 | 0 | T |
| AI686258 | UNKNOWN | 82 | 0 | T |
| AI686258 | UNKNOWN | 22 | 140 | A |
| AI686258 | UNKNOWN | 13 | 287 | G |
| AI686285 | UNKNOWN | 17 | 227 | T |
| AI686303 | UNKNOWN | 7 | 632 | AC |
| AI686303 | UNKNOWN | 6.5 | 620 | AT |
| AI686360 | UNKNOWN | 27 | 0 | T |
| AI686390 | UNKNOWN | 12 | 0 | T |
| AI686414 | UNKNOWN | 46 | 0 | T |
| AI686511 | UNKNOWN | 64 | 0 | T |

TABLE 1-continued

| Genbank # | Region | # reps | Position | Unit sequence |
|---|---|---|---|---|
| AI686511 | UNKNOWN | 28 | 157 | C |
| AI686522 | UNKNOWN | 9.5 | 394 | TG |
| AI686528 | UNKNOWN | 37 | 0 | T |
| AI686554 | UNKNOWN | 89 | 0 | T |
| AI686554 | UNKNOWN | 24 | 158 | C |
| AI686554 | UNKNOWN | 15 | 273 | G |
| AI686554 | UNKNOWN | 12 | 131 | A |
| AI686565 | UNKNOWN | 54 | 0 | T |
| AI686576 | UNKNOWN | 78 | 0 | T |
| AI686576 | UNKNOWN | 14 | 135 | A |
| AI686579 | UNKNOWN | 13 | 0 | T |
| AI686589 | UNKNOWN | 52 | 0 | T |
| AI686597 | UNKNOWN | 113 | 0 | T |
| AI686597 | UNKNOWN | 23 | 171 | G |
| AI686597 | UNKNOWN | 15 | 138 | C |
| AI686597 | UNKNOWN | 14 | 153 | A |
| AI686601 | UNKNOWN | 42 | 0 | T |
| AI686615 | UNKNOWN | 51 | 18 | T |
| AI686615 | UNKNOWN | 17 | 0 | T |
| AI686631 | UNKNOWN | 2.52 | 117 | AAAAAAAAAATTTTTG (SEQ ID NO: 139) |
| AI686631 | UNKNOWN | 74 | 0 | T |
| AI686631 | UNKNOWN | 14 | 113 | A |
| AI686634 | UNKNOWN | 23 | 0 | T |
| AI686643 | UNKNOWN | 36 | 0 | T |
| AI686643 | UNKNOWN | 13 | 231 | A |
| AI686643 | UNKNOWN | 12 | 138 | A |
| AI686675 | UNKNOWN | 13 | 0 | T |
| AI686690 | UNKNOWN | 50 | 0 | T |
| AI686702 | UNKNOWN | 53 | 4 | T |
| AI686703 | UNKNOWN | 17 | 0 | T |
| AI686704 | UNKNOWN | 15 | 0 | T |
| AI686714 | UNKNOWN | 37 | 0 | T |
| AI686716 | UNKNOWN | 78 | 0 | T |
| AI686716 | UNKNOWN | 15 | 253 | C |
| AI686716 | UNKNOWN | 12 | 94 | A |
| AI686716 | UNKNOWN | 12 | 166 | C |
| AI686749 | UNKNOWN | 60 | 0 | T |
| AI686749 | UNKNOWN | 18 | 110 | A |
| AI686768 | UNKNOWN | 35 | 4 | T |
| AI686809 | UNKNOWN | 21 | 0 | T |
| AI686817 | UNKNOWN | 94 | 0 | T |
| AI686817 | UNKNOWN | 20 | 155 | C |
| AI686817 | UNKNOWN | 15 | 94 | A |
| AI686823 | UNKNOWN | 79 | 0 | T |
| AI686823 | UNKNOWN | 16 | 129 | A |
| AI686852 | UNKNOWN | 51 | 0 | T |
| AI686852 | UNKNOWN | 18 | 149 | A |
| AI686862 | UNKNOWN | 43 | 0 | T |
| AI686862 | UNKNOWN | 13 | 124 | G |
| AI686877 | UNKNOWN | 115 | 0 | T |
| AI686877 | UNKNOWN | 22 | 212 | A |
| AI686877 | UNKNOWN | 20 | 307 | C |
| AI686890 | UNKNOWN | 15 | 0 | T |
| AI686906 | UNKNOWN | 88 | 0 | T |
| AI686906 | UNKNOWN | 18 | 203 | G |
| AI686923 | UNKNOWN | 6.33 | 191 | ACC |
| AI686923 | UNKNOWN | 32 | 0 | T |
| AI686926 | UNKNOWN | 127 | 0 | T |
| AI686926 | UNKNOWN | 16 | 287 | C |
| AI686926 | UNKNOWN | 13 | 200 | A |
| AI686949 | UNKNOWN | 40 | 0 | T |
| AI686964 | UNKNOWN | 83 | 0 | T |
| AI686964 | UNKNOWN | 14 | 222 | C |
| AI686964 | UNKNOWN | 12 | 180 | A |
| AI686986 | UNKNOWN | 24 | 0 | T |
| AI686989 | UNKNOWN | 43 | 0 | T |
| AI687065 | UNKNOWN | 100 | 0 | T |
| AI687065 | UNKNOWN | 12 | 163 | G |
| AI687068 | UNKNOWN | 55 | 0 | T |
| AI687115 | UNKNOWN | 26 | 0 | T |
| AI687127 | UNKNOWN | 119 | 0 | T |
| AI687127 | UNKNOWN | 17 | 259 | A |
| AI687127 | UNKNOWN | 14 | 119 | A |
| AI687127 | UNKNOWN | 13 | 240 | C |
| AI687130 | UNKNOWN | 10.5 | 181 | CA |
| AI687130 | UNKNOWN | 55 | 0 | T |
| AI687130 | UNKNOWN | 13 | 244 | A |

TABLE 1-continued

| Genbank # | Region | # reps | Position | Unit sequence |
|---|---|---|---|---|
| AI687166 | UNKNOWN | 68 | 0 | T |
| AI687166 | UNKNOWN | 14 | 177 | G |
| AI687168 | UNKNOWN | 62 | 0 | T |
| AI687168 | UNKNOWN | 14 | 172 | G |
| AI687277 | UNKNOWN | 76 | 0 | T |
| AI687277 | UNKNOWN | 16 | 243 | G |
| AI687277 | UNKNOWN | 13 | 101 | A |
| AI687287 | UNKNOWN | 93 | 0 | T |
| AI687287 | UNKNOWN | 14 | 158 | A |
| AI687291 | UNKNOWN | 64 | 54 | T |
| AI687291 | UNKNOWN | 33 | 11 | T |
| AI687295 | UNKNOWN | 80 | 0 | T |
| AI687300 | UNKNOWN | 15 | 0 | T |
| AI687319 | UNKNOWN | 16 | 98 | T |
| AI687331 | UNKNOWN | 23 | 0 | T |
| AI687350 | UNKNOWN | 13 | 0 | T |
| AI687375 | UNKNOWN | 121 | 0 | T |
| AI687375 | UNKNOWN | 18 | 210 | G |
| AI687376 | UNKNOWN | 140 | 0 | T |
| AI687376 | UNKNOWN | 16 | 280 | G |
| AI687376 | UNKNOWN | 14 | 178 | C |
| AI687376 | UNKNOWN | 13 | 149 | A |
| AI687412 | UNKNOWN | 45 | 0 | T |
| AI687415 | UNKNOWN | 137 | 0 | T |
| AI687415 | UNKNOWN | 24 | 254 | C |
| AI687415 | UNKNOWN | 14 | 284 | G |
| AI687415 | UNKNOWN | 13 | 178 | G |
| AI687424 | UNKNOWN | 45 | 0 | T |
| AI687424 | UNKNOWN | 21 | 130 | G |
| AI687426 | UNKNOWN | 19 | 23 | T |
| AI687447 | UNKNOWN | 20 | 223 | C |
| AI687447 | UNKNOWN | 17 | 48 | C |
| AI687447 | UNKNOWN | 16 | 135 | G |
| AI687447 | UNKNOWN | 12 | 107 | A |
| AI687465 | UNKNOWN | 117 | 0 | T |
| AI687465 | UNKNOWN | 20 | 198 | C |
| AI687465 | UNKNOWN | 14 | 270 | G |
| AI687473 | UNKNOWN | 49 | 0 | T |
| AI687473 | UNKNOWN | 13 | 227 | C |
| AI687475 | UNKNOWN | 52 | 0 | T |
| AI687481 | UNKNOWN | 39 | 0 | T |
| AI687568 | UNKNOWN | 59 | 0 | T |
| AI687570 | UNKNOWN | 4.75 | 24 | TTTA |
| AI687570 | UNKNOWN | 16 | 11 | T |
| AI687575 | UNKNOWN | 40 | 0 | T |
| AI687630 | UNKNOWN | 62 | 0 | T |
| AI687638 | UNKNOWN | 36 | 0 | T |
| AI687673 | UNKNOWN | 15 | 244 | A |
| AI687689 | UNKNOWN | 85 | 0 | T |
| AI687703 | UNKNOWN | 40 | 0 | T |
| AI687728 | UNKNOWN | 130 | 0 | T |
| AI687728 | UNKNOWN | 14 | 206 | A |
| AI687728 | UNKNOWN | 13 | 130 | A |
| AI687728 | UNKNOWN | 13 | 303 | C |
| AI687771 | UNKNOWN | 24 | 20 | T |
| AI687809 | UNKNOWN | 70 | 0 | T |
| AI688063 | UNKNOWN | 7.5 | 378 | TA |
| AI688063 | UNKNOWN | 14 | 363 | A |
| AI688076 | UNKNOWN | 18 | 0 | T |
| AI688094 | UNKNOWN | 19 | 0 | T |
| AI688140 | UNKNOWN | 25 | 0 | T |
| AI688140 | UNKNOWN | 12 | 178 | G |
| AI688146 | UNKNOWN | 48 | 0 | T |
| AI688146 | UNKNOWN | 20 | 175 | A |
| AI688187 | UNKNOWN | 13 | 233 | T |
| AI688241 | UNKNOWN | 43 | 0 | T |
| AI688241 | UNKNOWN | 15 | 153 | G |
| AI688287 | UNKNOWN | 33 | 0 | T |
| AI688381 | UNKNOWN | 59 | 0 | T |
| AI688381 | UNKNOWN | 14 | 115 | G |
| AI688457 | UNKNOWN | 28 | 0 | T |
| AI688469 | UNKNOWN | 5.5 | 460 | ATAC |
| AI688474 | UNKNOWN | 16 | 51 | TA |
| AI688474 | UNKNOWN | 7.5 | 82 | AC |
| AI688494 | UNKNOWN | 5.25 | 75 | AAAG |
| AI688494 | UNKNOWN | 12 | 0 | T |
| AI688533 | UNKNOWN | 26 | 5 | T |

TABLE 1-continued

| Genbank # | Region | # reps | Position | Unit sequence |
|---|---|---|---|---|
| AI688559 | UNKNOWN | 7.5 | 54 | TA |
| AI688638 | UNKNOWN | 12 | 0 | T |
| AI688650 | UNKNOWN | 18 | 1 | T |
| AI688658 | UNKNOWN | 13 | 0 | T |
| AI688707 | UNKNOWN | 13 | 232 | A |
| AI688840 | UNKNOWN | 65 | 15 | T |
| AI688840 | UNKNOWN | 18 | 222 | A |
| AI688840 | UNKNOWN | 14 | 413 | C |
| AI688847 | UNKNOWN | 73 | 0 | T |
| AI688848 | UNKNOWN | 54 | 0 | T |
| AI688848 | UNKNOWN | 13 | 98 | G |
| AI688853 | UNKNOWN | 88 | 0 | T |
| AI688853 | UNKNOWN | 17 | 224 | G |
| AI688853 | UNKNOWN | 17 | 250 | A |
| AI688854 | UNKNOWN | 54 | 0 | T |
| AI688854 | UNKNOWN | 16 | 122 | A |
| AI688855 | UNKNOWN | 59 | 0 | T |
| AI688855 | UNKNOWN | 13 | 165 | C |
| AI688856 | UNKNOWN | 16 | 0 | T |
| AI688858 | UNKNOWN | 85 | 0 | T |
| AI688858 | UNKNOWN | 20 | 281 | G |
| AI688858 | UNKNOWN | 16 | 180 | G |
| AI688858 | UNKNOWN | 13 | 108 | A |
| AI688878 | UNKNOWN | 66 | 0 | T |
| AI688878 | UNKNOWN | 15 | 169 | G |
| AI688918 | UNKNOWN | 63 | 0 | T |
| AI688918 | UNKNOWN | 12 | 213 | C |
| AI688983 | UNKNOWN | 42 | 0 | T |
| AI689020 | UNKNOWN | 14 | 0 | T |
| AI689066 | UNKNOWN | 20 | 0 | T |
| AI689071 | UNKNOWN | 54 | 0 | T |
| AI689154 | UNKNOWN | 33 | 0 | T |
| AI689170 | UNKNOWN | 18 | 0 | T |
| AI689175 | UNKNOWN | 89 | 0 | T |
| AI689175 | UNKNOWN | 12 | 102 | A |
| AI689184 | UNKNOWN | 38 | 0 | T |
| AI689184 | UNKNOWN | 16 | 233 | G |
| AI689243 | UNKNOWN | 24 | 0 | T |
| AI689248 | UNKNOWN | 89 | 0 | T |
| AI689248 | UNKNOWN | 22 | 195 | A |
| AI689248 | UNKNOWN | 15 | 110 | A |
| AI689263 | UNKNOWN | 48 | 0 | T |
| AI689379 | UNKNOWN | 101 | 0 | T |
| AI689379 | UNKNOWN | 13 | 171 | C |
| AI689388 | UNKNOWN | 73 | 0 | T |
| AI689388 | UNKNOWN | 17 | 172 | G |
| AI689388 | UNKNOWN | 14 | 105 | A |
| AI689388 | UNKNOWN | 12 | 241 | C |
| AI689420 | UNKNOWN | 93 | 0 | T |
| AI689420 | UNKNOWN | 19 | 151 | G |
| AI689420 | UNKNOWN | 12 | 137 | C |
| AI689427 | UNKNOWN | 17 | 414 | A |
| AI689463 | UNKNOWN | 50 | 0 | T |
| AI689463 | UNKNOWN | 15 | 140 | A |
| AI689528 | UNKNOWN | 84 | 0 | T |
| AI689528 | UNKNOWN | 18 | 253 | G |
| AI689528 | UNKNOWN | 17 | 193 | G |
| AI689528 | UNKNOWN | 15 | 272 | A |
| AI689555 | UNKNOWN | 31 | 0 | T |
| AI689557 | UNKNOWN | 3.6 | 94 | AAAGA |
| AI689557 | UNKNOWN | 50 | 0 | T |
| AI689571 | UNKNOWN | 107 | 0 | T |
| AI689579 | UNKNOWN | 84 | 0 | T |
| AI689579 | UNKNOWN | 15 | 152 | A |
| AI689637 | UNKNOWN | 57 | 0 | T |
| AI689637 | UNKNOWN | 12 | 242 | G |
| AI689640 | UNKNOWN | 91 | 0 | T |
| AI689640 | UNKNOWN | 15 | 158 | A |
| AI689702 | UNKNOWN | 73 | 0 | T |
| AI689702 | UNKNOWN | 12 | 138 | A |
| AI689742 | UNKNOWN | 2.75 | 298 | CTATGACAATAA (SEQ ID NO: 140) |
| AI689754 | UNKNOWN | 18 | 18 | A |
| AI689832 | UNKNOWN | 16 | 341 | A |
| AI689876 | UNKNOWN | 6.5 | 195 | TC |
| AI689901 | UNKNOWN | 4.75 | 11 | TTTA |
| AI689911 | UNKNOWN | 19 | 181 | T |
| AI690021 | UNKNOWN | 12 | 283 | T |

TABLE 1-continued

| Genbank # | Region | # reps | Position | Unit sequence |
|---|---|---|---|---|
| AI690241 | UNKNOWN | 13 | 193 | A |
| AI690301 | UNKNOWN | 10.75 | 245 | TTTA |
| AI690312 | UNKNOWN | 108 | 0 | T |
| AI690312 | UNKNOWN | 16 | 117 | A |
| AI690312 | UNKNOWN | 12 | 178 | G |
| AI690317 | UNKNOWN | 45 | 0 | T |
| AI690322 | UNKNOWN | 4.8 | 79 | AAAC |
| AI690327 | UNKNOWN | 52 | 0 | T |
| AI690389 | UNKNOWN | 70 | 0 | T |
| AI690389 | UNKNOWN | 14 | 118 | G |
| AI690410 | UNKNOWN | 89 | 0 | T |
| AI690410 | UNKNOWN | 17 | 117 | A |
| AI690410 | UNKNOWN | 12 | 144 | C |
| AI690411 | UNKNOWN | 72 | 0 | T |
| AI690426 | UNKNOWN | 114 | 0 | T |
| AI690426 | UNKNOWN | 17 | 222 | C |
| AI690427 | UNKNOWN | 55 | 0 | T |
| AI690480 | UNKNOWN | 119 | 0 | T |
| AI690480 | UNKNOWN | 15 | 270 | A |
| AI690480 | UNKNOWN | 15 | 355 | C |
| AI690480 | UNKNOWN | 13 | 303 | G |
| AI690480 | UNKNOWN | 12 | 139 | G |
| AI690490 | UNKNOWN | 107 | 0 | T |
| AI690490 | UNKNOWN | 21 | 350 | C |
| AI690490 | UNKNOWN | 14 | 144 | G |
| AI690490 | UNKNOWN | 14 | 161 | A |
| AI690490 | UNKNOWN | 14 | 175 | C |
| AI690509 | UNKNOWN | 64 | 0 | T |
| AI690509 | UNKNOWN | 13 | 99 | A |
| AI690536 | UNKNOWN | 61 | 0 | T |
| AI690536 | UNKNOWN | 19 | 135 | G |
| AI690585 | UNKNOWN | 94 | 0 | T |
| AI690585 | UNKNOWN | 14 | 124 | C |
| AI690585 | UNKNOWN | 13 | 215 | A |
| AI690598 | UNKNOWN | 44 | 0 | T |
| AI690613 | UNKNOWN | 23 | 0 | T |
| AI690620 | UNKNOWN | 76 | 0 | T |
| AI690620 | UNKNOWN | 12 | 126 | G |
| AI690620 | UNKNOWN | 12 | 173 | C |
| AI690650 | UNKNOWN | 40 | 0 | T |
| AI690650 | UNKNOWN | 18 | 80 | A |
| AI690687 | UNKNOWN | 70 | 0 | T |
| AI690687 | UNKNOWN | 16 | 379 | A |
| AI690687 | UNKNOWN | 15 | 264 | G |
| AI690693 | UNKNOWN | 32 | 0 | T |
| AI690706 | UNKNOWN | 58 | 0 | T |
| AI690706 | UNKNOWN | 19 | 158 | G |
| AI690738 | UNKNOWN | 79 | 0 | T |
| AI690738 | UNKNOWN | 12 | 274 | A |
| AI690748 | UNKNOWN | 77 | 0 | T |
| AI690748 | UNKNOWN | 12 | 146 | C |
| AI690751 | UNKNOWN | 140 | 0 | T |
| AI690751 | UNKNOWN | 21 | 184 | C |
| AI690751 | UNKNOWN | 17 | 315 | G |
| AI690751 | UNKNOWN | 12 | 227 | G |
| AI690752 | UNKNOWN | 18 | 0 | T |
| AI690752 | UNKNOWN | 12 | 218 | A |
| AI690757 | UNKNOWN | 21 | 0 | T |
| AI690770 | UNKNOWN | 20 | 0 | T |
| AI690781 | UNKNOWN | 92 | 0 | T |
| AI690781 | UNKNOWN | 14 | 127 | G |
| AI690782 | UNKNOWN | 57 | 0 | T |
| AI690784 | UNKNOWN | 80 | 0 | T |
| AI690784 | UNKNOWN | 17 | 118 | G |
| AI690784 | UNKNOWN | 14 | 80 | A |
| AI690835 | UNKNOWN | 129 | 0 | T |
| AI690835 | UNKNOWN | 20 | 345 | c |
| AI690835 | UNKNOWN | 15 | 211 | C |
| AI690835 | UNKNOWN | 14 | 143 | G |
| AI690835 | UNKNOWN | 14 | 181 | A |
| AI690860 | UNKNOWN | 38 | 0 | T |
| AI690911 | UNKNOWN | 33 | 0 | T |
| AI690916 | UNKNOWN | 53 | 0 | T |
| AI690921 | UNKNOWN | 41 | 0 | T |
| AI690924 | UNKNOWN | 81 | 0 | T |
| AI690927 | UNKNOWN | 55 | 0 | T |
| AI690930 | UNKNOWN | 102 | 0 | T |

TABLE 1-continued

| Genbank # | Region | # reps | Position | Unit sequence |
|---|---|---|---|---|
| AI690930 | UNKNOWN | 13 | 308 | A |
| AI690930 | UNKNOWN | 12 | 146 | G |
| AI690946 | UNKNOWN | 63 | 11 | T |
| AI690946 | UNKNOWN | 12 | 143 | A |
| AI690961 | UNKNOWN | 54 | 0 | T |
| AI690961 | UNKNOWN | 15 | 261 | G |
| AI691033 | UNKNOWN | 47 | 0 | T |
| AI691043 | UNKNOWN | 19 | 79 | T |
| AI691043 | UNKNOWN | 16 | 136 | G |
| AI691043 | UNKNOWN | 12 | 152 | C |
| AI691051 | UNKNOWN | 33 | 0 | T |
| AI691088 | UNKNOWN | 65 | 0 | T |
| AI691131 | UNKNOWN | 51 | 0 | T |
| AI691131 | UNKNOWN | 17 | 93 | A |
| AI692176 | UNKNOWN | 36 | 0 | T |
| AI692212 | UNKNOWN | 12 | 0 | T |
| AI692232 | UNKNOWN | 7.75 | 0 | TATT |
| AI692245 | UNKNOWN | 12 | 0 | T |
| AI692355 | UNKNOWN | 5.4 | 492 | AAAAC |
| AI692401 | UNKNOWN | 14 | 294 | A |
| AI692492 | UNKNOWN | 17 | 0 | T |
| AI692509 | UNKNOWN | 15 | 0 | T |
| AI692513 | UNKNOWN | 11 | 424 | AT |
| AI692568 | UNKNOWN | 48 | 0 | T |
| AI692624 | UNKNOWN | 17 | 427 | A |
| AI692696 | UNKNOWN | 25 | 0 | T |
| AI692745 | UNKNOWN | 14 | 61 | A |
| AI692852 | UNKNOWN | 17 | 418 | T |
| AI692938 | UNKNOWN | 13 | 3 | T |
| AI692941 | UNKNOWN | 55 | 0 | T |
| AI692945 | UNKNOWN | 14 | 198 | A |
| AI692976 | UNKNOWN | 12 | 382 | A |
| AI692980 | UNKNOWN | 14 | 0 | T |
| AI693016 | UNKNOWN | 55 | 0 | T |
| AI693024 | UNKNOWN | 28 | 0 | T |
| AI693024 | UNKNOWN | 19 | 353 | A |
| AI693035 | UNKNOWN | 18 | 0 | T |
| AI693178 | UNKNOWN | 4.75 | 134 | GGAG |
| AI693278 | UNKNOWN | 26 | 221 | T |
| AI693278 | UNKNOWN | 12 | 0 | T |
| AI693329 | UNKNOWN | 12 | 0 | T |
| AI693375 | UNKNOWN | 13 | 6 | T |
| AI693546 | UNKNOWN | 23 | 0 | T |
| AI693548 | UNKNOWN | 28 | 1 | T |
| AI693551 | UNKNOWN | 26 | 0 | T |
| AI693669 | UNKNOWN | 14 | 129 | A |
| AI693690 | UNKNOWN | 13 | 0 | T |
| AI693691 | UNKNOWN | 22 | 0 | T |
| AI693881 | UNKNOWN | 19 | 3 | T |
| AI693892 | UNKNOWN | 18 | 3 | T |
| AI693902 | UNKNOWN | 16 | 213 | AT |
| AI693942 | UNKNOWN | 16 | 361 | A |
| AI693942 | UNKNOWN | 15 | 290 | T |
| AI693952 | UNKNOWN | 42 | 0 | T |
| AI693955 | UNKNOWN | 43 | 0 | T |
| AI693975 | UNKNOWN | 42 | 0 | T |
| AI694023 | UNKNOWN | 18 | 0 | T |
| AI694076 | UNKNOWN | 40 | 0 | T |
| AI694084 | UNKNOWN | 66 | 0 | T |
| AI694084 | UNKNOWN | 14 | 398 | G |
| AI694091 | UNKNOWN | 60 | 0 | T |
| AI694130 | UNKNOWN | 30 | 55 | A |
| AI694156 | UNKNOWN | 48 | 0 | T |
| AI694157 | UNKNOWN | 87 | 0 | T |
| AI694157 | UNKNOWN | 15 | 87 | A |
| AI694157 | UNKNOWN | 12 | 111 | C |
| AI694157 | UNKNOWN | 12 | 228 | G |
| AI694177 | UNKNOWN | 12 | 0 | T |
| AI694189 | UNKNOWN | 33 | 0 | T |
| AI694231 | UNKNOWN | 15 | 309 | AC |
| AI694231 | UNKNOWN | 10.5 | 469 | TG |
| AI694241 | UNKNOWN | 20 | 0 | T |
| AI694280 | UNKNOWN | 56 | 43 | T |
| AI694280 | UNKNOWN | 42 | 0 | T |
| AI694280 | UNKNOWN | 21 | 428 | G |
| AI694280 | UNKNOWN | 20 | 274 | A |
| AI694280 | UNKNOWN | 19 | 335 | G |

TABLE 1-continued

| Genbank # | Region | # reps | Position | Unit sequence |
|---|---|---|---|---|
| AI694280 | UNKNOWN | 16 | 294 | G |
| AI694280 | UNKNOWN | 13 | 106 | A |
| AI694355 | UNKNOWN | 12 | 0 | T |
| AI694358 | UNKNOWN | 14 | 0 | T |
| AI694375 | UNKNOWN | 17 | 136 | A |
| AI694524 | UNKNOWN | 14 | 228 | A |
| AI694560 | UNKNOWN | 18 | 316 | A |
| AI694562 | UNKNOWN | 3.6 | 396 | AACAA |
| AI694585 | UNKNOWN | 17 | 0 | T |
| AI694591 | UNKNOWN | 12 | 60 | A |
| AI694593 | UNKNOWN | 19 | 383 | T |
| AI694657 | UNKNOWN | 42 | 0 | T |
| AI694720 | UNKNOWN | 6.5 | 225 | AC |
| AI694752 | UNKNOWN | 12 | 75 | T |
| AI694767 | UNKNOWN | 20 | 0 | T |
| AI694833 | UNKNOWN | 54 | 0 | T |
| AI694833 | UNKNOWN | 18 | 206 | C |
| AI694833 | UNKNOWN | 12 | 172 | C |
| AI694855 | UNKNOWN | 48 | 0 | T |
| AI694890 | UNKNOWN | 31 | 0 | T |
| AI694954 | UNKNOWN | 19 | 0 | T |
| AI694959 | UNKNOWN | 12 | 0 | T |
| AI694962 | UNKNOWN | 28 | 0 | T |
| AI694977 | UNKNOWN | 13 | 0 | T |
| AI695079 | UNKNOWN | 6 | 10 | AAC |
| AI695129 | UNKNOWN | 64 | 0 | T |
| AI695129 | UNKNOWN | 13 | 164 | A |
| AI695129 | UNKNOWN | 13 | 200 | C |
| AI695153 | UNKNOWN | 36 | 0 | T |
| AI695271 | UNKNOWN | 14 | 0 | T |
| AI695273 | UNKNOWN | 8 | 61 | TA |
| AI695273 | UNKNOWN | 7 | 343 | GA |
| AI695363 | UNKNOWN | 4.75 | 10 | TTAT |
| AI695404 | UNKNOWN | 12 | 409 | T |
| AI695418 | UNKNOWN | 13 | 39 | A |
| AI695509 | UNKNOWN | 45 | 0 | T |
| AI695548 | UNKNOWN | 23 | 0 | T |
| AI695647 | UNKNOWN | 16 | 0 | T |
| AI695678 | UNKNOWN | 19 | 102 | A |
| AI695678 | UNKNOWN | 16 | 65 | T |
| AI695751 | UNKNOWN | 13 | 0 | T |
| AI695794 | UNKNOWN | 48 | 0 | T |
| AI695813 | UNKNOWN | 23 | 0 | T |
| AI695835 | UNKNOWN | 3.8 | 84 | AAAAG |
| AI695835 | UNKNOWN | 4.5 | 0 | ATTT |
| AI695857 | UNKNOWN | 46 | 0 | T |
| AI695857 | UNKNOWN | 13 | 46 | A |
| AI695875 | UNKNOWN | 30 | 0 | T |
| AI695905 | UNKNOWN | 13 | 0 | T |
| AI695947 | UNKNOWN | 31 | 0 | T |
| AI695991 | UNKNOWN | 36 | 0 | T |
| AI696047 | UNKNOWN | 10.5 | 83 | AC |
| AI696064 | UNKNOWN | 55 | 0 | T |
| AI696064 | UNKNOWN | 18 | 220 | A |
| AI696081 | UNKNOWN | 35 | 0 | T |
| AI696089 | UNKNOWN | 16 | 232 | T |
| AI696186 | UNKNOWN | 69 | 0 | T |
| AI696229 | UNKNOWN | 12 | 315 | A |
| AI696245 | UNKNOWN | 38 | 0 | T |
| AI696249 | UNKNOWN | 23 | 0 | T |
| AI696277 | UNKNOWN | 12 | 322 | G |
| AI696284 | UNKNOWN | 58 | 0 | T |
| AI696340 | UNKNOWN | 49 | 0 | T |
| AI696378 | UNKNOWN | 79 | 0 | T |
| AI696398 | UNKNOWN | 122 | 0 | T |
| AI696398 | UNKNOWN | 19 | 154 | A |
| AI696398 | UNKNOWN | 13 | 393 | C |
| AI696434 | UNKNOWN | 58 | 0 | T |
| AI696529 | UNKNOWN | 25 | 0 | T |
| AI696533 | UNKNOWN | 80 | 0 | T |
| AI696533 | UNKNOWN | 12 | 229 | C |
| AI696570 | UNKNOWN | 74 | 0 | T |
| AI696588 | UNKNOWN | 45 | 0 | T |
| AI696596 | UNKNOWN | 19 | 0 | T |
| AI696606 | UNKNOWN | 37 | 56 | T |
| AI696606 | UNKNOWN | 27 | 10 | T |
| AI696606 | UNKNOWN | 23 | 178 | A |

TABLE 1-continued

| Genbank # | Region | # reps | Position | Unit sequence |
|---|---|---|---|---|
| AI696611 | UNKNOWN | 66 | 0 | T |
| AI696612 | UNKNOWN | 105 | 0 | T |
| AI696612 | UNKNOWN | 12 | 117 | A |
| AI696612 | UNKNOWN | 12 | 157 | C |
| AI696619 | UNKNOWN | 43 | 0 | T |
| AI696621 | UNKNOWN | 46 | 0 | T |
| AI696626 | UNKNOWN | 97 | 0 | T |
| AI696627 | UNKNOWN | 13 | 0 | T |
| AI696692 | UNKNOWN | 4.75 | 70 | AAAC |
| AI696692 | UNKNOWN | 21 | 0 | T |
| AI696692 | UNKNOWN | 15 | 249 | A |
| AI696714 | UNKNOWN | 49 | 0 | T |
| AI696714 | UNKNOWN | 13 | 100 | G |
| AI696739 | UNKNOWN | 27 | 0 | T |
| AI696809 | UNKNOWN | 63 | 0 | T |
| AI696809 | UNKNOWN | 20 | 314 | A |
| AI696809 | UNKNOWN | 16 | 130 | G |
| AI696809 | UNKNOWN | 12 | 171 | A |
| AI696819 | UNKNOWN | 90 | 0 | T |
| AI696819 | UNKNOWN | 23 | 147 | C |
| AI696819 | UNKNOWN | 14 | 174 | A |
| AI696829 | UNKNOWN | 114 | 0 | T |
| AI696829 | UNKNOWN | 13 | 181 | C |
| AI696846 | UNKNOWN | 101 | 0 | T |
| AI696846 | UNKNOWN | 16 | 129 | C |
| AI696846 | UNKNOWN | 15 | 167 | A |
| AI696846 | UNKNOWN | 15 | 340 | G |
| AI696846 | UNKNOWN | 13 | 145 | A |
| AI696846 | UNKNOWN | 13 | 284 | G |
| AI696862 | UNKNOWN | 42 | 0 | T |
| AI696883 | UNKNOWN | 27 | 0 | T |
| AI696927 | UNKNOWN | 54 | 0 | T |
| AI696927 | UNKNOWN | 24 | 265 | A |
| AI696940 | UNKNOWN | 14 | 378 | GT |
| AI696956 | UNKNOWN | 94 | 0 | T |
| AI696956 | UNKNOWN | 15 | 119 | C |
| AI696956 | UNKNOWN | 13 | 143 | A |
| AI696956 | UNKNOWN | 12 | 306 | G |
| AI696970 | UNKNOWN | 103 | 0 | T |
| AI696970 | UNKNOWN | 17 | 216 | C |
| AI696970 | UNKNOWN | 14 | 110 | G |
| AI696970 | UNKNOWN | 13 | 149 | A |
| AI696971 | UNKNOWN | 31 | 0 | T |
| AI696983 | UNKNOWN | 65 | 0 | T |
| AI696983 | UNKNOWN | 12 | 134 | A |
| AI697008 | UNKNOWN | 58 | 0 | T |
| AI697028 | UNKNOWN | 20 | 383 | T |
| AI697092 | UNKNOWN | 80 | 0 | T |
| AI697092 | UNKNOWN | 17 | 191 | G |
| AI697099 | UNKNOWN | 83 | 0 | T |
| AI697099 | UNKNOWN | 14 | 146 | G |
| AI697102 | UNKNOWN | 34 | 0 | T |
| AI697112 | UNKNOWN | 43 | 0 | T |
| AI697112 | UNKNOWN | 14 | 126 | A |
| AI697137 | UNKNOWN | 125 | 0 | T |
| AI697137 | UNKNOWN | 20 | 266 | A |
| AI697137 | UNKNOWN | 17 | 290 | C |
| AI697149 | UNKNOWN | 61 | 0 | T |
| AI697157 | UNKNOWN | 63 | 0 | T |
| AI697160 | UNKNOWN | 22 | 0 | T |
| AI697177 | UNKNOWN | 59 | 0 | T |
| AI697177 | UNKNOWN | 12 | 192 | G |
| AI697178 | UNKNOWN | 48 | 0 | T |
| AI697178 | UNKNOWN | 14 | 258 | A |
| AI697188 | UNKNOWN | 86 | 0 | T |
| AI697188 | UNKNOWN | 15 | 107 | A |
| AI697191 | UNKNOWN | 87 | 0 | T |
| AI697191 | UNKNOWN | 19 | 115 | C |
| AI697196 | UNKNOWN | 26 | 0 | T |
| AI697207 | UNKNOWN | 79 | 0 | T |
| AI697207 | UNKNOWN | 22 | 147 | C |
| AI697207 | UNKNOWN | 18 | 279 | A |
| AI697207 | UNKNOWN | 14 | 96 | A |
| AI697236 | UNKNOWN | 55 | 0 | T |
| AI697280 | UNKNOWN | 23 | 0 | T |
| AI697304 | UNKNOWN | 107 | 0 | T |
| AI697309 | UNKNOWN | 12 | 321 | T |

TABLE 1-continued

| Genbank # | Region | # reps | Position | Unit sequence |
|---|---|---|---|---|
| AI697321 | UNKNOWN | 108 | 0 | T |
| AI697321 | UNKNOWN | 19 | 296 | C |
| AI697321 | UNKNOWN | 17 | 142 | A |
| AI697321 | UNKNOWN | 15 | 116 | C |
| AI697321 | UNKNOWN | 14 | 253 | G |
| AI697324 | UNKNOWN | 80 | 0 | T |
| AI697354 | UNKNOWN | 15 | 0 | T |
| AI697372 | UNKNOWN | 78 | 0 | T |
| AI697372 | UNKNOWN | 15 | 332 | A |
| AI697372 | UNKNOWN | 14 | 115 | A |
| AI697396 | UNKNOWN | 14 | 0 | T |
| AI697407 | UNKNOWN | 36 | 0 | T |
| AI697410 | UNKNOWN | 53 | 0 | T |
| AI697417 | UNKNOWN | 8 | 0 | ATTT |
| AI697420 | UNKNOWN | 87 | 0 | T |
| AI697420 | UNKNOWN | 15 | 121 | C |
| AI697420 | UNKNOWN | 14 | 190 | G |
| AI697526 | UNKNOWN | 32 | 0 | T |
| AI697526 | UNKNOWN | 14 | 337 | C |
| AI697528 | UNKNOWN | 18 | 394 | T |
| AI697540 | UNKNOWN | 14 | 513 | T |
| AI697569 | UNKNOWN | 12 | 0 | T |
| AI697608 | UNKNOWN | 3.8 | 403 | TTTTC |
| AI697615 | UNKNOWN | 15 | 0 | T |
| AI697703 | UNKNOWN | 12 | 8 | T |
| AI697756 | UNKNOWN | 13 | 426 | A |
| AI697770 | UNKNOWN | 17 | 187 | T |
| AI697790 | UNKNOWN | 15 | 0 | T |
| AI697834 | UNKNOWN | 14 | 4 | T |
| AI697842 | UNKNOWN | 14 | 0 | T |
| AI697950 | UNKNOWN | 24 | 0 | T |
| AI698045 | UNKNOWN | 6 | 200 | ATT |
| AI698092 | UNKNOWN | 15 | 158 | T |
| AI698092 | UNKNOWN | 14 | 327 | A |
| AI698117 | UNKNOWN | 12 | 95 | A |
| AI698134 | UNKNOWN | 12 | 9 | A |
| AI698239 | UNKNOWN | 12 | 0 | T |
| AI698391 | UNKNOWN | 89 | 0 | T |
| AI698391 | UNKNOWN | 12 | 89 | A |
| AI698401 | UNKNOWN | 85 | 0 | T |
| AI698401 | UNKNOWN | 14 | 157 | G |
| AI698403 | UNKNOWN | 54 | 0 | T |
| AI698427 | UNKNOWN | 72 | 0 | T |
| AI698462 | UNKNOWN | 41 | 0 | T |
| AI698491 | UNKNOWN | 55 | 0 | T |
| AI698491 | UNKNOWN | 12 | 168 | G |
| AI698684 | UNKNOWN | 13 | 13 | T |
| AI698728 | UNKNOWN | 18 | 1 | T |
| AI698797 | UNKNOWN | 21 | 0 | T |
| AI698804 | UNKNOWN | 6.5 | 283 | AG |
| AI698902 | UNKNOWN | 12 | 0 | T |
| AI698927 | UNKNOWN | 17 | 0 | T |
| AI699011 | UNKNOWN | 90 | 0 | T |
| AI699011 | UNKNOWN | 15 | 148 | C |
| AI699011 | UNKNOWN | 13 | 165 | A |
| AI699026 | UNKNOWN | 41 | 0 | T |
| AI699046 | UNKNOWN | 43 | 0 | T |
| AI699055 | UNKNOWN | 36 | 0 | T |
| AI699060 | UNKNOWN | 14 | 0 | T |
| AI699061 | UNKNOWN | 35 | 0 | T |
| AI699067 | UNKNOWN | 50 | 0 | T |
| AI699143 | UNKNOWN | 71 | 0 | T |
| AI699143 | UNKNOWN | 12 | 204 | C |
| AI699160 | UNKNOWN | 19 | 0 | T |
| AI699175 | UNKNOWN | 47 | 0 | T |
| AI699184 | UNKNOWN | 49 | 0 | T |
| AI699184 | UNKNOWN | 14 | 151 | C |
| AI699184 | UNKNOWN | 12 | 94 | G |
| AI699186 | UNKNOWN | 38 | 0 | T |
| AI699194 | UNKNOWN | 27 | 0 | T |
| AI699211 | UNKNOWN | 57 | 0 | T |
| AI699228 | UNKNOWN | 14 | 0 | T |
| AI699255 | UNKNOWN | 77 | 0 | T |
| AI699274 | UNKNOWN | 55 | 0 | T |
| AI699344 | UNKNOWN | 15 | 0 | T |
| AI699458 | UNKNOWN | 19 | 0 | T |
| AI699467 | UNKNOWN | 3.6 | 136 | AAAAC |

TABLE 1-continued

| Genbank # | Region | # reps | Position | Unit sequence |
|---|---|---|---|---|
| AI699506 | UNKNOWN | 5.66 | 324 | CCG |
| AI699526 | UNKNOWN | 18 | 4 | T |
| AI699616 | UNKNOWN | 15 | 0 | T |
| AI699630 | UNKNOWN | 13 | 458 | A |
| AI699630 | UNKNOWN | 13 | 471 | T |
| AI699764 | UNKNOWN | 61 | 0 | T |
| AI699788 | UNKNOWN | 63 | 0 | T |
| AI699788 | UNKNOWN | 17 | 213 | C |
| AI699804 | UNKNOWN | 38 | 0 | T |
| AI699812 | UNKNOWN | 30 | 0 | T |
| AI699836 | UNKNOWN | 44 | 0 | T |
| AI699836 | UNKNOWN | 13 | 80 | A |
| AI699836 | UNKNOWN | 12 | 261 | G |
| AI699857 | UNKNOWN | 124 | 0 | T |
| AI699857 | UNKNOWN | 17 | 184 | A |
| AI699857 | UNKNOWN | 16 | 156 | G |
| AI699857 | UNKNOWN | 14 | 294 | C |
| AI699862 | UNKNOWN | 72 | 0 | T |
| AI699862 | UNKNOWN | 14 | 130 | G |
| AI699865 | UNKNOWN | 81 | 0 | T |
| AI699865 | UNKNOWN | 18 | 186 | G |
| AI699865 | UNKNOWN | 17 | 134 | A |
| AI699865 | UNKNOWN | 15 | 151 | G |
| AI699865 | UNKNOWN | 14 | 166 | C |
| AI699866 | UNKNOWN | 42 | 0 | T |
| AI699889 | UNKNOWN | 20 | 0 | T |
| AI699945 | UNKNOWN | 21 | 462 | G |
| AI699945 | UNKNOWN | 12 | 340 | A |
| AI700071 | UNKNOWN | 18 | 4 | T |
| AI700124 | UNKNOWN | 4.4 | 412 | AAAC |
| AI700146 | UNKNOWN | 72 | 0 | T |
| AI700158 | UNKNOWN | 51 | 0 | T |
| AI700159 | UNKNOWN | 73 | 0 | T |
| AI700159 | UNKNOWN | 12 | 173 | C |
| AI700168 | UNKNOWN | 43 | 0 | T |
| AI700190 | UNKNOWN | 22 | 0 | T |
| AI700225 | UNKNOWN | 18 | 126 | T |
| AI700225 | UNKNOWN | 14 | 180 | A |
| AI700233 | UNKNOWN | 12 | 399 | A |
| AI700305 | UNKNOWN | 72 | 0 | T |
| AI700305 | UNKNOWN | 18 | 260 | C |
| AI700305 | UNKNOWN | 13 | 243 | A |
| AI700305 | UNKNOWN | 12 | 185 | C |
| AI700358 | UNKNOWN | 66 | 0 | T |
| AI700358 | UNKNOWN | 18 | 138 | C |
| AI700358 | UNKNOWN | 12 | 189 | A |
| AI700415 | UNKNOWN | 3.83 | 304 | AAAAC |
| AI700460 | UNKNOWN | 18 | 1 | T |
| AI700465 | UNKNOWN | 18 | 1 | T |
| AI700468 | UNKNOWN | 15 | 0 | T |
| AI700477 | UNKNOWN | 48 | 0 | T |
| AI700499 | UNKNOWN | 26 | 0 | T |
| AI700500 | UNKNOWN | 6.5 | 128 | AG |
| AI700516 | UNKNOWN | 3.6 | 369 | TTTTA |
| AI700523 | UNKNOWN | 17 | 0 | T |
| AI700720 | UNKNOWN | 21 | 108 | A |
| AI700737 | UNKNOWN | 11.5 | 273 | AC |
| AI700780 | UNKNOWN | 15 | 95 | A |
| AI700810 | UNKNOWN | 19 | 0 | T |
| AI700907 | UNKNOWN | 21 | 0 | T |
| AI701034 | UNKNOWN | 20 | 0 | T |
| AI701066 | UNKNOWN | 16 | 0 | T |
| AI701074 | UNKNOWN | 101 | 0 | T |
| AI701074 | UNKNOWN | 14 | 122 | A |
| AI701074 | UNKNOWN | 14 | 148 | G |
| AI701133 | UNKNOWN | 5.66 | 51 | AAC |
| AI701229 | UNKNOWN | 45 | 0 | T |
| AI701229 | UNKNOWN | 12 | 108 | A |
| AI701230 | UNKNOWN | 17 | 0 | T |
| AI701406 | UNKNOWN | 13 | 0 | T |
| AI701500 | UNKNOWN | 14 | 0 | T |
| AI701550 | UNKNOWN | 4.5 | 24 | AAAT |
| AI701551 | UNKNOWN | 16 | 0 | T |
| AI701570 | UNKNOWN | 19 | 0 | T |
| AI701577 | UNKNOWN | 5.66 | 426 | CAG |
| AI701596 | UNKNOWN | 6.33 | 56 | TAT |
| AI701596 | UNKNOWN | 12 | 421 | A |

TABLE 1-continued

| Genbank # | Region | # reps | Position | Unit sequence |
|---|---|---|---|---|
| AI701609 | UNKNOWN | 21 | 0 | T |
| AI701613 | UNKNOWN | 14 | 0 | T |
| AI701670 | UNKNOWN | 21 | 1 | T |
| AI701796 | UNKNOWN | 17 | 0 | T |
| AI701830 | UNKNOWN | 30 | 0 | T |
| AI701835 | UNKNOWN | 16 | 0 | T |
| AI701857 | UNKNOWN | 19 | 3 | T |
| AI701868 | UNKNOWN | 40 | 0 | T |
| AI701882 | UNKNOWN | 68 | 0 | T |
| AI701882 | UNKNOWN | 13 | 104 | A |
| AI701890 | UNKNOWN | 64 | 0 | T |
| AI701890 | UNKNOWN | 15 | 226 | G |
| AI701890 | UNKNOWN | 13 | 250 | A |
| AI701891 | UNKNOWN | 45 | 0 | T |
| AI701891 | UNKNOWN | 12 | 119 | G |
| AI701897 | UNKNOWN | 81 | 0 | T |
| AI701897 | UNKNOWN | 12 | 112 | A |
| AI701905 | UNKNOWN | 18 | 0 | T |
| AI701948 | UNKNOWN | 49 | 0 | T |
| AI701948 | UNKNOWN | 14 | 204 | A |
| AI701975 | UNKNOWN | 71 | 0 | T |
| AI701975 | UNKNOWN | 14 | 127 | G |
| AI701975 | UNKNOWN | 13 | 187 | A |
| AI701978 | UNKNOWN | 55 | 0 | T |
| AI701995 | UNKNOWN | 3.83 | 22 | AAAAAC |
| AI702013 | UNKNOWN | 6.66 | 280 | TGT |
| AI702013 | UNKNOWN | 61 | 0 | T |
| AI702047 | UNKNOWN | 36 | 0 | T |
| AI702060 | UNKNOWN | 27 | 0 | T |
| AI702068 | UNKNOWN | 106 | 2 | T |
| AI702068 | UNKNOWN | 19 | 260 | A |
| AI702068 | UNKNOWN | 15 | 146 | G |
| AI702068 | UNKNOWN | 12 | 240 | C |
| AI702073 | UNKNOWN | 108 | 0 | T |
| AI702073 | UNKNOWN | 22 | 143 | G |
| AI702073 | UNKNOWN | 18 | 108 | A |
| AI702086 | UNKNOWN | 35 | 0 | T |
| AI702291 | UNKNOWN | 26 | 346 | C |
| AI702301 | UNKNOWN | 73 | 0 | T |
| AI702331 | UNKNOWN | 37 | 10 | T |
| AI702331 | UNKNOWN | 18 | 117 | A |
| AI702331 | UNKNOWN | 12 | 150 | C |
| AI702406 | UNKNOWN | 130 | 0 | T |
| AI702406 | UNKNOWN | 13 | 170 | A |
| AI702433 | UNKNOWN | 122 | 0 | T |
| AI702433 | UNKNOWN | 19 | 231 | G |
| AI702433 | UNKNOWN | 15 | 136 | A |
| AI702433 | UNKNOWN | 14 | 213 | C |
| AI702476 | UNKNOWN | 12 | 0 | T |
| AI702543 | UNKNOWN | 29 | 0 | T |
| AI702670 | UNKNOWN | 17 | 263 | T |
| AI702767 | UNKNOWN | 18 | 275 | A |
| AI702770 | UNKNOWN | 22 | 0 | T |
| AI702812 | UNKNOWN | 18 | 12 | T |
| AI702902 | UNKNOWN | 56 | 0 | T |
| AI702914 | UNKNOWN | 9.25 | 31 | TCAT |
| AI703017 | UNKNOWN | 14 | 0 | T |
| AI703040 | UNKNOWN | 3.04 | 385 | ATGTATCATTCAAACTAAATAC (SEQ ID NO: 141) |
| AI703072 | UNKNOWN | 6.25 | 22 | ATTC |
| AI703094 | UNKNOWN | 23 | 0 | T |
| AI703114 | UNKNOWN | 13 | 344 | A |
| AI703214 | UNKNOWN | 13 | 150 | A |
| AI703298 | UNKNOWN | 24 | 409 | T |
| AI703303 | UNKNOWN | 17 | 0 | T |
| AI703304 | UNKNOWN | 22 | 0 | T |
| AI703308 | UNKNOWN | 13 | 350 | A |
| AI703473 | UNKNOWN | 20 | 20 | T |
| AI703496 | UNKNOWN | 19 | 0 | T |
| AI707692 | UNKNOWN | 39 | 0 | T |
| AI707809 | UNKNOWN | 36 | 0 | T |
| AI707834 | UNKNOWN | 43 | 0 | T |
| AI708043 | UNKNOWN | 53 | 0 | T |
| AI708043 | UNKNOWN | 18 | 155 | G |
| AI708076 | UNKNOWN | 31 | 0 | T |
| AI708076 | UNKNOWN | 23 | 319 | G |
| AI708080 | UNKNOWN | 24 | 21 | T |
| AI708080 | UNKNOWN | 19 | 0 | T |

TABLE 1-continued

| Genbank # | Region | # reps | Position | Unit sequence |
|---|---|---|---|---|
| AI708080 | UNKNOWN | 13 | 170 | A |
| AI708125 | UNKNOWN | 4.59 | 126 | TTTCT |
| AI708125 | UNKNOWN | 16 | 145 | T |
| AI708219 | UNKNOWN | 46 | 0 | T |
| AI708248 | UNKNOWN | 38 | 1 | T |
| AI708339 | UNKNOWN | 14 | 330 | T |
| AI708503 | UNKNOWN | 18 | 0 | T |
| AI708648 | UNKNOWN | 18 | 0 | T |
| AI708725 | UNKNOWN | 34 | 0 | T |
| AI708979 | UNKNOWN | 21 | 0 | T |
| AI709153 | UNKNOWN | 21 | 0 | T |
| AI709203 | UNKNOWN | 12 | 103 | T |
| AI709215 | UNKNOWN | 22 | 0 | T |
| AI709236 | UNKNOWN | 5.66 | 404 | TTA |
| AI718009 | UNKNOWN | 32 | 0 | T |
| AI718113 | UNKNOWN | 13 | 297 | A |
| AI718161 | UNKNOWN | 61 | 0 | T |
| AI718161 | UNKNOWN | 15 | 362 | A |
| AI718161 | UNKNOWN | 14 | 285 | C |
| AI718161 | UNKNOWN | 13 | 253 | G |
| AI718513 | UNKNOWN | 77 | 0 | T |
| AI718513 | UNKNOWN | 12 | 381 | A |
| AI718580 | UNKNOWN | 27 | 321 | T |
| AI718938 | UNKNOWN | 16 | 273 | T |
| AI718946 | UNKNOWN | 18 | 0 | T |
| AI719043 | UNKNOWN | 39 | 20 | T |
| AI719043 | UNKNOWN | 18 | 0 | T |
| AI719043 | UNKNOWN | 13 | 106 | A |
| AI719289 | UNKNOWN | 13 | 0 | T |
| AI719664 | UNKNOWN | 44 | 0 | T |
| AI719768 | UNKNOWN | 49 | 0 | T |
| AI719817 | UNKNOWN | 63 | 0 | T |
| AI719817 | UNKNOWN | 16 | 65 | A |
| AI720018 | UNKNOWN | 24 | 0 | T |
| AI720048 | UNKNOWN | 13 | 0 | T |
| AI720052 | UNKNOWN | 40 | 0 | T |
| AI720258 | UNKNOWN | 43 | 20 | T |
| AI720258 | UNKNOWN | 15 | 0 | T |
| AI720258 | UNKNOWN | 14 | 270 | G |
| AI720663 | UNKNOWN | 22 | 0 | T |
| AI720881 | UNKNOWN | 15 | 0 | T |
| AI720923 | UNKNOWN | 3.57 | 74 | AAAACAA |
| AI721044 | UNKNOWN | 20 | 6 | T |
| AI721234 | UNKNOWN | 12 | 3 | T |
| AI732060 | UNKNOWN | 22 | 8 | T |
| AI732072 | UNKNOWN | 15 | 272 | A |
| AI732076 | UNKNOWN | 24 | 268 | A |
| AI732077 | UNKNOWN | 27 | 8 | T |
| AI732083 | UNKNOWN | 16 | 8 | T |
| AI732084 | UNKNOWN | 16 | 8 | T |
| AI732089 | UNKNOWN | 26 | 8 | T |
| AI732108 | UNKNOWN | 18 | 364 | A |
| AI732109 | UNKNOWN | 13 | 281 | A |
| AI732113 | UNKNOWN | 22 | 0 | T |
| AI732133 | UNKNOWN | 15 | 33 | T |
| AI732138 | UNKNOWN | 16 | 33 | T |
| AI732143 | UNKNOWN | 25 | 8 | T |
| AI732156 | UNKNOWN | 19 | 0 | T |
| AI732161 | UNKNOWN | 30 | 0 | T |
| AI732167 | UNKNOWN | 19 | 0 | T |
| AI732173 | UNKNOWN | 26 | 0 | T |
| AI732177 | UNKNOWN | 15 | 40 | T |
| AI732191 | UNKNOWN | 22 | 0 | T |
| AI732192 | UNKNOWN | 15 | 0 | T |
| AI732209 | UNKNOWN | 19 | 8 | T |
| AI732212 | UNKNOWN | 12 | 328 | A |
| AI732213 | UNKNOWN | 18 | 33 | T |
| AI732215 | UNKNOWN | 20 | 192 | A |
| AI732219 | UNKNOWN | 13 | 8 | T |
| AI732223 | UNKNOWN | 23 | 8 | T |
| AI732227 | UNKNOWN | 22 | 20 | T |
| AI732229 | UNKNOWN | 17 | 8 | T |
| AI732231 | UNKNOWN | 14 | 8 | T |
| AI732235 | UNKNOWN | 16 | 8 | T |
| AI732285 | UNKNOWN | 4.8 | 487 | ACAAA |
| AI732285 | UNKNOWN | 5.66 | 506 | AAC |
| AI732303 | UNKNOWN | 7.33 | 24 | CGG |

TABLE 1-continued

| Genbank # | Region | # reps | Position | Unit sequence |
|---|---|---|---|---|
| AI732313 | UNKNOWN | 5.5 | 446 | TTAA |
| AI732328 | UNKNOWN | 22 | 8 | T |
| AI732331 | UNKNOWN | 16 | 387 | A |
| AI732338 | UNKNOWN | 21 | 0 | T |
| AI732345 | UNKNOWN | 20 | 209 | T |
| AI732345 | UNKNOWN | 16 | 0 | T |
| AI732346 | UNKNOWN | 30 | 0 | T |
| AI732347 | UNKNOWN | 23 | 21 | T |
| AI732348 | UNKNOWN | 23 | 8 | T |
| AI732354 | UNKNOWN | 22 | 0 | T |
| AI732357 | UNKNOWN | 24 | 0 | T |
| AI732361 | UNKNOWN | 20 | 8 | T |
| AI732364 | UNKNOWN | 33 | 8 | T |
| AI732369 | UNKNOWN | 18 | 0 | T |
| AI732373 | UNKNOWN | 13 | 0 | T |
| AI732379 | UNKNOWN | 22 | 192 | A |
| AI732388 | UNKNOWN | 20 | 0 | T |
| AI732410 | UNKNOWN | 4.75 | 480 | TTTA |
| AI732433 | UNKNOWN | 18 | 0 | T |
| AI732437 | UNKNOWN | 17 | 0 | T |
| AI732459 | UNKNOWN | 14 | 0 | T |
| AI732480 | UNKNOWN | 17 | 8 | T |
| AI732483 | UNKNOWN | 26 | 8 | T |
| AI732484 | UNKNOWN | 31 | 39 | T |
| AI732487 | UNKNOWN | 23 | 0 | T |
| AI732493 | UNKNOWN | 14 | 0 | T |
| AI732497 | UNKNOWN | 18 | 206 | A |
| AI732498 | UNKNOWN | 19 | 39 | T |
| AI732501 | UNKNOWN | 15 | 404 | A |
| AI732508 | UNKNOWN | 17 | 33 | T |
| AI732517 | UNKNOWN | 15 | 9 | T |
| AI732535 | UNKNOWN | 23 | 0 | T |
| AI732536 | UNKNOWN | 9 | 255 | CAAAA |
| AI732536 | UNKNOWN | 26 | 0 | T |
| AI732544 | UNKNOWN | 12 | 509 | A |
| AI732548 | UNKNOWN | 17 | 8 | T |
| AI732550 | UNKNOWN | 22 | 8 | T |
| AI732569 | UNKNOWN | 21 | 0 | T |
| AI732578 | UNKNOWN | 16 | 2 | T |
| AI732596 | UNKNOWN | 22 | 0 | T |
| AI732598 | UNKNOWN | 19 | 0 | T |
| AI732602 | UNKNOWN | 12 | 0 | T |
| AI732621 | UNKNOWN | 12 | 0 | T |
| AI732625 | UNKNOWN | 22 | 0 | T |
| AI732625 | UNKNOWN | 14 | 364 | A |
| AI732627 | UNKNOWN | 17 | 0 | T |
| AI732629 | UNKNOWN | 7 | 549 | GA |
| AI732631 | UNKNOWN | 15 | 243 | A |
| AI732641 | UNKNOWN | 17 | 409 | A |
| AI732645 | UNKNOWN | 19 | 0 | T |
| AI732646 | UNKNOWN | 26 | 0 | T |
| AI732652 | UNKNOWN | 15 | 0 | T |
| AI732654 | UNKNOWN | 26 | 0 | T |
| AI732660 | UNKNOWN | 3.6 | 72 | AAAGA |
| AI732660 | UNKNOWN | 28 | 0 | T |
| AI732662 | UNKNOWN | 13 | 0 | T |
| AI732682 | UNKNOWN | 16 | 8 | T |
| AI732688 | UNKNOWN | 35 | 8 | T |
| AI732695 | UNKNOWN | 33 | 0 | T |
| AI732709 | UNKNOWN | 4 | 69 | AAAAC |
| AI732709 | UNKNOWN | 24 | 8 | T |
| AI732711 | UNKNOWN | 13 | 425 | A |
| AI732713 | UNKNOWN | 18 | 362 | T |
| AI732716 | UNKNOWN | 8.5 | 248 | TA |
| AI732716 | UNKNOWN | 17 | 33 | T |
| AI732720 | UNKNOWN | 23 | 396 | A |
| AI732722 | UNKNOWN | 20 | 39 | T |
| AI732761 | UNKNOWN | 22 | 6 | T |
| AI732769 | UNKNOWN | 13 | 0 | T |
| AI732785 | UNKNOWN | 19 | 0 | T |
| AI732790 | UNKNOWN | 19 | 0 | T |
| AI732793 | UNKNOWN | 15 | 0 | T |
| AI732798 | UNKNOWN | 14 | 406 | T |
| AI732800 | UNKNOWN | 20 | 90 | A |
| AI732804 | UNKNOWN | 14 | 71 | T |
| AI732807 | UNKNOWN | 22 | 4 | T |
| AI732808 | UNKNOWN | 19 | 0 | T |

TABLE 1-continued

| Genbank # | Region | # reps | Position | Unit sequence |
|---|---|---|---|---|
| AI732809 | UNKNOWN | 17 | 0 | T |
| AI732837 | UNKNOWN | 23 | 304 | A |
| AI732857 | UNKNOWN | 17 | 190 | A |
| AI732858 | UNKNOWN | 18 | 8 | T |
| AI732861 | UNKNOWN | 26 | 33 | T |
| AI732865 | UNKNOWN | 26 | 8 | T |
| AI732866 | UNKNOWN | 18 | 33 | T |
| AI732868 | UNKNOWN | 3.87 | 151 | ACTGCACC |
| AI732868 | UNKNOWN | 15 | 33 | T |
| AI732871 | UNKNOWN | 15 | 0 | T |
| AI732894 | UNKNOWN | 25 | 0 | T |
| AI732895 | UNKNOWN | 25 | 0 | T |
| AI732904 | UNKNOWN | 21 | 0 | T |
| AI732908 | UNKNOWN | 16 | 0 | T |
| AI732931 | UNKNOWN | 19 | 0 | T |
| AI732946 | UNKNOWN | 12 | 221 | A |
| AI732969 | UNKNOWN | 9.5 | 455 | AC |
| AI732971 | UNKNOWN | 15 | 0 | T |
| AI732994 | UNKNOWN | 3.8 | 411 | TTTG |
| AI733010 | UNKNOWN | 20 | 0 | T |
| AI733019 | UNKNOWN | 18 | 0 | T |
| AI733026 | UNKNOWN | 16 | 471 | A |
| AI733030 | UNKNOWN | 14 | 0 | T |
| AI733033 | UNKNOWN | 23 | 0 | T |
| AI733041 | UNKNOWN | 8 | 243 | CA |
| AI733044 | UNKNOWN | 15 | 0 | T |
| AI733059 | UNKNOWN | 19 | 0 | T |
| AI733062 | UNKNOWN | 18 | 0 | T |
| AI733077 | UNKNOWN | 17 | 0 | T |
| AI733079 | UNKNOWN | 14 | 0 | T |
| AI733108 | UNKNOWN | 4.5 | 252 | TTTA |
| AI733108 | UNKNOWN | 8 | 342 | AT |
| AI733112 | UNKNOWN | 16 | 52 | A |
| AI733115 | UNKNOWN | 5.66 | 105 | TTC |
| AI733144 | UNKNOWN | 4.75 | 172 | TTTG |
| AI733144 | UNKNOWN | 15 | 248 | A |
| AI733222 | UNKNOWN | 15 | 0 | T |
| AI733232 | UNKNOWN | 16 | 15 | A |
| AI733237 | UNKNOWN | 13 | 5 | T |
| AI733253 | UNKNOWN | 23 | 0 | T |
| AI733290 | UNKNOWN | 24 | 0 | T |
| AI733294 | UNKNOWN | 16 | 0 | T |
| AI733303 | UNKNOWN | 12 | 0 | T |
| AI733304 | UNKNOWN | 10 | 28 | TTTA |
| AI733315 | UNKNOWN | 16 | 0 | T |
| AI733318 | UNKNOWN | 13 | 231 | A |
| AI733322 | UNKNOWN | 19 | 304 | T |
| AI733323 | UNKNOWN | 23 | 0 | T |
| AI733328 | UNKNOWN | 12 | 315 | T |
| AI733338 | UNKNOWN | 16 | 0 | T |
| AI733348 | UNKNOWN | 13 | 152 | A |
| AI733353 | UNKNOWN | 12 | 396 | T |
| AI733363 | UNKNOWN | 15 | 228 | CA |
| AI733370 | UNKNOWN | 4.5 | 12 | TTAT |
| AI733387 | UNKNOWN | 23 | 0 | T |
| AI733399 | UNKNOWN | 12 | 425 | T |
| AI733404 | UNKNOWN | 12 | 201 | A |
| AI733405 | UNKNOWN | 14 | 330 | A |
| AI733406 | UNKNOWN | 15 | 204 | T |
| AI733431 | UNKNOWN | 18 | 0 | T |
| AI733445 | UNKNOWN | 17 | 0 | T |
| AI733456 | UNKNOWN | 17 | 0 | T |
| AI733456 | UNKNOWN | 16 | 118 | A |
| AI733459 | UNKNOWN | 4.75 | 350 | AAAC |
| AI733461 | UNKNOWN | 13 | 0 | T |
| AI733464 | UNKNOWN | 27 | 80 | A |
| AI733464 | UNKNOWN | 21 | 407 | T |
| AI733474 | UNKNOWN | 15 | 526 | T |
| AI733490 | UNKNOWN | 12 | 0 | T |
| AI733492 | UNKNOWN | 23 | 2 | T |
| AI733498 | UNKNOWN | 12 | 0 | T |
| AI733500 | UNKNOWN | 16 | 0 | T |
| AI733508 | UNKNOWN | 8.5 | 235 | TG |
| AI733532 | UNKNOWN | 6.5 | 328 | TC |
| AI733553 | UNKNOWN | 4.5 | 418 | GGAG |
| AI733553 | UNKNOWN | 16 | 0 | T |
| AI733554 | UNKNOWN | 6 | 136 | TAA |

TABLE 1-continued

| Genbank # | Region | # reps | Position | Unit sequence |
|---|---|---|---|---|
| AI733573 | UNKNOWN | 16 | 0 | T |
| AI733576 | UNKNOWN | 17 | 0 | T |
| AI733591 | UNKNOWN | 12 | 0 | T |
| AI733604 | UNKNOWN | 15 | 0 | T |
| AI733610 | UNKNOWN | 8 | 526 | TA |
| AI733610 | UNKNOWN | 7.5 | 512 | TC |
| AI733612 | UNKNOWN | 19 | 0 | T |
| AI733617 | UNKNOWN | 26 | 0 | T |
| AI733623 | UNKNOWN | 8.5 | 423 | GT |
| AI733625 | UNKNOWN | 12 | 457 | A |
| AI733629 | UNKNOWN | 13 | 0 | T |
| AI733633 | UNKNOWN | 14 | 362 | A |
| AI733649 | UNKNOWN | 13 | 0 | T |
| AI733651 | UNKNOWN | 14 | 287 | T |
| AI733667 | UNKNOWN | 17 | 0 | T |
| AI733678 | UNKNOWN | 6.5 | 402 | AG |
| AI733688 | UNKNOWN | 18 | 0 | T |
| AI733694 | UNKNOWN | 30 | 0 | T |
| AI733696 | UNKNOWN | 28 | 0 | T |
| AI733700 | UNKNOWN | 3.5 | 420 | TCTTCC |
| AI733794 | UNKNOWN | 30 | 0 | T |
| AI733795 | UNKNOWN | 14 | 0 | T |
| AI733830 | UNKNOWN | 15 | 0 | T |
| AI733916 | UNKNOWN | 10 | 100 | AC |
| AI733916 | UNKNOWN | 19 | 404 | A |
| AI733938 | UNKNOWN | 29 | 147 | A |
| AI733940 | UNKNOWN | 31 | 132 | A |
| AI733942 | UNKNOWN | 30 | 192 | A |
| AI733947 | UNKNOWN | 28 | 185 | A |
| AI733949 | UNKNOWN | 32 | 123 | A |
| AI733951 | UNKNOWN | 29 | 266 | A |
| AI733956 | UNKNOWN | 28 | 133 | A |
| AI733958 | UNKNOWN | 22 | 368 | A |
| AI733960 | UNKNOWN | 6.5 | 131 | CT |
| AI733960 | UNKNOWN | 26 | 340 | A |
| AI733961 | UNKNOWN | 3.1 | 82 | AGAAAGAAAG (SEQ ID NO: 142) |
| AI733961 | UNKNOWN | 3.8 | 115 | AAAAG |
| AI733961 | UNKNOWN | 30 | 247 | A |
| AI733964 | UNKNOWN | 24 | 225 | A |
| AI733971 | UNKNOWN | 19 | 0 | T |
| AI733983 | UNKNOWN | 25 | 366 | A |
| AI733986 | UNKNOWN | 23 | 227 | A |
| AI733995 | UNKNOWN | 29 | 168 | A |
| AI734011 | UNKNOWN | 17 | 0 | T |
| AI734016 | UNKNOWN | 8 | 67 | AG |
| AI734053 | UNKNOWN | 22 | 34 | T |
| AI734055 | UNKNOWN | 15 | 326 | A |
| AI734069 | UNKNOWN | 14 | 28 | T |
| AI734070 | UNKNOWN | 18 | 31 | T |
| AI734075 | UNKNOWN | 16 | 6 | T |
| AI734081 | UNKNOWN | 16 | 373 | T |
| AI734093 | UNKNOWN | 13 | 31 | T |
| AI734095 | UNKNOWN | 19 | 6 | T |
| AI734115 | UNKNOWN | 3.83 | 242 | AAAAAG |
| AI734115 | UNKNOWN | 8.5 | 490 | AT |
| AI734116 | UNKNOWN | 6.5 | 363 | TA |
| AI734116 | UNKNOWN | 20 | 31 | T |
| AI734120 | UNKNOWN | 16 | 31 | T |
| AI734156 | UNKNOWN | 13 | 369 | A |
| AI734188 | UNKNOWN | 17 | 30 | T |
| AI734212 | UNKNOWN | 12 | 139 | A |
| AI734258 | UNKNOWN | 12 | 251 | A |
| AI734852 | UNKNOWN | 12 | 305 | A |
| AI734962 | UNKNOWN | 9.5 | 557 | TC |
| AI734967 | UNKNOWN | 12 | 115 | T |
| AI735078 | UNKNOWN | 2.63 | 504 | CACACACCACA (SEQ ID NO: 143) |
| AI735171 | UNKNOWN | 13 | 257 | A |
| AI735372 | UNKNOWN | 29 | 0 | T |
| AI735372 | UNKNOWN | 13 | 165 | G |
| AI735489 | UNKNOWN | 17 | 0 | T |
| AI735698 | UNKNOWN | 32 | 29 | T |
| AI735698 | UNKNOWN | 28 | 0 | T |
| AI735698 | UNKNOWN | 13 | 256 | A |
| AI735723 | UNKNOWN | 12 | 404 | T |
| AI738436 | UNKNOWN | 16 | 63 | A |
| AI738493 | UNKNOWN | 35 | 0 | T |
| AI738550 | UNKNOWN | 18 | 0 | T |

TABLE 1-continued

| Genbank # | Region | # reps | Position | Unit sequence |
|---|---|---|---|---|
| AI738551 | UNKNOWN | 15 | 445 | T |
| AI738566 | UNKNOWN | 16 | 0 | T |
| AI738578 | UNKNOWN | 13 | 0 | T |
| AI738592 | UNKNOWN | 12 | 223 | A |
| AI738660 | UNKNOWN | 62 | 0 | T |
| AI738660 | UNKNOWN | 18 | 185 | G |
| AI738675 | UNKNOWN | 12 | 0 | T |
| AI738751 | UNKNOWN | 13 | 144 | T |
| AI738762 | UNKNOWN | 48 | 0 | T |
| AI738806 | UNKNOWN | 43 | 0 | T |
| AI738806 | UNKNOWN | 12 | 261 | C |
| AI738835 | UNKNOWN | 17 | 0 | T |
| AI738836 | UNKNOWN | 13 | 0 | T |
| AI738852 | UNKNOWN | 78 | 0 | T |
| AI738852 | UNKNOWN | 12 | 277 | G |
| AI738854 | UNKNOWN | 91 | 0 | T |
| AI738854 | UNKNOWN | 26 | 165 | A |
| AI738854 | UNKNOWN | 17 | 191 | C |
| AI738854 | UNKNOWN | 12 | 343 | G |
| AI738867 | UNKNOWN | 84 | 0 | T |
| AI738897 | UNKNOWN | 15 | 0 | T |
| AI738913 | UNKNOWN | 12 | 8 | T |
| AI738919 | UNKNOWN | 13 | 0 | T |
| AI738992 | UNKNOWN | 12 | 405 | T |
| AI739024 | UNKNOWN | 3.6 | 110 | TAAAA |
| AI739053 | UNKNOWN | 19 | 0 | T |
| AI739057 | UNKNOWN | 12 | 93 | T |
| AI739241 | UNKNOWN | 22 | 4 | T |
| AI739332 | UNKNOWN | 17 | 5 | T |
| AI739383 | UNKNOWN | 15 | 0 | T |
| AI739416 | UNKNOWN | 37 | 0 | T |
| AI739486 | UNKNOWN | 18 | 4 | T |
| AI739583 | UNKNOWN | 37 | 21 | T |
| AI739583 | UNKNOWN | 20 | 0 | T |
| AI739595 | UNKNOWN | 22 | 0 | T |
| AI739614 | UNKNOWN | 13 | 0 | T |
| AI739615 | UNKNOWN | 22 | 0 | T |
| AI739630 | UNKNOWN | 17 | 0 | T |
| AI740450 | UNKNOWN | 16 | 0 | T |
| AI740457 | UNKNOWN | 35 | 0 | T |
| AI740462 | UNKNOWN | 15 | 20 | T |
| AI740476 | UNKNOWN | 19 | 0 | T |
| AI740476 | UNKNOWN | 14 | 238 | A |
| AI740483 | UNKNOWN | 13 | 0 | T |
| AI740499 | UNKNOWN | 12 | 0 | T |
| AI740501 | UNKNOWN | 12 | 0 | T |
| AI740516 | UNKNOWN | 22 | 0 | T |
| AI740525 | UNKNOWN | 13 | 523 | A |
| AI740537 | UNKNOWN | 12 | 0 | T |
| AI740548 | UNKNOWN | 44 | 0 | T |
| AI740552 | UNKNOWN | 18 | 3 | T |
| AI740573 | UNKNOWN | 17 | 0 | T |
| AI740589 | UNKNOWN | 19 | 0 | T |
| AI740597 | UNKNOWN | 14 | 0 | T |
| AI740623 | UNKNOWN | 52 | 0 | T |
| AI740623 | UNKNOWN | 13 | 165 | G |
| AI740627 | UNKNOWN | 55 | 0 | T |
| AI740627 | UNKNOWN | 15 | 106 | A |
| AI740629 | UNKNOWN | 18 | 1 | T |
| AI740669 | UNKNOWN | 17 | 0 | T |
| AI740696 | UNKNOWN | 23 | 0 | T |
| AI740698 | UNKNOWN | 8.5 | 326 | TC |
| AI740721 | UNKNOWN | 14 | 0 | T |
| AI740733 | UNKNOWN | 15 | 0 | T |
| AI740735 | UNKNOWN | 16 | 0 | T |
| AI740744 | UNKNOWN | 15 | 0 | T |
| AI740796 | UNKNOWN | 13 | 0 | T |
| AI740817 | UNKNOWN | 43 | 0 | T |
| AI740817 | UNKNOWN | 14 | 376 | G |
| AI740825 | UNKNOWN | 14 | 0 | T |
| AI740836 | UNKNOWN | 12 | 140 | A |
| AI740845 | UNKNOWN | 40 | 0 | T |
| AI740856 | UNKNOWN | 22 | 0 | T |
| AI740938 | UNKNOWN | 12 | 0 | T |
| AI740989 | UNKNOWN | 25 | 453 | T |
| AI740992 | UNKNOWN | 16 | 0 | T |
| AI740999 | UNKNOWN | 13 | 0 | T |

TABLE 1-continued

| Genbank # | Region | # reps | Position | Unit sequence |
|---|---|---|---|---|
| AI741059 | UNKNOWN | 12 | 0 | T |
| AI741066 | UNKNOWN | 18 | 0 | T |
| AI741068 | UNKNOWN | 15 | 0 | T |
| AI741070 | UNKNOWN | 12 | 0 | T |
| AI741083 | UNKNOWN | 37 | 0 | T |
| AI741093 | UNKNOWN | 18 | 0 | T |
| AI741116 | UNKNOWN | 45 | 0 | T |
| AI741140 | UNKNOWN | 17 | 0 | T |
| AI741147 | UNKNOWN | 25 | 0 | T |
| AI741150 | UNKNOWN | 24 | 0 | T |
| AI741158 | UNKNOWN | 60 | 0 | T |
| AI741158 | UNKNOWN | 15 | 216 | C |
| AI741187 | UNKNOWN | 52 | 0 | T |
| AI741234 | UNKNOWN | 3.8 | 84 | TTTTG |
| AI741234 | UNKNOWN | 12 | 0 | T |
| AI741240 | UNKNOWN | 17 | 1 | T |
| AI741244 | UNKNOWN | 12 | 0 | T |
| AI741292 | UNKNOWN | 26 | 0 | T |
| AI741300 | UNKNOWN | 24 | 0 | T |
| AI741315 | UNKNOWN | 18 | 8 | T |
| AI741316 | UNKNOWN | 62 | 0 | T |
| AI741319 | UNKNOWN | 21 | 0 | T |
| AI741344 | UNKNOWN | 16 | 0 | T |
| AI741348 | UNKNOWN | 18 | 1 | T |
| AI741350 | UNKNOWN | 25 | 0 | T |
| AI741361 | UNKNOWN | 18 | 0 | T |
| AI741373 | UNKNOWN | 20 | 5 | T |
| AI741381 | UNKNOWN | 15 | 0 | T |
| AI741385 | UNKNOWN | 12 | 0 | T |
| AI741403 | UNKNOWN | 21 | 0 | T |
| AI741412 | UNKNOWN | 19 | 0 | T |
| AI741414 | UNKNOWN | 13 | 0 | T |
| AI741467 | UNKNOWN | 60 | 0 | T |
| AI741467 | UNKNOWN | 19 | 88 | A |
| AI741486 | UNKNOWN | 20 | 0 | T |
| AI741501 | UNKNOWN | 21 | 0 | T |
| AI741503 | UNKNOWN | 15 | 0 | T |
| AI741506 | UNKNOWN | 8 | 562 | TG |
| AI7A1506 | UNKNOWN | 14 | 0 | T |
| AI741513 | UNKNOWN | 15 | 0 | T |
| AI741518 | UNKNOWN | 12 | 0 | T |
| AI741524 | UNKNOWN | 13 | 82 | A |
| AI741530 | UNKNOWN | 16 | 0 | T |
| AI741535 | UNKNOWN | 21 | 0 | T |
| AI741560 | UNKNOWN | 14 | 0 | T |
| AI741561 | UNKNOWN | 29 | 0 | T |
| AI741577 | UNKNOWN | 18 | 0 | T |
| AI741593 | UNKNOWN | 28 | 0 | T |
| AI741597 | UNKNOWN | 13 | 0 | T |
| AI741627 | UNKNOWN | 44 | 0 | T |
| AI741633 | UNKNOWN | 16 | 0 | T |
| AI741639 | UNKNOWN | 20 | 304 | A |
| AI741639 | UNKNOWN | 18 | 0 | T |
| AI741655 | UNKNOWN | 20 | 0 | T |
| AI741684 | UNKNOWN | 14 | 185 | A |
| AI741711 | UNKNOWN | 15 | 0 | T |
| AI741719 | UNKNOWN | 18 | 0 | T |
| AI741723 | UNKNOWN | 19 | 0 | T |
| AI741736 | UNKNOWN | 6.5 | 251 | TA |
| AI741756 | UNKNOWN | 13 | 0 | T |
| AI741838 | UNKNOWN | 28 | 0 | T |
| AI741843 | UNKNOWN | 17 | 0 | T |
| AI741889 | UNKNOWN | 13 | 0 | T |
| AI741905 | UNKNOWN | 13 | 0 | T |
| AI741907 | UNKNOWN | 13 | 0 | T |
| AI741934 | UNKNOWN | 15 | 0 | T |
| AI741947 | UNKNOWN | 24 | 0 | T |
| AI742003 | UNKNOWN | 15 | 0 | T |
| AI742026 | UNKNOWN | 53 | 23 | T |
| AI742026 | UNKNOWN | 21 | 0 | T |
| AI742068 | UNKNOWN | 57 | 0 | T |
| AI742068 | UNKNOWN | 24 | 430 | C |
| AI742068 | UNKNOWN | 17 | 150 | A |
| AI742068 | UNKNOWN | 13 | 382 | G |
| AI742068 | UNKNOWN | 12 | 78 | G |
| AI742071 | UNKNOWN | 12 | 0 | T |
| AI742077 | UNKNOWN | 21 | 0 | T |

TABLE 1-continued

| Genbank # | Region | # reps | Position | Unit sequence |
|---|---|---|---|---|
| AI742088 | UNKNOWN | 15 | 0 | T |
| AI742111 | UNKNOWN | 25 | 0 | T |
| AI742142 | UNKNOWN | 6.75 | 91 | AAAC |
| AI742160 | UNKNOWN | 36 | 0 | T |
| AI742200 | UNKNOWN | 7 | 473 | CA |
| AI742206 | UNKNOWN | 17 | 392 | A |
| AI742206 | UNKNOWN | 15 | 0 | T |
| AI742251 | UNKNOWN | 3.09 | 65 | TCTTTCTTTCT (SEQ ID NO: 144) |
| AI742251 | UNKNOWN | 11.75 | 0 | CTTT |
| AI742278 | UNKNOWN | 29 | 6 | T |
| AI742294 | UNKNOWN | 17 | 0 | T |
| AI742328 | UNKNOWN | 14 | 0 | T |
| AI742332 | UNKNOWN | 82 | 0 | T |
| AI742332 | UNKNOWN | 16 | 192 | G |
| AI742332 | UNKNOWN | 15 | 145 | C |
| AI742332 | UNKNOWN | 14 | 214 | A |
| AI742336 | UNKNOWN | 20 | 151 | A |
| AI742336 | UNKNOWN | 18 | 57 | C |
| AI742336 | UNKNOWN | 15 | 86 | A |
| AI742336 | UNKNOWN | 14 | 19 | G |
| AI742336 | UNKNOWN | 13 | 6 | A |
| AI742356 | UNKNOWN | 12 | 0 | T |
| AI742358 | UNKNOWN | 7 | 537 | TA |
| AI742358 | UNKNOWN | 6.5 | 448 | TG |
| AI742397 | UNKNOWN | 47 | 0 | T |
| AI742397 | UNKNOWN | 14 | 71 | A |
| AI742418 | UNKNOWN | 20 | 238 | A |
| AI742418 | UNKNOWN | 16 | 0 | T |
| AI742427 | UNKNOWN | 7.5 | 63 | AT |
| AI742434 | UNKNOWN | 13 | 30 | T |
| AI742499 | UNKNOWN | 16 | 0 | T |
| AI742517 | UNKNOWN | 28 | 0 | T |
| AI742529 | UNKNOWN | 18 | 0 | T |
| AI742543 | UNKNOWN | 35 | 0 | T |
| AI742572 | UNKNOWN | 16 | 0 | T |
| AI742601 | UNKNOWN | 6.5 | 257 | CA |
| AI742601 | UNKNOWN | 28 | 0 | T |
| AI742629 | UNKNOWN | 3.66 | 350 | TTTTGT |
| AI742629 | UNKNOWN | 4 | 339 | GTTTT |
| AI742629 | UNKNOWN | 21 | 0 | T |
| AI742633 | UNKNOWN | 10.5 | 371 | AT |
| AI742633 | UNKNOWN | 15 | 0 | T |
| AI742636 | UNKNOWN | 17 | 0 | T |
| AI742655 | UNKNOWN | 12 | 0 | T |
| AI742681 | UNKNOWN | 14 | 50 | A |
| AI742685 | UNKNOWN | 29 | 0 | T |
| AI742691 | UNKNOWN | 34 | 0 | T |
| AI742694 | UNKNOWN | 12 | 8 | T |
| AI742712 | UNKNOWN | 16 | 0 | T |
| AI742713 | UNKNOWN | 24 | 0 | T |
| AI742722 | UNKNOWN | 6 | 25 | AAT |
| AI742728 | UNKNOWN | 52 | 0 | T |
| AI742728 | UNKNOWN | 16 | 133 | G |
| AI742737 | UNKNOWN | 13 | 0 | T |
| AI742738 | UNKNOWN | 16 | 0 | T |
| AI742744 | UNKNOWN | 23 | 2 | T |
| AI742796 | UNKNOWN | 22 | 0 | T |
| AI742815 | UNKNOWN | 21 | 0 | T |
| AI742850 | UNKNOWN | 14 | 0 | T |
| AI742858 | UNKNOWN | 14 | 0 | T |
| AI742878 | UNKNOWN | 17 | 0 | T |
| AI742894 | UNKNOWN | 19 | 0 | T |
| AI742927 | UNKNOWN | 12 | 0 | T |
| AI742931 | UNKNOWN | 13 | 476 | G |
| AI742944 | UNKNOWN | 30 | 0 | T |
| AI743012 | UNKNOWN | 12 | 0 | T |
| AI743079 | UNKNOWN | 5 | 218 | GTTTTT |
| AI743105 | UNKNOWN | 13 | 0 | T |
| AI743199 | UNKNOWN | 14 | 0 | T |
| AI743222 | UNKNOWN | 15 | 0 | T |
| AI743253 | UNKNOWN | 31 | 0 | T |
| AI743303 | UNKNOWN | 10.5 | 165 | TC |
| AI743303 | UNKNOWN | 19 | 4 | T |
| AI743312 | UNKNOWN | 14 | 0 | T |
| AI743315 | UNKNOWN | 12 | 45 | T |
| AI743347 | UNKNOWN | 37 | 0 | T |
| AI743362 | UNKNOWN | 50 | 0 | T |

TABLE 1-continued

| Genbank # | Region | # reps | Position | Unit sequence |
|---|---|---|---|---|
| AI743362 | UNKNOWN | 14 | 75 | A |
| AI743362 | UNKNOWN | 13 | 143 | C |
| AI743381 | UNKNOWN | 16 | 0 | T |
| AI743447 | UNKNOWN | 40 | 0 | T |
| AI743482 | UNKNOWN | 14 | 245 | T |
| AI743486 | UNKNOWN | 30 | 0 | T |
| AI743505 | UNKNOWN | 51 | 0 | T |
| AI743527 | UNKNOWN | 4.75 | 10 | TTTA |
| AI743560 | UNKNOWN | 32 | 0 | T |
| AI743574 | UNKNOWN | 33 | 0 | T |
| AI743575 | UNKNOWN | 12 | 74 | T |
| AI743592 | UNKNOWN | 5.66 | 315 | TTG |
| AI743599 | UNKNOWN | 13 | 111 | T |
| AI743613 | UNKNOWN | 2.8 | 282 | AGGGAGAGCAGAGGGGGTGCACTGGAGTGCCAACGGAGG GCTAGAC (SEQ ID NO: 145) |
| AI743651 | UNKNOWN | 16 | 0 | T |
| AI743689 | UNKNOWN | 8.5 | 357 | TA |
| AI743717 | UNKNOWN | 15 | 473 | A |
| AI743719 | UNKNOWN | 42 | 0 | T |
| AI743719 | UNKNOWN | 23 | 187 | G |
| AI743754 | UNKNOWN | 32 | 0 | T |
| AI743754 | UNKNOWN | 12 | 142 | A |
| AI743805 | UNKNOWN | 26 | 21 | T |
| AI743805 | UNKNOWN | 20 | 0 | T |
| AI743837 | UNKNOWN | 18 | 0 | T |
| AI743845 | UNKNOWN | 13 | 475 | A |
| AI743847 | UNKNOWN | 18 | 0 | T |
| AI743863 | UNKNOWN | 8.5 | 375 | AT |
| AI743879 | UNKNOWN | 30 | 0 | T |
| AI743937 | UNKNOWN | 19 | 1 | T |
| AI743947 | UNKNOWN | 12 | 0 | T |
| AI743989 | UNKNOWN | 18 | 4 | T |
| AI743990 | UNKNOWN | 24 | 0 | T |
| AI744009 | UNKNOWN | 25 | 0 | T |
| AI744152 | UNKNOWN | 42 | 0 | T |
| AI744168 | UNKNOWN | 104 | 0 | T |
| AI744168 | UNKNOWN | 12 | 299 | C |
| AI744168 | UNKNOWN | 12 | 311 | A |
| AI744173 | UNKNOWN | 93 | 0 | T |
| AI744173 | UNKNOWN | 12 | 330 | G |
| AI744175 | UNKNOWN | 16 | 0 | T |
| AI744181 | UNKNOWN | 76 | 0 | T |
| AI744181 | UNKNOWN | 16 | 154 | G |
| AI744185 | UNKNOWN | 78 | 0 | T |
| AI744185 | UNKNOWN | 16 | 92 | G |
| AI744185 | UNKNOWN | 14 | 170 | C |
| AI744204 | UNKNOWN | 53 | 0 | T |
| AI744204 | UNKNOWN | 13 | 121 | A |
| AI744234 | UNKNOWN | 41 | 0 | T |
| AI744234 | UNKNOWN | 12 | 219 | A |
| AI744238 | UNKNOWN | 44 | 0 | T |
| AI744243 | UNKNOWN | 61 | 0 | T |
| AI744243 | UNKNOWN | 18 | 88 | A |
| AI744256 | UNKNOWN | 87 | 0 | T |
| AI744256 | UNKNOWN | 14 | 119 | A |
| AI744256 | UNKNOWN | 14 | 382 | G |
| AI744268 | UNKNOWN | 51 | 0 | T |
| AI744279 | UNKNOWN | 72 | 0 | T |
| AI744322 | UNKNOWN | 61 | 0 | T |
| AI744322 | UNKNOWN | 13 | 240 | G |
| AI744330 | UNKNOWN | 105 | 0 | T |
| AI744330 | UNKNOWN | 17 | 350 | C |
| AI744330 | UNKNOWN | 15 | 173 | C |
| AI744330 | UNKNOWN | 13 | 275 | G |
| AI744330 | UNKNOWN | 12 | 322 | A |
| AI744335 | UNKNOWN | 21 | 0 | T |
| AI744348 | UNKNOWN | 20 | 0 | T |
| AI744402 | UNKNOWN | 35 | 0 | T |
| AI744405 | UNKNOWN | 4.8 | 246 | TTCAT |
| AI744421 | UNKNOWN | 26 | 0 | T |
| AI744485 | UNKNOWN | 61 | 0 | T |
| AI744485 | UNKNOWN | 19 | 162 | G |
| AI744485 | UNKNOWN | 13 | 363 | C |
| AI744512 | UNKNOWN | 9 | 468 | AGA |
| AI744524 | UNKNOWN | 16 | 157 | A |
| AI744525 | UNKNOWN | 84 | 0 | T |
| AI744525 | UNKNOWN | 20 | 94 | A |

TABLE 1-continued

| Genbank # | Region | # reps | Position | Unit sequence |
|---|---|---|---|---|
| AI744534 | UNKNOWN | 3.5 | 19 | AAAACA |
| AI744541 | UNKNOWN | 24 | 0 | T |
| AI744543 | UNKNOWN | 15 | 140 | A |
| AI744546 | UNKNOWN | 7 | 129 | TTG |
| AI744567 | UNKNOWN | 20 | 0 | T |
| AI744575 | UNKNOWN | 15 | 0 | T |
| AI744592 | UNKNOWN | 23 | 2 | T |
| AI744597 | UNKNOWN | 15 | 0 | T |
| AI744600 | UNKNOWN | 20 | 0 | T |
| AI744607 | UNKNOWN | 16 | 0 | T |
| AI744609 | UNKNOWN | 28 | 0 | T |
| AI744618 | UNKNOWN | 24 | 0 | T |
| AI744691 | UNKNOWN | 18 | 4 | T |
| AI744704 | UNKNOWN | 19 | 4 | T |
| AI744711 | UNKNOWN | 12 | 0 | T |
| AI744726 | UNKNOWN | 12 | 89 | A |
| AI744728 | UNKNOWN | 17 | 11 | T |
| AI744768 | UNKNOWN | 84 | 0 | T |
| AI744817 | UNKNOWN | 18 | 308 | T |
| AI744861 | UNKNOWN | 16 | 0 | T |
| AI744923 | UNKNOWN | 104 | 0 | T |
| AI744923 | UNKNOWN | 20 | 135 | G |
| AI744923 | UNKNOWN | 19 | 113 | C |
| AI744935 | UNKNOWN | 23 | 0 | T |
| AI744946 | UNKNOWN | 28 | 0 | T |
| AI744958 | UNKNOWN | 51 | 0 | T |
| AI744979 | UNKNOWN | 12 | 0 | T |
| AI744985 | UNKNOWN | 70 | 0 | T |
| AI744985 | UNKNOWN | 20 | 281 | A |
| AI744985 | UNKNOWN | 12 | 339 | G |
| AI744988 | UNKNOWN | 71 | 0 | T |
| AI745049 | UNKNOWN | 71 | 0 | T |
| AI745067 | UNKNOWN | 23 | 0 | T |
| AI745076 | UNKNOWN | 44 | 0 | T |
| AI745092 | UNKNOWN | 14 | 0 | T |
| AI745131 | UNKNOWN | 6.75 | 7 | TTAT |
| AI745131 | UNKNOWN | 22 | 330 | T |
| AI745189 | UNKNOWN | 37 | 0 | T |
| AI745197 | UNKNOWN | 17 | 0 | T |
| AI745199 | UNKNOWN | 12 | 0 | T |
| AI745209 | UNKNOWN | 10.5 | 232 | AC |
| AI745209 | UNKNOWN | 14 | 0 | T |
| AI745249 | UNKNOWN | 30 | 10 | T |
| AI745316 | UNKNOWN | 54 | 0 | T |
| AI745325 | UNKNOWN | 13 | 0 | T |
| AI745329 | UNKNOWN | 56 | 0 | T |
| AI745359 | UNKNOWN | 41 | 0 | T |
| AI745409 | UNKNOWN | 17 | 0 | T |
| AI745433 | UNKNOWN | 24 | 0 | T |
| AI745447 | UNKNOWN | 31 | 0 | T |
| AI745485 | UNKNOWN | 118 | 0 | T |
| AI745485 | UNKNOWN | 15 | 259 | C |
| AI745490 | UNKNOWN | 16 | 0 | T |
| AI745505 | UNKNOWN | 25.5 | 322 | TA |
| AI745505 | UNKNOWN | 21 | 176 | T |
| AI745524 | UNKNOWN | 35 | 0 | T |
| AI745527 | UNKNOWN | 16 | 0 | T |
| AI745595 | UNKNOWN | 17 | 0 | T |
| AI745646 | UNKNOWN | 66 | 0 | T |
| AI745656 | UNKNOWN | 87 | 0 | T |
| AI745656 | UNKNOWN | 28 | 365 | C |
| AI745656 | UNKNOWN | 12 | 307 | G |
| AI745659 | UNKNOWN | 26 | 0 | T |
| AI745684 | UNKNOWN | 80 | 0 | T |
| AI745684 | UNKNOWN | 12 | 84 | A |
| AI745684 | UNKNOWN | 12 | 403 | G |
| AI745713 | UNKNOWN | 105 | 0 | T |
| AI745713 | UNKNOWN | 14 | 128 | A |
| AI745713 | UNKNOWN | 12 | 178 | C |
| AI749231 | UNKNOWN | 41 | 0 | T |
| AI749373 | UNKNOWN | 55 | 25 | T |
| AI749373 | UNKNOWN | 21 | 0 | T |
| AI749373 | UNKNOWN | 13 | 214 | G |
| AI749444 | UNKNOWN | 16 | 0 | T |
| AI749623 | UNKNOWN | 16 | 14 | T |
| AI749642 | UNKNOWN | 17 | 0 | T |
| AI749855 | UNKNOWN | 14 | 0 | T |

TABLE 1-continued

| Genbank # | Region | # reps | Position | Unit sequence |
|---|---|---|---|---|
| AI750068 | UNKNOWN | 36 | 0 | T |
| AI750178 | UNKNOWN | 9 | 447 | TAA |
| AI750178 | UNKNOWN | 8.5 | 229 | AG |
| AI750927 | UNKNOWN | 12 | 351 | A |
| AI751060 | UNKNOWN | 12 | 239 | A |
| AI751725 | UNKNOWN | 30 | 8 | T |
| AI752485 | UNKNOWN | 12 | 726 | C |
| AI752834 | UNKNOWN | 22 | 0 | T |
| AI752861 | UNKNOWN | 18 | 0 | T |
| AI753091 | UNKNOWN | 21 | 0 | T |
| AI753092 | UNKNOWN | 18 | 0 | T |
| AI753104 | UNKNOWN | 18 | 0 | T |
| AI753158 | UNKNOWN | 19 | 0 | T |
| AI753241 | UNKNOWN | 19 | 0 | T |
| AI753291 | UNKNOWN | 19 | 0 | T |
| AI753316 | UNKNOWN | 20 | 0 | T |
| AI753390 | UNKNOWN | 19 | 0 | T |
| AI753474 | UNKNOWN | 28 | 0 | T |
| AI753474 | UNKNOWN | 17 | 483 | A |
| AI753488 | UNKNOWN | 18 | 0 | T |
| AI753525 | UNKNOWN | 18 | 0 | T |
| AI753538 | UNKNOWN | 18 | 0 | T |
| AI753557 | UNKNOWN | 19 | 0 | T |
| AI753655 | UNKNOWN | 38 | 0 | T |
| AI753683 | UNKNOWN | 109 | 24 | T |
| AI753683 | UNKNOWN | 22 | 0 | T |
| AI753725 | UNKNOWN | 22 | 0 | T |
| AI753726 | UNKNOWN | 18 | 0 | T |
| AI753729 | UNKNOWN | 18 | 0 | T |
| AI753732 | UNKNOWN | 18 | 0 | T |
| AI753969 | UNKNOWN | 21 | 0 | T |
| AI753988 | UNKNOWN | 19 | 0 | T |
| AI754032 | UNKNOWN | 19 | 0 | T |
| AI754064 | UNKNOWN | 19 | 0 | T |
| AI754075 | UNKNOWN | 19 | 0 | T |
| AI754086 | UNKNOWN | 28 | 0 | T |
| AI754092 | UNKNOWN | 18 | 0 | T |
| AI754163 | UNKNOWN | 28 | 0 | T |
| AI754246 | UNKNOWN | 18 | 0 | T |
| AI754296 | UNKNOWN | 20 | 0 | T |
| AI754397 | UNKNOWN | 18 | 0 | T |
| AI754502 | UNKNOWN | 19 | 0 | T |
| AI754534 | UNKNOWN | 32 | 0 | T |
| AI754605 | UNKNOWN | 18 | 0 | T |
| AI754625 | UNKNOWN | 19 | 0 | T |
| AI754629 | UNKNOWN | 18 | 0 | T |
| AI754641 | UNKNOWN | 21 | 0 | T |
| AI754652 | UNKNOWN | 22 | 0 | T |
| AI754675 | UNKNOWN | 18 | 0 | T |
| AI754692 | UNKNOWN | 20 | 0 | T |
| AI754693 | UNKNOWN | 18 | 0 | T |
| AI754693 | UNKNOWN | 14 | 93 | A |
| AI754701 | UNKNOWN | 22 | 0 | T |
| AI754722 | UNKNOWN | 18 | 0 | T |
| AI754756 | UNKNOWN | 18 | 0 | T |
| AI754789 | UNKNOWN | 21 | 0 | T |
| AI754827 | UNKNOWN | 26 | 0 | T |
| AI754838 | UNKNOWN | 18 | 0 | T |
| AI754862 | UNKNOWN | 28 | 0 | T |
| AI754871 | UNKNOWN | 28 | 0 | T |
| AI754897 | UNKNOWN | 119 | 0 | T |
| AI754944 | UNKNOWN | 19 | 0 | T |
| AI755014 | UNKNOWN | 23 | 0 | T |
| AI755014 | UNKNOWN | 15 | 204 | A |
| AI755024 | UNKNOWN | 9 | 474 | GT |
| AI755024 | UNKNOWN | 21 | 0 | T |
| AI755069 | UNKNOWN | 17 | 0 | T |
| AI755079 | UNKNOWN | 21 | 0 | T |
| AI755153 | UNKNOWN | 18 | 0 | T |
| AI755224 | UNKNOWN | 18 | 0 | T |
| AI755245 | UNKNOWN | 18 | 0 | T |
| AI758270 | UNKNOWN | 56 | 0 | T |
| AI758270 | UNKNOWN | 19 | 135 | A |
| AI758272 | UNKNOWN | 77 | 0 | T |
| AI758272 | UNKNOWN | 16 | 217 | A |
| AI758272 | UNKNOWN | 15 | 188 | G |
| AI758272 | UNKNOWN | 12 | 173 | C |

TABLE 1-continued

| Genbank # | Region | # reps | Position | Unit sequence |
|---|---|---|---|---|
| AI758290 | UNKNOWN | 29 | 0 | T |
| AI758295 | UNKNOWN | 70 | 0 | T |
| AI758295 | UNKNOWN | 14 | 221 | A |
| AI758437 | UNKNOWN | 122 | 0 | T |
| AI758445 | UNKNOWN | 52 | 0 | T |
| AI758473 | UNKNOWN | 6.5 | 290 | AG |
| AI758473 | UNKNOWN | 13 | 275 | A |
| AI758512 | UNKNOWN | 92 | 0 | T |
| AI758512 | UNKNOWN | 19 | 212 | A |
| AI758512 | UNKNOWN | 14 | 162 | A |
| AI758528 | UNKNOWN | 65 | 0 | T |
| AI758538 | UNKNOWN | 45 | 0 | T |
| AI758538 | UNKNOWN | 16 | 115 | G |
| AI758569 | UNKNOWN | 56 | 0 | T |
| AI758583 | UNKNOWN | 83 | 0 | T |
| AI758583 | UNKNOWN | 17 | 253 | C |
| AI758583 | UNKNOWN | 16 | 138 | G |
| AI758583 | UNKNOWN | 15 | 228 | A |
| AI758583 | UNKNOWN | 12 | 90 | A |
| AI758613 | UNKNOWN | 78 | 0 | T |
| AI758613 | UNKNOWN | 15 | 124 | G |
| AI758613 | UNKNOWN | 12 | 164 | A |
| AI758674 | UNKNOWN | 65 | 0 | T |
| AI758694 | UNKNOWN | 50 | 0 | T |
| AI758702 | UNKNOWN | 45 | 0 | T |
| AI758706 | UNKNOWN | 42 | 0 | T |
| AI758721 | UNKNOWN | 42 | 0 | T |
| AI758727 | UNKNOWN | 39 | 0 | T |
| AI758735 | UNKNOWN | 86 | 0 | T |
| AI758735 | UNKNOWN | 12 | 110 | G |
| AI758735 | UNKNOWN | 12 | 223 | A |
| AI758748 | UNKNOWN | 66 | 0 | T |
| AI758812 | UNKNOWN | 76 | 0 | T |
| AI758812 | UNKNOWN | 13 | 205 | A |
| AI758816 | UNKNOWN | 88 | 0 | T |
| AI758816 | UNKNOWN | 16 | 271 | C |
| AI758816 | UNKNOWN | 13 | 322 | G |
| AI758901 | UNKNOWN | 12 | 0 | T |
| AI758919 | UNKNOWN | 13 | 123 | A |
| AI758924 | UNKNOWN | 60 | 0 | T |
| AI758932 | UNKNOWN | 41 | 0 | T |
| AI758937 | UNKNOWN | 12 | 481 | T |
| AI758942 | UNKNOWN | 92 | 0 | T |
| AI758957 | UNKNOWN | 55 | 0 | T |
| AI758957 | UNKNOWN | 22 | 286 | A |
| AI758977 | UNKNOWN | 32 | 0 | T |
| AI758988 | UNKNOWN | 58 | 0 | T |
| AI759003 | UNKNOWN | 53 | 0 | T |
| AI759003 | UNKNOWN | 12 | 173 | A |
| AI760018 | UNKNOWN | 18.5 | 474 | AT |
| AI760018 | UNKNOWN | 8 | 376 | AC |
| AI760018 | UNKNOWN | 6.5 | 361 | AT |
| AI760020 | UNKNOWN | 3.5 | 188 | GCCAGG |
| AI760026 | UNKNOWN | 15 | 0 | T |
| AI760121 | UNKNOWN | 5.66 | 220 | TTG |
| AI760121 | UNKNOWN | 19 | 0 | T |
| AI760137 | UNKNOWN | 16 | 276 | T |
| AI760170 | UNKNOWN | 12 | 0 | T |
| AI760198 | UNKNOWN | 12 | 0 | T |
| AI760202 | UNKNOWN | 15 | 0 | T |
| AI760277 | UNKNOWN | 12 | 0 | T |
| AI760319 | UNKNOWN | 9 | 30 | GA |
| AI760319 | UNKNOWN | 6.5 | 463 | TA |
| AI760370 | UNKNOWN | 14 | 168 | T |
| AI760374 | UNKNOWN | 45 | 0 | T |
| AI760380 | UNKNOWN | 4.75 | 7 | TTTA |
| AI760416 | UNKNOWN | 16 | 6 | T |
| AI760427 | UNKNOWN | 23 | 0 | T |
| AI760435 | UNKNOWN | 72 | 0 | T |
| AI760435 | UNKNOWN | 15 | 300 | G |
| AI760508 | UNKNOWN | 8.5 | 190 | TG |
| AI760508 | UNKNOWN | 18 | 0 | T |
| AI760531 | UNKNOWN | 16 | 260 | A |
| AI760531 | UNKNOWN | 14 | 147 | T |
| AI760534 | UNKNOWN | 24 | 0 | T |
| AI760618 | UNKNOWN | 37 | 0 | T |
| AI760640 | UNKNOWN | 46 | 0 | T |

TABLE 1-continued

| Genbank # | Region | # reps | Position | Unit sequence |
|---|---|---|---|---|
| AI760640 | UNKNOWN | 13 | 139 | A |
| AI760655 | UNKNOWN | 27 | 0 | T |
| AI760667 | UNKNOWN | 16 | 0 | T |
| AI760674 | UNKNOWN | 45 | 0 | T |
| AI760770 | UNKNOWN | 15 | 0 | T |
| AI760827 | UNKNOWN | 13 | 0 | T |
| AI760835 | UNKNOWN | 14 | 0 | T |
| AI760991 | UNKNOWN | 55 | 0 | T |
| AI761029 | UNKNOWN | 67 | 0 | T |
| AI761029 | UNKNOWN | 13 | 409 | G |
| AI761029 | UNKNOWN | 12 | 311 | C |
| AI761064 | UNKNOWN | 13 | 80 | A |
| AI761065 | UNKNOWN | 14 | 3 | T |
| AI761092 | UNKNOWN | 15 | 246 | T |
| AI761130 | UNKNOWN | 12 | 179 | G |
| AI761164 | UNKNOWN | 3.5 | 192 | GGCAGC |
| AI761446 | UNKNOWN | 41 | 0 | T |
| AI761467 | UNKNOWN | 8.5 | 243 | AG |
| AI761468 | UNKNOWN | 62 | 0 | T |
| AI761545 | UNKNOWN | 41 | 0 | T |
| AI761553 | UNKNOWN | 8.66 | 420 | AAT |
| AI761622 | UNKNOWN | 12 | 0 | T |
| AI761623 | UNKNOWN | 7 | 213 | AC |
| AI761623 | UNKNOWN | 13 | 0 | T |
| AI761639 | UNKNOWN | 6.5 | 658 | TG |
| AI761656 | UNKNOWN | 11.33 | 10 | TTA |
| AI761694 | UNKNOWN | 13 | 242 | A |
| AI761703 | UNKNOWN | 16 | 0 | T |
| AI761708 | UNKNOWN | 24 | 0 | T |
| AI761715 | UNKNOWN | 24 | 0 | T |
| AI761740 | UNKNOWN | 17 | 0 | T |
| AI761745 | UNKNOWN | 21 | 0 | T |
| AI761804 | UNKNOWN | 7 | 196 | GT |
| AI761836 | UNKNOWN | 17 | 0 | T |
| AI761853 | UNKNOWN | 15 | 133 | T |
| AI761853 | UNKNOWN | 12 | 0 | T |
| AI761862 | UNKNOWN | 3.6 | 178 | TTTTG |
| AI761900 | UNKNOWN | 19 | 0 | T |
| AI761923 | UNKNOWN | 12 | 0 | T |
| AI761934 | UNKNOWN | 18 | 1 | T |
| AI761948 | UNKNOWN | 14 | 0 | T |
| AI761987 | UNKNOWN | 10 | 403 | TC |
| AI762019 | UNKNOWN | 15 | 106 | T |
| AI762023 | UNKNOWN | 4.75 | 195 | AAAC |
| AI762031 | UNKNOWN | 11 | 312 | AC |
| AI762035 | UNKNOWN | 17 | 0 | T |
| AI762144 | UNKNOWN | 19 | 4 | T |
| AI762152 | UNKNOWN | 18 | 4 | T |
| AI762317 | UNKNOWN | 14 | 357 | A |
| AI762334 | UNKNOWN | 13 | 428 | T |
| AI762372 | UNKNOWN | 21 | 0 | T |
| AI762422 | UNKNOWN | 30 | 0 | T |
| AI762477 | UNKNOWN | 19 | 58 | A |
| AI762495 | UNKNOWN | 18 | 9 | T |
| AI762535 | UNKNOWN | 26 | 0 | T |
| AI762557 | UNKNOWN | 16 | 114 | A |
| AI762568 | UNKNOWN | 17 | 148 | T |
| AI762617 | UNKNOWN | 15 | 0 | T |
| AI762636 | UNKNOWN | 32 | 0 | T |
| AI762707 | UNKNOWN | 53 | 0 | T |
| AI762707 | UNKNOWN | 13 | 199 | A |
| AI762719 | UNKNOWN | 58 | 0 | T |
| AI762737 | UNKNOWN | 27 | 226 | T |
| AI762739 | UNKNOWN | 84 | 0 | T |
| AI762856 | UNKNOWN | 19 | 255 | GT |
| AI762890 | UNKNOWN | 16 | 18 | T |
| AI762899 | UNKNOWN | 24 | 0 | T |
| AI762905 | UNKNOWN | 6.66 | 354 | GCG |
| AI762918 | UNKNOWN | 12 | 0 | T |
| AI762929 | UNKNOWN | 6 | 147 | GGC |
| AI762931 | UNKNOWN | 43 | 0 | T |
| AI762955 | UNKNOWN | 22 | 0 | T |
| AI762955 | UNKNOWN | 14 | 304 | A |
| AI763037 | UNKNOWN | 31 | 0 | T |
| AI763051 | UNKNOWN | 12 | 0 | T |
| AI763135 | UNKNOWN | 16 | 0 | T |
| AI763151 | UNKNOWN | 18 | 0 | T |

TABLE 1-continued

| Genbank # | Region | # reps | Position | Unit sequence |
|---|---|---|---|---|
| AI763152 | UNKNOWN | 19 | 0 | T |
| AI763163 | UNKNOWN | 22 | 105 | T |
| AI763163 | UNKNOWN | 15 | 0 | T |
| AI763163 | UNKNOWN | 13 | 220 | A |
| AI763176 | UNKNOWN | 15 | 0 | T |
| AI763187 | UNKNOWN | 15 | 0 | T |
| AI763188 | UNKNOWN | 15 | 0 | T |
| AI763194 | UNKNOWN | 16 | 0 | T |
| AI763195 | UNKNOWN | 15 | 0 | T |
| AI763278 | UNKNOWN | 34 | 0 | T |
| AI763282 | UNKNOWN | 3.6 | 107 | AAAAC |
| AI763282 | UNKNOWN | 19 | 4 | T |
| AI763300 | UNKNOWN | 20 | 4 | T |
| AI763325 | UNKNOWN | 12 | 0 | T |
| AI763344 | UNKNOWN | 15 | 0 | T |
| AI763366 | UNKNOWN | 13 | 0 | T |
| AI763414 | UNKNOWN | 62 | 0 | T |
| AI764986 | UNKNOWN | 17 | 0 | T |
| AI765027 | UNKNOWN | 14 | 319 | A |
| AI765050 | UNKNOWN | 2.5 | 198 | CATTAGGACA (SEQ ID NO: 146) |
| AI765082 | UNKNOWN | 26 | 0 | T |
| AI765087 | UNKNOWN | 12 | 0 | T |
| AI765103 | UNKNOWN | 46 | 0 | T |
| AI765121 | UNKNOWN | 3.57 | 324 | AAAAAAC |
| AI765121 | UNKNOWN | 22 | 18 | T |
| AI765121 | UNKNOWN | 16 | 0 | T |
| AI765121 | UNKNOWN | 13 | 317 | A |
| AI765125 | UNKNOWN | 18 | 4 | T |
| AI765134 | UNKNOWN | 18 | 0 | T |
| AI765180 | UNKNOWN | 8.5 | 247 | AC |
| AI765208 | UNKNOWN | 15 | 0 | T |
| AI765244 | UNKNOWN | 42 | 5 | T |
| AI765258 | UNKNOWN | 37 | 0 | T |
| AI765265 | UNKNOWN | 12 | 301 | A |
| AI765323 | UNKNOWN | 86 | 0 | T |
| AI765383 | UNKNOWN | 31 | 0 | T |
| AI765449 | UNKNOWN | 48 | 0 | T |
| AI765460 | UNKNOWN | 8.5 | 179 | TG |
| AI765469 | UNKNOWN | 75 | 0 | T |
| AI765469 | UNKNOWN | 13 | 241 | C |
| AI765537 | UNKNOWN | 26 | 0 | T |
| AI765553 | UNKNOWN | 21 | 0 | T |
| AI765602 | UNKNOWN | 12 | 71 | A |
| AI765621 | UNKNOWN | 15 | 0 | T |
| AI765698 | UNKNOWN | 19 | 0 | T |
| AI765761 | UNKNOWN | 14 | 0 | T |
| AI765793 | UNKNOWN | 4.8 | 104 | TTTTC |
| AI765793 | UNKNOWN | 13 | 124 | T |
| AI765890 | UNKNOWN | 13 | 392 | T |
| AI765967 | UNKNOWN | 17 | 294 | A |
| AI765984 | UNKNOWN | 16 | 0 | T |
| AI765991 | UNKNOWN | 16 | 0 | T |
| AI766017 | UNKNOWN | 5.66 | 439 | GGC |
| AI766086 | UNKNOWN | 3.5 | 293 | TATTAA |
| AI766086 | UNKNOWN | 15 | 89 | T |
| AI766172 | UNKNOWN | 25 | 0 | T |
| AI766244 | UNKNOWN | 19 | 0 | T |
| AI766260 | UNKNOWN | 12 | 26 | T |
| AI766273 | UNKNOWN | 6.5 | 201 | TC |
| AI766348 | UNKNOWN | 54 | 20 | T |
| AI766348 | UNKNOWN | 19 | 0 | T |
| AI766348 | UNKNOWN | 12 | 151 | G |
| AI766416 | UNKNOWN | 7.5 | 427 | AT |
| AI766478 | UNKNOWN | 18 | 291 | A |
| AI766478 | UNKNOWN | 17 | 190 | A |
| AI766656 | UNKNOWN | 49 | 0 | T |
| AI766663 | UNKNOWN | 31 | 0 | T |
| AI766706 | UNKNOWN | 16 | 0 | T |
| AI766867 | UNKNOWN | 4 | 239 | AAAAG |
| AI766867 | UNKNOWN | 26 | 0 | T |
| AI766980 | UNKNOWN | 94 | 0 | T |
| AI766980 | UNKNOWN | 21 | 111 | G |
| AI766980 | UNKNOWN | 14 | 282 | C |
| AI766980 | UNKNOWN | 12 | 145 | C |
| AI767003 | UNKNOWN | 55 | 0 | T |
| AI767003 | UNKNOWN | 13 | 76 | A |
| AI767003 | UNKNOWN | 12 | 201 | C |

TABLE 1-continued

| Genbank # | Region | # reps | Position | Unit sequence |
|---|---|---|---|---|
| AI767338 | UNKNOWN | 42 | 0 | T |
| AI767343 | UNKNOWN | 18 | 0 | T |
| AI767388 | UNKNOWN | 19 | 0 | T |
| AI767394 | UNKNOWN | 30 | 0 | T |
| AI767394 | UNKNOWN | 16 | 225 | A |
| AI767472 | UNKNOWN | 5.25 | 341 | AAAC |
| AI767542 | UNKNOWN | 17 | 0 | T |
| AI767557 | UNKNOWN | 14.66 | 285 | AAC |
| AI767564 | UNKNOWN | 15 | 52 | A |
| AI767597 | UNKNOWN | 19 | 135 | T |
| AI767698 | UNKNOWN | 16 | 0 | T |
| AI767709 | UNKNOWN | 16 | 0 | T |
| AI767725 | UNKNOWN | 12 | 0 | T |
| AI767756 | UNKNOWN | 27 | 0 | T |
| AI767799 | UNKNOWN | 38 | 0 | T |
| AI767808 | UNKNOWN | 21 | 92 | A |
| AI767825 | UNKNOWN | 43 | 0 | T |
| AI767825 | UNKNOWN | 14 | 107 | C |
| AI767862 | UNKNOWN | 18 | 0 | T |
| AI767965 | UNKNOWN | 55 | 0 | T |
| AI768079 | UNKNOWN | 14 | 10 | T |
| AI768085 | UNKNOWN | 18 | 14 | T |
| AI768092 | UNKNOWN | 19 | 0 | T |
| AI768096 | UNKNOWN | 23 | 268 | A |
| AI768123 | UNKNOWN | 19 | 0 | T |
| AI768124 | UNKNOWN | 20 | 0 | T |
| AI768174 | UNKNOWN | 12 | 0 | T |
| AI768197 | UNKNOWN | 7 | 217 | GT |
| AI768198 | UNKNOWN | 12 | 416 | A |
| AI768405 | UNKNOWN | 7 | 32 | CAA |
| AI768440 | UNKNOWN | 15 | 0 | T |
| AI768452 | UNKNOWN | 12 | 0 | T |
| AI768466 | UNKNOWN | 32 | 0 | T |
| AI768496 | UNKNOWN | 88 | 0 | T |
| AI768496 | UNKNOWN | 14 | 135 | A |
| AI768496 | UNKNOWN | 13 | 275 | C |
| AI768529 | UNKNOWN | 22 | 0 | T |
| AI768629 | UNKNOWN | 9.5 | 45 | TG |
| AI768629 | UNKNOWN | 15 | 300 | T |
| AI768636 | UNKNOWN | 15 | 441 | T |
| AI768655 | UNKNOWN | 12 | 275 | A |
| AI768677 | UNKNOWN | 18 | 11 | T |
| AI768697 | UNKNOWN | 4 | 347 | CAAAAA |
| AI768720 | UNKNOWN | 13 | 142 | G |
| AI768804 | UNKNOWN | 18 | 0 | T |
| AI768810 | UNKNOWN | 13 | 12 | T |
| AI768858 | UNKNOWN | 15 | 463 | T |
| AI768895 | UNKNOWN | 12 | 201 | A |
| AI768974 | UNKNOWN | 29 | 0 | T |
| AI768983 | UNKNOWN | 16 | 4 | T |
| AI768997 | UNKNOWN | 40 | 0 | T |
| AI769212 | UNKNOWN | 13 | 0 | T |
| AI769281 | UNKNOWN | 18 | 0 | T |
| AI769290 | UNKNOWN | 15 | 0 | T |
| AI769293 | UNKNOWN | 42 | 0 | T |
| AI769323 | UNKNOWN | 32 | 0 | T |
| AI769331 | UNKNOWN | 15 | 0 | T |
| AI769352 | UNKNOWN | 14 | 0 | T |
| AI769387 | UNKNOWN | 35 | 0 | T |
| AI769392 | UNKNOWN | 16 | 0 | T |
| AI769422 | UNKNOWN | 12 | 70 | T |
| AI769453 | UNKNOWN | 12 | 0 | T |
| AI769466 | UNKNOWN | 29 | 0 | T |
| AI769492 | UNKNOWN | 15.25 | 13 | TCTT |
| AI769492 | UNKNOWN | 8.75 | 340 | TTTA |
| AI769492 | UNKNOWN | 8 | 0 | CT |
| AI769494 | UNKNOWN | 14 | 430 | A |
| AI769507 | UNKNOWN | 44 | 0 | T |
| AI769531 | UNKNOWN | 13 | 368 | A |
| AI769559 | UNKNOWN | 4.59 | 126 | AAGCC |
| AI769625 | UNKNOWN | 21 | 51 | A |
| AI769645 | UNKNOWN | 12 | 396 | T |
| AI769733 | UNKNOWN | 4.5 | 474 | ACACCC |
| AI769794 | UNKNOWN | 2.58 | 300 | TTAACCAGTATA (SEQ ID NO: 147) |
| AI769817 | UNKNOWN | 17 | 0 | T |
| AI769831 | UNKNOWN | 22 | 0 | T |
| AI769832 | UNKNOWN | 19 | 0 | T |

TABLE 1-continued

| Genbank # | Region | # reps | Position | Unit sequence |
|---|---|---|---|---|
| AI769869 | UNKNOWN | 12 | 263 | A |
| AI769922 | UNKNOWN | 18 | 0 | T |
| AI769947 | UNKNOWN | 16 | 0 | T |
| AI769948 | UNKNOWN | 15 | 0 | T |
| AI769954 | UNKNOWN | 15 | 0 | T |
| AI769954 | UNKNOWN | 12 | 339 | A |
| AI769960 | UNKNOWN | 17 | 0 | T |
| AI769961 | UNKNOWN | 22 | 3 | T |
| AI769965 | UNKNOWN | 16 | 0 | T |
| AI769970 | UNKNOWN | 16 | 0 | T |
| AI769979 | UNKNOWN | 4.75 | 416 | CTTG |
| AI769979 | UNKNOWN | 4.5 | 401 | TTTC |
| AI769985 | UNKNOWN | 17 | 180 | T |
| AI769989 | UNKNOWN | 53 | 0 | T |
| AI769989 | UNKNOWN | 14 | 176 | C |
| AI769991 | UNKNOWN | 5 | 527 | AAAAC |
| AI770064 | UNKNOWN | 16 | 0 | T |
| AI770108 | UNKNOWN | 22 | 0 | T |
| AI770139 | UNKNOWN | 34 | 0 | T |
| AI783493 | UNKNOWN | 40 | 0 | T |
| AI783504 | UNKNOWN | 115 | 0 | T |
| AI783504 | UNKNOWN | 17 | 170 | C |
| AI783519 | UNKNOWN | 33 | 0 | T |
| AI783530 | UNKNOWN | 75 | 0 | T |
| AI783530 | UNKNOWN | 15 | 94 | G |
| AI783535 | UNKNOWN | 42 | 0 | T |
| AI783549 | UNKNOWN | 15 | 0 | T |
| AI783569 | UNKNOWN | 52 | 0 | T |
| AI783785 | UNKNOWN | 46 | 0 | T |
| AI783792 | UNKNOWN | 98 | 0 | T |
| AI783792 | UNKNOWN | 17 | 204 | C |
| AI783792 | UNKNOWN | 13 | 151 | C |
| AI783792 | UNKNOWN | 12 | 118 | A |
| AI783792 | UNKNOWN | 12 | 241 | G |
| AI783805 | UNKNOWN | 45 | 0 | T |
| AI783808 | UNKNOWN | 63 | 0 | T |
| AI783821 | UNKNOWN | 71 | 0 | T |
| AI783821 | UNKNOWN | 14 | 211 | G |
| AI783825 | UNKNOWN | 59 | 0 | T |
| AI783838 | UNKNOWN | 42 | 0 | T |
| AI783849 | UNKNOWN | 17 | 27 | T |
| AI783861 | UNKNOWN | 81 | 0 | T |
| AI783861 | UNKNOWN | 18 | 105 | A |
| AI783861 | UNKNOWN | 18 | 165 | G |
| AI783890 | UNKNOWN | 23 | 0 | T |
| AI783939 | UNKNOWN | 20 | 0 | T |
| AI783972 | UNKNOWN | 13 | 0 | T |
| AI783997 | UNKNOWN | 78 | 0 | T |
| AI783997 | UNKNOWN | 12 | 107 | A |
| AI784041 | UNKNOWN | 23 | 0 | T |
| AI784046 | UNKNOWN | 22 | 19 | T |
| AI784071 | UNKNOWN | 14 | 162 | A |
| AI784135 | UNKNOWN | 13 | 0 | T |
| AI784166 | UNKNOWN | 25 | 0 | T |
| AI784214 | UNKNOWN | 58 | 0 | T |
| AI784214 | UNKNOWN | 17 | 98 | A |
| AI784219 | UNKNOWN | 59 | 0 | T |
| AI784219 | UNKNOWN | 12 | 159 | C |
| AI784230 | UNKNOWN | 77 | 0 | T |
| AI784230 | UNKNOWN | 18 | 171 | C |
| AI784252 | UNKNOWN | 109 | 0 | T |
| AI784252 | UNKNOWN | 14 | 189 | A |
| AI784317 | UNKNOWN | 3.66 | 98 | AAAAAG |
| AI784317 | UNKNOWN | 43 | 0 | T |
| AI784355 | UNKNOWN | 23 | 0 | T |
| AI784377 | UNKNOWN | 48 | 0 | T |
| AI784387 | UNKNOWN | 52 | 0 | T |
| AI784387 | UNKNOWN | 15 | 345 | G |
| AI784387 | UNKNOWN | 14 | 392 | A |
| AI784473 | UNKNOWN | 44 | 0 | T |
| AI784473 | UNKNOWN | 21 | 181 | A |
| AI784529 | UNKNOWN | 12 | 441 | T |
| AI784610 | UNKNOWN | 3.66 | 355 | GCTCCA |
| AI784610 | UNKNOWN | 12 | 0 | T |
| AI791123 | UNKNOWN | 12 | 0 | T |
| AI791128 | UNKNOWN | 12 | 144 | T |
| AI791134 | UNKNOWN | 26 | 79 | A |

TABLE 1-continued

| Genbank # | Region | # reps | Position | Unit sequence |
|---|---|---|---|---|
| AI791141 | UNKNOWN | 14 | 438 | A |
| AI791144 | UNKNOWN | 28 | 0 | T |
| AI791145 | UNKNOWN | 3.21 | 45 | TTTTATTTATTTAT (SEQ ID NO: 148) |
| AI791148 | UNKNOWN | 18 | 0 | T |
| AI791150 | UNKNOWN | 12 | 0 | T |
| AI791159 | UNKNOWN | 2.75 | 164 | ACACATATATAT (SEQ ID NO: 149) |
| AI791159 | UNKNOWN | 11.5 | 229 | AC |
| AI791159 | UNKNOWN | 20 | 0 | T |
| AI791163 | UNKNOWN | 12.5 | 390 | CA |
| AI791163 | UNKNOWN | 7 | 377 | TC |
| AI791171 | UNKNOWN | 6.5 | 275 | AG |
| AI791171 | UNKNOWN | 15 | 149 | A |
| AI791171 | UNKNOWN | 13 | 453 | T |
| AI791176 | UNKNOWN | 16 | 0 | T |
| AI791177 | UNKNOWN | 22 | 2 | T |
| AI791182 | UNKNOWN | 14 | 34 | T |
| AI791187 | UNKNOWN | 15 | 31 | T |
| AI791189 | UNKNOWN | 13 | 31 | T |
| AI791196 | UNKNOWN | 18 | 31 | T |
| AI791197 | UNKNOWN | 8 | 0 | CTA |
| AI791200 | UNKNOWN | 3.6 | 293 | AAAAG |
| AI791200 | UNKNOWN | 13 | 432 | A |
| AI791202 | UNKNOWN | 21.5 | 230 | AC |
| AI791202 | UNKNOWN | 19 | 156 | CA |
| AI791202 | UNKNOWN | 13 | 423 | A |
| AI791211 | UNKNOWN | 18 | 31 | T |
| AI791213 | UNKNOWN | 28 | 28 | T |
| AI791215 | UNKNOWN | 19 | 6 | T |
| AI791217 | UNKNOWN | 17 | 31 | T |
| AI791225 | UNKNOWN | 12 | 28 | T |
| AI791245 | UNKNOWN | 13 | 149 | A |
| AI791311 | UNKNOWN | 19 | 6 | T |
| AI791312 | UNKNOWN | 17 | 31 | T |
| AI791323 | UNKNOWN | 13 | 0 | T |
| AI791349 | UNKNOWN | 21 | 260 | A |
| AI791349 | UNKNOWN | 19 | 183 | T |
| AI791368 | UNKNOWN | 13 | 246 | A |
| AI791373 | UNKNOWN | 23 | 230 | A |
| AI791380 | UNKNOWN | 11 | 169 | GA |
| AI791388 | UNKNOWN | 3.8 | 451 | AAAAC |
| AI791396 | UNKNOWN | 77 | 283 | A |
| AI791453 | UNKNOWN | 18 | 34 | T |
| AI791456 | UNKNOWN | 22 | 31 | T |
| AI791460 | UNKNOWN | 15 | 30 | T |
| AI791465 | UNKNOWN | 16 | 30 | T |
| AI791508 | UNKNOWN | 17 | 32 | T |
| AI791510 | UNKNOWN | 21 | 31 | T |
| AI791512 | UNKNOWN | 18 | 31 | T |
| AI791521 | UNKNOWN | 22 | 237 | A |
| AI791527 | UNKNOWN | 15 | 49 | A |
| AI791557 | UNKNOWN | 15 | 39 | A |
| AI791578 | UNKNOWN | 5.75 | 419 | AAAT |
| AI791635 | UNKNOWN | 21 | 34 | T |
| AI791749 | UNKNOWN | 20 | 552 | A |
| AI791764 | UNKNOWN | 4.75 | 235 | AAAC |
| AI791777 | UNKNOWN | 17 | 0 | T |
| AI791792 | UNKNOWN | 19 | 423 | A |
| AI791820 | UNKNOWN | 17 | 31 | T |
| AI791822 | UNKNOWN | 3.8 | 346 | AAAAC |
| AI791822 | UNKNOWN | 15 | 367 | A |
| AI791828 | UNKNOWN | 16 | 34 | T |
| AI791834 | UNKNOWN | 21 | 31 | T |
| AI791835 | UNKNOWN | 17 | 31 | T |
| AI791842 | UNKNOWN | 17 | 31 | T |
| AI791845 | UNKNOWN | 57.5 | 8 | GA |
| AI791859 | UNKNOWN | 18 | 31 | T |
| AI791886 | UNKNOWN | 14 | 483 | A |
| AI791888 | UNKNOWN | 16 | 140 | A |
| AI791911 | UNKNOWN | 12 | 31 | T |
| AI791917 | UNKNOWN | 16 | 464 | A |
| AI791932 | UNKNOWN | 16 | 31 | T |
| AI791953 | UNKNOWN | 4.75 | 194 | AAAC |
| AI791972 | UNKNOWN | 19 | 28 | T |
| AI792031 | UNKNOWN | 6.5 | 435 | GT |
| AI792034 | UNKNOWN | 20 | 32 | T |
| AI792049 | UNKNOWN | 15 | 196 | T |
| AI792057 | UNKNOWN | 15 | 60 | T |

TABLE 1-continued

| Genbank # | Region | # reps | Position | Unit sequence |
|---|---|---|---|---|
| AI792080 | UNKNOWN | 35 | 304 | A |
| AI792092 | UNKNOWN | 13 | 31 | T |
| AI792175 | UNKNOWN | 3.57 | 326 | GCCCCGA |
| AI792176 | UNKNOWN | 22 | 354 | A |
| AI792186 | UNKNOWN | 28 | 32 | A |
| AI792203 | UNKNOWN | 12 | 436 | T |
| AI792240 | UNKNOWN | 12 | 315 | T |
| AI792244 | UNKNOWN | 15 | 91 | T |
| AI792256 | UNKNOWN | 37 | 6 | T |
| AI792267 | UNKNOWN | 19 | 357 | A |
| AI792305 | UNKNOWN | 15 | 315 | A |
| AI792439 | UNKNOWN | 30 | 24 | T |
| AI792443 | UNKNOWN | 3.5 | 129 | TCTTTC |
| AI792443 | UNKNOWN | 9 | 49 | TTTC |
| AI792443 | UNKNOWN | 13 | 145 | TC |
| AI792443 | UNKNOWN | 28 | 24 | T |
| AI792445 | UNKNOWN | 25 | 24 | T |
| AI792446 | UNKNOWN | 29 | 24 | T |
| AI792449 | UNKNOWN | 26 | 24 | T |
| AI792453 | UNKNOWN | 4.83 | 25 | TTTTTG |
| AI792455 | UNKNOWN | 28 | 24 | T |
| AI792456 | UNKNOWN | 26 | 24 | T |
| AI792487 | UNKNOWN | 28 | 24 | T |
| AI792496 | UNKNOWN | 27 | 24 | T |
| AI792499 | UNKNOWN | 28 | 24 | T |
| AI792501 | UNKNOWN | 27 | 34 | T |
| AI792508 | UNKNOWN | 28 | 24 | T |
| AI792513 | UNKNOWN | 29 | 24 | T |
| AI792515 | UNKNOWN | 27 | 24 | T |
| AI792517 | UNKNOWN | 27 | 24 | T |
| AI792518 | UNKNOWN | 17 | 24 | T |
| AI792519 | UNKNOWN | 27 | 24 | T |
| AI792522 | UNKNOWN | 28 | 24 | T |
| AI792523 | UNKNOWN | 29 | 24 | T |
| AI792524 | UNKNOWN | 29 | 34 | T |
| AI792525 | UNKNOWN | 30 | 51 | T |
| AI792526 | UNKNOWN | 23 | 34 | T |
| AI792527 | UNKNOWN | 23 | 24 | T |
| AI792528 | UNKNOWN | 31 | 24 | T |
| AI792529 | UNKNOWN | 29 | 24 | T |
| AI792532 | UNKNOWN | 30 | 24 | T |
| AI792533 | UNKNOWN | 27 | 24 | T |
| AI792536 | UNKNOWN | 30 | 24 | T |
| AI792540 | UNKNOWN | 26 | 24 | T |
| AI792545 | UNKNOWN | 30 | 34 | T |
| AI792547 | UNKNOWN | 23 | 34 | T |
| AI792554 | UNKNOWN | 27 | 24 | T |
| AI792557 | UNKNOWN | 15 | 41 | T |
| AI792560 | UNKNOWN | 32 | 24 | T |
| AI792561 | UNKNOWN | 30 | 24 | T |
| AI792562 | UNKNOWN | 25 | 21 | T |
| AI792563 | UNKNOWN | 24 | 24 | T |
| AI792564 | UNKNOWN | 25 | 24 | T |
| AI792568 | UNKNOWN | 21 | 26 | T |
| AI792572 | UNKNOWN | 22 | 26 | T |
| AI792575 | UNKNOWN | 21 | 24 | T |
| AI792578 | UNKNOWN | 28 | 24 | T |
| AI792585 | UNKNOWN | 21 | 34 | T |
| AI792618 | UNKNOWN | 14 | 0 | T |
| AI792621 | UNKNOWN | 29 | 24 | T |
| AI792628 | UNKNOWN | 32 | 34 | T |
| AI792628 | UNKNOWN | 13 | 86 | A |
| AI792629 | UNKNOWN | 21 | 34 | T |
| AI792648 | UNKNOWN | 28 | 481 | A |
| AI792658 | UNKNOWN | 18 | 7 | T |
| AI792675 | UNKNOWN | 13 | 363 | T |
| AI792692 | UNKNOWN | 28 | 34 | T |
| AI792696 | UNKNOWN | 30 | 39 | T |
| AI792702 | UNKNOWN | 15 | 24 | T |
| AI792709 | UNKNOWN | 28 | 24 | T |
| AI792803 | UNKNOWN | 13 | 121 | A |
| AI792841 | UNKNOWN | 29 | 37 | T |
| AI792848 | UNKNOWN | 27 | 34 | T |
| AI792853 | UNKNOWN | 22 | 42 | T |
| AI792857 | UNKNOWN | 5.75 | 115 | TTTG |
| AI792857 | UNKNOWN | 28 | 37 | T |
| AI792858 | UNKNOWN | 26 | 34 | T |

TABLE 1-continued

| Genbank # | Region | # reps | Position | Unit sequence |
|---|---|---|---|---|
| AI792860 | UNKNOWN | 28 | 33 | T |
| AI792862 | UNKNOWN | 21 | 40 | T |
| AI792869 | UNKNOWN | 30 | 34 | T |
| AI792888 | UNKNOWN | 20 | 34 | T |
| AI792890 | UNKNOWN | 28 | 34 | T |
| AI792891 | UNKNOWN | 19 | 37 | T |
| AI792893 | UNKNOWN | 15 | 24 | T |
| AI792900 | UNKNOWN | 30 | 34 | T |
| AI792901 | UNKNOWN | 21 | 38 | T |
| AI792908 | UNKNOWN | 20 | 428 | A |
| AI792991 | UNKNOWN | 25 | 164 | A |
| AI793021 | UNKNOWN | 5.75 | 199 | TTTG |
| AI793021 | UNKNOWN | 14 | 10 | T |
| AI793028 | UNKNOWN | 7.5 | 356 | TG |
| AI793028 | UNKNOWN | 14 | 6 | T |
| AI793040 | UNKNOWN | 8 | 132 | TG |
| AI793091 | UNKNOWN | 17 | 190 | A |
| AI793093 | UNKNOWN | 8.75 | 89 | AATA |
| AI793130 | UNKNOWN | 6.5 | 169 | AC |
| AI793172 | UNKNOWN | 20 | 39 | T |
| AI793194 | UNKNOWN | 20 | 0 | T |
| AI793203 | UNKNOWN | 13 | 0 | T |
| AI793204 | UNKNOWN | 12 | 0 | T |
| AI793210 | UNKNOWN | 34 | 0 | T |
| AI793211 | UNKNOWN | 12 | 132 | T |
| AI793223 | UNKNOWN | 2.7 | 71 | AAAAAAAAAG (SEQ ID NO: 150) |
| AI793223 | UNKNOWN | 12 | 68 | A |
| AI793267 | UNKNOWN | 14 | 4 | T |
| AI793299 | UNKNOWN | 21 | 515 | A |
| AI793301 | UNKNOWN | 16 | 0 | T |
| AI793304 | UNKNOWN | 18 | 468 | A |
| AI795913 | UNKNOWN | 16 | 0 | T |
| AI795919 | UNKNOWN | 7.66 | 261 | AAC |
| AI795953 | UNKNOWN | 14 | 102 | T |
| AI795964 | UNKNOWN | 12 | 0 | T |
| AI795970 | UNKNOWN | 14 | 207 | T |
| AI795974 | UNKNOWN | 7 | 213 | GT |
| AI796026 | UNKNOWN | 15 | 0 | T |
| AI796096 | UNKNOWN | 34 | 0 | T |
| AI796113 | UNKNOWN | 50 | 0 | T |
| AI796222 | UNKNOWN | 13 | 0 | T |
| AI796241 | UNKNOWN | 12 | 22 | T |
| AI796242 | UNKNOWN | 18 | 0 | T |
| AI796297 | UNKNOWN | 14 | 0 | T |
| AI796409 | UNKNOWN | 3.5 | 212 | TTTGTT |
| AI796413 | UNKNOWN | 6 | 8 | TTAT |
| AI796419 | UNKNOWN | 36 | 0 | T |
| AI796491 | UNKNOWN | 12.5 | 362 | TG |
| AI796520 | UNKNOWN | 13 | 0 | T |
| AI796562 | UNKNOWN | 21 | 0 | T |
| AI796564 | UNKNOWN | 13 | 0 | T |
| AI796566 | UNKNOWN | 6.5 | 0 | AT |
| AI796568 | UNKNOWN | 41 | 0 | T |
| AI796668 | UNKNOWN | 18 | 0 | T |
| AI796743 | UNKNOWN | 94 | 0 | T |
| AI796784 | UNKNOWN | 17 | 133 | A |
| AI796818 | UNKNOWN | 18 | 4 | T |
| AI796835 | UNKNOWN | 4.5 | 6 | TTCA |
| AI796839 | UNKNOWN | 18 | 377 | A |
| AI796914 | UNKNOWN | 16 | 3 | T |
| AI797023 | UNKNOWN | 12 | 37 | T |
| AI797036 | UNKNOWN | 6 | 289 | GGAG |
| AI797036 | UNKNOWN | 6.5 | 277 | GA |
| AI797036 | UNKNOWN | 17 | 0 | T |
| AI797062 | UNKNOWN | 15.5 | 371 | TC |
| AI797062 | UNKNOWN | 7 | 356 | CT |
| AI797063 | UNKNOWN | 12 | 172 | T |
| AI797073 | UNKNOWN | 3.6 | 271 | TTTGT |
| AI797087 | UNKNOWN | 22 | 0 | T |
| AI797169 | UNKNOWN | 13 | 0 | T |
| AI797236 | UNKNOWN | 13 | 0 | T |
| AI797248 | UNKNOWN | 14 | 451 | GT |
| AI797283 | UNKNOWN | 3.8 | 387 | AAATC |
| AI797436 | UNKNOWN | 13 | 0 | T |
| AI797478 | UNKNOWN | 14 | 0 | T |
| AI797512 | UNKNOWN | 25 | 0 | T |
| AI797538 | UNKNOWN | 68 | 0 | T |

TABLE 1-continued

| Genbank # | Region | # reps | Position | Unit sequence |
|---|---|---|---|---|
| AI797538 | UNKNOWN | 13 | 88 | A |
| AI797557 | UNKNOWN | 23 | 47 | A |
| AI797566 | UNKNOWN | 18 | 0 | T |
| AI797584 | UNKNOWN | 5 | 233 | CATT |
| AI797584 | UNKNOWN | 17 | 0 | T |
| AI797619 | UNKNOWN | 6 | 0 | CATT |
| AI797749 | UNKNOWN | 17 | 0 | T |
| AI797774 | UNKNOWN | 16 | 0 | T |
| AI797794 | UNKNOWN | 73 | 0 | T |
| AI797794 | UNKNOWN | 24 | 339 | G |
| AI797794 | UNKNOWN | 18 | 154 | G |
| AI797794 | UNKNOWN | 15 | 324 | A |
| AI797813 | UNKNOWN | 44 | 32 | T |
| AI797813 | UNKNOWN | 31 | 0 | T |
| AI797813 | UNKNOWN | 12 | 260 | C |
| AI797869 | UNKNOWN | 17 | 326 | T |
| AI797908 | UNKNOWN | 87 | 0 | T |
| AI797908 | UNKNOWN | 19 | 190 | C |
| AI797972 | UNKNOWN | 30 | 0 | T |
| AI797988 | UNKNOWN | 17 | 0 | T |
| AI797998 | UNKNOWN | 12 | 5 | T |
| AI798089 | UNKNOWN | 3.66 | 110 | AAAAAG |
| AI798089 | UNKNOWN | 21 | 19 | T |
| AI798089 | UNKNOWN | 16 | 0 | T |
| AI798099 | UNKNOWN | 18 | 0 | T |
| AI798100 | UNKNOWN | 36 | 0 | T |
| AI798100 | UNKNOWN | 18 | 173 | G |
| AI798100 | UNKNOWN | 16 | 315 | A |
| AI798101 | UNKNOWN | 71 | 0 | T |
| AI798101 | UNKNOWN | 12 | 92 | G |
| AI798114 | UNKNOWN | 49 | 0 | T |
| AI798114 | UNKNOWN | 13 | 72 | A |
| AI798117 | UNKNOWN | 3.4 | 190 | GGGCTCCTGGCCTCACATCT (SEQ ID NO: 151) |
| AI798164 | UNKNOWN | 4 | 143 | AAAAT |
| AI798258 | UNKNOWN | 87 | 0 | T |
| AI798258 | UNKNOWN | 12 | 288 | G |
| AI798279 | UNKNOWN | 29 | 0 | T |
| AI798303 | UNKNOWN | 64 | 0 | T |
| AI798303 | UNKNOWN | 17 | 164 | A |
| AI798303 | UNKNOWN | 12 | 80 | A |
| AI798315 | UNKNOWN | 14 | 0 | T |
| AI798317 | UNKNOWN | 38 | 0 | T |
| AI798327 | UNKNOWN | 15 | 59 | T |
| AI798327 | UNKNOWN | 13 | 124 | A |
| AI798371 | UNKNOWN | 38 | 0 | T |
| AI798373 | UNKNOWN | 79 | 0 | T |
| AI798373 | UNKNOWN | 20 | 84 | A |
| AI798373 | UNKNOWN | 13 | 223 | G |
| AI798385 | UNKNOWN | 62 | 0 | T |
| AI798396 | UNKNOWN | 18 | 93 | T |
| AI798404 | UNKNOWN | 56 | 0 | T |
| AI798404 | UNKNOWN | 19 | 209 | C |
| AI798434 | UNKNOWN | 37 | 0 | T |
| AI798434 | UNKNOWN | 15 | 126 | A |
| AI798455 | UNKNOWN | 16 | 0 | T |
| AI798456 | UNKNOWN | 92 | 0 | T |
| AI798456 | UNKNOWN | 17 | 226 | A |
| AI798456 | UNKNOWN | 13 | 93 | A |
| AI798464 | UNKNOWN | 8.5 | 75 | AC |
| AI798464 | UNKNOWN | 42 | 0 | T |
| AI798501 | UNKNOWN | 73 | 0 | T |
| AI798510 | UNKNOWN | 67 | 0 | T |
| AI798544 | UNKNOWN | 57 | 0 | T |
| AI798544 | UNKNOWN | 12 | 81 | A |
| AI798545 | UNKNOWN | 17 | 0 | T |
| AI798563 | UNKNOWN | 14 | 0 | T |
| AI798590 | UNKNOWN | 12 | 414 | T |
| AI798608 | UNKNOWN | 65 | 0 | T |
| AI798608 | UNKNOWN | 15 | 292 | C |
| AI798608 | UNKNOWN | 12 | 181 | A |
| AI798610 | UNKNOWN | 38 | 0 | T |
| AI798666 | UNKNOWN | 18 | 0 | T |
| AI798723 | UNKNOWN | 16 | 201 | T |
| AI798723 | UNKNOWN | 12 | 277 | A |
| AI798793 | UNKNOWN | 13 | 0 | T |
| AI798839 | UNKNOWN | 47 | 0 | T |
| AI798863 | UNKNOWN | 19 | 0 | T |

TABLE 1-continued

| Genbank # | Region | # reps | Position | Unit sequence |
|---|---|---|---|---|
| AI798890 | UNKNOWN | 13 | 0 | T |
| AI798958 | UNKNOWN | 8.33 | 306 | TGC |
| AI798960 | UNKNOWN | 16 | 0 | T |
| AI798967 | UNKNOWN | 2.63 | 234 | AGAGGGAGAGG (SEQ ID NO: 152) |
| AI799004 | UNKNOWN | 15.5 | 155 | AT |
| AI799004 | UNKNOWN | 9 | 191 | AC |
| AI799024 | UNKNOWN | 5.66 | 363 | GTT |
| AI799038 | UNKNOWN | 6.5 | 330 | CA |
| AI799038 | UNKNOWN | 25 | 0 | T |
| AI799038 | UNKNOWN | 13 | 112 | G |
| AI799053 | UNKNOWN | 17 | 0 | T |
| AI799087 | UNKNOWN | 14 | 143 | A |
| AI799104 | UNKNOWN | 12 | 0 | T |
| AI799158 | UNKNOWN | 88 | 0 | T |
| AI799158 | UNKNOWN | 22 | 315 | A |
| AI799183 | UNKNOWN | 102 | 0 | T |
| AI799183 | UNKNOWN | 16 | 258 | G |
| AI799183 | UNKNOWN | 13 | 291 | C |
| AI799195 | UNKNOWN | 82 | 0 | T |
| AI799199 | UNKNOWN | 115 | 0 | T |
| AI799199 | UNKNOWN | 21 | 149 | A |
| AI799199 | UNKNOWN | 21 | 181 | G |
| AI799220 | UNKNOWN | 36 | 0 | T |
| AI799220 | UNKNOWN | 21 | 123 | A |
| AI799233 | UNKNOWN | 50 | 0 | T |
| AI799234 | UNKNOWN | 90 | 0 | T |
| AI799234 | UNKNOWN | 15 | 151 | A |
| AI799239 | UNKNOWN | 58 | 0 | T |
| AI799268 | UNKNOWN | 65 | 0 | T |
| AI799273 | UNKNOWN | 96 | 0 | T |
| AI799273 | UNKNOWN | 23 | 270 | G |
| AI799273 | UNKNOWN | 14 | 164 | A |
| AI799336 | UNKNOWN | 66 | 0 | T |
| AI799336 | UNKNOWN | 12 | 203 | C |
| AI799344 | UNKNOWN | 83 | 0 | T |
| AI799385 | UNKNOWN | 44 | 0 | T |
| AI799470 | UNKNOWN | 118 | 0 | T |
| AI799470 | UNKNOWN | 18 | 335 | A |
| AI799470 | UNKNOWN | 14 | 118 | A |
| AI799470 | UNKNOWN | 14 | 132 | C |
| AI799472 | UNKNOWN | 97 | 3 | T |
| AI799472 | UNKNOWN | 13 | 173 | C |
| AI799472 | UNKNOWN | 12 | 102 | G |
| AI799472 | UNKNOWN | 12 | 377 | A |
| AI799482 | UNKNOWN | 12 | 0 | T |
| AI799487 | UNKNOWN | 20 | 0 | T |
| AI799496 | UNKNOWN | 22 | 0 | T |
| AI799540 | UNKNOWN | 57 | 0 | T |
| AI799568 | UNKNOWN | 52 | 0 | T |
| AI799607 | UNKNOWN | 25 | 4 | T |
| AI799618 | UNKNOWN | 38 | 0 | T |
| AI799637 | UNKNOWN | 41 | 0 | T |
| AI799642 | UNKNOWN | 18 | 0 | T |
| AI799646 | UNKNOWN | 5.75 | 128 | TTGC |
| AI799646 | UNKNOWN | 4.75 | 112 | TTGG |
| AI799652 | UNKNOWN | 22 | 0 | T |
| AI799657 | UNKNOWN | 68 | 1 | T |
| AI799674 | UNKNOWN | 65 | 0 | T |
| AI799674 | UNKNOWN | 12 | 157 | A |
| AI799681 | UNKNOWN | 55 | 0 | T |
| AI799681 | UNKNOWN | 13 | 223 | A |
| AI799766 | UNKNOWN | 45 | 0 | T |
| AI799784 | UNKNOWN | 20 | 330 | T |
| AI799804 | UNKNOWN | 13 | 10 | T |
| AI799822 | UNKNOWN | 14 | 97 | A |
| AI799854 | UNKNOWN | 44 | 0 | T |
| AI799872 | UNKNOWN | 13 | 0 | T |
| AI799893 | UNKNOWN | 15 | 0 | T |
| AI799909 | UNKNOWN | 13 | 0 | T |
| AI799963 | UNKNOWN | 52 | 0 | T |
| AI799968 | UNKNOWN | 49 | 0 | T |
| AI800109 | UNKNOWN | 53 | 0 | T |
| AI800109 | UNKNOWN | 15 | 376 | A |
| AI800112 | UNKNOWN | 19 | 0 | T |
| AI800138 | UNKNOWN | 77 | 0 | T |
| AI800138 | UNKNOWN | 14 | 139 | C |
| AI800152 | UNKNOWN | 105 | 0 | T |

TABLE 1-continued

| Genbank # | Region | # reps | Position | Unit sequence |
|---|---|---|---|---|
| AI800152 | UNKNOWN | 13 | 390 | C |
| AI800155 | UNKNOWN | 85 | 0 | T |
| AI800155 | UNKNOWN | 14 | 116 | C |
| AI800155 | UNKNOWN | 13 | 291 | A |
| AI800159 | UNKNOWN | 63 | 0 | T |
| AI800160 | UNKNOWN | 38 | 0 | T |
| AI800162 | UNKNOWN | 21 | 52 | A |
| AI800168 | UNKNOWN | 14 | 0 | T |
| AI800171 | UNKNOWN | 63 | 0 | T |
| AI800179 | UNKNOWN | 56 | 0 | T |
| AI800182 | UNKNOWN | 16 | 0 | T |
| AI800185 | UNKNOWN | 39 | 16 | T |
| AI800185 | UNKNOWN | 22 | 170 | G |
| AI800185 | UNKNOWN | 15 | 0 | T |
| AI800185 | UNKNOWN | 15 | 151 | A |
| AI800185 | UNKNOWN | 14 | 137 | C |
| AI800217 | UNKNOWN | 15 | 0 | T |
| AI800236 | UNKNOWN | 14 | 0 | T |
| AI800250 | UNKNOWN | 15 | 0 | T |
| AI800280 | UNKNOWN | 13 | 9 | T |
| AI800289 | UNKNOWN | 14 | 393 | CA |
| AI800289 | UNKNOWN | 9.5 | 375 | CT |
| AI800341 | UNKNOWN | 74 | 0 | T |
| AI800364 | UNKNOWN | 21 | 252 | T |
| AI800364 | UNKNOWN | 16 | 224 | A |
| AI800367 | UNKNOWN | 70 | 0 | T |
| AI800370 | UNKNOWN | 53 | 0 | T |
| AI800380 | UNKNOWN | 99 | 0 | T |
| AI800380 | UNKNOWN | 19 | 139 | A |
| AI800380 | UNKNOWN | 12 | 169 | C |
| AI800380 | UNKNOWN | 12 | 230 | G |
| AI800382 | UNKNOWN | 81 | 0 | T |
| AI800382 | UNKNOWN | 14 | 89 | A |
| AI800384 | UNKNOWN | 117 | 0 | T |
| AI800411 | UNKNOWN | 123 | 0 | T |
| AI800411 | UNKNOWN | 18 | 192 | A |
| AI800411 | UNKNOWN | 16 | 163 | C |
| AI800411 | UNKNOWN | 15 | 313 | G |
| AI800411 | UNKNOWN | 14 | 236 | G |
| AI800411 | UNKNOWN | 12 | 151 | A |
| AI800433 | UNKNOWN | 122 | 0 | T |
| AI800433 | UNKNOWN | 18 | 157 | C |
| AI800433 | UNKNOWN | 13 | 210 | G |
| AI800437 | UNKNOWN | 15 | 0 | T |
| AI800440 | UNKNOWN | 90 | 0 | T |
| AI800440 | UNKNOWN | 18 | 177 | A |
| AI800440 | UNKNOWN | 15 | 162 | C |
| AI800440 | UNKNOWN | 13 | 142 | A |
| AI800441 | UNKNOWN | 41 | 0 | T |
| AI800446 | UNKNOWN | 19 | 157 | T |
| AI800453 | UNKNOWN | 122 | 0 | T |
| AI800453 | UNKNOWN | 18 | 157 | C |
| AI800453 | UNKNOWN | 14 | 210 | G |
| AI800470 | UNKNOWN | 23 | 0 | T |
| AI800473 | UNKNOWN | 68 | 0 | T |
| AI800590 | UNKNOWN | 21 | 0 | T |
| AI800595 | UNKNOWN | 34 | 0 | T |
| AI800648 | UNKNOWN | 50 | 0 | T |
| AI800648 | UNKNOWN | 14 | 97 | G |
| AI800648 | UNKNOWN | 13 | 113 | A |
| AI800661 | UNKNOWN | 57 | 0 | T |
| AI800661 | UNKNOWN | 12 | 81 | C |
| AI800674 | UNKNOWN | 22 | 0 | T |
| AI800681 | UNKNOWN | 38 | 0 | T |
| AI800681 | UNKNOWN | 15 | 137 | G |
| AI800735 | UNKNOWN | 13 | 0 | T |
| AI800768 | UNKNOWN | 4.66 | 173 | TTTTAT |
| AI800768 | UNKNOWN | 5.75 | 335 | TTTG |
| AI800780 | UNKNOWN | 17 | 0 | T |
| AI800806 | UNKNOWN | 20 | 0 | T |
| AI800829 | UNKNOWN | 20 | 0 | T |
| AI800852 | UNKNOWN | 4.75 | 14 | TCTT |
| AI800852 | UNKNOWN | 12 | 0 | T |
| AI800895 | UNKNOWN | 16 | 90 | T |
| AI800896 | UNKNOWN | 17 | 0 | T |
| AI800919 | UNKNOWN | 3.5 | 28 | TTTTAT |
| AI801013 | UNKNOWN | 16 | 0 | T |

TABLE 1-continued

| Genbank # | Region | # reps | Position | Unit sequence |
|---|---|---|---|---|
| AI801029 | UNKNOWN | 18 | 394 | A |
| AI801032 | UNKNOWN | 46 | 0 | T |
| AI801044 | UNKNOWN | 61 | 0 | T |
| AI801048 | UNKNOWN | 52 | 0 | T |
| AI801048 | UNKNOWN | 13 | 139 | A |
| AI801067 | UNKNOWN | 18 | 0 | T |
| AI801088 | UNKNOWN | 43 | 0 | T |
| AI801088 | UNKNOWN | 19 | 93 | A |
| AI801091 | UNKNOWN | 37 | 0 | T |
| AI801091 | UNKNOWN | 14 | 162 | A |
| AI801100 | UNKNOWN | 14 | 0 | T |
| AI801112 | UNKNOWN | 92 | 0 | T |
| AI801112 | UNKNOWN | 14 | 137 | A |
| AI801112 | UNKNOWN | 13 | 264 | C |
| AI801146 | UNKNOWN | 43 | 0 | T |
| AI801152 | UNKNOWN | 100 | 0 | T |
| AI801152 | UNKNOWN | 12 | 157 | A |
| AI801167 | UNKNOWN | 75 | 0 | T |
| AI801187 | UNKNOWN | 73 | 0 | T |
| AI801187 | UNKNOWN | 17 | 102 | A |
| AI801187 | UNKNOWN | 12 | 207 | C |
| AI801197 | UNKNOWN | 16 | 0 | T |
| AI801205 | UNKNOWN | 19 | 0 | T |
| AI801213 | UNKNOWN | 116 | 0 | T |
| AI801213 | UNKNOWN | 15 | 153 | G |
| AI801213 | UNKNOWN | 14 | 162 | A |
| AI801237 | UNKNOWN | 74 | 0 | T |
| AI801237 | UNKNOWN | 14 | 234 | G |
| AI801257 | UNKNOWN | 56 | 0 | T |
| AI801257 | UNKNOWN | 15 | 170 | A |
| AI801276 | UNKNOWN | 37 | 0 | T |
| AI801276 | UNKNOWN | 18 | 144 | A |
| AI801295 | UNKNOWN | 12 | 11 | T |
| AI801322 | UNKNOWN | 112 | 0 | T |
| AI801322 | UNKNOWN | 20 | 232 | A |
| AI801322 | UNKNOWN | 15 | 216 | G |
| AI801325 | UNKNOWN | 98 | 11 | T |
| AI801351 | UNKNOWN | 46 | 0 | T |
| AI801395 | UNKNOWN | 24 | 23 | T |
| AI801404 | UNKNOWN | 64 | 0 | T |
| AI801404 | UNKNOWN | 13 | 165 | G |
| AI801406 | UNKNOWN | 22 | 220 | A |
| AI801450 | UNKNOWN | 14 | 10 | T |
| AI801460 | UNKNOWN | 94 | 0 | T |
| AI801460 | UNKNOWN | 14 | 235 | C |
| AI801505 | UNKNOWN | 19 | 0 | T |
| AI801505 | UNKNOWN | 18 | 425 | A |
| AI801515 | UNKNOWN | 72 | 0 | T |
| AI801523 | UNKNOWN | 83 | 0 | T |
| AI801523 | UNKNOWN | 19 | 209 | A |
| AI801523 | UNKNOWN | 14 | 122 | A |
| AI801533 | UNKNOWN | 48 | 0 | T |
| AI801533 | UNKNOWN | 12 | 306 | G |
| AI801535 | UNKNOWN | 64 | 0 | T |
| AI801544 | UNKNOWN | 107 | 0 | T |
| AI801544 | UNKNOWN | 14 | 193 | G |
| AI801544 | UNKNOWN | 13 | 229 | A |
| AI801544 | UNKNOWN | 12 | 270 | C |
| AI801545 | UNKNOWN | 20 | 68 | A |
| AI801556 | UNKNOWN | 64 | 0 | T |
| AI801557 | UNKNOWN | 45 | 0 | T |
| AI801561 | UNKNOWN | 82 | 0 | T |
| AI801561 | UNKNOWN | 15 | 317 | G |
| AI801561 | UNKNOWN | 12 | 159 | A |
| AI801592 | UNKNOWN | 90 | 0 | T |
| AI801592 | UNKNOWN | 26 | 209 | A |
| AI801605 | UNKNOWN | 91 | 0 | T |
| AI801605 | UNKNOWN | 18 | 163 | G |
| AI801605 | UNKNOWN | 17 | 205 | C |
| AI801608 | UNKNOWN | 117 | 0 | T |
| AI801608 | UNKNOWN | 22 | 326 | A |
| AI801608 | UNKNOWN | 18 | 189 | C |
| AI801608 | UNKNOWN | 15 | 252 | G |
| AI801608 | UNKNOWN | 13 | 148 | G |
| AI801620 | UNKNOWN | 73 | 0 | T |
| AI801620 | UNKNOWN | 19 | 173 | G |
| AI801647 | UNKNOWN | 60 | 0 | T |

TABLE 1-continued

| Genbank # | Region | # reps | Position | Unit sequence |
|---|---|---|---|---|
| AI801725 | UNKNOWN | 45 | 0 | T |
| AI801766 | UNKNOWN | 103 | 0 | T |
| AI801766 | UNKNOWN | 15 | 106 | A |
| AI801766 | UNKNOWN | 15 | 184 | G |
| AI801766 | UNKNOWN | 14 | 241 | C |
| AI801777 | UNKNOWN | 12 | 655 | A |
| AI801793 | UNKNOWN | 69 | 0 | T |
| AI801793 | UNKNOWN | 12 | 190 | A |
| AI801818 | UNKNOWN | 41 | 0 | T |
| AI801890 | UNKNOWN | 20 | 8 | T |
| AI801897 | UNKNOWN | 5.66 | 526 | CAG |
| AI801902 | UNKNOWN | 8.5 | 537 | TG |
| AI801969 | UNKNOWN | 6.5 | 154 | AC |
| AI801987 | UNKNOWN | 6.5 | 143 | TTCA |
| AI802036 | UNKNOWN | 25 | 0 | T |
| AI802060 | UNKNOWN | 12 | 352 | A |
| AI802099 | UNKNOWN | 20 | 0 | T |
| AI802240 | UNKNOWN | 65 | 25 | T |
| AI802240 | UNKNOWN | 24 | 0 | T |
| AI802240 | UNKNOWN | 23 | 146 | G |
| AI802244 | UNKNOWN | 44 | 15 | T |
| AI802244 | UNKNOWN | 14 | 0 | T |
| AI802384 | UNKNOWN | 19 | 0 | T |
| AI802408 | UNKNOWN | 13 | 0 | T |
| AI802450 | UNKNOWN | 22 | 226 | T |
| AI802453 | UNKNOWN | 15 | 379 | T |
| AI802477 | UNKNOWN | 37 | 59 | T |
| AI802477 | UNKNOWN | 26 | 0 | T |
| AI802477 | UNKNOWN | 19 | 147 | A |
| AI802477 | UNKNOWN | 14 | 129 | A |
| AI802491 | UNKNOWN | 49 | 0 | T |
| AI802491 | UNKNOWN | 13 | 159 | A |
| AI802542 | UNKNOWN | 118 | 0 | T |
| AI802542 | UNKNOWN | 14 | 118 | A |
| AI802542 | UNKNOWN | 13 | 175 | C |
| AI802554 | UNKNOWN | 69 | 0 | T |
| AI802581 | UNKNOWN | 48 | 0 | T |
| AI802581 | UNKNOWN | 12 | 174 | C |
| AI802654 | UNKNOWN | 85 | 0 | T |
| AI802654 | UNKNOWN | 18 | 193 | C |
| AI802654 | UNKNOWN | 13 | 171 | C |
| AI802659 | UNKNOWN | 16 | 399 | A |
| AI802695 | UNKNOWN | 56 | 0 | T |
| AI802695 | UNKNOWN | 12 | 250 | A |
| AI802711 | UNKNOWN | 58 | 0 | T |
| AI802725 | UNKNOWN | 41 | 0 | T |
| AI802801 | UNKNOWN | 17 | 164 | A |
| AI802804 | UNKNOWN | 19 | 350 | A |
| AI802830 | UNKNOWN | 23 | 270 | A |
| AI802835 | UNKNOWN | 29 | 150 | A |
| AI802946 | UNKNOWN | 30 | 0 | T |
| AI802957 | UNKNOWN | 23 | 378 | T |
| AI803126 | UNKNOWN | 18 | 0 | T |
| AI803314 | UNKNOWN | 18 | 0 | T |
| AI803328 | UNKNOWN | 10 | 318 | CA |
| AI803356 | UNKNOWN | 15 | 80 | T |
| AI803434 | UNKNOWN | 12 | 0 | T |
| AI803527 | UNKNOWN | 12 | 464 | A |
| AI803535 | UNKNOWN | 18 | 0 | T |
| AI803545 | UNKNOWN | 17 | 0 | T |
| AI803740 | UNKNOWN | 47 | 0 | T |
| AI803749 | UNKNOWN | 28 | 29 | T |
| AI803749 | UNKNOWN | 26 | 0 | T |
| AI803778 | UNKNOWN | 82 | 0 | T |
| AI803778 | UNKNOWN | 19 | 234 | G |
| AI803779 | UNKNOWN | 18 | 0 | T |
| AI803786 | UNKNOWN | 63 | 0 | T |
| AI803793 | UNKNOWN | 12 | 0 | T |
| AI803802 | UNKNOWN | 21 | 0 | T |
| AI803816 | UNKNOWN | 89 | 0 | T |
| AI803880 | UNKNOWN | 17.5 | 149 | AT |
| AI803887 | UNKNOWN | 49 | 0 | T |
| AI803935 | UNKNOWN | 51 | 0 | T |
| AI803937 | UNKNOWN | 43 | 0 | T |
| AI803955 | UNKNOWN | 44 | 0 | T |
| AI804071 | UNKNOWN | 15 | 383 | T |
| AI804190 | UNKNOWN | 13 | 125 | A |

TABLE 1-continued

| Genbank # | Region | # reps | Position | Unit sequence |
|---|---|---|---|---|
| AI804244 | UNKNOWN | 21 | 0 | T |
| AI804505 | UNKNOWN | 55 | 11 | T |
| AI804529 | UNKNOWN | 17 | 1 | T |
| AI804553 | UNKNOWN | 73 | 0 | T |
| AI804563 | UNKNOWN | 72 | 0 | T |
| AI804563 | UNKNOWN | 16 | 321 | A |
| AI804564 | UNKNOWN | 13 | 0 | T |
| AI804585 | UNKNOWN | 119 | 0 | T |
| AI804585 | UNKNOWN | 17 | 153 | G |
| AI804585 | UNKNOWN | 15 | 127 | A |
| AI804586 | UNKNOWN | 58 | 0 | T |
| AI804586 | UNKNOWN | 15 | 935 | A |
| AI804667 | UNKNOWN | 17 | 0 | T |
| AI804754 | UNKNOWN | 34 | 0 | T |
| AI804780 | UNKNOWN | 22 | 0 | T |
| AI804808 | UNKNOWN | 20 | 0 | T |
| AI804831 | UNKNOWN | 29 | 0 | T |
| AI804839 | UNKNOWN | 27 | 29 | T |
| AI804839 | UNKNOWN | 18 | 0 | T |
| AI804839 | UNKNOWN | 12 | 120 | C |
| AI804842 | UNKNOWN | 48 | 0 | T |
| AI804929 | UNKNOWN | 24 | 0 | T |
| AI804965 | UNKNOWN | 60 | 0 | T |
| AI804983 | UNKNOWN | 87 | 0 | T |
| AI804983 | UNKNOWN | 17 | 117 | A |
| AI805042 | UNKNOWN | 13 | 22 | T |
| AI805062 | UNKNOWN | 5.25 | 91 | GGAG |
| AI805106 | UNKNOWN | 16 | 0 | T |
| AI805144 | UNKNOWN | 66 | 0 | T |
| AI805144 | UNKNOWN | 12 | 154 | G |
| AI805288 | UNKNOWN | 12 | 0 | T |
| AI805301 | UNKNOWN | 17 | 0 | T |
| AI805385 | UNKNOWN | 97 | 0 | T |
| AI805385 | UNKNOWN | 12 | 316 | G |
| AI805408 | UNKNOWN | 17 | 0 | T |
| AI805463 | UNKNOWN | 15 | 49 | T |
| AI805547 | UNKNOWN | 16 | 0 | T |
| AI805547 | UNKNOWN | 16 | 369 | A |
| AI805550 | UNKNOWN | 12 | 0 | T |
| AI805598 | UNKNOWN | 62 | 0 | T |
| AI805598 | UNKNOWN | 12 | 245 | A |
| AI805601 | UNKNOWN | 31 | 0 | T |
| AI805603 | UNKNOWN | 85 | 0 | T |
| AI805603 | UNKNOWN | 13 | 142 | G |
| AI805603 | UNKNOWN | 12 | 178 | C |
| AI805638 | UNKNOWN | 71 | 32 | T |
| AI805638 | UNKNOWN | 30 | 1 | T |
| AI805638 | UNKNOWN | 13 | 149 | G |
| AI805638 | UNKNOWN | 12 | 137 | C |
| AI805670 | UNKNOWN | 6.66 | 22 | TTA |
| AI805671 | UNKNOWN | 73 | 0 | T |
| AI805671 | UNKNOWN | 14 | 103 | A |
| AI805672 | UNKNOWN | 1T | 0 | T |
| AI805688 | UNKNOWN | 80 | 0 | T |
| AI805730 | UNKNOWN | 26 | 0 | T |
| AI805760 | UNKNOWN | 20 | 11 | T |
| AI805914 | UNKNOWN | 12 | 0 | T |
| AI805917 | UNKNOWN | 25 | 0 | T |
| AI805943 | UNKNOWN | 20 | 0 | T |
| AI805947 | UNKNOWN | 19 | 0 | T |
| AI805966 | UNKNOWN | 14 | 27 | A |
| AI805985 | UNKNOWN | 22 | 0 | T |
| AI806010 | UNKNOWN | 37 | 0 | T |
| AI806010 | UNKNOWN | 17 | 164 | G |
| AI806010 | UNKNOWN | 13 | 150 | G |
| AI806074 | UNKNOWN | 15 | 0 | T |
| AI806097 | UNKNOWN | 16 | 11 | T |
| AI806129 | UNKNOWN | 3.8 | 167 | TGGGG |
| AI806183 | UNKNOWN | 5 | 508 | AAAT |
| AI806217 | UNKNOWN | 13 | 0 | T |
| AI806223 | UNKNOWN | 15 | 0 | T |
| AI806240 | UNKNOWN | 36 | 0 | T |
| AI806250 | UNKNOWN | 13 | 0 | T |
| AI806296 | UNKNOWN | 42 | 0 | T |
| AI806348 | UNKNOWN | 18 | 1 | T |
| AI806355 | UNKNOWN | 18 | 0 | T |
| AI806372 | UNKNOWN | 14 | 502 | A |

TABLE 1-continued

| Genbank # | Region | # reps | Position | Unit sequence |
|---|---|---|---|---|
| AI806384 | UNKNOWN | 17 | 0 | T |
| AI806432 | UNKNOWN | 14 | 0 | T |
| AI806498 | UNKNOWN | 18 | 0 | T |
| AI806581 | UNKNOWN | 7 | 354 | TA |
| AI806583 | UNKNOWN | 23 | 137 | T |
| AI806602 | UNKNOWN | 7.5 | 278 | TA |
| AI806629 | UNKNOWN | 23.5 | 253 | AC |
| AI806635 | UNKNOWN | 15 | 0 | T |
| AI806707 | UNKNOWN | 25 | 371 | T |
| AI806710 | UNKNOWN | 12 | 0 | T |
| AI806719 | UNKNOWN | 12 | 0 | T |
| AI806738 | UNKNOWN | 16 | 0 | T |
| AI806748 | UNKNOWN | 14 | 0 | T |
| AI806832 | UNKNOWN | 8 | 63 | AATC |
| AI806832 | UNKNOWN | 13 | 0 | T |
| AI806867 | UNKNOWN | 15 | 0 | T |
| AI806909 | UNKNOWN | 12 | 0 | T |
| AI806927 | UNKNOWN | 12 | 162 | A |
| AI807023 | UNKNOWN | 20 | 0 | T |
| AI807036 | UNKNOWN | 31 | 0 | T |
| AI807052 | UNKNOWN | 5.66 | 416 | GGA |
| AI807069 | UNKNOWN | 15 | 0 | T |
| AI807160 | UNKNOWN | 42 | 0 | T |
| AI807173 | UNKNOWN | 13 | 0 | T |
| AI807189 | UNKNOWN | 21 | 0 | T |
| AI807219 | UNKNOWN | 13 | 0 | T |
| AI807242 | UNKNOWN | 16 | 0 | T |
| AI807257 | UNKNOWN | 15 | 0 | T |
| AI807267 | UNKNOWN | 20 | 2 | T |
| AI807281 | UNKNOWN | 18 | 0 | T |
| AI807329 | UNKNOWN | 18 | 0 | T |
| AI807334 | UNKNOWN | 12 | 0 | T |
| AI807345 | UNKNOWN | 18 | 0 | T |
| AI807350 | UNKNOWN | 5.75 | 146 | TTTG |
| AI807377 | UNKNOWN | 42 | 0 | T |
| AI807377 | UNKNOWN | 20 | 456 | A |
| AI807397 | UNKNOWN | 6 | 152 | GTTTT |
| AI807397 | UNKNOWN | 18 | 196 | A |
| AI807401 | UNKNOWN | 27 | 0 | T |
| AI807470 | UNKNOWN | 14 | 0 | T |
| AI807478 | UNKNOWN | 14 | 0 | T |
| AI807529 | UNKNOWN | 14 | 302 | A |
| AI807537 | UNKNOWN | 18.5 | 146 | AC |
| AI807538 | UNKNOWN | 28 | 0 | T |
| AI807625 | UNKNOWN | 15 | 0 | T |
| AI807638 | UNKNOWN | 5 | 90 | AAAC |
| AI807638 | UNKNOWN | 12 | 150 | A |
| AI807649 | UNKNOWN | 18 | 0 | T |
| AI807710 | UNKNOWN | 3.8 | 382 | TTTTG |
| AI807756 | UNKNOWN | 3.6 | 275 | GTTTT |
| AI807790 | UNKNOWN | 19 | 0 | T |
| AI807804 | UNKNOWN | 12 | 694 | G |
| AI807851 | UNKNOWN | 15 | 0 | T |
| AI807852 | UNKNOWN | 15 | 0 | T |
| AI807929 | UNKNOWN | 13 | 0 | T |
| AI807939 | UNKNOWN | 15 | 0 | T |
| AI807945 | UNKNOWN | 13 | 347 | A |
| AI807950 | UNKNOWN | 13 | 341 | T |
| AI807982 | UNKNOWN | 13 | 245 | A |
| AI808009 | UNKNOWN | 18 | 0 | T |
| AI808078 | UNKNOWN | 20 | 0 | T |
| AI808113 | UNKNOWN | 15 | 0 | T |
| AI808120 | UNKNOWN | 22 | 447 | A |
| AI808141 | UNKNOWN | 15 | 0 | T |
| AI808142 | UNKNOWN | 19 | 0 | T |
| AI808149 | UNKNOWN | 13 | 329 | T |
| AI808216 | UNKNOWN | 12 | 0 | T |
| AI808248 | UNKNOWN | 16 | 227 | A |
| AI808284 | UNKNOWN | 13 | 0 | T |
| AI808311 | UNKNOWN | 19 | 0 | T |
| AI808329 | UNKNOWN | 6.5 | 199 | TC |
| AI808329 | UNKNOWN | 18 | 0 | T |
| AI808358 | UNKNOWN | 15 | 0 | T |
| AI808390 | UNKNOWN | 22 | 0 | T |
| AI808395 | UNKNOWN | 13 | 0 | T |
| AI808395 | UNKNOWN | 12 | 241 | A |
| AI808499 | UNKNOWN | 16 | 0 | T |

TABLE 1-continued

| Genbank # | Region | # reps | Position | Unit sequence |
|---|---|---|---|---|
| AI808525 | UNKNOWN | 18 | 0 | T |
| AI808548 | UNKNOWN | 22 | 0 | T |
| AI808549 | UNKNOWN | 14 | 0 | T |
| AI808551 | UNKNOWN | 39 | 0 | T |
| AI808551 | UNKNOWN | 12 | 39 | G |
| AI808568 | UNKNOWN | 18 | 0 | T |
| AI808596 | UNKNOWN | 17 | 0 | T |
| AI808691 | UNKNOWN | 15 | 0 | T |
| AI808724 | UNKNOWN | 14 | 0 | T |
| AI808913 | UNKNOWN | 17 | 2 | T |
| AI808964 | UNKNOWN | 7 | 10 | TG |
| AI808970 | UNKNOWN | 14 | 0 | T |
| AI809077 | UNKNOWN | 15 | 252 | A |
| AI809100 | UNKNOWN | 13 | 0 | T |
| AI809101 | UNKNOWN | 14 | 0 | T |
| AI809113 | UNKNOWN | 19 | 426 | T |
| AI809131 | UNKNOWN | 18 | 0 | T |
| AI809147 | UNKNOWN | 13 | 0 | T |
| AI809150 | UNKNOWN | 16 | 0 | T |
| AI809181 | UNKNOWN | 21 | 0 | T |
| AI809184 | UNKNOWN | 41 | 0 | T |
| AI809252 | UNKNOWN | 7 | 226 | AC |
| AI809255 | UNKNOWN | 34 | 0 | T |
| AI809257 | UNKNOWN | 13 | 143 | A |
| AI809310 | UNKNOWN | 18 | 0 | T |
| AI809325 | UNKNOWN | 12 | 0 | T |
| AI809329 | UNKNOWN | 13 | 0 | T |
| AI809373 | UNKNOWN | 16 | 366 | A |
| AI809444 | UNKNOWN | 12 | 157 | T |
| AI809484 | UNKNOWN | 13 | 0 | T |
| AI809544 | UNKNOWN | 21 | 0 | T |
| AI809545 | UNKNOWN | 21 | 0 | T |
| AI809550 | UNKNOWN | 6.66 | 131 | GTG |
| AI809561 | UNKNOWN | 29 | 0 | T |
| AI809595 | UNKNOWN | 20 | 215 | T |
| AI809617 | UNKNOWN | 33 | 0 | T |
| AI809641 | UNKNOWN | 13 | 0 | T |
| AI809669 | UNKNOWN | 12 | 0 | T |
| AI809682 | UNKNOWN | 3.8 | 159 | AAAAC |
| AI809688 | UNKNOWN | 13 | 0 | T |
| AI809752 | UNKNOWN | 6 | 329 | TTG |
| AI809753 | UNKNOWN | 18 | 0 | T |
| AI809753 | UNKNOWN | 13 | 30 | G |
| AI809829 | UNKNOWN | 18 | 0 | T |
| AI809831 | UNKNOWN | 18 | 36 | T |
| AI809872 | UNKNOWN | 17 | 0 | T |
| AI809874 | UNKNOWN | 32 | 0 | T |
| AI809894 | UNKNOWN | 15 | 0 | T |
| AI809920 | UNKNOWN | 31 | 0 | T |
| AI809944 | UNKNOWN | 12 | 0 | T |
| AI809950 | UNKNOWN | 15 | 0 | T |
| AI809964 | UNKNOWN | 12 | 0 | T |
| AI809981 | UNKNOWN | 13 | 494 | A |
| AI809997 | UNKNOWN | 22 | 0 | T |
| AI810018 | UNKNOWN | 22 | 0 | T |
| AI810054 | UNKNOWN | 12 | 0 | T |
| AI810095 | UNKNOWN | 14 | 0 | T |
| AI810166 | UNKNOWN | 31 | 0 | T |
| AI810186 | UNKNOWN | 3.8 | 218 | AAAAC |
| AI810186 | UNKNOWN | 12 | 0 | T |
| AI810195 | UNKNOWN | 22 | 0 | T |
| AI810205 | UNKNOWN | 30 | 0 | T |
| AI810223 | UNKNOWN | 16 | 179 | T |
| AI810278 | UNKNOWN | 31 | 0 | T |
| AI810296 | UNKNOWN | 19 | 430 | T |
| AI810296 | UNKNOWN | 13 | 0 | T |
| AI810317 | UNKNOWN | 46 | 0 | T |
| AI810367 | UNKNOWN | 23 | 0 | T |
| AI810379 | UNKNOWN | 21 | 0 | T |
| AI810397 | UNKNOWN | 15 | 0 | T |
| AI810534 | UNKNOWN | 19 | 12 | T |
| AI810544 | UNKNOWN | 50 | 0 | T |
| AI810589 | UNKNOWN | 59 | 0 | T |
| AI810589 | UNKNOWN | 16 | 141 | G |
| AI810593 | UNKNOWN | 22 | 0 | T |
| AI810665 | UNKNOWN | 28 | 0 | T |
| AI810751 | UNKNOWN | 44 | 0 | T |

TABLE 1-continued

| Genbank # | Region | # reps | Position | Unit sequence |
|---|---|---|---|---|
| AI810779 | UNKNOWN | 44 | 0 | T |
| AI810827 | UNKNOWN | 18 | 398 | T |
| AI810845 | UNKNOWN | 34 | 0 | T |
| AI810944 | UNKNOWN | 14 | 0 | T |
| AI810964 | UNKNOWN | 61 | 0 | T |
| AI810964 | UNKNOWN | 13 | 328 | C |
| AI810964 | UNKNOWN | 12 | 86 | G |
| AI810964 | UNKNOWN | 12 | 316 | A |
| AI811097 | UNKNOWN | 16 | 436 | A |
| AI811111 | UNKNOWN | 16 | 0 | T |
| AI811147 | UNKNOWN | 41 | 0 | T |
| AI811147 | UNKNOWN | 15 | 139 | A |
| AI811148 | UNKNOWN | 40 | 0 | T |
| AI811160 | UNKNOWN | 48 | 0 | T |
| AI811168 | UNKNOWN | 96 | 2 | T |
| AI811168 | UNKNOWN | 22 | 191 | C |
| AI811168 | UNKNOWN | 15 | 248 | A |
| AI811171 | UNKNOWN | 56 | 0 | T |
| AI811173 | UNKNOWN | 52 | 0 | T |
| AI811195 | UNKNOWN | 29 | 0 | T |
| AI811195 | UNKNOWN | 13 | 53 | A |
| AI811210 | UNKNOWN | 16 | 0 | T |
| AI811221 | UNKNOWN | 3.8 | 69 | GCTCT |
| AI811307 | UNKNOWN | 69 | 0 | T |
| AI811307 | UNKNOWN | 12 | 71 | G |
| AI811311 | UNKNOWN | 42 | 0 | T |
| AI811311 | UNKNOWN | 20 | 126 | G |
| AI811311 | UNKNOWN | 13 | 109 | A |
| AI811336 | UNKNOWN | 43 | 0 | T |
| AI811336 | UNKNOWN | 14 | 252 | A |
| AI811342 | UNKNOWN | 39 | 0 | T |
| AI811344 | UNKNOWN | 113 | 1 | T |
| AI811344 | UNKNOWN | 22 | 167 | C |
| AI811344 | UNKNOWN | 16 | 118 | A |
| AI811344 | UNKNOWN | 16 | 139 | G |
| AI811345 | UNKNOWN | 22 | 270 | T |
| AI811353 | UNKNOWN | 120 | 0 | T |
| AI811353 | UNKNOWN | 17 | 362 | C |
| AI811353 | UNKNOWN | 14 | 166 | G |
| AI811353 | UNKNOWN | 13 | 201 | A |
| AI811353 | UNKNOWN | 13 | 221 | C |
| AI811373 | UNKNOWN | 58 | 1 | T |
| AI811373 | UNKNOWN | 18 | 183 | C |
| AI811373 | UNKNOWN | 18 | 218 | G |
| AI811373 | UNKNOWN | 12 | 141 | C |
| AI811387 | UNKNOWN | 14 | 0 | T |
| AI811478 | UNKNOWN | 39 | 0 | T |
| AI811520 | UNKNOWN | 90 | 0 | T |
| AI811520 | UNKNOWN | 15 | 233 | C |
| AI811529 | UNKNOWN | 83 | 0 | T |
| AI811572 | UNKNOWN | 25 | 0 | T |
| AI811603 | UNKNOWN | 54 | 0 | T |
| AI811603 | UNKNOWN | 13 | 122 | G |
| AI811612 | UNKNOWN | 46 | 0 | T |
| AI811626 | UNKNOWN | 38 | 0 | T |
| AI811631 | UNKNOWN | 59 | 0 | T |
| AI811639 | UNKNOWN | 38 | 0 | T |
| AI811639 | UNKNOWN | 14 | 241 | A |
| AI811644 | UNKNOWN | 73 | 0 | T |
| AI811666 | UNKNOWN | 87 | 0 | T |
| AI811666 | UNKNOWN | 18 | 285 | G |
| AI811666 | UNKNOWN | 12 | 149 | G |
| AI811684 | UNKNOWN | 76 | 0 | T |
| AI811684 | UNKNOWN | 14 | 320 | G |
| AI811688 | UNKNOWN | 14 | 0 | T |
| AI811774 | UNKNOWN | 18 | 0 | T |
| AI811785 | UNKNOWN | 88 | 0 | T |
| AI811785 | UNKNOWN | 13 | 170 | A |
| AI811785 | UNKNOWN | 12 | 189 | C |
| AI811808 | UNKNOWN | 20 | 0 | T |
| AI811811 | UNKNOWN | 82 | 0 | T |
| AI811811 | UNKNOWN | 13 | 177 | A |
| AI811815 | UNKNOWN | 15 | 0 | T |
| AI811820 | UNKNOWN | 45 | 0 | T |
| AI811820 | UNKNOWN | 12 | 709 | A |
| AI811821 | UNKNOWN | 77 | 0 | T |
| AI811840 | UNKNOWN | 68 | 0 | T |

TABLE 1-continued

| Genbank # | Region | # reps | Position | Unit sequence |
|---|---|---|---|---|
| AI811840 | UNKNOWN | 14 | 150 | C |
| AI811840 | UNKNOWN | 12 | 225 | A |
| AI811845 | UNKNOWN | 119 | 0 | T |
| AI811845 | UNKNOWN | 23 | 312 | G |
| AI811845 | UNKNOWN | 21 | 227 | C |
| AI811845 | UNKNOWN | 16 | 134 | C |
| AI811845 | UNKNOWN | 16 | 156 | A |
| AI811845 | UNKNOWN | 12 | 122 | G |
| AI811846 | UNKNOWN | 4.5 | 373 | AATA |
| AI811860 | UNKNOWN | 78 | 0 | T |
| AI811860 | UNKNOWN | 15 | 141 | A |
| AI811860 | UNKNOWN | 15 | 215 | G |
| AI811863 | UNKNOWN | 121 | 0 | T |
| AI811863 | UNKNOWN | 21 | 167 | C |
| AI811863 | UNKNOWN | 18 | 224 | G |
| AI811863 | UNKNOWN | 12 | 147 | A |
| AI811865 | UNKNOWN | 39 | 0 | T |
| AI811868 | UNKNOWN | 45 | 0 | T |
| AI811911 | UNKNOWN | 51 | 0 | T |
| AI811912 | UNKNOWN | 82 | 0 | T |
| AI811957 | UNKNOWN | 38 | 0 | T |
| AI812003 | UNKNOWN | 63 | 0 | T |
| AI812003 | UNKNOWN | 12 | 191 | C |
| AI812014 | UNKNOWN | 25 | 0 | T |
| AI812015 | UNKNOWN | 84 | 0 | T |
| AI812015 | UNKNOWN | 17 | 158 | G |
| AI812015 | UNKNOWN | 13 | 135 | C |
| AI812032 | UNKNOWN | 87 | 0 | T |
| AI812032 | UNKNOWN | 15 | 173 | G |
| AI812032 | UNKNOWN | 14 | 159 | A |
| AI812032 | UNKNOWN | 12 | 272 | C |
| AI812075 | UNKNOWN | 27 | 388 | T |
| AI812080 | UNKNOWN | 117 | 0 | T |
| AI812080 | UNKNOWN | 25 | 126 | A |
| AI812080 | UNKNOWN | 19 | 166 | C |
| AI812080 | UNKNOWN | 12 | 151 | G |
| AI812107 | UNKNOWN | 113 | 0 | T |
| AI812107 | UNKNOWN | 24 | 117 | A |
| AI812107 | UNKNOWN | 17 | 163 | G |
| AI812107 | UNKNOWN | 12 | 194 | C |
| AI813522 | UNKNOWN | 16 | 0 | T |
| AI813533 | UNKNOWN | 52 | 0 | T |
| AI813533 | UNKNOWN | 12 | 93 | C |
| AI813547 | UNKNOWN | 24 | 0 | T |
| AI813579 | UNKNOWN | 100 | 0 | T |
| AI813579 | UNKNOWN | 22 | 157 | G |
| AI813579 | UNKNOWN | 15 | 123 | C |
| AI813579 | UNKNOWN | 14 | 138 | A |
| AI813586 | UNKNOWN | 44 | 0 | T |
| AI813614 | UNKNOWN | 17.5 | 289 | CA |
| AI813633 | UNKNOWN | 64 | 0 | T |
| AI813654 | UNKNOWN | 18 | 5 | T |
| AI813799 | UNKNOWN | 4.5 | 25 | TTAT |
| AI813799 | UNKNOWN | 20 | 0 | T |
| AI813868 | UNKNOWN | 69 | 0 | T |
| AI813868 | UNKNOWN | 14 | 335 | G |
| AI813872 | UNKNOWN | 42 | 0 | T |
| AI813875 | UNKNOWN | 5.25 | 52 | ATTT |
| AI813875 | UNKNOWN | 41 | 0 | T |
| AI813882 | UNKNOWN | 45 | 0 | T |
| AI813885 | UNKNOWN | 12 | 0 | T |
| AI813889 | UNKNOWN | 21 | 0 | T |
| AI813893 | UNKNOWN | 8 | 218 | AC |
| AI813893 | UNKNOWN | 16 | 0 | T |
| AI813901 | UNKNOWN | 61 | 17 | T |
| AI813901 | UNKNOWN | 23 | 250 | C |
| AI813901 | UNKNOWN | 15 | 0 | T |
| AI813901 | UNKNOWN | 14 | 275 | G |
| AI813905 | UNKNOWN | 84 | 0 | T |
| AI813905 | UNKNOWN | 22 | 160 | G |
| AI813905 | UNKNOWN | 21 | 98 | C |
| AI813905 | UNKNOWN | 18 | 126 | A |
| AI813913 | UNKNOWN | 59 | 0 | T |
| AI813914 | UNKNOWN | 104 | 27 | T |
| AI813914 | UNKNOWN | 30 | 453 | C |
| AI813914 | UNKNOWN | 22 | 505 | G |
| AI813914 | UNKNOWN | 21 | 5 | T |

TABLE 1-continued

| Genbank # | Region | # reps | Position | Unit sequence |
|---|---|---|---|---|
| AI813914 | UNKNOWN | 21 | 195 | A |
| AI813914 | UNKNOWN | 17 | 223 | G |
| AI813914 | UNKNOWN | 17 | 321 | C |
| AI813919 | UNKNOWN | 84 | 0 | T |
| AI813919 | UNKNOWN | 13 | 278 | A |
| AI813979 | UNKNOWN | 22 | 0 | T |
| AI813986 | UNKNOWN | 73 | 0 | T |
| AI813986 | UNKNOWN | 14 | 267 | A |
| AI814021 | UNKNOWN | 6 | 20 | TATT |
| AI814021 | UNKNOWN | 14 | 0 | T |
| AI814021 | UNKNOWN | 14 | 81 | A |
| AI814025 | UNKNOWN | 62 | 0 | T |
| AI814052 | UNKNOWN | 45 | 0 | T |
| AI814063 | UNKNOWN | 46 | 0 | T |
| AI814063 | UNKNOWN | 14 | 201 | A |
| AI814087 | UNKNOWN | 78 | 0 | T |
| AI814087 | UNKNOWN | 12 | 179 | C |
| AI814118 | UNKNOWN | 24 | 0 | T |
| AI814128 | UNKNOWN | 19 | 0 | T |
| AI814140 | UNKNOWN | 46 | 0 | T |
| AI814156 | UNKNOWN | 35 | 0 | T |
| AI814165 | UNKNOWN | 30 | 0 | T |
| AI814168 | UNKNOWN | 40 | 0 | T |
| AI814203 | UNKNOWN | 35 | 0 | T |
| AI814218 | UNKNOWN | 58 | 0 | T |
| AI814317 | UNKNOWN | 85 | 0 | T |
| AI814317 | UNKNOWN | 14 | 402 | A |
| AI814317 | UNKNOWN | 13 | 386 | G |
| AI814594 | UNKNOWN | 61 | 0 | T |
| AI814594 | UNKNOWN | 16 | 214 | G |
| AI614594 | UNKNOWN | 15 | 154 | G |
| AI814774 | UNKNOWN | 43 | 0 | T |
| AI814828 | UNKNOWN | 56 | 0 | T |
| AI814828 | UNKNOWN | 17 | 102 | C |
| AI814838 | UNKNOWN | 36 | 0 | T |
| AI814838 | UNKNOWN | 17 | 195 | A |
| AI814841 | UNKNOWN | 47 | 0 | T |
| AI814848 | UNKNOWN | 43 | 0 | T |
| AI814892 | UNKNOWN | 21 | 95 | A |
| AI814892 | UNKNOWN | 19 | 0 | T |
| AI814916 | UNKNOWN | 43 | 0 | T |
| AI814965 | UNKNOWN | 2.81 | 0 | TTTTTTTTTTTTTTTTTTTTTTATTT (SEQ ID NO: 153) |
| AI814965 | UNKNOWN | 26 | 24 | T |
| AI814965 | UNKNOWN | 23 | 0 | T |
| AI814965 | UNKNOWN | 17 | 236 | G |
| AI815019 | UNKNOWN | 51 | 0 | T |
| AI815028 | UNKNOWN | 15 | 0 | T |
| AI815065 | UNKNOWN | 61 | 0 | T |
| AI815065 | UNKNOWN | 15 | 164 | G |
| AI815074 | UNKNOWN | 38 | 0 | T |
| AI815080 | UNKNOWN | 49 | 0 | T |
| AI815087 | UNKNOWN | 42 | 0 | T |
| AI815087 | UNKNOWN | 12 | 273 | G |
| AI815128 | UNKNOWN | 15 | 0 | T |
| AI815141 | UNKNOWN | 31 | 0 | T |
| AI815162 | UNKNOWN | 55 | 0 | T |
| AI815162 | UNKNOWN | 13 | 334 | G |
| AI815165 | UNKNOWN | 17 | 0 | T |
| AI815237 | UNKNOWN | 90 | 0 | T |
| AI815237 | UNKNOWN | 17 | 209 | C |
| AI815237 | UNKNOWN | 17 | 416 | A |
| AI815237 | UNKNOWN | 16 | 130 | C |
| AI815237 | UNKNOWN | 12 | 146 | G |
| AI815781 | UNKNOWN | 51 | 0 | T |
| AI815876 | UNKNOWN | 18 | 292 | G |
| AI815915 | UNKNOWN | 60 | 0 | T |
| AI815932 | UNKNOWN | 16 | 0 | T |
| AI816010 | UNKNOWN | 97 | 0 | T |
| AI816010 | UNKNOWN | 25 | 231 | G |
| AI816010 | UNKNOWN | 14 | 113 | A |
| AI816010 | UNKNOWN | 12 | 140 | C |
| AI816010 | UNKNOWN | 12 | 191 | G |
| AI816047 | UNKNOWN | 12 | 0 | T |
| AI816067 | UNKNOWN | 28 | 0 | T |
| AI816136 | UNKNOWN | 27 | 0 | T |
| AI816138 | UNKNOWN | 4.8 | 73 | AAAAC |

TABLE 1-continued

| Genbank # | Region | # reps | Position | Unit sequence |
|---|---|---|---|---|
| AI816138 | UNKNOWN | 14 | 0 | T |
| AI816257 | UNKNOWN | 45 | 0 | T |
| AI816257 | UNKNOWN | 12 | 207 | G |
| AI816306 | UNKNOWN | 46 | 0 | T |
| AI816306 | UNKNOWN | 24 | 108 | A |
| AI816306 | UNKNOWN | 14 | 206 | G |
| AI816306 | UNKNOWN | 12 | 46 | A |
| AI816422 | UNKNOWN | 13 | 15 | T |
| AI816793 | UNKNOWN | 14 | 0 | T |
| AI816797 | UNKNOWN | 37 | 0 | T |
| AI816884 | UNKNOWN | 69 | 0 | T |
| AI816947 | UNKNOWN | 100 | 0 | T |
| AI816947 | UNKNOWN | 12 | 219 | G |
| AI816947 | UNKNOWN | 12 | 261 | C |
| AI816954 | UNKNOWN | 75 | 0 | T |
| AI816954 | UNKNOWN | 16 | 75 | G |
| AI816956 | UNKNOWN | 43 | 0 | T |
| AI816980 | UNKNOWN | 48 | 0 | T |
| AI816980 | UNKNOWN | 13 | 163 | G |
| AI816987 | UNKNOWN | 41 | 0 | T |
| AI817029 | UNKNOWN | 5.66 | 482 | TGC |
| AI817103 | UNKNOWN | 69 | 0 | T |
| AI817103 | UNKNOWN | 13 | 93 | C |
| AI817125 | UNKNOWN | 19 | 0 | T |
| AI817150 | UNKNOWN | 14 | 360 | T |
| AI817152 | UNKNOWN | 42 | 0 | T |
| AI817172 | UNKNOWN | 14 | 157 | A |
| AI817179 | UNKNOWN | 48 | 0 | T |
| AI817179 | UNKNOWN | 13 | 82 | A |
| AI817226 | UNKNOWN | 17 | 11 | T |
| AI817237 | UNKNOWN | 89 | 0 | T |
| AI817237 | UNKNOWN | 16 | 407 | C |
| AI817237 | UNKNOWN | 12 | 338 | G |
| AI817242 | UNKNOWN | 12 | 85 | A |
| AI817244 | UNKNOWN | 96 | 11 | T |
| AI817253 | UNKNOWN | 50 | 0 | T |
| AI817279 | UNKNOWN | 12 | 0 | T |
| AI817292 | UNKNOWN | 14 | 0 | T |
| AI817381 | UNKNOWN | 4.75 | 33 | TTTA |
| AI817403 | UNKNOWN | 23 | 0 | T |
| AI817458 | UNKNOWN | 16 | 0 | T |
| AI817468 | UNKNOWN | 14 | 0 | T |
| AI817487 | UNKNOWN | 55 | 0 | T |
| AI817492 | UNKNOWN | 55 | 0 | T |
| AI817504 | UNKNOWN | 33 | 0 | T |
| AI817516 | UNKNOWN | 4.5 | 148 | TTAT |
| AI817523 | UNKNOWN | 71 | 0 | T |
| AI817523 | UNKNOWN | 14 | 114 | C |
| AI817543 | UNKNOWN | 104 | 0 | T |
| AI817543 | UNKNOWN | 14 | 377 | C |
| AI817543 | UNKNOWN | 13 | 149 | A |
| AI817543 | UNKNOWN | 12 | 162 | G |
| AI817545 | UNKNOWN | 44 | 12 | T |
| AI817552 | UNKNOWN | 85 | 0 | T |
| AI817552 | UNKNOWN | 15 | 112 | A |
| AI817584 | UNKNOWN | 51 | 0 | T |
| AI817584 | UNKNOWN | 16 | 374 | G |
| AI817584 | UNKNOWN | 12 | 264 | G |
| AI817584 | UNKNOWN | 12 | 411 | C |
| AI817608 | UNKNOWN | 14 | 0 | T |
| AI817708 | UNKNOWN | 18 | 1 | T |
| AI817717 | UNKNOWN | 4.75 | 355 | AATC |
| AI817717 | UNKNOWN | 19 | 1 | T |
| AI817732 | UNKNOWN | 28 | 0 | T |
| AI817736 | UNKNOWN | 18 | 0 | T |
| AI817785 | UNKNOWN | 22 | 0 | T |
| AI817796 | UNKNOWN | 55 | 0 | T |
| AI817833 | UNKNOWN | 35 | 0 | T |
| AI817881 | UNKNOWN | 7.5 | 47 | AG |
| AI817925 | UNKNOWN | 51 | 0 | T |
| AI817969 | UNKNOWN | 16 | 321 | A |
| AI817975 | UNKNOWN | 16 | 276 | T |
| AI818003 | UNKNOWN | 13 | 432 | T |
| AI818065 | UNKNOWN | 45 | 0 | T |
| AI818101 | UNKNOWN | 4.2 | 85 | AACAA |
| AI818109 | UNKNOWN | 6.33 | 13 | TGG |
| AI818133 | UNKNOWN | 22 | 0 | T |

TABLE 1-continued

| Genbank # | Region | # reps | Position | Unit sequence |
|---|---|---|---|---|
| AI818151 | UNKNOWN | 23 | 0 | T |
| AI818204 | UNKNOWN | 72 | 0 | T |
| AI818204 | UNKNOWN | 16 | 299 | G |
| AI818206 | UNKNOWN | 124 | 0 | T |
| AI818206 | UNKNOWN | 17 | 349 | G |
| AI818206 | UNKNOWN | 14 | 262 | C |
| AI818206 | UNKNOWN | 13 | 161 | C |
| AI818206 | UNKNOWN | 13 | 203 | G |
| AI818213 | UNKNOWN | 68 | 0 | T |
| AI818213 | UNKNOWN | 14 | 193 | C |
| AI818213 | UNKNOWN | 14 | 349 | G |
| AI818215 | UNKNOWN | 39 | 0 | T |
| AI818225 | UNKNOWN | 98 | 0 | T |
| AI818225 | UNKNOWN | 15 | 134 | G |
| AI818225 | UNKNOWN | 13 | 149 | C |
| AI818320 | UNKNOWN | 55 | 0 | T |
| AI818324 | UNKNOWN | 61 | 0 | T |
| AI818324 | UNKNOWN | 15 | 119 | C |
| AI818349 | UNKNOWN | 20 | 191 | T |
| AI818350 | UNKNOWN | 52 | 0 | T |
| AI818350 | UNKNOWN | 14 | 52 | A |
| AI818353 | UNKNOWN | 70 | 0 | T |
| AI818365 | UNKNOWN | 19 | 0 | T |
| AI818436 | UNKNOWN | 27 | 0 | T |
| AI818485 | UNKNOWN | 36 | 0 | T |
| AI818574 | UNKNOWN | 77 | 0 | T |
| AI818574 | UNKNOWN | 12 | 99 | A |
| AI818578 | UNKNOWN | 78 | 0 | T |
| AI818578 | UNKNOWN | 15 | 137 | G |
| AI818596 | UNKNOWN | 31 | 0 | T |
| AI818669 | UNKNOWN | 14 | 0 | T |
| AI818676 | UNKNOWN | 25 | 0 | T |
| AI818683 | UNKNOWN | 130 | 0 | T |
| AI818683 | UNKNOWN | 26 | 260 | G |
| AI818683 | UNKNOWN | 24 | 229 | C |
| AI818683 | UNKNOWN | 13 | 130 | A |
| AI818728 | UNKNOWN | 60 | 0 | T |
| AI818728 | UNKNOWN | 15 | 135 | G |
| AI818728 | UNKNOWN | 15 | 286 | A |
| AI818731 | UNKNOWN | 36 | 0 | T |
| AI818737 | UNKNOWN | 16 | 203 | T |
| AI818767 | UNKNOWN | 30 | 0 | T |
| AI818772 | UNKNOWN | 41 | 0 | T |
| AI818772 | UNKNOWN | 15 | 41 | A |
| AI818777 | UNKNOWN | 41 | 0 | T |
| AI818778 | UNKNOWN | 33 | 0 | T |
| AI818784 | UNKNOWN | 52 | 0 | T |
| AI818784 | UNKNOWN | 19 | 196 | G |
| AI818784 | UNKNOWN | 12 | 135 | C |
| AI818805 | UNKNOWN | 42 | 0 | T |
| AI818866 | UNKNOWN | 31 | 0 | T |
| AI818887 | UNKNOWN | 88 | 0 | T |
| AI818887 | UNKNOWN | 22 | 147 | G |
| AI818887 | UNKNOWN | 17 | 325 | C |
| AI818887 | UNKNOWN | 15 | 88 | C |
| AI818896 | UNKNOWN | 39 | 0 | T |
| AI818900 | UNKNOWN | 41 | 0 | T |
| AI818900 | UNKNOWN | 14 | 390 | A |
| AI818921 | UNKNOWN | 19 | 335 | T |
| AI818936 | UNKNOWN | 67 | 0 | T |
| AI818954 | UNKNOWN | 67 | 0 | T |
| AI818977 | UNKNOWN | 108 | 0 | T |
| AI818977 | UNKNOWN | 28 | 327 | C |
| AI818977 | UNKNOWN | 15 | 207 | G |
| AI818977 | UNKNOWN | 13 | 309 | A |
| AI818980 | UNKNOWN | 93 | 0 | T |
| AI818980 | UNKNOWN | 13 | 188 | G |
| AI818980 | UNKNOWN | 13 | 247 | A |
| AI818980 | UNKNOWN | 12 | 93 | A |
| AI819008 | UNKNOWN | 48 | 0 | T |
| AI819016 | UNKNOWN | 54 | 0 | T |
| AI819035 | UNKNOWN | 16 | 0 | T |
| AI819052 | UNKNOWN | 13 | 0 | T |
| AI819106 | UNKNOWN | 65 | 0 | T |
| AI819140 | UNKNOWN | 4.75 | 305 | ATAC |
| AI819140 | UNKNOWN | 14 | 321 | AT |
| AI819140 | UNKNOWN | 29 | 348 | T |

TABLE 1-continued

| Genbank # | Region | # reps | Position | Unit sequence |
|---|---|---|---|---|
| AI819164 | UNKNOWN | 3.6 | 186 | CAGAA |
| AI819198 | UNKNOWN | 14 | 0 | T |
| AI819202 | UNKNOWN | 68 | 0 | T |
| AI819202 | UNKNOWN | 16 | 378 | C |
| AI819202 | UNKNOWN | 15 | 363 | G |
| AI819202 | UNKNOWN | 12 | 241 | A |
| AI819224 | UNKNOWN | 13 | 0 | T |
| AI819282 | UNKNOWN | 2.75 | 320 | ATATATATAGTT (SEQ ID NO: 154) |
| AI819326 | UNKNOWN | 102 | 0 | T |
| AI819326 | UNKNOWN | 20 | 221 | A |
| AI819326 | UNKNOWN | 14 | 102 | A |
| AI819326 | UNKNOWN | 13 | 171 | C |
| AI819327 | UNKNOWN | 13 | 302 | A |
| AI819419 | UNKNOWN | 22 | 26 | A |
| AI819425 | UNKNOWN | 13 | 0 | T |
| AI819460 | UNKNOWN | 13 | 2 | T |
| AI819498 | UNKNOWN | 23 | 0 | T |
| AI819516 | UNKNOWN | 40 | 19 | T |
| AI819516 | UNKNOWN | 17 | 1 | T |
| AI819516 | UNKNOWN | 13 | 240 | C |
| AI819522 | UNKNOWN | 72 | 0 | T |
| AI819522 | UNKNOWN | 16 | 195 | G |
| AI819522 | UNKNOWN | 15 | 121 | C |
| AI819545 | UNKNOWN | 57 | 0 | T |
| AI819545 | UNKNOWN | 12 | 57 | A |
| AI819555 | UNKNOWN | 68 | 0 | T |
| AI819555 | UNKNOWN | 12 | 334 | G |
| AI819631 | UNKNOWN | 45 | 0 | T |
| AI819663 | UNKNOWN | 54 | 0 | T |
| AI819700 | UNKNOWN | 44 | 0 | T |
| AI819925 | UNKNOWN | 15 | 203 | T |
| AI819958 | UNKNOWN | 81 | 0 | T |
| AI819958 | UNKNOWN | 15 | 223 | G |
| AI819958 | UNKNOWN | 13 | 241 | C |
| AI819970 | UNKNOWN | 109 | 0 | T |
| AI819970 | UNKNOWN | 26 | 324 | C |
| AI819970 | UNKNOWN | 15 | 208 | G |
| AI819970 | UNKNOWN | 14 | 139 | C |
| AI819970 | UNKNOWN | 14 | 158 | G |
| AI819976 | UNKNOWN | 92 | 0 | T |
| AI819976 | UNKNOWN | 13 | 229 | G |
| AI819976 | UNKNOWN | 13 | 246 | A |
| AI820047 | UNKNOWN | 58 | 0 | T |
| AI820047 | UNKNOWN | 15 | 166 | G |
| AI820049 | UNKNOWN | 13 | 195 | T |
| AI820050 | UNKNOWN | 10 | 8 | AT |
| AI820076 | UNKNOWN | 24 | 0 | T |
| AI820535 | UNKNOWN | 5 | 437 | TTAT |
| AI820535 | UNKNOWN | 19.5 | 505 | CA |
| AI820567 | UNKNOWN | 8.5 | 345 | TTTA |
| AI820580 | UNKNOWN | 15 | 423 | T |
| AI820598 | UNKNOWN | 4.75 | 147 | TTTG |
| AI820617 | UNKNOWN | 16 | 404 | T |
| AI820628 | UNKNOWN | 6.33 | 349 | TTG |
| AI820642 | UNKNOWN | 14.5 | 30 | CT |
| AI820642 | UNKNOWN | 12 | 58 | CA |
| AI820646 | UNKNOWN | 13 | 33 | GT |
| AI820646 | UNKNOWN | 17 | 0 | T |
| AI820650 | UNKNOWN | 13 | 313 | T |
| AI820651 | UNKNOWN | 11 | 334 | ATACA |
| AI820664 | UNKNOWN | 24 | 310 | T |
| AI820669 | UNKNOWN | 16 | 450 | T |
| AI820693 | UNKNOWN | 16 | 17 | A |
| AI820740 | UNKNOWN | 6.5 | 332 | CT |
| AI820751 | UNKNOWN | 7 | 399 | GT |
| AI820751 | UNKNOWN | 19 | 512 | A |
| AI820772 | UNKNOWN | 4.75 | 154 | TAAA |
| AI820794 | UNKNOWN | 19 | 0 | T |
| AI820796 | UNKNOWN | 13 | 299 | A |
| AI820797 | UNKNOWN | 3.83 | 163 | GAAGAG |
| AI820797 | UNKNOWN | 17 | 109 | AAG |
| AI820797 | UNKNOWN | 18 | 0 | T |
| AI820798 | UNKNOWN | 31 | 0 | T |
| AI820840 | UNKNOWN | 5.75 | 498 | AAAT |
| AI820840 | UNKNOWN | 23 | 400 | T |
| AI820859 | UNKNOWN | 24 | 437 | A |
| AI820863 | UNKNOWN | 12 | 432 | A |

TABLE 1-continued

| Genbank # | Region | # reps | Position | Unit sequence |
|---|---|---|---|---|
| AI820883 | UNKNOWN | 15 | 0 | T |
| AI820887 | UNKNOWN | 30 | 231 | A |
| AI820888 | UNKNOWN | 12 | 171 | A |
| AI820891 | UNKNOWN | 19 | 137 | A |
| AI820909 | UNKNOWN | 14 | 438 | A |
| AI820928 | UNKNOWN | 22 | 433 | A |
| AI820950 | UNKNOWN | 4.4 | 365 | TTTTA |
| AI820950 | UNKNOWN | 19 | 6 | T |
| AI820954 | UNKNOWN | 4.5 | 331 | AAAC |
| AI820954 | UNKNOWN | 12 | 482 | A |
| AI820955 | UNKNOWN | 14 | 34 | T |
| AI820964 | UNKNOWN | 15 | 31 | T |
| AI820966 | UNKNOWN | 35 | 31 | T |
| AI820983 | UNKNOWN | 16 | 31 | T |
| AI820988 | UNKNOWN | 9.6 | 38 | TTTGT |
| AI820988 | UNKNOWN | 16 | 6 | T |
| AI821008 | UNKNOWN | 16 | 114 | A |
| AI821062 | UNKNOWN | 62 | 334 | A |
| AI821072 | UNKNOWN | 14 | 31 | T |
| AI821076 | UNKNOWN | 14 | 31 | T |
| AI821079 | UNKNOWN | 17 | 31 | T |
| AI821081 | UNKNOWN | 16 | 31 | T |
| AI821101 | UNKNOWN | 15 | 6 | T |
| AI821102 | UNKNOWN | 16 | 31 | T |
| AI821116 | UNKNOWN | 13 | 135 | A |
| AI821116 | UNKNOWN | 12 | 31 | T |
| AI821118 | UNKNOWN | 16 | 30 | T |
| AI821126 | UNKNOWN | 13 | 30 | T |
| AI821135 | UNKNOWN | 14 | 31 | T |
| AI821136 | UNKNOWN | 17 | 32 | T |
| AI821188 | UNKNOWN | 3.8 | 131 | CAAAA |
| AI821230 | UNKNOWN | 15 | 6 | T |
| AI821232 | UNKNOWN | 15 | 404 | A |
| AI821234 | UNKNOWN | 15 | 6 | T |
| AI821235 | UNKNOWN | 17 | 6 | T |
| AI821239 | UNKNOWN | 15 | 244 | A |
| AI821241 | UNKNOWN | 15 | 441 | A |
| AI821243 | UNKNOWN | 16 | 6 | T |
| AI821251 | UNKNOWN | 19 | 106 | T |
| AI821259 | UNKNOWN | 58 | 141 | A |
| AI821270 | UNKNOWN | 17 | 0 | T |
| AI821273 | UNKNOWN | 15 | 0 | T |
| AI821276 | UNKNOWN | 19 | 0 | T |
| AI821293 | UNKNOWN | 17 | 0 | T |
| AI821299 | UNKNOWN | 14 | 28 | A |
| AI821302 | UNKNOWN | 9 | 203 | AC |
| AI821309 | UNKNOWN | 17 | 5 | T |
| AI821318 | UNKNOWN | 21 | 173 | A |
| AI821329 | UNKNOWN | 17 | 294 | T |
| AI821331 | UNKNOWN | 3.8 | 80 | TTTTG |
| AI821358 | UNKNOWN | 5.16 | 0 | ATTTTT |
| AI821379 | UNKNOWN | 17 | 0 | T |
| AI821401 | UNKNOWN | 8 | 27 | TG |
| AI821401 | UNKNOWN | 19 | 0 | T |
| AI821415 | UNKNOWN | 15 | 299 | A |
| AI821416 | UNKNOWN | 17 | 8 | T |
| AI821417 | UNKNOWN | 14 | 191 | A |
| AI821420 | UNKNOWN | 20 | 26 | T |
| AI821421 | UNKNOWN | 18 | 39 | T |
| AI821430 | UNKNOWN | 13 | 8 | T |
| AI821438 | UNKNOWN | 21 | 6 | T |
| AI821440 | UNKNOWN | 18 | 8 | T |
| AI821444 | UNKNOWN | 20 | 0 | T |
| AI821450 | UNKNOWN | 31 | 0 | T |
| AI821465 | UNKNOWN | 13 | 303 | A |
| AI821466 | UNKNOWN | 18 | 318 | A |
| AI821467 | UNKNOWN | 33 | 17 | T |
| AI821468 | UNKNOWN | 16 | 41 | T |
| AI821469 | UNKNOWN | 3.8 | 359 | AAAAC |
| AI821479 | UNKNOWN | 18 | 5 | T |
| AI821480 | UNKNOWN | 21 | 5 | T |
| AI821482 | UNKNOWN | 22 | 5 | T |
| AI821486 | UNKNOWN | 14 | 5 | T |
| AI821496 | UNKNOWN | 22 | 8 | T |
| AI821503 | UNKNOWN | 15 | 325 | A |
| AI821504 | UNKNOWN | 14 | 122 | T |
| AI821517 | UNKNOWN | 12 | 8 | T |

TABLE 1-continued

| Genbank # | Region | # reps | Position | Unit sequence |
|---|---|---|---|---|
| AI821551 | UNKNOWN | 17 | 0 | T |
| AI821595 | UNKNOWN | 18 | 8 | T |
| AI821602 | UNKNOWN | 18 | 8 | T |
| AI821602 | UNKNOWN | 12 | 94 | A |
| AI821605 | UNKNOWN | 15 | 9 | T |
| AI821620 | UNKNOWN | 27 | 0 | T |
| AI821631 | UNKNOWN | 7 | 244 | TC |
| AI821691 | UNKNOWN | 6.5 | 220 | AC |
| AI821699 | UNKNOWN | 12 | 0 | T |
| AI821701 | UNKNOWN | 13 | 0 | T |
| AI821706 | UNKNOWN | 40 | 0 | T |
| AI821711 | UNKNOWN | 13 | 0 | T |
| AI821721 | UNKNOWN | 12 | 0 | T |
| AI821726 | UNKNOWN | 12 | 0 | T |
| AI821740 | UNKNOWN | 13 | 0 | T |
| AI821745 | UNKNOWN | 35 | 8 | T |
| AI821746 | UNKNOWN | 17 | 8 | T |
| AI821752 | UNKNOWN | 6.5 | 432 | GT |
| AI821764 | UNKNOWN | 19 | 0 | T |
| AI821778 | UNKNOWN | 18 | 0 | T |
| AI821780 | UNKNOWN | 23 | 0 | T |
| AI821787 | UNKNOWN | 14 | 8 | T |
| AI821790 | UNKNOWN | 13 | 0 | T |
| AI821803 | UNKNOWN | 20 | 33 | T |
| AI821804 | UNKNOWN | 14 | 33 | T |
| AI821807 | UNKNOWN | 27 | 0 | T |
| AI821809 | UNKNOWN | 52 | 0 | T |
| AI821815 | UNKNOWN | 19 | 8 | T |
| AI821822 | UNKNOWN | 18 | 26 | T |
| AI821837 | UNKNOWN | 25 | 8 | T |
| AI821841 | UNKNOWN | 17 | 33 | T |
| AI821858 | UNKNOWN | 37 | 0 | T |
| AI821864 | UNKNOWN | 22 | 39 | T |
| AI821866 | UNKNOWN | 24 | 39 | T |
| AI821867 | UNKNOWN | 19 | 38 | T |
| AI821871 | UNKNOWN | 15 | 401 | A |
| AI821886 | UNKNOWN | 12 | 33 | T |
| AI821900 | UNKNOWN | 16 | 9 | T |
| AI821904 | UNKNOWN | 18 | 361 | A |
| AI821913 | UNKNOWN | 15 | 33 | T |
| AI821914 | UNKNOWN | 13 | 21 | T |
| AI821916 | UNKNOWN | 19 | 8 | T |
| AI821917 | UNKNOWN | 27 | 8 | T |
| AI821928 | UNKNOWN | 15 | 445 | A |
| AI821935 | UNKNOWN | 19 | 24 | T |
| AI821953 | UNKNOWN | 18 | 33 | T |
| AI821955 | UNKNOWN | 16 | 21 | T |
| AI821957 | UNKNOWN | 15 | 0 | T |
| AI821968 | UNKNOWN | 12 | 0 | T |
| AI821975 | UNKNOWN | 24 | 24 | T |
| AI821978 | UNKNOWN | 17 | 8 | T |
| AI821980 | UNKNOWN | 18 | 367 | A |
| AI821981 | UNKNOWN | 16 | 354 | A |
| AI821982 | UNKNOWN | 23 | 21 | T |
| AI821986 | UNKNOWN | 34 | 8 | T |
| AI822027 | UNKNOWN | 12 | 137 | T |
| AI822027 | UNKNOWN | 12 | 455 | A |
| AI822028 | UNKNOWN | 14 | 1 | T |
| AI822047 | UNKNOWN | 2.6 | 285 | GGAAGGTTGT (SEQ ID NO: 155) |
| AI822092 | UNKNOWN | 12 | 0 | T |
| AI822094 | UNKNOWN | 26 | 0 | T |
| AI822097 | UNKNOWN | 13 | 19 | T |
| AI822106 | UNKNOWN | 12 | 0 | T |
| AI822111 | UNKNOWN | 15 | 0 | T |
| AI822120 | UNKNOWN | 4.83 | 189 | TTTTTA |
| AI822125 | UNKNOWN | 12 | 36 | A |
| AI822128 | UNKNOWN | 12 | 203 | T |
| AI823365 | UNKNOWN | 12 | 0 | T |
| AI823392 | UNKNOWN | 18 | 4 | T |
| AI823398 | UNKNOWN | 13 | 404 | A |
| AI823411 | UNKNOWN | 23 | 4 | T |
| AI823457 | UNKNOWN | 26 | 0 | T |
| AI823458 | UNKNOWN | 15 | 4 | T |
| AI823464 | UNKNOWN | 45 | 0 | T |
| AI823484 | UNKNOWN | 20 | 15 | A |
| AI823487 | UNKNOWN | 23 | 0 | T |
| AI823503 | UNKNOWN | 40 | 0 | T |

TABLE 1-continued

| Genbank # | Region | # reps | Position | Unit sequence |
|---|---|---|---|---|
| AI823587 | UNKNOWN | 12 | 0 | T |
| AI823645 | UNKNOWN | 7.5 | 340 | TA |
| AI823670 | UNKNOWN | 95 | 0 | T |
| AI823670 | UNKNOWN | 15 | 126 | G |
| AI823670 | UNKNOWN | 13 | 372 | A |
| AI823670 | UNKNOWN | 12 | 318 | A |
| AI823703 | UNKNOWN | 46 | 0 | T |
| AI823719 | UNKNOWN | 64 | 0 | T |
| AI823719 | UNKNOWN | 14 | 303 | G |
| AI823719 | UNKNOWN | 13 | 69 | A |
| AI823738 | UNKNOWN | 35 | 0 | T |
| AI823780 | UNKNOWN | 17 | 190 | T |
| AI823793 | UNKNOWN | 12 | 0 | T |
| AI823926 | UNKNOWN | 18 | 0 | T |
| AI823935 | UNKNOWN | 15 | 0 | T |
| AI823943 | UNKNOWN | 15 | 0 | T |
| AI823948 | UNKNOWN | 15 | 0 | T |
| AI823958 | UNKNOWN | 16 | 0 | T |
| AI823998 | UNKNOWN | 17 | 0 | T |
| AI824010 | UNKNOWN | 34 | 250 | T |
| AI824060 | UNKNOWN | 18 | 0 | T |
| AI824064 | UNKNOWN | 13.5 | 88 | AC |
| AI824087 | UNKNOWN | 40 | 0 | T |
| AI824149 | UNKNOWN | 13 | 0 | T |
| AI824335 | UNKNOWN | 12 | 19 | A |
| AI824348 | UNKNOWN | 37 | 0 | T |
| AI824360 | UNKNOWN | 74 | 0 | T |
| AI824360 | UNKNOWN | 16 | 271 | G |
| AI824361 | UNKNOWN | 66 | 0 | T |
| AI824361 | UNKNOWN | 25 | 161 | A |
| AI824428 | UNKNOWN | 31 | 0 | T |
| AI824432 | UNKNOWN | 19 | 0 | T |
| AI824437 | UNKNOWN | 37 | 0 | T |
| AI824444 | UNKNOWN | 107 | 13 | T |
| AI824444 | UNKNOWN | 18 | 228 | A |
| AI824444 | UNKNOWN | 16 | 139 | A |
| AI824444 | UNKNOWN | 14 | 159 | G |
| AI824455 | UNKNOWN | 28 | 0 | T |
| AI824497 | UNKNOWN | 67 | 0 | T |
| AI824497 | UNKNOWN | 13 | 292 | G |
| AI824501 | UNKNOWN | 41 | 0 | T |
| AI824503 | UNKNOWN | 56 | 0 | T |
| AI824557 | UNKNOWN | 104 | 0 | T |
| AI824557 | UNKNOWN | 17 | 224 | C |
| AI824557 | UNKNOWN | 16 | 134 | A |
| AI824576 | UNKNOWN | 83 | 0 | T |
| AI824576 | UNKNOWN | 12 | 178 | G |
| AI824591 | UNKNOWN | 23 | 5 | T |
| AI824688 | UNKNOWN | 55 | 0 | T |
| AI824688 | UNKNOWN | 14 | 55 | A |
| AI824706 | UNKNOWN | 8.75 | 12 | TTTA |
| AI824723 | UNKNOWN | 21 | 0 | T |
| AI824746 | UNKNOWN | 101 | 0 | T |
| AI824746 | UNKNOWN | 19 | 169 | G |
| AI824746 | UNKNOWN | 14 | 246 | C |
| AI824748 | UNKNOWN | 59 | 0 | T |
| AI824761 | UNKNOWN | 58 | 0 | T |
| AI824764 | UNKNOWN | 102 | 0 | T |
| AI824764 | UNKNOWN | 20 | 169 | A |
| AI824765 | UNKNOWN | 12 | 2 | T |
| AI824894 | UNKNOWN | 18 | 0 | T |
| AI824954 | UNKNOWN | 32 | 0 | T |
| AI825073 | UNKNOWN | 17 | 0 | T |
| AI825078 | UNKNOWN | 20 | 0 | T |
| AI825101 | UNKNOWN | 5.75 | 7 | TTTA |
| AI825114 | UNKNOWN | 18 | 274 | T |
| AI825133 | UNKNOWN | 32 | 0 | T |
| AI825139 | UNKNOWN | 24 | 0 | T |
| AI825256 | UNKNOWN | 12 | 172 | A |
| AI825264 | UNKNOWN | 72 | 0 | T |
| AI825264 | UNKNOWN | 15 | 249 | G |
| AI825264 | UNKNOWN | 13 | 216 | G |
| AI825264 | UNKNOWN | 12 | 116 | A |
| AI825330 | UNKNOWN | 12 | 107 | T |
| AI825335 | UNKNOWN | 29 | 0 | T |
| AI825339 | UNKNOWN | 14 | 4 | T |
| AI825341 | UNKNOWN | 19 | 0 | T |

TABLE 1-continued

| Genbank # | Region | # reps | Position | Unit sequence |
|---|---|---|---|---|
| AI825372 | UNKNOWN | 13 | 0 | T |
| AI825891 | UNKNOWN | 29 | 0 | T |
| AI825956 | UNKNOWN | 91 | 0 | T |
| AI825956 | UNKNOWN | 16 | 403 | A |
| AI825956 | UNKNOWN | 14 | 136 | C |
| AI825956 | UNKNOWN | 12 | 202 | G |
| AI825964 | UNKNOWN | 57 | 0 | T |
| AI825964 | UNKNOWN | 18 | 92 | A |
| AI825964 | UNKNOWN | 13 | 228 | G |
| AI826029 | UNKNOWN | 16 | 0 | T |
| AI826091 | UNKNOWN | 17 | 0 | T |
| AI826123 | UNKNOWN | 41 | 0 | T |
| AI826212 | UNKNOWN | 49 | 0 | T |
| AI826216 | UNKNOWN | 26 | 0 | T |
| AI826216 | UNKNOWN | 14 | 144 | A |
| AI826225 | UNKNOWN | 88 | 0 | T |
| AI826225 | UNKNOWN | 14 | 169 | A |
| AI826225 | UNKNOWN | 12 | 189 | C |
| AI826230 | UNKNOWN | 52 | 0 | T |
| AI826244 | UNKNOWN | 38 | 0 | T |
| AI826245 | UNKNOWN | 33 | 0 | T |
| AI826300 | UNKNOWN | 35 | 0 | T |
| AI826331 | UNKNOWN | 62 | 0 | T |
| AI826331 | UNKNOWN | 12 | 223 | C |
| AI826336 | UNKNOWN | 64 | 0 | T |
| AI826406 | UNKNOWN | 34 | 0 | T |
| AI826415 | UNKNOWN | 61 | 0 | T |
| AI826422 | UNKNOWN | 12 | 492 | T |
| AI826431 | UNKNOWN | 53 | 0 | T |
| AI826431 | UNKNOWN | 18 | 371 | A |
| AI826431 | UNKNOWN | 14 | 241 | C |
| AI826434 | UNKNOWN | 18 | 4 | T |
| AI826449 | UNKNOWN | 53 | 0 | T |
| AI826449 | UNKNOWN | 19 | 241 | C |
| AI826449 | UNKNOWN | 18 | 371 | A |
| AI826453 | UNKNOWN | 23 | 0 | T |
| AI826481 | UNKNOWN | 45 | 38 | T |
| AI826481 | UNKNOWN | 37 | 0 | T |
| AI826481 | UNKNOWN | 12 | 201 | A |
| AI826481 | UNKNOWN | 12 | 226 | C |
| AI826498 | UNKNOWN | 14 | 16 | T |
| AI826553 | UNKNOWN | 14 | 25 | T |
| AI826631 | UNKNOWN | 35 | 0 | T |
| AI826636 | UNKNOWN | 46 | 0 | T |
| AI826761 | UNKNOWN | 4.75 | 22 | TTTA |
| AI826809 | UNKNOWN | 5.66 | 335 | AAC |
| AI826857 | UNKNOWN | 5.8 | 44 | TTTTC |
| AI826857 | UNKNOWN | 14 | 69 | T |
| AI826868 | UNKNOWN | 49 | 0 | T |
| AI826891 | UNKNOWN | 38 | 0 | T |
| AI826996 | UNKNOWN | 12 | 0 | T |
| AI826999 | UNKNOWN | 16 | 17 | T |
| AI827003 | UNKNOWN | 57 | 0 | T |
| AI827003 | UNKNOWN | 12 | 88 | C |
| AI827019 | UNKNOWN | 21 | 0 | T |
| AI827053 | UNKNOWN | 33 | 0 | T |
| AI827058 | UNKNOWN | 62 | 0 | T |
| AI827058 | UNKNOWN | 18 | 135 | C |
| AI827058 | UNKNOWN | 13 | 90 | C |
| AI827058 | UNKNOWN | 13 | 260 | G |
| AI827122 | UNKNOWN | 15 | 0 | T |
| AI827131 | UNKNOWN | 23 | 0 | T |
| AI827154 | UNKNOWN | 77 | 0 | T |
| AI827154 | UNKNOWN | 17 | 245 | G |
| AI827154 | UNKNOWN | 13 | 77 | A |
| AI827212 | UNKNOWN | 57 | 0 | T |
| AI827222 | UNKNOWN | 6 | 99 | AGC |
| AI827226 | UNKNOWN | 69 | 0 | T |
| AI827226 | UNKNOWN | 12 | 98 | A |
| AI827229 | UNKNOWN | 44 | 0 | T |
| AI827230 | UNKNOWN | 12 | 0 | T |
| AI827238 | UNKNOWN | 12 | 357 | T |
| AI827309 | UNKNOWN | 28 | 0 | T |
| AI827311 | UNKNOWN | 82 | 0 | T |
| AI827311 | UNKNOWN | 15 | 212 | A |
| AI827311 | UNKNOWN | 12 | 144 | A |
| AI827328 | UNKNOWN | 43 | 0 | T |

TABLE 1-continued

| Genbank # | Region | # reps | Position | Unit sequence |
|---|---|---|---|---|
| AI827356 | UNKNOWN | 43 | 0 | T |
| AI827387 | UNKNOWN | 6.5 | 208 | CG |
| AI827387 | UNKNOWN | 6.5 | 222 | TG |
| AI827431 | UNKNOWN | 2.6 | 173 | ATATATATAC (SEQ ID NO: 156) |
| AI827431 | UNKNOWN | 11 | 138 | TA |
| AI827439 | UNKNOWN | 32 | 0 | T |
| AI827440 | UNKNOWN | 67 | 0 | T |
| AI827440 | UNKNOWN | 17 | 164 | C |
| AI827440 | UNKNOWN | 17 | 347 | G |
| AI827440 | UNKNOWN | 15 | 197 | G |
| AI827451 | UNKNOWN | 28 | 0 | T |
| AI827463 | UNKNOWN | 25 | 0 | T |
| AI827466 | UNKNOWN | 15 | 0 | T |
| AI827512 | UNKNOWN | 19 | 0 | T |
| AI827525 | UNKNOWN | 16 | 0 | T |
| AI827561 | UNKNOWN | 16 | 247 | A |
| AI827563 | UNKNOWN | 18 | 1 | T |
| AI827687 | UNKNOWN | 13 | 0 | T |
| AI827749 | UNKNOWN | 28 | 0 | T |
| AI827770 | UNKNOWN | 13 | 0 | T |
| AI827779 | UNKNOWN | 24 | 0 | T |
| AI827799 | UNKNOWN | 14 | 194 | A |
| AI827830 | UNKNOWN | 12.5 | 497 | GA |
| AI827867 | UNKNOWN | 22 | 2 | T |
| AI827900 | UNKNOWN | 21 | 0 | T |
| AI827928 | UNKNOWN | 12 | 0 | T |
| AI827993 | UNKNOWN | 14 | 36 | T |
| AI827998 | UNKNOWN | 34 | 0 | T |
| AI828012 | UNKNOWN | 12 | 358 | A |
| AI828076 | UNKNOWN | 6.66 | 285 | GCC |
| AI828179 | UNKNOWN | 14 | 0 | T |
| AI828226 | UNKNOWN | 62 | 0 | T |
| AI828226 | UNKNOWN | 15 | 126 | C |
| AI828226 | UNKNOWN | 15 | 141 | A |
| AI828239 | UNKNOWN | 58 | 0 | T |
| AI828239 | UNKNOWN | 26 | 210 | G |
| AI828266 | UNKNOWN | 46 | 0 | T |
| AI828285 | UNKNOWN | 45 | 0 | T |
| AI828285 | UNKNOWN | 14 | 91 | C |
| AI828367 | UNKNOWN | 95 | 0 | T |
| AI828367 | UNKNOWN | 20 | 125 | G |
| AI828367 | UNKNOWN | 16 | 109 | A |
| AI828367 | UNKNOWN | 14 | 145 | C |
| AI828412 | UNKNOWN | 65 | 0 | T |
| AI828412 | UNKNOWN | 12 | 342 | C |
| AI828417 | UNKNOWN | 38 | 0 | T |
| AI828418 | UNKNOWN | 54 | 0 | T |
| AI828432 | UNKNOWN | 34 | 0 | T |
| AI828436 | UNKNOWN | 75 | 0 | T |
| AI828436 | UNKNOWN | 25 | 137 | C |
| AI828436 | UNKNOWN | 20 | 117 | A |
| AI828477 | UNKNOWN | 16 | 0 | T |
| AI828489 | UNKNOWN | 23 | 0 | T |
| AI828549 | UNKNOWN | 33 | 0 | T |
| AI828568 | UNKNOWN | 105 | 0 | T |
| AI828568 | UNKNOWN | 20 | 155 | G |
| AI828568 | UNKNOWN | 19 | 206 | C |
| AI828568 | UNKNOWN | 16 | 122 | A |
| AI828589 | UNKNOWN | 17 | 11 | T |
| AI828682 | UNKNOWN | 114 | 0 | T |
| AI828682 | UNKNOWN | 30 | 211 | C |
| AI828682 | UNKNOWN | 13 | 241 | A |
| AI828705 | UNKNOWN | 96 | 0 | T |
| AI828705 | UNKNOWN | 22 | 344 | G |
| AI828705 | UNKNOWN | 21 | 191 | G |
| AI828705 | UNKNOWN | 15 | 176 | C |
| AI828705 | UNKNOWN | 12 | 117 | A |
| AI828714 | UNKNOWN | 99 | 0 | T |
| AI828714 | UNKNOWN | 15 | 253 | C |
| AI828731 | UNKNOWN | 110 | 0 | T |
| AI828731 | UNKNOWN | 20 | 142 | A |
| AI828731 | UNKNOWN | 16 | 180 | C |
| AI828733 | UNKNOWN | 12 | 10 | T |
| AI828734 | UNKNOWN | 62 | 0 | T |
| AI828734 | UNKNOWN | 12 | 382 | A |
| AI828760 | UNKNOWN | 27 | 0 | T |
| AI828795 | UNKNOWN | 64 | 0 | T |

TABLE 1-continued

| Genbank # | Region | # reps | Position | Unit sequence |
|---|---|---|---|---|
| AI828806 | UNKNOWN | 48 | 0 | T |
| AI828818 | UNKNOWN | 111 | 0 | T |
| AI828818 | UNKNOWN | 26 | 296 | G |
| AI828818 | UNKNOWN | 20 | 276 | A |
| AI828818 | UNKNOWN | 16 | 169 | G |
| AI828818 | UNKNOWN | 14 | 155 | A |
| AI828818 | UNKNOWN | 13 | 111 | C |
| AI828827 | UNKNOWN | 14 | 0 | T |
| AI828857 | UNKNOWN | 31 | 0 | T |
| AI828865 | UNKNOWN | 28 | 0 | T |
| AI828887 | UNKNOWN | 11.5 | 512 | TA |
| AI828978 | UNKNOWN | 12 | 0 | T |
| AI829026 | UNKNOWN | 14 | 0 | T |
| AI829036 | UNKNOWN | 15 | 0 | T |
| AI829038 | UNKNOWN | 40 | 0 | T |
| AI829139 | UNKNOWN | 14 | 0 | T |
| AI829176 | UNKNOWN | 41 | 0 | T |
| AI829192 | UNKNOWN | 37 | 0 | T |
| AI829313 | UNKNOWN | 4.5 | 114 | AAGG |
| AI829313 | UNKNOWN | 46 | 0 | T |
| AI829313 | UNKNOWN | 15 | 247 | G |
| AI829327 | UNKNOWN | 91 | 0 | T |
| AI829327 | UNKNOWN | 23 | 148 | G |
| AI829327 | UNKNOWN | 22 | 114 | C |
| AI829330 | UNKNOWN | 78 | 0 | T |
| AI829330 | UNKNOWN | 18 | 348 | C |
| AI829330 | UNKNOWN | 17 | 125 | C |
| AI829330 | UNKNOWN | 14 | 309 | G |
| AI829333 | UNKNOWN | 65 | 0 | T |
| AI829333 | UNKNOWN | 17 | 166 | A |
| AI829342 | UNKNOWN | 50 | 0 | T |
| AI829342 | UNKNOWN | 13 | 333 | G |
| AI829350 | UNKNOWN | 74 | 0 | T |
| AI829350 | UNKNOWN | 18 | 245 | C |
| AI829350 | UNKNOWN | 13 | 118 | A |
| AI829350 | UNKNOWN | 12 | 161 | G |
| AI829377 | UNKNOWN | 91 | 0 | T |
| AI829377 | UNKNOWN | 17 | 148 | C |
| AI829377 | UNKNOWN | 15 | 165 | A |
| AI829423 | UNKNOWN | 43 | 0 | T |
| AI829423 | UNKNOWN | 15 | 70 | C |
| AI829423 | UNKNOWN | 13 | 123 | A |
| AI829432 | UNKNOWN | 44 | 0 | T |
| AI829433 | UNKNOWN | 21 | 0 | T |
| AI829435 | UNKNOWN | 7.5 | 293 | GT |
| AI829435 | UNKNOWN | 7.5 | 330 | TA |
| AI829445 | UNKNOWN | 14 | 0 | T |
| AI829457 | UNKNOWN | 35 | 0 | T |
| AI829457 | UNKNOWN | 12 | 88 | A |
| AI829480 | UNKNOWN | 23 | 0 | T |
| AI829495 | UNKNOWN | 73 | 0 | T |
| AI829495 | UNKNOWN | 19 | 145 | C |
| AI829495 | UNKNOWN | 14 | 102 | A |
| AI829521 | UNKNOWN | 25 | 0 | T |
| AI829532 | UNKNOWN | 16 | 0 | T |
| AI829537 | UNKNOWN | 12.5 | 319 | AC |
| AI829550 | UNKNOWN | 55 | 0 | T |
| AI829570 | UNKNOWN | 15 | 0 | T |
| AI829587 | UNKNOWN | 15 | 331 | T |
| AI829587 | UNKNOWN | 13 | 74 | A |
| AI829596 | UNKNOWN | 23 | 2 | T |
| AI829610 | UNKNOWN | 28 | 0 | T |
| AI829696 | UNKNOWN | 30 | 0 | T |
| AI829707 | UNKNOWN | 15 | 0 | T |
| AI829729 | UNKNOWN | 14 | 207 | A |
| AI829765 | UNKNOWN | 15 | 0 | T |
| AI829773 | UNKNOWN | 40 | 0 | T |
| AI829793 | UNKNOWN | 39 | 0 | T |
| AI829839 | UNKNOWN | 18 | 0 | T |
| AI829842 | UNKNOWN | 88 | 0 | T |
| AI829842 | UNKNOWN | 13 | 174 | A |
| AI829990 | UNKNOWN | 49 | 0 | T |
| AI829998 | UNKNOWN | 11.5 | 11 | AT |
| AI829998 | UNKNOWN | 19 | 36 | T |
| AI830016 | UNKNOWN | 60 | 0 | T |
| AI830024 | UNKNOWN | 52 | 0 | T |
| AI830026 | UNKNOWN | 65 | 0 | T |

TABLE 1-continued

| Genbank # | Region | # reps | Position | Unit sequence |
|---|---|---|---|---|
| AI830026 | UNKNOWN | 13 | 173 | C |
| AI830028 | UNKNOWN | 8 | 45 | GA |
| AI830029 | UNKNOWN | 76 | 0 | T |
| AI830029 | UNKNOWN | 21 | 322 | G |
| AI830029 | UNKNOWN | 18 | 139 | A |
| AI830030 | UNKNOWN | 86 | 0 | T |
| AI830030 | UNKNOWN | 19 | 186 | G |
| AI830030 | UNKNOWN | 13 | 209 | A |
| AI830132 | UNKNOWN | 19 | 61 | A |
| AI830141 | UNKNOWN | 36 | 0 | T |
| AI830187 | UNKNOWN | 67 | 0 | T |
| AI830195 | UNKNOWN | 35 | 0 | T |
| AI830195 | UNKNOWN | 14 | 195 | A |
| AI830259 | UNKNOWN | 81 | 0 | T |
| AI830259 | UNKNOWN | 16 | 322 | C |
| AI830259 | UNKNOWN | 15 | 346 | G |
| AI830319 | UNKNOWN | 5.66 | 106 | AAC |
| AI830448 | UNKNOWN | 24 | 0 | T |
| AI830474 | UNKNOWN | 12 | 0 | T |
| AI830481 | UNKNOWN | 47 | 0 | T |
| AI830481 | UNKNOWN | 12 | 197 | A |
| AI830489 | UNKNOWN | 24 | 0 | T |
| AI830491 | UNKNOWN | 16 | 0 | T |
| AI830579 | UNKNOWN | 11.5 | 101 | AC |
| AI830603 | UNKNOWN | 14 | 0 | T |
| AI830627 | UNKNOWN | 12 | 0 | T |
| AI830707 | UNKNOWN | 16 | 0 | T |
| AI830937 | UNKNOWN | 20 | 10 | T |
| AI830951 | UNKNOWN | 48 | 0 | T |
| AI830969 | UNKNOWN | 21 | 0 | T |
| AI830992 | UNKNOWN | 29 | 0 | T |
| AI831030 | UNKNOWN | 20 | 0 | T |
| AI831109 | UNKNOWN | 18 | 0 | T |
| AI831122 | UNKNOWN | 22 | 0 | T |
| AI831138 | UNKNOWN | 37 | 0 | T |
| AI831138 | UNKNOWN | 16 | 50 | G |
| AI831138 | UNKNOWN | 12 | 295 | A |
| AI831140 | UNKNOWN | 90 | 0 | T |
| AI831140 | UNKNOWN | 15 | 347 | G |
| AI831148 | UNKNOWN | 48 | 2 | T |
| AI831174 | UNKNOWN | 38 | 17 | T |
| AI831174 | UNKNOWN | 14 | 224 | A |
| AI831174 | UNKNOWN | 12 | 0 | T |
| AI831174 | UNKNOWN | 12 | 76 | A |
| AI831174 | UNKNOWN | 12 | 168 | C |
| AI831178 | UNKNOWN | 78 | 0 | T |
| AI831178 | UNKNOWN | 13 | 88 | A |
| AI831178 | UNKNOWN | 13 | 101 | G |
| AI831190 | UNKNOWN | 5.66 | 18 | GCG |
| AI831201 | UNKNOWN | 8 | 189 | AT |
| AI831201 | UNKNOWN | 16 | 0 | T |
| AI831241 | UNKNOWN | 30 | 0 | T |
| AI831308 | UNKNOWN | 55 | 0 | T |
| AI831315 | UNKNOWN | 28 | 0 | T |
| AI831323 | UNKNOWN | 48 | 0 | T |
| AI831333 | UNKNOWN | 43 | 0 | T |
| AI831347 | UNKNOWN | 29 | 0 | T |
| AI831351 | UNKNOWN | 41 | 0 | T |
| AI831383 | UNKNOWN | 6.5 | 1 | TA |
| AI831402 | UNKNOWN | 15 | 0 | T |
| AI831472 | UNKNOWN | 2.63 | 355 | GGGGGGGGCCC (SEQ ID NO: 157) |
| AI831472 | UNKNOWN | 51 | 0 | T |
| AI831506 | UNKNOWN | 14 | 191 | A |
| AI831517 | UNKNOWN | 13 | 0 | T |
| AI831541 | UNKNOWN | 16 | 0 | T |
| AI831544 | UNKNOWN | 14 | 352 | T |
| AI831656 | UNKNOWN | 20 | 0 | T |
| AI831733 | UNKNOWN | 13 | 140 | A |
| AI831849 | UNKNOWN | 24 | 0 | T |
| AI831874 | UNKNOWN | 7.5 | 295 | AG |
| AI831904 | UNKNOWN | 24 | 0 | T |
| AI831949 | UNKNOWN | 12 | 0 | T |
| AI831975 | UNKNOWN | 21 | 0 | T |
| AI831993 | UNKNOWN | 15 | 274 | A |
| AI832013 | UNKNOWN | 17 | 0 | T |
| AI832029 | UNKNOWN | 34 | 2 | T |
| AI832038 | UNKNOWN | 62 | 0 | T |

TABLE 1-continued

| Genbank # | Region | # reps | Position | Unit sequence |
|---|---|---|---|---|
| AI832065 | UNKNOWN | 80 | 1 | T |
| AI832076 | UNKNOWN | 20 | 125 | T |
| AI832183 | UNKNOWN | 19 | 0 | T |
| AI832244 | UNKNOWN | 46 | 0 | T |
| AI832245 | UNKNOWN | 78 | 0 | T |
| AI832457 | UNKNOWN | 63 | 0 | T |
| AI832477 | UNKNOWN | 13 | 0 | T |
| AI832576 | UNKNOWN | 3.66 | 186 | TAATCA |
| AI832729 | UNKNOWN | 29 | 0 | T |
| AI833039 | UNKNOWN | 13 | 4 | T |
| AI833040 | UNKNOWN | 12.5 | 95 | AT |
| AI833128 | UNKNOWN | 36 | 16 | T |
| AI833128 | UNKNOWN | 15 | 0 | T |
| AI833128 | UNKNOWN | 15 | 226 | G |
| AI833128 | UNKNOWN | 14 | 162 | A |
| AI833128 | UNKNOWN | 13 | 132 | A |
| AI833196 | UNKNOWN | 30 | 0 | T |
| AI857241 | UNKNOWN | 55 | 0 | T |
| AI857250 | UNKNOWN | 13 | 0 | T |
| AI857296 | UNKNOWN | 123 | 0 | T |
| AI857296 | UNKNOWN | 17 | 182 | G |
| AI857296 | UNKNOWN | 16 | 162 | A |
| AI857296 | UNKNOWN | 15 | 147 | C |
| AI857299 | UNKNOWN | 75 | 0 | T |
| AI857360 | UNKNOWN | 29 | 0 | T |
| AI857453 | UNKNOWN | 46 | 0 | T |
| AI857496 | UNKNOWN | 15 | 0 | T |
| AI857555 | UNKNOWN | 33 | 0 | T |
| AI857724 | UNKNOWN | 86 | 0 | T |
| AI857724 | UNKNOWN | 14 | 350 | G |
| AI857760 | UNKNOWN | 90 | 0 | T |
| AI857760 | UNKNOWN | 22 | 111 | C |
| AI857760 | UNKNOWN | 15 | 146 | G |
| AI857788 | UNKNOWN | 15 | 148 | A |
| AI857797 | UNKNOWN | 76 | 0 | T |
| AI857797 | UNKNOWN | 19 | 136 | A |
| AI857797 | UNKNOWN | 16 | 273 | G |
| AI857856 | UNKNOWN | 15 | 514 | A |
| AI857868 | UNKNOWN | 43 | 0 | T |
| AI857869 | UNKNOWN | 38 | 0 | T |
| AI857889 | UNKNOWN | 34 | 0 | T |
| AI857892 | UNKNOWN | 34 | 0 | T |
| AI857997 | UNKNOWN | 14 | 503 | T |
| AI858031 | UNKNOWN | 14 | 0 | T |
| AI858037 | UNKNOWN | 12 | 154 | T |
| AI858054 | UNKNOWN | 12 | 0 | T |
| AI858137 | UNKNOWN | 80 | 0 | T |
| AI858137 | UNKNOWN | 15 | 140 | G |
| AI858137 | UNKNOWN | 14 | 231 | A |
| AI858256 | UNKNOWN | 47 | 0 | T |
| AI858266 | UNKNOWN | 19 | 0 | T |
| AI858293 | UNKNOWN | 28 | 0 | T |
| AI858304 | UNKNOWN | 21 | 0 | T |
| AI858310 | UNKNOWN | 93 | 0 | T |
| AI858310 | UNKNOWN | 14 | 203 | C |
| AI858310 | UNKNOWN | 13 | 355 | A |
| AI858364 | UNKNOWN | 41 | 0 | T |
| AI858378 | UNKNOWN | 19 | 0 | T |
| AI858378 | UNKNOWN | 13 | 156 | A |
| AI858436 | UNKNOWN | 15 | 0 | T |
| AI858465 | UNKNOWN | 68 | 0 | T |
| AI858465 | UNKNOWN | 18 | 175 | C |
| AI858465 | UNKNOWN | 17 | 148 | C |
| AI858465 | UNKNOWN | 15 | 84 | C |
| AI858476 | UNKNOWN | 33 | 0 | T |
| AI858527 | UNKNOWN | 26 | 0 | T |
| AI858572 | UNKNOWN | 51 | 0 | T |
| AI858579 | UNKNOWN | 38 | 8 | T |
| AI858620 | UNKNOWN | 33 | 0 | T |
| AI858626 | UNKNOWN | 5.66 | 261 | TCA |
| AI858626 | UNKNOWN | 13 | 0 | T |
| AI858663 | UNKNOWN | 36 | 0 | T |
| AI858677 | UNKNOWN | 24 | 0 | T |
| AI858691 | UNKNOWN | 16 | 0 | T |
| AI858724 | UNKNOWN | 35 | 0 | T |
| AI858739 | UNKNOWN | 45 | 0 | T |
| AI858786 | UNKNOWN | 89 | 15 | T |

TABLE 1-continued

| Genbank # | Region | # reps | Position | Unit sequence |
|---|---|---|---|---|
| AI858786 | UNKNOWN | 16 | 305 | A |
| AI858786 | UNKNOWN | 13 | 226 | A |
| AI858836 | UNKNOWN | 52 | 0 | T |
| AI858838 | UNKNOWN | 20 | 354 | A |
| AI858846 | UNKNOWN | 21 | 0 | T |
| AI858865 | UNKNOWN | 57 | 0 | T |
| AI858874 | UNKNOWN | 55 | 0 | T |
| AI858914 | UNKNOWN | 5.75 | 200 | AAAC |
| AI858914 | UNKNOWN | 22 | 153 | T |
| AI858920 | UNKNOWN | 13 | 0 | T |
| AI858988 | UNKNOWN | 40 | 0 | T |
| AI858988 | UNKNOWN | 19 | 79 | A |
| AI858994 | UNKNOWN | 57 | 0 | T |
| AI859106 | UNKNOWN | 31 | 0 | T |
| AI859114 | UNKNOWN | 16 | 0 | T |
| AI859123 | UNKNOWN | 45 | 0 | T |
| AI859127 | UNKNOWN | 54 | 0 | T |
| AI859127 | UNKNOWN | 22 | 308 | G |
| AI859127 | UNKNOWN | 15 | 213 | C |
| AI859127 | UNKNOWN | 14 | 270 | G |
| AI859134 | UNKNOWN | 66 | 0 | T |
| AI859157 | UNKNOWN | 18 | 363 | A |
| AI859157 | UNKNOWN | 14 | 0 | T |
| AI859199 | UNKNOWN | 70 | 0 | T |
| AI859199 | UNKNOWN | 16 | 266 | G |
| AI859199 | UNKNOWN | 13 | 103 | A |
| AI859199 | UNKNOWN | 12 | 363 | C |
| AI859233 | UNKNOWN | 23 | 0 | T |
| AI859240 | UNKNOWN | 58 | 0 | T |
| AI859242 | UNKNOWN | 14 | 416 | AC |
| AI859242 | UNKNOWN | 31 | 0 | T |
| AI859248 | UNKNOWN | 46 | 0 | T |
| AI859253 | UNKNOWN | 19 | 0 | T |
| AI859309 | UNKNOWN | 39 | 0 | T |
| AI859375 | UNKNOWN | 51 | 0 | T |
| AI859375 | UNKNOWN | 15 | 230 | C |
| AI859402 | UNKNOWN | 111 | 0 | T |
| AI859402 | UNKNOWN | 22 | 185 | A |
| AI859402 | UNKNOWN | 16 | 157 | G |
| AI859402 | UNKNOWN | 12 | 270 | C |
| AI859429 | UNKNOWN | 87 | 12 | T |
| AI859429 | UNKNOWN | 30 | 342 | C |
| AI859429 | UNKNOWN | 18 | 187 | A |
| AI859429 | UNKNOWN | 15 | 150 | G |
| AI859429 | UNKNOWN | 14 | 99 | C |
| AI859470 | UNKNOWN | 38 | 0 | T |
| AI859492 | UNKNOWN | 16 | 0 | T |
| AI859494 | UNKNOWN | 4.5 | 301 | TTGG |
| AI859494 | UNKNOWN | 31 | 0 | T |
| AI859511 | UNKNOWN | 102 | 0 | T |
| AI859511 | UNKNOWN | 15 | 166 | A |
| AI859511 | UNKNOWN | 13 | 122 | C |
| AI859536 | UNKNOWN | 15 | 230 | A |
| AI859536 | UNKNOWN | 13 | 175 | G |
| AI859536 | UNKNOWN | 12 | 283 | C |
| AI859609 | UNKNOWN | 85 | 0 | T |
| AI859644 | UNKNOWN | 62 | 0 | T |
| AI859654 | UNKNOWN | 60 | 0 | T |
| AI859733 | UNKNOWN | 122 | 0 | T |
| AI859733 | UNKNOWN | 20 | 322 | G |
| AI859733 | UNKNOWN | 16 | 236 | A |
| AI859733 | UNKNOWN | 13 | 138 | A |
| AI859760 | UNKNOWN | 15 | 72 | A |
| AI859766 | UNKNOWN | 47 | 0 | T |
| AI859772 | UNKNOWN | 16 | 0 | T |
| AI859782 | UNKNOWN | 59 | 0 | T |
| AI859782 | UNKNOWN | 13 | 307 | G |
| AI859800 | UNKNOWN | 65 | 0 | T |
| AI859801 | UNKNOWN | 47 | 0 | T |
| AI859801 | UNKNOWN | 12 | 141 | A |
| AI859828 | UNKNOWN | 19 | 0 | T |
| AI859833 | UNKNOWN | 48 | 0 | T |
| AI859840 | UNKNOWN | 51 | 0 | T |
| AI859840 | UNKNOWN | 13 | 160 | A |
| AI859849 | UNKNOWN | 19 | 10 | T |
| AI859880 | UNKNOWN | 85 | 0 | T |
| AI859880 | UNKNOWN | 12 | 195 | C |

TABLE 1-continued

| Genbank # | Region | # reps | Position | Unit sequence |
|---|---|---|---|---|
| AI859899 | UNKNOWN | 57 | 0 | T |
| AI859915 | UNKNOWN | 96 | 0 | T |
| AI859915 | UNKNOWN | 22 | 155 | G |
| AI859920 | UNKNOWN | 58 | 0 | T |
| AI859932 | UNKNOWN | 59 | 0 | T |
| AI859932 | UNKNOWN | 14 | 207 | C |
| AI859932 | UNKNOWN | 13 | 62 | A |
| AI859990 | UNKNOWN | 11.5 | 144 | TCTA |
| AI860012 | UNKNOWN | 12 | 14 | T |
| AI860020 | UNKNOWN | 4.59 | 103 | TTTCT |
| AI860037 | UNKNOWN | 4.5 | 123 | AAGG |
| AI860037 | UNKNOWN | 52 | 0 | T |
| AI860045 | UNKNOWN | 75 | 0 | T |
| AI860045 | UNKNOWN | 27 | 168 | G |
| AI860150 | UNKNOWN | 21 | 349 | A |
| AI860152 | UNKNOWN | 49 | 0 | T |
| AI860323 | UNKNOWN | 14 | 0 | T |
| AI860348 | UNKNOWN | 55 | 0 | T |
| AI860348 | UNKNOWN | 13 | 60 | A |
| AI860360 | UNKNOWN | 5.66 | 319 | TTC |
| AI860360 | UNKNOWN | 17 | 373 | A |
| AI860360 | UNKNOWN | 15 | 0 | T |
| AI860370 | UNKNOWN | 92 | 0 | T |
| AI860370 | UNKNOWN | 22 | 336 | C |
| AI860370 | UNKNOWN | 15 | 160 | C |
| AI860370 | UNKNOWN | 15 | 246 | G |
| AI860370 | UNKNOWN | 12 | 312 | A |
| AI860381 | UNKNOWN | 35 | 0 | T |
| AI860407 | UNKNOWN | 21 | 0 | T |
| AI860422 | UNKNOWN | 43 | 0 | T |
| AI860423 | UNKNOWN | 4.5 | 23 | TTAT |
| AI860476 | UNKNOWN | 54 | 0 | T |
| AI860496 | UNKNOWN | 96 | 0 | T |
| AI860496 | UNKNOWN | 18 | 330 | G |
| AI860496 | UNKNOWN | 12 | 293 | G |
| AI860509 | UNKNOWN | 57 | 0 | T |
| AI860537 | UNKNOWN | 110 | 0 | T |
| AI860537 | UNKNOWN | 27 | 156 | C |
| AI860537 | UNKNOWN | 16 | 135 | G |
| AI860537 | UNKNOWN | 13 | 122 | C |
| AI860537 | UNKNOWN | 13 | 367 | A |
| AI860546 | UNKNOWN | 59 | 0 | T |
| AI860609 | UNKNOWN | 84 | 0 | T |
| AI860609 | UNKNOWN | 17 | 232 | G |
| AI860619 | UNKNOWN | 39 | 0 | T |
| AI860619 | UNKNOWN | 20 | 275 | G |
| AI860636 | UNKNOWN | 24 | 0 | T |
| AI860639 | UNKNOWN | 71 | 0 | T |
| AI860647 | UNKNOWN | 18 | 13 | T |
| AI860652 | UNKNOWN | 66 | 0 | T |
| AI860655 | UNKNOWN | 49 | 0 | T |
| AI860673 | UNKNOWN | 54 | 0 | T |
| AI860673 | UNKNOWN | 14 | 350 | C |
| AI860674 | UNKNOWN | 87 | 17 | T |
| AI860674 | UNKNOWN | 17 | 137 | C |
| AI860674 | UNKNOWN | 16 | 0 | T |
| AI860674 | UNKNOWN | 16 | 180 | A |
| AI860674 | UNKNOWN | 14 | 267 | G |
| AI860691 | UNKNOWN | 62 | 0 | T |
| AI860691 | UNKNOWN | 13 | 166 | A |
| AI860694 | UNKNOWN | 83 | 0 | T |
| AI860694 | UNKNOWN | 20 | 129 | C |
| AI860694 | UNKNOWN | 19 | 185 | G |
| AI860694 | UNKNOWN | 14 | 107 | A |
| AI860697 | UNKNOWN | 64 | 0 | T |
| AI860697 | UNKNOWN | 16 | 201 | C |
| AI860742 | UNKNOWN | 27 | 0 | T |
| AI860750 | UNKNOWN | 41 | 0 | T |
| AI860775 | UNKNOWN | 13 | 0 | T |
| AI860783 | UNKNOWN | 73 | 0 | T |
| AI860783 | UNKNOWN | 16 | 183 | G |
| AI860787 | UNKNOWN | 47 | 0 | T |
| AI860809 | UNKNOWN | 62 | 0 | T |
| AI860809 | UNKNOWN | 14 | 237 | A |
| AI860809 | UNKNOWN | 13 | 107 | C |
| AI860809 | UNKNOWN | 12 | 136 | A |
| AI860822 | UNKNOWN | 23 | 0 | T |

TABLE 1-continued

| Genbank # | Region | # reps | Position | Unit sequence |
|---|---|---|---|---|
| AI860830 | UNKNOWN | 59 | 0 | T |
| AI860833 | UNKNOWN | 63 | 0 | T |
| AI860833 | UNKNOWN | 18 | 307 | G |
| AI860856 | UNKNOWN | 18 | 0 | T |
| AI860860 | UNKNOWN | 42 | 0 | T |
| AI860860 | UNKNOWN | 14 | 264 | A |
| AI860874 | UNKNOWN | 6.5 | 51 | TA |
| AI860885 | UNKNOWN | 75 | 0 | T |
| AI860885 | UNKNOWN | 16 | 154 | G |
| AI860885 | UNKNOWN | 12 | 273 | C |
| AI860897 | UNKNOWN | 72 | 0 | T |
| AI860897 | UNKNOWN | 17 | 182 | G |
| AI861836 | UNKNOWN | 7 | 398 | GT |
| AI861854 | UNKNOWN | 25 | 0 | T |
| AI861927 | UNKNOWN | 3.8 | 60 | AAATA |
| AI861927 | UNKNOWN | 17 | 24 | T |
| AI861962 | UNKNOWN | 19 | 0 | T |
| AI861972 | UNKNOWN | 75 | 0 | T |
| AI861972 | UNKNOWN | 14 | 350 | A |
| AI861972 | UNKNOWN | 12 | 284 | G |
| AI861973 | UNKNOWN | 62 | 0 | T |
| AI861973 | UNKNOWN | 14 | 266 | G |
| AI861976 | UNKNOWN | 82 | 0 | T |
| AI861976 | UNKNOWN | 15 | 220 | C |
| AI861976 | UNKNOWN | 14 | 107 | G |
| AI861983 | UNKNOWN | 6.2 | 13 | TTTTA |
| AI861983 | UNKNOWN | 17 | 0 | T |
| AI862024 | UNKNOWN | 89 | 0 | T |
| AI862024 | UNKNOWN | 12 | 147 | C |
| AI862043 | UNKNOWN | 51 | 0 | T |
| AI862062 | UNKNOWN | 12 | 0 | T |
| AI862063 | UNKNOWN | 13 | 224 | A |
| AI862066 | UNKNOWN | 61 | 0 | T |
| AI862066 | UNKNOWN | 19 | 170 | A |
| AI862067 | UNKNOWN | 63 | 0 | T |
| AI862067 | UNKNOWN | 12 | 356 | G |
| AI862097 | UNKNOWN | 14 | 0 | T |
| AI862135 | UNKNOWN | 82 | 0 | T |
| AI862135 | UNKNOWN | 12 | 224 | C |
| AI862135 | UNKNOWN | 12 | 323 | G |
| AI862139 | UNKNOWN | 100 | 0 | T |
| AI862139 | UNKNOWN | 25 | 118 | A |
| AI862139 | UNKNOWN | 12 | 100 | A |
| AI862142 | UNKNOWN | 119 | 0 | T |
| AI862142 | UNKNOWN | 18 | 195 | G |
| AI862142 | UNKNOWN | 17 | 240 | A |
| AI862142 | UNKNOWN | 12 | 164 | C |
| AI862144 | UNKNOWN | 114 | 0 | T |
| AI862144 | UNKNOWN | 15 | 125 | C |
| AI862144 | UNKNOWN | 15 | 147 | A |
| AI862190 | UNKNOWN | 13 | 15 | T |
| AI862200 | UNKNOWN | 55 | 0 | T |
| AI862242 | UNKNOWN | 29 | 94 | A |
| AI862253 | UNKNOWN | 22 | 299 | A |
| AI862258 | UNKNOWN | 31 | 125 | A |
| AI862263 | UNKNOWN | 14 | 115 | A |
| AI862266 | UNKNOWN | 32 | 197 | A |
| AI862282 | UNKNOWN | 27 | 223 | A |
| AI862284 | UNKNOWN | 23 | 132 | A |
| AI862295 | UNKNOWN | 17 | 71 | A |
| AI862324 | UNKNOWN | 81 | 0 | T |
| AI862324 | UNKNOWN | 16 | 141 | C |
| AI862347 | UNKNOWN | 23 | 0 | T |
| AI862358 | UNKNOWN | 19 | 0 | T |
| AI862385 | UNKNOWN | 45 | 0 | T |
| AI862395 | UNKNOWN | 23 | 0 | T |
| AI862430 | UNKNOWN | 15 | 0 | T |
| AI862471 | UNKNOWN | 14 | 42 | A |
| AI862487 | UNKNOWN | 20 | 124 | A |
| AI862515 | UNKNOWN | 32 | 134 | A |
| AI862587 | UNKNOWN | 16 | 0 | T |
| AI862668 | UNKNOWN | 12 | 0 | T |
| AI862742 | UNKNOWN | 37 | 0 | T |
| AI862759 | UNKNOWN | 81 | 0 | T |
| AI862759 | UNKNOWN | 17 | 329 | C |
| AI862759 | UNKNOWN | 13 | 163 | G |
| AI862777 | UNKNOWN | 37 | 0 | T |

TABLE 1-continued

| Genbank # | Region | # reps | Position | Unit sequence |
|---|---|---|---|---|
| AI862777 | UNKNOWN | 20 | 88 | A |
| AI862825 | UNKNOWN | 74 | 0 | T |
| AI862825 | UNKNOWN | 19 | 140 | G |
| AI862825 | UNKNOWN | 12 | 240 | A |
| AI862839 | UNKNOWN | 67 | 0 | T |
| AI862839 | UNKNOWN | 15 | 89 | A |
| AI862880 | UNKNOWN | 86 | 0 | T |
| AI862880 | UNKNOWN | 16 | 274 | G |
| AI862880 | UNKNOWN | 14 | 229 | C |
| AI862880 | UNKNOWN | 13 | 215 | G |
| AI862880 | UNKNOWN | 13 | 261 | A |
| AI862892 | UNKNOWN | 7.5 | 225 | AC |
| AI862896 | UNKNOWN | 45 | 0 | T |
| AI862913 | UNKNOWN | 12 | 0 | T |
| AI862919 | UNKNOWN | 3.8 | 37 | AAAAC |
| AI862947 | UNKNOWN | 7 | 36 | TATT |
| AI862947 | UNKNOWN | 24 | 0 | T |
| AI862991 | UNKNOWN | 16 | 0 | T |
| AI863014 | UNKNOWN | 137 | 11 | T |
| AI863014 | UNKNOWN | 24 | 353 | G |
| AI863014 | UNKNOWN | 20 | 275 | A |
| AI863014 | UNKNOWN | 16 | 181 | G |
| AI863029 | UNKNOWN | 59 | 0 | T |
| AI863047 | UNKNOWN | 67 | 0 | T |
| AI863047 | UNKNOWN | 22 | 197 | G |
| AI863067 | UNKNOWN | 67 | 0 | T |
| AI863067 | UNKNOWN | 13 | 124 | A |
| AI863082 | UNKNOWN | 86 | 0 | T |
| AI863082 | UNKNOWN | 14 | 157 | G |
| AI863082 | UNKNOWN | 13 | 140 | A |
| AI863098 | UNKNOWN | 18 | 9 | T |
| AI863111 | UNKNOWN | 4 | 0 | GTTTT |
| AI863132 | UNKNOWN | 31 | 0 | T |
| AI863133 | UNKNOWN | 97 | 0 | T |
| AI863133 | UNKNOWN | 24 | 358 | C |
| AI863133 | UNKNOWN | 20 | 231 | G |
| AI863133 | UNKNOWN | 20 | 338 | A |
| AI863133 | UNKNOWN | 15 | 130 | A |
| AI863133 | UNKNOWN | 13 | 218 | C |
| AI863158 | UNKNOWN | 2.73 | 6 | TTTTTTTTTTTNTTT (SEQ ID NO: 158) |
| AI863158 | UNKNOWN | 45 | 33 | T |
| AI863158 | UNKNOWN | 15 | 234 | A |
| AI863158 | UNKNOWN | 14 | 18 | T |
| AI863158 | UNKNOWN | 12 | 180 | A |
| AI863166 | UNKNOWN | 13 | 4 | T |
| AI863191 | UNKNOWN | 76 | 0 | T |
| AI863191 | UNKNOWN | 13 | 114 | A |
| AI863191 | UNKNOWN | 12 | 81 | G |
| AI863209 | UNKNOWN | 21 | 14 | T |
| AI863226 | UNKNOWN | 15 | 376 | T |
| AI863231 | UNKNOWN | 55 | 0 | T |
| AI863231 | UNKNOWN | 12 | 220 | G |
| AI863237 | UNKNOWN | 42 | 0 | T |
| AI863237 | UNKNOWN | 15 | 162 | G |
| AI863239 | UNKNOWN | 16 | 0 | T |
| AI863240 | UNKNOWN | 91 | 0 | T |
| AI863240 | UNKNOWN | 20 | 232 | A |
| AI863241 | UNKNOWN | 96 | 0 | T |
| AI863241 | UNKNOWN | 16 | 175 | C |
| AI863241 | UNKNOWN | 15 | 272 | G |
| AI863241 | UNKNOWN | 12 | 191 | G |
| AI863249 | UNKNOWN | 17 | 0 | T |
| AI863249 | UNKNOWN | 12 | 420 | A |
| AI863256 | UNKNOWN | 82 | 0 | T |
| AI863256 | UNKNOWN | 12 | 282 | G |
| AI863260 | UNKNOWN | 45 | 0 | T |
| AI863264 | UNKNOWN | 25 | 0 | T |
| AI863266 | UNKNOWN | 15 | 11 | T |
| AI863279 | UNKNOWN | 24 | 2 | T |
| AI863292 | UNKNOWN | 51 | 0 | T |
| AI863302 | UNKNOWN | 30 | 0 | T |
| AI863319 | UNKNOWN | 44 | 0 | T |
| AI863321 | UNKNOWN | 83 | 0 | T |
| AI863321 | UNKNOWN | 21 | 145 | A |
| AI863322 | UNKNOWN | 36 | 0 | T |
| AI863335 | UNKNOWN | 15 | 11 | T |
| AI863338 | UNKNOWN | 16 | 11 | T |

TABLE 1-continued

| Genbank # | Region | # reps | Position | Unit sequence |
|---|---|---|---|---|
| AI863344 | UNKNOWN | 18 | 0 | T |
| AI863351 | UNKNOWN | 15 | 11 | T |
| AI863353 | UNKNOWN | 17 | 11 | T |
| AI863355 | UNKNOWN | 15 | 0 | T |
| AI863358 | UNKNOWN | 5.5 | 43 | AAAG |
| AI863373 | UNKNOWN | 54 | 0 | T |
| AI863382 | UNKNOWN | 78 | 0 | T |
| AI863382 | UNKNOWN | 22 | 126 | A |
| AI863382 | UNKNOWN | 16 | 186 | C |
| AI863397 | UNKNOWN | 64 | 0 | T |
| AI863397 | UNKNOWN | 12 | 80 | G |
| AI863411 | UNKNOWN | 80 | 0 | T |
| AI863411 | UNKNOWN | 16 | 221 | C |
| AI863411 | UNKNOWN | 13 | 119 | G |
| AI863414 | UNKNOWN | 15 | 0 | T |
| AI863415 | UNKNOWN | 28 | 0 | T |
| AI863416 | UNKNOWN | 12 | 336 | A |
| AI863425 | UNKNOWN | 15 | 11 | T |
| AI863437 | UNKNOWN | 91 | 0 | T |
| AI863437 | UNKNOWN | 16 | 362 | C |
| AI863437 | UNKNOWN | 12 | 293 | G |
| AI863438 | UNKNOWN | 19 | 11 | T |
| AI863441 | UNKNOWN | 88 | 0 | T |
| AI863444 | UNKNOWN | 22 | 15 | T |
| AI863446 | UNKNOWN | 24 | 15 | T |
| AI863458 | UNKNOWN | 20 | 422 | A |
| AI863458 | UNKNOWN | 12 | 15 | T |
| AI863466 | UNKNOWN | 78 | 0 | T |
| AI863466 | UNKNOWN | 23 | 141 | G |
| AI863466 | UNKNOWN | 20 | 116 | A |
| AI863466 | UNKNOWN | 16 | 95 | A |
| AI863466 | UNKNOWN | 14 | 182 | C |
| AI863466 | UNKNOWN | 12 | 164 | C |
| AI863477 | UNKNOWN | 107 | 0 | T |
| AI863477 | UNKNOWN | 12 | 308 | G |
| AI863479 | UNKNOWN | 8.5 | 136 | AC |
| AI863479 | UNKNOWN | 59 | 0 | T |
| AI863479 | UNKNOWN | 17 | 120 | A |
| AI863479 | UNKNOWN | 13 | 86 | A |
| AI863505 | UNKNOWN | 12 | 0 | T |
| AI863665 | UNKNOWN | 74 | 0 | T |
| AI863665 | UNKNOWN | 15 | 249 | C |
| AI863710 | UNKNOWN | 3.5 | 233 | CACGCC |
| AI863710 | UNKNOWN | 18 | 0 | T |
| AI863800 | UNKNOWN | 13 | 461 | A |
| AI864102 | UNKNOWN | 70 | 0 | T |
| AI864102 | UNKNOWN | 16 | 304 | G |
| AI864102 | UNKNOWN | 14 | 171 | G |
| AI864301 | UNKNOWN | 44 | 0 | T |
| AI864340 | UNKNOWN | 20 | 0 | T |
| AI864348 | UNKNOWN | 20 | 0 | T |
| AI864617 | UNKNOWN | 13 | 0 | T |
| AI864748 | UNKNOWN | 21 | 0 | T |
| AI864806 | UNKNOWN | 41 | 0 | T |
| AI864827 | UNKNOWN | 75 | 0 | T |
| AI834836 | UNKNOWN | 89 | 0 | T |
| AI864836 | UNKNOWN | 16 | 287 | C |
| AI864836 | UNKNOWN | 14 | 110 | A |
| AI864857 | UNKNOWN | 87 | 0 | T |
| AI864857 | UNKNOWN | 16 | 291 | A |
| AI864857 | UNKNOWN | 14 | 276 | C |
| AI864892 | UNKNOWN | 6 | 3 | GCC |
| AI864933 | UNKNOWN | 9 | 203 | TA |
| AI864933 | UNKNOWN | 7.5 | 171 | TA |
| AI864960 | UNKNOWN | 10.25 | 12 | TATT |
| AI864969 | UNKNOWN | 15 | 0 | T |
| AI864970 | UNKNOWN | 14 | 8 | T |
| AI865010 | UNKNOWN | 74 | 0 | T |
| AI865010 | UNKNOWN | 12 | 275 | G |
| AI865040 | UNKNOWN | 44 | 0 | T |
| AI865070 | UNKNOWN | 34 | 0 | T |
| AI865097 | UNKNOWN | 34 | 0 | T |
| AI865105 | UNKNOWN | 56 | 0 | T |
| AI865105 | UNKNOWN | 17 | 248 | A |
| AI865116 | UNKNOWN | 59 | 48 | A |
| AI865189 | UNKNOWN | 50 | 0 | T |
| AI865189 | UNKNOWN | 16 | 100 | A |

TABLE 1-continued

| Genbank # | Region | # reps | Position | Unit sequence |
|---|---|---|---|---|
| AI865213 | UNKNOWN | 16 | 0 | T |
| AI865297 | UNKNOWN | 63 | 0 | T |
| AI865320 | UNKNOWN | 64 | 0 | T |
| AI865324 | UNKNOWN | 41 | 0 | T |
| AI865334 | UNKNOWN | 66 | 0 | T |
| AI865394 | UNKNOWN | 36 | 0 | T |
| AI865400 | UNKNOWN | 15 | 0 | T |
| AI865584 | UNKNOWN | 34 | 0 | T |
| AI865713 | UNKNOWN | 46 | 0 | T |
| AI865730 | UNKNOWN | 20 | 203 | T |
| AI865735 | UNKNOWN | 27 | 79 | T |
| AI865823 | UNKNOWN | 19 | 0 | T |
| AI865880 | UNKNOWN | 68 | 0 | T |
| AI865880 | UNKNOWN | 12 | 211 | A |
| AI865900 | UNKNOWN | 62 | 0 | T |
| AI865900 | UNKNOWN | 12 | 195 | C |
| AI865906 | UNKNOWN | 90 | 0 | T |
| AI865906 | UNKNOWN | 13 | 133 | A |
| AI865906 | UNKNOWN | 12 | 270 | G |
| AI865907 | UNKNOWN | 58 | 0 | T |
| AI865923 | UNKNOWN | 36 | 0 | T |
| AI865931 | UNKNOWN | 94 | 0 | T |
| AI865931 | UNKNOWN | 16 | 125 | G |
| AI865942 | UNKNOWN | 49 | 0 | T |
| AI865942 | UNKNOWN | 14 | 125 | G |
| AI865972 | UNKNOWN | 3.8 | 218 | CCAAC |
| AI865972 | UNKNOWN | 52 | 0 | T |
| AI865982 | UNKNOWN | 40 | 0 | T |
| AI865998 | UNKNOWN | 55 | 0 | T |
| AI865998 | UNKNOWN | 23 | 202 | A |
| AI866002 | UNKNOWN | 121 | 0 | T |
| AI866002 | UNKNOWN | 20 | 121 | G |
| AI866002 | UNKNOWN | 16 | 184 | C |
| AI866004 | UNKNOWN | 33 | 0 | T |
| AI866032 | UNKNOWN | 14 | 390 | G |
| AI866040 | UNKNOWN | 72 | 0 | T |
| AI866040 | UNKNOWN | 18 | 305 | G |
| AI866040 | UNKNOWN | 15 | 131 | G |
| AI866040 | UNKNOWN | 14 | 72 | A |
| AI866060 | UNKNOWN | 39 | 0 | T |
| AI866078 | UNKNOWN | 42 | 0 | T |
| AI866082 | UNKNOWN | 76 | 0 | T |
| AI866083 | UNKNOWN | 79 | 0 | T |
| AI866083 | UNKNOWN | 15 | 304 | G |
| AI866083 | UNKNOWN | 14 | 186 | C |
| AI866083 | UNKNOWN | 12 | 167 | G |
| AI866090 | UNKNOWN | 90 | 0 | T |
| AI866090 | UNKNOWN | 13 | 143 | G |
| AI866100 | UNKNOWN | 109 | 0 | T |
| AI866100 | UNKNOWN | 18 | 270 | C |
| AI866100 | UNKNOWN | 16 | 236 | G |
| AI866100 | UNKNOWN | 13 | 127 | A |
| AI866110 | UNKNOWN | 60 | 0 | T |
| AI866110 | UNKNOWN | 17 | 230 | G |
| AI866110 | UNKNOWN | 13 | 196 | G |
| AI866110 | UNKNOWN | 12 | 121 | A |
| AI866111 | UNKNOWN | 110 | 0 | T |
| AI866111 | UNKNOWN | 22 | 201 | C |
| AI866111 | UNKNOWN | 12 | 133 | G |
| AI866127 | UNKNOWN | 75 | 0 | T |
| AI866127 | UNKNOWN | 14 | 185 | G |
| AI866131 | UNKNOWN | 77 | 0 | T |
| AI866131 | UNKNOWN | 13 | 131 | G |
| AI866139 | UNKNOWN | 41 | 0 | T |
| AI866146 | UNKNOWN | 18 | 0 | T |
| AI866162 | UNKNOWN | 85 | 0 | T |
| AI866162 | UNKNOWN | 17 | 164 | A |
| AI866162 | UNKNOWN | 16 | 256 | G |
| AI866162 | UNKNOWN | 13 | 145 | C |
| AI866169 | UNKNOWN | 57 | 0 | T |
| AI866263 | UNKNOWN | 16 | 130 | A |
| AI866281 | UNKNOWN | 32 | 0 | T |
| AI866284 | UNKNOWN | 41 | 0 | T |
| AI866430 | UNKNOWN | 35 | 0 | T |
| AI866430 | UNKNOWN | 14 | 161 | A |
| AI866437 | UNKNOWN | 23 | 0 | T |
| AI866457 | UNKNOWN | 107 | 16 | T |

TABLE 1-continued

| Genbank # | Region | # reps | Position | Unit sequence |
|---|---|---|---|---|
| AI866457 | UNKNOWN | 17 | 338 | G |
| AI866457 | UNKNOWN | 14 | 217 | G |
| AI866460 | UNKNOWN | 15 | 11 | T |
| AI866477 | UNKNOWN | 37 | 0 | T |
| AI866487 | UNKNOWN | 23 | 15 | T |
| AI866488 | UNKNOWN | 9.5 | 177 | CA |
| AI866488 | UNKNOWN | 45 | 11 | T |
| AI866493 | UNKNOWN | 15 | 11 | T |
| AI866504 | UNKNOWN | 12 | 14 | T |
| AI866529 | UNKNOWN | 46 | 5 | T |
| AI866537 | UNKNOWN | 16 | 0 | T |
| AI866550 | UNKNOWN | 20 | 0 | T |
| AI866556 | UNKNOWN | 29 | 0 | T |
| AI866572 | UNKNOWN | 24 | 11 | T |
| AI866585 | UNKNOWN | 118 | 0 | T |
| AI866585 | UNKNOWN | 27 | 378 | C |
| AI866585 | UNKNOWN | 19 | 151 | C |
| AI866585 | UNKNOWN | 12 | 320 | G |
| AI866600 | UNKNOWN | 35 | 0 | T |
| AI866608 | UNKNOWN | 123 | 16 | T |
| AI866624 | UNKNOWN | 57 | 0 | T |
| AI866627 | UNKNOWN | 6.5 | 344 | AG |
| AI866627 | UNKNOWN | 17 | 0 | T |
| AI866632 | UNKNOWN | 44 | 0 | T |
| AI866644 | UNKNOWN | 54 | 0 | T |
| AI866646 | UNKNOWN | 60 | 5 | T |
| AI866646 | UNKNOWN | 12 | 108 | G |
| AI866653 | UNKNOWN | 19 | 0 | T |
| AI866666 | UNKNOWN | 17 | 11 | T |
| AI866666 | UNKNOWN | 12 | 109 | A |
| AI866703 | UNKNOWN | 19 | 0 | T |
| AI866741 | UNKNOWN | 83 | 0 | T |
| AI866743 | UNKNOWN | 25 | 0 | T |
| AI866751 | UNKNOWN | 111 | 0 | T |
| AI866751 | UNKNOWN | 21 | 237 | G |
| AI866751 | UNKNOWN | 12 | 149 | G |
| AI866751 | UNKNOWN | 12 | 268 | A |
| AI866757 | UNKNOWN | 6.5 | 26 | TTTA |
| AI866759 | UNKNOWN | 30 | 0 | T |
| AI866759 | UNKNOWN | 18 | 70 | A |
| AI866770 | UNKNOWN | 90 | 0 | T |
| AI866773 | UNKNOWN | 7.5 | 428 | CT |
| AI866780 | UNKNOWN | 127 | 0 | T |
| AI866780 | UNKNOWN | 25 | 420 | C |
| AI866780 | UNKNOWN | 12 | 455 | G |
| AI866781 | UNKNOWN | 16 | 3 | T |
| AI866798 | UNKNOWN | 90 | 0 | T |
| AI866798 | UNKNOWN | 25 | 161 | G |
| AI866801 | UNKNOWN | 106 | 0 | T |
| AI866801 | UNKNOWN | 19 | 201 | C |
| AI866801 | UNKNOWN | 14 | 106 | A |
| AI866801 | UNKNOWN | 14 | 169 | G |
| AI866805 | UNKNOWN | 23 | 0 | T |
| AI866811 | UNKNOWN | 88 | 0 | T |
| AI866811 | UNKNOWN | 24 | 88 | C |
| AI866811 | UNKNOWN | 12 | 314 | G |
| AI866815 | UNKNOWN | 40 | 0 | T |
| AI866820 | UNKNOWN | 63 | 14 | T |
| AI866835 | UNKNOWN | 13.5 | 222 | AG |
| AI866852 | UNKNOWN | 29 | 0 | T |
| AI866856 | UNKNOWN | 16 | 0 | T |
| AI866857 | UNKNOWN | 47 | 0 | T |
| AI866861 | UNKNOWN | 71 | 0 | T |
| AI866861 | UNKNOWN | 19 | 153 | C |
| AI866861 | UNKNOWN | 13 | 110 | A |
| AI866862 | UNKNOWN | 21 | 0 | T |
| AI866887 | UNKNOWN | 122 | 0 | T |
| AI866887 | UNKNOWN | 16 | 122 | G |
| AI866887 | UNKNOWN | 12 | 161 | C |
| AI866916 | UNKNOWN | 27 | 0 | T |
| AI866919 | UNKNOWN | 51 | 0 | T |
| AI866919 | UNKNOWN | 17 | 83 | A |
| AI866994 | UNKNOWN | 98 | 0 | T |
| AI867017 | UNKNOWN | 42 | 0 | T |
| AI867042 | UNKNOWN | 94 | 0 | T |
| AI867042 | UNKNOWN | 16 | 94 | G |
| AI867042 | UNKNOWN | 16 | 153 | C |

TABLE 1-continued

| Genbank # | Region | # reps | Position | Unit sequence |
|---|---|---|---|---|
| AI867042 | UNKNOWN | 13 | 169 | A |
| AI867048 | UNKNOWN | 63 | 0 | T |
| AI867066 | UNKNOWN | 42 | 11 | T |
| AI867076 | UNKNOWN | 44 | 0 | T |
| AI867458 | UNKNOWN | 11 | 112 | TG |
| AI867559 | UNKNOWN | 16 | 0 | T |
| AI867569 | UNKNOWN | 31 | 0 | T |
| AI867574 | UNKNOWN | 16 | 0 | T |
| AI867771 | UNKNOWN | 21 | 0 | T |
| AI867806 | UNKNOWN | 12 | 298 | A |
| AI867886 | UNKNOWN | 14 | 0 | T |
| AI868005 | UNKNOWN | 7 | 208 | AC |
| AI868048 | UNKNOWN | 39 | 0 | T |
| AI868122 | UNKNOWN | 44 | 0 | T |
| AI868134 | UNKNOWN | 52 | 0 | T |
| AI868156 | UNKNOWN | 41 | 0 | T |
| AI868157 | UNKNOWN | 50 | 0 | T |
| AI868180 | UNKNOWN | 54 | 0 | T |
| AI868180 | UNKNOWN | 16 | 112 | G |
| AI868204 | UNKNOWN | 80 | 0 | T |
| AI868204 | UNKNOWN | 24 | 112 | A |
| AI868292 | UNKNOWN | 12 | 0 | T |
| AI868302 | UNKNOWN | 32 | 0 | T |
| AI868330 | UNKNOWN | 23 | 0 | T |
| AI868336 | UNKNOWN | 15 | 1 | T |
| AI868475 | UNKNOWN | 67 | 0 | T |
| AI868706 | UNKNOWN | 12 | 0 | T |
| AI868740 | UNKNOWN | 73 | 16 | T |
| AI868740 | UNKNOWN | 15 | 0 | T |
| AI868740 | UNKNOWN | 15 | 167 | C |
| AI868774 | UNKNOWN | 25 | 389 | C |
| AI868774 | UNKNOWN | 16 | 306 | C |
| AI868774 | UNKNOWN | 12 | 287 | C |
| AI868827 | UNKNOWN | 37 | 0 | T |
| AI868831 | UNKNOWN | 155 | 0 | T |
| AI868831 | UNKNOWN | 17 | 183 | C |
| AI868892 | UNKNOWN | 16 | 0 | T |
| AI868913 | UNKNOWN | 28 | 0 | T |
| AI868931 | UNKNOWN | 77 | 0 | T |
| AI868931 | UNKNOWN | 12 | 170 | G |
| AI869071 | UNKNOWN | 30 | 0 | T |
| AI869098 | UNKNOWN | 12 | 13 | T |
| AI869125 | UNKNOWN | 78 | 0 | T |
| AI869125 | UNKNOWN | 13 | 215 | G |
| AI869172 | UNKNOWN | 30 | 0 | T |
| AI869172 | UNKNOWN | 17 | 158 | A |
| AI869183 | UNKNOWN | 19 | 0 | T |
| AI869289 | UNKNOWN | 16 | 0 | T |
| AI869346 | UNKNOWN | 44 | 0 | T |
| AI869359 | UNKNOWN | 28 | 31 | T |
| AI869359 | UNKNOWN | 14 | 16 | T |
| AI869361 | UNKNOWN | 22 | 0 | T |
| AI869367 | UNKNOWN | 115 | 0 | T |
| AI869367 | UNKNOWN | 20 | 205 | A |
| AI869367 | UNKNOWN | 16 | 189 | C |
| AI869367 | UNKNOWN | 15 | 160 | G |
| AI869369 | UNKNOWN | 15 | 0 | T |
| AI869377 | UNKNOWN | 66 | 0 | T |
| AI869377 | UNKNOWN | 14 | 98 | G |
| AI869403 | UNKNOWN | 50 | 0 | T |
| AI869420 | UNKNOWN | 12 | 0 | T |
| AI869499 | UNKNOWN | 56 | 0 | T |
| AI869550 | UNKNOWN | 25 | 0 | T |
| AI869671 | UNKNOWN | 15 | 46 | A |
| AI869750 | UNKNOWN | 51 | 0 | T |
| AI869765 | UNKNOWN | 57 | 0 | T |
| AI869796 | UNKNOWN | 13 | 0 | T |
| AI869869 | UNKNOWN | 77 | 0 | T |
| AI869873 | UNKNOWN | 37 | 0 | T |
| AI870187 | UNKNOWN | 98 | 0 | T |
| AI870187 | UNKNOWN | 18 | 144 | G |
| AI870187 | UNKNOWN | 14 | 347 | C |
| AI870187 | UNKNOWN | 12 | 162 | A |
| AI870190 | UNKNOWN | 52 | 0 | T |
| AI870190 | UNKNOWN | 17 | 219 | A |
| AI870192 | UNKNOWN | 85 | 0 | T |
| AI870192 | UNKNOWN | 12 | 123 | G |

TABLE 1-continued

| Genbank # | Region | # reps | Position | Unit sequence |
|---|---|---|---|---|
| AI870198 | UNKNOWN | 58 | 0 | T |
| AI870198 | UNKNOWN | 12 | 82 | C |
| AI870223 | UNKNOWN | 57 | 0 | T |
| AI870238 | UNKNOWN | 51 | 0 | T |
| AI870238 | UNKNOWN | 12 | 84 | G |
| AI870238 | UNKNOWN | 12 | 109 | A |
| AI870242 | UNKNOWN | 21 | 0 | T |
| AI870308 | UNKNOWN | 41 | 0 | T |
| AI870399 | UNKNOWN | 16 | 5 | T |
| AI870401 | UNKNOWN | 6 | 429 | T |
| AI870404 | UNKNOWN | 12 | 0 | T |
| AI870428 | UNKNOWN | 17 | 0 | T |
| AI870457 | UNKNOWN | 28 | 0 | T |
| AI870526 | UNKNOWN | 50 | 0 | T |
| AI870526 | UNKNOWN | 20 | 410 | G |
| AI870526 | UNKNOWN | 15 | 456 | C |
| AI870653 | UNKNOWN | 42 | 0 | T |
| AI870661 | UNKNOWN | 30 | 0 | T |
| AI870706 | UNKNOWN | 29 | 0 | T |
| AI870745 | UNKNOWN | 31 | 0 | T |
| AI870772 | UNKNOWN | 50 | 0 | T |
| AI870868 | UNKNOWN | 8.33 | 103 | ACA |
| AI870894 | UNKNOWN | 15 | 357 | A |
| AI870990 | UNKNOWN | 3.83 | 120 | ATGAGG |
| AI870991 | UNKNOWN | 5 | 47 | AAAAC |
| AI871000 | UNKNOWN | 17 | 47 | T |
| AI871028 | UNKNOWN | 20 | 0 | T |
| AI871103 | UNKNOWN | 5.5 | 15 | TTTA |
| AI871174 | UNKNOWN | 31 | 0 | T |
| AI871174 | UNKNOWN | 27 | 256 | A |
| AI871218 | UNKNOWN | 41 | 0 | T |
| AI871218 | UNKNOWN | 14 | 208 | C |
| AI871222 | UNKNOWN | 17 | 0 | T |
| AI871225 | UNKNOWN | 5.5 | 6 | TTAT |
| AI871284 | UNKNOWN | 2.8 | 262 | GGGCCGGGCT (SEQ ID NO: 159) |
| AI871432 | UNKNOWN | 13 | 72 | A |
| AI871462 | UNKNOWN | 18 | 0 | T |
| AI871468 | UNKNOWN | 42 | 0 | T |
| AI871468 | UNKNOWN | 19 | 160 | A |
| AI871483 | UNKNOWN | 12 | 496 | A |
| AI871583 | UNKNOWN | 13 | 56 | A |
| AI871616 | UNKNOWN | 13 | 0 | T |
| AI871629 | UNKNOWN | 12.5 | 118 | CA |
| AI871643 | UNKNOWN | 17 | 467 | A |
| AI871658 | UNKNOWN | 23 | 267 | T |
| AI871659 | UNKNOWN | 71 | 0 | T |
| AI871660 | UNKNOWN | 49 | 0 | T |
| AI871678 | UNKNOWN | 65 | 0 | T |
| AI871695 | UNKNOWN | 39 | 0 | T |
| AI871697 | UNKNOWN | 108 | 0 | T |
| AI871697 | UNKNOWN | 19 | 260 | G |
| AI871697 | UNKNOWN | 18 | 279 | A |
| AI871697 | UNKNOWN | 15 | 108 | A |
| AI871697 | UNKNOWN | 12 | 148 | C |
| AI871697 | UNKNOWN | 12 | 219 | G |
| AI871703 | UNKNOWN | 56 | 0 | T |
| AI871703 | UNKNOWN | 16 | 158 | C |
| AI871703 | UNKNOWN | 12 | 110 | C |
| AI871709 | UNKNOWN | 72 | 0 | T |
| AI871709 | UNKNOWN | 14 | 272 | A |
| AI871709 | UNKNOWN | 13 | 301 | C |
| AI871735 | UNKNOWN | 56 | 0 | T |
| AI871807 | UNKNOWN | 40 | 0 | T |
| AI871808 | UNKNOWN | 16 | 0 | T |
| AI871810 | UNKNOWN | 15 | 0 | T |
| AI871811 | UNKNOWN | 6.5 | 118 | AC |
| AI871825 | UNKNOWN | 21 | 0 | T |
| AI871826 | UNKNOWN | 15 | 0 | T |
| AI871839 | UNKNOWN | 7 | 217 | TA |
| AI871839 | UNKNOWN | 45 | 0 | T |
| AI871861 | UNKNOWN | 31 | 0 | T |
| AI871883 | UNKNOWN | 16 | 0 | T |
| AI871892 | UNKNOWN | 13 | 301 | T |
| AI871913 | UNKNOWN | 13 | 0 | T |
| AI871923 | UNKNOWN | 100 | 0 | T |
| AI871923 | UNKNOWN | 30 | 249 | G |
| AI871923 | UNKNOWN | 17 | 222 | C |

TABLE 1-continued

| Genbank # | Region | # reps | Position | Unit sequence |
|---|---|---|---|---|
| AI871923 | UNKNOWN | 16 | 125 | A |
| AI871923 | UNKNOWN | 15 | 107 | A |
| AI871933 | UNKNOWN | 4.33 | 286 | GGCCTT |
| AI871933 | UNKNOWN | 72 | 0 | T |
| AI871933 | UNKNOWN | 18 | 138 | G |
| AI871933 | UNKNOWN | 16 | 92 | A |
| AI871970 | UNKNOWN | 15 | 353 | A |
| AI871976 | UNKNOWN | 31 | 0 | T |
| AI871977 | UNKNOWN | 79 | 0 | T |
| AI871977 | UNKNOWN | 13 | 265 | G |
| AI871981 | UNKNOWN | 65 | 0 | T |
| AI871981 | UNKNOWN | 19 | 156 | A |
| AI872028 | UNKNOWN | 39 | 0 | T |
| AI872051 | UNKNOWN | 94 | 0 | T |
| AI872064 | UNKNOWN | 78 | 0 | T |
| AI872064 | UNKNOWN | 13 | 101 | A |
| AI872064 | UNKNOWN | 13 | 253 | G |
| AI872072 | UNKNOWN | 72 | 0 | T |
| AI872074 | UNKNOWN | 2.83 | 116 | CCCCGGGGGGGG (SEQ ID NO: 160) |
| AI872074 | UNKNOWN | 112 | 0 | T |
| AI872074 | UNKNOWN | 20 | 168 | C |
| AI872076 | UNKNOWN | 34 | 0 | T |
| AI872077 | UNKNOWN | 74 | 0 | T |
| AI872077 | UNKNOWN | 16 | 351 | C |
| AI872077 | UNKNOWN | 12 | 282 | G |
| AI872082 | UNKNOWN | 37 | 0 | T |
| AI872091 | UNKNOWN | 61 | 0 | T |
| AI872091 | UNKNOWN | 19 | 301 | G |
| AI872091 | UNKNOWN | 15 | 380 | C |
| AI872091 | UNKNOWN | 12 | 267 | A |
| AI872092 | UNKNOWN | 12 | 7 | T |
| AI872105 | UNKNOWN | 35 | 0 | T |
| AI872131 | UNKNOWN | 27 | 0 | T |
| AI872148 | UNKNOWN | 65 | 0 | T |
| AI872150 | UNKNOWN | 6 | 0 | GTT |
| AI872154 | UNKNOWN | 76 | 0 | T |
| AI872154 | UNKNOWN | 23 | 112 | A |
| AI872154 | UNKNOWN | 15 | 222 | G |
| AI872154 | UNKNOWN | 12 | 188 | G |
| AI872159 | UNKNOWN | 99 | 0 | T |
| AI872164 | UNKNOWN | 75 | 5 | T |
| AI872167 | UNKNOWN | 74 | 0 | T |
| AI872175 | UNKNOWN | 16 | 0 | T |
| AI872177 | UNKNOWN | 23 | 0 | T |
| AI872184 | UNKNOWN | 80 | 0 | T |
| AI872184 | UNKNOWN | 16 | 196 | G |
| AI872184 | UNKNOWN | 12 | 144 | G |
| AI872202 | UNKNOWN | 51 | 0 | T |
| AI872215 | UNKNOWN | 15 | 0 | T |
| AI872253 | UNKNOWN | 24 | 0 | T |
| AI872264 | UNKNOWN | 52 | 0 | T |
| AI872264 | UNKNOWN | 12 | 158 | A |
| AI872267 | UNKNOWN | 18 | 0 | T |
| AI872294 | UNKNOWN | 18 | 11 | T |
| AI872296 | UNKNOWN | 25 | 0 | T |
| AI872302 | UNKNOWN | 16 | 0 | T |
| AI872314 | UNKNOWN | 26 | 10 | T |
| AI872343 | UNKNOWN | 59 | 0 | T |
| AI872343 | UNKNOWN | 13 | 107 | G |
| AI872421 | UNKNOWN | 19 | 11 | T |
| AI872437 | UNKNOWN | 61 | 0 | T |
| AI872437 | UNKNOWN | 12 | 235 | G |
| AI872446 | UNKNOWN | 25 | 0 | T |
| AI872457 | UNKNOWN | 27 | 0 | T |
| AI872458 | UNKNOWN | 32 | 0 | T |
| AI872472 | UNKNOWN | 56 | 0 | T |
| AI872479 | UNKNOWN | 13 | 0 | T |
| AI672506 | UNKNOWN | 22 | 0 | T |
| AI872523 | UNKNOWN | 18 | 314 | C |
| AI872523 | UNKNOWN | 17 | 262 | G |
| AI872523 | UNKNOWN | 14 | 110 | G |
| AI872523 | UNKNOWN | 13 | 149 | A |
| AI672545 | UNKNOWN | 99 | 0 | T |
| AI872545 | UNKNOWN | 21 | 233 | G |
| AI872545 | UNKNOWN | 13 | 123 | C |
| AI672555 | UNKNOWN | 54 | 0 | T |
| AI872555 | UNKNOWN | 12 | 153 | C |

TABLE 1-continued

| Genbank # | Region | # reps | Position | Unit sequence |
|---|---|---|---|---|
| AI872568 | UNKNOWN | 36 | 0 | T |
| AI872573 | UNKNOWN | 35 | 0 | T |
| AI872621 | UNKNOWN | 23 | 0 | T |
| AI872625 | UNKNOWN | 12 | 347 | A |
| AI872669 | UNKNOWN | 40 | 0 | T |
| AI872711 | UNKNOWN | 115 | 0 | T |
| AI872711 | UNKNOWN | 18 | 230 | C |
| AI872711 | UNKNOWN | 17 | 207 | A |
| AI872711 | UNKNOWN | 14 | 131 | A |
| AI872719 | UNKNOWN | 12 | 0 | T |
| AI872722 | UNKNOWN | 62 | 0 | T |
| AI872722 | UNKNOWN | 12 | 86 | C |
| AI872724 | UNKNOWN | 102 | 0 | T |
| AI872763 | UNKNOWN | 36 | 0 | T |
| AI872768 | UNKNOWN | 18 | 259 | A |
| AI872768 | UNKNOWN | 17 | 73 | T |
| AI872768 | UNKNOWN | 16 | 158 | C |
| AI872768 | UNKNOWN | 13 | 143 | G |
| AI872786 | UNKNOWN | 41 | 0 | T |
| AI872786 | UNKNOWN | 13 | 119 | A |
| AI872787 | UNKNOWN | 41 | 0 | T |
| AI872798 | UNKNOWN | 34 | 0 | T |
| AI872804 | UNKNOWN | 66 | 0 | T |
| AI872810 | UNKNOWN | 69 | 0 | T |
| AI872847 | UNKNOWN | 52 | 0 | T |
| AI872869 | UNKNOWN | 46 | 0 | T |
| AI872914 | UNKNOWN | 95 | 0 | T |
| AI872914 | UNKNOWN | 13 | 318 | G |
| AI872914 | UNKNOWN | 12 | 183 | A |
| AI872916 | UNKNOWN | 3.6 | 165 | TTTAT |
| AI872916 | UNKNOWN | 16 | 0 | T |
| AI873058 | UNKNOWN | 17 | 586 | G |
| AI873058 | UNKNOWN | 12 | 407 | A |
| AI873302 | UNKNOWN | 22 | 2 | T |
| AI873363 | UNKNOWN | 17 | 0 | T |
| AI873550 | UNKNOWN | 51 | 0 | T |
| AI873550 | UNKNOWN | 16 | 157 | A |
| AI873552 | UNKNOWN | 30 | 0 | T |
| AI873604 | UNKNOWN | 97 | 0 | T |
| AI873604 | UNKNOWN | 13 | 152 | A |
| AI873604 | UNKNOWN | 13 | 250 | G |
| AI873605 | UNKNOWN | 74 | 0 | T |
| AI873605 | UNKNOWN | 13 | 245 | G |
| AI873605 | UNKNOWN | 12 | 105 | C |
| AI873613 | UNKNOWN | 106 | 0 | T |
| AI873613 | UNKNOWN | 12 | 161 | G |
| AI873619 | UNKNOWN | 35 | 0 | T |
| AI873630 | UNKNOWN | 18 | 0 | T |
| AI873638 | UNKNOWN | 67 | 0 | T |
| AI873644 | UNKNOWN | 98 | 0 | T |
| AI873644 | UNKNOWN | 21 | 176 | C |
| AI873644 | UNKNOWN | 12 | 125 | A |
| AI873675 | UNKNOWN | 35 | 0 | T |
| AI873703 | UNKNOWN | 26 | 0 | T |
| AI873704 | UNKNOWN | 107 | 0 | T |
| AI873704 | UNKNOWN | 21 | 236 | G |
| AI873704 | UNKNOWN | 19 | 153 | A |
| AI873704 | UNKNOWN | 14 | 172 | C |
| AI873704 | UNKNOWN | 12 | 193 | G |
| AI873731 | UNKNOWN | 119 | 0 | T |
| AI873731 | UNKNOWN | 27 | 271 | G |
| AI873731 | UNKNOWN | 23 | 225 | A |
| AI873731 | UNKNOWN | 14 | 196 | C |
| AI873731 | UNKNOWN | 13 | 147 | A |
| AI873746 | UNKNOWN | 2.9 | 6 | TTTTTTTTN (SEQ ID NO: 161) |
| AI873746 | UNKNOWN | 24 | 26 | T |
| AI873746 | UNKNOWN | 15 | 0 | T |
| AI873761 | UNKNOWN | 5.75 | 48 | TTTC |
| AI873761 | UNKNOWN | 22 | 68 | T |
| AI873804 | UNKNOWN | 22 | 220 | T |
| AI873866 | UNKNOWN | 14 | 0 | T |
| AI873919 | UNKNOWN | 50 | 0 | T |
| AI873923 | UNKNOWN | 81 | 0 | T |
| AI873923 | UNKNOWN | 19 | 91 | A |
| AI873923 | UNKNOWN | 15 | 231 | G |
| AI873995 | UNKNOWN | 32 | 0 | T |
| AI873998 | UNKNOWN | 52 | 0 | T |

TABLE 1-continued

| Genbank # | Region | # reps | Position | Unit sequence |
|---|---|---|---|---|
| AI874004 | UNKNOWN | 71 | 0 | T |
| AI874004 | UNKNOWN | 21 | 383 | A |
| AI874004 | UNKNOWN | 19 | 279 | C |
| AI874004 | UNKNOWN | 12 | 322 | G |
| AI874070 | UNKNOWN | 36 | 14 | T |
| AI874107 | UNKNOWN | 53 | 0 | T |
| AI874109 | UNKNOWN | 125 | 0 | T |
| AI874109 | UNKNOWN | 21 | 152 | A |
| AI874109 | UNKNOWN | 20 | 125 | C |
| AI874109 | UNKNOWN | 19 | 200 | G |
| AI874134 | UNKNOWN | 4.75 | 347 | AAAT |
| AI874151 | UNKNOWN | 76 | 0 | T |
| AI874166 | UNKNOWN | 94 | 0 | T |
| AI874189 | UNKNOWN | 63 | 0 | T |
| AI874189 | UNKNOWN | 23 | 245 | A |
| AI874189 | UNKNOWN | 15 | 119 | A |
| AI874219 | UNKNOWN | 32 | 0 | T |
| AI874222 | UNKNOWN | 41 | 0 | T |
| AI874226 | UNKNOWN | 34 | 0 | T |
| AI874228 | UNKNOWN | 68 | 0 | T |
| AI874238 | UNKNOWN | 53 | 0 | T |
| AI874243 | UNKNOWN | 85 | 0 | T |
| AI874243 | UNKNOWN | 17 | 217 | C |
| AI874243 | UNKNOWN | 14 | 307 | G |
| AI874245 | UNKNOWN | 13 | 256 | A |
| AI874248 | UNKNOWN | 35 | 0 | T |
| AI874248 | UNKNOWN | 16 | 254 | C |
| AI874261 | UNKNOWN | 96 | 0 | T |
| AI874261 | UNKNOWN | 19 | 271 | A |
| AI874261 | UNKNOWN | 18 | 132 | A |
| AI874263 | UNKNOWN | 41 | 0 | T |
| AI874341 | UNKNOWN | 23 | 433 | A |
| AI874343 | UNKNOWN | 4.59 | 54 | AAACC |
| AI874351 | UNKNOWN | 99 | 0 | T |
| AI874351 | UNKNOWN | 27 | 358 | C |
| AI874371 | UNKNOWN | 49 | 0 | T |
| AI874394 | UNKNOWN | 27 | 0 | T |
| AI874394 | UNKNOWN | 14 | 207 | A |
| AI874410 | UNKNOWN | 97 | 0 | T |
| AI874410 | UNKNOWN | 15 | 377 | G |
| AI874410 | UNKNOWN | 14 | 266 | C |
| AI874410 | UNKNOWN | 12 | 180 | A |
| AI878897 | UNKNOWN | 13 | 186 | A |
| AI879281 | UNKNOWN | 19 | 497 | AC |
| AI879330 | UNKNOWN | 16 | 6 | C |
| AI879587 | UNKNOWN | 55 | 0 | T |
| AI879693 | UNKNOWN | 73 | 0 | T |
| AI879863 | UNKNOWN | 13 | 0 | T |
| AI879951 | UNKNOWN | 17 | 0 | T |
| AI880009 | UNKNOWN | 63 | 0 | T |
| AI880111 | UNKNOWN | 51 | 0 | T |
| AI880562 | UNKNOWN | 15 | 290 | A |
| AI884303 | UNKNOWN | 53 | 0 | T |
| AI884303 | UNKNOWN | 14 | 240 | A |
| AI884310 | UNKNOWN | 49 | 0 | T |
| AI884310 | UNKNOWN | 15 | 412 | A |
| AI884320 | UNKNOWN | 39 | 0 | T |
| AI884332 | UNKNOWN | 7 | 346 | AT |
| AI884354 | UNKNOWN | 79 | 0 | T |
| AI884354 | UNKNOWN | 18 | 331 | G |
| AI884399 | UNKNOWN | 46 | 0 | T |
| AI884414 | UNKNOWN | 51 | 0 | T |
| AI884414 | UNKNOWN | 12 | 264 | G |
| AI884419 | UNKNOWN | 47 | 0 | T |
| AI884419 | UNKNOWN | 16 | 110 | A |
| AI884422 | UNKNOWN | 17 | 0 | T |
| AI884429 | UNKNOWN | 23 | 0 | T |
| AI884459 | UNKNOWN | 56 | 0 | T |
| AI884466 | UNKNOWN | 15 | 0 | T |
| AI884467 | UNKNOWN | 40 | 0 | T |
| AI884467 | UNKNOWN | 12 | 228 | G |
| AI884469 | UNKNOWN | 112 | 0 | T |
| AI884469 | UNKNOWN | 15 | 116 | A |
| AI884497 | UNKNOWN | 41 | 0 | T |
| AI884510 | UNKNOWN | 48 | 0 | T |
| AI884510 | UNKNOWN | 21 | 239 | A |
| AI884516 | UNKNOWN | 17 | 0 | T |

TABLE 1-continued

| Genbank # | Region | # reps | Position | Unit sequence |
|---|---|---|---|---|
| AI884527 | UNKNOWN | 55 | 0 | T |
| AI884528 | UNKNOWN | 71 | 0 | T |
| AI884528 | UNKNOWN | 17 | 447 | G |
| AI884528 | UNKNOWN | 12 | 76 | A |
| AI884529 | UNKNOWN | 43 | 0 | T |
| AI884560 | UNKNOWN | 20 | 0 | T |
| AI884570 | UNKNOWN | 12 | 14 | T |
| AI884573 | UNKNOWN | 26 | 0 | T |
| AI884574 | UNKNOWN | 58 | 0 | T |
| AI884574 | UNKNOWN | 14 | 170 | G |
| AI884598 | UNKNOWN | 3.8 | 206 | AAAAC |
| AI884598 | UNKNOWN | 51 | 0 | T |
| AI884619 | UNKNOWN | 12 | 0 | T |
| AI884635 | UNKNOWN | 37 | 0 | T |
| AI884660 | UNKNOWN | 18 | 0 | T |
| AI884687 | UNKNOWN | 19 | 0 | T |
| AI884688 | UNKNOWN | 14 | 0 | T |
| AI884801 | UNKNOWN | 14 | 0 | T |
| AI884945 | UNKNOWN | 13 | 0 | T |
| AI885003 | UNKNOWN | 15 | 0 | T |
| AI885012 | UNKNOWN | 3.5 | 255 | CAGATT |
| AI885036 | UNKNOWN | 18 | 1 | T |
| AI885078 | UNKNOWN | 30 | 0 | T |
| AI885078 | UNKNOWN | 12 | 369 | G |
| AI885087 | UNKNOWN | 3.8 | 19 | TTTTA |
| AI885183 | UNKNOWN | 17 | 18 | T |
| AI885260 | UNKNOWN | 30 | 0 | T |
| AI885296 | UNKNOWN | 13 | 0 | T |
| AI885321 | UNKNOWN | 20 | 0 | T |
| AI885329 | UNKNOWN | 15 | 0 | T |
| AI885371 | UNKNOWN | 16 | 564 | A |
| AI885374 | UNKNOWN | 20 | 4 | T |
| AI885390 | UNKNOWN | 15 | 350 | T |
| AI885403 | UNKNOWN | 12 | 0 | T |
| AI885411 | UNKNOWN | 13 | 0 | T |
| AI885420 | UNKNOWN | 17 | 0 | T |
| AI885420 | UNKNOWN | 12 | 71 | A |
| AI885438 | UNKNOWN | 21 | 0 | T |
| AI885453 | UNKNOWN | 16 | 0 | T |
| AI885466 | UNKNOWN | 13 | 472 | A |
| AI885488 | UNKNOWN | 16 | 95 | T |
| AI885491 | UNKNOWN | 4 | 235 | TTTTA |
| AI885501 | UNKNOWN | 49 | 0 | T |
| AI885512 | UNKNOWN | 58 | 0 | T |
| AI885512 | UNKNOWN | 12 | 158 | C |
| AI885520 | UNKNOWN | 71 | 0 | T |
| AI885610 | UNKNOWN | 38 | 0 | T |
| AI885664 | UNKNOWN | 32 | 15 | T |
| AI885664 | UNKNOWN | 14 | 0 | T |
| AI885665 | UNKNOWN | 20 | 0 | T |
| AI885666 | UNKNOWN | 12 | 0 | T |
| AI885677 | UNKNOWN | 9 | 151 | TG |
| AI885756 | UNKNOWN | 43 | 0 | T |
| AI885756 | UNKNOWN | 12 | 70 | G |
| AI885843 | UNKNOWN | 30 | 0 | T |
| AI885843 | UNKNOWN | 17 | 158 | A |
| AI885879 | UNKNOWN | 112 | 0 | T |
| AI885879 | UNKNOWN | 15 | 318 | A |
| AI885879 | UNKNOWN | 14 | 218 | G |
| AI885879 | UNKNOWN | 13 | 163 | A |
| AI885879 | UNKNOWN | 13 | 301 | C |
| AI885884 | UNKNOWN | 5.75 | 377 | AATA |
| AI885884 | UNKNOWN | 12 | 0 | T |
| AI885905 | UNKNOWN | 71 | 0 | T |
| AI885916 | UNKNOWN | 13 | 0 | T |
| AI885943 | UNKNOWN | 54 | 0 | T |
| AI885943 | UNKNOWN | 24 | 211 | C |
| AI885950 | UNKNOWN | 54 | 0 | T |
| AI885950 | UNKNOWN | 16 | 285 | A |
| AI885969 | UNKNOWN | 15 | 4 | T |
| AI885974 | UNKNOWN | 100 | 0 | T |
| AI885974 | UNKNOWN | 18 | 116 | A |
| AI885974 | UNKNOWN | 15 | 155 | C |
| AI885982 | UNKNOWN | 72 | 0 | T |
| AI885982 | UNKNOWN | 17 | 140 | G |
| AI885982 | UNKNOWN | 12 | 221 | C |
| AI885989 | UNKNOWN | 64 | 0 | T |

TABLE 1-continued

| Genbank # | Region | # reps | Position | Unit sequence |
|---|---|---|---|---|
| AI885989 | UNKNOWN | 19 | 140 | G |
| AI885999 | UNKNOWN | 62 | 0 | T |
| AI886016 | UNKNOWN | 63 | 0 | T |
| AI886016 | UNKNOWN | 12 | 290 | G |
| AI886016 | UNKNOWN | 12 | 380 | A |
| AI886022 | UNKNOWN | 84 | 0 | T |
| AI886034 | UNKNOWN | 18 | 0 | T |
| AI886036 | UNKNOWN | 7 | 349 | GT |
| AI886036 | UNKNOWN | 14 | 0 | T |
| AI886063 | UNKNOWN | 44 | 0 | T |
| AI886063 | UNKNOWN | 14 | 136 | A |
| AI886123 | UNKNOWN | 80 | 0 | T |
| AI886124 | UNKNOWN | 99 | 0 | T |
| AI886124 | UNKNOWN | 15 | 180 | A |
| AI886126 | UNKNOWN | 17 | 0 | T |
| AI886149 | UNKNOWN | 16 | 237 | T |
| AI886153 | UNKNOWN | 8.5 | 143 | TA |
| AI886181 | UNKNOWN | 80 | 0 | T |
| AI886181 | UNKNOWN | 15 | 123 | C |
| AI886181 | UNKNOWN | 14 | 186 | G |
| AI886192 | UNKNOWN | 78 | 0 | T |
| AI886192 | UNKNOWN | 17 | 171 | C |
| AI886206 | UNKNOWN | 96 | 6 | T |
| AI886206 | UNKNOWN | 33 | 126 | A |
| AI886206 | UNKNOWN | 16 | 178 | G |
| AI886269 | UNKNOWN | 19 | 83 | T |
| AI886269 | UNKNOWN | 19 | 280 | A |
| AI886269 | UNKNOWN | 16 | 228 | A |
| AI886269 | UNKNOWN | 14 | 321 | G |
| AI886269 | UNKNOWN | 13 | 212 | G |
| AI886270 | UNKNOWN | 41 | 0 | T |
| AI886275 | UNKNOWN | 13 | 0 | T |
| AI886321 | UNKNOWN | 55 | 0 | T |
| AI886331 | UNKNOWN | 15 | 0 | T |
| AI886355 | UNKNOWN | 51 | 0 | T |
| AI886355 | UNKNOWN | 20 | 103 | G |
| AI886355 | UNKNOWN | 19 | 74 | C |
| AI886368 | UNKNOWN | 38 | 0 | T |
| AI886381 | UNKNOWN | 30 | 176 | T |
| AI886381 | UNKNOWN | 17 | 154 | T |
| AI886415 | UNKNOWN | 62 | 0 | T |
| AI886415 | UNKNOWN | 17 | 140 | A |
| AI886421 | UNKNOWN | 22 | 0 | T |
| AI886440 | UNKNOWN | 80 | 0 | T |
| AI886440 | UNKNOWN | 15 | 103 | A |
| AI886440 | UNKNOWN | 13 | 247 | C |
| AI886452 | UNKNOWN | 44 | 0 | T |
| AI886467 | UNKNOWN | 12 | 0 | T |
| AI886468 | UNKNOWN | 3.66 | 195 | AAAACA |
| AI886468 | UNKNOWN | 17 | 222 | G |
| AI886504 | UNKNOWN | 14 | 114 | C |
| AI886504 | UNKNOWN | 12 | 155 | A |
| AI886532 | UNKNOWN | 74 | 65 | T |
| AI886532 | UNKNOWN | 33 | 0 | T |
| AI886532 | UNKNOWN | 15 | 240 | C |
| AI886532 | UNKNOWN | 13 | 213 | C |
| AI886532 | UNKNOWN | 13 | 255 | A |
| AI886546 | UNKNOWN | 38 | 2 | T |
| AI886715 | UNKNOWN | 56 | 0 | T |
| AI886715 | UNKNOWN | 13 | 114 | G |
| AI886715 | UNKNOWN | 12 | 170 | A |
| AI886751 | UNKNOWN | 36 | 0 | T |
| AI886753 | UNKNOWN | 103 | 0 | T |
| AI886753 | UNKNOWN | 14 | 178 | A |
| AI886784 | UNKNOWN | 58 | 0 | T |
| AI886884 | UNKNOWN | 44 | 0 | T |
| AI886940 | UNKNOWN | 37 | 21 | T |
| AI886940 | UNKNOWN | 18 | 0 | T |
| AI887029 | UNKNOWN | 12 | 0 | T |
| AI887055 | UNKNOWN | 26 | 0 | T |
| AI887139 | UNKNOWN | 82 | 0 | T |
| AI887139 | UNKNOWN | 13 | 283 | A |
| AI887139 | UNKNOWN | 12 | 102 | A |
| AI887141 | UNKNOWN | 46 | 0 | T |
| AI887141 | UNKNOWN | 18 | 283 | A |
| AI887141 | UNKNOWN | 15 | 86 | A |
| AI887151 | UNKNOWN | 92 | 0 | T |

TABLE 1-continued

| Genbank # | Region | # reps | Position | Unit sequence |
|---|---|---|---|---|
| AI887151 | UNKNOWN | 23 | 209 | A |
| AI887151 | UNKNOWN | 15 | 175 | G |
| AI887151 | UNKNOWN | 12 | 130 | C |
| AI887163 | UNKNOWN | 54 | 0 | T |
| AI887163 | UNKNOWN | 24 | 140 | A |
| AI887166 | UNKNOWN | 51 | 0 | T |
| AI887170 | UNKNOWN | 104 | 0 | T |
| AI887170 | UNKNOWN | 25 | 398 | A |
| AI887170 | UNKNOWN | 20 | 162 | G |
| AI887170 | UNKNOWN | 19 | 214 | C |
| AI887170 | UNKNOWN | 12 | 279 | A |
| AI887174 | UNKNOWN | 31 | 0 | T |
| AI887194 | UNKNOWN | 104 | 0 | T |
| AI887194 | UNKNOWN | 14 | 331 | C |
| AI887194 | UNKNOWN | 13 | 200 | G |
| AI887209 | UNKNOWN | 6.33 | 384 | TAT |
| AI887211 | UNKNOWN | 77 | 0 | T |
| AI887214 | UNKNOWN | 49 | 0 | T |
| AI887222 | UNKNOWN | 52 | 0 | T |
| AI887222 | UNKNOWN | 12 | 266 | G |
| AI887235 | UNKNOWN | 26 | 0 | T |
| AI887241 | UNKNOWN | 42 | 0 | T |
| AI887242 | UNKNOWN | 82 | 0 | T |
| AI887242 | UNKNOWN | 22 | 229 | A |
| AI887242 | UNKNOWN | 12 | 173 | C |
| AI887244 | UNKNOWN | 26 | 0 | T |
| AI887247 | UNKNOWN | 85 | 0 | T |
| AI887247 | UNKNOWN | 17 | 141 | C |
| AI887247 | UNKNOWN | 13 | 200 | A |
| AI887308 | UNKNOWN | 90 | 0 | T |
| AI887308 | UNKNOWN | 13 | 285 | G |
| AI887311 | UNKNOWN | 12 | 18 | A |
| AI887338 | UNKNOWN | 85 | 0 | T |
| AI887338 | UNKNOWN | 12 | 156 | C |
| AI887360 | UNKNOWN | 45 | 0 | T |
| AI887360 | UNKNOWN | 18 | 425 | A |
| AI887363 | UNKNOWN | 38 | 0 | T |
| AI887380 | UNKNOWN | 87 | 0 | T |
| AI887380 | UNKNOWN | 18 | 322 | G |
| AI887380 | UNKNOWN | 15 | 277 | A |
| AI887381 | UNKNOWN | 73 | 0 | T |
| AI887381 | UNKNOWN | 12 | 73 | A |
| AI887389 | UNKNOWN | 71 | 0 | T |
| AI887389 | UNKNOWN | 12 | 164 | C |
| AI887396 | UNKNOWN | 114 | 0 | T |
| AI887396 | UNKNOWN | 18 | 298 | A |
| AI887396 | UNKNOWN | 13 | 114 | A |
| AI887396 | UNKNOWN | 12 | 322 | G |
| AI887430 | UNKNOWN | 72 | 0 | T |
| AI887434 | UNKNOWN | 53 | 2 | T |
| AI887450 | UNKNOWN | 117 | 0 | T |
| AI887450 | UNKNOWN | 19 | 234 | C |
| AI887450 | UNKNOWN | 16 | 207 | C |
| AI887450 | UNKNOWN | 15 | 192 | G |
| AI887450 | UNKNOWN | 14 | 146 | A |
| AI887488 | UNKNOWN | 42 | 0 | T |
| AI887521 | UNKNOWN | 19 | 0 | T |
| AI887544 | UNKNOWN | 15 | 0 | T |
| AI887550 | UNKNOWN | 29 | 0 | T |
| AI887567 | UNKNOWN | 46 | 0 | T |
| AI887569 | UNKNOWN | 77 | 0 | T |
| AI887569 | UNKNOWN | 15 | 127 | G |
| AI887611 | UNKNOWN | 25 | 0 | T |
| AI887613 | UNKNOWN | 25 | 0 | T |
| AI887615 | UNKNOWN | 31 | 0 | T |
| AI887620 | UNKNOWN | 65 | 0 | T |
| AI887620 | UNKNOWN | 14 | 120 | G |
| AI887659 | UNKNOWN | 109 | 0 | T |
| AI887659 | UNKNOWN | 18 | 234 | C |
| AI887659 | UNKNOWN | 18 | 277 | G |
| AI887659 | UNKNOWN | 12 | 214 | A |
| AI887688 | UNKNOWN | 55 | 0 | T |
| AI887721 | UNKNOWN | 37 | 0 | T |
| AI887726 | UNKNOWN | 19 | 0 | T |
| AI887749 | UNKNOWN | 24 | 11 | T |
| AI887752 | UNKNOWN | 44 | 0 | T |
| AI887752 | UNKNOWN | 14 | 211 | A |

TABLE 1-continued

| Genbank # | Region | # reps | Position | Unit sequence |
|---|---|---|---|---|
| AI887765 | UNKNOWN | 76 | 0 | T |
| AI887765 | UNKNOWN | 13 | 260 | C |
| AI887772 | UNKNOWN | 73 | 0 | T |
| AI887772 | UNKNOWN | 19 | 101 | G |
| AI887772 | UNKNOWN | 14 | 130 | C |
| AI887772 | UNKNOWN | 13 | 78 | A |
| AI887773 | UNKNOWN | 5.25 | 48 | ATTT |
| AI887773 | UNKNOWN | 26 | 0 | T |
| AI887776 | UNKNOWN | 17 | 11 | T |
| AI887786 | UNKNOWN | 20 | 0 | T |
| AI887787 | UNKNOWN | 30 | 0 | T |
| AI887816 | UNKNOWN | 13 | 305 | A |
| AI887840 | UNKNOWN | 14 | 277 | T |
| AI887849 | UNKNOWN | 15 | 15 | A |
| AI887868 | UNKNOWN | 31 | 0 | T |
| AI887868 | UNKNOWN | 13 | 76 | G |
| AI887898 | UNKNOWN | 12 | 477 | A |
| AI888033 | UNKNOWN | 30 | 0 | T |
| AI888057 | UNKNOWN | 9.5 | 510 | TA |
| AI888057 | UNKNOWN | 13 | 486 | A |
| AI888057 | UNKNOWN | 12 | 0 | T |
| AI888095 | UNKNOWN | 49 | 0 | T |
| AI888180 | UNKNOWN | 13 | 511 | TA |
| AI888203 | UNKNOWN | 63 | 0 | T |
| AI888208 | UNKNOWN | 60 | 4 | T |
| AI888208 | UNKNOWN | 14 | 118 | A |
| AI888208 | UNKNOWN | 12 | 268 | G |
| AI888225 | UNKNOWN | 65 | 0 | T |
| AI888231 | UNKNOWN | 43 | 0 | T |
| AI888247 | UNKNOWN | 54 | 0 | T |
| AI888257 | UNKNOWN | 35 | 0 | T |
| AI888257 | UNKNOWN | 14 | 343 | A |
| AI888269 | UNKNOWN | 34 | 0 | T |
| AI888293 | UNKNOWN | 20 | 0 | T |
| AI888303 | UNKNOWN | 14 | 292 | T |
| AI888308 | UNKNOWN | 20 | 0 | T |
| AI888416 | UNKNOWN | 47 | 0 | T |
| AI888428 | UNKNOWN | 18 | 11 | T |
| AI888429 | UNKNOWN | 82 | 0 | T |
| AI888429 | UNKNOWN | 12 | 82 | G |
| AI888429 | UNKNOWN | 12 | 339 | A |
| AI888432 | UNKNOWN | 49 | 0 | T |
| AI888460 | UNKNOWN | 78 | 49 | T |
| AI888460 | UNKNOWN | 12 | 171 | A |
| AI888460 | UNKNOWN | 12 | 183 | G |
| AI888480 | UNKNOWN | 47 | 0 | T |
| AI888482 | UNKNOWN | 75 | 0 | T |
| AI888482 | UNKNOWN | 15 | 345 | C |
| AI888482 | UNKNOWN | 13 | 371 | G |
| AI888482 | UNKNOWN | 12 | 275 | G |
| AI888488 | UNKNOWN | 43 | 0 | T |
| AI888521 | UNKNOWN | 13 | 235 | C |
| AI888522 | UNKNOWN | 80 | 0 | T |
| AI888522 | UNKNOWN | 14 | 226 | A |
| AI888523 | UNKNOWN | 58 | 0 | T |
| AI888570 | UNKNOWN | 18 | 0 | T |
| AI888608 | UNKNOWN | 2.5 | 505 | TGTGTGTGTA (SEQ ID NO: 162) |
| AI888621 | UNKNOWN | 80 | 0 | T |
| AI888621 | UNKNOWN | 17 | 114 | A |
| AI888624 | UNKNOWN | 37 | 0 | T |
| AI888671 | UNKNOWN | 83 | 0 | T |
| AI888671 | UNKNOWN | 16 | 135 | A |
| AI888705 | UNKNOWN | 32 | 0 | T |
| AI888725 | UNKNOWN | 32 | 0 | T |
| AI888746 | UNKNOWN | 51 | 0 | T |
| AI888746 | UNKNOWN | 13 | 104 | A |
| AI888818 | UNKNOWN | 17 | 5 | T |
| AI888849 | UNKNOWN | 2.53 | 326 | AAAATGATAGACA (SEQ ID NO: 163) |
| AI888849 | UNKNOWN | 29 | 11 | T |
| AI888856 | UNKNOWN | 42 | 0 | T |
| AI888856 | UNKNOWN | 13 | 106 | A |
| AI888856 | UNKNOWN | 13 | 200 | C |
| AI888869 | UNKNOWN | 54 | 0 | T |
| AI888944 | UNKNOWN | 92 | 0 | T |
| AI888953 | UNKNOWN | 102 | 0 | T |
| AI888953 | UNKNOWN | 12 | 150 | A |
| AI888956 | UNKNOWN | 61 | 0 | T |

TABLE 1-continued

| Genbank # | Region | # reps | Position | Unit sequence |
|---|---|---|---|---|
| AI888956 | UNKNOWN | 12 | 197 | C |
| AI888978 | UNKNOWN | 75 | 38 | T |
| AI888978 | UNKNOWN | 21 | 0 | T |
| AI888978 | UNKNOWN | 20 | 163 | G |
| AI888978 | UNKNOWN | 19 | 253 | A |
| AI888978 | UNKNOWN | 14 | 212 | C |
| AI888991 | UNKNOWN | 12 | 0 | T |
| AI889034 | UNKNOWN | 33 | 0 | T |
| AI889049 | UNKNOWN | 20 | 0 | T |
| AI889074 | UNKNOWN | 16 | 4 | T |
| AI889075 | UNKNOWN | 13 | 0 | T |
| AI889085 | UNKNOWN | 14 | 0 | T |
| AI889109 | UNKNOWN | 54 | 0 | T |
| AI889110 | UNKNOWN | 18 | 0 | T |
| AI889114 | UNKNOWN | 19 | 0 | T |
| AI889118 | UNKNOWN | 3.8 | 9 | TTTTC |
| AI889118 | UNKNOWN | 7 | 139 | AT |
| AI889118 | UNKNOWN | 17 | 24 | T |
| AI889133 | UNKNOWN | 101 | 11 | T |
| AI889133 | UNKNOWN | 14 | 250 | C |
| AI889185 | UNKNOWN | 43 | 0 | T |
| AI889195 | UNKNOWN | 55 | 0 | T |
| AI889203 | UNKNOWN | 131 | 0 | T |
| AI889203 | UNKNOWN | 15 | 274 | C |
| AI889203 | UNKNOWN | 14 | 181 | C |
| AI889213 | UNKNOWN | 105 | 0 | T |
| AI889213 | UNKNOWN | 20 | 206 | C |
| AI889213 | UNKNOWN | 13 | 110 | A |
| AI889214 | UNKNOWN | 38 | 0 | T |
| AI889244 | UNKNOWN | 51 | 0 | T |
| AI889256 | UNKNOWN | 55 | 0 | T |
| AI889256 | UNKNOWN | 14 | 104 | C |
| AI889257 | UNKNOWN | 47 | 0 | T |
| AI889262 | UNKNOWN | 55 | 0 | T |
| AI889280 | UNKNOWN | 67 | 0 | T |
| AI889280 | UNKNOWN | 12 | 310 | C |
| AI889292 | UNKNOWN | 8.5 | 503 | AT |
| AI889306 | UNKNOWN | 93 | 0 | T |
| AI889306 | UNKNOWN | 22 | 139 | C |
| AI889306 | UNKNOWN | 19 | 119 | A |
| AI889323 | UNKNOWN | 67 | 0 | T |
| AI889348 | UNKNOWN | 45 | 0 | T |
| AI889372 | UNKNOWN | 74 | 0 | T |
| AI889376 | UNKNOWN | 106 | 0 | T |
| AI889376 | UNKNOWN | 16 | 211 | A |
| AI889376 | UNKNOWN | 13 | 118 | A |
| AI889376 | UNKNOWN | 13 | 174 | C |
| AI889379 | UNKNOWN | 56 | 0 | T |
| AI889379 | UNKNOWN | 14 | 286 | G |
| AI889396 | UNKNOWN | 35 | 0 | T |
| AI889403 | UNKNOWN | 91 | 0 | T |
| AI889403 | UNKNOWN | 16 | 155 | C |
| AI889403 | UNKNOWN | 14 | 128 | A |
| AI889403 | UNKNOWN | 13 | 429 | G |
| AI889449 | UNKNOWN | 46 | 0 | T |
| AI889449 | UNKNOWN | 14 | 94 | A |
| AI889462 | UNKNOWN | 52 | 0 | T |
| AI889486 | UNKNOWN | 34 | 0 | T |
| AI889493 | UNKNOWN | 89 | 0 | T |
| AI889493 | UNKNOWN | 17 | 243 | A |
| AI889493 | UNKNOWN | 16 | 344 | C |
| AI889493 | UNKNOWN | 15 | 126 | G |
| AI889493 | UNKNOWN | 15 | 141 | A |
| AI889498 | UNKNOWN | 16 | 11 | T |
| AI889501 | UNKNOWN | 29 | 0 | T |
| AI889508 | UNKNOWN | 15 | 11 | T |
| AI889509 | UNKNOWN | 43 | 0 | T |
| AI889536 | UNKNOWN | 14 | 294 | ATT |
| AI889536 | UNKNOWN | 16 | 11 | T |
| AI889565 | UNKNOWN | 16 | 0 | T |
| AI889582 | UNKNOWN | 46 | 0 | T |
| AI889586 | UNKNOWN | 34 | 0 | T |
| AI889601 | UNKNOWN | 37 | 0 | T |
| AI889640 | UNKNOWN | 83 | 0 | T |
| AI889640 | UNKNOWN | 14 | 287 | C |
| AI889640 | UNKNOWN | 13 | 253 | G |
| AI889640 | UNKNOWN | 12 | 161 | G |

TABLE 1-continued

| Genbank # | Region | # reps | Position | Unit sequence |
|---|---|---|---|---|
| AI889708 | UNKNOWN | 14 | 153 | T |
| AI889728 | UNKNOWN | 48 | 0 | T |
| AI889795 | UNKNOWN | 19 | 0 | T |
| AI889816 | UNKNOWN | 25 | 0 | T |
| AI889818 | UNKNOWN | 52 | 0 | T |
| AI889818 | UNKNOWN | 22 | 132 | A |
| AI889839 | UNKNOWN | 124 | 0 | T |
| AI889839 | UNKNOWN | 24 | 384 | C |
| AI889839 | UNKNOWN | 15 | 162 | C |
| AI889839 | UNKNOWN | 13 | 280 | G |
| AI889850 | UNKNOWN | 3.8 | 315 | AAAC |
| AI889850 | UNKNOWN | 37 | 0 | T |
| AI889855 | UNKNOWN | 18 | 0 | T |
| AI889862 | UNKNOWN | 49 | 0 | T |
| AI889862 | UNKNOWN | 13 | 147 | A |
| AI889862 | UNKNOWN | 13 | 242 | G |
| AI889872 | UNKNOWN | 37 | 0 | T |
| AI889882 | UNKNOWN | 82 | 0 | T |
| AI889882 | UNKNOWN | 13 | 265 | C |
| AI889882 | UNKNOWN | 12 | 140 | A |
| AI889884 | UNKNOWN | 41 | 0 | T |
| AI889932 | UNKNOWN | 65 | 0 | T |
| AI889932 | UNKNOWN | 17 | 180 | G |
| AI889932 | UNKNOWN | 13 | 364 | C |
| AI889932 | UNKNOWN | 12 | 129 | G |
| AI889953 | UNKNOWN | 88 | 0 | T |
| AI889953 | UNKNOWN | 22 | 145 | G |
| AI889953 | UNKNOWN | 15 | 111 | C |
| AI889959 | UNKNOWN | 16 | 0 | T |
| AI889968 | UNKNOWN | 41 | 0 | T |
| AI889971 | UNKNOWN | 63 | 0 | T |
| AI889971 | UNKNOWN | 14 | 333 | A |
| AI889974 | UNKNOWN | 76 | 0 | T |
| AI889974 | UNKNOWN | 14 | 160 | A |
| AI889994 | UNKNOWN | 18 | 0 | T |
| AI890047 | UNKNOWN | 44 | 0 | T |
| AI890051 | UNKNOWN | 56 | 0 | T |
| AI890057 | UNKNOWN | 64 | 0 | T |
| AI890154 | UNKNOWN | 58 | 0 | T |
| AI890154 | UNKNOWN | 12 | 376 | C |
| AI890165 | UNKNOWN | 48 | 0 | T |
| AI890182 | UNKNOWN | 72 | 0 | T |
| AI890182 | UNKNOWN | 13 | 178 | C |
| AI890183 | UNKNOWN | 79 | 0 | T |
| AI890183 | UNKNOWN | 12 | 194 | G |
| AI890193 | UNKNOWN | 18 | 0 | T |
| AI890204 | UNKNOWN | 48 | 0 | T |
| AI890205 | UNKNOWN | 12 | 0 | T |
| AI890206 | UNKNOWN | 33 | 0 | T |
| AI890214 | UNKNOWN | 91 | 0 | T |
| AI890214 | UNKNOWN | 14 | 332 | A |
| AI890214 | UNKNOWN | 13 | 284 | G |
| AI890214 | UNKNOWN | 12 | 214 | A |
| AI890223 | UNKNOWN | 94 | 0 | T |
| AI890223 | UNKNOWN | 29 | 223 | G |
| AI890223 | UNKNOWN | 21 | 147 | C |
| AI890223 | UNKNOWN | 13 | 168 | G |
| AI890232 | UNKNOWN | 15 | 0 | T |
| AI890232 | UNKNOWN | 14 | 216 | G |
| AI890268 | UNKNOWN | 16 | 217 | G |
| AI890336 | UNKNOWN | 21 | 0 | T |
| AI890346 | UNKNOWN | 19 | 0 | T |
| AI890347 | UNKNOWN | 17 | 11 | T |
| AI890349 | UNKNOWN | 27 | 0 | T |
| AI890367 | UNKNOWN | 47 | 1 | T |
| AI890386 | UNKNOWN | 52 | 0 | T |
| AI890391 | UNKNOWN | 59 | 0 | T |
| AI890391 | UNKNOWN | 13 | 356 | C |
| AI890391 | UNKNOWN | 12 | 172 | G |
| AI890394 | UNKNOWN | 42 | 0 | T |
| AI890399 | UNKNOWN | 19 | 158 | T |
| AI890400 | UNKNOWN | 19 | 126 | T |
| AI890407 | UNKNOWN | 22 | 0 | T |
| AI890412 | UNKNOWN | 66 | 0 | T |
| AI890412 | UNKNOWN | 15 | 181 | A |
| AI890412 | UNKNOWN | 14 | 167 | C |
| AI890443 | UNKNOWN | 47 | 0 | T |

TABLE 1-continued

| Genbank # | Region | # reps | Position | Unit sequence |
|---|---|---|---|---|
| AI890448 | UNKNOWN | 53 | 0 | T |
| AI890448 | UNKNOWN | 12 | 78 | C |
| AI890451 | UNKNOWN | 35 | 11 | T |
| AI890456 | UNKNOWN | 21 | 11 | T |
| AI890469 | UNKNOWN | 25 | 11 | T |
| AI890481 | UNKNOWN | 15 | 11 | T |
| AI890488 | UNKNOWN | 7 | 431 | AT |
| AI890507 | UNKNOWN | 78 | 0 | T |
| AI890507 | UNKNOWN | 22 | 133 | G |
| AI890507 | UNKNOWN | 16 | 99 | C |
| AI890509 | UNKNOWN | 70 | 0 | T |
| AI890509 | UNKNOWN | 13 | 94 | A |
| AI890509 | UNKNOWN | 13 | 218 | G |
| AI890530 | UNKNOWN | 49 | 0 | T |
| AI890533 | UNKNOWN | 65 | 0 | T |
| AI890550 | UNKNOWN | 78 | 0 | T |
| AI890550 | UNKNOWN | 12 | 151 | C |
| AI890550 | UNKNOWN | 12 | 261 | G |
| AI890561 | UNKNOWN | 31 | 0 | T |
| AI890570 | UNKNOWN | 26 | 0 | T |
| AI890574 | UNKNOWN | 62 | 0 | T |
| AI890574 | UNKNOWN | 14 | 164 | C |
| AI890574 | UNKNOWN | 13 | 302 | A |
| AI890576 | UNKNOWN | 60 | 0 | T |
| AI890617 | UNKNOWN | 27 | 0 | T |
| AI890628 | UNKNOWN | 76 | 0 | T |
| AI890628 | UNKNOWN | 22 | 133 | G |
| AI890628 | UNKNOWN | 13 | 99 | C |
| AI890636 | UNKNOWN | 33 | 0 | T |
| AI890646 | UNKNOWN | 22 | 1 | T |
| AI890647 | UNKNOWN | 26 | 0 | T |
| AI890654 | UNKNOWN | 41 | 0 | T |
| AI890654 | UNKNOWN | 14 | 112 | G |
| AI890654 | UNKNOWN | 14 | 343 | C |
| AI890654 | UNKNOWN | 13 | 245 | C |
| AI890700 | UNKNOWN | 39 | 0 | T |
| AI890714 | UNKNOWN | 42 | 0 | T |
| AI890757 | UNKNOWN | 46 | 0 | T |
| AI890761 | UNKNOWN | 20 | 0 | T |
| AI890780 | UNKNOWN | 37 | 0 | T |
| AI890782 | UNKNOWN | 56 | 0 | T |
| AI890784 | UNKNOWN | 86 | 0 | T |
| AI890784 | UNKNOWN | 13 | 218 | A |
| AI890799 | UNKNOWN | 12 | 0 | T |
| AI890806 | UNKNOWN | 95 | 0 | T |
| AI890806 | UNKNOWN | 15 | 100 | G |
| AI890806 | UNKNOWN | 13 | 140 | A |
| AI890833 | UNKNOWN | 105 | 0 | T |
| AI890833 | UNKNOWN | 18 | 168 | C |
| AI890833 | UNKNOWN | 14 | 105 | A |
| AI890838 | UNKNOWN | 94 | 4 | T |
| AI890838 | UNKNOWN | 23 | 364 | A |
| AI890838 | UNKNOWN | 18 | 240 | G |
| AI890838 | UNKNOWN | 15 | 207 | C |
| AI890838 | UNKNOWN | 14 | 100 | A |
| AI890840 | UNKNOWN | 14 | 284 | T |
| AI890852 | UNKNOWN | 66 | 0 | T |
| AI890852 | UNKNOWN | 25 | 369 | A |
| AI890852 | UNKNOWN | 17 | 121 | G |
| AI890852 | UNKNOWN | 14 | 199 | A |
| AI890852 | UNKNOWN | 12 | 151 | A |
| AI890866 | UNKNOWN | 16 | 0 | T |
| AI890868 | UNKNOWN | 20 | 0 | T |
| AI890887 | UNKNOWN | 68 | 0 | T |
| AI890918 | UNKNOWN | 16 | 0 | T |
| AI890954 | UNKNOWN | 74 | 0 | T |
| AI890954 | UNKNOWN | 15 | 89 | A |
| AI891041 | UNKNOWN | 49 | 0 | T |
| AI891080 | UNKNOWN | 25 | 0 | T |
| AI891084 | UNKNOWN | 77 | 0 | T |
| AI891084 | UNKNOWN | 19 | 112 | A |
| AI891102 | UNKNOWN | 61 | 0 | T |
| AI891102 | UNKNOWN | 12 | 148 | A |
| AI891125 | UNKNOWN | 65 | 0 | T |
| AI891125 | UNKNOWN | 16 | 173 | G |
| AI891126 | UNKNOWN | 73 | 0 | T |
| AI891126 | UNKNOWN | 14 | 309 | G |

TABLE 1-continued

| Genbank # | Region | # reps | Position | Unit sequence |
|---|---|---|---|---|
| AI891127 | UNKNOWN | 31 | 2 | T |
| AI891157 | UNKNOWN | 113 | 0 | T |
| AI891157 | UNKNOWN | 24 | 259 | C |
| AI891157 | UNKNOWN | 19 | 240 | G |
| AI891157 | UNKNOWN | 12 | 113 | G |
| AI891158 | UNKNOWN | 46 | 0 | T |
| AI902194 | UNKNOWN | 13 | 173 | A |
| AI904095 | UNKNOWN | 12 | 216 | T |
| AI904455 | UNKNOWN | 10.25 | 33 | TATT |
| AI904455 | UNKNOWN | 22 | 130 | T |
| AI904611 | UNKNOWN | 15 | 83 | A |
| AI905408 | UNKNOWN | 5.5 | 158 | TTAT |
| AI905527 | UNKNOWN | 15 | 69 | T |
| AI906339 | UNKNOWN | 12 | 762 | G |
| AI906424 | UNKNOWN | 23 | 430 | A |
| AI907083 | UNKNOWN | 26 | 531 | T |
| AI907083 | UNKNOWN | 12 | 511 | T |
| AI907506 | UNKNOWN | 30 | 143 | T |
| AI908903 | UNKNOWN | 19 | 33 | A |
| AI909118 | UNKNOWN | 20.5 | 150 | CA |
| AI909642 | UNKNOWN | 100 | 10 | T |
| AI909662 | UNKNOWN | 114 | 61 | T |
| AI909662 | UNKNOWN | 26 | 9 | T |
| AI909662 | UNKNOWN | 12 | 369 | A |
| AI909694 | UNKNOWN | 13 | 13 | T |
| AI910393 | UNKNOWN | 13 | 0 | T |
| AI910464 | UNKNOWN | 60 | 16 | T |
| AI910464 | UNKNOWN | 16 | 207 | G |
| AI910464 | UNKNOWN | 15 | 0 | T |
| AI910471 | UNKNOWN | 19 | 0 | T |
| AI910504 | UNKNOWN | 22 | 2 | T |
| AI910513 | UNKNOWN | 30 | 0 | T |
| AI910602 | UNKNOWN | 21 | 0 | T |
| AI910639 | UNKNOWN | 76 | 0 | T |
| AI910639 | UNKNOWN | 19 | 166 | C |
| AI910639 | UNKNOWN | 14 | 239 | G |
| AI910639 | UNKNOWN | 12 | 201 | G |
| AI910657 | UNKNOWN | 21 | 60 | TG |
| AI910660 | UNKNOWN | 63 | 0 | T |
| AI910718 | UNKNOWN | 13 | 181 | A |
| AI910732 | UNKNOWN | 16 | 0 | T |
| AI910824 | UNKNOWN | 26 | 0 | T |
| AI910844 | UNKNOWN | 26 | 0 | T |
| AI910848 | UNKNOWN | 39 | 0 | T |
| AI910852 | UNKNOWN | 18 | 4 | T |
| AI910855 | UNKNOWN | 14 | 0 | T |
| AI910882 | UNKNOWN | 17 | 0 | T |
| AI910964 | UNKNOWN | 12 | 57 | A |
| AI911011 | UNKNOWN | 13 | 0 | T |
| AI911020 | UNKNOWN | 54 | 0 | T |
| AI911033 | UNKNOWN | 17 | 321 | T |
| AI911044 | UNKNOWN | 23 | 72 | A |
| AI911044 | UNKNOWN | 16 | 1 | T |
| AI911070 | UNKNOWN | 13 | 146 | A |
| AI911173 | UNKNOWN | 16 | 0 | T |
| AI911186 | UNKNOWN | 9.5 | 157 | AG |
| AI911207 | UNKNOWN | 15 | 0 | T |
| AI911218 | UNKNOWN | 3.8 | 52 | CCCCG |
| AI911321 | UNKNOWN | 18 | 1 | T |
| AI911352 | UNKNOWN | 28 | 0 | T |
| AI911362 | UNKNOWN | 12 | 26 | A |
| AI911369 | UNKNOWN | 13 | 0 | T |
| AI911385 | UNKNOWN | 15 | 181 | A |
| AI911385 | UNKNOWN | 13 | 0 | T |
| AI911392 | UNKNOWN | 14 | 0 | T |
| AI911397 | UNKNOWN | 15 | 0 | T |
| AI911402 | UNKNOWN | 15 | 0 | T |
| AI911414 | UNKNOWN | 22 | 2 | T |
| AI911430 | UNKNOWN | 12 | 0 | T |
| AI911449 | UNKNOWN | 12 | 0 | T |
| AI911469 | UNKNOWN | 18 | 0 | T |
| AI911488 | UNKNOWN | 15 | 210 | T |
| AI911488 | UNKNOWN | 12 | 34 | T |
| AI911509 | UNKNOWN | 12 | 0 | T |
| AI911548 | UNKNOWN | 2.53 | 28 | TTTTTTTTATTTTT (SEQ ID NO: 164) |
| AI911548 | UNKNOWN | 27 | 0 | T |
| AI911620 | UNKNOWN | 55 | 0 | T |

TABLE 1-continued

| Genbank # | Region | # reps | Position | Unit sequence |
|---|---|---|---|---|
| AI911648 | UNKNOWN | 73 | 0 | T |
| AI911648 | UNKNOWN | 14 | 285 | A |
| AI911659 | UNKNOWN | 18 | 0 | T |
| AI911700 | UNKNOWN | 34 | 0 | T |
| AI911700 | UNKNOWN | 13 | 291 | G |
| AI911703 | UNKNOWN | 22 | 0 | T |
| AI911726 | UNKNOWN | 12 | 0 | T |
| AI911837 | UNKNOWN | 15 | 0 | T |
| AI911839 | UNKNOWN | 28 | 0 | T |
| AI911868 | UNKNOWN | 64 | 0 | T |
| AI911873 | UNKNOWN | 22 | 0 | T |
| AI911885 | UNKNOWN | 36 | 0 | T |
| AI911888 | UNKNOWN | 19 | 4 | T |
| AI911922 | UNKNOWN | 19 | 0 | T |
| AI911933 | UNKNOWN | 71 | 0 | T |
| AI911938 | UNKNOWN | 56 | 0 | T |
| AI911974 | UNKNOWN | 14 | 255 | A |
| AI911986 | UNKNOWN | 14 | 35 | A |
| AI912018 | UNKNOWN | 12 | 295 | G |
| AI912031 | UNKNOWN | 12 | 0 | A |
| AI912079 | UNKNOWN | 12 | 0 | T |
| AI912084 | UNKNOWN | 11 | 184 | AG |
| AI912221 | UNKNOWN | 5.6 | 19 | TTTAT |
| AI912259 | UNKNOWN | 16 | 93 | A |
| AI912275 | UNKNOWN | 12 | 310 | T |
| AI912288 | UNKNOWN | 100 | 0 | T |
| AI912288 | UNKNOWN | 19 | 123 | A |
| AI912288 | UNKNOWN | 18 | 360 | C |
| AI912288 | UNKNOWN | 14 | 391 | G |
| AI912288 | UNKNOWN | 13 | 321 | G |
| AI912297 | UNKNOWN | 58 | 0 | T |
| AI912297 | UNKNOWN | 12 | 229 | G |
| AI912333 | UNKNOWN | 64 | 0 | T |
| AI912333 | UNKNOWN | 14 | 179 | G |
| AI912333 | UNKNOWN | 13 | 98 | A |
| AI912343 | UNKNOWN | 24 | 0 | T |
| AI912356 | UNKNOWN | 86 | 0 | T |
| AI912356 | UNKNOWN | 15 | 238 | A |
| AI912356 | UNKNOWN | 14 | 86 | A |
| AI912376 | UNKNOWN | 50 | 0 | T |
| AI912393 | UNKNOWN | 12 | 0 | T |
| AI912409 | UNKNOWN | 91 | 0 | T |
| AI912409 | UNKNOWN | 21 | 281 | G |
| AI912409 | UNKNOWN | 16 | 173 | C |
| AI912409 | UNKNOWN | 13 | 142 | C |
| AI912429 | UNKNOWN | 40 | 0 | T |
| AI912429 | UNKNOWN | 20 | 181 | A |
| AI912429 | UNKNOWN | 16 | 160 | C |
| AI912434 | UNKNOWN | 58 | 0 | T |
| AI912434 | UNKNOWN | 25 | 102 | A |
| AI912434 | UNKNOWN | 19 | 170 | C |
| AI912435 | UNKNOWN | 87 | 0 | T |
| AI912435 | UNKNOWN | 16 | 121 | G |
| AI912435 | UNKNOWN | 16 | 384 | C |
| AI912437 | UNKNOWN | 85 | 0 | T |
| AI912438 | UNKNOWN | 64 | 0 | T |
| AI912438 | UNKNOWN | 16 | 181 | A |
| AI912438 | UNKNOWN | 15 | 274 | G |
| AI912469 | UNKNOWN | 40 | 0 | T |
| AI912474 | UNKNOWN | 55 | 0 | T |
| AI912477 | UNKNOWN | 76 | 0 | T |
| AI912496 | UNKNOWN | 51 | 10 | T |
| AI912510 | UNKNOWN | 90 | 0 | T |
| AI912510 | UNKNOWN | 12 | 180 | A |
| AI912526 | UNKNOWN | 35 | 0 | T |
| AI912526 | UNKNOWN | 15 | 326 | A |
| AI912531 | UNKNOWN | 57 | 0 | T |
| AI912533 | UNKNOWN | 88 | 0 | T |
| AI912533 | UNKNOWN | 20 | 109 | A |
| AI912533 | UNKNOWN | 19 | 90 | G |
| AI912544 | UNKNOWN | 43 | 0 | T |
| AI912555 | UNKNOWN | 22 | 0 | T |
| AI912571 | UNKNOWN | 12 | 118 | T |
| AI912573 | UNKNOWN | 46 | 4 | T |
| AI912575 | UNKNOWN | 12 | 0 | T |
| AI912617 | UNKNOWN | 16 | 439 | T |
| AI912678 | UNKNOWN | 13 | 0 | T |

TABLE 1-continued

| Genbank # | Region | # reps | Position | Unit sequence |
|---|---|---|---|---|
| AI912702 | UNKNOWN | 15 | 50 | A |
| AI912795 | UNKNOWN | 3.6 | 179 | AAACC |
| AI912795 | UNKNOWN | 7.66 | 196 | AAC |
| AI912827 | UNKNOWN | 12 | 431 | A |
| AI912864 | UNKNOWN | 13 | 0 | T |
| AI912866 | UNKNOWN | 113 | 0 | T |
| AI912909 | UNKNOWN | 23 | 0 | T |
| AI912937 | UNKNOWN | 4.75 | 381 | TTTG |
| AI912953 | UNKNOWN | 13 | 0 | T |
| AI912976 | UNKNOWN | 13 | 0 | T |
| AI913008 | UNKNOWN | 18 | 0 | T |
| AI913008 | UNKNOWN | 13 | 237 | A |
| AI913011 | UNKNOWN | 8.5 | 0 | ATTT |
| AI913041 | UNKNOWN | 50 | 0 | T |
| AI913066 | UNKNOWN | 40 | 0 | T |
| AI913066 | UNKNOWN | 18 | 307 | A |
| AI913067 | UNKNOWN | 41 | 0 | T |
| AI913082 | UNKNOWN | 80 | 0 | T |
| AI913082 | UNKNOWN | 15 | 211 | A |
| AI913094 | UNKNOWN | 20 | 0 | T |
| AI913113 | UNKNOWN | 12 | 10 | T |
| AI913146 | UNKNOWN | 19 | 0 | T |
| AI913173 | UNKNOWN | 6.5 | 119 | AT |
| AI913173 | UNKNOWN | 34 | 0 | T |
| AI913258 | UNKNOWN | 7.5 | 242 | TG |
| AI913276 | UNKNOWN | 42 | 0 | T |
| AI913290 | UNKNOWN | 41 | 0 | T |
| AI913296 | UNKNOWN | 56 | 0 | T |
| AI913312 | UNKNOWN | 77 | 0 | T |
| AI913312 | UNKNOWN | 17 | 269 | A |
| AI913312 | UNKNOWN | 16 | 169 | A |
| AI913312 | UNKNOWN | 12 | 201 | G |
| AI913312 | UNKNOWN | 12 | 235 | C |
| AI913320 | UNKNOWN | 23 | 0 | T |
| AI913323 | UNKNOWN | 69 | 0 | T |
| AI913330 | UNKNOWN | 83 | 0 | T |
| AI913330 | UNKNOWN | 19 | 252 | G |
| AI913330 | UNKNOWN | 13 | 182 | C |
| AI913351 | UNKNOWN | 46 | 0 | T |
| AI913351 | UNKNOWN | 14 | 361 | A |
| AI913359 | UNKNOWN | 21 | 151 | A |
| AI913366 | UNKNOWN | 76 | 0 | T |
| AI913366 | UNKNOWN | 14 | 206 | A |
| AI913366 | UNKNOWN | 12 | 142 | A |
| AI913376 | UNKNOWN | 13 | 0 | T |
| AI913437 | UNKNOWN | 99 | 0 | T |
| AI913437 | UNKNOWN | 21 | 124 | C |
| AI913437 | UNKNOWN | 15 | 271 | G |
| AI913437 | UNKNOWN | 13 | 245 | G |
| AI913452 | UNKNOWN | 87 | 0 | T |
| AI913452 | UNKNOWN | 13 | 206 | G |
| AI913542 | UNKNOWN | 7 | 351 | CA |
| AI913608 | UNKNOWN | 36 | 0 | T |
| AI913783 | UNKNOWN | 18 | 0 | T |
| AI913828 | UNKNOWN | 42 | 0 | T |
| AI913867 | UNKNOWN | 16 | 0 | T |
| AI913978 | UNKNOWN | 18 | 0 | T |
| AI913988 | UNKNOWN | 51 | 0 | T |
| AI914044 | UNKNOWN | 21 | 0 | T |
| AI914105 | UNKNOWN | 19 | 417 | T |
| AI914182 | UNKNOWN | 5 | 49 | TATT |
| AI914182 | UNKNOWN | 30 | 0 | T |
| AI914182 | UNKNOWN | 12 | 216 | G |
| AI914220 | UNKNOWN | 14 | 0 | T |
| AI914328 | UNKNOWN | 3.83 | 23 | TTTTTA |
| AI914345 | UNKNOWN | 17 | 0 | T |
| AI914418 | UNKNOWN | 12 | 443 | T |
| AI914508 | UNKNOWN | 20 | 0 | T |
| AI914630 | UNKNOWN | 23 | 2 | T |
| AI914685 | UNKNOWN | 28 | 0 | T |
| AI914736 | UNKNOWN | 60 | 0 | T |
| AI914747 | UNKNOWN | 21 | 0 | T |
| AI914753 | UNKNOWN | 58 | 0 | T |
| AI914760 | UNKNOWN | 55 | 0 | T |
| AI914760 | UNKNOWN | 15 | 189 | A |
| AI914816 | UNKNOWN | 25 | 64 | T |
| AI914816 | UNKNOWN | 19 | 146 | C |

TABLE 1-continued

| Genbank # | Region | # reps | Position | Unit sequence |
|---|---|---|---|---|
| AI914816 | UNKNOWN | 15 | 0 | T |
| AI914816 | UNKNOWN | 13 | 122 | A |
| AI914819 | UNKNOWN | 21 | 0 | T |
| AI914862 | UNKNOWN | 97 | 0 | T |
| AI914862 | UNKNOWN | 15 | 423 | G |
| AI914862 | UNKNOWN | 13 | 369 | C |
| AI914862 | UNKNOWN | 12 | 147 | A |
| AI914886 | UNKNOWN | 26 | 64 | A |
| AI914931 | UNKNOWN | 51 | 0 | T |
| AI914931 | UNKNOWN | 17 | 232 | G |
| AI915020 | UNKNOWN | 12 | 0 | T |
| AI915118 | UNKNOWN | 19 | 0 | T |
| AI915131 | UNKNOWN | 53 | 0 | T |
| AI915232 | UNKNOWN | 28 | 79 | T |
| AI915232 | UNKNOWN | 26 | 0 | T |
| AI915232 | UNKNOWN | 19 | 202 | G |
| AI915232 | UNKNOWN | 13 | 297 | A |
| AI915279 | UNKNOWN | 39 | 0 | T |
| AI915291 | UNKNOWN | 86 | 0 | T |
| AI915291 | UNKNOWN | 14 | 86 | A |
| AI915295 | UNKNOWN | 60 | 0 | T |
| AI915344 | UNKNOWN | 12 | 0 | T |
| AI915467 | UNKNOWN | 18 | 0 | T |
| AI915528 | UNKNOWN | 6.4 | 43 | GCCCT |
| AI915569 | UNKNOWN | 36 | 22 | T |
| AI915569 | UNKNOWN | 20 | 0 | T |
| AI915569 | UNKNOWN | 19 | 601 | G |
| AI915569 | UNKNOWN | 15 | 155 | G |
| AI915593 | UNKNOWN | 15 | 0 | T |
| AI915657 | UNKNOWN | 57 | 0 | T |
| AI915657 | UNKNOWN | 18 | 420 | G |
| AI915657 | UNKNOWN | 15 | 148 | C |
| AI915657 | UNKNOWN | 13 | 224 | G |
| AI915686 | UNKNOWN | 41 | 0 | T |
| AI915701 | UNKNOWN | 63 | 0 | T |
| AI915761 | UNKNOWN | 35 | 0 | T |
| AI915795 | UNKNOWN | 47 | 0 | T |
| AI915834 | UNKNOWN | 15 | 0 | T |
| AI915944 | UNKNOWN | 20 | 0 | T |
| AI915986 | UNKNOWN | 26 | 0 | T |
| AI916180 | UNKNOWN | 14 | 377 | T |
| AI916189 | UNKNOWN | 19 | 4 | T |
| AI916196 | UNKNOWN | 20 | 0 | T |
| AI916227 | UNKNOWN | 37 | 0 | T |
| AI916271 | UNKNOWN | 15 | 392 | T |
| AI916309 | UNKNOWN | 14 | 157 | A |
| AI916313 | UNKNOWN | 19 | 0 | T |
| AI916327 | UNKNOWN | 12 | 5 | T |
| AI916403 | UNKNOWN | 52 | 0 | T |
| AI916413 | UNKNOWN | 22 | 0 | T |
| AI916419 | UNKNOWN | 90 | 0 | T |
| AI916419 | UNKNOWN | 18 | 127 | G |
| AI916419 | UNKNOWN | 13 | 113 | C |
| AI916419 | UNKNOWN | 12 | 95 | A |
| AI916486 | UNKNOWN | 47 | 0 | T |
| AI916495 | UNKNOWN | 81 | 0 | T |
| AI916495 | UNKNOWN | 16 | 223 | A |
| AI916539 | UNKNOWN | 17 | 0 | T |
| AI916543 | UNKNOWN | 25 | 0 | T |
| AI916560 | UNKNOWN | 17 | 0 | T |
| AI916586 | UNKNOWN | 12 | 0 | T |
| AI916591 | UNKNOWN | 20 | 0 | T |
| AI916595 | UNKNOWN | 20 | 4 | T |
| AI916599 | UNKNOWN | 18 | 4 | T |
| AI916618 | UNKNOWN | 26 | 0 | T |
| AI916641 | UNKNOWN | 16 | 0 | T |
| AI916691 | UNKNOWN | 50 | 0 | T |
| AI916691 | UNKNOWN | 23 | 64 | A |
| AI916691 | UNKNOWN | 13 | 271 | G |
| AI916691 | UNKNOWN | 12 | 167 | G |
| AI916695 | UNKNOWN | 18 | 0 | T |
| AI916720 | UNKNOWN | 47 | 0 | T |
| AI916732 | UNKNOWN | 7 | 33 | TAA |
| AI916734 | UNKNOWN | 13 | 0 | T |
| AI916783 | UNKNOWN | 13 | 0 | T |
| AI916812 | UNKNOWN | 14 | 360 | CA |
| AI916812 | UNKNOWN | 10 | 341 | TC |

TABLE 1-continued

| Genbank # | Region | # reps | Position | Unit sequence |
|---|---|---|---|---|
| AI916859 | UNKNOWN | 14 | 0 | T |
| AI916890 | UNKNOWN | 13 | 782 | T |
| AI916890 | UNKNOWN | 13 | 811 | C |
| AI916928 | UNKNOWN | 22 | 0 | T |
| AI916943 | UNKNOWN | 40 | 0 | T |
| AI917026 | UNKNOWN | 46 | 0 | T |
| AI917038 | UNKNOWN | 24 | 108 | A |
| AI917051 | UNKNOWN | 45 | 0 | T |
| AI917055 | UNKNOWN | 74 | 0 | T |
| AI917145 | UNKNOWN | 91 | 0 | T |
| AI917154 | UNKNOWN | 65 | 0 | T |
| AI917235 | UNKNOWN | 66 | 0 | T |
| AI917235 | UNKNOWN | 13 | 301 | G |
| AI917252 | UNKNOWN | 87 | 0 | T |
| AI917252 | UNKNOWN | 12 | 205 | G |
| AI917253 | UNKNOWN | 107 | 0 | T |
| AI917253 | UNKNOWN | 16 | 296 | A |
| AI917331 | UNKNOWN | 51 | 0 | T |
| AI917339 | UNKNOWN | 12 | 2 | T |
| AI917348 | UNKNOWN | 41 | 0 | T |
| AI917369 | UNKNOWN | 12 | 0 | T |
| AI917381 | UNKNOWN | 41 | 0 | T |
| AI917428 | UNKNOWN | 72 | 0 | T |
| AI917428 | UNKNOWN | 14 | 154 | G |
| AI917442 | UNKNOWN | 12 | 234 | T |
| AI917516 | UNKNOWN | 3.8 | 46 | TTTTA |
| AI917516 | UNKNOWN | 28 | 0 | T |
| AI917523 | UNKNOWN | 37 | 0 | T |
| AI917574 | UNKNOWN | 39 | 0 | T |
| AI917602 | UNKNOWN | 16 | 0 | T |
| AI917636 | UNKNOWN | 3.6 | 103 | TTTCT |
| AI917636 | UNKNOWN | 16 | 431 | T |
| AI917928 | UNKNOWN | 79 | 0 | T |
| AI917928 | UNKNOWN | 13 | 320 | G |
| AI917928 | UNKNOWN | 12 | 105 | C |
| AI917938 | UNKNOWN | 84 | 0 | T |
| AI917938 | UNKNOWN | 15 | 229 | G |
| AI917938 | UNKNOWN | 12 | 348 | A |
| AI917940 | UNKNOWN | 17 | 0 | T |
| AI917951 | UNKNOWN | 43 | 0 | T |
| AI917955 | UNKNOWN | 70 | 0 | T |
| AI917959 | UNKNOWN | 99 | 0 | T |
| AI917959 | UNKNOWN | 19 | 338 | A |
| AI917959 | UNKNOWN | 17 | 362 | C |
| AI917959 | UNKNOWN | 12 | 118 | A |
| AI917959 | UNKNOWN | 12 | 172 | C |
| AI917963 | UNKNOWN | 76 | 0 | T |
| AI917963 | UNKNOWN | 21 | 133 | G |
| AI917994 | UNKNOWN | 81 | 0 | T |
| AI917994 | UNKNOWN | 24 | 213 | G |
| AI917994 | UNKNOWN | 13 | 116 | C |
| AI918009 | UNKNOWN | 41 | 0 | T |
| AI918031 | UNKNOWN | 12 | 168 | T |
| AI918042 | UNKNOWN | 13 | 0 | T |
| AI918054 | UNKNOWN | 15 | 0 | T |
| AI918118 | UNKNOWN | 39 | 0 | T |
| AI918195 | UNKNOWN | 39 | 0 | T |
| AI918358 | UNKNOWN | 60 | 0 | T |
| AI918370 | UNKNOWN | 49 | 0 | T |
| AI918370 | UNKNOWN | 12 | 174 | A |
| AI918376 | UNKNOWN | 50 | 23 | T |
| AI918376 | UNKNOWN | 14 | 0 | T |
| AI918404 | UNKNOWN | 28 | 0 | T |
| AI918404 | UNKNOWN | 22 | 225 | G |
| AI918404 | UNKNOWN | 17 | 173 | G |
| AI918408 | UNKNOWN | 60 | 0 | T |
| AI918408 | UNKNOWN | 18 | 126 | G |
| AI918408 | UNKNOWN | 12 | 81 | A |
| AI918427 | UNKNOWN | 44 | 0 | T |
| AI918435 | UNKNOWN | 45 | 55 | T |
| AI918435 | UNKNOWN | 26 | 0 | T |
| AI918435 | UNKNOWN | 15 | 136 | A |
| AI918437 | UNKNOWN | 47 | 0 | T |
| AI918445 | UNKNOWN | 4.5 | 3 | TATT |
| AI918449 | UNKNOWN | 70 | 0 | T |
| AI918500 | UNKNOWN | 76 | 0 | T |
| AI918500 | UNKNOWN | 17 | 236 | A |

TABLE 1-continued

| Genbank # | Region | # reps | Position | Unit sequence |
|---|---|---|---|---|
| AI918500 | UNKNOWN | 12 | 140 | G |
| AI918554 | UNKNOWN | 65 | 0 | T |
| AI918582 | UNKNOWN | 42 | 84 | T |
| AI918582 | UNKNOWN | 18 | 55 | T |
| AI918582 | UNKNOWN | 12 | 0 | T |
| AI918588 | UNKNOWN | 30 | 18 | T |
| AI918600 | UNKNOWN | 36 | 0 | T |
| AI918655 | UNKNOWN | 92 | 0 | T |
| AI918655 | UNKNOWN | 17 | 220 | C |
| AI918655 | UNKNOWN | 12 | 111 | A |
| AI918677 | UNKNOWN | 48 | 0 | T |
| AI918738 | UNKNOWN | 25 | 0 | T |
| AI918786 | UNKNOWN | 21 | 0 | T |
| AI918955 | UNKNOWN | 56 | 0 | T |
| AI918955 | UNKNOWN | 18 | 231 | A |
| AI919058 | UNKNOWN | 128 | 0 | T |
| AI919058 | UNKNOWN | 20 | 272 | G |
| AI919058 | UNKNOWN | 16 | 166 | G |
| AI919058 | UNKNOWN | 16 | 319 | C |
| AI919058 | UNKNOWN | 13 | 440 | A |
| AI919107 | UNKNOWN | 83 | 0 | T |
| AI919124 | UNKNOWN | 6.5 | 22 | AAAT |
| AI919145 | UNKNOWN | 6.66 | 89 | AAG |
| AI919147 | UNKNOWN | 65 | 0 | T |
| AI919158 | UNKNOWN | 31 | 0 | T |
| AI919158 | UNKNOWN | 16 | 53 | A |
| AI919232 | UNKNOWN | 50 | 0 | T |
| AI919253 | UNKNOWN | 6.5 | 59 | AC |
| AI919253 | UNKNOWN | 12 | 0 | T |
| AI919265 | UNKNOWN | 22 | 0 | T |
| AI919319 | UNKNOWN | 25 | 0 | T |
| AI919345 | UNKNOWN | 103 | 0 | T |
| AI919345 | UNKNOWN | 12 | 135 | A |
| AI919431 | UNKNOWN | 7.75 | 92 | CATT |
| AI919500 | UNKNOWN | 80 | 0 | T |
| AI919500 | UNKNOWN | 12 | 104 | A |
| AI919504 | UNKNOWN | 46 | 0 | T |
| AI919504 | UNKNOWN | 19 | 212 | A |
| AI919506 | UNKNOWN | 94 | 1 | T |
| AI919506 | UNKNOWN | 12 | 215 | G |
| AI919506 | UNKNOWN | 12 | 268 | A |
| AI919516 | UNKNOWN | 48 | 0 | T |
| AI919534 | UNKNOWN | 68 | 0 | T |
| AI919534 | UNKNOWN | 21 | 189 | A |
| AI919593 | UNKNOWN | 71 | 0 | T |
| AI919593 | UNKNOWN | 21 | 128 | G |
| AI919600 | UNKNOWN | 55 | 0 | T |
| AI920782 | UNKNOWN | 72 | 0 | T |
| AI920809 | UNKNOWN | 61 | 0 | T |
| AI920809 | UNKNOWN | 18 | 100 | A |
| AI920817 | UNKNOWN | 46 | 0 | T |
| AI920817 | UNKNOWN | 19 | 198 | A |
| AI920817 | UNKNOWN | 14 | 237 | G |
| AI920829 | UNKNOWN | 41 | 0 | T |
| AI920833 | UNKNOWN | 83 | 0 | T |
| AI920833 | UNKNOWN | 15 | 313 | A |
| AI920833 | UNKNOWN | 12 | 103 | A |
| AI920834 | UNKNOWN | 43 | 0 | T |
| AI920835 | UNKNOWN | 66 | 0 | T |
| AI920835 | UNKNOWN | 17 | 90 | A |
| AI920835 | UNKNOWN | 15 | 317 | C |
| AI920842 | UNKNOWN | 2.88 | 64 | TGTTTCTTATTTCCTTGTCTAGCTT (SEQ ID NO. 165) |
| AI920842 | UNKNOWN | 13 | 388 | A |
| AI920851 | UNKNOWN | 27 | 0 | T |
| AI920851 | UNKNOWN | 20 | 392 | A |
| AI920882 | UNKNOWN | 46 | 0 | T |
| AI920950 | UNKNOWN | 80 | 0 | T |
| AI920950 | UNKNOWN | 17 | 238 | G |
| AI920950 | UNKNOWN | 15 | 85 | G |
| AI920950 | UNKNOWN | 12 | 275 | A |
| AI920968 | UNKNOWN | 139 | 5 | T |
| AI920968 | UNKNOWN | 19 | 158 | G |
| AI920968 | UNKNOWN | 18 | 232 | A |
| AI920968 | UNKNOWN | 14 | 206 | A |
| AI920968 | UNKNOWN | 14 | 257 | C |
| AI920968 | UNKNOWN | 13 | 185 | A |

TABLE 1-continued

| Genbank # | Region | # reps | Position | Unit sequence |
|---|---|---|---|---|
| AI920983 | UNKNOWN | 41 | 0 | T |
| AI921055 | UNKNOWN | 53 | 0 | T |
| AI921055 | UNKNOWN | 13 | 87 | G |
| AI921082 | UNKNOWN | 116 | 0 | T |
| AI921082 | UNKNOWN | 22 | 154 | A |
| AI921082 | UNKNOWN | 12 | 244 | G |
| AI921087 | UNKNOWN | 51 | 0 | T |
| AI921087 | UNKNOWN | 12 | 95 | C |
| AI921092 | UNKNOWN | 72 | 0 | T |
| AI921122 | UNKNOWN | 22 | 0 | T |
| AI921130 | UNKNOWN | 69 | 0 | T |
| AI921130 | UNKNOWN | 15 | 128 | C |
| AI921130 | UNKNOWN | 14 | 540 | A |
| AI921132 | UNKNOWN | 62 | 0 | T |
| AI921158 | UNKNOWN | 20 | 230 | T |
| AI921162 | UNKNOWN | 38 | 0 | T |
| AI921176 | UNKNOWN | 95 | 0 | T |
| AI921176 | UNKNOWN | 16 | 103 | A |
| AI921176 | UNKNOWN | 14 | 196 | C |
| AI921180 | UNKNOWN | 74 | 0 | T |
| AI921180 | UNKNOWN | 16 | 314 | C |
| AI921180 | UNKNOWN | 13 | 339 | G |
| AI921180 | UNKNOWN | 12 | 174 | C |
| AI921194 | UNKNOWN | 20 | 0 | T |
| AI921197 | UNKNOWN | 58 | 0 | T |
| AI921197 | UNKNOWN | 14 | 150 | G |
| AI921205 | UNKNOWN | 30 | 0 | T |
| AI921232 | UNKNOWN | 103 | 0 | T |
| AI921232 | UNKNOWN | 21 | 161 | G |
| AI921232 | UNKNOWN | 15 | 141 | A |
| AI921232 | UNKNOWN | 14 | 127 | C |
| AI921236 | UNKNOWN | 58 | 0 | T |
| AI921244 | UNKNOWN | 104 | 0 | T |
| AI921244 | UNKNOWN | 24 | 411 | G |
| AI921244 | UNKNOWN | 21 | 163 | G |
| AI921244 | UNKNOWN | 16 | 142 | A |
| AI921244 | UNKNOWN | 14 | 128 | C |
| AI921248 | UNKNOWN | 108 | 0 | T |
| AI921248 | UNKNOWN | 18 | 166 | C |
| AI921248 | UNKNOWN | 18 | 195 | G |
| AI921254 | UNKNOWN | 68 | 0 | T |
| AI921254 | UNKNOWN | 20 | 146 | G |
| AI921266 | UNKNOWN | 45 | 0 | T |
| AI921281 | UNKNOWN | 77 | 0 | T |
| AI921287 | UNKNOWN | 25 | 0 | T |
| AI921300 | UNKNOWN | 13 | 0 | T |
| AI921345 | UNKNOWN | 46 | 0 | T |
| AI921371 | UNKNOWN | 46 | 0 | T |
| AI921371 | UNKNOWN | 16 | 128 | A |
| AI921379 | UNKNOWN | 123 | 8 | T |
| AI921379 | UNKNOWN | 28 | 173 | C |
| AI921379 | UNKNOWN | 20 | 219 | G |
| AI921379 | UNKNOWN | 15 | 201 | A |
| AI921379 | UNKNOWN | 12 | 152 | A |
| AI921381 | UNKNOWN | 44 | 0 | T |
| AI921386 | UNKNOWN | 89 | 0 | T |
| AI921395 | UNKNOWN | 12 | 16 | T |
| AI921396 | UNKNOWN | 52 | 0 | T |
| AI921406 | UNKNOWN | 41 | 0 | T |
| AI921420 | UNKNOWN | 94 | 0 | T |
| AI921420 | UNKNOWN | 15 | 224 | C |
| AI921438 | UNKNOWN | 63 | 0 | T |
| AI921442 | UNKNOWN | 62 | 0 | T |
| AI921442 | UNKNOWN | 14 | 283 | G |
| AI921464 | UNKNOWN | 88 | 0 | T |
| AI921464 | UNKNOWN | 29 | 88 | A |
| AI921464 | UNKNOWN | 14 | 263 | G |
| AI921469 | UNKNOWN | 67 | 0 | T |
| AI921469 | UNKNOWN | 13 | 375 | G |
| AI921469 | UNKNOWN | 12 | 117 | A |
| AI921479 | UNKNOWN | 59 | 0 | T |
| AI921506 | UNKNOWN | 43 | 0 | T |
| AI921573 | UNKNOWN | 12 | 235 | G |
| AI921586 | UNKNOWN | 34 | 0 | T |
| AI921597 | UNKNOWN | 24 | 0 | T |
| AI921609 | UNKNOWN | 43 | 0 | T |
| AI921619 | UNKNOWN | 24 | 0 | T |

TABLE 1-continued

| Genbank # | Region | # reps | Position | Unit sequence |
|---|---|---|---|---|
| AI921633 | UNKNOWN | 55 | 0 | T |
| AI921633 | UNKNOWN | 12 | 258 | G |
| AI921667 | UNKNOWN | 21 | 1 | T |
| AI921671 | UNKNOWN | 32 | 0 | T |
| AI921718 | UNKNOWN | 23 | 0 | T |
| AI921734 | UNKNOWN | 3.83 | 309 | CCCCGGGGGGGA (SEQ ID NO: 166) |
| AI921734 | UNKNOWN | 101 | 0 | T |
| AI921734 | UNKNOWN | 12 | 139 | A |
| AI921735 | UNKNOWN | 15 | 0 | T |
| AI921744 | UNKNOWN | 14 | 0 | T |
| AI921746 | UNKNOWN | 83 | 0 | T |
| AI921746 | UNKNOWN | 17 | 287 | A |
| AI921746 | UNKNOWN | 14 | 272 | C |
| AI921753 | UNKNOWN | 98 | 16 | T |
| AI921753 | UNKNOWN | 22 | 155 | A |
| AI921753 | UNKNOWN | 20 | 286 | C |
| AI921753 | UNKNOWN | 16 | 139 | C |
| AI921753 | UNKNOWN | 13 | 0 | T |
| AI921837 | UNKNOWN | 16 | 280 | A |
| AI921915 | UNKNOWN | 47 | 0 | T |
| AI921915 | UNKNOWN | 18 | 92 | C |
| AI921915 | UNKNOWN | 13 | 264 | G |
| AI921922 | UNKNOWN | 50 | 0 | T |
| AI921997 | UNKNOWN | 62 | 0 | T |
| AI921997 | UNKNOWN | 14 | 152 | C |
| AI921997 | UNKNOWN | 13 | 320 | G |
| AI922000 | UNKNOWN | 67 | 0 | T |
| AI922009 | UNKNOWN | 37 | 0 | T |
| AI922037 | UNKNOWN | 55 | 0 | T |
| AI922067 | UNKNOWN | 13 | 0 | T |
| AI922075 | UNKNOWN | 92 | 0 | T |
| AI922075 | UNKNOWN | 17 | 334 | C |
| AI922075 | UNKNOWN | 14 | 360 | G |
| AI922075 | UNKNOWN | 13 | 174 | A |
| AI922075 | UNKNOWN | 13 | 237 | C |
| AI922076 | UNKNOWN | 56 | 0 | T |
| AI922089 | UNKNOWN | 73 | 0 | T |
| AI922089 | UNKNOWN | 15 | 91 | A |
| AI922089 | UNKNOWN | 14 | 138 | C |
| AI922091 | UNKNOWN | 73 | 0 | T |
| AI922091 | UNKNOWN | 17 | 175 | C |
| AI922091 | UNKNOWN | 13 | 228 | G |
| AI922093 | UNKNOWN | 42 | 0 | T |
| AI922093 | UNKNOWN | 19 | 420 | A |
| AI922094 | UNKNOWN | 7 | 167 | TAT |
| AI922094 | UNKNOWN | 16.5 | 27 | TA |
| AI922110 | UNKNOWN | 58 | 0 | T |
| AI922178 | UNKNOWN | 31 | 11 | T |
| AI922189 | UNKNOWN | 15 | 0 | T |
| AI922191 | UNKNOWN | 31 | 0 | T |
| AI922215 | UNKNOWN | 98 | 0 | T |
| AI922215 | UNKNOWN | 18 | 140 | C |
| AI922215 | UNKNOWN | 16 | 117 | A |
| AI922216 | UNKNOWN | 81 | 0 | T |
| AI922216 | UNKNOWN | 15 | 254 | C |
| AI922216 | UNKNOWN | 14 | 128 | A |
| AI922216 | UNKNOWN | 13 | 112 | G |
| AI922269 | UNKNOWN | 104 | 0 | T |
| AI922269 | UNKNOWN | 19 | 134 | A |
| AI922269 | UNKNOWN | 16 | 238 | G |
| AI922269 | UNKNOWN | 15 | 167 | C |
| AI922278 | UNKNOWN | 55 | 0 | T |
| AI922293 | UNKNOWN | 38 | 0 | T |
| AI922315 | UNKNOWN | 78 | 0 | T |
| AI922315 | UNKNOWN | 17 | 234 | G |
| AI922315 | UNKNOWN | 12 | 219 | C |
| AI922365 | UNKNOWN | 90 | 0 | T |
| AI922365 | UNKNOWN | 24 | 91 | G |
| AI922365 | UNKNOWN | 19 | 138 | A |
| AI922365 | UNKNOWN | 14 | 201 | C |
| AI922371 | UNKNOWN | 37 | 0 | T |
| AI922375 | UNKNOWN | 49 | 0 | T |
| AI922465 | UNKNOWN | 30 | 0 | T |
| AI922494 | UNKNOWN | 13 | 146 | T |
| AI922496 | UNKNOWN | 29 | 0 | T |
| AI922502 | UNKNOWN | 16 | 62 | A |
| AI922520 | UNKNOWN | 19.5 | 286 | AC |

TABLE 1-continued

| Genbank # | Region | # reps | Position | Unit sequence |
|---|---|---|---|---|
| AI922521 | UNKNOWN | 22 | 486 | T |
| AI922521 | UNKNOWN | 19 | 0 | T |
| AI922540 | UNKNOWN | 58 | 0 | T |
| AI922540 | UNKNOWN | 13 | 172 | G |
| AI922543 | UNKNOWN | 51 | 0 | T |
| AI922550 | UNKNOWN | 70 | 0 | T |
| AI922556 | UNKNOWN | 35 | 0 | T |
| AI922557 | UNKNOWN | 37 | 0 | T |
| AI922561 | UNKNOWN | 76 | 0 | T |
| AI922561 | UNKNOWN | 19 | 95 | A |
| AI922572 | UNKNOWN | 14 | 155 | T |
| AI922577 | UNKNOWN | 84 | 0 | T |
| AI922577 | UNKNOWN | 14 | 142 | C |
| AI922597 | UNKNOWN | 49 | 0 | T |
| AI922597 | UNKNOWN | 14 | 332 | A |
| AI922607 | UNKNOWN | 59 | 0 | T |
| AI922607 | UNKNOWN | 22 | 115 | G |
| AI922618 | UNKNOWN | 80 | 0 | T |
| AI922618 | UNKNOWN | 19 | 336 | A |
| AI922618 | UNKNOWN | 15 | 263 | C |
| AI922618 | UNKNOWN | 15 | 305 | A |
| AI922618 | UNKNOWN | 14 | 118 | A |
| AI922641 | UNKNOWN | 36 | 0 | T |
| AI922665 | UNKNOWN | 116 | 0 | T |
| AI922665 | UNKNOWN | 20 | 328 | C |
| AI922665 | UNKNOWN | 19 | 309 | A |
| AI922665 | UNKNOWN | 15 | 124 | G |
| AI922665 | UNKNOWN | 14 | 231 | C |
| AI922665 | UNKNOWN | 13 | 164 | A |
| AI922668 | UNKNOWN | 74 | 0 | T |
| AI922676 | UNKNOWN | 95 | 0 | T |
| AI922676 | UNKNOWN | 23 | 152 | G |
| AI922676 | UNKNOWN | 15 | 119 | C |
| AI922677 | UNKNOWN | 24 | 0 | T |
| AI922689 | UNKNOWN | 84 | 0 | T |
| AI922689 | UNKNOWN | 16 | 114 | A |
| AI922689 | UNKNOWN | 14 | 310 | C |
| AI922699 | UNKNOWN | 47 | 0 | T |
| AI922707 | UNKNOWN | 2.63 | 92 | AAAAAAATTA (SEQ ID NO: 167) |
| AI922707 | UNKNOWN | 85 | 0 | T |
| AI922707 | UNKNOWN | 12 | 260 | C |
| AI922754 | UNKNOWN | 8 | 322 | CA |
| AI922756 | UNKNOWN | 87 | 0 | T |
| AI922756 | UNKNOWN | 14 | 287 | C |
| AI922812 | UNKNOWN | 74 | 0 | T |
| AI922812 | UNKNOWN | 17 | 314 | C |
| AI922812 | UNKNOWN | 14 | 339 | G |
| AI922837 | UNKNOWN | 28 | 0 | T |
| AI922838 | UNKNOWN | 16 | 27 | T |
| AI922901 | UNKNOWN | 113 | 0 | T |
| AI922901 | UNKNOWN | 16 | 138 | C |
| AI922901 | UNKNOWN | 14 | 177 | A |
| AI922901 | UNKNOWN | 13 | 191 | G |
| AI922913 | UNKNOWN | 20 | 0 | T |
| AI922921 | UNKNOWN | 7.5 | 289 | AT |
| AI922921 | UNKNOWN | 25 | 0 | T |
| AI922923 | UNKNOWN | 16 | 0 | T |
| AI922923 | UNKNOWN | 15 | 367 | A |
| AI923034 | UNKNOWN | 71 | 0 | T |
| AI923034 | UNKNOWN | 13 | 109 | G |
| AI923034 | UNKNOWN | 12 | 396 | C |
| AI923050 | UNKNOWN | 25 | 0 | T |
| AI923052 | UNKNOWN | 16 | 6 | T |
| AI923069 | UNKNOWN | 36 | 0 | T |
| AI923069 | UNKNOWN | 21 | 148 | G |
| AI923112 | UNKNOWN | 38 | 0 | T |
| AI923124 | UNKNOWN | 98 | 0 | T |
| AI923124 | UNKNOWN | 13 | 98 | A |
| AI923125 | UNKNOWN | 7 | 301 | ATTT |
| AI923125 | UNKNOWN | 4.5 | 282 | TTTA |
| AI923190 | UNKNOWN | 70 | 0 | T |
| AI923190 | UNKNOWN | 14 | 351 | G |
| AI923190 | UNKNOWN | 13 | 196 | C |
| AI923226 | UNKNOWN | 13 | 0 | T |
| AI923249 | UNKNOWN | 66 | 0 | T |
| AI923249 | UNKNOWN | 14 | 116 | G |
| AI923249 | UNKNOWN | 13 | 89 | C |

TABLE 1-continued

| Genbank # | Region | # reps | Position | Unit sequence |
|---|---|---|---|---|
| AI923264 | UNKNOWN | 33 | 0 | T |
| AI923328 | UNKNOWN | 51 | 0 | T |
| AI923357 | UNKNOWN | 96 | 0 | T |
| AI923357 | UNKNOWN | 24 | 229 | C |
| AI923357 | UNKNOWN | 18 | 123 | A |
| AI923370 | UNKNOWN | 90 | 0 | T |
| AI923370 | UNKNOWN | 14 | 160 | C |
| AI923370 | UNKNOWN | 13 | 123 | G |
| AI923370 | UNKNOWN | 12 | 90 | A |
| AI923376 | UNKNOWN | 27 | 0 | T |
| AI923397 | UNKNOWN | 20 | 133 | A |
| AI923397 | UNKNOWN | 13 | 0 | T |
| AI923412 | UNKNOWN | 49 | 0 | T |
| AI923412 | UNKNOWN | 15 | 110 | C |
| AI923422 | UNKNOWN | 69 | 0 | T |
| AI923437 | UNKNOWN | 15 | 11 | T |
| AI923486 | UNKNOWN | 36 | 0 | T |
| AI923513 | UNKNOWN | 46 | 0 | T |
| AI923559 | UNKNOWN | 51 | 0 | T |
| AI923590 | UNKNOWN | 40 | 13 | T |
| AI923590 | UNKNOWN | 19 | 206 | G |
| AI923590 | UNKNOWN | 17 | 174 | A |
| AI923590 | UNKNOWN | 15 | 147 | C |
| AI923607 | UNKNOWN | 6 | 53 | TTA |
| AI923607 | UNKNOWN | 37 | 0 | T |
| AI923673 | UNKNOWN | 18 | 5 | T |
| AI923708 | UNKNOWN | 4.83 | 403 | CACCAG |
| AI923734 | UNKNOWN | 43 | 0 | T |
| AI923750 | UNKNOWN | 63 | 0 | T |
| AI923750 | UNKNOWN | 12 | 121 | A |
| AI923768 | UNKNOWN | 96 | 0 | T |
| AI923768 | UNKNOWN | 13 | 108 | A |
| AI923768 | UNKNOWN | 12 | 174 | G |
| AI923782 | UNKNOWN | 78 | 0 | T |
| AI923782 | UNKNOWN | 13 | 294 | A |
| AI923782 | UNKNOWN | 12 | 212 | C |
| AI923833 | UNKNOWN | 76 | 0 | T |
| AI923833 | UNKNOWN | 16 | 182 | C |
| AI923837 | UNKNOWN | 102 | 0 | T |
| AI923837 | UNKNOWN | 15 | 137 | C |
| AI923842 | UNKNOWN | 42 | 0 | T |
| AI923871 | UNKNOWN | 59 | 0 | T |
| AI923872 | UNKNOWN | 21 | 0 | T |
| AI923987 | UNKNOWN | 14 | 0 | T |
| AI924024 | UNKNOWN | 42 | 11 | T |
| AI924030 | UNKNOWN | 34 | 0 | T |
| AI924035 | UNKNOWN | 51 | 0 | T |
| AI924046 | UNKNOWN | 21 | 11 | T |
| AI924065 | UNKNOWN | 15 | 0 | T |
| AI924216 | UNKNOWN | 13 | 0 | T |
| AI924235 | UNKNOWN | 14 | 468 | A |
| AI924237 | UNKNOWN | 12 | 0 | T |
| AI924241 | UNKNOWN | 30 | 0 | T |
| AI924246 | UNKNOWN | 24 | 0 | T |
| AI924270 | UNKNOWN | 47 | 0 | T |
| AI924270 | UNKNOWN | 17 | 211 | A |
| AI924322 | UNKNOWN | 21 | 0 | T |
| AI924324 | UNKNOWN | 32 | 0 | T |
| AI924520 | UNKNOWN | 19 | 5 | T |
| AI924533 | UNKNOWN | 18 | 5 | T |
| AI924559 | UNKNOWN | 26 | 0 | T |
| AI924621 | UNKNOWN | 55 | 0 | T |
| AI924669 | UNKNOWN | 57 | 0 | T |
| AI924669 | UNKNOWN | 13 | 110 | C |
| AI924686 | UNKNOWN | 83 | 0 | T |
| AI924711 | UNKNOWN | 52 | 0 | T |
| AI924711 | UNKNOWN | 15 | 143 | G |
| AI924713 | UNKNOWN | 64 | 0 | T |
| AI924713 | UNKNOWN | 18 | 291 | A |
| AI924713 | UNKNOWN | 15 | 106 | C |
| AI924720 | UNKNOWN | 33 | 0 | T |
| AI924721 | UNKNOWN | 66 | 0 | T |
| AI924792 | UNKNOWN | 47 | 0 | T |
| AI924806 | UNKNOWN | 12 | 0 | T |
| AI924811 | UNKNOWN | 48 | 0 | T |
| AI924832 | UNKNOWN | 19 | 0 | T |
| AI924846 | UNKNOWN | 91 | 0 | T |

TABLE 1-continued

| Genbank # | Region | # reps | Position | Unit sequence |
|---|---|---|---|---|
| AI924846 | UNKNOWN | 21 | 229 | C |
| AI924846 | UNKNOWN | 15 | 351 | G |
| AI924846 | UNKNOWN | 12 | 100 | A |
| AI924851 | UNKNOWN | 43 | 0 | T |
| AI924872 | UNKNOWN | 19 | 289 | T |
| AI924896 | UNKNOWN | 14 | 0 | T |
| AI924900 | UNKNOWN | 24 | 0 | T |
| AI924911 | UNKNOWN | 94 | 0 | T |
| AI924911 | UNKNOWN | 19 | 399 | G |
| AI924911 | UNKNOWN | 15 | 101 | A |
| AI924911 | UNKNOWN | 14 | 241 | G |
| AI924923 | UNKNOWN | 93 | 0 | T |
| AI924923 | UNKNOWN | 16 | 375 | G |
| AI924923 | UNKNOWN | 15 | 103 | A |
| AI924923 | UNKNOWN | 13 | 313 | C |
| AI924948 | UNKNOWN | 30 | 0 | T |
| AI924963 | UNKNOWN | 14 | 0 | T |
| AI924969 | UNKNOWN | 34 | 0 | T |
| AI924971 | UNKNOWN | 93 | 0 | T |
| AI924971 | UNKNOWN | 19 | 203 | A |
| AI924971 | UNKNOWN | 12 | 100 | A |
| AI925004 | UNKNOWN | 28 | 0 | T |
| AI925010 | UNKNOWN | 42 | 0 | T |
| AI925036 | UNKNOWN | 16 | 0 | T |
| AI925047 | UNKNOWN | 13 | 0 | T |
| AI925083 | UNKNOWN | 28 | 0 | T |
| AI925140 | UNKNOWN | 25 | 0 | T |
| AI925156 | UNKNOWN | 105 | 0 | T |
| AI925156 | UNKNOWN | 19 | 173 | G |
| AI925156 | UNKNOWN | 15 | 105 | C |
| AI925156 | UNKNOWN | 14 | 125 | A |
| AI925163 | UNKNOWN | 37 | 0 | T |
| AI925163 | UNKNOWN | 16 | 90 | A |
| AI925164 | UNKNOWN | 57 | 0 | T |
| AI925164 | UNKNOWN | 16 | 139 | A |
| AI925180 | UNKNOWN | 15 | 0 | T |
| AI925183 | UNKNOWN | 24 | 0 | T |
| AI925183 | UNKNOWN | 19 | 304 | A |
| AI925196 | UNKNOWN | 110 | 0 | T |
| AI925196 | UNKNOWN | 26 | 174 | C |
| AI925196 | UNKNOWN | 16 | 296 | G |
| AI925196 | UNKNOWN | 15 | 123 | A |
| AI925273 | UNKNOWN | 52 | 0 | T |
| AI925281 | UNKNOWN | 55 | 0 | T |
| AI925281 | UNKNOWN | 18 | 249 | C |
| AI925281 | UNKNOWN | 12 | 200 | C |
| AI925299 | UNKNOWN | 35 | 0 | T |
| AI925310 | UNKNOWN | 12 | 36 | T |
| AI925321 | UNKNOWN | 23 | 0 | T |
| AI925324 | UNKNOWN | 76 | 0 | T |
| AI925324 | UNKNOWN | 16 | 205 | C |
| AI925404 | UNKNOWN | 57 | 0 | T |
| AI925432 | UNKNOWN | 53 | 0 | T |
| AI925463 | UNKNOWN | 73 | 0 | T |
| AI925502 | UNKNOWN | 84 | 0 | T |
| AI925502 | UNKNOWN | 12 | 95 | A |
| AI925503 | UNKNOWN | 34 | 0 | T |
| AI925510 | UNKNOWN | 50 | 0 | T |
| AI925514 | UNKNOWN | 45 | 0 | T |
| AI925541 | UNKNOWN | 47 | 0 | T |
| AI925579 | UNKNOWN | 33 | 0 | T |
| AI925680 | UNKNOWN | 63 | 0 | T |
| AI925705 | UNKNOWN | 41 | 0 | T |
| AI925733 | UNKNOWN | 33 | 10 | T |
| AI925736 | UNKNOWN | 51 | 0 | T |
| AI925744 | UNKNOWN | 85 | 0 | T |
| AI925744 | UNKNOWN | 13 | 254 | G |
| AI925923 | UNKNOWN | 16 | 0 | T |
| AI925958 | UNKNOWN | 20 | 0 | T |
| AI925966 | UNKNOWN | 30 | 0 | T |
| AI925987 | UNKNOWN | 79 | 0 | T |
| AI925988 | UNKNOWN | 28 | 0 | T |
| AI926007 | UNKNOWN | 54 | 0 | T |
| AI926041 | UNKNOWN | 59 | 0 | T |
| AI926106 | UNKNOWN | 39 | 0 | T |
| AI926143 | UNKNOWN | 64 | 0 | T |
| AI926143 | UNKNOWN | 12 | 113 | G |

TABLE 1-continued

| Genbank # | Region | # reps | Position | Unit sequence |
|---|---|---|---|---|
| AI926146 | UNKNOWN | 24 | 0 | T |
| AI926146 | UNKNOWN | 15 | 175 | A |
| AI926147 | UNKNOWN | 49 | 0 | T |
| AI926167 | UNKNOWN | 30 | 0 | T |
| AI926182 | UNKNOWN | 43 | 0 | T |
| AI926185 | UNKNOWN | 14 | 132 | A |
| AI926190 | UNKNOWN | 34 | 0 | T |
| AI926190 | UNKNOWN | 15 | 413 | A |
| AI926229 | UNKNOWN | 23 | 0 | T |
| AI926238 | UNKNOWN | 40 | 0 | T |
| AI926253 | UNKNOWN | 19 | 0 | T |
| AI926286 | UNKNOWN | 31 | 0 | T |
| AI926289 | UNKNOWN | 43 | 0 | T |
| AI926333 | UNKNOWN | 78 | 0 | T |
| AI926333 | UNKNOWN | 13 | 173 | G |
| AI926333 | UNKNOWN | 13 | 269 | C |
| AI926346 | UNKNOWN | 74 | 0 | T |
| AI926346 | UNKNOWN | 17 | 270 | A |
| AI926346 | UNKNOWN | 13 | 180 | G |
| AI926346 | UNKNOWN | 12 | 127 | A |
| AI926353 | UNKNOWN | 14 | 0 | T |
| AI926358 | UNKNOWN | 45 | 0 | T |
| AI926367 | UNKNOWN | 93 | 0 | T |
| AI926367 | UNKNOWN | 13 | 93 | A |
| AI926378 | UNKNOWN | 40 | 0 | T |
| AI926419 | UNKNOWN | 49 | 0 | T |
| AI926493 | UNKNOWN | 32 | 0 | T |
| AI926531 | UNKNOWN | 58 | 0 | T |
| AI926554 | UNKNOWN | 3.6 | 254 | TTTGT |
| AI926568 | UNKNOWN | 14 | 0 | T |
| AI926573 | UNKNOWN | 13 | 0 | T |
| AI926604 | UNKNOWN | 27 | 0 | T |
| AI926605 | UNKNOWN | 15 | 0 | T |
| AI926614 | UNKNOWN | 35 | 0 | T |
| AI926661 | UNKNOWN | 44 | 0 | T |
| AI926669 | UNKNOWN | 63 | 0 | T |
| AI926669 | UNKNOWN | 14 | 327 | G |
| AI926700 | UNKNOWN | 34 | 0 | T |
| AI926700 | UNKNOWN | 12 | 136 | C |
| AI926728 | UNKNOWN | 25 | 0 | T |
| AI926730 | UNKNOWN | 6.5 | 153 | AT |
| AI926755 | UNKNOWN | 36 | 11 | T |
| AI926790 | UNKNOWN | 108 | 0 | T |
| AI926790 | UNKNOWN | 17 | 149 | A |
| AI926790 | UNKNOWN | 14 | 108 | A |
| AI926790 | UNKNOWN | 12 | 166 | C |
| AI926794 | UNKNOWN | 66 | 0 | T |
| AI926800 | UNKNOWN | 94 | 0 | T |
| AI926800 | UNKNOWN | 18 | 196 | G |
| AI926800 | UNKNOWN | 16 | 126 | C |
| AI926800 | UNKNOWN | 13 | 174 | A |
| AI926807 | UNKNOWN | 33 | 5 | T |
| AI926850 | UNKNOWN | 15 | 0 | T |
| AI926878 | UNKNOWN | 75 | 0 | T |
| AI926878 | UNKNOWN | 15 | 187 | G |
| AI926900 | UNKNOWN | 43 | 0 | T |
| AI926900 | UNKNOWN | 14 | 90 | A |
| AI926921 | UNKNOWN | 18 | 6 | T |
| AI927026 | UNKNOWN | 16 | 0 | T |
| AI927030 | UNKNOWN | 3.06 | 235 | GATGATCAAAGGTCG (SEQ ID NO: 168) |
| AI927080 | UNKNOWN | 15 | 0 | T |
| AI927084 | UNKNOWN | 15 | 0 | T |
| AI927092 | UNKNOWN | 79 | 0 | T |
| AI927092 | UNKNOWN | 13 | 154 | C |
| AI927104 | UNKNOWN | 44 | 0 | T |
| AI927191 | UNKNOWN | 12 | 0 | T |
| AI927192 | UNKNOWN | 12 | 0 | T |
| AI927202 | UNKNOWN | 16 | 0 | T |
| AI927204 | UNKNOWN | 19 | 4 | T |
| AI927212 | UNKNOWN | 16 | 0 | T |
| AI927216 | UNKNOWN | 15 | 0 | T |
| AI927256 | UNKNOWN | 58 | 0 | T |
| AI927261 | UNKNOWN | 17 | 0 | T |
| AI927273 | UNKNOWN | 22 | 0 | T |
| AI927277 | UNKNOWN | 58 | 0 | T |
| AI927375 | UNKNOWN | 18 | 452 | AC |
| AI927378 | UNKNOWN | 28 | 0 | T |

TABLE 1-continued

| Genbank # | Region | # reps | Position | Unit sequence |
| --- | --- | --- | --- | --- |
| AI927394 | UNKNOWN | 20 | 0 | T |
| AI927399 | UNKNOWN | 32 | 0 | T |
| AI927399 | UNKNOWN | 14 | 299 | G |
| AI927410 | UNKNOWN | 13 | 0 | T |
| AI927444 | UNKNOWN | 25 | 0 | T |
| AI927495 | UNKNOWN | 14 | 0 | T |
| AI927605 | UNKNOWN | 13 | 492 | A |
| AI927610 | UNKNOWN | 14 | 414 | T |
| AI927666 | UNKNOWN | 23 | 389 | T |
| AI927688 | UNKNOWN | 12 | 0 | T |
| AI927694 | UNKNOWN | 14 | 0 | T |
| AI927695 | UNKNOWN | 14 | 0 | T |
| AI927700 | UNKNOWN | 32 | 0 | T |
| AI927700 | UNKNOWN | 12 | 47 | G |
| AI927755 | UNKNOWN | 75 | 0 | T |
| AI927755 | UNKNOWN | 13 | 130 | G |
| AI927755 | UNKNOWN | 13 | 158 | A |
| AI927766 | UNKNOWN | 32 | 0 | T |
| AI927767 | UNKNOWN | 30 | 0 | T |
| AI927811 | UNKNOWN | 12 | 0 | T |
| AI927836 | UNKNOWN | 16 | 0 | T |
| AI927837 | UNKNOWN | 14 | 7 | T |
| AI927846 | UNKNOWN | 25 | 0 | T |
| AI927919 | UNKNOWN | 12 | 0 | T |
| AI927925 | UNKNOWN | 18 | 0 | T |
| AI927927 | UNKNOWN | 14 | 0 | T |
| AI927943 | UNKNOWN | 18 | 0 | T |
| AI927983 | UNKNOWN | 25 | 0 | T |
| AI928021 | UNKNOWN | 21 | 6 | T |
| AI928024 | UNKNOWN | 18 | 4 | T |
| AI928039 | UNKNOWN | 43 | 0 | T |
| AI928039 | UNKNOWN | 13 | 211 | A |
| AI928162 | UNKNOWN | 13 | 0 | T |
| AI928201 | UNKNOWN | 12 | 0 | T |
| AI928203 | UNKNOWN | 19 | 37 | T |
| AI928218 | UNKNOWN | 3.18 | 426 | TCTCTGGGCTCTGTGACGTTCCTACAGGACGC (SEQ ID NO: 169) |
| AI928227 | UNKNOWN | 23 | 0 | T |
| AI928229 | UNKNOWN | 34 | 0 | T |
| AI928230 | UNKNOWN | 24 | 0 | T |
| AI928240 | UNKNOWN | 12 | 0 | T |
| AI928247 | UNKNOWN | 19 | 4 | T |
| AI928293 | UNKNOWN | 54 | 0 | T |
| AI928293 | UNKNOWN | 14 | 297 | G |
| AI928294 | UNKNOWN | 50 | 0 | T |
| AI928294 | UNKNOWN | 12 | 298 | C |
| AI928298 | UNKNOWN | 18 | 0 | T |
| AI928298 | UNKNOWN | 14 | 360 | G |
| AI928344 | UNKNOWN | 14 | 0 | T |
| AI928373 | UNKNOWN | 17 | 0 | T |
| AI928392 | UNKNOWN | 14 | 0 | T |
| AI928402 | UNKNOWN | 14 | 0 | T |
| AI928447 | UNKNOWN | 12 | 0 | T |
| AI928448 | UNKNOWN | 20 | 0 | T |
| AI928451 | UNKNOWN | 22 | 0 | T |
| AI928453 | UNKNOWN | 15 | 0 | T |
| AI928456 | UNKNOWN | 20 | 0 | T |
| AI928457 | UNKNOWN | 12 | 0 | T |
| AI928481 | UNKNOWN | 45 | 0 | T |
| AI928482 | UNKNOWN | 15 | 19 | T |
| AI928482 | UNKNOWN | 14 | 0 | T |
| AI928489 | UNKNOWN | 35 | 0 | T |
| AI928490 | UNKNOWN | 20 | 4 | T |
| AI928505 | UNKNOWN | 17 | 0 | T |
| AI928506 | UNKNOWN | 14 | 0 | T |
| AI928513 | UNKNOWN | 16 | 0 | T |
| AI928515 | UNKNOWN | 14 | 0 | T |
| AI928517 | UNKNOWN | 17 | 4 | T |
| AI928524 | UNKNOWN | 4.5 | 0 | ATTT |
| AI928587 | UNKNOWN | 26 | 8 | T |
| AI928587 | UNKNOWN | 22 | 170 | A |
| AI928635 | UNKNOWN | 14 | 115 | T |
| AI928677 | UNKNOWN | 15 | 1 | T |
| AI928807 | UNKNOWN | 13 | 0 | T |
| AI928868 | UNKNOWN | 17 | 0 | T |
| AI928897 | UNKNOWN | 12 | 112 | T |
| AI929101 | UNKNOWN | 15 | 0 | T |

TABLE 1-continued

| Genbank # | Region | # reps | Position | Unit sequence |
|---|---|---|---|---|
| AI929247 | UNKNOWN | 9 | 297 | AT |
| AI929533 | UNKNOWN | 12 | 0 | T |
| AI929564 | UNKNOWN | 89 | 0 | T |
| AI929564 | UNKNOWN | 27 | 207 | G |
| AI929564 | UNKNOWN | 18 | 329 | C |
| AI929564 | UNKNOWN | 13 | 189 | C |
| AI929702 | UNKNOWN | 13 | 172 | A |
| AI929772 | UNKNOWN | 13 | 40 | C |
| AI932266 | UNKNOWN | 16 | 294 | A |
| AI932266 | UNKNOWN | 14 | 232 | T |
| AI932290 | UNKNOWN | 4.5 | 145 | TTTA |
| AI932301 | UNKNOWN | 14 | 327 | A |
| AI932329 | UNKNOWN | 14 | 256 | T |
| AI932345 | UNKNOWN | 13 | 0 | T |
| AI932419 | UNKNOWN | 13 | 0 | T |
| AI932458 | UNKNOWN | 67 | 0 | T |
| AI932502 | UNKNOWN | 14 | 0 | T |
| AI932503 | UNKNOWN | 81 | 0 | T |
| AI932503 | UNKNOWN | 13 | 327 | G |
| AI932503 | UNKNOWN | 12 | 99 | A |
| AI932503 | UNKNOWN | 12 | 243 | C |
| AI932510 | UNKNOWN | 93 | 0 | T |
| AI932510 | UNKNOWN | 15 | 232 | G |
| AI932636 | UNKNOWN | 19 | 0 | T |
| AI932638 | UNKNOWN | 83 | 0 | T |
| AI932638 | UNKNOWN | 15 | 119 | A |
| AI932638 | UNKNOWN | 12 | 174 | C |
| AI932660 | UNKNOWN | 49 | 0 | T |
| AI932794 | UNKNOWN | 91 | 0 | T |
| AI932794 | UNKNOWN | 14 | 202 | G |
| AI932794 | UNKNOWN | 12 | 167 | C |
| AI932818 | UNKNOWN | 68 | 0 | T |
| AI932867 | UNKNOWN | 59 | 0 | T |
| AI932915 | UNKNOWN | 77 | 0 | T |
| AI932949 | UNKNOWN | 76 | 0 | T |
| AI932949 | UNKNOWN | 15 | 101 | A |
| AI932949 | UNKNOWN | 13 | 136 | C |
| AI932953 | UNKNOWN | 50 | 5 | T |
| AI932953 | UNKNOWN | 13 | 173 | G |
| AI932953 | UNKNOWN | 12 | 147 | C |
| AI932966 | UNKNOWN | 89 | 0 | T |
| AI932966 | UNKNOWN | 13 | 229 | A |
| AI932970 | UNKNOWN | 51 | 0 | T |
| AI932970 | UNKNOWN | 12 | 81 | A |
| AI932980 | UNKNOWN | 44 | 0 | T |
| AI932988 | UNKNOWN | 72 | 0 | T |
| AI932988 | UNKNOWN | 19 | 219 | G |
| AI933001 | UNKNOWN | 90 | 0 | T |
| AI933001 | UNKNOWN | 14 | 94 | C |
| AI933001 | UNKNOWN | 13 | 138 | A |
| AI933010 | UNKNOWN | 42 | 0 | T |
| AI933012 | UNKNOWN | 81 | 0 | T |
| AI933012 | UNKNOWN | 15 | 210 | C |
| AI933012 | UNKNOWN | 12 | 176 | C |
| AI933012 | UNKNOWN | 12 | 188 | G |
| AI933029 | UNKNOWN | 19 | 0 | T |
| AI933486 | UNKNOWN | 16 | 11 | T |
| AI933518 | UNKNOWN | 78 | 0 | T |
| AI933518 | UNKNOWN | 16 | 288 | A |
| AI933528 | UNKNOWN | 56 | 0 | T |
| AI933542 | UNKNOWN | 14 | 0 | T |
| AI933574 | UNKNOWN | 66 | 0 | T |
| AI933574 | UNKNOWN | 13 | 181 | C |
| AI933574 | UNKNOWN | 12 | 96 | G |
| AI933589 | UNKNOWN | 95 | 0 | T |
| AI933589 | UNKNOWN | 14 | 137 | G |
| AI933589 | UNKNOWN | 12 | 166 | C |
| AI933591 | UNKNOWN | 17 | 0 | T |
| AI933600 | UNKNOWN | 18 | 0 | T |
| AI933607 | UNKNOWN | 37 | 0 | T |
| AI933607 | UNKNOWN | 24 | 139 | A |
| AI933607 | UNKNOWN | 14 | 58 | A |
| AI933633 | UNKNOWN | 16 | 0 | T |
| AI933704 | UNKNOWN | 44 | 0 | T |
| AI933721 | UNKNOWN | 44 | 0 | T |
| AI933726 | UNKNOWN | 45 | 0 | T |
| AI933726 | UNKNOWN | 14 | 317 | G |

TABLE 1-continued

| Genbank # | Region | # reps | Position | Unit sequence |
|---|---|---|---|---|
| AI933727 | UNKNOWN | 54 | 0 | T |
| AI933756 | UNKNOWN | 45 | 0 | T |
| AI933780 | UNKNOWN | 68 | 0 | T |
| AI933780 | UNKNOWN | 15 | 122 | A |
| AI933785 | UNKNOWN | 88 | 0 | T |
| AI933785 | UNKNOWN | 20 | 150 | G |
| AI933811 | UNKNOWN | 21 | 0 | T |
| AI933836 | UNKNOWN | 14 | 297 | A |
| AI933840 | UNKNOWN | 66 | 0 | T |
| AI933903 | UNKNOWN | 74 | 0 | T |
| AI933926 | UNKNOWN | 78 | 0 | T |
| AI933926 | UNKNOWN | 13 | 100 | G |
| AI933938 | UNKNOWN | 43 | 0 | T |
| AI933952 | UNKNOWN | 27 | 0 | T |
| AI933962 | UNKNOWN | 60 | 0 | T |
| AI933992 | UNKNOWN | 69 | 0 | T |
| AI934011 | UNKNOWN | 115 | 0 | T |
| AI934011 | UNKNOWN | 20 | 183 | G |
| AI934011 | UNKNOWN | 15 | 116 | A |
| AI934011 | UNKNOWN | 13 | 261 | C |
| AI934012 | UNKNOWN | 71 | 0 | T |
| AI934012 | UNKNOWN | 14 | 256 | C |
| AI934012 | UNKNOWN | 12 | 163 | G |
| AI934026 | UNKNOWN | 87 | 0 | T |
| AI934026 | UNKNOWN | 20 | 114 | A |
| AI934026 | UNKNOWN | 15 | 295 | C |
| AI934026 | UNKNOWN | 14 | 224 | G |
| AI934035 | UNKNOWN | 118 | 0 | T |
| AI934035 | UNKNOWN | 16 | 250 | A |
| AI934035 | UNKNOWN | 12 | 303 | G |
| AI934036 | UNKNOWN | 135 | 0 | T |
| AI934036 | UNKNOWN | 27 | 222 | G |
| AI934036 | UNKNOWN | 19 | 252 | A |
| AI934036 | UNKNOWN | 14 | 399 | C |
| AI934036 | UNKNOWN | 13 | 155 | C |
| AI934039 | UNKNOWN | 84 | 0 | T |
| AI934039 | UNKNOWN | 20 | 239 | G |
| AI934039 | UNKNOWN | 16 | 162 | C |
| AI934039 | UNKNOWN | 14 | 184 | A |
| AI934052 | UNKNOWN | 54 | 0 | T |
| AI934052 | UNKNOWN | 18 | 224 | A |
| AI934061 | UNKNOWN | 52 | 0 | T |
| AI934065 | UNKNOWN | 45 | 0 | T |
| AI934098 | UNKNOWN | 22 | 0 | T |
| AI934127 | UNKNOWN | 19 | 0 | T |
| AI934132 | UNKNOWN | 38 | 0 | T |
| AI934137 | UNKNOWN | 111 | 0 | T |
| AI934137 | UNKNOWN | 15 | 146 | C |
| AI934137 | UNKNOWN | 13 | 218 | G |
| AI934147 | UNKNOWN | 78 | 0 | T |
| AI934147 | UNKNOWN | 17 | 197 | C |
| AI934147 | UNKNOWN | 12 | 111 | A |
| AI934154 | UNKNOWN | 47 | 0 | T |
| AI934233 | UNKNOWN | 36 | 0 | T |
| AI934233 | UNKNOWN | 14 | 214 | A |
| AI934259 | UNKNOWN | 95 | 0 | T |
| AI934259 | UNKNOWN | 16 | 95 | A |
| AI934259 | UNKNOWN | 12 | 135 | G |
| AI934276 | UNKNOWN | 63 | 0 | T |
| AI934276 | UNKNOWN | 13 | 210 | C |
| AI934295 | UNKNOWN | 61 | 0 | T |
| AI934295 | UNKNOWN | 18 | 239 | G |
| AI934295 | UNKNOWN | 13 | 169 | C |
| AI934308 | UNKNOWN | 44 | 0 | T |
| AI934322 | UNKNOWN | 54 | 0 | T |
| AI934370 | UNKNOWN | 38 | 0 | T |
| AI934404 | UNKNOWN | 31 | 0 | T |
| AI934415 | UNKNOWN | 15 | 0 | T |
| AI934432 | UNKNOWN | 19 | 0 | T |
| AI934445 | UNKNOWN | 13 | 0 | T |
| AI934517 | UNKNOWN | 17 | 0 | T |
| AI934529 | UNKNOWN | 33 | 0 | T |
| AI934535 | UNKNOWN | 8 | 407 | GT |
| AI934540 | UNKNOWN | 6.5 | 325 | AG |
| AI934540 | UNKNOWN | 12 | 205 | A |
| AI934552 | UNKNOWN | 8.5 | 251 | GT |
| AI934552 | UNKNOWN | 6.5 | 238 | AT |

TABLE 1-continued

| Genbank # | Region | # reps | Position | Unit sequence |
|---|---|---|---|---|
| AI934577 | UNKNOWN | 12 | 470 | A |
| AI934608 | UNKNOWN | 3.66 | 179 | TTTTGT |
| AI934819 | UNKNOWN | 13 | 0 | T |
| AI934838 | UNKNOWN | 17 | 369 | A |
| AI934857 | UNKNOWN | 16 | 0 | T |
| AI934946 | UNKNOWN | 15 | 0 | T |
| AI934965 | UNKNOWN | 12 | 0 | T |
| AI935054 | UNKNOWN | 18 | 229 | A |
| AI935069 | UNKNOWN | 14 | 214 | T |
| AI935076 | UNKNOWN | 14 | 0 | T |
| AI935182 | UNKNOWN | 16 | 0 | T |
| AI935244 | UNKNOWN | 21 | 146 | A |
| AI935271 | UNKNOWN | 19 | 5 | T |
| AI935344 | UNKNOWN | 34 | 0 | T |
| AI935382 | UNKNOWN | 14 | 0 | T |
| AI935391 | UNKNOWN | 17 | 0 | T |
| AI935508 | UNKNOWN | 14 | 184 | A |
| AI935630 | UNKNOWN | 16 | 473 | T |
| AI935687 | UNKNOWN | 13 | 0 | T |
| AI935827 | UNKNOWN | 5.25 | 432 | AAAG |
| AI935846 | UNKNOWN | 40 | 0 | T |
| AI935874 | UNKNOWN | 24 | 0 | T |
| AI935874 | UNKNOWN | 12 | 123 | A |
| AI935915 | UNKNOWN | 23.5 | 343 | GA |
| AI935968 | UNKNOWN | 56 | 0 | T |
| AI935995 | UNKNOWN | 40 | 0 | T |
| AI935995 | UNKNOWN | 14 | 338 | C |
| AI935995 | UNKNOWN | 12 | 105 | A |
| AI936003 | UNKNOWN | 58 | 0 | T |
| AI936003 | UNKNOWN | 12 | 351 | A |
| AI936008 | UNKNOWN | 16 | 0 | T |
| AI936069 | UNKNOWN | 25 | 0 | T |
| AI936089 | UNKNOWN | 13 | 0 | T |
| AI936092 | UNKNOWN | 13 | 2 | T |
| AI936197 | UNKNOWN | 13 | 0 | T |
| AI936312 | UNKNOWN | 37 | 0 | T |
| AI936325 | UNKNOWN | 13 | 0 | T |
| AI936345 | UNKNOWN | 5.75 | 403 | TTTC |
| AI936345 | UNKNOWN | 28 | 0 | T |
| AI936345 | UNKNOWN | 13 | 205 | A |
| AI936370 | UNKNOWN | 22 | 0 | T |
| AI936373 | UNKNOWN | 21 | 0 | T |
| AI936379 | UNKNOWN | 28 | 0 | T |
| AI936482 | UNKNOWN | 7.66 | 295 | GAA |
| AI936482 | UNKNOWN | 14 | 274 | A |
| AI936520 | UNKNOWN | 13 | 310 | T |
| AI936540 | UNKNOWN | 15 | 0 | T |
| AI936560 | UNKNOWN | 14 | 423 | A |
| AI936562 | UNKNOWN | 20 | 419 | T |
| AI936593 | UNKNOWN | 13 | 0 | T |
| AI936604 | UNKNOWN | 22 | 409 | T |
| AI936604 | UNKNOWN | 18 | 0 | T |
| AI936643 | UNKNOWN | 3.6 | 338 | AAACA |
| AI936657 | UNKNOWN | 6 | 321 | ATTT |
| AI936974 | UNKNOWN | 43 | 0 | T |
| AI936987 | UNKNOWN | 15 | 170 | T |
| AI937002 | UNKNOWN | 25 | 0 | T |
| AI937029 | UNKNOWN | 13 | 54 | A |
| AI937085 | UNKNOWN | 45 | 0 | T |
| AI937085 | UNKNOWN | 14 | 391 | G |
| AI937089 | UNKNOWN | 15 | 0 | T |
| AI937132 | UNKNOWN | 17 | 0 | T |
| AI937250 | UNKNOWN | 3.6 | 109 | AAAAT |
| AI937250 | UNKNOWN | 22 | 26 | T |
| AI937254 | UNKNOWN | 11.5 | 562 | AC |
| AI937254 | UNKNOWN | 17 | 4 | T |
| AI937310 | UNKNOWN | 31 | 0 | T |
| AI937310 | UNKNOWN | 12 | 144 | G |
| AI937322 | UNKNOWN | 3.6 | 16 | TTTAT |
| AI937370 | UNKNOWN | 13 | 367 | T |
| AI937405 | UNKNOWN | 5.75 | 2 | TTTA |
| AI937408 | UNKNOWN | 36 | 0 | T |
| AI937456 | UNKNOWN | 35 | 0 | T |
| AI937457 | UNKNOWN | 26 | 0 | T |
| AI937612 | UNKNOWN | 18 | 7 | T |
| AI937617 | UNKNOWN | 35 | 0 | T |
| AI937704 | UNKNOWN | 12 | 5 | T |

TABLE 1-continued

| Genbank # | Region | # reps | Position | Unit sequence |
|---|---|---|---|---|
| AI937869 | UNKNOWN | 46 | 0 | T |
| AI939299 | UNKNOWN | 15 | 0 | T |
| AI939317 | UNKNOWN | 14 | 45 | T |
| AI939331 | UNKNOWN | 28 | 0 | T |
| AI939332 | UNKNOWN | 17 | 433 | A |
| AI939343 | UNKNOWN | 15 | 304 | A |
| AI939350 | UNKNOWN | 23 | 0 | T |
| AI939353 | UNKNOWN | 12 | 4 | T |
| AI939354 | UNKNOWN | 15 | 0 | T |
| AI939357 | UNKNOWN | 16 | 464 | T |
| AI939361 | UNKNOWN | 18 | 0 | T |
| AI939364 | UNKNOWN | 36 | 0 | T |
| AI939364 | UNKNOWN | 21 | 199 | A |
| AI939371 | UNKNOWN | 13 | 0 | T |
| AI939372 | UNKNOWN | 18 | 0 | T |
| AI939373 | UNKNOWN | 14 | 5 | T |
| AI939379 | UNKNOWN | 17 | 86 | A |
| AI939391 | UNKNOWN | 19 | 0 | T |
| AI939411 | UNKNOWN | 12 | 0 | T |
| AI939413 | UNKNOWN | 14 | 312 | A |
| AI939434 | UNKNOWN | 19 | 118 | A |
| AI939435 | UNKNOWN | 13 | 244 | A |
| AI939437 | UNKNOWN | 26 | 170 | A |
| AI939445 | UNKNOWN | 14 | 5 | T |
| AI939464 | UNKNOWN | 29 | 0 | T |
| AI939486 | UNKNOWN | 13 | 85 | A |
| AI939491 | UNKNOWN | 2.63 | 124 | AGGCAATGGGA (SEQ ID NO: 170) |
| AI939495 | UNKNOWN | 14 | 438 | A |
| AI939500 | UNKNOWN | 27 | 0 | T |
| AI939503 | UNKNOWN | 13 | 136 | T |
| AI939505 | UNKNOWN | 12 | 393 | T |
| AI939513 | UNKNOWN | 14 | 188 | A |
| AI939514 | UNKNOWN | 27 | 0 | T |
| AI939521 | UNKNOWN | 14 | 0 | T |
| AI939524 | UNKNOWN | 25 | 0 | T |
| AI939528 | UNKNOWN | 15 | 0 | T |
| AI939532 | UNKNOWN | 4.83 | 227 | GGGCGA |
| AI939533 | UNKNOWN | 22 | 0 | T |
| AI939538 | UNKNOWN | 12.5 | 497 | AC |
| AI939541 | UNKNOWN | 16 | 399 | T |
| AI939546 | UNKNOWN | 23 | 17 | T |
| AI939562 | UNKNOWN | 6.5 | 238 | TC |
| AI939567 | UNKNOWN | 20 | 0 | T |
| AI939569 | UNKNOWN | 23 | 0 | T |
| AI939570 | UNKNOWN | 5.66 | 346 | GCC |
| AI939575 | UNKNOWN | 18 | 174 | T |
| AI939581 | UNKNOWN | 2.96 | 91 | AGAACAGACTAATACAGGGACTTTG (SEQ ID NO: 171) |
| AI939590 | UNKNOWN | 15 | 0 | T |
| AI939604 | UNKNOWN | 25 | 0 | T |
| AI939610 | UNKNOWN | 12 | 10 | T |
| AI939627 | UNKNOWN | 7.5 | 149 | AC |
| AI942283 | UNKNOWN | 13 | 0 | T |
| AI942292 | UNKNOWN | 12 | 0 | T |
| AI942328 | UNKNOWN | 38 | 0 | T |
| AI942328 | UNKNOWN | 17 | 301 | G |
| AI942331 | UNKNOWN | 17 | 0 | T |
| AI942436 | UNKNOWN | 65 | 0 | T |
| AI942451 | UNKNOWN | 10.5 | 67 | TC |
| AI942454 | UNKNOWN | 6.5 | 173 | TA |
| AI948431 | UNKNOWN | 38 | 0 | T |
| AI948465 | UNKNOWN | 16 | 0 | T |
| AI948478 | UNKNOWN | 15 | 0 | T |
| AI948480 | UNKNOWN | 19 | 0 | T |
| AI948490 | UNKNOWN | 18 | 0 | T |
| AI948491 | UNKNOWN | 13 | 116 | T |
| AI948498 | UNKNOWN | 42 | 0 | T |
| AI948537 | UNKNOWN | 21 | 0 | T |
| AI948629 | UNKNOWN | 17 | 0 | T |
| AI948772 | UNKNOWN | 14 | 0 | T |
| AI948790 | UNKNOWN | 12 | 0 | T |
| AI948831 | UNKNOWN | 18 | 4 | T |
| AI948831 | UNKNOWN | 13 | 95 | A |
| AI948985 | UNKNOWN | 9 | 101 | AT |
| AI949113 | UNKNOWN | 66 | 0 | T |
| AI949113 | UNKNOWN | 15 | 350 | A |
| AI949113 | UNKNOWN | 12 | 227 | G |

TABLE 1-continued

| Genbank # | Region | # reps | Position | Unit sequence |
|---|---|---|---|---|
| AI949165 | UNKNOWN | 12 | 229 | T |
| AI949205 | UNKNOWN | 65 | 0 | T |
| AI949211 | UNKNOWN | 84 | 0 | T |
| AI949211 | UNKNOWN | 12 | 464 | G |
| AI949235 | UNKNOWN | 57 | 0 | T |
| AI949235 | UNKNOWN | 17 | 96 | A |
| AI949251 | UNKNOWN | 15 | 0 | T |
| AI949333 | UNKNOWN | 23 | 195 | T |
| AI949344 | UNKNOWN | 18 | 15 | T |
| AI949344 | UNKNOWN | 14 | 0 | T |
| AI949348 | UNKNOWN | 33 | 0 | T |
| AI949371 | UNKNOWN | 15 | 0 | T |
| AI949384 | UNKNOWN | 15 | 136 | T |
| AI949435 | UNKNOWN | 15 | 230 | A |
| AI949450 | UNKNOWN | 19 | 0 | T |
| AI949465 | UNKNOWN | 14 | 0 | T |
| AI949498 | UNKNOWN | 38 | 0 | T |
| AI949498 | UNKNOWN | 12 | 88 | A |
| AI949510 | UNKNOWN | 86 | 0 | T |
| AI949510 | UNKNOWN | 25 | 287 | G |
| AI949510 | UNKNOWN | 21 | 137 | A |
| AI949510 | UNNNOWN | 12 | 216 | G |
| AI949512 | UNKNOWN | 58 | 0 | T |
| AI949606 | UNKNOWN | 12 | 0 | T |
| AI949637 | UNKNOWN | 12 | 8 | T |
| AI949638 | UNKNOWN | 12 | 328 | A |
| AI949645 | UNKNOWN | 33 | 0 | T |
| AI949650 | UNKNOWN | 3.66 | 405 | CTGTCC |
| AI949650 | UNKNOWN | 14 | 0 | T |
| AI949732 | UNKNOWN | 6.5 | 160 | TA |
| AI949756 | UNKNOWN | 21 | 0 | T |
| AI949775 | UNKNOWN | 22 | 180 | T |
| AI949775 | UNKNOWN | 17 | 222 | A |
| AI949799 | UNKNOWN | 12 | 0 | T |
| AI949833 | UNKNOWN | 14 | 0 | T |
| AI949916 | UNKNOWN | 17 | 0 | T |
| AI949940 | UNKNOWN | 12 | 0 | T |
| AI949941 | UNKNOWN | 14 | 0 | T |
| AI949960 | UNKNOWN | 90 | 0 | T |
| AI949960 | UNKNOWN | 22 | 289 | G |
| AI949960 | UNKNOWN | 13 | 105 | A |
| AI949983 | UNNNOWN | 16 | 510 | A |
| AI950007 | UNKNOWN | 13 | 3 | T |
| AI950094 | UNKNOWN | 15 | 0 | T |
| AI950099 | UNKNOWN | 46 | 0 | T |
| AI950100 | UNKNOWN | 51 | 0 | T |
| AI950106 | UNKNOWN | 13 | 405 | T |
| AI950205 | UNKNOWN | 12 | 0 | T |
| AI950300 | UNKNOWN | 15 | 0 | T |
| AI950302 | UNKNOWN | 13 | 0 | T |
| AI950306 | UNKNOWN | 16 | 0 | T |
| AI950319 | UNKNOWN | 15 | 0 | T |
| AI950337 | UNKNOWN | 9.5 | 148 | AC |
| AI950349 | UNKNOWN | 12 | 436 | T |
| AI950358 | UNKNOWN | 22 | 0 | T |
| AI950360 | UNKNOWN | 22 | 36 | T |
| AI950372 | UNKNOWN | 13 | 0 | T |
| AI950381 | UNKNOWN | 37 | 0 | T |
| AI950405 | UNKNOWN | 12 | 0 | T |
| AI950451 | UNKNOWN | 7.33 | 416 | TAA |
| AI950462 | UNKNOWN | 12 | 0 | T |
| AI950472 | UNKNOWN | 15 | 50 | T |
| AI950502 | UNKNOWN | 36 | 0 | T |
| AI950502 | UNKNOWN | 17 | 279 | A |
| AI950511 | UNKNOWN | 20 | 0 | T |
| AI950642 | UNKNOWN | 50 | 0 | T |
| AI950664 | UNKNOWN | 111 | 0 | T |
| AI950688 | UNKNOWN | 79 | 0 | T |
| AI950692 | UNKNOWN | 88 | 0 | T |
| AI950697 | UNKNOWN | 29 | 0 | T |
| AI950702 | UNKNOWN | 38 | 0 | T |
| AI950729 | UNKNOWN | 70 | 0 | T |
| AI950729 | UNKNOWN | 29 | 138 | C |
| AI950729 | UNKNOWN | 18 | 93 | A |
| AI950838 | UNKNOWN | 72 | 0 | T |
| AI950838 | UNKNOWN | 16 | 189 | A |
| AI950838 | UNKNOWN | 12 | 155 | A |

TABLE 1-continued

| Genbank # | Region | # reps | Position | Unit sequence |
|---|---|---|---|---|
| AI950856 | UNKNOWN | 42 | 0 | T |
| AI950862 | UNKNOWN | 65 | 0 | T |
| AI950862 | UNKNOWN | 12 | 204 | C |
| AI950862 | UNKNOWN | 12 | 341 | G |
| AI950865 | UNKNOWN | 75 | 0 | T |
| AI950865 | UNKNOWN | 19 | 129 | A |
| AI950865 | UNKNOWN | 12 | 103 | A |
| AI950877 | UNKNOWN | 80 | 0 | T |
| AI950877 | UNKNOWN | 15 | 101 | A |
| AI950877 | UNKNOWN | 13 | 201 | C |
| AI950877 | UNKNOWN | 12 | 265 | G |
| AI950892 | UNKNOWN | 88 | 8 | T |
| AI950892 | UNKNOWN | 15 | 160 | C |
| AI950895 | UNKNOWN | 61 | 2 | T |
| AI950911 | UNKNOWN | 26 | 0 | T |
| AI950934 | UNKNOWN | 18 | 255 | T |
| AI950973 | UNKNOWN | 60 | 0 | T |
| AI950973 | UNKNOWN | 12 | 202 | A |
| AI950983 | UNKNOWN | 22 | 293 | T |
| AI951062 | UNKNOWN | 63 | 0 | T |
| AI951062 | UNKNOWN | 13 | 113 | G |
| AI951076 | UNKNOWN | 81 | 0 | T |
| AI951076 | UNKNOWN | 19 | 164 | C |
| AI951076 | UNKNOWN | 15 | 303 | G |
| AI951076 | UNKNOWN | 12 | 110 | A |
| AI951076 | UNKNOWN | 12 | 137 | G |
| AI951123 | UNKNOWN | 49 | 0 | T |
| AI951123 | UNKNOWN | 12 | 337 | C |
| AI951149 | UNKNOWN | 60 | 0 | T |
| AI951158 | UNKNOWN | 32 | 14 | T |
| AI951161 | UNKNOWN | 19 | 0 | T |
| AI951163 | UNKNOWN | 37 | 0 | T |
| AI951198 | UNKNOWN | 32 | 0 | T |
| AI951198 | UNKNOWN | 12 | 84 | G |
| AI951203 | UNKNOWN | 29 | 0 | T |
| AI951222 | UNKNOWN | 58 | 0 | T |
| AI951287 | UNKNOWN | 20 | 0 | T |
| AI951335 | UNKNOWN | 46 | 0 | T |
| AI951356 | UNKNOWN | 18 | 424 | A |
| AI951373 | UNKNOWN | 63 | 0 | T |
| AI951373 | UNKNOWN | 13 | 131 | A |
| AI951435 | UNKNOWN | 48 | 0 | T |
| AI951444 | UNKNOWN | 47 | 0 | T |
| AI951446 | UNKNOWN | 64 | 0 | T |
| AI951446 | UNKNOWN | 17 | 138 | A |
| AI951516 | UNKNOWN | 56 | 0 | T |
| AI951562 | UNKNOWN | 12 | 71 | T |
| AI951683 | UNKNOWN | 18 | 293 | T |
| AI951740 | UNKNOWN | 6.66 | 3 | TTG |
| AI951752 | UNKNOWN | 14 | 0 | T |
| AI951805 | UNKNOWN | 77 | 0 | T |
| AI951805 | UNKNOWN | 15 | 236 | A |
| AI951805 | UNKNOWN | 14 | 77 | C |
| AI951805 | UNKNOWN | 13 | 167 | G |
| AI951805 | UNKNOWN | 12 | 113 | A |
| AI951868 | UNKNOWN | 75 | 0 | T |
| AI951868 | UNKNOWN | 20 | 124 | G |
| AI951868 | UNKNOWN | 18 | 79 | A |
| AI951868 | UNKNOWN | 15 | 234 | C |
| AI951868 | UNKNOWN | 13 | 162 | C |
| AI951950 | UNKNOWN | 74 | 0 | T |
| AI951950 | UNKNOWN | 12 | 76 | A |
| AI952064 | UNKNOWN | 76 | 0 | T |
| AI952064 | UNKNOWN | 16 | 134 | C |
| AI952077 | UNKNOWN | 49 | 0 | T |
| AI952114 | UNKNOWN | 126 | 0 | T |
| AI952114 | UNKNOWN | 20 | 337 | C |
| AI952114 | UNKNOWN | 15 | 134 | G |
| AI952114 | UNKNOWN | 14 | 308 | C |
| AI952114 | UNKNOWN | 13 | 173 | A |
| AI952114 | UNKNOWN | 12 | 202 | C |
| AI952145 | UNKNOWN | 79 | 0 | T |
| AI952145 | UNKNOWN | 19 | 279 | G |
| AI952145 | UNKNOWN | 17 | 126 | C |
| AI952172 | UNKNOWN | 12 | 404 | T |
| AI952182 | UNKNOWN | 13 | 180 | A |
| AI952183 | UNKNOWN | 12 | 392 | A |

TABLE 1-continued

| Genbank # | Region | # reps | Position | Unit sequence |
|---|---|---|---|---|
| AI952206 | UNKNOWN | 22 | 0 | T |
| AI952209 | UNKNOWN | 16 | 0 | T |
| AI952212 | UNKNOWN | 13 | 578 | A |
| AI952245 | UNKNOWN | 38 | 0 | T |
| AI952249 | UNKNOWN | 99 | 0 | T |
| AI952249 | UNKNOWN | 12 | 235 | A |
| AI952264 | UNKNOWN | 40 | 0 | T |
| AI952265 | UNKNOWN | 16 | 0 | T |
| AI952274 | UNKNOWN | 36 | 0 | T |
| AI952278 | UNKNOWN | 73 | 0 | T |
| AI952278 | UNKNOWN | 16 | 324 | G |
| AI952302 | UNKNOWN | 70 | 0 | T |
| AI952302 | UNKNOWN | 16 | 164 | A |
| AI952302 | UNKNOWN | 13 | 129 | C |
| AI952306 | UNKNOWN | 54 | 0 | T |
| AI952318 | UNKNOWN | 43 | 0 | T |
| AI952341 | UNKNOWN | 16 | 0 | T |
| AI952360 | UNKNOWN | 107 | 0 | T |
| AI952360 | UNKNOWN | 14 | 119 | A |
| AI952360 | UNKNOWN | 12 | 107 | G |
| AI952412 | UNKNOWN | 23 | 0 | T |
| AI952463 | UNKNOWN | 13 | 0 | T |
| AI952466 | UNKNOWN | 15 | 0 | T |
| AI952471 | UNKNOWN | 43 | 0 | T |
| AI952493 | UNKNOWN | 63 | 0 | T |
| AI952542 | UNKNOWN | 78 | 0 | T |
| AI952542 | UNKNOWN | 15 | 231 | A |
| AI952546 | UNKNOWN | 14 | 0 | T |
| AI952584 | UNKNOWN | 58 | 0 | T |
| AI952593 | UNKNOWN | 6.5 | 114 | AT |
| AI952593 | UNKNOWN | 42 | 0 | T |
| AI952593 | UNKNOWN | 20 | 339 | A |
| AI952628 | UNKNOWN | 16 | 0 | T |
| AI952638 | UNKNOWN | 13 | 350 | T |
| AI952641 | UNKNOWN | 44 | 0 | T |
| AI952645 | UNKNOWN | 43 | 0 | T |
| AI952645 | UNKNOWN | 12 | 135 | A |
| AI952653 | UNKNOWN | 27 | 0 | T |
| AI952677 | UNKNOWN | 31 | 0 | T |
| AI952677 | UNKNOWN | 14 | 173 | G |
| AI952687 | UNKNOWN | 45 | 0 | T |
| AI952717 | UNKNOWN | 3.5 | 188 | AAAACA |
| AI952752 | UNKNOWN | 33 | 0 | T |
| AI952761 | UNKNOWN | 79 | 0 | T |
| AI952761 | UNKNOWN | 15 | 386 | C |
| AI952761 | UNKNOWN | 14 | 98 | G |
| AI952761 | UNKNOWN | 13 | 373 | A |
| AI952783 | UNKNOWN | 42 | 0 | T |
| AI952790 | UNKNOWN | 20 | 0 | T |
| AI952813 | UNKNOWN | 13 | 0 | T |
| AI952900 | UNKNOWN | 13 | 0 | T |
| AI952914 | UNKNOWN | 63 | 0 | T |
| AI952914 | UNKNOWN | 12 | 272 | G |
| AI952920 | UNKNOWN | 79 | 0 | T |
| AI952920 | UNKNOWN | 15 | 202 | A |
| AI952999 | UNKNOWN | 6.5 | 148 | AT |
| AI953001 | UNKNOWN | 14 | 87 | T |
| AI953008 | UNKNOWN | 7 | 239 | AC |
| AI953087 | UNKNOWN | 25 | 244 | T |
| AI953169 | UNKNOWN | 14 | 166 | T |
| AI953201 | UNKNOWN | 18 | 1 | T |
| AI953205 | UNKNOWN | 7 | 220 | GT |
| AI953227 | UNKNOWN | 21 | 4 | T |
| AI953229 | UNKNOWN | 2.93 | 478 | GCCCTCCAACCGCCA (SEQ ID NO: 172) |
| AI953229 | UNKNOWN | 2.6 | 453 | CCAACCGCCTGCCCT (SEQ ID NO: 173) |
| AI953229 | UNKNOWN | 18 | 55 | T |
| AI953380 | UNKNOWN | 44 | 0 | T |
| AI953393 | UNKNOWN | 65 | 0 | T |
| AI953393 | UNKNOWN | 28 | 136 | A |
| AI953418 | UNKNOWN | 6.5 | 123 | TC |
| AI953418 | UNKNOWN | 15 | 11 | T |
| AI953438 | UNKNOWN | 73 | 0 | T |
| AI953481 | UNKNOWN | 6.5 | 141 | AC |
| AI953546 | UNKNOWN | 47 | 0 | T |
| AI953593 | UNKNOWN | 13 | 411 | A |
| AI953614 | UNKNOWN | 16 | 1 | T |
| AI953662 | UNKNOWN | 19 | 4 | T |

TABLE 1-continued

| Genbank # | Region | # reps | Position | Unit sequence |
|---|---|---|---|---|
| AI953677 | UNKNOWN | 12 | 5 | G |
| AI953704 | UNKNOWN | 19 | 0 | T |
| AI953730 | UNKNOWN | 2.92 | 123 | GCGGGGCGGGGCTC (SEQ ID NO: 174) |
| AI953761 | UNKNOWN | 7 | 350 | TC |
| AI953761 | UNKNOWN | 53 | 0 | T |
| AI953764 | UNKNOWN | 15 | 31 | T |
| AI953765 | UNKNOWN | 58 | 0 | T |
| AI953769 | UNKNOWN | 18 | 0 | T |
| AI953776 | UNKNOWN | 44 | 0 | T |
| AI953778 | UNKNOWN | 41 | 0 | T |
| AI953803 | UNKNOWN | 68 | 0 | T |
| AI953804 | UNKNOWN | 88 | 0 | T |
| AI953804 | UNKNOWN | 15 | 384 | G |
| AI953817 | UNKNOWN | 62 | 0 | T |
| AI953817 | UNKNOWN | 12 | 258 | G |
| AI953838 | UNKNOWN | 16 | 0 | T |
| AI953852 | UNKNOWN | 45 | 0 | T |
| AI953863 | UNKNOWN | 41 | 0 | T |
| AI953863 | UNKNOWN | 12 | 129 | A |
| AI953880 | UNKNOWN | 79 | 0 | T |
| AI953900 | UNKNOWN | 59 | 0 | T |
| AI953900 | UNKNOWN | 13 | 115 | G |
| AI954060 | UNKNOWN | 47 | 0 | T |
| AI954075 | UNKNOWN | 94 | 0 | T |
| AI954075 | UNKNOWN | 13 | 215 | A |
| AI954080 | UNKNOWN | 64 | 0 | T |
| AIS4080 | UNKNOWN | 14 | 191 | A |
| AI954095 | UNKNOWN | 64 | 0 | T |
| AI954112 | UNKNOWN | 3.8 | 270 | AAAAC |
| AI954130 | UNKNOWN | 85 | 0 | T |
| AIS4130 | UNKNOWN | 14 | 152 | C |
| AI954183 | UNKNOWN | 106 | 0 | T |
| AI954183 | UNKNOWN | 15 | 113 | A |
| AI954183 | UNKNOWN | 14 | 241 | G |
| AI954183 | UNKNOWN | 12 | 128 | C |
| AI954192 | UNKNOWN | 21 | 311 | T |
| AI954194 | UNKNOWN | 47 | 0 | T |
| AI954194 | UNKNOWN | 18 | 202 | G |
| AI954194 | UNKNOWN | 13 | 160 | A |
| AI954265 | UNKNOWN | 46 | 0 | T |
| AI954287 | UNKNOWN | 13 | 0 | T |
| AI954414 | UNKNOWN | 32 | 11 | T |
| AI954422 | UNKNOWN | 76 | 0 | T |
| AI954422 | UNKNOWN | 13 | 95 | A |
| AI954424 | UNKNOWN | 17 | 0 | T |
| AI954439 | UNKNOWN | 27 | 0 | T |
| AI954475 | UNKNOWN | 58 | 0 | T |
| AI954476 | UNKNOWN | 43 | 0 | T |
| AI954481 | UNKNOWN | 87 | 0 | T |
| AI954481 | UNKNOWN | 17 | 289 | A |
| AI954481 | UNKNOWN | 14 | 275 | C |
| AI954504 | UNKNOWN | 78 | 0 | T |
| AI954504 | UNKNOWN | 12 | 129 | A |
| AI954507 | UNKNOWN | 108 | 0 | T |
| AI954507 | UNKNOWN | 20 | 238 | C |
| AI954507 | UNKNOWN | 17 | 120 | G |
| AI954507 | UNKNOWN | 15 | 137 | A |
| AI954507 | UNKNOWN | 12 | 172 | C |
| AI954523 | UNKNOWN | 43 | 0 | T |
| AI954540 | UNKNOWN | 15 | 11 | T |
| AI954605 | UNKNOWN | 12 | 0 | T |
| AI954666 | UNKNOWN | 30 | 0 | T |
| AI954712 | UNKNOWN | 13 | 0 | T |
| AI954776 | UNKNOWN | 18 | 4 | T |
| AI954805 | UNNNOWN | 26 | 0 | T |
| AI954832 | UNKNOWN | 21 | 0 | T |
| AI954885 | UNKNOWN | 16 | 0 | T |
| AI954890 | UNKNOWN | 34 | 28 | T |
| AI954897 | UNKNOWN | 17 | 0 | T |
| AI954945 | UNKNOWN | 53 | 0 | T |
| AI954945 | UNKNOWN | 14 | 411 | A |
| AI954988 | UNKNOWN | 3.83 | 362 | ATATAC |
| AI954988 | UNKNOWN | 19.5 | 380 | AT |
| AI954988 | UNKNOWN | 13 | 220 | A |
| AI955025 | UNKNOWN | 51 | 0 | T |
| AI955117 | UNKNOWN | 71 | 0 | T |
| AI955117 | UNKNOWN | 20 | 238 | A |

TABLE 1-continued

| Genbank # | Region | # reps | Position | Unit sequence |
|---|---|---|---|---|
| AI955121 | UNKNOWN | 34 | 0 | T |
| AI955202 | UNKNOWN | 15 | 474 | A |
| AI955281 | UNKNOWN | 15 | 0 | T |
| AI955301 | UNKNOWN | 6.75 | 88 | AATA |
| AI955310 | UNKNOWN | 48 | 0 | T |
| AI955339 | UNKNOWN | 24 | 0 | T |
| AI955420 | UNKNOWN | 16 | 0 | T |
| AI955488 | UNKNOWN | 33 | 20 | T |
| AI955488 | UNKNOWN | 16 | 0 | T |
| AI955491 | UNKNOWN | 12 | 0 | T |
| AI955493 | UNKNOWN | 23 | 0 | T |
| AI955587 | UNKNOWN | 73 | 0 | T |
| AI955587 | UNKNOWN | 14 | 208 | G |
| AI955604 | UNKNOWN | 72 | 0 | T |
| AI955604 | UNKNOWN | 13 | 223 | A |
| AI955609 | UNKNOWN | 12 | 0 | T |
| AI955621 | UNKNOWN | 18 | 0 | T |
| AI955654 | UNKNOWN | 25 | 0 | T |
| AI955689 | UNKNOWN | 30 | 0 | T |
| AI955713 | UNKNOWN | 10.5 | 96 | AT |
| AI955832 | UNKNOWN | 12 | 0 | T |
| AI955849 | UNKNOWN | 19 | 0 | T |
| AI955849 | UNKNOWN | 16 | 65 | A |
| AI955859 | UNKNOWN | 59 | 0 | T |
| AI955859 | UNKNOWN | 19 | 97 | C |
| AI955866 | UNKNOWN | 84 | 0 | T |
| AI955866 | UNKNOWN | 22 | 141 | G |
| AI955866 | UNKNOWN | 17 | 106 | C |
| AI955869 | UNKNOWN | 41 | 0 | T |
| AI955899 | UNKNOWN | 61 | 0 | T |
| AI955906 | UNKNOWN | 93 | 0 | T |
| AI955906 | UNKNOWN | 16 | 125 | A |
| AI955917 | UNKNOWN | 98 | 0 | T |
| AI955943 | UNKNOWN | 67 | 0 | T |
| AI955945 | UNKNOWN | 63 | 0 | T |
| AI955987 | UNKNOWN | 86 | 0 | T |
| AI955987 | UNKNOWN | 24 | 168 | G |
| AI955987 | UNKNOWN | 12 | 204 | C |
| AI956004 | UNKNOWN | 45 | 0 | T |
| AI956063 | UNKNOWN | 35 | 0 | T |
| AI956063 | UNKNOWN | 12 | 251 | A |
| AI956066 | UNKNOWN | 38 | 0 | T |
| AI956080 | UNKNOWN | 84 | 0 | T |
| AI956080 | UNKNOWN | 14 | 84 | A |
| AI956080 | UNKNOWN | 12 | 398 | G |
| AI956086 | UNKNOWN | 81 | 0 | T |
| AI956100 | UNKNOWN | 24 | 13 | T |
| AI956108 | UNKNOWN | 21 | 0 | T |
| AI956141 | UNKNOWN | 48 | 0 | T |
| AI961027 | UNKNOWN | 14 | 155 | T |
| AI961029 | UNKNOWN | 4.75 | 124 | AAAC |
| AI961029 | UNKNOWN | 14 | 5 | T |
| AI961100 | UNKNOWN | 12 | 231 | A |
| AI961177 | UNKNOWN | 15 | 25 | T |
| AI961226 | UNKNOWN | 38 | 0 | T |
| AI961242 | UNKNOWN | 13 | 0 | T |
| AI961258 | UNKNOWN | 14 | 0 | T |
| AI961278 | UNKNOWN | 60 | 0 | T |
| AI961278 | UNKNOWN | 13 | 297 | A |
| AI961280 | UNKNOWN | 51 | 0 | T |
| AI961283 | UNKNOWN | 36 | 0 | T |
| AI961286 | UNKNOWN | 83 | 0 | T |
| AI961286 | UNKNOWN | 17 | 274 | G |
| AI961286 | UNKNOWN | 15 | 175 | A |
| AI961286 | UNKNOWN | 14 | 246 | G |
| AI961309 | UNKNOWN | 47 | 0 | T |
| AI961310 | UNKNOWN | 93 | 0 | T |
| AI961310 | UNKNOWN | 13 | 119 | C |
| AI961315 | UNKNOWN | 6.5 | 436 | TA |
| AI961350 | UNKNOWN | 39 | 0 | T |
| AI961390 | UNKNOWN | 7 | 152 | TA |
| AI961393 | UNKNOWN | 69 | 0 | T |
| AI961393 | UNKNOWN | 12 | 237 | C |
| AI961403 | UNKNOWN | 62 | 0 | T |
| AI961403 | UNKNOWN | 22 | 86 | A |
| AI961405 | UNKNOWN | 50 | 0 | T |
| AI961405 | UNKNOWN | 16 | 125 | G |

TABLE 1-continued

| Genbank # | Region | # reps | Position | Unit sequence |
|---|---|---|---|---|
| AI961414 | UNKNOWN | 66 | 0 | T |
| AI961414 | UNKNOWN | 14 | 124 | G |
| AI961414 | UNKNOWN | 14 | 187 | A |
| AI961561 | UNKNOWN | 23 | 0 | T |
| AI961587 | UNKNOWN | 57 | 0 | T |
| AI961589 | UNKNOWN | 72 | 0 | T |
| AI961589 | UNKNOWN | 17 | 131 | A |
| AI961589 | UNKNOWN | 13 | 148 | G |
| AI961599 | UNKNOWN | 55 | 0 | T |
| AI961631 | UNKNOWN | 53 | 0 | T |
| AI961631 | UNKNOWN | 17 | 229 | A |
| AI961799 | UNKNOWN | 22 | 0 | T |
| AI961808 | UNKNOWN | 43 | 0 | T |
| AI961818 | UNKNOWN | 12 | 1 | T |
| AI961835 | UNKNOWN | 19 | 0 | T |
| AI961838 | UNKNOWN | 3.13 | 138 | TATATATGTATACATATATGTG (SEQ ID NO: 175) |
| AI961838 | UNKNOWN | 7.5 | 302 | TA |
| AI961838 | UNKNOWN | 13 | 1 | T |
| AI961887 | UNKNOWN | 48 | 0 | T |
| AI961961 | UNKNOWN | 49 | 0 | T |
| AI961961 | UNKNOWN | 18 | 91 | A |
| AI961988 | UNKNOWN | 22 | 0 | T |
| AI962013 | UNKNOWN | 32 | 11 | T |
| AI962040 | UNKNOWN | 58 | 0 | T |
| AI962187 | UNKNOWN | 15 | 0 | T |
| AI962247 | UNKNOWN | 14 | 0 | T |
| AI962402 | UNKNOWN | 20 | 4 | T |
| AI962439 | UNKNOWN | 15 | 0 | T |
| AI962469 | UNKNOWN | 12 | 0 | T |
| AI962474 | UNKNOWN | 18 | 0 | T |
| AI962487 | UNKNOWN | 15 | 0 | T |
| AI962552 | UNKNOWN | 15 | 0 | T |
| AI962561 | UNKNOWN | 7 | 10 | CTG |
| AI962570 | UNKNOWN | 13 | 0 | T |
| AI962589 | UNKNOWN | 39 | 0 | T |
| AI962616 | UNKNOWN | 13 | 416 | A |
| AI962616 | UNKNOWN | 12 | 0 | T |
| AI962732 | UNKNOWN | 15 | 300 | A |
| AI962740 | UNKNOWN | 3.66 | 126 | TTTATT |
| AI962740 | UNKNOWN | 19 | 265 | T |
| AI962751 | UNKNOWN | 12 | 0 | T |
| AI962760 | UNKNOWN | 12 | 0 | T |
| AI962764 | UNKNOWN | 28 | 0 | T |
| AI962796 | UNKNOWN | 18 | 0 | T |
| AI962823 | UNKNOWN | 33 | 0 | T |
| AI962831 | UNKNOWN | 16 | 0 | T |
| AI962858 | UNKNOWN | 64 | 37 | T |
| AI962858 | UNKNOWN | 36 | 0 | T |
| AI962858 | UNKNOWN | 16 | 356 | G |
| AI962858 | UNKNOWN | 14 | 332 | C |
| AI962858 | UNKNOWN | 13 | 152 | A |
| AI962879 | UNKNOWN | 13 | 0 | T |
| AI962900 | UNKNOWN | 48 | 0 | T |
| AI962906 | UNKNOWN | 42 | 0 | T |
| AI962922 | UNKNOWN | 81 | 0 | T |
| AI962932 | UNKNOWN | 31 | 0 | T |
| AI962986 | UNKNOWN | 3.5 | 17 | TTTCTT |
| AI963009 | UNKNOWN | 19 | 0 | T |
| AI963019 | UNKNOWN | 66 | 0 | T |
| AI963019 | UNKNOWN | 18 | 149 | A |
| AI963038 | UNKNOWN | 60 | 0 | T |
| AI963038 | UNKNOWN | 13 | 191 | C |
| AI963038 | UNKNOWN | 12 | 103 | A |
| AI963038 | UNKNOWN | 12 | 204 | G |
| AI963040 | UNKNOWN | 81 | 0 | T |
| AI963042 | UNKNOWN | 34 | 0 | T |
| AI963051 | UNKNOWN | 70 | 0 | T |
| AI963051 | UNKNOWN | 14 | 286 | A |
| AI963051 | UNKNOWN | 12 | 191 | C |
| AI963053 | UNKNOWN | 52 | 0 | T |
| AI963053 | UNKNOWN | 13 | 391 | G |
| AI963058 | UNKNOWN | 75 | 0 | T |
| AI963058 | UNKNOWN | 20 | 211 | G |
| AI963058 | UNKNOWN | 14 | 193 | C |
| AI963062 | UNKNOWN | 88 | 0 | T |
| AI963062 | UNKNOWN | 14 | 327 | G |
| AI963062 | UNKNOWN | 12 | 180 | G |

TABLE 1-continued

| Genbank # | Region | # reps | Position | Unit sequence |
|---|---|---|---|---|
| AI963068 | UNKNOWN | 111 | 0 | T |
| AI963068 | UNKNOWN | 13 | 161 | A |
| AI963083 | UNKNOWN | 12 | 0 | T |
| AI963101 | UNKNOWN | 44 | 0 | T |
| AI963130 | UNKNOWN | 21 | 55 | T |
| AI963130 | UNKNOWN | 18 | 157 | G |
| AI963130 | UNKNOWN | 15 | 109 | G |
| AI963130 | UNKNOWN | 13 | 76 | A |
| AI963144 | UNKNOWN | 19 | 0 | T |
| AI963164 | UNKNOWN | 58 | 0 | T |
| AI963167 | UNKNOWN | 60 | 0 | T |
| AI963167 | UNKNOWN | 13 | 106 | G |
| AI963172 | UNKNOWN | 80 | 0 | T |
| AI963172 | UNKNOWN | 23 | 145 | C |
| AI963172 | UNKNOWN | 19 | 126 | A |
| AI963193 | UNKNOWN | 101 | 0 | T |
| AI963193 | UNKNOWN | 15 | 192 | G |
| AI963194 | UNKNOWN | 94 | 0 | T |
| AI963194 | UNKNOWN | 14 | 509 | G |
| AI963194 | UNKNOWN | 13 | 264 | G |
| AI963194 | UNKNOWN | 13 | 299 | C |
| AI963209 | UNKNOWN | 96 | 0 | T |
| AI963209 | UNKNOWN | 12 | 163 | A |
| AI963216 | UNKNOWN | 96 | 0 | T |
| AI963216 | UNKNOWN | 16 | 173 | A |
| AI963224 | UNKNOWN | 90 | 0 | T |
| AI963224 | UNKNOWN | 15 | 355 | G |
| AI963224 | UNKNOWN | 13 | 172 | A |
| AI963224 | UNKNOWN | 12 | 191 | C |
| AI963230 | UNKNOWN | 27 | 0 | T |
| AI963285 | UNKNOWN | 60 | 0 | T |
| AI963291 | UNKNOWN | 66 | 0 | T |
| AI963291 | UNKNOWN | 22 | 123 | G |
| AI963343 | UNKNOWN | 17 | 0 | T |
| AI963346 | UNKNOWN | 75 | 3 | T |
| AI963346 | UNKNOWN | 14 | 292 | A |
| AI963346 | UNKNOWN | 12 | 356 | G |
| AI963349 | UNKNOWN | 25 | 0 | T |
| AI963367 | UNKNOWN | 36 | 0 | T |
| AI963387 | UNKNOWN | 58 | 0 | T |
| AI963400 | UNKNOWN | 17 | 0 | T |
| AI963445 | UNKNOWN | 25 | 0 | T |
| AI963449 | UNKNOWN | 44 | 9 | T |
| AI963458 | UNKNOWN | 87 | 0 | T |
| AI963458 | UNKNOWN | 13 | 264 | G |
| AI963514 | UNKNOWN | 6.75 | 25 | TTTA |
| AI963514 | UNKNOWN | 14 | 0 | T |
| AI963524 | UNKNOWN | 14 | 0 | T |
| AI963564 | UNKNOWN | 45 | 0 | T |
| AI963564 | UNKNOWN | 20 | 95 | A |
| AI963615 | UNKNOWN | 52 | 0 | T |
| AI963615 | UNKNOWN | 16 | 95 | A |
| AI963617 | UNKNOWN | 66 | 0 | T |
| AI963617 | UNKNOWN | 18 | 163 | C |
| AI963625 | UNKNOWN | 68 | 0 | T |
| AI963625 | UNKNOWN | 19 | 103 | C |
| AI963625 | UNKNOWN | 13 | 256 | G |
| AI963631 | UNKNOWN | 64 | 0 | T |
| AI963631 | UNKNOWN | 19 | 123 | A |
| AI963631 | UNKNOWN | 12 | 84 | A |
| AI963639 | UNKNOWN | 45 | 0 | T |
| AI963655 | UNKNOWN | 38 | 0 | T |
| AI963668 | UNKNOWN | 79 | 0 | T |
| AI963668 | UNKNOWN | 17 | 234 | G |
| AI963690 | UNKNOWN | 68 | 0 | T |
| AI963714 | UNKNOWN | 16 | 401 | T |
| AI963757 | UNKNOWN | 13 | 0 | T |
| AI963763 | UNKNOWN | 77 | 0 | T |
| AI963769 | UNKNOWN | 21 | 0 | T |
| AI963776 | UNKNOWN | 4 | 293 | CTGGC |
| AI963785 | UNKNOWN | 25 | 11 | T |
| AI963794 | UNKNOWN | 52 | 0 | T |
| AI963808 | UNKNOWN | 22 | 11 | T |
| AI963811 | UNKNOWN | 36 | 0 | T |
| AI963835 | UNKNOWN | 36 | 0 | T |
| AI963835 | UNKNOWN | 18 | 361 | A |
| AI963912 | UNKNOWN | 22 | 0 | T |

TABLE 1-continued

| Genbank # | Region | # reps | Position | Unit sequence |
|---|---|---|---|---|
| AI963964 | UNKNOWN | 13 | 318 | T |
| AI963969 | UNKNOWN | 14 | 0 | T |
| AI963995 | UNKNOWN | 25 | 0 | T |
| AI964011 | UNKNOWN | 50 | 0 | T |
| AI964055 | UNKNOWN | 15 | 0 | T |
| AI964086 | UNKNOWN | 14 | 0 | T |
| AI967945 | UNKNOWN | 14 | 135 | T |
| AI967945 | UNKNOWN | 13 | 186 | A |
| AI968002 | UNKNOWN | 16 | 0 | T |
| AI968014 | UNKNOWN | 6 | 536 | GGC |
| AI968018 | UNKNOWN | 13 | 0 | T |
| AI968034 | UNKNOWN | 24 | 246 | T |
| AI968040 | UNKNOWN | 16 | 0 | T |
| AI968097 | UNKNOWN | 13 | 0 | T |
| AI968158 | UNKNOWN | 23 | 0 | T |
| AI968184 | UNKNOWN | 14 | 0 | T |
| AI968190 | UNKNOWN | 20 | 0 | T |
| AI968215 | UNKNOWN | 22 | 4 | T |
| AI968240 | UNKNOWN | 11 | 179 | GT |
| AI968241 | UNKNOWN | 12 | 0 | T |
| AI968309 | UNKNOWN | 5 | 27 | TTTC |
| AI968316 | UNKNOWN | 58 | 0 | T |
| AI968316 | UNKNOWN | 13 | 421 | A |
| AI968316 | UNKNOWN | 12 | 357 | A |
| AI968327 | UNKNOWN | 15 | 0 | T |
| AI968349 | UNKNOWN | 5.66 | 26 | TCT |
| AI968349 | UNKNOWN | 5.66 | 127 | GCC |
| AI968381 | UNKNOWN | 37 | 6 | T |
| AI968387 | UNKNOWN | 17 | 179 | A |
| AI968391 | UNKNOWN | 45 | 0 | T |
| AI968416 | UNKNOWN | 14 | 0 | T |
| AI968575 | UNKNOWN | 15 | 0 | T |
| AI968644 | UNKNOWN | 46 | 424 | C |
| AI968644 | UNKNOWN | 21 | 320 | C |
| AI968644 | UNKNOWN | 17 | 239 | C |
| AI968928 | UNKNOWN | 3.66 | 406 | CCCTGC |
| AI969014 | UNKNOWN | 54 | 0 | T |
| AI969173 | UNKNOWN | 3.6 | 304 | AAACA |
| AI969230 | UNKNOWN | 50 | 0 | T |
| AI969342 | UNKNOWN | 16 | 0 | T |
| AI969355 | UNKNOWN | 15 | 0 | T |
| AI969373 | UNKNOWN | 13 | 0 | T |
| AI969395 | UNKNOWN | 19 | 0 | T |
| AI969396 | UNKNOWN | 43 | 0 | T |
| AI969419 | UNKNOWN | 7.5 | 330 | TC |
| AI969419 | UNKNOWN | 21 | 354 | A |
| AI969419 | UNKNOWN | 18 | 0 | T |
| AI969420 | UNKNOWN | 31 | 0 | T |
| AI969435 | UNKNOWN | 7 | 253 | TC |
| AI969522 | UNKNOWN | 35 | 0 | T |
| AI969567 | UNKNOWN | 75 | 62 | T |
| AI969567 | UNKNOWN | 61 | 0 | T |
| AI969567 | UNKNOWN | 18 | 483 | G |
| AI969567 | UNKNOWN | 16 | 381 | A |
| AI969567 | UNKNOWN | 14 | 337 | C |
| AI969567 | UNKNOWN | 12 | 146 | A |
| AI969601 | UNKNOWN | 136 | 0 | T |
| AI969601 | UNKNOWN | 16 | 453 | A |
| AI969601 | UNKNOWN | 14 | 273 | A |
| AI969601 | UNKNOWN | 13 | 228 | A |
| AI969601 | UNKNOWN | 12 | 171 | A |
| AI969631 | UNKNOWN | 20 | 0 | T |
| AI969641 | UNKNOWN | 92 | 0 | T |
| AI969641 | UNKNOWN | 15 | 388 | G |
| AI969655 | UNKNOWN | 78 | 0 | T |
| AI969655 | UNKNOWN | 14 | 380 | G |
| AI969727 | UNKNOWN | 17 | 4 | T |
| AI969727 | UNKNOWN | 15 | 238 | A |
| AI970142 | UNKNOWN | 22 | 0 | T |
| AI970197 | UNKNOWN | 13 | 4 | T |
| AI970238 | UNKNOWN | 15 | 4 | T |
| AI970274 | UNKNOWN | 44 | 0 | T |
| AI970298 | UNKNOWN | 42 | 0 | T |
| AI970305 | UNKNOWN | 5.66 | 457 | GAG |
| AI970336 | UNKNOWN | 28 | 16 | T |
| AI970387 | UNKNOWN | 26 | 0 | T |
| AI970392 | UNKNOWN | 13 | 0 | T |

TABLE 1-continued

| Genbank # | Region | # reps | Position | Unit sequence |
|---|---|---|---|---|
| AI970401 | UNKNOWN | 30 | 0 | T |
| AI970415 | UNKNOWN | 15 | 307 | T |
| AI970464 | UNKNOWN | 5.5 | 499 | ACAA |
| AI970472 | UNKNOWN | 12 | 0 | T |
| AI970475 | UNKNOWN | 18 | 4 | T |
| AI970491 | UNKNOWN | 14 | 50 | T |
| AT970520 | UNKNOWN | 36 | 0 | T |
| AI970797 | UNKNOWN | 15 | 0 | T |
| AI970831 | UNKNOWN | 17 | 0 | T |
| AI970860 | UNKNOWN | 48 | 0 | T |
| AI970883 | UNKNOWN | 41 | 0 | T |
| AI970896 | UNKNOWN | 15 | 0 | T |
| AI970952 | UNKNOWN | 16 | 6 | T |
| AI970952 | UNKNOWN | 13 | 43 | A |
| AI971025 | UNKNOWN | 16.75 | 188 | GAAG |
| AI971025 | UNKNOWN | 17 | 0 | T |
| AI971029 | UNKNOWN | 7 | 58 | TAA |
| AI971180 | UNKNOWN | 13 | 0 | T |
| AI971194 | UNKNOWN | 15 | 0 | T |
| AI971203 | UNKNOWN | 12 | 66 | A |
| AI971290 | UNKNOWN | 15 | 0 | T |
| AI971301 | UNKNOWN | 24 | 0 | T |
| AI971310 | UNKNOWN | 15 | 0 | T |
| AI971314 | UNKNOWN | 40 | 0 | T |
| AI971367 | UNKNOWN | 13 | 58 | A |
| AI971557 | UNKNOWN | 13 | 62 | A |
| AI971563 | UNKNOWN | 24 | 0 | T |
| AI971615 | UNKNOWN | 74 | 0 | T |
| AI971885 | UNKNOWN | 7.33 | 372 | CCT |
| AI971954 | UNKNOWN | 6.5 | 87 | AATG |
| AI971965 | UNKNOWN | 25 | 5 | T |
| AI972029 | UNKNOWN | 8.5 | 220 | AGGG |
| AI972070 | UNKNOWN | 53 | 0 | T |
| AI972074 | UNKNOWN | 77 | 0 | T |
| AI972074 | UNKNOWN | 12 | 135 | A |
| AI972079 | UNKNOWN | 14 | 0 | T |
| AI972094 | UNKNOWN | 18 | 126 | T |
| AI972104 | UNKNOWN | 18 | 11 | T |
| AI972108 | UNKNOWN | 41 | 0 | T |
| AI972108 | UNKNOWN | 17 | 331 | G |
| AI972109 | UNKNOWN | 67 | 0 | T |
| AI972112 | UNKNOWN | 65 | 0 | T |
| AI972112 | UNKNOWN | 12 | 106 | A |
| AI972118 | UNKNOWN | 33 | 0 | T |
| AI972118 | UNKNOWN | 12 | 310 | G |
| AI972131 | UNKNOWN | 48 | 0 | T |
| AI972131 | UNKNOWN | 20 | 69 | A |
| AI972155 | UNKNOWN | 77 | 0 | T |
| AI972170 | UNKNOWN | 51 | 0 | T |
| AI972170 | UNKNOWN | 14 | 139 | G |
| AI972270 | UNKNOWN | 12 | 18 | T |
| AI972342 | UNKNOWN | 5.66 | 112 | TTG |
| AI972342 | UNKNOWN | 16 | 0 | T |
| AI972368 | UNKNOWN | 14 | 0 | T |
| AI972395 | UNKNOWN | 16 | 188 | T |
| AI972433 | UNKNOWN | 18 | 0 | T |
| AI972460 | UNKNOWN | 18 | 0 | T |
| AI972461 | UNKNOWN | 14 | 442 | A |
| AI972473 | UNKNOWN | 46 | 0 | T |
| AI972479 | UNKNOWN | 25 | 0 | T |
| AI972497 | UNKNOWN | 43 | 0 | T |
| AI972511 | UNKNOWN | 13 | 129 | T |
| AI972580 | UNKNOWN | 22 | 0 | T |
| AI972623 | UNKNOWN | 8 | 370 | AC |
| AI972643 | UNKNOWN | 45 | 0 | T |
| AI972652 | UNKNOWN | 10.5 | 0 | CTTT |
| AI972652 | UNKNOWN | 5.75 | 39 | TCTA |
| AI972712 | UNKNOWN | 4.5 | 381 | TGTT |
| AI972722 | UNKNOWN | 40 | 0 | T |
| AI972779 | UNKNOWN | 12 | 47 | A |
| AI972779 | UNKNOWN | 12 | 385 | T |
| AI972789 | UNKNOWN | 14 | 177 | T |
| AI972798 | UNKNOWN | 18 | 0 | T |
| AI972836 | UNKNOWN | 16 | 0 | T |
| AI972845 | UNKNOWN | 9 | 160 | TA |
| AI972845 | UNKNOWN | 6.5 | 326 | TG |
| AI972846 | UNKNOWN | 6.5 | 276 | TG |

TABLE 1-continued

| Genbank # | Region | # reps | Position | Unit sequence |
|---|---|---|---|---|
| AI972903 | UNKNOWN | 21 | 0 | T |
| AI972905 | UNKNOWN | 18 | 0 | T |
| AI972919 | UNKNOWN | 39 | 0 | T |
| AI972944 | UNKNOWN | 59 | 0 | T |
| AI972944 | UNKNOWN | 15 | 164 | A |
| AI972944 | UNKNOWN | 12 | 231 | G |
| AI972953 | UNKNOWN | 15 | 0 | T |
| AI972964 | UNKNOWN | 19 | 0 | T |
| AI972981 | UNKNOWN | 15 | 0 | T |
| AI972985 | UNKNOWN | 44 | 0 | T |
| AI973021 | UNKNOWN | 35 | 0 | T |
| AI973021 | UNKNOWN | 14 | 324 | G |
| AI973076 | UNKNOWN | 41 | 0 | T |
| AI973088 | UNKNOWN | 14 | 0 | T |
| AI973104 | UNKNOWN | 46 | 0 | T |
| AI973104 | UNKNOWN | 22 | 112 | G |
| AI973104 | UNKNOWN | 14 | 78 | A |
| AI973110 | UNKNOWN | 21 | 0 | T |
| AI973128 | UNKNOWN | 19 | 0 | T |
| AI973152 | UNKNOWN | 78 | 0 | T |
| AI973152 | UNKNOWN | 17 | 213 | C |
| AI973152 | UNKNOWN | 16 | 295 | A |
| AI973152 | UNKNOWN | 12 | 129 | C |
| AI973230 | UNKNOWN | 16 | 0 | T |
| AI973234 | UNKNOWN | 48 | 0 | T |
| AI973236 | UNKNOWN | 57 | 0 | T |
| AI973272 | UNKNOWN | 56 | 0 | T |
| AI973288 | UNKNOWN | 75 | 0 | T |
| AI978604 | UNKNGWN | 12 | 217 | G |
| AI978606 | UNKNOWN | 15 | 10 | T |
| AI978626 | UNKNOWN | 14 | 162 | A |
| AI978654 | UNKNOWN | 5.66 | 124 | ATT |
| AI978677 | UNKNOWN | 6 | 382 | TGC |
| AI978703 | UNKNOWN | 95 | 0 | T |
| AI978703 | UNKNOWN | 23 | 114 | A |
| AI978720 | UNKNOWN | 54 | 0 | T |
| AI978720 | UNKNOWN | 21 | 226 | A |
| AI978720 | UNKNOWN | 15 | 123 | A |
| AI978720 | UNKNOWN | 13 | 70 | A |
| AI978753 | UNKNOWN | 20 | 0 | T |
| AI978941 | UNKNOWN | 14 | 0 | T |
| AI978945 | UNKNOWN | 23 | 145 | C |
| AI978958 | UNKNOWN | 25 | 0 | T |
| AI978958 | UNKNOWN | 12 | 182 | A |
| AI978979 | UNKNOWN | 26 | 0 | T |
| AI979129 | UNKNOWN | 57 | 0 | T |
| AI979129 | UNKNOWN | 17 | 342 | A |
| AI979134 | UNKNOWN | 14 | 0 | T |
| AI979145 | UNKNOWN | 22 | 0 | T |
| AI979165 | UNKNOWN | 13 | 234 | G |
| AI979221 | UNKNOWN | 38 | 0 | T |
| AI979221 | UNKNOWN | 14 | 85 | A |
| AI979288 | UNKNOWN | 16 | 516 | A |
| AI979338 | UNKNOWN | 13 | 140 | T |
| AI982547 | UNKNOWN | 16 | 267 | A |
| AI982590 | UNKNOWN | 17 | 1 | T |
| AI982607 | UNKNOWN | 22 | 0 | T |
| AI982648 | UNKNOWN | 48 | 0 | T |
| AI982648 | UNKNOWN | 13 | 109 | C |
| AI982723 | UNKNOWN | 14 | 0 | T |
| AI982736 | UNKNOWN | 12 | 293 | T |
| AI982766 | UNKNOWN | 14.5 | 224 | AC |
| AI983188 | UNKNOWN | 15 | 0 | T |
| AI983207 | UNKNOWN | 5 | 45 | CCAG |
| AI983332 | UNKNOWN | 14 | 0 | T |
| AI983334 | UNKNOWN | 3.8 | 58 | AAAGG |
| AI983352 | UNKNOWN | 12 | 17 | A |
| AI983359 | UNKNOWN | 18 | 0 | T |
| AI983457 | UNKNOWN | 57 | 0 | T |
| AI983457 | UNKNOWN | 13 | 226 | C |
| AI983478 | UNKNOWN | 12 | 9 | T |
| AI983634 | UNKNOWN | 20 | 0 | T |
| AI983634 | UNKNOWN | 17 | 62 | C |
| AI983634 | UNKNOWN | 14 | 36 | A |
| AI983642 | UNKNOWN | 13 | 355 | C |
| AI983789 | UNKNOWN | 27 | 0 | T |
| AI983789 | UNKNOWN | 20 | 67 | A |

TABLE 1-continued

| Genbank # | Region | # reps | Position | Unit sequence |
|---|---|---|---|---|
| AI983850 | UNKNOWN | 15 | 410 | T |
| AI983850 | UNKNOWN | 12 | 197 | A |
| AI983870 | UNKNOWN | 12 | 0 | T |
| AI983889 | UNKNOWN | 18 | 0 | T |
| AI983889 | UNKNOWN | 18 | 261 | A |
| AI983915 | UNKNOWN | 19 | 316 | G |
| AI983915 | UNKNOWN | 16 | 102 | A |
| AI983921 | UNKNOWN | 12 | 0 | T |
| AI983937 | UNKNOWN | 21 | 0 | T |
| AI984034 | UNKNOWN | 16 | 0 | T |
| AI984144 | UNKNOWN | 14 | 0 | T |
| AI984176 | UNKNOWN | 29 | 11 | T |
| AI984180 | UNKNOWN | 15 | 11 | T |
| AI984197 | UNKNOWN | 15 | 11 | T |
| AI984203 | UNKNOWN | 8.5 | 343 | CA |
| AI984203 | UNKNOWN | 21 | 3 | T |
| AI984205 | UNKNOWN | 13 | 40 | A |
| AI984205 | UNKNOWN | 13 | 69 | C |
| AI984253 | UNKNOWN | 24 | 0 | T |
| AI984253 | UNKNOWN | 14 | 231 | A |
| AI984368 | UNKNOWN | 19 | 0 | T |
| AI984378 | UNKNOWN | 15 | 0 | T |
| AI984472 | UNKNOWN | 15 | 0 | T |
| AI984480 | UNKNOWN | 21 | 240 | T |
| AI984495 | UNKNOWN | 22 | 127 | C |
| AI984495 | UNKNOWN | 18 | 162 | A |
| AI984710 | UNKNOWN | 22 | 29 | C |
| AI985104 | UNKNOWN | 14 | 0 | T |
| AI985115 | UNKNOWN | 12 | 0 | T |
| AI985120 | UNKNOWN | 13 | 0 | T |
| AI985161 | UNKNOWN | 18 | 315 | A |
| AI985251 | UNKNOWN | 18 | 0 | T |
| AI985274 | UNKNOWN | 14 | 166 | T |
| AI985407 | UNKNOWN | 18 | 0 | T |
| AI985432 | UNKNOWN | 12 | 0 | T |
| AI985534 | UNKNOWN | 22 | 0 | T |
| AI985592 | UNKNOWN | 6.25 | 293 | TCAT |
| AI985654 | UNKNOWN | 13 | 60 | A |
| AI985677 | UNKNOWN | 5.5 | 68 | TGAA |
| AI985688 | UNKNOWN | 13 | 134 | A |
| AI985708 | UNKNOWN | 7.5 | 0 | TG |
| AI985753 | UNKNOWN | 14 | 0 | T |
| AI985759 | UNKNOWN | 12 | 0 | T |
| AI985836 | UNKNOWN | 19 | 0 | T |
| AI985906 | UNKNOWN | 25 | 0 | T |
| AI985906 | UNKNOWN | 22 | 34 | A |
| AI985906 | UNKNOWN | 17 | 183 | G |
| AI985906 | UNKNOWN | 16 | 98 | C |
| AI985906 | UNKNOWN | 12 | 56 | G |
| AI985983 | UNKNOWN | 43 | 0 | T |
| AI985983 | UNKNOWN | 19 | 134 | A |
| AI985987 | UNKNOWN | 16 | 0 | T |
| AI985996 | UNKNOWN | 7 | 289 | TG |
| AI986023 | UNKNOWN | 6.33 | 387 | TCC |
| AI986102 | UNKNOWN | 16 | 377 | T |
| AI986157 | UNKNOWN | 9.8 | 134 | AATAT |
| AI986157 | UNKNOWN | 22 | 0 | T |
| AI986165 | UNKNOWN | 15 | 5 | T |
| AI986165 | UNKNOWN | 14 | 466 | A |
| AI986175 | UNKNOWN | 13 | 72 | C |
| AI986182 | UNKNOWn | 9.75 | 194 | ATAC |
| AI986182 | UNKNOWN | 9.5 | 230 | AT |
| AI986182 | UNKNOWN | 16 | 0 | T |
| AI986194 | UNKNOWN | 12 | 186 | T |
| AI986195 | UNKNOWN | 13 | 305 | A |
| AI986197 | UNKNOWN | 13 | 0 | T |
| AI986201 | UNKNOWN | 15 | 0 | T |
| AI986300 | UNKNOWN | 20 | 0 | T |
| AI986323 | UNKNOWN | 24 | 0 | T |
| AI986356 | UNKNOWN | 17 | 171 | A |
| AI986356 | UNKNOWN | 16 | 0 | T |
| AI986393 | UNKNOWN | 41 | 0 | T |
| AI986393 | UNKNOWN | 24 | 365 | A |
| AI986413 | UNKNOWN | 13 | 46 | G |
| AI986413 | UNKNOWN | 13 | 62 | A |
| AI986424 | UNKNOWN | 20 | 0 | T |
| AI989364 | UNKNOWN | 3.8 | 18 | TTTTG |

TABLE 1-continued

| Genbank # | Region | # reps | Position | Unit sequence |
|---|---|---|---|---|
| AI989419 | UNKNOWN | 12 | 0 | T |
| AI989490 | UNKNOWN | 13 | 322 | A |
| AI989552 | UNKNOWN | 18 | 4 | T |
| AI989600 | UNKNOWN | 21 | 0 | T |
| AI989677 | UNKNOWN | 12 | 0 | T |
| AI989709 | UNKNOWN | 18 | 4 | T |
| AI989716 | UNKNOWN | 5 | 555 | CATT |
| AI989716 | UNKNOWN | 12 | 0 | T |
| AI989772 | UNKNOWN | 3.5 | 24 | TTTATT |
| AI989776 | UNKNOWN | 12 | 0 | T |
| AI989781 | UNKNOWN | 19 | 0 | T |
| AI989803 | UNKNOWN | 21 | 0 | T |
| AI989828 | UNKNOWN | 20 | 0 | T |
| AI989906 | UNKNOWN | 14 | 0 | T |
| AI989941 | UNKNOWN | 39 | 0 | T |
| AI989941 | UNKNOWN | 20 | 272 | A |
| AI989955 | UNKNOWN | 13 | 0 | T |
| AI990020 | UNKNOWN | 15 | 0 | T |
| AI990027 | UNKNOWN | 4.5 | 533 | AGCC |
| AI990036 | UNKNOWN | 20 | 35 | T |
| AI990071 | UNKNOWN | 14 | 202 | T |
| AI990084 | UNKNOWN | 18 | 0 | T |
| AI990107 | UNKNOWN | 14 | 124 | A |
| AI990110 | UNKNOWN | 13 | 0 | T |
| AI990114 | UNKNOWN | 12 | 0 | T |
| AI990151 | UNKNOWN | 12 | 0 | T |
| AI990274 | UNKNOWN | 20 | 0 | T |
| AI990290 | UNKNOWN | 13 | 0 | T |
| AI990291 | UNKNOWN | 15 | 0 | T |
| AI990292 | UNKNOWN | 21 | 0 | T |
| AI990312 | UNKNOWN | 13 | 0 | T |
| AI990370 | UNKNOWN | 2.88 | 460 | GCACATAGTACATGTTC (SEQ ID NO: 176) |
| AI990489 | UNKNOWN | 19 | 0 | T |
| AI990507 | UNKNOWN | 16 | 0 | T |
| AI990593 | UNKNOWN | 15 | 0 | T |
| AI990610 | UNKNOWN | 6.5 | 174 | TA |
| AI990638 | UNKNOWN | 8 | 243 | AC |
| AI990747 | UNKNOWN | 12 | 0 | T |
| AI990790 | UNKNOWN | 18 | 0 | T |
| AI990847 | UNKNOWN | 12 | 0 | T |
| AI990862 | UNKNOWN | 2.55 | 137 | TTTCATTTCTCTTAGGGA (SEQ ID NO: 177) |
| AI990939 | UNKNOWN | 2.68 | 399 | CCCTCCGTGTCCCCCATGT (SEQ ID NO: 178) |
| AI991155 | UNKNOWN | 13 | 134 | C |
| AI991158 | UNKNOWN | 6.25 | 407 | AACC |
| AI991451 | UNKNOWN | 6.5 | 487 | AG |
| AI991581 | UNKNOWN | 13 | 0 | T |
| AI991661 | UNKNOWN | 17 | 0 | T |
| AI991726 | UNKNOWN | 43 | 0 | T |
| AI991952 | UNKNOWN | 19 | 0 | T |
| AI992058 | UNKNOWN | 19 | 1 | T |
| AI992077 | UNKNOWN | 12 | 0 | T |
| AI992176 | UNKNOWN | 22 | 0 | T |
| AI992191 | UNKNOWN | 5.66 | 151 | GGC |
| AI992210 | UNKNOWN | 16 | 0 | T |
| AI992275 | UNKNOWN | 14 | 0 | T |
| AI992286 | UNKNOWN | 18 | 0 | T |
| AJ000041 | 3' UTR | 15 | 1692 | T |
| AJ000098 | 5' UTR | 23 | 52 | A |
| AJ000099 | 3' UTR | 5.66 | 1784 | TTA |
| AJ000388 | 5' UTR | 12.33 | 111 | GCA |
| AJ000388 | 3' UTR | 6.66 | 2635 | ACC |
| AJ000503 | 5' UTR | 7 | 366 | AG |
| AJ000517 | CDS | 10.66 | 647 | GCA |
| AJ001019 | 5' UTR | 13 | 59 | T |
| AJ001183 | 5' UTR | 5.66 | 93 | GCG |
| AJ001189 | 3' UTR | 2.63 | 6822 | TTTTTTTTTCT (SEQ ID NO: 179) |
| AJ001340 | CDS | 7 | 223 | GAG |
| AJ001383 | 3' UTR | 23 | 1184 | A |
| AJ001383 | 3' UTR | 15 | 1138 | T |
| AJ001402 | CDS | 2.6 | 569 | CTCTGTGGCATCCAG (SEQ ID NO: 180) |
| AJ001625 | 3' UTR | 7.5 | 1490 | AT |
| AJ001696 | 3' UTR | 17 | 2031 | T |
| AJ003112 | 3' UTR | 13.5 | 4217 | AC |
| AJ003112 | 3' UTR | 9 | 3177 | TG |
| AJ003112 | 3' UTR | 7 | 3139 | TG |
| AJ003112 | 3' UTR | 18 | 6411 | T |
| AJ003112 | 3' UTR | 14 | 2555 | A |

TABLE 1-continued

| Genbank # | Region | # reps | Position | Unit sequence |
|---|---|---|---|---|
| AJ003125 | CDS | 8.66 | 44 | GCT |
| AJ003125 | CDS | 6 | 83 | GCC |
| AJ005579 | CDS | 7.5 | 267 | GA |
| AJ005670 | 5' UTR | 6.66 | 19 | GCG |
| AJ005670 | 5' UTR | 6.33 | 91 | GCA |
| AJ005670 | 3' UTR | 14 | 1945 | A |
| AJ005698 | 3' UTR | 20 | 2749 | TG |
| AJ005814 | 3' UTR | 17 | 881 | A |
| AJ006266 | CDS | 5.66 | 2529 | GAA |
| AJ006973 | 3' UTR | 5.25 | 1820 | GGCT |
| AJ007395 | CDS | 7 | 65 | TGC |
| AJ007509 | 3' UTR | 12 | 3217 | A |
| AJ007590 | 3' UTR | 8.33 | 2919 | TAT |
| AJ009936 | UNKNOWN | 30 | 4418 | A |
| AJ010014 | 3' UTR | 15 | 2117 | A |
| AJ010230 | UNKNOWN | 21 | 3929 | A |
| AJ010277 | 3' UTR | 6 | 2316 | AAAG |
| AJ010901 | 3' UTR | 10.5 | 3735 | CA |
| AJ011679 | 3' UTR | 31.5 | 3694 | AT |
| AJ011679 | 3' UTR | 19.5 | 4085 | TG |
| AJ012370 | 3' UTR | 12 | 2415 | T |
| AJ012506 | UNKNOWN | 35 | 1261 | A |
| AJ012582 | CDS | 7 | 115 | GCC |
| AJ012582 | 5' UTR | 6.33 | 3 | CGG |
| AJ130978 | CDS | 5.66 | 216 | GAA |
| AJ131693 | 5' UTR | 5.66 | 6 | GGC |
| AJ131730 | UNKNOWN | 18.5 | 993 | AC |
| AJ132583 | 3' UTR | 13 | 3219 | T |
| AJ133355 | CDS | 7.33 | 309 | GAT |
| AJ223321 | 3' UTR | 7.5 | 2111 | AT |
| AJ224874 | CDS | 3.88 | 2468 | GAGGAAGAA |
| AJ224874 | CDS | 7 | 2452 | GGA |
| AJ224979 | CDS | 7 | 3 | CGG |
| AJ224979 | 3' UTR | 4.5 | 2427 | TAAG |
| AJ225109 | 5' UTR | 18 | 36 | T |
| AJ228139 | CDS | 2.5 | 2527 | AGGAGCAATACAGGAGAA (SEQ ID NO: 181) |
| AJ230787 | UNKNOWN | 5.66 | 33 | AAC |
| AJ230790 | UNKNOWN | 3.8 | 429 | CAGGC |
| AJ236885 | BORDER | 15 | 2774 | A |
| AJ237724 | CDS | 6 | 39 | GGC |
| AJ237724 | 3' UTR | 17 | 3672 | T |
| AJ237724 | 3' UTR | 13 | 3738 | A |
| AJ239394 | UNKNOWN | 15 | 317 | A |
| AJ239434 | UNKNOWN | 16 | 175 | A |
| AJ239446 | UNKNOWN | 24 | 459 | A |
| AJ239466 | UNKNOWN | 16 | 531 | A |
| AJ243425 | CDS | 6.66 | 514 | CAG |
| AJ243425 | CDS | 6.33 | 463 | CAG |
| AJ243425 | 3' UTR | 16 | 2417 | A |
| AJ243425 | 3' UTR | 12 | 2617 | T |
| AJ243721 | 3' UTR | 12 | 1161 | T |
| AJ243874 | 3' UTR | 22 | 3109 | A |
| AJ243936 | 3' UTR | 7.66 | 1069 | AAT |
| AJ245433 | 3' UTR | 15 | 1950 | A |
| AJ245433 | 3' UTR | 14 | 1915 | T |
| AJ249732 | 5' UTR | 14 | 1 | T |
| AJ249921 | UNKNOWN | 13 | 147 | T |
| AL008583 | 5' UTR | 5.83 | 20 | GCTCCG |
| AL008583 | 3' UTR | 2.6 | 5692 | TGTGTGCGTG (SEQ ID NO: 182) |
| AL008583 | 3' UTR | 8 | 5709 | GT |
| AL008583 | 3' UTR | 27 | 4931 | T |
| AL008583 | 3' UTR | 12 | 2190 | C |
| AL008726 | CDS | 8.66 | 163 | CTG |
| AL009172 | 5' UTR | 6 | 756 | CCA |
| AL009172 | 5' UTR | 19 | 3412 | A |
| AL009172 | 5' UTR | 12 | 746 | C |
| AL009183 | 3' UTR | 15 | 1067 | T |
| AL009266 | 3' UTR | 4.75 | 1366 | AAAC |
| AL009266 | 3' UTR | 15 | 1524 | A |
| AL021155 | 5' UTR | 7.33 | 173 | GCA |
| AL021331 | 3' UTR | 14 | 1157 | T |
| AL021366 | 3' UTR | 26.5 | 2202 | TG |
| AL021546 | 3' UTR | 12 | 825 | T |
| AL021938 | 3' UTR | 8.5 | 4134 | CA |
| AL021938 | 3' UTR | 20 | 4516 | A |
| AL021938 | 3' UTR | 13 | 3999 | T |
| AL022310 | 3' UTR | 10.5 | 2481 | TG |

TABLE 1-continued

| Genbank # | Region | # reps | Position | Unit sequence |
|---|---|---|---|---|
| AL022312 | 5' UTR | 19 | 314 | T |
| AL022312 | 3' UTR | 5 | 5103 | GTCT |
| AL022326 | 3' UTR | 7 | 4202 | TG |
| AL022328 | 3' UTR | 4.5 | 1989 | GGGT |
| AL022329 | 5' UTR | 5.66 | 27 | CCG |
| AL022394 | 3' UTR | 8 | 4862 | TA |
| AL022394 | 3' UTR | 16 | 8414 | A |
| AL022718 | 3' UTR | 5.8 | 7827 | AAAAC |
| AL022726 | CDS | 6.66 | 488 | GCG |
| AL023282 | 3' UTR | 17 | 2549 | T |
| AL023282 | 3' UTR | 13 | 2812 | A |
| AL031177 | 3' UTR | 4.59 | 1342 | AAAAC |
| AL031178 | 3' UTR | 24.5 | 1783 | TA |
| AL031228 | CDS | 6.33 | 310 | GCG |
| AL031282 | CDS | 9.33 | 1350 | GAG |
| AL031588 | 3' UTR | 13 | 2495 | A |
| AL031652 | 3' UTR | 3.6 | 3765 | ATCAA |
| AL031652 | 3' UTR | 16 | 774 | A |
| AL031670 | 5' UTR | 6.5 | 70 | CA |
| AL031670 | 3' UTR | 24 | 1674 | A |
| AL031681 | 3' UTR | 37 | 1683 | T |
| AL031685 | 3' UTR | 4.59 | 2075 | GTTTT |
| AL031685 | 3' UTR | 25 | 3460 | AT |
| AL031687 | CDS | 6.33 | 461 | CTG |
| AL031775 | 3' UTR | 6 | 1053 | GTTTT |
| AL031775 | 3' UTR | 13 | 1311 | T |
| AL031778 | 3' UTR | 7 | 2195 | AG |
| AL031778 | 3' UTR | 14 | 3525 | T |
| AL031846 | 5' UTR | 3.6 | 46 | CCCGG |
| AL033538 | 3' UTR | 37 | 2891 | A |
| AL033538 | 3' UTR | 15 | 4664 | T |
| AL033543 | 3' UTR | 5.75 | 412 | TTTG |
| AL034396 | CDS | 5.66 | 42 | GGC |
| AL034562 | 3' UTR | 10.33 | 1491 | CCA |
| AL034562 | 3' UTR | 7.33 | 1253 | GCA |
| AL035289 | 3' UTR | 10 | 2538 | AC |
| AL035305 | 3' UTR | 21 | 1831 | A |
| AL035306 | 3' UTR | 7.66 | 1725 | TTG |
| AL035364 | 5' UTR | 6.5 | 42 | AG |
| AL035403 | CDS | 3.5 | 160 | GCTCCT |
| AL035424 | 3' UTR | 13 | 2767 | A |
| AL035461 | 3' UTR | 22.5 | 1909 | AC |
| AL035461 | 3' UTR | 18 | 2165 | A |
| AL035562 | 3' UTR | 3.6 | 2552 | AAAAC |
| AL035562 | 3' UTR | 5.66 | 2568 | AAC |
| AL035588 | CDS | 7 | 123 | GCA |
| AL035593 | 3' UTR | 21 | 991 | A |
| AL035604 | CDS | 5.66 | 614 | AGG |
| AL035683 | 3' UTR | 2.81 | 1385 | CTGCCGTGGTC (SEQ ID NO: 183) |
| AL035683 | 3' UTR | 5.25 | 3150 | TTTG |
| AL035700 | 3' UTR | 19 | 2372 | T |
| AL035765 | UNKNOWN | 18 | 0 | T |
| AL035767 | UNKNOWN | 6 | 82 | CAG |
| AL035767 | UNKNOWN | 18 | 0 | T |
| AL035785 | UNKNOWN | 18 | 0 | T |
| AL035860 | UNKNOWN | 20 | 0 | T |
| AL035883 | UNKNOWN | 13 | 264 | A |
| AL035893 | UNKNOWN | 19 | 0 | T |
| AL035902 | UNKNOWN | 15 | 38 | T |
| AL035957 | UNKNOWN | 19 | 0 | T |
| AL035963 | UNKNOWN | 18 | 0 | T |
| AL035981 | UNKNOWN | 11.75 | 29 | AAAT |
| AL035981 | UNKNOWN | 16 | 0 | T |
| AL035987 | UNKNOWN | 19 | 0 | T |
| AL035992 | UNKNOWN | 17 | 0 | T |
| AL036009 | UNKNOWN | 19 | 0 | T |
| AL036129 | UNKNOWN | 20 | 375 | A |
| AL036130 | UNKNOWN | 17 | 203 | A |
| AL036183 | UNKNOWN | 18 | 0 | T |
| AL036215 | UNKNOWN | 79 | 20 | T |
| AL036215 | UNKNOWN | 19 | 0 | T |
| AL036230 | UNKNOWN | 52 | 0 | T |
| AL036233 | UNKNOWN | 18 | 185 | A |
| AL036237 | UNKNOWN | 14 | 0 | T |
| AL036239 | UNKNOWN | 18 | 0 | T |
| AL036250 | UNKNOWN | 75 | 23 | T |
| AL036250 | UNKNOWN | 17 | 0 | T |

TABLE 1-continued

| Genbank # | Region | # reps | Position | Unit sequence |
|---|---|---|---|---|
| AL036250 | UNKNOWN | 14 | 297 | A |
| AL036250 | UNKNOWN | 13 | 746 | G |
| AL036252 | UNKNOWN | 18 | 0 | T |
| AL036274 | UNKNOWN | 103 | 49 | T |
| AL036274 | UNKNOWN | 20 | 28 | T |
| AL036275 | UNKNOWN | 20 | 168 | A |
| AL036285 | UNKNOWN | 22 | 293 | A |
| AL036289 | UNKNOWN | 20 | 136 | A |
| AL036328 | UNKNOWN | 16 | 0 | T |
| AL036330 | UNKNOWN | 24 | 0 | T |
| AL036334 | UNKNOWN | 3.8 | 506 | TTTC |
| AL036334 | UNKNOWN | 32 | 25 | T |
| AL036356 | UNKNOWN | 13 | 137 | A |
| AL036364 | UNKNOWN | 19 | 0 | T |
| AL036382 | UNKNOWN | 20 | 0 | T |
| AL036396 | UNKNOWN | 143 | 10 | A |
| AL036413 | UNKNOWN | 19 | 0 | T |
| AL036437 | UNKNOWN | 18 | 0 | T |
| AL036437 | UNKNOWN | 17 | 399 | A |
| AL036449 | UNKNOWN | 19 | 0 | T |
| AL036451 | UNKNOWN | 21 | 6 | T |
| AL036490 | UNKNOWN | 17 | 9 | T |
| AL036490 | UNKNOWN | 13 | 474 | A |
| AL036499 | UNKNOWN | 23 | 26 | T |
| AL036527 | UNKNOWN | 20 | 7 | T |
| AL036532 | UNKNOWN | 20 | 5 | T |
| AL036547 | UNKNOWN | 28 | 0 | T |
| AL036589 | UNKNOWN | 20 | 26 | T |
| AL036605 | UNKNOWN | 20 | 26 | T |
| AL036656 | UNKNOWN | 112 | 0 | T |
| AL036656 | UNKNOWN | 24 | 150 | A |
| AL036656 | UNKNOWN | 14 | 335 | C |
| AL036656 | UNKNOWN | 13 | 123 | A |
| AL036659 | UNKNOWN | 19 | 0 | T |
| AL036662 | UNKNOWN | 18 | 0 | T |
| AL036665 | UNKNOWN | 19 | 27 | T |
| AL036666 | UNKNOWN | 33 | 23 | T |
| AL036704 | UNKNOWN | 53 | 20 | T |
| AL036704 | UNKNOWN | 19 | 0 | T |
| AL036710 | UNKNOWN | 21 | 15 | T |
| AL036715 | UNKNOWN | 29 | 26 | T |
| AL036715 | UNKNOWN | 18 | 0 | T |
| AL036753 | UNKNOWN | 27 | 28 | T |
| AL036753 | UNKNOWN | 12 | 562 | A |
| AL036771 | UNKNOWN | 80 | 20 | T |
| AL036771 | UNKNOWN | 19 | 0 | T |
| AL036776 | UNKNOWN | 13 | 6 | T |
| AL036786 | UNKNOWN | 22 | 27 | T |
| AL036802 | UNKNOWN | 97 | 58 | A |
| AL036802 | UNKNOWN | 44 | 13 | A |
| AL036804 | UNKNOWN | 98 | 0 | T |
| AL036804 | UNKNOWN | 15 | 337 | G |
| AL036819 | UNKNOWN | 30 | 51 | T |
| AL036819 | UNKNOWN | 25 | 25 | T |
| AL036819 | UNKNOWN | 20 | 0 | T |
| AL036854 | UNKNOWN | 19 | 0 | T |
| AL036878 | UNKNOWN | 83 | 22 | T |
| AL036878 | UNKNOWN | 19 | 0 | T |
| AL036889 | UNKNOWN | 19 | 0 | T |
| AL036898 | UNKNOWN | 18 | 26 | T |
| AL036914 | UNKNOWN | 6 | 11 | CTA |
| AL036914 | UNKNOWN | 41 | 93 | A |
| AL036914 | UNKNOWN | 37 | 55 | A |
| AL036915 | UNKNOWN | 5.75 | 42 | TTTG |
| AL036915 | UNKNOWN | 19 | 26 | T |
| AL036932 | UNKNOWN | 18 | 473 | T |
| AL036936 | UNKNOWN | 13 | 0 | T |
| AL036949 | UNKNOWN | 27 | 26 | T |
| AL036980 | UNKNOWN | 103 | 41 | A |
| AL037041 | UNKNOWN | 44 | 117 | A |
| AL037041 | UNKNOWN | 28 | 88 | A |
| AL037041 | UNKNOWN | 19 | 26 | T |
| AL037050 | UNKNOWN | 22 | 22 | T |
| AL037052 | UNKNOWN | 20 | 23 | T |
| AL037068 | UNKNOWN | 18 | 24 | T |
| AL037070 | UNKNOWN | 16 | 0 | T |
| AL037075 | UNKNOWN | 19 | 0 | T |

TABLE 1-continued

| Genbank # | Region | # reps | Position | Unit sequence |
|---|---|---|---|---|
| AL037075 | UNKNOWN | 12 | 120 | A |
| AL037081 | UNKNOWN | 64 | 42 | T |
| AL037081 | UNKNOWN | 21 | 20 | T |
| AL037081 | UNKNOWN | 19 | 160 | A |
| AL037101 | UNKNOWN | 19 | 0 | T |
| AL037103 | UNKNOWN | 28 | 0 | T |
| AL037104 | UNKNOWN | 65 | 44 | T |
| AL037104 | UNKNOWN | 21 | 22 | T |
| AL037104 | UNKNOWN | 18 | 162 | A |
| AL037116 | UNKNOWN | 19 | 0 | T |
| AL037131 | UNKNOWN | 47 | 45 | T |
| AL037131 | UNKNOWN | 21 | 23 | T |
| AL037141 | UNKNOWN | 18 | 0 | T |
| AL037148 | UNKNOWN | 50 | 43 | T |
| AL037148 | UNKNOWN | 19 | 23 | T |
| AL037158 | UNKNOWN | 40 | 75 | T |
| AL037158 | UNKNOWN | 20 | 28 | T |
| AL037164 | UNKNOWN | 15 | 0 | T |
| AL037172 | UNKNOWN | 72 | 0 | T |
| AL037258 | UNKNOWN | 19 | 0 | T |
| AL037260 | UNKNOWN | 19 | 0 | T |
| AL037261 | UNKNOWN | 20 | 0 | T |
| AL037303 | UNKNOWN | 6 | 376 | TTA |
| AL037304 | UNKNOWN | 20 | 0 | T |
| AL037305 | UNKNOWN | 17 | 0 | T |
| AL037330 | UNKNOWN | 16 | 0 | T |
| AL037331 | UNKNOWN | 5.75 | 163 | CTTA |
| AL037331 | UNKNOWN | 18 | 0 | T |
| AL037364 | UNKNOWN | 13 | 0 | T |
| AL037367 | UNKNOWN | 19 | 0 | T |
| AL037396 | UNKNOWN | 19 | 0 | T |
| AL037403 | UNKNOWN | 18 | 0 | T |
| AL037405 | UNKNOWN | 8 | 733 | AG |
| AL037414 | UNKNOWN | 13 | 0 | T |
| AL037433 | UNKNOWN | 18 | 0 | T |
| AL037440 | UNKNOWN | 12 | 473 | T |
| AL037445 | UNKNOWN | 17 | 572 | AC |
| AL037446 | UNKNOWN | 21 | 0 | T |
| AL037447 | UNKNOWN | 20 | 672 | A |
| AL037447 | UNKNOWN | 19 | 0 | T |
| AL037460 | UNKNOWN | 18 | 864 | A |
| AL037473 | UNKNOWN | 20 | 24 | T |
| AL037555 | UNKNOWN | 18 | 621 | A |
| AL037557 | UNKNOWN | 16 | 776 | A |
| AL037585 | UNKNOWN | 19 | 25 | T |
| AL037590 | UNKNOWN | 20 | 38 | T |
| AL037590 | UNKNOWN | 17 | 158 | A |
| AL037595 | UNKNOWN | 15 | 27 | T |
| AL037601 | UNKNOWN | 30 | 70 | A |
| AL037617 | UNKNOWN | 19 | 0 | T |
| AL037639 | UNKNOWN | 46 | 98 | A |
| AL037666 | UNKNOWN | 20 | 0 | T |
| AL037674 | UNKNOWN | 17 | 142 | A |
| AL037683 | UNKNOWN | 23 | 346 | A |
| AL037711 | UNKNOWN | 20 | 0 | T |
| AL037723 | UNKNOWN | 20 | 0 | T |
| AL037738 | UNKNOWN | 18 | 0 | T |
| AL037745 | UNKNOWN | 19 | 0 | T |
| AL037747 | UNKNOWN | 19 | 0 | T |
| AL037764 | UNKNOWN | 19 | 0 | T |
| AL037769 | UNKNOWN | 18 | 0 | T |
| AL037771 | UNKNOWN | 20 | 228 | A |
| AL037777 | UNKNOWN | 18 | 0 | T |
| AL037786 | UNKNOWN | 17 | 449 | A |
| AL037805 | UNKNOWN | 20 | 0 | T |
| AL037805 | UNKNOWN | 12 | 275 | A |
| AL037820 | UNKNOWN | 21 | 298 | AC |
| AL037820 | UNKNOWN | 20 | 0 | T |
| AL037850 | UNKNOWN | 24 | 0 | T |
| AL037860 | UNKNOWN | 18 | 445 | A |
| AL037876 | UNKNOWN | 20 | 0 | T |
| AL037888 | UNKNOWN | 4.8 | 16 | TTTTC |
| AL037888 | UNKNOWN | 20 | 0 | T |
| AL037903 | UNKNOWN | 19 | 0 | T |
| AL037906 | UNKNOWN | 22 | 0 | T |
| AL037907 | UNKNOWN | 20 | 0 | T |
| AL037910 | UNKNOWN | 17 | 0 | T |

TABLE 1-continued

| Genbank # | Region | # reps | Position | Unit sequence |
|---|---|---|---|---|
| AL037921 | UNKNOWN | 19 | 0 | T |
| AL037927 | UNKNOWN | 20 | 0 | T |
| AL037927 | UNKNOWN | 20 | 50 | A |
| AL037950 | UNKNOWN | 19 | 0 | T |
| AL037984 | UNKNOWN | 20 | 0 | T |
| AL037998 | UNKNOWN | 21 | 4 | T |
| AL038004 | UNKNOWN | 18 | 470 | A |
| AL038004 | UNKNOWN | 14 | 451 | A |
| AL038005 | UNKNOWN | 18 | 0 | T |
| AL038008 | UNKNOWN | 17 | 7 | T |
| AL038011 | UNKNOWN | 12 | 22 | T |
| AL038023 | UNKNOWN | 20 | 34 | T |
| AL038027 | UNKNOWN | 20 | 43 | T |
| AL038072 | UNKNOWN | 23 | 2 | T |
| AL038090 | UNKNOWN | 13 | 313 | T |
| AL038090 | UNKNOWN | 12 | 0 | T |
| AL038092 | UNKNOWN | 20 | 32 | T |
| AL038114 | UNKNOWN | 19 | 43 | T |
| AL038114 | UNKNOWN | 19 | 455 | A |
| AL038114 | UNKNOWN | 14 | 148 | A |
| AL038125 | UNKNOWN | 20 | 0 | T |
| AL038162 | UNKNOWN | 21 | 0 | T |
| AL038167 | UNKNOWN | 20 | 0 | T |
| AL038182 | UNKNOWN | 17 | 0 | T |
| AL038191 | UNKNOWN | 19 | 0 | T |
| AL038228 | UNKNOWN | 80 | 51 | A |
| AL038228 | UNKNOWN | 50 | 0 | A |
| AL038258 | UNKNOWN | 20 | 494 | A |
| AL038273 | UNKNOWN | 78 | 30 | T |
| AL038273 | UNKNOWN | 20 | 0 | T |
| AL038273 | UNKNOWN | 12 | 129 | A |
| AL038279 | UNKNOWN | 50 | 21 | T |
| AL038279 | UNKNOWN | 20 | 0 | T |
| AL038308 | UNKNOWN | 129 | 33 | A |
| AL038334 | UNKNOWN | 20 | 0 | T |
| AL038375 | UNKNOWN | 22 | 0 | T |
| AL038377 | UNKNOWN | 41 | 0 | T |
| AL038388 | UNKNOWN | 100 | 0 | T |
| AL038389 | UNKNOWN | 20 | 0 | T |
| AL038392 | UNKNOWN | 20 | 0 | T |
| AL038405 | UNKNOWN | 79 | 21 | T |
| AL038405 | UNKNOWN | 20 | 0 | T |
| AL038409 | UNKNOWN | 20 | 0 | T |
| AL038435 | UNKNOWN | 21 | 0 | T |
| AL038435 | UNKNOWN | 21 | 368 | A |
| AL038437 | UNKNOWN | 43 | 21 | T |
| AL038437 | UNKNOWN | 18 | 0 | T |
| AL038445 | UNKNOWN | 91 | 95 | A |
| AL038450 | UNKNOWN | 20 | 0 | T |
| AL038456 | UNKNOWN | 59 | 20 | T |
| AL038456 | UNKNOWN | 19 | 0 | T |
| AL038457 | UNKNOWN | 63 | 0 | T |
| AL038463 | UNKNOWN | 57 | 20 | T |
| AL038463 | UNKNOWN | 19 | 0 | T |
| AL038488 | UNKNOWN | 19 | 0 | T |
| AL038504 | UNKNOWN | 70 | 22 | T |
| AL038504 | UNKNOWN | 21 | 0 | T |
| AL038511 | UNKNOWN | 20 | 0 | T |
| AL038527 | UNKNOWN | 26 | 0 | T |
| AL038534 | UNKNOWN | 19 | 0 | T |
| AL038541 | UNKNOWN | 62 | 381 | A |
| AL038565 | UNKNOWN | 112 | 0 | T |
| AL038573 | UNKNOWN | 19 | 0 | T |
| AL038575 | UNKNOWN | 60 | 0 | T |
| AL038581 | UNKNOWN | 21 | 0 | T |
| AL038591 | UNKNOWN | 19 | 0 | T |
| AL038605 | UNKNOWN | 107 | 21 | T |
| AL038605 | UNKNOWN | 20 | 0 | T |
| AL038612 | UNKNOWN | 9.5 | 507 | AC |
| AL038612 | UNKNOWN | 18 | 0 | T |
| AL038624 | UNKNOWN | 21 | 0 | T |
| AL038636 | UNKNOWN | 5.66 | 274 | AAC |
| AL038637 | UNKNOWN | 20 | 0 | T |
| AL038645 | UNKNOWN | 62 | 43 | T |
| AL038645 | UNKNOWN | 41 | 0 | T |
| AL038665 | UNKNOWN | 68 | 0 | T |
| AL038677 | UNKNOWN | 20 | 0 | T |

TABLE 1-continued

| Genbank # | Region | # reps | Position | Unit sequence |
|---|---|---|---|---|
| AL038704 | UNKNOWN | 20 | 0 | T |
| AL038714 | UNKNOWN | 19 | 0 | T |
| AL038727 | UNKNOWN | 19 | 0 | T |
| AL038745 | UNKNOWN | 23 | 20 | T |
| AL038745 | UNKNOWN | 19 | 0 | T |
| AL038757 | UNKNOWN | 20 | 0 | T |
| AL038759 | UNKNOWN | 20 | 0 | T |
| AL038763 | UNKNOWN | 36 | 0 | T |
| AL038765 | UNKNOWN | 20 | 0 | T |
| AL038775 | UNKNOWN | 54 | 0 | T |
| AL038779 | UNKNOWN | 105 | 18 | T |
| AL038779 | UNKNOWN | 17 | 0 | T |
| AL038779 | UNKNOWN | 12 | 139 | A |
| AL038781 | UNKNOWN | 14 | 0 | T |
| AL038784 | UNKNOWN | 20 | 0 | T |
| AL038787 | UNKNOWN | 13 | 0 | T |
| AL038799 | UNKNOWN | 18 | 0 | T |
| AL038817 | UNKNOWN | 42 | 0 | T |
| AL038852 | UNKNOWN | 48 | 20 | T |
| AL038852 | UNKNOWN | 19 | 0 | T |
| AL038860 | UNKNOWN | 20 | 0 | T |
| AL038864 | UNKNOWN | 64 | 21 | T |
| AL038864 | UNKNOWN | 20 | 0 | T |
| AL038887 | UNKNOWN | 19 | 0 | T |
| AL038901 | UNKNOWN | 20 | 0 | T |
| AL038936 | UNKNOWN | 20 | 0 | T |
| AL038952 | UNKNOWN | 21 | 0 | T |
| AL038956 | UNKNOWN | 62 | 0 | T |
| AL038962 | UNKNOWN | 19 | 0 | T |
| AL038963 | UNKNOWN | 18 | 0 | T |
| AL038967 | UNKNOWN | 22 | 333 | A |
| AL038971 | UNKNOWN | 20 | 0 | T |
| AL038972 | UNKNOWN | 19 | 0 | T |
| AL038973 | UNKNOWN | 19 | 0 | T |
| AL038977 | UNKNOWN | 19 | 0 | T |
| AL038993 | UNKNOWN | 19 | 335 | A |
| AL038999 | UNKNOWN | 18 | 0 | T |
| AL039003 | UNKNOWN | 16 | 0 | T |
| AL039013 | UNKNOWN | 12.5 | 176 | AC |
| AL039013 | UNKNOWN | 20 | 200 | A |
| AL039013 | UNKNOWN | 19 | 15 | A |
| AL039039 | UNKNOWN | 19 | 0 | T |
| AL039041 | UNKNOWN | 20 | 331 | A |
| AL039056 | UNKNOWN | 22 | 0 | T |
| AL039057 | UNKNOWN | 16 | 0 | T |
| AL039083 | UNKNOWN | 23 | 0 | T |
| AL039086 | UNKNOWN | 97 | 54 | A |
| AL039096 | UNKNOWN | 21 | 139 | A |
| AL039107 | UNKNOWN | 20 | 157 | A |
| AL039145 | UNKNOWN | 19 | 0 | T |
| AL039172 | UNKNOWN | 19 | 0 | T |
| AL039179 | UNKNOWN | 18 | 0 | T |
| AL039189 | UNKNOWN | 19 | 0 | T |
| AL039191 | UNKNOWN | 17 | 341 | A |
| AL039194 | UNKNOWN | 18 | 217 | A |
| AL039196 | UNKNOWN | 19 | 0 | T |
| AL039200 | UNKNOWN | 17 | 0 | T |
| AL039379 | UNKNOWN | 23 | 10 | T |
| AL039389 | UNKNOWN | 25 | 17 | T |
| AL039400 | UNKNOWN | 17 | 200 | T |
| AL039400 | UNKNOWN | 15 | 12 | T |
| AL039434 | UNKNOWN | 17 | 394 | A |
| AL039478 | UNKNOWN | 43 | 13 | T |
| AL039483 | UNKNOWN | 22 | 12 | T |
| AL039633 | UNKNOWN | 16 | 7 | T |
| AL039671 | UNKNOWN | 21 | 7 | T |
| AL039676 | UNKNOWN | 17 | 138 | T |
| AL039706 | UNKNOWN | 25 | 1 | T |
| AL039718 | UNKNOWN | 33 | 0 | T |
| AL039730 | UNKNOWN | 54 | 1 | T |
| AL039730 | UNKNOWN | 13 | 486 | A |
| AL039753 | UNKNOWN | 67 | 2 | T |
| AL039788 | UNKNOWN | 49 | 0 | T |
| AL039800 | UNKNOWN | 36 | 1 | T |
| AL039806 | UNKNOWN | 2.9 | 39 | TTTTTTTTN (SEQ ID NO: 184) |
| AL039806 | UNKNOWN | 48 | 0 | T |
| AL039811 | UNKNOWN | 39 | 0 | T |

TABLE 1-continued

| Genbank # | Region | # reps | Position | Unit sequence |
|---|---|---|---|---|
| AL039826 | UNKNOWN | 23 | 1 | T |
| AL039831 | UNKNOWN | 18 | 1 | T |
| AL039857 | UNKNOWN | 3.6 | 275 | GGAAT |
| AL039858 | UNKNOWN | 82 | 0 | T |
| AL039862 | UNKNOWN | 30 | 1 | T |
| AL039868 | UNKNOWN | 15 | 1 | T |
| AL039870 | UNKNOWN | 16 | 1 | T |
| AL039876 | UNKNOWN | 4.5 | 453 | TATT |
| AL039876 | UNKNOWN | 23 | 1 | T |
| AL039884 | UNKNOWN | 36 | 0 | T |
| AL039887 | UNKNOWN | 37 | 0 | T |
| AL039893 | UNKNOWN | 5.66 | 62 | GAA |
| AL039893 | UNKNOWN | 19 | 207 | A |
| AL039930 | UNKNOWN | 13 | 0 | T |
| AL039945 | UNKNOWN | 22 | 1 | T |
| AL039958 | UNKNOWN | 24 | 1 | T |
| AL039963 | UNKNOWN | 30 | 1 | T |
| AL039969 | UNKNOWN | 28 | 1 | T |
| AL039978 | UNKNOWN | 51 | 1 | T |
| AL039995 | UNKNOWN | 35 | 0 | T |
| AL039996 | UNKNOWN | 7 | 14 | AT |
| AL039996 | UNKNOWN | 16 | 461 | A |
| AL040011 | UNKNOWN | 63 | 0 | T |
| AL040011 | UNKNOWN | 14 | 96 | A |
| AL040054 | UNKNOWN | 5 | 42 | ATTTT |
| AL040054 | UNKNOWN | 38 | 0 | T |
| AL040100 | UNKNOWN | 47 | 0 | T |
| AL040109 | UNKNOWN | 16 | 345 | A |
| AL040130 | UNKNOWN | 15 | 0 | T |
| AL040153 | UNKNOWN | 15 | 0 | T |
| AL040153 | UNKNOWN | 12 | 757 | A |
| AL040160 | UNKNOWN | 5 | 222 | CCCCA |
| AL040169 | UNKNOWN | 136 | 737 | A |
| AL040178 | UNKNOWN | 54 | 0 | T |
| AL040182 | UNKNOWN | 46 | 0 | T |
| AL040184 | UNKNOWN | 73 | 0 | T |
| AL040197 | UNKNOWN | 7 | 764 | CTC |
| AL040205 | UNKNOWN | 96 | 365 | A |
| AL040241 | UNKNOWN | 91 | 0 | T |
| AL040259 | UNKNOWN | 30 | 0 | T |
| AL040287 | UNKNOWN | 42 | 0 | T |
| AL040313 | UNKNOWN | 29 | 0 | T |
| AL040319 | UNKNOWN | 49 | 0 | T |
| AL040354 | UNKNOWN | 21 | 0 | T |
| AL040360 | UNKNOWN | 20 | 0 | T |
| AL040364 | UNKNOWN | 37 | 212 | A |
| AL040366 | UNKNOWN | 49 | 0 | T |
| AL040372 | UNKNOWN | 42 | 0 | T |
| AL040374 | UNKNOWN | 27 | 0 | T |
| AL040379 | UNKNOWN | 38 | 0 | T |
| AL040403 | UNKNOWN | 33 | 0 | T |
| AL040416 | UNKNOWN | 42 | 0 | T |
| AL040416 | UNKNOWN | 20 | 607 | A |
| AL040420 | UNKNOWN | 19 | 0 | T |
| AL040430 | UNKNOWN | 22 | 319 | A |
| AL040449 | UNKNOWN | 67 | 0 | T |
| AL040454 | UNKNOWN | 33 | 298 | A |
| AL040498 | UNKNOWN | 14 | 371 | A |
| AL040547 | UNKNOWN | 13 | 1 | T |
| AL040581 | UNKNOWN | 33 | 0 | T |
| AL040581 | UNKNOWN | 18 | 472 | A |
| AL040586 | UNKNOWN | 61 | 94 | A |
| AL040600 | UNKNOWN | 11.5 | 506 | CA |
| AL040600 | UNKNOWN | 28 | 0 | T |
| AL040616 | UNKNOWN | 36 | 0 | T |
| AL040663 | UNKNOWN | 15 | 0 | T |
| AL040681 | UNKNOWN | 20 | 0 | T |
| AL040693 | UNKNOWN | 21 | 728 | A |
| AL040705 | UNKNOWN | 34 | 0 | T |
| AL040712 | UNKNOWN | 16 | 376 | A |
| AL040748 | UNKNOWN | 15 | 0 | T |
| AL040789 | UNKNOWN | 16 | 427 | A |
| AL040827 | UNKNOWN | 95 | 330 | A |
| AL040907 | UNKNOWN | 3.8 | 423 | AAAAC |
| AL041068 | UNKNOWN | 46 | 0 | T |
| AL041080 | UNKNOWN | 15 | 0 | T |
| AL041105 | UNKNOWN | 75 | 0 | T |

TABLE 1-continued

| Genbank # | Region | # reps | Position | Unit sequence |
|---|---|---|---|---|
| AL041115 | UNKNOWN | 72 | 0 | T |
| AL041118 | UNKNOWN | 30 | 0 | T |
| AL041122 | UNKNOWN | 27 | 0 | T |
| AL041126 | UNKNOWN | 34 | 0 | T |
| AL041146 | UNKNOWN | 19 | 0 | T |
| AL041154 | UNKNOWN | 4.59 | 67 | TTTAT |
| AL041154 | UNKNOWN | 47 | 0 | T |
| AL041162 | UNKNOWN | 37 | 0 | T |
| AL041170 | UNKNOWN | 31 | 0 | T |
| AL041174 | UNKNOWN | 26 | 0 | T |
| AL041196 | UNKNOWN | 30 | 0 | T |
| AL041208 | UNKNOWN | 55 | 0 | T |
| AL041224 | UNKNOWN | 37 | 0 | T |
| AL041224 | UNKNOWN | 12 | 230 | A |
| AL041226 | UNKNdWN | 43 | 0 | T |
| AL041229 | UNKNOWN | 68 | 0 | T |
| AL041243 | UNKNOWN | 51 | 0 | T |
| AL041272 | UNKNOWN | 19 | 558 | A |
| AL041294 | UNKNOWN | 46 | 220 | A |
| AL041300 | UNKNOWN | 26 | 0 | T |
| AL041308 | UNKNOWN | 27 | 0 | T |
| AL041318 | UNKNOWN | 37 | 0 | T |
| AL041325 | UNKNOWN | 14 | 443 | A |
| AL041339 | UNKNOWN | 19 | 911 | A |
| AL041383 | UNKNOWN | 15 | 357 | A |
| AL041408 | UNKNOWN | 15 | 0 | T |
| AL041444 | UNKNOWN | 6.33 | 209 | AAG |
| AL041450 | UNKNOWN | 13 | 5 | T |
| AL041475 | UNKNOWN | 17 | 155 | A |
| AL041527 | UNKNOWN | 12 | 291 | T |
| AL041540 | UNKNOWN | 9 | 48 | CA |
| AL041555 | UNKNOWN | 16 | 0 | T |
| AL041561 | UNKNOWN | 24 | 0 | T |
| AL041562 | UNKNOWN | 73 | 397 | A |
| AL041573 | UNKNOWN | 119 | 316 | A |
| AL041632 | UNKNOWN | 15 | 0 | T |
| AL041638 | UNKNOWN | 7.5 | 545 | GT |
| AL041649 | UNKNOWN | 16 | 410 | A |
| AL041690 | UNKNOWN | 22 | 0 | T |
| AL041693 | UNKNOWN | 8 | 150 | TC |
| AL041712 | UNKNOWN | 16 | 31 | T |
| AL041734 | UNKNOWN | 73 | 266 | A |
| AL041761 | UNKNOWN | 11.5 | 450 | AT |
| AL041761 | UNKNOWN | 7 | 472 | AC |
| AL041765 | UNKNOWN | 20 | 2 | T |
| AL041801 | UNKNOWN | 19 | 2 | T |
| AL041806 | UNKNOWN | 15 | 2 | T |
| AL041815 | UNKNOWN | 12 | 368 | A |
| AL041820 | UNKNOWN | 16 | 447 | A |
| AL041928 | UNKNOWN | 54 | 462 | A |
| AL041964 | UNKNOWN | 23 | 409 | A |
| AL042088 | UNKNOWN | 24 | 2 | T |
| AL042162 | UNKNOWN | 7.5 | 345 | AT |
| AL042244 | UNKNOWN | 17 | 2 | T |
| AL042310 | UNKNOWN | 13 | 285 | T |
| AL042372 | UNKNOWN | 17 | 1 | T |
| AL042374 | UNNNOWN | 46 | 417 | A |
| AL042374 | UNKNOWN | 12 | 376 | T |
| AL042377 | UNKNOWN | 4.75 | 83 | TTTA |
| AL042377 | UNKNOWN | 76 | 10 | T |
| AL042392 | UNKNOWN | 17 | 435 | A |
| AL042395 | UNKNOWN | 32 | 1 | T |
| AL042468 | UNNNOWN | 17 | 64 | T |
| AL042471 | UNKNOWN | 27 | 10 | T |
| AL042483 | UNKNOWN | 44 | 11 | T |
| AL042496 | UNKNOWN | 13.5 | 574 | AC |
| AL042496 | UNKNOWN | 31 | 1 | T |
| AL042503 | UNKNOWN | 23 | 26 | T |
| AL042512 | UNKNOWN | 36 | 7 | T |
| AL042523 | UNKNOWN | 25 | 77 | T |
| AL042538 | UNKNOWN | 100 | 52 | T |
| AL042546 | UNKNOWN | 21 | 0 | T |
| AL042557 | UNKNOWN | 9.5 | 420 | CT |
| AL042557 | UNKNOWN | 7 | 445 | TG |
| AL042557 | UNKNOWN | 82 | 10 | T |
| AL042567 | UNKNOWN | 55 | 11 | T |
| AL042593 | UNKNOWN | 44 | 10 | T |

TABLE 1-continued

| Genbank # | Region | # reps | Position | Unit sequence |
|---|---|---|---|---|
| AL042595 | UNKNOWN | 59 | 11 | T |
| AL042605 | UNKNOWN | 42 | 1 | T |
| AL042615 | UNKNOWN | 21 | 1 | T |
| AL042618 | UNKNOWN | 9.5 | 451 | AC |
| AL042630 | UNKNOWN | 35 | 248 | A |
| AL042655 | UNKNOWN | 46 | 53 | T |
| AL042660 | UNKNOWN | 22 | 11 | T |
| AL042667 | UNKNOWN | 19 | 10 | T |
| AL042694 | UNKNOWN | 53 | 10 | T |
| AL042699 | UNKNOWN | 22 | 10 | T |
| AL042704 | UNKNOWN | 13 | 162 | T |
| AL042716 | UNKNOWN | 28 | 71 | T |
| AL042727 | UNKNOWN | 18 | 1 | T |
| AL042756 | UNKNOWN | 30 | 41 | T |
| AL042759 | UNKNOWN | 39 | 47 | T |
| AL042765 | UNKNOWN | 34 | 69 | T |
| AL042785 | UNKNOWN | 67 | 12 | T |
| AL042790 | UNKNOWN | 23 | 47 | T |
| AL042793 | UNKNOWN | 29 | 39 | T |
| AL042817 | UNKNOWN | 15 | 41 | T |
| AL042823 | UNKNOWN | 15 | 46 | T |
| AL042837 | UNKNOWN | 30 | 36 | T |
| AL042861 | UNKNOWN | 22 | 1 | T |
| AL042883 | UNKNOWN | 14 | 0 | T |
| AL042891 | UNKNOWN | 21 | 341 | T |
| AL042891 | UNKNOWN | 18 | 58 | T |
| AL042912 | UNKNOWN | 31 | 287 | A |
| AL042940 | UNKNOWN | 2.72 | 305 | ATATATATGAT (SEQ ID NO: 185) |
| AL042940 | UNKNOWN | 8 | 286 | AT |
| AL042955 | UNKNOWN | 6.5 | 396 | TC |
| AL042959 | UNKNOWN | 48 | 0 | T |
| AL042970 | UNKNOWN | 3.8 | 266 | GCCCA |
| AL042980 | UNKNOWN | 6.5 | 735 | AT |
| AL043020 | UNKNOWN | 3.2 | 89 | CCTCAGTCTGCAGCCTGCTAGGGACGCACGGCCACACTC CTGTCTTTCAG (SEQ ID NO: 186) |
| AL043048 | UNKNOWN | 13 | 381 | A |
| AL043050 | UNKNOWN | 15 | 1 | T |
| AL043052 | UNKNOWN | 79 | 1 | T |
| AL043064 | UNKNOWN | 18 | 0 | T |
| AL043067 | UNKNOWN | 13 | 156 | T |
| AL043081 | UNKNOWN | 29 | 1 | T |
| AL043083 | UNKNOWN | 14 | 0 | T |
| AL043084 | UNKNOWN | 67 | 209 | A |
| AL043093 | UNKNOWN | 34 | 1 | T |
| AL043095 | UNKNOWN | 6.5 | 300 | TTTA |
| AL043095 | UNKNOWN | 14 | 0 | T |
| AL043096 | UNKNOWN | 18 | 522 | A |
| AL043104 | UNKNOWN | 25 | 0 | T |
| AL043122 | UNKNOWN | 20 | 680 | A |
| AL043125 | UNKNOWN | 14 | 0 | T |
| AL043148 | UNKNOWN | 21 | 622 | A |
| AL043148 | UNKNOWN | 16 | 2 | T |
| AL043152 | UNKNOWN | 59 | 497 | A |
| AL043159 | UNKNOWN | 29 | 1 | T |
| AL043161 | UNKNOWN | 37 | 0 | T |
| AL043166 | UNKNOWN | 44 | 27 | T |
| AL043170 | UNKNOWN | 30 | 1 | T |
| AL043178 | UNKNOWN | 26 | 1 | T |
| AL043180 | UNKNOWN | 22 | 166 | A |
| AL043196 | UNKNOWN | 63 | 40 | T |
| AL043237 | UNKNOWN | 16 | 682 | A |
| AL043239 | UNKNOWN | 58 | 41 | T |
| AL043273 | UNKNOWN | 46 | 0 | T |
| AL043282 | UNKNOWN | 30 | 521 | A |
| AL043282 | UNKNOWN | 18 | 502 | A |
| AL043282 | UNKNOWN | 15 | 234 | T |
| AL043288 | UNKNOWN | 45 | 1 | T |
| AL043289 | UNKNOWN | 43 | 241 | A |
| AL043294 | UNKNOWN | 14 | 567 | T |
| AL043296 | UNKNOWN | 12 | 136 | A |
| AL043308 | UNKNOWN | 28 | 294 | A |
| AL043351 | UNKNOWN | 27 | 361 | A |
| AL043376 | UNKNOWN | 12 | 0 | T |
| AL043390 | UNKNOWN | 12 | 0 | T |
| AL043556 | UNKNOWN | 19 | 112 | T |
| AL043632 | UNKNOWN | 65 | 172 | A |
| AL043632 | UNKNOWN | 15 | 98 | A |

TABLE 1-continued

| Genbank # | Region | # reps | Position | Unit sequence |
|---|---|---|---|---|
| AL043656 | UNKNOWN | 7.5 | 129 | TG |
| AL043676 | UNKNOWN | 5.25 | 11 | TTTA |
| AL043676 | UNKNOWN | 14 | 0 | T |
| AL043707 | UNKNOWN | 21 | 302 | A |
| AL043718 | UNKNOWN | 17 | 0 | T |
| AL043727 | UNKNOWN | 19 | 465 | A |
| AL043748 | UNKNOWN | 28 | 0 | T |
| AL043782 | UNKNOWN | 46 | 530 | A |
| AL043846 | UNKNOWN | 21 | 575 | GT |
| AL043846 | UNKNOWN | 6.5 | 560 | TC |
| AL043897 | UNKNOWN | 21 | 0 | T |
| AL043937 | UNKNOWN | 16 | 0 | T |
| AL043956 | UNKNOWN | 20 | 479 | A |
| AL043977 | UNKNOWN | 13 | 855 | A |
| AL043979 | UNKNOWN | 12 | 544 | T |
| AL043980 | UNKNOWN | 29 | 0 | T |
| AL044007 | UNKNOWN | 5.66 | 485 | AAC |
| AL044007 | UNKNOWN | 15 | 0 | T |
| AL044019 | UNKNOWN | 28 | 0 | T |
| AL044056 | UNKNOWN | 16 | 0 | T |
| AL044079 | UNKNOWN | 24 | 0 | T |
| AL044092 | UNKNOWN | 16 | 0 | T |
| AL044137 | UNKNOWN | 18 | 266 | T |
| AL044207 | UNKNOWN | 117 | 168 | A |
| AL044209 | UNKNOWN | 15 | 586 | A |
| AL044267 | UNKNOWN | 12 | 250 | T |
| AL044304 | UNKNOWN | 13.5 | 332 | CA |
| AL044304 | UNKNOWN | 70 | 370 | A |
| AL044394 | UNKNOWN | 16 | 0 | T |
| AL044423 | UNKNOWN | 14 | 406 | A |
| AL044425 | UNKNOWN | 15 | 0 | T |
| AL044445 | UNKNOWN | 14 | 0 | T |
| AL044454 | UNKNOWN | 16 | 0 | T |
| AL044456 | UNKNOWN | 14 | 0 | T |
| AL044470 | UNKNOWN | 9 | 637 | TC |
| AL044498 | UNKNOWN | 4.5 | 706 | AATA |
| AL044500 | UNKNOWN | 14 | 0 | T |
| AL044520 | UNKNOWN | 12 | 0 | T |
| AL044523 | UNKNOWN | 28 | 232 | A |
| AL044528 | UNKNOWN | 12 | 0 | T |
| AL044545 | UNKNOWN | 12 | 0 | T |
| AL044570 | UNKNOWN | 12 | 0 | T |
| AL044574 | UNKNOWN | 16 | 158 | T |
| AL044574 | UNKNOWN | 12 | 0 | T |
| AL044589 | UNKNOWN | 12 | 0 | T |
| AL044599 | UNKNOWN | 13 | 0 | T |
| AL044904 | UNKNOWN | 30 | 8 | T |
| AL044914 | UNKNOWN | 16 | 8 | T |
| AL044934 | UNKNOWN | 17 | 8 | T |
| AL044946 | UNKNOWN | 8 | 496 | AT |
| AL044946 | UNKNOWN | 15 | 8 | T |
| AL044989 | UNKNOWN | 19 | 8 | T |
| AL045166 | UNKNOWN | 51 | 23 | T |
| AL045181 | UNKNOWN | 12 | 303 | A |
| AL045285 | UNKNOWN | 13 | 364 | T |
| AL045349 | UNKNOWN | 62 | 2 | T |
| AL045360 | UNKNOWN | 60 | 7 | T |
| AL045379 | UNKNOWN | 34 | 15 | T |
| AL045398 | UNKNOWN | 27 | 11 | T |
| AL045406 | UNKNOWN | 44 | 67 | A |
| AL045421 | UNKNOWN | 65 | 12 | T |
| AL045441 | UNKNOWN | 18 | 1 | T |
| AL045455 | UNKNOWN | 8.5 | 267 | TG |
| AL045482 | UNKNOWN | 16 | 13 | T |
| AL045500 | UNKNOWN | 134 | 12 | T |
| AL045606 | UNKNOWN | 2.9 | 414 | AAAAAAAAN (SEQ ID NO: 187) |
| AL045606 | UNKNOWN | 51 | 372 | A |
| AL045619 | UNKNOWN | 51 | 8 | T |
| AL045620 | UNKNOWN | 91 | 189 | A |
| AL045626 | UNKNOWN | 70 | 11 | T |
| AL045628 | UNKNOWN | 36 | 9 | T |
| AL045641 | UNKNOWN | 16 | 12 | T |
| AL045659 | UNKNOWN | 3.5 | 21 | GGGCAG |
| AL045661 | UNKNOWN | 28 | 0 | T |
| AL045664 | UNKNOWN | 55 | 0 | T |
| AL045666 | UNKNOWN | 9.5 | 363 | AC |
| AL045666 | UNKNOWN | 24 | 0 | T |

TABLE 1-continued

| Genbank # | Region | # reps | Position | Unit sequence |
|---|---|---|---|---|
| AL045672 | UNKNOWN | 40 | 134 | A |
| AL045711 | UNKNOWN | 54 | 0 | T |
| AL045714 | UNKNOWN | 32 | 0 | T |
| AL045730 | UNKNOWN | 32 | 553 | A |
| AL045772 | UNKNOWN | 44 | 0 | T |
| AL045781 | UNKNOWN | 14 | 321 | A |
| AL045798 | UNKNOWN | 43 | 0 | T |
| AL045808 | UNKNOWN | 28 | 333 | A |
| AL045813 | UNKNOWN | 21 | 0 | T |
| AL045816 | UNKNOWN | 23 | 0 | T |
| AL045825 | UNKNOWN | 46 | 588 | A |
| AL045882 | UNKNOWN | 21 | 0 | T |
| AL045911 | UNKNOWN | 65 | 0 | T |
| AL045916 | UNKNOWN | 23 | 0 | T |
| AL045916 | UNKNOWN | 13 | 653 | A |
| AL045919 | UNKNOWN | 16 | 0 | T |
| AL045922 | UNKNOWN | 52 | 238 | A |
| AL045922 | UNKNOWN | 24 | 213 | A |
| AL045929 | UNKNOWN | 38 | 0 | T |
| AL045950 | UNKNOWN | 49 | 0 | T |
| AL045965 | UNKNOWN | 29 | 0 | T |
| AL045971 | UNKNOWN | 35 | 0 | T |
| AL045977 | UNKNOWN | 28 | 0 | T |
| AL045983 | UNKNOWN | 51 | 0 | T |
| AL045988 | UNKNOWN | 20 | 0 | T |
| AL046023 | UNKNOWN | 17 | 0 | T |
| AL046134 | UNKNOWN | 40 | 503 | A |
| AL046161 | UNKNOWN | 14 | 0 | T |
| AL046175 | UNKNOWN | 20 | 17 | T |
| AL046175 | UNKNOWN | 16 | 0 | T |
| AL046192 | UNKNOWN | 34 | 0 | T |
| AL046199 | UNKNOWN | 17 | 0 | T |
| AL046202 | UNKNOWN | 38 | 0 | T |
| AL046227 | UNKNOWN | 48 | 0 | T |
| AL046246 | UNKNOWN | 17 | 0 | T |
| AL046250 | UNKNOWN | 17 | 0 | T |
| AL046262 | UNKNOWN | 57 | 430 | A |
| AL046264 | UNKNOWN | 25 | 0 | T |
| AL046276 | UNKNOWN | 17 | 551 | CA |
| AL046276 | UNKNOWN | 16 | 0 | T |
| AL046301 | UNKNOWN | 17 | 0 | T |
| AL046345 | UNKNOWN | 55 | 0 | T |
| AL046345 | UNKNOWN | 12 | 291 | C |
| AL046389 | UNKNOWN | 18 | 0 | T |
| AL046412 | UNKNOWN | 6.5 | 239 | TC |
| AL046412 | UNKNOWN | 15 | 0 | T |
| AL046428 | UNKNOWN | 29 | 248 | A |
| AL046454 | UNKNOWN | 61 | 2 | T |
| AL046457 | UNKNOWN | 19 | 2 | T |
| AL046463 | UNKNOWN | 76 | 2 | T |
| AL046466 | UNKNOWN | 67 | 2 | T |
| AL046466 | UNKNOWN | 12 | 69 | A |
| AL046473 | UNKNOWN | 67 | 2 | T |
| AL046485 | UNKNOWN | 37 | 2 | T |
| AL046503 | UNKNOWN | 30 | 2 | T |
| AL046562 | UNKNOWN | 59 | 2 | T |
| AL046583 | UNKNOWN | 33 | 2 | T |
| AL046595 | UNKNOWN | 73 | 2 | T |
| AL046595 | UNKNOWN | 12 | 76 | A |
| AL046618 | UNKNOWN | 69 | 2 | T |
| AL046628 | UNKNOWN | 20 | 2 | T |
| AL046653 | UNKNOWN | 12 | 287 | A |
| AL046854 | UNKNOWN | 73 | 0 | T |
| AL046863 | UNKNOWN | 17 | 0 | T |
| AL046876 | UNKNOWN | 17 | 0 | T |
| AL046885 | UNKNOWN | 17 | 12 | T |
| AL046886 | UNKNOWN | 10 | 680 | CAG |
| AL046886 | UNKNOWN | 8.66 | 559 | CAG |
| AL046886 | UNKNOWN | 7.66 | 457 | CAG |
| AL046893 | UNKNOWN | 3.6 | 151 | TTTTA |
| AL046893 | UNKNOWN | 17 | 0 | T |
| AL046920 | UNKNOWN | 57 | 0 | T |
| AL046938 | UNKNOWN | 69 | 18 | T |
| AL046938 | UNKNOWN | 17 | 0 | T |
| AL046973 | UNKNOWN | 16 | 0 | T |
| AL047025 | UNKNOWN | 79 | 0 | T |
| AL047034 | UNKNOWN | 17 | 0 | T |

TABLE 1-continued

| Genbank # | Region | # reps | Position | Unit sequence |
|---|---|---|---|---|
| AL047041 | UNKNOWN | 124 | 0 | T |
| AL047041 | UNKNOWN | 12 | 142 | A |
| AL047047 | UNKNOWN | 95 | 0 | T |
| AL047052 | UNKNOWN | 6 | 119 | AAAC |
| AL047052 | UNKNOWN | 5 | 102 | TAAA |
| AL047052 | UNKNOWN | 17 | 0 | T |
| AL047209 | UNKNOWN | 23 | 301 | A |
| AL047265 | UNKNOWN | 17 | 8 | T |
| AL047271 | UNKNOWN | 16 | 22 | T |
| AL047309 | UNKNOWN | 17 | 8 | T |
| AL047387 | UNKNOWN | 78 | 31 | T |
| AL047387 | UNKNOWN | 15 | 14 | T |
| AL047426 | UNKNOWN | 12 | 7 | A |
| AL047441 | UNKNOWN | 17 | 8 | T |
| AL047491 | UNKNOWN | 13 | 0 | T |
| AL047559 | UNKNOWN | 17 | 104 | A |
| AL047570 | UNKNOWN | 46 | 19 | T |
| AL047570 | UNKNOWN | 13 | 5 | T |
| AL047600 | UNKNOWN | 13 | 0 | T |
| AL047692 | UNKNOWN | 17 | 125 | A |
| AL047725 | UNKNOWN | 14 | 0 | T |
| AL047731 | UNKNOWN | 12 | 1 | T |
| AL047843 | UNKNOWN | 88 | 0 | T |
| AL047843 | UNKNOWN | 12 | 223 | G |
| AL047849 | UNKNOWN | 45 | 18 | T |
| AL047849 | UNKNOWN | 17 | 0 | T |
| AL047854 | UNKNOWN | 50 | 18 | T |
| AL047854 | UNKNOWN | 17 | 0 | T |
| AL047858 | UNKNOWN | 17 | 312 | A |
| AL047877 | UNKNOWN | 50 | 0 | T |
| AL047887 | UNKNOWN | 17 | 0 | T |
| AL047998 | UNKNOWN | 5.5 | 299 | AATG |
| AL047998 | UNKNOWN | 17 | 574 | A |
| AL048296 | UNKNOWN | 17 | 10 | T |
| AL048304 | UNKNOWN | 17 | 10 | T |
| AL048307 | UNKNOWN | 3.8 | 4 | AAAAT |
| AL048307 | UNKNOWN | 15 | 174 | A |
| AL048312 | UNKNOWN | 68 | 28 | T |
| AL048312 | UNKNOWN | 17 | 10 | T |
| AL048312 | UNKNOWN | 13 | 377 | A |
| AL048326 | UNKNOWN | 17 | 8 | T |
| AL048338 | UNKNOWN | 17 | 10 | T |
| AL048361 | UNKNOWN | 4.75 | 24 | TTTG |
| AL048361 | UNKNOWN | 17 | 10 | T |
| AL048368 | UNKNOWN | 17 | 9 | T |
| AL048372 | UNKNOWN | 17 | 9 | T |
| AL048376 | UNKNOWN | 17 | 11 | T |
| AL048377 | UNKNOWN | 88 | 12 | T |
| AL048386 | UNKNOWN | 17 | 12 | T |
| AL048397 | UNKNOWN | 100 | 21 | T |
| AL048397 | UNKNOWN | 17 | 1 | T |
| AL048397 | UNKNOWN | 16 | 171 | A |
| AL048399 | UNKNOWN | 6.5 | 166 | TA |
| AL048399 | UNKNOWN | 17 | 9 | T |
| AL048402 | UNKNOWN | 17 | 7 | T |
| AL048409 | UNKNOWN | 17 | 8 | T |
| AL048410 | UNKNOWN | 43 | 10 | T |
| AL048433 | UNKNOWN | 17 | 5 | T |
| AL048480 | UNKNOWN | 17 | 10 | T |
| AL048492 | UNKNOWN | 17 | 10 | T |
| AL048496 | UNKNOWN | 87 | 28 | T |
| AL048496 | UNKNOWN | 17 | 10 | T |
| AL048508 | UNKNOWN | 17 | 9 | T |
| AL048542 | UNKNOWN | 17 | 13 | T |
| AL048552 | UNKNOWN | 56 | 17 | T |
| AL048552 | UNKNOWN | 16 | 0 | T |
| AL048596 | UNKNOWN | 2.66 | 450 | GAGCGAGAGAGA (SEQ ID NO: 188) |
| AL048596 | UNKNOWN | 8.5 | 95 | AT |
| AL048596 | UNKNOWN | 16 | 432 | A |
| AL048632 | UNKNOWN | 19 | 0 | T |
| AL048633 | UNKNOWN | 21 | 7 | T |
| AL048633 | UNKNOWN | 12 | 213 | A |
| AL048651 | UNKNOWN | 20 | 0 | T |
| AL048790 | UNKNOWN | 18 | 93 | A |
| AL048853 | UNKNOWN | 14 | 325 | A |
| AL048858 | UNKNOWN | 22 | 2 | T |
| AL048916 | UNKNOWN | 76 | 2 | T |

TABLE 1-continued

| Genbank # | Region | # reps | Position | Unit sequence |
|---|---|---|---|---|
| AL048920 | UNKNOWN | 25 | 2 | T |
| AL048950 | UNKNOWN | 42 | 2 | T |
| AL048961 | UNKNOWN | 12 | 346 | A |
| AL048966 | UNKNOWN | 18 | 2 | T |
| AL048969 | UNKNOWN | 20 | 548 | A |
| AL048969 | UNKNOWN | 16 | 254 | A |
| AL048994 | UNKNOWN | 15 | 575 | A |
| AL048996 | UNKNOWN | 15 | 2 | T |
| AL049000 | UNKNOWN | 20 | 2 | T |
| AL049003 | UNKNOWN | 61 | 2 | T |
| AL049053 | UNKNOWN | 62 | 2 | T |
| AL049176 | 3' UTR | 24 | 2493 | TG |
| AL049176 | 3' UTR | 17 | 1288 | AC |
| AL049176 | 3' UTR | 10 | 1252 | TC |
| AL049215 | UNKNOWN | 18 | 1933 | A |
| AL049218 | UNKNOWN | 18 | 1474 | A |
| AL049219 | UNKNOWN | 19 | 1704 | A |
| AL049219 | UNKNOWN | 12 | 594 | T |
| AL049223 | UNKNOWN | 19 | 1570 | A |
| AL049223 | UNKNOWN | 13 | 879 | A |
| AL049226 | UNKNOWN | 3.8 | 1140 | AAACA |
| AL049226 | UNKNOWN | 19 | 1402 | A |
| AL049226 | UNKNOWN | 12 | 96 | A |
| AL049227 | UNKNOWN | 18 | 1869 | A |
| AL049227 | UNKNOWN | 17 | 18 | T |
| AL049228 | UNKNOWN | 19 | 1619 | A |
| AL049228 | UNKNOWN | 17 | 244 | T |
| AL049229 | UNKNOWN | 23 | 68 | T |
| AL049229 | UNKNOWN | 19 | 1767 | A |
| AL049232 | UNKNOWN | 20 | 26 | T |
| AL049232 | UNKNOWN | 19 | 2135 | A |
| AL049232 | UNKNOWN | 18 | 1953 | A |
| AL049233 | UNKNOWN | 20 | 3613 | A |
| AL049242 | UNKNOWN | 19 | 1262 | A |
| AL049242 | UNKNOWN | 14 | 652 | A |
| AL049246 | UNKNOWN | 21 | 3650 | A |
| AL049246 | UNKNOWN | 15 | 357 | A |
| AL049250 | UNKNOWN | 19 | 2481 | A |
| AL049257 | UNKNOWN | 16 | 2465 | A |
| AL049257 | UNKNOWN | 13 | 978 | A |
| AL049259 | UNKNOWN | 17 | 1674 | A |
| AL049259 | UNKNOWN | 14 | 1330 | T |
| AL049261 | UNKNOWN | 18 | 2997 | A |
| AL049261 | UNKNOWN | 13 | 2368 | A |
| AL049263 | UNKNOWN | 3.85 | 2896 | TTTTTA |
| AL049263 | UNKNOWN | 23 | 1209 | T |
| AL049263 | UNKNOWN | 22 | 4420 | A |
| AL049263 | UNKNOWN | 12 | 1050 | T |
| AL049265 | UNKNOWN | 14 | 2850 | A |
| AL049266 | UNKNOWN | 18 | 2943 | A |
| AL049268 | UNKNOWN | 20 | 2427 | A |
| AL049270 | UNKNOWN | 13.25 | 46 | AGAA |
| AL049270 | UNKNOWN | 17 | 1701 | A |
| AL049274 | UNKNOWN | 20 | 742 | A |
| AL049274 | UNKNOWN | 13 | 42 | T |
| AL049278 | UNKNOWN | 17 | 1119 | A |
| AL049279 | UNKNOWN | 20 | 3683 | A |
| AL049279 | UNKNOWN | 14 | 567 | A |
| AL049280 | UNKNOWN | 7 | 3352 | AG |
| AL049280 | UNKNOWN | 17 | 3386 | A |
| AL049282 | UNKNOWN | 19 | 1190 | A |
| AL049288 | UNKNOWN | 7.5 | 1442 | TG |
| AL049288 | UNKNOWN | 20 | 2018 | A |
| AL049296 | UNKNOWN | 20 | 1093 | A |
| AL049299 | UNKNOWN | 22 | 2517 | A |
| AL049301 | UNKNOWN | 28 | 541 | A |
| AL049305 | UNKNOWN | 17 | 1652 | A |
| AL049309 | UNKNOWN | 19 | 1055 | A |
| AL049313 | UNKNOWN | 18 | 2190 | A |
| AL049319 | UNKNOWN | 21 | 1342 | A |
| AL049321 | UNKNOWN | 18 | 1440 | A |
| AL049325 | UNKNOWN | 20 | 1591 | A |
| AL049325 | UNKNOWN | 17 | 1232 | A |
| AL049328 | UNKNOWN | 21 | 1785 | A |
| AL049331 | UNKNOWN | 19 | 1950 | A |
| AL049332 | UNKNOWN | 20 | 3750 | A |
| AL049335 | UNKNOWN | 19 | 996 | A |

TABLE 1-continued

| Genbank # | Region | # reps | Position | Unit sequence |
|---|---|---|---|---|
| AL049337 | UNKNOWN | 5.75 | 1618 | TTTA |
| AL049337 | UNKNOWN | 20 | 1918 | A |
| AL049338 | UNKNOWN | 6.5 | 1177 | TA |
| AL049338 | UNKNOWN | 20 | 1466 | A |
| AL049340 | UNKNOWN | 16 | 1245 | A |
| AL049346 | UNKNOWN | 20 | 1554 | A |
| AL049354 | UNKNOWN | 20 | 1255 | A |
| AL049365 | UNKNOWN | 17 | 2544 | A |
| AL049365 | UNKNOWN | 12 | 2252 | T |
| AL049367 | UNKNOWN | 30 | 2322 | A |
| AL049367 | UNKNOWN | 12 | 1239 | T |
| AL049369 | UNKNOWN | 17 | 2046 | A |
| AL049369 | UNKNOWN | 14 | 915 | T |
| AL049370 | UNKNOWN | 17 | 2705 | A |
| AL049378 | UNKNOWN | 17 | 1752 | A |
| AL049378 | UNKNOWN | 15 | 1076 | A |
| AL049381 | UNKNOWN | 17 | 780 | A |
| AL049382 | UNKNOWN | 95 | 1599 | A |
| AL049385 | UNKNOWN | 17 | 2419 | A |
| AL049386 | UNKNOWN | 17 | 2103 | A |
| AL049387 | UNKNOWN | 17 | 3358 | A |
| AL049389 | UNKNOWN | 17 | 2309 | A |
| AL049390 | UNKNOWN | 17 | 2322 | A |
| AL049397 | UNKNOWN | 17 | 1720 | A |
| AL049404 | UNKNOWN | 17 | 2434 | A |
| AL049409 | UNKNOWN | 17 | 1419 | A |
| AL049415 | UNKNOWN | 22 | 230 | T |
| AL049415 | UNKNOWN | 17 | 1232 | A |
| AL049417 | UNKNOWN | 17 | 2665 | A |
| AL049417 | UNKNOWN | 16 | 2275 | A |
| AL049422 | UNKNOWN | 17 | 2317 | A |
| AL049423 | UNKNOWN | 4.5 | 712 | CATT |
| AL049423 | UNKNOWN | 21 | 576 | AC |
| AL049423 | UNKNOWN | 48 | 1689 | A |
| AL049423 | UNKNOWN | 14 | 1670 | A |
| AL049428 | UNKNOWN | 8 | 3143 | CA |
| AL049428 | UNKNOWN | 17 | 3196 | A |
| AL049428 | UNKNOWN | 13 | 423 | G |
| AL049430 | UNKNOWN | 91 | 1515 | A |
| AL049430 | UNKNOWN | 24 | 678 | A |
| AL049430 | UNKNOWN | 17 | 115 | A |
| AL049430 | UNKNOWN | 13 | 799 | T |
| AL049432 | UNKNOWN | 3.6 | 1839 | AAACA |
| AL049432 | UNKNOWN | 17 | 2510 | A |
| AL049435 | UNKNOWN | 17 | 2685 | A |
| AL049437 | UNKNOWN | 17 | 2124 | A |
| AL049437 | UNKNOWN | 12 | 186 | T |
| AL049442 | UNKNOWN | 17 | 2003 | A |
| AL049443 | UNKNOWN | 17 | 1983 | A |
| AL049449 | UNKNOWN | 17 | 1036 | A |
| AL049450 | UNKNOWN | 17 | 1416 | A |
| AL049470 | UNKNOWN | 17 | 2243 | A |
| AL049470 | UNKNOWN | 12 | 1125 | T |
| AL049471 | UNKNOWN | 8 | 1037 | AT |
| AL049471 | UNKNOWN | 17 | 2879 | A |
| AL049538 | 3' UTR | 26 | 1842 | T |
| AL049544 | 3' UTR | 14 | 466 | T |
| AL049548 | 3' UTR | 13 | 3225 | T |
| AL049610 | 3' UTR | 13 | 1576 | T |
| AL049634 | 3' UTR | 8.5 | 2983 | CT |
| AL049654 | CDS | 7 | 1369 | GGA |
| AL049685 | 3' UTR | 28 | 2627 | TC |
| AL049685 | 3' UTR | 19 | 1190 | T |
| AL049782 | UNKNOWN | 21 | 2876 | A |
| AL049782 | UNKNOWN | 12 | 2274 | A |
| AL049925 | 3' UTR | 12 | 1581 | A |
| AL049932 | UNKNOWN | 21 | 1844 | A |
| AL049932 | UNKNOWN | 19 | 0 | T |
| AL049932 | UNKNOWN | 14 | 1636 | A |
| AL049935 | UNKNOWN | 3.6 | 1632 | TTTCT |
| AL049935 | UNKNOWN | 25.5 | 704 | TG |
| AL049935 | UNKNOWN | 8 | 2710 | TC |
| AL049935 | UNKNOWN | 19 | 5938 | A |
| AL049935 | UNKNOWN | 15 | 1953 | T |
| AL049938 | 3' UTR | 58 | 1306 | A |
| AL049938 | 3' UTR | 38 | 1267 | A |
| AL049940 | UNKNOWN | 6 | 1360 | AAT |

TABLE 1-continued

| Genbank # | Region | # reps | Position | Unit sequence |
|---|---|---|---|---|
| AL049940 | UNKNOWN | 20 | 3555 | A |
| AL049940 | UNKNOWN | 14 | 170 | A |
| AL049941 | UNKNOWN | 8.33 | 2531 | AAC |
| AL049941 | UNKNOWN | 16 | 2708 | A |
| AL049946 | 3' UTR | 7 | 2281 | AT |
| AL049948 | UNKNOWN | 19 | 1027 | A |
| AL049949 | UNKNOWN | 20 | 2738 | A |
| AL049949 | UNKNOWN | 12 | 1424 | A |
| AL049951 | UNKNOWN | 8 | 1425 | AT |
| AL049951 | UNKNOWN | 20 | 1707 | A |
| AL049957 | UNKNOWN | 21 | 890 | T |
| AL049957 | UNKNOWN | 19 | 2180 | A |
| AL049962 | UNKNOWN | 18 | 1839 | A |
| AL049963 | UNKNOWN | 18 | 1322 | A |
| AL049966 | UNKNOWN | 19 | 2143 | A |
| AL049966 | UNKNOWN | 18 | 2115 | A |
| AL049969 | UNKNOWN | 20 | 2460 | A |
| AL049973 | UNKNOWN | 6.66 | 2215 | TGA |
| AL049973 | UNKNOWN | 5.66 | 145 | AAC |
| AL049973 | UNKNOWN | 6.5 | 1567 | GT |
| AL049973 | UNKNOWN | 26 | 53 | T |
| AL049973 | UNKNOWN | 19 | 2170 | A |
| AL049974 | UNKNOWN | 10 | 2280 | ATG |
| AL049974 | UNKNOWN | 24 | 2231 | A |
| AL049974 | UNKNOWN | 19 | 0 | T |
| AL049977 | UNKNOWN | 19 | 1071 | A |
| AL049979 | UNKNOWN | 19 | 2167 | A |
| AL049983 | UNKNOWN | 7.5 | 32 | TC |
| AL049983 | UNKNOWN | 19 | 1766 | A |
| AL049983 | UNKNOWN | 13 | 46 | T |
| AL049985 | UNKNOWN | 6 | 8 | CTA |
| AL049985 | UNKNOWN | 20 | 1023 | A |
| AL049985 | UNKNOWN | 19 | 73 | T |
| AL049987 | UNKNOWN | 19 | 1196 | A |
| AL049990 | UNKNOWN | 18 | 1701 | A |
| AL049991 | UNKNOWN | 19 | 1383 | A |
| AL049992 | UNKNOWN | 18 | 1211 | A |
| AL049997 | UNKNOWN | 19 | 1449 | A |
| AL049998 | UNKNOWN | 4.75 | 216 | AAAC |
| AL049998 | UNKNOWN | 18 | 1286 | A |
| AL050002 | UNKNOWN | 5.5 | 536 | TTGT |
| AL050002 | UNKNOWN | 19 | 1546 | A |
| AL050005 | UNKNOWN | 20 | 2172 | A |
| AL050007 | CDS | 20 | 27 | T |
| AL050012 | UNKNOWN | 20 | 4491 | A |
| AL050012 | UNKNOWN | 14 | 3414 | T |
| AL050019 | 3' UTR | 4 | 2432 | GCTGG |
| AL050021 | UNKNOWN | 20 | 3084 | A |
| AL050021 | UNKNOWN | 12 | 9 | T |
| AL050025 | 3' UTR | 7 | 2965 | TG |
| AL050025 | 3' UTR | 23 | 2817 | A |
| AL050035 | UNKNOWN | 20 | 1289 | A |
| AL050037 | 3' UTR | 23 | 1363 | T |
| AL050041 | UNKNOWN | 22 | 1768 | A |
| AL050041 | UNKNOWN | 17 | 836 | A |
| AL050043 | UNKNOWN | 31 | 910 | A |
| AL050043 | UNKNOWN | 24 | 736 | A |
| AL050047 | UNKNOWN | 18 | 2611 | A |
| AL050053 | UNKNOWN | 19 | 1734 | A |
| AL050061 | UNKNOWN | 20 | 2051 | A |
| AL050063 | UNKNOWN | 18 | 1978 | A |
| AL050064 | UNKNOWN | 22 | 2989 | A |
| AL050064 | UNKNOWN | 14 | 179 | A |
| AL050064 | UNKNOWN | 12 | 855 | T |
| AL050065 | UNKNOWN | 17 | 1568 | A |
| AL050065 | UNKNOWN | 16 | 28 | T |
| AL050066 | UNKNOWN | 19 | 1173 | A |
| AL050074 | UNKNOWN | 20 | 2201 | A |
| AL050078 | UNKNOWN | 5.75 | 1547 | TTTG |
| AL050078 | UNKNOWN | 19 | 5028 | A |
| AL050081 | UNKNOWN | 20 | 1365 | A |
| AL050084 | 3' UTR | 16 | 1028 | A |
| AL050087 | UNKNOWN | 3.5 | 813 | TCTTTC |
| AL050087 | UNKNOWN | 10 | 829 | TC |
| AL050100 | 3' UTR | 15 | 1582 | T |
| AL050105 | 3' UTR | 19.5 | 732 | TG |
| AL050105 | 3' UTR | 8.5 | 770 | TA |

TABLE 1-continued

| Genbank # | Region | # reps | Position | Unit sequence |
|---|---|---|---|---|
| AL050106 | UNKNOWN | 22 | 1599 | T |
| AL050106 | UNKNOWN | 17 | 2254 | A |
| AL050107 | CDS | 6 | 245 | CAG |
| AL050107 | 3' UTR | 4.75 | 3101 | AAAT |
| AL050107 | 3' UTR | 12 | 1594 | T |
| AL050119 | UNKNOWN | 17 | 776 | A |
| AL050119 | UNKNOWN | 14 | 216 | T |
| AL050120 | 3' UTR | 8 | 1019 | TA |
| AL050125 | UNKNOWN | 5.2 | 2322 | TTTTG |
| AL050125 | UNKNOWN | 4.8 | 2633 | AAAAC |
| AL050125 | UNKNOWN | 17 | 3518 | A |
| AL050126 | 3' UTR | 12 | 1569 | A |
| AL050127 | UNKNOWN | 17 | 1686 | A |
| AL050128 | UNKNOWN | 17 | 1950 | A |
| AL050130 | UNKNOWN | 17 | 1776 | A |
| AL050136 | UNKNOWN | 17 | 3473 | A |
| AL050139 | UNKNOWN | 22 | 814 | T |
| AL050139 | UNKNOWN | 17 | 3293 | A |
| AL050141 | UNKNOWN | 17.5 | 574 | TG |
| AL050141 | UNKNOWN | 7.5 | 1695 | CT |
| AL050141 | UNKNOWN | 17 | 2353 | A |
| AL050143 | 3' UTR | 2.92 | 570 | GCCACACAGCAAATGCTAATATGCTCCAGTGTTAGCTTAGAAGCCTTGTGTCAACAAGAACTGGCTCCTGAGTCCCAAGCTTGGT (SEQ ID NO: 189) |
| AL050143 | 3' UTR | 17 | 2214 | C |
| AL050145 | UNKNOWN | 6.5 | 453 | AC |
| AL050145 | UNKNOWN | 17 | 1989 | A |
| AL050148 | UNKNOWN | 17 | 3013 | A |
| AL050151 | UNKNOWN | 17 | 2344 | A |
| AL050152 | UNKNOWN | 17 | 2821 | A |
| AL050153 | 3' UTR | 13 | 957 | GA |
| AL050154 | UNKNOWN | 17 | 1868 | A |
| AL050159 | 3' UTR | 16 | 857 | T |
| AL050159 | 3' UTR | 14 | 1119 | A |
| AL050166 | UNKNOWN | 17 | 2654 | A |
| AL050171 | UNKNOWN | 17 | 1472 | A |
| AL050172 | UNKNOWN | 65 | 1762 | A |
| AL050173 | 3' UTR | 7 | 3627 | GT |
| AL050173 | 3' UTR | 13 | 2999 | A |
| AL050179 | 3' UTR | 4 | 957 | GTTTT |
| AL050187 | UNKNOWN | 19 | 953 | T |
| AL050187 | UNKNOWN | 14 | 1787 | A |
| AL050189 | UNKNOWN | 9.5 | 1128 | TA |
| AL050199 | UNKNOWN | 15 | 1779 | A |
| AL050199 | UNKNOWN | 13 | 758 | A |
| AL050201 | UNKNOWN | 16 | 1810 | A |
| AL050201 | UNKNOWN | 15 | 994 | A |
| AL050202 | UNKNOWN | 13 | 1169 | A |
| AL050204 | UNRNOWN | 8 | 49 | ATT |
| AL050204 | UNKNOWN | 21 | 1634 | A |
| AL050205 | UNKNOWN | 7 | 618 | GT |
| AL050209 | UNKNOWN | 16 | 1278 | A |
| AL050217 | UNKNOWN | 12 | 1111 | A |
| AL050223 | UNKNOWN | 38 | 223 | A |
| AL050224 | UNKNOWN | 18 | 1250 | A |
| AL050227 | UNKNOWN | 15 | 1269 | A |
| AL050257 | 3' UTR | 12 | 652 | A |
| AL050260 | 5' UTR | 15 | 562 | T |
| AL050263 | 3' UTR | 13 | 2029 | T |
| AL050270 | 3' UTR | 2.8 | 3082 | AAGAAGAACT (SEQ ID NO: 190) |
| AL050270 | 3' UTR | 5.5 | 1831 | GTAA |
| AL050270 | 3' UTR | 6.66 | 3070 | AAG |
| AL050283 | 3' UTR | 17 | 1673 | TA |
| AL050284 | 3' UTR | 20 | 1753 | TG |
| AL050284 | 3' UTR | 13 | 1792 | GC |
| AL050337 | 3' UTR | 14 | 1779 | T |
| AL050353 | UNKNOWN | 14 | 1077 | T |
| AL050355 | UNKNOWN | 37 | 0 | T |
| AL050355 | UNKNOWN | 18 | 2202 | A |
| AL050356 | UNKNOWN | 21 | 2396 | A |
| AL050358 | UNKNOWN | 20 | 2988 | A |
| AL050361 | UNKNOWN | 19 | 1608 | A |
| AL050361 | UNKNOWN | 15 | 1313 | A |
| AL050364 | UNKNOWN | 5 | 1039 | TGTA |
| AL050364 | UNKNOWN | 19 | 1903 | A |
| AL050366 | UNKNOWN | 42 | 5465 | A |
| AL050366 | UNKNOWN | 13 | 5449 | T |

TABLE 1-continued

| Genbank # | Region | # reps | Position | Unit sequence |
|---|---|---|---|---|
| AL050367 | UNKNOWN | 20 | 3938 | A |
| AL050367 | UNKNOWN | 12 | 3823 | A |
| AL050370 | UNKNOWN | 6.5 | 685 | TG |
| AL050370 | UNKNOWN | 20 | 2495 | A |
| AL050371 | UNKNOWN | 19 | 2530 | A |
| AL050373 | UNKNOWN | 17 | 1965 | A |
| AL050378 | UNKNOWN | 17 | 2743 | A |
| AL050379 | UNKNOWN | 3.57 | 458 | AAAACAA |
| AL050379 | UNKNOWN | 3.83 | 144 | AAAAAC |
| AL050379 | UNKNOWN | 17 | 1478 | A |
| AL050379 | UNKNOWN | 12 | 477 | A |
| AL050381 | UNRNOWN | 16 | 1485 | A |
| AL050385 | UNKNOWN | 18 | 5493 | A |
| AL050386 | UNKNOWN | 20 | 1848 | A |
| AL050388 | UNKNOWN | 20 | 1964 | A |
| AL050388 | UNKNOWN | 12 | 1224 | T |
| AL050390 | UNKNOWN | 20 | 2495 | A |
| AL050391 | UNKNOWN | 4.75 | 3070 | CAAT |
| AL050391 | UNKNOWN | 12.5 | 3250 | AG |
| AL050391 | UNKNOWN | 12 | 1009 | GT |
| AL050391 | UNKNOWN | 11.5 | 3228 | AC |
| AL050391 | UNKNOWN | 17 | 4747 | A |
| AL050393 | UNKNOWN | 156 | 3326 | A |
| AL050395 | UNKNOWN | 17 | 1342 | A |
| AL050397 | UNKNOWN | 19 | 2194 | A |
| AL078636 | UNKNOWN | 15 | 45 | A |
| AL079275 | UNKNOWN | 22 | 2082 | A |
| AL079279 | UNKNOWN | 22 | 2428 | A |
| AL079283 | UNKNOWN | 18 | 1454 | A |
| AL079286 | UNKNOWN | 20 | 1717 | A |
| AL079289 | UNKNOWN | 22 | 1319 | A |
| AL079294 | UNKNOWN | 19 | 1160 | A |
| AL079310 | CDS | 7 | 1431 | AG |
| AL079366 | UNKNOWN | 19 | 0 | T |
| AL079370 | UNKNOWN | 20 | 0 | T |
| AL079372 | UNKNOWN | 17 | 0 | T |
| AL079374 | UNKNOWN | 19 | 0 | T |
| AL079376 | UNKNOWN | 20 | 0 | T |
| AL079392 | UNKNOWN | 27 | 0 | T |
| AL079447 | UNKNOWN | 50 | 1 | T |
| AL079457 | UNKNOWN | 4.8 | 144 | AAAAT |
| AL079457 | UNKNOWN | 9 | 37 | AC |
| AL079466 | UNKNOWN | 29 | 347 | A |
| AL079493 | UNKNOWN | 19 | 0 | T |
| AL079648 | UNKNOWN | 35 | 0 | T |
| AL079689 | UNKNOWN | 19 | 342 | A |
| AL079689 | UNKNOWN | 17 | 17 | T |
| AL079728 | UNKNOWN | 70 | 267 | A |
| AL079734 | UNKNOWN | 38 | 346 | A |
| AL079740 | UNKNOWN | 87 | 156 | A |
| AL079834 | UNKNOWN | 29 | 270 | A |
| AL079838 | UNKNOWN | 26 | 8 | T |
| AL079907 | UNKNOWN | 5 | 648 | CCTC |
| AL079907 | UNKNOWN | 8 | 618 | TC |
| AL079908 | UNKNOWN | 17 | 523 | A |
| AL079947 | UNKNOWN | 15 | 123 | A |
| AL079960 | UNKNOWN | 53 | 102 | A |
| AL079999 | UNKNOWN | 22 | 639 | A |
| AL080045 | UNKNOWN | 55 | 219 | A |
| AL080059 | UNKNOWN | 19 | 2607 | A |
| AL080060 | UNKNOWN | 130 | 0 | T |
| AL080060 | UNKNOWN | 19 | 1064 | A |
| AL080062 | 3' UTR | 21 | 1070 | T |
| AL080062 | 3' UTR | 16 | 1251 | A |
| AL080066 | UNKNOWN | 17 | 1291 | A |
| AL080068 | UNKNOWN | 18 | 2095 | A |
| AL080072 | UNKNOWN | 21 | 1300 | A |
| AL080075 | UNNNOWN | 20 | 1150 | A |
| AL080077 | UNKNOWN | 19 | 1457 | A |
| AL080077 | UNKNOWN | 16 | 198 | A |
| AL080078 | UNKNOWN | 15 | 559 | TG |
| AL080078 | UNKNOWN | 17 | 1876 | A |
| AL080080 | 3' UTR | 15 | 1740 | T |
| AL080082 | UNKNOWN | 19 | 1006 | A |
| AL080093 | UNKNOWN | 5.25 | 1019 | ATTT |
| AL080093 | UNKNOWN | 20 | 1809 | A |
| AL080094 | UNKNOWN | 21 | 1062 | A |

TABLE 1-continued

| Genbank # | Region | # reps | Position | Unit sequence |
|---|---|---|---|---|
| AL080095 | UNKNOWN | 20 | 2017 | A |
| AL080101 | UNKNOWN | 19 | 1058 | A |
| AL080102 | CDS | 7.66 | 1008 | CAC |
| AL060103 | UNKNOWN | 20 | 2020 | A |
| AL080107 | UNKNOWN | 5 | 165 | GTTT |
| AL080107 | UNKNOWN | 17 | 1566 | A |
| AL080107 | UNKNOWN | 15 | 266 | A |
| AL080110 | UNKNOWN | 58 | 1808 | A |
| AL080111 | UNKNOWN | 17 | 1650 | A |
| AL080112 | UNKNOWN | 17 | 1509 | A |
| AL080112 | UNKNOWN | 16 | 49 | T |
| AL080113 | UNKNOWN | 17 | 1665 | A |
| AL080114 | UNKNOWN | 5.75 | 803 | AAAC |
| AL080114 | UNKNOWN | 18 | 1805 | A |
| AL080122 | 3' UTR | 13 | 967 | A |
| AL080130 | UNKNOWN | 30 | 3960 | A |
| AL080130 | UNKNOWN | 20 | 3390 | T |
| AL080130 | UNKNOWN | 13 | 2433 | T |
| AL080132 | UNKNOWN | 43 | 2856 | A |
| AL080134 | UNKNOWN | 27 | 3095 | A |
| AL080135 | UNKNOWN | 21 | 5242 | A |
| AL080135 | UNKNOWN | 13 | 3188 | A |
| AL080142 | UNKNOWN | 23 | 2166 | A |
| AL080142 | UNKNOWN | 16 | 1302 | A |
| AL080151 | UNKNOWN | 41 | 2821 | A |
| AL080153 | CDS | 6.5 | 502 | GA |
| AL080155 | 3' UTR | 13 | 1699 | A |
| AL080157 | 3' UTR | 4.75 | 1996 | AAAT |
| AL080161 | UNKNOWN | 27 | 2668 | A |
| AL080162 | 3' UTR | 7 | 1724 | GA |
| AL080170 | CDS | 8.33 | 97 | CTC |
| AL080170 | 3' UTR | 6.5 | 1806 | CT |
| AL080172 | UNKNOWN | 2.9 | 3315 | TTTTTTTTG (SEQ ID NO: 191) |
| AL080172 | UNKNOWN | 12 | 3312 | T |
| AL080180 | UNKNOWN | 5.66 | 2575 | TTG |
| AL080181 | UNNOWN | 3.83 | 720 | AAAAAC |
| AL080181 | UNKNOWN | 7 | 255 | TA |
| AL080181 | UNKNOWN | 12 | 738 | A |
| AL080188 | UNKNOWN | 15 | 3754 | A |
| AL080190 | UNKNOWN | 16 | 1469 | A |
| AL080191 | 3' UTR | 27.5 | 1096 | AC |
| AL080192 | UNKNOWN | 12 | 1718 | A |
| AL080202 | UNKNOWN | 13 | 2768 | A |
| AL080209 | UNKNOWN | 15 | 2863 | AC |
| AL080209 | UNKNOWN | 13 | 4124 | A |
| AL080210 | UNKNOWN | 12 | 1388 | A |
| AL080213 | UNKNOWN | 12 | 2640 | A |
| AL080215 | UNKNOWN | 17 | 2463 | A |
| AL080215 | UNKNOWN | 14 | 340 | T |
| AL080216 | UNKNOWN | 25 | 2204 | A |
| AL080222 | UNKNOWN | 20 | 1843 | A |
| AL080222 | UNKNOWN | 13 | 1884 | T |
| AL080223 | UNKNOWN | 21 | 1782 | A |
| AL080232 | UNKNOWN | 17 | 3033 | A |
| AL080232 | UNKNOWN | 14 | 2493 | A |
| AL080232 | UNKNOWN | 12 | 806 | T |
| AL080233 | UNKNOWN | 5 | 564 | TCTCCC |
| AL080233 | UNKNOWN | 20 | 42 | A |
| AL080234 | UNKNOWN | 4.8 | 282 | TTTTG |
| AL080234 | UNKNOWN | 51 | 2088 | A |
| AL080235 | CDS | 6.66 | 387 | GCC |
| AL096713 | UNNOWN | 18 | 4827 | A |
| AL096714 | UNKNOWN | 19 | 1904 | A |
| AL096716 | 3' UTR | 8.5 | 1262 | TA |
| AL096716 | 3' UTR | 6.5 | 1278 | TG |
| AL096719 | UNKNOWN | 21 | 2185 | A |
| AL096719 | UNKNOWN | 12 | 232 | T |
| AL096723 | UNKNOWN | 5.66 | 1031 | AGG |
| AL096723 | UNKNOWN | 18 | 2965 | A |
| AL096727 | UNKNOWN | 45 | 1681 | A |
| AL096729 | UNKNOWN | 6.25 | 797 | ATTC |
| AL096729 | UNKNOWN | 6.5 | 2130 | GT |
| AL096729 | UNKNOWN | 32 | 2393 | A |
| AL096732 | UNKNOWN | 17 | 2941 | A |
| AL096734 | UNKNOWN | 15 | 375 | T |
| AL096738 | UNKNOWN | 15 | 4392 | A |
| AL096739 | UNKNOWN | 17 | 3147 | A |

TABLE 1-continued

| Genbank # | Region | # reps | Position | Unit sequence |
|---|---|---|---|---|
| AL096744 | UNKNOWN | 85 | 2517 | A |
| AL096748 | 3' UTR | 2.5 | 2075 | AAAAAAAAAG (SEQ ID NO: 192) |
| AL096749 | UNKNOWN | 30 | 2658 | A |
| AL096750 | UNKNOWN | 46 | 3095 | A |
| AL096751 | UNKNOWN | 65 | 3414 | A |
| AL096857 | 3' UTR | 8.5 | 9918 | AT |
| AL096879 | 3' UTR | 12 | 3054 | T |
| AL109666 | UNKNOWN | 18 | 1782 | A |
| AL109667 | UNKNOWN | 18 | 3618 | A |
| AL109669 | UNKNOWN | 23 | 2756 | A |
| AL109671 | UNKNOWN | 19 | 2320 | A |
| AL109674 | UNKNOWN | 22 | 1101 | A |
| AL109678 | UNKNOWN | 6.5 | 439 | AG |
| AL109678 | UNKNOWN | 19 | 1407 | A |
| AL109679 | 3' UTR | 12 | 905 | A |
| AL109681 | UNKNOWN | 20 | 1459 | A |
| AL109682 | UNKNOWN | 20 | 2316 | A |
| AL109690 | UNKNOWN | 17 | 1221 | A |
| AL109690 | UNKNOWN | 16 | 1174 | T |
| AL109691 | UNKNOWN | 19 | 1434 | A |
| AL109693 | UNKNOWN | 20 | 1233 | A |
| AL109695 | UNKNOWN | 33 | 1564 | A |
| AL109696 | UNNNOWN | 15.5 | 1513 | TG |
| AL109696 | UNKNOWN | 19 | 1999 | A |
| AL109698 | UNKNOWN | 23 | 2035 | A |
| AL109699 | UNKNOWN | 19 | 1167 | A |
| AL109700 | UNKNOWN | 22 | 2194 | A |
| AL109700 | UNKNOWN | 14 | 1454 | A |
| AL109702 | UNKNOWN | 18 | 1869 | A |
| AL109703 | UNKNOWN | 3.62 | 262 | ATATGATATATAAATGTTATATGTTATATATG (SEQ ID NO: 193) |
| AL109703 | UNKNOWN | 3.25 | 57 | TATGTTATATATAATATGATATATAAATGTTA (SEQ ID NO: 194) |
| AL109703 | UNKNOWN | 2.96 | 130 | TATAAATATGATATATAAATGTTATATGTTATG (SEQ ID NO: 195) |
| AL109703 | UNKNOWN | 2.96 | 1 | TTATATATAATATGATATATAAATGTTATG (SEQ ID NO: 196) |
| AL109703 | UNKNOWN | 10 | 600 | TA |
| AL109703 | UNKNOWN | 19 | 1539 | A |
| AL109705 | UNKNOWN | 24 | 62 | A |
| AL109706 | UNKNOWN | 7.8 | 0 | GTTTA |
| AL109706 | UNKNOWN | 19 | 2501 | A |
| AL109707 | UNKNOWN | 4 | 203 | GTTTT |
| AL109707 | UNKNOWN | 19 | 1335 | A |
| AL109708 | UNKNOWN | 18 | 1053 | A |
| AL109709 | UNKNOWN | 18 | 2082 | A |
| AL109712 | UNKNOWN | 24 | 992 | A |
| AL109714 | UNKNOWN | 22 | 1004 | A |
| AL109716 | UNKNOWN | 25 | 1297 | A |
| AL109722 | UNKNOWN | 18 | 1698 | A |
| AL109724 | UNKNOWN | 20 | 1369 | A |
| AL109725 | UNKNOWN | 45 | 1396 | A |
| AL109726 | UNKNOWN | 18 | 1091 | A |
| AL109730 | UNKNOWN | 18 | 1014 | A |
| AL109779 | UNKNOWN | 27 | 1304 | A |
| AL109779 | UNKNOWN | 12 | 159 | T |
| AL109780 | UNKNOWN | 41 | 1559 | A |
| AL109781 | UNKNOWN | 19 | 1376 | A |
| AL109783 | UNKNOWN | 23 | 1779 | A |
| AL109786 | UNKNOWN | 26 | 1856 | A |
| AL109788 | UNKNOWN | 5.66 | 356 | AGC |
| AL109788 | UNKNOWN | 13 | 1875 | A |
| AL109788 | UNKNOWN | 12 | 1111 | T |
| AL109791 | UNKNOWN | 18 | 2092 | A |
| AL109792 | UNKNOWN | 6.5 | 1107 | AG |
| AL109792 | UNKNOWN | 18 | 1387 | A |
| AL109793 | UNKNOWN | 19 | 2155 | A |
| AL109793 | UNKNOWN | 14 | 1198 | T |
| AL109795 | UNKNOWN | 24 | 1937 | A |
| AL109817 | UNKNOWN | 31 | 1295 | A |
| AL109959 | UNKNOWN | 6 | 135 | AAT |
| AL109959 | UNKNOWN | 21 | 1216 | A |
| AL109978 | CDS | 6.5 | 259 | AG |
| AL110125 | UNKNOWN | 19 | 1651 | A |
| AL110126 | UNKNOWN | 20 | 1445 | A |
| AL110126 | UNKNOWN | 14 | 181 | T |
| AL110126 | UNKNOWN | 13 | 612 | A |

TABLE 1-continued

| Genbank # | Region | # reps | Position | Unit sequence |
|---|---|---|---|---|
| AL110129 | UNKNOWN | 20 | 2158 | A |
| AL110130 | UNKNOWN | 20 | 2389 | A |
| AL110130 | UNKNOWN | 13 | 2045 | A |
| AL110131 | UNKNOWN | 21 | 2874 | A |
| AL110132 | UNKNOWN | 3.85 | 309 | GTTTTTT |
| AL110132 | UNKNOWN | 23 | 381 | A |
| AL110132 | UNKNOWN | 19 | 0 | T |
| AL110133 | UNKNOWN | 20 | 6393 | A |
| AL110133 | UNKNOWN | 12 | 3324 | T |
| AL110135 | UNKNOWN | 22 | 0 | T |
| AL110135 | UNKNOWN | 21 | 4070 | A |
| AL110136 | UNKNOWN | 20 | 1865 | A |
| AL110136 | UNKNOWN | 13 | 1340 | A |
| AL110137 | UNKNOWN | 20 | 1257 | A |
| AL110139 | UNKNOWN | 8.5 | 14 | GT |
| AL110139 | UNKNOWN | 20 | 1325 | A |
| AL110145 | UNKNOWN | 17 | 1286 | A |
| AL110145 | UNKNOWN | 15 | 406 | A |
| AL110147 | 3' UTR | 16 | 1164 | A |
| AL110150 | UNKNOWN | 17 | 63 | T |
| AL110150 | UNKNOWN | 17 | 1247 | A |
| AL110152 | UNKNOWN | 17 | 1324 | A |
| AL110153 | UNKNOWN | 17 | 1473 | A |
| AL110161 | UNKNOWN | 17 | 2663 | A |
| AL110163 | UNKNOWN | 17 | 1526 | A |
| AL110164 | UNKNOWN | 17 | 1688 | A |
| AL110164 | UNKNOWN | 16 | 1218 | A |
| AL110167 | UNKNOWN | 17 | 1202 | A |
| AL110169 | UNKNOWN | 17 | 1443 | A |
| AL110171 | UNKNOWN | 67 | 991 | A |
| AL110174 | UNKNOWN | 20 | 1467 | A |
| AL110174 | UNKNOWN | 13 | 298 | A |
| AL110176 | UNKNOWN | 14 | 2098 | A |
| AL110176 | UNKNOWN | 13 | 423 | T |
| AL110179 | UNKNOWN | 6.5 | 1077 | TA |
| AL110179 | UNKNOWN | 20 | 2613 | A |
| AL110180 | UNKNOWN | 25 | 2310 | A |
| AL110181 | UNKNOWN | 19 | 1759 | A |
| AL110187 | UNKNOWN | 21 | 1890 | A |
| AL110189 | UNKNOWN | 5.25 | 1168 | TTTA |
| AL110189 | UNKNOWN | 28 | 1321 | A |
| AL110189 | UNKNOWN | 12 | 1054 | T |
| AL110194 | UNKNOWN | 21 | 1991 | A |
| AL110196 | UNKNOWN | 117 | 1422 | A |
| AL110197 | UNKNOWN | 68 | 1810 | A |
| AL110200 | UNKNOWN | 2.53 | 2250 | TCAGGAACATGTCAGTGTCCCAGAGCCA (SEQ ID NO: 197) |
| AL110200 | UNKNOWN | 17 | 2923 | A |
| AL110200 | UNKNOWN | 13 | 1894 | T |
| AL110202 | UNKNOWN | 17 | 2518 | A |
| AL110203 | UNKNOWN | 17 | 2043 | A |
| AL110203 | UNKNOWN | 16 | 1611 | T |
| AL110204 | UNKNOWN | 7.5 | 2853 | TG |
| AL110204 | UNKNOWN | 7.5 | 2887 | TA |
| AL110204 | UNKNOWN | 17 | 3544 | A |
| AL110205 | UNKNOWN | 4 | 1062 | TTTTG |
| AL110205 | UNKNOWN | 17 | 2068 | A |
| AL110207 | UNKNOWN | 6.5 | 1437 | AC |
| AL110207 | UNKNOWN | 17 | 1576 | A |
| AL110211 | UNKNOWN | 21 | 5314 | A |
| AL110211 | UNKNOWN | 14 | 2452 | T |
| AL110212 | UNKNOWN | 20 | 4441 | A |
| AL110212 | UNKNOWN | 15 | 1619 | T |
| AL110217 | 3' UTR | 12 | 2301 | A |
| AL110227 | UNKNOWN | 3.8 | 328 | TTTTA |
| AL110227 | UNKNOWN | 37 | 2288 | A |
| AL110229 | UNKNOWN | 5.75 | 2456 | TTTA |
| AL110229 | UNKNOWN | 40 | 3434 | A |
| AL110229 | UNKNOWN | 16 | 3329 | A |
| AL110236 | UNKNOWN | 20 | 2247 | A |
| AL110236 | UNKNOWN | 12 | 1413 | T |
| AL110237 | UNKNOWN | 20 | 1386 | A |
| AL110242 | UNKNOWN | 19 | 1161 | A |
| AL110252 | UNKNOWN | 30 | 2157 | A |
| AL110255 | UNKNOWN | 19 | 2154 | A |
| AL110255 | UNKNOWN | 12 | 1981 | T |
| AL110257 | UNKNOWN | 20 | 1801 | A |

TABLE 1-continued

| Genbank # | Region | # reps | Position | Unit sequence |
|---|---|---|---|---|
| AL110262 | UNKNOWN | 32 | 1041 | A |
| AL110265 | 5' UTR | 13 | 536 | T |
| AL110269 | 5' UTR | 12 | 1461 | A |
| AL110269 | 3' UTR | 14 | 3793 | T |
| AL110269 | 3' UTR | 13 | 3417 | A |
| AL110270 | UNKNOWN | 17 | 1356 | A |
| AL110272 | UNKNOWN | 20 | 1648 | A |
| AL110274 | UNKNOWN | 21 | 4393 | A |
| AL110280 | UNKNOWN | 82 | 4665 | A |
| AL110283 | UNKNOWN | 38 | 4666 | A |
| AL110300 | UNKNOWN | 20 | 1076 | A |
| AL110312 | UNKNOWN | 43 | 0 | T |
| AL110335 | UNKNOWN | 19 | 284 | A |
| AL110335 | UNKNOWN | 18 | 0 | T |
| AL110353 | UNKNOWN | 3.83 | 341 | TTTTTC |
| AL110353 | UNKNOWN | 19 | 0 | T |
| AL110359 | UNKNOWN | 15 | 498 | A |
| AL110380 | UNKNOWN | 8 | 545 | TC |
| AL110388 | UNKNOWN | 23 | 438 | A |
| AL110402 | UNKNOWN | 101 | 240 | A |
| AL110409 | UNKNOWN | 17 | 1 | T |
| AL110454 | UNKNOWN | 13 | 505 | A |
| AL117392 | 3' UTR | 2.9 | 4221 | AAAAAAAAAC (SEQ ID NO: 198) |
| AL117395 | 5' UTR | 5.6 | 940 | TTTTG |
| AL117397 | 5' UTR | 14 | 994 | A |
| AL117397 | 5' UTR | 13 | 1198 | T |
| AL117398 | UNKNOWN | 17 | 764 | T |
| AL117400 | 5' UTR | 6.5 | 5 | GA |
| AL117400 | 5' UTR | 17 | 769 | T |
| AL117401 | UNKNOWN | 16 | 4586 | A |
| AL117401 | UNKNOWN | 12 | 4226 | A |
| AL117406 | UNKNOWN | 12 | 1812 | A |
| AL117408 | CDS | 2.71 | 1384 | CAGGAGAAGGAGCGGCAGAAA (SEQ ID NO: 199) |
| AL117409 | UNKNOWN | 15 | 3237 | A |
| AL117413 | UNKNOWN | 20 | 1908 | A |
| AL117415 | UNKNOWN | 31 | 3001 | A |
| AL117416 | UNKNOWN | 72 | 1838 | A |
| AL117420 | UNKNOWN | 19 | 1320 | A |
| AL117421 | UNKNOWN | 18 | 1730 | A |
| AL117422 | UNKNOWN | 5.66 | 244 | GAG |
| AL117422 | UNKNOWN | 17 | 2774 | A |
| AL117422 | UNKNOWN | 13 | 2042 | A |
| AL117424 | 5' UTR | 7 | 143 | AGC |
| AL117425 | UNKNOWN | 20 | 4293 | A |
| AL117425 | UNKNOWN | 16 | 1562 | T |
| AL117426 | UNKNOWN | 20 | 4130 | A |
| AL117426 | UNKNOWN | 17 | 3419 | T |
| AL117426 | UNKNOWN | 14 | 3485 | A |
| AL117427 | UNKNOWN | 4 | 1297 | AAAAC |
| AL117427 | UNKNOWN | 20 | 3577 | A |
| AL117427 | UNKNOWN | 15 | 1871 | T |
| AL117427 | UNKNOWN | 12 | 1502 | A |
| AL117431 | UNKNOWN | 15 | 3112 | A |
| AL117433 | 3' UTR | 4 | 1517 | CCCCA |
| AL117436 | UNKNOWN | 15.5 | 1687 | TG |
| AL117436 | UNKNOWN | 23 | 4678 | A |
| AL117436 | UNKNOWN | 13 | 3859 | T |
| AL117437 | UNKNOWN | 39 | 2563 | A |
| AL117440 | UNKNOWN | 80 | 2736 | A |
| AL117441 | 3' UTR | 15 | 1739 | T |
| AL117445 | 3' UTR | 6.5 | 2246 | TG |
| AL117450 | UNKNOWN | 17 | 2612 | A |
| AL117450 | UNKNOWN | 13 | 2359 | A |
| AL117454 | UNKNOWN | 17 | 2216 | A |
| AL117454 | UNKNOWN | 14 | 1574 | A |
| AL117457 | UNKNOWN | 115 | 2284 | A |
| AL117461 | UNKNOWN | 17 | 3926 | A |
| AL117461 | UNKNOWN | 12 | 971 | T |
| AL117471 | 3' UTR | 17 | 1991 | A |
| AL117472 | 3' UTR | 5.66 | 4730 | TTG |
| AL117472 | 3' UTR | 13 | 4719 | T |
| AL117474 | UNKNOWN | 16 | 2955 | AT |
| AL117476 | 3' UTR | 16 | 1530 | T |
| AL117477 | 3' UTR | 5.5 | 1554 | CCTG |
| AL117481 | CDS | 2.92 | 304 | GGGACGCCGTCAAGGGCATCGCTGATC (SEQ ID NO: 200) |
| AL117489 | 3' UTR | 5.25 | 1471 | GGAT |

TABLE 1-continued

| Genbank # | Region | # reps | Position | Unit sequence |
|---|---|---|---|---|
| AL117490 | UNKNOWN | 12 | 762 | A |
| AL117496 | CDS | 5.66 | 3663 | AAG |
| AL117498 | 3' UTR | 5.75 | 1649 | AAAC |
| AL117499 | 3' UTR | 19.5 | 931 | TG |
| AL117499 | 3' UTR | 12 | 843 | T |
| AL117511 | 3' UTR | 4.2 | 500 | TGTTT |
| AL117511 | 3' UTR | 19 | 1021 | A |
| AL117513 | 3' UTR | 7 | 1841 | CA |
| AL117519 | UNKNOWN | 6.5 | 211 | TA |
| AL117530 | 3' UTR | 6.5 | 1980 | TG |
| AL117531 | UNKNOWN | 12 | 1710 | A |
| AL117533 | UNKNOWN | 16 | 1630 | A |
| AL117535 | UNKNOWN | 16 | 4572 | A |
| AL117537 | 3' UTR | 16.5 | 983 | AG |
| AL117543 | UNKNOWN | 13 | 998 | A |
| AL117546 | UNKNOWN | 4.75 | 2220 | TTTA |
| AL117546 | UNKNOWN | 12 | 3025 | A |
| AL117550 | UNKNOWN | 17 | 1762 | A |
| AL117553 | UNKNOWN | 20 | 1841 | A |
| AL117559 | UNKNOWN | 22 | 24 | T |
| AL117559 | UNKNOWN | 21 | 1633 | A |
| AL117560 | UNKNOWN | 19 | 2265 | A |
| AL117561 | UNKNOWN | 19 | 1970 | A |
| AL117565 | UNKNOWN | 19 | 1386 | A |
| AL117568 | UNKNOWN | 20 | 1514 | A |
| AL117571 | UNKNOWN | 18 | 1790 | A |
| AL117571 | UNKNOWN | 13 | 1044 | A |
| AL117574 | UNKNOWN | 29 | 2974 | A |
| AL117574 | UNKNOWN | 16 | 1266 | T |
| AL117574 | UNKNOWN | 14 | 838 | T |
| AL117580 | 3' UTR | 13.5 | 1141 | GT |
| AL117584 | 3' UTR | 3.6 | 2408 | TTTTG |
| AL117586 | UNKNOWN | 27 | 3438 | A |
| AL117587 | 3' UTR | 7.5 | 769 | AT |
| AL117587 | 3' UTR | 13 | 1346 | T |
| AL117590 | UNKNOWN | 45 | 2904 | A |
| AL117592 | UNKNOWN | 17 | 2105 | A |
| AL117592 | UNKNOWN | 14 | 1636 | T |
| AL117593 | UNKNOWN | 19 | 4491 | A |
| AL117593 | UNKNOWN | 13 | 719 | T |
| AL117595 | UNKNOWN | 6.5 | 594 | TA |
| AL117595 | UNKNOWN | 20 | 1424 | A |
| AL117596 | UNKNOWN | 20 | 2398 | A |
| AL117597 | UNKNOWN | 21 | 2437 | A |
| AL117597 | UNNNOWN | 13 | 187 | T |
| AL117598 | UNKNOWN | 20 | 2347 | A |
| AL117599 | UNKNOWN | 25 | 1940 | A |
| AL117601 | UNKNOWN | 19 | 2567 | A |
| AL117604 | UNKNOWN | 20 | 1592 | A |
| AL117604 | UNKNOWN | 15 | 1576 | A |
| AL117604 | UNKNOWN | 14 | 319 | T |
| AL117605 | UNKNOWN | 16 | 1138 | A |
| AL117606 | UNKNOWN | 25.5 | 1224 | CT |
| AL117606 | UNKNOWN | 9 | 1207 | AC |
| AL117606 | UNKNOWN | 20 | 1752 | A |
| AL117607 | UNKNOWN | 11.5 | 510 | CT |
| AL117607 | UNKNOWN | 27 | 3663 | A |
| AL117611 | UNKNOWN | 20 | 1888 | A |
| AL117612 | UNKNOWN | 19 | 2105 | A |
| AL117613 | UNKNOWN | 22 | 1406 | A |
| AL117616 | UNKNOWN | 20 | 1161 | A |
| AL117617 | UNKNOWN | 3.83 | 703 | TGTTTT |
| AL117617 | UNKNOWN | 20 | 1327 | A |
| AL117617 | UNKNOWN | 12 | 987 | A |
| AL117621 | UNKNOWN | 21 | 1777 | A |
| AL117622 | UNKNOWN | 17 | 1109 | A |
| AL117623 | UNKNOWN | 19 | 1443 | A |
| AL117623 | UNKNOWN | 17 | 1302 | A |
| AL117627 | UNKNOWN | 32 | 1342 | A |
| AL117630 | UNKNOWN | 38 | 965 | A |
| AL117636 | UNKNOWN | 40 | 2518 | A |
| AL117636 | UNKNOWN | 12 | 1300 | T |
| AL117643 | UNKNOWN | 30 | 1139 | A |
| AL117645 | UNKNOWN | 22 | 1619 | A |
| AL117651 | UNKNOWN | 17 | 1775 | A |
| AL117653 | UNKNOWN | 22 | 1738 | A |
| AL117657 | UNKNOWN | 17 | 1557 | A |

TABLE 1-continued

| Genbank # | Region | # reps | Position | Unit sequence |
|---|---|---|---|---|
| AL117658 | UNKNOWN | 19 | 159 | T |
| AL117658 | UNKNOWN | 17 | 1334 | A |
| AL117662 | 3' UTR | 9 | 1010 | AT |
| AL118646 | UNKNOWN | 18 | 0 | T |
| AL118653 | UNKNOWN | 13 | 134 | T |
| AL118664 | UNKNOWN | 11.5 | 311 | TC |
| AL118676 | UNKNOWN | 18 | 449 | A |
| AL118754 | UNKNOWN | 7 | 59 | TA |
| AL118768 | UNKNOWN | 4.8 | 110 | TTTTG |
| AL118768 | UNKNOWN | 22 | 536 | T |
| AL118823 | UNKNOWN | 27 | 144 | A |
| AL118860 | UNKNOWN | 18 | 0 | T |
| AL118865 | UNKNOWN | 19 | 501 | A |
| AL118943 | UNKNOWN | 19 | 0 | T |
| AL118969 | UNKNOWN | 19 | 0 | T |
| AL118985 | UNKNOWN | 5.6 | 264 | AAAAC |
| AL118985 | UNKNOWN | 19 | 0 | T |
| AL118998 | UNKNOWN | 19 | 0 | T |
| AL119006 | UNKNOWN | 13 | 172 | A |
| AL119009 | UNKNOWN | 19 | 0 | T |
| AL119010 | UNKNOWN | 17 | 278 | T |
| AL119016 | UNKNOWN | 19 | 0 | T |
| AL119025 | UNKNOWN | 19 | 631 | A |
| AL119027 | UNKNOWN | 19 | 0 | T |
| AL119055 | UNKNOWN | 26 | 219 | T |
| AL119055 | UNKNOWN | 13 | 0 | T |
| AL119084 | UNKNOWN | 13 | 119 | A |
| AL119123 | UNKNOWN | 18 | 118 | A |
| AL119177 | UNKNOWN | 15 | 212 | A |
| AL119177 | UNKNOWN | 12 | 123 | A |
| AL119189 | UNKNOWN | 13 | 294 | T |
| AL119220 | UNKNOWN | 16 | 628 | A |
| AL119305 | UNKNOWN | 18 | 681 | A |
| AL119331 | UNKNOWN | 33 | 262 | A |
| AL119387 | UNKNOWN | 11.5 | 237 | TC |
| AL119394 | UNKNOWN | 13 | 672 | A |
| AL119418 | UNKNOWN | 17 | 668 | A |
| AL119438 | UNKNOWN | 19 | 0 | T |
| AL119491 | UNKNOWN | 12 | 280 | A |
| AL119494 | UNKNOWN | 13 | 637 | T |
| AL119552 | UNKNOWN | 19 | 0 | T |
| AL119576 | UNKNOWN | 19 | 0 | T |
| AL119608 | UNKNOWN | 14.5 | 76 | TG |
| AL119608 | UNNNOWN | 18 | 423 | A |
| AL119612 | UNKNOWN | 19 | 0 | T |
| AL119622 | UNKNOWN | 18 | 179 | A |
| AL119625 | UNNNOWN | 3.5 | 32 | TTTATT |
| AL119625 | UNNNOWN | 5.75 | 16 | TTTA |
| AL119625 | UNKNOWN | 19 | 0 | T |
| AL119632 | UNKNOWN | 18 | 0 | T |
| AL119649 | UNKNOWN | 19 | 0 | T |
| AL119691 | UNKNOWN | 19 | 3 | T |
| AL119791 | UNKNOWN | 88 | 29 | A |
| AL119856 | UNKNOWN | 4.75 | 35 | TTTG |
| AL119856 | UNNNOWN | 19 | 0 | T |
| AL119863 | UNKNOWN | 101 | 81 | A |
| AL119897 | UNKNOWN | 12 | 497 | A |
| AL119946 | UNKNOWN | 19 | 0 | T |
| AL119946 | UNNNOWN | 16 | 245 | A |
| AL120035 | UNKNOWN | 19 | 645 | A |
| AL120121 | UNKNOWN | 6 | 408 | GTT |
| AL120121 | UNKNOWN | 19 | 0 | T |
| AL120129 | UNKNOWN | 13 | 0 | T |
| AL120133 | UNKNOWN | 14 | 0 | T |
| AL120155 | UNKNOWN | 19 | 264 | A |
| AL120158 | UNKNOWN | 19 | 354 | A |
| AL120177 | UNKNOWN | 19 | 416 | A |
| AL120181 | UNKNOWN | 19 | 0 | T |
| AL120207 | UNKNOWN | 19 | 509 | A |
| AL120213 | UNKNOWN | 19 | 0 | T |
| AL120241 | UNKNOWN | 16 | 4 | T |
| AL120254 | UNKNOWN | 59 | 20 | T |
| AL120254 | UNKNOWN | 19 | 0 | T |
| AL120260 | UNKNOWN | 19 | 451 | A |
| AL120283 | UNKNOWN | 17.5 | 46 | CA |
| AL120283 | UNKNOWN | 19 | 407 | A |
| AL120287 | UNKNOWN | 19 | 0 | T |

TABLE 1-continued

| Genbank # | Region | # reps | Position | Unit sequence |
|---|---|---|---|---|
| AL120288 | UNKNOWN | 19 | 353 | A |
| AL120295 | UNKNOWN | 11.5 | 830 | AT |
| AL120295 | UNKNOWN | 7 | 781 | TA |
| AL120295 | UNKNOWN | 19 | 0 | T |
| AL120320 | UNKNOWN | 19 | 0 | T |
| AL120370 | UNKNOWN | 19 | 0 | T |
| AL120375 | UNKNOWN | 42 | 20 | T |
| AL120375 | UNKNOWN | 19 | 0 | T |
| AL120388 | UNNNOWN | 19 | 0 | T |
| AL120518 | UNKNOWN | 17 | 844 | A |
| AL120616 | UNKNOWN | 18 | 0 | T |
| AL120651 | UNKNOWN | 14 | 548 | A |
| AL120660 | UNKNOWN | 18 | 338 | A |
| AL120662 | UNKNOWN | 20 | 92 | A |
| AL120664 | UNKNOWN | 18 | 3 | A |
| AL120704 | UNKNOWN | 15 | 962 | A |
| AL120708 | UNKNOWN | 19 | 518 | A |
| AL120756 | UNKNOWN | 55 | 185 | A |
| AL120789 | UNKNOWN | 19 | 272 | A |
| AL120789 | UNKNOWN | 17 | 24 | T |
| AL120853 | UNKNOWN | 93 | 0 | T |
| AL120927 | UNKNOWN | 21 | 234 | A |
| AL120986 | UNKNOWN | 20 | 543 | T |
| AL120986 | UNKNOWN | 17 | 0 | T |
| AL120995 | UNKNOWN | 66 | 445 | A |
| AL121021 | UNKNOWN | 17 | 0 | T |
| AL121027 | UNKNOWN | 17 | 0 | T |
| AL121143 | UNKNOWN | 20 | 28 | T |
| AL121235 | UNKNOWN | 17 | 0 | T |
| AL121338 | UNKNOWN | 40 | 434 | A |
| AL121382 | UNKNOWN | 17 | 0 | T |
| AL121733 | CDS | 5.66 | 206 | GAA |
| AL121739 | 5' UTR | 13 | 2 | A |
| AL133672 | UNKNOWN | 18 | 0 | T |
| AL133682 | UNKNOWN | 18 | 0 | T |
| AL133688 | UNKNOWN | 18 | 0 | T |
| AL133696 | UNKNOWN | 18 | 0 | T |
| AL133698 | UNKNOWN | 6.5 | 240 | AC |
| AL133698 | UNKNOWN | 18 | 0 | T |
| AL133698 | UNKNOWN | 12 | 355 | G |
| AL133700 | UNKNOWN | 18 | 0 | T |
| AL133706 | UNKNOWN | 18 | 0 | T |
| AL133721 | UNKNOWN | 13 | 377 | A |
| AL133730 | UNKNOWN | 19 | 175 | A |
| AL133776 | UNKNOWN | 45 | 51 | T |
| AL133776 | UNKNOWN | 19 | 31 | T |
| AL133784 | UNKNOWN | 15 | 983 | A |
| AL133830 | UNKNOWN | 17 | 5 | T |
| AL133908 | UNKNOWN | 16 | 173 | A |
| AL133952 | UNKNOWN | 18 | 429 | A |
| AL133952 | UNKNOWN | 13 | 244 | T |
| AL133990 | UNKNOWN | 16 | 547 | A |
| AL134044 | UNKNOWN | 39 | 294 | A |
| AL134095 | UNKNOWN | 17 | 0 | T |
| AL134242 | UNKNOWN | 34 | 144 | A |
| AL134343 | UNKNOWN | 15 | 0 | T |
| AL134350 | UNKNOWN | 13 | 321 | A |
| AL134369 | UNKNOWN | 19 | 257 | T |
| AL134402 | UNKNOWN | 16 | 559 | A |
| AL134419 | UNKNOWN | 24 | 505 | T |
| AL134435 | UNKNOWN | 12 | 95 | A |
| AL134448 | UNKNOWN | 2.9 | 6 | TTTAAATAAAT (SEQ ID NO: 201) |
| AL134451 | UNKNOWN | 17 | 516 | A |
| AL134489 | UNKNOWN | 13 | 580 | A |
| AL134540 | UNKNOWN | 17 | 1 | T |
| AL134547 | UNKNOWN | 15 | 16 | A |
| AL134574 | UNKNOWN | 16 | 31 | T |
| AL134616 | UNKNOWN | 12 | 543 | A |
| AL134650 | UNKNOWN | 15 | 0 | T |
| AL134652 | UNKNOWN | 12 | 477 | A |
| AL134654 | UNKNOWN | 16 | 1 | T |
| AL134679 | UNKNOWN | 18 | 43 | A |
| AL134698 | UNKNOWN | 12 | 24 | T |
| AL134708 | UNKNOWN | 17 | 1 | T |
| AL134832 | UNKNOWN | 42 | 19 | T |
| AL134832 | UNKNOWN | 17 | 1 | T |
| AL134850 | UNKNOWN | 41 | 167 | A |

TABLE 1-continued

| Genbank # | Region | # reps | Position | Unit sequence |
|---|---|---|---|---|
| AL134856 | UNKNOWN | 7.5 | 104 | CT |
| AL134856 | UNKNOWN | 7 | 91 | AC |
| AL134920 | UNKNOWN | 17 | 351 | A |
| AL134928 | UNKNOWN | 12 | 467 | A |
| AL134947 | UNKNOWN | 3.57 | 59 | GAGGAGAGGCTGTGTGAACAGGAGGAGAGGCTACGTGAACAG (SEQ ID NO: 202) |
| AL134947 | UNKNOWN | 3.76 | 464 | TTTATTTGTGTTTCTAATTTATAGTTTAAA (SEQ ID NO: 203) |
| AL134949 | UNKNOWN | 17 | 512 | A |
| AL134965 | UNKNOWN | 9.5 | 464 | AT |
| AL134965 | UNKNOWN | 17 | 629 | A |
| AL134980 | UNKNOWN | 12 | 325 | A |
| AL134985 | UNKNOWN | 4.75 | 131 | AAAT |
| AL134985 | UNKNOWN | 12 | 559 | T |
| AL134988 | UNKNOWN | 15 | 123 | A |
| AL135018 | UNKNOWN | 13 | 389 | A |
| AL135063 | UNKNOWN | 16 | 399 | A |
| AL135117 | UNKNOWN | 15 | 0 | T |
| AL135222 | UNKNOWN | 14 | 329 | T |
| AL135269 | UNNNOWN | 15 | 959 | A |
| AL135295 | UNKNOWN | 18 | 618 | T |
| AL135296 | UNKNOWN | 16 | 293 | T |
| AL135342 | UNKNOWN | 34 | 776 | A |
| AL135347 | UNKNOWN | 16 | 624 | A |
| AL135352 | UNKNOWN | 15 | 500 | A |
| AL135357 | UNKNOWN | 35 | 283 | A |
| AL135357 | UNKNOWN | 22 | 110 | A |
| AL135396 | UNKNOWN | 3.8 | 585 | TTTGC |
| AL135396 | UNKNOWN | 14 | 796 | A |
| AL135407 | UNKNOWN | 17 | 241 | A |
| AL135423 | UNKNOWN | 19 | 647 | A |
| AL135435 | UNKNOWN | 29 | 0 | T |
| AL135517 | UNKNOWN | 73 | 220 | A |
| AL135558 | UNKNOWN | 17 | 0 | T |
| AL135633 | UNKNOWN | 16 | 310 | T |
| AL135664 | UNKNOWN | 16 | 225 | A |
| AL135688 | UNKNOWN | 14 | 832 | A |
| AL135706 | UNKNOWN | 15 | 585 | A |
| AL135712 | UNKNOWN | 6.5 | 587 | CA |
| AL135739 | UNKNOWN | 17 | 0 | T |
| AW000713 | UNKNOWN | 39 | 0 | T |
| AW000721 | UNKNOWN | 43 | 0 | T |
| AW000738 | UNKNOWN | 49 | 0 | T |
| AW001000 | UNKNOWN | 16 | 0 | T |
| AW001036 | UNKNOWN | 5.25 | 259 | ATTC |
| AW001212 | UNKNOWN | 12 | 0 | T |
| AW001397 | UNKNOWN | 4.8 | 369 | CCTGG |
| AW001412 | UNKNOWN | 6.33 | 350 | CAG |
| AW001414 | UNKNOWN | 5.66 | 198 | TGC |
| AW001424 | UNKNOWN | 22 | 16 | T |
| AW001424 | UNKNOWN | 15 | 0 | T |
| AW001424 | UNKNOWN | 14 | 168 | A |
| AW001426 | UNKNOWN | 83 | 0 | T |
| AW001426 | UNKNOWN | 16 | 83 | C |
| AW001426 | UNKNOWN | 14 | 407 | G |
| AW001428 | UNKNOWN | 29 | 0 | T |
| AW001726 | UNKNOWN | 12 | 0 | T |
| AW001850 | UNKNOWN | 69 | 0 | T |
| AW001850 | UNKNOWN | 15 | 288 | C |
| AW001850 | UNKNOWN | 13 | 327 | G |
| AW001850 | UNKNOWN | 12 | 75 | A |
| AW001997 | UNKNOWN | 13 | 0 | T |
| AW002045 | UNKNOWN | 19 | 297 | A |
| AW002047 | UNKNOWN | 19 | 10 | T |
| AW002098 | UNKNOWN | 20 | 0 | T |
| AW002123 | UNKNOWN | 44 | 0 | T |
| AW002133 | UNKNOWN | 29 | 0 | T |
| AW002133 | UNKNOWN | 17 | 120 | A |
| AW002164 | UNKNOWN | 16 | 16 | T |
| AW002174 | UNKNOWN | 76 | 0 | T |
| AW002327 | UNKNOWN | 47 | 0 | T |
| AW002342 | UNKNOWN | 116 | 0 | T |
| AW002342 | UNKNOWN | 18 | 221 | G |
| AW002342 | UNKNOWN | 16 | 239 | C |
| AW002342 | UNKNOWN | 15 | 191 | A |
| AW002344 | UNKNOWN | 37 | 0 | T |
| AW002362 | UNKNOWN | 104 | 0 | T |

TABLE 1-continued

| Genbank # | Region | # reps | Position | Unit sequence |
|---|---|---|---|---|
| AW002362 | UNKNOWN | 18 | 164 | A |
| AW002362 | UNKNOWN | 16 | 112 | C |
| AW002362 | UNKNOWN | 15 | 320 | G |
| AW002362 | UNKNOWN | 12 | 129 | A |
| AW002393 | UNKNOWN | 38 | 0 | T |
| AW002489 | UNNNOWN | 15 | 0 | T |
| AW002505 | UNKNOWN | 19 | 0 | T |
| AW002522 | UNKNOWN | 16 | 0 | T |
| AW002599 | UNKNOWN | 15 | 0 | T |
| AW002645 | UNKNOWN | 24 | 0 | T |
| AW002673 | UNKNOWN | 19 | 0 | T |
| AW002673 | UNKNOWN | 15 | 290 | A |
| AW002685 | UNKNOWN | 15 | 0 | T |
| AW002698 | UNKNOWN | 60 | 0 | T |
| AW002722 | UNKNOWN | 26 | 0 | T |
| AW002727 | UNKNOWN | 47 | 0 | T |
| AW002727 | UNKNOWN | 13 | 136 | C |
| AW002740 | UNKNOWN | 32 | 0 | T |
| AW002794 | UNKNOWN | 22 | 0 | T |
| AW002807 | UNKNOWN | 50 | 0 | T |
| AW002838 | UNKNOWN | 84 | 0 | T |
| AW002838 | UNKNOWN | 20 | 171 | C |
| AW002838 | UNKNOWN | 16 | 146 | A |
| AW002838 | UNKNOWN | 13 | 277 | G |
| AW002843 | UNKNOWN | 21 | 0 | T |
| AW002876 | UNKNOWN | 12 | 15 | T |
| AW002965 | UNKNOWN | 3.8 | 0 | ATTTT |
| AW002965 | UNKNOWN | 16 | 29 | T |
| AW002969 | UNKNOWN | 26 | 19 | T |
| AW002986 | UNKNOWN | 17 | 261 | T |
| AW003107 | UNKNOWN | 25 | 417 | T |
| AW003127 | UNKNOWN | 27 | 0 | T |
| AW003150 | UNKNOWN | 32 | 0 | T |
| AW003187 | UNKNOWN | 5.66 | 260 | GCT |
| AW003204 | UNKNOWN | 29 | 0 | T |
| AW003218 | UNKNOWN | 3.66 | 107 | AAAACC |
| AW003218 | UNKNOWN | 4.75 | 134 | AAAC |
| AW003229 | UNKNOWN | 41 | 0 | T |
| AW003229 | UNKNOWN | 18 | 407 | A |
| AW003229 | UNKNOWN | 12 | 132 | A |
| AW003230 | UNKNOWN | 13 | 369 | T |
| AW003251 | UNKNOWN | 12 | 0 | T |
| AW003266 | UNKNOWN | 13 | 180 | T |
| AW003286 | UNKNOWN | 41 | 0 | T |
| AW003350 | UNKNOWN | 14 | 0 | T |
| AW003479 | UNKNOWN | 26 | 0 | T |
| AW003501 | UNKNOWN | 25 | 0 | T |
| AW003525 | UNKNOWN | 17 | 0 | T |
| AW003571 | UNKNOWN | 15 | 93 | T |
| AW003572 | UNKNOWN | 43 | 0 | T |
| AW003576 | UNKNOWN | 14 | 0 | T |
| AW003578 | UNKNOWN | 9 | 250 | CT |
| AW003582 | UNKNOWN | 28 | 0 | T |
| AW003634 | UNKNOWN | 7 | 3 | TC |
| AW003645 | UNKNOWN | 12 | 0 | T |
| AW003686 | UNKNOWN | 34 | 0 | T |
| AW003821 | UNKNOWN | 7 | 198 | CA |
| AW003829 | UNKNOWN | 5.5 | 299 | CTGT |
| AW003866 | UNKNOWN | 59 | 0 | T |
| AW003866 | UNKNOWN | 20 | 206 | G |
| AW003879 | UNKNOWN | 46 | 0 | T |
| AW003898 | UNKNOWN | 6.5 | 280 | AC |
| AW003997 | UNKNOWN | 19 | 4 | T |
| AW004079 | UNKNOWN | 21 | 0 | T |
| AW004595 | UNKNOWN | 49 | 0 | T |
| AW004595 | UNKNOWN | 12 | 70 | A |
| AW004654 | UNKNOWN | 32 | 0 | T |
| AW004683 | UNKNOWN | 17 | 0 | T |
| AW004689 | UNKNOWN | 31 | 0 | T |
| AW004689 | UNKNOWN | 16 | 110 | A |
| AW004762 | UNKNOWN | 30 | 0 | T |
| AW004872 | UNKNOWN | 18 | 0 | T |
| AW004886 | UNKNOWN | 75 | 0 | T |
| AW004886 | UNKNOWN | 26 | 169 | C |
| AW004886 | UNKNOWN | 15 | 140 | G |
| AW004886 | UNKNOWN | 14 | 126 | C |
| AW004894 | UNKNOWN | 48 | 0 | T |

TABLE 1-continued

| Genbank # | Region | # reps | Position | Unit sequence |
|---|---|---|---|---|
| AW004896 | UNKNOWN | 77 | 0 | T |
| AW004911 | UNKNOWN | 18 | 2 | T |
| AW004926 | UNKNOWN | 36 | 0 | T |
| AW005085 | UNKNOWN | 19 | 131 | A |
| AW005085 | UNKNOWN | 13 | 0 | T |
| AW005115 | UNKNOWN | 35 | 0 | T |
| AW005129 | UNKNOWN | 13.5 | 381 | TG |
| AW005167 | UNKNOWN | 50 | 0 | T |
| AW005174 | UNKNOWN | 6.33 | 496 | TCT |
| AW005253 | UNKNOWN | 15 | 0 | T |
| AW005316 | UNKNOWN | 14 | 22 | T |
| AW005554 | UNKNOWN | 12.5 | 211 | TG |
| AW005558 | UNKNOWN | 13 | 169 | T |
| AW005565 | UNKNOWN | 36 | 0 | T |
| AW005604 | UNKNOWN | 3.83 | 31 | TATTTT |
| AW005612 | UNKNOWN | 82 | 0 | T |
| AW005612 | UNKNOWN | 14 | 170 | G |
| AW005614 | UNKNOWN | 75 | 0 | T |
| AW005614 | UNKNOWN | 15 | 138 | A |
| AW005614 | UNKNOWN | 13 | 168 | C |
| AW005697 | UNKNOWN | 39 | 0 | T |
| AW005772 | UNKNOWN | 47 | 0 | T |
| AW005772 | UNKNOWN | 13 | 179 | C |
| AW005832 | UNKNOWN | 39 | 0 | T |
| AW005834 | UNKNOWN | 12 | 204 | A |
| AW005852 | UNKNOWN | 31 | 0 | T |
| AW005858 | UNKNOWN | 111 | 0 | T |
| AW005858 | UNKNOWN | 17 | 335 | C |
| AW005858 | UNKNOWN | 16 | 156 | G |
| AW005858 | UNKNOWN | 16 | 199 | C |
| AW005858 | UNKNOWN | 15 | 240 | A |
| AW005858 | UNKNOWN | 13 | 142 | C |
| AW005866 | UNKNOWN | 7.5 | 392 | TC |
| AW005866 | UNKNOWN | 12 | 406 | T |
| AW005882 | UNKNOWN | 34 | 0 | T |
| AW005897 | UNKNOWN | 27 | 0 | T |
| AW005901 | UNKNOWN | 26 | 0 | T |
| AW006032 | UNKNOWN | 76 | 0 | T |
| AW006032 | UNKNOWN | 30 | 145 | G |
| AW006032 | UNKNOWN | 12 | 76 | A |
| AW006032 | UNKNOWN | 12 | 175 | C |
| AW006046 | UNKNOWN | 88 | 0 | T |
| AW006046 | UNKNOWN | 13 | 131 | C |
| AW006063 | UNKNOWN | 38 | 0 | T |
| AW006063 | UNKNOWN | 14 | 163 | A |
| AW006085 | UNKNOWN | 32 | 0 | T |
| AW006095 | UNKNOWN | 4.8 | 109 | AAAAC |
| AW006096 | UNKNOWN | 23 | 1 | T |
| AW006109 | UNKNOWN | 56 | 0 | T |
| AW006109 | UNKNOWN | 17 | 187 | C |
| AW006109 | UNKNOWN | 15 | 93 | A |
| AW006113 | UNKNOWN | 17 | 0 | T |
| AW006138 | UNKNOWN | 18 | 0 | T |
| AW006163 | UNKNOWN | 5.2 | 160 | AACAA |
| AW006204 | UNKNOWN | 14 | 438 | T |
| AW006235 | UNKNOWN | 13 | 508 | AC |
| AW006235 | UNKNOWN | 6.5 | 494 | AC |
| AW006258 | UNKNOWN | 15 | 393 | T |
| AW006265 | UNKNOWN | 18 | 0 | T |
| AW006270 | UNKNOWN | 86 | 0 | T |
| AW006270 | UNKNOWN | 17 | 327 | G |
| AW006294 | UNKNOWN | 12 | 0 | T |
| AW006296 | UNKNOWN | 12 | 0 | T |
| AW006302 | UNKNOWN | 58 | 0 | T |
| AW006341 | UNKNOWN | 44 | 0 | T |
| AW006351 | UNKNOWN | 13 | 0 | T |
| AW006387 | UNKNOWN | 15 | 0 | T |
| AW006409 | UNKNOWN | 13 | 362 | T |
| AW006428 | UNKNOWN | 3.66 | 69 | GGAGGG |
| AW006428 | UNKNOWN | 47 | 0 | T |
| AW006453 | UNKNOWN | 15 | 10 | T |
| AW006504 | UNKNOWN | 22 | 0 | T |
| AW006505 | UNKNOWN | 22 | 0 | T |
| AW006505 | UNKNOWN | 18 | 52 | G |
| AW006617 | UNKNOWN | 7 | 351 | TTG |
| AW006617 | UNKNOWN | 21 | 197 | T |
| AW006636 | UNKNOWN | 15 | 398 | A |

TABLE 1-continued

| Genbank # | Region | # reps | Position | Unit sequence |
|---|---|---|---|---|
| AW006664 | UNKNOWN | 25 | 0 | T |
| AW006709 | UNKNOWN | 19 | 413 | A |
| AW006709 | UNKNOWN | 17 | 358 | T |
| AW006763 | UNKNOWN | 14 | 0 | T |
| AW006784 | UNKNOWN | 15 | 0 | T |
| AW006788 | UNKNOWN | 30 | 0 | T |
| AW006830 | UNKNOWN | 45 | 0 | T |
| AW006832 | UNKNOWN | 19 | 0 | T |
| AW006850 | UNKNOWN | 24 | 0 | T |
| AW006856 | UNKNOWN | 32 | 0 | T |
| AW006862 | UNKNOWN | 29 | 0 | T |
| AW006876 | UNKNOWN | 27 | 0 | T |
| AW006942 | UNKNOWN | 23 | 0 | T |
| AW006947 | UNKNOWN | 58 | 0 | T |
| AW006947 | UNKNOWN | 15 | 103 | G |
| AW007031 | UNKNOWN | 28 | 0 | T |
| AW007063 | UNKNOWN | 24 | 316 | T |
| AW007089 | UNKNOWN | 34 | 0 | T |
| AW007146 | UNKNOWN | 12 | 433 | T |
| AW007189 | UNKNOWN | 12 | 0 | T |
| AW007211 | UNKNOWN | 12 | 159 | T |
| AW007262 | UNKNOWN | 33 | 0 | T |
| AW007284 | UNKNOWN | 52 | 0 | T |
| AW007284 | UNKNOWN | 12 | 79 | A |
| AW007293 | UNKNOWN | 48 | 0 | T |
| AW007293 | UNKNOWN | 12 | 238 | A |
| AW007300 | UNKNOWN | 66 | 0 | T |
| AW007300 | UNKNOWN | 16 | 134 | G |
| AW007309 | UNKNOWN | 63 | 0 | T |
| AW007309 | UNKNOWN | 14 | 221 | A |
| AW007319 | UNKNOWN | 19 | 539 | AC |
| AW007327 | UNKNOWN | 5.66 | 175 | AAC |
| AW007401 | UNKNOWN | 48 | 0 | T |
| AW007410 | UNKNOWN | 14.5 | 102 | TA |
| AW007410 | UNKNOWN | 13 | 0 | T |
| AW007414 | UNKNOWN | 54 | 0 | T |
| AW007431 | UNKNOWN | 32 | 0 | T |
| AW007455 | UNKNOWN | 27 | 301 | A |
| AW007466 | UNKNOWN | 29 | 17 | T |
| AW007466 | UNKNOWN | 16 | 0 | T |
| AW007555 | UNKNOWN | 67 | 0 | T |
| AW007555 | UNKNOWN | 14 | 155 | C |
| AW007555 | UNKNOWN | 12 | 129 | G |
| AW007562 | UNKNOWN | 73 | 0 | T |
| AW007562 | UNKNOWN | 13 | 143 | A |
| AW007562 | UNKNOWN | 12 | 199 | C |
| AW007580 | UNKNOWN | 52 | 0 | T |
| AW007811 | UNKNOWN | 12 | 0 | T |
| AW007833 | UNKNOWN | 51 | 0 | T |
| AW007843 | UNKNOWN | 13 | 0 | T |
| AW007855 | UNKNOWN | 13 | 0 | T |
| AW007916 | UNKNOWN | 11 | 55 | GT |
| AW007939 | UNKNOWN | 75 | 0 | T |
| AW007939 | UNKNOWN | 17 | 256 | C |
| AW007939 | UNKNOWN | 12 | 394 | G |
| AW007955 | UNKNOWN | 59 | 0 | T |
| AW007988 | UNKNOWN | 17 | 0 | T |
| AW007992 | UNKNOWN | 18 | 0 | T |
| AW007996 | UNKNOWN | 30 | 0 | T |
| AW008015 | UNKNOWN | 16 | 0 | T |
| AW008033 | UNKNOWN | 39 | 0 | T |
| AW008048 | UNKNOWN | 111 | 0 | T |
| AW008048 | UNKNOWN | 15 | 145 | C |
| AW008048 | UNKNOWN | 15 | 218 | G |
| AW008048 | UNKNOWN | 13 | 192 | A |
| AW008064 | UNKNOWN | 38 | 0 | T |
| AW008071 | UNKNOWN | 54 | 0 | T |
| AW008071 | UNKNOWN | 12 | 106 | G |
| AW008075 | UNKNOWN | 20 | 0 | T |
| AW008085 | UNKNOWN | 55 | 17 | T |
| AW008085 | UNKNOWN | 23 | 128 | G |
| AW008085 | UNKNOWN | 16 | 0 | T |
| AW008085 | UNKNOWN | 12 | 98 | C |
| AW008090 | UNKNOWN | 78 | 0 | T |
| AW008090 | UNKNOWN | 14 | 101 | C |
| AW008090 | UNKNOWN | 14 | 239 | G |
| AW008090 | UNKNOWN | 14 | 319 | A |

TABLE 1-continued

| Genbank # | Region | # reps | Position | Unit sequence |
|---|---|---|---|---|
| AW008120 | UNKNOWN | 39 | 0 | T |
| AW008129 | UNKNOWN | 80 | 0 | T |
| AW008129 | UNKNOWN | 13 | 136 | A |
| AW008129 | UNKNOWN | 12 | 316 | C |
| AW008166 | UNKNOWN | 68 | 0 | T |
| AW008166 | UNKNOWN | 19 | 165 | G |
| AW008166 | UNKNOWN | 15 | 125 | C |
| AW008247 | UNKNOWN | 31 | 0 | T |
| AW008253 | UNKNOWN | 55 | 0 | T |
| AW008253 | UNKNOWN | 14 | 111 | C |
| AW008264 | UNKNOWN | 42 | 0 | T |
| AW008265 | UNKNOWN | 44 | 1 | T |
| AW008333 | UNKNOWN | 23 | 0 | T |
| AW008353 | UNKNOWN | 83 | 0 | T |
| AW008353 | UNKNOWN | 14 | 119 | C |
| AW008353 | UNKNOWN | 14 | 196 | G |
| AW008358 | UNKNOWN | 39 | 0 | T |
| AW008373 | UNKNOWN | 68 | 0 | T |
| AW008434 | UNKNOWN | 61 | 0 | T |
| AW008434 | UNKNOWN | 12 | 129 | A |
| AW008456 | UNKNOWN | 12 | 0 | T |
| AW008551 | UNKNOWN | 44 | 0 | T |
| AW008589 | UNKNOWN | 79 | 0 | T |
| AW008589 | UNKNOWN | 18 | 142 | G |
| AW008589 | UNKNOWN | 17 | 220 | C |
| AW008597 | UNKNOWN | 21 | 1 | T |
| AW008605 | UNKNOWN | 31 | 0 | T |
| AW008605 | UNKNOWN | 13 | 70 | C |
| AW008720 | UNKNOWN | 42 | 0 | T |
| AW008720 | UNKNOWN | 29 | 207 | A |
| AW008720 | UNKNOWN | 22 | 78 | C |
| AW008720 | UNKNOWN | 20 | 153 | A |
| AW008720 | UNKNOWN | 12 | 128 | A |
| AW008737 | UNKNOWN | 59 | 0 | T |
| AW008737 | UNKNOWN | 12 | 79 | G |
| AW008737 | UNKNOWN | 12 | 274 | C |
| AW008779 | UNKNOWN | 48 | 0 | T |
| AW008781 | UNKNOWN | 63 | 0 | T |
| AW008781 | UNKNOWN | 19 | 176 | C |
| AW008781 | UNKNOWN | 18 | 86 | A |
| AW008781 | UNKNOWN | 13 | 158 | G |
| AW008782 | UNKNOWN | 16 | 457 | A |
| AW008784 | UNKNOWN | 28 | 202 | T |
| AW008784 | UNKNOWN | 15 | 0 | T |
| AW008848 | UNKNOWN | 12 | 0 | T |
| AW008919 | UNKNOWN | 43 | 0 | T |
| AW008994 | UNKNOWN | 44 | 0 | T |
| AW009070 | UNKNOWN | 44 | 0 | T |
| AW009070 | UNKNOWN | 12 | 282 | G |
| AW009070 | UNKNOWN | 12 | 384 | A |
| AW009077 | UNKNOWN | 18 | 0 | T |
| AW009081 | UNKNOWN | 17 | 283 | A |
| AW009280 | UNKNOWN | 32 | 0 | T |
| AW009280 | UNKNOWN | 12 | 243 | A |
| AW009306 | UNKNOWN | 60 | 0 | T |
| AW009306 | UNKNOWN | 23 | 91 | A |
| AW009306 | UNKNOWN | 23 | 184 | G |
| AW009306 | UNKNOWN | 22 | 144 | C |
| AW009364 | UNKNOWN | 2.65 | 226 | AGGAAAAGGCGGCGTGGAGAGACGGGACGCGCGGG (SEQ ID NO: 204) |
| AW009370 | UNKNOWN | 12 | 0 | T |
| AW009409 | UNKNOWN | 31 | 0 | T |
| AW009409 | UNKNOWN | 13 | 59 | G |
| AW009426 | UNKNOWN | 46 | 0 | T |
| AW009500 | UNKNOWN | 46 | 0 | T |
| AW009500 | UNKNOWN | 12 | 119 | C |
| AW009540 | UNKNOWN | 13 | 0 | T |
| AW009551 | UNKNOWN | 13 | 0 | T |
| AW009562 | UNKNOWN | 6.5 | 106 | CA |
| AW009562 | UNKNOWN | 21 | 310 | T |
| AW009589 | UNKNOWN | 42 | 0 | T |
| AW009602 | UNKNOWN | 14 | 0 | T |
| AW009619 | UNKNOWN | 40 | 0 | T |
| AW009619 | UNKNOWN | 13 | 243 | A |
| AW009624 | UNKNOWN | 68 | 0 | T |
| AW009624 | UNKNOWN | 13 | 327 | C |
| AW009624 | UNKNOWN | 12 | 167 | C |

TABLE 1-continued

| Genbank # | Region | # reps | Position | Unit sequence |
|---|---|---|---|---|
| AW009745 | UNKNOWN | 25 | 375 | T |
| AW009856 | UNKNOWN | 17 | 0 | T |
| AW009856 | UNKNOWN | 12 | 292 | A |
| AW009896 | UNKNOWN | 49 | 0 | T |
| AW009955 | UNKNOWN | 28 | 0 | T |
| AW013808 | UNKNOWN | 15 | 0 | T |
| AW013809 | UNKNOWN | 14 | 0 | T |
| AW013821 | UNKNOWN | 17 | 0 | T |
| AW013821 | UNKNOWN | 13 | 259 | A |
| AW013836 | UNKNOWN | 17 | 0 | T |
| AW013839 | UNKNOWN | 17 | 0 | T |
| AW013849 | UNKNOWN | 16 | 0 | T |
| AW013852 | UNKNOWN | 17 | 0 | T |
| AW013857 | UNKNOWN | 17 | 0 | T |
| AW013858 | UNKNOWN | 17 | 0 | T |
| AW013863 | UNKNOWN | 17 | 0 | T |
| AW013872 | UNKNOWN | 17 | 0 | T |
| AW013891 | UNKNOWN | 15 | 0 | T |
| AW013912 | UNKNOWN | 17 | 0 | T |
| AW013920 | UNKNOWN | 17 | 0 | T |
| AW013933 | UNKNOWN | 15 | 0 | T |
| AW013952 | UNKNOWN | 17 | 0 | T |
| AW013968 | UNKNOWN | 17 | 0 | T |
| AW013993 | UNKNOWN | 15 | 0 | T |
| AW013997 | UNKNOWN | 17 | 0 | T |
| AW014000 | UNKNOWN | 17 | 0 | T |
| AW014016 | UNKNOWN | 17 | 0 | T |
| AW014022 | UNKNOWN | 17 | 0 | T |
| AW014041 | UNKNOWN | 17 | 0 | T |
| AW014049 | UNKNOWN | 17 | 0 | T |
| AW014078 | UNKNOWN | 17 | 0 | T |
| AW014086 | UNKNOWN | 17 | 0 | T |
| AW014096 | UNKNOWN | 2.68 | 92 | GTGGTTTGGGCCCGACCGAGCTGGTCCCGCAGTGGGCG (SEQ ID NO: 205) |
| AW014096 | UNKNOWN | 17 | 0 | T |
| AW014100 | UNKNOWN | 17 | 0 | T |
| AW014105 | UNKNOWN | 17 | 0 | T |
| AW014109 | UNKNOWN | 17 | 0 | T |
| AW014118 | UNKNOWN | 17 | 0 | T |
| AW014126 | UNKNOWN | 17 | 0 | T |
| AW014128 | UNKNOWN | 17 | 0 | T |
| AW014130 | UNKNOWN | 17 | 0 | T |
| AW014131 | UNKNOWN | 17 | 0 | T |
| AW014133 | UNKNOWN | 17 | 0 | T |
| AW014144 | UNKNOWN | 14 | 0 | T |
| AW014155 | UNKNOWN | 17 | 0 | T |
| AW014166 | UNKNOWN | 17 | 0 | T |
| AW014172 | UNKNOWN | 17 | 0 | T |
| AW014181 | UNKNOWN | 17 | 0 | T |
| AW014185 | UNKNOWN | 12 | 0 | T |
| AW014212 | UNKNOWN | 17 | 0 | T |
| AW014237 | UNKNOWN | 17 | 0 | T |
| AW014249 | UNKNOWN | 17 | 0 | T |
| AW014251 | UNKNOWN | 17 | 0 | T |
| AW014267 | UNKNOWN | 17 | 0 | T |
| AW014272 | UNKNOWN | 15 | 0 | T |
| AW014275 | UNKNOWN | 17 | 0 | T |
| AW014285 | UNKNOWN | 17 | 0 | T |
| AW014288 | UNKNOWN | 17 | 0 | T |
| AW014300 | UNKNOWN | 17 | 0 | T |
| AW014327 | UNKNOWN | 15 | 0 | T |
| AW014329 | UNKNOWN | 17 | 0 | T |
| AW014356 | UNKNOWN | 17 | 0 | T |
| AW014371 | UNKNOWN | 14 | 0 | T |
| AW014375 | UNKNOWN | 17 | 0 | T |
| AW014383 | UNKNOWN | 17 | 0 | T |
| AW014391 | UNKNOWN | 14 | 0 | T |
| AW014413 | UNKNOWN | 17 | 0 | T |
| AW014468 | UNKNOWN | 17 | 0 | T |
| AW014470 | UNKNOWN | 17 | 0 | T |
| AW014487 | UNKNOWN | 15 | 0 | T |
| AW014517 | UNKNOWN | 17 | 0 | T |
| AW014518 | UNKNOWN | 17 | 0 | T |
| AW014552 | UNKNOWN | 15 | 0 | T |
| AW014554 | UNKNOWN | 15 | 0 | T |
| AW014557 | UNKNOWN | 2.9 | 285 | AGGCATACAGGTTGATTATTTT (SEQ ID NO: 206) |
| AW014557 | UNKNOWN | 17 | 0 | T |

TABLE 1-continued

| Genbank # | Region | # reps | Position | Unit sequence |
|---|---|---|---|---|
| AW014560 | UNKNOWN | 17 | 0 | T |
| AW014561 | UNKNOWN | 17 | 0 | T |
| AW014567 | UNKNOWN | 17 | 0 | T |
| AW014570 | UNKNOWN | 17 | 0 | T |
| AW014571 | UNKNOWN | 15 | 0 | T |
| AW014582 | UNKNOWN | 17 | 0 | T |
| AW014583 | UNKNOWN | 17 | 0 | T |
| AW014599 | UNKNOWN | 17 | 0 | T |
| AW014600 | UNKNOWN | 17 | 0 | T |
| AW014606 | UNKNOWN | 17 | 0 | T |
| AW014613 | UNKNOWN | 17 | 0 | T |
| AW014618 | UNKNOWN | 17 | 0 | T |
| AW014619 | UNKNOWN | 17 | 0 | T |
| AW014624 | UNKNOWN | 17 | 0 | T |
| AW014633 | UNKNOWN | 17 | 0 | T |
| AW014647 | UNKNOWN | 17 | 0 | T |
| AW014648 | UNKNOWN | 17 | 0 | T |
| AW014673 | UNKNOWN | 15 | 0 | T |
| AW014682 | UNKNOWN | 17 | 0 | T |
| AW014699 | UNKNOWN | 17 | 0 | T |
| AW014717 | UNKNOWN | 17 | 0 | T |
| AW014719 | UNKNOWN | 17 | 0 | T |
| AW014721 | UNKNOWN | 17 | 0 | T |
| AW014722 | UNKNOWN | 17 | 0 | T |
| AW014723 | UNKNOWN | 17 | 0 | T |
| AW014730 | UNKNOWN | 17 | 0 | T |
| AW014734 | UNKNOWN | 17 | 0 | T |
| AW014735 | UNKNOWN | 17 | 0 | T |
| AW014736 | UNKNOWN | 15 | 0 | T |
| AW014739 | UNKNOWN | 17 | 0 | T |
| AW014742 | UNKNOWN | 17 | 0 | T |
| AW014743 | UNKNOWN | 17 | 0 | T |
| AW014746 | UNKNOWN | 17 | 0 | T |
| AW014763 | UNKNOWN | 17 | 0 | T |
| AW014764 | UNKNOWN | 17 | 0 | T |
| AW014769 | UNKNOWN | 12 | 0 | T |
| AW014775 | UNKNOWN | 17 | 0 | T |
| AW014780 | UNKNOWN | 15 | 0 | T |
| AW014798 | UNKNOWN | 13 | 0 | T |
| AW014804 | UNKNOWN | 17 | 0 | T |
| AW014808 | UNKNOWN | 17 | 0 | T |
| AW014815 | UNKNOWN | 17 | 0 | T |
| AW014824 | UNKNOWN | 12 | 0 | T |
| AW014841 | UNKNOWN | 17 | 0 | T |
| AW014847 | UNKNOWN | 15 | 0 | T |
| AW014865 | UNKNOWN | 17 | 0 | T |
| AW014883 | UNKNOWN | 14 | 3 | T |
| AW014908 | UNKNOWN | 17 | 0 | T |
| AW014916 | UNKNOWN | 17 | 0 | T |
| AW014918 | UNKNOWN | 17 | 0 | T |
| AW014947 | UNKNOWN | 17 | 0 | T |
| AW014949 | UNKNOWN | 17 | 0 | T |
| AW014994 | UNKNOWN | 15 | 0 | T |
| AW015003 | UNKNOWN | 17 | 0 | T |
| AW015020 | UNKNOWN | 17 | 0 | T |
| AW015022 | UNKNOWN | 17 | 0 | T |
| AW015027 | UNKNOWN | 10.5 | 64 | AC |
| AW015027 | UNKNOWN | 17 | 0 | T |
| AW015038 | UNKNOWN | 17 | 0 | T |
| AW015040 | UNKNOWN | 16 | 0 | T |
| AW015043 | UNKNOWN | 17 | 0 | T |
| AW015053 | UNKNOWN | 17 | 0 | T |
| AW015063 | UNKNOWN | 17 | 0 | T |
| AW015073 | UNKNOWN | 17 | 0 | T |
| AW015074 | UNKNOWN | 17 | 0 | T |
| AW015103 | UNKNOWN | 17 | 0 | T |
| AW015120 | UNKNOWN | 15 | 0 | T |
| AW015135 | UNKNOWN | 5.66 | 298 | GGC |
| AW015138 | UNKNOWN | 17 | 0 | T |
| AW015140 | UNKNOWN | 17 | 0 | T |
| AW015147 | UNKNOWN | 17 | 0 | T |
| AW015148 | UNKNOWN | 17 | 0 | T |
| AW015154 | UNKNOWN | 17 | 0 | T |
| AW015162 | UNKNOWN | 17 | 0 | T |
| AW015169 | UNKNOWN | 17 | 0 | T |
| AW015170 | UNKNOWN | 17 | 0 | T |
| AW015176 | UNKNOWN | 17 | 0 | T |

TABLE 1-continued

| Genbank # | Region | # reps | Position | Unit sequence |
|---|---|---|---|---|
| AW015185 | UNKNOWN | 17 | 0 | T |
| AW015189 | UNKNOWN | 17 | 0 | T |
| AW015203 | UNKNOWN | 17 | 0 | T |
| AW015211 | UNKNOWN | 17 | 0 | T |
| AW015236 | UNKNOWN | 16 | 0 | T |
| AW015238 | UNKNOWN | 17 | 0 | T |
| AW015262 | UNKNOWN | 17 | 0 | T |
| AW015263 | UNKNOWN | 17 | 0 | T |
| AW015266 | UNKNOWN | 17 | 0 | T |
| AW015275 | UNKNOWN | 15 | 0 | T |
| AW015297 | UNKNOWN | 14 | 0 | T |
| AW015311 | UNKNOWN | 17 | 0 | T |
| AW015340 | UNKNOWN | 17 | 0 | T |
| AW015342 | UNKNOWN | 17 | 0 | T |
| AW015369 | UNKNOWN | 17 | 0 | T |
| AW015406 | UNKNOWN | 17 | 0 | T |
| AW015417 | UNKNOWN | 17 | 0 | T |
| AW015429 | UNKNOWN | 17 | 0 | T |
| AW015436 | UNKNOWN | 17 | 0 | T |
| AW015446 | UNKNOWN | 14 | 0 | T |
| AW015461 | UNKNOWN | 17 | 0 | T |
| AW015477 | UNKNOWN | 17 | 0 | T |
| AW015506 | UNKNOWN | 17 | 0 | T |
| AW015536 | UNKNOWN | 17 | 0 | T |
| AW015543 | UNKNOWN | 17 | 0 | T |
| AW015549 | UNKNOWN | 13 | 0 | T |
| AW015564 | UNKNOWN | 17 | 0 | T |
| AW015571 | UNKNOWN | 17 | 0 | T |
| AW015572 | UNKNOWN | 17 | 0 | T |
| AW015574 | UNKNOWN | 7 | 152 | TG |
| AW015574 | UNKNOWN | 17 | 0 | T |
| AW015598 | UNKNOWN | 17 | 0 | T |
| AW015599 | UNKNOWN | 17 | 0 | T |
| AW015602 | UNKNOWN | 14 | 0 | T |
| AW015623 | UNKNOWN | 17 | 0 | T |
| AW015632 | UNKNOWN | 17 | 0 | T |
| AW015635 | UNKNOWN | 17 | 0 | T |
| AW015656 | UNKNOWN | 15 | 0 | T |
| AW015678 | UNKNOWN | 17 | 0 | T |
| AW015699 | UNKNOWN | 17 | 0 | T |
| AW015706 | UNKNOWN | 14 | 0 | T |
| AW015711 | UNKNOWN | 17 | 0 | T |
| AW015736 | UNKNOWN | 17 | 0 | T |
| AW015754 | UNKNOWN | 17 | 0 | T |
| AW015794 | UNKNOWN | 17 | 0 | T |
| AW015800 | UNKNOWN | 17 | 0 | T |
| AW015805 | UNKNOWN | 17 | 0 | T |
| AW015807 | UNKNOWN | 17 | 0 | T |
| AW015819 | UNKNOWN | 17 | 0 | T |
| AW015852 | UNKNOWN | 17 | 0 | T |
| AW015870 | UNKNOWN | 17 | 0 | T |
| AW015877 | UNKNOWN | 14 | 0 | T |
| AW015880 | UNKNOWN | 17 | 0 | T |
| AW015894 | UNKNOWN | 16 | 0 | T |
| AW015901 | UNKNOWN | 17 | 0 | T |
| AW015907 | UNKNOWN | 17 | 0 | T |
| AW015920 | UNKNOWN | 17 | 0 | T |
| AW015927 | UNKNOWN | 15 | 0 | T |
| AW015947 | UNKNOWN | 15 | 0 | T |
| AW015955 | UNKNOWN | 17 | 0 | T |
| AW015960 | UNKNOWN | 17 | 0 | T |
| AW015975 | UNKNOWN | 17 | 0 | T |
| AW016002 | UNKNOWN | 17 | 0 | T |
| AW016026 | UNKNOWN | 17 | 0 | T |
| AW016037 | UNKNOWN | 17 | 0 | T |
| AW016057 | UNKNOWN | 14 | 0 | T |
| AW016060 | UNKNOWN | 17 | 0 | T |
| AW016066 | UNKNOWN | 17 | 0 | T |
| AW016076 | UNKNOWN | 17 | 0 | T |
| AW016094 | UNKNOWN | 17 | 0 | T |
| AW016099 | UNKNOWN | 15 | 0 | T |
| AW016110 | UNKNOWN | 17 | 0 | T |
| AW016120 | UNKNOWN | 15 | 0 | T |
| AW016127 | UNKNOWN | 17 | 0 | T |
| AW016128 | UNKNOWN | 17 | 0 | T |
| AW016167 | UNKNOWN | 15 | 0 | T |
| AW016175 | UNKNOWN | 17 | 0 | T |

TABLE 1-continued

| Genbank # | Region | # reps | Position | Unit sequence |
|---|---|---|---|---|
| AW016182 | UNKNOWN | 17 | 0 | T |
| AW016182 | UNKNOWN | 13 | 288 | A |
| AW016203 | UNKNOWN | 17 | 0 | T |
| AW016228 | UNKNOWN | 17 | 0 | T |
| AW016250 | UNKNOWN | 17 | 0 | T |
| AW016256 | UNKNOWN | 6.5 | 33 | AC |
| AW016256 | UNKNOWN | 17 | 0 | T |
| AW016280 | UNKNOWN | 17 | 0 | T |
| AW016288 | UNKNOWN | 17 | 0 | T |
| AW016288 | UNKNOWN | 16 | 275 | A |
| AW016288 | UNKNOWN | 14 | 245 | A |
| AW016290 | UNKNOWN | 17 | 0 | T |
| AW016304 | UNKNOWN | 17 | 0 | T |
| AW016308 | UNKNOWN | 17 | 0 | T |
| AW016310 | UNKNOWN | 17 | 0 | T |
| AW016325 | UNKNOWN | 13 | 0 | T |
| AW016342 | UNKNOWN | 17 | 0 | T |
| AW016364 | UNKNOWN | 17 | 0 | T |
| AW016364 | UNKNOWN | 16 | 205 | A |
| AW016378 | UNKNOWN | 17 | 0 | T |
| AW016398 | UNKNOWN | 17 | 0 | T |
| AW016399 | UNKNOWN | 16 | 0 | T |
| AW016418 | UNKNOWN | 15 | 0 | T |
| AW016437 | UNKNOWN | 14 | 0 | T |
| AW016439 | UNKNOWN | 17 | 0 | T |
| AW016454 | UNKNOWN | 17 | 0 | T |
| AW016503 | UNKNOWN | 17 | 0 | T |
| AW016508 | UNKNOWN | 17 | 0 | T |
| AW016522 | UNKNOWN | 17 | 0 | T |
| AW016523 | UNKNOWN | 17 | 0 | T |
| AW016532 | UNKNOWN | 17 | 0 | T |
| AW016556 | UNKNOWN | 17 | 0 | T |
| AW016572 | UNKNOWN | 17 | 0 | T |
| AW016607 | UNKNOWN | 17 | 0 | T |
| AW016637 | UNKNOWN | 17 | 0 | T |
| AW016645 | UNKNOWN | 17 | 0 | T |
| AW016680 | UNKNOWN | 12 | 5 | T |
| AW016682 | UNKNOWN | 17 | 0 | T |
| AW016696 | UNKNOWN | 17 | 0 | T |
| AW016697 | UNKNOWN | 17 | 0 | T |
| AW016721 | UNKNOWN | 17 | 0 | T |
| AW016732 | UNKNOWN | 17 | 0 | T |
| AW016740 | UNKNOWN | 17 | 0 | T |
| AW016741 | UNKNOWN | 17 | 0 | T |
| AW016751 | UNKNOWN | 14 | 0 | T |
| AW016761 | UNKNOWN | 17 | 0 | T |
| AW016777 | UNKNOWN | 17 | 0 | T |
| AW016788 | UNKNOWN | 14 | 0 | T |
| AW016801 | UNKNOWN | 17 | 0 | T |
| AW016806 | UNKNOWN | 15 | 0 | T |
| AW016812 | UNKNOWN | 3.6 | 91 | AAAAC |
| AW016812 | UNKNOWN | 17 | 0 | T |
| AW016819 | UNKNOWN | 15 | 0 | T |
| AW016825 | UNKNOWN | 17 | 0 | T |
| AW016830 | UNKNOWN | 15 | 0 | T |
| AW016853 | UNKNOWN | 17 | 0 | T |
| AW016859 | UNKNOWN | 17 | 0 | T |
| AW016868 | UNKNOWN | 17 | 0 | T |
| AW016869 | UNKNOWN | 17 | 0 | T |
| AW016879 | UNKNOWN | 17 | 0 | T |
| AW016882 | UNKNOWN | 17 | 0 | T |
| AW016886 | UNKNOWN | 15 | 0 | T |
| AW016903 | UNKNOWN | 17 | 0 | T |
| AW016911 | UNKNOWN | 15 | 0 | T |
| AW016921 | UNKNOWN | 17 | 0 | T |
| AW016926 | UNKNOWN | 17 | 0 | T |
| AW019881 | UNKNOWN | 21 | 411 | A |
| AW019900 | UNKNOWN | 18 | 106 | A |
| AW019903 | UNKNOWN | 20 | 137 | A |
| AW019923 | UNKNOWN | 18 | 505 | A |
| AW019945 | UNKNOWN | 24 | 258 | A |
| AW019950 | UNKNOWN | 19 | 320 | A |
| AW019966 | UNKNOWN | 18 | 260 | A |
| AW019994 | UNKNOWN | 20 | 246 | A |
| AW019998 | UNKNOWN | 18 | 438 | A |
| AW020037 | UNKNOWN | 19 | 430 | A |
| AW020044 | UNKNOWN | 12.75 | 51 | TAGA |

TABLE 1-continued

| Genbank # | Region | # reps | Position | Unit sequence |
|---|---|---|---|---|
| AW020044 | UNKNOWN | 9.25 | 7 | GATA |
| AW020044 | UNKNOWN | 17 | 299 | A |
| AW020088 | UNKNOWN | 18 | 347 | A |
| AW020089 | UNKNOWN | 20 | 518 | A |
| AW020113 | UNKNOWN | 19 | 387 | A |
| AW020122 | UNKNOWN | 6.5 | 409 | CA |
| AW020122 | UNKNOWN | 19 | 423 | A |
| AW020260 | UNKNOWN | 16 | 387 | A |
| AW020341 | UNKNOWN | 46 | 137 | A |
| AW020380 | UNKNOWN | 18 | 293 | A |
| AW020419 | UNKNOWN | 73 | 31 | A |
| AW020449 | UNKNOWN | 17 | 166 | A |
| AW020456 | UNKNOWN | 19 | 229 | A |
| AW020469 | UNKNOWN | 15 | 594 | A |
| AW020470 | UNKNOWN | 18 | 260 | A |
| AW020496 | UNKNOWN | 18 | 432 | A |
| AW020549 | UNKNOWN | 8 | 16 | TC |
| AW020549 | UNKNOWN | 20 | 260 | A |
| AW020592 | UNKNOWN | 55 | 68 | A |
| AW020593 | UNKNOWN | 19 | 373 | A |
| AW020612 | UNKNOWN | 16 | 392 | A |
| AW020636 | UNKNOWN | 25 | 195 | A |
| AW020654 | UNKNOWN | 30 | 71 | A |
| AW020657 | UNKNOWN | 19 | 508 | A |
| AW020674 | UNKNOWN | 20 | 460 | A |
| AW020677 | UNKNOWN | 18 | 293 | A |
| AW020693 | UNKNOWN | 95 | 27 | A |
| AW020697 | UNKNOWN | 18 | 273 | A |
| AW020717 | UNKNOWN | 19 | 176 | A |
| AW020719 | UNKNOWN | 26 | 331 | A |
| AW020762 | UNKNOWN | 42 | 206 | A |
| AW020852 | UNKNOWN | 18 | 315 | A |
| AW020872 | UNKNOWN | 19 | 247 | A |
| AW020893 | UNKNOWN | 20 | 315 | A |
| AW020912 | UNKNOWN | 24 | 242 | A |
| AW020912 | UNKNOWN | 16 | 28 | A |
| AW020991 | UNKNOWN | 19 | 487 | A |
| AW020995 | UNKNOWN | 18 | 322 | A |
| AW021015 | UNKNOWN | 18 | 373 | A |
| AW021052 | UNKNOWN | 18 | 317 | A |
| AW021102 | UNKNOWN | 16 | 497 | A |
| AW021138 | UNKNOWN | 8 | 197 | AT |
| AW021195 | UNKNOWN | 61 | 194 | A |
| AW021195 | UNKNOWN | 17 | 19 | A |
| AW021219 | UNKNOWN | 20 | 296 | A |
| AW021282 | UNKNOWN | 19 | 84 | A |
| AW021313 | UNKNOWN | 17 | 391 | A |
| AW021349 | UNKNOWN | 19 | 403 | A |
| AW021373 | UNKNOWN | 72 | 29 | A |
| AW021399 | UNKNOWN | 31 | 336 | A |
| AW021399 | UNKNOWN | 14 | 15 | A |
| AW021429 | UNKNOWN | 20 | 432 | A |
| AW021440 | UNKNOWN | 18 | 273 | A |
| AW021540 | UNKNOWN | 30 | 18 | T |
| AW021540 | UNKNOWN | 17 | 739 | A |
| AW021559 | UNKNOWN | 23 | 451 | A |
| AW021579 | UNKNOWN | 24 | 534 | A |
| AW021581 | UNKNOWN | 18 | 467 | A |
| AW021627 | UNKNOWN | 20 | 267 | A |
| AW021639 | UNKNOWN | 13 | 431 | GT |
| AW021717 | UNKNOWN | 64 | 41 | A |
| AW021725 | UNKNOWN | 20 | 179 | A |
| AW021740 | UNKNOWN | 17 | 7 | T |
| AW021780 | UNKNOWN | 31 | 117 | A |
| AW021874 | UNKNOWN | 19 | 389 | A |
| AW021886 | UNKNOWN | 18 | 441 | A |
| AW021952 | UNKNOWN | 20 | 104 | A |
| AW021998 | UNKNOWN | 23 | 372 | A |
| AW022009 | UNKNOWN | 20 | 305 | A |
| AW022047 | UNKNOWN | 17 | 436 | A |
| AW022081 | UNKNOWN | 12 | 350 | A |
| AW022082 | UNKNOWN | 20 | 183 | A |
| AW022108 | UNKNOWN | 18 | 360 | A |
| AW022114 | UNKNOWN | 18 | 422 | A |
| AW022140 | UNKNOWN | 13 | 727 | A |
| AW022148 | UNKNOWN | 22 | 480 | A |
| AW022162 | UNKNOWN | 14 | 174 | T |

TABLE 1-continued

| Genbank # | Region | # reps | Position | Unit sequence |
|---|---|---|---|---|
| AW022211 | UNKNOWN | 18 | 396 | A |
| AW022213 | UNKNOWN | 15 | 53 | T |
| AW022237 | UNKNOWN | 18 | 359 | A |
| AW022257 | UNKNOWN | 14 | 506 | A |
| AW022259 | UNKNOWN | 18 | 242 | A |
| AW022311 | UNKNOWN | 18 | 179 | A |
| AW022311 | UNKNOWN | 15 | 8 | A |
| AW022315 | UNKNOWN | 18 | 337 | A |
| AW022317 | UNKNOWN | 22 | 343 | A |
| AW022376 | UNKNOWN | 20 | 279 | A |
| AW022410 | UNKNOWN | 13 | 443 | A |
| AW022419 | UNKNOWN | 17 | 399 | A |
| AW022433 | UNKNOWN | 24 | 298 | A |
| AW022454 | UNKNOWN | 18 | 131 | A |
| AW022455 | UNKNOWN | 18 | 316 | A |
| AW022504 | UNKNOWN | 20 | 268 | A |
| AW022580 | UNKNOWN | 24 | 426 | A |
| AW022580 | UNKNOWN | 13 | 87 | T |
| AW022607 | UNKNOWN | 20 | 545 | A |
| AW022623 | UNKNOWN | 7 | 58 | CA |
| AW022623 | UNKNOWN | 23 | 302 | A |
| AW022670 | UNKNOWN | 18 | 277 | A |
| AW022690 | UNKNOWN | 18 | 341 | A |
| AW022699 | UNKNOWN | 77 | 104 | A |
| AW022703 | UNKNOWN | 12 | 464 | A |
| AW022706 | UNKNOWN | 19 | 245 | A |
| AW022713 | UNKNOWN | 59 | 225 | A |
| AW022715 | UNKNOWN | 27 | 451 | A |
| AW022732 | UNKNOWN | 14 | 295 | A |
| AW022761 | UNKNOWN | 18 | 490 | A |
| AW022773 | UNKNOWN | 18 | 428 | A |
| AW022819 | UNKNOWN | 22 | 704 | C |
| AW022844 | UNKNOWN | 18 | 304 | A |
| AW022844 | UNKNOWN | 12 | 78 | A |
| AW022851 | UNKNOWN | 26 | 173 | A |
| AW022895 | UNKNOWN | 18 | 195 | A |
| AW023018 | UNKNOWN | 18 | 368 | A |
| AW023068 | UNKNOWN | 18 | 222 | A |
| AW023188 | UNKNOWN | 22 | 253 | A |
| AW023265 | UNKNOWN | 23 | 148 | A |
| AW023327 | UNKNOWN | 4.5 | 329 | AGAGAA |
| AW023327 | UNKNOWN | 7 | 320 | GA |
| AW023327 | UNKNOWN | 19 | 361 | A |
| AW023358 | UNKNOWN | 14 | 246 | A |
| AW023375 | UNKNOWN | 18 | 221 | A |
| AW023383 | UNKNOWN | 18 | 351 | A |
| AW023390 | UNKNOWN | 29 | 320 | A |
| AW023406 | UNKNOWN | 20 | 355 | A |
| AW023410 | UNKNOWN | 22 | 374 | A |
| AW023411 | UNKNOWN | 18 | 413 | A |
| AW023517 | UNKNOWN | 20 | 200 | A |
| AW023595 | UNKNOWN | 20 | 266 | A |
| AW023713 | UNKNOWN | 18 | 296 | A |
| AW023867 | UNKNOWN | 20 | 137 | A |
| AW023933 | UNKNOWN | 20 | 420 | A |
| AW023951 | UNKNOWN | 18 | 431 | A |
| AW023993 | UNKNOWN | 23 | 125 | A |
| AW024003 | UNKNOWN | 19 | 386 | A |
| AW024184 | UNKNOWN | 18 | 0 | T |
| AW024185 | UNKNOWN | 49 | 0 | T |
| AW024204 | UNKNOWN | 34 | 0 | T |
| AW024273 | UNKNOWN | 17 | 0 | T |
| AW024275 | UNKNOWN | 82 | 0 | T |
| AW024275 | UNKNOWN | 14 | 138 | A |
| AW024275 | UNKNOWN | 14 | 391 | C |
| AW024275 | UNKNOWN | 13 | 406 | G |
| AW024311 | UNKNOWN | 24 | 202 | A |
| AW024360 | UNKNOWN | 72 | 0 | T |
| AW024374 | UNKNOWN | 55 | 0 | T |
| AW024374 | UNKNOWN | 19 | 208 | A |
| AW024425 | UNKNOWN | 49 | 0 | T |
| AW024527 | UNKNOWN | 13 | 149 | T |
| AW024539 | UNKNOWN | 32 | 0 | T |
| AW024539 | UNKNOWN | 18 | 327 | A |
| AW024564 | UNKNOWN | 81 | 0 | T |
| AW024564 | UNKNOWN | 14 | 207 | C |
| AW024594 | UNKNOWN | 59 | 0 | T |

TABLE 1-continued

| Genbank # | Region | # reps | Position | Unit sequence |
|---|---|---|---|---|
| AW024594 | UNKNOWN | 12 | 137 | A |
| AW024627 | UNKNOWN | 6.33 | 187 | GCA |
| AW024653 | UNKNOWN | 3.5 | 30 | TCTTCC |
| AW024666 | UNKNOWN | 17 | 239 | A |
| AW024793 | UNKNOWN | 63 | 0 | T |
| AW024889 | UNKNOWN | 68 | 0 | T |
| AW024889 | UNKNOWN | 14 | 134 | C |
| AW024907 | UNKNOWN | 13 | 239 | A |
| AW024907 | UNKNOWN | 12 | 0 | T |
| AW024911 | UNKNOWN | 42 | 0 | T |
| AW024921 | UNKNOWN | 52 | 0 | T |
| AW024933 | UNKNOWN | 13 | 0 | T |
| AW024954 | UNKNOWN | 55 | 0 | T |
| AW024954 | UNKNOWN | 17 | 406 | A |
| AW024974 | UNKNOWN | 6 | 133 | GGCG |
| AW024976 | UNKNOWN | 38 | 0 | T |
| AW024976 | UNKNOWN | 22 | 209 | A |
| AW025060 | UNKNOWN | 15 | 394 | A |
| AW025123 | UNKNOWN | 50 | 0 | T |
| AW025138 | UNKNOWN | 13 | 0 | T |
| AW025169 | UNKNOWN | 14 | 0 | T |
| AW025336 | UNKNOWN | 25 | 0 | T |
| AW025399 | UNKNOWN | 18 | 81 | T |
| AW025412 | UNKNOWN | 66 | 0 | T |
| AW025412 | UNKNOWN | 30 | 123 | A |
| AW025412 | UNKNOWN | 25 | 272 | G |
| AW025463 | UNKNOWN | 3.8 | 197 | AAAAT |
| AW025463 | UNKNOWN | 9 | 90 | AC |
| AW025463 | UNKNOWN | 43 | 0 | T |
| AW025464 | UNKNOWN | 87 | 0 | T |
| AW025464 | UNKNOWN | 13 | 204 | A |
| AW025472 | UNKNOWN | 21 | 0 | T |
| AW025529 | UNKNOWN | 13 | 0 | T |
| AW025533 | UNKNOWN | 84 | 0 | T |
| AW025533 | UNKNOWN | 21 | 125 | A |
| AW025535 | UNKNOWN | 15 | 0 | T |
| AW025539 | UNKNOWN | 26 | 0 | T |
| AW025583 | UNKNOWN | 15 | 349 | A |
| AW025602 | UNKNOWN | 15 | 448 | A |
| AW025602 | UNKNOWN | 12 | 422 | T |
| AW025687 | UNKNOWN | 12 | 0 | T |
| AW025720 | UNKNOWN | 13 | 0 | T |
| AW025723 | UNKNOWN | 16 | 28 | T |
| AW025757 | UNKNOWN | 25 | 0 | T |
| AW025762 | UNKNOWN | 17 | 0 | T |
| AW025766 | UNKNOWN | 12 | 7 | T |
| AW025844 | UNKNOWN | 3.5 | 114 | AAAAAC |
| AW025844 | UNKNOWN | 16 | 0 | T |
| AW025958 | UNKNOWN | 23 | 0 | T |
| AW025980 | UNKNOWN | 14 | 0 | T |
| AW025988 | UNKNOWN | 17 | 330 | A |
| AW026000 | UNKNOWN | 35 | 0 | T |
| AW026021 | UNKNOWN | 30 | 0 | T |
| AW026074 | UNKNOWN | 36 | 0 | T |
| AW026087 | UNKNOWN | 70 | 0 | T |
| AW026087 | UNKNOWN | 20 | 130 | C |
| AW026087 | UNKNOWN | 15 | 248 | G |
| AW026092 | UNKNOWN | 29 | 0 | T |
| AW026120 | UNKNOWN | 18 | 0 | T |
| AW026121 | UNKNOWN | 67 | 0 | T |
| AW026123 | UNKNOWN | 50 | 0 | T |
| AW026123 | UNKNOWN | 12 | 220 | G |
| AW026135 | UNKNOWN | 27 | 0 | T |
| AW026144 | UNKNOWN | 15 | 12 | T |
| AW026188 | UNKNOWN | 33 | 0 | T |
| AW026198 | UNKNOWN | 4.75 | 7 | TTTC |
| AW026198 | UNKNOWN | 21 | 23 | T |
| AW026257 | UNKNOWN | 21 | 426 | AC |
| AW026271 | UNKNOWN | 12 | 0 | T |
| AW026286 | UNKNOWN | 15 | 0 | T |
| AW026305 | UNKNOWN | 19 | 38 | T |
| AW026425 | UNKNOWN | 73 | 0 | T |
| AW026425 | UNKNOWN | 21 | 90 | A |
| AW026425 | UNKNOWN | 12 | 158 | G |
| AW026477 | UNKNOWN | 61 | 0 | T |
| AW026477 | UNKNOWN | 18 | 93 | C |
| AW026485 | UNKNOWN | 23 | 483 | TG |

TABLE 1-continued

| Genbank # | Region | # reps | Position | Unit sequence |
|---|---|---|---|---|
| AW026528 | UNKNOWN | 12 | 0 | T |
| AW026557 | UNKNOWN | 54 | 0 | T |
| AW026567 | UNKNOWN | 62 | 0 | T |
| AW026567 | UNKNOWN | 17 | 203 | A |
| AW026607 | UNKNOWN | 28 | 0 | T |
| AW026610 | UNKNOWN | 111 | 0 | T |
| AW026610 | UNKNOWN | 19 | 283 | C |
| AW026610 | UNKNOWN | 14 | 233 | C |
| AW026610 | UNKNOWN | 14 | 346 | G |
| AW026610 | UNKNOWN | 13 | 169 | C |
| AW026610 | UNKNOWN | 12 | 199 | A |
| AW026618 | UNKNOWN | 54 | 0 | T |
| AW026630 | UNKNOWN | 67 | 0 | T |
| AW026630 | UNKNOWN | 15 | 227 | C |
| AW026635 | UNKNOWN | 40 | 0 | T |
| AW026641 | UNKNOWN | 13 | 0 | T |
| AW026665 | UNKNOWN | 12 | 8 | G |
| AW026667 | UNKNOWN | 18 | 0 | T |
| AW026707 | UNKNOWN | 63 | 0 | T |
| AW026707 | UNKNOWN | 16 | 161 | A |
| AW026718 | UNKNOWN | 38 | 0 | T |
| AW026730 | UNKNOWN | 64 | 0 | T |
| AW026732 | UNKNOWN | 14 | 52 | T |
| AW026735 | UNKNOWN | 15 | 0 | T |
| AW026750 | UNKNOWN | 12 | 28 | T |
| AW026766 | UNKNOWN | 16 | 0 | T |
| AW026780 | UNKNOWN | 28 | 0 | T |
| AW026786 | UNKNOWN | 11.5 | 261 | AT |
| AW026786 | UNKNOWN | 25 | 0 | T |
| AW026796 | UNKNOWN | 12 | 0 | T |
| AW026815 | UNKNOWN | 24 | 0 | T |
| AW026817 | UNKNOWN | 43 | 0 | T |
| AW026817 | UNKNOWN | 12 | 344 | C |
| AW026853 | UNKNOWN | 23 | 141 | A |
| AW026882 | UNKNOWN | 118 | 0 | T |
| AW026882 | UNKNOWN | 13 | 118 | A |
| AW026882 | UNKNOWN | 13 | 147 | C |
| AW026887 | UNKNOWN | 17 | 0 | T |
| AW026896 | UNKNOWN | 57 | 0 | T |
| AW026896 | UNKNOWN | 13 | 125 | G |
| AW026905 | UNKNOWN | 61 | 0 | T |
| AW026905 | UNKNOWN | 18 | 263 | A |
| AW026905 | UNKNOWN | 13 | 123 | C |
| AW027221 | UNKNOWN | 44 | 0 | T |
| AW027221 | UNKNOWN | 12 | 44 | A |
| AW027363 | UNKNOWN | 18 | 115 | A |
| AW027374 | UNKNOWN | 59 | 0 | T |
| AW027374 | UNKNOWN | 15 | 142 | A |
| AW027374 | UNKNOWN | 14 | 126 | C |
| AW027456 | UNKNOWN | 12 | 306 | AC |
| AW027492 | UNKNOWN | 8.5 | 401 | CA |
| AW027492 | UNKNOWN | 20 | 4 | T |
| AW027644 | UNKNOWN | 13 | 393 | T |
| AW027898 | UNKNOWN | 55 | 0 | T |
| AW027898 | UNKNOWN | 24 | 265 | G |
| AW027904 | UNKNOWN | 67 | 0 | T |
| AW027904 | UNKNOWN | 20 | 268 | A |
| AW027904 | UNKNOWN | 12 | 106 | A |
| AW027926 | UNKNOWN | 13 | 0 | T |
| AW028007 | UNKNOWN | 81 | 0 | T |
| AW028007 | UNKNOWN | 15 | 286 | G |
| AW028007 | UNKNOWN | 12 | 161 | G |
| AW028033 | UNKNOWN | 55 | 0 | T |
| AW028033 | UNKNOWN | 22 | 148 | A |
| AW028192 | UNKNOWN | 20 | 0 | T |
| AW028192 | UNKNOWN | 16 | 126 | G |
| AW028193 | UNKNOWN | 35 | 0 | T |
| AW028196 | UNKNOWN | 60 | 0 | T |
| AW028196 | UNKNOWN | 12 | 178 | G |
| AW028330 | UNKNOWN | 4.75 | 379 | TTTA |
| AW028359 | UNKNOWN | 36 | 0 | T |
| AW028362 | UNKNOWN | 48 | 0 | T |
| AW028369 | UNKNOWN | 3.16 | 171 | GGGCGGACCCCT (SEQ ID NO: 207) |
| AW028369 | UNKNOWN | 45 | 0 | T |
| AW028379 | UNKNOWN | 37 | 0 | T |
| AW028392 | UNKNOWN | 21 | 0 | T |
| AW028416 | UNKNOWN | 69 | 0 | T |

TABLE 1-continued

| Genbank # | Region | # reps | Position | Unit sequence |
|---|---|---|---|---|
| AW028416 | UNKNOWN | 16 | 287 | C |
| AW028416 | UNKNOWN | 15 | 150 | G |
| AW028416 | UNKNOWN | 13 | 137 | C |
| AW028419 | UNKNOWN | 41 | 0 | T |
| AW028442 | UNKNOWN | 56 | 0 | T |
| AW028442 | UNKNOWN | 13 | 128 | A |
| AW028447 | UNKNOWN | 12 | 0 | T |
| AW028454 | UNKNOWN | 53 | 0 | T |
| AW028491 | UNKNOWN | 12 | 90 | A |
| AW028809 | UNKNOWN | 3.6 | 67 | GGGCG |
| AW028840 | UNKNOWN | 67 | 0 | T |
| AW028840 | UNKNOWN | 12 | 92 | C |
| AW028890 | UNKNOWN | 3.8 | 63 | TTTTG |
| AW028911 | UNKNOWN | 21 | 29 | T |
| AW028911 | UNKNOWN | 15 | 288 | C |
| AW028911 | UNKNOWN | 12 | 90 | A |
| AW028924 | UNKNOWN | 27 | 0 | T |
| AW028943 | UNKNOWN | 3.6 | 41 | CTTTC |
| AW028943 | UNKNOWN | 4.5 | 0 | CTTT |
| AW028943 | UNKNOWN | 13 | 77 | T |
| AW028951 | UNKNOWN | 24 | 0 | T |
| AW028964 | UNKNOWN | 37 | 0 | T |
| AW029009 | UNKNOWN | 41 | 0 | T |
| AW029072 | UNKNOWN | 72 | 0 | T |
| AW029072 | UNKNOWN | 18 | 201 | C |
| AW029072 | UNKNOWN | 17 | 277 | A |
| AW029072 | UNKNOWN | 12 | 236 | A |
| AW029081 | UNKNOWN | 93 | 0 | T |
| AW029081 | UNKNOWN | 27 | 167 | G |
| AW029081 | UNKNOWN | 17 | 141 | A |
| AW029081 | UNKNOWN | 12 | 207 | C |
| AW029086 | UNKNOWN | 27 | 0 | T |
| AW029095 | UNKNOWN | 21 | 149 | T |
| AW029102 | UNKNOWN | 111 | 3 | T |
| AW029102 | UNKNOWN | 23 | 366 | G |
| AW029102 | UNKNOWN | 16 | 126 | A |
| AW029102 | UNKNOWN | 15 | 233 | C |
| AW029102 | UNKNOWN | 13 | 175 | G |
| AW029124 | UNKNOWN | 61 | 0 | T |
| AW029124 | UNKNOWN | 18 | 390 | G |
| AW029124 | UNKNOWN | 13 | 82 | A |
| AW029186 | UNKNOWN | 74 | 0 | T |
| AW029186 | UNKNOWN | 12 | 112 | A |
| AW029197 | UNKNOWN | 80 | 0 | T |
| AW029197 | UNKNOWN | 14 | 121 | A |
| AW029199 | UNKNOWN | 47 | 0 | T |
| AW029201 | UNKNOWN | 82 | 0 | T |
| AW029201 | UNKNOWN | 25 | 138 | C |
| AW029201 | UNKNOWN | 19 | 119 | A |
| AW029216 | UNKNOWN | 63 | 0 | T |
| AW029216 | UNKNOWN | 15 | 97 | A |
| AW029234 | UNKNOWN | 26 | 0 | T |
| AW029238 | UNKNOWN | 63 | 0 | T |
| AW029238 | UNKNOWN | 16 | 222 | A |
| AW029263 | UNKNOWN | 76 | 0 | T |
| AW029263 | UNKNOWN | 17 | 135 | C |
| AW029263 | UNKNOWN | 15 | 200 | G |
| AW029265 | UNKNOWN | 45 | 0 | T |
| AW029265 | UNKNOWN | 13 | 124 | G |
| AW029271 | UNKNOWN | 86 | 0 | T |
| AW029271 | UNKNOWN | 22 | 157 | C |
| AW029275 | UNKNOWN | 79 | 0 | T |
| AW029275 | UNKNOWN | 14 | 351 | G |
| AW029275 | UNKNOWN | 13 | 263 | A |
| AW029289 | UNKNOWN | 47 | 0 | T |
| AW029294 | UNKNOWN | 69 | 0 | T |
| AW029294 | UNKNOWN | 12 | 297 | G |
| AW029294 | UNKNOWN | 12 | 329 | A |
| AW029317 | UNKNOWN | 56 | 0 | T |
| AW029317 | UNKNOWN | 20 | 110 | A |
| AW029317 | UNKNOWN | 15 | 87 | C |
| AW029329 | UNKNOWN | 86 | 0 | T |
| AW029329 | UNKNOWN | 18 | 141 | G |
| AW029349 | UNKNOWN | 90 | 0 | T |
| AW029349 | UNKNOWN | 15 | 125 | A |
| AW029349 | UNKNOWN | 13 | 219 | G |
| AW029401 | UNKNOWN | 68 | 0 | T |

TABLE 1-continued

| Genbank # | Region | # reps | Position | Unit sequence |
|---|---|---|---|---|
| AW029401 | UNKNOWN | 25 | 160 | A |
| AW029401 | UNKNOWN | 12 | 126 | A |
| AW029408 | UNKNOWN | 14 | 396 | A |
| AW029454 | UNKNOWN | 18 | 0 | T |
| AW029457 | UNKNOWN | 51 | 0 | T |
| AW029489 | UNKNOWN | 48 | 0 | T |
| AW029533 | UNKNOWN | 69 | 0 | T |
| AW029533 | UNKNOWN | 12 | 111 | G |
| AW029566 | UNKNOWN | 59 | 0 | T |
| AW029571 | UNKNOWN | 13 | 264 | T |
| AW029579 | UNKNOWN | 79 | 0 | T |
| AW029579 | UNKNOWN | 13 | 323 | G |
| AW029606 | UNKNOWN | 70 | 0 | T |
| AW029606 | UNKNOWN | 20 | 349 | C |
| AW029606 | UNKNOWN | 15 | 254 | G |
| AW029611 | UNKNOWN | 84 | 0 | T |
| AW029611 | UNKNOWN | 30 | 186 | A |
| AW029611 | UNKNOWN | 13 | 154 | C |
| AW029638 | UNKNOWN | 72 | 0 | T |
| AW029638 | UNKNOWN | 24 | 270 | G |
| AW029638 | UNKNOWN | 14 | 159 | C |
| AW029638 | UNKNOWN | 13 | 72 | A |
| AW043556 | UNKNOWN | 14 | 0 | T |
| AW043577 | UNKNOWN | 14 | 0 | T |
| AW043579 | UNKNOWN | 18 | 0 | T |
| AW043613 | UNKNOWN | 13 | 0 | T |
| AW043631 | UNKNOWN | 13 | 281 | T |
| AW043635 | UNKNOWN | 24 | 0 | T |
| AW043668 | UNKNOWN | 5.66 | 90 | GCG |
| AW043683 | UNKNOWN | 16 | 36 | A |
| AW043738 | UNKNOWN | 14 | 44 | A |
| AW043782 | UNKNOWN | 18 | 31 | A |
| AW043793 | UNKNOWN | 8.5 | 60 | AC |
| AW043803 | UNKNOWN | 31 | 0 | T |
| AW043817 | UNKNOWN | 13 | 15 | T |
| AW043848 | UNKNOWN | 50 | 0 | T |
| AW043848 | UNKNOWN | 13 | 375 | A |
| AW043904 | UNKNOWN | 12 | 354 | T |
| AW043983 | UNKNOWN | 20 | 0 | T |
| AW044029 | UNKNOWN | 66 | 0 | T |
| AW044029 | UNKNOWN | 14 | 133 | C |
| AW044045 | UNKNOWN | 14 | 157 | T |
| AW044061 | UNKNOWN | 15 | 0 | T |
| AW044083 | UNKNOWN | 17 | 0 | T |
| AW044118 | UNKNOWN | 26 | 0 | T |
| AW044190 | UNKNOWN | 4.75 | 100 | AAAC |
| AW044226 | UNKNOWN | 12 | 0 | T |
| AW044251 | UNKNOWN | 19 | 337 | T |
| AW044299 | UNKNOWN | 13 | 0 | T |
| AW044305 | UNKNOWN | 8 | 66 | GCG |
| AW044344 | UNKNOWN | 12 | 69 | A |
| AW044347 | UNKNOWN | 32 | 0 | T |
| AW044357 | UNKNOWN | 7 | 39 | CT |
| AW044386 | UNKNOWN | 59 | 0 | T |
| AW044386 | UNKNOWN | 15 | 225 | A |
| AW044386 | UNKNOWN | 12 | 138 | A |
| AW044391 | UNKNOWN | 98 | 0 | T |
| AW044391 | UNKNOWN | 16 | 126 | G |
| AW044391 | UNKNOWN | 15 | 223 | C |
| AW044396 | UNKNOWN | 18 | 0 | T |
| AW044404 | UNKNOWN | 89 | 0 | T |
| AW044404 | UNKNOWN | 18 | 136 | C |
| AW044404 | UNKNOWN | 18 | 174 | G |
| AW044404 | UNKNOWN | 16 | 156 | A |
| AW044404 | UNKNOWN | 13 | 115 | A |
| AW044420 | UNKNOWN | 13 | 0 | T |
| AW044506 | UNKNOWN | 14 | 165 | A |
| AW044625 | UNKNOWN | 18 | 0 | T |
| AW044626 | UNKNOWN | 66 | 0 | T |
| AW044626 | UNKNOWN | 13 | 172 | C |
| AW044676 | UNKNOWN | 23 | 0 | T |
| AW051169 | UNKNOWN | 18 | 72 | AG |
| AW051169 | UNKNOWN | 10 | 53 | CA |
| AW051169 | UNKNOWN | 22 | 0 | T |
| AW051169 | UNKNOWN | 13 | 356 | G |
| AW051318 | UNKNOWN | 9 | 165 | AC |
| AW051338 | UNKNOWN | 13 | 0 | T |

TABLE 1-continued

| Genbank # | Region | # reps | Position | Unit sequence |
|---|---|---|---|---|
| AW051339 | UNKNOWN | 8.5 | 310 | TA |
| AW051339 | UNKNOWN | 7 | 336 | CA |
| AW051518 | UNKNOWN | 23 | 1 | T |
| AW051591 | UNKNOWN | 18 | 0 | T |
| AW051597 | UNKNOWN | 13 | 28 | T |
| AW051603 | UNKNOWN | 7 | 29 | TA |
| AW051699 | UNKNOWN | 13 | 9 | T |
| AW051767 | UNKNOWN | 15 | 0 | T |
| AW051796 | UNKNOWN | 5.75 | 170 | TTTA |
| AW051879 | UNKNOWN | 3.6 | 97 | GGGCA |
| AW052033 | UNKNOWN | 15 | 0 | T |
| AW052126 | UNKNOWN | 22 | 0 | T |
| AW052142 | UNKNOWN | 7.66 | 287 | TTC |
| AW054703 | UNKNOWN | 20 | 4 | T |
| AW054710 | UNKNOWN | 3.8 | 306 | TTTTC |
| AW054793 | UNKNOWN | 13 | 0 | T |
| AW054859 | UNKNOWN | 25 | 0 | T |
| AW054939 | UNKNOWN | 59 | 2 | T |
| AW055226 | UNKNOWN | 12 | 437 | T |
| AW057513 | UNKNOWN | 12 | 0 | T |
| AW057685 | UNKNOWN | 48 | 0 | T |
| AW057685 | UNKNOWN | 12 | 381 | A |
| AW057779 | UNKNOWN | 33 | 0 | T |
| AW058278 | UNKNOWN | 18 | 0 | T |
| AW058459 | UNKNOWN | 14 | 0 | T |
| AW058493 | UNKNOWN | 12 | 70 | T |
| AW058544 | UNKNOWN | 17 | 384 | T |
| AW058607 | UNKNOWN | 21 | 0 | T |
| AW062247 | UNKNOWN | 15 | 440 | A |
| AW062310 | UNKNOWN | 13 | 119 | A |
| AW062314 | UNKNOWN | 13 | 676 | A |
| AW062338 | UNKNOWN | 19 | 0 | T |
| AW062359 | UNKNOWN | 15 | 331 | A |
| AW063026 | UNKNOWN | 14 | 919 | A |
| AW068647 | UNKNOWN | 14 | 201 | A |
| AW068845 | UNKNOWN | 124 | 8 | A |
| AW068901 | UNKNOWN | 18 | 0 | T |
| AW068972 | UNKNOWN | 17 | 0 | T |
| AW068977 | UNKNOWN | 20 | 0 | T |
| AW069001 | UNKNOWN | 18 | 0 | T |
| AW069016 | UNKNOWN | 19 | 0 | T |
| AW069047 | UNKNOWN | 19 | 0 | T |
| AW069073 | UNKNOWN | 19 | 0 | T |
| AW069084 | UNKNOWN | 27 | 0 | T |
| AW069142 | UNKNOWN | 7.5 | 17 | TA |
| AW069142 | UNKNOWN | 18 | 0 | T |
| AW069158 | UNKNOWN | 18 | 0 | T |
| AW069167 | UNKNOWN | 20 | 0 | T |
| AW069181 | UNKNOWN | 18 | 0 | T |
| AW069191 | UNKNOWN | 18 | 0 | T |
| AW069285 | UNKNOWN | 17 | 0 | T |
| AW069365 | UNKNOWN | 18 | 0 | T |
| AW069415 | UNKNOWN | 24 | 0 | T |
| AW069445 | UNKNOWN | 8.5 | 422 | AG |
| AW069445 | UNKNOWN | 18 | 0 | T |
| AW069445 | UNKNOWN | 15 | 399 | A |
| AW069453 | UNKNOWN | 18 | 0 | T |
| AW069467 | UNKNOWN | 4 | 39 | ATTTT |
| AW069467 | UNKNOWN | 31 | 0 | T |
| AW069500 | UNKNOWN | 17 | 0 | T |
| AW069546 | UNKNOWN | 18 | 0 | T |
| AW069550 | UNKNOWN | 18 | 0 | T |
| AW069577 | UNKNOWN | 20 | 0 | T |
| AW069657 | UNKNOWN | 19 | 0 | T |
| AW069660 | UNKNOWN | 18 | 0 | T |
| AW069679 | UNKNOWN | 18 | 0 | T |
| AW069729 | UNKNOWN | 27 | 16 | T |
| AW069744 | UNKNOWN | 7 | 556 | TA |
| AW069744 | UNKNOWN | 18 | 0 | T |
| AW069762 | UNKNOWN | 20 | 0 | T |
| AW069787 | UNKNOWN | 18 | 0 | T |
| AW069832 | UNKNOWN | 19 | 0 | T |
| AW069838 | UNKNOWN | 18 | 0 | T |
| AW069867 | UNKNOWN | 28 | 0 | T |
| AW070220 | UNKNOWN | 25 | 0 | T |
| AW070231 | UNKNOWN | 13 | 0 | T |
| AW070240 | UNKNOWN | 23 | 0 | T |

TABLE 1-continued

| Genbank # | Region | # reps | Position | Unit sequence |
|---|---|---|---|---|
| AW070323 | UNKNOWN | 25 | 0 | T |
| AW070327 | UNKNOWN | 12 | 0 | T |
| AW070346 | UNKNOWN | 37 | 0 | T |
| AW070419 | UNKNOWN | 14 | 286 | T |
| AW070466 | UNKNOWN | 12 | 400 | A |
| AW070522 | UNKNOWN | 12 | 0 | T |
| AW070549 | UNKNOWN | 24 | 0 | T |
| AW070598 | UNKNOWN | 14 | 0 | T |
| AW070764 | UNKNOWN | 12 | 470 | T |
| AW070766 | UNKNOWN | 6.5 | 0 | GT |
| AW070767 | UNKNOWN | 75 | 0 | T |
| AW070854 | UNKNOWN | 4.5 | 71 | TAAA |
| AW070854 | UNKNOWN | 14 | 0 | T |
| AW070967 | UNKNOWN | 43 | 0 | T |
| AW070967 | UNKNOWN | 14 | 176 | A |
| AW071014 | UNKNOWN | 78 | 0 | T |
| AW071014 | UNKNOWN | 12 | 137 | A |
| AW071138 | UNKNOWN | 14 | 80 | G |
| AW071177 | UNKNOWN | 99 | 4 | T |
| AW071177 | UNKNOWN | 23 | 280 | G |
| AW071177 | UNKNOWN | 12 | 111 | A |
| AW071177 | UNKNOWN | 12 | 161 | G |
| AW071254 | UNKNOWN | 15 | 352 | A |
| AW071303 | UNKNOWN | 22 | 153 | A |
| AW071365 | UNKNOWN | 28 | 179 | A |
| AW071377 | UNKNOWN | 70 | 19 | A |
| AW071377 | UNKNOWN | 13 | 121 | T |
| AW071395 | UNKNOWN | 69 | 19 | A |
| AW071412 | UNKNOWN | 77 | 19 | A |
| AW071431 | UNKNOWN | 41 | 0 | T |
| AW071516 | UNKNOWN | 57 | 0 | T |
| AW071516 | UNKNOWN | 18 | 363 | G |
| AW071593 | UNKNOWN | 49 | 0 | T |
| AW071644 | UNKNOWN | 19 | 0 | T |
| AW071689 | UNKNOWN | 71 | 0 | T |
| AW071689 | UNKNOWN | 20 | 115 | C |
| AW071689 | UNKNOWN | 13 | 169 | G |
| AW071689 | UNKNOWN | 12 | 95 | A |
| AW071705 | UNKNOWN | 14 | 0 | T |
| AW071709 | UNKNOWN | 13 | 0 | T |
| AW071753 | UNKNOWN | 27 | 0 | T |
| AW071880 | UNKNOWN | 30 | 0 | T |
| AW072171 | UNKNOWN | 16 | 0 | T |
| AW072187 | UNKNOWN | 26 | 0 | T |
| AW072346 | UNKNOWN | 18 | 0 | T |
| AW072349 | UNKNOWN | 54 | 0 | T |
| AW072349 | UNKNOWN | 12 | 83 | G |
| AW072349 | UNKNOWN | 12 | 180 | A |
| AW072387 | UNKNOWN | 15 | 0 | T |
| AW072395 | UNKNOWN | 3.16 | 224 | GGGGTGGCGTATTCTGGTCTCCTACAGTCATATTTT (SEQ ID NO: 208) |
| AW072395 | UNKNOWN | 2.63 | 108 | CATATTTTGGGGTGACGTATTCTGGTCTCCTACAGT (SEQ ID NO: 209) |
| AW072413 | UNKNOWN | 54 | 0 | T |
| AW072413 | UNKNOWN | 14 | 81 | A |
| AW072487 | UNKNOWN | 28 | 404 | A |
| AW072492 | UNKNOWN | 29 | 270 | A |
| AW072515 | UNKNOWN | 27 | 191 | A |
| AW072530 | UNKNOWN | 34 | 0 | T |
| AW072588 | UNKNOWN | 72 | 0 | T |
| AW072588 | UNKNOWN | 20 | 156 | A |
| AW072715 | UNKNOWN | 28 | 177 | A |
| AW072817 | UNKNOWN | 43 | 0 | T |
| AW072817 | UNKNOWN | 13 | 208 | A |
| AW072817 | UNKNOWN | 12 | 395 | C |
| AW072845 | UNKNOWN | 29 | 0 | T |
| AW072904 | UNKNOWN | 27 | 0 | T |
| AW072919 | UNKNOWN | 54 | 0 | T |
| AW072930 | UNKNOWN | 101 | 0 | T |
| AW072930 | UNKNOWN | 13 | 203 | C |
| AW072963 | UNKNOWN | 17 | 0 | T |
| AW073046 | UNKNOWN | 29 | 266 | A |
| AW073270 | UNKNOWN | 105 | 0 | T |
| AW073270 | UNKNOWN | 21 | 105 | A |
| AW073270 | UNKNOWN | 20 | 223 | C |
| AW073270 | UNKNOWN | 14 | 209 | G |
| AW073354 | UNKNOWN | 24 | 0 | T |

TABLE 1-continued

| Genbank # | Region | # reps | Position | Unit sequence |
|---|---|---|---|---|
| AW073434 | UNKNOWN | 26 | 337 | A |
| AW073444 | UNKNOWN | 24 | 177 | A |
| AW073476 | UNKNOWN | 26 | 191 | A |
| AW073507 | UNKNOWN | 12 | 20 | T |
| AW073562 | UNKNOWN | 57 | 0 | T |
| AW073562 | UNKNOWN | 15 | 183 | A |
| AW073563 | UNKNOWN | 17 | 0 | T |
| AW073598 | UNKNOWN | 23 | 0 | T |
| AW073612 | UNKNOWN | 26 | 356 | A |
| AW073631 | UNKNOWN | 26 | 240 | A |
| AW073643 | UNKNOWN | 28 | 146 | A |
| AW073660 | UNKNOWN | 7.5 | 18 | TA |
| AW073660 | UNKNOWN | 28 | 302 | A |
| AW073664 | UNKNOWN | 53 | 0 | T |
| AW073677 | UNKNOWN | 80 | 0 | T |
| AW073677 | UNKNOWN | 24 | 398 | A |
| AW073677 | UNKNOWN | 15 | 379 | A |
| AW073677 | UNKNOWN | 14 | 82 | A |
| AW073681 | UNKNOWN | 78 | 0 | T |
| AW073681 | UNKNOWN | 13 | 312 | C |
| AW073684 | UNKNOWN | 55 | 0 | T |
| AW073685 | UNKNOWN | 42 | 0 | T |
| AW073697 | UNKNOWN | 80 | 0 | T |
| AW073697 | UNKNOWN | 22 | 143 | G |
| AW073697 | UNKNOWN | 14 | 109 | C |
| AW073699 | UNKNOWN | 73 | 0 | T |
| AW073699 | UNKNOWN | 20 | 324 | G |
| AW073699 | UNKNOWN | 14 | 150 | G |
| AW073708 | UNKNOWN | 84 | 0 | T |
| AW073708 | UNKNOWN | 20 | 110 | A |
| AW073708 | UNKNOWN | 17 | 182 | G |
| AW073708 | UNKNOWN | 14 | 201 | C |
| AW073708 | UNKNOWN | 12 | 134 | C |
| AW073710 | UNKNOWN | 48 | 0 | T |
| AW073721 | UNKNOWN | 57 | 0 | T |
| AW073721 | UNKNOWN | 13 | 321 | G |
| AW073784 | UNKNOWN | 26 | 0 | T |
| AW073791 | UNKNOWN | 16 | 2 | T |
| AW073796 | UNKNOWN | 46 | 0 | T |
| AW073796 | UNKNOWN | 13 | 149 | A |
| AW073824 | UNKNOWN | 60 | 0 | T |
| AW073824 | UNKNOWN | 16 | 114 | C |
| AW073824 | UNKNOWN | 14 | 192 | G |
| AW073843 | UNKNOWN | 50 | 0 | T |
| AW073850 | UNKNOWN | 28 | 0 | T |
| AW073850 | UNKNOWN | 17 | 92 | C |
| AW073858 | UNKNOWN | 59 | 0 | T |
| AW073858 | UNKNOWN | 15 | 291 | G |
| AW073868 | UNKNOWN | 78 | 0 | T |
| AW073868 | UNKNOWN | 13 | 290 | A |
| AW073868 | UNKNOWN | 12 | 78 | G |
| AW073868 | UNKNOWN | 12 | 137 | A |
| AW073877 | UNKNOWN | 47 | 0 | T |
| AW073877 | UNKNOWN | 12 | 231 | C |
| AW073880 | UNKNOWN | 19 | 0 | T |
| AW073882 | UNKNOWN | 90 | 0 | T |
| AW073882 | UNKNOWN | 21 | 274 | C |
| AW073882 | UNKNOWN | 14 | 100 | A |
| AW073882 | UNKNOWN | 12 | 177 | C |
| AW073888 | UNKNOWN | 40 | 0 | T |
| AW073896 | UNKNOWN | 25 | 0 | T |
| AW073898 | UNKNOWN | 59 | 0 | T |
| AW073907 | UNKNOWN | 59 | 0 | T |
| AW073907 | UNKNOWN | 12 | 185 | C |
| AW073926 | UNKNOWN | 64 | 0 | T |
| AW073926 | UNKNOWN | 15 | 122 | C |
| AW073936 | UNKNOWN | 17 | 0 | T |
| AW073946 | UNKNOWN | 61 | 0 | T |
| AW073946 | UNKNOWN | 12 | 247 | C |
| AW073953 | UNKNOWN | 37 | 0 | T |
| AW073956 | UNKNOWN | 57 | 0 | T |
| AW073956 | UNKNOWN | 16 | 219 | C |
| AW073956 | UNKNOWN | 12 | 133 | A |
| AW073956 | UNKNOWN | 12 | 178 | C |
| AW073994 | UNKNOWN | 89 | 0 | T |
| AW073994 | UNKNOWN | 22 | 146 | G |
| AW073994 | UNKNOWN | 15 | 112 | C |

TABLE 1-continued

| Genbank # | Region | # reps | Position | Unit sequence |
|---|---|---|---|---|
| AW073994 | UNKNOWN | 15 | 127 | A |
| AW073996 | UNKNOWN | 60 | 0 | T |
| AW073996 | UNKNOWN | 23 | 126 | A |
| AW074009 | UNKNOWN | 80 | 0 | T |
| AW074018 | UNKNOWN | 45 | 0 | T |
| AW074018 | UNKNOWN | 13 | 160 | A |
| AW074049 | UNKNOWN | 6.5 | 328 | TG |
| AW074085 | UNKNOWN | 18 | 0 | T |
| AW074086 | UNKNOWN | 35 | 0 | T |
| AW074095 | UNKNOWN | 49 | 0 | T |
| AW074095 | UNKNOWN | 14 | 149 | C |
| AW074095 | UNKNOWN | 12 | 137 | A |
| AW074114 | UNKNOWN | 18 | 0 | T |
| AW074142 | UNKNOWN | 62 | 0 | T |
| AW074142 | UNKNOWN | 12 | 72 | A |
| AW074143 | UNKNOWN | 13 | 0 | T |
| AW074154 | UNKNOWN | 29 | 0 | T |
| AW074161 | UNKNOWN | 93 | 0 | T |
| AW074161 | UNKNOWN | 19 | 115 | G |
| AW074161 | UNKNOWN | 17 | 201 | C |
| AW074161 | UNKNOWN | 14 | 163 | C |
| AW074172 | UNKNOWN | 98 | 0 | T |
| AW074172 | UNKNOWN | 16 | 134 | C |
| AW074172 | UNKNOWN | 15 | 233 | G |
| AW074172 | UNKNOWN | 14 | 117 | A |
| AW074172 | UNKNOWN | 14 | 150 | G |
| AW074199 | UNKNOWN | 50 | 0 | T |
| AW074209 | UNKNOWN | 13 | 0 | T |
| AW074212 | UNKNOWN | 19 | 0 | T |
| AW074230 | UNKNOWN | 13 | 0 | T |
| AW074236 | UNKNOWN | 54 | 0 | T |
| AW074236 | UNKNOWN | 13 | 110 | A |
| AW074259 | UNKNOWN | 28 | 0 | T |
| AW074274 | UNKNOWN | 66 | 0 | T |
| AW074274 | UNKNOWN | 13 | 103 | A |
| AW074301 | UNKNOWN | 77 | 0 | T |
| AW074301 | UNKNOWN | 14 | 143 | A |
| AW074301 | UNKNOWN | 12 | 117 | G |
| AW074315 | UNKNOWN | 46 | 0 | T |
| AW074315 | UNKNOWN | 12 | 258 | G |
| AW074362 | UNKNOWN | 18 | 0 | T |
| AW074365 | UNKNOWN | 50 | 0 | T |
| AW074374 | UNKNOWN | 60 | 0 | T |
| AW074374 | UNKNOWN | 12 | 86 | A |
| AW074376 | UNKNOWN | 59 | 0 | T |
| AW074376 | UNKNOWN | 13 | 291 | G |
| AW074443 | UNKNOWN | 38 | 0 | T |
| AW074459 | UNKNOWN | 94 | 0 | T |
| AW074459 | UNKNOWN | 12 | 148 | A |
| AW074476 | UNKNOWN | 35 | 0 | T |
| AW074476 | UNKNOWN | 12 | 344 | G |
| AW074556 | UNKNOWN | 33 | 0 | T |
| AW074557 | UNKNOWN | 41 | 0 | T |
| AW074624 | UNKNOWN | 14 | 0 | T |
| AW074638 | UNKNOWN | 56 | 0 | T |
| AW074651 | UNKNOWN | 52 | 0 | T |
| AW074663 | UNKNOWN | 50 | 0 | T |
| AW074663 | UNKNOWN | 16 | 109 | C |
| AW074663 | UNKNOWN | 12 | 222 | A |
| AW074702 | UNKNOWN | 62 | 0 | T |
| AW074702 | UNKNOWN | 15 | 99 | A |
| AW074702 | UNKNOWN | 14 | 230 | C |
| AW074702 | UNKNOWN | 13 | 114 | C |
| AW074702 | UNKNOWN | 12 | 85 | A |
| AW074707 | UNKNOWN | 4.75 | 82 | ATAG |
| AW074727 | UNKNOWN | 46 | 0 | T |
| AW074742 | UNKNOWN | 12 | 0 | T |
| AW074754 | UNKNOWN | 5.2 | 267 | TATTA |
| AW074777 | UNKNOWN | 29 | 179 | A |
| AW074793 | UNKNOWN | 29 | 322 | A |
| AW074803 | UNKNOWN | 30 | 201 | A |
| AW074804 | UNKNOWN | 28 | 179 | A |
| AW074816 | UNKNOWN | 27 | 290 | A |
| AW074839 | UNKNOWN | 13 | 0 | T |
| AW074853 | UNKNOWN | 20 | 0 | T |
| AW074900 | UNKNOWN | 22 | 176 | A |
| AW074910 | UNKNOWN | 29 | 199 | A |

TABLE 1-continued

| Genbank # | Region | # reps | Position | Unit sequence |
|---|---|---|---|---|
| AW074933 | UNKNOWN | 6.5 | 303 | AC |
| AW074970 | UNKNOWN | 30 | 188 | A |
| AW074977 | UNKNOWN | 28 | 174 | A |
| AW075022 | UNKNOWN | 27 | 226 | A |
| AW075034 | UNKNOWN | 26 | 192 | A |
| AW075067 | UNKNOWN | 30 | 356 | A |
| AW075094 | UNKNOWN | 25 | 395 | A |
| AW075104 | UNKNOWN | 13 | 219 | A |
| AW075108 | UNKNOWN | 24 | 245 | A |
| AW075153 | UNKNOWN | 20 | 228 | A |
| AW075178 | UNKNOWN | 25 | 210 | A |
| AW075188 | UNKNOWN | 16 | 409 | A |
| AW075242 | UNKNOWN | 21 | 438 | A |
| AW075248 | UNKNOWN | 13 | 1 | T |
| AW075251 | UNKNOWN | 28 | 0 | T |
| AW075305 | UNKNOWN | 81 | 0 | T |
| AW075305 | UNKNOWN | 13 | 210 | C |
| AW075334 | UNKNOWN | 3.85 | 170 | TTTTTTC |
| AW075351 | UNKNOWN | 118 | 0 | T |
| AW075351 | UNKNOWN | 27 | 205 | G |
| AW075351 | UNKNOWN | 13 | 118 | C |
| AW075351 | UNKNOWN | 12 | 169 | A |
| AW075382 | UNKNOWN | 57 | 0 | T |
| AW075397 | UNKNOWN | 53 | 0 | T |
| AW075409 | UNKNOWN | 55 | 0 | T |
| AW075413 | UNKNOWN | 112 | 0 | T |
| AW075413 | UNKNOWN | 25 | 128 | A |
| AW075413 | UNKNOWN | 21 | 199 | C |
| AW075413 | UNKNOWN | 19 | 180 | G |
| AW075413 | UNKNOWN | 14 | 153 | C |
| AW075418 | UNKNOWN | 78 | 0 | T |
| AW075418 | UNKNOWN | 12 | 284 | C |
| AW075426 | UNKNOWN | 53 | 0 | T |
| AW075446 | UNKNOWN | 7.5 | 157 | AC |
| AW075482 | UNKNOWN | 67 | 0 | T |
| AW075482 | UNKNOWN | 23 | 124 | A |
| AW075482 | UNKNOWN | 15 | 247 | G |
| AW075484 | UNKNOWN | 70 | 0 | T |
| AW075484 | UNKNOWN | 13 | 149 | A |
| AW075484 | UNKNOWN | 12 | 169 | C |
| AW075487 | UNKNOWN | 61 | 0 | T |
| AW075487 | UNKNOWN | 12 | 80 | A |
| AW075502 | UNKNOWN | 33 | 0 | T |
| AW075505 | UNKNOWN | 40 | 0 | T |
| AW075505 | UNKNOWN | 12 | 228 | A |
| AW075506 | UNKNOWN | 48 | 0 | T |
| AW075517 | UNKNOWN | 30 | 0 | T |
| AW075519 | UNKNOWN | 87 | 0 | T |
| AW075519 | UNKNOWN | 25 | 141 | A |
| AW075519 | UNKNOWN | 21 | 248 | C |
| AW075519 | UNKNOWN | 16 | 91 | C |
| AW075522 | UNKNOWN | 84 | 0 | T |
| AW075522 | UNKNOWN | 13 | 124 | A |
| AW075608 | UNKNOWN | 63 | 0 | T |
| AW075608 | UNKNOWN | 20 | 282 | A |
| AW075610 | UNKNOWN | 62 | 0 | T |
| AW075610 | UNKNOWN | 15 | 174 | C |
| AW075636 | UNKNOWN | 41 | 0 | T |
| AW075637 | UNKNOWN | 44 | 0 | T |
| AW075637 | UNKNOWN | 14 | 239 | C |
| AW075638 | UNKNOWN | 48 | 0 | T |
| AW075638 | UNKNOWN | 20 | 160 | C |
| AW075638 | UNKNOWN | 17 | 70 | A |
| AW075638 | UNKNOWN | 14 | 140 | G |
| AW075642 | UNKNOWN | 74 | 0 | T |
| AW075645 | UNKNOWN | 66 | 0 | T |
| AW075645 | UNKNOWN | 14 | 129 | A |
| AW075648 | UNKNOWN | 55 | 0 | T |
| AW075648 | UNKNOWN | 28 | 220 | A |
| AW075648 | UNKNOWN | 14 | 176 | A |
| AW075650 | UNKNOWN | 32 | 0 | T |
| AW075653 | UNKNOWN | 53 | 0 | T |
| AW075657 | UNKNOWN | 85 | 0 | T |
| AW075657 | UNKNOWN | 14 | 194 | C |
| AW075657 | UNKNOWN | 13 | 145 | C |
| AW075657 | UNKNOWN | 12 | 236 | G |
| AW075657 | UNKNOWN | 12 | 248 | A |

TABLE 1-continued

| Genbank # | Region | # reps | Position | Unit sequence |
| --- | --- | --- | --- | --- |
| AW075658 | UNKNOWN | 40 | 0 | T |
| AW075665 | UNKNOWN | 59 | 0 | T |
| AW075665 | UNKNOWN | 16 | 141 | G |
| AW075667 | UNKNOWN | 2.54 | 142 | CCCCCCGGGGG (SEQ ID NO: 210) |
| AW075667 | UNKNOWN | 115 | 0 | T |
| AW075667 | UNKNOWN | 23 | 177 | A |
| AW075667 | UNKNOWN | 22 | 221 | G |
| AW075667 | UNKNOWN | 19 | 115 | A |
| AW075667 | UNKNOWN | 13 | 164 | C |
| AW075669 | UNKNOWN | 72 | 0 | T |
| AW075669 | UNKNOWN | 14 | 72 | A |
| AW075669 | UNKNOWN | 14 | 185 | G |
| AW075671 | UNKNOWN | 50 | 0 | T |
| AW075671 | UNKNOWN | 13 | 202 | C |
| AW075671 | UNKNOWN | 12 | 50 | A |
| AW075671 | UNKNOWN | 12 | 298 | G |
| AW075672 | UNKNOWN | 35 | 0 | T |
| AW075677 | UNKNOWN | 22 | 0 | T |
| AW075685 | UNKNOWN | 46 | 0 | T |
| AW075712 | UNKNOWN | 3.8 | 1 | ATTTT |
| AW075715 | UNKNOWN | 64 | 0 | T |
| AW075715 | UNKNOWN | 16 | 278 | A |
| AW075802 | UNKNOWN | 13 | 146 | A |
| AW075862 | UNKNOWN | 35 | 0 | T |
| AW075894 | UNKNOWN | 47 | 0 | T |
| AW075905 | UNKNOWN | 39 | 0 | T |
| AW075905 | UNKNOWN | 12 | 78 | G |
| AW075929 | UNKNOWN | 43 | 0 | T |
| AW075979 | UNKNOWN | 19 | 0 | T |
| AW076093 | UNKNOWN | 93 | 0 | T |
| AW076093 | UNKNOWN | 15 | 256 | G |
| AW076093 | UNKNOWN | 14 | 119 | A |
| AW076103 | UNKNOWN | 13 | 0 | T |
| AW076116 | UNKNOWN | 50 | 0 | T |
| AW076116 | UNKNOWN | 22 | 89 | G |
| AW076116 | UNKNOWN | 12 | 265 | C |
| AW076124 | UNKNOWN | 55 | 0 | T |
| AW076124 | UNKNOWN | 18 | 279 | A |
| AW076124 | UNKNOWN | 14 | 76 | A |
| AW076124 | UNKNOWN | 14 | 98 | C |
| AW076127 | UNKNOWN | 70 | 0 | T |
| AW078498 | UNKNOWN | 13 | 17 | A |
| AW078513 | UNKNOWN | 44 | 0 | T |
| AW078513 | UNKNOWN | 16 | 270 | A |
| AW078529 | UNKNOWN | 116 | 0 | T |
| AW078529 | UNKNOWN | 19 | 290 | A |
| AW078529 | UNKNOWN | 18 | 178 | C |
| AW078529 | UNKNOWN | 14 | 237 | A |
| AW078529 | UNKNOWN | 12 | 278 | G |
| AW078538 | UNKNOWN | 14 | 0 | T |
| AW078541 | UNKNOWN | 42 | 0 | T |
| AW078543 | UNKNOWN | 53 | 0 | T |
| AW078543 | UNKNOWN | 13 | 135 | C |
| AW078574 | UNKNOWN | 68 | 0 | T |
| AW078593 | UNKNOWN | 46 | 0 | T |
| AW078593 | UNKNOWN | 12 | 118 | G |
| AW078606 | UNKNOWN | 64 | 0 | T |
| AW078647 | UNKNOWN | 33 | 0 | T |
| AW078647 | UNKNOWN | 13 | 328 | G |
| AW078672 | UNKNOWN | 83 | 0 | T |
| AW078680 | UNKNOWN | 91 | 0 | T |
| AW078680 | UNKNOWN | 15 | 154 | C |
| AW078680 | UNKNOWN | 15 | 171 | G |
| AW078680 | UNKNOWN | 15 | 371 | A |
| AW078681 | UNKNOWN | 18 | 0 | T |
| AW078689 | UNKNOWN | 55 | 0 | T |
| AW078689 | UNKNOWN | 14 | 139 | A |
| AW078703 | UNKNOWN | 42 | 0 | T |
| AW078703 | UNKNOWN | 12 | 198 | A |
| AW078710 | UNKNOWN | 88 | 0 | T |
| AW078710 | UNKNOWN | 18 | 358 | G |
| AW078710 | UNKNOWN | 17 | 164 | C |
| AW078710 | UNKNOWN | 15 | 109 | A |
| AW078711 | UNKNOWN | 91 | 0 | T |
| AW078711 | UNKNOWN | 16 | 149 | C |
| AW078711 | UNKNOWN | 15 | 211 | G |
| AW078711 | UNKNOWN | 14 | 275 | A |

TABLE 1-continued

| Genbank # | Region | # reps | Position | Unit sequence |
|---|---|---|---|---|
| AW078712 | UNKNOWN | 88 | 0 | T |
| AW078712 | UNKNOWN | 23 | 109 | G |
| AW078712 | UNKNOWN | 14 | 88 | A |
| AW078712 | UNKNOWN | 14 | 158 | C |
| AW078718 | UNKNOWN | 20 | 0 | T |
| AW078720 | UNKNOWN | 80 | 0 | T |
| AW078720 | UNKNOWN | 15 | 138 | C |
| AW078720 | UNKNOWN | 15 | 199 | G |
| AW078720 | UNKNOWN | 13 | 265 | A |
| AW078720 | UNKNOWN | 12 | 240 | A |
| AW078729 | UNKNOWN | 59 | 0 | T |
| AW078735 | UNKNOWN | 79 | 0 | T |
| AW078735 | UNKNOWN | 16 | 142 | C |
| AW078739 | UNKNOWN | 45 | 0 | T |
| AW078741 | UNKNOWN | 37 | 0 | T |
| AW078748 | UNKNOWN | 50 | 0 | T |
| AW078753 | UNKNOWN | 80 | 0 | T |
| AW078753 | UNKNOWN | 12 | 166 | A |
| AW078755 | UNKNOWN | 53 | 0 | T |
| AW078755 | UNKNOWN | 20 | 142 | C |
| AW078755 | UNKNOWN | 13 | 93 | A |
| AW078760 | UNKNOWN | 35 | 0 | T |
| AW078764 | UNKNOWN | 45 | 0 | T |
| AW078767 | UNKNOWN | 65 | 0 | T |
| AW078767 | UNKNOWN | 15 | 196 | G |
| AW078767 | UNKNOWN | 12 | 94 | A |
| AW078771 | UNKNOWN | 54 | 0 | T |
| AW078776 | UNKNOWN | 54 | 0 | T |
| AW078777 | UNKNOWN | 62 | 0 | T |
| AW078777 | UNKNOWN | 13 | 247 | G |
| AW078797 | UNKNOWN | 41 | 0 | T |
| AW078797 | UNKNOWN | 13 | 229 | C |
| AW078800 | UNKNOWN | 76 | 0 | T |
| AW078800 | UNKNOWN | 17 | 158 | C |
| AW078800 | UNKNOWN | 13 | 175 | A |
| AW078805 | UNKNOWN | 66 | 0 | T |
| AW078807 | UNKNOWN | 38 | 0 | T |
| AW078818 | UNKNOWN | 76 | 0 | T |
| AW078818 | UNKNOWN | 13 | 160 | G |
| AW078839 | UNKNOWN | 77 | 0 | T |
| AW078839 | UNKNOWN | 15 | 257 | C |
| AW078847 | UNKNOWN | 43 | 0 | T |
| AW078895 | UNKNOWN | 71 | 0 | T |
| AW078895 | UNKNOWN | 15 | 266 | G |
| AW078898 | UNKNOWN | 29 | 0 | T |
| AW078900 | UNKNOWN | 67 | 14 | T |
| AW078900 | UNKNOWN | 19 | 135 | A |
| AW078900 | UNKNOWN | 14 | 221 | G |
| AW078929 | UNKNOWN | 109 | 0 | T |
| AW078929 | UNKNOWN | 15 | 248 | G |
| AW078929 | UNKNOWN | 14 | 218 | C |
| AW078945 | UNKNOWN | 84 | 0 | T |
| AW078945 | UNKNOWN | 21 | 177 | G |
| AW078945 | UNKNOWN | 13 | 203 | C |
| AW078961 | UNKNOWN | 43 | 0 | T |
| AW079000 | UNKNOWN | 15 | 0 | T |
| AW079007 | UNKNOWN | 23 | 0 | T |
| AW079032 | UNKNOWN | 79 | 0 | T |
| AW079032 | UNKNOWN | 13 | 269 | C |
| AW079034 | UNKNOWN | 11.5 | 94 | CA |
| AW079034 | UNKNOWN | 17 | 0 | T |
| AW079045 | UNKNOWN | 75 | 0 | T |
| AW079045 | UNKNOWN | 17 | 136 | A |
| AW079059 | UNKNOWN | 32 | 0 | T |
| AW079062 | UNKNOWN | 33 | 1 | T |
| AW079075 | UNKNOWN | 95 | 4 | T |
| AW079075 | UNKNOWN | 16 | 135 | C |
| AW079075 | UNKNOWN | 14 | 151 | G |
| AW079075 | UNKNOWN | 14 | 196 | A |
| AW079119 | UNKNOWN | 73 | 0 | T |
| AW079119 | UNKNOWN | 25 | 363 | G |
| AW079119 | UNKNOWN | 12 | 77 | A |
| AW079120 | UNKNOWN | 14 | 141 | A |
| AW079141 | UNKNOWN | 12 | 515 | A |
| AW079148 | UNKNOWN | 49 | 0 | T |
| AW079158 | UNKNOWN | 70 | 0 | T |
| AW079158 | UNKNOWN | 18 | 386 | G |

TABLE 1-continued

| Genbank # | Region | # reps | Position | Unit sequence |
|---|---|---|---|---|
| AW079158 | UNKNOWN | 13 | 160 | A |
| AW079159 | UNKNOWN | 93 | 0 | T |
| AW079159 | UNKNOWN | 21 | 166 | G |
| AW079159 | UNKNOWN | 19 | 138 | C |
| AW079286 | UNKNOWN | 17 | 0 | T |
| AW079286 | UNKNOWN | 15 | 122 | G |
| AW079334 | UNKNOWN | 61 | 0 | T |
| AW079336 | UNKNOWN | 77 | 0 | T |
| AW079336 | UNKNOWN | 14 | 159 | A |
| AW079346 | UNKNOWN | 50 | 0 | T |
| AW079368 | UNKNOWN | 85 | 0 | T |
| AW079368 | UNKNOWN | 15 | 230 | A |
| AW079368 | UNKNOWN | 14 | 216 | G |
| AW079383 | UNKNOWN | 56 | 0 | T |
| AW079383 | UNKNOWN | 13 | 158 | G |
| AW079409 | UNKNOWN | 84 | 0 | T |
| AW079409 | UNKNOWN | 16 | 104 | G |
| AW079432 | UNKNOWN | 59 | 0 | T |
| AW079436 | UNKNOWN | 51 | 0 | T |
| AW079486 | UNKNOWN | 18 | 145 | T |
| AW079498 | UNKNOWN | 39 | 0 | T |
| AW079508 | UNKNOWN | 14 | 0 | T |
| AW079511 | UNKNOWN | 50 | 0 | T |
| AW079522 | UNKNOWN | 15 | 0 | T |
| AW079525 | UNKNOWN | 46 | 0 | T |
| AW079541 | UNKNOWN | 46 | 0 | T |
| AW079572 | UNKNOWN | 84 | 0 | T |
| AW079572 | UNKNOWN | 15 | 118 | A |
| AW079572 | UNKNOWN | 15 | 180 | C |
| AW079572 | UNKNOWN | 12 | 136 | C |
| AW079640 | UNKNOWN | 63 | 0 | T |
| AW079640 | UNKNOWN | 13 | 283 | G |
| AW079654 | UNKNOWN | 91 | 0 | T |
| AW079654 | UNKNOWN | 15 | 179 | A |
| AW079654 | UNKNOWN | 13 | 115 | A |
| AW079654 | UNKNOWN | 13 | 305 | G |
| AW079654 | UNKNOWN | 12 | 161 | G |
| AW079656 | UNKNOWN | 54 | 0 | T |
| AW079669 | UNKNOWN | 17 | 0 | T |
| AW079699 | UNKNOWN | 54 | 0 | T |
| AW079718 | UNKNOWN | 34 | 0 | T |
| AW079753 | UNKNOWN | 73 | 0 | T |
| AW079753 | UNKNOWN | 21 | 118 | A |
| AW079753 | UNKNOWN | 13 | 330 | C |
| AW079753 | UNKNOWN | 13 | 343 | G |
| AW079753 | UNKNOWN | 12 | 264 | C |
| AW079768 | UNKNOWN | 53 | 4 | T |
| AW079771 | UNKNOWN | 76 | 4 | T |
| AW079772 | UNKNOWN | 52 | 4 | T |
| AW079811 | UNKNOWN | 42 | 0 | T |
| AW079818 | UNKNOWN | 101 | 0 | T |
| AW079818 | UNKNOWN | 17 | 128 | C |
| AW079818 | UNKNOWN | 13 | 182 | G |
| AW079859 | UNKNOWN | 82 | 0 | T |
| AW079859 | UNKNOWN | 17 | 360 | A |
| AW079859 | UNKNOWN | 12 | 112 | C |
| AW079859 | UNKNOWN | 12 | 211 | A |
| AW079915 | UNKNOWN | 5.66 | 54 | TTA |
| AW079922 | UNKNOWN | 45 | 0 | T |
| AW079996 | UNKNOWN | 46 | 0 | T |
| AW080011 | UNKNOWN | 12 | 0 | T |
| AW080058 | UNKNOWN | 12 | 0 | T |
| AW080067 | UNKNOWN | 56 | 0 | T |
| AW080070 | UNKNOWN | 15 | 186 | T |
| AW080076 | UNKNOWN | 53 | 0 | T |
| AW080079 | UNKNOWN | 107 | 0 | T |
| AW080079 | UNKNOWN | 20 | 188 | A |
| AW080079 | UNKNOWN | 14 | 153 | G |
| AW080079 | UNKNOWN | 12 | 208 | C |
| AW080080 | UNKNOWN | 82 | 0 | T |
| AW080080 | UNKNOWN | 15 | 391 | C |
| AW080090 | UNKNOWN | 93 | 0 | T |
| AW080090 | UNKNOWN | 13 | 161 | C |
| AW080090 | UNKNOWN | 12 | 93 | A |
| AW080090 | UNKNOWN | 12 | 130 | G |
| AW080095 | UNKNOWN | 85 | 0 | T |
| AW080095 | UNKNOWN | 21 | 332 | A |

TABLE 1-continued

| Genbank # | Region | # reps | Position | Unit sequence |
|---|---|---|---|---|
| AW080095 | UNKNOWN | 20 | 280 | A |
| AW080095 | UNKNOWN | 13 | 97 | G |
| AW080107 | UNKNOWN | 54 | 0 | T |
| AW080135 | UNKNOWN | 88 | 0 | T |
| AW080135 | UNKNOWN | 15 | 138 | G |
| AW080135 | UNKNOWN | 14 | 254 | A |
| AW080135 | UNKNOWN | 13 | 125 | C |
| AW080135 | UNKNOWN | 13 | 153 | A |
| AW080140 | UNKNOWN | 50 | 0 | T |
| AW080160 | UNKNOWN | 12 | 376 | A |
| AW080173 | UNKNOWN | 60 | 0 | T |
| AW080173 | UNKNOWN | 15 | 287 | G |
| AW080173 | UNKNOWN | 12 | 107 | C |
| AW080173 | UNKNOWN | 12 | 184 | G |
| AW080191 | UNKNOWN | 48 | 0 | T |
| AW080205 | UNKNOWN | 92 | 0 | T |
| AW080205 | UNKNOWN | 23 | 158 | C |
| AW080211 | UNKNOWN | 32 | 0 | T |
| AW080211 | UNKNOWN | 12 | 128 | A |
| AW080214 | UNKNOWN | 66 | 0 | T |
| AW080234 | UNKNOWN | 46 | 0 | T |
| AW080277 | UNKNOWN | 51 | 0 | T |
| AW080279 | UNKNOWN | 109 | 0 | T |
| AW080279 | UNKNOWN | 17 | 350 | C |
| AW080279 | UNKNOWN | 15 | 375 | G |
| AW080279 | UNKNOWN | 14 | 190 | A |
| AW080279 | UNKNOWN | 14 | 251 | C |
| AW080279 | UNKNOWN | 13 | 209 | C |
| AW080279 | UNKNOWN | 12 | 155 | G |
| AW080286 | UNKNOWN | 68 | 0 | T |
| AW080286 | UNKNOWN | 21 | 130 | A |
| AW080286 | UNKNOWN | 14 | 75 | A |
| AW080288 | UNKNOWN | 45 | 0 | T |
| AW080290 | UNKNOWN | 62 | 0 | T |
| AW080290 | UNKNOWN | 14 | 182 | G |
| AW080298 | UNKNOWN | 69 | 0 | T |
| AW080298 | UNKNOWN | 15 | 114 | A |
| AW080326 | UNKNOWN | 65 | 0 | T |
| AW080326 | UNKNOWN | 12 | 127 | A |
| AW080327 | UNKNOWN | 109 | 0 | T |
| AW080327 | UNKNOWN | 16 | 218 | C |
| AW080327 | UNKNOWN | 12 | 270 | A |
| AW080335 | UNKNOWN | 53 | 0 | T |
| AW080337 | UNKNOWN | 59 | 0 | T |
| AW080337 | UNKNOWN | 15 | 163 | C |
| AW080341 | UNKNOWN | 15 | 0 | T |
| AW080357 | UNKNOWN | 104 | 0 | T |
| AW080357 | UNKNOWN | 17 | 134 | C |
| AW080357 | UNKNOWN | 16 | 393 | G |
| AW080373 | UNKNOWN | 64 | 0 | T |
| AW080373 | UNKNOWN | 15 | 77 | C |
| AW080373 | UNKNOWN | 12 | 418 | A |
| AW080374 | UNKNOWN | 85 | 0 | T |
| AW080374 | UNKNOWN | 14 | 197 | C |
| AW080376 | UNKNOWN | 86 | 0 | T |
| AW080376 | UNKNOWN | 21 | 111 | A |
| AW080379 | UNKNOWN | 86 | 0 | T |
| AW080379 | UNKNOWN | 14 | 115 | A |
| AW080379 | UNKNOWN | 12 | 198 | C |
| AW080436 | UNKNOWN | 4.8 | 137 | TTTG |
| AW080456 | UNKNOWN | 60 | 0 | T |
| AW080526 | UNKNOWN | 51 | 0 | T |
| AW080531 | UNKNOWN | 49 | 0 | T |
| AW080532 | UNKNOWN | 19 | 0 | T |
| AW080558 | UNKNOWN | 32 | 0 | T |
| AW080563 | UNKNOWN | 4.5 | 31 | TATT |
| AW080563 | UNKNOWN | 16 | 4 | T |
| AW080609 | UNKNOWN | 13 | 0 | T |
| AW080611 | UNKNOWN | 38 | 0 | T |
| AW080619 | UNKNOWN | 39 | 0 | T |
| AW080652 | UNKNOWN | 43 | 9 | T |
| AW080672 | UNKNOWN | 15 | 4 | T |
| AW080709 | UNKNOWN | 15 | 4 | T |
| AW080717 | UNKNOWN | 47 | 0 | T |
| AW080723 | UNKNOWN | 71 | 0 | T |
| AW080730 | UNKNOWN | 79 | 0 | T |
| AW080730 | UNKNOWN | 12 | 279 | G |

TABLE 1-continued

| Genbank # | Region | # reps | Position | Unit sequence |
|---|---|---|---|---|
| AW080739 | UNKNOWN | 31 | 0 | T |
| AW080746 | UNKNOWN | 88 | 0 | T |
| AW080746 | UNKNOWN | 19 | 123 | C |
| AW080746 | UNKNOWN | 14 | 109 | A |
| AW080746 | UNKNOWN | 12 | 88 | A |
| AW080763 | UNKNOWN | 15 | 0 | T |
| AW080766 | UNKNOWN | 54 | 0 | T |
| AW080766 | UNKNOWN | 13 | 109 | A |
| AW080790 | UNKNOWN | 27 | 0 | T |
| AW080793 | UNKNOWN | 40 | 0 | T |
| AW080793 | UNKNOWN | 12 | 105 | A |
| AW080839 | UNKNOWN | 17 | 4 | T |
| AW080842 | UNKNOWN | 17 | 0 | T |
| AW080843 | UNKNOWN | 26 | 0 | T |
| AW080856 | UNKNOWN | 68 | 4 | T |
| AW080859 | UNKNOWN | 35 | 7 | T |
| AW080872 | UNKNOWN | 40 | 3 | T |
| AW080872 | UNKNOWN | 12 | 112 | A |
| AW080893 | UNKNOWN | 56 | 0 | T |
| AW080896 | UNKNOWN | 46 | 0 | T |
| AW080920 | UNKNOWN | 53 | 0 | T |
| AW080939 | UNKNOWN | 3.6 | 475 | AAAAT |
| AW080939 | UNKNOWN | 12 | 610 | A |
| AW080951 | UNKNOWN | 43 | 0 | T |
| AW080965 | UNKNOWN | 31 | 0 | T |
| AW080965 | UNKNOWN | 14 | 411 | A |
| AW080977 | UNKNOWN | 12 | 414 | A |
| AW080979 | UNKNOWN | 50 | 0 | T |
| AW080992 | UNKNOWN | 104 | 7 | T |
| AW080992 | UNKNOWN | 20 | 337 | C |
| AW080992 | UNKNOWN | 18 | 132 | A |
| AW080992 | UNKNOWN | 15 | 208 | G |
| AW080992 | UNKNOWN | 13 | 169 | G |
| AW080994 | UNKNOWN | 47 | 0 | T |
| AW080995 | UNKNOWN | 79 | 0 | T |
| AW080997 | UNKNOWN | 23 | 4 | T |
| AW080999 | UNKNOWN | 16 | 4 | T |
| AW081003 | UNKNOWN | 21 | 0 | T |
| AW081007 | UNKNOWN | 44 | 0 | T |
| AW081008 | UNKNOWN | 64 | 4 | T |
| AW081014 | UNKNOWN | 4.8 | 187 | AAAAC |
| AW081014 | UNKNOWN | 47 | 0 | T |
| AW081026 | UNKNOWN | 15 | 4 | T |
| AW081033 | UNKNOWN | 15 | 10 | T |
| AW081034 | UNKNOWN | 65 | 4 | T |
| AW081034 | UNKNOWN | 17 | 226 | A |
| AW081034 | UNKNOWN | 12 | 386 | G |
| AW081036 | UNKNOWN | 95 | 6 | T |
| AW081036 | UNKNOWN | 16 | 212 | C |
| AW081036 | UNKNOWN | 12 | 101 | A |
| AW081041 | UNKNOWN | 17 | 4 | T |
| AW081047 | UNKNOWN | 60 | 5 | T |
| AW081047 | UNKNOWN | 16 | 179 | G |
| AW081092 | UNKNOWN | 18 | 5 | T |
| AW081122 | UNKNOWN | 48 | 0 | T |
| AW081128 | UNKNOWN | 15 | 1 | T |
| AW081136 | UNKNOWN | 15 | 0 | T |
| AW081137 | UNKNOWN | 24 | 0 | T |
| AW081140 | UNKNOWN | 40 | 0 | T |
| AW081145 | UNKNOWN | 33 | 0 | T |
| AW081162 | UNKNOWN | 15 | 1 | T |
| AW081166 | UNKNOWN | 15 | 4 | T |
| AW081169 | UNKNOWN | 58 | 4 | T |
| AW081171 | UNKNOWN | 25 | 0 | T |
| AW081177 | UNKNOWN | 24 | 4 | T |
| AW081196 | UNKNOWN | 16 | 4 | T |
| AW081197 | UNKNOWN | 15 | 4 | T |
| AW081202 | UNKNOWN | 15 | 4 | T |
| AW081231 | UNKNOWN | 3.6 | 157 | CCCAA |
| AW081231 | UNKNOWN | 63 | 3 | T |
| AW081231 | UNKNOWN | 15 | 190 | G |
| AW081231 | UNKNOWN | 13 | 177 | A |
| AW081231 | UNKNOWN | 12 | 73 | A |
| AW081231 | UNKNOWN | 12 | 148 | C |
| AW081232 | UNKNOWN | 45 | 0 | T |
| AW081234 | UNKNOWN | 59 | 0 | T |
| AW081242 | UNKNOWN | 87 | 0 | T |

TABLE 1-continued

| Genbank # | Region | # reps | Position | Unit sequence |
|---|---|---|---|---|
| AW081242 | UNKNOWN | 23 | 177 | G |
| AW081242 | UNKNOWN | 14 | 87 | C |
| AW081250 | UNKNOWN | 57 | 0 | T |
| AW081252 | UNKNOWN | 53 | 0 | T |
| AW081255 | UNKNOWN | 97 | 0 | T |
| AW081255 | UNKNOWN | 28 | 129 | G |
| AW081255 | UNKNOWN | 13 | 157 | A |
| AW081256 | UNKNOWN | 67 | 0 | T |
| AW081270 | UNKNOWN | 30 | 4 | T |
| AW081298 | UNKNOWN | 99 | 4 | T |
| AW081298 | UNKNOWN | 18 | 191 | C |
| AW081298 | UNKNOWN | 15 | 128 | A |
| AW081311 | UNKNOWN | 71 | 0 | T |
| AW081322 | UNKNOWN | 65 | 0 | T |
| AW081322 | UNKNOWN | 19 | 68 | A |
| AW081342 | UNKNOWN | 48 | 4 | T |
| AW081343 | UNKNOWN | 55 | 4 | T |
| AW081353 | UNKNOWN | 32 | 0 | T |
| AW081361 | UNKNOWN | 26 | 0 | T |
| AW081364 | UNKNOWN | 22 | 4 | T |
| AW081368 | UNKNOWN | 15 | 4 | T |
| AW081369 | UNKNOWN | 15 | 4 | T |
| AW081375 | UNKNOWN | 4.75 | 7 | TTTA |
| AW081377 | UNKNOWN | 15 | 4 | T |
| AW081402 | UNKNOWN | 22 | 0 | T |
| AW081402 | UNKNOWN | 13 | 297 | A |
| AW081424 | UNKNOWN | 46 | 0 | T |
| AW081439 | UNKNOWN | 67 | 4 | T |
| AW081449 | UNKNOWN | 94 | 18 | T |
| AW081449 | UNKNOWN | 23 | 376 | G |
| AW081449 | UNKNOWN | 17 | 352 | C |
| AW081449 | UNKNOWN | 15 | 157 | G |
| AW081449 | UNKNOWN | 13 | 4 | T |
| AW081449 | UNKNOWN | 13 | 213 | C |
| AW081451 | UNKNOWN | 62 | 0 | T |
| AW081465 | UNKNOWN | 43 | 0 | T |
| AW081465 | UNKNOWN | 18 | 140 | A |
| AW081484 | UNKNOWN | 15 | 0 | T |
| AW081486 | UNKNOWN | 17 | 4 | T |
| AW081507 | UNKNOWN | 32 | 0 | T |
| AW081513 | UNKNOWN | 55 | 0 | T |
| AW081513 | UNKNOWN | 14 | 216 | A |
| AW081513 | UNKNOWN | 12 | 139 | A |
| AW081514 | UNKNOWN | 31 | 0 | T |
| AW081515 | UNKNOWN | 83 | 4 | T |
| AW081515 | UNKNOWN | 16 | 587 | G |
| AW081515 | UNKNOWN | 13 | 165 | G |
| AW081515 | UNKNOWN | 12 | 187 | C |
| AW081523 | UNKNOWN | 8.5 | 369 | CA |
| AW081524 | UNKNOWN | 14 | 0 | T |
| AW081528 | UNKNOWN | 86 | 0 | T |
| AW081528 | UNKNOWN | 26 | 107 | A |
| AW081606 | UNKNOWN | 93 | 9 | T |
| AW081606 | UNKNOWN | 22 | 433 | C |
| AW081606 | UNKNOWN | 18 | 342 | C |
| AW081606 | UNKNOWN | 16 | 367 | G |
| AW081606 | UNKNOWN | 14 | 147 | G |
| AW081606 | UNKNOWN | 14 | 182 | A |
| AW081606 | UNKNOWN | 13 | 202 | C |
| AW081626 | UNKNOWN | 14 | 191 | T |
| AW081647 | UNKNOWN | 38 | 2 | T |
| AW081648 | UNKNOWN | 50 | 2 | T |
| AW081648 | UNKNOWN | 14 | 120 | A |
| AW081648 | UNKNOWN | 42 | 207 | G |
| AW081653 | UNKNOWN | 100 | 3 | T |
| AW081653 | UNKNOWN | 14 | 126 | C |
| AW081670 | UNKNOWN | 52 | 0 | T |
| AW081702 | UNKNOWN | 16 | 0 | T |
| AW081706 | UNKNOWN | 36 | 0 | T |
| AW081797 | UNKNOWN | 90 | 1 | T |
| AW081797 | UNKNOWN | 13 | 143 | G |
| AW081797 | UNKNOWN | 13 | 213 | A |
| AW081812 | UNKNOWN | 61 | 0 | T |
| AW081852 | UNKNOWN | 32 | 0 | T |
| AW081866 | UNKNOWN | 68 | 0 | T |
| AW081866 | UNKNOWN | 13 | 310 | G |
| AW081893 | UNKNOWN | 15 | 0 | T |

TABLE 1-continued

| Genbank # | Region | # reps | Position | Unit sequence |
|---|---|---|---|---|
| AW081894 | UNKNOWN | 48 | 0 | T |
| AW081915 | UNKNOWN | 43 | 0 | T |
| AW081917 | UNKNOWN | 49 | 0 | T |
| AW081959 | UNKNOWN | 17 | 0 | T |
| AW082008 | UNKNOWN | 61 | 0 | T |
| AW082017 | UNKNOWN | 34 | 0 | T |
| AW082017 | UNKNOWN | 26 | 198 | A |
| AW082018 | UNKNOWN | 48 | 0 | T |
| AW082033 | UNKNOWN | 87 | 0 | T |
| AW082033 | UNKNOWN | 20 | 115 | A |
| AW082034 | UNKNOWN | 45 | 0 | T |
| AW082034 | UNKNOWN | 12 | 100 | C |
| AW082040 | UNKNOWN | 109 | 0 | T |
| AW082040 | UNKNOWN | 19 | 136 | C |
| AW082040 | UNKNOWN | 14 | 119 | A |
| AW082041 | UNKNOWN | 44 | 0 | T |
| AW082041 | UNKNOWN | 15 | 287 | G |
| AW082042 | UNKNOWN | 22 | 336 | A |
| AW082042 | UNKNOWN | 21 | 3 | T |
| AW082050 | UNKNOWN | 13 | 161 | T |
| AW082052 | UNKNOWN | 29 | 11 | T |
| AW082058 | UNKNOWN | 56 | 0 | T |
| AW082058 | UNKNOWN | 12 | 73 | A |
| AW082060 | UNKNOWN | 108 | 2 | T |
| AW082060 | UNKNOWN | 17 | 271 | A |
| AW082060 | UNKNOWN | 16 | 181 | C |
| AW082062 | UNKNOWN | 44 | 0 | T |
| AW082066 | UNKNOWN | 52 | 0 | T |
| AW082080 | UNKNOWN | 37 | 0 | T |
| AW082088 | UNKNOWN | 85 | 0 | T |
| AW082088 | UNKNOWN | 13 | 276 | A |
| AW082092 | UNKNOWN | 30 | 159 | T |
| AW082105 | UNKNOWN | 37 | 0 | T |
| AW082117 | UNKNOWN | 40 | 0 | T |
| AW082124 | UNKNOWN | 87 | 0 | T |
| AW082124 | UNKNOWN | 16 | 215 | C |
| AW082124 | UNKNOWN | 12 | 152 | C |
| AW082137 | UNKNOWN | 3.8 | 11 | TTTAT |
| AW082220 | UNKNOWN | 19 | 0 | T |
| AW082247 | UNKNOWN | 17 | 0 | T |
| AW082270 | UNKNOWN | 17 | 0 | T |
| AW082341 | UNKNOWN | 16 | 0 | T |
| AW082369 | UNKNOWN | 6.5 | 151 | CA |
| AW082408 | UNKNOWN | 17 | 0 | T |
| AW082412 | UNKNOWN | 31 | 0 | T |
| AW082422 | UNKNOWN | 33 | 0 | T |
| AW082506 | UNKNOWN | 15 | 0 | T |
| AW082532 | UNKNOWN | 62 | 0 | T |
| AW082532 | UNKNOWN | 12 | 94 | A |
| AW082556 | UNKNOWN | 12 | 0 | T |
| AW082588 | UNKNOWN | 73 | 0 | T |
| AW082588 | UNKNOWN | 27 | 130 | A |
| AW082588 | UNKNOWN | 13 | 271 | C |
| AW082594 | UNKNOWN | 91 | 0 | T |
| AW082594 | UNKNOWN | 12 | 157 | C |
| AW082623 | UNKNOWN | 64 | 0 | T |
| AW082623 | UNKNOWN | 18 | 114 | A |
| AW082625 | UNKNOWN | 51 | 0 | T |
| AW082665 | UNKNOWN | 14 | 329 | A |
| AW082698 | UNKNOWN | 16 | 0 | T |
| AW082801 | UNKNOWN | 15 | 0 | T |
| AW082807 | UNKNOWN | 49 | 0 | T |
| AW082809 | UNKNOWN | 36 | 0 | T |
| AW082827 | UNKNOWN | 22 | 0 | T |
| AW082835 | UNKNOWN | 54 | 0 | T |
| AW082835 | UNKNOWN | 20 | 156 | C |
| AW082843 | UNKNOWN | 60 | 0 | T |
| AW082843 | UNKNOWN | 16 | 204 | C |
| AW082964 | UNKNOWN | 39 | 0 | T |
| AW082964 | UNKNOWN | 21 | 110 | G |
| AW082966 | UNKNOWN | 16 | 0 | T |
| AW082969 | UNKNOWN | 5.75 | 199 | TTTG |
| AW082969 | UNKNOWN | 18 | 282 | A |
| AW082972 | UNKNOWN | 13 | 0 | T |
| AW082972 | UNKNOWN | 12 | 431 | A |
| AW082997 | UNKNOWN | 56 | 0 | T |
| AW082997 | UNKNOWN | 17 | 146 | A |

TABLE 1-continued

| Genbank # | Region | # reps | Position | Unit sequence |
|---|---|---|---|---|
| AW082997 | UNKNOWN | 12 | 170 | G |
| AW083000 | UNKNOWN | 8 | 58 | AT |
| AW083000 | UNKNOWN | 45 | 0 | T |
| AW083018 | UNKNOWN | 19 | 0 | T |
| AW083021 | UNKNOWN | 14 | 0 | T |
| AW083084 | UNKNOWN | 12 | 0 | T |
| AW083090 | UNKNOWN | 45 | 0 | T |
| AW083090 | UNKNOWN | 15 | 80 | A |
| AW083098 | UNKNOWN | 13 | 143 | A |
| AW083109 | UNKNOWN | 35 | 0 | T |
| AW083111 | UNKNOWN | 49 | 0 | T |
| AW083111 | UNKNOWN | 16 | 130 | G |
| AW083115 | UNKNOWN | 24 | 1 | T |
| AW083120 | UNKNOWN | 46 | 0 | T |
| AW083135 | UNKNOWN | 20 | 0 | T |
| AW083135 | UNKNOWN | 14 | 381 | A |
| AW083149 | UNKNOWN | 61 | 1 | T |
| AW083175 | UNKNOWN | 98 | 3 | T |
| AW083175 | UNKNOWN | 27 | 280 | C |
| AW083175 | UNKNOWN | 20 | 126 | A |
| AW083175 | UNKNOWN | 18 | 307 | G |
| AW083175 | UNKNOWN | 17 | 101 | C |
| AW083181 | UNKNOWN | 17 | 0 | T |
| AW083181 | UNKNOWN | 12 | 76 | G |
| AW083188 | UNKNOWN | 45 | 0 | T |
| AW083189 | UNKNOWN | 84 | 0 | T |
| AW083189 | UNKNOWN | 16 | 324 | C |
| AW083189 | UNKNOWN | 13 | 144 | C |
| AW083219 | UNKNOWN | 42 | 0 | T |
| AW083239 | UNKNOWN | 33 | 180 | A |
| AW083277 | UNKNOWN | 6.5 | 268 | TG |
| AW083314 | UNKNOWN | 33 | 0 | T |
| AW083352 | UNKNOWN | 18 | 0 | T |
| AW083353 | UNKNOWN | 17 | 0 | T |
| AW083361 | UNKNOWN | 31 | 2 | T |
| AW083374 | UNKNOWN | 78 | 0 | T |
| AW083374 | UNKNOWN | 21 | 136 | C |
| AW083374 | UNKNOWN | 12 | 119 | A |
| AW083438 | UNKNOWN | 12 | 0 | T |
| AW083448 | UNKNOWN | 15 | 306 | A |
| AW083452 | UNKNOWN | 47 | 0 | T |
| AW083454 | UNKNOWN | 46 | 0 | T |
| AW083454 | UNKNOWN | 13 | 193 | A |
| AW083454 | UNKNOWN | 12 | 49 | G |
| AW083489 | UNKNOWN | 60 | 0 | T |
| AW083491 | UNKNOWN | 18 | 0 | T |
| AW083499 | UNKNOWN | 80 | 0 | T |
| AW083499 | UNKNOWN | 12 | 195 | |
| AW083524 | UNKNOWN | 33 | 7 | T |
| AW083573 | UNKNOWN | 83 | 0 | T |
| AW083573 | UNKNOWN | 15 | 222 | G |
| AW083577 | UNKNOWN | 47 | 0 | T |
| AW083587 | UNKNOWN | 28 | 10 | T |
| AW083730 | UNKNOWN | 67 | 0 | T |
| AW083750 | UNKNOWN | 80 | 0 | T |
| AW083750 | UNKNOWN | 22 | 211 | G |
| AW083758 | UNKNOWN | 28 | 0 | T |
| AW083775 | UNKNOWN | 48 | 0 | T |
| AW083778 | UNKNOWN | 77 | 2 | T |
| AW083778 | UNKNOWN | 13 | 149 | C |
| AW083783 | UNKNOWN | 115 | 6 | T |
| AW083783 | UNKNOWN | 32 | 294 | C |
| AW083783 | UNKNOWN | 18 | 245 | C |
| AW083783 | UNKNOWN | 15 | 166 | A |
| AW083783 | UNKNOWN | 15 | 200 | C |
| AW083788 | UNKNOWN | 25 | 0 | T |
| AW083804 | UNKNOWN | 95 | 4 | T |
| AW083804 | UNKNOWN | 12 | 99 | G |
| AW083807 | UNKNOWN | 13 | 65 | A |
| AW083825 | UNKNOWN | 60 | 0 | T |
| AW083826 | UNKNOWN | 62 | 0 | T |
| AW083840 | UNKNOWN | 27 | 0 | T |
| AW083846 | UNKNOWN | 42 | 23 | T |
| AW083857 | UNKNOWN | 30 | 16 | T |
| AW083863 | UNKNOWN | 20 | 216 | A |
| AW083866 | UNKNOWN | 50 | 5 | T |
| AW083866 | UNKNOWN | 14 | 115 | A |

TABLE 1-continued

| Genbank # | Region | # reps | Position | Unit sequence |
|---|---|---|---|---|
| AW083866 | UNKNOWN | 12 | 153 | C |
| AW083866 | UNKNOWN | 12 | 306 | G |
| AW083873 | UNKNOWN | 48 | 0 | T |
| AW083890 | UNKNOWN | 52 | 0 | T |
| AW083895 | UNKNOWN | 30 | 0 | T |
| AW083895 | UNKNOWN | 16 | 30 | A |
| AW083936 | UNKNOWN | 4.75 | 430 | AAAT |
| AW083951 | UNKNOWN | 15 | 160 | A |
| AW083970 | UNKNOWN | 57 | 0 | T |
| AW083985 | UNKNOWN | 80 | 6 | T |
| AW083985 | UNKNOWN | 20 | 254 | G |
| AW083985 | UNKNOWN | 14 | 274 | C |
| AW083985 | UNKNOWN | 13 | 185 | C |
| AW084000 | UNKNOWN | 70 | 0 | T |
| AW084020 | UNKNOWN | 47 | 4 | T |
| AW084041 | UNKNOWN | 15 | 0 | T |
| AW084046 | UNKNOWN | 63 | 1 | T |
| AW084056 | UNKNOWN | 61 | 4 | T |
| AW084057 | UNKNOWN | 26 | 4 | T |
| AW084059 | UNKNOWN | 85 | 0 | T |
| AW084065 | UNKNOWN | 62 | 4 | T |
| AW084065 | UNKNOWN | 15 | 308 | A |
| AW084065 | UNKNOWN | 13 | 113 | A |
| AW084077 | UNKNOWN | 45 | 0 | T |
| AW084077 | UNKNOWN | 13 | 91 | C |
| AW084078 | UNKNOWN | 15 | 4 | T |
| AW084096 | UNKNOWN | 48 | 0 | T |
| AW084097 | UNKNOWN | 66 | 0 | T |
| AW084097 | UNKNOWN | 12 | 125 | G |
| AW084105 | UNKNOWN | 45 | 7 | T |
| AW084107 | UNKNOWN | 15 | 4 | T |
| AW084113 | UNKNOWN | 15 | 4 | T |
| AW084117 | UNKNOWN | 78 | 7 | T |
| AW084117 | UNKNOWN | 18 | 355 | G |
| AW084117 | UNKNOWN | 15 | 95 | A |
| AW084117 | UNKNOWN | 12 | 163 | G |
| AW084117 | UNKNOWN | 12 | 175 | C |
| AW084118 | UNKNOWN | 19 | 4 | T |
| AW084120 | UNKNOWN | 15 | 9 | T |
| AW084123 | UNKNOWN | 15 | 8 | T |
| AW084131 | UNKNOWN | 84 | 0 | T |
| AW084131 | UNKNOWN | 13 | 345 | A |
| AW084132 | UNKNOWN | 65 | 8 | T |
| AW084132 | UNKNOWN | 16 | 91 | A |
| AW084137 | UNKNOWN | 19 | 10 | T |
| AW084141 | UNKNOWN | 17 | 4 | T |
| AW084145 | UNKNOWN | 40 | 0 | T |
| AW084149 | UNKNOWN | 15 | 4 | T |
| AW084151 | UNKNOWN | 57 | 4 | T |
| AW084184 | UNKNOWN | 3.8 | 53 | TTAAA |
| AW084184 | UNKNOWN | 55 | 0 | T |
| AW084190 | UNKNOWN | 29 | 398 | T |
| AW084190 | UNKNOWN | 15 | 0 | T |
| AW084194 | UNKNOWN | 97 | 0 | T |
| AW084194 | UNKNOWN | 15 | 103 | G |
| AW084194 | UNKNOWN | 15 | 208 | C |
| AW084194 | UNKNOWN | 14 | 294 | A |
| AW084219 | UNKNOWN | 87 | 0 | T |
| AW084219 | UNKNOWN | 18 | 134 | G |
| AW084224 | UNKNOWN | 16 | 63 | T |
| AW084227 | UNKNOWN | 19 | 0 | T |
| AW084256 | UNKNOWN | 66 | 0 | T |
| AW084312 | UNKNOWN | 40 | 0 | T |
| AW084368 | UNKNOWN | 51 | 0 | T |
| AW084373 | UNKNOWN | 37 | 0 | T |
| AW084396 | UNKNOWN | 47 | 0 | T |
| AW084396 | UNKNOWN | 18 | 161 | A |
| AW084425 | UNKNOWN | 92 | 0 | T |
| AW084425 | UNKNOWN | 16 | 184 | G |
| AW084425 | UNKNOWN | 15 | 151 | A |
| AW084440 | UNKNOWN | 88 | 0 | T |
| AW084440 | UNKNOWN | 18 | 254 | G |
| AW084447 | UNKNOWN | 63 | 0 | T |
| AW084447 | UNKNOWN | 23 | 168 | A |
| AW084447 | UNKNOWN | 20 | 86 | A |
| AW084447 | UNKNOWN | 14 | 251 | C |
| AW084476 | UNKNOWN | 22 | 0 | T |

TABLE 1-continued

| Genbank # | Region | # reps | Position | Unit sequence |
|---|---|---|---|---|
| AW084590 | UNKNOWN | 12 | 0 | T |
| AW084755 | UNKNOWN | 25 | 604 | T |
| AW084772 | UNKNOWN | 61 | 0 | T |
| AW084790 | UNKNOWN | 3.8 | 186 | AAAAC |
| AW084790 | UNKNOWN | 44 | 0 | T |
| AW084797 | UNKNOWN | 74 | 0 | T |
| AW084797 | UNKNOWN | 17 | 171 | G |
| AW084797 | UNKNOWN | 14 | 275 | C |
| AW084801 | UNKNOWN | 63 | 0 | T |
| AW084807 | UNKNOWN | 46 | 0 | T |
| AW084812 | UNKNOWN | 72 | 0 | T |
| AW084812 | UNKNOWN | 19 | 77 | G |
| AW084812 | UNKNOWN | 12 | 365 | A |
| AW084815 | UNKNOWN | 45 | 0 | T |
| AW084815 | UNKNOWN | 12 | 206 | A |
| AW084844 | UNKNOWN | 41 | 0 | T |
| AW084850 | UNKNOWN | 85 | 0 | T |
| AW084850 | UNKNOWN | 13 | 149 | G |
| AW084850 | UNKNOWN | 12 | 133 | C |
| AW084850 | UNKNOWN | 12 | 369 | A |
| AW084865 | UNKNOWN | 57 | 0 | T |
| AW084869 | UNKNOWN | 89 | 0 | T |
| AW084869 | UNKNOWN | 15 | 126 | C |
| AW084881 | UNKNOWN | 50 | 0 | T |
| AW084881 | UNKNOWN | 20 | 229 | A |
| AW084883 | UNKNOWN | 15 | 0 | T |
| AW084884 | UNKNOWN | 26 | 0 | T |
| AW084896 | UNKNOWN | 3.8 | 191 | AAAAC |
| AW084896 | UNKNOWN | 49 | 0 | T |
| AW084914 | UNKNOWN | 57 | 0 | T |
| AW084915 | UNKNOWN | 3.83 | 237 | CTTTTC |
| AW084915 | UNKNOWN | 46 | 5 | T |
| AW084940 | UNKNOWN | 38 | 0 | T |
| AW084940 | UNKNOWN | 12 | 248 | A |
| AW084972 | UNKNOWN | 13 | 327 | T |
| AW085012 | UNKNOWN | 6.5 | 63 | AT |
| AW085156 | UNKNOWN | 14 | 0 | T |
| AW085197 | UNKNOWN | 16 | 0 | T |
| AW085201 | UNKNOWN | 17 | 0 | T |
| AW085236 | UNKNOWN | 46 | 0 | T |
| AW085236 | UNKNOWN | 28 | 163 | A |
| AW085236 | UNKNOWN | 16 | 102 | A |
| AW085267 | UNKNOWN | 20 | 0 | T |
| AW085270 | UNKNOWN | 16 | 0 | T |
| AW085300 | UNKNOWN | 12 | 289 | A |
| AW085319 | UNKNOWN | 14 | 0 | T |
| AW085321 | UNKNOWN | 15 | 0 | T |
| AW085322 | UNKNOWN | 32 | 0 | T |
| AW085324 | UNKNOWN | 26 | 0 | T |
| AW085325 | UNKNOWN | 20 | 0 | T |
| AW085325 | UNKNOWN | 12 | 351 | A |
| AW085329 | UNKNOWN | 28 | 0 | T |
| AW085329 | UNKNOWN | 12 | 439 | A |
| AW085331 | UNKNOWN | 31 | 0 | T |
| AW085332 | UNKNOWN | 25 | 0 | T |
| AW085333 | UNKNOWN | 12 | 9 | T |
| AW085334 | UNKNOWN | 15 | 0 | T |
| AW085335 | UNKNOWN | 23 | 0 | T |
| AW085337 | UNKNOWN | 13 | 0 | T |
| AW085338 | UNKNOWN | 20 | 0 | T |
| AW085339 | UNKNOWN | 16 | 0 | T |
| AW085340 | UNKNOWN | 22 | 0 | T |
| AW085342 | UNKNOWN | 14 | 0 | T |
| AW085344 | UNKNOWN | 20 | 0 | T |
| AW085345 | UNKNOWN | 22 | 0 | T |
| AW085346 | UNKNOWN | 12 | 162 | T |
| AW085347 | UNKNOWN | 29 | 0 | T |
| AW085348 | UNKNOWN | 23 | 0 | T |
| AW085348 | UNKNOWN | 13 | 323 | A |
| AW085351 | UNKNOWN | 15 | 0 | T |
| AW085353 | UNKNOWN | 22 | 0 | T |
| AW085354 | UNKNOWN | 35 | 0 | T |
| AW085355 | UNKNOWN | 19 | 0 | T |
| AW085357 | UNKNOWN | 14 | 0 | T |
| AW085358 | UNKNOWN | 14 | 0 | T |
| AW085359 | UNKNOWN | 17 | 296 | A |
| AW085360 | UNKNOWN | 8 | 379 | CA |

TABLE 1-continued

| Genbank # | Region | # reps | Position | Unit sequence |
|---|---|---|---|---|
| AW085360 | UNKNOWN | 27 | 0 | T |
| AW085364 | UNKNOWN | 20 | 0 | T |
| AW085365 | UNKNOWN | 14 | 0 | T |
| AW085368 | UNKNOWN | 14 | 0 | T |
| AW085370 | UNKNOWN | 51 | 0 | T |
| AW085371 | UNKNOWN | 18 | 0 | T |
| AW085373 | UNKNOWN | 55 | 0 | T |
| AW085374 | UNKNOWN | 46 | 0 | T |
| AW085376 | UNKNOWN | 19 | 0 | T |
| AW085377 | UNKNOWN | 29 | 0 | T |
| AW085378 | UNKNOWN | 23 | 0 | T |
| AW085380 | UNKNOWN | 16 | 0 | T |
| AW085381 | UNKNOWN | 24 | 0 | T |
| AW085383 | UNKNOWN | 16 | 3 | T |
| AW085384 | UNKNOWN | 15 | 0 | T |
| AW085385 | UNKNOWN | 15 | 0 | T |
| AW085385 | UNKNOWN | 12 | 257 | A |
| AW085386 | UNKNOWN | 18 | 3 | T |
| AW085389 | UNKNOWN | 27 | 0 | T |
| AW085390 | UNKNOWN | 21 | 0 | T |
| AW085391 | UNKNOWN | 19 | 0 | T |
| AW085393 | UNKNOWN | 47 | 0 | T |
| AW085396 | UNKNOWN | 15 | 0 | T |
| AW085397 | UNKNOWN | 15 | 0 | T |
| AW085398 | UNKNOWN | 22 | 2 | T |
| AW085401 | UNKNOWN | 8 | 296 | CA |
| AW085403 | UNKNOWN | 21 | 0 | T |
| AW085408 | UNKNOWN | 18 | 0 | T |
| AW085410 | UNKNOWN | 23 | 0 | T |
| AW085411 | UNKNOWN | 12 | 0 | T |
| AW085412 | UNKNOWN | 20 | 0 | T |
| AW085413 | UNKNOWN | 17 | 0 | T |
| AW085417 | UNKNOWN | 16 | 0 | T |
| AW085418 | UNKNOWN | 26 | 0 | T |
| AW085419 | UNKNOWN | 24 | 0 | T |
| AW085420 | UNKNOWN | 17 | 0 | T |
| AW085421 | UNKNOWN | 18 | 0 | T |
| AW085422 | UNKNOWN | 21 | 0 | T |
| AW085423 | UNKNOWN | 37 | 0 | T |
| AW085425 | UNKNOWN | 39 | 0 | T |
| AW085426 | UNKNOWN | 18 | 0 | T |
| AW085427 | UNKNOWN | 22 | 0 | T |
| AW085428 | UNKNOWN | 24 | 0 | T |
| AW085429 | UNKNOWN | 24 | 0 | T |
| AW085430 | UNKNOWN | 15 | 0 | T |
| AW085431 | UNKNOWN | 19 | 0 | T |
| AW085432 | UNKNOWN | 17 | 0 | T |
| AW085433 | UNKNOWN | 19 | 1 | T |
| AW085434 | UNKNOWN | 15 | 0 | T |
| AW085435 | UNKNOWN | 28 | 4 | T |
| AW085435 | UNKNOWN | 14 | 91 | A |
| AW085436 | UNKNOWN | 28 | 0 | T |
| AW085438 | UNKNOWN | 29 | 0 | T |
| AW085440 | UNKNOWN | 13 | 0 | T |
| AW085442 | UNKNOWN | 23 | 0 | T |
| AW085443 | UNKNOWN | 8.5 | 197 | CT |
| AW085443 | UNKNOWN | 29 | 0 | T |
| AW085446 | UNKNOWN | 32 | 0 | T |
| AW085447 | UNKNOWN | 15 | 0 | T |
| AW085449 | UNKNOWN | 21 | 0 | T |
| AW085450 | UNKNOWN | 6 | 213 | TAA |
| AW085450 | UNKNOWN | 22 | 0 | T |
| AW085452 | UNKNOWN | 22 | 0 | T |
| AW085454 | UNKNOWN | 21 | 0 | T |
| AW085455 | UNKNOWN | 29 | 0 | T |
| AW085456 | UNKNOWN | 55 | 0 | T |
| AW085457 | UNKNOWN | 37 | 2 | T |
| AW085458 | UNKNOWN | 29 | 0 | T |
| AW085460 | UNKNOWN | 6.5 | 273 | GT |
| AW085460 | UNKNOWN | 24 | 0 | T |
| AW085461 | UNKNOWN | 17 | 0 | T |
| AW085462 | UNKNOWN | 28 | 2 | T |
| AW085463 | UNKNOWN | 17 | 3 | T |
| AW085464 | UNKNOWN | 28 | 2 | T |
| AW085465 | UNKNOWN | 13 | 0 | T |
| AW085467 | UNKNOWN | 16 | 0 | T |
| AW085469 | UNKNOWN | 16 | 0 | T |

TABLE 1-continued

| Genbank # | Region | # reps | Position | Unit sequence |
|---|---|---|---|---|
| AW085471 | UNKNOWN | 35 | 0 | T |
| AW085472 | UNKNOWN | 15 | 0 | T |
| AW085473 | UNKNOWN | 18 | 0 | T |
| AW085476 | UNKNOWN | 18 | 0 | T |
| AW085478 | UNKNOWN | 25 | 0 | T |
| AW085479 | UNKNOWN | 21 | 0 | T |
| AW085480 | UNKNOWN | 16 | 1 | T |
| AW085481 | UNKNOWN | 15 | 0 | T |
| AW085507 | UNKNOWN | 9.5 | 317 | AC |
| AW085507 | UNKNOWN | 7.5 | 295 | AT |
| AW085518 | UNKNOWN | 18 | 0 | T |
| AW085610 | UNKNOWN | 59 | 0 | T |
| AW085610 | UNKNOWN | 16 | 116 | A |
| AW085620 | UNKNOWN | 41 | 0 | T |
| AW085626 | UNKNOWN | 15 | 304 | A |
| AW085639 | UNKNOWN | 66 | 0 | T |
| AW085639 | UNKNOWN | 13 | 166 | C |
| AW085654 | UNKNOWN | 6 | 62 | TTA |
| AW085654 | UNKNOWN | 40 | 0 | T |
| AW085660 | UNKNOWN | 18 | 0 | T |
| AW085667 | UNKNOWN | 93 | 0 | T |
| AW085667 | UNKNOWN | 16 | 276 | C |
| AW085667 | UNKNOWN | 15 | 157 | C |
| AW085667 | UNKNOWN | 13 | 93 | G |
| AW085673 | UNKNOWN | 41 | 27 | T |
| AW085673 | UNKNOWN | 26 | 0 | T |
| AW085673 | UNKNOWN | 19 | 115 | A |
| AW085673 | UNKNOWN | 18 | 91 | C |
| AW085673 | UNKNOWN | 15 | 76 | A |
| AW085681 | UNKNOWN | 86 | 0 | T |
| AW085681 | UNKNOWN | 16 | 191 | C |
| AW085681 | UNKNOWN | 12 | 234 | A |
| AW085698 | UNKNOWN | 14 | 0 | T |
| AW085698 | UNKNOWN | 12 | 88 | G |
| AW085709 | UNKNOWN | 69 | 0 | T |
| AW085709 | UNKNOWN | 19 | 206 | A |
| AW085709 | UNKNOWN | 12 | 307 | C |
| AW085718 | UNKNOWN | 21 | 0 | T |
| AW085721 | UNKNOWN | 71 | 0 | T |
| AW085721 | UNKNOWN | 14 | 93 | G |
| AW085734 | UNKNOWN | 79 | 0 | T |
| AW085734 | UNKNOWN | 15 | 413 | C |
| AW085734 | UNKNOWN | 13 | 145 | G |
| AW085735 | UNKNOWN | 34 | 0 | T |
| AW085786 | UNKNOWN | 74 | 0 | T |
| AW085786 | UNKNOWN | 17 | 95 | A |
| AW085799 | UNKNOWN | 121 | 0 | T |
| AW085799 | UNKNOWN | 19 | 317 | C |
| AW085799 | UNKNOWN | 17 | 289 | A |
| AW085799 | UNKNOWN | 14 | 270 | G |
| AW085799 | UNKNOWN | 13 | 216 | C |
| AW085890 | UNKNOWN | 13 | 358 | G |
| AW085906 | UNKNOWN | 97 | 0 | T |
| AW085906 | UNKNOWN | 26 | 188 | C |
| AW085906 | UNKNOWN | 17 | 114 | A |
| AW085906 | UNKNOWN | 14 | 144 | C |
| AW085906 | UNKNOWN | 14 | 307 | G |
| AW085906 | UNKNOWN | 13 | 172 | G |
| AW085910 | UNKNOWN | 23 | 0 | T |
| AW085913 | UNKNOWN | 15 | 0 | T |
| AW085935 | UNKNOWN | 23 | 0 | T |
| AW085940 | UNKNOWN | 13 | 0 | T |
| AW085947 | UNKNOWN | 60 | 0 | T |
| AW085947 | UNKNOWN | 12 | 108 | A |
| AW085958 | UNKNOWN | 17 | 0 | T |
| AW085963 | UNKNOWN | 39 | 0 | T |
| AW085964 | UNKNOWN | 13 | 0 | T |
| AW085982 | UNKNOWN | 13 | 0 | T |
| AW085986 | UNKNOWN | 16 | 0 | T |
| AW085988 | UNKNOWN | 13 | 0 | T |
| AW086022 | UNKNOWN | 13 | 0 | T |
| AW086030 | UNKNOWN | 16 | 0 | T |
| AW086034 | UNKNOWN | 16 | 0 | T |
| AW086053 | UNKNOWN | 27 | 0 | T |
| AW086056 | UNKNOWN | 13 | 0 | T |
| AW086074 | UNKNOWN | 23 | 0 | T |
| AW086075 | UNKNOWN | 23 | 0 | T |

TABLE 1-continued

| Genbank # | Region | # reps | Position | Unit sequence |
|---|---|---|---|---|
| AW086081 | UNKNOWN | 40 | 0 | T |
| AW086082 | UNKNOWN | 58 | 0 | T |
| AW086113 | UNKNOWN | 116 | 0 | T |
| AW086113 | UNKNOWN | 19 | 324 | C |
| AW086113 | UNKNOWN | 16 | 154 | G |
| AW086113 | UNKNOWN | 13 | 141 | C |
| AW086121 | UNKNOWN | 22 | 82 | A |
| AW086125 | UNKNOWN | 20 | 0 | T |
| AW086136 | UNKNOWN | 24 | 0 | T |
| AW086140 | UNKNOWN | 13 | 0 | T |
| AW086148 | UNKNOWN | 30 | 0 | T |
| AW086168 | UNKNOWN | 14 | 0 | T |
| AW086179 | UNKNOWN | 13 | 0 | T |
| AW086183 | UNKNOWN | 14 | 0 | T |
| AW086185 | UNKNOWN | 25 | 0 | T |
| AW086205 | UNKNOWN | 13 | 0 | T |
| AW086220 | UNKNOWN | 14 | 80 | A |
| AW086231 | UNKNOWN | 30 | 308 | A |
| AW086233 | UNKNOWN | 29 | 220 | A |
| AW086238 | UNKNOWN | 14 | 83 | A |
| AW086249 | UNKNOWN | 30 | 114 | A |
| AW086256 | UNKNOWN | 20 | 277 | A |
| AW086261 | UNKNOWN | 23 | 189 | A |
| AW086268 | UNKNOWN | 22 | 137 | A |
| AW086270 | UNKNOWN | 23 | 279 | A |
| AW086279 | UNKNOWN | 21 | 104 | A |
| AW086291 | UNKNOWN | 17 | 377 | A |
| AW086309 | UNKNOWN | 27 | 213 | A |
| AW086310 | UNKNOWN | 16 | 152 | A |
| AW086312 | UNKNOWN | 5.25 | 48 | AAGG |
| AW086312 | UNKNOWN | 4.5 | 121 | AAAG |
| AW086312 | UNKNOWN | 13 | 149 | A |
| AW086317 | UNKNOWN | 21 | 172 | A |
| AW086331 | UNKNOWN | 26 | 184 | A |
| AW086332 | UNKNOWN | 32 | 94 | A |
| AW086339 | UNKNOWN | 12.25 | 130 | AGAA |
| AW086339 | UNKNOWN | 14 | 25 | GA |
| AW086339 | UNKNOWN | 28 | 176 | A |
| AW086342 | UNKNOWN | 19 | 327 | A |
| AW086353 | UNKNOWN | 29 | 184 | A |
| AW086398 | UNKNOWN | 25 | 171 | A |
| AW086400 | UNKNOWN | 27 | 149 | A |
| AW086407 | UNKNOWN | 17 | 192 | A |
| AW086411 | UNKNOWN | 5 | 171 | AGAAA |
| AW086411 | UNKNOWN | 5.75 | 189 | AAAG |
| AW086411 | UNKNOWN | 30 | 319 | A |
| AW086416 | UNKNOWN | 36 | 149 | A |
| AW086420 | UNKNOWN | 13 | 0 | T |
| AW086427 | UNKNOWN | 13 | 0 | T |
| AW086428 | UNKNOWN | 16 | 0 | T |
| AW086439 | UNKNOWN | 14 | 0 | T |
| AW086449 | UNKNOWN | 15 | 0 | T |
| AW086462 | UNKNOWN | 14 | 0 | T |
| AW086486 | UNKNOWN | 12 | 0 | T |
| AW086493 | UNKNOWN | 13 | 0 | T |
| AW086494 | UNKNOWN | 16 | 0 | T |
| AW086495 | UNKNOWN | 13 | 0 | T |
| AW087160 | UNKNOWN | 99 | 0 | T |
| AW087160 | UNKNOWN | 26 | 181 | G |
| AW087160 | UNKNOWN | 16 | 130 | A |
| AW087160 | UNKNOWN | 14 | 213 | C |
| AW087161 | UNKNOWN | 63 | 0 | T |
| AW087161 | UNKNOWN | 19 | 123 | C |
| AW087163 | UNKNOWN | 60 | 0 | T |
| AW087163 | UNKNOWN | 20 | 340 | G |
| AW087163 | UNKNOWN | 14 | 203 | A |
| AW087163 | UNKNOWN | 13 | 100 | C |
| AW087178 | UNKNOWN | 47 | 0 | T |
| AW087186 | UNKNOWN | 72 | 0 | T |
| AW087186 | UNKNOWN | 23 | 211 | C |
| AW087186 | UNKNOWN | 15 | 109 | C |
| AW087187 | UNKNOWN | 28 | 0 | T |
| AW087190 | UNKNOWN | 43 | 0 | T |
| AW087191 | UNKNOWN | 46 | 0 | T |
| AW087191 | UNKNOWN | 12 | 322 | C |
| AW087193 | UNKNOWN | 83 | 0 | T |
| AW087193 | UNKNOWN | 13 | 132 | C |

TABLE 1-continued

| Genbank # | Region | # reps | Position | Unit sequence |
|---|---|---|---|---|
| AW087194 | UNKNOWN | 33 | 0 | T |
| AW087199 | UNKNOWN | 65 | 0 | T |
| AW087199 | UNKNOWN | 14 | 167 | G |
| AW087200 | UNKNOWN | 69 | 0 | T |
| AW087200 | UNKNOWN | 25 | 302 | G |
| AW087200 | UNKNOWN | 16 | 272 | C |
| AW087200 | UNKNOWN | 12 | 96 | C |
| AW087203 | UNKNOWN | 59 | 0 | T |
| AW087207 | UNKNOWN | 108 | 0 | T |
| AW087207 | UNKNOWN | 21 | 108 | A |
| AW087207 | UNKNOWN | 17 | 206 | G |
| AW087207 | UNKNOWN | 17 | 320 | C |
| AW087208 | UNKNOWN | 25 | 0 | T |
| AW087217 | UNKNOWN | 45 | 0 | T |
| AW087250 | UNKNOWN | 38 | 0 | T |
| AW087252 | UNKNOWN | 22 | 0 | T |
| AW087261 | UNKNOWN | 14 | 281 | A |
| AW087262 | UNKNOWN | 84 | 0 | T |
| AW087262 | UNKNOWN | 14 | 239 | G |
| AW087270 | UNKNOWN | 48 | 0 | T |
| AW087336 | UNKNOWN | 59 | 0 | T |
| AW087361 | UNKNOWN | 34 | 0 | T |
| AW087369 | UNKNOWN | 25 | 0 | T |
| AW087369 | UNKNOWN | 18 | 150 | A |
| AW087385 | UNKNOWN | 66 | 0 | T |
| AW087385 | UNKNOWN | 16 | 107 | A |
| AW087385 | UNKNOWN | 16 | 235 | G |
| AW087455 | UNKNOWN | 86 | 0 | T |
| AW087455 | UNKNOWN | 22 | 95 | A |
| AW087455 | UNKNOWN | 16 | 254 | C |
| AW087455 | UNKNOWN | 14 | 133 | G |
| AW087459 | UNKNOWN | 24 | 0 | T |
| AW087462 | UNKNOWN | 108 | 0 | T |
| AW087462 | UNKNOWN | 12 | 167 | A |
| AW087528 | UNKNOWN | 4.2 | 53 | AAAAC |
| AW087534 | UNKNOWN | 95 | 0 | T |
| AW087534 | UNKNOWN | 31 | 117 | A |
| AW087534 | UNKNOWN | 13 | 238 | G |
| AW087534 | UNKNOWN | 12 | 95 | C |
| AW087538 | UNKNOWN | 49 | 0 | T |
| AW087538 | UNKNOWN | 12 | 202 | C |
| AW087545 | UNKNOWN | 4.75 | 184 | TTTG |
| AW087545 | UNKNOWN | 15 | 0 | T |
| AW087560 | UNKNOWN | 42 | 0 | T |
| AW087564 | UNKNOWN | 40 | 0 | T |
| AW087566 | UNKNOWN | 61 | 0 | T |
| AW087566 | UNKNOWN | 14 | 204 | G |
| AW087566 | UNKNOWN | 13 | 77 | A |
| AW087570 | UNKNOWN | 95 | 0 | T |
| AW087570 | UNKNOWN | 19 | 187 | A |
| AW087570 | UNKNOWN | 15 | 172 | C |
| AW087570 | UNKNOWN | 13 | 122 | C |
| AW087570 | UNKNOWN | 12 | 154 | A |
| AW087628 | UNKNOWN | 18 | 295 | T |
| AW087647 | UNKNOWN | 18 | 0 | T |
| AW087651 | UNKNOWN | 12 | 0 | T |
| AW087741 | UNKNOWN | 19 | 0 | T |
| AW087755 | UNKNOWN | 36 | 0 | T |
| AW087804 | UNKNOWN | 58 | 0 | T |
| AW087808 | UNKNOWN | 42 | 0 | T |
| AW087813 | UNKNOWN | 50 | 0 | T |
| AW087813 | UNKNOWN | 12 | 58 | A |
| AW087814 | UNKNOWN | 72 | 0 | T |
| AW087814 | UNKNOWN | 13 | 224 | G |
| AW087815 | UNKNOWN | 86 | 0 | T |
| AW087815 | UNKNOWN | 15 | 245 | C |
| AW087824 | UNKNOWN | 54 | 0 | T |
| AW087830 | UNKNOWN | 57 | 0 | T |
| AW087830 | UNKNOWN | 14 | 322 | G |
| AW087837 | UNKNOWN | 49 | 0 | T |
| AW087838 | UNKNOWN | 93 | 0 | T |
| AW087838 | UNKNOWN | 17 | 336 | C |
| AW087838 | UNKNOWN | 15 | 139 | G |
| AW087838 | UNKNOWN | 15 | 174 | A |
| AW087838 | UNKNOWN | 14 | 238 | C |
| AW087838 | UNKNOWN | 13 | 195 | C |
| AW087839 | UNKNOWN | 42 | 0 | T |

TABLE 1-continued

| Genbank # | Region | # reps | Position | Unit sequence |
| --- | --- | --- | --- | --- |
| AW087842 | UNKNOWN | 70 | 0 | T |
| AW087842 | UNKNOWN | 16 | 261 | G |
| AW087842 | UNKNOWN | 12 | 123 | C |
| AW087843 | UNKNOWN | 66 | 0 | T |
| AW087843 | UNKNOWN | 12 | 212 | C |
| AW087848 | UNKNOWN | 54 | 0 | T |
| AW087855 | UNKNOWN | 66 | 0 | T |
| AW087855 | UNKNOWN | 19 | 120 | C |
| AW087856 | UNKNOWN | 37 | 0 | T |
| AW087857 | UNKNOWN | 64 | 0 | T |
| AW087857 | UNKNOWN | 19 | 145 | A |
| AW087857 | UNKNOWN | 18 | 250 | G |
| AW087862 | UNKNOWN | 60 | 0 | T |
| AW087862 | UNKNOWN | 15 | 118 | C |
| AW087863 | UNKNOWN | 60 | 0 | T |
| AW087868 | UNKNOWN | 37 | 0 | T |
| AW087877 | UNKNOWN | 51 | 0 | T |
| AW087877 | UNKNOWN | 13 | 275 | A |
| AW087880 | UNKNOWN | 32 | 0 | T |
| AW087888 | UNKNOWN | 54 | 0 | T |
| AW087888 | UNKNOWN | 16 | 112 | C |
| AW087901 | UNKNOWN | 77 | 0 | T |
| AW087901 | UNKNOWN | 18 | 186 | A |
| AW087901 | UNKNOWN | 15 | 91 | C |
| AW087902 | UNKNOWN | 93 | 0 | T |
| AW087902 | UNKNOWN | 19 | 368 | G |
| AW087902 | UNKNOWN | 13 | 165 | G |
| AW087902 | UNKNOWN | 12 | 295 | A |
| AW087907 | UNKNOWN | 63 | 0 | T |
| AW087907 | UNKNOWN | 16 | 96 | A |
| AW087907 | UNKNOWN | 12 | 141 | C |
| AW087915 | UNKNOWN | 81 | 0 | T |
| AW087915 | UNKNOWN | 16 | 129 | G |
| AW087915 | UNKNOWN | 14 | 209 | C |
| AW087915 | UNKNOWN | 13 | 145 | A |
| AW087915 | UNKNOWN | 12 | 117 | C |
| AW087916 | UNKNOWN | 85 | 0 | T |
| AW087916 | UNKNOWN | 19 | 250 | C |
| AW087916 | UNKNOWN | 18 | 156 | A |
| AW087928 | UNKNOWN | 49 | 0 | T |
| AW087932 | UNKNOWN | 91 | 0 | T |
| AW087932 | UNKNOWN | 17 | 177 | A |
| AW087932 | UNKNOWN | 15 | 103 | G |
| AW087938 | UNKNOWN | 81 | 0 | T |
| AW087938 | UNKNOWN | 16 | 162 | A |
| AW087938 | UNKNOWN | 13 | 142 | C |
| AW087955 | UNKNOWN | 2.5 | 342 | ATTGCTCCTTTCTCCTGT (SEQ ID NO: 211) |
| AW087955 | UNKNOWN | 21 | 11 | T |
| AW088017 | UNKNOWN | 37 | 0 | T |
| AW088037 | UNKNOWN | 85 | 0 | T |
| AW088037 | UNKNOWN | 18 | 194 | C |
| AW088037 | UNKNOWN | 16 | 148 | C |
| AW088037 | UNKNOWN | 16 | 328 | A |
| AW088043 | UNKNOWN | 101 | 0 | T |
| AW088043 | UNKNOWN | 24 | 198 | C |
| AW088043 | UNKNOWN | 21 | 166 | A |
| AW088043 | UNKNOWN | 17 | 110 | A |
| AW088043 | UNKNOWN | 13 | 139 | G |
| AW088043 | UNKNOWN | 12 | 127 | C |
| AW088087 | UNKNOWN | 51 | 0 | T |
| AW088087 | UNKNOWN | 16 | 149 | G |
| AW088089 | UNKNOWN | 35 | 0 | T |
| AW088089 | UNKNOWN | 13 | 248 | G |
| AW088118 | UNKNOWN | 43 | 0 | T |
| AW088129 | UNKNOWN | 83 | 0 | T |
| AW088129 | UNKNOWN | 16 | 142 | G |
| AW088129 | UNKNOWN | 15 | 257 | A |
| AW088129 | UNKNOWN | 13 | 158 | A |
| AW088129 | UNKNOWN | 13 | 222 | C |
| AW088129 | UNKNOWN | 12 | 130 | C |
| AW088131 | UNKNOWN | 53 | 0 | T |
| AW088133 | UNKNOWN | 15 | 2 | T |
| AW088134 | UNKNOWN | 99 | 0 | T |
| AW088134 | UNKNOWN | 18 | 112 | C |
| AW088141 | UNKNOWN | 38 | 18 | T |
| AW088141 | UNKNOWN | 17 | 0 | T |
| AW088141 | UNKNOWN | 13 | 114 | C |

TABLE 1-continued

| Genbank # | Region | # reps | Position | Unit sequence |
|---|---|---|---|---|
| AW088144 | UNKNOWN | 90 | 0 | T |
| AW088145 | UNKNOWN | 53 | 0 | T |
| AW088145 | UNKNOWN | 15 | 88 | A |
| AW088155 | UNKNOWN | 13 | 0 | T |
| AW088162 | UNKNOWN | 95 | 0 | T |
| AW088162 | UNKNOWN | 16 | 123 | A |
| AW088162 | UNKNOWN | 14 | 179 | C |
| AW088162 | UNKNOWN | 13 | 277 | G |
| AW088183 | UNKNOWN | 52 | 0 | T |
| AW088190 | UNKNOWN | 20 | 0 | T |
| AW088216 | UNKNOWN | 37 | 0 | T |
| AW088216 | UNKNOWN | 12 | 38 | A |
| AW088223 | UNKNOWN | 66 | 0 | T |
| AW088223 | UNKNOWN | 14 | 134 | A |
| AW088259 | UNKNOWN | 39 | 0 | T |
| AW088261 | UNKNOWN | 26 | 0 | T |
| AW088287 | UNKNOWN | 65 | 0 | T |
| AW088312 | UNKNOWN | 23 | 2 | T |
| AW088328 | UNKNOWN | 85 | 0 | T |
| AW088328 | UNKNOWN | 12 | 116 | A |
| AW088345 | UNKNOWN | 12 | 0 | T |
| AW088366 | UNKNOWN | 6.5 | 327 | AC |
| AW088403 | UNKNOWN | 36 | 0 | T |
| AW088422 | UNKNOWN | 17 | 0 | T |
| AW088438 | UNKNOWN | 53 | 0 | T |
| AW088439 | UNKNOWN | 17 | 0 | T |
| AW088469 | UNKNOWN | 12 | 41 | T |
| AW088478 | UNKNOWN | 15 | 0 | T |
| AW088484 | UNKNOWN | 45 | 0 | T |
| AW088485 | UNKNOWN | 56 | 0 | T |
| AW088485 | UNKNOWN | 12 | 95 | G |
| AW088489 | UNKNOWN | 55 | 0 | T |
| AW088494 | UNKNOWN | 7.25 | 185 | CAAA |
| AW088521 | UNKNOWN | 71 | 0 | T |
| AW088521 | UNKNOWN | 13 | 361 | G |
| AW088527 | UNKNOWN | 20 | 0 | T |
| AW088535 | UNKNOWN | 39 | 0 | T |
| AW088538 | UNKNOWN | 76 | 0 | T |
| AW088538 | UNKNOWN | 16 | 148 | G |
| AW088538 | UNKNOWN | 13 | 263 | C |
| AW088546 | UNKNOWN | 47 | 0 | T |
| AW088546 | UNKNOWN | 20 | 214 | A |
| AW088553 | UNKNOWN | 52 | 0 | T |
| AW088553 | UNKNOWN | 12 | 128 | A |
| AW088560 | UNKNOWN | 66 | 2 | T |
| AW088560 | UNKNOWN | 18 | 90 | A |
| AW088581 | UNKNOWN | 3.5 | 431 | AAAAAT |
| AW088581 | UNKNOWN | 13 | 6 | T |
| AW088591 | UNKNOWN | 74 | 0 | T |
| AW088591 | UNKNOWN | 22 | 130 | G |
| AW088638 | UNKNOWN | 12 | 10 | T |
| AW088672 | UNKNOWN | 12 | 141 | A |
| AW088685 | UNKNOWN | 52 | 0 | T |
| AW088691 | UNKNOWN | 78 | 4 | T |
| AW088691 | UNKNOWN | 17 | 184 | A |
| AW088691 | UNKNOWN | 13 | 213 | C |
| AW088695 | UNKNOWN | 25 | 0 | T |
| AW088697 | UNKNOWN | 71 | 0 | T |
| AW088698 | UNKNOWN | 65 | 0 | T |
| AW088698 | UNKNOWN | 20 | 380 | A |
| AW088698 | UNKNOWN | 15 | 275 | A |
| AW088698 | UNKNOWN | 14 | 160 | C |
| AW088717 | UNKNOWN | 49 | 0 | T |
| AW088718 | UNKNOWN | 19 | 0 | T |
| AW088723 | UNKNOWN | 47 | 0 | T |
| AW088723 | UNKNOWN | 12 | 374 | A |
| AW088736 | UNKNOWN | 16 | 252 | T |
| AW088763 | UNKNOWN | 13 | 310 | T |
| AW088773 | UNKNOWN | 54 | 0 | T |
| AW088802 | UNKNOWN | 48 | 0 | T |
| AW088805 | UNKNOWN | 79 | 0 | T |
| AW088805 | UNKNOWN | 19 | 236 | A |
| AW088805 | UNKNOWN | 13 | 104 | A |
| AW088805 | UNKNOWN | 12 | 166 | G |
| AW088821 | UNKNOWN | 46 | 0 | T |
| AW088827 | UNKNOWN | 43 | 0 | T |
| AW088838 | UNKNOWN | 14 | 0 | T |

TABLE 1-continued

| Genbank # | Region | # reps | Position | Unit sequence |
|---|---|---|---|---|
| AW088839 | UNKNOWN | 47 | 0 | T |
| AW088839 | UNKNOWN | 16 | 113 | G |
| AW088839 | UNKNOWN | 12 | 184 | C |
| AW088839 | UNKNOWN | 12 | 213 | A |
| AW088841 | UNKNOWN | 27 | 0 | T |
| AW088843 | UNKNOWN | 3.8 | 161 | TTTTG |
| AW088882 | UNKNOWN | 66 | 0 | T |
| AW088882 | UNKNOWN | 17 | 169 | G |
| AW088899 | UNKNOWN | 89 | 0 | T |
| AW088903 | UNKNOWN | 100 | 0 | T |
| AW088903 | UNKNOWN | 12 | 165 | C |
| AW088919 | UNKNOWN | 13 | 0 | T |
| AW088929 | UNKNOWN | 53 | 0 | T |
| AW088929 | UNKNOWN | 14 | 350 | G |
| AW088929 | UNKNOWN | 12 | 328 | C |
| AW088944 | UNKNOWN | 56 | 0 | T |
| AW089006 | UNKNOWN | 68 | 0 | T |
| AW089009 | UNKNOWN | 53 | 0 | T |
| AW089009 | UNKNOWN | 19 | 103 | A |
| AW089016 | UNKNOWN | 8.5 | 318 | ATAC |
| AW089016 | UNKNOWN | 12 | 10 | A |
| AW089036 | UNKNOWN | 59 | 0 | T |
| AW089036 | UNKNOWN | 32 | 139 | C |
| AW089036 | UNKNOWN | 14 | 225 | G |
| AW089048 | UNKNOWN | 28 | 0 | T |
| AW089084 | UNKNOWN | 21 | 0 | T |
| AW089091 | UNKNOWN | 28 | 0 | T |
| AW089091 | UNKNOWN | 14 | 196 | A |
| AW089120 | UNKNOWN | 29 | 0 | T |
| AW089122 | UNKNOWN | 61 | 0 | T |
| AW089122 | UNKNOWN | 16 | 148 | G |
| AW089139 | UNKNOWN | 17 | 0 | T |
| AW089157 | UNKNOWN | 32 | 0 | T |
| AW089171 | UNKNOWN | 39 | 0 | T |
| AW089179 | UNKNOWN | 90 | 0 | T |
| AW089179 | UNKNOWN | 23 | 146 | C |
| AW089179 | UNKNOWN | 12 | 177 | A |
| AW089221 | UNKNOWN | 80 | 0 | T |
| AW089221 | UNKNOWN | 15 | 211 | A |
| AW089226 | UNKNOWN | 59 | 0 | T |
| AW089252 | UNKNOWN | 61 | 0 | T |
| AW089252 | UNKNOWN | 15 | 119 | C |
| AW089258 | UNKNOWN | 82 | 0 | T |
| AW089258 | UNKNOWN | 20 | 190 | A |
| AW089272 | UNKNOWN | 61 | 0 | T |
| AW089272 | UNKNOWN | 13 | 205 | A |
| AW089272 | UNKNOWN | 12 | 232 | C |
| AW089275 | UNKNOWN | 76 | 0 | T |
| AW089275 | UNKNOWN | 13 | 114 | G |
| AW089285 | UNKNOWN | 2.8 | 100 | AAAAAAAACC (SEQ ID NO: 212) |
| AW089285 | UNKNOWN | 35 | 0 | T |
| AW089293 | UNKNOWN | 53 | 0 | T |
| AW089310 | UNKNOWN | 87 | 0 | T |
| AW089310 | UNKNOWN | 16 | 331 | C |
| AW089310 | UNKNOWN | 14 | 239 | G |
| AW089310 | UNKNOWN | 12 | 156 | C |
| AW089310 | UNKNOWN | 12 | 304 | A |
| AW089327 | UNKNOWN | 89 | 0 | T |
| AW089327 | UNKNOWN | 15 | 226 | G |
| AW089328 | UNKNOWN | 56 | 0 | T |
| AW089340 | UNKNOWN | 50 | 0 | T |
| AW089340 | UNKNOWN | 14 | 88 | A |
| AW089350 | UNKNOWN | 91 | 0 | T |
| AW089350 | UNKNOWN | 14 | 166 | C |
| AW089350 | UNKNOWN | 13 | 130 | C |
| AW089350 | UNKNOWN | 12 | 182 | A |
| AW089351 | UNKNOWN | 53 | 0 | T |
| AW089373 | UNKNOWN | 37 | 0 | T |
| AW089373 | UNKNOWN | 16 | 174 | A |
| AW089379 | UNKNOWN | 47 | 0 | T |
| AW089379 | UNKNOWN | 13 | 273 | C |
| AW089387 | UNKNOWN | 57 | 0 | T |
| AW089387 | UNKNOWN | 12 | 163 | A |
| AW089405 | UNKNOWN | 95 | 0 | T |
| AW089405 | UNKNOWN | 16 | 310 | G |
| AW089405 | UNKNOWN | 15 | 295 | A |
| AW089405 | UNKNOWN | 13 | 223 | A |

TABLE 1-continued

| Genbank # | Region | # reps | Position | Unit sequence |
|---|---|---|---|---|
| AW089424 | UNKNOWN | 59 | 0 | T |
| AW089424 | UNKNOWN | 14 | 196 | G |
| AW089436 | UNKNOWN | 73 | 0 | T |
| AW089436 | UNKNOWN | 12 | 265 | C |
| AW089438 | UNKNOWN | 66 | 0 | T |
| AW089438 | UNKNOWN | 14 | 158 | C |
| AW089438 | UNKNOWN | 12 | 66 | A |
| AW089438 | UNKNOWN | 12 | 172 | G |
| AW089439 | UNKNOWN | 63 | 33 | T |
| AW089439 | UNKNOWN | 32 | 0 | T |
| AW089439 | UNKNOWN | 20 | 246 | G |
| AW089439 | UNKNOWN | 19 | 132 | G |
| AW089439 | UNKNOWN | 14 | 118 | A |
| AW089439 | UNKNOWN | 14 | 266 | C |
| AW089439 | UNKNOWN | 12 | 99 | A |
| AW089457 | UNKNOWN | 45 | 0 | T |
| AW089457 | UNKNOWN | 16 | 209 | A |
| AW089471 | UNKNOWN | 85 | 0 | T |
| AW089495 | UNKNOWN | 55 | 0 | T |
| AW089495 | UNKNOWN | 20 | 469 | A |
| AW089517 | UNKNOWN | 50 | 0 | T |
| AW089562 | UNKNOWN | 81 | 0 | T |
| AW089562 | UNKNOWN | 23 | 148 | C |
| AW089562 | UNKNOWN | 19 | 129 | A |
| AW089562 | UNKNOWN | 12 | 511 | G |
| AW089567 | UNKNOWN | 28 | 0 | T |
| AW089638 | UNKNOWN | 44 | 0 | T |
| AW089640 | UNKNOWN | 69 | 0 | T |
| AW089664 | UNKNOWN | 78 | 0 | T |
| AW089664 | UNKNOWN | 15 | 142 | C |
| AW089664 | UNKNOWN | 14 | 203 | G |
| AW089684 | UNKNOWN | 61 | 0 | T |
| AW089684 | UNKNOWN | 14 | 195 | A |
| AW089689 | UNKNOWN | 74 | 0 | T |
| AW089689 | UNKNOWN | 14 | 118 | A |
| AW089707 | UNKNOWN | 7.5 | 376 | AG |
| AW089707 | UNKNOWN | 28 | 349 | A |
| AW089726 | UNKNOWN | 54 | 0 | T |
| AW089732 | UNKNOWN | 60 | 0 | T |
| AW089732 | UNKNOWN | 16 | 126 | G |
| AW089743 | UNKNOWN | 8 | 280 | CA |
| AW089743 | UNKNOWN | 24 | 0 | T |
| AW089776 | UNKNOWN | 41 | 0 | T |
| AW089777 | UNKNOWN | 58 | 0 | T |
| AW089801 | UNKNOWN | 81 | 0 | T |
| AW089801 | UNKNOWN | 18 | 144 | C |
| AW089811 | UNKNOWN | 53 | 0 | T |
| AW089823 | UNKNOWN | 42 | 0 | T |
| AW089840 | UNKNOWN | 86 | 0 | T |
| AW089840 | UNKNOWN | 16 | 155 | C |
| AW089840 | UNKNOWN | 16 | 253 | A |
| AW089840 | UNKNOWN | 12 | 123 | G |
| AW089844 | UNKNOWN | 53 | 4 | T |
| AW089853 | UNKNOWN | 45 | 2 | T |
| AW089858 | UNKNOWN | 89 | 0 | T |
| AW089858 | UNKNOWN | 12 | 285 | G |
| AW089877 | UNKNOWN | 8 | 51 | AT |
| AW089877 | UNKNOWN | 25 | 449 | A |
| AW089890 | UNKNOWN | 55 | 0 | T |
| AW089900 | UNKNOWN | 56 | 0 | T |
| AW089905 | UNKNOWN | 55 | 0 | T |
| AW089905 | UNKNOWN | 12 | 342 | G |
| AW089922 | UNKNOWN | 41 | 0 | T |
| AW089936 | UNKNOWN | 4.5 | 197 | TTGG |
| AW089936 | UNKNOWN | 52 | 0 | T |
| AW089959 | UNKNOWN | 4.75 | 17 | TTTA |
| AW089959 | UNKNOWN | 15 | 530 | G |
| AW090001 | UNKNOWN | 58 | 0 | T |
| AW090001 | UNKNOWN | 14 | 242 | A |
| AW090001 | UNKNOWN | 12 | 107 | A |
| AW090006 | UNKNOWN | 75 | 0 | T |
| AW090006 | UNKNOWN | 14 | 93 | A |
| AW090007 | UNKNOWN | 49 | 0 | T |
| AW090007 | UNKNOWN | 14 | 123 | C |
| AW090011 | UNKNOWN | 26 | 0 | T |
| AW090013 | UNKNOWN | 112 | 0 | T |
| AW090013 | UNKNOWN | 16 | 126 | G |

TABLE 1-continued

| Genbank # | Region | # reps | Position | Unit sequence |
|---|---|---|---|---|
| AW090013 | UNKNOWN | 14 | 254 | C |
| AW090019 | UNKNOWN | 35 | 0 | T |
| AW090019 | UNKNOWN | 15 | 161 | A |
| AW090021 | UNKNOWN | 31 | 0 | T |
| AW090021 | UNKNOWN | 13 | 396 | G |
| AW090052 | UNKNOWN | 34 | 0 | T |
| AW090058 | UNKNOWN | 70 | 0 | T |
| AW090058 | UNKNOWN | 15 | 186 | A |
| AW090071 | UNKNOWN | 99 | 1 | T |
| AW090071 | UNKNOWN | 25 | 284 | C |
| AW090071 | UNKNOWN | 17 | 206 | G |
| AW090071 | UNKNOWN | 16 | 262 | A |
| AW090071 | UNKNOWN | 14 | 245 | A |
| AW090086 | UNKNOWN | 54 | 0 | T |
| AW090086 | UNKNOWN | 36 | 390 | C |
| AW090086 | UNKNOWN | 15 | 108 | A |
| AW090086 | UNKNOWN | 13 | 89 | A |
| AW090087 | UNKNOWN | 58 | 0 | T |
| AW090093 | UNKNOWN | 86 | 0 | T |
| AW090093 | UNKNOWN | 17 | 154 | C |
| AW090093 | UNKNOWN | 14 | 132 | C |
| AW090093 | UNKNOWN | 13 | 324 | A |
| AW090102 | UNKNOWN | 61 | 0 | T |
| AW090103 | UNKNOWN | 77 | 0 | T |
| AW090103 | UNKNOWN | 17 | 227 | C |
| AW090103 | UNKNOWN | 15 | 175 | A |
| AW090103 | UNKNOWN | 13 | 150 | G |
| AW090103 | UNKNOWN | 12 | 163 | C |
| AW090128 | UNKNOWN | 63 | 0 | T |
| AW090128 | UNKNOWN | 15 | 192 | C |
| AW090131 | UNKNOWN | 50 | 0 | T |
| AW090131 | UNKNOWN | 16 | 147 | G |
| AW090141 | UNKNOWN | 72 | 3 | T |
| AW090158 | UNKNOWN | 58 | 0 | T |
| AW090158 | UNKNOWN | 13 | 141 | C |
| AW090206 | UNKNOWN | 59 | 0 | T |
| AW090206 | UNKNOWN | 18 | 219 | G |
| AW090207 | UNKNOWN | 13 | 166 | T |
| AW090225 | UNKNOWN | 50 | 0 | T |
| AW090246 | UNKNOWN | 33 | 0 | T |
| AW090273 | UNKNOWN | 56 | 0 | T |
| AW090273 | UNKNOWN | 20 | 193 | A |
| AW090273 | UNKNOWN | 18 | 123 | G |
| AW090278 | UNKNOWN | 33 | 0 | T |
| AW090279 | UNKNOWN | 69 | 0 | T |
| AW090283 | UNKNOWN | 20 | 0 | T |
| AW090285 | UNKNOWN | 51 | 0 | T |
| AW090290 | UNKNOWN | 46 | 0 | T |
| AW090292 | UNKNOWN | 40 | 0 | T |
| AW090351 | UNKNOWN | 46 | 0 | T |
| AW090360 | UNKNOWN | 76 | 0 | T |
| AW090360 | UNKNOWN | 12 | 300 | G |
| AW090375 | UNKNOWN | 61 | 0 | T |
| AW090393 | UNKNOWN | 78 | 0 | T |
| AW090398 | UNKNOWN | 62 | 0 | T |
| AW090429 | UNKNOWN | 43 | 0 | T |
| AW090429 | UNKNOWN | 23 | 168 | C |
| AW090429 | UNKNOWN | 18 | 147 | A |
| AW090437 | UNKNOWN | 16 | 0 | T |
| AW090446 | UNKNOWN | 36 | 0 | T |
| AW090451 | UNKNOWN | 71 | 0 | T |
| AW090451 | UNKNOWN | 16 | 193 | A |
| AW090451 | UNKNOWN | 13 | 138 | A |
| AW090485 | UNKNOWN | 8.5 | 32 | AC |
| AW090492 | UNKNOWN | 64 | 0 | T |
| AW090492 | UNKNOWN | 16 | 389 | A |
| AW090492 | UNKNOWN | 13 | 220 | C |
| AW099494 | UNKNOWN | 88 | 0 | T |
| AW090494 | UNKNOWN | 17 | 262 | C |
| AW090494 | UNKNOWN | 15 | 154 | A |
| AW090494 | UNKNOWN | 12 | 129 | G |
| AW090498 | UNKNOWN | 63 | 0 | T |
| AW090498 | UNKNOWN | 26 | 115 | A |
| AW090498 | UNKNOWN | 13 | 282 | C |
| AW090505 | UNKNOWN | 44 | 0 | T |
| AW090505 | UNKNOWN | 12 | 195 | A |
| AW090539 | UNKNOWN | 70 | 0 | T |

TABLE 1-continued

| Genbank # | Region | # reps | Position | Unit sequence |
|---|---|---|---|---|
| AW090539 | UNKNOWN | 20 | 172 | C |
| AW090539 | UNKNOWN | 15 | 103 | A |
| AW090539 | UNKNOWN | 12 | 124 | G |
| AW090550 | UNKNOWN | 87 | 0 | T |
| AW090550 | UNKNOWN | 20 | 87 | A |
| AW090589 | UNKNOWN | 45 | 0 | T |
| AW090589 | UNKNOWN | 14 | 341 | C |
| AW090589 | UNKNOWN | 12 | 155 | A |
| AW090594 | UNKNOWN | 45 | 1 | T |
| AW090594 | UNKNOWN | 12 | 163 | G |
| AW090599 | UNKNOWN | 82 | 0 | T |
| AW090599 | UNKNOWN | 17 | 155 | C |
| AW090599 | UNKNOWN | 14 | 324 | A |
| AW090601 | UNKNOWN | 13 | 0 | T |
| AW090610 | UNKNOWN | 16 | 0 | T |
| AW090622 | UNKNOWN | 35 | 0 | T |
| AW090625 | UNKNOWN | 37 | 0 | T |
| AW090643 | UNKNOWN | 44 | 0 | T |
| AW090662 | UNKNOWN | 62 | 0 | T |
| AW090662 | UNKNOWN | 15 | 147 | G |
| AW090662 | UNKNOWN | 12 | 208 | A |
| AW090667 | UNKNOWN | 47 | 0 | T |
| AW090681 | UNKNOWN | 69 | 0 | T |
| AW090700 | UNKNOWN | 98 | 0 | T |
| AW090700 | UNKNOWN | 25 | 171 | C |
| AW090700 | UNKNOWN | 18 | 112 | A |
| AW090700 | UNKNOWN | 14 | 411 | G |
| AW090726 | UNKNOWN | 92 | 0 | T |
| AW090726 | UNKNOWN | 24 | 229 | C |
| AW090726 | UNKNOWN | 17 | 92 | C |
| AW090726 | UNKNOWN | 16 | 172 | A |
| AW090726 | UNKNOWN | 16 | 314 | G |
| AW090726 | UNKNOWN | 13 | 216 | G |
| AW090736 | UNKNOWN | 81 | 0 | T |
| AW090736 | UNKNOWN | 18 | 142 | G |
| AW090736 | UNKNOWN | 15 | 348 | C |
| AW090736 | UNKNOWN | 12 | 251 | C |
| AW090738 | UNKNOWN | 26 | 0 | T |
| AW090764 | UNKNOWN | 29 | 0 | T |
| AW090768 | UNKNOWN | 80 | 0 | T |
| AW090768 | UNKNOWN | 17 | 148 | C |
| AW090768 | UNKNOWN | 14 | 126 | C |
| AW090768 | UNKNOWN | 12 | 319 | A |
| AW090769 | UNKNOWN | 12 | 0 | T |
| AW090782 | UNKNOWN | 5.5 | 54 | TTAA |
| AW090782 | UNKNOWN | 49 | 0 | T |
| AW090806 | UNKNOWN | 77 | 0 | T |
| AW090830 | UNKNOWN | 13 | 548 | A |
| AW102632 | UNKNOWN | 13 | 303 | A |
| AW102654 | UNKNOWN | 17 | 42 | T |
| AW102696 | UNKNOWN | 14 | 35 | A |
| AW102740 | UNKNOWN | 14 | 0 | T |
| AW102754 | UNKNOWN | 84 | 0 | T |
| AW102754 | UNKNOWN | 18 | 102 | A |
| AW102754 | UNKNOWN | 12 | 203 | G |
| AW102761 | UNKNOWN | 115 | 0 | T |
| AW102761 | UNKNOWN | 16 | 164 | G |
| AW102761 | UNKNOWN | 12 | 152 | A |
| AW102778 | UNKNOWN | 30 | 0 | T |
| AW102778 | UNKNOWN | 16 | 227 | C |
| AW102778 | UNKNOWN | 14 | 136 | C |
| AW102785 | UNKNOWN | 103 | 0 | T |
| AW102785 | UNKNOWN | 20 | 170 | C |
| AW102785 | UNKNOWN | 19 | 132 | A |
| AW102794 | UNKNOWN | 76 | 0 | T |
| AW102794 | UNKNOWN | 21 | 384 | C |
| AW102794 | UNKNOWN | 12 | 316 | C |
| AW102798 | UNKNOWN | 95 | 0 | T |
| AW102798 | UNKNOWN | 17 | 129 | A |
| AW102798 | UNKNOWN | 13 | 166 | C |
| AW102814 | UNKNOWN | 28 | 19 | T |
| AW102814 | UNKNOWN | 13 | 126 | C |
| AW102816 | UNKNOWN | 69 | 0 | T |
| AW102816 | UNKNOWN | 14 | 106 | A |
| AW102816 | UNKNOWN | 12 | 146 | C |
| AW102816 | UNKNOWN | 12 | 236 | G |
| AW102821 | UNKNOWN | 71 | 0 | T |

TABLE 1-continued

| Genbank # | Region | # reps | Position | Unit sequence |
|---|---|---|---|---|
| AW102821 | UNKNOWN | 14 | 253 | G |
| AW102836 | UNKNOWN | 31 | 0 | T |
| AW102836 | UNKNOWN | 15 | 286 | A |
| AW102858 | UNKNOWN | 46 | 0 | T |
| AW102861 | UNKNOWN | 88 | 0 | T |
| AW102861 | UNKNOWN | 20 | 238 | C |
| AW102861 | UNKNOWN | 15 | 119 | A |
| AW102864 | UNKNOWN | 67 | 0 | T |
| AW102864 | UNKNOWN | 15 | 78 | A |
| AW102868 | UNKNOWN | 41 | 0 | T |
| AW102900 | UNKNOWN | 66 | 0 | T |
| AW102902 | UNKNOWN | 71 | 2 | T |
| AW102902 | UNKNOWN | 15 | 338 | G |
| AW102902 | UNKNOWN | 14 | 119 | G |
| AW102902 | UNKNOWN | 14 | 404 | C |
| AW102907 | UNKNOWN | 46 | 0 | T |
| AW102913 | UNKNOWN | 52 | 0 | T |
| AW102924 | UNKNOWN | 93 | 9 | T |
| AW102924 | UNKNOWN | 17 | 287 | C |
| AW102924 | UNKNOWN | 14 | 199 | A |
| AW102924 | UNKNOWN | 14 | 224 | C |
| AW102928 | UNKNOWN | 45 | 0 | T |
| AW102941 | UNKNOWN | 12.5 | 258 | TG |
| AW102950 | UNKNOWN | 83 | 0 | T |
| AW102950 | UNKNOWN | 13 | 280 | G |
| AW102966 | UNKNOWN | 49 | 0 | T |
| AW102966 | UNKNOWN | 18 | 126 | A |
| AW102966 | UNKNOWN | 17 | 193 | G |
| AW102966 | UNKNOWN | 13 | 235 | C |
| AW102968 | UNKNOWN | 28 | 0 | T |
| AW102970 | UNKNOWN | 43 | 0 | T |
| AW102970 | UNKNOWN | 16 | 109 | A |
| AW102989 | UNKNOWN | 61 | 0 | T |
| AW102989 | UNKNOWN | 12 | 177 | C |
| AW102993 | UNKNOWN | 42 | 0 | T |
| AW103012 | UNKNOWN | 67 | 0 | T |
| AW103012 | UNKNOWN | 16 | 195 | C |
| AW103029 | UNKNOWN | 38 | 0 | T |
| AW103029 | UNKNOWN | 13 | 166 | C |
| AW103036 | UNKNOWN | 15 | 0 | T |
| AW103040 | UNKNOWN | 59 | 0 | T |
| AW103051 | UNKNOWN | 15 | 0 | T |
| AW103063 | UNKNOWN | 91 | 5 | T |
| AW103063 | UNKNOWN | 14 | 123 | A |
| AW103063 | UNKNOWN | 13 | 316 | G |
| AW103068 | UNKNOWN | 30 | 0 | T |
| AW103079 | UNKNOWN | 45 | 0 | T |
| AW103079 | UNKNOWN | 14 | 323 | A |
| AW103079 | UNKNOWN | 13 | 173 | G |
| AW103079 | UNKNOWN | 12 | 159 | A |
| AW103095 | UNKNOWN | 45 | 0 | T |
| AW103107 | UNKNOWN | 40 | 0 | T |
| AW103122 | UNKNOWN | 13 | 25 | A |
| AW103168 | UNKNOWN | 14 | 0 | T |
| AW103176 | UNKNOWN | 12 | 0 | T |
| AW103195 | UNKNOWN | 82 | 0 | T |
| AW103195 | UNKNOWN | 20 | 98 | A |
| AW103195 | UNKNOWN | 18 | 258 | G |
| AW103195 | UNKNOWN | 17 | 357 | C |
| AW103195 | UNKNOWN | 14 | 167 | C |
| AW103195 | UNKNOWN | 13 | 82 | G |
| AW103228 | UNKNOWN | 94 | 0 | T |
| AW103228 | UNKNOWN | 14 | 364 | C |
| AW103241 | UNKNOWN | 53 | 0 | T |
| AW103245 | UNKNOWN | 20 | 0 | T |
| AW103307 | UNKNOWN | 4.8 | 27 | AAAAG |
| AW103317 | UNKNOWN | 35 | 0 | T |
| AW103338 | UNKNOWN | 32 | 0 | T |
| AW103338 | UNKNOWN | 16 | 156 | C |
| AW103338 | UNKNOWN | 12 | 172 | A |
| AW103345 | UNKNOWN | 4.5 | 154 | AAAT |
| AW103360 | UNKNOWN | 41 | 0 | T |
| AW103362 | UNKNOWN | 53 | 0 | T |
| AW103371 | UNKNOWN | 127 | 95 | A |
| AW103372 | UNKNOWN | 64 | 0 | T |
| AW103372 | UNKNOWN | 20 | 167 | C |
| AW103398 | UNKNOWN | 58 | 0 | T |

TABLE 1-continued

| Genbank # | Region | # reps | Position | Unit sequence |
| --- | --- | --- | --- | --- |
| AW103421 | UNKNOWN | 37 | 0 | T |
| AW103431 | UNKNOWN | 56 | 0 | T |
| AW103431 | UNKNOWN | 12 | 172 | A |
| AW103433 | UNKNOWN | 27 | 0 | T |
| AW103441 | UNKNOWN | 89 | 0 | T |
| AW103441 | UNKNOWN | 24 | 242 | G |
| AW103441 | UNKNOWN | 18 | 165 | C |
| AW103441 | UNKNOWN | 12 | 134 | G |
| AW103441 | UNKNOWN | 12 | 146 | C |
| AW103442 | UNKNOWN | 82 | 0 | T |
| AW103442 | UNKNOWN | 14 | 202 | A |
| AW103442 | UNKNOWN | 14 | 216 | G |
| AW103442 | UNKNOWN | 13 | 231 | C |
| AW103442 | UNKNOWN | 12 | 170 | C |
| AW103449 | UNKNOWN | 74 | 0 | T |
| AW103458 | UNKNOWN | 18 | 0 | T |
| AW103501 | UNKNOWN | 66 | 0 | T |
| AW103501 | UNKNOWN | 16 | 306 | A |
| AW103507 | UNKNOWN | 39 | 0 | T |
| AW103507 | UNKNOWN | 12 | 260 | G |
| AW103523 | UNKNOWN | 45 | 0 | T |
| AW103523 | UNKNOWN | 13 | 220 | G |
| AW103553 | UNKNOWN | 45 | 0 | T |
| AW103555 | UNKNOWN | 34 | 0 | T |
| AW103555 | UNKNOWN | 22 | 235 | A |
| AW103555 | UNKNOWN | 14 | 257 | C |
| AW103600 | UNKNOWN | 45 | 0 | T |
| AW103628 | UNKNOWN | 80 | 0 | T |
| AW103691 | UNKNOWN | 40 | 0 | T |
| AW103710 | UNKNOWN | 60 | 0 | T |
| AW103710 | UNKNOWN | 15 | 153 | C |
| AW103726 | UNKNOWN | 61 | 0 | T |
| AW103751 | UNKNOWN | 31 | 0 | T |
| AW103751 | UNKNOWN | 16 | 246 | A |
| AW103765 | UNKNOWN | 43 | 0 | T |
| AW103831 | UNKNOWN | 4.66 | 266 | GAGAGG |
| AW103868 | UNKNOWN | 12 | 0 | T |
| AW103878 | UNKNOWN | 89 | 0 | T |
| AW103878 | UNKNOWN | 17 | 134 | G |
| AW103878 | UNKNOWN | 12 | 89 | A |
| AW103886 | UNKNOWN | 81 | 0 | T |
| AW103886 | UNKNOWN | 16 | 188 | G |
| AW103886 | UNKNOWN | 14 | 204 | C |
| AW103893 | UNKNOWN | 104 | 0 | T |
| AW103893 | UNKNOWN | 20 | 200 | C |
| AW103923 | UNKNOWN | 53 | 0 | T |
| AW103928 | UNKNOWN | 68 | 0 | T |
| AW103947 | UNKNOWN | 42 | 0 | T |
| AW103979 | UNKNOWN | 21 | 0 | T |
| AW104049 | UNKNOWN | 44 | 0 | T |
| AW104049 | UNKNOWN | 14 | 267 | A |
| AW104056 | UNKNOWN | 65 | 0 | T |
| AW104056 | UNKNOWN | 12 | 159 | G |
| AW104062 | UNKNOWN | 71 | 0 | T |
| AW104062 | UNKNOWN | 16 | 334 | C |
| AW104062 | UNKNOWN | 13 | 89 | C |
| AW104095 | UNKNOWN | 13 | 1 | T |
| AW104108 | UNKNOWN | 80 | 0 | T |
| AW104108 | UNKNOWN | 16 | 295 | G |
| AW104108 | UNKNOWN | 12 | 101 | A |
| AW104117 | UNKNOWN | 63 | 0 | T |
| AW104117 | UNKNOWN | 16 | 394 | C |
| AW104117 | UNKNOWN | 13 | 114 | C |
| AW104125 | UNKNOWN | 16 | 352 | T |
| AW104129 | UNKNOWN | 50 | 0 | T |
| AW104129 | UNKNOWN | 17 | 262 | G |
| AW104141 | UNKNOWN | 70 | 0 | T |
| AW104141 | UNKNOWN | 12 | 89 | C |
| AW104145 | UNKNOWN | 83 | 0 | T |
| AW104145 | UNKNOWN | 14 | 113 | G |
| AW104145 | UNKNOWN | 13 | 301 | C |
| AW104146 | UNKNOWN | 91 | 0 | T |
| AW104146 | UNKNOWN | 18 | 259 | A |
| AW104146 | UNKNOWN | 14 | 91 | G |
| AW104146 | UNKNOWN | 13 | 137 | A |
| AW104146 | UNKNOWN | 12 | 357 | C |
| AW104149 | UNKNOWN | 15 | 84 | A |

TABLE 1-continued

| Genbank # | Region | # reps | Position | Unit sequence |
|---|---|---|---|---|
| AW104151 | UNKNOWN | 72 | 0 | T |
| AW104151 | UNKNOWN | 17 | 161 | G |
| AW104153 | UNKNOWN | 35 | 0 | T |
| AW104237 | UNKNOWN | 31 | 0 | T |
| AW104283 | UNKNOWN | 14 | 0 | T |
| AW104308 | UNKNOWN | 12 | 78 | A |
| AW104345 | UNKNOWN | 5 | 198 | CAAAA |
| AW104387 | UNKNOWN | 13 | 0 | T |
| AW104406 | UNKNOWN | 5.75 | 295 | TTTG |
| AW104412 | UNKNOWN | 15 | 0 | T |
| AW104500 | UNKNOWN | 4.5 | 11 | TTTA |
| AW104518 | UNKNOWN | 37 | 0 | T |
| AW104531 | UNKNOWN | 15 | 0 | T |
| AW104533 | UNKNOWN | 12 | 0 | T |
| AW104539 | UNKNOWN | 17 | 182 | A |
| AW104633 | UNKNOWN | 54 | 0 | T |
| AW104641 | UNKNOWN | 77 | 0 | T |
| AW104641 | UNKNOWN | 17 | 104 | A |
| AW104641 | UNKNOWN | 15 | 221 | G |
| AW104641 | UNKNOWN | 14 | 135 | G |
| AW104646 | UNKNOWN | 103 | 0 | T |
| AW104646 | UNKNOWN | 27 | 383 | C |
| AW104646 | UNKNOWN | 15 | 254 | C |
| AW104646 | UNKNOWN | 14 | 110 | A |
| AW104666 | UNKNOWN | 43 | 0 | T |
| AW104683 | UNKNOWN | 65 | 0 | T |
| AW104683 | UNKNOWN | 16 | 92 | C |
| AW104684 | UNKNOWN | 91 | 0 | T |
| AW104684 | UNKNOWN | 27 | 351 | C |
| AW104713 | UNKNOWN | 71 | 0 | T |
| AW104713 | UNKNOWN | 15 | 183 | C |
| AW104713 | UNKNOWN | 13 | 265 | A |
| AW104719 | UNKNOWN | 46 | 0 | T |
| AW104720 | UNKNOWN | 45 | 0 | T |
| AW104724 | UNKNOWN | 117 | 0 | T |
| AW104724 | UNKNOWN | 24 | 117 | A |
| AW104724 | UNKNOWN | 24 | 230 | C |
| AW104724 | UNKNOWN | 22 | 151 | G |
| AW104724 | UNKNOWN | 16 | 173 | C |
| AW104733 | UNKNOWN | 15 | 318 | A |
| AW104746 | UNKNOWN | 53 | 0 | T |
| AW104746 | UNKNOWN | 15 | 155 | G |
| AW104746 | UNKNOWN | 12 | 89 | A |
| AW104780 | UNKNOWN | 48 | 0 | T |
| AW104790 | UNKNOWN | 97 | 0 | T |
| AW104790 | UNKNOWN | 18 | 185 | A |
| AW104790 | UNKNOWN | 15 | 98 | C |
| AW104790 | UNKNOWN | 13 | 141 | G |
| AW104827 | UNKNOWN | 96 | 0 | T |
| AW104827 | UNKNOWN | 23 | 96 | A |
| AW104827 | UNKNOWN | 19 | 237 | C |
| AW104827 | UNKNOWN | 16 | 202 | G |
| AW104827 | UNKNOWN | 15 | 150 | G |
| AW104836 | UNKNOWN | 84 | 0 | T |
| AW104859 | UNKNOWN | 42 | 0 | T |
| AW104948 | UNKNOWN | 21 | 0 | T |
| AW105011 | UNKNOWN | 12 | 14 | T |
| AW105041 | UNKNOWN | 15 | 0 | T |
| AW105087 | UNKNOWN | 77 | 0 | T |
| AW105087 | UNKNOWN | 20 | 179 | C |
| AW105087 | UNKNOWN | 14 | 276 | A |
| AW105110 | UNKNOWN | 12 | 0 | T |
| AW105117 | UNKNOWN | 5.66 | 50 | AAC |
| AW105128 | UNKNOWN | 21 | 0 | T |
| AW105143 | UNKNOWN | 16 | 0 | T |
| AW105157 | UNKNOWN | 31 | 0 | T |
| AW105179 | UNKNOWN | 22 | 0 | T |
| AW105194 | UNKNOWN | 12 | 214 | T |
| AW105199 | UNKNOWN | 15 | 0 | T |
| AW105218 | UNKNOWN | 24 | 0 | T |
| AW105237 | UNKNOWN | 6.66 | 52 | GCC |
| AW105278 | UNKNOWN | 14 | 0 | T |
| AW105313 | UNKNOWN | 50 | 0 | T |
| AW105330 | UNKNOWN | 50 | 0 | T |
| AW105342 | UNKNOWN | 2.66 | 3 | TTTTTTTTGCAA (SEQ ID NO: 213) |
| AW105342 | UNKNOWN | 15 | 27 | T |
| AW105383 | UNKNOWN | 101 | 0 | T |

TABLE 1-continued

| Genbank # | Region | # reps | Position | Unit sequence |
|---|---|---|---|---|
| AW105383 | UNKNOWN | 26 | 333 | C |
| AW105383 | UNKNOWN | 18 | 110 | A |
| AW105383 | UNKNOWN | 12 | 141 | G |
| AW105412 | UNKNOWN | 75 | 0 | T |
| AW105412 | UNKNOWN | 19 | 390 | A |
| AW105412 | UNKNOWN | 15 | 170 | C |
| AW105412 | UNKNOWN | 15 | 285 | A |
| AW105421 | UNKNOWN | 57 | 0 | T |
| AW105429 | UNKNOWN | 92 | 0 | T |
| AW105429 | UNKNOWN | 28 | 406 | C |
| AW105429 | UNKNOWN | 17 | 277 | C |
| AW105429 | UNKNOWN | 14 | 186 | C |
| AW105429 | UNKNOWN | 14 | 305 | G |
| AW105429 | UNKNOWN | 13 | 143 | C |
| AW105431 | UNKNOWN | 94 | 0 | T |
| AW105431 | UNKNOWN | 15 | 312 | C |
| AW105431 | UNKNOWN | 12 | 148 | G |
| AW105441 | UNKNOWN | 13 | 0 | T |
| AW105446 | UNKNOWN | 39 | 0 | T |
| AW105446 | UNKNOWN | 24 | 281 | A |
| AW105448 | UNKNOWN | 42 | 0 | T |
| AW105455 | UNKNOWN | 76 | 0 | T |
| AW105459 | UNKNOWN | 64 | 0 | T |
| AW105459 | UNKNOWN | 12 | 179 | A |
| AW105460 | UNKNOWN | 74 | 0 | T |
| AW105460 | UNKNOWN | 16 | 369 | C |
| AW105460 | UNKNOWN | 13 | 229 | C |
| AW105464 | UNKNOWN | 87 | 0 | T |
| AW105464 | UNKNOWN | 13 | 364 | C |
| AW105464 | UNKNOWN | 12 | 351 | C |
| AW105474 | UNKNOWN | 45 | 0 | T |
| AW105503 | UNKNOWN | 17 | 0 | T |
| AW105503 | UNKNOWN | 14 | 305 | A |
| AW105512 | UNKNOWN | 21 | 0 | T |
| AW105568 | UNKNOWN | 3.5 | 28 | CTCTCC |
| AW105591 | UNKNOWN | 54 | 0 | T |
| AW105601 | UNKNOWN | 97 | 0 | T |
| AW105601 | UNKNOWN | 24 | 139 | G |
| AW105601 | UNKNOWN | 15 | 163 | C |
| AW105620 | UNKNOWN | 79 | 0 | T |
| AW105620 | UNKNOWN | 14 | 114 | G |
| AW105620 | UNKNOWN | 13 | 128 | A |
| AW105627 | UNKNOWN | 43 | 0 | T |
| AW105665 | UNKNOWN | 50 | 0 | T |
| AW105716 | UNKNOWN | 3.6 | 12 | TTTTA |
| AW105724 | UNKNOWN | 16 | 0 | T |
| AW117261 | UNKNOWN | 25 | 2 | T |
| AW117269 | UNKNOWN | 30 | 0 | T |
| AW117275 | UNKNOWN | 16 | 63 | T |
| AW117297 | UNKNOWN | 16 | 191 | A |
| AW117335 | UNKNOWN | 15 | 356 | T |
| AW117354 | UNKNOWN | 18 | 0 | T |
| AW117355 | UNKNOWN | 65 | 0 | T |
| AW117355 | UNKNOWN | 16 | 177 | C |
| AW117355 | UNKNOWN | 13 | 374 | A |
| AW117360 | UNKNOWN | 30 | 0 | T |
| AW117399 | UNKNOWN | 17 | 0 | T |
| AW117412 | UNKNOWN | 18 | 0 | T |
| AW117452 | UNKNOWN | 16 | 0 | T |
| AW117477 | UNKNOWN | 2.7 | 440 | TCCACGTTGCACTGGATGTTCTAGCCGGTTCTGA (SEQ ID NO: 214) |
| AW117487 | UNKNOWN | 6.25 | 24 | TTAT |
| AW117487 | UNKNOWN | 23 | 0 | T |
| AW117576 | UNKNOWN | 19 | 239 | A |
| AW117576 | UNKNOWN | 15 | 127 | T |
| AW117629 | UNKNOWN | 41 | 0 | T |
| AW117652 | UNKNOWN | 73 | 0 | T |
| AW117675 | UNKNOWN | 55 | 13 | T |
| AW117675 | UNKNOWN | 16 | 239 | G |
| AW117675 | UNKNOWN | 12 | 111 | G |
| AW117740 | UNKNOWN | 14 | 318 | A |
| AW117743 | UNKNOWN | 77 | 0 | T |
| AW117743 | UNKNOWN | 16 | 185 | C |
| AW117743 | UNKNOWN | 13 | 164 | A |
| AW117746 | UNKNOWN | 94 | 0 | T |
| AW117746 | UNKNOWN | 15 | 140 | C |
| AW117746 | UNKNOWN | 13 | 167 | G |

TABLE 1-continued

| Genbank # | Region | # reps | Position | Unit sequence |
|---|---|---|---|---|
| AW117779 | UNKNOWN | 77 | 0 | T |
| AW117779 | UNKNOWN | 15 | 258 | C |
| AW117803 | UNKNOWN | 28 | 0 | T |
| AW117843 | UNKNOWN | 52 | 0 | T |
| AW117846 | UNKNOWN | 43 | 0 | T |
| AW117848 | UNKNOWN | 22 | 107 | T |
| AW117855 | UNKNOWN | 43 | 0 | T |
| AW117855 | UNKNOWN | 12 | 108 | C |
| AW117903 | UNKNOWN | 88 | 0 | T |
| AW117903 | UNKNOWN | 14 | 409 | C |
| AW117903 | UNKNOWN | 12 | 338 | G |
| AW117907 | UNKNOWN | 88 | 0 | T |
| AW117907 | UNKNOWN | 22 | 153 | A |
| AW117907 | UNKNOWN | 19 | 88 | G |
| AW117907 | UNKNOWN | 14 | 108 | A |
| AW117907 | UNKNOWN | 13 | 361 | C |
| AW117914 | UNKNOWN | 29 | 0 | T |
| AW117919 | UNKNOWN | 76 | 0 | T |
| AW117919 | UNKNOWN | 16 | 97 | G |
| AW117919 | UNKNOWN | 15 | 189 | C |
| AW117926 | UNKNOWN | 76 | 0 | T |
| AW117926 | UNKNOWN | 17 | 348 | G |
| AW117926 | UNKNOWN | 15 | 250 | G |
| AW117926 | UNKNOWN | 12 | 228 | G |
| AW117938 | UNKNOWN | 68 | 0 | T |
| AW117938 | UNKNOWN | 20 | 221 | A |
| AW117938 | UNKNOWN | 16 | 126 | C |
| AW117972 | UNKNOWN | 30 | 0 | T |
| AW117997 | UNKNOWN | 76 | 0 | T |
| AW117997 | UNKNOWN | 17 | 351 | G |
| AW117997 | UNKNOWN | 15 | 128 | A |
| AW118001 | UNKNOWN | 54 | 0 | T |
| AW118010 | UNKNOWN | 74 | 0 | T |
| AW118010 | UNKNOWN | 19 | 167 | G |
| AW118010 | UNKNOWN | 17 | 80 | A |
| AW118042 | UNKNOWN | 42 | 0 | T |
| AW118066 | UNKNOWN | 40 | 0 | T |
| AW118096 | UNKNOWN | 12 | 147 | A |
| AW118097 | UNKNOWN | 21 | 184 | A |
| AW118101 | UNKNOWN | 6 | 311 | TGC |
| AW118101 | UNKNOWN | 31 | 0 | T |
| AW118108 | UNKNOWN | 20 | 0 | T |
| AW118147 | UNKNOWN | 6.5 | 223 | AT |
| AW118161 | UNKNOWN | 16 | 0 | T |
| AW118163 | UNKNOWN | 18 | 0 | T |
| AW118189 | UNKNOWN | 17 | 0 | T |
| AW118221 | UNKNOWN | 28 | 0 | T |
| AW118248 | UNKNOWN | 3.5 | 143 | AAAAAT |
| AW118252 | UNKNOWN | 35 | 0 | T |
| AW118252 | UNKNOWN | 13 | 135 | G |
| AW118279 | UNKNOWN | 50 | 0 | T |
| AW118279 | UNKNOWN | 12 | 176 | A |
| AW118311 | UNKNOWN | 53 | 13 | T |
| AW118311 | UNKNOWN | 12 | 222 | G |
| AW118332 | UNKNOWN | 95 | 0 | T |
| AW118332 | UNKNOWN | 25 | 231 | G |
| AW118333 | UNKNOWN | 59 | 0 | T |
| AW118353 | UNKNOWN | 56 | 0 | T |
| AW118359 | UNKNOWN | 35 | 0 | T |
| AW118373 | UNKNOWN | 87 | 0 | T |
| AW118382 | UNKNOWN | 100 | 0 | T |
| AW118398 | UNKNOWN | 103 | 0 | T |
| AW118398 | UNKNOWN | 21 | 133 | A |
| AW118398 | UNKNOWN | 18 | 171 | C |
| AW118414 | UNKNOWN | 74 | 0 | T |
| AW118414 | UNKNOWN | 14 | 209 | G |
| AW118433 | UNKNOWN | 2.81 | 28 | TTTTTTTTTNT (SEQ ID NO: 215) |
| AW118433 | UNKNOWN | 2.9 | 18 | TTTTTTTTN (SEQ ID NO: 216) |
| AW118433 | UNKNOWN | 30 | 76 | T |
| AW118433 | UNKNOWN | 26 | 49 | T |
| AW118433 | UNKNOWN | 12 | 15 | T |
| AW118448 | UNKNOWN | 52 | 0 | T |
| AW118457 | UNKNOWN | 81 | 0 | T |
| AW118457 | UNKNOWN | 15 | 212 | A |
| AW118457 | UNKNOWN | 13 | 93 | A |
| AW118459 | UNKNOWN | 35 | 0 | T |
| AW118459 | UNKNOWN | 20 | 180 | A |

TABLE 1-continued

| Genbank # | Region | # reps | Position | Unit sequence |
|---|---|---|---|---|
| AW118475 | UNKNOWN | 55 | 0 | T |
| AW118475 | UNKNOWN | 14 | 155 | A |
| AW118477 | UNKNOWN | 83 | 0 | T |
| AW118477 | UNKNOWN | 14 | 87 | C |
| AW118477 | UNKNOWN | 14 | 261 | G |
| AW118477 | UNKNOWN | 12 | 126 | A |
| AW118496 | UNKNOWN | 94 | 0 | T |
| AW118496 | UNKNOWN | 16 | 213 | C |
| AW118496 | UNKNOWN | 15 | 262 | A |
| AW118496 | UNKNOWN | 12 | 245 | A |
| AW118508 | UNKNOWN | 54 | 0 | T |
| AW118512 | UNKNOWN | 114 | 0 | T |
| AW118512 | UNKNOWN | 19 | 207 | C |
| AW118512 | UNKNOWN | 12 | 226 | A |
| AW118518 | UNKNOWN | 89 | 0 | T |
| AW118518 | UNKNOWN | 13 | 151 | C |
| AW118518 | UNKNOWN | 12 | 181 | A |
| AW118552 | UNKNOWN | 11.5 | 186 | CA |
| AW118552 | UNKNOWN | 7 | 212 | GA |
| AW118552 | UNKNOWN | 22 | 0 | T |
| AW118553 | UNKNOWN | 47 | 0 | T |
| AW118553 | UNKNOWN | 16 | 299 | G |
| AW118553 | UNKNOWN | 13 | 85 | A |
| AW118554 | UNKNOWN | 36 | 0 | T |
| AW118554 | UNKNOWN | 12 | 60 | A |
| AW118557 | UNKNOWN | 120 | 0 | T |
| AW118557 | UNKNOWN | 25 | 337 | C |
| AW118557 | UNKNOWN | 18 | 160 | G |
| AW118557 | UNKNOWN | 16 | 227 | C |
| AW118557 | UNKNOWN | 13 | 278 | A |
| AW118569 | UNKNOWN | 12 | 0 | T |
| AW118624 | UNKNOWN | 14 | 0 | T |
| AW118646 | UNKNOWN | 16 | 0 | T |
| AW118717 | UNKNOWN | 15 | 0 | T |
| AW118756 | UNKNOWN | 23 | 37 | T |
| AW118815 | UNKNOWN | 3.8 | 146 | AAAAC |
| AW118847 | UNKNOWN | 12 | 0 | T |
| AW118861 | UNKNOWN | 15 | 295 | A |
| AW118862 | UNKNOWN | 26 | 462 | A |
| AW118904 | UNKNOWN | 22 | 296 | T |
| AW118924 | UNKNOWN | 16 | 0 | T |
| AW118972 | UNKNOWN | 12 | 0 | T |
| AW119006 | UNKNOWN | 5.5 | 305 | AAAC |
| AW119031 | UNKNOWN | 3.8 | 124 | AAAAC |
| AW119031 | UNKNOWN | 20 | 90 | T |
| AW119031 | UNKNOWN | 14 | 0 | T |
| AW119051 | UNKNOWN | 18 | 0 | T |
| AW119129 | UNKNOWN | 13.5 | 263 | AT |
| AW119129 | UNKNOWN | 8.5 | 229 | AC |
| AW119129 | UNKNOWN | 8.5 | 245 | AT |
| AW128834 | UNKNOWN | 61 | 1 | T |
| AW128834 | UNKNOWN | 13 | 62 | A |
| AW128834 | UNKNOWN | 12 | 236 | G |
| AW128841 | UNKNOWN | 80 | 0 | T |
| AW128841 | UNKNOWN | 23 | 190 | A |
| AW128855 | UNKNOWN | 54 | 0 | T |
| AW128866 | UNKNOWN | 16 | 0 | T |
| AW128867 | UNKNOWN | 15 | 0 | T |
| AW128878 | UNKNOWN | 28 | 0 | T |
| AW128880 | UNKNOWN | 15 | 0 | T |
| AW128895 | UNKNOWN | 60 | 2 | T |
| AW128901 | UNKNOWN | 3.8 | 154 | TTCTT |
| AW128901 | UNKNOWN | 15 | 0 | T |
| AW128931 | UNKNOWN | 61 | 0 | T |
| AW128931 | UNKNOWN | 15 | 118 | C |
| AW128945 | UNKNOWN | 68 | 0 | T |
| AW128945 | UNKNOWN | 25 | 171 | G |
| AW128971 | UNKNOWN | 48 | 0 | T |
| AW128971 | UNKNOWN | 13 | 76 | C |
| AW128983 | UNKNOWN | 75 | 0 | T |
| AW128983 | UNKNOWN | 13 | 235 | G |
| AW128983 | UNKNOWN | 12 | 181 | G |
| AW129019 | UNKNOWN | 41 | 0 | T |
| AW129030 | UNKNOWN | 16 | 0 | T |
| AW129036 | UNKNOWN | 86 | 0 | T |
| AW129036 | UNKNOWN | 19 | 325 | G |
| AW129036 | UNKNOWN | 18 | 194 | A |

TABLE 1-continued

| Genbank # | Region | # reps | Position | Unit sequence |
|---|---|---|---|---|
| AW129036 | UNKNOWN | 13 | 387 | C |
| AW129057 | UNKNOWN | 57 | 0 | T |
| AW129057 | UNKNOWN | 15 | 180 | A |
| AW129080 | UNKNOWN | 80 | 0 | T |
| AW129080 | UNKNOWN | 17 | 149 | C |
| AW129080 | UNKNOWN | 12 | 177 | G |
| AW129093 | UNKNOWN | 2.73 | 367 | ATATATATATATATTATGG (SEQ ID NO: 217) |
| AW129093 | UNKNOWN | 8 | 365 | AT |
| AW129106 | UNKNOWN | 94 | 6 | T |
| AW129106 | UNKNOWN | 13 | 164 | A |
| AW129113 | UNKNOWN | 35 | 0 | T |
| AW129117 | UNKNOWN | 62 | 0 | T |
| AW129133 | UNKNOWN | 15 | 0 | T |
| AW129140 | UNKNOWN | 57 | 0 | T |
| AW129140 | UNKNOWN | 17 | 119 | G |
| AW129140 | UNKNOWN | 14 | 160 | A |
| AW129142 | UNKNOWN | 57 | 0 | T |
| AW129142 | UNKNOWN | 17 | 119 | G |
| AW129142 | UNKNOWN | 14 | 160 | A |
| AW129143 | UNKNOWN | 15 | 0 | T |
| AW129148 | UNKNOWN | 48 | 0 | T |
| AW129160 | UNKNOWN | 49 | 0 | T |
| AW129170 | UNKNOWN | 108 | 0 | T |
| AW129170 | UNKNOWN | 17 | 243 | C |
| AW129170 | UNKNOWN | 14 | 184 | A |
| AW129171 | UNKNOWN | 112 | 0 | T |
| AW129171 | UNKNOWN | 25 | 243 | C |
| AW129171 | UNKNOWN | 16 | 112 | C |
| AW129171 | UNKNOWN | 12 | 193 | A |
| AW129200 | UNKNOWN | 49 | 0 | T |
| AW129202 | UNKNOWN | 114 | 0 | T |
| AW129202 | UNKNOWN | 16 | 223 | C |
| AW129206 | UNKNOWN | 39 | 0 | T |
| AW129217 | UNKNOWN | 42 | 0 | T |
| AW129230 | UNKNOWN | 83 | 0 | T |
| AW129230 | UNKNOWN | 15 | 146 | A |
| AW129231 | UNKNOWN | 29 | 0 | T |
| AW129264 | UNKNOWN | 63 | 0 | T |
| AW129269 | UNKNOWN | 60 | 0 | T |
| AW129271 | UNKNOWN | 76 | 0 | T |
| AW129271 | UNKNOWN | 16 | 93 | A |
| AW129271 | UNKNOWN | 12 | 109 | C |
| AW129284 | UNKNOWN | 8.5 | 332 | TC |
| AW129284 | UNKNOWN | 20 | 0 | T |
| AW129306 | UNKNOWN | 6.66 | 287 | TCC |
| AW129306 | UNKNOWN | 15 | 0 | T |
| AW129359 | UNKNOWN | 16 | 0 | T |
| AW129365 | UNKNOWN | 31 | 0 | T |
| AW129393 | UNKNOWN | 39 | 0 | T |
| AW129433 | UNKNOWN | 46 | 0 | T |
| AW129433 | UNKNOWN | 12 | 84 | A |
| AW129434 | UNKNOWN | 24 | 0 | T |
| AW129456 | UNKNOWN | 57 | 0 | T |
| AW129518 | UNKNOWN | 31 | 0 | T |
| AW129541 | UNKNOWN | 41 | 0 | T |
| AW129592 | UNKNOWN | 56 | 0 | T |
| AW129597 | UNKNOWN | 64 | 0 | T |
| AW129597 | UNKNOWN | 13 | 170 | C |
| AW129597 | UNKNOWN | 12 | 92 | A |
| AW129604 | UNKNOWN | 49 | 0 | T |
| AW129616 | UNKNOWN | 67 | 0 | T |
| AW129616 | UNKNOWN | 14 | 267 | A |
| AW129639 | UNKNOWN | 31 | 0 | T |
| AW129659 | UNKNOWN | 114 | 0 | T |
| AW129659 | UNKNOWN | 24 | 263 | C |
| AW129659 | UNKNOWN | 14 | 153 | A |
| AW129659 | UNKNOWN | 13 | 187 | C |
| AW129659 | UNKNOWN | 12 | 114 | A |
| AW129659 | UNKNOWN | 12 | 293 | G |
| AW129661 | UNKNOWN | 15 | 0 | T |
| AW129676 | UNKNOWN | 36 | 0 | T |
| AW129678 | UNKNOWN | 42 | 0 | T |
| AW129686 | UNKNOWN | 15 | 8 | T |
| AW129689 | UNKNOWN | 112 | 0 | T |
| AW129689 | UNKNOWN | 15 | 122 | A |
| AW129689 | UNKNOWN | 12 | 153 | G |
| AW129689 | UNKNOWN | 12 | 315 | C |

TABLE 1-continued

| Genbank # | Region | # reps | Position | Unit sequence |
|---|---|---|---|---|
| AW129698 | UNKNOWN | 103 | 0 | T |
| AW129698 | UNKNOWN | 26 | 189 | A |
| AW129698 | UNKNOWN | 20 | 152 | C |
| AW129698 | UNKNOWN | 14 | 175 | G |
| AW129717 | UNKNOWN | 59 | 0 | T |
| AW129717 | UNKNOWN | 13 | 136 | G |
| AW129722 | UNKNOWN | 92 | 0 | T |
| AW129722 | UNKNOWN | 23 | 92 | A |
| AW129722 | UNKNOWN | 18 | 387 | C |
| AW129722 | UNKNOWN | 17 | 148 | G |
| AW129722 | UNKNOWN | 17 | 248 | C |
| AW129722 | UNKNOWN | 12 | 183 | C |
| AW129731 | UNKNOWN | 69 | 0 | T |
| AW129731 | UNKNOWN | 12 | 117 | A |
| AW129740 | UNKNOWN | 87 | 0 | T |
| AW129745 | UNKNOWN | 43 | 0 | T |
| AW129758 | UNKNOWN | 16 | 0 | T |
| AW129781 | UNKNOWN | 76 | 0 | T |
| AW129781 | UNKNOWN | 12 | 332 | A |
| AW129916 | UNKNOWN | 92 | 0 | T |
| AW129916 | UNKNOWN | 13 | 98 | A |
| AW129918 | UNKNOWN | 70 | 0 | T |
| AW129918 | UNKNOWN | 20 | 125 | C |
| AW129918 | UNKNOWN | 14 | 281 | G |
| AW129944 | UNKNOWN | 48 | 0 | T |
| AW129944 | UNKNOWN | 16 | 155 | C |
| AW129947 | UNKNOWN | 47 | 0 | T |
| AW129947 | UNKNOWN | 17 | 322 | A |
| AW129966 | UNKNOWN | 60 | 0 | T |
| AW129968 | UNKNOWN | 49 | 0 | T |
| AW129979 | UNKNOWN | 54 | 0 | T |
| AW129979 | UNKNOWN | 20 | 206 | A |
| AW129979 | UNKNOWN | 14 | 245 | G |
| AW129993 | UNKNOWN | 56 | 0 | T |
| AW130038 | UNKNOWN | 21 | 0 | T |
| AW130064 | UNKNOWN | 37 | 0 | T |
| AW130064 | UNKNOWN | 29 | 109 | A |
| AW130068 | UNKNOWN | 108 | 2 | T |
| AW130068 | UNKNOWN | 26 | 402 | C |
| AW130068 | UNKNOWN | 13 | 157 | A |
| AW130068 | UNKNOWN | 13 | 271 | C |
| AW130088 | UNKNOWN | 48 | 0 | T |
| AW130088 | UNKNOWN | 12 | 163 | G |
| AW130104 | UNKNOWN | 72 | 0 | T |
| AW130104 | UNKNOWN | 13 | 209 | G |
| AW130129 | UNKNOWN | 50 | 0 | T |
| AW130134 | UNKNOWN | 81 | 0 | T |
| AW130134 | UNKNOWN | 23 | 87 | A |
| AW130134 | UNKNOWN | 14 | 279 | C |
| AW130155 | UNKNOWN | 58 | 0 | T |
| AW130155 | UNKNOWN | 14 | 94 | A |
| AW130155 | UNKNOWN | 12 | 82 | C |
| AW130165 | UNKNOWN | 37 | 0 | T |
| AW130165 | UNKNOWN | 12 | 222 | G |
| AW130168 | UNKNOWN | 53 | 0 | T |
| AW130187 | UNKNOWN | 39 | 0 | T |
| AW130224 | UNKNOWN | 43 | 0 | T |
| AW130224 | UNKNOWN | 15 | 152 | A |
| AW130257 | UNKNOWN | 15 | 0 | T |
| AW130307 | UNKNOWN | 68 | 0 | T |
| AW130307 | UNKNOWN | 16 | 307 | C |
| AW130307 | UNKNOWN | 15 | 331 | G |
| AW130309 | UNKNOWN | 75 | 0 | T |
| AW130309 | UNKNOWN | 14 | 405 | C |
| AW130309 | UNKNOWN | 12 | 127 | G |
| AW130356 | UNKNOWN | 69 | 0 | T |
| AW130356 | UNKNOWN | 15 | 102 | G |
| AW130362 | UNKNOWN | 51 | 0 | T |
| AW130362 | UNKNOWN | 13 | 218 | G |
| AW130398 | UNKNOWN | 64 | 0 | T |
| AW130403 | UNKNOWN | 64 | 0 | T |
| AW130403 | UNKNOWN | 14 | 134 | C |
| AW130421 | UNKNOWN | 40 | 0 | T |
| AW130421 | UNKNOWN | 13 | 107 | A |
| AW130428 | UNKNOWN | 10 | 16 | GT |
| AW130428 | UNKNOWN | 14 | 0 | T |
| AW130430 | UNKNOWN | 61 | 0 | T |

TABLE 1-continued

| Genbank # | Region | # reps | Position | Unit sequence |
|---|---|---|---|---|
| AW130430 | UNKNOWN | 22 | 206 | A |
| AW130430 | UNKNOWN | 13 | 145 | A |
| AW130430 | UNKNOWN | 12 | 127 | C |
| AW130439 | UNKNOWN | 24 | 0 | T |
| AW130463 | UNKNOWN | 66 | 0 | T |
| AW130463 | UNKNOWN | 21 | 166 | C |
| AW130525 | UNKNOWN | 37 | 0 | T |
| AW130533 | UNKNOWN | 27 | 0 | T |
| AW130534 | UNKNOWN | 85 | 0 | T |
| AW130534 | UNKNOWN | 14 | 141 | G |
| AW130534 | UNKNOWN | 14 | 322 | A |
| AW130584 | UNKNOWN | 92 | 0 | T |
| AW130584 | UNKNOWN | 21 | 305 | A |
| AW130584 | UNKNOWN | 15 | 199 | A |
| AW130584 | UNKNOWN | 13 | 218 | C |
| AW130584 | UNKNOWN | 12 | 169 | G |
| AW130585 | UNKNOWN | 29 | 0 | T |
| AW130585 | UNKNOWN | 15 | 148 | A |
| AW130605 | UNKNOWN | 45 | 0 | T |
| AW130623 | UNKNOWN | 17 | 0 | T |
| AW130635 | UNKNOWN | 23 | 0 | T |
| AW130648 | UNKNOWN | 14 | 0 | T |
| AW130681 | UNKNOWN | 70 | 0 | T |
| AW130681 | UNKNOWN | 14 | 84 | A |
| AW130689 | UNKNOWN | 70 | 0 | T |
| AW130689 | UNKNOWN | 16 | 378 | C |
| AW130689 | UNKNOWN | 13 | 85 | A |
| AW130689 | UNKNOWN | 12 | 195 | C |
| AW130695 | UNKNOWN | 33 | 0 | T |
| AW130695 | UNKNOWN | 12 | 331 | A |
| AW130697 | UNKNOWN | 6.5 | 104 | AT |
| AW130697 | UNKNOWN | 17 | 0 | T |
| AW130711 | UNKNOWN | 62 | 0 | T |
| AW130711 | UNKNOWN | 18 | 253 | G |
| AW130776 | UNKNOWN | 102 | 0 | T |
| AW130776 | UNKNOWN | 17 | 149 | A |
| AW130776 | UNKNOWN | 17 | 310 | C |
| AW130776 | UNKNOWN | 12 | 108 | A |
| AW130776 | UNKNOWN | 12 | 374 | G |
| AW130785 | UNKNOWN | 82 | 0 | T |
| AW130785 | UNKNOWN | 21 | 315 | C |
| AW130789 | UNKNOWN | 51 | 0 | T |
| AW130804 | UNKNOWN | 60 | 0 | T |
| AW130804 | UNKNOWN | 13 | 177 | G |
| AW130829 | UNKNOWN | 63 | 0 | T |
| AW130829 | UNKNOWN | 14 | 356 | C |
| AW130829 | UNKNOWN | 12 | 157 | A |
| AW130849 | UNKNOWN | 85 | 0 | T |
| AW130849 | UNKNOWN | 12 | 558 | A |
| AW130856 | UNKNOWN | 24 | 0 | T |
| AW130863 | UNKNOWN | 77 | 0 | T |
| AW130882 | UNKNOWN | 104 | 0 | T |
| AW130882 | UNKNOWN | 20 | 315 | C |
| AW130882 | UNKNOWN | 19 | 296 | A |
| AW130882 | UNKNOWN | 14 | 111 | G |
| AW130882 | UNKNOWN | 13 | 150 | A |
| AW130890 | UNKNOWN | 5 | 346 | AAAT |
| AW130920 | UNKNOWN | 50 | 0 | T |
| AW130922 | UNKNOWN | 103 | 0 | T |
| AW130922 | UNKNOWN | 14 | 252 | C |
| AW130922 | UNKNOWN | 12 | 131 | A |
| AW130922 | UNKNOWN | 12 | 310 | G |
| AW130930 | UNKNOWN | 79 | 0 | T |
| AW130930 | UNKNOWN | 14 | 127 | C |
| AW130930 | UNKNOWN | 13 | 161 | G |
| AW130938 | UNKNOWN | 15 | 200 | A |
| AW130949 | UNKNOWN | 91 | 0 | T |
| AW130992 | UNKNOWN | 56 | 0 | T |
| AW130994 | UNKNOWN | 44 | 0 | T |
| AW131018 | UNKNOWN | 73 | 0 | T |
| AW131018 | UNKNOWN | 13 | 275 | A |
| AW131024 | UNKNOWN | 73 | 0 | T |
| AW131024 | UNKNOWN | 13 | 278 | A |
| AW131026 | UNKNOWN | 40 | 0 | T |
| AW131026 | UNKNOWN | 12 | 134 | A |
| AW131047 | UNKNOWN | 67 | 0 | T |
| AW131047 | UNKNOWN | 16 | 112 | A |

TABLE 1-continued

| Genbank # | Region | # reps | Position | Unit sequence |
|---|---|---|---|---|
| AW131047 | UNKNOWN | 15 | 289 | C |
| AW131047 | UNKNOWN | 14 | 83 | C |
| AW131047 | UNKNOWN | 13 | 342 | G |
| AW131065 | UNKNOWN | 72 | 0 | T |
| AW131065 | UNKNOWN | 15 | 130 | C |
| AW131112 | UNKNOWN | 59 | 0 | T |
| AW131112 | UNKNOWN | 15 | 116 | C |
| AW131119 | UNKNOWN | 60 | 0 | T |
| AW131119 | UNKNOWN | 13 | 197 | G |
| AW131131 | UNKNOWN | 23 | 0 | T |
| AW131139 | UNKNOWN | 70 | 0 | T |
| AW131146 | UNKNOWN | 13 | 0 | T |
| AW131149 | UNKNOWN | 34 | 0 | T |
| AW131149 | UNKNOWN | 18 | 201 | A |
| AW131165 | UNKNOWN | 71 | 0 | T |
| AW131165 | UNKNOWN | 17 | 172 | C |
| AW131211 | UNKNOWN | 34 | 0 | T |
| AW131211 | UNKNOWN | 15 | 166 | C |
| AW131217 | UNKNOWN | 15 | 0 | T |
| AW131277 | UNKNOWN | 16 | 0 | T |
| AW131280 | UNKNOWN | 28 | 0 | T |
| AW131281 | UNKNOWN | 35 | 0 | T |
| AW131282 | UNKNOWN | 103 | 0 | T |
| AW131282 | UNKNOWN | 18 | 125 | A |
| AW131282 | UNKNOWN | 18 | 166 | C |
| AW131282 | UNKNOWN | 15 | 349 | G |
| AW131283 | UNKNOWN | 86 | 0 | T |
| AW131283 | UNKNOWN | 18 | 185 | A |
| AW131283 | UNKNOWN | 17 | 125 | A |
| AW131283 | UNKNOWN | 13 | 160 | C |
| AW131283 | UNKNOWN | 12 | 99 | A |
| AW131283 | UNKNOWN | 12 | 203 | G |
| AW131288 | UNKNOWN | 86 | 0 | T |
| AW131288 | UNKNOWN | 18 | 160 | G |
| AW131288 | UNKNOWN | 18 | 251 | C |
| AW131288 | UNKNOWN | 16 | 88 | C |
| AW131288 | UNKNOWN | 16 | 121 | G |
| AW131292 | UNKNOWN | 42 | 0 | T |
| AW131292 | UNKNOWN | 19 | 188 | G |
| AW131292 | UNKNOWN | 18 | 133 | C |
| AW131294 | UNKNOWN | 82 | 0 | T |
| AW131294 | UNKNOWN | 18 | 159 | A |
| AW131294 | UNKNOWN | 14 | 82 | A |
| AW131308 | UNKNOWN | 82 | 0 | T |
| AW131308 | UNKNOWN | 12 | 127 | A |
| AW131309 | UNKNOWN | 47 | 0 | T |
| AW131331 | UNKNOWN | 87 | 0 | T |
| AW131331 | UNKNOWN | 18 | 218 | G |
| AW131360 | UNKNOWN | 3.5 | 338 | AATATATA |
| AW131369 | UNKNOWN | 19 | 0 | T |
| AW131376 | UNKNOWN | 31 | 0 | T |
| AW131394 | UNKNOWN | 13 | 305 | A |
| AW131402 | UNKNOWN | 66 | 0 | T |
| AW131428 | UNKNOWN | 105 | 0 | T |
| AW131428 | UNKNOWN | 18 | 288 | G |
| AW131428 | UNKNOWN | 17 | 237 | G |
| AW131428 | UNKNOWN | 13 | 146 | C |
| AW131438 | UNKNOWN | 13 | 184 | T |
| AW131450 | UNKNOWN | 13 | 0 | T |
| AW131457 | UNKNOWN | 9 | 0 | ATTT |
| AW131600 | UNKNOWN | 27 | 0 | T |
| AW131743 | UNKNOWN | 14 | 0 | T |
| AW131750 | UNKNOWN | 32 | 0 | T |
| AW131888 | UNKNOWN | 8.66 | 48 | CAG |
| AW131888 | UNKNOWN | 5.66 | 72 | CAA |
| AW131912 | UNKNOWN | 16 | 0 | T |
| AW131930 | UNKNOWN | 73 | 0 | T |
| AW131930 | UNKNOWN | 15 | 398 | G |
| AW131930 | UNKNOWN | 14 | 186 | G |
| AW131952 | UNKNOWN | 73 | 0 | T |
| AW131954 | UNKNOWN | 112 | 0 | T |
| AW131954 | UNKNOWN | 16 | 253 | A |
| AW131954 | UNKNOWN | 15 | 151 | G |
| AW131954 | UNKNOWN | 14 | 215 | A |
| AW131954 | UNKNOWN | 12 | 112 | G |
| AW131969 | UNKNOWN | 38 | 0 | T |
| AW131989 | UNKNOWN | 90 | 0 | T |

TABLE 1-continued

| Genbank # | Region | # reps | Position | Unit sequence |
|---|---|---|---|---|
| AW131989 | UNKNOWN | 13 | 299 | G |
| AW131994 | UNKNOWN | 48 | 0 | T |
| AW131994 | UNKNOWN | 17 | 87 | A |
| AW131999 | UNKNOWN | 70 | 0 | T |
| AW131999 | UNKNOWN | 13 | 152 | C |
| AW132001 | UNKNOWN | 97 | 0 | T |
| AW132001 | UNKNOWN | 13 | 127 | A |
| AW132003 | UNKNOWN | 42 | 0 | T |
| AW132034 | UNKNOWN | 109 | 0 | T |
| AW132034 | UNKNOWN | 19 | 224 | G |
| AW132039 | UNKNOWN | 56 | 0 | T |
| AW132039 | UNKNOWN | 12 | 173 | C |
| AW132056 | UNKNOWN | 105 | 0 | T |
| AW132056 | UNKNOWN | 17 | 151 | G |
| AW132056 | UNKNOWN | 16 | 195 | C |
| AW132056 | UNKNOWN | 12 | 139 | C |
| AW132061 | UNKNOWN | 69 | 0 | T |
| AW132071 | UNKNOWN | 65 | 0 | T |
| AW132071 | UNKNOWN | 12 | 261 | C |
| AW132096 | UNKNOWN | 15 | 233 | T |
| AW132096 | UNKNOWN | 14 | 0 | T |
| AW132104 | UNKNOWN | 70 | 0 | T |
| AW132104 | UNKNOWN | 26 | 268 | A |
| AW132104 | UNKNOWN | 15 | 123 | C |
| AW132115 | UNKNOWN | 52 | 0 | T |
| AW132148 | UNKNOWN | 6.33 | 15 | TTA |
| AW132153 | UNKNOWN | 40 | 0 | T |
| AW134485 | UNKNOWN | 17 | 0 | T |
| AW134492 | UNKNOWN | 17 | 0 | T |
| AW134504 | UNKNOWN | 17 | 0 | T |
| AW134510 | UNKNOWN | 17 | 0 | T |
| AW134523 | UNKNOWN | 17 | 0 | T |
| AW134536 | UNKNOWN | 17 | 0 | T |
| AW134538 | UNKNOWN | 17 | 0 | T |
| AW134542 | UNKNOWN | 15 | 0 | T |
| AW134548 | UNKNOWN | 14 | 0 | T |
| AW134551 | UNKNOWN | 15 | 0 | T |
| AW134584 | UNKNOWN | 15 | 2 | T |
| AW134608 | UNKNOWN | 17 | 0 | T |
| AW134613 | UNKNOWN | 6.5 | 351 | TA |
| AW134613 | UNKNOWN | 17 | 0 | T |
| AW134632 | UNKNOWN | 17 | 0 | T |
| AW134636 | UNKNOWN | 17 | 0 | T |
| AW134645 | UNKNOWN | 17 | 0 | T |
| AW134664 | UNKNOWN | 17 | 0 | T |
| AW134677 | UNKNOWN | 17 | 0 | T |
| AW134679 | UNKNOWN | 17 | 0 | T |
| AW134693 | UNKNOWN | 17 | 0 | T |
| AW134701 | UNKNOWN | 12 | 0 | T |
| AW134708 | UNKNOWN | 4.75 | 351 | TTTG |
| AW134708 | UNKNOWN | 17 | 0 | T |
| AW134719 | UNKNOWN | 17 | 0 | T |
| AW134726 | UNKNOWN | 15 | 0 | T |
| AW134729 | UNKNOWN | 17 | 0 | T |
| AW134761 | UNKNOWN | 12 | 0 | T |
| AW134791 | UNKNOWN | 12 | 0 | T |
| AW134792 | UNKNOWN | 17.5 | 572 | AT |
| AW134792 | UNKNOWN | 17 | 0 | T |
| AW134795 | UNKNOWN | 17 | 0 | T |
| AW134812 | UNKNOWN | 17 | 0 | T |
| AW134818 | UNKNOWN | 15 | 0 | T |
| AW134822 | UNKNOWN | 15 | 0 | T |
| AW134825 | UNKNOWN | 17 | 0 | T |
| AW134826 | UNKNOWN | 17 | 0 | T |
| AW134829 | UNKNOWN | 17 | 0 | T |
| AW134832 | UNKNOWN | 7.5 | 331 | CA |
| AW134832 | UNKNOWN | 17 | 0 | T |
| AW134835 | UNKNOWN | 15 | 0 | T |
| AW134837 | UNKNOWN | 6 | 176 | GAG |
| AW134837 | UNKNOWN | 17 | 0 | T |
| AW134839 | UNKNOWN | 15 | 0 | T |
| AW134844 | UNKNOWN | 17 | 0 | T |
| AW134862 | UNKNOWN | 17 | 0 | T |
| AW134877 | UNKNOWN | 17 | 0 | T |
| AW134878 | UNKNOWN | 17 | 0 | T |
| AW134949 | UNKNOWN | 17 | 0 | T |
| AW134977 | UNKNOWN | 13 | 0 | T |

TABLE 1-continued

| Genbank # | Region | # reps | Position | Unit sequence |
|---|---|---|---|---|
| AW134979 | UNKNOWN | 17 | 0 | T |
| AW134980 | UNKNOWN | 17 | 0 | T |
| AW134981 | UNKNOWN | 14 | 0 | T |
| AW134984 | UNKNOWN | 17 | 0 | T |
| AW134993 | UNKNOWN | 17 | 0 | T |
| AW134996 | UNKNOWN | 17 | 0 | T |
| AW134997 | UNKNOWN | 17 | 0 | T |
| AW135000 | UNKNOWN | 16 | 0 | T |
| AW135002 | UNKNOWN | 17 | 0 | T |
| AW135003 | UNKNOWN | 17 | 0 | T |
| AW135015 | UNKNOWN | 15 | 0 | T |
| AW135016 | UNKNOWN | 17 | 0 | T |
| AW135017 | UNKNOWN | 17 | 0 | T |
| AW135021 | UNKNOWN | 17 | 0 | T |
| AW135022 | UNKNOWN | 14 | 0 | T |
| AW135024 | UNKNOWN | 13 | 0 | T |
| AW135030 | UNKNOWN | 17 | 0 | T |
| AW135036 | UNKNOWN | 15 | 0 | T |
| AW135045 | UNKNOWN | 17 | 0 | T |
| AW135056 | UNKNOWN | 17 | 0 | T |
| AW135066 | UNKNOWN | 17 | 0 | T |
| AW135067 | UNKNOWN | 7.75 | 208 | TCAT |
| AW135067 | UNKNOWN | 17 | 0 | T |
| AW135070 | UNKNOWN | 14 | 0 | T |
| AW135173 | UNKNOWN | 17 | 0 | T |
| AW135226 | UNKNOWN | 13 | 4 | T |
| AW135241 | UNKNOWN | 17 | 0 | T |
| AW135243 | UNKNOWN | 7 | 18 | GA |
| AW135243 | UNKNOWN | 17 | 0 | T |
| AW135255 | UNKNOWN | 17 | 0 | T |
| AW135259 | UNKNOWN | 17 | 0 | T |
| AW135282 | UNKNOWN | 6.75 | 153 | TTTA |
| AW135282 | UNKNOWN | 17 | 0 | T |
| AW135297 | UNKNOWN | 15 | 0 | T |
| AW135306 | UNKNOWN | 5.66 | 117 | AAT |
| AW135306 | UNKNOWN | 16 | 0 | T |
| AW135310 | UNKNOWN | 17 | 0 | T |
| AW135314 | UNKNOWN | 17 | 0 | T |
| AW135322 | UNKNOWN | 17 | 0 | T |
| AW135323 | UNKNOWN | 17 | 0 | T |
| AW135324 | UNKNOWN | 17 | 0 | T |
| AW135326 | UNKNOWN | 17 | 0 | T |
| AW135330 | UNKNOWN | 17 | 0 | T |
| AW135336 | UNKNOWN | 17 | 0 | T |
| AW135348 | UNKNOWN | 17 | 0 | T |
| AW135359 | UNKNOWN | 17 | 0 | T |
| AW135360 | UNKNOWN | 17 | 0 | T |
| AW135366 | UNKNOWN | 17 | 0 | T |
| AW135371 | UNKNOWN | 17 | 0 | T |
| AW135374 | UNKNOWN | 17 | 0 | T |
| AW135375 | UNKNOWN | 15 | 0 | T |
| AW135401 | UNKNOWN | 17 | 0 | T |
| AW135402 | UNKNOWN | 17 | 0 | T |
| AW135404 | UNKNOWN | 17 | 0 | T |
| AW135405 | UNKNOWN | 17 | 0 | T |
| AW135410 | UNKNOWN | 17 | 0 | T |
| AW135412 | UNKNOWN | 17 | 0 | T |
| AW135453 | UNKNOWN | 15 | 0 | T |
| AW135478 | UNKNOWN | 15 | 0 | T |
| AW135481 | UNKNOWN | 17 | 0 | T |
| AW135492 | UNKNOWN | 17 | 0 | T |
| AW135502 | UNKNOWN | 17 | 0 | T |
| AW135543 | UNKNOWN | 15 | 0 | T |
| AW135551 | UNKNOWN | 15 | 0 | T |
| AW135554 | UNKNOWN | 17 | 0 | T |
| AW135555 | UNKNOWN | 17 | 0 | T |
| AW135556 | UNKNOWN | 17 | 0 | T |
| AW135557 | UNKNOWN | 16 | 0 | T |
| AW135564 | UNKNOWN | 15 | 0 | T |
| AW135566 | UNKNOWN | 17 | 0 | T |
| AW135570 | UNKNOWN | 17 | 0 | T |
| AW135581 | UNKNOWN | 4.5 | 74 | TCAT |
| AW135581 | UNKNOWN | 17 | 0 | T |
| AW135595 | UNKNOWN | 17 | 0 | T |
| AW135610 | UNKNOWN | 17 | 0 | T |
| AW135616 | UNKNOWN | 17 | 0 | T |
| AW135641 | UNKNOWN | 17 | 0 | T |

TABLE 1-continued

| Genbank # | Region | # reps | Position | Unit sequence |
|---|---|---|---|---|
| AW135666 | UNKNOWN | 17 | 0 | T |
| AW135667 | UNKNOWN | 17 | 0 | T |
| AW135711 | UNKNOWN | 17 | 0 | T |
| AW135713 | UNKNOWN | 17 | 0 | T |
| AW135735 | UNKNOWN | 17 | 0 | T |
| AW135855 | UNKNOWN | 17 | 0 | T |
| AW135866 | UNKNOWN | 17 | 0 | T |
| AW135911 | UNKNOWN | 12 | 0 | T |
| AW135946 | UNKNOWN | 17 | 0 | T |
| AW135961 | UNKNOWN | 17 | 0 | T |
| AW135982 | UNKNOWN | 17 | 0 | T |
| AW135987 | UNKNOWN | 17 | 0 | T |
| AW136003 | UNKNOWN | 17 | 0 | T |
| AW136025 | UNKNOWN | 17 | 0 | T |
| AW136029 | UNKNOWN | 6 | 2 | GCC |
| AW136035 | UNKNOWN | 15 | 0 | T |
| AW136040 | UNKNOWN | 17 | 0 | T |
| AW136056 | UNKNOWN | 17 | 0 | T |
| AW136061 | UNKNOWN | 17 | 0 | T |
| AW136062 | UNKNOWN | 17 | 0 | T |
| AW136064 | UNKNOWN | 17 | 0 | T |
| AW136065 | UNKNOWN | 17 | 0 | T |
| AW136091 | UNKNOWN | 17 | 0 | T |
| AW136096 | UNKNOWN | 17 | 0 | T |
| AW136102 | UNKNOWN | 17 | 0 | T |
| AW136107 | UNKNOWN | 17 | 0 | T |
| AW136115 | UNKNOWN | 17 | 0 | T |
| AW136126 | UNKNOWN | 17 | 0 | T |
| AW136176 | UNKNOWN | 17 | 0 | T |
| AW136183 | UNKNOWN | 13 | 0 | T |
| AW136184 | UNKNOWN | 17 | 0 | T |
| AW136198 | UNKNOWN | 17 | 0 | T |
| AW136202 | UNKNOWN | 15 | 0 | T |
| AW136217 | UNKNOWN | 17 | 0 | T |
| AW136221 | UNKNOWN | 17 | 0 | T |
| AW136223 | UNKNOWN | 16 | 0 | T |
| AW136238 | UNKNOWN | 15 | 0 | T |
| AW136242 | UNKNOWN | 17 | 0 | T |
| AW136261 | UNKNOWN | 13 | 0 | T |
| AW136307 | UNKNOWN | 17 | 0 | T |
| AW136321 | UNKNOWN | 13 | 547 | A |
| AW136338 | UNKNOWN | 17 | 0 | T |
| AW136339 | UNKNOWN | 15 | 0 | T |
| AW136340 | UNKNOWN | 17 | 0 | T |
| AW136343 | UNKNOWN | 17 | 0 | T |
| AW136354 | UNKNOWN | 17 | 0 | T |
| AW136358 | UNKNOWN | 17 | 0 | T |
| AW136363 | UNKNOWN | 17 | 0 | T |
| AW136378 | UNKNOWN | 17 | 0 | T |
| AW136396 | UNKNOWN | 17 | 0 | T |
| AW136397 | UNKNOWN | 17 | 0 | T |
| AW136401 | UNKNOWN | 17 | 0 | T |
| AW136403 | UNKNOWN | 14 | 0 | T |
| AW136414 | UNKNOWN | 15 | 0 | T |
| AW136430 | UNKNOWN | 6.5 | 110 | GT |
| AW136445 | UNKNOWN | 17 | 0 | T |
| AW136450 | UNKNOWN | 17 | 0 | T |
| AW136452 | UNKNOWN | 17 | 0 | T |
| AW136466 | UNKNOWN | 15 | 0 | T |
| AW136468 | UNKNOWN | 17 | 0 | T |
| AW136493 | UNKNOWN | 17 | 0 | T |
| AW136515 | UNKNOWN | 18 | 327 | T |
| AW136515 | UNKNOWN | 16 | 0 | T |
| AW136559 | UNKNOWN | 17 | 0 | T |
| AW136573 | UNKNOWN | 17 | 0 | T |
| AW136575 | UNKNOWN | 17 | 0 | T |
| AW136581 | UNKNOWN | 17 | 0 | T |
| AW136594 | UNKNOWN | 17 | 0 | T |
| AW136642 | UNKNOWN | 12 | 0 | T |
| AW136646 | UNKNOWN | 17 | 0 | T |
| AW136649 | UNKNOWN | 17 | 0 | T |
| AW136654 | UNKNOWN | 17 | 0 | T |
| AW136659 | UNKNOWN | 17 | 0 | T |
| AW136677 | UNKNOWN | 17 | 0 | T |
| AW136696 | UNKNOWN | 15 | 0 | T |
| AW136712 | UNKNOWN | 17 | 0 | T |
| AW136713 | UNKNOWN | 17 | 0 | T |

TABLE 1-continued

| Genbank # | Region | # reps | Position | Unit sequence |
|---|---|---|---|---|
| AW136717 | UNKNOWN | 17 | 0 | T |
| AW136736 | UNKNOWN | 17 | 0 | T |
| AW136740 | UNKNOWN | 6.66 | 132 | TGG |
| AW136740 | UNKNOWN | 17 | 0 | T |
| AW136742 | UNKNOWN | 17 | 0 | T |
| AW136750 | UNKNOWN | 17 | 0 | T |
| AW136771 | UNKNOWN | 16 | 1 | T |
| AW136785 | UNKNOWN | 17 | 0 | T |
| AW136820 | UNKNOWN | 16 | 0 | T |
| AW136822 | UNKNOWN | 17 | 0 | T |
| AW136824 | UNKNOWN | 17 | 0 | T |
| AW136834 | UNKNOWN | 17 | 0 | T |
| AW136839 | UNKNOWN | 17 | 0 | T |
| AW136848 | UNKNOWN | 17 | 0 | T |
| AW136853 | UNKNOWN | 17 | 0 | T |
| AW136860 | UNKNOWN | 17 | 0 | T |
| AW136869 | UNKNOWN | 17 | 0 | T |
| AW136885 | UNKNOWN | 17 | 0 | T |
| AW136911 | UNKNOWN | 15 | 0 | T |
| AW136930 | UNKNOWN | 17 | 0 | T |
| AW136969 | UNKNOWN | 17 | 0 | T |
| AW136975 | UNKNOWN | 17 | 0 | T |
| AW136978 | UNKNOWN | 17 | 0 | T |
| AW137017 | UNKNOWN | 17 | 0 | T |
| AW137072 | UNKNOWN | 17 | 0 | T |
| AW137078 | UNKNOWN | 17 | 0 | T |
| AW137085 | UNKNOWN | 17 | 0 | T |
| AW137088 | UNKNOWN | 17 | 0 | T |
| AW137094 | UNKNOWN | 15 | 0 | T |
| AW137099 | UNKNOWN | 17 | 0 | T |
| AW137106 | UNKNOWN | 17 | 0 | T |
| AW137116 | UNKNOWN | 17 | 0 | T |
| AW137117 | UNKNOWN | 17 | 0 | T |
| AW137123 | UNKNOWN | 15 | 0 | T |
| AW137130 | UNKNOWN | 17 | 0 | T |
| AW137131 | UNKNOWN | 16 | 0 | T |
| AW137133 | UNKNOWN | 17 | 0 | T |
| AW137137 | UNKNOWN | 17 | 0 | T |
| AW137145 | UNKNOWN | 16 | 0 | T |
| AW137148 | UNKNOWN | 14 | 0 | T |
| AW137150 | UNKNOWN | 17 | 0 | T |
| AW137161 | UNKNOWN | 17 | 0 | T |
| AW137166 | UNKNOWN | 17 | 0 | T |
| AW137170 | UNKNOWN | 17 | 0 | T |
| AW137180 | UNKNOWN | 6.5 | 472 | AC |
| AW137180 | UNKNOWN | 17 | 0 | T |
| AW137202 | UNKNOWN | 20 | 298 | A |
| AW137208 | UNKNOWN | 17 | 0 | T |
| AW137219 | UNKNOWN | 10.66 | 45 | AAC |
| AW137219 | UNKNOWN | 17 | 0 | T |
| AW137224 | UNKNOWN | 17 | 0 | T |
| AW137260 | UNKNOWN | 17 | 0 | T |
| AW137288 | UNKNOWN | 17 | 0 | T |
| AW137299 | UNKNOWN | 17 | 0 | T |
| AW137300 | UNKNOWN | 17 | 0 | T |
| AW137302 | UNKNOWN | 17 | 0 | T |
| AW137322 | UNKNOWN | 17 | 0 | T |
| AW137342 | UNKNOWN | 17 | 0 | T |
| AW137375 | UNKNOWN | 17 | 325 | A |
| AW137384 | UNKNOWN | 17 | 0 | T |
| AW137408 | UNKNOWN | 17 | 0 | T |
| AW137419 | UNKNOWN | 14 | 0 | T |
| AW137421 | UNKNOWN | 17 | 0 | T |
| AW137422 | UNKNOWN | 15 | 0 | T |
| AW137425 | UNKNOWN | 17 | 0 | T |
| AW137452 | UNKNOWN | 17 | 0 | T |
| AW137461 | UNKNOWN | 10.5 | 229 | GC |
| AW137461 | UNKNOWN | 7 | 256 | TA |
| AW137461 | UNKNOWN | 17 | 0 | T |
| AW137465 | UNKNOWN | 17 | 0 | T |
| AW137468 | UNKNOWN | 17 | 0 | T |
| AW137469 | UNKNOWN | 17 | 0 | T |
| AW137472 | UNKNOWN | 17 | 0 | T |
| AW137495 | UNKNOWN | 17 | 0 | T |
| AW137500 | UNKNOWN | 17 | 0 | T |
| AW137508 | UNKNOWN | 17 | 0 | T |
| AW137512 | UNKNOWN | 17 | 0 | T |

TABLE 1-continued

| Genbank # | Region | # reps | Position | Unit sequence |
|---|---|---|---|---|
| AW137517 | UNKNOWN | 17 | 0 | T |
| AW137532 | UNKNOWN | 17 | 0 | T |
| AW137539 | UNKNOWN | 17 | 0 | T |
| AW137564 | UNKNOWN | 17 | 0 | T |
| AW137565 | UNKNOWN | 17 | 0 | T |
| AW137570 | UNKNOWN | 17 | 0 | T |
| AW137591 | UNKNOWN | 2.75 | 241 | TGTGTGTGTAATGTGTGTTTGTCATCGTGATGT (SEQ ID NO: 218) |
| AW137591 | UNKNOWN | 17 | 0 | T |
| AW137603 | UNKNOWN | 15 | 0 | T |
| AW137632 | UNKNOWN | 17 | 0 | T |
| AW137636 | UNKNOWN | 13 | 521 | GT |
| AW137636 | UNKNOWN | 17 | 0 | T |
| AW137637 | UNKNOWN | 17 | 0 | T |
| AW137640 | UNKNOWN | 17 | 0 | T |
| AW137649 | UNKNOWN | 14 | 0 | T |
| AW137664 | UNKNOWN | 17 | 0 | T |
| AW137674 | UNKNOWN | 17 | 0 | T |
| AW137676 | UNKNOWN | 17 | 0 | T |
| AW137710 | UNKNOWN | 17 | 0 | T |
| AW137743 | UNKNOWN | 15 | 0 | T |
| AW137762 | UNKNOWN | 17 | 0 | T |
| AW137785 | UNKNOWN | 17 | 0 | T |
| AW137802 | UNKNOWN | 17 | 0 | T |
| AW137804 | UNKNOWN | 17 | 0 | T |
| AW137811 | UNKNOWN | 17 | 0 | T |
| AW137859 | UNKNOWN | 17 | 0 | T |
| AW137859 | UNKNOWN | 12 | 116 | A |
| AW137863 | UNKNOWN | 17 | 0 | T |
| AW137867 | UNKNOWN | 15 | 0 | T |
| AW137896 | UNKNOWN | 17 | 0 | T |
| AW137902 | UNKNOWN | 17 | 0 | T |
| AW137936 | UNKNOWN | 17 | 0 | T |
| AW137954 | UNKNOWN | 17 | 0 | T |
| AW137957 | UNKNOWN | 17 | 0 | T |
| AW137967 | UNKNOWN | 17 | 0 | T |
| AW137980 | UNKNOWN | 15 | 0 | T |
| AW137982 | UNKNOWN | 17 | 0 | T |
| AW137997 | UNKNOWN | 17 | 0 | T |
| AW138027 | UNKNOWN | 17 | 0 | T |
| AW138032 | UNKNOWN | 17 | 0 | T |
| AW138041 | UNKNOWN | 17 | 0 | T |
| AW138045 | UNKNOWN | 13 | 0 | T |
| AW138098 | UNKNOWN | 14 | 0 | T |
| AW138112 | UNKNOWN | 15 | 0 | T |
| AW138118 | UNKNOWN | 17 | 0 | T |
| AW138125 | UNKNOWN | 13 | 4 | T |
| AW138128 | UNKNOWN | 17 | 0 | T |
| AW138130 | UNKNOWN | 17 | 0 | T |
| AW138134 | UNKNOWN | 15 | 0 | T |
| AW138136 | UNKNOWN | 17 | 0 | T |
| AW138137 | UNKNOWN | 16 | 0 | T |
| AW138143 | UNKNOWN | 17 | 0 | T |
| AW138155 | UNKNOWN | 15 | 0 | T |
| AW138168 | UNKNOWN | 15 | 0 | T |
| AW138174 | UNKNOWN | 17 | 0 | T |
| AW138181 | UNKNOWN | 17 | 0 | T |
| AW138182 | UNKNOWN | 17 | 0 | T |
| AW138183 | UNKNOWN | 17 | 0 | T |
| AW138188 | UNKNOWN | 15 | 0 | T |
| AW138195 | UNKNOWN | 17 | 0 | T |
| AW138196 | UNKNOWN | 15 | 0 | T |
| AW138206 | UNKNOWN | 17 | 0 | T |
| AW138207 | UNKNOWN | 17 | 0 | T |
| AW138218 | UNKNOWN | 17 | 0 | T |
| AW138235 | UNKNOWN | 17 | 0 | T |
| AW138237 | UNKNOWN | 17 | 0 | T |
| AW138247 | UNKNOWN | 22 | 353 | T |
| AW138247 | UNKNOWN | 17 | 0 | T |
| AW138251 | UNKNOWN | 17 | 0 | T |
| AW138253 | UNKNOWN | 13 | 0 | T |
| AW138275 | UNKNOWN | 17 | 0 | T |
| AW138280 | UNKNOWN | 6.5 | 515 | CT |
| AW138280 | UNKNOWN | 15 | 0 | T |
| AW138288 | UNKNOWN | 17 | 0 | T |
| AW138295 | UNKNOWN | 17 | 0 | T |
| AW138319 | UNKNOWN | 17 | 0 | T |

TABLE 1-continued

| Genbank # | Region | # reps | Position | Unit sequence |
|---|---|---|---|---|
| AW138320 | UNKNOWN | 17 | 0 | T |
| AW138321 | UNKNOWN | 14 | 0 | T |
| AW138322 | UNKNOWN | 17 | 0 | T |
| AW138343 | UNKNOWN | 17 | 0 | T |
| AW138355 | UNKNOWN | 17 | 0 | T |
| AW138363 | UNKNOWN | 17 | 0 | T |
| AW138371 | UNKNOWN | 17 | 0 | T |
| AW138375 | UNKNOWN | 17 | 0 | T |
| AW138389 | UNKNOWN | 8.5 | 14 | TG |
| AW138389 | UNKNOWN | 15 | 0 | T |
| AW138393 | UNKNOWN | 17 | 0 | T |
| AW138455 | UNKNOWN | 17 | 0 | T |
| AW138461 | UNKNOWN | 17 | 0 | T |
| AW138480 | UNKNOWN | 17 | 0 | T |
| AW138487 | UNKNOWN | 17 | 0 | T |
| AW138498 | UNKNOWN | 17 | 0 | T |
| AW138499 | UNKNOWN | 15 | 0 | T |
| AW138514 | UNKNOWN | 17 | 0 | T |
| AW138516 | UNKNOWN | 17 | 0 | T |
| AW138521 | UNKNOWN | 17 | 0 | T |
| AW138522 | UNKNOWN | 17 | 0 | T |
| AW138529 | UNKNOWN | 17 | 0 | T |
| AW138581 | UNKNOWN | 17 | 0 | T |
| AW138587 | UNKNOWN | 17 | 0 | T |
| AW138615 | UNKNOWN | 15 | 0 | T |
| AW138625 | UNKNOWN | 17 | 0 | T |
| AW138631 | UNKNOWN | 17 | 0 | T |
| AW138649 | UNKNOWN | 17 | 0 | T |
| AW138672 | UNKNOWN | 15 | 0 | T |
| AW138673 | UNKNOWN | 17 | 0 | T |
| AW138675 | UNKNOWN | 17 | 0 | T |
| AW138679 | UNKNOWN | 17 | 0 | T |
| AW138681 | UNKNOWN | 17 | 0 | T |
| AW138691 | UNKNOWN | 16 | 0 | T |
| AW138693 | UNKNOWN | 15 | 0 | T |
| AW138695 | UNKNOWN | 17 | 0 | T |
| AW138703 | UNKNOWN | 15 | 0 | T |
| AW138704 | UNKNOWN | 17 | 0 | T |
| AW138704 | UNKNOWN | 12 | 393 | A |
| AW138722 | UNKNOWN | 15 | 0 | T |
| AW138725 | UNKNOWN | 17 | 0 | T |
| AW138739 | UNKNOWN | 17 | 0 | T |
| AW138740 | UNKNOWN | 17 | 0 | T |
| AW138743 | UNKNOWN | 17 | 0 | T |
| AW138747 | UNKNOWN | 17 | 0 | T |
| AW138758 | UNKNOWN | 17 | 0 | T |
| AW138760 | UNKNOWN | 17 | 0 | T |
| AW138763 | UNKNOWN | 17 | 0 | T |
| AW138771 | UNKNOWN | 17 | 0 | T |
| AW138772 | UNKNOWN | 17 | 0 | T |
| AW138775 | UNKNOWN | 17 | 0 | T |
| AW138782 | UNKNOWN | 14 | 0 | T |
| AW138785 | UNKNOWN | 17 | 0 | T |
| AW138788 | UNKNOWN | 5.66 | 138 | GCC |
| AW138791 | UNKNOWN | 17 | 0 | T |
| AW138793 | UNKNOWN | 17 | 0 | T |
| AW138797 | UNKNOWN | 4.75 | 359 | TGTT |
| AW138797 | UNKNOWN | 15 | 0 | T |
| AW138801 | UNKNOWN | 17 | 0 | T |
| AW138811 | UNKNOWN | 17 | 0 | T |
| AW138814 | UNKNOWN | 17 | 0 | T |
| AW138815 | UNKNOWN | 17 | 0 | T |
| AW138819 | UNKNOWN | 15 | 0 | T |
| AW138824 | UNKNOWN | 17 | 0 | T |
| AW138825 | UNKNOWN | 17 | 0 | T |
| AW138830 | UNKNOWN | 17 | 0 | T |
| AW138833 | UNKNOWN | 17 | 0 | T |
| AW138835 | UNKNOWN | 17 | 0 | T |
| AW138839 | UNKNOWN | 17 | 0 | T |
| AW138840 | UNKNOWN | 17 | 0 | T |
| AW138842 | UNKNOWN | 17 | 0 | T |
| AW138845 | UNKNOWN | 17 | 0 | T |
| AW138846 | UNKNOWN | 17 | 0 | T |
| AW138847 | UNKNOWN | 17 | 0 | T |
| AW138852 | UNKNOWN | 17 | 0 | T |
| AW138869 | UNKNOWN | 17 | 0 | T |
| AW138872 | UNKNOWN | 17 | 0 | T |

TABLE 1-continued

| Genbank # | Region | # reps | Position | Unit sequence |
|---|---|---|---|---|
| AW138879 | UNKNOWN | 17 | 0 | T |
| AW138881 | UNKNOWN | 17 | 0 | T |
| AW138883 | UNKNOWN | 17 | 0 | T |
| AW138886 | UNKNOWN | 4.8 | 358 | TTTTG |
| AW138886 | UNKNOWN | 17 | 0 | T |
| AW138895 | UNKNOWN | 17 | 0 | T |
| AW138907 | UNKNOWN | 17 | 0 | T |
| AW138908 | UNKNOWN | 5.75 | 26 | TTTG |
| AW138908 | UNKNOWN | 5.75 | 113 | AAAG |
| AW138908 | UNKNOWN | 17 | 0 | T |
| AW138909 | UNKNOWN | 17 | 0 | T |
| AW138910 | UNKNOWN | 6.5 | 58 | AG |
| AW138910 | UNKNOWN | 17 | 0 | T |
| AW138920 | UNKNOWN | 17 | 0 | T |
| AW138943 | UNKNOWN | 17 | 0 | T |
| AW138959 | UNKNOWN | 15 | 0 | T |
| AW138968 | UNKNOWN | 15 | 0 | T |
| AW138973 | UNKNOWN | 17 | 0 | T |
| AW138975 | UNKNOWN | 17 | 0 | T |
| AW138984 | UNKNOWN | 17 | 0 | T |
| AW138989 | UNKNOWN | 17 | 0 | T |
| AW139005 | UNKNOWN | 17 | 0 | T |
| AW139015 | UNKNOWN | 15 | 0 | T |
| AW139027 | UNKNOWN | 17 | 0 | T |
| AW139043 | UNKNOWN | 17 | 0 | T |
| AW139046 | UNKNOWN | 17 | 0 | T |
| AW139052 | UNKNOWN | 17 | 0 | T |
| AW139053 | UNKNOWN | 17 | 0 | T |
| AW139056 | UNKNOWN | 9 | 189 | CA |
| AW139056 | UNKNOWN | 13 | 0 | T |
| AW139061 | UNKNOWN | 17 | 0 | T |
| AW139064 | UNKNOWN | 17 | 0 | T |
| AW139067 | UNKNOWN | 17 | 0 | T |
| AW139072 | UNKNOWN | 15 | 0 | T |
| AW139077 | UNKNOWN | 17 | 0 | T |
| AW139091 | UNKNOWN | 17 | 0 | T |
| AW139099 | UNKNOWN | 17 | 0 | T |
| AW139103 | UNKNOWN | 17 | 0 | T |
| AW139104 | UNKNOWN | 17 | 0 | T |
| AW139113 | UNKNOWN | 17 | 0 | T |
| AW139121 | UNKNOWN | 17 | 0 | T |
| AW139123 | UNKNOWN | 17 | 0 | T |
| AW139128 | UNKNOWN | 17 | 0 | T |
| AW139129 | UNKNOWN | 17 | 0 | T |
| AW139150 | UNKNOWN | 17 | 0 | T |
| AW139151 | UNKNOWN | 17 | 0 | T |
| AW139155 | UNKNOWN | 17 | 0 | T |
| AW139157 | UNKNOWN | 14 | 0 | T |
| AW139161 | UNKNOWN | 17 | 0 | T |
| AW139163 | UNKNGWN | 17 | 0 | T |
| AW139165 | UNKNOWN | 17 | 0 | T |
| AW139180 | UNKNOWN | 17 | 0 | T |
| AW139182 | UNKNOWN | 17 | 0 | T |
| AW139183 | UNKNOWN | 17 | 0 | T |
| AW139193 | UNKNOWN | 17 | 0 | T |
| AW139194 | UNKNOWN | 13 | 0 | T |
| AW139225 | UNKNOWN | 17 | 0 | T |
| AW139232 | UNKNOWN | 17 | 0 | T |
| AW139246 | UNKNOWN | 17 | 0 | T |
| AW139248 | UNKNOWN | 17 | 0 | T |
| AW139255 | UNKNOWN | 17 | 0 | T |
| AW139262 | UNKNOWN | 16 | 180 | T |
| AW139264 | UNKNOWN | 17 | 0 | T |
| AW139297 | UNKNOWN | 17 | 0 | T |
| AW139328 | UNKNOWN | 17 | 0 | T |
| AW139330 | UNKNOWN | 17 | 0 | T |
| AW139340 | UNKNOWN | 17 | 0 | T |
| AW139344 | UNKNOWN | 17 | 0 | T |
| AW139345 | UNKNOWN | 17 | 0 | T |
| AW139359 | UNKNOWN | 17 | 0 | T |
| AW139369 | UNKNOWN | 17 | 0 | T |
| AW139377 | UNKNOWN | 15 | 483 | A |
| AW139381 | UNKNOWN | 17 | 0 | T |
| AW139381 | UNKNOWN | 14 | 388 | A |
| AW139384 | UNKNOWN | 17 | 0 | T |
| AW139388 | UNKNOWN | 17 | 0 | T |
| AW139388 | UNKNOWN | 12 | 188 | A |

TABLE 1-continued

| Genbank # | Region | # reps | Position | Unit sequence |
|---|---|---|---|---|
| AW139393 | UNKNOWN | 17 | 0 | T |
| AW139403 | UNKNOWN | 17 | 0 | T |
| AW139406 | UNKNOWN | 17 | 0 | T |
| AW139412 | UNKNOWN | 17 | 0 | T |
| AW139425 | UNKNOWN | 17 | 0 | T |
| AW139426 | UNKNOWN | 17 | 0 | T |
| AW139464 | UNKNOWN | 17 | 0 | T |
| AW139470 | UNKNOWN | 17 | 0 | T |
| AW139474 | UNKNOWN | 17 | 0 | T |
| AW139477 | UNKNOWN | 17 | 0 | T |
| AW139492 | UNKNOWN | 17 | 0 | T |
| AW139503 | UNKNOWN | 17 | 0 | T |
| AW139512 | UNKNOWN | 17 | 0 | T |
| AW139525 | UNKNOWN | 5 | 209 | CAAA |
| AW139528 | UNKNOWN | 17 | 0 | T |
| AW139541 | UNKNOWN | 17 | 0 | T |
| AW139544 | UNKNOWN | 17 | 0 | T |
| AW139549 | UNKNOWN | 17 | 0 | T |
| AW139550 | UNKNOWN | 17 | 0 | T |
| AW139556 | UNKNOWN | 17 | 0 | T |
| AW139557 | UNKNOWN | 17 | 0 | T |
| AW139559 | UNKNOWN | 17 | 0 | T |
| AW139562 | UNKNOWN | 17 | 0 | T |
| AW139567 | UNKNOWN | 17 | 0 | T |
| AW139582 | UNKNOWN | 17 | 0 | T |
| AW139584 | UNKNOWN | 17 | 0 | T |
| AW139588 | UNKNOWN | 17 | 0 | T |
| AW139594 | UNKNOWN | 17 | 0 | T |
| AW139602 | UNKNOWN | 17 | 0 | T |
| AW139611 | UNKNOWN | 17 | 0 | T |
| AW139651 | UNKNOWN | 17 | 0 | T |
| AW139660 | UNKNOWN | 17 | 0 | T |
| AW139674 | UNKNOWN | 17 | 0 | T |
| AW139678 | UNKNOWN | 17 | 0 | T |
| AW139704 | UNKNOWN | 17 | 0 | T |
| AW139707 | UNKNOWN | 17 | 0 | T |
| AW139709 | UNKNOWN | 17 | 0 | T |
| AW139715 | UNKNOWN | 17 | 0 | T |
| AW139719 | UNKNOWN | 17 | 0 | T |
| AW139723 | UNKNOWN | 12 | 0 | T |
| AW139729 | UNKNOWN | 17 | 0 | T |
| AW139742 | UNKNOWN | 17 | 0 | T |
| AW139744 | UNKNOWN | 17 | 0 | T |
| AW139750 | UNKNOWN | 17 | 0 | T |
| AW139752 | UNKNOWN | 17 | 0 | T |
| AW139752 | UNKNOWN | 15 | 43 | A |
| AW139754 | UNKNOWN | 12 | 0 | T |
| AW139757 | UNKNOWN | 17 | 0 | T |
| AW139760 | UNKNOWN | 17 | 0 | T |
| AW139766 | UNKNOWN | 15 | 0 | T |
| AW139769 | UNKNOWN | 17 | 0 | T |
| AW139773 | UNKNOWN | 17 | 0 | T |
| AW139776 | UNKNOWN | 17 | 0 | T |
| AW139786 | UNKNOWN | 4.8 | 296 | GGGCC |
| AW139788 | UNKNOWN | 17 | 0 | T |
| AW139789 | UNKNOWN | 19 | 81 | T |
| AW139789 | UNKNOWN | 17 | 0 | T |
| AW139808 | UNKNOWN | 17 | 0 | T |
| AW139823 | UNKNOWN | 3.6 | 135 | CCCTC |
| AW139840 | UNKNOWN | 17 | 0 | T |
| AW139860 | UNKNOWN | 16 | 1 | T |
| AW139867 | UNKNOWN | 17 | 0 | T |
| AW139876 | UNKNOWN | 17 | 0 | T |
| AW139885 | UNKNOWN | 17 | 0 | T |
| AW139890 | UNKNOWN | 17 | 0 | T |
| AW139896 | UNKNOWN | 17 | 0 | T |
| AW139901 | UNKNOWN | 17 | 0 | T |
| AW139902 | UNKNOWN | 17 | 0 | T |
| AW139915 | UNKNOWN | 12 | 0 | T |
| AW139918 | UNKNOWN | 17 | 0 | T |
| AW139919 | UNKNOWN | 17 | 0 | T |
| AW139926 | UNKNOWN | 17 | 0 | T |
| AW139939 | UNKNOWN | 17 | 0 | T |
| AW139941 | UNKNOWN | 17 | 0 | T |
| AW139949 | UNKNOWN | 17 | 0 | T |
| AW139951 | UNKNOWN | 17 | 0 | T |
| AW139964 | UNKNOWN | 17 | 0 | T |

TABLE 1-continued

| Genbank # | Region | # reps | Position | Unit sequence |
|---|---|---|---|---|
| AW139982 | UNKNOWN | 13 | 4 | T |
| AW140031 | UNKNOWN | 17 | 0 | T |
| AW140059 | UNKNOWN | 17 | 0 | T |
| AW140073 | UNKNOWN | 17 | 0 | T |
| AW140083 | UNKNOWN | 17 | 0 | T |
| AW140084 | UNKNOWN | 16 | 0 | T |
| AW140089 | UNKNOWN | 16 | 0 | T |
| AW140092 | UNKNOWN | 14 | 0 | T |
| AW140093 | UNKNOWN | 15 | 0 | T |
| AW140098 | UNKNOWN | 6 | 79 | CCG |
| AW140111 | UNKNOWN | 17 | 0 | T |
| AW140135 | UNKNOWN | 17 | 0 | T |
| AW148294 | UNKNOWN | 91 | 0 | T |
| AW148294 | UNKNOWN | 14 | 148 | A |
| AW148303 | UNKNOWN | 51 | 0 | T |
| AW148303 | UNKNOWN | 12 | 82 | C |
| AW148320 | UNKNOWN | 123 | 0 | T |
| AW148320 | UNKNOWN | 18 | 201 | G |
| AW148320 | UNKNOWN | 14 | 151 | A |
| AW148320 | UNKNOWN | 12 | 123 | C |
| AW148336 | UNKNOWN | 16 | 0 | T |
| AW148350 | UNKNOWN | 43 | 0 | T |
| AW148354 | UNKNOWN | 52 | 0 | T |
| AW148356 | UNKNOWN | 79 | 0 | T |
| AW148356 | UNKNOWN | 12 | 146 | G |
| AW148363 | UNKNOWN | 104 | 0 | T |
| AW148363 | UNKNOWN | 17 | 104 | A |
| AW148363 | UNKNOWN | 14 | 175 | C |
| AW148374 | UNKNOWN | 48 | 0 | T |
| AW148382 | UNKNOWN | 52 | 0 | T |
| AW148382 | UNKNOWN | 12 | 212 | A |
| AW148408 | UNKNOWN | 114 | 0 | T |
| AW148408 | UNKNOWN | 28 | 114 | A |
| AW148408 | UNKNOWN | 20 | 188 | C |
| AW148408 | UNKNOWN | 15 | 173 | G |
| AW148412 | UNKNOWN | 52 | 0 | T |
| AW148412 | UNKNOWN | 17 | 122 | A |
| AW148412 | UNKNOWN | 15 | 216 | C |
| AW148413 | UNKNOWN | 12 | 0 | T |
| AW148414 | UNKNOWN | 85 | 0 | T |
| AW148414 | UNKNOWN | 22 | 303 | C |
| AW148414 | UNKNOWN | 13 | 112 | C |
| AW148414 | UNKNOWN | 13 | 195 | G |
| AW148446 | UNKNOWN | 19 | 0 | T |
| AW148457 | UNKNOWN | 89 | 0 | T |
| AW148457 | UNKNOWN | 13 | 151 | G |
| AW148457 | UNKNOWN | 13 | 209 | A |
| AW148465 | UNKNOWN | 14 | 108 | G |
| AW148465 | UNKNOWN | 12 | 0 | T |
| AW148466 | UNKNOWN | 48 | 0 | T |
| AW148470 | UNKNOWN | 38 | 0 | T |
| AW148478 | UNKNOWN | 60 | 0 | T |
| AW148478 | UNKNOWN | 14 | 184 | A |
| AW148484 | UNKNOWN | 70 | 0 | T |
| AW148484 | UNKNOWN | 17 | 169 | G |
| AW148484 | UNKNOWN | 13 | 151 | A |
| AW148505 | UNKNOWN | 42 | 0 | T |
| AW148527 | UNKNOWN | 47 | 0 | T |
| AW148528 | UNKNOWN | 50 | 0 | T |
| AW148528 | UNKNOWN | 12 | 107 | A |
| AW148536 | UNKNOWN | 101 | 0 | T |
| AW148536 | UNKNOWN | 14 | 225 | G |
| AW148536 | UNKNOWN | 13 | 153 | C |
| AW148544 | UNKNOWN | 61 | 0 | T |
| AW148545 | UNKNOWN | 22 | 0 | T |
| AW148551 | UNKNOWN | 29 | 0 | T |
| AW148559 | UNKNOWN | 6 | 74 | TTG |
| AW148561 | UNKNOWN | 17 | 0 | T |
| AW148585 | UNKNOWN | 40 | 0 | T |
| AW148589 | UNKNOWN | 60 | 0 | T |
| AW148589 | UNKNOWN | 12 | 308 | C |
| AW148590 | UNKNOWN | 70 | 0 | T |
| AW148590 | UNKNOWN | 13 | 103 | A |
| AW148593 | UNKNOWN | 40 | 0 | T |
| AW148593 | UNKNOWN | 15 | 85 | G |
| AW148593 | UNKNOWN | 12 | 255 | A |
| AW148599 | UNKNOWN | 41 | 0 | T |

TABLE 1-continued

| Genbank # | Region | # reps | Position | Unit sequence |
|---|---|---|---|---|
| AW148621 | UNKNOWN | 81 | 0 | T |
| AW148621 | UNKNOWN | 26 | 341 | C |
| AW148634 | UNKNOWN | 25 | 0 | T |
| AW148639 | UNKNOWN | 53 | 0 | T |
| AW148639 | UNKNOWN | 16 | 121 | C |
| AW148653 | UNKNOWN | 48 | 0 | T |
| AW148658 | UNKNOWN | 49 | 0 | T |
| AW148663 | UNKNOWN | 54 | 0 | T |
| AW148663 | UNKNOWN | 19 | 223 | G |
| AW148678 | UNKNOWN | 43 | 0 | T |
| AW148678 | UNKNOWN | 16 | 318 | G |
| AW148685 | UNKNOWN | 60 | 0 | T |
| AW148693 | UNKNOWN | 50 | 0 | T |
| AW148716 | UNKNOWN | 80 | 0 | T |
| AW148730 | UNKNOWN | 16 | 0 | T |
| AW148743 | UNKNOWN | 50 | 0 | T |
| AW148743 | UNKNOWN | 15 | 84 | G |
| AW148758 | UNKNOWN | 72 | 0 | T |
| AW148758 | UNKNOWN | 13 | 187 | G |
| AW148831 | UNKNOWN | 33 | 0 | T |
| AW148841 | UNKNOWN | 55 | 0 | T |
| AW148841 | UNKNOWN | 17 | 216 | G |
| AW148846 | UNKNOWN | 70 | 0 | T |
| AW148846 | UNKNOWN | 15 | 140 | G |
| AW148865 | UNKNOWN | 46 | 0 | T |
| AW148865 | UNKNOWN | 12 | 79 | A |
| AW148872 | UNKNOWN | 13 | 403 | T |
| AW148876 | UNKNOWN | 56 | 0 | T |
| AW148876 | UNKNOWN | 22 | 91 | A |
| AW148895 | UNKNOWN | 60 | 0 | T |
| AW148904 | UNKNOWN | 63 | 0 | T |
| AW148904 | UNKNOWN | 21 | 347 | A |
| AW148904 | UNKNOWN | 14 | 304 | G |
| AW148904 | UNKNOWN | 12 | 162 | C |
| AW148909 | UNKNOWN | 67 | 0 | T |
| AW148928 | UNKNOWN | 28 | 0 | T |
| AW148935 | UNKNOWN | 9.5 | 0 | TTAT |
| AW148935 | UNKNOWN | 15 | 96 | A |
| AW148940 | UNKNOWN | 38 | 0 | T |
| AW148967 | UNKNOWN | 45 | 0 | T |
| AW148970 | UNKNOWN | 78 | 0 | T |
| AW148970 | UNKNOWN | 12 | 198 | A |
| AW148994 | UNKNOWN | 23 | 0 | T |
| AW149022 | UNKNOWN | 8 | 471 | GT |
| AW149026 | UNKNOWN | 72 | 0 | T |
| AW149026 | UNKNOWN | 14 | 189 | C |
| AW149026 | UNKNOWN | 13 | 391 | A |
| AW149041 | UNKNOWN | 37 | 0 | T |
| AW149041 | UNKNOWN | 17 | 277 | C |
| AW149041 | UNKNOWN | 12 | 132 | A |
| AW149069 | UNKNOWN | 53 | 0 | T |
| AW149069 | UNKNOWN | 12 | 126 | G |
| AW149076 | UNKNOWN | 54 | 0 | T |
| AW149076 | UNKNOWN | 16 | 128 | A |
| AW149076 | UNKNOWN | 12 | 106 | A |
| AW149092 | UNKNOWN | 78 | 0 | T |
| AW149092 | UNKNOWN | 15 | 126 | A |
| AW149109 | UNKNOWN | 58 | 0 | T |
| AW149109 | UNKNOWN | 12 | 141 | C |
| AW149112 | UNKNOWN | 101 | 0 | T |
| AW149112 | UNKNOWN | 17 | 226 | G |
| AW149112 | UNKNOWN | 13 | 213 | C |
| AW149125 | UNKNOWN | 48 | 0 | T |
| AW149150 | UNKNOWN | 27 | 0 | T |
| AW149159 | UNKNOWN | 51 | 0 | T |
| AW149181 | UNKNOWN | 33 | 16 | T |
| AW149181 | UNKNOWN | 15 | 0 | T |
| AW149181 | UNKNOWN | 13 | 103 | A |
| AW149181 | UNKNOWN | 13 | 289 | C |
| AW149219 | UNKNOWN | 50 | 0 | T |
| AW149219 | UNKNOWN | 18 | 169 | A |
| AW149219 | UNKNOWN | 13 | 91 | A |
| AW149227 | UNKNOWN | 99 | 0 | T |
| AW149227 | UNKNOWN | 14 | 182 | G |
| AW149227 | UNKNOWN | 13 | 169 | C |
| AW149232 | UNKNOWN | 47 | 0 | T |
| AW149236 | UNKNOWN | 90 | 0 | T |

TABLE 1-continued

| Genbank # | Region | # reps | Position | Unit sequence |
|---|---|---|---|---|
| AW149236 | UNKNOWN | 20 | 246 | C |
| AW149268 | UNKNOWN | 49 | 0 | T |
| AW149268 | UNKNOWN | 12 | 456 | G |
| AW149285 | UNKNOWN | 39 | 17 | T |
| AW149285 | UNKNOWN | 14 | 0 | T |
| AW149287 | UNKNOWN | 112 | 0 | T |
| AW149287 | UNKNOWN | 19 | 220 | G |
| AW149287 | UNKNOWN | 17 | 203 | C |
| AW149287 | UNKNOWN | 17 | 331 | A |
| AW149287 | UNKNOWN | 14 | 127 | G |
| AW149311 | UNKNOWN | 100 | 0 | T |
| AW149311 | UNKNOWN | 25 | 103 | A |
| AW149311 | UNKNOWN | 16 | 164 | C |
| AW149311 | UNKNOWN | 14 | 184 | G |
| AW149321 | UNKNOWN | 21 | 399 | A |
| AW149329 | UNKNOWN | 42 | 0 | T |
| AW149334 | UNKNOWN | 37 | 0 | T |
| AW149336 | UNKNOWN | 16 | 98 | T |
| AW149336 | UNKNOWN | 12 | 18 | T |
| AW149336 | UNKNOWN | 12 | 228 | C |
| AW149501 | UNKNOWN | 3.8 | 28 | AAAC |
| AW149546 | UNKNOWN | 29 | 0 | T |
| AW149546 | UNKNOWN | 23 | 237 | A |
| AW149557 | UNKNOWN | 13 | 421 | T |
| AW149738 | UNKNOWN | 6.5 | 61 | AAAT |
| AW149743 | UNKNOWN | 6.5 | 310 | AT |
| AW149754 | UNKNOWN | 14 | 317 | T |
| AW149827 | UNKNOWN | 15 | 373 | A |
| AW149851 | UNKNOWN | 109 | 0 | T |
| AW149851 | UNKNOWN | 19 | 231 | G |
| AW149851 | UNKNOWN | 13 | 216 | A |
| AW149869 | UNKNOWN | 110 | 0 | T |
| AW149869 | UNKNOWN | 24 | 143 | A |
| AW149869 | UNKNOWN | 13 | 179 | C |
| AW149869 | UNKNOWN | 12 | 241 | G |
| AW149876 | UNKNOWN | 67 | 0 | T |
| AW149878 | UNKNOWN | 74 | 0 | T |
| AW149878 | UNKNOWN | 14 | 221 | G |
| AW149878 | UNKNOWN | 12 | 166 | G |
| AW149925 | UNKNOWN | 78 | 0 | T |
| AW149925 | UNKNOWN | 14 | 119 | A |
| AW149925 | UNKNOWN | 13 | 133 | G |
| AW149937 | UNKNOWN | 47 | 1 | T |
| AW149941 | UNKNOWN | 20 | 300 | C |
| AW149941 | UNKNOWN | 17 | 112 | G |
| AW149941 | UNKNOWN | 15 | 146 | C |
| AW149941 | UNKNOWN | 12 | 129 | C |
| AW149982 | UNKNOWN | 49 | 0 | T |
| AW149983 | UNKNOWN | 27 | 0 | T |
| AW149994 | UNKNOWN | 93 | 0 | T |
| AW150008 | UNKNOWN | 82 | 0 | T |
| AW150008 | UNKNOWN | 17 | 123 | A |
| AW150011 | UNKNOWN | 44 | 0 | T |
| AW150031 | UNKNOWN | 41 | 0 | T |
| AW150084 | UNKNOWN | 38 | 0 | T |
| AW150108 | UNKNOWN | 33 | 0 | T |
| AW150108 | UNKNOWN | 13 | 104 | C |
| AW150143 | UNKNOWN | 15 | 240 | A |
| AW150175 | UNKNOWN | 42 | 0 | T |
| AW150175 | UNKNOWN | 18 | 209 | A |
| AW150179 | UNKNOWN | 41 | 0 | T |
| AW150182 | UNKNOWN | 38 | 0 | T |
| AW150214 | UNKNOWN | 46 | 0 | T |
| AW150214 | UNKNOWN | 16 | 98 | A |
| AW150225 | UNKNOWN | 84 | 0 | T |
| AW150225 | UNKNOWN | 18 | 109 | C |
| AW150225 | UNKNOWN | 14 | 179 | G |
| AW150226 | UNKNOWN | 12 | 0 | T |
| AW150242 | UNKNOWN | 42 | 0 | T |
| AW150245 | UNKNOWN | 41 | 0 | T |
| AW150308 | UNKNOWN | 63 | 0 | T |
| AW150308 | UNKNOWN | 13 | 191 | A |
| AW150326 | UNKNOWN | 68 | 0 | T |
| AW150326 | UNKNOWN | 12 | 149 | G |
| AW150343 | UNKNOWN | 19 | 0 | T |
| AW150351 | UNKNOWN | 48 | 0 | T |
| AW150351 | UNKNOWN | 14 | 198 | A |

TABLE 1-continued

| Genbank # | Region | # reps | Position | Unit sequence |
|---|---|---|---|---|
| AW150359 | UNKNOWN | 46 | 0 | T |
| AW150359 | UNKNOWN | 12 | 111 | A |
| AW150367 | UNKNOWN | 35 | 31 | T |
| AW150374 | UNKNOWN | 4.5 | 75 | ATAC |
| AW150374 | UNKNOWN | 21 | 0 | T |
| AW150389 | UNKNOWN | 11 | 270 | AC |
| AW150423 | UNKNOWN | 13 | 0 | T |
| AW150439 | UNKNOWN | 37 | 0 | T |
| AW150439 | UNKNOWN | 17 | 322 | G |
| AW150440 | UNKNOWN | 26 | 0 | T |
| AW150453 | UNKNOWN | 98 | 0 | T |
| AW150453 | UNKNOWN | 12 | 139 | G |
| AW150457 | UNKNOWN | 80 | 0 | T |
| AW150457 | UNKNOWN | 12 | 230 | G |
| AW150511 | UNKNOWN | 66 | 0 | T |
| AW150511 | UNKNOWN | 12 | 191 | C |
| AW150557 | UNKNOWN | 62 | 0 | T |
| AW150609 | UNKNOWN | 45 | 0 | T |
| AW150621 | UNKNOWN | 38 | 0 | T |
| AW150621 | UNKNOWN | 13 | 318 | G |
| AW150622 | UNKNOWN | 74 | 0 | T |
| AW150679 | UNKNOWN | 23 | 356 | C |
| AW150679 | UNKNOWN | 21 | 0 | T |
| AW150679 | UNKNOWN | 21 | 323 | C |
| AW150679 | UNKNOWN | 12 | 262 | C |
| AW150703 | UNKNOWN | 44 | 0 | T |
| AW150703 | UNKNOWN | 15 | 322 | G |
| AW150736 | UNKNOWN | 48 | 0 | T |
| AW150736 | UNKNOWN | 13 | 156 | C |
| AW150762 | UNKNOWN | 85 | 0 | T |
| AW150762 | UNKNOWN | 16 | 145 | G |
| AW150762 | UNKNOWN | 13 | 184 | A |
| AW150778 | UNKNOWN | 51 | 0 | T |
| AW150778 | UNKNOWN | 18 | 327 | A |
| AW150778 | UNKNOWN | 12 | 179 | A |
| AW150785 | UNKNOWN | 18 | 0 | T |
| AW150794 | UNKNOWN | 77 | 0 | T |
| AW150803 | UNKNOWN | 32 | 0 | T |
| AW150803 | UNKNOWN | 12 | 149 | A |
| AW150804 | UNKNOWN | 81 | 0 | T |
| AW150804 | UNKNOWN | 15 | 171 | G |
| AW150809 | UNKNOWN | 62 | 0 | T |
| AW150826 | UNKNOWN | 68 | 0 | T |
| AW150826 | UNKNOWN | 12 | 336 | C |
| AW150833 | UNKNOWN | 18 | 0 | T |
| AW150843 | UNKNOWN | 34 | 0 | T |
| AW150893 | UNKNOWN | 81 | 0 | T |
| AW150893 | UNKNOWN | 13 | 133 | C |
| AW150955 | UNKNOWN | 33 | 0 | T |
| AW151031 | UNKNOWN | 52 | 0 | T |
| AW151034 | UNKNOWN | 78 | 0 | T |
| AW151034 | UNKNOWN | 20 | 319 | G |
| AW151034 | UNKNOWN | 19 | 101 | A |
| AW151034 | UNKNOWN | 13 | 138 | C |
| AW151056 | UNKNOWN | 41 | 0 | T |
| AW151056 | UNKNOWN | 16 | 130 | G |
| AW151113 | UNKNOWN | 18 | 11 | T |
| AW151114 | UNKNOWN | 32 | 11 | T |
| AW151134 | UNKNOWN | 15 | 0 | T |
| AW151136 | UNKNOWN | 86 | 11 | T |
| AW151136 | UNKNOWN | 18 | 129 | A |
| AW151163 | UNKNOWN | 3.8 | 25 | TTTTA |
| AW151163 | UNKNOWN | 15 | 0 | T |
| AW151165 | UNKNOWN | 14 | 354 | T |
| AW151200 | UNKNOWN | 13 | 419 | T |
| AW151204 | UNKNOWN | 13 | 0 | T |
| AW151221 | UNKNOWN | 35 | 0 | T |
| AW151229 | UNKNOWN | 28 | 0 | T |
| AW151254 | UNKNOWN | 25 | 0 | T |
| AW151279 | UNKNOWN | 42 | 0 | T |
| AW151283 | UNKNOWN | 59 | 0 | T |
| AW151285 | UNKNOWN | 47 | 0 | T |
| AW151285 | UNKNOWN | 12 | 82 | C |
| AW151286 | UNKNOWN | 21 | 24 | AC |
| AW151298 | UNKNOWN | 53 | 0 | T |
| AW151301 | UNKNOWN | 13 | 161 | T |
| AW151326 | UNKNOWN | 5.66 | 2 | TTA |

TABLE 1-continued

| Genbank # | Region | # reps | Position | Unit sequence |
|---|---|---|---|---|
| AW151346 | UNKNOWN | 14 | 0 | T |
| AW151429 | UNKNOWN | 43 | 0 | T |
| AW151429 | UNKNOWN | 19 | 292 | A |
| AW151437 | UNKNOWN | 26 | 2 | T |
| AW151446 | UNKNOWN | 21 | 0 | T |
| AW151448 | UNKNOWN | 59 | 0 | T |
| AW151448 | UNKNOWN | 13 | 84 | A |
| AW151456 | UNKNOWN | 61 | 0 | T |
| AW151466 | UNKNOWN | 12 | 13 | A |
| AW151485 | UNKNOWN | 114 | 0 | T |
| AW151485 | UNKNOWN | 14 | 126 | G |
| AW151487 | UNKNOWN | 12 | 157 | T |
| AW151533 | UNKNOWN | 26 | 282 | T |
| AW151541 | UNKNOWN | 25 | 1 | T |
| AW151547 | UNKNOWN | 17 | 232 | A |
| AW151548 | UNKNOWN | 44 | 0 | T |
| AW151548 | UNKNOWN | 15 | 362 | A |
| AW151586 | UNKNOWN | 38 | 0 | T |
| AW151586 | UNKNOWN | 12 | 119 | A |
| AW151595 | UNKNOWN | 38 | 0 | T |
| AW151625 | UNKNOWN | 88 | 0 | T |
| AW151625 | UNKNOWN | 12 | 131 | G |
| AW151633 | UNKNOWN | 15 | 479 | A |
| AW151657 | UNKNOWN | 20 | 6 | T |
| AW151660 | UNKNOWN | 5 | 325 | CAAA |
| AW151660 | UNKNOWN | 15 | 0 | T |
| AW151664 | UNKNOWN | 43 | 0 | T |
| AW151681 | UNKNOWN | 87 | 0 | T |
| AW151681 | UNKNOWN | 16 | 132 | C |
| AW151681 | UNKNOWN | 13 | 152 | G |
| AW151714 | UNKNOWN | 83 | 0 | T |
| AW151726 | UNKNOWN | 32 | 0 | T |
| AW151729 | UNKNOWN | 85 | 0 | T |
| AW151729 | UNKNOWN | 14 | 131 | G |
| AW151729 | UNKNOWN | 13 | 164 | C |
| AW151729 | UNKNOWN | 12 | 118 | A |
| AW151737 | UNKNOWN | 36 | 0 | T |
| AW151739 | UNKNOWN | 40 | 0 | T |
| AW151740 | UNKNOWN | 59 | 0 | T |
| AW151740 | UNKNOWN | 15 | 77 | A |
| AW151740 | UNKNOWN | 12 | 201 | G |
| AW151744 | UNKNOWN | 14 | 0 | T |
| AW151748 | UNKNOWN | 41 | 0 | T |
| AW151750 | UNKNOWN | 76 | 0 | T |
| AW151775 | UNKNOWN | 61 | 0 | T |
| AW151775 | UNKNOWN | 18 | 280 | A |
| AW151785 | UNKNOWN | 84 | 0 | T |
| AW151785 | UNKNOWN | 20 | 192 | G |
| AW151785 | UNKNOWN | 12 | 117 | A |
| AW151786 | UNKNOWN | 85 | 0 | T |
| AW151786 | UNKNOWN | 18 | 105 | A |
| AW151786 | UNKNOWN | 17 | 219 | C |
| AW151786 | UNKNOWN | 12 | 151 | G |
| AW151817 | UNKNOWN | 63 | 0 | T |
| AW151817 | UNKNOWN | 14 | 373 | G |
| AW151817 | UNKNOWN | 13 | 88 | G |
| AW151831 | UNKNOWN | 51 | 0 | T |
| AW151831 | UNKNOWN | 15 | 313 | C |
| AW151835 | UNKNOWN | 51 | 0 | T |
| AW151835 | UNKNOWN | 20 | 192 | A |
| AW151844 | UNKNOWN | 47 | 0 | T |
| AW151847 | UNKNGWN | 81 | 0 | T |
| AW151850 | UNKNOWN | 65 | 0 | T |
| AW151850 | UNKNOWN | 13 | 108 | C |
| AW151850 | UNKNOWN | 12 | 121 | A |
| AW151867 | UNKNOWN | 24 | 0 | T |
| AW151889 | UNKNOWN | 92 | 0 | T |
| AW151889 | UNKNOWN | 17 | 334 | G |
| AW151889 | UNKNOWN | 13 | 236 | A |
| AW151889 | UNKNOWN | 12 | 283 | G |
| AW151890 | UNKNOWN | 34 | 0 | T |
| AW151892 | UNKNOWN | 88 | 0 | T |
| AW151892 | UNKNOWN | 24 | 283 | G |
| AW151892 | UNKNOWN | 21 | 151 | G |
| AW151892 | UNKNOWN | 16 | 88 | C |
| AW151892 | UNKNOWN | 16 | 224 | A |
| AW151892 | UNKNOWN | 12 | 109 | G |

TABLE 1-continued

| Genbank # | Region | # reps | Position | Unit sequence |
|---|---|---|---|---|
| AW151892 | UNKNOWN | 12 | 121 | A |
| AW151893 | UNKNOWN | 81 | 0 | T |
| AW151893 | UNKNOWN | 20 | 243 | C |
| AW151893 | UNKNOWN | 19 | 81 | A |
| AW151893 | UNKNOWN | 17 | 191 | C |
| AW151893 | UNKNOWN | 13 | 139 | C |
| AW151893 | UNKNOWN | 12 | 332 | G |
| AW151902 | UNKNOWN | 80 | 0 | T |
| AW151902 | UNKNOWN | 24 | 125 | C |
| AW151902 | UNKNOWN | 17 | 185 | A |
| AW151926 | UNKNOWN | 75 | 0 | T |
| AW151926 | UNKNOWN | 16 | 373 | G |
| AW151926 | UNKNOWN | 15 | 283 | G |
| AW151926 | UNKNOWN | 14 | 351 | A |
| AW151926 | UNKNOWN | 12 | 239 | G |
| AW151948 | UNKNOWN | 73 | 0 | T |
| AW151948 | UNKNOWN | 14 | 223 | C |
| AW151959 | UNKNOWN | 41 | 0 | T |
| AW151959 | UNKNOWN | 12 | 126 | A |
| AW151970 | UNKNOWN | 53 | 12 | T |
| AW151977 | UNKNOWN | 50 | 0 | T |
| AW152000 | UNKNOWN | 74 | 0 | T |
| AW152000 | UNKNOWN | 21 | 284 | A |
| AW152000 | UNKNOWN | 14 | 196 | C |
| AW152000 | UNKNOWN | 12 | 174 | A |
| AW152024 | UNKNOWN | 95 | 0 | T |
| AW152024 | UNKNOWN | 19 | 313 | C |
| AW152024 | UNKNOWN | 18 | 158 | A |
| AW152024 | UNKNOWN | 13 | 133 | A |
| AW152024 | UNKNOWN | 13 | 269 | G |
| AW152024 | UNKNOWN | 12 | 190 | C |
| AW152026 | UNKNOWN | 15 | 11 | T |
| AW152035 | UNKNOWN | 50 | 0 | T |
| AW152053 | UNKNOWN | 22 | 0 | T |
| AW152054 | UNKNOWN | 7 | 90 | TTAT |
| AW152067 | UNKNOWN | 60 | 0 | T |
| AW152118 | UNKNOWN | 44 | 0 | T |
| AW152134 | UNKNOWN | 41 | 0 | T |
| AW152136 | UNKNOWN | 6.8 | 0 | ATTTT |
| AW152144 | UNKNOWN | 66 | 0 | T |
| AW152149 | UNKNOWN | 46 | 0 | T |
| AW152163 | UNKNOWN | 46 | 0 | T |
| AW152166 | UNKNOWN | 26 | 0 | T |
| AW152186 | UNKNOWN | 86 | 0 | T |
| AW152186 | UNKNOWN | 18 | 111 | A |
| AW152186 | UNKNOWN | 16 | 346 | C |
| AW152186 | UNKNOWN | 13 | 172 | G |
| AW152190 | UNKNOWN | 56 | 0 | T |
| AW152190 | UNKNOWN | 12 | 129 | G |
| AW152190 | UNKNOWN | 12 | 330 | C |
| AW152195 | UNKNOWN | 51 | 0 | T |
| AW152195 | UNKNOWN | 13 | 229 | C |
| AW152214 | UNKNOWN | 57 | 0 | T |
| AW152214 | UNKNOWN | 15 | 374 | G |
| AW152214 | UNKNOWN | 12 | 87 | A |
| AW152214 | UNKNOWN | 12 | 336 | G |
| AW152216 | UNKNOWN | 24 | 0 | T |
| AW152240 | UNKNOWN | 47 | 0 | T |
| AW152243 | UNKNOWN | 30 | 0 | T |
| AW152246 | UNKNOWN | 35 | 0 | T |
| AW152246 | UNKNOWN | 16 | 37 | G |
| AW152253 | UNKNOWN | 40 | 0 | T |
| AW152346 | UNKNOWN | 14 | 0 | T |
| AW152365 | UNKNOWN | 2.9 | 7 | TTTTTTTTTA (SEQ ID NO: 219) |
| AW152365 | UNKNOWN | 44 | 29 | T |
| AW152365 | UNKNOWN | 23 | 257 | A |
| AW152365 | UNKNOWN | 22 | 78 | G |
| AW152365 | UNKNOWN | 17 | 172 | A |
| AW152365 | UNKNOWN | 12 | 5 | T |
| AW152369 | UNKNOWN | 54 | 0 | T |
| AW152369 | UNKNOWN | 12 | 172 | A |
| AW152392 | UNKNOWN | 6 | 47 | CGG |
| AW152393 | UNKNOWN | 46 | 0 | T |
| AW152415 | UNKNOWN | 54 | 0 | T |
| AW152415 | UNKNOWN | 12 | 200 | G |
| AW152416 | UNKNOWN | 14 | 7 | A |
| AW152433 | UNKNOWN | 14 | 129 | A |

TABLE 1-continued

| Genbank # | Region | # reps | Position | Unit sequence |
|---|---|---|---|---|
| AW152448 | UNKNOWN | 78 | 0 | T |
| AW152448 | UNKNOWN | 15 | 216 | C |
| AW152448 | UNKNOWN | 12 | 144 | G |
| AW152459 | UNKNOWN | 96 | 0 | T |
| AW152459 | UNKNOWN | 20 | 296 | G |
| AW152459 | UNKNOWN | 16 | 202 | G |
| AW152459 | UNKNOWN | 15 | 281 | C |
| AW152459 | UNKNOWN | 14 | 158 | A |
| AW152459 | UNKNOWN | 13 | 103 | A |
| AW152469 | UNKNOWN | 89 | 0 | T |
| AW152469 | UNKNOWN | 18 | 174 | G |
| AW152469 | UNKNOWN | 16 | 156 | A |
| AW152469 | UNKNOWN | 13 | 114 | A |
| AW152487 | UNKNOWN | 53 | 0 | T |
| AW152494 | UNKNOWN | 80 | 0 | T |
| AW152494 | UNKNOWN | 12 | 157 | C |
| AW152520 | UNKNOWN | 21 | 0 | T |
| AW152533 | UNKNOWN | 47 | 0 | T |
| AW152533 | UNKNOWN | 18 | 249 | A |
| AW152536 | UNKNOWN | 72 | 0 | T |
| AW152536 | UNKNOWN | 17 | 190 | G |
| AW152536 | UNKNOWN | 15 | 207 | C |
| AW152538 | UNKNOWN | 25 | 0 | T |
| AW152550 | UNKNOWN | 67 | 0 | T |
| AW152550 | UNKNOWN | 17 | 138 | C |
| AW152550 | UNKNOWN | 12 | 85 | C |
| AW152559 | UNKNOWN | 51 | 2 | T |
| AW152559 | UNKNOWN | 12 | 124 | A |
| AW152568 | UNKNOWN | 71 | 0 | T |
| AW152587 | UNKNOWN | 71 | 0 | T |
| AW152587 | UNKNOWN | 19 | 285 | A |
| AW152587 | UNKNOWN | 13 | 189 | C |
| AW152590 | UNKNOWN | 27 | 0 | T |
| AW152604 | UNKNOWN | 76 | 0 | T |
| AW152604 | UNKNOWN | 15 | 164 | C |
| AW152604 | UNKNOWN | 14 | 341 | A |
| AW152604 | UNKNOWN | 13 | 90 | G |
| AW152604 | UNKNOWN | 13 | 141 | A |
| AW152615 | UNKNOWN | 47 | 0 | T |
| AW152621 | UNKNOWN | 43 | 0 | T |
| AW152624 | UNKNOWN | 15 | 0 | T |
| AW152637 | UNKNOWN | 78 | 0 | T |
| AW152637 | UNKNOWN | 12 | 363 | G |
| AW156888 | UNKNOWN | 52 | 0 | T |
| AW157035 | UNKNOWN | 32 | 0 | T |
| AW157096 | UNKNOWN | 53 | 0 | T |
| AW157096 | UNKNOWN | 12 | 280 | A |
| AW157099 | UNKNOWN | 19 | 173 | AC |
| AW157163 | UNKNOWN | 58 | 0 | T |
| AW157163 | UNKNOWN | 21 | 157 | A |
| AW157183 | UNKNOWN | 83 | 0 | T |
| AW157183 | UNKNOWN | 18 | 309 | C |
| AW157183 | UNKNOWN | 15 | 275 | G |
| AW157183 | UNKNOWN | 15 | 293 | C |
| AW157183 | UNKNOWN | 14 | 251 | A |
| AW157241 | UNKNOWN | 6.66 | 25 | TTA |
| AW157241 | UNKNOWN | 10.5 | 580 | TG |
| AW157250 | UNKNOWN | 53 | 0 | T |
| AW157289 | UNKNOWN | 21 | 0 | T |
| AW157301 | UNKNOWN | 63 | 0 | T |
| AW157370 | UNKNOWN | 57 | 0 | T |
| AW157392 | UNKNOWN | 60 | 0 | T |
| AW157392 | UNKNOWN | 14 | 221 | C |
| AW157424 | UNKNOWN | 20 | 430 | A |
| AW157424 | UNKNOWN | 12 | 10 | T |
| AW157558 | UNKNOWN | 57 | 0 | T |
| AW157558 | UNKNOWN | 16 | 114 | C |
| AW157573 | UNKNOWN | 51 | 0 | T |
| AW157599 | UNKNOWN | 3.8 | 3 | TTTTG |
| AW157767 | UNKNOWN | 86 | 0 | T |
| AW157767 | UNKNOWN | 23 | 133 | A |
| AW157767 | UNKNOWN | 14 | 266 | C |
| AW157772 | UNKNOWN | 19 | 0 | T |
| AW157789 | UNKNOWN | 41 | 0 | T |
| AW160916 | UNKNOWN | 83 | 217 | A |
| AW161567 | UNKNOWN | 8.33 | 105 | GCG |
| AW161670 | UNKNOWN | 38 | 0 | T |

TABLE 1-continued

| Genbank # | Region | # reps | Position | Unit sequence |
|---|---|---|---|---|
| AW161701 | UNKNOWN | 12 | 0 | T |
| AW161710 | UNKNOWN | 58 | 0 | T |
| AW161735 | UNKNOWN | 75 | 0 | T |
| AW161735 | UNKNOWN | 26 | 128 | C |
| AW161735 | UNKNOWN | 22 | 375 | G |
| AW161790 | UNKNOWN | 14 | 0 | T |
| AW161810 | UNKNOWN | 45 | 0 | T |
| AW161810 | UNKNOWN | 12 | 45 | C |
| AW161812 | UNKNOWN | 51 | 0 | T |
| AW161892 | UNKNOWN | 77 | 0 | T |
| AW161892 | UNKNOWN | 14 | 142 | A |
| AW161892 | UNKNOWN | 12 | 116 | G |
| AW161894 | UNKNOWN | 75 | 0 | T |
| AW161894 | UNKNOWN | 14 | 287 | G |
| AW161894 | UNKNOWN | 13 | 418 | C |
| AW161921 | UNKNOWN | 17 | 498 | G |
| AW162118 | UNKNOWN | 83 | 0 | T |
| AW162118 | UNKNOWN | 20 | 158 | A |
| AW162118 | UNKNOWN | 17 | 130 | G |
| AW162118 | UNKNOWN | 17 | 436 | C |
| AW162118 | UNKNOWN | 16 | 313 | C |
| AW162118 | UNKNOWN | 12 | 92 | A |
| AW162118 | UNKNOWN | 12 | 279 | C |
| AW162210 | UNKNOWN | 16 | 0 | T |
| AW162210 | UNKNOWN | 15 | 107 | A |
| AW162214 | UNKNOWN | 64 | 0 | T |
| AW162214 | UNKNOWN | 13 | 172 | C |
| AW162234 | UNKNOWN | 57 | 0 | T |
| AW162247 | UNKNOWN | 48 | 0 | T |
| AW162247 | UNKNOWN | 15 | 439 | G |
| AW162256 | UNKNOWN | 15 | 0 | T |
| AW162275 | UNKNOWN | 37 | 0 | T |
| AW162275 | UNKNOWN | 14 | 102 | G |
| AW162315 | UNKNOWN | 48 | 0 | T |
| AW162319 | UNKNOWN | 52 | 0 | T |
| AW162324 | UNKNOWN | 16 | 0 | T |
| AW162466 | UNKNOWN | 55 | 0 | T |
| AW162658 | UNKNOWN | 33 | 0 | T |
| AW162671 | UNKNOWN | 12 | 0 | T |
| AW162690 | UNKNOWN | 48 | 0 | T |
| AW162690 | UNKNOWN | 15 | 302 | A |
| AW162719 | UNKNOWN | 23 | 0 | T |
| AW162719 | UNKNOWN | 14 | 50 | A |
| AW162846 | UNKNOWN | 3.6 | 65 | AGCGC |
| AW163178 | UNKNOWN | 14 | 129 | A |
| AW163293 | UNKNOWN | 32 | 269 | A |
| AW165970 | UNKNOWN | 27 | 0 | T |
| AW165980 | UNKNOWN | 3.83 | 120 | GGCGGG |
| AW166119 | UNKNOWN | 3.8 | 498 | AAAAC |
| AW166133 | UNKNOWN | 6.5 | 519 | AG |
| AW166176 | UNKNOWN | 38 | 0 | T |
| AW166182 | UNKNOWN | 85 | 0 | T |
| AW166182 | UNKNOWN | 24 | 302 | G |
| AW166182 | UNKNOWN | 18 | 239 | A |
| AW166182 | UNKNOWN | 16 | 103 | A |
| AW166182 | UNKNOWN | 15 | 328 | C |
| AW166182 | UNKNOWN | 12 | 174 | C |
| AW166256 | UNKNOWN | 40 | 0 | T |
| AW166561 | UNKNOWN | 57 | 0 | T |
| AW166562 | UNKNOWN | 14 | 410 | G |
| AW166583 | UNKNOWN | 105 | 0 | T |
| AW166583 | UNKNOWN | 16 | 145 | A |
| AW166583 | UNKNOWN | 15 | 161 | G |
| AW166583 | UNKNOWN | 12 | 237 | C |
| AW166612 | UNKNOWN | 65 | 0 | T |
| AW166612 | UNKNOWN | 18 | 94 | A |
| AW166612 | UNKNOWN | 13 | 130 | C |
| AW166638 | UNKNOWN | 61 | 0 | T |
| AW166638 | UNKNOWN | 15 | 182 | G |
| AW166638 | UNKNOWN | 12 | 197 | A |
| AW166638 | UNKNOWN | 12 | 290 | C |
| AW166666 | UNKNOWN | 38 | 9 | T |
| AW166681 | UNKNOWN | 59 | 0 | T |
| AW166681 | UNKNOWN | 15 | 248 | G |
| AW166681 | UNKNOWN | 12 | 392 | C |
| AW166722 | UNKNOWN | 54 | 0 | T |
| AW166742 | UNKNOWN | 56 | 0 | T |

TABLE 1-continued

| Genbank # | Region | # reps | Position | Unit sequence |
|---|---|---|---|---|
| AW166746 | UNKNOWN | 63 | 0 | T |
| AW166746 | UNKNOWN | 12 | 129 | C |
| AW166760 | UNKNOWN | 28 | 0 | T |
| AW166801 | UNKNOWN | 47 | 0 | T |
| AW166801 | UNKNOWN | 12 | 149 | C |
| AW166808 | UNKNOWN | 20 | 365 | A |
| AW166842 | UNKNOWN | 35 | 0 | T |
| AW166847 | UNKNOWN | 20 | 0 | T |
| AW166861 | UNKNOWN | 56 | 0 | T |
| AW166861 | UNKNOWN | 15 | 326 | G |
| AW166864 | UNKNOWN | 35 | 0 | T |
| AW166870 | UNKNOWN | 62 | 0 | T |
| AW166870 | UNKNOWN | 13 | 62 | A |
| AW166887 | UNKNOWN | 32 | 0 | T |
| AW166903 | UNKNOWN | 107 | 0 | T |
| AW166903 | UNKNOWN | 16 | 179 | G |
| AW166903 | UNKNOWN | 13 | 107 | A |
| AW166903 | UNKNOWN | 13 | 255 | C |
| AW166906 | UNKNOWN | 19 | 0 | T |
| AW166908 | UNKNOWN | 69 | 0 | T |
| AW166908 | UNKNOWN | 13 | 422 | G |
| AW166922 | UNKNOWN | 27 | 0 | T |
| AW166926 | UNKNOWN | 51 | 0 | T |
| AW166934 | UNKNOWN | 37 | 0 | T |
| AW166937 | UNKNOWN | 64 | 0 | T |
| AW166959 | UNKNOWN | 50 | 0 | T |
| AW166959 | UNKNOWN | 16 | 91 | G |
| AW166959 | UNKNOWN | 16 | 384 | A |
| AW166963 | UNKNOWN | 63 | 0 | T |
| AW166963 | UNKNOWN | 13 | 239 | C |
| AW166963 | UNKNOWN | 12 | 270 | A |
| AW166968 | UNKNOWN | 14 | 345 | A |
| AW166970 | UNKNOWN | 119 | 0 | T |
| AW166970 | UNKNOWN | 23 | 242 | G |
| AW166970 | UNKNOWN | 21 | 322 | C |
| AW166970 | UNKNOWN | 18 | 152 | A |
| AW166970 | UNKNOWN | 12 | 120 | A |
| AW166970 | UNKNOWN | 12 | 140 | C |
| AW166975 | UNKNOWN | 75 | 0 | T |
| AW166975 | UNKNOWN | 12 | 170 | C |
| AW166975 | UNKNOWN | 12 | 224 | G |
| AW166977 | UNKNOWN | 61 | 0 | T |
| AW166979 | UNKNOWN | 72 | 0 | T |
| AW166979 | UNKNOWN | 17 | 255 | A |
| AW166999 | UNKNOWN | 64 | 0 | T |
| AW166999 | UNKNOWN | 13 | 354 | A |
| AW167000 | UNKNOWN | 43 | 0 | T |
| AW167006 | UNKNOWN | 43 | 0 | T |
| AW167006 | UNKNOWN | 19 | 417 | A |
| AW167007 | UNKNOWN | 62 | 0 | T |
| AW167021 | UNKNOWN | 77 | 0 | T |
| AW167021 | UNKNOWN | 16 | 164 | C |
| AW167021 | UNKNOWN | 14 | 77 | A |
| AW167022 | UNKNOWN | 12 | 0 | T |
| AW167033 | UNKNOWN | 51 | 0 | T |
| AW167060 | UNKNOWN | 13 | 417 | T |
| AW167083 | UNKNOWN | 76 | 0 | T |
| AW167083 | UNKNOWN | 15 | 187 | C |
| AW167083 | UNKNOWN | 14 | 247 | G |
| AW167086 | UNKNOWN | 72 | 0 | T |
| AW167086 | UNKNOWN | 13 | 311 | A |
| AW167091 | UNKNOWN | 36 | 0 | T |
| AW167098 | UNKNOWN | 41 | 0 | T |
| AW167105 | UNKNOWN | 58 | 0 | T |
| AW167146 | UNKNOWN | 77 | 0 | T |
| AW167146 | UNKNOWN | 18 | 105 | A |
| AW167146 | UNKNOWN | 13 | 428 | C |
| AW167146 | UNKNOWN | 12 | 142 | G |
| AW167148 | UNKNOWN | 13 | 409 | A |
| AW167155 | UNKNOWN | 47 | 0 | T |
| AW167157 | UNKNOWN | 62 | 0 | T |
| AW167157 | UNKNOWN | 25 | 327 | G |
| AW167157 | UNKNOWN | 12 | 85 | G |
| AW167161 | UNKNOWN | 36 | 0 | T |
| AW167174 | UNKNOWN | 54 | 0 | T |
| AW167174 | UNKNOWN | 24 | 395 | C |
| AW167174 | UNKNOWN | 12 | 87 | A |

TABLE 1-continued

| Genbank # | Region | # reps | Position | Unit sequence |
|---|---|---|---|---|
| AW167201 | UNKNOWN | 48 | 0 | T |
| AW167203 | UNKNOWN | 115 | 0 | T |
| AW167203 | UNKNOWN | 16 | 398 | C |
| AW167203 | UNKNOWN | 15 | 216 | A |
| AW167203 | UNKNOWN | 14 | 266 | G |
| AW167215 | UNKNOWN | 48 | 0 | T |
| AW167215 | UNKNOWN | 13 | 369 | A |
| AW167222 | UNKNOWN | 78 | 0 | T |
| AW167222 | UNKNOWN | 16 | 204 | C |
| AW167222 | UNKNOWN | 13 | 190 | G |
| AW167228 | UNKNOWN | 96 | 0 | T |
| AW167228 | UNKNOWN | 18 | 151 | C |
| AW167228 | UNKNOWN | 15 | 96 | A |
| AW167228 | UNKNOWN | 12 | 227 | G |
| AW167229 | UNKNOWN | 67 | 0 | T |
| AW167229 | UNKNOWN | 12 | 289 | A |
| AW167238 | UNKNOWN | 83 | 0 | T |
| AW167238 | UNKNOWN | 15 | 169 | A |
| AW167297 | UNKNOWN | 39 | 0 | T |
| AW167303 | UNKNOWN | 35 | 0 | T |
| AW167322 | UNKNOWN | 34 | 0 | T |
| AW167327 | UNKNOWN | 68 | 0 | T |
| AW167327 | UNKNOWN | 20 | 174 | G |
| AW167327 | UNKNOWN | 13 | 132 | C |
| AW167328 | UNKNOWN | 43 | 0 | T |
| AW167330 | UNKNOWN | 4.75 | 42 | TTTA |
| AW167336 | UNKNOWN | 27 | 0 | T |
| AW167343 | UNKNOWN | 24 | 215 | A |
| AW167358 | UNKNOWN | 44 | 0 | T |
| AW167362 | UNKNOWN | 31 | 0 | T |
| AW167397 | UNKNOWN | 50 | 0 | T |
| AW167397 | UNKNOWN | 12 | 247 | G |
| AW167406 | UNKNOWN | 18 | 295 | C |
| AW167410 | UNKNOWN | 97 | 0 | T |
| AW167410 | UNKNOWN | 18 | 159 | A |
| AW167410 | UNKNOWN | 12 | 190 | C |
| AW167422 | UNKNOWN | 55 | 0 | T |
| AW167448 | UNKNOWN | 74 | 0 | T |
| AW167448 | UNKNOWN | 14 | 125 | A |
| AW167469 | UNKNOWN | 66 | 15 | T |
| AW167469 | UNKNOWN | 15 | 298 | G |
| AW167469 | UNKNOWN | 12 | 274 | C |
| AW167469 | UNKNOWN | 12 | 286 | A |
| AW167470 | UNKNOWN | 40 | 0 | T |
| AW167509 | UNKNOWN | 26 | 0 | T |
| AW167563 | UNKNOWN | 28 | 0 | T |
| AW167569 | UNKNOWN | 45 | 0 | T |
| AW167664 | UNKNOWN | 39 | 0 | T |
| AW167763 | UNKNOWN | 30 | 0 | T |
| AW167776 | UNKNOWN | 124 | 0 | T |
| AW167776 | UNKNOWN | 22 | 367 | C |
| AW167776 | UNKNOWN | 21 | 412 | G |
| AW167776 | UNKNOWN | 16 | 177 | A |
| AW167776 | UNKNOWN | 16 | 193 | C |
| AW167776 | UNKNOWN | 15 | 278 | G |
| AW167776 | UNKNOWN | 12 | 165 | G |
| AW167777 | UNKNOWN | 56 | 0 | T |
| AW167777 | UNKNOWN | 16 | 118 | C |
| AW167777 | UNKNOWN | 14 | 195 | A |
| AW167777 | UNKNOWN | 12 | 85 | A |
| AW167795 | UNKNOWN | 41 | 0 | T |
| AW167796 | UNKNOWN | 45 | 0 | T |
| AW167829 | UNKNOWN | 7.5 | 15 | AT |
| AW167857 | UNKNOWN | 34 | 0 | T |
| AW167879 | UNKNOWN | 34 | 0 | T |
| AW167882 | UNKNOWN | 90 | 0 | T |
| AW167882 | UNKNOWN | 22 | 123 | G |
| AW167882 | UNKNOWN | 17 | 364 | C |
| AW167882 | UNKNOWN | 15 | 169 | A |
| AW167895 | UNKNOWN | 59 | 0 | T |
| AW167908 | UNKNOWN | 43 | 0 | T |
| AW167916 | UNKNOWN | 38 | 0 | T |
| AW167918 | UNKNOWN | 85 | 0 | T |
| AW167918 | UNKNOWN | 13 | 153 | G |
| AW167919 | UNKNOWN | 37 | 0 | T |
| AW167924 | UNKNOWN | 101 | 0 | T |
| AW167924 | UNKNOWN | 14 | 132 | G |

TABLE 1-continued

| Genbank # | Region | # reps | Position | Unit sequence |
|---|---|---|---|---|
| AW167926 | UNKNOWN | 64 | 0 | T |
| AW167926 | UNKNOWN | 14 | 200 | G |
| AW167926 | UNKNOWN | 12 | 188 | C |
| AW167943 | UNKNOWN | 44 | 0 | T |
| AW167972 | UNKNOWN | 24 | 0 | T |
| AW167975 | UNKNOWN | 18 | 0 | T |
| AW167975 | UNKNOWN | 15 | 96 | A |
| AW167975 | UNKNOWN | 12 | 133 | G |
| AW167983 | UNKNOWN | 48 | 0 | T |
| AW167998 | UNKNOWN | 6.33 | 82 | TCT |
| AW167998 | UNKNOWN | 17 | 256 | T |
| AW168001 | UNKNOWN | 96 | 0 | T |
| AW168001 | UNKNOWN | 15 | 197 | C |
| AW168001 | UNKNOWN | 13 | 172 | G |
| AW168008 | UNKNOWN | 28 | 0 | T |
| AW168008 | UNKNOWN | 17 | 310 | A |
| AW168012 | UNKNOWN | 68 | 0 | T |
| AW168031 | UNKNOWN | 79 | 0 | T |
| AW168031 | UNKNOWN | 12 | 101 | A |
| AW168031 | UNKNOWN | 12 | 139 | G |
| AW168080 | UNKNOWN | 38 | 0 | T |
| AW168086 | UNKNOWN | 65 | 0 | T |
| AW168086 | UNKNOWN | 13 | 90 | A |
| AW168087 | UNKNOWN | 21 | 0 | T |
| AW168121 | UNKNOWN | 98 | 0 | T |
| AW168121 | UNKNOWN | 16 | 154 | A |
| AW168121 | UNKNOWN | 15 | 361 | G |
| AW168161 | UNKNOWN | 20 | 0 | T |
| AW168200 | UNKNOWN | 59 | 0 | T |
| AW168200 | UNKNOWN | 15 | 116 | C |
| AW168221 | UNKNOWN | 38 | 15 | T |
| AW168221 | UNKNOWN | 13 | 1 | T |
| AW168255 | UNKNOWN | 33 | 0 | T |
| AW168296 | UNKNOWN | 77 | 0 | T |
| AW168296 | UNKNOWN | 16 | 317 | C |
| AW168296 | UNKNOWN | 14 | 342 | G |
| AW168296 | UNKNOWN | 12 | 158 | A |
| AW168313 | UNKNOWN | 31 | 0 | T |
| AW168313 | UNKNOWN | 12 | 166 | A |
| AW168315 | UNKNOWN | 20 | 0 | T |
| AW168320 | UNKNOWN | 74 | 0 | T |
| AW168320 | UNKNOWN | 15 | 172 | C |
| AW168333 | UNKNOWN | 50 | 0 | T |
| AW168373 | UNKNOWN | 77 | 0 | T |
| AW168382 | UNKNOWN | 12 | 306 | A |
| AW168384 | UNKNOWN | 118 | 0 | T |
| AW168384 | UNKNOWN | 30 | 313 | C |
| AW168384 | UNKNOWN | 16 | 296 | G |
| AW168384 | UNKNOWN | 14 | 206 | C |
| AW168400 | UNKNOWN | 61 | 0 | T |
| AW168400 | UNKNOWN | 13 | 337 | A |
| AW168402 | UNKNOWN | 78 | 0 | T |
| AW168406 | UNKNOWN | 59 | 0 | T |
| AW168407 | UNKNOWN | 16 | 0 | T |
| AW168410 | UNKNOWN | 19 | 0 | T |
| AW168417 | UNKNOWN | 46 | 0 | T |
| AW168417 | UNKNOWN | 13 | 145 | C |
| AW168417 | UNKNOWN | 12 | 215 | G |
| AW168425 | UNKNOWN | 98 | 0 | T |
| AW168425 | UNKNOWN | 15 | 222 | C |
| AW168428 | UNKNOWN | 23 | 0 | T |
| AW168433 | UNKNOWN | 17 | 375 | A |
| AW168451 | UNKNOWN | 70 | 0 | T |
| AW168451 | UNKNOWN | 21 | 168 | C |
| AW168451 | UNKNOWN | 17 | 144 | G |
| AW168451 | UNKNOWN | 13 | 121 | C |
| AW168452 | UNKNOWN | 88 | 0 | T |
| AW168452 | UNKNOWN | 18 | 263 | G |
| AW168452 | UNKNOWN | 17 | 128 | C |
| AW168452 | UNKNOWN | 16 | 145 | A |
| AW168452 | UNKNOWN | 16 | 223 | G |
| AW168452 | UNKNOWN | 12 | 113 | A |
| AW168472 | UNKNOWN | 44 | 0 | T |
| AW168473 | UNKNOWN | 58 | 0 | T |
| AW168473 | UNKNOWN | 13 | 86 | G |
| AW168485 | UNKNOWN | 81 | 0 | T |
| AW168485 | UNKNOWN | 12 | 112 | C |

TABLE 1-continued

| Genbank # | Region | # reps | Position | Unit sequence |
|---|---|---|---|---|
| AW168494 | UNKNOWN | 38 | 0 | T |
| AW168496 | UNKNOWN | 79 | 0 | T |
| AW168496 | UNKNOWN | 15 | 232 | C |
| AW168497 | UNKNOWN | 45 | 0 | T |
| AW168497 | UNKNOWN | 13 | 183 | A |
| AW168501 | UNKNOWN | 45 | 0 | T |
| AW168501 | UNKNOWN | 17 | 230 | A |
| AW168503 | UNKNOWN | 71 | 0 | T |
| AW168503 | UNKNOWN | 23 | 115 | G |
| AW168520 | UNKNOWN | 12 | 10 | TATT |
| AW168524 | UNKNOWN | 31 | 0 | T |
| AW168544 | UNKNOWN | 65 | 0 | T |
| AW168544 | UNKNOWN | 23 | 231 | A |
| AW168564 | UNKNOWN | 62 | 0 | T |
| AW168564 | UNKNOWN | 14 | 172 | C |
| AW168582 | UNKNOWN | 24 | 0 | T |
| AW168582 | UNKNOWN | 15 | 168 | C |
| AW168602 | UNKNOWN | 58 | 0 | T |
| AW168602 | UNKNOWN | 12 | 134 | A |
| AW168619 | UNKNOWN | 13 | 0 | T |
| AW168619 | UNKNOWN | 13 | 284 | G |
| AW168620 | UNKNOWN | 21 | 0 | T |
| AW168621 | UNKNOWN | 26 | 0 | T |
| AW168629 | UNKNOWN | 46 | 0 | T |
| AW168650 | UNKNOWN | 116 | 0 | T |
| AW168650 | UNKNOWN | 14 | 170 | C |
| AW168663 | UNKNOWN | 87 | 0 | T |
| AW168663 | UNKNOWN | 16 | 303 | G |
| AW168667 | UNKNOWN | 12 | 142 | T |
| AW168677 | UNKNOWN | 63 | 0 | T |
| AW168693 | UNKNOWN | 82 | 0 | T |
| AW168693 | UNKNOWN | 13 | 288 | C |
| AW168695 | UNKNOWN | 48 | 0 | T |
| AW168700 | UNKNOWN | 64 | 0 | T |
| AW168700 | UNKNOWN | 13 | 138 | C |
| AW168708 | UNKNOWN | 53 | 0 | T |
| AW168709 | UNKNOWN | 79 | 0 | T |
| AW168709 | UNKNOWN | 18 | 215 | C |
| AW168709 | UNKNOWN | 12 | 172 | C |
| AW168718 | UNKNOWN | 88 | 0 | T |
| AW168718 | UNKNOWN | 18 | 142 | C |
| AW168718 | UNKNOWN | 14 | 257 | G |
| AW168718 | UNKNOWN | 12 | 112 | A |
| AW168723 | UNKNOWN | 99 | 0 | T |
| AW168768 | UNKNOWN | 61 | 0 | T |
| AW168768 | UNKNOWN | 16 | 302 | C |
| AW168768 | UNKNOWN | 14 | 326 | G |
| AW168768 | UNKNOWN | 12 | 161 | C |
| AW168773 | UNKNOWN | 23 | 0 | T |
| AW168773 | UNKNOWN | 19 | 192 | A |
| AW168788 | UNKNOWN | 78 | 0 | T |
| AW168788 | UNKNOWN | 16 | 220 | A |
| AW168788 | UNKNOWN | 13 | 206 | G |
| AW168788 | UNKNOWN | 12 | 78 | A |
| AW168791 | UNKNOWN | 62 | 0 | T |
| AW168795 | UNKNOWN | 101 | 0 | T |
| AW168795 | UNKNOWN | 15 | 231 | C |
| AW168802 | UNKNOWN | 104 | 0 | T |
| AW168802 | UNKNOWN | 23 | 197 | A |
| AW168802 | UNKNOWN | 21 | 105 | C |
| AW168815 | UNKNOWN | 32 | 0 | T |
| AW168818 | UNKNOWN | 45 | 0 | T |
| AW168818 | UNKNOWN | 14 | 72 | G |
| AW168822 | UNKNOWN | 75 | 0 | T |
| AW168822 | UNKNOWN | 13 | 274 | C |
| AW168823 | UNKNOWN | 71 | 0 | T |
| AW168823 | UNKNOWN | 17 | 275 | C |
| AW168823 | UNKNOWN | 16 | 121 | A |
| AW168846 | UNKNOWN | 5 | 0 | ATTT |
| AW168848 | UNKNOWN | 14 | 0 | T |
| AW168849 | UNKNOWN | 63 | 0 | T |
| AW168849 | UNKNOWN | 15 | 81 | A |
| AW168857 | UNKNOWN | 16 | 71 | C |
| AW168857 | UNKNOWN | 12 | 40 | C |
| AW168864 | UNKNOWN | 71 | 0 | T |
| AW168871 | UNKNOWN | 27 | 0 | T |
| AW168875 | UNKNOWN | 63 | 0 | T |

TABLE 1-continued

| Genbank # | Region | # reps | Position | Unit sequence |
|---|---|---|---|---|
| AW168910 | UNKNOWN | 47 | 0 | T |
| AW168910 | UNKNOWN | 22 | 230 | A |
| AW168910 | UNKNOWN | 17 | 252 | C |
| AW168923 | UNKNOWN | 56 | 0 | T |
| AW168923 | UNKNOWN | 12 | 87 | A |
| AW168932 | UNKNOWN | 3.6 | 242 | AAATA |
| AW168932 | UNKNOWN | 28 | 0 | T |
| AW168934 | UNKNOWN | 51 | 0 | T |
| AW168934 | UNKNOWN | 15 | 315 | C |
| AW169001 | UNKNOWN | 79 | 0 | T |
| AW169001 | UNKNOWN | 17 | 139 | A |
| AW169001 | UNKNOWN | 13 | 197 | G |
| AW169001 | UNKNOWN | 13 | 212 | C |
| AW169001 | UNKNOWN | 12 | 87 | A |
| AW169001 | UNKNOWN | 12 | 100 | C |
| AW169024 | UNKNOWN | 9 | 465 | TA |
| AW169024 | UNKNOWN | 6.5 | 504 | AC |
| AW169029 | UNKNOWN | 21 | 0 | T |
| AW169039 | UNKNOWN | 87 | 0 | T |
| AW169039 | UNKNOWN | 20 | 164 | C |
| AW169039 | UNKNOWN | 13 | 144 | G |
| AW169056 | UNKNOWN | 70 | 0 | T |
| AW169130 | UNKNOWN | 84 | 0 | T |
| AW169130 | UNKNOWN | 21 | 299 | C |
| AW169130 | UNKNOWN | 15 | 205 | C |
| AW169130 | UNKNOWN | 13 | 286 | A |
| AW169130 | UNKNOWN | 12 | 136 | A |
| AW169132 | UNKNOWN | 110 | 4 | T |
| AW169132 | UNKNOWN | 15 | 149 | C |
| AW169132 | UNKNOWN | 15 | 168 | A |
| AW169132 | UNKNOWN | 14 | 135 | A |
| AW169132 | UNKNOWN | 12 | 205 | G |
| AW169141 | UNKNOWN | 37 | 0 | T |
| AW169149 | UNKNOWN | 89 | 0 | T |
| AW169149 | UNKNOWN | 25 | 322 | A |
| AW169149 | UNKNOWN | 22 | 224 | C |
| AW169149 | UNKNOWN | 12 | 143 | C |
| AW169199 | UNKNOWN | 45 | 0 | T |
| AW169199 | UNKNOWN | 16 | 119 | C |
| AW169199 | UNKNOWN | 12 | 172 | G |
| AW169209 | UNKNOWN | 58 | 0 | T |
| AW169209 | UNKNOWN | 13 | 310 | A |
| AW169213 | UNKNOWN | 63 | 0 | T |
| AW169224 | UNKNOWN | 18 | 0 | T |
| AW169234 | UNKNOWN | 81 | 0 | T |
| AW169234 | UNKNOWN | 18 | 109 | A |
| AW169234 | UNKNOWN | 15 | 229 | C |
| AW169234 | UNKNOWN | 13 | 190 | C |
| AW169234 | UNKNOWN | 12 | 162 | G |
| AW169240 | UNKNOWN | 14 | 0 | T |
| AW169270 | UNKNOWN | 16 | 0 | T |
| AW169275 | UNKNOWN | 96 | 0 | T |
| AW169275 | UNKNOWN | 13 | 149 | G |
| AW169291 | UNKNOWN | 59 | 0 | T |
| AW169291 | UNKNOWN | 12 | 160 | A |
| AW169297 | UNKNOWN | 72 | 0 | T |
| AW169297 | UNKNOWN | 15 | 416 | A |
| AW169315 | UNKNOWN | 6.5 | 5 | AC |
| AW169323 | UNKNOWN | 12 | 0 | T |
| AW169328 | UNKNOWN | 43 | 0 | T |
| AW169363 | UNKNOWN | 83 | 0 | T |
| AW169363 | UNKNOWN | 16 | 203 | C |
| AW169363 | UNKNOWN | 14 | 285 | A |
| AW169368 | UNKNOWN | 81 | 0 | T |
| AW169368 | UNKNOWN | 14 | 134 | A |
| AW169379 | UNKNOWN | 44 | 0 | T |
| AW169383 | UNKNOWN | 50 | 0 | T |
| AW169383 | UNKNOWN | 14 | 181 | C |
| AW169389 | UNKNOWN | 43 | 0 | T |
| AW169424 | UNKNOWN | 34 | 0 | T |
| AW169462 | UNKNOWN | 79 | 0 | T |
| AW169462 | UNKNOWN | 18 | 141 | C |
| AW169462 | UNKNOWN | 14 | 108 | A |
| AW169462 | UNKNOWN | 13 | 167 | G |
| AW169467 | UNKNOWN | 48 | 0 | T |
| AW169486 | UNKNOWN | 40 | 0 | T |
| AW169496 | UNKNOWN | 84 | 0 | T |

TABLE 1-continued

| Genbank # | Region | # reps | Position | Unit sequence |
|---|---|---|---|---|
| AW169496 | UNKNOWN | 14 | 111 | A |
| AW169514 | UNKNOWN | 46 | 0 | T |
| AW169514 | UNKNOWN | 12 | 146 | C |
| AW169518 | UNKNOWN | 27 | 0 | T |
| AW169518 | UNKNOWN | 12 | 213 | A |
| AW169527 | UNKNOWN | 94 | 8 | T |
| AW169527 | UNKNOWN | 20 | 177 | G |
| AW169527 | UNKNOWN | 17 | 134 | A |
| AW169527 | UNKNOWN | 14 | 109 | A |
| AW169527 | UNKNOWN | 14 | 225 | C |
| AW169587 | UNKNOWN | 65 | 2 | T |
| AW169587 | UNKNOWN | 16 | 198 | C |
| AW169587 | UNKNOWN | 12 | 104 | A |
| AW169597 | UNKNOWN | 29 | 0 | T |
| AW169598 | UNKNOWN | 67 | 0 | T |
| AW169598 | UNKNOWN | 25 | 122 | C |
| AW169604 | UNKNOWN | 82 | 3 | T |
| AW169604 | UNKNOWN | 24 | 127 | G |
| AW169604 | UNKNOWN | 13 | 157 | C |
| AW169618 | UNKNOWN | 62 | 0 | T |
| AW169624 | UNKNOWN | 74 | 0 | T |
| AW169624 | UNKNOWN | 12 | 154 | A |
| AW169626 | UNKNOWN | 51 | 0 | T |
| AW169628 | UNKNOWN | 55 | 0 | T |
| AW169629 | UNKNOWN | 24 | 0 | T |
| AW169630 | UNKNOWN | 47 | 0 | T |
| AW169634 | UNKNOWN | 97 | 0 | T |
| AW169634 | UNKNOWN | 21 | 155 | G |
| AW169634 | UNKNOWN | 15 | 120 | C |
| AW169634 | UNKNOWN | 13 | 260 | A |
| AW169635 | UNKNOWN | 41 | 0 | T |
| AW169643 | UNKNOWN | 55 | 0 | T |
| AW169653 | UNKNOWN | 124 | 0 | T |
| AW169653 | UNKNOWN | 19 | 162 | G |
| AW169653 | UNKNOWN | 17 | 130 | A |
| AW169653 | UNKNOWN | 15 | 147 | C |
| AW169654 | UNKNOWN | 45 | 4 | T |
| AW169658 | UNKNOWN | 63 | 53 | T |
| AW169658 | UNKNOWN | 50 | 0 | T |
| AW169658 | UNKNOWN | 16 | 223 | A |
| AW169658 | UNKNOWN | 14 | 272 | C |
| AW169671 | UNKNOWN | 113 | 0 | T |
| AW169671 | UNKNOWN | 15 | 194 | G |
| AW169684 | UNKNOWN | 53 | 0 | T |
| AW169684 | UNKNOWN | 12 | 61 | A |
| AW169782 | UNKNOWN | 5 | 0 | GTTT |
| AW169784 | UNKNOWN | 66 | 0 | T |
| AW169790 | UNKNOWN | 90 | 0 | T |
| AW169790 | UNKNOWN | 16 | 131 | C |
| AW169790 | UNKNOWN | 15 | 94 | A |
| AW169814 | UNKNOWN | 49 | 0 | T |
| AW169814 | UNKNOWN | 18 | 149 | G |
| AW169827 | UNKNOWN | 71 | 0 | T |
| AW169827 | UNKNOWN | 12 | 134 | C |
| AW169834 | UNKNOWN | 17 | 0 | T |
| AW169838 | UNKNOWN | 4.4 | 154 | AACCC |
| AW169838 | UNKNOWN | 31 | 0 | T |
| AW169848 | UNKNOWN | 79 | 0 | T |
| AW169848 | UNKNOWN | 13 | 208 | G |
| AW169848 | UNKNOWN | 12 | 196 | C |
| AW169853 | UNKNOWN | 78 | 0 | T |
| AW169853 | UNKNOWN | 15 | 208 | G |
| AW169853 | UNKNOWN | 12 | 187 | A |
| AW169896 | UNKNOWN | 15 | 0 | T |
| AW169951 | UNKNOWN | 18 | 0 | T |
| AW169987 | UNKNOWN | 11 | 347 | CAG |
| AW170100 | UNKNOWN | 19 | 0 | T |
| AW170100 | UNKNOWN | 16 | 72 | A |
| AW170310 | UNKNOWN | 12 | 27 | T |
| AW170496 | UNKNOWN | 17 | 0 | T |
| AW170632 | UNKNOWN | 29 | 0 | T |
| AW170635 | UNKNOWN | 86 | 0 | T |
| AW170635 | UNKNOWN | 17 | 172 | A |
| AW170673 | UNKNOWN | 68 | 0 | T |
| AW170674 | UNKNOWN | 74 | 0 | T |
| AW170674 | UNKNOWN | 20 | 96 | A |
| AW170682 | UNKNOWN | 77 | 0 | T |

TABLE 1-continued

| Genbank # | Region | # reps | Position | Unit sequence |
|---|---|---|---|---|
| AW170682 | UNKNOWN | 18 | 260 | C |
| AW170682 | UNKNOWN | 16 | 121 | A |
| AW170682 | UNKNOWN | 15 | 97 | A |
| AW170697 | UNKNOWN | 14 | 0 | T |
| AW170700 | UNKNOWN | 80 | 0 | T |
| AW170700 | UNKNOWN | 16 | 138 | G |
| AW170700 | UNKNOWN | 14 | 84 | A |
| AW170725 | UNKNOWN | 66 | 0 | T |
| AW170725 | UNKNOWN | 24 | 127 | A |
| AW170725 | UNKNOWN | 13 | 226 | G |
| AW170731 | UNKNOWN | 75 | 0 | T |
| AW170734 | UNKNOWN | 89 | 0 | T |
| AW170734 | UNKNOWN | 12 | 283 | G |
| AW170737 | UNKNOWN | 44 | 0 | T |
| AW170741 | UNKNOWN | 97 | 0 | T |
| AW170741 | UNKNOWN | 21 | 340 | C |
| AW170741 | UNKNOWN | 14 | 250 | G |
| AW170741 | UNKNOWN | 13 | 167 | C |
| AW170741 | UNKNOWN | 12 | 315 | A |
| AW170750 | UNKNOWN | 53 | 0 | T |
| AW170750 | UNKNOWN | 17 | 163 | A |
| AW170757 | UNKNOWN | 40 | 0 | T |
| AW170764 | UNKNOWN | 47 | 0 | T |
| AW170773 | UNKNOWN | 61 | 0 | T |
| AW170773 | UNKNOWN | 23 | 117 | G |
| AW170787 | UNKNOWN | 51 | 0 | T |
| AW170788 | UNKNOWN | 64 | 0 | T |
| AW170788 | UNKNOWN | 17 | 304 | C |
| AW170788 | UNKNOWN | 14 | 329 | G |
| AW170792 | UNKNOWN | 18 | 0 | T |
| AW172333 | UNKNOWN | 13 | 0 | T |
| AW172504 | UNKNOWN | 14 | 0 | T |
| AW172561 | UNKNOWN | 25 | 0 | T |
| AW172569 | UNKNOWN | 17 | 0 | T |
| AW172578 | UNKNOWN | 20 | 0 | T |
| AW172607 | UNKNOWN | 48 | 35 | T |
| AW172607 | UNKNOWN | 34 | 0 | T |
| AW172607 | UNKNOWN | 17 | 428 | C |
| AW172607 | UNKNOWN | 16 | 258 | C |
| AW172607 | UNKNOWN | 15 | 335 | G |
| AW172607 | UNKNOWN | 12 | 107 | A |
| AW172612 | UNKNOWN | 41 | 0 | T |
| AW172652 | UNKNOWN | 13 | 0 | T |
| AW172676 | UNKNOWN | 21 | 0 | T |
| AW172692 | UNKNOWN | 40 | 0 | T |
| AW172692 | UNKNOWN | 24 | 249 | A |
| AW172711 | UNKNOWN | 38 | 0 | T |
| AW172729 | UNKNOWN | 18 | 0 | T |
| AW172787 | UNKNOWN | 54 | 0 | T |
| AW172787 | UNKNOWN | 12 | 118 | C |
| AW172790 | UNKNOWN | 22 | 0 | T |
| AW172815 | UNKNOWN | 28 | 0 | T |
| AW172844 | UNKNOWN | 13 | 11 | T |
| AW172860 | UNKNOWN | 49 | 0 | T |
| AW172878 | UNKNOWN | 64 | 0 | T |
| AW172878 | UNKNOWN | 14 | 172 | C |
| AW172878 | UNKNOWN | 12 | 114 | G |
| AW172892 | UNKNOWN | 44 | 0 | T |
| AW172896 | UNKNOWN | 50 | 0 | T |
| AW172910 | UNKNOWN | 41 | 0 | T |
| AW172918 | UNKNOWN | 3.8 | 189 | TTTTA |
| AW172918 | UNKNOWN | 54 | 0 | T |
| AW172918 | UNKNOWN | 17 | 169 | C |
| AW172923 | UNKNOWN | 12 | 248 | T |
| AW172930 | UNKNOWN | 47 | 0 | T |
| AW172959 | UNKNOWN | 19 | 0 | T |
| AW172975 | UNKNOWN | 60 | 0 | T |
| AW172981 | UNKNOWN | 69 | 0 | T |
| AW172981 | UNKNOWN | 16 | 339 | C |
| AW172981 | UNKNOWN | 13 | 117 | C |
| AW172981 | UNKNOWN | 12 | 197 | G |
| AW172982 | UNKNOWN | 57 | 0 | T |
| AW172982 | UNKNOWN | 13 | 142 | C |
| AW173013 | UNKNOWN | 22 | 0 | T |
| AW173017 | UNKNOWN | 19 | 0 | T |
| AW173092 | UNKNOWN | 12 | 198 | A |
| AW173103 | UNKNOWN | 16 | 328 | A |

TABLE 1-continued

| Genbank # | Region | # reps | Position | Unit sequence |
|---|---|---|---|---|
| AW173114 | UNKNOWN | 23 | 164 | T |
| AW173190 | UNKNOWN | 13 | 421 | T |
| AW173191 | UNKNOWN | 22 | 0 | T |
| AW173191 | UNKNOWN | 15 | 241 | A |
| AW173248 | UNKNOWN | 16 | 367 | T |
| AW173251 | UNKNOWN | 3.6 | 120 | AAACA |
| AW173274 | UNKNOWN | 9 | 341 | AT |
| AW173370 | UNKNOWN | 14 | 0 | T |
| AW173396 | UNKNOWN | 12 | 0 | T |
| AW173401 | UNKNOWN | 13 | 91 | A |
| AW173422 | UNKNOWN | 38 | 0 | T |
| AW173422 | UNKNOWN | 18 | 383 | A |
| AW173428 | UNKNOWN | 60 | 0 | T |
| AW173436 | UNKNOWN | 17 | 49 | T |
| AW173443 | UNKNOWN | 12 | 153 | T |
| AW173453 | UNKNOWN | 37 | 0 | T |
| AW173500 | UNKNOWN | 40 | 0 | T |
| AW173534 | UNKNOWN | 12 | 0 | T |
| AW173558 | UNKNOWN | 32 | 0 | T |
| AW173605 | UNKNOWN | 48 | 0 | T |
| AW173605 | UNKNOWN | 15 | 105 | C |
| AW173608 | UNKNOWN | 12 | 0 | T |
| AW173633 | UNKNOWN | 63 | 0 | T |
| AW173633 | UNKNOWN | 19 | 116 | C |
| AW173633 | UNKNOWN | 13 | 341 | G |
| AW173633 | UNKNOWN | 12 | 82 | A |
| AW173633 | UNKNOWN | 12 | 163 | G |
| AW173642 | UNKNOWN | 50 | 0 | T |
| AW173673 | UNKNOWN | 62 | 0 | T |
| AW173673 | UNKNOWN | 18 | 88 | G |
| AW173673 | UNKNOWN | 13 | 312 | C |
| AW175973 | UNKNOWN | 16 | 658 | A |
| AW176112 | UNKNOWN | 12 | 218 | A |
| AW176270 | UNKNOWN | 15 | 252 | T |
| AW177224 | UNKNOWN | 23 | 384 | A |
| AW179349 | UNKNOWN | 16 | 89 | A |
| AW181907 | UNKNOWN | 24 | 0 | T |
| AW181916 | UNKNOWN | 42 | 0 | T |
| AW181916 | UNKNOWN | 13 | 375 | C |
| AW182051 | UNKNOWN | 17 | 0 | T |
| AW182090 | UNKNOWN | 12 | 12 | G |
| AW182137 | UNKNOWN | 13 | 0 | T |
| AW182141 | UNKNOWN | 17 | 528 | A |
| AW182203 | UNKNOWN | 19 | 0 | T |
| AW182258 | UNKNOWN | 37 | 0 | T |
| AW182263 | UNKNOWN | 12 | 0 | T |
| AW182284 | UNKNOWN | 7.5 | 411 | TG |
| AW182315 | UNKNOWN | 18 | 0 | T |
| AW182330 | UNKNOWN | 16 | 0 | T |
| AW182392 | UNKNOWN | 5.66 | 287 | GAG |
| AW182462 | UNKNOWN | 12 | 0 | T |
| AW182464 | UNKNOWN | 2.6 | 28 | AACATATATA (SEQ ID NO: 220) |
| AW182481 | UNKNOWN | 24 | 0 | T |
| AW182563 | UNKNOWN | 6.5 | 101 | TG |
| AW182675 | UNKNOWN | 5.75 | 308 | AAAC |
| AW182790 | UNKNOWN | 63 | 0 | T |
| AW182790 | UNKNOWN | 18 | 95 | G |
| AW182790 | UNKNOWN | 13 | 310 | A |
| AW182813 | UNKNOWN | 18 | 1 | T |
| AW182816 | UNKNOWN | 23 | 2 | T |
| AW182820 | UNKNOWN | 7 | 288 | GAGAATGGGTCCAGTTAATC (SEQ ID NO: 221) |
| AW182822 | UNKNOWN | 19 | 0 | T |
| AW182839 | UNKNOWN | 12 | 0 | T |
| AW182842 | UNKNOWN | 18 | 1 | T |
| AW182843 | UNKNOWN | 19 | 1 | T |
| AW182849 | UNKNOWN | 32 | 1 | T |
| AW182857 | UNKNOWN | 21 | 1 | T |
| AW182861 | UNKNOWN | 23 | 2 | T |
| AW182866 | UNKNOWN | 18 | 1 | T |
| AW182928 | UNKNOWN | 36 | 0 | T |
| AW182942 | UNKNOWN | 17 | 1 | T |
| AW182974 | UNKNOWN | 7 | 229 | TC |
| AW183052 | UNKNOWN | 13 | 428 | A |
| AW183061 | UNKNOWN | 5.66 | 314 | AAC |
| AW183130 | UNKNOWN | 118 | 0 | T |
| AW183130 | UNKNOWN | 14 | 141 | G |
| AW183130 | UNKNOWN | 12 | 198 | A |

TABLE 1-continued

| Genbank # | Region | # reps | Position | Unit sequence |
|---|---|---|---|---|
| AW183130 | UNKNOWN | 12 | 308 | C |
| AW183256 | UNKNOWN | 14 | 0 | T |
| AW183286 | UNKNOWN | 51 | 0 | T |
| AW183365 | UNKNOWN | 15 | 483 | G |
| AW183381 | UNKNOWN | 28 | 0 | T |
| AW183480 | UNKNOWN | 13 | 297 | A |
| AW183497 | UNKNOWN | 30 | 0 | T |
| AW183562 | UNKNOWN | 31 | 0 | T |
| AW183562 | UNKNOWN | 16 | 193 | G |
| AW183587 | UNKNOWN | 14 | 0 | T |
| AW183599 | UNKNOWN | 72 | 0 | T |
| AW183599 | UNKNOWN | 14 | 302 | C |
| AW183599 | UNKNOWN | 14 | 356 | G |
| AW183601 | UNKNOWN | 67 | 0 | T |
| AW183610 | UNKNOWN | 67 | 0 | T |
| AW183620 | UNKNOWN | 69 | 0 | T |
| AW183620 | UNKNOWN | 19 | 246 | C |
| AW183620 | UNKNOWN | 12 | 175 | G |
| AW183621 | UNKNOWN | 108 | 0 | T |
| AW183621 | UNKNOWN | 15 | 114 | G |
| AW183621 | UNKNOWN | 15 | 223 | C |
| AW183621 | UNKNOWN | 14 | 153 | A |
| AW183621 | UNKNOWN | 12 | 183 | C |
| AW183701 | UNKNOWN | 16 | 0 | T |
| AW183704 | UNKNOWN | 17 | 0 | T |
| AW183711 | UNKNOWN | 19 | 0 | T |
| AW183871 | UNKNOWN | 29 | 0 | T |
| AW183883 | UNKNOWN | 6.5 | 177 | CT |
| AW183940 | UNKNOWN | 15 | 0 | T |
| AW184038 | UNKNOWN | 23 | 0 | T |
| AW187988 | UNKNOWN | 13 | 0 | T |
| AW187993 | UNKNOWN | 14 | 194 | T |
| AW188017 | UNKNOWN | 15 | 0 | T |
| AW188041 | UNKNOWN | 19 | 0 | T |
| AW188050 | UNKNOWN | 16 | 41 | A |
| AW188086 | UNKNOWN | 15 | 0 | T |
| AW188135 | UNKNOWN | 12 | 0 | T |
| AW188199 | UNKNOWN | 6.5 | 272 | TA |
| AW188212 | UNKNOWN | 30 | 0 | T |
| AW188243 | UNKNOWN | 28 | 0 | T |
| AW188301 | UNKNOWN | 26 | 3 | T |
| AW188305 | UNKNOWN | 12 | 312 | A |
| AW188366 | UNKNOWN | 12 | 0 | T |
| AW188375 | UNKNOWN | 8.8 | 74 | GTTTT |
| AW188382 | UNKNOWN | 94 | 0 | T |
| AW188382 | UNKNOWN | 22 | 159 | C |
| AW188382 | UNKNOWN | 15 | 125 | A |
| AW188382 | UNKNOWN | 12 | 285 | G |
| AW188390 | UNKNOWN | 53 | 4 | T |
| AW188390 | UNKNOWN | 15 | 109 | A |
| AW188400 | UNKNOWN | 45 | 0 | T |
| AW188401 | UNKNOWN | 32 | 0 | T |
| AW188416 | UNKNOWN | 16 | 4 | T |
| AW188434 | UNKNOWN | 65 | 2 | T |
| AW188434 | UNKNOWN | 15 | 228 | A |
| AW188438 | UNKNOWN | 75 | 12 | T |
| AW188438 | UNKNOWN | 14 | 347 | C |
| AW188438 | UNKNOWN | 13 | 224 | G |
| AW188478 | UNKNOWN | 20 | 0 | T |
| AW188489 | UNKNOWN | 46 | 0 | T |
| AW188491 | UNKNOWN | 95 | 0 | T |
| AW188491 | UNKNOWN | 19 | 313 | C |
| AW188491 | UNKNOWN | 15 | 263 | G |
| AW188491 | UNKNOWN | 14 | 299 | A |
| AW188491 | UNKNOWN | 13 | 201 | G |
| AW188498 | UNKNOWN | 71 | 0 | T |
| AW188498 | UNKNOWN | 15 | 261 | G |
| AW188507 | UNKNOWN | 56 | 0 | T |
| AW188507 | UNKNOWN | 12 | 235 | C |
| AW188521 | UNKNOWN | 68 | 1 | T |
| AW188525 | UNKNOWN | 49 | 1 | T |
| AW188539 | UNKNOWN | 111 | 0 | T |
| AW188539 | UNKNOWN | 26 | 129 | A |
| AW188539 | UNKNOWN | 22 | 155 | C |
| AW188539 | UNKNOWN | 19 | 209 | G |
| AW188539 | UNKNOWN | 15 | 111 | C |
| AW188554 | UNKNOWN | 82 | 0 | T |

TABLE 1-continued

| Genbank # | Region | # reps | Position | Unit sequence |
|---|---|---|---|---|
| AW188554 | UNKNOWN | 13 | 170 | A |
| AW188568 | UNKNOWN | 15 | 4 | T |
| AW188575 | UNKNOWN | 19 | 0 | T |
| AW188587 | UNKNOWN | 37 | 0 | T |
| AW188591 | UNKNOWN | 36 | 0 | T |
| AW188592 | UNKNOWN | 35 | 0 | T |
| AW188595 | UNKNOWN | 53 | 0 | T |
| AW188599 | UNKNOWN | 7 | 144 | GT |
| AW188599 | UNKNOWN | 15 | 0 | T |
| AW188630 | UNKNOWN | 53 | 1 | T |
| AW188650 | UNKNOWN | 49 | 0 | T |
| AW188662 | UNKNOWN | 13 | 0 | T |
| AW188693 | UNKNOWN | 61 | 0 | T |
| AW188693 | UNKNOWN | 13 | 84 | A |
| AW188701 | UNKNOWN | 14 | 0 | T |
| AW188752 | UNKNOWN | 23 | 0 | T |
| AW188769 | UNKNOWN | 13 | 0 | T |
| AW188781 | UNKNOWN | 41 | 0 | T |
| AW188814 | UNKNOWN | 43 | 0 | T |
| AW188814 | UNKNOWN | 15 | 107 | C |
| AW188825 | UNKNOWN | 4.5 | 106 | AAGG |
| AW188825 | UNKNOWN | 40 | 0 | T |
| AW188834 | UNKNOWN | 14 | 0 | T |
| AW188954 | UNKNOWN | 20 | 0 | T |
| AW189002 | UNKNOWN | 75 | 0 | T |
| AW189002 | UNKNOWN | 20 | 100 | A |
| AW189003 | UNKNOWN | 43 | 0 | T |
| AW189036 | UNKNOWN | 38 | 0 | T |
| AW189085 | UNKNOWN | 39 | 0 | T |
| AW189113 | UNKNOWN | 25 | 80 | T |
| AW189126 | UNKNOWN | 56 | 0 | T |
| AW189126 | UNKNOWN | 14 | 219 | A |
| AW189134 | UNKNOWN | 56 | 0 | T |
| AW189148 | UNKNOWN | 63 | 0 | T |
| AW189148 | UNKNOWN | 13 | 360 | G |
| AW189159 | UNKNOWN | 12 | 0 | T |
| AW189164 | UNKNOWN | 51 | 0 | T |
| AW189164 | UNKNOWN | 13 | 185 | G |
| AW189189 | UNKNOWN | 53 | 0 | T |
| AW189189 | UNKNOWN | 17 | 74 | C |
| AW189190 | UNKNOWN | 44 | 0 | T |
| AW189190 | UNKNOWN | 12 | 76 | A |
| AW189191 | UNKNOWN | 42 | 0 | T |
| AW189196 | UNKNOWN | 52 | 0 | T |
| AW189245 | UNKNOWN | 79 | 0 | T |
| AW189245 | UNKNOWN | 16 | 400 | C |
| AW189250 | UNKNOWN | 44 | 0 | T |
| AW189268 | UNKNOWN | 83 | 0 | T |
| AW189268 | UNKNOWN | 18 | 160 | A |
| AW189268 | UNKNOWN | 18 | 263 | C |
| AW189268 | UNKNOWN | 14 | 146 | C |
| AW189270 | UNKNOWN | 78 | 0 | T |
| AW189274 | UNKNOWN | 33 | 29 | T |
| AW189274 | UNKNOWN | 19 | 0 | T |
| AW189274 | UNKNOWN | 13 | 125 | C |
| AW189274 | UNKNOWN | 13 | 356 | G |
| AW189290 | UNKNOWN | 23 | 0 | T |
| AW189299 | UNKNOWN | 33 | 0 | T |
| AW189301 | UNKNOWN | 78 | 0 | T |
| AW189415 | UNKNOWN | 78 | 0 | T |
| AW189415 | UNKNOWN | 17 | 129 | C |
| AW189415 | UNKNOWN | 17 | 151 | G |
| AW189415 | UNKNOWN | 17 | 168 | A |
| AW189424 | UNKNOWN | 81 | 0 | T |
| AW189424 | UNKNOWN | 15 | 220 | C |
| AW189424 | UNKNOWN | 15 | 348 | G |
| AW189424 | UNKNOWN | 12 | 155 | C |
| AW189473 | UNKNOWN | 51 | 0 | T |
| AW189473 | UNKNOWN | 15 | 236 | C |
| AW189473 | UNKNOWN | 12 | 157 | C |
| AW189504 | UNKNOWN | 37 | 0 | T |
| AW189548 | UNKNOWN | 45 | 0 | T |
| AW189549 | UNKNOWN | 74 | 0 | T |
| AW189549 | UNKNOWN | 13 | 222 | A |
| AW189563 | UNKNOWN | 49 | 0 | T |
| AW189563 | UNKNOWN | 12 | 158 | A |
| AW189602 | UNKNOWN | 23 | 0 | T |

TABLE 1-continued

| Genbank # | Region | # reps | Position | Unit sequence |
|---|---|---|---|---|
| AW189602 | UNKNOWN | 12 | 233 | G |
| AW189614 | UNKNOWN | 27 | 0 | T |
| AW189614 | UNKNOWN | 13 | 362 | G |
| AW189625 | UNKNOWN | 23 | 0 | T |
| AW189629 | UNKNOWN | 24 | 112 | T |
| AW189644 | UNKNOWN | 80 | 0 | T |
| AW189644 | UNKNOWN | 16 | 153 | A |
| AW189644 | UNKNOWN | 12 | 301 | G |
| AW189716 | UNKNOWN | 68 | 0 | T |
| AW189736 | UNKNOWN | 14 | 43 | T |
| AW189743 | UNKNOWN | 20 | 0 | T |
| AW189777 | UNKNOWN | 60 | 0 | T |
| AW189777 | UNKNOWN | 13 | 155 | C |
| AW189802 | UNKNOWN | 78 | 56 | A |
| AW189802 | UNKNOWN | 25 | 148 | T |
| AW189832 | UNKNOWN | 14 | 425 | A |
| AW189835 | UNKNOWN | 37 | 4 | T |
| AW189835 | UNKNOWN | 15 | 346 | A |
| AW189835 | UNKNOWN | 13 | 288 | G |
| AW189904 | UNKNOWN | 31 | 7 | T |
| AW189911 | UNKNOWN | 29 | 0 | T |
| AW189911 | UNKNOWN | 13 | 184 | A |
| AW189951 | UNKNOWN | 46 | 3 | T |
| AW189956 | UNKNOWN | 44 | 0 | T |
| AW189964 | UNKNOWN | 67 | 0 | T |
| AW190042 | UNKNOWN | 96 | 0 | T |
| AW190042 | UNKNOWN | 22 | 153 | G |
| AW190042 | UNKNOWN | 16 | 133 | A |
| AW190042 | UNKNOWN | 13 | 120 | C |
| AW190053 | UNKNOWN | 90 | 0 | T |
| AW190053 | UNKNOWN | 16 | 375 | C |
| AW190053 | UNKNOWN | 13 | 111 | A |
| AW190068 | UNKNOWN | 36 | 0 | T |
| AW190069 | UNKNOWN | 88 | 9 | T |
| AW190069 | UNKNOWN | 14 | 157 | C |
| AW190069 | UNKNOWN | 12 | 220 | G |
| AW190143 | UNKNOWN | 22 | 0 | T |
| AW190183 | UNKNOWN | 5.66 | 156 | GAG |
| AW190194 | UNKNOWN | 85 | 8 | T |
| AW190194 | UNKNOWN | 18 | 93 | A |
| AW190194 | UNKNOWN | 12 | 273 | G |
| AW190215 | UNKNOWN | 20 | 0 | T |
| AW190233 | UNKNOWN | 38 | 0 | T |
| AW190242 | UNKNOWN | 56 | 0 | T |
| AW190254 | UNKNOWN | 9.5 | 434 | AT |
| AW190254 | UNKNOWN | 16 | 0 | T |
| AW190263 | UNKNOWN | 51 | 0 | T |
| AW190266 | UNKNOWN | 67 | 0 | T |
| AW190286 | UNKNOWN | 97 | 10 | T |
| AW190286 | UNKNOWN | 23 | 198 | C |
| AW190286 | UNKNOWN | 15 | 145 | A |
| AW190286 | UNKNOWN | 13 | 160 | G |
| AW190297 | UNKNOWN | 53 | 0 | T |
| AW190297 | UNKNOWN | 19 | 91 | A |
| AW190305 | UNKNOWN | 29 | 0 | T |
| AW190314 | UNKNOWN | 50 | 9 | T |
| AW190334 | UNKNOWN | 4 | 207 | AAAAT |
| AW190408 | UNKNOWN | 40 | 0 | T |
| AW190428 | UNKNOWN | 55 | 0 | T |
| AW190428 | UNKNOWN | 14 | 216 | C |
| AW190452 | UNKNOWN | 37 | 7 | T |
| AW190454 | UNKNOWN | 12 | 0 | T |
| AW190465 | UNKNOWN | 46 | 0 | T |
| AW190465 | UNKNOWN | 14 | 200 | G |
| AW190471 | UNKNOWN | 48 | 0 | T |
| AW190480 | UNKNOWN | 16 | 307 | A |
| AW190480 | UNKNOWN | 15 | 0 | T |
| AW190482 | UNKNOWN | 49 | 8 | T |
| AW190482 | UNKNOWN | 12 | 107 | A |
| AW190487 | UNKNOWN | 56 | 0 | T |
| AW190487 | UNKNOWN | 14 | 343 | G |
| AW190487 | UNKNOWN | 13 | 188 | C |
| AW190487 | UNKNOWN | 12 | 236 | A |
| AW190493 | UNKNOWN | 14 | 285 | A |
| AW190493 | UNKNOWN | 12 | 310 | C |
| AW190494 | UNKNOWN | 31 | 0 | T |
| AW190505 | UNKNOWN | 16 | 193 | T |

TABLE 1-continued

| Genbank # | Region | # reps | Position | Unit sequence |
|---|---|---|---|---|
| AW190517 | UNKNOWN | 14 | 0 | T |
| AW190523 | UNKNOWN | 37 | 0 | T |
| AW190540 | UNKNOWN | 36 | 0 | T |
| AW190563 | UNKNOWN | 17 | 247 | A |
| AW190618 | UNKNOWN | 32 | 0 | T |
| AW190621 | UNKNOWN | 17 | 0 | T |
| AW190660 | UNKNOWN | 60 | 0 | T |
| AW190662 | UNKNOWN | 83 | 4 | T |
| AW190662 | UNKNOWN | 15 | 92 | G |
| AW190662 | UNKNOWN | 15 | 297 | C |
| AW190688 | UNKNOWN | 44 | 0 | T |
| AW190694 | UNKNOWN | 37 | 7 | T |
| AW190694 | UNKNOWN | 12 | 129 | A |
| AW190722 | UNKNOWN | 38 | 7 | T |
| AW190722 | UNKNOWN | 13 | 83 | C |
| AW190762 | UNKNOWN | 39 | 0 | T |
| AW190808 | UNKNOWN | 49 | 8 | T |
| AW190823 | UNKNOWN | 14 | 0 | T |
| AW190881 | UNKNOWN | 18 | 0 | T |
| AW190891 | UNKNOWN | 59 | 10 | T |
| AW190891 | UNKNOWN | 14 | 178 | G |
| AW190891 | UNKNOWN | 12 | 102 | C |
| AW190913 | UNKNOWN | 35 | 10 | T |
| AW190928 | UNKNOWN | 15 | 0 | T |
| AW190943 | UNKNOWN | 20 | 0 | T |
| AW190944 | UNKNOWN | 25 | 6 | T |
| AW190957 | UNKNOWN | 23 | 0 | T |
| AW191012 | UNKNOWN | 48 | 11 | T |
| AW191012 | UNKNOWN | 15 | 274 | G |
| AW191012 | UNKNOWN | 12 | 187 | G |
| AW191032 | UNKNOWN | 18 | 0 | T |
| AW191056 | UNKNOWN | 37 | 0 | T |
| AW191892 | UNKNOWN | 92 | 0 | T |
| AW191892 | UNKNOWN | 18 | 137 | A |
| AW191892 | UNKNOWN | 16 | 204 | G |
| AW191892 | UNKNOWN | 14 | 245 | C |
| AW191897 | UNKNOWN | 7 | 96 | TA |
| AW191897 | UNKNOWN | 38 | 0 | T |
| AW191901 | UNKNOWN | 36 | 0 | T |
| AW191916 | UNKNOWN | 99 | 0 | T |
| AW191916 | UNKNOWN | 12 | 282 | C |
| AW191929 | UNKNOWN | 43 | 0 | T |
| AW191959 | UNKNOWN | 76 | 0 | T |
| AW191959 | UNKNOWN | 13 | 100 | A |
| AW191959 | UNKNOWN | 12 | 242 | G |
| AW191976 | UNKNOWN | 14 | 0 | T |
| AW192042 | UNKNOWN | 74 | 0 | T |
| AW192042 | UNKNOWN | 15 | 84 | A |
| AW192052 | UNKNOWN | 77 | 0 | T |
| AW192052 | UNKNOWN | 17 | 196 | G |
| AW192109 | UNKNOWN | 58 | 0 | T |
| AW192109 | UNKNOWN | 16 | 247 | G |
| AW192111 | UNKNOWN | 23 | 352 | A |
| AW192111 | UNKNOWN | 17 | 322 | A |
| AW192156 | UNKNOWN | 36 | 0 | T |
| AW192161 | UNKNOWN | 45 | 0 | T |
| AW192226 | UNKNOWN | 115 | 0 | T |
| AW192226 | UNKNOWN | 14 | 182 | A |
| AW192226 | UNKNOWN | 13 | 115 | G |
| AW192228 | UNKNOWN | 79 | 0 | T |
| AW192228 | UNKNOWN | 13 | 102 | A |
| AW192228 | UNKNOWN | 12 | 251 | G |
| AW192241 | UNKNOWN | 66 | 0 | T |
| AW192241 | UNKNOWN | 19 | 141 | C |
| AW192245 | UNKNOWN | 53 | 19 | T |
| AW192245 | UNKNOWN | 16 | 130 | C |
| AW192245 | UNKNOWN | 12 | 146 | A |
| AW192268 | UNKNOWN | 19.5 | 310 | TG |
| AW192268 | UNKNOWN | 22 | 0 | T |
| AW192278 | UNKNOWN | 15 | 0 | T |
| AW192288 | UNKNOWN | 83 | 0 | T |
| AW192288 | UNKNOWN | 16 | 156 | A |
| AW192288 | UNKNOWN | 15 | 141 | C |
| AW192294 | UNKNOWN | 26 | 0 | T |
| AW192300 | UNKNOWN | 59 | 0 | T |
| AW192300 | UNKNOWN | 25 | 91 | G |
| AW192346 | UNKNOWN | 32 | 0 | T |

TABLE 1-continued

| Genbank # | Region | # reps | Position | Unit sequence |
|---|---|---|---|---|
| AW192363 | UNKNOWN | 53 | 0 | T |
| AW192375 | UNKNOWN | 101 | 0 | T |
| AW192375 | UNKNOWN | 23 | 101 | G |
| AW192375 | UNKNOWN | 16 | 124 | C |
| AW192375 | UNKNOWN | 14 | 151 | A |
| AW192461 | UNKNOWN | 78 | 0 | T |
| AW192461 | UNKNOWN | 13 | 167 | G |
| AW192525 | UNKNOWN | 15 | 0 | T |
| AW192547 | UNKNOWN | 17 | 0 | T |
| AW192633 | UNKNOWN | 42 | 0 | T |
| AW192652 | UNKNOWN | 93 | 0 | T |
| AW192652 | UNKNOWN | 21 | 106 | A |
| AW192652 | UNKNOWN | 12 | 233 | C |
| AW192687 | UNKNOWN | 89 | 0 | T |
| AW192687 | UNKNOWN | 17 | 306 | G |
| AW192687 | UNKNOWN | 14 | 151 | A |
| AW192687 | UNKNOWN | 13 | 183 | G |
| AW192687 | UNKNOWN | 13 | 281 | C |
| AW192701 | UNKNOWN | 96 | 0 | T |
| AW192701 | UNKNOWN | 20 | 131 | G |
| AW192701 | UNKNOWN | 16 | 98 | A |
| AW192701 | UNKNOWN | 12 | 172 | C |
| AW192703 | UNKNOWN | 12 | 416 | A |
| AW192712 | UNKNOWN | 87 | 0 | T |
| AW192712 | UNKNOWN | 18 | 171 | A |
| AW192712 | UNKNOWN | 13 | 196 | C |
| AW192770 | UNKNOWN | 38 | 11 | T |
| AW192782 | UNKNOWN | 38 | 9 | T |
| AW192842 | UNKNOWN | 44 | 0 | T |
| AW192881 | UNKNOWN | 4.59 | 361 | AAAG |
| AW192881 | UNKNOWN | 16 | 349 | A |
| AW192976 | UNKNOWN | 79 | 0 | T |
| AW192976 | UNKNOWN | 16 | 339 | C |
| AW192976 | UNKNOWN | 14 | 223 | C |
| AW193000 | UNKNOWN | 100 | 0 | T |
| AW193000 | UNKNOWN | 13 | 221 | G |
| AW193000 | UNKNOWN | 12 | 242 | A |
| AW193007 | UNKNOWN | 82 | 6 | T |
| AW193007 | UNKNOWN | 17 | 114 | G |
| AW193007 | UNKNOWN | 12 | 132 | A |
| AW193026 | UNKNOWN | 90 | 0 | T |
| AW193027 | UNKNOWN | 85 | 0 | T |
| AW193027 | UNKNOWN | 16 | 184 | G |
| AW193027 | UNKNOWN | 13 | 92 | A |
| AW193027 | UNKNOWN | 13 | 153 | G |
| AW193038 | UNKNOWN | 63 | 0 | T |
| AW193049 | UNKNOWN | 49 | 0 | T |
| AW193049 | UNKNOWN | 13 | 256 | A |
| AW193092 | UNKNOWN | 45 | 0 | T |
| AW193092 | UNKNOWN | 12 | 114 | A |
| AW193120 | UNKNOWN | 61 | 0 | T |
| AW193125 | UNKNOWN | 2.83 | 209 | CCCCGGGGGGGG (SEQ ID NO: 222) |
| AW193125 | UNKNOWN | 79 | 0 | T |
| AW193125 | UNKNOWN | 13 | 146 | A |
| AW193125 | UNKNOWN | 12 | 178 | C |
| AW193134 | UNKNOWN | 98 | 0 | T |
| AW193134 | UNKNOWN | 14 | 104 | G |
| AW193134 | UNKNOWN | 14 | 143 | A |
| AW193T39 | UNKNOWN | 79 | 0 | T |
| AW193139 | UNKNOWN | 12 | 122 | C |
| AW193141 | UNKNOWN | 85 | 0 | T |
| AW193141 | UNKNOWN | 12 | 125 | A |
| AW193177 | UNKNOWN | 46 | 0 | T |
| AW193203 | UNKNOWN | 72 | 0 | T |
| AW193203 | UNKNOWN | 12 | 150 | G |
| AW193231 | UNKNOWN | 79 | 0 | T |
| AW193231 | UNKNOWN | 16 | 85 | A |
| AW193236 | UNKNOWN | 81 | 0 | T |
| AW193236 | UNKNOWN | 21 | 233 | A |
| AW193246 | UNKNOWN | 54 | 0 | T |
| AW193274 | UNKNOWN | 77 | 0 | T |
| AW193288 | UNKNOWN | 89 | 0 | T |
| AW193288 | UNKNOWN | 17 | 299 | A |
| AW193299 | UNKNOWN | 49 | 0 | T |
| AW193300 | UNKNOWN | 33 | 0 | T |
| AW193344 | UNKNOWN | 54 | 0 | T |
| AW193358 | UNKNOWN | 21 | 0 | T |

TABLE 1-continued

| Genbank # | Region | # reps | Position | Unit sequence |
|---|---|---|---|---|
| AW193389 | UNKNOWN | 42 | 0 | T |
| AW193410 | UNKNOWN | 13.33 | 19 | TTA |
| AW193416 | UNKNOWN | 7 | 58 | TG |
| AW193416 | UNKNOWN | 6.5 | 45 | TA |
| AW193426 | UNKNOWN | 32 | 0 | T |
| AW193449 | UNKNOWN | 39 | 0 | T |
| AW193457 | UNKNOWN | 64 | 0 | T |
| AW193457 | UNKNOWN | 14 | 190 | G |
| AW193465 | UNKNOWN | 57 | 0 | T |
| AW193465 | UNKNOWN | 13 | 171 | G |
| AW193467 | UNKNOWN | 65 | 0 | T |
| AW193496 | UNKNOWN | 33 | 0 | T |
| AW193499 | UNKNOWN | 12 | 0 | T |
| AW193524 | UNKNOWN | 53 | 0 | T |
| AW193524 | UNKNOWN | 13 | 161 | G |
| AW193528 | UNKNOWN | 54 | 0 | T |
| AW193528 | UNKNOWN | 13 | 248 | G |
| AW193530 | UNKNOWN | 99 | 0 | T |
| AW193530 | UNKNOWN | 23 | 239 | C |
| AW193530 | UNKNOWN | 22 | 159 | C |
| AW193530 | UNKNOWN | 21 | 99 | A |
| AW193537 | UNKNOWN | 15 | 0 | T |
| AW193606 | UNKNOWN | 43 | 11 | T |
| AW193606 | UNKNOWN | 12 | 658 | G |
| AW193620 | UNKNOWN | 46 | 0 | T |
| AW193622 | UNKNOWN | 32 | 0 | T |
| AW193635 | UNKNOWN | 108 | 0 | T |
| AW193635 | UNKNOWN | 14 | 263 | C |
| AW193635 | UNKNOWN | 13 | 114 | A |
| AW193635 | UNKNOWN | 12 | 293 | G |
| AW193670 | UNKNOWN | 41 | 0 | T |
| AW193743 | UNKNOWN | 33 | 26 | T |
| AW193743 | UNKNOWN | 25 | 0 | T |
| AW193760 | UNKNOWN | 4.75 | 97 | TTTG |
| AW193761 | UNKNOWN | 15 | 11 | T |
| AW193841 | UNKNOWN | 52 | 24 | T |
| AW193841 | UNKNOWN | 23 | 0 | T |
| AW193841 | UNKNOWN | 14 | 211 | C |
| AW193841 | UNKNOWN | 12 | 185 | A |
| AW193843 | UNKNOWN | 74 | 0 | T |
| AW193843 | UNKNOWN | 17 | 260 | A |
| AW193843 | UNKNOWN | 13 | 188 | A |
| AW193850 | UNKNOWN | 60 | 0 | T |
| AW193854 | UNKNOWN | 22 | 0 | T |
| AW193872 | UNKNOWN | 69 | 8 | T |
| AW193872 | UNKNOWN | 17 | 109 | G |
| AW193883 | UNKNOWN | 19 | 186 | A |
| AW193883 | UNKNOWN | 13 | 306 | G |
| AW193883 | UNKNOWN | 12 | 249 | G |
| AW193883 | UNKNOWN | 12 | 284 | C |
| AW193886 | UNKNOWN | 20 | 0 | T |
| AW193887 | UNKNOWN | 57 | 0 | T |
| AW193888 | UNKNOWN | 66 | 0 | T |
| AW193888 | UNKNOWN | 15 | 146 | C |
| AW193894 | UNKNOWN | 65 | 0 | T |
| AW193894 | UNKNOWN | 16 | 392 | A |
| AW193911 | UNKNOWN | 96 | 0 | T |
| AW193911 | UNKNOWN | 16 | 136 | A |
| AW193911 | UNKNOWN | 14 | 224 | G |
| AW193922 | UNKNOWN | 49 | 0 | T |
| AW193922 | UNKNOWN | 13 | 259 | G |
| AW193922 | UNKNOWN | 12 | 194 | C |
| AW193949 | UNKNOWN | 69 | 0 | T |
| AW193949 | UNKNOWN | 32 | 251 | A |
| AW193949 | UNKNOWN | 27 | 121 | C |
| AW193949 | UNKNOWN | 17 | 213 | A |
| AW193975 | UNKNOWN | 44 | 0 | T |
| AW193975 | UNKNOWN | 14 | 119 | A |
| AW193988 | UNKNOWN | 25 | 0 | T |
| AW193988 | UNKNOWN | 13 | 80 | A |
| AW194014 | UNKNOWN | 57 | 0 | T |
| AW194014 | UNKNOWN | 16 | 90 | C |
| AW194053 | UNKNOWN | 27 | 0 | T |
| AW194054 | UNKNOWN | 14 | 208 | A |
| AW194079 | UNKNOWN | 59 | 0 | T |
| AW194126 | UNKNOWN | 20 | 0 | T |
| AW194185 | UNKNOWN | 72 | 0 | T |

TABLE 1-continued

| Genbank # | Region | # reps | Position | Unit sequence |
|---|---|---|---|---|
| AW194185 | UNKNOWN | 15 | 284 | G |
| AW194189 | UNKNOWN | 4.5 | 104 | AAGG |
| AW194189 | UNKNOWN | 40 | 0 | T |
| AW194213 | UNKNOWN | 29 | 0 | T |
| AW194213 | UNKNOWN | 14 | 160 | A |
| AW194230 | UNKNOWN | 36 | 0 | T |
| AW194232 | UNKNOWN | 53 | 0 | T |
| AW194253 | UNKNOWN | 18 | 128 | A |
| AW194260 | UNKNOWN | 33 | 0 | T |
| AW194266 | UNKNOWN | 3.66 | 256 | CCTTGG |
| AW194266 | UNKNOWN | 44 | 0 | T |
| AW194266 | UNKNOWN | 13 | 117 | G |
| AW194292 | UNKNOWN | 14 | 0 | T |
| AW194293 | UNKNOWN | 26 | 11 | T |
| AW194299 | UNKNOWN | 6.75 | 427 | TTTA |
| AW194299 | UNKNOWN | 17 | 11 | T |
| AW194305 | UNKNOWN | 51 | 0 | T |
| AW194305 | UNKNOWN | 13 | 291 | A |
| AW194312 | UNKNOWN | 37 | 0 | T |
| AW194312 | UNKNOWN | 14 | 126 | C |
| AW194318 | UNKNOWN | 43 | 0 | T |
| AW194318 | UNKNOWN | 13 | 232 | A |
| AW194379 | UNKNOWN | 12 | 0 | T |
| AW194410 | UNKNOWN | 57 | 0 | T |
| AW194433 | UNKNOWN | 60 | 0 | T |
| AW194441 | UNKNOWN | 87 | 1 | T |
| AW194441 | UNKNOWN | 22 | 146 | C |
| AW194441 | UNKNOWN | 19 | 327 | A |
| AW194441 | UNKNOWN | 18 | 128 | A |
| AW194625 | UNKNOWN | 3.6 | 186 | AGTTT |
| AW194742 | UNKNOWN | 37 | 0 | T |
| AW194742 | UNKNOWN | 13 | 70 | G |
| AW194747 | UNKNOWN | 50 | 0 | T |
| AW194747 | UNKNOWN | 16 | 234 | C |
| AW194771 | UNKNOWN | 35 | 0 | T |
| AW194907 | UNKNOWN | 13 | 43 | A |
| AW194981 | UNKNOWN | 29 | 0 | T |
| AW195019 | UNKNOWN | 15 | 107 | A |
| AW195169 | UNKNOWN | 52 | 0 | T |
| AW195183 | UNKNOWN | 16 | 0 | T |
| AW195238 | UNKNOWN | 31 | 0 | T |
| AW195250 | UNKNOWN | 17 | 2 | T |
| AW195270 | UNKNOWN | 70 | 0 | T |
| AW195284 | UNKNOWN | 46 | 7 | T |
| AW195313 | UNKNOWN | 46 | 0 | T |
| AW195336 | UNKNOWN | 12 | 1 | T |
| AW195351 | UNKNOWN | 23 | 0 | T |
| AW195444 | UNKNOWN | 41 | 0 | T |
| AW195582 | UNKNOWN | 21 | 0 | T |
| AW195586 | UNKNOWN | 15 | 0 | T |
| AW195640 | UNKNOWN | 5 | 407 | AAAAC |
| AW195806 | UNKNOWN | 12 | 0 | T |
| AW195854 | UNKNOWN | 42 | 0 | T |
| AW195880 | UNKNOWN | 6.66 | 118 | AGC |
| AW195892 | UNKNOWN | 17 | 222 | T |
| AW195932 | UNKNOWN | 16 | 0 | T |
| AW195933 | UNKNOWN | 15 | 143 | A |
| AW195943 | UNKNOWN | 58 | 0 | T |
| AW195943 | UNKNOWN | 19 | 249 | A |
| AW195943 | UNKNOWN | 13 | 154 | A |
| AW195957 | UNKNOWN | 125 | 0 | T |
| AW195957 | UNKNOWN | 20 | 144 | A |
| AW195957 | UNKNOWN | 15 | 125 | G |
| AW195957 | UNKNOWN | 15 | 244 | C |
| AW195968 | UNKNOWN | 108 | 0 | T |
| AW195968 | UNKNOWN | 16 | 200 | C |
| AW195968 | UNKNOWN | 14 | 253 | G |
| AW195969 | UNKNOWN | 112 | 0 | T |
| AW195969 | UNKNOWN | 17 | 152 | A |
| AW195969 | UNKNOWN | 17 | 205 | C |
| AW195999 | UNKNOWN | 41 | 0 | T |
| AW196029 | UNKNOWN | 38 | 0 | T |
| AW196037 | UNKNOWN | 83 | 0 | T |
| AW196037 | UNKNOWN | 22 | 237 | C |
| AW196037 | UNKNOWN | 16 | 142 | A |
| AW196037 | UNKNOWN | 15 | 159 | C |
| AW196075 | UNKNOWN | 73 | 0 | T |

TABLE 1-continued

| Genbank # | Region | # reps | Position | Unit sequence |
|---|---|---|---|---|
| AW196078 | UNKNOWN | 72 | 0 | T |
| AW196078 | UNKNOWN | 12 | 198 | C |
| AW196083 | UNKNOWN | 32 | 0 | T |
| AW196097 | UNKNOWN | 88 | 0 | T |
| AW196097 | UNKNOWN | 12 | 246 | C |
| AW196105 | UNKNOWN | 81 | 0 | T |
| AW196105 | UNKNOWN | 17 | 171 | G |
| AW196114 | UNKNOWN | 20 | 173 | A |
| AW196114 | UNKNOWN | 14 | 2 | A |
| AW196138 | UNKNOWN | 39 | 0 | T |
| AW196138 | UNKNOWN | 20 | 141 | A |
| AW196141 |UN5NOWN | 114 | 0 | T |
| AW196141 | UNKNOWN | 21 | 185 | C |
| AW196141 | UNKNOWN | 13 | 172 | G |
| AW196141 | UNKNOWN | 12 | 245 | A |
| AW196161 | UNKNOWN | 49 | 0 | T |
| AW196172 | UNKNOWN | 33 | 0 | T |
| AW196182 | UNKNOWN | 44 | 0 | T |
| AW196199 | UNKNOWN | 16 | 0 | T |
| AW196271 | UNKNOWN | 17 | 0 | T |
| AW196287 | UNKNOWN | 9.5 | 315 | AT |
| AW196289 | UNKNOWN | 56 | 0 | T |
| AW196299 | UNKNOWN | 78 | 0 | T |
| AW196299 | UNKNOWN | 13 | 153 | A |
| AW196302 | UNKNOWN | 13 | 29 | A |
| AW196472 | UNKNOWN | 44 | 11 | T |
| AW196472 | UNKNOWN | 12 | 187 | A |
| AW196495 | UNKNOWN | 15 | 10 | T |
| AW196504 | UNKNOWN | 27 | 0 | T |
| AW196543 | UNKNOWN | 12 | 0 | T |
| AW196548 | UNKNOWN | 16 | 0 | T |
| AW196574 | UNKNOWN | 45 | 0 | T |
| AW196666 | UNKNOWN | 13 | 235 | A |
| AW196679 | UNKNOWN | 17 | 0 | T |
| AW196722 | UNKNOWN | 4.66 | 255 | CCTTGG |
| AW196722 | UNKNOWN | 46 | 0 | T |
| AW196722 | UNKNOWN | 12 | 116 | G |
| AW196775 | UNKNOWN | 33 | 0 | T |
| AW196794 | UNKNOWN | 16 | 0 | T |
| AW196813 | UNKNOWN | 30 | 0 | T |
| AW196814 | UNKNOWN | 16 | 0 | T |
| AW196825 | UNKNOWN | 16 | 0 | T |
| AW196825 | UNKNOWN | 12 | 361 | A |
| AW196848 | UNKNOWN | 59 | 0 | T |
| AW196868 | UNKNOWN | 95 | 0 | T |
| AW196868 | UNKNOWN | 16 | 173 | C |
| AW196868 | UNKNOWN | 15 | 213 | A |
| AW196936 | UNKNOWN | 36 | 0 | T |
| AW196952 | UNKNOWN | 17 | 0 | T |
| AW197005 | UNKNOWN | 69 | 0 | T |
| AW197005 | UNKNOWN | 18 | 242 | G |
| AW197087 | UNKNOWN | 14 | 0 | T |
| AW197162 | UNKNOWN | 41 | 0 | T |
| AW197174 | UNKNOWN | 45 | 0 | T |
| AW197196 | UNKNOWN | 9 | 339 | TC |
| AW197212 | UNKNOWN | 19 | 338 | T |
| AW197213 | UNKNOWN | 19 | 0 | T |
| AW197229 | UNKNOWN | 12 | 156 | A |
| AW197273 | UNKNOWN | 14 | 363 | T |
| AW197282 | UNKNOWN | 37 | 0 | T |
| AW197312 | UNKNOWN | 15 | 0 | T |
| AW197329 | UNKNOWN | 37 | 0 | T |
| AW197343 | UNKNOWN | 14 | 0 | T |
| AW197437 | UNKNOWN | 31 | 0 | T |
| AW197600 | UNKNOWN | 22 | 0 | T |
| AW197661 | UNKNOWN | 19 | 0 | T |
| AW197756 | UNKNOWN | 31 | 0 | T |
| AW197943 | UNKNOWN | 18 | 0 | T |
| AW197943 | UNKNOWN | 17 | 379 | G |
| AW197948 | UNKNOWN | 39 | 0 | T |
| AW197948 | UNKNOWN | 16 | 218 | G |
| AW197949 | UNKNOWN | 43 | 0 | T |
| AW197949 | UNKNOWN | 12 | 329 | A |
| AW197980 | UNKNOWN | 37 | 0 | T |
| AW198021 | UNKNOWN | 74 | 0 | T |
| AW198021 | UNKNOWN | 12 | 98 | C |
| AW198075 | UNKNOWN | 81 | 0 | T |

TABLE 1-continued

| Genbank # | Region | # reps | Position | Unit sequence |
|---|---|---|---|---|
| AW198075 | UNKNOWN | 21 | 138 | G |
| AW198090 | UNKNOWN | 104 | 0 | T |
| AW198090 | UNKNOWN | 28 | 205 | C |
| AW198090 | UNKNOWN | 17 | 104 | A |
| AW198112 | UNKNOWN | 72 | 0 | T |
| AW198115 | UNKNOWN | 48 | 0 | T |
| AW198115 | UNKNOWN | 12 | 267 | C |
| AW198133 | UNKNOWN | 54 | 0 | T |
| AW198137 | UNKNOWN | 45 | 0 | T |
| AW198144 | UNKNOWN | 81 | 0 | T |
| AW198144 | UNKNOWN | 12 | 178 | A |
| AW198148 | UNKNOWN | 63 | 0 | T |
| AW198153 | UNKNOWN | 44 | 0 | T |
| AW203954 | UNKNOWN | 17 | 0 | T |
| AW203959 | UNKNOWN | 17 | 0 | T |
| AW203960 | UNKNOWN | 17 | 0 | T |
| AW203967 | UNKNOWN | 17 | 0 | T |
| AW203969 | UNKNOWN | 17 | 0 | T |
| AW203973 | UNKNOWN | 17 | 0 | T |
| AW203982 | UNKNOWN | 17 | 0 | T |
| AW203986 | UNKNOWN | 17 | 0 | T |
| AW204018 | UNKNOWN | 17 | 0 | T |
| AW204029 | UNKNOWN | 17 | 0 | T |
| AW204033 | UNKNOWN | 17 | 0 | T |
| AW204038 | UNKNOWN | 17 | 0 | T |
| AW204053 | UNKNOWN | 17 | 0 | T |
| AW204058 | UNKNOWN | 17 | 0 | T |
| AW204072 | UNKNOWN | 17 | 0 | T |
| AW204080 | UNKNOWN | 5.25 | 192 | TAAA |
| AW204080 | UNKNOWN | 17 | 0 | T |
| AW204090 | UNKNOWN | 17 | 0 | T |
| AW204095 | UNKNOWN | 13 | 0 | T |
| AW204099 | UNKNOWN | 17 | 0 | T |
| AW204111 | UNKNOWN | 17 | 0 | T |
| AW204116 | UNKNOWN | 18 | 536 | A |
| AW204116 | UNKNOWN | 12 | 0 | T |
| AW204126 | UNKNOWN | 17 | 0 | T |
| AW204137 | UNKNOWN | 15 | 0 | T |
| AW204145 | UNKNOWN | 17 | 0 | T |
| AW204148 | UNKNOWN | 17 | 0 | T |
| AW204153 | UNKNOWN | 15 | 0 | T |
| AW204156 | UNKNOWN | 17 | 0 | T |
| AW204162 | UNKNOWN | 17 | 0 | T |
| AW204171 | UNKNOWN | 17 | 0 | T |
| AW204184 | UNKNOWN | 17 | 0 | T |
| AW204190 | UNKNOWN | 17 | 0 | T |
| AW204215 | UNKNOWN | 17 | 0 | T |
| AW204220 | UNKNOWN | 15 | 0 | T |
| AW204233 | UNKNOWN | 17 | 0 | T |
| AW204237 | UNKNOWN | 15 | 0 | T |
| AW204239 | UNKNOWN | 17 | 0 | T |
| AW204241 | UNKNOWN | 17 | 0 | T |
| AW204262 | UNKNOWN | 3.83 | 66 | AAAAT |
| AW204262 | UNKNOWN | 17 | 0 | T |
| AW204267 | UNKNOWN | 17 | 0 | T |
| AW204302 | UNKNOWN | 17 | 0 | T |
| AW204319 | UNKNOWN | 17 | 0 | T |
| AW204359 | UNKNOWN | 17 | 0 | T |
| AW204380 | UNKNOWN | 17 | 0 | T |
| AW204430 | UNKNOWN | 17 | 0 | T |
| AW204435 | UNKNOWN | 17 | 0 | T |
| AW204441 | UNKNOWN | 15 | 0 | T |
| AW204455 | UNKNOWN | 17 | 0 | T |
| AW204480 | UNKNOWN | 17 | 0 | T |
| AW204485 | UNKNOWN | 17 | 0 | T |
| AW204491 | UNKNOWN | 17 | 0 | T |
| AW204502 | UNKNOWN | 17 | 0 | T |
| AW204503 | UNKNOWN | 17 | 0 | T |
| AW204509 | UNKNOWN | 17 | 0 | T |
| AW204518 | UNKNOWN | 17 | 0 | T |
| AW204542 | UNKNOWN | 17 | 0 | T |
| AW204555 | UNKNOWN | 15 | 0 | T |
| AW204561 | UNKNOWN | 17 | 0 | T |
| AW204566 | UNKNOWN | 17 | 0 | T |
| AW204581 | UNKNOWN | 14 | 0 | T |
| AW204583 | UNKNOWN | 16 | 0 | T |
| AW204620 | UNKNOWN | 17 | 0 | T |

TABLE 1-continued

| Genbank # | Region | # reps | Position | Unit sequence |
|---|---|---|---|---|
| AW204690 | UNKNOWN | 17 | 0 | T |
| AW204690 | UNKNOWN | 14 | 445 | A |
| AW204694 | UNKNOWN | 17 | 0 | T |
| AW204698 | UNKNOWN | 15 | 0 | T |
| AW204707 | UNKNOWN | 17 | 0 | T |
| AW204709 | UNKNOWN | 17 | 0 | T |
| AW204724 | UNKNOWN | 17 | 0 | T |
| AW204742 | UNKNOWN | 12 | 0 | T |
| AW204743 | UNKNOWN | 17 | 0 | T |
| AW204745 | UNKNOWN | 17 | 0 | T |
| AW204748 | UNKNOWN | 17 | 0 | T |
| AW204760 | UNKNOWN | 17 | 0 | T |
| AW204765 | UNKNOWN | 17 | 0 | T |
| AW204766 | UNKNOWN | 17 | 0 | T |
| AW204827 | UNKNOWN | 17 | 0 | T |
| AW204840 | UNKNOWN | 17 | 0 | T |
| AW204850 | UNKNOWN | 17 | 0 | T |
| AW204868 | UNKNOWN | 17 | 0 | T |
| AW204871 | UNKNOWN | 17 | 0 | T |
| AW204876 | UNKNOWN | 17 | 0 | T |
| AW204905 | UNKNOWN | 17 | 0 | T |
| AW204913 | UNKNOWN | 17 | 0 | T |
| AW204920 | UNKNOWN | 17 | 0 | T |
| AW204932 | UNKNOWN | 17 | 0 | T |
| AW204936 | UNKNOWN | 17 | 0 | T |
| AW204952 | UNKNOWN | 17 | 0 | T |
| AW204953 | UNKNOWN | 17 | 0 | T |
| AW204958 | UNKNOWN | 17 | 0 | T |
| AW204995 | UNKNOWN | 17 | 0 | T |
| AW205002 | UNKNOWN | 15 | 0 | T |
| AW205003 | UNKNOWN | 17 | 0 | T |
| AW205017 | UNKNOWN | 14 | 543 | A |
| AW205024 | UNKNOWN | 17 | 0 | T |
| AW205026 | UNKNOWN | 17 | 0 | T |
| AW205043 | UNKNOWN | 17 | 0 | T |
| AW205046 | UNKNOWN | 17 | 0 | T |
| AW205048 | UNKNOWN | 17 | 0 | T |
| AW205051 | UNKNOWN | 17 | 0 | T |
| AW205059 | UNKNOWN | 17 | 0 | T |
| AW205061 | UNKNOWN | 17 | 0 | T |
| AW205064 | UNKNOWN | 17 | 0 | T |
| AW205089 | UNKNOWN | 17 | 0 | T |
| AW205092 | UNKNOWN | 17 | 0 | T |
| AW205098 | UNKNOWN | 17 | 0 | T |
| AW205118 | UNKNOWN | 17 | 0 | T |
| AW205123 | UNKNOWN | 17 | 0 | T |
| AW205124 | UNKNOWN | 17 | 0 | T |
| AW205130 | UNKNOWN | 3.8 | 298 | ATTTT |
| AW205139 | UNKNOWN | 17 | 0 | T |
| AW205150 | UNKNOWN | 17 | 0 | T |
| AW205173 | UNKNOWN | 17 | 0 | T |
| AW205180 | UNKNOWN | 17 | 0 | T |
| AW205184 | UNKNOWN | 17 | 0 | T |
| AW205186 | UNKNOWN | 17 | 0 | T |
| AW205188 | UNKNOWN | 17 | 0 | T |
| AW205196 | UNKNOWN | 17 | 0 | T |
| AW205219 | UNKNOWN | 17 | 0 | T |
| AW205227 | UNKNOWN | 15 | 0 | T |
| AW205244 | UNKNOWN | 16 | 0 | T |
| AW205266 | UNKNOWN | 17 | 0 | T |
| AW205275 | UNKNOWN | 17 | 0 | T |
| AW205283 | UNKNOWN | 18 | 197 | A |
| AW205283 | UNKNOWN | 13 | 0 | T |
| AW205318 | UNKNOWN | 17 | 0 | T |
| AW205322 | UNKNOWN | 17 | 0 | T |
| AW205323 | UNKNOWN | 17 | 0 | T |
| AW205336 | UNKNOWN | 17 | 0 | T |
| AW205339 | UNKNOWN | 15 | 0 | T |
| AW205347 | UNKNOWN | 17 | 0 | T |
| AW205348 | UNKNOWN | 17 | 0 | T |
| AW205351 | UNKNOWN | 17 | 0 | T |
| AW205355 | UNKNOWN | 17 | 0 | T |
| AW205358 | UNKNOWN | 16 | 0 | T |
| AW205370 | UNKNOWN | 7 | 223 | CAA |
| AW205370 | UNKNOWN | 17 | 0 | T |
| AW205381 | UNKNOWN | 15 | 0 | T |
| AW205383 | UNKNOWN | 17 | 0 | T |

TABLE 1-continued

| Genbank # | Region | # reps | Position | Unit sequence |
|---|---|---|---|---|
| AW205384 | UNKNOWN | 17 | 0 | T |
| AW205390 | UNKNOWN | 17 | 0 | T |
| AW205394 | UNKNOWN | 17 | 0 | T |
| AW205402 | UNKNOWN | 17 | 0 | T |
| AW205403 | UNKNOWN | 17 | 0 | T |
| AW205412 | UNKNOWN | 17 | 0 | T |
| AW205417 | UNKNOWN | 17 | 0 | T |
| AW205421 | UNKNOWN | 16 | 0 | T |
| AW205428 | UNKNOWN | 17 | 0 | T |
| AW205438 | UNKNOWN | 17 | 0 | T |
| AW205439 | UNKNOWN | 17 | 0 | T |
| AW205453 | UNKNOWN | 5 | 178 | CAAAA |
| AW205453 | UNKNOWN | 17 | 0 | T |
| AW205468 | UNKNOWN | 17 | 0 | T |
| AW205471 | UNKNOWN | 18 | 192 | A |
| AW205473 | UNKNOWN | 17 | 0 | T |
| AW205474 | UNKNOWN | 17 | 0 | T |
| AW205475 | UNKNOWN | 17 | 0 | T |
| AW205487 | UNKNOWN | 17 | 0 | T |
| AW205500 | UNKNOWN | 17 | 0 | T |
| AW205500 | UNKNOWN | 13 | 156 | A |
| AW205511 | UNKNOWN | 15 | 0 | T |
| AW205526 | UNKNOWN | 15 | 0 | T |
| AW205529 | UNKNOWN | 17 | 0 | T |
| AW205542 | UNKNOWN | 17 | 0 | T |
| AW205587 | UNKNOWN | 17 | 0 | T |
| AW205588 | UNKNOWN | 15 | 0 | T |
| AW205595 | UNKNOWN | 17 | 0 | T |
| AW205597 | UNKNOWN | 17 | 0 | T |
| AW205604 | UNKNOWN | 17 | 522 | A |
| AW205605 | UNKNOWN | 17 | 0 | T |
| AW205607 | UNKNOWN | 17 | 0 | T |
| AW205610 | UNKNOWN | 16 | 0 | T |
| AW205612 | UNKNOWN | 17 | 0 | T |
| AW205616 | UNKNOWN | 15 | 0 | T |
| AW205616 | UNKNOWN | 12 | 407 | A |
| AW205624 | UNKNOWN | 15 | 0 | T |
| AW205629 | UNKNOWN | 17 | 0 | T |
| AW205632 | UNKNOWN | 17 | 0 | T |
| AW205640 | UNKNOWN | 17 | 0 | T |
| AW205659 | UNKNOWN | 17 | 0 | T |
| AW205664 | UNKNOWN | 17 | 0 | T |
| AW205668 | UNKNOWN | 17 | 0 | T |
| AW205673 | UNKNOWN | 17 | 0 | T |
| AW205677 | UNKNOWN | 17 | 0 | T |
| AW205681 | UNKNOWN | 17 | 0 | T |
| AW205691 | UNKNOWN | 15 | 0 | T |
| AW205700 | UNKNOWN | 17 | 0 | T |
| AW205701 | UNKNOWN | 17 | 0 | T |
| AW205728 | UNKNOWN | 5.2 | 88 | AAAAC |
| AW205728 | UNKNOWN | 17 | 0 | T |
| AW205729 | UNKNOWN | 17 | 0 | T |
| AW205742 | UNKNOWN | 15 | 0 | T |
| AW205750 | UNKNOWN | 17 | 0 | T |
| AW205751 | UNKNOWN | 17 | 0 | T |
| AW205752 | UNKNOWN | 15 | 0 | T |
| AW205756 | UNKNOWN | 17 | 0 | T |
| AW205760 | UNKNOWN | 17 | 0 | T |
| AW205763 | UNKNOWN | 15 | 0 | T |
| AW205772 | UNKNOWN | 17 | 0 | T |
| AW205775 | UNKNOWN | 13 | 0 | T |
| AW205788 | UNKNOWN | 17 | 0 | T |
| AW205790 | UNKNOWN | 17 | 0 | T |
| AW205791 | UNKNOWN | 17 | 0 | T |
| AW205798 | UNKNOWN | 17 | 0 | T |
| AW205799 | UNKNOWN | 17 | 0 | T |
| AW205811 | UNKNOWN | 15 | 0 | T |
| AW205815 | UNKNOWN | 6.66 | 165 | GCG |
| AW205818 | UNKNOWN | 17 | 0 | T |
| AW205833 | UNKNOWN | 17 | 0 | T |
| AW205837 | UNKNOWN | 17 | 0 | T |
| AW205861 | UNKNOWN | 17 | 0 | T |
| AW205868 | UNKNOWN | 17 | 0 | T |
| AW205877 | UNKNOWN | 17 | 0 | T |
| AW205881 | UNKNOWN | 17 | 0 | T |
| AW205887 | UNKNOWN | 17 | 0 | T |
| AW205896 | UNKNOWN | 17 | 0 | T |

TABLE 1-continued

| Genbank # | Region | # reps | Position | Unit sequence |
|---|---|---|---|---|
| AW205900 | UNKNOWN | 17 | 0 | T |
| AW205908 | UNKNOWN | 17 | 0 | T |
| AW205909 | UNKNOWN | 17 | 0 | T |
| AW205925 | UNKNOWN | 17 | 0 | T |
| AW205930 | UNKNOWN | 17 | 0 | T |
| AW205933 | UNKNOWN | 17 | 0 | T |
| AW205938 | UNKNOWN | 17 | 0 | T |
| AW205942 | UNKNOWN | 14 | 0 | T |
| AW205962 | UNKNOWN | 12 | 0 | T |
| AW205964 | UNKNOWN | 15 | 0 | T |
| AW205969 | UNKNOWN | 17 | 0 | T |
| AW205973 | UNKNOWN | 17 | 0 | T |
| AW206012 | UNKNOWN | 17 | 0 | T |
| AW206015 | UNKNOWN | 17 | 0 | T |
| AW206025 | UNKNOWN | 15 | 0 | T |
| AW206037 | UNKNOWN | 7.75 | 416 | GATA |
| AW206037 | UNKNOWN | 17 | 0 | T |
| AW206053 | UNKNOWN | 17 | 0 | T |
| AW206077 | UNKNOWN | 17 | 0 | T |
| AW206095 | UNKNOWN | 17 | 0 | T |
| AW206099 | UNKNOWN | 14 | 0 | T |
| AW206102 | UNKNOWN | 17 | 0 | T |
| AW206112 | UNKNOWN | 15 | 0 | T |
| AW206123 | UNKNOWN | 17 | 0 | T |
| AW206124 | UNKNOWN | 17 | 0 | T |
| AW206130 | UNKNOWN | 17 | 0 | T |
| AW206138 | UNKNOWN | 17 | 0 | T |
| AW206148 | UNKNOWN | 15 | 0 | T |
| AW206164 | UNKNOWN | 17 | 0 | T |
| AW206172 | UNKNOWN | 17 | 0 | T |
| AW206192 | UNKNOWN | 17 | 0 | T |
| AW206202 | UNKNOWN | 17 | 0 | T |
| AW206211 | UNKNOWN | 17 | 0 | T |
| AW206222 | UNKNOWN | 17 | 0 | T |
| AW206229 | UNKNOWN | 14 | 0 | T |
| AW206247 | UNKNOWN | 17 | 0 | T |
| AW206257 | UNKNOWN | 17 | 0 | T |
| AW206266 | UNKNOWN | 17 | 0 | T |
| AW206285 | UNKNOWN | 17 | 0 | T |
| AW206286 | UNKNOWN | 17 | 0 | T |
| AW206292 | UNKNOWN | 15 | 0 | T |
| AW206308 | UNKNOWN | 17 | 0 | T |
| AW206315 | UNKNOWN | 17 | 0 | T |
| AW206335 | UNKNOWN | 17 | 0 | T |
| AW206350 | UNKNOWN | 17 | 0 | T |
| AW206362 | UNKNOWN | 15 | 0 | T |
| AW206364 | UNKNOWN | 16 | 0 | T |
| AW206404 | UNKNOWN | 17 | 0 | T |
| AW206414 | UNKNOWN | 17 | 0 | T |
| AW206421 | UNKNOWN | 17 | 0 | T |
| AW206426 | UNKNOWN | 17 | 0 | T |
| AW206429 | UNKNOWN | 17 | 0 | T |
| AW206435 | UNKNOWN | 15 | 0 | T |
| AW206438 | UNKNOWN | 17 | 0 | T |
| AW206439 | UNKNOWN | 17 | 0 | T |
| AW206440 | UNKNOWN | 17 | 0 | T |
| AW206445 | UNKNOWN | 4.75 | 376 | AAAC |
| AW206445 | UNKNOWN | 17 | 0 | T |
| AW206452 | UNKNOWN | 17 | 0 | T |
| AW206456 | UNKNOWN | 17 | 0 | T |
| AW206465 | UNKNOWN | 17 | 0 | T |
| AW206478 | UNKNOWN | 17 | 0 | T |
| AW206485 | UNKNOWN | 17 | 0 | T |
| AW206487 | UNKNOWN | 15 | 0 | T |
| AW206490 | UNKNOWN | 17 | 0 | T |
| AW206494 | UNKNOWN | 17 | 0 | T |
| AW206500 | UNKNOWN | 17 | 0 | T |
| AW206504 | UNKNOWN | 17 | 0 | T |
| AW206515 | UNKNOWN | 15 | 0 | T |
| AW206518 | UNKNOWN | 17 | 0 | T |
| AW206520 | UNKNOWN | 17 | 0 | T |
| AW206525 | UNKNOWN | 17 | 0 | T |
| AW206532 | UNKNOWN | 17 | 0 | T |
| AW206548 | UNKNOWN | 17 | 0 | T |
| AW206555 | UNKNOWN | 16 | 0 | T |
| AW206558 | UNKNOWN | 17 | 0 | T |
| AW206559 | UNKNOWN | 15 | 0 | T |

TABLE 1-continued

| Genbank # | Region | # reps | Position | Unit sequence |
|---|---|---|---|---|
| AW206568 | UNKNOWN | 17 | 0 | T |
| AW206570 | UNKNOWN | 15 | 352 | A |
| AW206604 | UNKNOWN | 14 | 0 | T |
| AW206609 | UNKNOWN | 17 | 0 | T |
| AW206612 | UNKNOWN | 17 | 0 | T |
| AW206616 | UNKNOWN | 12 | 0 | T |
| AW206654 | UNKNOWN | 17 | 0 | T |
| AW206656 | UNKNOWN | 17 | 0 | T |
| AW206680 | UNKNOWN | 17 | 0 | T |
| AW206681 | UNKNOWN | 17 | 0 | T |
| AW206686 | UNKNOWN | 17 | 0 | T |
| AW206708 | UNKNOWN | 12 | 0 | T |
| AW206716 | UNKNOWN | 17 | 0 | T |
| AW206737 | UNKNOWN | 17 | 0 | T |
| AW206737 | UNKNOWN | 12 | 423 | A |
| AW206740 | UNKNOWN | 17 | 0 | T |
| AW206772 | UNKNOWN | 17 | 0 | T |
| AW206802 | UNKNOWN | 17 | 0 | T |
| AW206806 | UNKNOWN | 17 | 0 | T |
| AW206812 | UNKNOWN | 17 | 0 | T |
| AW206836 | UNKNOWN | 17 | 0 | T |
| AW206837 | UNKNOWN | 17 | 0 | T |
| AW206854 | UNKNOWN | 15 | 0 | T |
| AW206860 | UNKNOWN | 17 | 0 | T |
| AW206870 | UNKNOWN | 15 | 0 | T |
| AW206879 | UNKNOWN | 8.5 | 434 | TG |
| AW206879 | UNKNOWN | 17 | 0 | T |
| AW206890 | UNKNOWN | 17 | 0 | T |
| AW206896 | UNKNOWN | 17 | 0 | T |
| AW206920 | UNKNOWN | 15 | 0 | T |
| AW206939 | UNKNOWN | 4.4 | 343 | ATTTT |
| AW206939 | UNKNOWN | 5 | 26 | TTTA |
| AW206939 | UNKNOWN | 17 | 0 | T |
| AW206950 | UNKNOWN | 17 | 0 | T |
| AW206953 | UNKNOWN | 17 | 0 | T |
| AW206956 | UNKNOWN | 17 | 0 | T |
| AW206962 | UNKNOWN | 17 | 0 | T |
| AW206972 | UNKNOWN | 17 | 0 | T |
| AW206973 | UNKNOWN | 18 | 185 | A |
| AW206978 | UNKNOWN | 17 | 0 | T |
| AW206988 | UNKNOWN | 17 | 0 | T |
| AW206989 | UNKNOWN | 17 | 0 | T |
| AW207003 | UNKNOWN | 17 | 0 | T |
| AW207025 | UNKNOWN | 17 | 0 | T |
| AW207037 | UNKNOWN | 17 | 0 | T |
| AW207144 | UNKNOWN | 15 | 0 | T |
| AW207150 | UNKNOWN | 17 | 0 | T |
| AW207155 | UNKNOWN | 17 | 0 | T |
| AW207165 | UNKNOWN | 17 | 0 | T |
| AW207178 | UNKNOWN | 17 | 0 | T |
| AW207179 | UNKNOWN | 17 | 0 | T |
| AW207199 | UNKNOWN | 17 | 0 | T |
| AW207200 | UNKNOWN | 17 | 0 | T |
| AW207205 | UNKNOWN | 17 | 0 | T |
| AW207210 | UNKNOWN | 17 | 0 | T |
| AW207212 | UNKNOWN | 17 | 0 | T |
| AW207233 | UNKNOWN | 17 | 0 | T |
| AW207243 | UNKNOWN | 17 | 0 | T |
| AW207253 | UNKNOWN | 17 | 0 | T |
| AW207255 | UNKNOWN | 17 | 0 | T |
| AW207263 | UNKNOWN | 17 | 0 | T |
| AW207291 | UNKNOWN | 17 | 0 | T |
| AW207308 | UNKNOWN | 17 | 0 | T |
| AW207323 | UNKNOWN | 17 | 0 | T |
| AW207354 | UNKNOWN | 15 | 0 | T |
| AW207379 | UNKNOWN | 15 | 0 | T |
| AW207381 | UNKNOWN | 15 | 0 | T |
| AW207388 | UNKNOWN | 16 | 479 | A |
| AW207390 | UNKNOWN | 17 | 0 | T |
| AW207393 | UNKNOWN | 14 | 575 | A |
| AW207395 | UNKNOWN | 17 | 0 | T |
| AW207404 | UNKNOWN | 17 | 0 | T |
| AW207407 | UNKNOWN | 17 | 0 | T |
| AW207413 | UNKNOWN | 17 | 0 | T |
| AW207423 | UNKNOWN | 17 | 0 | T |
| AW207427 | UNKNOWN | 17 | 0 | T |
| AW207436 | UNKNOWN | 17 | 0 | T |

TABLE 1-continued

| Genbank # | Region | # reps | Position | Unit sequence |
|---|---|---|---|---|
| AW207437 | UNKNOWN | 17 | 0 | T |
| AW207470 | UNKNOWN | 17 | 0 | T |
| AW207474 | UNKNOWN | 17 | 0 | T |
| AW207489 | UNKNOWN | 17 | 0 | T |
| AW207540 | UNKNOWN | 6 | 35 | TTC |
| AW207540 | UNKNOWN | 17 | 0 | T |
| AW207553 | UNKNOWN | 17 | 0 | T |
| AW207563 | UNKNOWN | 17 | 0 | T |
| AW207565 | UNKNOWN | 8.29 | 94 | TGGACACCGGAGACTGTTGAGACGCCGACTGGAGTCACACACGGCAGTCAACGCG (SEQ ID NO: 223) |
| AW207565 | UNKNOWN | 14 | 0 | T |
| AW207577 | UNKNOWN | 17 | 0 | T |
| AW207578 | UNKNOWN | 17 | 0 | T |
| AW207581 | UNKNOWN | 17 | 0 | T |
| AW207582 | UNKNOWN | 17 | 0 | T |
| AW207585 | UNKNOWN | 17 | 0 | T |
| AW207666 | UNKNOWN | 17 | 0 | T |
| AW207619 | UNKNOWN | 17 | 0 | T |
| AW207619 | UNKNOWN | 12 | 221 | A |
| AW207631 | UNKNOWN | 17 | 0 | T |
| AW207632 | UNKNOWN | 17 | 0 | T |
| AW207640 | UNKNOWN | 17 | 0 | T |
| AW207641 | UNKNOWN | 17 | 0 | T |
| AW207642 | UNKNOWN | 17 | 0 | T |
| AW207654 | UNKNOWN | 17 | 0 | T |
| AW207674 | UNKNOWN | 15 | 0 | T |
| AW207676 | UNKNOWN | 17 | 0 | T |
| AW207690 | UNKNOWN | 14 | 0 | T |
| AW207692 | UNKNOWN | 17 | 0 | T |
| AW207699 | UNKNOWN | 17 | 0 | T |
| AW207701 | UNKNOWN | 17 | 0 | T |
| AW207704 | UNKNOWN | 17 | 0 | T |
| AW207712 | UNKNOWN | 17 | 0 | T |
| AW207713 | UNKNOWN | 17 | 0 | T |
| AW207714 | UNKNOWN | 17 | 0 | T |
| AW207723 | UNKNOWN | 17 | 0 | T |
| AW207725 | UNKNOWN | 17 | 0 | T |
| AW207726 | UNKNOWN | 17 | 0 | T |
| AW207728 | UNKNOWN | 14 | 189 | A |
| AW207735 | UNKNOWN | 17 | 0 | T |
| AW207738 | UNKNOWN | 16 | 0 | T |
| AW207749 | UNKNOWN | 13 | 227 | A |
| AW207777 | UNKNOWN | 17 | 0 | T |
| AW207797 | UNKNOWN | 4.75 | 26 | TTAT |
| AW207797 | UNKNOWN | 15 | 0 | T |
| AW207824 | UNKNOWN | 17 | 0 | T |
| AW207827 | UNKNOWN | 17 | 0 | T |
| AW207835 | UNKNOWN | 17 | 0 | T |
| AW207846 | UNKNOWN | 17 | 0 | T |
| AW207848 | UNKNOWN | 17 | 0 | T |
| AW207853 | UNKNOWN | 17 | 0 | T |
| AW207856 | UNKNOWN | 15 | 0 | T |
| AW207858 | UNKNOWN | 17 | 0 | T |
| AW207859 | UNKNOWN | 17 | 0 | T |
| AW207864 | UNKNOWN | 18 | 25 | T |
| AW207864 | UNKNOWN | 17 | 0 | T |
| AW207868 | UNKNOWN | 7 | 94 | CA |
| AW207868 | UNKNOWN | 17 | 0 | T |
| AW207873 | UNKNOWN | 17 | 0 | T |
| AW207877 | UNKNOWN | 17 | 0 | T |
| AW207882 | UNKNOWN | 17 | 0 | T |
| AW207884 | UNKNOWN | 17 | 0 | T |
| AW207896 | UNKNOWN | 3.8 | 66 | TTTAA |
| AW207896 | UNKNOWN | 17 | 0 | T |
| AW207898 | UNKNOWN | 15 | 0 | T |
| AW235028 | UNKNOWN | 96 | 0 | T |
| AW235028 | UNKNOWN | 26 | 349 | C |
| AW235028 | UNKNOWN | 12 | 291 | G |
| AW235031 | UNKNOWN | 13 | 0 | T |
| AW235035 | UNKNOWN | 94 | 37 | T |
| AW235035 | UNKNOWN | 36 | 0 | T |
| AW235035 | UNKNOWN | 18 | 199 | C |
| AW235035 | UNKNOWN | 14 | 152 | G |
| AW235092 | UNKNOWN | 29 | 0 | T |
| AW235109 | UNKNOWN | 23 | 0 | T |
| AW235121 | UNKNOWN | 41 | 0 | T |
| AW235121 | UNKNOWN | 14 | 373 | C |

TABLE 1-continued

| Genbank # | Region | # reps | Position | Unit sequence |
|---|---|---|---|---|
| AW235123 | UNKNOWN | 12 | 416 | T |
| AW235233 | UNKNOWN | 4.2 | 77 | AAAAC |
| AW235435 | UNKNOWN | 17 | 0 | T |
| AW235442 | UNKNOWN | 3.6 | 204 | TTTGT |
| AW235475 | UNKNOWN | 18 | 343 | T |
| AW235482 | UNKNOWN | 96 | 0 | T |
| AW235482 | UNKNOWN | 21 | 293 | A |
| AW235482 | UNKNOWN | 18 | 199 | G |
| AW235482 | UNKNOWN | 16 | 168 | A |
| AW235482 | UNKNOWN | 13 | 96 | A |
| AW235483 | UNKNOWN | 25 | 0 | T |
| AW235487 | UNKNOWN | 46 | 0 | T |
| AW235489 | UNKNOWN | 59 | 0 | T |
| AW235489 | UNKNOWN | 15 | 118 | A |
| AW235489 | UNKNOWN | 15 | 258 | C |
| AW235501 | UNKNOWN | 62 | 0 | T |
| AW235501 | UNKNOWN | 13 | 129 | G |
| AW235545 | UNKNOWN | 13 | 0 | T |
| AW235582 | UNKNOWN | 22 | 0 | T |
| AW235584 | UNKNOWN | 41 | 0 | T |
| AW235638 | UNKNOWN | 20 | 0 | T |
| AW235660 | UNKNOWN | 19 | 0 | T |
| AW235671 | UNKNOWN | 15 | 0 | T |
| AW235745 | UNKNOWN | 85 | 0 | T |
| AW235827 | UNKNOWN | 41 | 0 | T |
| AW235834 | UNKNOWN | 24 | 0 | T |
| AW235862 | UNKNOWN | 13 | 514 | T |
| AW236062 | UNKNOWN | 22 | 0 | T |
| AW236118 | UNKNOWN | 41 | 0 | T |
| AW236168 | UNKNOWN | 19 | 0 | T |
| AW236186 | UNKNOWN | 49 | 0 | T |
| AW236208 | UNKNOWN | 51 | 0 | T |
| AW236271 | UNKNOWN | 28 | 0 | T |
| AW236277 | UNKNOWN | 22 | 28 | T |
| AW236345 | UNKNOWN | 27 | 0 | T |
| AW236370 | UNKNOWN | 2.75 | 347 | ATATATATACAT (SEQ ID NO: 224) |
| AW236370 | UNKNOWN | 8.5 | 369 | AT |
| AW236370 | UNKNOWN | 6.5 | 385 | AC |
| AW236464 | UNKNOWN | 17 | 171 | A |
| AW236466 | UNKNOWN | 68 | 0 | T |
| AW236466 | UNKNOWN | 12 | 117 | A |
| AW236486 | UNKNOWN | 18 | 207 | A |
| AW236566 | UNKNOWN | 13 | 432 | AC |
| AW236681 | UNKNOWN | 3.75 | 438 | ACACACAT |
| AW236780 | UNKNOWN | 28 | 0 | T |
| AW236987 | UNKNOWN | 13 | 460 | A |
| AW236990 | UNKNOWN | 20 | 271 | A |
| AW237022 | UNKNOWN | 32 | 0 | T |
| AW237096 | UNKNOWN | 60 | 0 | T |
| AW237151 | UNKNOWN | 13 | 0 | T |
| AW237188 | UNKNOWN | 14 | 284 | T |
| AW237299 | UNKNOWN | 55 | 0 | T |
| AW237299 | UNKNOWN | 12 | 113 | C |
| AW237390 | UNKNOWN | 29 | 0 | T |
| AW237401 | UNKNOWN | 17 | 0 | T |
| AW237560 | UNKNOWN | 13 | 0 | T |
| AW237577 | UNKNOWN | 21 | 18 | T |
| AW237587 | UNKNOWN | 13 | 0 | T |
| AW237618 | UNKNOWN | 16 | 0 | T |
| AW237631 | UNKNOWN | 20 | 0 | T |
| AW237729 | UNKNOWN | 7.5 | 144 | TG |
| AW237754 | UNKNOWN | 12 | 174 | T |
| AW237818 | UNKNOWN | 15 | 202 | A |
| AW237843 | UNKNOWN | 26 | 351 | T |
| AW237857 | UNKNOWN | 85 | 0 | T |
| AW237857 | UNKNOWN | 12 | 244 | C |
| AW237887 | UNKNOWN | 13 | 320 | A |
| AW237903 | UNKNOWN | 15 | 8 | T |
| AW237985 | UNKNOWN | 17 | 101 | A |
| AW237994 | UNKNOWN | 13 | 250 | A |
| AW238024 | UNKNOWN | 13 | 8 | T |
| AW238025 | UNKNOWN | 27 | 36 | T |
| AW238092 | UNKNOWN | 21 | 279 | A |
| AW238108 | UNKNOWN | 19 | 8 | T |
| AW238121 | UNKNOWN | 18 | 8 | T |
| AW238175 | UNKNOWN | 15 | 356 | A |
| AW238203 | UNKNOWN | 12 | 22 | T |

TABLE 1-continued

| Genbank # | Region | # reps | Position | Unit sequence |
|---|---|---|---|---|
| AW238385 | UNKNOWN | 16 | 8 | T |
| AW238438 | UNKNOWN | 16 | 47 | T |
| AW238488 | UNKNOWN | 16 | 8 | T |
| AW238490 | UNKNOWN | 14 | 8 | T |
| AW238505 | UNKNOWN | 17 | 8 | T |
| AW238542 | UNKNOWN | 12 | 0 | T |
| AW238628 | UNKNOWN | 14 | 8 | T |
| AW238655 | UNKNOWN | 14 | 8 | T |
| AW238690 | UNKNOWN | 14 | 395 | A |
| AW238691 | UNKNOWN | 79 | 8 | T |
| AW238691 | UNKNOWN | 15 | 221 | G |
| AW238691 | UNKNOWN | 13 | 199 | C |
| AW238721 | UNKNOWN | 18 | 33 | T |
| AW238725 | UNKNOWN | 13 | 381 | A |
| AW238741 | UNKNOWN | 16 | 8 | T |
| AW238745 | UNKNOWN | 18 | 330 | A |
| AW238750 | UNKNOWN | 13 | 314 | T |
| AW238764 | UNKNOWN | 99 | 21 | T |
| AW241252 | UNKNOWN | 19 | 175 | G |
| AW241286 | UNKNOWN | 13 | 0 | T |
| AW241325 | UNKNOWN | 21 | 0 | T |
| AW241463 | UNKNOWN | 13 | 15 | T |
| AW241592 | UNKNOWN | 33 | 4 | T |
| AW241606 | UNKNOWN | 15 | 4 | T |
| AW241720 | UNKNOWN | 13 | 0 | T |
| AW241818 | UNKNOWN | 3.5 | 261 | TTTTGT |
| AW241827 | UNKNOWN | 7.5 | 67 | AC |
| AW241827 | UNKNOWN | 13 | 0 | T |
| AW241834 | UNKNOWN | 33 | 0 | T |
| AW241838 | UNKNOWN | 18 | 0 | T |
| AW241867 | UNKNOWN | 18 | 0 | T |
| AW241926 | UNKNOWN | 17 | 0 | T |
| AW241932 | UNKNOWN | 7.25 | 152 | GAAT |
| AW241932 | UNKNOWN | 8 | 128 | AG |
| AW242001 | UNKNOWN | 27 | 0 | T |
| AW242002 | UNKNOWN | 20 | 0 | T |
| AW242034 | UNKNOWN | 28 | 0 | T |
| AW242065 | UNKNOWN | 20 | 0 | T |
| AW242116 | UNKNOWN | 75 | 10 | T |
| AW242116 | UNKNOWN | 13 | 121 | C |
| AW242116 | UNKNOWN | 12 | 134 | G |
| AW242197 | UNKNOWN | 58 | 0 | T |
| AW242197 | UNKNOWN | 14 | 157 | G |
| AW242197 | UNKNOWN | 12 | 127 | G |
| AW242220 | UNKNOWN | 13 | 189 | AC |
| AW242325 | UNKNOWN | 13 | 73 | T |
| AW242328 | UNKNOWN | 16 | 0 | T |
| AW242348 | UNKNOWN | 13 | 0 | T |
| AW242410 | UNKNOWN | 16 | 125 | A |
| AW242419 | UNKNOWN | 14 | 427 | C |
| AW242432 | UNKNOWN | 7 | 305 | AT |
| AW242439 | UNKNOWN | 7.5 | 263 | AC |
| AW242479 | UNKNOWN | 65 | 0 | T |
| AW242528 | UNKNOWN | 15 | 433 | A |
| AW242528 | UNKNOWN | 12 | 0 | T |
| AW242543 | UNKNOWN | 3.6 | 69 | TTTCT |
| AW242543 | UNKNOWN | 17 | 0 | T |
| AW242606 | UNKNOWN | 35 | 0 | T |
| AW242614 | UNKNOWN | 13 | 73 | A |
| AW242708 | UNKNOWN | 12 | 0 | T |
| AW242717 | UNKNOWN | 16 | 0 | T |
| AW242721 | UNKNOWN | 35 | 0 | T |
| AW242732 | UNKNOWN | 20.33 | 476 | TGC |
| AW242891 | UNKNOWN | 24 | 70 | A |
| AW242891 | UNKNOWN | 17 | 0 | T |
| AW242904 | UNKNOWN | 20 | 0 | T |
| AW242991 | UNKNOWN | 5.66 | 292 | TCC |
| AW243046 | UNKNOWN | 12 | 417 | T |
| AW243089 | UNKNOWN | 13 | 0 | T |
| AW243102 | UNKNOWN | 7 | 74 | AT |
| AW243154 | UNKNOWN | 13 | 0 | T |
| AW243204 | UNKNOWN | 13 | 21 | T |
| AW243223 | UNKNOWN | 28 | 0 | T |
| AW243302 | UNKNOWN | 13 | 0 | T |
| AW243308 | UNKNOWN | 19 | 4 | T |
| AW243346 | UNKNOWN | 25 | 0 | T |
| AW243435 | UNKNOWN | 5 | 20 | TTTA |

TABLE 1-continued

| Genbank # | Region | # reps | Position | Unit sequence |
|---|---|---|---|---|
| AW243451 | UNKNOWN | 33 | 25 | T |
| AW243451 | UNKNOWN | 24 | 0 | T |
| AW243574 | UNKNOWN | 98 | 0 | T |
| AW243574 | UNKNOWN | 18 | 210 | C |
| AW243574 | UNKNOWN | 15 | 105 | G |
| AW243574 | UNKNOWN | 14 | 294 | A |
| AW243574 | UNKNOWN | 13 | 144 | A |
| AW243574 | UNKNOWN | 12 | 172 | C |
| AW243586 | UNKNOWN | 42 | 0 | T |
| AW243587 | UNKNOWN | 49 | 0 | T |
| AW243619 | UNKNOWN | 61 | 0 | T |
| AW243619 | UNKNOWN | 14 | 181 | G |
| AW243637 | UNKNOWN | 71 | 0 | T |
| AW243637 | UNKNOWN | 13 | 106 | A |
| AW243637 | UNKNOWN | 12 | 167 | C |
| AW243639 | UNKNOWN | 23 | 0 | T |
| AW243642 | UNKNOWN | 51 | 0 | T |
| AW243642 | UNKNOWN | 16 | 303 | G |
| AW243687 | UNKNOWN | 17 | 0 | T |
| AW243691 | UNKNOWN | 63 | 0 | T |
| AW243691 | UNKNOWN | 21 | 220 | G |
| AW243691 | UNKNOWN | 13 | 80 | A |
| AW243705 | UNKNOWN | 54 | 0 | T |
| AW243705 | UNKNOWN | 19 | 152 | A |
| AW243712 | UNKNOWN | 72 | 0 | T |
| AW243712 | UNKNOWN | 13 | 224 | A |
| AW243712 | UNKNOWN | 12 | 107 | C |
| AW243741 | UNKNOWN | 71 | 0 | T |
| AW243741 | UNKNOWN | 19 | 144 | A |
| AW243741 | UNKNOWN | 15 | 405 | G |
| AW243741 | UNKNOWN | 13 | 126 | A |
| AW243752 | UNKNOWN | 43 | 0 | T |
| AW243766 | UNKNOWN | 8.66 | 153 | AGG |
| AW243766 | UNKNOWN | 10.5 | 130 | GA |
| AW243766 | UNKNOWN | 13 | 0 | T |
| AW243767 | UNKNOWN | 45 | 0 | T |
| AW243814 | UNKNOWN | 96 | 0 | T |
| AW243814 | UNKNOWN | 17 | 142 | C |
| AW243814 | UNKNOWN | 17 | 238 | G |
| AW243820 | UNKNOWN | 101 | 0 | T |
| AW243820 | UNKNOWN | 25 | 233 | C |
| AW243820 | UNKNOWN | 17 | 128 | A |
| AW243876 | UNKNOWN | 54 | 0 | T |
| AW243878 | UNKNOWN | 48 | 0 | T |
| AW243878 | UNKNOWN | 14 | 117 | A |
| AW243886 | UNKNOWN | 75 | 0 | T |
| AW243886 | UNKNOWN | 14 | 82 | A |
| AW243913 | UNKNOWN | 46 | 0 | T |
| AW243923 | UNKNOWN | 65 | 0 | T |
| AW243923 | UNKNOWN | 18 | 97 | G |
| AW243954 | UNKNOWN | 16 | 102 | A |
| AW243955 | UNKNOWN | 16 | 8 | T |
| AW243964 | UNKNOWN | 13 | 222 | A |
| AW244016 | UNKNOWN | 7.5 | 199 | TA |
| AW245889 | UNKNOWN | 9.5 | 491 | GT |
| AW245919 | UNKNOWN | 21 | 626 | A |
| AW245993 | UNKNOWN | 8 | 86 | AC |
| AW247348 | UNKNOWN | 5.66 | 435 | GCG |
| AW248588 | UNKNOWN | 14 | 21 | T |
| AW249151 | UNKNOWN | 12 | 355 | A |
| AW250349 | UNKNOWN | 6 | 497 | GAA |
| AW250865 | UNKNOWN | 11.5 | 22 | TC |
| AW250915 | UNKNOWN | 2.54 | 171 | CCCTTCCTTTAGGGCTGGAAAGACACGGGTCTA (SEQ ID NO:225) |
| C03791 | UNKNOWN | 28 | 13 | T |
| C04538 | UNKNOWN | 13 | 26 | T |
| C05246 | UNKNOWN | 27 | 18 | T |
| C06058 | UNKNOWN | 11 | 234 | AC |
| C06350 | UNNNOWN | 12 | 82 | A |
| C06494 | UNKNOWN | 13 | 20 | T |
| C14358 | UNKNOWN | 18 | 5 | T |
| C14394 | UNKNOWN | 46 | 1 | T |
| C14486 | UNKNOWN | 28.5 | 0 | AG |
| C14486 | UNKNOWN | 20 | 215 | T |
| C14489 | UNKNOWN | 20.5 | 0 | AG |
| C15810 | UNKNOWN | 21 | 1 | T |
| C15907 | UNKNOWN | 22 | 38 | A |

TABLE 1-continued

| Genbank # | Region | # reps | Position | Unit sequence |
|---|---|---|---|---|
| C16135 | UNKNOWN | 17 | 8 | S |
| C16653 | UNKNOWN | 22 | 17 | T |
| C16654 | UNKNOWN | 18 | 10 | T |
| C20768 | UNKNOWN | 10.5 | 87 | AATA |
| C21272 | UNKNOWN | 15 | 17 | T |
| D10522 | 3'UTR | 15 | 1862 | T |
| D10522 | 3'UTR | 13 | 1982 | A |
| D10656 | 3'UTR | 16 | 1058 | T |
| D10704 | CDS | 4.5 | 206 | GCCGCT |
| D10925 | 3'UTR | 6.66 | 2104 | AAT |
| D12008 | UNKNOWN | 18 | 200 | AC |
| D12439 | UNKNOWN | 13 | 40 | T |
| D12676 | 3'UTR | 15 | 2312 | G |
| D13292 | 3'UTR | 3.66 | 1426 | GTTTTT |
| D13292 | 3'UTR | 23 | 1493 | T |
| D13630 | 3'UTR | 6 | 1891 | TTTTG |
| D13639 | 3'UTR | 7 | 6059 | TC |
| D13639 | 3'UTR | 17 | 2601 | T |
| D13639 | 3'UTR | 14 | 2481 | T |
| D13640 | 3'UTR | 3.6 | 4668 | CCTCT |
| D13641 | 3'UTR | 13 | 878 | A |
| D13644 | 5'UTR | 4 | 105 | CGCCG |
| D13644 | 5'UTR | 5.66 | 94 | GCC |
| D13644 | 3'UTR | 10.5 | 4554 | TA |
| D13969 | 3'UTR | 7 | 1368 | AT |
| D13969 | 3'UTR | 14 | 1918 | T |
| D14041 | 3'UTR | 3.8 | 4712 | TTTTG |
| D14041 | 3'UTR | 4.75 | 1759 | GTTG |
| D14041 | 3'UTR | 28 | 1678 | A |
| D14539 | CDS | 4.66 | 977 | CCCCCA |
| D14539 | CDS | 6 | 1116 | CCT |
| D14539 | 5'UTR | 8.66 | 38 | CGG |
| D14664 | 3'UTR | 8.5 | 2886 | TA |
| D14838 | 5'UTR | 6.5 | 61 | TC |
| D14838 | 3'UTR | 15.5 | 1079 | TG |
| D14838 | 3'UTR | 7 | 1043 | GA |
| D14887 | 5'UTR | 14 | 170 | T |
| D14889 | 5'UTR | 6.5 | 270 | CG |
| D15050 | CDS | 5.66 | 3195 | GAG |
| D15050 | 3'UTR | 3.85 | 3989 | GGCTCAT |
| D15050 | 3'UTR | 7.66 | 4692 | CTG |
| D16532 | 5'UTR | 8.33 | 572 | CGG |
| D16626 | 3'UTR | 15 | 2610 | T |
| D16815 | 5'UTR | 6 | 236 | GGC |
| D17427 | 3'UTR | 12 | 3006 | T |
| D17525 | 3'UTR | 8 | 4030 | AT |
| D17532 | 3'UTR | 9.5 | 2773 | AT |
| D17547 | 5'UTR | 7 | 381 | AG |
| D20065 | UNKNOWN | 7 | 31 | TC |
| D20847 | UNKNOWN | 4.75 | 90 | TTTC |
| D21089 | CDS | 5.66 | 192 | GAG |
| D21262 | CDS | 5.66 | 653 | AGC |
| D21267 | 3'UTR | 7.5 | 1431 | AC |
| D21853 | 5'UTR | 2.S | 88 | CAGCGAGGTCGGCAGCGGCACAGCGAGGTCGGCAGCGG (SEQ ID NO:226) |
| D21853 | 5'UTR | 6.4 | 0 | CAGCGGCACAGCGAGGTCGG (SEQ ID NO:227) |
| D25217 | CDS | 7.33 | 1022 | TGC |
| D25272 | UNKNOWN | 14 | 160 | T |
| D25304 | 3'UTR | 8 | 2432 | TC |
| D25538 | 3'UTR | 6 | 5958 | AACA |
| D26067 | 3'UTR | 19 | 1471 | T |
| D26069 | 3'UTR | 15 | 3126 | T |
| D26135 | 3'UTR | 8 | 2981 | CA |
| D26158 | 3'UTR | 8.5 | 1364 | AG |
| D26350 | BORDER | 2.5 | 397 | CATGAAGCAG (SEQ ID NO:228) |
| D26350 | 5'UTR | 5.66 | 78 | AGG |
| D26361 | 3'UTR | 5 | 5830 | TAAA |
| D26361 | 3'UTR | 4.5 | 5811 | AAAT |
| D26488 | 3'UTR | 23 | 3148 | T |
| D28114 | CDS | 4.23 | 294 | AGCCACGGTCCCCTCCGAGGTCTGAGCGTC (SEQ ID NO:229) |
| D28118 | CDS | 8.33 | 1047 | AGC |
| D28118 | CDS | 6.66 | 1070 | CAA |
| D28539 | 3'UTR | 2.54 | 4296 | CTTTTTTCTTT (SEQ ID NO:230) |
| D28767 | 5'UTR | 7 | 393 | AG |
| D28767 | 3'UTR | 7.5 | 1182 | TC |
| D29805 | 3'UTR | 29 | 3443 | T |

TABLE 1-continued

| Genbank # | Region | # reps | Position | Unit sequence |
|---|---|---|---|---|
| D30036 | 5'UTR | 3.6 | 116 | GCCGG |
| D30742 | 5'UTR | 7.66 | 33 | GCG |
| D30783 | 3'UTR | 12 | 2658 | T |
| D31762 | 3'UTR | 16 | 3838 | A |
| D31763 | 3'UTR | 7 | 3120 | TG |
| D31763 | 3'UTR | 6.5 | 3100 | TG |
| D31840 | CDS | 10.66 | 1699 | CAG |
| D31883 | 3'UTR | 24 | 3539 | GT |
| D31888 | 3'UTR | 7 | 2771 | TTG |
| D31888 | 3'UTR | 6.66 | 2618 | TTG |
| D32202 | 3'UTR | 6.5 | 2152 | AC |
| D32202 | 3'UTR | 12 | 2002 | T |
| D37933 | 3'UTR | 13 | 1046 | C |
| D38024 | CDS | 3.87 | 47 | AGGGAGGC |
| D38024 | CDS | 5.25 | 1246 | GGCT |
| D38024 | CDS | 7.66 | 1099 | CCA |
| D38024 | CDS | 12 | 1089 | C |
| D38076 | 5'UTR | 5.66 | 126 | GCC |
| D38081 | 3'UTR | 16 | 2615 | T |
| D38522 | 3'UTR | 5.5 | 2347 | AATT |
| D38522 | 3'UTR | 12 | 854 | T |
| D38524 | CDS | 5.66 | 1745 | GAG |
| D38550 | 3'UTR | 12 | 2244 | A |
| D42038 | 3'UTR | 17 | 2783 | T |
| D42039 | CDS | 5.66 | 52 | CTG |
| D42040 | 5'UTR | 6.5 | 890 | GC |
| D42044 | 3'UTR | 13 | 4492 | T |
| D42055 | 3'UTR | 6.5 | 4377 | AT |
| D42087 | 3'UTR | 2.72 | 692 | TTTTTTTTGT (SEQ ID NO:231) |
| D42087 | 3'UTR | 3 | 703 | TTTTTTTTG (SEQ ID NO:232) |
| D42108 | 3'UTR | 19.5 | 3438 | GT |
| D43951 | 3'UTR | 12.5 | 4161 | AT |
| D43968 | 3'UTR | 3.8 | 3618 | TTTTG |
| D43968 | 3'UTR | 9.5 | 5470 | GT |
| D43968 | 3'UTR | 7 | 5455 | TG |
| D44652 | UNKNOWN | 14 | 446 | A |
| D44697 | UNKNOWN | 13 | 509 | A |
| D44708 | UNKNOWN | 16 | 559 | GA |
| D44708 | UNKNOWN | 10.5 | 539 | GT |
| D44756 | UNKNOWN | 15 | 4 | T |
| D45027 | 5'UTR | 15 | 5 | C |
| D45027 | 3'UTR | 6.5 | 1311 | TA |
| D45325 | UNKNOWN | 14 | 215 | A |
| D45371 | 3'UTR | 2.56 | 3948 | TTTCTTTCTTCCTTCC (SEQ ID NO:233) |
| D45371 | 3'UTR | 5.66 | 2506 | TTG |
| D45371 | 3'UTR | 12.5 | 4021 | TC |
| D45371 | 3'UTR | 6.5 | 3986 | TC |
| D45371 | 3'UTR | 14 | 1516 | T |
| D49410 | 3'UTR | 13 | 1380 | T |
| D49493 | CDS | 6.66 | 471 | GCT |
| D49677 | CDS | 4.83 | 1338 | AGCCGG |
| D49835 | 5'UTR | 9.66 | 76 | CGC |
| D49835 | 3'UTR | 18 | 5611 | GA |
| D49958 | 5'UTR | 20 | 0 | A |
| D50030 | CDS | 6.33 | 144 | CTG |
| D50370 | CDS | 6.66 | 396 | CAG |
| D50402 | 3'UTR | 4.75 | 2088 | AAAC |
| D50419 | 3'UTR | 5.25 | 3283 | GTAT |
| D50550 | 3'UTR | 14 | 3572 | T |
| D50683 | 5'UTR | 17 | 1502 | A |
| D50683 | 5'UTR | 14 | 83 | T |
| D50683 | 3'UTR | 9.5 | 3585 | TA |
| D50863 | 5'UTR | 3.72 | 103 | GGATCTTCGGC (SEQ ID NO:234) |
| D50911 | 5'UTR | 13 | 245 | T |
| D50911 | 3'UTR | 13 | 1408 | A |
| D50912 | CDS | 8 | 579 | GGA |
| D5091S | 3'UTR | 11 | 2757 | AG |
| D50916 | 3'UTR | 17 | 3401 | T |
| D50917 | 3'UTR | 6.5 | 1631 | TA |
| D50917 | 3'UTR | 16 | 4906 | A |
| D50918 | 3'UTR | 16 | 4428 | AC |
| D50918 | 3'UTR | 18 | 3394 | A |
| D50920 | 3'UTR | 13.5 | 3367 | TG |
| D50924 | 3'UTR | 6 | 2297 | GGA |
| D50927 | 3'UTR | 18 | 2827 | T |
| D50928 | 3'UTR | 16 | 3037 | T |
| D50929 | CDS | 3.56 | 3356 | CGGGGTCCCAGGCGAGGCATGGATGATGAC (SEQ ID |

TABLE 1-continued

| Genbank # | Region | # reps | Position | Unit sequence |
|---|---|---|---|---|
| | | | | NO:235) |
| D50930 | 3'UTR | 14 | 5053 | T |
| D55639 | UNKNOWN | 14 | 8 | T |
| D55655 | CDS | 6 | 1240 | GAT |
| D55655 | 3'UTR | 13 | 2313 | A |
| D60517 | UNKNOWN | 12 | 110 | G |
| D61026 | UNKNOWN | 26 | 5 | T |
| D61473 | UNKNOWN | 7.5 | 134 | AT |
| D61473 | UNKNOWN | 17 | 1 | T |
| D63480 | 3'UTR | 6.33 | 2799 | GGT |
| D63481 | CDS | 6.33 | 1779 | AGG |
| D63484 | CDS | 7.66 | 2605 | TCC |
| D63486 | CDS | 6.33 | 176 | CTG |
| D63486 | CDS | 6 | 824 | GAA |
| D63486 | 3'UTR | 3.66 | 3519 | TTTTG |
| D63486 | 3'UTR | 4.75 | 1771 | TTTG |
| D63710 | 3'UTR | 21 | 3334 | A |
| D63710 | 3'UTR | 16 | 3035 | A |
| D63874 | 3'UTR | 15 | 1111 | A |
| D63878 | CDS | 3.66 | 1280 | GCAGAT |
| D63880 | 3'UTR | 12 | 5104 | A |
| D63881 | CDS | 5.66 | 354 | CCT |
| D63881 | 3'UTR | 17 | 4043 | A |
| D63881 | 3'UTR | 12 | 3155 | T |
| D63997 | 3'UTR | 19 | 5299 | T |
| D64108 | 3'UTR | 7.5 | 1291 | TG |
| D64108 | 3'UTR | 18 | 2017 | A |
| D64108 | 3'UTR | 13 | 1855 | A |
| D67029 | 3'UTR | 3.05 | 4138 | GGTAGGGTTCGTAGGTAGGGCTAGTAGGTAGGGTTAGTA GGTAGGGCTAGTAGGTAGGGCTAGTAGGTAGGGTTAGTA GGTAGGGTTCGTAGGTAGGGCTGGTAGGTAGGGTTAGTA GGTAGGGCTAGTA (SEQ ID NO:236) |
| D67029 | 3'UTR | 7.92 | 4640 | TAGTAGGTAGGGC (SEQ ID NO:237) |
| D67029 | 3'UTR | 3.92 | 4733 | GTAGGTAGGGTTC (SEQ ID NO:238) |
| D67029 | 3'UTR | 2.92 | 4172 | TAGTAGGTAGGGC (SEQ ID NO:239) |
| D67029 | 3'UTR | 6.5 | 3487 | GT |
| D76435 | 5'UTR | 18 | 194 | T |
| D76435 | 3'UTR | 3.66 | 2616 | GGGGGA |
| D79986 | 3'UTR | 6.5 | 4325 | TG |
| D79990 | 3'UTR | 14 | 4467 | T |
| D79992 | 3'UTR | 4.75 | 6460 | TTTG |
| D79994 | CDS | 5.66 | 2967 | GAG |
| D79996 | CDS | 3.83 | 750 | ATGCCC |
| D80003 | CDS | 8.66 | 632 | CAG |
| D80004 | CDS | 3.83 | 844 | GAGCGC |
| D80004 | 3'UTR | 14 | 4405 | A |
| D80005 | 3'UTR | 13 | 4492 | A |
| D80006 | 3'UTR | 3.8 | 2834 | AAGGA |
| D80008 | 3'UTR | 3.8 | 1711 | TTTTG |
| D80010 | 3'UTR | 23 | 4423 | A |
| D80011 | 3'UTR | 14 | 4542 | AT |
| D80011 | 3'UTR | 10.5 | 4569 | TG |
| D80143 | UNKNOWN | 17 | 400 | G |
| D80519 | UNKNOWN | 19 | 3 | T |
| D81363 | UNKNOWN | 16 | 14 | T |
| D82326 | 3'UTR | 18 | 2258 | A |
| D82326 | 3'UTR | 18 | 2276 | T |
| D82344 | 3'UTR | 7 | 1316 | GCG |
| D82347 | 3'UTR | 34 | 1823 | A |
| D83004 | 3'UTR | 5.8 | 860 | TTTTA |
| D83402 | 5'UTR | 4.44 | 8 | CCGCCAGCC |
| D83402 | 3'UTR | 2.8 | 1587 | CCCAGCCTGC (SEQ ID NO:240) |
| D83492 | CDS | 8.33 | 1246 | CCT |
| D83492 | 5'UTR | 13 | 641 | A |
| D83646 | 3'UTR | 4.5 | 2235 | TTTTTCTT |
| D83699 | UNKNOWN | 16 | 797 | T |
| D83735 | 3'UTR | 15 | 1026 | T |
| D84110 | 5'UTR | 5 | 219 | CTTC |
| D85376 | 3'UTR | 12 | 2909 | T |
| D86062 | 3'UTR | 12 | 832 | T |
| D86407 | CDS | 11.66 | 274 | GCT |
| D86407 | 5'UTR | 7.33 | 111 | GCG |
| D86407 | 3'UTR | 16 | 3578 | A |
| D86550 | CDS | 5.66 | 3273 | CAC |
| D86864 | 3'UTR | 14 | 2872 | T |
| D86959 | 3'UTR | 3.8 | 4259 | TTTTG |
| D86960 | 3'UTR | 2.69 | 1820 | TTGCAGTAACAAACTCCAGTCTG (SEQ ID NO:241) |

TABLE 1-continued

| Genbank # | Region | # reps | Position | Unit sequence |
|---|---|---|---|---|
| D86965 | 5'UTR | 14 | 558 | T |
| D86965 | 3'UTR | 12 | 4625 | A |
| D86967 | 3'UTR | 7 | 3860 | AT |
| D86967 | 3'UTR | 19 | 4468 | T |
| D86969 | 3'UTR | 12 | 3930 | G |
| D86970 | CDS | 2.8 | 3532 | CAGCGGGAGAAGCTG (SEQ ID NO:242) |
| D86971 | 3'UTR | 6.5 | 4376 | GT |
| D86971 | 3'UTR | 17 | 2389 | T |
| D86971 | 3'UTR | 16 | 4147 | A |
| D86974 | 3'UTR | 4.73 | 3306 | CTTCCACCCTCAGCGGATGATAATCTCAAGACACCTTCCGAGCGTCAGCTCACTCCCCTTCCACCCTCAGCTCCACCCTCAGCAGATGATAATATCAAGACACCTGCCGAGCGTCTGCGGGGGCCG (SEQ ID NO:243) |
| D86974 | 3'UTR | 2.85 | 2986 | TGCTCACTCCCCTTCCACCCTCAGCGGATGATAATCTCAAGACACCTCCCGAGTGTG (SEQ ID NO:244) |
| D86975 | 3'UTR | 9.33 | 5485 | TAT |
| D86975 | 3'UTR | 15.5 | 5628 | TA |
| D86975 | 3'UTR | 7.5 | 5409 | AC |
| D86975 | 3'UTR | 17 | 5658 | T |
| D86979 | 3'UTR | 18 | 2968 | T |
| D86980 | CDS | 7.33 | 281 | GCG |
| D86980 | CDS | 6 | 135 | GGC |
| D86981 | 3'UTR | 17 | 5479 | T |
| D86982 | CDS | 6.66 | 278 | GCG |
| D86984 | 3'UTR | 16 | 1765 | A |
| D86985 | 3'UTR | 11.5 | 5282 | GT |
| D87071 | CDS | 7.33 | 792 | AGG |
| D87074 | 3'UTR | 8 | 1577 | GT |
| D87075 | 3'UTR | 13 | 3548 | AC |
| D87076 | CDS | 6 | 1158 | ACC |
| D87077 | 3'UTR | 20 | 4255 | T |
| D87078 | CDS | 5.66 | 793 | GCA |
| D87258 | CDS | 6.33 | 77 | GCT |
| D87434 | 3'UTR | 19 | 4037 | T |
| D87440 | 3'UTR | 6.5 | 2589 | TG |
| D87440 | 3'UTR | 12 | 2552 | G |
| D87445 | 3'UTR | 12 | 6434 | A |
| D87450 | 3'UTR | 3.8 | 5738 | TTTTG |
| D87457 | 3'UTR | 19 | 1912 | T |
| D87465 | 3'UTR | 8 | 1797 | TG |
| D87466 | 3'UTR | 21 | 2171 | T |
| D87467 | 3'UTR | 17 | 2960 | T |
| D87470 | 3'UTR | 9.66 | 6528 | AAT |
| D87675 | CDS | 7.33 | 964 | CCA |
| D87682 | 3'UTR | 15 | 2435 | G |
| D87735 | CDS | 15.66 | 462 | CTG |
| D87930 | BORDER | 12 | 3091 | A |
| D87942 | 3'UTR | 13 | 1576 | A |
| D87942 | 3'UTR | 13 | 2254 | T |
| D88153 | 3'UTR | 5.66 | 3581 | ATATCT |
| D88153 | 3'UTR | 17 | 1432 | A |
| D88308 | 5'UTR | 12 | 8 | A |
| D88460 | CDS | 4 | 1708 | AGATGA |
| D89077 | 3'UTR | 14 | 1743 | A |
| D89078 | 5'UTR | 14 | 271 | T |
| D89094 | 5'UTR | 7 | 0 | GCC |
| D89618 | 5'UTR | 6 | 36 | CGC |
| D89859 | 3'UTR | 13 | 1666 | T |
| D89937 | CDS | 3.5 | 90 | GCTCGC |
| D90041 | 3'UTR | 8.66 | 1209 | AAT |
| D90064 | 3'UTR | 20 | 1431 | T |
| D90150 | 5'UTR | 4.2 | 106 | CCGCC |
| D90150 | 3'UTR | 15 | 2469 | T |
| F00361 | UNKNOWN | 15 | 26 | T |
| F00751 | UNKNOWN | 19 | 32 | A |
| F01901 | UNKNOWN | 30 | 54 | A |
| F02199 | UNKNOWN | 14 | 141 | TA |
| F02459 | UNKNOWN | 13 | 16 | T |
| F02740 | UNKNOWN | 13 | 97 | A |
| F03001 | UNKNOWN | 14 | 252 | A |
| F04105 | UNKNOWN | 26 | 12 | T |
| F04275 | UNKNOWN | 5.8 | 152 | ACATC |
| F04275 | UNKNOWN | 14 | 193 | T |
| F04503 | UNKNOWN | 18 | 30 | A |
| F04504 | UNKNOWN | 13 | 130 | T |
| F09493 | UNKNOWN | 8 | 89 | TA |
| F09745 | UNKNOWN | 15 | 162 | A |

TABLE 1-continued

| Genbank # | Region | # reps | Position | Unit sequence |
|---|---|---|---|---|
| F10324 | UNKNOWN | 14 | 46 | T |
| F13687 | UNKNOWN | 6.5 | 9 | TA |
| F23223 | UNKNOWN | 15 | 319 | A |
| F23327 | UNKNOWN | 23 | 314 | A |
| F24633 | UNKNOWN | 12 | 370 | A |
| F24781 | UNKNOWN | 15 | 377 | A |
| F25504 | UNKNOWN | 12 | 459 | A |
| F25759 | UNKNOWN | 14 | 359 | A |
| F26408 | UNKNOWN | 13 | 322 | A |
| F27284 | UNKNOWN | 14 | 377 | A |
| F28428 | UNKNOWN | 5 | 180 | CAAA |
| F28428 | UNKNOWN | 16 | 410 | A |
| F30114 | UNKNOWN | 13 | 115 | A |
| F30369 | UNKNOWN | 19 | 379 | A |
| F30631 | UNKNOWN | 15 | 373 | A |
| F30828 | UNKNOWN | 15 | 431 | A |
| F31447 | UNKNOWN | 18 | 90 | A |
| F32774 | UNKNOWN | 16 | 122 | A |
| F33126 | UNKNOWN | 25 | 325 | A |
| F33131 | UNKNOWN | 15 | 402 | A |
| F33254 | UNKNOWN | 89 | 208 | A |
| F33254 | UNKNOWN | 17 | 26 | T |
| F34074 | UNKNOWN | 15 | 184 | A |
| F34243 | UNKNOWN | 35 | 212 | A |
| F34445 | UNKNOWN | 23 | 209 | A |
| F34445 | UNKNOWN | 13 | 184 | A |
| F34509 | UNKNOWN | 14 | 195 | A |
| F34721 | UNKNOWN | 22 | 130 | A |
| F34725 | UNKNOWN | 55 | 291 | A |
| F34725 | UNKNOWN | 14 | 116 | A |
| F35151 | UNKNOWN | 20 | 144 | A |
| F35374 | UNKNOWN | 28 | 306 | A |
| F35390 | UNKNOWN | 14 | 337 | A |
| F35463 | UNKNOWN | 63 | 127 | A |
| F35571 | UNKNOWN | 14 | 195 | A |
| F35692 | UNKNOWN | 16 | 404 | A |
| F35893 | UNKNOWN | 25 | 319 | A |
| F36186 | UNKNOWN | 31 | 168 | A |
| F36195 | UNKNOWN | 14 | 462 | A |
| F36359 | UNKNOWN | 17 | 127 | A |
| F36936 | UNKNOWN | 14 | 328 | A |
| F37276 | UNKNOWN | 24 | 366 | A |
| F37398 | UNKNOWN | 29 | 410 | A |
| F37541 | UNKNOWN | 36 | 382 | A |
| H01418 | UNKNOWN | 12 | 201 | AC |
| H01596 | UNKNOWN | 13 | 487 | A |
| H02612 | UNKNOWN | 6.5 | 85 | AC |
| H03347 | UNKNOWN | 15 | 1 | T |
| H04006 | UNKNOWN | 7.5 | 235 | AC |
| H04150 | UNKNOWN | 4 | 271 | TTTTG |
| H04482 | UNKNOWN | 21 | 7 | T |
| H04658 | UNKNOWN | 15 | 0 | T |
| H04811 | UNKNOWN | 13 | 0 | T |
| H04817 | UNKNOWN | 13 | 0 | T |
| H04833 | UNKNOWN | 6 | 216 | AAGT |
| H04977 | UNKNOWN | 15 | 0 | T |
| H05218 | UNKNOWN | 14 | 0 | T |
| H05252 | UNKNOWN | 13 | 0 | T |
| H05254 | UNKNOWN | 12 | 0 | T |
| H05255 | UNKNOWN | 26 | 0 | T |
| H05303 | UNKNOWN | 16 | 0 | T |
| H05315 | UNKNOWN | 16 | 12 | T |
| H05322 | UNKNOWN | 21 | 0 | T |
| H05386 | UNKNOWN | 16 | 0 | T |
| H05653 | UNKNOWN | 15 | 0 | T |
| H05742 | UNKNOWN | 29 | 0 | T |
| H05758 | UNNNOWN | 21 | 0 | T |
| H05782 | UNKNOWN | 13 | 0 | T |
| H05821 | UNKNOWN | 17 | 0 | T |
| H05826 | UNKNOWN | 14 | 0 | T |
| H05911 | UNKNOWN | 12 | 0 | T |
| H05923 | UNKNOWN | 14 | 0 | T |
| H05940 | UNKNOWN | 21 | 0 | T |
| H05944 | UNKNOWN | 23 | 0 | T |
| H05958 | UNKNOWN | 23 | 0 | T |
| H05959 | UNKNOWN | 17 | 0 | T |
| H05961 | UNKNOWN | 14 | 0 | T |

TABLE 1-continued

| Genbank # | Region | # reps | Position | Unit sequence |
|---|---|---|---|---|
| H05986 | UNKNOWN | 27 | 0 | T |
| H05992 | UNKNOWN | 8.66 | 366 | TTG |
| H06050 | UNKNOWN | 45 | 0 | T |
| H06053 | UNKNOWN | 40 | 0 | T |
| H06068 | UNKNOWN | 18 | 0 | T |
| H06071 | UNKNOWN | 23 | 0 | T |
| H06211 | UNKNOWN | 37 | 0 | T |
| H06233 | UNKNOWN | 12 | 0 | T |
| H06377 | UNKNOWN | 24 | 0 | T |
| H06391 | UNKNOWN | 15 | 0 | T |
| H06475 | UNKNOWN | 20 | 0 | T |
| H06476 | UNKNOWN | 24 | 0 | T |
| H06509 | UNKNOWN | 14 | 46 | A |
| H06803 | UNKNOWN | 21 | 0 | T |
| H06805 | UNKNOWN | 12 | 0 | T |
| H06810 | UNKNOWN | 12 | 0 | T |
| H07093 | UNKNOWN | 13 | 0 | T |
| H07095 | UNKNOWN | 14 | 0 | T |
| H07100 | UNKNOWN | 14 | 0 | T |
| H07101 | UNKNOWN | 13 | 535 | A |
| H07119 | UNKNOWN | 18 | 0 | T |
| H07134 | UNKNOWN | 16 | 0 | T |
| H07143 | UNKNOWN | 13 | 0 | T |
| H07855 | UNKNOWN | 17 | 0 | T |
| H07865 | UNKNOWN | 18 | 0 | T |
| H07900 | UNKNOWN | 18 | 0 | T |
| H08162 | UNKNOWN | 3.8 | 304 | TTTTG |
| H08162 | UNKNOWN | 20 | 0 | T |
| H08168 | UNKNOWN | 14 | 0 | T |
| H08170 | UNKNOWN | 23 | 0 | T |
| H08202 | UNKNOWN | 15 | 0 | T |
| H08341 | UNKNOWN | 14 | 46 | T |
| H08580 | UNKNOWN | 21 | 0 | T |
| H08627 | UNKNOWN | 13 | 0 | T |
| H08722 | UNKNOWN | 25 | 221 | T |
| H08722 | UNKNOWN | 17 | 0 | T |
| H08756 | UNKNOWN | 30 | 0 | T |
| H08857 | UNKNOWN | 12 | 0 | T |
| H08867 | UNKNOWN | 17 | 0 | T |
| H09029 | UNKNOWN | 17 | 0 | T |
| H09086 | UNKNOWN | 13 | 0 | T |
| H09088 | UNKNOWN | 24 | 0 | T |
| H09103 | UNKNOWN | 15 | 0 | T |
| H09128 | UNKNOWN | 15 | 0 | T |
| H09132 | UNKNOWN | 18 | 0 | T |
| H09243 | UNKNOWN | 8.66 | 178 | TTG |
| H09317 | UNKNOWN | 13 | 0 | T |
| H09320 | UNKNOWN | 19 | 0 | T |
| H09324 | UNKNOWN | 21 | 0 | T |
| H09356 | UNKNOWN | 16 | 0 | T |
| H09570 | UNKNOWN | 5.75 | 7 | TAGA |
| H09716 | UNKNOWN | 19 | 0 | T |
| H09742 | UNKNOWN | 35 | 0 | T |
| H09749 | UNKNOWN | 21 | 0 | T |
| H09778 | UNKNOWN | 4.59 | 47 | AAAAC |
| H10030 | UNKNOWN | 15 | 0 | T |
| H10051 | UNKNOWN | 13 | 0 | T |
| H10059 | UNKNOWN | 26 | 0 | T |
| H10168 | UNKNOWN | 34 | 0 | T |
| H10322 | UNKNOWN | 6.5 | 92 | TA |
| H10372 | UNKNOWN | 18 | 0 | T |
| H10387 | UNKNOWN | 12 | 0 | T |
| H10441 | UNKNOWN | 15 | 0 | T |
| H10652 | UNKNOWN | 24 | 0 | T |
| H10775 | UNKNOWN | 15 | 0 | T |
| H10827 | UNKNOWN | 22 | 0 | T |
| H10830 | UNKNOWN | 24 | 0 | T |
| H10967 | UNKNOWN | 4.16 | 168 | TATTTT |
| H10967 | UNSNOWN | 14 | 0 | T |
| H10992 | UNKNOWN | 13 | 0 | T |
| H11031 | UNKNOWN | 15 | 0 | T |
| H11093 | UNKNOWN | 12 | 0 | |
| H11238 | UNKNOWN | 6.5 | 251 | CT |
| H11238 | UNKNOWN | 25 | 0 | T |
| H11252 | UNKNOWN | 15 | 0 | T |
| H11326 | UNKNOWN | 15 | 0 | T |
| H11333 | UNKNOWN | 17 | 0 | T |

TABLE 1-continued

| Genbank # | Region | # reps | Position | Unit sequence |
|---|---|---|---|---|
| H11341 | UNKNOWN | 15 | 0 | T |
| H11379 | UNKNOWN | 5.66 | 321 | TTA |
| H11380 | UNKNOWN | 14 | 0 | T |
| H11488 | UNKNOWN | 26 | 0 | T |
| H11522 | UNKNOWN | 22 | 0 | T |
| H11557 | UNKNOWN | 16 | 73 | T |
| H11641 | UNKNOWN | 15 | 0 | T |
| H11658 | UNKNOWN | 19 | 0 | T |
| H11724 | UNKNOWN | 12 | 0 | T |
| H11968 | UNKNOWN | 3.83 | 240 | TGTTTT |
| H11968 | UNKNOWN | 12 | 0 | T |
| H12081 | UNKNOWN | 21 | 0 | T |
| H12290 | UNKNOWN | 17 | 0 | T |
| H12320 | UNKNOWN | 14 | 332 | T |
| H12340 | UNKNOWN | 4 | 212 | AAAAG |
| H13440 | UNKNOWN | 12 | 116 | A |
| H14149 | UNKNOWN | 9 | 292 | TG |
| H14453 | UNKNOWN | 54 | 291 | A |
| H14523 | UNKNOWN | 60 | 56 | T |
| H14523 | UNKNOWN | 30 | 22 | T |
| H14598 | UNKNOWN | 6.5 | 89 | CA |
| H14629 | UNKNOWN | 4.5 | 81 | AAAAC |
| H14920 | UNKNOWN | 8 | 84 | AC |
| H15093 | UNKNOWN | 14 | 0 | T |
| H15173 | UNKNOWN | 14 | 0 | T |
| H15358 | UNKNOWN | 16 | 0 | T |
| H15364 | UNKNOWN | 28 | 0 | T |
| H15407 | UNKNOWN | 18 | 0 | T |
| H15555 | UNKNOWN | 16 | 0 | T |
| H15560 | UNKNOWN | 29 | 0 | T |
| H15563 | UNNNOWN | 22 | 0 | T |
| H15650 | UNKNOWN | 7 | 476 | TG |
| H15665 | UNKNOWN | 3.6 | 353 | TTTGT |
| H15665 | UNKNOWN | 15 | 0 | T |
| H16098 | UNKNOWN | 17 | 0 | T |
| H16240 | UNKNOWN | 6.5 | 300 | AG |
| H16240 | UNKNOWN | 12 | 0 | T |
| H16251 | UNKNOWN | 14 | 0 | T |
| H16258 | UNKNOWN | 12 | 0 | T |
| H16398 | UNKNOWN | 15 | 0 | T |
| H16572 | UNKNOWN | 4.75 | 216 | TTTG |
| H16584 | UNKNOWN | 16 | 0 | T |
| H16595 | UNKNOWN | 14 | 0 | T |
| H16714 | UNKNOWN | 27 | 0 | T |
| H16725 | UNKNOWN | 15 | 0 | T |
| H16870 | UNKNOWN | 6.66 | 99 | AAC |
| H16885 | UNKNOWN | 13 | 66 | A |
| H17024 | UNKNOWN | 3.6 | 438 | TTTTA |
| H17137 | UNKNOWN | 27 | 0 | T |
| H17213 | UNKNOWN | 13 | 101 | T |
| H17272 | UNKNOWN | 21 | 307 | T |
| H17304 | UNKNOWN | 16 | 0 | T |
| H17315 | UNKNOWN | 19 | 227 | A |
| H17448 | UNKNOWN | 14 | 0 | T |
| H17543 | UNKNOWN | 13 | 0 | T |
| H17618 | UNKNOWN | 3.8 | 358 | TTTTG |
| H17670 | UNKNOWN | 8 | 250 | TA |
| H17730 | UNNNOWN | 9.5 | 481 | AC |
| H17752 | UNKNOWN | 6.5 | 508 | TA |
| H17810 | UNKNOWN | 16 | 0 | T |
| H17854 | UNKNOWN | 13 | 0 | T |
| H17934 | UNKNOWN | 27 | 0 | T |
| H17953 | UNKNOWN | 14 | 0 | T |
| H17954 | UNKNOWN | 13 | 0 | T |
| H18072 | UNKNOWN | 13 | 0 | T |
| H18074 | UNKNOWN | 25 | 0 | T |
| H18218 | UNKNOWN | 18 | 141 | A |
| H18229 | UNKNOWN | 14 | 191 | TG |
| H18354 | UNKNOWN | 24 | 144 | A |
| H18471 | UNKNOWN | 17 | 0 | T |
| H18554 | UNKNOWN | 6.75 | 122 | GATA |
| H18651 | UNKNOWN | 22 | 0 | T |
| H18652 | UNNNOWN | 19 | 0 | T |
| H18657 | UNKNOWN | 17 | 0 | T |
| H18668 | UNKNOWN | 25 | 0 | T |
| H18913 | UNKNOWN | 13 | 0 | T |
| H18914 | UNKNOWN | 26 | 0 | T |

TABLE 1-continued

| Genbank # | Region | # reps | Position | Unit sequence |
|---|---|---|---|---|
| H18941 | UNKNOWN | 36 | 0 | T |
| H18953 | UNKNOWN | 12 | 0 | T |
| H19137 | UNKNOWN | 13 | 0 | T |
| H19217 | UNKNOWN | 16 | | T |
| H19232 | UNKNOWN | 13 | 0 | T |
| H19334 | UNKNOWN | 12 | 333 | A |
| H19343 | UNKNOWN | 15 | 0 | T |
| H19429 | UNKNOWN | 15 | 0 | T |
| H19442 | UNKNOWN | 13 | 186 | A |
| H19808 | UNKNOWN | 17 | 228 | A |
| H19921 | UNKNOWN | 16 | 214 | A |
| H20551 | UNKNOWN | 28 | 0 | T |
| H20754 | UNKNOWN | 12 | 310 | A |
| H20757 | UNKNOWN | 18 | 240 | T |
| H20757 | UNKNOWN | 12 | 0 | T |
| H20826 | UNKNOWN | 12 | 0 | T |
| H20851 | UNKNOWN | 24 | 0 | T |
| H20851 | UNKNOWN | 14 | 84 | A |
| H22352 | UNKNOWN | 26 | 286 | T |
| H22552 | UNKNOWN | 14 | 0 | T |
| H22558 | UNKNOWN | 14 | 0 | T |
| H22560 | UNKNOWN | 30 | 0 | T |
| H22561 | UNKNOWN | 15 | 0 | T |
| H22570 | UNKNOWN | 15 | 193 | A |
| H22570 | UNKNOWN | 12 | 0 | T |
| H22842 | UNKNOWN | 17 | 0 | T |
| H22851 | UNKNOWN | 15 | 263 | A |
| H22921 | UNKNOWN | 13 | 0 | T |
| H22934 | UNKNOWN | 17 | 0 | T |
| H23067 | UNKNOWN | 7 | 446 | CA |
| H23108 | UNKNOWN | 33 | 0 | T |
| H23230 | UNKNOWN | 5 | 313 | ATTT |
| H23329 | UNKNOWN | 5.8 | 429 | AAAAC |
| H23462 | UNKNOWN | 14 | 0 | T |
| H23467 | UNKNOWN | 10.66 | 52 | TTG |
| H23540 | UNKNOWN | 27 | 0 | T |
| H23542 | UNKNOWN | 16 | 0 | T |
| H23545 | UNKNOWN | 17 | 0 | T |
| H23546 | UNKNOWN | 26 | 0 | T |
| H23549 | UNKNOWN | 37 | 0 | T |
| H23560 | UNKNOWN | 13 | 0 | T |
| H23814 | UNKNOWN | 17 | 156 | T |
| H24018 | UNKNOWN | 14 | 0 | T |
| H24021 | UNKNOWN | 12 | 0 | T |
| H24025 | UNKNOWN | 14.5 | 395 | AC |
| H24025 | UNKNOWN | 12 | 0 | T |
| H24085 | UNKNOWN | 14 | 0 | T |
| H24302 | UNKNOWN | 14 | 0 | T |
| H24306 | UNKNOWN | 17 | 0 | T |
| H24317 | UNKNOWN | 35 | 0 | T |
| H24353 | UNKNOWN | 17 | 0 | T |
| H24355 | UNKNOWN | 16 | 0 | T |
| H24382 | UNKNOWN | 31 | 0 | T |
| H24458 | UNKNOWN | 16 | 0 | T |
| H24467 | UNKNOWN | 16 | 397 | A |
| H24467 | UNKNOWN | 13 | 0 | T |
| H24513 | UNKNOWN | 12 | 423 | T |
| H24556 | UNKNOWN | 13 | 0 | T |
| H25446 | UNKNOWN | 6.5 | 106 | AT |
| H25735 | UNKNOWN | 16 | 223 | A |
| H27234 | UNKNOWN | 17.5 | 144 | AC |
| H27234 | UNKNOWN | 14 | 199 | CT |
| H27234 | UNKNOWN | 9 | 107 | AC |
| H28701 | UNKNOWN | 18 | 0 | T |
| H28716 | UNKNOWN | 28 | 0 | T |
| H28723 | UNKNOWN | 3.6 | 162 | CACCC |
| H28738 | UNKNOWN | 4.8 | 6 | TTTTC |
| H28738 | UNKNOWN | 13 | 26 | T |
| H29016 | UNKNOWN | 12 | 0 | T |
| H29023 | UNKNOWN | 17 | 0 | T |
| H29187 | UNKNOWN | 7.5 | 131 | AC |
| H29241 | UNKNOWN | 15 | 0 | T |
| H29291 | UNKNOWN | 15 | 0 | T |
| H29335 | UNKNOWN | 18 | 0 | T |
| H29443 | UNKNOWN | 12 | 116 | A |
| H29444 | UNKNOWN | 16 | 0 | T |
| H29444 | UNKNOWN | 12 | 309 | A |

TABLE 1-continued

| Genbank # | Region | # reps | Position | Unit sequence |
|---|---|---|---|---|
| H29511 | UNKNOWN | 22 | 8 | T |
| H29546 | UNKNOWN | 42 | 0 | T |
| H29582 | UNKNOWN | 15 | 0 | T |
| H29590 | UNKNOWN | 15 | 0 | T |
| H29610 | UNKNOWN | 14 | 20 | T |
| H29627 | UNKNOWN | 16 | 0 | T |
| H29810 | UNKNOWN | 16 | 0 | T |
| H30064 | UNKNOWN | 12 | 81 | A |
| H30069 | UNKNOWN | 7 | 291 | TG |
| H30382 | UNKNOWN | 13 | 253 | T |
| H38110 | UNKNOWN | 19.5 | 156 | GT |
| H38186 | UNKNOWN | 14 | 0 | T |
| H38245 | UNKNOWN | 4.59 | 11 | AAACA |
| H38247 | UNKNOWN | 16 | 59 | T |
| H38478 | UNKNOWN | 19 | 188 | A |
| H39119 | UNKNOWN | 14 | 355 | T |
| H40374 | UNKNOWN | 15 | 0 | T |
| H40393 | UNKNOWN | 14 | 1 | T |
| H40440 | UNKNOWN | 13 | 231 | T |
| H40612 | UNKNOWN | 20 | 303 | A |
| H40837 | UNKNOWN | 42 | 259 | A |
| H41238 | UNKNOWN | 9.5 | 39 | GT |
| H41572 | UNKNOWN | 5.66 | 83 | AGG |
| H41644 | UNKNOWN | 30 | 129 | A |
| H41789 | UNKNOWN | 6.66 | 185 | TTA |
| H41889 | UNKNOWN | 29 | 307 | A |
| H42085 | UNKNOWN | 12 | 139 | T |
| H42271 | UNKNOWN | 9.5 | 225 | TA |
| H42271 | UNKNOWN | 37 | 185 | A |
| H42320 | UNKNOWN | 29 | 75 | A |
| H42935 | UNKNOWN | 26 | 189 | A |
| H43374 | UNKNOWN | 7.5 | 189 | AC |
| H43374 | UNKNOWN | 6.5 | 161 | AT |
| H43374 | UNKNOWN | 6.5 | 173 | AC |
| H43493 | UNKNOWN | 14 | 345 | T |
| H44404 | UNKNOWN | 6.33 | 69 | TTA |
| H46109 | UNKNOWN | 26 | 148 | T |
| H47519 | UNKNOWN | 4.8 | 21S | TTTTG |
| H48322 | UNKNOWN | 12 | 221 | A |
| H48471 | UNKNOWN | 7.5 | 305 | AC |
| H48471 | UNKNOWN | 7 | 292 | TA |
| H48546 | UNKNOWN | 13 | 280 | T |
| H48767 | UNKNOWN | 12 | 68 | T |
| H49254 | UNKNOWN | 6.5 | 255 | TG |
| H49798 | UNKNOWN | 12 | 163 | A |
| H49988 | UNKNOWN | 5 | 141 | TTTA |
| H49997 | UNKNOWN | 10.5 | 85 | CT |
| H50682 | UNKNOWN | 21 | 180 | T |
| H50984 | UNKNOWN | 16 | 211 | T |
| H52158 | UNKNOWN | 18 | 473 | A |
| H52431 | UNKNOWN | 15 | 0 | T |
| H52622 | UNKNOWN | 13 | 2 | T |
| H52726 | UNKNOWN | 18 | 151 | A |
| H53253 | UNKNOWN | 12 | 340 | T |
| H53262 | UNKNOWN | 15 | 0 | T |
| H53285 | UNKNOWN | 15 | 163 | T |
| H53436 | UNKNOWN | 12 | 10 | A |
| H53841 | UNKNOWN | 19 | 351 | A |
| H54394 | UNKNOWN | 5.6 | 275 | TTTTG |
| H54631 | UNKNOWN | 7.5 | 168 | TG |
| H54631 | UNKNOWN | 13 | 275 | A |
| H55789 | UNKNOWN | 8 | 144 | GT |
| H56152 | UNKNOWN | 7 | 219 | AC |
| H56191 | UNKNOWN | 18 | 292 | A |
| H56424 | UNKNOWN | 6.75 | 192 | TTTA |
| H56424 | UNKNOWN | 14 | 383 | A |
| H56926 | UNKNOWN | 13 | 228 | T |
| H57647 | UNKNOWN | 24 | 20 | T |
| H57946 | UNKNOWN | 18.5 | 238 | TG |
| H57964 | UNKNOWN | 16 | 258 | A |
| H57978 | UNKNOWN | 19 | 177 | A |
| H58369 | UNKNOWN | 9.5 | 149 | GT |
| H58372 | UNKNOWN | 10.5 | 51 | GA |
| H58495 | UNKNOWN | 8 | 144 | GT |
| H59627 | UNKNOWN | 16 | 229 | A |
| H59628 | UNKNOWN | 8 | 16 | TA |
| H59628 | UNKNOWN | 7 | 275 | GA |

TABLE 1-continued

| Genbank # | Region | # reps | Position | Unit sequence |
|---|---|---|---|---|
| H59670 | UNKNOWN | 8.5 | 128 | TG |
| H59865 | UNKNOWN | 12 | 165 | A |
| H59946 | UNKNOWN | 13 | 163 | A |
| H60097 | UNKNOWN | 14 | 0 | T |
| H60164 | UNKNOWN | 15 | 255 | A |
| H60313 | UNKNOWN | 5.5 | 318 | TAAA |
| H60331 | UNKNOWN | 13 | 2 | T |
| H60850 | UNKNOWN | 18 | 244 | A |
| H61003 | UNKNOWN | 15 | 31 | A |
| H61919 | UNKNOWN | 4.75 | 388 | CAAA |
| H61919 | UNKNOWN | 12 | 104 | T |
| H62010 | UNKNOWN | 4 | 156 | GTTTT |
| H62010 | UNKNOWN | 15 | 0 | T |
| H63111 | UNKNOWN | 8 | 396 | GT |
| H63253 | UNKNOWN | 16 | 135 | A |
| H63447 | UNKNOWN | 21 | 9 | T |
| H63504 | UNKNOWN | 22 | 108 | A |
| H63771 | UNKNOWN | 12 | 104 | A |
| H64017 | UNKNOWN | 12 | 131 | A |
| H64145 | UNKNOWN | 14 | 80 | A |
| H64937 | UNKNOWN | 16 | 401 | T |
| H65044 | UNKNOWN | 13.5 | 211 | TG |
| H65280 | UNKNOWN | 5 | 1 | GTTTT |
| H65331 | UNKNOWN | 7 | 253 | CCAT |
| H65951 | UNKNOWN | 15 | 89 | A |
| H65988 | UNKNOWN | 4.75 | 56 | AAAC |
| H67117 | UNKNOWN | 4.75 | 167 | TAAA |
| H67242 | UNKNOWN | 37 | 3 | T |
| H67296 | UNKNOWN | 24 | 90 | A |
| H67560 | UNKNOWN | 13 | 75 | A |
| H67707 | UNKNOWN | 18 | 144 | T |
| H68146 | UNKNOWN | 15 | 144 | T |
| H68713 | UNKNOWN | 13.5 | 399 | GT |
| H68862 | UNKNOWN | 12 | 17 | A |
| H68878 | UNKNOWN | 12 | 342 | A |
| H69127 | UNKNOWN | 14 | 428 | A |
| H69498 | UNKNOWN | 5 | 76 | AAAAC |
| H69675 | UNKNOWN | 6.5 | 117 | TC |
| H69675 | UNKNOWN | 6.5 | 129 | TA |
| H69958 | UNKNOWN | 22 | 312 | T |
| H70868 | UNKNOWN | 5 | 389 | GTTTT |
| H71270 | UNKNOWN | 15 | 0 | T |
| H71462 | UNKNOWN | 10 | 6 | CA |
| H71593 | UNKNOWN | 13 | 202 | T |
| H72029 | UNKNOWN | 23 | 61 | A |
| H72644 | UNKNOWN | 15 | 89 | A |
| H73013 | UNKNOWN | 13 | 353 | T |
| H73289 | UNKNOWN | 19 | 94 | A |
| H73636 | UNKNOWN | 26 | 142 | TG |
| H73649 | UNKNOWN | 13 | 139 | A |
| H73724 | UNKNOWN | 16.5 | 203 | AC |
| H75558 | UNKNOWN | 22 | 82 | A |
| H77479 | UNKNOWN | 15.5 | 137 | AC |
| H77772 | UNKNOWN | 14 | 350 | T |
| H78384 | UNKNOWN | 13 | 179 | A |
| H78573 | UNKNOWN | 3.66 | 276 | TTTAT |
| H78653 | UNKNOWN | 4.75 | 11 | TTTA |
| H79034 | UNKNOWN | 12 | 107 | A |
| H79324 | UNKNOWN | 13 | 157 | A |
| H79536 | UNKNOWN | 14 | 1 | T |
| H79719 | UNKNOWN | 27 | 202 | A |
| H79736 | UNKNOWN | 7 | 114 | AT |
| H79832 | UNKNOWN | 6.5 | 15 | TTAT |
| H79977 | UNKNOWN | 14 | 154 | T |
| H80203 | UNKNOWN | 15 | 0 | T |
| H80374 | UNKNOWN | 4.75 | 201 | TTTG |
| H81271 | UNKNOWN | 14 | 363 | A |
| H81641 | UNKNOWN | 12 | 259 | T |
| H82528 | UNKNOWN | 5.66 | 61 | TTA |
| H82528 | UNKNOWN | 16 | 0 | T |
| H82636 | UNKNOWN | 19 | 1 | T |
| H83935 | UNKNOWN | 19 | 105 | A |
| H84105 | UNKNOWN | 18 | 1 | T |
| H84783 | UNKNOWN | 20 | 283 | A |
| H84790 | UNKNOWN | 14 | 143 | T |
| H85328 | UNKNOWN | 14 | 416 | A |
| H86839 | UNKNOWN | 18 | 1 | T |

TABLE 1-continued

| Genbank # | Region | # reps | Position | Unit sequence |
|---|---|---|---|---|
| H87064 | UNKNOWN | 16 | 76 | T |
| H87181 | UNKNOWN | 15 | 191 | T |
| H88053 | UNKNOWN | 12 | 557 | A |
| H89435 | UNKNOWN | 15 | 206 | A |
| H90123 | UNKNOWN | 21 | 156 | T |
| H90123 | UNKNOWN | 13 | 1 | T |
| H90305 | UNKNOWN | 15 | 87 | A |
| H90328 | UNKNOWN | 13 | 253 | A |
| H90688 | UNKNOWN | 12 | 114 | A |
| H91849 | UNKNOWN | 18 | 47 | A |
| H92026 | UNKNOWN | 5.75 | 156 | TTTG |
| H92085 | UNKNOWN | 36 | 260 | A |
| H92724 | UNKNOWN | 39 | 271 | A |
| H92994 | UNKNOWN | 20 | 19 | T |
| H93001 | UNKNOWN | 16 | 376 | A |
| H93010 | UNKNOWN | 19 | 410 | GT |
| H93040 | UNKNOWN | 12 | 0 | T |
| H93143 | UNKNOWN | 12 | 126 | T |
| H93339 | UNKNOWN | 12 | 0 | T |
| H93959 | UNKNOWN | 8 | 61 | CA |
| H94842 | UNKNOWN | 7.5 | 185 | AT |
| H95251 | UNKNOWN | 6 | 148 | GTTT |
| H95280 | UNKNOWN | 18 | 493 | A |
| H95651 | UNKNOWN | 12 | 58 | A |
| H96124 | UNKNOWN | 17 | 26 | T |
| H96566 | UNKNOWN | 15 | 1 | T |
| H96659 | UNKNOWN | 24 | 30 | A |
| H98103 | UNKNOWN | 3.8 | 282 | AAAAC |
| H98103 | UNKNOWN | 8 | 266 | CA |
| H98167 | UNKNOWN | 11 | 401 | CA |
| H98683 | UNKNOWN | 6.33 | 148 | CAA |
| H98748 | UNKNOWN | 11 | 109 | GA |
| H98748 | UNKNOWN | 9 | 92 | TG |
| H98757 | UNKNOWN | 14 | 176 | A |
| H98780 | UNKNOWN | 8 | 429 | TC |
| H98792 | UNKNOWN | 12 | 400 | T |
| H98896 | UNKNOWN | 21 | 70 | T |
| H98987 | UNKNOWN | 3.8 | 6 | TTTTG |
| H98987 | UNKNOWN | 12 | 39 | A |
| H99398 | UNKNOWN | 6 | 185 | ATT |
| H99538 | UNKNOWN | 12.5 | 123 | TA |
| H99538 | UNKNOWN | 7 | 153 | GA |
| H99538 | UNKNOWN | 1S | 36 | T |
| J00124 | CDS | 6.33 | 279 | CAG |
| J00140 | 5'UTR | 16 | 4 | G |
| J02761 | CDS | 5.66 | 39 | GCT |
| J02931 | 3'UTR | 20 | 1361 | T |
| J02973 | 3'UTR | 6.5 | 2710 | TC |
| J03019 | CDS | 3.83 | 900 | CGCCCT |
| J03019 | CDS | 5.66 | 960 | CCG |
| J03019 | CDS | 5.66 | 1370 | GAC |
| J03069 | 3'UTR | 4.18 | 1761 | ATATATGTATATATATATGTATGTATATATGT (SEQ ID NO:245) |
| J03069 | 3'UTR | 17 | 2563 | T |
| J03075 | CDS | 9.66 | 1072 | GAG |
| J03133 | 3'UTR | 10 | 2505 | TA |
| J03258 | 3'UTR | 21 | 3498 | A |
| J03592 | 3'UTR | 8.5 | 805 | CA |
| J03634 | 3'UTR | 3.8 | 1471 | AAAAC |
| J03798 | CDS | 4 | 447 | AGAGGA |
| J03798 | 5'UTR | 14 | 5 | C |
| J03890 | CDS | 5.66 | 139 | GTG |
| J04076 | CDS | 6 | 962 | GCC |
| J04130 | 5'UTR | 22 | 2 | C |
| J04513 | UNKNOWN | 13 | 4717 | T |
| J04543 | 3'UTR | 13 | 1467 | T |
| J04755 | UNKNOWN | 3.5 | 397 | AAAAAT |
| J04809 | 3'UTR | 21 | 1635 | A |
| J05008 | 3'UTR | 6.5 | 1199 | GA |
| J05016 | UNKNOWN | 5.66 | 168 | GAG |
| J05016 | UNKNOWN | 37 | 2351 | A |
| J05016 | UNKNOWN | 15 | 2086 | T |
| J05032 | 3'UTR | 62 | 1650 | A |
| J05096 | 3'UTR | 14 | 4649 | A |
| J05158 | 3'UTR | 7 | 2480 | CT |
| J05428 | 3'UTR | 14 | 1704 | A |
| J05582 | CDS | 40.48 | 451 | GCCCCGGGCTCCACCGCCCCCCCAGCCCACGGTGTCACC |

TABLE 1-continued

| Genbank # | Region | # reps | Position | Unit sequence |
|---|---|---|---|---|
| | | | | TCGGCCCCGGACACCAGGCCG (SEQ ID NO:246) |
| J05682 | 3'UTR | 6.5 | 1218 | AT |
| L00352 | 3'UTR | 7 | 4874 | TA |
| L00972 | UNKNOWN | 42 | 2668 | A |
| L01087 | 5'UTR | 2.63 | 18 | CAGTCCCCGCG (SEQ ID NO:247) |
| L02321 | 3'UTR | 8.5 | 1235 | GT |
| L02867 | 3'UTR | 13 | 1962 | T |
| L04510 | 3'UTR | 10.5 | 1849 | AT |
| L05144 | 3'UTR | 16 | 2371 | TG |
| L05148 | UNKNOWN | 21 | 2431 | A |
| L05424 | 3'UTR | 9.5 | 2384 | AT |
| L05779 | 5'UTR | 13.5 | 8 | CT |
| L06133 | 3'UTR | 11 | 5633 | TTG |
| L06147 | CDS | 7.33 | 996 | GAG |
| L07648 | 5'UTR | 19 | 64 | T |
| L07648 | 3'UTR | 5 | 992 | AAAAC |
| L07868 | 3'UTR | 3.5 | 4271 | TTTTTC |
| L07868 | 3.UTR | 17 | 4314 | T |
| L08096 | 3'UTR | 3.8 | 759 | ATTTT |
| L08424 | CDS | 14.33 | 581 | GCA |
| L08424 | 3'UTR | 5.66 | 1272 | AAG |
| L08835 | 5'UTR | 24 | 122 | A |
| L08835 | 3'UTR | 11.66 | 2887 | TGC |
| L08895 | 5'UTR | 8.5 | 193 | TC |
| L08895 | 3'UTR | 6.5 | 1861 | GT |
| L08895 | 3'UTR | 13 | 1842 | T |
| L09190 | CDS | 3.97 | 1259 | AGGAGGAGAGGCGCGAGCAGCAGCTGAGGCGCGAGCAGG (SEQ ID NO:248) |
| L09190 | CDS | 10.72 | 1383 | GAGGCGCGAGCAGCAGCT (SEQ ID NO:249) |
| L09190 | CDS | 5.66 | 3002 | AGG |
| L10284 | 3'UTR | 12 | 2130 | T |
| L10373 | UNKNOWN | 7.33 | 19 | GCC |
| L10374 | UNKNOWN | 9.33 | 380 | GCA |
| L10374 | UNKNOWN | 6.33 | 560 | CGG |
| L10377 | UNKNOWN | 15.66 | 739 | CAG |
| L10378 | UNKNOWN | 10 | 448 | CAG |
| L10378 | UNKNOWN | 5.66 | 403 | CAG |
| L10844 | 3'UTR | 5.75 | 1942 | TTTA |
| L10910 | 5'UTR | 8 | 65 | GCA |
| L11066 | UNKNOWN | 20 | 2825 | A |
| L11066 | UNKNOWN | 13 | 2795 | T |
| L11284 | UNKNOWN | 39 | 2183 | A |
| L11285 | UNKNOWN | 18 | 1558 | A |
| L11695 | CDS | 9.33 | 126 | GGC |
| L11695 | 5'UTR | 3.8 | 36 | GGCCG |
| L12168 | 3'UTR | 15 | 2186 | A |
| L12350 | 3'UTR | 3.5 | 5126 | TTTGTT |
| L12392 | CDS | 21.66 | 366 | CAG |
| L12392 | CDS | 7.66 | 441 | CCG |
| L12398 | CDS | 2.5 | 57 | GCGGGGGCATCT (SEQ ID NO:250) |
| L12535 | 5'UTR | 12 | 8 | T |
| L13266 | CDS | 5.66 | 2872 | GAG |
| L13266 | 5'UTR | 6.33 | 806 | GCC |
| L13286 | 3'UTR | 6.5 | 2619 | TG |
| L13385 | 3'UTR | 7 | 4166 | TG |
| L13434 | CDS | 6.33 | 1880 | CCA |
| L13689 | 5'UTR | 6.33 | 154 | GAG |
| L13720 | CDS | 6.33 | 184 | GCT |
| L13720 | 5'UTR | 7.66 | 5 | GCC |
| L13744 | CDS | 3.09 | 638 | CAGCAGCAGCAGCAGCAGCAGCAGTAGCAGCAG (SEQ ID NO:251) |
| L13744 | CDS | 5 | 1339 | CCAGCT |
| L13744 | CDS | 10.66 | 663 | AGC |
| L13744 | CDS | 8 | 638 | CAG |
| L13744 | 3'UTR | 12 | 1937 | T |
| L13744 | 3'UTR | 12 | 2868 | A |
| L13773 | 3'UTR | 5.8 | 7690 | TTTTG |
| L13773 | 3'UTR | 4 | 8818 | TATAT |
| L13773 | 3'UTR | 10 | 6841 | GT |
| L13943 | 3'UTR | 13 | 1841 | T |
| L14561 | 3'UTR | 3.8 | 4102 | AAAAC |
| L14561 | 3'UTR | 12 | 3558 | A |
| L14723 | UNKNOWN | 32 | 3078 | T |
| L14812 | 3'UTR | 8.5 | 3793 | AT |
| L14837 | 3'UTR | 4.8 | 7275 | TTTTC |
| L14837 | 3'UTR | 16 | 7295 | T |
| L16991 | 3'UTR | 29 | 1067 | T |

TABLE 1-continued

| Genbank # | Region | # reps | Position | Unit sequence |
|---|---|---|---|---|
| L17131 | 5'UTR | 4.16 | 322 | GAGCCC |
| L17328 | 5'UTR | 13 | 884 | T |
| L19160 | UNKNOWN | 16 | 257 | A |
| L19183 | 3'UTR | 16 | 739 | T |
| L19593 | 3'UTR | 15 | 1874 | A |
| L19778 | 3'UTR | 18 | 1571 | T |
| L19872 | 3'UTR | 19 | 4493 | T |
| L20298 | 3'UTR | 14 | 1215 | T |
| L20433 | CDS | 9.66 | 531 | CAC |
| L20861 | 3'UTR | 3.83 | 3028 | ATATAA |
| L20861 | 3'UTR | 4.59 | 2066 | AAAAC |
| L20861 | 3'UTR | 7.5 | 3008 | AT |
| L20861 | 3'UTR | 23 | 3521 | T |
| L20977 | 5'UTR | 4.16 | 59 | CAGCGG |
| L20977 | 5'UTR | 3.8 | 34 | GGGCC |
| L20977 | 3'UTR | 4.75 | 4559 | TTTG |
| L20977 | 3'UTR | 9.5 | 4846 | AT |
| L21998 | CDS | 100 | 5712 | CCAACCACGACACCCATCACCACCACCACTACGGTGACC CCAACCCCAACACCCACCGGCACACAGACC (SEQ ID NO:252) |
| L21998 | CDS | 3.23 | 4422 | CCAACCACCACTCCCAGCCCT (SEQ ID NO:253) |
| L21998 | CDS | 6 | 3873 | ACC |
| L22075 | 5'UTR | 6 | 20 | GGC |
| L23852 | 3'UTR | 20 | 499 | T |
| L24123 | UNKNOWN | 4.33 | 3209 | CTGGAC |
| L24123 | UNKNOWN | 4.75 | 3533 | GAAG |
| L24123 | UNKNOWN | 7 | 4936 | GA |
| L24123 | UNKNOWN | 13 | 3552 | C |
| L25110 | UNKNOWN | 4.5 | 1347 | TGGG |
| L25286 | 3'UTR | 13 | 4351 | T |
| L26339 | CDS | 6.66 | 1990 | AGC |
| L26494 | CDS | 7.66 | 122 | GCG |
| L26494 | CDS | 6 | 1346 | CAC |
| L26494 | 5'UTR | 6 | 6 | CGG |
| L26494 | 3'UTR | 14 | 1481 | A |
| L26953 | CDS | 32 | 1577 | A |
| L26953 | CDS | 12 | 1159 | A |
| L26953 | 3'UTR | 4.16 | 2797 | CAAAAA |
| L27560 | UNKNOWN | 6 | 3438 | GTT |
| L27560 | UNKNOWN | 14 | 3658 | A |
| L27745 | CDS | 7 | 1067 | AG |
| L30117 | UNKNOWN | 79 | 652 | T |
| L31881 | 3'UTR | 4.59 | 1481 | CCCAG |
| L32832 | CDS | 2.93 | 2092 | GAGGAGGAGGAAGAA (SEQ ID NO:254) |
| L32832 | CDS | 10 | 5866 | CAA |
| L32832 | CDS | 7.66 | 10261 | CAG |
| L32832 | CDS | 7 | 2985 | GGC |
| L33075 | 3'UTR | 16 | 6723 | A |
| L33243 | 3'UTR | 9 | 13947 | TG |
| L33477 | 3'UTR | 10 | 3557 | CA |
| L34357 | CDS | 6 | 590 | GGC |
| L34408 | UNKNOWN | 15 | 706 | A |
| L35592 | UNKNOWN | 14 | 1577 | AC |
| L36140 | 5'UTR | 24 | 1 | T |
| L36642 | 3'UTR | 4 | 4333 | CAAAA |
| L36983 | 3'UTR | 5.66 | 3368 | CTC |
| L37112 | CDS | 3.5 | 1257 | CCTCAG |
| L37198 | UNKNOWN | 23 | 7 | A |
| L38707 | CDS | 3.83 | 146 | CCGGGG |
| L38951 | 3'UTR | 31 | 3653 | A |
| L38951 | 3'UTR | 13 | 3736 | T |
| L38961 | 3'UTR | 22 | 2283 | T |
| L39064 | CDS | 8.33 | 1504 | AGC |
| L39833 | 3'UTR | 13 | 1809 | A |
| L39833 | 3'UTR | 13 | 2713 | T |
| L40377 | 5'UTR | 6.66 | 33 | GCG |
| L40377 | 5'UTR | 6.33 | 51 | GCA |
| L40392 | 3'UTR | 14 | 2209 | T |
| L40992 | CDS | 6 | 18 | CAG |
| L40992 | BORDER | 5.66 | 0 | CAG |
| L41690 | CDS | 6 | 620 | GCC |
| L41887 | 3'UTR | 14 | 2046 | A |
| L41919 | CDS | 8 | 440 | GGC |
| L42025 | 5'UTR | 5.66 | 1 | GGC |
| L42243 | 3'UTR | 7 | 3934 | GT |
| L42243 | 3'UTR | 16 | 2217 | T |
| L42243 | 3'UTR | 15 | 1137 | T |

TABLE 1-continued

| Genbank # | Region | # reps | Position | Unit sequence |
|---|---|---|---|---|
| L42243 | 3'UTR | 12 | 2874 | A |
| L44505 | UNKNOWN | 13 | 309 | A |
| L46353 | 5'UTR | 2.8 | 2094 | CACACTCACA (SEQ ID NO:255) |
| L46353 | 5'UTR | 19 | 2401 | TC |
| L46353 | 5'UTR | 9.5 | 2381 | TC |
| L46353 | 5'UTR | 6.5 | 1394 | TG |
| L46353 | 5'UTR | 13 | 264 | A |
| L46353 | 3'UTR | 5 | 3378 | TGGGG |
| L48796 | UNKNOWN | 15 | 147 | A |
| L49169 | 3'UTR | 6 | 1661 | GAG |
| L49169 | 3'UTR | 6.5 | 2689 | CT |
| L49380 | CDS | 6 | 1771 | GCC |
| L76702 | CDS | 4.33 | 301 | CAGCCC |
| L76703 | 3'UTR | 12 | 2219 | A |
| L77864 | CDS | 5.66 | 571 | GAG |
| L78833 | 3'UTR | 18 | 6465 | A |
| M10901 | 3'UTR | 18 | 3217 | A |
| M11220 | 3'UTR | 5.5 | 693 | TATT |
| M11353 | 3'UTR | 16 | 817 | A |
| M11722 | 5'UTR | 14 | 216 | G |
| M12783 | UNKNOWN | 3.85 | 296 | CGCAGCT |
| M12783 | UNKNOWN | 7.5 | 3612 | AC |
| M12783 | UNKNOWN | 16 | 238 | A |
| M13232 | 3'UTR | 6.5 | 1889 | CA |
| M13452 | 3'UTR | 8.5 | 2030 | GA |
| M13452 | 3'UTR | 15 | 1745 | A |
| M13903 | CDS | 5 | 528 | GAGCAGCAGGAGGGGCAGCTGGAGCTCCCA (SEQ ID NO:256) |
| M13903 | CDS | 3.43 | 679 | AGCAGCAGGAGGGGCAGCTGGAGCTCTCTG (SEQ ID NO:257) |
| M14058 | 3'UTR | 12 | 2221 | A |
| M14083 | 3'UTR | 7 | 2667 | AT |
| M14170 | CDS | 7.66 | 30 | TGC |
| M14219 | 3'UTR | 13 | 1660 | T |
| M14630 | UNKNOWN | 12 | 538 | A |
| M14648 | 3'UTR | 10.66 | 3535 | TTG |
| M14745 | 3'UTR | 7.5 | 897 | AC |
| M14764 | 5'UTR | 3.6 | 36 | AGCGC |
| M14764 | 3'UTR | 7 | 2444 | CA |
| M15169 | UNKNOWN | 13 | 2852 | C |
| M15353 | 3'UTR | 18 | 847 | T |
| M16276 | UNKNOWN | 12 | 1368 | A |
| M16505 | UNKNOWN | 6.5 | 2611 | AC |
| M16505 | UNKNOWN | 18 | 3645 | A |
| M16801 | CDS | 3.83 | 2295 | CCCCCA |
| M16937 | 3'UTR | 2.7 | 865 | AAACAAA (SEQ ID NO:258) |
| M16938 | 5'UTR | 7 | 172 | TG |
| M16965 | CDS | 2.94 | 115 | TACCTTTGTTGGAAGACG (SEQ ID NO:259) |
| M16965 | CDS | 2.5 | 591 | CTGGAAGACATGGATTTT (SEQ ID NO:260) |
| M18533 | UNKNOWN | 5.25 | 12297 | TTGA |
| M18533 | UNKNOWN | 8.5 | 11725 | AC |
| M18728 | UNKNOWN | 12 | 2266 | A |
| M19154 | 3'UTR | 7.33 | 2117 | ACA |
| M19961 | 5'UTR | 13 | 0 | T |
| M20681 | UNKNOWN | 13 | 2233 | T |
| M20681 | UNKNOWN | 13 | 3705 | A |
| M21305 | CDS | 6.4 | 56 | TGGAA |
| M21305 | BORDER | 3.8 | 0 | ATGGA |
| M21574 | 3'UTR | 14 | 4503 | T |
| M23114 | 3'UTR | 3.8 | 3839 | CACCC |
| M23263 | CDS | 20.33 | 1884 | GGC |
| M23263 | CDS | 17 | 701 | GCA |
| M24069 | CDS | 7.66 | 229 | CCA |
| M24283 | 3'UTR | 9 | 2742 | GT |
| M24486 | 3'UTR | 16 | 2350 | T |
| M24902 | 3'UTR | 12.5 | 2338 | AATA |
| M25667 | 3'UTR | 9 | 1153 | CT |
| M25667 | 3'UTR | 17 | 973 | A |
| M28170 | 3'UTR | 17 | 1816 | GT |
| M28713 | 5'UTR | 6.66 | 253 | CGG |
| M29053 | 3'UTR | 3.8 | 1579 | AAAAT |
| M29204 | UNKNOWN | 21 | 288 | A |
| M29873 | 3'UTR | 6.5 | 1687 | TA |
| M29874 | 3'UTR | 7 | 1688 | AT |
| M29874 | 3'UTR | 15 | 2510 | T |
| M30448 | 3'UTR | 26 | 887 | A |
| M31165 | BORDER | 12 | 900 | A |

TABLE 1-continued

| Genbank # | Region | # reps | Position | Unit sequence |
|---|---|---|---|---|
| M31523 | 3'UTR | 12 | 2316 | T |
| M31525 | 3'UTR | 6.5 | 1037 | AC |
| M31682 | 3'UTR | 8 | 1601 | AG |
| M31682 | 3'UTR | 6.5 | 1886 | TG |
| M31732 | 3'UTR | 15 | 1474 | C |
| M31899 | CDS | 5.66 | 869 | GAA |
| M31932 | 3'UTR | 13 | 1430 | T |
| M32315 | 3'UTR | 7.75 | 1814 | TTTG |
| M32315 | 3'UTR | 6.5 | 3589 | TG |
| M32315 | 3'UTR | 12 | 2368 | A |
| M34041 | CDS | 6.66 | 903 | GAG |
| M34309 | 5'UTR | 6.S | 4 | CA |
| M34539 | 3'UTR | 12 | 1120 | T |
| M35531 | 3'UTR | 6.25 | 2068 | TTAT |
| M35531 | 3'UTR | 18 | 1752 | T |
| M35663 | 3'UTR | 18 | 2056 | T |
| M36089 | UNKNOWN | 17 | 2462 | AC |
| M36542 | 3'UTR | 18 | 1886 | A |
| M36711 | 3'UTR | 6.66 | 1494 | GCC |
| M36820 | 3'UTR | 6.25 | 540 | TATT |
| M36860 | CDS | 3.66 | 950 | CAGCTG |
| M37981 | CDS | 6.33 | 113 | GCT |
| M54915 | 5'UTR | 3.8 | 246 | CAGCA |
| M54915 | 5'UTR | 9 | 45 | GCA |
| M54915 | 3'UTR | 5.25 | 2191 | TATT |
| M54927 | 3'UTR | 14 | 2476 | A |
| M55047 | 3'UTR | 22.5 | 2095 | GT |
| M55053 | 3'UTR | 12 | 1915 | T |
| M55172 | CDS | 7.96 | 3238 | CTGCCCCTGGAGTAGAGGACATCAGCGGGCTTCCTTCTG GAGAAGTTCTAGAGACCG (SEQ ID NO:261) |
| M55172 | CDS | 5.52 | 2979 | GGGCTTCCTTCTGGAGAAGTTCTAGAGACCACTGCCCCT GGAGTAGAGGACATCAGC (SEQ ID NO:262) |
| M55172 | CDS | 5 | 3636 | GCTGCCCCTGGAGTAGAGGACATCAGCGGGCTTCCTTCT GGAGAAGTTCTAGAGACT (SEQ ID NO:263) |
| M55422 | 5'UTR | 5.66 | 944 | TTG |
| M55542 | 3'UTR | 14 | 2006 | A |
| M55593 | 5'UTR | 7.33 | 87 | GCG |
| M55630 | UNKNOWN | 22 | 126 | GT |
| M55630 | UNKNOWN | 12 | 1538 | A |
| M55654 | CDS | 18.66 | 466 | CAG |
| M55654 | CDS | 9.66 | 430 | CAG |
| M55654 | 3'UTR | 13 | 1297 | T |
| M55683 | 3'UTR | 12 | 1203 | TG |
| M57627 | 3'UTR | 3.5 | 1457 | AAAAAT |
| M58583 | 3'UTR | 5.66 | 1354 | TTG |
| M59305 | 5'UTR | 4.16 | 129 | CTTTTT |
| M59465 | 3'UTR | 12 | 3986 | A |
| M59499 | 3'UTR | 2.91 | 2093 | TAGCTTCATGAA (SEQ ID NO:264) |
| M59499 | 3'UTR | 15 | 2248 | T |
| M59941 | 3'UTR | 8 | 2912 | AC |
| M60052 | CDS | 14.33 | 911 | GAT |
| M60052 | CDS | 8.66 | 749 | GAG |
| M60314 | 5'UTR | 13 | 637 | T |
| M60315 | CDS | 7 | 493 | AGC |
| M60626 | 3'UTR | 13 | 1206 | A |
| M61108 | 3'UTR | 12 | 3880 | TG |
| M61108 | 3'UTR | 14 | 4060 | T |
| M61877 | 5'UTR | 11.5 | 123 | TC |
| M61877 | 5'UTR | 12 | 45 | T |
| M61877 | 3'UTR | 17.5 | 7539 | GT |
| M62302 | UNKNOWN | 5.66 | 1799 | GCG |
| M62626 | 5'UTR | 3.6 | 658 | CCCCT |
| M62831 | 3'UTR | 4.75 | 1112 | TTTG |
| M63175 | 3'UTR | 24 | 1503 | T |
| M64347 | 3'UTR | 8 | 2317 | TG |
| M64347 | 3'UTR | 6.5 | 2831 | AT |
| M64716 | 5'UTR | 16 | 0 | T |
| M64930 | UNKNOWN | 14 | 3427 | A |
| M64936 | UNKNOWN | 50 | 3307 | A |
| M65131 | UNKNOWN | 28 | 2770 | A |
| M65290 | 3'UTR | 4.75 | 2256 | TTTA |
| M68520 | 3'UTR | 17 | 2047 | T |
| M69013 | 3'UTR | 12 | 1386 | T |
| M73047 | 3'UTR | 22 | 4250 | T |
| M73531 | 3'UTR | 19 | 1757 | T |
| M73547 | 3'UTR | 26.5 | 1412 | AC |
| M73746 | CDS | 5.66 | 73 | GCT |

TABLE 1-continued

| Genbank # | Region | # reps | Position | Unit sequence |
|---|---|---|---|---|
| M74047 | 3'UTR | 19 | 881 | AT |
| M74047 | 3'UTR | 13 | 1966 | T |
| M74491 | 3'UTR | 7 | 2744 | TG |
| M74491 | 3'UTR | 6.5 | 1124 | CT |
| M74525 | 5'UTR | 11.66 | 296 | CGG |
| M74525 | 5'UTR | 12 | 381 | T |
| M74719 | 5'UTR | 7.66 | 37 | GGC |
| M76558 | CDS | 3.S | 2987 | GGAAGA |
| M76558 | BORDER | 7.66 | 509 | GAT |
| M76729 | CDS | 6.33 | 294 | GCT |
| M77140 | 3'UTR | 12 | 461 | T |
| M77235 | 3'UTR | 7 | 6773 | CA |
| M77498 | CDS | 3.73 | 447 | GGTGGTTCTGGTGGT (SEQ ID NO:265) |
| M77698 | CDS | 6 | 446 | CCA |
| M77698 | CDS | 5.66 | 366 | GAG |
| M77698 | 3'UTR | 13 | 2018 | A |
| M77698 | 3'UTR | 12 | 1641 | A |
| M80482 | CDS | 3.66 | 243 | GGGCGCGGG |
| M80899 | 3'UTR | 7.5 | 3857 | AT |
| M81601 | 5'UTR | 7.66 | 0 | GCC |
| M83216 | CDS | 3 | 1182 | GGAGGAAGAGAAAAGGGCAGCAGAGGAGAGGCAGAGGAT AAA (SEQ ID NO:266) |
| M83738 | 3'UTR | 9 | 2798 | TG |
| M83751 | CDS | 8 | 256 | GGA |
| M84424 | 3'UTR | 8.5 | 1341 | AC |
| M84739 | 5'UTR | 14 | 25 | C |
| M85169 | 3'UTR | 12 | 1712 | T |
| M85590 | UNKNOWN | 17 | 0 | T |
| M85670 | UNKNOWN | 13 | 227 | A |
| M86400 | 3'UTR | 18 | 1632 | T |
| M86406 | 5'UTR | 3.57 | 71 | CGCCCGC |
| M86406 | 3'UTR | 6.5 | 2952 | GA |
| M86699 | 5'UTR | 15 | 8 | T |
| M87503 | CDS | 7 | 574 | AGC |
| M87503 | 3'UTR | 13 | 1400 | T |
| M88108 | 3'UTR | 12 | 1749 | A |
| M88282 | 3'UTR | 7.75 | 4728 | AAAG |
| M88282 | 3'UTR | 16 | 4715 | A |
| M89796 | 3'UTR | 23 | 2068 | A |
| M89796 | 3'UTR | 14 | 1205 | T |
| M90391 | CDS | 6.66 | 694 | CCT |
| M90656 | 5'UTR | 9.66 | 55 | GGA |
| M91463 | 3'UTR | 23 | 2202 | T |
| M91467 | 3'UTR | 4.5 | 1793 | TTGT |
| M92287 | 5'UTR | 6.5 | 18 | GC |
| M92299 | 3'UTR | 15 | 1396 | A |
| M92357 | CDS | 6.66 | 442 | GGC |
| M92357 | 3'UTR | 18 | 3256 | T |
| M92439 | UNKNOWN | 64 | 4718 | A |
| M92642 | 3'UTR | 12 | 5048 | T |
| M93056 | UNKNOWN | 18 | 1298 | A |
| M93650 | BORDER | 14 | 1684 | A |
| M93651 | CDS | 5.66 | 705 | GAT |
| M93651 | 3'UTR | 23 | 907 | T |
| M94046 | UNKNOWN | 15 | 1887 | T |
| M95178 | 5'UTR | 3.6 | 4 | CCAGC |
| M95767 | CDS | 3.77 | 66 | GCGCTGCTG |
| M96684 | CDS | 5.66 | 188 | GGC |
| M96684 | 3'UTR | 7 | 1047 | CA |
| M96739 | UNKNOWN | 6 | 2046 | TATT |
| M96739 | UNKNOWN | 36 | 2565 | A |
| M96739 | UNKNOWN | 12 | 1603 | A |
| M96824 | CDS | 7.33 | 1234 | AGC |
| M96859 | CDS | 7 | 310 | GCG |
| M96859 | 5'UTR | 6 | 15 | TGC |
| M96859 | 3'UTR | 4 | 2827 | GGGGC |
| M96956 | 3'UTR | 12 | 1641 | T |
| M96982 | CDS | 3.66 | 669 | GTGGCG |
| M97287 | CDS | 7 | 2014 | CAG |
| M97287 | 5'UTR | 13 | 61 | T |
| M97675 | 5'UTR | 6 | 342 | GCC |
| M97676 | 3'UTR | 28 | 1542 | A |
| M98343 | 3'UTR | 30 | 1913 | T |
| M98447 | CDS | 3.83 | 162 | CCAGAG |
| M98776 | CDS | 3.4 | 281 | TGGTGGTGGTGGCTT (SEQ ID NO:267) |
| M98776 | CDS | 5.66 | 145 | GTG |
| M98833 | 3'UTR | 12 | 2231 | T |

TABLE 1-continued

| Genbank # | Region | # reps | Position | Unit sequence |
|---|---|---|---|---|
| M99063 | CDS | 7.66 | 1649 | GCA |
| N20081 | UNKNOWN | 15 | 1 | T |
| N20320 | UNKNOWN | 35 | 1 | T |
| N20522 | UNKNOWN | 3.5 | 40 | ACATAC |
| N20653 | UNKNOWN | 20 | 23 | A |
| N21103 | UNKNOWN | 5.75 | 182 | TTTG |
| N21103 | UNKNOWN | 4.75 | 166 | TTTA |
| N21111 | UNKNOWN | 16 | 269 | T |
| N21207 | UNKNOWN | 14 | 363 | T |
| N21297 | UNKNOWN | 23 | 93 | T |
| N21460 | UNKNOWN | 20 | 49 | T |
| N21555 | UNKNOWN | 2.56 | 180 | TATATATATATCTCTT (SEQ ID NO:268) |
| N21555 | UNKNOWN | 6.5 | 224 | TA |
| N21613 | UNKNOWN | 8 | 0 | GTT |
| N21613 | UNKNOWN | 19 | 90 | A |
| N22032 | UNKNOWN | 20 | 0 | T |
| N22058 | UNKNOWN | 15 | 0 | T |
| N22180 | UNKNOWN | 24 | 0 | T |
| N22378 | UNKNOWN | 13 | 27 | T |
| N22415 | UNKNOWN | 13 | 0 | T |
| N22687 | UNKNOWN | 22 | 43 | T |
| N22760 | UNKNOWN | 15 | 445 | T |
| N22770 | UNKNOWN | 8.5 | 367 | GT |
| N22959 | UNKNOWN | 22 | 147 | A |
| N23052 | UNKNOWN | 13 | 1 | T |
| N23130 | UNKNOWN | 17 | 400 | T |
| N23377 | UNKNOWN | 6.5 | 372 | GA |
| N23489 | UNKNOWN | 15 | 431 | T |
| N23599 | UNKNOWN | 7.5 | 203 | AT |
| N23666 | UNKNOWN | 5 | 76 | AAAT |
| N23666 | UNKNOWN | 17 | 250 | A |
| N23674 | UNKNOWN | 18 | 0 | T |
| N23685 | UNKNOWN | 20 | 0 | T |
| N23766 | UNKNOWN | 22 | 390 | A |
| N23781 | UNKNOWN | 8 | 62 | TTA |
| N23846 | UNKNOWN | 22 | 0 | T |
| N23858 | UNKNOWN | 3.83 | 223 | TTTTTG |
| N23870 | UNKNOWN | 21 | 174 | T |
| N23872 | UNKNOWN | 18 | 0 | T |
| N23885 | UNKNOWN | 5.25 | 186 | TGTT |
| N23885 | UNKNOWN | 9 | 75 | CT |
| N23885 | UNKNOWN | 12 | 426 | A |
| N23913 | UNKNOWN | 16 | 198 | T |
| N23949 | UNKNOWN | 35 | 1 | T |
| N23990 | UNKNOWN | 14 | 322 | A |
| N24046 | UNKNOWN | 30 | 169 | AC |
| N24046 | UNKNOWN | 15 | 318 | T |
| N25043 | UNKNOWN | 18 | 0 | T |
| N25096 | UNKNOWN | 3.66 | 463 | GTTTTG |
| N25532 | UNKNOWN | 20 | 170 | T |
| N25670 | UNKNOWN | 6.5 | 508 | CA |
| N25708 | UNKNOWN | 4 | 98 | GTTTT |
| N25708 | UNKNOWN | 26 | 1 | T |
| N26011 | UNKNOWN | 3.8 | 121 | TTTTA |
| N26213 | UNKNOWN | 7.5 | 309 | AG |
| N26213 | UNKNOWN | 13 | 291 | A |
| N26656 | UNKNOWN | 23 | 0 | T |
| N26727 | UNKNOWN | 30 | 0 | T |
| N26740 | UNKNOWN | 22.5 | 143 | AC |
| N26740 | UNKNOWN | 7 | 193 | AG |
| N26908 | UNKNOWN | 19 | 180 | T |
| N27028 | UNKNOWN | 20 | 257 | T |
| N27272 | UNKNOWN | 16 | 476 | T |
| N27321 | UNKNOWN | 22 | 0 | T |
| N27422 | UNKNOWN | 15 | 0 | T |
| N27448 | UNKNOWN | 18 | 91 | A |
| N27553 | UNKNOWN | 14 | 376 | A |
| N28600 | UNKNOWN | 12 | 474 | A |
| N28704 | UNKNOWN | 22 | 7 | T |
| N28842 | UNKNOWN | 13 | 44 | A |
| N29756 | UNKNOWN | 23 | 0 | T |
| N30008 | UNKNOWN | 6 | 176 | CCG |
| N30180 | UNKNOWN | 23 | 221 | T |
| N30205 | UNKNOWN | 18 | 224 | T |
| N30417 | UNKNOWN | 14.5 | 354 | GT |
| N30696 | UNKNOWN | 10 | 225 | GA |
| N30697 | UNKNOWN | 16 | 103 | A |

TABLE 1-continued

| Genbank # | Region | # reps | Position | Unit sequence |
|---|---|---|---|---|
| N30764 | UNKNOWN | 37 | 0 | T |
| N31574 | UNKNOWN | 25 | 1 | T |
| N32030 | UNKNOWN | 5.5 | 0 | ATTT |
| N32341 | UNKNOWN | 6 | 159 | TGT |
| N32547 | UNKNOWN | 12.5 | 355 | GT |
| N32669 | UNKNOWN | 6.5 | 209 | TG |
| N32764 | UNKNOWN | 15 | 0 | T |
| N32820 | UNKNOWN | 3.87 | 15 | AAAAACAA |
| N32820 | UNKNOWN | 6.5 | 43 | AC |
| N32821 | UNKNOWN | 22 | 0 | T |
| N32833 | UNKNOWN | 13 | 116 | G |
| N32840 | UNKNOWN | 15 | 1 | T |
| N33006 | UNKNOWN | 24 | 294 | T |
| N33161 | UNKNOWN | 16 | 3 | T |
| N33234 | UNKNOWN | 20 | 1 | T |
| N33458 | UNKNOWN | 15 | 299 | A |
| N33474 | UNKNOWN | 26 | 188 | T |
| N33939 | UNKNOWN | 13 | 80 | T |
| N33966 | UNKNOWN | 4.66 | 201 | AGTTCT |
| N34477 | UNKNOWN | 18 | 319 | A |
| N34500 | UNKNOWN | 13 | 382 | T |
| N34987 | UNKNOWN | 2.5 | 220 | ATACATATAT (SEQ ID NO:269) |
| N35073 | UNKNOWN | 7.5 | 378 | AG |
| N35361 | UNKNOWN | 11.66 | 2 | TTA |
| N35380 | UNKNOWN | 14 | 429 | A |
| N35602 | UNKNOWN | 17 | 219 | T |
| N35894 | UNKNOWN | 5.66 | 344 | AAC |
| N36090 | UNKNOWN | 14 | 219 | A |
| N36094 | UNKNOWN | 17 | 493 | A |
| N36303 | UNKNOWN | 6.66 | 76 | CTG |
| N36411 | UNKNOWN | 25 | 1 | T |
| N36621 | UNKNOWN | 18 | 73 | A |
| N36770 | UNKNOWN | 16 | 91 | A |
| N36786 | UNKNOWN | 16 | 33 | T |
| N36807 | UNKNOWN | 6.5 | 202 | AT |
| N36811 | UNKNOWN | 13 | 347 | A |
| N36994 | UNKNOWN | 4.5 | 443 | ATCA |
| N36995 | UNKNOWN | 14 | 265 | T |
| N37028 | UNKNOWN | 14 | 0 | T |
| N37065 | UNKNOWN | 12 | 479 | A |
| N38730 | UNKNOWN | 12 | 482 | A |
| N38732 | UNKNOWN | 4 | 124 | CAAAA |
| N38951 | UNKNOWN | 19 | 0 | T |
| N38953 | UNKNOWN | 19 | 142 | A |
| N38960 | UNKNOWN | 3.5 | 322 | TTTGTT |
| N38966 | UNKNOWN | 5.2 | 162 | TTTTG |
| N39014 | UNKNOWN | 20 | 496 | A |
| N39029 | UNKNOWN | 16 | 170 | A |
| N39104 | UNKNOWN | 17 | 0 | T |
| N39265 | UNKNOWN | 12 | 0 | T |
| N39928 | UNKNOWN | 21 | 288 | GT |
| N39954 | UNKNOWN | 12 | 86 | T |
| N40928 | UNKNOWN | 38 | 0 | T |
| N41038 | UNKNOWN | 8 | 426 | GCA |
| N41598 | UNKNOWN | 17 | 122 | A |
| N41944 | UNKNOWN | 14 | 121 | T |
| N45228 | UNKNOWN | 18 | 371 | A |
| N45369 | UNKNOWN | 20 | 498 | A |
| N45369 | UNKNOWN | 19 | 210 | A |
| N45600 | UNKNOWN | 14 | 100 | A |
| N46092 | UNKNOWN | 13 | 371 | A |
| N46096 | UNKNOWN | 21 | 124 | AC |
| N46100 | UNKNOWN | 20 | 168 | T |
| N46220 | UNKNOWN | 17 | 0 | T |
| N46322 | UNKNOWN | 17 | 159 | T |
| N46346 | UNKNOWN | 12 | 243 | T |
| N46826 | UNKNOWN | 19 | 208 | A |
| N47009 | UNKNOWN | 18 | 0 | T |
| N47115 | UNKNOWN | 14 | 183 | A |
| N47315 | UNKNOWN | 7 | 45 | AT |
| N47579 | UNKNOWN | 16 | 330 | A |
| N47786 | UNKNOWN | 6.5 | 109 | AT |
| N47989 | UNKNOWN | 16 | 0 | T |
| N48057 | UNKNOWN | 32 | 209 | T |
| N48143 | UNKNOWN | 13 | 347 | A |
| N48230 | UNKNOWN | 17 | 147 | T |
| N48286 | UNKNOWN | 14 | 185 | A |

TABLE 1-continued

| Genbank # | Region | # reps | Position | Unit sequence |
|---|---|---|---|---|
| N48573 | UNKNOWN | 6 | 38 | CGC |
| N48707 | UNKNOWN | 12 | 0 | T |
| N49186 | UNKNOWN | 14 | 268 | A |
| N49201 | UNKNOWN | 7.5 | 203 | AT |
| N49290 | UNKNOWN | 5.5 | 221 | ATAA |
| N49732 | UNKNOWN | 6 | 256 | CAA |
| N49769 | UNKNOWN | 16 | 309 | T |
| N49902 | UNKNOWN | 17 | 413 | A |
| N49958 | UNKNOWN | 6.66 | 243 | TTA |
| N50058 | UNKNOWN | 8 | 120 | AT |
| N50104 | UNKNOWN | 15 | 0 | T |
| N50545 | UNKNOWN | 3.8 | 7 | TTTTG |
| N50545 | UNKNOWN | 13 | 22 | T |
| N50585 | UNKNOWN | 12 | 450 | T |
| N50792 | UNKNOWN | 24 | 0 | T |
| N50910 | UNKNOWN | 17 | 79 | T |
| N51107 | UNKNOWN | 16 | 0 | T |
| N51223 | UNKNOWN | 12 | 4 | T |
| N51320 | UNKNOWN | 5.25 | 10 | TTTA |
| N51323 | UNKNOWN | 12 | 112 | A |
| N51413 | UNKNOWN | 12 | 37 | A |
| N51444 | UNKNOWN | 12.25 | 131 | ATCT |
| N51444 | UNKNOWN | 16 | 431 | T |
| N51511 | UNKNOWN | 12 | 0 | T |
| N51585 | UNKNOWN | 3.8 | 182 | AAAAC |
| N51682 | UNKNOWN | 15 | 450 | T |
| N52017 | UNKNOWN | 4 | 129 | GGGATG |
| N52039 | UNKNOWN | 4.5 | 8 | TTAT |
| N52189 | UNKNOWN | 3.83 | 164 | TTTTTC |
| N52189 | UNKNOWN | 17 | 182 | T |
| N52189 | UNKNOWN | 12 | 157 | T |
| N52234 | UNKNOWN | 17 | 0 | T |
| N52337 | UNKNOWN | 13 | 144 | T |
| N52545 | UNKNOWN | 14 | 596 | A |
| N52589 | UNKNOWN | 6.5 | 449 | AT |
| N52641 | UNKNOWN | 16 | 139 | A |
| N52759 | UNKNOWN | 15 | 6 | T |
| N52824 | UNKNOWN | 18.5 | 273 | TG |
| N52876 | UNKNOWN | 4.4 | 300 | AACAA |
| N52876 | UNKNOWN | 13.66 | 264 | AAC |
| N52914 | UNKNOWN | 21 | 161 | AC |
| N52938 | UNKNOWN | 16 | 289 | T |
| N52946 | UNKNOWN | 13 | 42 | A |
| N52990 | UNKNOWN | 5 | 85 | CAAAAA |
| N53075 | UNKNOWN | 30 | 0 | T |
| N53160 | UNKNOWN | 14 | 393 | A |
| N53167 | UNKNOWN | 14 | 318 | A |
| N53453 | UNKNOWN | 12 | 302 | A |
| N53462 | UNKNOWN | 12.75 | 15 | TTTC |
| N53462 | UNKNOWN | 7.5 | 67 | TC |
| N53462 | UNKNOWN | 15 | 91 | T |
| N53470 | UNKNOWN | 14 | 0 | T |
| N53574 | UNKNOWN | 8 | 354 | AT |
| N53578 | UNKNOWN | 6.5 | 377 | AG |
| N53674 | UNKNOWN | 31 | 0 | T |
| N53754 | UNKNOWN | 5.66 | 281 | GGT |
| N53757 | UNKNOWN | 14 | 0 | T |
| N53840 | UNKNOWN | 19 | 297 | T |
| N54136 | UNKNOWN | 19 | 116 | T |
| N54163 | UNKNOWN | 15 | 449 | T |
| N54175 | UNKNOWN | 12 | 66 | A |
| N54370 | UNKNOWN | 18 | 0 | T |
| N54498 | UNKNOWN | 15 | 0 | T |
| N54890 | UNKNOWN | 19.5 | 417 | AC |
| N54916 | UNKNOWN | 3.5 | 40 | CTCAGC |
| N54935 | UNKNOWN | 16 | 144 | T |
| N54957 | UNKNOWN | 9.5 | 90 | TC |
| N55019 | UNKNOWN | 4.75 | 6 | TTTA |
| N55024 | UNKNOWN | 13 | 292 | A |
| N55189 | UNKNOWN | 13 | 295 | A |
| N55581 | UNKNOWN | 18 | 246 | GT |
| N56920 | UNKNOWN | 18 | 400 | A |
| N56947 | UNKNOWN | 13 | 465 | T |
| N56948 | UNKNOWN | 12 | 0 | T |
| N57482 | UNKNOWN | 12 | 107 | A |
| N57483 | UNKNOWN | 9 | 170 | AT |
| N57483 | UNKNOWN | 6.5 | 66 | AC |

TABLE 1-continued

| Genbank # | Region | # reps | Position | Unit sequence |
|---|---|---|---|---|
| N57666 | UNKNOWN | 16 | 0 | T |
| N57775 | UNKNOWN | 16 | 26 | T |
| N58192 | UNKNOWN | 7 | 99 | TG |
| N58301 | UNKNOWN | 15 | 401 | A |
| N583T9 | UNKNOWN | 13 | 337 | A |
| N58323 | UNKNOWN | 13 | 101 | T |
| N58336 | UNKNOWN | 13 | 138 | A |
| N58361 | UNKNOWN | 15 | 0 | T |
| N58370 | UNKNOWN | 14 | 0 | T |
| N58386 | UNKNOWN | 13 | 31 | T |
| N58487 | UNKNOWN | 7.5 | 305 | TA |
| N58488 | UNKNOWN | 15 | 0 | T |
| N58508 | UNKNOWN | 12 | 0 | T |
| N58512 | UNKNOWN | 14 | 561 | A |
| N59220 | UNKNOWN | 12 | 0 | T |
| N59238 | UNKNOWN | 10.5 | 99 | TG |
| N59238 | UNKNOWN | 7 | 84 | GT |
| N59278 | UNKNOWN | 5.5 | 337 | TGTT |
| N59776 | UNKNOWN | 13 | 430 | A |
| N59800 | UNKNOWN | 14 | 68 | A |
| N59854 | UNKNOWN | 16 | 191 | A |
| N59866 | UNKNOWN | 16 | 1 | T |
| N62225 | UNKNOWN | 19 | 0 | T |
| N62468 | UNKNOWN | 13 | 471 | A |
| N62484 | UNKNOWN | 18 | 386 | A |
| N62516 | UNKNOWN | 14 | 0 | T |
| N62532 | UNKNOWN | 6 | 149 | TCTA |
| N62578 | UNKNOWN | 24.5 | 201 | TG |
| N62603 | UNKNOWN | 13 | 3 | T |
| N62797 | UNKNOWN | 3.5 | 230 | GTCTGCTG |
| N62812 | UNKNOWN | 18 | 0 | T |
| N62920 | UNKNOWN | 8.19 | 114 | TATTT |
| N62920 | UNKNOWN | 14 | 213 | A |
| N62960 | UNKNOWN | 13 | 0 | T |
| N62991 | UNKNOWN | 27 | 158 | T |
| N63010 | UNKNOWN | 13 | 527 | T |
| N63020 | UNKNOWN | 12 | 1 | T |
| N63027 | UNKNOWN | 7 | 200 | CA |
| N63056 | UNKNOWN | 15 | 83 | T |
| N63312 | UNKNOWN | 9 | 134 | AT |
| N63316 | UNKNOWN | 16 | 186 | GT |
| N63316 | UNKNOWN | 12.5 | 162 | GA |
| N63316 | UNKNOWN | 17 | 0 | T |
| N63346 | UNKNOWN | 34 | 0 | T |
| N63375 | UNKNOWN | 14 | 119 | A |
| N63392 | UNKNOWN | 15 | 0 | T |
| N63455 | UNKNOWN | 16 | 0 | T |
| N63479 | UNKNOWN | 20 | 155 | T |
| N63582 | UNKNOWN | 13 | 446 | A |
| N63609 | UNKNOWN | 14 | 244 | A |
| N63706 | UNKNOWN | 7.33 | 55 | AAC |
| N63708 | UNKNOWN | 14 | 81 | A |
| N63786 | UNKNOWN | 12 | 158 | T |
| N63794 | UNKNOWN | 10 | 403 | AT |
| N63877 | UNKNOWN | 15 | 0 | T |
| N63894 | UNKNOWN | 13 | 102 | G |
| N63995 | UNKNOWN | 19 | 80 | A |
| N64478 | UNKNOWN | 15 | 192 | A |
| N64493 | UNKNOWN | 15 | 1 | T |
| N64568 | UNKNOWN | 42 | 0 | T |
| N64581 | UNKNOWN | 12 | 0 | T |
| N64619 | UNKNOWN | 8.5 | 248 | TA |
| N64662 | UNKNOWN | 9 | 232 | AAAC |
| N64662 | UNKNOWN | 22 | 146 | T |
| N64716 | UNKNOWN | 3.5 | 208 | AGAAAG |
| N64716 | UNKNOWN | 7 | 194 | GT |
| N64767 | UNKNOWN | 23 | 0 | T |
| N64861 | UNKNOWN | 40 | 0 | T |
| N66062 | UNKNOWN | 13 | 32 | A |
| N66072 | UNKNOWN | 16 | 225 | T |
| N66169 | UNKNOWN | 19 | 181 | T |
| N66283 | UNKNOWN | 15 | 0 | T |
| N66296 | UNKNOWN | 12 | 0 | T |
| N66378 | UNKNOWN | 18 | 45 | T |
| N66458 | UNKNOWN | 23 | 0 | T |
| N66468 | UNKNOWN | 23 | 0 | T |
| N66530 | UNKNOWN | 14 | 0 | T |

TABLE 1-continued

| Genbank # | Region | # reps | Position | Unit sequence |
|---|---|---|---|---|
| N66563 | UNKNOWN | 12 | 344 | A |
| N66591 | UNKNOWN | 12 | 274 | A |
| N66597 | UNKNOWN | 2.7 | 389 | GATATACGTATACAGCATATACGA (SEQ ID NO:270) |
| N66704 | UNKNOWN | 22 | 0 | T |
| N66712 | UNKNOWN | 17 | 0 | T |
| N66776 | UNKNOWN | 15 | 0 | T |
| N66784 | UNKNOWN | 21 | 0 | T |
| N66869 | UNKNOWN | 10.66 | 55 | AAC |
| N66869 | UNKNOWN | 24 | 0 | T |
| N66930 | UNKNOWN | 15 | 310 | T |
| N66966 | UNKNOWN | 4.81 | 33 | AATATATTTTATTACATATAATGTCAC (SEQ ID NO: 271) |
| N67117 | UNKNOWN | 18 | 0 | T |
| N67148 | UNKNOWN | 23 | 0 | T |
| N67158 | UNKNOWN | 14.5 | 242 | AC |
| N67251 | UNKNOWN | 38 | 0 | T |
| N67332 | UNKNOWN | 15 | 68 | T |
| N67370 | UNKNOWN | 27 | 0 | T |
| N67591 | UNKNOWN | 13 | 409 | A |
| N67684 | UNKNOWN | 20 | 0 | T |
| N68022 | UNKNOWN | 32 | 0 | T |
| N68032 | UNKNOWN | 13 | 30 | T |
| N68097 | UNKNOWN | 14 | 0 | T |
| N68163 | UNKNOWN | 16.5 | 145 | AC |
| N68163 | UNKNOWN | 6.5 | 126 | TC |
| N68198 | UNKNOWN | 17 | 0 | T |
| N68393 | UNKNOWN | 7.66 | 387 | TTG |
| N68489 | UNKNOWN | 22 | 9 | T |
| N68595 | UNKNOWN | 12 | 5 | A |
| N68662 | UNKNOWN | 29 | 7 | T |
| N68677 | UNKNOWN | 22 | 0 | T |
| N68744 | UNKNOWN | 7.5 | 0 | ATTT |
| N68997 | UNKNOWN | 15 | 213 | T |
| N68997 | UNKNOWN | 12 | 266 | A |
| N69101 | UNKNOWN | 15 | 209 | A |
| N69368 | UNKNOWN | 19 | 0 | T |
| N69368 | UNKNOWN | 12 | 62 | A |
| N69371 | UNKNOWN | 17 | 200 | T |
| N69476 | UNKNOWN | 7 | 264 | CA |
| N69517 | UNKNOWN | 4.5 | 346 | AACA |
| N69541 | UNKNOWN | 25 | 0 | T |
| N69645 | UNKNOWN | 22 | 0 | T |
| N69645 | UNKNOWN | 13 | 96 | A |
| N69666 | UNKNOWN | 3.6 | 365 | AAATT |
| N69666 | UNKNOWN | 13 | 355 | A |
| N69691 | UNKNOWN | 4.75 | 420 | AAAT |
| N69862 | UNKNOWN | 4.75 | 298 | TTTG |
| N69862 | UNKNOWN | 16 | 387 | A |
| N70000 | UNKNOWN | 32 | 0 | T |
| N70176 | UNKNOWN | 6.5 | 47 | GA |
| N70176 | UNKNOWN | 16 | 163 | A |
| N70302 | UNKNOWN | 6.5 | 21 | AC |
| N70324 | UNKNOWN | 4 | 170 | TTTTA |
| N70688 | UNKNOWN | 13.5 | 376 | AC |
| N70943 | UNKNOWN | 17 | 0 | T |
| N71060 | UNKNOWN | 17 | 0 | T |
| N71180 | UNKNOWN | 86 | 28 | A |
| N71183 | UNKNOWN | 18 | 216 | A |
| N71229 | UNKNOWN | 19 | 155 | A |
| N71241 | UNKNOWN | 17 | 439 | A |
| N71340 | UNKNOWN | 15 | 313 | T |
| N71432 | UNKNOWN | 14 | 171 | T |
| N71583 | UNKNOWN | 7 | 408 | AC |
| N71600 | UNKNOWN | 24 | 214 | A |
| N71656 | UNKNOWN | 28 | 0 | T |
| N71720 | UNKNOWN | 20 | 153 | A |
| N71731 | UNKNOWN | 20 | 152 | A |
| N71739 | UNKNOWN | 18 | 409 | A |
| N71746 | UNKNOWN | 27 | 226 | A |
| N71792 | UNKNOWN | 5.8 | 241 | AAAAT |
| N71792 | UNKNOWN | 18 | 164 | T |
| N71888 | UNKNOWN | 23 | 0 | T |
| N72270 | UNKNOWN | 12 | 141 | T |
| N72680 | UNKNOWN | 11.5 | 101 | TA |
| N72680 | UNKNOWN | 6.5 | 89 | TG |
| N72903 | UNKNOWN | 16 | 101 | A |

TABLE 1-continued

| Genbank # | Region | # reps | Position | Unit sequence |
|---|---|---|---|---|
| N72944 | UNKNOWN | 18 | 150 | A |
| N73185 | UNKNOWN | 12 | 238 | A |
| N73274 | UNKNOWN | 30 | 1 | T |
| N73337 | UNKNOWN | 19 | 231 | A |
| N73477 | UNKNOWN | 15 | 281 | A |
| N73673 | UNKNOWN | 6.66 | 397 | AAT |
| N73724 | UNKNOWN | 16 | 313 | A |
| N73773 | UNKNOWN | 23 | 0 | T |
| N73802 | UNKNOWN | 5.25 | 214 | TAAA |
| N73807 | UNKNOWN | 4.5 | 258 | TTTATT |
| N73872 | UNKNOWN | 6.75 | 217 | AATA |
| N73872 | UNKNOWN | 17 | 150 | T |
| N74880 | UNKNOWN | 5 | 242 | TTTA |
| N75281 | UNKNOWN | 18 | 271 | A |
| N75489 | UNKNOWN | 12 | 386 | A |
| N75725 | UNKNOWN | 5 | 177 | ATTT |
| N75789 | UNKNOWN | 13 | 306 | A |
| N75835 | UNKNOWN | 19.5 | 188 | TG |
| N75835 | UNKNOWN | 6.5 | 231 | AG |
| N76856 | UNKNOWN | 14 | 458 | A |
| N77229 | UNKNOWN | 9.5 | 179 | AG |
| N77554 | UNKNOWN | 8.5 | 460 | AC |
| N78018 | UNKNOWN | 8.5 | 317 | TG |
| N78018 | UNKNOWN | 13 | 604 | A |
| N78337 | UNKNOWN | 14 | 634 | A |
| N78437 | UNKNOWN | 13 | 620 | A |
| N78510 | UNKNOWN | 19 | 488 | A |
| N78656 | UNKNOWN | 4.5 | 6 | TTAT |
| N79206 | UNKNOWN | 4.5 | 60 | AAAT |
| N79253 | UNKNOWN | 13 | 422 | T |
| N79287 | UNKNOWN | 27 | 160 | A |
| N79287 | UNKNOWN | 15 | 98 | T |
| N79406 | UNKNOWN | 8.5 | 57 | AC |
| N79619 | UNKNOWN | 17 | 349 | A |
| N79740 | UNKNOWN | 28 | 2 | T |
| N79930 | UNKNOWN | 19 | 309 | A |
| N80094 | UNKNOWN | 88 | 121 | A |
| N80159 | UNKNOWN | 12 | 260 | T |
| N80383 | UNKNOWN | 14 | 177 | A |
| N80395 | UNKNOWN | 3.8 | 173 | AAAAG |
| N80395 | UNKNOWN | 64 | 194 | A |
| N80739 | UNKNOWN | 15 | 3 | T |
| N80972 | UNKNOWN | 14 | 177 | A |
| N80972 | UNKNOWN | 12 | 63 | T |
| N81167 | UNKNOWN | 14 | 385 | A |
| N81177 | UNKNOWN | 18 | 235 | A |
| N81191 | UNKNOWN | 2.81 | 0 | ATCTAACAGATAACAGTTTGTTTAAAATAAGAATAATAA AATATTTTATTATTCTTATTTG (SEQ ID NO:272) |
| N81191 | UNKNOWN | 14 | 296 | A |
| N85903 | UNKNOWN | 14 | 307 | A |
| N85943 | UNKNOWN | 17 | 3 | T |
| N90348 | UNKNOWN | 19 | 496 | A |
| N90533 | UNKNOWN | 21 | 0 | T |
| N92086 | UNKNOWN | 19 | 19 | A |
| N92136 | UNKNOWN | 12 | 95 | T |
| N92198 | UNKNOWN | 23 | 445 | A |
| N92311 | UNKNOWN | 13 | 6 | T |
| N92541 | UNKNOWN | 15 | 0 | T |
| N92578 | UNKNOWN | 15 | 0 | T |
| N92589 | UNKNOWN | 15 | 0 | T |
| N92618 | UNKNOWN | 26 | 0 | T |
| N92629 | UNKNOWN | 19 | 0 | T |
| N92751 | UNKNOWN | 23 | 0 | T |
| N92752 | UNKNOWN | 34 | 27 | T |
| N92870 | UNKNOWN | 7 | 448 | CA |
| N93515 | UNKNOWN | 14 | 391 | A |
| N93728 | UNKNOWN | 16 | 0 | T |
| N94144 | UNKNOWN | 15.5 | 413 | AC |
| N94160 | UNKNOWN | 7 | 85 | TG |
| N94160 | UNKNOWN | 12 | 244 | T |
| N94198 | UNKNOWN | 7 | 313 | TG |
| N94320 | UNKNOWN | 4.75 | 74 | AAAC |
| N94362 | UNKNOWN | 10 | 330 | AT |
| N94362 | UNKNOWN | 8.5 | 456 | AC |
| N94362 | UNKNOWN | 8 | 481 | GA |
| N94362 | UNRNOWN | 13 | 0 | T |
| N94591 | UNKNOWN | 7.5 | io | TTTA |

TABLE 1-continued

| Genbank # | Region | # reps | Position | Unit sequence |
|---|---|---|---|---|
| N94591 | UNKNOWN | 13 | 0 | T |
| N94998 | UNKNOWN | 17 | 0 | T |
| N9S041 | UNKNOWN | 12.5 | 111 | TN |
| N95059 | UNKNOWN | 6.66 | 271 | AAC |
| N95068 | UNKNOWN | 40 | 0 | T |
| N95170 | UNKNOWN | 31 | 0 | T |
| N95476 | UNKNOWN | 21 | 0 | T |
| N95618 | UNKNOWN | 2.7 | 562 | AATTTTTTGG (SEQ ID NO:273) |
| N95663 | UNKNOWN | 10.5 | 403 | TG |
| N95663 | UNKNOWN | 6.5 | 283 | GT |
| N98235 | UNKNOWN | 4.75 | 24 | TTTA |
| N98242 | UNKNOWN | 14 | 407 | T |
| N98756 | UNKNOWN | 13 | 0 | T |
| N98877 | UNKNOWN | 20 | 0 | T |
| N99017 | UNKNOWN | 14 | 382 | A |
| N99056 | UNKNOWN | 12 | 0 | T |
| N99081 | UNKNOWN | 13 | 480 | A |
| N99174 | UNKNOWN | 16 | 69 | T |
| N99553 | UNKNOWN | 3.6 | 262 | TTTTG |
| N99764 | UNKNOWN | 31 | 0 | T |
| N99898 | UNKNOWN | 20 | 0 | T |
| R00010 | UNKNOWN | 5.25 | 275 | TATT |
| R00311 | UNKNOWN | 6.75 | 192 | TTTA |
| R00805 | UNKNOWN | 26 | 0 | T |
| R01450 | UNKNOWN | 12 | 204 | A |
| R02171 | UNKNOWN | 6.25 | 38 | ATAA |
| R02232 | UNKNOWN | 14 | 227 | T |
| R02271 | UNKNOWN | 20 | 0 | T |
| R02S22 | UNKNOWN | 18 | 106 | T |
| R02546 | UNKNOWN | 20 | 1 | T |
| R02742 | UNKNOWN | 8 | 37 | GT |
| R02742 | UNKNOWN | 14 | 263 | A |
| R05283 | UNKNOWN | 12 | 149 | A |
| R05292 | UNKNOWN | 5.5 | 257 | CAGA |
| R05292 | UNKNOWN | 14 | 213 | GA |
| R05292 | UNKNOWN | 12 | 1 | T |
| R05826 | UNKNOWN | 3.02 | 212 | CAAGGAGAGTAGTTAGACAACACGTCAGCCACGGAGCAGG (SEQ ID NO:274) |
| R06207 | UNKNOWN | 14 | 173 | A |
| R06262 | UNKNOWN | 21 | 194 | T |
| R06351 | UNKNOWN | 31 | 240 | A |
| R06374 | UNKNOWN | 13 | 211 | A |
| R06655 | UNKNOWN | 25 | 33 | T |
| R06720 | UNKNOWN | 23 | 0 | T |
| R06743 | UNKNOWN | 18 | 17 | T |
| R06750 | UNKNOWN | 18 | 16 | T |
| R06753 | UNKNOWN | 14 | 23 | T |
| R06754 | UNKNOWN | 19 | 16 | T |
| R06781 | UNKNOWN | 20 | 30 | T |
| R06857 | UNKNOWN | 21 | 32 | T |
| R06862 | UNKNOWN | 20 | 18 | T |
| R06874 | UNKNOWN | 19 | 17 | T |
| R08115 | UNKNOWN | 18 | 311 | T |
| R08311 | UNKNOWN | 12 | 9 | T |
| R08866 | UNKNOWN | 13 | 290 | T |
| R09989 | UNKNOWN | 12 | 379 | T |
| R10270 | UNKNOWN | 22 | 204 | A |
| R10270 | UNKNOWN | 13 | 85 | T |
| R10325 | UNKNOWN | 6 | 151 | TTG |
| R10610 | UNKNOWN | 5.75 | 140 | TAGG |
| R10610 | UNKNOWN | 4.75 | 182 | GATT |
| R11657 | UNKNOWN | 30 | 0 | T |
| R11664 | UNKNOWN | 19 | 0 | T |
| R11666 | UNKNOWN | 13 | 0 | T |
| R12499 | UNKNOWN | 6.75 | 328 | TTTG |
| R12598 | UNKNOWN | 29 | 0 | T |
| R12598 | UNKNOWN | 12 | 84 | A |
| R12700 | UNKNOWN | 24 | 26 | T |
| R12996 | UNKNOWN | 12 | 79 | T |
| R13208 | UNKNOWN | 2.6 | 281 | TAATAATAAT (SEQ ID NO:275) |
| R13901 | UNKNOWN | 6.75 | 145 | AAAC |
| R14606 | UNKNOWN | 13 | 0 | T |
| R15076 | UNKNOWN | 29 | 0 | T |
| R15742 | UNKNOWN | 12 | 0 | T |
| R15779 | UNKNOWN | 14 | 0 | T |
| R15794 | UNKNOWN | 17 | 0 | T |
| R15913 | UNKNOWN | 20 | 0 | T |

TABLE 1-continued

| Genbank # | Region | # reps | Position | Unit sequence |
|---|---|---|---|---|
| R15934 | UNKNOWN | 8 | 124 | GT |
| R15934 | UNKNOWN | 14 | 0 | T |
| R16074 | UNKNOWN | 11.5 | 377 | AC |
| R16081 | UNKNOWN | 12 | 0 | T |
| R16119 | UNKNOWN | 31 | 0 | T |
| R16171 | UNKNOWN | 13 | 0 | T |
| R16229 | UNKNOWN | 17 | 0 | T |
| R16241 | UNKNOWN | 17 | 0 | T |
| R16985 | UNKNOWN | 21 | 0 | T |
| R17661 | UNKNOWN | 3.83 | 121 | TTTTTG |
| R17661 | UNKNOWN | 15 | 139 | T |
| R17685 | UNKNOWN | 14 | 10 | T |
| R17744 | UNKNOWN | 17 | 0 | T |
| R17746 | UNKNOWN | 21 | 0 | T |
| R17762 | UNKNOWN | 18 | 0 | T |
| R18374 | UNKNOWN | 12 | 269 | A |
| R19406 | UNKNOWN | 3.8 | 408 | CAAAA |
| R20547 | UNKNOWN | 18 | 126 | AC |
| R20550 | UNKNOWN | 26 | 0 | T |
| R20617 | UNKNOWN | 18 | 0 | T |
| R20627 | UNKNOWN | 12 | 0 | T |
| R20628 | UNKNOWN | 13 | 0 | T |
| R20632 | UNKNOWN | 12 | 0 | T |
| R20648 | UNKNOWN | 12 | 0 | T |
| R20749 | UNKNOWN | 21 | 0 | T |
| R20764 | UNKNOWN | 25 | 0 | T |
| R20786 | UNKNOWN | 17 | 0 | T |
| R21018 | UNKNOWN | 3.71 | 275 | TTTTGT |
| R21114 | UNKNOWN | 3.8 | 494 | AGGGG |
| R21218 | UNKNOWN | 19 | 0 | T |
| R21779 | UNKNOWN | 19 | 193 | T |
| R22506 | UNKNOWN | 4.8 | 24 | TTTTN |
| R22506 | UNKNOWN | 21 | 0 | T |
| R22524 | UNKNOWN | 6 | 361 | CCA |
| R22524 | UNKNOWN | 15 | 176 | A |
| R22582 | UNKNOWN | 27 | 89 | A |
| R22582 | UNKNOWN | 25 | 0 | T |
| R22954 | UNKNOWN | 32 | 0 | T |
| R22954 | UNKNOWN | 18 | 109 | A |
| R23166 | UNKNOWN | 20 | 0 | T |
| R23249 | UNKNOWN | 14 | 187 | A |
| R23701 | UNKNOWN | 32 | 281 | A |
| R24011 | UNKNOWN | 11 | 39 | CA |
| R24061 | UNKNOWN | 13 | 290 | T |
| R24205 | UNKNOWN | 16 | 10 | T |
| R24500 | UNKNOWN | 18 | 1 | T |
| R25196 | UNKNOWN | 21 | 0 | T |
| R26061 | UNKNOWN | 12 | 0 | T |
| R26089 | UNKNOWN | 23 | 0 | T |
| R26125 | UNKNOWN | 18 | 0 | T |
| R26367 | UNKNOWN | 19 | 0 | T |
| R26709 | UNKNOWN | 21 | 0 | T |
| R26768 | UNKNOWN | 12 | 161 | A |
| R27186 | UNKNOWN | 14 | 85 | T |
| R27774 | UNKNOWN | 4.75 | 3 | TTTA |
| R28285 | UNKNOWN | 17 | 0 | T |
| R28363 | UNKNOWN | 18 | 0 | T |
| R28384 | UNKNOWN | 15 | 344 | AC |
| R28574 | UNKNOWN | 22 | 138 | A |
| R28952 | UNKNOWN | 18 | 132 | A |
| R29077 | UNKNOWN | 19 | 0 | T |
| R29387 | UNKNOWN | 27 | 163 | A |
| R29387 | UNKNOWN | 13 | 0 | A |
| R30814 | UNKNOWN | 6.5 | 329 | AT |
| R30814 | UNKNOWN | 15 | 0 | T |
| R31333 | UNKNOWN | 13 | 70 | T |
| R31692 | UNKNOWN | 8 | 342 | TA |
| R31908 | UNKNOWN | 12 | 9 | C |
| R32033 | UNKNOWN | 20 | 336 | A |
| R32322 | UNKNOWN | 12 | 226 | C |
| R32328 | UNKNOWN | 19 | 0 | T |
| R33013 | UNKNOWN | 4.8 | 24 | TTTTG |
| R33013 | UNKNOWN | 21 | 0 | T |
| R33104 | UNKNOWN | 18 | 0 | T |
| R33331 | UNKNOWN | 21 | 276 | A |
| R33779 | UNKNOWN | 13 | 12 | A |
| R33835 | UNKNOWN | 28 | 0 | T |

TABLE 1-continued

| Genbank # | Region | # reps | Position | Unit sequence |
|---|---|---|---|---|
| R34062 | UNKNOWN | 18 | 120 | T |
| R36217 | UNKNOWN | 59 | 0 | T |
| R36217 | UNKNOWN | 15 | 186 | A |
| R36221 | UNKNOWN | 24 | 354 | A |
| R36222 | UNKNOWN | 28 | 0 | T |
| R36222 | UNKNOWN | 15 | 63 | G |
| R36628 | UNKNOWN | 12 | 177 | T |
| R36852 | UNKNOWN | 12 | 0 | T |
| R36937 | UNKNOWN | 15 | 0 | T |
| R36939 | UNKNOWN | 13 | 0 | T |
| R36944 | UNKNOWN | 14 | 0 | T |
| R37012 | UNKNOWN | 14 | 0 | T |
| R37047 | UNKNOWN | 13 | 0 | T |
| R37181 | UNKNOWN | 21 | 0 | T |
| R37245 | UNKNOWN | 14 | 0 | T |
| R37268 | UNKNOWN | 23 | 0 | T |
| R37300 | UNKNOWN | 18 | 0 | T |
| R37316 | UNKNOWN | 31 | 0 | T |
| R37358 | UNKNOWN | 6.5 | 13 | AT |
| R37377 | UNKNOWN | 12 | 0 | T |
| R37390 | UNKNOWN | 34 | 0 | T |
| R37472 | UNKNOWN | 13 | 0 | T |
| R37608 | UNKNOWN | 10.5 | 9 | TTAT |
| R37637 | UNKNOWN | 33 | 0 | T |
| R37827 | UNKNOWN | 6.66 | 156 | TCC |
| R37827 | UNKNOWN | 6.33 | 136 | CAT |
| R38017 | UNKNOWN | 14 | 0 | T |
| R38086 | UNKNOWN | 16 | 0 | T |
| R38089 | UNKNOWN | 12 | 0 | T |
| R38408 | UNKNOWN | 20 | 0 | T |
| R38416 | UNKNOWN | 17 | 0 | T |
| R38421 | UNKNOWN | 13 | 0 | T |
| R38585 | UNKNOWN | 13 | 47 | A |
| R38644 | UNKNOWN | 13 | 0 | T |
| R38676 | UNKNOWN | 14 | 0 | T |
| R38700 | UNKNOWN | 14 | 0 | T |
| R38802 | UNKNOWN | 12 | 0 | T |
| R38816 | UNKNOWN | 18 | 0 | T |
| R38838 | UNKNOWN | 15 | 0 | T |
| R38899 | UNKNOWN | 12 | 151 | A |
| R38964 | UNKNOWN | 13 | 0 | T |
| R38985 | UNKNOWN | 14 | 0 | T |
| R39039 | UNKNOWN | 7.5 | 337 | GT |
| R39206 | UNKNOWN | 14 | 0 | T |
| R39357 | UNKNOWN | 27 | 0 | T |
| R39454 | UNKNOWN | 17 | 348 | A |
| R39460 | UNKNOWN | 12 | 0 | T |
| R39677 | UNKNOWN | 15 | 0 | T |
| R39789 | UNKNOWN | 35 | 0 | T |
| R39794 | UNKNOWN | 15 | 0 | T |
| R39803 | UNKNOWN | 12 | 0 | T |
| R39804 | UNKNOWN | 18 | 0 | T |
| R39984 | UNKNOWN | 20 | 0 | T |
| R40033 | UNKNOWN | 12 | 198 | T |
| R40038 | UNKNOWN | 20 | 0 | T |
| R40045 | UNKNOWN | 38 | 0 | T |
| R40105 | UNKNOWN | 9 | 250 | GA |
| R40105 | UNKNOWN | 12 | 0 | T |
| R40120 | UNKNOWN | 22 | 0 | T |
| R40128 | UNKNOWN | 5.75 | 168 | TTTG |
| R40129 | UNKNOWN | 18 | 0 | T |
| R40191 | UNKNOWN | 27 | 0 | T |
| R40193 | UNKNOWN | 17 | 0 | T |
| R40316 | UNKNOWN | 16 | 0 | T |
| R40328 | UNKNOWN | 8.5 | 152 | CA |
| R40328 | UNKNOWN | 17 | 0 | T |
| R40398 | UNKNOWN | 16 | 0 | T |
| R40425 | UNKNOWN | 17 | 0 | T |
| R40433 | UNKNOWN | 13 | 0 | T |
| R40435 | UNKNOWN | 12.75 | 37 | TTTA |
| R40449 | UNKNOWN | 20 | 0 | T |
| R40471 | UNKNOWN | 12 | 0 | T |
| R40480 | UNKNOWN | 14 | 0 | T |
| R40546 | UNKNOWN | 21 | 0 | T |
| R40569 | UNKNOWN | 16 | 0 | T |
| R40604 | UNKNOWN | 14 | 0 | T |
| R40611 | UNKNOWN | 19 | 0 | T |

TABLE 1-continued

| Genbank # | Region | # reps | Position | Unit sequence |
|---|---|---|---|---|
| R40650 | UNKNOWN | 17 | 0 | T |
| R40699 | UNKNOWN | 8.5 | 151 | CA |
| R40753 | UNKNOWN | 18 | 0 | T |
| R40781 | UNKNOWN | 7 | 37 | TCC |
| R40819 | UNKNOWN | 19 | 0 | T |
| R40855 | UNKNOWN | 24 | 0 | T |
| R40926 | UNKNOWN | 12 | 0 | T |
| R40945 | UNKNOWN | 14 | 0 | T |
| R40977 | UNKNOWN | 7.66 | 24 | GGT |
| R40977 | UNKNOWN | 19 | 0 | T |
| R41169 | UNKNOWN | 13 | 0 | T |
| R41173 | UNKNOWN | 14 | 0 | T |
| R41180 | UNKNOWN | 21 | 0 | T |
| R41184 | UNKNOWN | 14 | 0 | T |
| R41198 | UNKNOWN | 15 | 0 | T |
| R41227 | UNKNOWN | 16 | 0 | T |
| R41233 | UNKNOWN | 13 | 0 | T |
| R41295 | UNKNOWN | 12 | 0 | T |
| R41347 | UNKNOWN | 15 | 0 | T |
| R41384 | UNKNOWN | 22 | 0 | T |
| R41431 | UNKNOWN | 13 | 0 | T |
| R41494 | UNKNOWN | 12 | 0 | T |
| R41533 | UNKNOWN | 18 | 0 | T |
| R41627 | UNKNOWN | 26 | 0 | T |
| R41682 | UNKNOWN | 12 | 0 | T |
| R41686 | UNKNOWN | 27 | 0 | T |
| R41725 | UNKNOWN | 12 | 0 | T |
| R41749 | UNKNOWN | 15 | 0 | T |
| R41771 | UNKNOWN | 12 | 0 | T |
| R41772 | UNKNOWN | 23 | 0 | T |
| R41784 | UNKNOWN | 17 | 0 | T |
| R41800 | UNKNOWN | 18 | 0 | T |
| R41979 | UNKNOWN | 22 | 0 | T |
| R42061 | UNKNOWN | 7.66 | 104 | AAT |
| R42061 | UNKNOWN | 15 | 0 | T |
| R42121 | UNKNOWN | 14 | 0 | T |
| R42166 | UNKNOWN | 18 | 0 | T |
| R42228 | UNKNOWN | 16 | 10 | T |
| R42241 | UNKNOWN | 14 | 0 | T |
| R42302 | UNKNOWN | 12 | 6 | T |
| R42352 | UNKNOWN | 14 | 0 | T |
| R42359 | UNKNOWN | 26 | 0 | T |
| R42368 | UNKNOWN | 7 | 14 | TG |
| R42456 | UNKNOWN | 21 | 0 | T |
| R42480 | UNKNOWN | 16 | 0 | T |
| R42487 | UNKNOWN | 15 | 0 | T |
| R42508 | UNKNOWN | 34 | 0 | T |
| R42532 | UNKNOWN | 11 | 319 | GT |
| R42532 | UNKNOWN | 7.5 | 302 | GT |
| R42543 | UNKNOWN | 24 | 0 | T |
| R42553 | UNKNOWN | 18 | 0 | T |
| R42566 | UNKNOWN | 14 | 0 | T |
| R42569 | UNKNOWN | 13 | 0 | T |
| R42580 | UNKNOWN | 19 | 0 | T |
| R42604 | UNKNOWN | 40 | 0 | T |
| R42627 | UNKNOWN | 12 | 0 | T |
| R42635 | UNKNOWN | 30 | 0 | T |
| R42640 | UNKNOWN | 12 | 0 | T |
| R42760 | UNKNOWN | 28 | 0 | T |
| R42778 | UNKNOWN | 12 | 0 | T |
| R42779 | UNKNOWN | 16 | 0 | T |
| R42861 | UNKNOWN | 15 | 0 | T |
| R42887 | UNKNOWN | 2.67 | 176 | CCGGGCCCCTTCACCTGGGGNTCAGGTGAGAGCAGGTTT T (SEQ ID NO:276) |
| R42887 | UNKNOWN | 15 | 0 | T |
| R42900 | UNKNOWN | 4.8 | 221 | AAAAC |
| R42989 | UNKNOWN | 15 | 0 | T |
| R42999 | UNKNOWN | 15 | 0 | T |
| R43001 | UNKNOWN | 13 | 0 | T |
| R43010 | UNKNOWN | 15 | 14 | T |
| R43010 | UNKNOWN | 13 | 0 | T |
| R43017 | UNKNOWN | 31 | 0 | T |
| R43020 | UNKNOWN | 7 | 200 | CA |
| R43020 | UNKNOWN | 14 | 0 | T |
| R43077 | UNKNOWN | 12 | 0 | T |
| R43082 | UNKNOWN | 20 | 0 | T |
| R43093 | UNKNOWN | 12 | 0 | T |

TABLE 1-continued

| Genbank # | Region | # reps | Position | Unit sequence |
|---|---|---|---|---|
| R43158 | UNKNOWN | 20 | 0 | T |
| R43189 | UNKNOWN | 12 | 0 | T |
| R43204 | UNKNOWN | 15 | 0 | T |
| R43218 | UNKNOWN | 35 | 0 | T |
| R43254 | UNKNOWN | 27 | 0 | T |
| R43269 | UNKNOWN | 29 | 0 | T |
| R43309 | UNKNOWN | 17 | 0 | T |
| R43335 | UNKNOWN | 39 | 0 | T |
| R43481 | UNKNOWN | 12 | 0 | T |
| R43523 | UNKNOWN | 33 | 0 | T |
| R43528 | UNKNOWN | 13 | 0 | T |
| R43529 | UNKNOWN | 35 | 0 | T |
| R43535 | UNKNOWN | 25 | 0 | T |
| R43543 | UNKNOWN | 20 | 0 | T |
| R43564 | UNKNOWN | 13 | 0 | T |
| R43566 | UNKNOWN | 20 | 0 | T |
| R43597 | UNKNOWN | 16 | 0 | T |
| R43619 | UNKNOWN | 30 | 0 | T |
| R43631 | UNKNOWN | 22 | 0 | T |
| R43643 | UNKNOWN | 17 | 0 | T |
| R43644 | UNKNOWN | 20 | 259 | T |
| R43675 | UNKNOWN | 15 | 0 | T |
| R43678 | UNKNOWN | 19.5 | 232 | GT |
| R43678 | UNKNOWN | 11.5 | 273 | AG |
| R43721 | UNKNOWN | 5 | 14 | GATG |
| R43725 | UNKNOWN | 12 | 0 | T |
| R43774 | UNKNOWN | 14 | 0 | T |
| R43822 | UNKNOWN | 12 | 0 | T |
| R43896 | UNKNOWN | 12 | 0 | T |
| R43957 | UNKNOWN | 12 | 0 | T |
| R43976 | UNKNOWN | 25 | 261 | GT |
| R43987 | UNKNOWN | 9.5 | 212 | TA |
| R44042 | UNKNOWN | 17 | 0 | T |
| R44045 | UNKNOWN | 15 | 0 | T |
| R44077 | UNKNOWN | 12 | 0 | T |
| R44102 | UNKNOWN | 14 | 0 | T |
| R44111 | UNKNOWN | 17 | 0 | T |
| R44118 | UNKNOWN | 14 | 0 | T |
| R44193 | UNKNOWN | 13 | 0 | T |
| R44218 | UNKNOWN | 17 | 0 | T |
| R44259 | UNKNOWN | 37 | 0 | T |
| R44308 | UNKNOWN | 12 | 0 | T |
| R44338 | UNKNOWN | 18 | 0 | T |
| R44381 | UNKNOWN | 25 | 0 | T |
| R44473 | UNKNOWN | 20 | 0 | T |
| R44519 | UNKNOWN | 15 | 0 | T |
| R44567 | UNKNOWN | 19 | 0 | T |
| R44591 | UNKNOWN | 12 | 0 | T |
| R44779 | UNKNOWN | 24 | 0 | T |
| R44867 | UNKNOWN | 8 | 114 | TA |
| R44867 | UNKNOWN | 17 | 0 | T |
| R44912 | UNKNOWN | 20 | 0 | T |
| R44927 | UNKNOWN | 15 | 0 | T |
| R44949 | UNKNOWN | 17 | 0 | T |
| R44987 | UNKNOWN | 16 | 0 | T |
| R44995 | UNKNOWN | 19 | 0 | T |
| R45047 | UNKNOWN | 16 | 0 | T |
| R45073 | UNKNOWN | 22 | 0 | T |
| R45086 | UNKNOWN | 15 | 0 | T |
| R43269 | UNKNOWN | 29 | 0 | T |
| R43309 | UNKNOWN | 17 | 0 | T |
| R43335 | UNKNOWN | 39 | 0 | T |
| R43481 | UNKNOWN | 12 | 0 | T |
| R43523 | UNKNOWN | 33 | 0 | T |
| R43528 | UNKNOWN | 13 | 0 | T |
| R43529 | UNKNOWN | 35 | 0 | T |
| R43535 | UNKNOWN | 25 | 0 | T |
| R43543 | UNKNOWN | 20 | 0 | T |
| R43564 | UNKNOWN | 13 | 0 | T |
| R43566 | UNKNOWN | 20 | 0 | T |
| R43597 | UNKNOWN | 16 | 0 | T |
| R43619 | UNKNOWN | 30 | 0 | T |
| R43631 | UNKNOWN | 22 | 0 | T |
| R43643 | UNKNOWN | 17 | 0 | T |
| R43644 | UNKNOWN | 20 | 259 | T |
| R43675 | UNKNOWN | 15 | 0 | T |
| R43678 | UNKNOWN | 19.5 | 232 | GT |

TABLE 1-continued

| Genbank # | Region | # reps | Position | Unit sequence |
|---|---|---|---|---|
| R43678 | UNKNOWN | 11.5 | 273 | AG |
| R43721 | UNKNOWN | 5 | 14 | GATG |
| R43725 | UNKNOWN | 12 | 0 | T |
| R43774 | UNKNOWN | 14 | 0 | T |
| R43822 | UNKNOWN | 12 | 0 | T |
| R43896 | UNKNOWN | 12 | 0 | T |
| R43957 | UNKNOWN | 12 | 0 | T |
| R43976 | UNKNOWN | 25 | 261 | GT |
| R43987 | UNKNOWN | 9.5 | 212 | TA |
| R44042 | UNKNOWN | 17 | 0 | T |
| R44045 | UNKNOWN | 15 | 0 | T |
| R44077 | UNKNOWN | 12 | 0 | T |
| R44102 | UNKNOWN | 14 | 0 | T |
| R44111 | UNKNOWN | 17 | 0 | T |
| R44118 | UNKNOWN | 14 | 0 | T |
| R44193 | UNKNOWN | 13 | 0 | T |
| R44218 | UNKNOWN | 17 | 0 | T |
| R44259 | UNKNOWN | 37 | 0 | T |
| R44308 | UNKNOWN | 12 | 0 | T |
| R44338 | UNKNOWN | 18 | 0 | T |
| R44381 | UNKNOWN | 25 | 0 | T |
| R44473 | UNKNOWN | 20 | 0 | T |
| R44519 | UNKNOWN | 15 | 0 | T |
| R44567 | UNKNOWN | 19 | 0 | T |
| R44591 | UNKNOWN | 12 | 0 | T |
| R44779 | UNKNOWN | 24 | 0 | T |
| R44867 | UNKNOWN | 8 | 114 | TA |
| R44867 | UNKNOWN | 17 | 0 | T |
| R44912 | UNKNOWN | 20 | 0 | T |
| R44927 | UNKNOWN | 15 | 0 | T |
| R44949 | UNKNOWN | 17 | 0 | T |
| R44987 | UNKNOWN | 16 | 0 | T |
| R44995 | UNKNOWN | 19 | 0 | T |
| R45047 | UNKNOWN | 16 | 0 | T |
| R45073 | UNKNOWN | 22 | 0 | T |
| R45086 | UNKNOWN | 15 | 0 | T |
| R50801 | UNKNOWN | 38 | 0 | T |
| R50967 | UNKNOWN | 14 | 0 | T |
| R50975 | UNKNOWN | 15 | 0 | T |
| R51089 | UNKNOWN | 24 | 0 | T |
| R51089 | UNKNOWN | 16 | 122 | A |
| R51273 | UNKNOWN | 14 | 0 | T |
| R51280 | UNKNOWN | 25 | 0 | T |
| R51357 | UNKNOWN | 16 | 0 | T |
| R51386 | UNKNOWN | 25 | 0 | T |
| R51520 | UNKNOWN | 30 | 0 | T |
| R51520 | UNKNOWN | 13 | 410 | A |
| R51524 | UNKNOWN | 15 | 0 | T |
| R51529 | UNKNOWN | 16 | 0 | T |
| R51758 | UNKNOWN | 13 | 0 | T |
| R51857 | UNKNOWN | 13 | 11 | T |
| R51872 | UNKNOWN | 13 | 0 | T |
| R52008 | UNKNOWN | 19 | 346 | A |
| R52054 | UNKNOWN | 19 | 185 | A |
| R52536 | UNKNOWN | 17 | 0 | T |
| R52631 | UNKNOWN | 13 | 0 | T |
| R52684 | UNKNOWN | 15 | 156 | T |
| R53054 | UNKNOWN | 6.33 | 366 | GTT |
| R53169 | UNKNOWN | 15 | 63 | T |
| R53411 | UNKNOWN | 12 | 137 | T |
| R53442 | UNKNOWN | 27 | 0 | T |
| R53469 | UNKNOWN | 5 | 291 | AATT |
| R53469 | UNKNOWN | 18 | 0 | T |
| R53556 | UNKNOWN | 16 | 0 | T |
| R53573 | UNKNOWN | 32 | 0 | T |
| R53757 | UNKNOWN | 12 | 155 | T |
| R53940 | UNKNOWN | 16 | 0 | T |
| R53956 | UNKNOWN | 18 | 0 | T |
| R54081 | UNKNOWN | 16 | 0 | T |
| R54179 | UNKNOWN | 6.5 | 81 | AT |
| R54797 | UNKNOWN | 15 | 0 | T |
| R54803 | UNKNOWN | 13 | 411 | A |
| R54825 | UNKNOWN | 12 | 0 | T |
| R55241 | UNKNOWN | 12 | 0 | T |
| R55723 | UNKNOWN | 21 | 0 | T |
| R55757 | UNKNOWN | 20 | 0 | T |
| R56029 | UNKNOWN | 17 | 0 | T |

TABLE 1-continued

| Genbank # | Region | # reps | Position | Unit sequence |
|---|---|---|---|---|
| R56094 | UNKNOWN | 19 | 0 | T |
| R56107 | UNKNOWN | 18 | 0 | T |
| R56122 | UNKNOWN | 14 | 0 | T |
| R56130 | UNKNOWN | 14 | 0 | T |
| R56146 | UNKNOWN | 19 | 0 | T |
| R56228 | UNKNOWN | 18 | 0 | T |
| R56239 | UNKNOWN | 14 | 0 | T |
| R56250 | UNKNOWN | 15 | 0 | T |
| R56419 | UNKNOWN | 3.8 | 53 | AAACC |
| R56457 | UNKNOWN | 13 | 0 | T |
| R56583 | UNKNOWN | 39 | 0 | T |
| R56589 | UNKNOWN | 34 | 0 | T |
| R56657 | UNKNOWN | 7 | 302 | AT |
| R56769 | UNKNOWN | 18 | 0 | T |
| R56799 | UNKNOWN | 7 | 387 | AT |
| R56879 | UNKNOWN | 19 | 0 | T |
| R56903 | UNKNOWN | 12 | 0 | T |
| R56906 | UNKNOWN | 16 | 0 | T |
| R56912 | UNKNOWN | 34 | 0 | T |
| R58627 | UNKNOWN | 13 | 87 | A |
| R58925 | UNKNOWN | 9 | 318 | TG |
| R58974 | UNKNOWN | 13 | 0 | T |
| R59071 | UNKNOWN | 6.5 | 327 | GT |
| R59091 | UNKNOWN | 18 | 0 | T |
| R59138 | UNKNOWN | 20 | 0 | T |
| R59210 | UNKNOWN | 14 | 0 | T |
| R59210 | UNKNOWN | 14 | 180 | A |
| R59325 | UNKNOWN | 15 | 0 | T |
| R59334 | UNKNOWN | 15 | 0 | T |
| R59355 | UNKNOWN | 15 | 0 | T |
| R59369 | UNKNOWN | 19 | 0 | T |
| R59497 | UNKNOWN | 15 | 0 | T |
| R59581 | UNKNOWN | 14 | 0 | T |
| R59583 | UNKNOWN | 39 | 0 | T |
| R59593 | UNKNOWN | 16 | 0 | T |
| R59595 | UNKNOWN | 20 | 0 | T |
| R59702 | UNKNOWN | 3.83 | 46 | AAAAAC |
| R59765 | UNKNOWN | 5 | 81 | TTTTG |
| R59967 | UNKNOWN | 17 | 0 | T |
| R60030 | UNKNOWN | 34 | 0 | T |
| R60061 | UNKNOWN | 13 | 0 | T |
| R60138 | UNKNOWN | 9 | 112 | GT |
| R60198 | UNKNOWN | 9.25 | 34 | TTTA |
| R60198 | UNKNOWN | 12 | 0 | T |
| R60224 | UNKNOWN | 15 | 0 | T |
| R60352 | UNKNOWN | 16 | 0 | T |
| R60505 | UNKNOWN | 17 | 0 | T |
| R60569 | UNKNOWN | 16 | 0 | T |
| R60584 | UNKNOWN | 13 | 0 | T |
| R60755 | UNKNOWN | 19 | 0 | T |
| R60885 | UNKNOWN | 13 | 12 | A |
| R60891 | UNKNOWN | 14 | 0 | T |
| R60893 | UNKNOWN | 14 | 0 | T |
| R60981 | UNKNOWN | 13 | 0 | T |
| R60997 | UNKNOWN | 20 | 0 | T |
| R61231 | UNKNOWN | 7.5 | 298 | CT |
| R61291 | UNKNOWN | 17 | 0 | T |
| R61304 | UNKNOWN | 15 | 0 | T |
| R61390 | UNKNOWN | 22 | 0 | T |
| R61551 | UNKNOWN | 4.75 | 61 | AAAC |
| R61551 | UNKNOWN | 26 | 0 | T |
| R61746 | UNKNOWN | 16 | 0 | T |
| R61847 | UNKNOWN | 17 | 0 | T |
| R61877 | UNKNOWN | 16 | 0 | T |
| R61886 | UNKNOWN | 16 | 0 | T |
| R61889 | UNKNOWN | 12 | 0 | T |
| R62432 | UNKNOWN | 12 | 0 | T |
| R62748 | UNKNOWN | 13 | 349 | T |
| R63460 | UNKNOWN | 20 | 197 | A |
| R63899 | UNKNOWN | 15 | 198 | A |
| R64097 | UNKNOWN | 13 | 3 | T |
| R64696 | UNKNOWN | 16 | 49 | A |
| R66118 | UNKNOWN | 5.66 | 77 | GGA |
| R66868 | UNKNOWN | 18 | 263 | T |
| R66923 | UNRNOWN | 19 | 154 | T |
| R67259 | UNKNOWN | 18 | 0 | T |
| R67267 | UNKNOWN | 22 | 0 | T |

TABLE 1-continued

| Genbank # | Region | # reps | Position | Unit sequence |
|---|---|---|---|---|
| R68563 | UNKNOWN | 16.5 | 60 | AC |
| R68563 | UNKNOWN | 6.5 | 46 | AC |
| R68653 | UNKNOWN | 17 | 249 | AC |
| R68748 | UNKNOWN | 13 | 360 | A |
| R69245 | UNKNOWN | 15 | 72 | T |
| R69289 | UNKNOWN | 8 | 169 | CA |
| R69566 | UNKNOWN | 16 | 20 | T |
| R70319 | UNKNOWN | 12 | 269 | T |
| R70481 | UNKNOWN | 14 | 386 | A |
| R70986 | UNKNOWN | 21 | 55 | T |
| R71245 | UNKNOWN | 3.8 | 7 | TTTAT |
| R71245 | UNKNOWN | 13 | 87 | A |
| R71269 | UNKNOWN | 8 | 215 | CT |
| R71301 | UNKNOWN | 3.8 | 190 | TTTTG |
| R71573 | UNKNOWN | 13 | 544 | A |
| R71653 | UNKNOWN | 7.5 | 21 | TA |
| R71737 | UNNNOWN | 20 | 22 | T |
| R73220 | UNKNOWN | 25 | 230 | T |
| R73675 | UNKNOWN | 5.5 | 14 | AAAT |
| R74602 | UNKNOWN | 12 | 425 | TG |
| R76178 | UNKNOWN | 14 | 481 | T |
| R76493 | UNKNOWN | 8.5 | 88 | AC |
| R76600 | UNKNOWN | 14 | 144 | T |
| R76636 | UNKNOWN | 24.5 | 191 | AC |
| R76879 | UNKNOWN | 13 | 357 | A |
| R76882 | UNKNOWN | 12 | 10 | T |
| R76960 | UNKNOWN | 13 | 287 | T |
| R78444 | UNKNOWN | 19 | 334 | A |
| R78554 | UNKNOWN | 16 | 103 | A |
| R78575 | UNKNOWN | 13 | 289 | A |
| R78603 | UNKNOWN | 15 | 308 | T |
| R79063 | UNKNOWN | 5.66 | 41 | AAC |
| R79221 | UNKNOWN | 13 | 180 | T |
| R79367 | UNKNOWN | 4.5 | 85 | TTAA |
| R79570 | UNKNOWN | 13 | 46 | A |
| R79611 | UNKNOWN | 7 | 306 | GGA |
| R80459 | UNKNOWN | 13 | 140 | T |
| R81679 | UNKNOWN | 77 | 250 | A |
| R82846 | UNKNOWN | 13 | 390 | A |
| R83634 | UNKNOWN | 13 | 2 | T |
| R83740 | UNKNOWN | 5.5 | 336 | TTTA |
| R83905 | UNKNOWN | 16 | 221 | T |
| R84907 | UNKNOWN | 13 | 383 | A |
| R85255 | UNKNOWN | 19 | 102 | A |
| R85326 | UNKNOWN | 6.75 | 16 | AAAT |
| R85442 | UNKNOWN | 4 | 191 | GTTTT |
| R85549 | UNKNOWN | 13 | 9 | T |
| R85773 | UNKNOWN | 11 | 394 | CA |
| R86217 | UNKNOWN | 15 | 64 | A |
| R87488 | UNKNOWN | 3.8 | 149 | TTTTG |
| R87752 | UNKNOWN | 7 | 33 | AC |
| R87878 | UNKNOWN | 14 | 355 | A |
| R88428 | UNKNOWN | 5 | 146 | TAAA |
| R88723 | UNKNOWN | 4.75 | 103 | AAAC |
| R88723 | UNKNOWN | 19 | 144 | A |
| R88760 | UNKNOWN | 14 | 9 | T |
| R91075 | UNKNOWN | 12 | 147 | A |
| R91253 | UNKNOWN | 13 | 1 | T |
| R91299 | UNKNOWN | 14 | 185 | T |
| R91696 | UNKNOWN | 13 | 321 | A |
| R91839 | UNKNOWN | 7.75 | 49 | AAAC |
| R91868 | UNKNOWN | 6.5 | 126 | TA |
| R92200 | UNKNOWN | 5.75 | 68 | TTTG |
| R92941 | UNKNOWN | 19 | 12 | T |
| R92941 | UNKNOWN | 15 | 111 | A |
| R93315 | UNKNOWN | 5.25 | 187 | GGAT |
| R93444 | UNKNOWN | 7.5 | 422 | TA |
| R93657 | UNKNOWN | 26 | 0 | T |
| R93759 | UNKNOWN | 14 | 0 | T |
| R93999 | UNKNOWN | 14 | 242 | T |
| R94010 | UNKNOWN | 7.5 | 173 | TGTT |
| R94487 | UNKNOWN | 13 | 53 | T |
| R94852 | UNKNOWN | 16 | 257 | T |
| R96095 | UNKNOWN | 16 | 185 | A |
| R96525 | UNKNOWN | 14 | 181 | GT |
| R96753 | UNKNOWN | 29 | 101 | A |
| R96783 | UNKNOWN | 22 | 147 | A |

TABLE 1-continued

| Genbank # | Region | # reps | Position | Unit sequence |
|---|---|---|---|---|
| R97041 | UNKNOWN | 11.33 | 182 | AAT |
| R97240 | UNKNOWN | 6.5 | 91 | TG |
| R97612 | UNKNOWN | 15 | 0 | T |
| R98002 | UNKNOWN | 16 | 264 | A |
| R98170 | UNKNOWN | 18 | 12 | A |
| R98468 | UNKNOWN | 19 | 377 | A |
| R98468 | UNKNOWN | 13 | 164 | G |
| R98518 | UNKNOWN | 5.5 | 246 | AACC |
| R98895 | UNKNOWN | 17 | 249 | AC |
| R99532 | UNKNOWN | 14 | 1 | T |
| R99598 | UNKNOWN | 15 | 346 | A |
| R99820 | UNKNOWN | 12 | 1 | T |
| R99821 | UNKNOWN | 17 | 184 | T |
| R99923 | UNKNOWN | 6.5 | 143 | AT |
| R99990 | UNKNOWN | 7 | 98 | TA |
| S40719 | 3'UTR | 6.66 | 2942 | CTG |
| S40832 | 3'UTR | 4 | 3396 | TTTTG |
| S40832 | 3'UTR | 12 | 3858 | A |
| S41458 | 3'UTR | 22 | 2718 | T |
| S42303 | 5'UTR | 9.66 | 397 | CCG |
| S42303 | 3'UTR | 14 | 3697 | T |
| S43855 | 3'UTR | 9 | 884 | CA |
| S43855 | 3'UTR | 7 | 852 | CA |
| S49953 | BORDER | 4.5 | 741 | AAAT |
| S54641 | 5'UTR | 16 | 0 | T |
| S57235 | 3'UTR | 17 | 1586 | C |
| S58722 | CDS | 27 | 276 | T |
| S58722 | BORDER | 19 | 1 | T |
| S59184 | 5'UTR | 7.33 | 108 | CGG |
| S60415 | 3'UTR | 8 | 2654 | AT |
| S60415 | 3'UTR | 22 | 2058 | T |
| S62539 | 5'UTR | 9 | 367 | GCA |
| S62539 | 5'UTR | 6.33 | 79 | GAG |
| S62539 | 5'UTR | 9 | 602 | GC |
| S62907 | 5'UTR | 35 | 66 | TC |
| S63912 | 3'UTR | 2.7 | 2614 | ATATATATAG (SEQ ID NO:277) |
| S63912 | 3'UTR | 7 | 2666 | TA |
| S66431 | 5'UTR | 12 | 130 | C |
| S71018 | 3'UTR | 15 | 840 | GT |
| S71486 | CDS | 14 | 29 | A |
| S71824 | 3'UTR | 7 | 2835 | CA |
| S72487 | UNKNOWN | 9 | 1012 | CT |
| S73885 | 5'UTR | 6.33 | 117 | CGC |
| S73885 | 5'UTR | 21.5 | 9 | AC |
| S73885 | 3'UTR | 14 | 2001 | T |
| S75174 | CDS | 16.66 | 971 | CAG |
| S75174 | 3'UTR | 2.5 | 1466 | CTGTGCTGGCACTT (SEQ ID NO:278) |
| S75546 | 3'UTR | 4.5 | 2919 | CCCCTG |
| S76965 | 3'UTR | 10 | 1603 | AT |
| S78187 | 5'UTR | 18 | 0 | G |
| S78187 | 5'UTR | 12 | 127 | C |
| S78187 | 3'UTR | 2.7 | 2794 | GTGGATGGCC (SEQ ID NO:279) |
| S78203 | 5'UTR | 6.5 | 4 | GA |
| S78296 | CDS | 6.33 | 1374 | GAG |
| S79267 | UNKNOWN | 15 | 2755 | T |
| S79267 | UNKNOWN | 12 | 2314 | T |
| S79432 | 3'UTR | 7.66 | 392 | GGA |
| S79812 | 3'UTR | 12 | 1034 | A |
| S79869 | CDS | 8 | 185 | CCA |
| S80562 | 3'UTR | 17 | 1421 | T |
| S81734 | 3'UTR | 3.8 | 1756 | AAAAT |
| S81734 | 3'UTR | 29 | 1920 | A |
| S87759 | 3'UTR | 20 | 1673 | T |
| T02860 | UNKNOWN | 13 | 202 | A |
| T03075 | UNKNOWN | 15 | 106 | A |
| T03368 | UNKNOWN | 11.75 | 304 | TTTA |
| T03428 | UNKNOWN | 5.75 | 23 | ATAG |
| T03583 | UNKNOWN | 13 | 99 | T |
| T03667 | UNKNOWN | 29 | 65 | T |
| T03842 | UNKNOWN | 26 | 432 | A |
| T03941 | UNKNOWN | 2.52 | 0 | AAATACTGTATTTATAAAT (SEQ ID NO:280) |
| T03941 | UNKNOWN | 30 | 99 | A |
| T05118 | UNKNOWN | 17 | 0 | T |
| T05426 | UNKNOWN | 22 | 171 | A |
| T05426 | UNKNOWN | 12 | 11 | A |
| T05440 | UNKNOWN | 12 | 3 | T |
| T05595 | UNKNOWN | 14 | 0 | T |

TABLE 1-continued

| Genbank # | Region | # reps | Position | Unit sequence |
|---|---|---|---|---|
| T06016 | UNKNOWN | 15 | 227 | A |
| T07518 | UNKNOWN | 13 | 0 | T |
| T07954 | UNKNOWN | 1S | 3 | T |
| T10430 | UNKNOWN | 15 | 33 | A |
| T10577 | UNKNOWN | 22.5 | 109 | TG |
| T11686 | UNKNOWN | 16 | 97 | A |
| T11723 | UNKNOWN | 19 | 88 | A |
| T12157 | UNKNOWN | 7 | 92 | AT |
| T12232 | UNKNOWN | 15 | 107 | A |
| T15450 | UNKNOWN | 7 | 103 | AT |
| T15740 | UNKNOWN | 19 | 139 | A |
| T15740 | UNKNOWN | 15 | 111 | T |
| T16257 | UNKNOWN | 12 | 16 | T |
| T16378 | UNKNOWN | 8.5 | 133 | CA |
| T16443 | UNKNOWN | 12 | 173 | A |
| T16612 | UNKNOWN | 11.5 | 167 | TG |
| T16938 | UNKNOWN | 12 | 187 | T |
| T17258 | UNKNOWN | 18 | 132 | A |
| T17434 | UNKNOWN | 8 | 357 | TC |
| T23065 | UNKNOWN | 23 | 231 | A |
| T23069 | UNKNOWN | 25 | 307 | A |
| T23810 | UNKNOWN | 7 | 160 | AT |
| T24683 | UNKNOWN | 23 | 0 | T |
| T25327 | UNKNOWN | 17 | 0 | T |
| T25328 | UNKNOWN | 13 | 209 | A |
| T25399 | UNKNOWN | 15 | 0 | T |
| T25921 | UNKNOWN | 15 | 0 | T |
| T27182 | UNKNOWN | 22 | 0 | T |
| T27341 | UNKNOWN | 15 | 1 | T |
| T28421 | UNKNOWN | 59 | 15 | T |
| T39311 | UNKNOWN | 12.5 | 124 | AC |
| T39311 | UNKNOWN | 17 | 0 | T |
| T39322 | UNKNOWN | 19 | 199 | T |
| T39322 | UNKNOWN | 14 | 159 | T |
| T40344 | UNKNOWN | 21 | 304 | A |
| T40769 | UNKNOWN | 17 | 2 | T |
| T40789 | UNKNOWN | 16 | 0 | T |
| T40971 | UNKNOWN | 6.25 | 33 | AAAC |
| T41134 | UNKNOWN | 14 | 328 | A |
| T41153 | UNKNOWN | 7.66 | 80 | AAC |
| T41153 | UNKNOWN | 16 | 261 | A |
| T47055 | UNKNOWN | 15 | 114 | T |
| T47762 | UNKNOWN | 10.5 | 101 | GA |
| T47938 | UNKNOWN | 3.8 | 237 | AAAAC |
| T47972 | UNKNOWN | 24 | 259 | A |
| T48250 | UNKNOWN | 18 | 0 | T |
| T48750 | UNKNOWN | 3.6 | 265 | AGGAA |
| T49154 | UNKNOWN | 13 | 0 | T |
| T49783 | UNKNOWN | 16 | 78 | T |
| T49787 | UNKNOWN | 15 | 10 | T |
| T5041S | UNKNOWN | 18 | 210 | A |
| T50788 | UNKNOWN | 12 | 134 | T |
| T51136 | UNKNOWN | 18 | 166 | GT |
| T51259 | UNKNOWN | 13 | 7 | T |
| T51524 | UNKNOWN | 12 | 10 | T |
| T51619 | UNKNOWN | 17 | 0 | T |
| T52097 | UNKNOWN | 32 | 0 | T |
| T52246 | UNKNOWN | 16 | 126 | T |
| T52475 | UNKNOWN | 25 | 0 | T |
| T52648 | UNKNOWN | 21 | 0 | T |
| T54146 | UNKNOWN | 5 | 9 | ATTT |
| T54624 | UNKNOWN | 12 | 202 | A |
| T54792 | UNKNOWN | 17 | 0 | T |
| T55189 | UNKNOWN | 20 | 0 | T |
| T55423 | UNKNOWN | 17 | 12 | T |
| T55433 | UNKNOWN | 3.8 | 1 | TTTTA |
| T55451 | UNKNOWN | 31 | 0 | T |
| T55451 | UNKNOWN | 14 | 105 | A |
| T55543 | UNKNOWN | 17 | 10 | T |
| T55586 | UNKNOWN | 18 | 0 | T |
| T55714 | UNKNOWN | 14 | 452 | T |
| T55745 | UNKNOWN | 12 | 355 | T |
| T57049 | UNKNOWN | 21 | 0 | T |
| T57119 | UNKNOWN | 19 | 0 | T |
| T57458 | UNKNOWN | 7 | 295 | GT |
| T57458 | UNKNOWN | 6.5 | 281 | GT |
| T57458 | UNKNOWN | 6.5 | 330 | TA |

TABLE 1-continued

| Genbank # | Region | # reps | Position | Unit sequence |
|---|---|---|---|---|
| T57525 | UNKNOWN | 17 | 315 | T |
| T57865 | UNKNOWN | 17 | 155 | A |
| T58129 | UNKNOWN | 11 | 332 | CA |
| T58376 | UNKNOWN | 4.8 | 197 | AAAAG |
| T58376 | UNKNOWN | 16 | 185 | A |
| T58376 | UNKNOWN | 14 | 32 | A |
| T58500 | UNKNOWN | 18 | 0 | T |
| T59305 | UNKNOWN | 12 | 344 | T |
| T59578 | UNKNOWN | 22 | 163 | T |
| T59669 | UNKNOWN | 16 | 160 | T |
| T59887 | UNKNOWN | 12 | 10 | T |
| T59891 | UNKNOWN | 18 | 11 | T |
| T59943 | UNKNOWN | 8 | 124 | GTTT |
| T60156 | UNKNOWN | 16 | 308 | A |
| T60216 | UNKNOWN | 17 | 57 | A |
| T60689 | UNKNOWN | 13 | 202 | A |
| T61447 | UNKNOWN | 24 | 0 | T |
| T61512 | UNKNOWN | 20 | 229 | T |
| T61552 | UNKNOWN | 26 | 308 | A |
| T61595 | UNKNOWN | 19 | 278 | A |
| T61796 | UNKNOWN | 16 | 310 | GT |
| T63272 | UNKNOWN | 13 | 352 | A |
| T63510 | UNKNOWN | 2.9 | 184 | GAAGAAGAAA (SEQ ID NO:281) |
| T63510 | UNKNOWN | 2.6 | 167 | GAAGAAGGAA (SEQ ID NO:282) |
| T63510 | UNKNOWN | 4.83 | 136 | GAAGAG |
| T63510 | UNKNOWN | 12 | 85 | T |
| T63527 | UNKNOWN | 14 | 10 | T |
| T64319 | UNKNOWN | 18 | 11 | T |
| T64924 | UNKNOWN | 3.66 | 47 | AAAAAT |
| T64961 | UNKNOWN | 6.5 | 64 | TG |
| T65012 | UNKNOWN | 22 | 0 | T |
| T65014 | UNKNOWN | 13 | 0 | T |
| T65058 | UNKNOWN | 15 | 0 | T |
| T65206 | UNKNOWN | 25 | 0 | T |
| T65235 | UNKNOWN | 15 | 0 | T |
| T65308 | UNKNOWN | 18 | 214 | A |
| T65383 | UNKNOWN | 14 | 0 | T |
| T65556 | UNKNOWN | 18 | 0 | T |
| T65568 | UNKNOWN | 12 | 0 | T |
| T65590 | UNKNOWN | 12 | 0 | T |
| T66089 | UNKNOWN | 7.5 | 167 | CA |
| T66132 | UNKNOWN | 14 | 0 | T |
| T66831 | UNKNOWN | 15 | 50 | T |
| T66883 | UNKNOWN | 14 | 0 | T |
| T66990 | UNKNOWN | 17 | 0 | T |
| T67020 | UNKNOWN | 15 | 135 | A |
| T67137 | UNKNOWN | 6.66 | 172 | ATT |
| T67165 | UNKNOWN | 14 | 148 | T |
| T67499 | UNKNOWN | 10.5 | 38 | AGAT |
| T69738 | UNKNOWN | 3.8 | 341 | CACTC |
| T70259 | UNKNOWN | 19 | 8 | T |
| T70600 | UNKNOWN | 12.5 | 57 | AC |
| T70600 | UNKNOWN | 9.5 | 37 | AC |
| T71258 | UNKNOWN | 5.75 | 149 | TTTA |
| T71258 | UNKNOWN | 12 | 221 | A |
| T71320 | UNKNOWN | 12 | 285 | A |
| T71614 | UNKNOWN | 6 | 328 | AAC |
| T72541 | UNKNOWN | 5.75 | 154 | TGTT |
| T72642 | UNKNOWN | 6.25 | 0 | TCAT |
| T72934 | UNKNOWN | 3.6 | 316 | TTGTT |
| T72937 | UNKNOWN | 23 | 0 | T |
| T74893 | UNKNOWN | 12.5 | 11 | TG |
| T75208 | UNKNOWN | 9 | 257 | CT |
| T75208 | UNKNOWN | 15 | 274 | T |
| T76931 | UNKNOWN | 9.5 | 284 | GT |
| T76931 | UNKNOWN | 17 | 192 | T |
| T76931 | UNKNOWN | 12 | 209 | A |
| T77004 | UNKNOWN | 12 | 117 | T |
| T77167 | UNKNOWN | 13 | 1 | T |
| T77567 | UNKNOWN | 7 | 0 | TG |
| T77714 | UNKNOWN | 26 | 12 | A |
| T77781 | UNKNOWN | 17 | 151 | A |
| T77890 | UNKNOWN | 13 | 125 | T |
| T77990 | UNKNOWN | 4.75 | 9 | TATT |
| T78395 | UNKNOWN | 18 | 0 | T |
| T78398 | UNKNOWN | 12 | 46 | A |
| T78404 | UNKNOWN | 12 | 5 | G |

TABLE 1-continued

| Genbank # | Region | # reps | Position | Unit sequence |
|---|---|---|---|---|
| T78463 | UNKNOWN | 7 | 156 | TC |
| T78476 | UNKNOWN | 5.66 | 212 | AGC |
| T78540 | UNKNOWN | 19 | 318 | A |
| T78590 | UNKNOWN | 16.5 | 381 | CA |
| T78717 | UNKNOWN | 14 | 217 | T |
| T78991 | UNKNOWN | 14 | 181 | T |
| T79196 | UNKNOWN | 9.5 | 14 | TTAT |
| T79217 | UNKNOWN | 34 | 0 | T |
| T79374 | UNKNOWN | 47 | 226 | A |
| T79374 | UNKNOWN | 16 | 100 | A |
| T79401 | UNKNOWN | 5.2 | 143 | TATTT |
| T79443 | UNKNOWN | 16 | 0 | T |
| T79761 | UNKNOWN | 26 | 0 | T |
| T79766 | UNKNOWN | 26 | 0 | T |
| T79782 | UNKNOWN | 23.5 | 76 | AC |
| T79844 | UNKNOWN | 18 | 0 | T |
| T79944 | UNKNOWN | 27 | 0 | T |
| T79954 | UNKNOWN | 20 | 0 | T |
| T79963 | UNKNOWN | 6.5 | 347 | AAAT |
| T80587 | UNKNOWN | 12 | 100 | A |
| T80716 | UNKNOWN | 14 | 6 | T |
| T81438 | UNKNOWN | 26 | 0 | T |
| T82081 | UNKNOWN | 21 | 137 | A |
| T82181 | UNKNOWN | 12 | 0 | T |
| T82304 | UNKNOWN | 13 | 0 | T |
| T82330 | UNKNOWN | 14 | 0 | T |
| T82459 | UNKNOWN | 13 | 126 | A |
| T82468 | UNKNOWN | 15 | 0 | T |
| T83087 | UNKNOWN | 12 | 433 | T |
| T83663 | UNKNOWN | 9 | 375 | GT |
| T83852 | UNKNOWN | 10.5 | 256 | TG |
| T83852 | UNKNOWN | 13 | 69 | A |
| T83966 | UNKNOWN | 14 | 151 | T |
| T84348 | UNKNOWN | 6.5 | 25 | AC |
| T84348 | UNKNOWN | 14 | 12 | A |
| T84438 | UNKNOWN | 6 | 262 | GCT |
| T84542 | UNKNOWN | 14 | 0 | T |
| T84833 | UNKNOWN | 25 | 338 | A |
| T84833 | UNKNOWN | 12 | 230 | T |
| T85271 | UNKNOWN | 17 | 0 | T |
| T85304 | UNKNOWN | 12 | 217 | A |
| T85312 | UNKNOWN | 15 | 156 | A |
| T85349 | UNKNOWN | 5 | 60 | AAAC |
| T85352 | UNKNOWN | 7 | 124 | GTT |
| T85427 | UNKNOWN | 19 | 309 | A |
| T85427 | UNKNOWN | 12 | 296 | A |
| T85581 | UNKNOWN | 24 | 0 | T |
| T85628 | UNKNOWN | 14 | 81 | T |
| T86081 | UNKNOWN | 19 | 80 | A |
| T86130 | UNKNOWN | 6.75 | 16 | TTTA |
| T86185 | UNKNOWN | 21 | 209 | T |
| T86270 | UNKNOWN | 21 | 282 | T |
| T86282 | UNKNOWN | 18 | 327 | A |
| T86285 | UNKNOWN | 30 | 0 | T |
| T86307 | UNKNOWN | 12 | 0 | T |
| T86622 | UNKNOWN | 13 | 104 | T |
| T86732 | UNKNOWN | 15 | 0 | T |
| T86742 | UNKNOWN | 22 | 0 | T |
| T86957 | UNKNOWN | 15 | 0 | T |
| T86971 | UNKNOWN | 14 | 499 | T |
| T87062 | UNKNOWN | 15 | 381 | A |
| T87067 | UNKNOWN | 15 | 260 | T |
| T87103 | UNKNOWN | 15 | 193 | T |
| T87109 | UNKNOWN | 17 | 304 | T |
| T87326 | UNKNOWN | 12 | 426 | T |
| T88698 | UNKNOWN | 14 | 89 | T |
| T88801 | UNKNOWN | 15 | 121 | A |
| T88880 | UNKNOWN | 12 | 199 | A |
| T88999 | UNKNOWN | 14 | 0 | T |
| T89299 | UNKNOWN | 14 | 286 | A |
| T89407 | UNKNOWN | 15 | 288 | T |
| T89419 | UNKNOWN | 13 | 6 | T |
| T89441 | UNKNOWN | 12 | 0 | T |
| T89477 | UNKNOWN | 12 | 66 | A |
| T89638 | UNKNOWN | 6 | 427 | TTG |
| T89638 | UNKNOWN | 11.5 | 484 | AG |
| T89693 | UNKNOWN | 14 | 7 | T |

TABLE 1-continued

| Genbank # | Region | # reps | Position | Unit sequence |
|---|---|---|---|---|
| T89716 | UNKNOWN | 5.25 | 30 | AGGA |
| T89848 | UNKNOWN | 11 | 401 | GT |
| T89848 | UNKNOWN | 10 | 380 | TG |
| T89955 | UNKNOWN | 14 | 87 | GT |
| T89972 | UNKNOWN | 14 | 235 | A |
| T90054 | UNKNOWN | 13 | 137 | A |
| T90290 | UNKNOWN | 14 | 516 | T |
| T90346 | UNKNOWN | 10.25 | 336 | CCAT |
| T90453 | UNKNOWN | 12 | 1 | T |
| T90476 | UNKNOWN | 14 | 35 | T |
| T90522 | UNKNOWN | 6.5 | 487 | CA |
| T90913 | UNKNOWN | 19 | 6 | T |
| T90991 | UNKNOWN | 2.76 | 59 | TTTCTTTCTTTCT (SEQ ID NO:283) |
| T90991 | UNKNOWN | 17 | 6 | CTTT |
| T91086 | UNKNOWN | 11 | 58 | TA |
| T91086 | UNKNOWN | 10 | 39 | CT |
| T91092 | UNKNOWN | 5.4 | 0 | TCCTT |
| T91293 | UNKNOWN | 12 | 424 | T |
| T91502 | UNKNOWN | 8.8 | 13 | AATAA |
| T91502 | UNKNOWN | 14 | 112 | A |
| T91504 | UNKNOWN | 6.5 | 151 | CA |
| T91770 | UNKNOWN | 12 | 0 | T |
| T91799 | UNKNOWN | 5.25 | 20 | TCTA |
| T91942 | UNKNOWN | 16 | 290 | A |
| T92370 | UNKNOWN | 17 | 85 | A |
| T93956 | UNKNOWN | 12 | 195 | A |
| T94209 | UNKNOWN | 24 | 201 | T |
| T95064 | UNKNOWN | 4.75 | 110 | AAAC |
| T95404 | UNKNOWN | 40 | 313 | A |
| T96151 | UNKNOWN | 18 | 0 | T |
| T96491 | UNKNOWN | 8 | 0 | GA |
| T96491 | UNKNOWN | 13 | 424 | A |
| T96522 | UNKNOWN | 13 | 242 | A |
| T96875 | UNKNOWN | 14 | 6 | T |
| T96909 | UNKNOWN | 3.8 | 378 | TTTTG |
| T97295 | UNKNOWN | 5.5 | 140 | TATC |
| T97317 | UNKNOWN | 3.66 | 275 | AAAGGA |
| T97361 | UNKNOWN | 5.4 | 221 | AAAAC |
| T97361 | UNKNOWN | 4.4 | 181 | TTAGT |
| T97361 | UNKNOWN | 5.66 | 243 | AAC |
| T97431 | UNKNOWN | 13 | 66 | A |
| T97477 | UNKNOWN | 12 | 308 | A |
| T97493 | UNKNOWN | 6.75 | 365 | CTTC |
| T97592 | UNKNOWN | 16 | 0 | T |
| T97613 | UNKNOWN | 12 | 6 | T |
| T97684 | UNKNOWN | 13 | 138 | A |
| T97794 | UNKNOWN | 9 | 126 | TG |
| T97834 | UNKNOWN | 13 | 206 | A |
| T97981 | UNKNOWN | 2.83 | 214 | GAGCTGGGGTATTTATGTTCCAGGGTNAGG (SEQ ID NO:284) |
| T97991 | UNKNOWN | 37 | 6 | T |
| T98030 | UNKNOWN | 40 | 0 | T |
| T98276 | UNKNOWN | 15 | 158 | T |
| T98390 | UNKNOWN | 14 | 0 | T |
| T98594 | UNKNOWN | 5.75 | 0 | ATTT |
| T98594 | UNKNOWN | 13 | 137 | A |
| T98739 | UNKNOWN | 23 | 263 | A |
| T98756 | UNKNOWN | 15 | 94 | A |
| T98816 | UNKNOWN | 18 | 309 | A |
| T98886 | UNKNOWN | 7 | 288 | CAAA |
| T99068 | UNKNOWN | 26 | 169 | T |
| T99074 | UNKNOWN | 14 | 130 | A |
| T99356 | UNKNOWN | 3.66 | 52 | AATTTG |
| T99513 | UNKNOWN | 12 | 262 | A |
| T99753 | UNKNOWN | 13 | 3 | T |
| T99757 | UNKNOWN | 14 | 125 | TA |
| U00115 | 3'UTR | 7.5 | 2932 | AT |
| U00238 | 3'UTR | 18 | 2082 | A |
| U00238 | 3'UTR | 13 | 1737 | T |
| U00943 | UNKNOWN | 13 | 186 | A |
| U00944 | UNKNOWN | 16 | 586 | ACC |
| U00944 | UNKNOWN | 12 | 632 | CCT |
| U00951 | UNKNOWN | 5.66 | 881 | GCA |
| U00952 | UNKNOWN | 5.66 | 767 | CCA |
| U00956 | UNKNOWN | 15.33 | 142 | GGT |
| U00956 | UNKNOWN | 6 | 122 | TTG |
| U00957 | UNKNOWN | 17 | 1161 | T |

TABLE 1-continued

| Genbank # | Region | # reps | Position | Unit sequence |
|---|---|---|---|---|
| U01120 | 3'UTR | 15 | 2365 | T |
| U01157 | 3'UTR | 17.5 | 1485 | AC |
| U01160 | 3'UTR | 13 | 1192 | T |
| U01877 | 3'UTR | 2.8 | 8952 | ATATATATAA (SEQ ID NO:285) |
| U01923 | UNKNOWN | 13 | 2035 | T |
| U02493 | 3'UTR | 14 | 1812 | T |
| U02570 | 3'UTR | 15 | 2468 | T |
| U02683 | 3'UTR | 8 | 2908 | AT |
| U02882 | 3'UTR | 12 | 1944 | T |
| U03272 | 3'UTR | 14 | 9046 | T |
| U03398 | CDS | 7 | 104 | GCT |
| U03398 | 3'UTR | 8.5 | 989 | TA |
| U03644 | CDS | 5.66 | 820 | TCC |
| U03688 | 3'UTR | 12 | 2775 | A |
| U03749 | CDS | 8.33 | 897 | GAG |
| U03749 | CDS | 6.33 | 732 | GAG |
| U03886 | 3'UTR | 24 | 1897 | TC |
| U04840 | 3'UTR | 14 | 3379 | T |
| U05012 | 5'UTR | 8.66 | 57 | CGG |
| U05040 | 3'UTR | 20 | 2083 | T |
| U05237 | CDS | 6.66 | 82 | GAG |
| U05237 | 5'UTR | 21 | 34 | G |
| U05875 | 3'UTR | 14 | 1826 | T |
| U06233 | CDS | 12.66 | 377 | GGC |
| U06233 | CDS | 6.66 | 743 | CAC |
| U06233 | CDS | 5.66 | 725 | CAC |
| U06233 | 3'UTR | 14 | 2493 | AC |
| U06454 | 5'UTR | 5.66 | 4 | GCG |
| U06631 | CDS | 2.5 | 482 | GAAGAGGAGGAA (SEQ ID NO:286) |
| U06632 | 3'UTR | 13 | 1816 | T |
| U07000 | CDS | 5.66 | 386 | GGA |
| U07358 | 3'UTR | 8 | 2735 | AT |
| U07620 | 3'UTR | 8.5 | 1690 | AC |
| U07664 | CDS | 11.66 | 550 | GCC |
| U07664 | CDS | 6 | 475 | GGC |
| U07664 | CDS | 5.66 | 307 | GGC |
| U07802 | CDS | 7 | 1467 | CAG |
| U07802 | 3'UTR | 17 | 2051 | A |
| U07857 | CDS | 9.33 | 341 | AGC |
| U08438 | 5'UTR | 5.66 | 0 | GGC |
| U09002 | 3'UTR | 6 | 4668 | TTG |
| U09303 | 3'UTR | 17 | 2443 | CA |
| U09414 | 3'UTR | 12 | 1565 | T |
| U09607 | 3'UTR | 3.83 | 3806 | TTTTTA |
| U09848 | 3'UTR | 13 | 2199 | T |
| U09850 | 3'UTR | 21 | 2572 | A |
| U09850 | 3'UTR | 17 | 2285 | A |
| U10868 | 3'UTR | 23 | 2191 | A |
| U10886 | CDS | 6.66 | 414 | GCT |
| U10886 | 3'UTR | 12 | 4602 | T |
| U10991 | CDS | 6 | 3114 | TCA |
| U11690 | 5'UTR | 3.5 | 466 | CGGGGC |
| U12022 | 5'UTR | 8.33 | 92 | AGC |
| U12134 | 3'UTR | 18 | 1934 | T |
| U12767 | CDS | 9.66 | 383 | CAC |
| U12767 | 3'UTR | 9.5 | 3396 | AT |
| U12779 | 5'UTR | 15 | 77 | A |
| U12897 | UNKNOWN | 14.5 | 554 | TG |
| U13045 | 3'UTR | 13 | 1568 | T |
| U13219 | 5'UTR | 8 | 53 | CGG |
| U13219 | 3'UTR | 13 | 2317 | T |
| U13220 | CDS | 9.66 | 208 | CCG |
| U13220 | CDS | 7 | 909 | CAC |
| U13220 | 3'UTR | 9.5 | 1792 | TG |
| U13395 | 3'UTR | 5.66 | 1152 | ACC |
| U13616 | 3'UTR | 3.8 | 13473 | AAAAG |
| U13913 | CDS | 7.66 | 192 | TCC |
| U13913 | CDS | 7.33 | 112 | GCG |
| U13913 | CDS | 6 | 90 | GGC |
| U13913 | 3'UTR | 5.66 | 4023 | TTG |
| U14187 | CDS | 7 | 71 | GCT |
| U14187 | 5'UTR | 6 | 32 | GGC |
| U14383 | CDS | 3.36 | 144 | TCCAGGAAGGGACCCCGGGTTCACGAGCTGCCCACGTCCTC (SEQ ID NO:287) |
| U14550 | 3'UTR | 14 | 1681 | T |
| U14603 | 5'UTR | 17 | 1 | T |
| U15131 | 3'UTR | 5.25 | 3891 | GCCT |

TABLE 1-continued

| Genbank # | Region | # reps | Position | Unit sequence |
|---|---|---|---|---|
| U15932 | 5'UTR | 5.66 | 193 | GCG |
| U15979 | 5'UTR | 2.7 | 24 | GCAGCCCGGT (SEQ ID NO:288) |
| U16306 | CDS | 5.66 | 4433 | GAA |
| U16752 | 5'UTR | 6 | 53 | CCGC |
| U17032 | 5'UTR | 13 | 83 | C |
| U17033 | CDS | 7.33 | 223 | GCT |
| U17077 | 3'UTR | 21 | 2123 | T |
| U17327 | 3'UTR | 17 | 5431 | TG |
| U17566 | 3'UTR | 12 | 2351 | T |
| U17838 | CDS | 5.66 | 1686 | GAA |
| U17838 | CDS | 5.66 | 1701 | GAT |
| U17989 | 3'UTR | 28 | 2676 | T |
| U17989 | 3'UTR | 16 | 2849 | A |
| U18062 | 5'UTR | 4.5 | 349 | CTAG |
| U18932 | UNKNOWN | 13 | 923 | TA |
| U19495 | 5'UTR | 6 | 446 | CCGC |
| U19878 | 5'UTR | 17 | 9 | A |
| U20489 | 3'UTR | 14 | 5057 | A |
| U20648 | 3'UTR | 12 | 722 | T |
| U21092 | 3'UTR | 9 | 2274 | AC |
| U21936 | 3'UTR | 20 | 2338 | T |
| U22055 | CDS | 3.5 | 1968 | GAGGTG |
| U22055 | 3'UTR | 12 | 3194 | A |
| U22398 | CDS | 3.25 | 744 | CGGCTCCGGTCG (SEQ ID NO:289) |
| U22398 | CDS | 4.5 | 793 | GGCCCC |
| U23752 | CDS | 2.58 | 1106 | CAGCAGCAGCGG (SEQ ID NO:290) |
| U23752 | CDS | 9.66 | 747 | GAC |
| U23752 | 3'UTR | 6.33 | 1471 | TGA |
| U23803 | CDS | 6.33 | 1072 | GCG |
| U23841 | UNKNOWN | 9 | 611 | TAA |
| U23842 | UNKNOWN | 14.5 | 901 | CT |
| U23942 | 3'UTR | 22 | 2471 | T |
| U23946 | BORDER | 11 | 2515 | GA |
| U24152 | CDS | 6.33 | 924 | GAT |
| U24389 | CDS | 6 | 1225 | GCC |
| U25849 | 5'UTR | 6.5 | 418 | CA |
| U25997 | 5'UTR | 6.66 | 37 | GCA |
| U25997 | 5'UTR | 12 | 242 | A |
| U25997 | 3'UTR | 22 | 3293 | T |
| U26032 | UNKNOWN | 18 | 1580 | A |
| U26032 | UNKNOWN | 16 | 1800 | T |
| U26032 | UNKNOWN | 12 | 509 | T |
| U26424 | 3'UTR | 12 | 2637 | A |
| U26726 | 5'UTR | 3.8 | 100 | CCCCG |
| U27328 | 3'UTR | 2.56 | 1904 | TGGGGACCTCACCTGC (SEQ ID NO:291) |
| U28042 | CDS | 8.66 | 2404 | TGA |
| U28049 | CDS | 5.66 | 203 | GCG |
| U28055 | 3'UTR | 5.66 | 1923 | GTG |
| U28727 | CDS | 7.66 | 3384 | CGC |
| U28727 | 5'UTR | 2.63 | 43 | GTCCAGGGTGAGGAGTGAGGGA (SEQ ID NO:292) |
| U29175 | CDS | 3.83 | 768 | GGCCCT |
| U29185 | CDS | 2.83 | 402 | GGTGGTGGCTGGGGGCAGCCTCAT (SEQ ID NO:293) |
| U29195 | 3'UTR | 12 | 2460 | T |
| U29344 | 3'UTR | 4.8 | 7692 | CCCCA |
| U29589 | 3'UTR | 12 | 3151 | A |
| U29926 | 3'UTR | 10.5 | 3789 | TG |
| U30246 | CDS | 7.66 | 449 | GCG |
| U31116 | 3'UTR | 15 | 1855 | T |
| U31289 | UNKNOWN | 12 | 98 | A |
| U31468 | CDS | 8 | 164 | GCC |
| U31814 | 5'UTR | 8.33 | 142 | GCA |
| U31930 | 3'UTR | 13 | 568 | A |
| U32439 | 3'UTR | 9 | 1546 | TC |
| U32986 | 3'UTR | 7 | 3857 | GT |
| U33635 | 5'UTR | 2.6 | 36 | CTCGGGACGC (SEQ ID NO:294) |
| U33635 | 3'UTR | 3.83 | 4181 | TTTTTG |
| U33749 | 3'UTR | 16 | 1902 | T |
| U33931 | 3'UTR | 17 | 1385 | T |
| U34249 | 5'UTR | 8 | 328 | CT |
| U34360 | CDS | 7.66 | 1288 | GCA |
| U34605 | 5'UTR | 3.5 | 6 | CGCGCA |
| U34605 | 3'UTR | 5.66 | 3143 | TTA |
| U34962 | CDS | 5.66 | 800 | CCG |
| U35612 | CDS | 6 | 962 | GCC |
| U35612 | 3'UTR | 19 | 2924 | T |
| U36336 | 3'UTR | 4.8 | 2645 | CAAAA |

TABLE 1-continued

| Genbank # | Region | # reps | Position | Unit sequence |
| --- | --- | --- | --- | --- |
| U36336 | 3'UTR | 4.75 | 2662 | AAAC |
| U36336 | 3'UTR | 17 | 1790 | TG |
| U36336 | 3'UTR | 8 | 3198 | AT |
| U36336 | 3'UTR | 12 | 3090 | T |
| U36341 | 5'UTR | 8 | 334 | GCC |
| U36341 | 5'UTR | 6 | 95 | GCC |
| U36798 | 3'UTR | 22 | 3983 | TG |
| U37219 | 5'UTR | 14 | 0 | C |
| U37230 | 3'UTR | 9 | 519 | AT |
| U37574 | 5'UTR | 6 | 459 | CAAAA |
| U38276 | 3'UTR | 14.5 | 2636 | AT |
| U38810 | 5'UTR | 21.66 | 595 | AGC |
| U38980 | 5'UTR | 3.6 | 444 | CAGAG |
| U39196 | 5'UTR | 2.7 | 329 | AAAAAAAAAC (SEQ ID NO:295) |
| U39965 | 3'UTR | 12 | 2385 | T |
| U40215 | CDS | 6 | 154 | GCC |
| U40705 | UNKNOWN | 8.66 | 177 | GAG |
| U40705 | UNKNOWN | 12 | 1620 | A |
| U41315 | 3'UTR | 2.57 | 3004 | GTGTGTGAGTGTGG (SEQ ID NO:296) |
| U41344 | CDS | 3.66 | 121 | CCCAGG |
| U41635 | CDS | 4.33 | 1333 | GAGGAT |
| U43142 | CDS | 5.66 | 447 | CCG |
| U43148 | 3'UTR | 10.5 | 6197 | GT |
| U43185 | 3'UTR | 9.5 | 3134 | TG |
| U43188 | 3'UTR | 12 | 2505 | TA |
| U43292 | 5'UTR | 25 | 155 | GA |
| U43374 | UNKNOWN | 29 | 1238 | A |
| U43527 | 5'UTR | 30.5 | 0 | CT |
| U43604 | UNKNOWN | 16 | 1652 | A |
| U43628 | CDS | 3.75 | 766 | CTCCCGACACCACCTCCCAGGAGC (SEQ ID NO:297) |
| U43628 | CDS | 2.5 | 724 | ACACCACCTCCCCGGAGTCTCCCG (SEQ ID NO:298) |
| U43628 | CDS | 5.66 | 505 | AGG |
| U43747 | 3'UTR | 5.66 | 1235 | TTG |
| U43842 | 3'UTR | 6.5 | 1699 | CA |
| U43842 | 3'UTR | 19 | 1792 | A |
| U43843 | 3'UTR | 4.75 | 1260 | CTCC |
| U43899 | 3'UTR | 7 | 2273 | AT |
| U44060 | 5'UTR | 15 | 482 | AG |
| U44111 | 5'UTR | 15 | 135 | T |
| U44839 | 3'UTR | 16 | 2773 | A |
| U45984 | 3'UTR | 22 | 2794 | A |
| U45984 | 3'UTR | 14 | 2175 | T |
| U46023 | CDS | 8.66 | 1543 | CAG |
| U46120 | UNKNOWN | 22 | 2 | T |
| U46120 | UNKNOWN | 12 | 1234 | A |
| U46573 | 3'UTR | 9.5 | 461 | TA |
| U46691 | 5'UTR | 27 | 683 | T |
| U46751 | 3'UTR | 7 | 1549 | TG |
| U47292 | 3'UTR | 2.9 | 620 | CATGTATGGGTGTGTGTACC (SEQ ID NO:299) |
| U47621 | 3'UTR | 18 | 1987 | A |
| U47686 | 3'UTR | 15 | 2693 | TG |
| U47742 | 3'UTR | 6.66 | 6965 | TAT |
| U47742 | 3'UTR | 6.5 | 7035 | CA |
| U47924 | 5'UTR | 4.2 | 235 | GGCCA |
| U47924 | 3'UTR | 13 | 1651 | A |
| U48231 | 3'UTR | 5.6 | 1534 | TTTGC |
| U48251 | 3'UTR | 17 | 1997 | A |
| U48251 | 3'UTR | 13 | 1965 | A |
| U48436 | 5'UTR | 15.66 | 19 | GCC |
| U48436 | 3'UTR | 11.5 | 12611 | GT |
| U48436 | 3'UTR | 8 | 10316 | AC |
| U48436 | 3'UTR | 7.5 | 11301 | TC |
| U48436 | 3'UTR | 6.5 | 9592 | AC |
| U49020 | CDS | 10.33 | 1399 | CAG |
| U49089 | 5'UTR | 6 | 145 | CGG |
| U49089 | 3'UTR | 12 | 2842 | T |
| U49184 | CDS | 3.5 | 514 | TGGCTA |
| U49250 | 3'UTR | 7.5 | 2536 | TGGA |
| U49957 | 3'UTR | 3.8 | 5291 | AAAAT |
| U50383 | CDS | 5.66 | 1173 | GAG |
| U50535 | UNKNOWN | 12 | 2308 | A |
| U50928 | CDS | 6.33 | 354 | GAG |
| U50928 | 3'UTR | 12 | 4315 | A |
| U51003 | UNKNOWN | 6.33 | 1105 | CAG |
| U51003 | UNKNOWN | 5.66 | 1208 | GGC |

TABLE 1-continued

| Genbank # | Region | # reps | Position | Unit sequence |
|---|---|---|---|---|
| U51333 | 3'UTR | 6.5 | 3026 | AT |
| U51336 | 5'UTR | 5.66 | 80 | GGC |
| U51704 | UNKNOWN | 9 | 348 | AT |
| U51713 | UNKNOWN | 21 | 686 | A |
| U51869 | UNKNOWN | 31 | 2616 | A |
| U52112 | 3'UTR | 4.8 | 7283 | TTTTG |
| U52152 | 3'UTR | 7 | 1515 | GGA |
| U52152 | 3'UTR | 7 | 2256 | AG |
| U52154 | 5'UTR | 16.5 | 91 | AG |
| U52154 | 5'UTR | 13.5 | 65 | AC |
| U52154 | 3'UTR | 7.2 | 2499 | TGTTT |
| U52219 | CDS | 2.76 | 1394 | CTCTGTCCATTTCAAGGGTGA (SEQ ID NO:300) |
| U52682 | 3'UTR | 18 | 1509 | T |
| U52840 | 3'UTR | 6.5 | 6223 | TC |
| U52852 | 3'UTR | 3.8 | 1557 | AAAAT |
| U53003 | 3'UTR | 12 | 991 | T |
| U53209 | 3'UTR | 20 | 1044 | T |
| U53347 | 3'UTR | 18 | 2664 | GT |
| U54778 | 3'UTR | 20 | 967 | T |
| U54804 | 5'UTR | 4.8 | 220 | AAAAG |
| U54804 | 5'UTR | 23 | 137 | T |
| U54804 | 5'UTR | 15 | 209 | A |
| U55184 | 3'UTR | 20 | 5892 | A |
| U55184 | 3'UTR | 12 | 6896 | T |
| U55764 | 3'UTR | 17 | 480 | T |
| U55777 | UNKNOWN | 21 | 0 | T |
| U55967 | UNKNOWN | 16 | 417 | GT |
| U55983 | UNKNOWN | 13 | 0 | T |
| U55984 | UNKNOWN | 7 | 27 | AT |
| U56637 | 3'UTR | 21 | 1091 | T |
| U56725 | 5'UTR | 28.5 | 1187 | AC |
| U56725 | 5'UTR | 20 | 7 | T |
| U56725 | 5'UTR | 13 | 2260 | A |
| U56725 | 5'UTR | 12 | 1412 | A |
| U56725 | 3'UTR | 6.5 | 4415 | TC |
| U57623 | 3'UTR | 18 | 596 | T |
| U57650 | 5'UTR | 7.5 | 280 | TC |
| U57693 | UNKNOWN | 17 | 1055 | A |
| U57911 | 3'UTR | 3.6 | 1153 | TTATT |
| U58197 | 3'UTR | 2.58 | 2288 | GGCCACACCTGC (SEQ ID NO:301) |
| U58658 | 5'UTR | 12 | 57 | A |
| U59111 | 5'UTR | 14 | 0 | T |
| U59185 | 3'UTR | 19 | 1767 | T |
| U59289 | 3'UTR | 12 | 2406 | A |
| U59305 | 5'UTR | 15 | 943 | T |
| U59831 | CDS | 7 | 1300 | GCC |
| U59831 | CDS | 6 | 564 | GCG |
| U60207 | 3'UTR | 6.5 | 1876 | AT |
| U60519 | 3'UTR | 18 | 3161 | T |
| U60800 | 3'UTR | 13 | 3398 | T |
| U61145 | 5'UTR | 6.66 | 14 | CGG |
| U61374 | CDS | 5.66 | 67 | GCT |
| U61412 | 3'UTR | 20 | 3280 | A |
| U61849 | 3'UTR | 9.S | 2821 | TG |
| U62317 | CDS | 7.33 | 207 | GAG |
| U62317 | 3'UTR | 5.5 | 1780 | CCTC |
| U62317 | 3'UTR | 7 | 1778 | CA |
| U63332 | CDS | 2.58 | 70 | TGCTGCTGCTGT (SEQ ID NO:302) |
| U63332 | CDS | 17.33 | 29 | GCT |
| U63721 | 5'UTR | 4.8 | 39 | CCCGG |
| U64520 | CDS | 5.66 | 289 | TCA |
| U64820 | CDS | 8 | 948 | CAG |
| U64863 | 3'UTR | 10.33 | 1238 | CTG |
| U65002 | 3'UTR | 8.5 | 3890 | AC |
| U65002 | 3'UTR | 6.5 | 3875 | AT |
| U65002 | 3'UTR | 27 | 4992 | A |
| U66043 | UNKNOWN | 43 | 1312 | A |
| U66047 | UNKNOWN | 20 | 0 | T |
| U66306 | UNKNOWN | 5 | 2040 | GCTG |
| U66589 | UNKNOWN | 18 | 3555 | A |
| U66616 | CDS | 6 | 3280 | CCT |
| U66799 | CDS | 5.66 | 507 | CCG |
| U66799 | CDS | 5.66 | 1054 | GCG |
| U66871 | 3'UTR | 14 | 582 | T |
| U67058 | UNKNOWN | 3.6 | 749 | ATAAA |
| U67058 | UNKNOWN | 7 | 256 | AT |
| U67156 | 3'UTR | 14 | 4613 | T |

TABLE 1-continued

| Genbank # | Region | # reps | Position | Unit sequence |
|---|---|---|---|---|
| U67733 | CDS | 5.66 | 265 | GCC |
| U68140 | 3'UTR | 3.5 | 2762 | AAGCTG |
| U68162 | 3'UTR | 35 | 2627 | T |
| U68382 | 3'UTR | 16 | 1740 | T |
| U68494 | UNKNOWN | 7 | 1441 | TA |
| U68723 | CDS | 6 | 1196 | CTC |
| U68723 | 3'UTR | 20.5 | 2422 | CA |
| U68727 | 3'UTR | 10.5 | 1552 | GT |
| U69127 | 3'UTR | 3.6 | 2109 | TTTGG |
| U69185 | UNKNOWN | 22 | 1684 | A |
| U69189 | UNKNOWN | 23 | 1415 | A |
| U69191 | UNKNOWN | 18 | 2031 | A |
| U69192 | UNKNOWN | 27 | 2171 | A |
| U69196 | UNKNOWN | 3.8 | 1064 | TTTTG |
| U69196 | UNKNOWN | 9.5 | 591 | CA |
| U69199 | UNKNOWN | 19 | 1209 | A |
| U69201 | UNKNOWN | 34 | 1412 | A |
| U69205 | UNKNOWN | 21 | 1530 | A |
| U69566 | UNKNOWN | 19 | 1013 | A |
| U70136 | CDS | 3.5 | 2058 | ACCCCTAAGGAGCCTGCTCCAACT (SEQ ID NO:303) |
| U70136 | CDS | 6.66 | 528 | TCC |
| U70323 | CDS | 2.93 | 669 | CAGCAGCAGCAGCAA (SEQ ID NO:304) |
| U70323 | CDS | 8.66 | 657 | CAG |
| U70370 | 3'UTR | 22 | 1255 | A |
| U70426 | 3'UTR | 26 | 810 | A |
| U70660 | 5'UTR | 2.9 | 71 | ACACCGCCGCC (SEQ ID NO:305) |
| U72518 | CDS | 14 | 673 | T |
| U72621 | 3'UTR | 15 | 2729 | A |
| U72936 | CDS | 5.66 | 4695 | GAG |
| U72936 | 3'UTR | 27 | 9240 | A |
| U72936 | 3'UTR | 14 | 7948 | T |
| U73338 | 3'UTR | 4 | 4929 | TTTTG |
| U73338 | 3'UTR | 13 | 4193 | T |
| U73377 | 3'UTR | 19 | 3454 | A |
| U75285 | 3'UTR | 8.5 | 698 | TC |
| U75285 | 3'UTR | 12 | 988 | T |
| U75308 | CDS | 4.33 | 213 | CCCGGC |
| U75655 | UNKNOWN | 18 | 1660 | A |
| U76010 | 3'UTR | 3.5 | 1397 | CAGCCC |
| U76010 | 3'UTR | 19.5 | 1763 | TG |
| U76343 | UNKNOWN | 19 | 1375 | A |
| U76421 | 5'UTR | 7.66 | 0 | GCG |
| U76702 | 3'UTR | 3.06 | 1364 | GTATGGAGGGTCTAGCCTGGGTGAGTATGGAGGGTCTAGCCTGGGTGT (SEQ ID NO:306) |
| U76702 | 3'UTR | 3.33 | 1244 | GTACGGAGGGTCTAGCCTGGGTGA (SEQ ID NO:307) |
| U76702 | 3'UTR | 2.54 | 1350 | TCTAGCCTGGGTGAGTATGGAGGG (SEQ ID NO:308) |
| U77456 | 3'UTR | 15 | 1894 | T |
| U77735 | CDS | 4.59 | 1122 | GCCTG |
| U77735 | 3'UTR | 21 | 1678 | T |
| U77970 | 5'UTR | 7.66 | 96 | GCG |
| U78168 | 3'UTR | 8 | 3242 | AG |
| U78308 | CDS | 4 | 817 | GTGGCG |
| U79242 | UNNNOWN | 18 | 1614 | A |
| U79245 | UNKNOWN | 17 | 1584 | A |
| U79246 | UNKNOWN | 25 | 1809 | A |
| U79247 | UNKNOWN | 18 | 1662 | A |
| U79248 | UNKNOWN | 19 | 1596 | A |
| U79249 | UNKNOWN | 18 | 1438 | A |
| U79251 | UNKNOWN | 18 | 1820 | A |
| U79256 | UNKNOWN | 22 | 1196 | A |
| U79257 | UNKNOWN | 19 | 780 | T |
| U79257 | UNKNOWN | 18 | 1475 | A |
| U79260 | CDS | 14 | 754 | T |
| U79263 | 3'UTR | 4.75 | 1425 | TTTG |
| U79265 | UNKNOWN | 24 | 1744 | A |
| U79273 | UNKNOWN | 18 | 1422 | A |
| U79276 | UNKNOWN | 18 | 1641 | A |
| U79277 | UNKNOWN | 29 | 1545 | A |
| U79282 | UNKNOWN | 25 | 1694 | A |
| U79289 | UNKNOWN | 29 | 1846 | A |
| U79289 | UNKNOWN | 22 | 1724 | A |
| U79290 | UNKNOWN | 20 | 1813 | A |
| U79291 | UNKNOWN | 20 | 1342 | A |
| U79293 | UNKNOWN | 18 | 1774 | A |

TABLE 1-continued

| Genbank # | Region | # reps | Position | Unit sequence |
|---|---|---|---|---|
| U79295 | UNKNOWN | 18 | 1400 | A |
| U79297 | UNKNOWN | 25 | 1612 | A |
| U79300 | UNKNOWN | 22 | 1465 | A |
| U79301 | UNKNOWN | 28 | 1582 | A |
| U79301 | UNKNOWN | 16 | 14 | A |
| U79528 | 3'UTR | 9.5 | 1550 | AC |
| U79666 | CDS | 3.5 | 3184 | GGCGAG |
| U79666 | CDS | 11.33 | 7155 | GCA |
| U79666 | CDS | 9.66 | 6847 | CAC |
| U79666 | 5'UTR | 9 | 138 | GCG |
| U79745 | 3'UTR | 4.8 | 1892 | TTTTG |
| U80017 | 31UTR | 4.2 | 4661 | AAAAC |
| U80456 | 3'UTR | 18 | 3452 | T |
| U80735 | CDS | 7 | 679 | CAG |
| U80735 | CDS | 6.66 | 619 | CAG |
| U80736 | CDS | 7 | 599 | GCA |
| U80743 | CDS | 15.66 | 904 | CAG |
| U80743 | CDS | 8 | 879 | GCA |
| U80744 | CDS | 9 | 436 | TGC |
| U80747 | CDS | 8.66 | 601 | CAG |
| U80747 | 3'UTR | 7.66 | 1659 | AAC |
| U80756 | CDS | 7 | 182 | GCA |
| U80757 | UNKNOWN | 15 | 1914 | CAG |
| U80757 | UNKNOWN | 7 | 1249 | CA |
| U80759 | CDS | 8.66 | 763 | CAG |
| U80760 | CDS | 13.66 | 1287 | TGC |
| U80760 | 5'UTR | 6.5 | 196 | TA |
| U80760 | 3'UTR | 3.5 | 1340 | GGCCTG |
| U80761 | CDS | 13.33 | 301 | GCT |
| U80774 | UNKNOWN | 12 | 1436 | A |
| U81001 | UNKNOWN | 17 | 3212 | A |
| U81001 | UNKNOWN | 13 | 2826 | A |
| U82010 | 3'UTR | 14 | 1674 | T |
| U82382 | 3'UTR | 2.52 | 634 | GGGGGCCCTTCCAGACT (SEQ ID NO:309) |
| U82467 | 3'UTR | 8 | 2908 | CT |
| U82812 | 3'UTR | 12 | 1614 | T |
| U82828 | 3'UTR | 18 | 10487 | A |
| U82984 | UNKNOWN | 18 | 1750 | A |
| U82987 | 3'UTR | 14 | 991 | G |
| U83171 | 3'UTR | 20 | 1191 | T |
| U83192 | 3'UTR | 15 | 3777 | T |
| U83410 | 5'UTR | 6 | 11 | GCC |
| U83460 | 3'UTR | 18 | 832 | AC |
| U84388 | 3'UTR | 7 | 949 | AT |
| U84551 | 3'UTR | 5.8 | 2543 | AAATT |
| U84551 | 3'UTR | 12 | 2427 | T |
| U85245 | 5'UTR | 6.33 | 455 | CGC |
| U85642 | UNKNOWN | 13 | 59 | T |
| U85658 | 3'UTR | 21 | 2165 | T |
| U85992 | 3'UTR | 19 | 624 | T |
| U85996 | UNKNOWN | 12 | 1016 | A |
| U86453 | 3'UTR | 17 | 4092 | T |
| U86527 | UNKNOWN | 15 | 264 | A |
| U86751 | CDS | 6.66 | 1751 | AAG |
| U86751 | CDS | 6 | 199S | AGC |
| U86751 | 3'UTR | 6.66 | 2397 | TTA |
| U86751 | 3'UTR | 16 | 3085 | TG |
| U86751 | 3'UTR | 14 | 2415 | T |
| U87223 | 5'UTR | 5.5 | 22 | AG |
| U87309 | 3'UTR | 4.59 | 4233 | AAAAG |
| U87800 | UNKNOWN | 2.71 | 538 | AAAAAAAAAACAAA (SEQ ID NO:310) |
| U87800 | UNKNOWN | 14 | 563 | A |
| U88047 | CDS | 6.66 | 617 | GAG |
| U88047 | CDS | 6 | 1850 | GGC |
| U88047 | 5'UTR | 10.33 | 153 | GTG |
| U88047 | 3'UTR | 13.5 | 2139 | AT |
| U88153 | CDS | 2.53 | 3036 | GAAGAAGAAGAAGAG (SEQ ID NO:311) |
| U88153 | CDS | 8.66 | 3024 | GAA |
| U88154 | CDS | 2.53 | 2346 | GAAGAAGAAGAAGAG (SEQ ID NO:312) |
| U88154 | CDS | 8.66 | 2334 | GAA |
| U88666 | CDS | 5.66 | 271 | CCA |
| U88834 | UNKNOWN | 5.66 | 98 | CCG |
| U89012 | 3'UTR | 12 | 2393 | T |
| U89293 | CDS | 6 | 230 | AGC |
| U89331 | 5'UTR | 12 | 47 | T |
| U89331 | 3'UTR | 4.75 | 4378 | AAAC |
| U89331 | 3'UTR | 28 | 2324 | T |

TABLE 1-continued

| Genbank # | Region | # reps | Position | Unit sequence |
|---|---|---|---|---|
| U89331 | 3'UTR | 23 | 3777 | A |
| U89331 | 3'UTR | 12 | 3730 | A |
| U89387 | 5'UTR | 3.6 | 5 | GCGCG |
| U89387 | 3'UTR | 17 | 908 | T |
| U89505 | 3'UTR | 4 | 1309 | TTCCT |
| U89995 | CDS | 9 | 1207 | GCC |
| U90543 | CDS | 6.33 | 251 | CCT |
| U90545 | 5'UTR | 2.75 | 0 | ACGCGTCCGCCC (SEQ ID NO:313) |
| U90552 | 3'UTR | 15 | 2899 | T |
| U90840 | 3'UTR | 16.5 | 1048 | CA |
| U90840 | 3'UTR | 6.5 | 1027 | AC |
| U90902 | UNKNOWN | 20 | 1528 | A |
| U90902 | UNKNOWN | 16 | 822 | T |
| U90902 | UNKNOWN | 13 | 462 | T |
| U90902 | UNKNOWN | 12 | 121 | T |
| U90904 | UNKNOWN | 22 | 1421 | A |
| U90905 | UNKNOWN | 18 | 1017 | A |
| U90907 | UNKNOWN | 20 | 1655 | A |
| U90909 | UNKNOWN | 31 | 1485 | A |
| U90909 | UNKNOWN | 13 | 1250 | A |
| U90910 | UNKNOWN | 19 | 1791 | A |
| U90912 | UNKNOWN | 34 | 1633 | A |
| U90913 | UNKNOWN | 43 | 1260 | A |
| U90916 | UNKNOWN | 28 | 1868 | A |
| U90918 | UNKNOWN | 18 | 2317 | A |
| U90920 | 5'UTR | 3.83 | 5 | GGCTGC |
| U90920 | 3'UTR | 9.5 | 5202 | AT |
| U91329 | 3'UTR | 4.5 | 3816 | GTCT |
| U91540 | CDS | 3.5 | 168 | GAGCCA |
| U91543 | CDS | 5.66 | 789 | GCA |
| U91616 | 5'UTR | 5.25 | 8 | AATG |
| U91935 | CDS | 3.66 | 623 | CAGCTC |
| U91935 | CDS | 11.33 | 641 | CAG |
| U91935 | 3'UTR | 6.33 | 2117 | ACA |
| U91939 | CDS | 5.66 | 607 | TGC |
| U92021 | UNKNOWN | 14 | 795 | A |
| U92285 | UNKNOWN | 5.66 | 4678 | AGC |
| U92436 | 5'UTR | 6.66 | 484 | GCG |
| U92649 | 3'UTR | 24 | 3064 | T |
| U92981 | UNKNOWN | 6.66 | 158 | GCA |
| U92992 | UNKNOWN | 6 | 46 | GCA |
| U92992 | UNKNOWN | 52 | 1162 | T |
| U93091 | UNKNOWN | 19 | 4849 | A |
| U93181 | CDS | 3.6 | 5044 | CCCCG |
| U93305 | 3'UTR | 7 | 1066 | AT |
| U94333 | CDS | 7.66 | 166 | CTG |
| U94592 | 3'UTR | 19 | 1579 | A |
| U94832 | 5'UTR | 7 | 29 | GCC |
| U94832 | 3'UTR | 7.5 | 2557 | TA |
| U94832 | 3'UTR | 14 | 2499 | A |
| U94836 | CDS | 6.66 | 979 | CAG |
| U95032 | 3'UTR | 20 | 1420 | T |
| U95299 | CDS | 10.66 | 105 | CTG |
| U95301 | CDS | 6 | 493 | GCT |
| U95740 | 3'UTR | 6.5 | 2109 | TG |
| U95740 | 3'UTR | 14 | 2308 | A |
| U96136 | CDS | 8 | 655 | CGC |
| U96136 | 3'UTR | 14 | 4341 | A |
| U96769 | 3'UTR | 16 | 1504 | C |
| U97105 | 5'UTR | 3.8 | 1242 | AAAAC |
| U97105 | 5'UTR | 11.5 | 1077 | TC |
| U97105 | 3'UTR | 17 | 3517 | T |
| U97105 | 3'UTR | 12 | 3131 | T |
| U97188 | 3'UTR | 5.75 | 2197 | AAAC |
| U97188 | 3'UTR | 18 | 3225 | A |
| U97276 | CDS | 6.33 | 112 | GCT |
| U97519 | CDS | 5.16 | 314 | CGTCGC |
| U97519 | 5'UTR | 5.66 | 19 | GCC |
| U97670 | CDS | 7.66 | 62 | GGC |
| U97670 | 3'UTR | 3.6 | 1564 | TTTCC |
| W00605 | UNKNOWN | 14 | 515 | A |
| W00874 | UNKNOWN | 16 | 7 | T |
| W00931 | UNKNOWN | 7.5 | 239 | TA |
| W01374 | UNKNOWN | 4.75 | 307 | AAAC |
| W01374 | UNKNOWN | 7.5 | 329 | AT |
| W01475 | UNKNOWN | 17 | 4 | T |
| W01766 | UNKNOWN | 15 | 390 | A |

TABLE 1-continued

| Genbank # | Region | # reps | Position | Unit sequence |
|---|---|---|---|---|
| W01799 | UNKNOWN | 3.6 | 77 | TTTGT |
| W01987 | UNKNOWN | 13 | 138 | A |
| W02250 | UNKNOWN | 13 | 341 | T |
| W02281 | UNKNOWN | 7 | 130 | TA |
| W02281 | UNKNOWN | 23 | 96 | A |
| W03436 | UNKNOWN | 2.77 | 65 | CACACAGGGCACAGACCCCACGCACCC (SEQ ID NO:314) |
| W03527 | UNKNOWN | 5.25 | 186 | TTTG |
| W03531 | UNKNOWN | 13 | 398 | A |
| W03667 | UNKNOWN | 14 | 0 | T |
| W03725 | UNKNOWN | 14 | 1 | T |
| W03857 | UNKNOWN | 17 | 0 | T |
| W04238 | UNKNOWN | 5.75 | 60 | TTTA |
| W04238 | UNKNOWN | 5.66 | 389 | TTG |
| W04238 | UNKNOWN | 19 | 7 | T |
| W04244 | UNKNOWN | 13 | 424 | A |
| W04509 | UNKNOWN | 4.2 | 425 | CCTCA |
| W04558 | UNKNOWN | 13 | 157 | A |
| W04854 | UNKNOWN | 12 | 1 | T |
| W04991 | UNKNOWN | 26 | 10 | T |
| W05355 | UNKNOWN | 18 | 0 | T |
| W05448 | UNKNOWN | 16 | 136 | A |
| W05520 | UNKNOWN | 13 | 13 | A |
| W05842 | UNKNOWN | 22 | 589 | A |
| W06843 | UNKNOWN | 3.83 | 309 | TTTTG |
| W07032 | UNKNOWN | 24 | 145 | A |
| W15279 | UNKNOWN | 12 | 0 | T |
| W15281 | UNKNOWN | 14 | 0 | T |
| W15282 | UNKNOWN | 9 | 296 | AT |
| W15282 | UNKNOWN | 12 | 133 | T |
| W15284 | UNKNOWN | 14 | 248 | AC |
| W15284 | UNKNOWN | 8 | 275 | CT |
| W15542 | UNKNOWN | 14 | 6 | T |
| W15652 | UNKNOWN | 9.5 | 96 | GA |
| W16700 | UNKNOWN | 20 | 471 | A |
| W18190 | UNKNOWN | 5.8 | 155 | TTATT |
| W18192 | UNKNOWN | 3.8 | 171 | TTTTG |
| W18192 | UNKNOWN | 8.5 | 129 | AG |
| W18192 | UNKNOWN | 7 | 116 | TA |
| W18193 | UNKNOWN | 4.5 | 997 | AAAT |
| W19881 | UNKNOWN | 23 | 647 | A |
| W20054 | UNKNOWN | 16 | 1 | T |
| W20141 | UNKNOWN | 20 | 75 | A |
| W21841 | UNKNOWN | 12 | 549 | G |
| W21867 | UNKNOWN | 15 | 693 | A |
| W21916 | UNKNOWN | 13 | 594 | A |
| W22165 | UNKNOWN | 65 | 230 | A |
| W22240 | UNKNOWN | 13 | 39 | T |
| W22258 | UNKNOWN | 14 | 705 | C |
| W22264 | UNKNOWN | 13 | 464 | G |
| W22366 | UNKNOWN | 13 | 599 | T |
| W22440 | UNKNOWN | 20 | 491 | G |
| W22457 | UNKNOWN | 15 | 697 | A |
| W22457 | UNKNOWN | 12 | 16 | T |
| W22541 | UNKNOWN | 13 | 619 | A |
| W22575 | UNKNOWN | 15 | 655 | A |
| W22576 | UNKNOWN | 13 | 645 | T |
| W22604 | UNKNOWN | 15 | 664 | A |
| W22627 | UNKNOWN | 19 | 590 | A |
| W22670 | UNKNOWN | 14 | 772 | A |
| W22670 | UNKNOWN | 12 | 664 | G |
| W22886 | UNKNOWN | 12 | 604 | C |
| W22895 | UNKNOWN | 13 | 584 | A |
| W23186 | UNKNOWN | 7.5 | 371 | AG |
| W23237 | UNKNOWN | 13 | 822 | C |
| W23726 | UNKNOWN | 21 | 0 | T |
| W23726 | UNKNOWN | 15 | 309 | A |
| W24320 | UNKNOWN | 12 | 167 | T |
| W25776 | UNKNOWN | 20 | 502 | C |
| W25783 | UNKNOWN | 15 | 0 | T |
| W25793 | UNKNOWN | 12 | 673 | C |
| W25921 | UNKNOWN | 17 | 454 | C |
| W25998 | UNKNOWN | 15 | 592 | C |
| W26068 | UNKNOWN | 3.6 | 88 | ATTCC |
| W26104 | UNKNOWN | 16 | 157 | TC |
| W26466 | UNKNOWN | 13 | 26 | T |
| W26582 | UNKNOWN | 15 | 392 | TG |

TABLE 1-continued

| Genbank # | Region | # reps | Position | Unit sequence |
|---|---|---|---|---|
| W26634 | UNKNOWN | 7 | 251 | CA |
| W26640 | UNKNOWN | 12 | 498 | A |
| W26789 | UNKNOWN | 12 | 538 | G |
| W26851 | UNKNOWN | 19 | 285 | A |
| W26939 | UNKNOWN | 12 | 464 | C |
| W27026 | UNKNOWN | 17.5 | 346 | CA |
| W27921 | UNKNOWN | 12 | 295 | T |
| W27966 | UNKNOWN | 22 | 163 | T |
| W27966 | UNKNOWN | 12 | 303 | G |
| W28072 | UNKNOWN | 16 | 314 | T |
| W28074 | UNKNOWN | 16 | 319 | T |
| W28075 | UNKNOWN | 7 | 360 | AG |
| W28075 | UNKNOWN | 15 | 318 | T |
| W28306 | UNKNOWN | 15 | 342 | T |
| W28316 | UNKNOWN | 14 | 348 | T |
| W28322 | UNKNOWN | 22 | 445 | T |
| W28330 | UNKNOWN | 28 | 501 | T |
| W28418 | UNKNOWN | 15 | 565 | G |
| W28498 | UNKNOWN | 21 | 1 | G |
| W28504 | UNKNOWN | 12 | 434 | G |
| W28545 | UNKNOWN | 13 | 1 | C |
| W28729 | UNKNOWN | 14 | 578 | G |
| W28828 | UNKNOWN | 14 | 748 | C |
| W28842 | UNKNOWN | 14 | 838 | C |
| W28842 | UNKNOWN | 12 | 722 | C |
| W28846 | UNKNOWN | 14 | 705 | C |
| W28870 | UNKNOWN | 12 | 817 | C |
| W28887 | UNKNOWN | 15 | 388 | A |
| W28887 | UNKNOWN | 15 | 429 | T |
| W28979 | UNKNOWN | 66 | 251 | A |
| W32404 | UNKNOWN | 12 | 0 | T |
| W32407 | UNKNOWN | 20 | 0 | T |
| W32480 | UNKNOWN | 21 | 449 | A |
| W33199 | UNKNOWN | 24 | 0 | T |
| W37075 | UNKNOWN | 14 | 156 | T |
| W37109 | UNKNOWN | 21 | 211 | A |
| W37318 | UNKNOWN | 7 | 521 | AC |
| W37532 | UNKNOWN | 12 | 207 | T |
| W37659 | UNKNOWN | 12 | 564 | A |
| W37866 | UNKNOWN | 24 | 0 | T |
| W37880 | UNKNOWN | 14 | 0 | T |
| W37880 | UNKNOWN | 12 | 202 | A |
| W37897 | UNKNOWN | 15 | 238 | A |
| W38349 | UNKNOWN | 4.75 | 1 | TTTC |
| W38349 | UNKNOWN | 12 | 21 | T |
| W38619 | UNKNOWN | 12 | 128 | A |
| W39141 | UNKNOWN | 25 | 138 | A |
| W40251 | UNKNOWN | 15 | 0 | T |
| W42626 | UNKNOWN | 22 | 0 | T |
| W42996 | UNKNOWN | 22 | 0 | T |
| W44516 | UNKNOWN | 21 | 0 | T |
| W44633 | UNKNOWN | 16.5 | 147 | TG |
| W44657 | UNKNOWN | 13 | 0 | T |
| W44723 | UNKNOWN | 5.5 | 11 | TTAT |
| W45419 | UNKNOWN | 20 | 0 | T |
| W45562 | UNKNOWN | 14 | 0 | T |
| W46180 | UNKNOWN | 13 | 0 | T |
| W47196 | UNKNOWN | 13 | 187 | CA |
| W47480 | UNKNOWN | 12 | 431 | A |
| W49566 | UNKNOWN | 12 | 433 | T |
| W51746 | UNKNOWN | 21 | 615 | A |
| W51835 | UNKNOWN | 20 | 0 | T |
| W51988 | UNKNOWN | 14 | 134 | T |
| W52076 | UNKNOWN | 13 | 688 | A |
| W52242 | UNKNOWN | 25 | 0 | T |
| W52243 | UNKNOWN | 20 | 0 | T |
| W52245 | UNKNOWN | 24 | 0 | T |
| W52245 | UNKNOWN | 14 | 260 | A |
| W52248 | UNKNOWN | 17 | 0 | T |
| W52292 | UNKNOWN | 21 | 0 | T |
| W52294 | UNKNOWN | 16 | 0 | T |
| W52295 | UNKNOWN | 22 | 0 | T |
| W52297 | UNKNOWN | 19 | 0 | T |
| W52299 | UNKNOWN | 18 | 0 | T |
| W52321 | UNKNOWN | 13 | 0 | T |
| W52338 | UNKNOWN | 20 | 0 | T |
| W52339 | UNKNOWN | 21 | 0 | T |

TABLE 1-continued

| Genbank # | Region | # reps | Position | Unit sequence |
|---|---|---|---|---|
| W52339 | UNKNOWN | 13 | 413 | A |
| W52340 | UNKNOWN | 19 | 0 | T |
| W52341 | UNKNOWN | 18 | 0 | T |
| W52347 | UNKNOWN | 22 | 0 | T |
| W52348 | UNKNOWN | 17 | 0 | T |
| W52351 | UNKNOWN | 19 | 0 | T |
| W52353 | UNKNOWN | 23 | 0 | T |
| W52354 | UNKNOWN | 31 | 0 | T |
| W52355 | UNKNOWN | 7.5 | 56 | AC |
| W52355 | UNKNOWN | 19 | 0 | T |
| W52356 | UNKNOWN | 29 | 0 | T |
| W52377 | UNKNOWN | 19 | 0 | T |
| W52378 | UNKNOWN | 18 | 0 | T |
| W52379 | UNKNOWN | 29 | 0 | T |
| W52380 | UNKNOWN | 18 | 0 | T |
| W52381 | UNKNOWN | 41 | 0 | T |
| W52382 | UNKNOWN | 19 | 0 | T |
| W52383 | UNKNOWN | 19 | 0 | T |
| W52384 | UNKNOWN | 21 | 0 | T |
| W52385 | UNKNOWN | 18 | 0 | T |
| W52386 | UNKNOWN | 21 | 0 | T |
| W52825 | UNKNOWN | 11 | 402 | GT |
| W56067 | UNKNOWN | 15 | 8 | T |
| W56900 | UNKNOWN | 13 | 285 | T |
| W57618 | UNKNOWN | 14 | 203 | T |
| W57655 | UNKNOWN | 14 | 541 | T |
| W58074 | UNKNOWN | 12 | 0 | T |
| W58181 | UNKNOWN | 43 | 0 | T |
| W58361 | UNKNOWN | 18 | 61 | A |
| W60220 | UNKNOWN | 3.6 | 110 | CGGGG |
| W60681 | UNKNOWN | 15 | 0 | T |
| W61017 | UNKNOWN | 15 | 623 | A |
| W61019 | UNKNOWN | 15 | 617 | A |
| W61056 | UNKNOWN | 23 | 616 | A |
| W63576 | UNKNOWN | 25 | 518 | A |
| W63638 | UNKNOWN | 8.5 | 298 | AG |
| W63644 | UNKNOWN | 28 | 305 | A |
| W63698 | UNKNOWN | 20 | 625 | A |
| W63707 | UNKNOWN | 19 | 564 | A |
| W67267 | UNKNOWN | 15 | 40 | T |
| W67645 | UNKNOWN | 16.5 | 47 | AC |
| W67645 | UNKNOWN | 9.5 | 79 | AT |
| W67870 | UNKNOWN | 6 | 80 | ATT |
| W68051 | UNKNOWN | 14 | 2 | T |
| W68101 | UNKNOWN | 4.5 | 297 | AAAT |
| W68101 | UNKNOWN | 14 | 654 | A |
| W68633 | UNKNOWN | 19 | 535 | A |
| W68737 | UNKNOWN | 15 | 0 | T |
| W72157 | UNKNOWN | 5.8 | 166 | TTTTG |
| W72265 | UNKNOWN | 36 | 0 | T |
| W72274 | UNKNOWN | 13 | 493 | T |
| W72291 | UNKNOWN | 44 | 0 | T |
| W72300 | UNKNOWN | 23 | 148 | T |
| W72350 | UNKNOWN | 13 | 0 | T |
| W72416 | UNKNOWN | 12 | 0 | T |
| W72557 | UNKNOWN | 14 | 0 | T |
| W72564 | UNKNOWN | 16 | 0 | T |
| W72660 | UNKNOWN | 8.5 | 500 | GT |
| W72752 | UNKNOWN | 24 | 0 | T |
| W72774 | UNKNOWN | 13 | 252 | T |
| W72879 | UNKNOWN | 15 | 259 | T |
| W72920 | UNKNOWN | 12 | 227 | A |
| W73033 | UNKNOWN | 32 | 0 | T |
| W73113 | UNKNOWN | 6.5 | 69 | TG |
| W73113 | UNKNOWN | 20 | 537 | A |
| W73128 | UNKNOWN | 44 | 11 | T |
| W73224 | UNKNOWN | 21 | 566 | A |
| W73230 | UNKNOWN | 16 | 256 | A |
| W73792 | UNKNOWN | 14 | 384 | T |
| W73808 | UNKNOWN | 14 | 648 | A |
| W73823 | UNKNOWN | 25 | 430 | T |
| W73841 | UNKNOWN | 14 | 352 | T |
| W73841 | UNKNOWN | 13 | 580 | A |
| W73855 | UNKNOWN | 22 | 577 | A |
| W73872 | UNKNOWN | 16 | 46 | A |
| W73890 | UNKNOWN | 16 | 70 | A |
| W74144 | UNKNOWN | 27 | 73 | A |

TABLE 1-continued

| Genbank # | Region | # reps | Position | Unit sequence |
|---|---|---|---|---|
| W74216 | UNKNOWN | 7 | 327 | GA |
| W74257 | UNKNOWN | 4.75 | 395 | TTTG |
| W74543 | UNKNOWN | 20 | 154 | T |
| W74543 | UNKNOWN | 19 | 187 | A |
| W76548 | UNKNOWN | 20 | 0 | T |
| W78076 | UNKNOWN | 18 | 1 | T |
| W78847 | UNKNOWN | 7 | 68 | TC |
| W78912 | UNKNOWN | 17 | 17 | A |
| W79740 | UNKNOWN | 48 | 274 | A |
| W79740 | UNKNOWN | 13 | 18 | A |
| W79782 | UNKNOWN | 27 | 0 | T |
| W80478 | UNKNOWN | 14 | 107 | A |
| W80496 | UNKNOWN | 3.8 | 364 | TTTTG |
| W80496 | UNKNOWN | 4.75 | 31 | TTTC |
| W80510 | UNKNOWN | 9 | 6 | GA |
| W81031 | UNKNOWN | 19 | 459 | A |
| W81045 | UNKNOWN | 8.5 | 426 | AC |
| W81175 | UNKNOWN | 12 | 585 | T |
| W84432 | UNKNOWN | 7 | 330 | GA |
| W84448 | UNKNOWN | 14 | 227 | A |
| W84491 | UNKNOWN | 4.75 | 2 | ATTT |
| W84540 | UNKNOWN | 17 | 0 | T |
| W84705 | UNKNOWN | 8.5 | 171 | AC |
| W84705 | UNKNOWN | 7.5 | 145 | CT |
| W84714 | UNKNOWN | 19 | 181 | GA |
| W85788 | UNKNOWN | 19 | 439 | A |
| W85829 | UNKNOWN | 9 | 105 | AC |
| W85908 | UNKNOWN | 15 | 329 | A |
| W86048 | UNKNOWN | 17 | 145 | T |
| W86058 | UNKNOWN | 6.5 | 7 | TA |
| W86251 | UNKNOWN | 6 | 144 | AACAA |
| W86376 | UNKNOWN | 17 | 354 | A |
| W86423 | UNKNOWN | 12 | 358 | T |
| W86447 | UNKNOWN | 2.6 | 85 | GTTAAACAAAAAGTTACCTT (SEQ ID NO:315) |
| W86447 | UNKNOWN | 13 | 54 | A |
| W86742 | UNKNOWN | 6.5 | 246 | AT |
| W86781 | UNKNOWN | 6.5 | 206 | GT |
| W87310 | UNKNOWN | 14 | 203 | A |
| W87374 | UNKNOWN | 14 | 8 | T |
| W87427 | UNKNOWN | 14 | 387 | A |
| W87446 | UNKNOWN | 3.18 | 182 | CGTTCGATCAGGAACGAGACGAGGACGTGTGCTCTCACCACCG (SEQ ID NO:316) |
| W87492 | UNKNOWN | 5.66 | 163 | TTG |
| W87585 | UNKNOWN | 5.66 | 102 | TAT |
| W87649 | UNKNOWN | 6.5 | 416 | CA |
| W87759 | UNKNOWN | 8 | 94 | AATA |
| W87816 | UNKNOWN | 18 | 0 | T |
| W87828 | UNKNOWN | 6 | 170 | ATT |
| W87828 | UNKNOWN | 12 | 186 | T |
| W87865 | UNKNOWN | 3.8 | 2 | CACCG |
| W88653 | UNKNOWN | 15 | 140 | T |
| W88747 | UNKNOWN | 12 | 277 | T |
| W89093 | UNKNOWN | 13 | 5 | C |
| W89097 | UNKNOWN | 11 | 243 | CA |
| W89188 | UNKNOWN | 5.66 | 225 | TTG |
| W89200 | UNKNOWN | 4.5 | 37 | AATA |
| W90065 | UNKNOWN | 13 | 31 | A |
| W90297 | UNKNOWN | 6.5 | 118 | CA |
| W90361 | UNKNOWN | 12 | 487 | A |
| W90538 | UNKNOWN | 4 | 0 | ATTTT |
| W90591 | UNKNOWN | 16 | 275 | T |
| W90745 | UNKNOWN | 18 | 81 | A |
| W92002 | UNKNOWN | 14 | 212 | T |
| W92070 | UNKNOWN | 22 | 94 | A |
| W92084 | UNKNOWN | 4 | 394 | AAATA |
| W92084 | UNKNOWN | 5 | 381 | TAAA |
| W92197 | UNKNOWN | 18 | 62 | A |
| W92471 | UNKNOWN | 18 | 0 | T |
| W92738 | UNKNOWN | 13 | 0 | T |
| W92780 | UNKNOWN | 3.6 | 159 | TAAAA |
| W93496 | UNKNOWN | 21 | 103 | T |
| W93705 | UNKNOWN | 7.5 | 86 | AG |
| W94051 | UNKNOWN | 12.5 | 109 | AC |
| W94115 | UNKNOWN | 7 | 105 | TG |
| W94620 | UNKNOWN | 4.5 | 316 | TTTA |
| W95012 | UNKNOWN | 14 | 607 | A |
| W95023 | UNKNOWN | 13 | 452 | T |

TABLE 1-continued

| Genbank # | Region | # reps | Position | Unit sequence |
|---|---|---|---|---|
| W95035 | UNKNOWN | 5.75 | 164 | AAAC |
| W95117 | UNKNOWN | 7.75 | 302 | AAAC |
| W95522 | UNKNOWN | 16 | 576 | A |
| W96144 | UNKNOWN | 20 | 0 | T |
| W96225 | UNKNOWN | 12 | 403 | A |
| W96334 | UNKNOWN | 20 | 0 | T |
| W99251 | UNKNOWN | 12 | 1275 | A |
| 00588 | 3'UTR | 15 | 4100 | A |
| 01057 | 5'UTR | 16 | 5 | C |
| 01059 | 5'UTR | 12 | 35 | A |
| 01388 | 5'UTR | 17 | 6 | T |
| 01683 | 5'UTR | 14 | 5 | G |
| 02160 | 3'UTR | 21 | 4495 | T |
| 02162 | 5'UTR | 30 | 17 | A |
| 02308 | 5'UTR | 12 | 0 | G |
| 02404 | 3'UTR | 5.66 | 757 | ATG |
| 02596 | 5'UTR | 7 | 94 | GGC |
| 02596 | 5'UTR | 6 | 357 | CGC |
| 02750 | 5'UTR | 20 | 5 | G |
| 02812 | 3'UTR | 4.8 | 2020 | CCCGC |
| 02910 | 3'UTR | 2.81 | 1345 | TTATTTATTAT (SEQ ID NO:317) |
| 03484 | 3'UTR | 5 | 2800 | AACA |
| 03635 | 3'UTR | 17 | 4212 | T |
| 03635 | 3'UTR | 16 | 3949 | A |
| 03663 | 5'UTR | 4 | 70 | GAAGAG |
| 03747 | 3'UTR | 12 | 1503 | T |
| 04011 | 3'UTR | 21 | 4017 | T |
| 04106 | CDS | 10.66 | 269 | GGC |
| 04106 | CDS | 6.66 | 185 | GGC |
| 04327 | 5'UTR | 8.33 | 9 | GCT |
| 04412 | 3'UTR | 10 | 2459 | GT |
| 04434 | 5'UTR | 14 | 0 | T |
| 04506 | CDS | 6.33 | 175 | GCT |
| 04526 | UNKNOWN | 13 | 2556 | A |
| 05299 | CDS | 5.66 | 1206 | GAG |
| 05360 | 5'UTR | 12 | 0 | G |
| 05610 | 3'UTR | 14 | 1469 | A |
| 06026 | 5'UTR | 5.25 | 24 | GGCT |
| 06182 | 3'UTR | 4.8 | 4416 | AAAAC |
| 06290 | CDS | 22.6 | 241 | ACTACCCAAATGCTGGCTTGATCATGAACTACTGCAGGA ATCCAGATGCTGTGGCAGCTCCTTATTGTTATACGAGGG ATCCCGGTGTCAGGTGGGAGTACTGCAACCTGACGCAAT GCTCAGACGCAGAAGGGACTGCCGTCGCGCCTCCGACTG TTACCCCGGTTCCAAGCCTAGAGGCTCCTTCCGAACAAG CACCGACTGAGCAAAGGCCTGGGGTGCAGGAGTGCTACC ATGGTAATGGACAGAGTTATCGAGGCACATACTCCACCA CTGTCACAGGAAGAACCTGCCAAGCTTGGTCATCTATGA CACCACACTCGCATAGTCGGACCCCAGAAT (SEQ ID NO:318) |
| 06290 | CDS | 4.31 | 8730 | GGAAGAACCTGCCAAGCTTGGTCATCTATGACACCACAC TCGCATAGTCGGACCCCAGAATACTACCCAAATGCTGGC TTGATCATGAACTACTGCAGGAATCCAGATGCTGTGGCA GCTCCTTATTGTTATACGAGGGATCCCGGTGTCAGGTGG GAGTACTGCAACCTGACGCAATGCTCAGACGCAGAAGGG ACTGCCGTCGCGCCTCCGACTGTTACCCCGGTTCCAAGC CTAGAGGCTCCTTCCGAACAAGCACCGACTGAGCAGAGG CCTGGGGTGCAGGAGTGCTACCACGGTAATGGACAGAGT TATCGAGGCACATACTCCACCACTGTCACT (SEQ ID NO:319) |
| 06374 | 3'UTR | 12.5 | 1222 | AG |
| 06374 | 3'UTR | 31 | 1667 | T |
| 06374 | 3'UTR | 24 | 1598 | T |
| 06374 | 3'UTR | 14 | 1583 | T |
| 06562 | 3'UTR | 7 | 3457 | TTG |
| 07109 | 3'UTR | 2.63 | 2980 | AAAAAAAGAA (SEQ ID NO:320) |
| 07315 | 3'UTR | 22 | 732 | T |
| 07495 | 5'UTR | 7 | 366 | TG |
| 07495 | 3'UTR | 12.5 | 1482 | AT |
| 07743 | 3'UTR | 13 | 1443 | A |
| 07767 | 3'UTR | 3.57 | 1159 | TTTTCTT |
| 07868 | 3'UTR | 16 | 2632 | T |
| 07876 | CDS | 4.2 | 815 | AAAGG |
| 07881 | CDS | 4.04 | 443 | TCCGGGAAAGCCAGAAGGACCACCCCCACAAGGAGGAAA CCAGTCCCAAGGTCCCCCACCTCG (SEQ ID NO:321) |
| 12458 | 5'UTR | 5.66 | 155 | GCC |
| 13238 | 5'UTR | 13 | 0 | G |

TABLE 1-continued

| Genbank # | Region | # reps | Position | Unit sequence |
|---|---|---|---|---|
| 13403 | CDS | 3.5 | 431 | CAGGCA |
| 13403 | 3'UTR | 16 | 2422 | A |
| 13546 | 3'UTR | 15 | 478 | T |
| 13956 | 5'UTR | 13 | 1 | C |
| 14008 | 3'UTR | 24 | 753 | T |
| 14253 | 3'UTR | 17 | 1075 | T |
| 14487 | CDS | 2.6 | 1443 | CGGCGGCGGAAGCTC (SEQ ID NO:322) |
| 14487 | CDS | 8 | 73 | GGA |
| 14487 | CDS | 6.33 | 1656 | CGG |
| 14640 | CDS | 2.5 | 223 | TTGGAGGTGGCTATGGAGGTGGCC (SEQ ID NO:323) |
| 14885 | 3'UTR | 16 | 1960 | T |
| 15183 | CDS | 6.33 | 879 | AAG |
| 15306 | CDS | 3.23 | 2057 | AGAAGCAAAGTCCCCTGAGAAGGCCAAGTCCCCAGTGAAGGA (SEQ ID NO:324) |
| 15306 | CDS | 2.8 | 1980 | AAGTCCCCTGAGAAGGCCAAGTCCCCAGTGAAGGCAGAAGCA (SEQ ID NO:325) |
| 15376 | 5'UTR | 15 | 208 | A |
| 15653 | 3'UTR | 8 | 1886 | AT |
| 15949 | 3'UTR | 8 | 1660 | ATCCC |
| 16135 | 3'UTR | 21 | 1802 | T |
| 16155 | CDS | 6 | 76 | GCG |
| 16277 | 5'UTR | 6 | 16 | GCC |
| 16323 | 3'UTR | 14 | 3599 | T |
| 16609 | 3'UTR | 14 | 6303 | AC |
| 16609 | 3'UTR | 14 | 6137 | A |
| 16663 | CDS | 2.75 | 1134 | GAGCCTGAGCCC (SEQ ID NO:326) |
| 16663 | CDS | 3.83 | 1298 | GGCTGG |
| 16667 | 5'UTR | 13 | 253 | G |
| 16699 | 3'UTR | 6.5 | 1980 | TG |
| 17360 | 5'UTR | 8.5 | 235 | AG |
| 17360 | 3'UTR | 12 | 3131 | A |
| 17644 | 5'UTR | 10.66 | 248 | GGC |
| 51435 | 5'UTR | 6 | 109 | CGC |
| 51602 | 3'UTR | 21 | 6972 | TG |
| 51602 | 3'UTR | 16 | 6345 | T |
| 51804 | 5'UTR | 13 | 2 | C |
| 51956 | 5'UTR | 4 | 158 | CGCCAC |
| 51956 | 3'UTR | 5.25 | 2015 | TATT |
| 51985 | CDS | 3.83 | 1745 | CCGGAG |
| 51985 | CDS | 3.83 | 1772 | GAGCCC |
| 52075 | 3'UTR | 13.5 | 2955 | CA |
| 52075 | 3'UTR | 12.5 | 2981 | CG |
| 52075 | 3'UTR | 11.5 | 2933 | CT |
| 52947 | 3'UTR | 12 | 2069 | T |
| 53390 | 3'UTR | 17 | 2568 | A |
| 53586 | UNKNOWN | 20 | 5591 | A |
| 53586 | UNKNOWN | 12 | 3561 | A |
| 53587 | UNKNOWN | 76 | 5918 | A |
| 54150 | 3'UTR | 4.16 | 1461 | TTTATT |
| 54150 | 3'UTR | 14 | 1004 | T |
| 54156 | 3'UTR | 18 | 2079 | T |
| 54199 | UNKNOWN | 23 | 3268 | A |
| 54232 | 5'UTR | 5.66 | 44 | CGC |
| 55284 | UNKNOWN | 3.83 | 162 | CCAGCT |
| 55284 | UNKNOWN | 3.8 | 148 | CAGCC |
| 55313 | 3'UTR | 4.8 | 1975 | TTTTG |
| 55666 | UNKNOWN | 27 | 1673 | T |
| 55666 | UNKNOWN | 12 | 1655 | T |
| 55733 | CDS | 3.08 | 694 | GGTATCGGGATG (SEQ ID NO:327) |
| 55777 | CDS | 4 | 226 | CAAAA |
| 56465 | CDS | 6.33 | 1643 | GAT |
| 56465 | 5'UTR | 8 | 612 | GGC |
| 56681 | CDS | 7.33 | 651 | GCC |
| 56681 | 3'UTR | 7.5 | 1668 | TG |
| 57025 | 3'UTR | 4.75 | 4087 | AAAC |
| 57025 | 3'UTR | 20.5 | 3985 | AC |
| 57025 | 3'UTR | 9 | 888 | AT |
| 57025 | 3'UTR | 17 | 5031 | T |
| 57025 | 3'UTR | 12 | 2987 | A |
| 57110 | CDS | 7.33 | 253 | CAC |
| 57110 | CDS | 6.33 | 1511 | ATG |
| 57110 | 5'UTR | 11.33 | 20 | CGG |
| 57147 | UNKNOWN | 14 | 3904 | A |
| 57346 | 5'UTR | 7 | 39 | CGC |
| 57348 | 3'UTR | 15.5 | 1285 | GT |
| 58377 | 3'UTR | 4.5 | 704 | TTAT |

TABLE 1-continued

| Genbank # | Region | # reps | Position | Unit sequence |
|---|---|---|---|---|
| 58431 | 3'UTR | 7 | 2317 | GAT |
| 58431 | 3'UTR | 6.33 | 2336 | ATA |
| 58431 | 3'UTR | 5.66 | 2353 | AAC |
| 58851 | CDS | 3.83 | 117 | CCAGCT |
| 58964 | 5'UTR | 14 | 46 | A |
| 59350 | 3'UTR | 9.5 | 2721 | CA |
| 59350 | 3'UTR | 8.5 | 2703 | CA |
| 59405 | UNKNOWN | 13 | 3305 | A |
| 59739 | 3'UTR | 21 | 4801 | T |
| 59770 | UNKNOWN | 22 | 1286 | A |
| 59798 | 3'UTR | 13.5 | 2532 | AC |
| 59798 | 3'UTR | 6.5 | 1246 | AG |
| 59798 | 3'UTR | 16 | 4226 | C |
| 59798 | 3'UTR | 14 | 3174 | T |
| 59841 | UNKNOWN | 3.66 | 7 | CCTCCC |
| 59841 | UNKNOWN | 7.33 | 47 | CGC |
| 59842 | UNKNOWN | 7.33 | 2339 | TGG |
| 59842 | UNKNOWN | 12 | 2260 | T |
| 59871 | 3'UTR | 21 | 2651 | A |
| 59960 | CDS | 4.83 | 224 | CTGGCG |
| 60188 | 5'UTR | 6.33 | 43 | CAG |
| 60188 | 3'UTR | 5.66 | 1460 | GCT |
| 60435 | 3'UTR | 11.5 | 770 | AT |
| 61100 | UNKNOWN | 19 | 2506 | A |
| 61118 | UNKNOWN | 6.66 | 921 | CGG |
| 61118 | UNKNOWN | 12 | 2292 | A |
| 61123 | 3'UTR | 15 | 959 | A |
| 62078 | UNKNOWN | 12 | 1004 | T |
| 62167 | 3'UTR | 12 | 2024 | A |
| 62534 | CDS | 5.66 | 781 | GAG |
| 63097 | 3'UTR | 30 | 1582 | T |
| 63338 | CDS | 2.83 | 64 | CCAGCTGCTGCCAGCCAAGCTGCTGTGAGA (SEQ ID NO:328) |
| 63432 | 3'UTR | 15 | 1309 | T |
| 63468 | 3'UTR | 16 | 1619 | T |
| 63469 | 5'UTR | 6 | 49 | GCC |
| 63547 | UNKNOWN | 22 | 8179 | A |
| 63657 | 3'UTR | 5.87 | 1546 | TCTCTCTG |
| 63657 | 3'UTR | 9.5 | 1586 | TC |
| 63657 | 3'UTR | 15 | 2047 | A |
| 64037 | CDS | 5.66 | 1139 | AGG |
| 64037 | 3'UTR | 12 | 2256 | A |
| 64229 | CDS | 6.66 | 153 | GAG |
| 64330 | 3'UTR | 15 | 3833 | T |
| 64643 | 3'UTR | 14 | 1805 | A |
| 64878 | 3'UTR | 12.5 | 2248 | CA |
| 65233 | 3'UTR | 13 | 1365 | T |
| 65550 | CDS | 7.5 | 5173 | AC |
| 65724 | UNKNOWN | 2.91 | 11 | CTCTCTCTCTCC (SEQ ID NO:329) |
| 65724 | UNKNOWN | 6.5 | 9 | CT |
| 65724 | UNKNOWN | 36 | 1836 | A |
| 65923 | CDS | 6 | 345 | AGA |
| 66087 | 3'UTR | 7.5 | 2830 | TA |
| 66397 | CDS | 5.66 | 6165 | GAT |
| 66839 | CDS | 3.05 | 276 | GGAGAGGAGGATCTACCT (SEQ ID NO:330) |
| 66945 | CDS | 6.66 | 1104 | GAT |
| 67734 | 3'UTR | 12 | 4506 | C |
| 68060 | CDS | 6 | 4130 | TGA |
| 68264 | 3'UTR | 6.5 | 3262 | TA |
| 68486 | 5'UTR | 13 | 284 | T |
| 68550 | 3'UTR | 30.5 | 1530 | AC |
| 68550 | 3'UTR | 14 | 1347 | C |
| 68561 | CDS | 6 | 197 | AGG |
| 69295 | 3'UTR | 7 | 1101 | TA |
| 69699 | UNKNOWN | 33 | 2678 | A |
| 69804 | UNKNOWN | 28 | 1770 | A |
| 69804 | UNKNOWN | 23 | 0 | T |
| 69910 | CDS | 2.83 | 230 | GCACCCGCAGCA (SEQ ID NO:331) |
| 69910 | CDS | 7.66 | 292 | GCG |
| 69910 | CDS | 6 | 318 | TCC |
| 69910 | 3'UTR | 14 | 2237 | A |
| 69962 | 5'UTR | 2.96 | 61 | GGCGGCGGCGGCGGCGGCGGCGGCGGCGGA (SEQ ID NO:332) |
| 69962 | 5'UTR | 10.33 | 59 | GCG |
| 70340 | 3'UTR | 7 | 3719 | AG |
| 70683 | CDS | 5.66 | 851 | GGC |
| 70811 | 3'UTR | 11 | 2391 | GT |

TABLE 1-continued

| Genbank # | Region | # reps | Position | Unit sequence |
|---|---|---|---|---|
| 70811 | 3'UTR | 9.5 | 2371 | GT |
| 70944 | 3'UTR | 13 | 2498 | T |
| 71125 | UNKNOWN | 17 | 1556 | A |
| 71348 | UNKNOWN | 22 | 2608 | T |
| 71348 | UNKNOWN | 14 | 3436 | A |
| 71490 | 3'UTR | 13 | 1243 | C |
| 72304 | 5'UTR | 4.8 | 43 | GCCGG |
| 72315 | CDS | 16 | 127 | T |
| 72889 | CDS | 13.66 | 888 | CAG |
| 72925 | UNKNOWN | 17 | 4254 | A |
| 73882 | CDS | 2.88 | 1386 | GGCCCCAGCTCCAGCCTC (SEQ ID NO:333) |
| 74142 | CDS | 7.66 | 356 | CAC |
| 74142 | CDS | 5.66 | 442 | GCC |
| 74143 | CDS | 7.66 | 339 | CAC |
| 74262 | 3'UTR | 18 | 2012 | T |
| 74328 | UNKNOWN | 15 | 1775 | A |
| 74331 | 3'UTR | 13 | 1968 | T |
| 75208 | 3'UTR | 9.5 | 3655 | GT |
| 75208 | 3'UTR | 7.5 | 3673 | GC |
| 75252 | 3'UTR | 21 | 1039 | A |
| 75363 | UNKNOWN | 3.83 | 1014 | TTGGGG |
| 75917 | 3'UTR | 2.7 | 1586 | CAGAGAGAGA (SEQ ID NO:334) |
| 75918 | 3'UTR | 4.75 | 2266 | AAAC |
| 75918 | 3'UTR | 9.5 | 2512 | AC |
| 75918 | 3'UTR | 6.5 | 2498 | AC |
| 76029 | CDS | 6.66 | 171 | CTG |
| 76104 | 3'UTR | 6.5 | 5773 | TA |
| 76785 | CDS | 2.95 | 190 | CCTCGTCACTCAGCCCTGGA (SEQ ID NO:335) |
| 76785 | CDS | 2.7 | 115 | TCACTCAGCCCTGGACCTCC (SEQ ID NO:336) |
| 77567 | 5'UTR | 6 | 52 | GCC |
| 77748 | 3'UTR | 12 | 3175 | A |
| 77777 | 5'UTR | 7.66 | 15 | GGT |
| 78261 | UNKNOWN | 19.5 | 2704 | CA |
| 78261 | UNKNOWN | 9.5 | 953 | CA |
| 78261 | UNKNOWN | 8.5 | 837 | AC |
| 78338 | UNKNOWN | 6.33 | 0 | CGC |
| 78520 | UNKNOWN | 16.5 | 3465 | TC |
| 78565 | 3'UTR | 6.33 | 7429 | ATG |
| 78686 | CDS | 5.66 | 173 | TGC |
| 78947 | 3'UTR | 10.5 | 1793 | TG |
| 78947 | 3'UTR | 8.5 | 1813 | TA |
| 79067 | UNKNOWN | 12 | 2656 | A |
| 79204 | CDS | 15.66 | 1568 | CAG |
| 79204 | CDS | 13.33 | 1521 | AGC |
| 79204 | 3'UTR | 3.8 | 7749 | TTTTG |
| 79204 | 3'UTR | 14 | 9029 | A |
| 79204 | 3'UTR | 13 | 8106 | T |
| 79204 | 3'UTR | 12 | 4427 | T |
| 79563 | 3'UTR | 18 | 368 | A |
| 79568 | 3'UTR | 6.5 | 1984 | AG |
| 79568 | 3'UTR | 14 | 2531 | T |
| 80199 | 5'UTR | 2.8 | 28 | ACACACACACACACACCCCA (SEQ ID NO:337) |
| 80199 | 5'UTR | 23.5 | 68 | AC |
| 80199 | 5'UTR | 13.5 | 17 | CA |
| 80240 | CDS | 12 | 185 | A |
| 80910 | 3'UTR | 23 | 2165 | T |
| 81001 | UNKNOWN | 21 | 3512 | A |
| 81002 | UNKNOWN | 16 | 1505 | A |
| 81006 | UNKNOWN | 23 | 1224 | A |
| 81198 | 3'UTR | 8.66 | 1830 | TTA |
| 81422 | CDS | 5.66 | 174 | CTG |
| 81637 | UNKNOWN | 2.95 | 872 | GCTGTGGGGACATGAGAGGGA (SEQ ID NO:338) |
| 81637 | UNKNOWN | 3.75 | 914 | GCTGTGGGGACATGAGAGGG (SEQ ID NO:339) |
| 81637 | UNKNOWN | 3.77 | 3163 | GGGATGGTG |
| 81637 | UNKNOWN | 8 | 1655 | TC |
| 81637 | UNKNOWN | 14 | 3453 | T |
| 81789 | 3'UTR | 16 | 2730 | A |
| 81832 | 5'UTR | 17 | 383 | A |
| 81882 | 3'UTR | 14 | 3285 | T |
| 81895 | UNKNOWN | 14 | 1360 | A |
| 81896 | UNKNOWN | 12 | 324 | T |
| 82209 | CDS | 2.61 | 1837 | GCAGCAGCAGCCCCAGCA (SEQ ID NO:340) |
| 82209 | CDS | 3.83 | 2570 | CAGCAA |
| 82209 | CDS | 9.66 | 2525 | CAG |
| 82209 | CDS | 5.66 | 1868 | CAG |
| 82209 | 3'UTR | 12 | 5037 | T |
| 82240 | UNKNOWN | 15 | 1309 | A |

TABLE 1-continued

| Genbank # | Region | # reps | Position | Unit sequence |
|---|---|---|---|---|
| 82260 | CDS | 5.66 | 1086 | GAG |
| 82324 | 3'UTR | 4.4 | 1347 | CCCTT |
| 82456 | 3'UTR | 4.2 | 3268 | GGGCT |
| 82540 | 3'UTR | 22 | 1989 | T |
| 82629 | CDS | 8.66 | 466 | CAC |
| 82629 | 5'UTR | 12 | 165 | A |
| 82676 | CDS | 6.33 | 2324 | GAG |
| 82895 | 3'UTR | 9 | 2964 | GT |
| 83368 | 3'UTR | 15 | 5075 | T |
| 83467 | 3'UTR | 12 | 2082 | A |
| 83703 | 3'UTR | 32 | 1753 | T |
| 84373 | 3'UTR | 10 | 6430 | TA |
| 84373 | 3'UTR | 8 | 6029 | TG |
| 85133 | UNKNOWN | 17 | 2994 | A |
| 85134 | UNKNOWN | 20 | 2942 | T |
| 85134 | UNKNOWN | 17 | 3301 | A |
| 85545 | 3'UTR | 20 | 5339 | GT |
| 85545 | 3'UTR | 18.5 | 1788 | TG |
| 85545 | 3'UTR | 20 | 2504 | A |
| 85695 | UNKNOWN | 16 | 132 | A |
| 85750 | 3'UTR | 14 | 1866 | T |
| 86163 | 3'UTR | 2.66 | 1704 | GCTAGAACCTGGAGG (SEQ ID NO:341) |
| 86163 | 3'UTR | 14 | 2261 | A |
| 86691 | CDS | 6.33 | 486 | AGG |
| 86691 | CDS | 6 | 428 | AAG |
| 86691 | CDS | 6 | 503 | GAT |
| 86693 | CDS | 2.58 | 1333 | GATGATGATGGC (SEQ ID NO:342) |
| 87160 | 3'UTR | 4 | 3099 | ATTTT |
| 87344 | 3'UTR | 4.4 | 2268 | GGTGG |
| 87838 | 3'UTR | 27 | 2900 | T |
| 87838 | 3'UTR | 19 | 2835 | T |
| 89102 | 3'UTR | 16 | 1603 | GT |
| 89214 | CDS | 8 | 156 | GT |
| 89426 | 3'UTR | 15 | 1098 | T |
| 89887 | CDS | 5.66 | 1440 | GCA |
| 89984 | 5'UTR | 5.66 | 690 | CGG |
| 89984 | 5'UTR | 15 | 789 | TG |
| 89984 | 3'UTR | 14 | 3373 | A |
| 90846 | 5'UTR | 3.6 | 68 | CCCCG |
| 90857 | 5'UTR | 4.5 | 114 | GCCTGC |
| 91148 | 3'UTR | 15 | 3145 | A |
| 91249 | 3'UTR | 16 | 2287 | T |
| 91625 | 3'UTR | 5.5 | 1777 | TTGTTT |
| 91648 | UNKNOWN | 7 | 22 | CA |
| 91648 | UNKNOWN | 15 | 114 | A |
| 91817 | UNKNOWN | 14 | 2404 | A |
| 92715 | 5'UTR | 16 | 574 | T |
| 92841 | CDS | 6.33 | 983 | TGC |
| 92972 | 3'UTR | 13 | 1058 | T |
| 93207 | UNKNOWN | 32 | 3819 | A |
| 93921 | 3'UTR | 19 | 1378 | T |
| 94553 | 5'UTR | 13 | 605 | C |
| 95097 | 3'UTR | 20 | 1755 | T |
| 95263 | CDS | 5.66 | 757 | GAG |
| 95701 | CDS | 10.33 | 1244 | ACC |
| 95808 | UNKNOWN | 20.5 | 48 | AG |
| 95808 | UNKNOWN | 6.5 | 32 | AG |
| 95808 | UNKNOWN | 22 | 6092 | A |
| 96381 | 3'UTR | 20 | 3701 | T |
| 96401 | 3'UTR | 19 | 4216 | AC |
| 97335 | CDS | 2.95 | 1049 | GCTTGGATAGAAATGAGGAGG (SEQ ID NO:343) |
| 97548 | 5'UTR | 5.66 | 252 | GCG |
| 97675 | 3'UTR | 4.75 | 3361 | AAAT |
| 98093 | CDS | 11 | 407 | GCA |
| 98172 | 3'UTR | 4.59 | 1744 | TTTGT |
| 98426 | UNKNOWN | 15 | 812 | A |
| 98427 | UNKNOWN | 18 | 1375 | A |
| 98428 | UNKNOWN | 21 | 1629 | A |
| 98834 | UNKNOWN | 3.6 | 524 | GAGAG |
| 98834 | UNKNOWN | 5.66 | 950 | TCC |
| 98834 | UNKNOWN | 5.66 | 2693 | CCA |
| 98834 | UNKNOWN | 8 | 7 | AG |
| 98834 | UNKNOWN | 79 | 4836 | A |
| 99268 | CDS | 9 | 371 | GGC |
| 99268 | 3'UTR | 19 | 1023 | T |
| 99459 | 3'UTR | 12 | 1215 | T |
| 99894 | 5'UTR | 4 | 49 | CTCCCGG |

TABLE 1-continued

| Genbank # | Region | # reps | Position | Unit sequence |
|---|---|---|---|---|
| Y00067 | CDS | 2.89 | 1857 | TCACCAGTGGAAGAGAAAGGCAAGTCTCCTGTGCCCAAG (SEG ID NO:344) |
| Y00093 | 3'UTR | 15 | 3894 | T |
| Y00093 | 3'UTR | 14 | 3874 | T |
| Y00281 | 3'UTR | 15 | 2143 | T |
| Y00285 | 3'UTR | 16 | 8444 | TG |
| Y00815 | CDS | 5.66 | 3858 | GCG |
| Y00815 | 5'UTR | 5 | 67 | GGCTCC |
| Y00815 | 3'UTR | 17 | 6933 | A |
| Y00815 | 3'UTR | 16 | 6507 | T |
| Y00970 | CDS | 4.5 | 1098 | ACCCCC |
| Y00971 | 3'UTR | 18 | 1537 | T |
| Y07661 | 3'UTR | 7 | 1504 | GT |
| Y07759 | 5'UTR | 4.59 | 90 | CGCCC |
| Y07969 | 3'UTR | 12 | 1051 | A |
| Y08302 | CDS | 3.66 | 386 | GAGGCC |
| Y08639 | 5'UTR | 5.5 | 351 | AAAC |
| Y09048 | 3'UTR | 13 | 3248 | A |
| Y09160 | 5'UTR | 17 | 63 | A |
| Y09445 | 3'UTR | 7 | 2248 | AG |
| Y09538 | CDS | 7.33 | 94 | GAG |
| Y10043 | CDS | 7.66 | 659 | GAG |
| Y10256 | 3'UTR | 4 | 4136 | GGCAG |
| Y10275 | 3'UTR | 15 | 1022 | T |
| Y10571 | 3'UTR | 12 | 1265 | T |
| Y10659 | CDS | 3.66 | 97 | GGCGGG |
| Y10659 | 3'UTR | 5.8 | 2119 | AAAAC |
| Y10936 | CDS | 13 | 709 | T |
| Y11251 | 5'UTR | 15 | 1079 | T |
| Y11251 | 5'UTR | 14 | 803 | A |
| Y11306 | 5'UTR | 12 | 2 | T |
| Y11306 | 3'UTR | 6.5 | 2370 | AT |
| Y11312 | 3'UTR | 17 | 6807 | T |
| Y11312 | 3'UTR | 12 | 5922 | T |
| Y11525 | CDS | 3.5 | 714 | CGCACC |
| Y11525 | CDS | 7 | 691 | GCC |
| Y11525 | CDS | 6.66 | 439 | CGG |
| Y11681 | UNKNOWN | 19 | 1075 | A |
| Y12661 | 3'UTR | 6.5 | 2098 | CG |
| Y12781 | CDS | 5.66 | 1126 | GCG |
| Y12781 | 5'UTR | 6.66 | 127 | GCC |
| Y12781 | 3'UTR | 7 | 3219 | TC |
| Y12781 | 3'UTR | 13 | 2793 | T |
| Y13247 | CDS | 6.66 | 2681 | CCT |
| Y13286 | 3'UTR | 12 | 1716 | T |
| Y13350 | 3'UTR | 20 | 1547 | T |
| Y13436 | CDS | 4 | 463 | TGGGCG |
| Y13436 | CDS | 8 | 878 | GGC |
| Y13436 | CDS | 5.66 | 108 | GGC |
| Y13436 | CDS | 5.66 | 843 | GCC |
| Y13936 | CDS | 5.66 | 939 | GAA |
| Y15718 | 3'UTR | 13 | 2332 | T |
| Y15723 | 3'UTR | 13 | 2780 | A |
| Y15906 | 3'UTR | 8.5 | 2386 | TG |
| Y15906 | 3'UTR | 7.5 | 2402 | TA |
| Y15909 | 3'UTR | 15 | 7496 | T |
| Y16270 | 5'UTR | 3.8 | 64 | CCCCT |
| Y16280 | CDS | 7 | 1337 | CTG |
| Y16521 | 3'UTR | 15 | 1703 | T |
| Y17979 | 3'UTR | 3.83 | 2946 | TTTTTG |
| Y17979 | 3'UTR | 13 | 2988 | T |
| Y18046 | 3'UTR | 13 | 1338 | T |
| Y18198 | CDS | 8.66 | 559 | CAC |
| Y18264 | CDS | 10 | 687 | AGC |
| Y18264 | 5'UTR | 6.66 | 147 | GCC |
| Y18418 | 3'UTR | 9.5 | 1705 | TC |
| Y18483 | 5'UTR | 25 | 482 | T |
| Z11933 | CDS | 6.66 | 585 | CAG |
| Z12173 | 5'UTR | 3.6 | 45 | CCGTC |
| Z13009 | CDS | 5.66 | 123 | GCT |
| Z13009 | 3'UTR | 15 | 3204 | T |
| Z13009 | 3'UTR | 12 | 2952 | T |
| Z14244 | 5'UTR | 16 | 0 | T |
| Z17227 | 3'UTR | 5.66 | 1535 | GGA |
| Z17227 | 3'UTR | 18 | 1615 | A |
| Z18956 | 3'UTR | 11 | 2031 | GT |
| Z18956 | 3'UTR | 13 | 1976 | T |

TABLE 1-continued

| Genbank # | Region | # reps | Position | Unit sequence |
|---|---|---|---|---|
| Z19836 | UNKNOWN | 15 | 341 | A |
| Z19946 | UNKNOWN | 7.33 | 121 | CTG |
| Z19946 | UNKNOWN | 26 | 16 | T |
| Z19955 | UNKNOWN | 14 | 0 | T |
| Z21517 | UNKNOWN | 17 | 0 | T |
| Z21545 | UNKNOWN | 16 | 0 | T |
| Z21546 | UNKNOWN | 16 | 0 | T |
| Z21563 | UNKNOWN | 16 | 0 | T |
| Z21569 | UNKNOWN | 16 | 0 | T |
| Z22536 | 3'UTR | 7 | 2135 | GT |
| Z22942 | UNKNOWN | 27 | 71 | A |
| Z25909 | UNKNOWN | 18 | 0 | T |
| Z26308 | UNKNOWN | 23 | 2 | T |
| Z28339 | 3'UTR | 12 | 2412 | A |
| Z28407 | 5'UTR | 11.5 | 0 | TC |
| Z29064 | 3'UTR | 15 | 3755 | T |
| Z29064 | 3'UTR | 12 | 2923 | T |
| Z29331 | 3'UTR | 8 | 1140 | GT |
| Z30040 | UNKNOWN | 39 | 17 | T |
| Z35278 | CDS | 5.66 | 73 | GCG |
| Z35278 | 3'UTR | 18 | 2323 | A |
| Z36248 | UNKNOWN | 13 | 10 | T |
| Z36714 | 3'UTR | 18 | 3636 | T |
| Z37544 | 3'UTR | 17 | 4105 | T |
| Z37986 | 5'UTR | 18 | 52 | T |
| Z37987 | 3'UTR | 13 | 1935 | T |
| Z39654 | UNKNOWN | 6.5 | 193 | TA |
| Z40838 | UNKNOWN | 12 | 26 | A |
| Z41161 | UNKNOWN | 12 | 5 | A |
| Z41192 | UNKNOWN | 6.5 | 233 | TC |
| Z46606 | UNKNOWN | 18 | 5439 | A |
| Z46629 | 3'UTR | 6 | 2013 | TTC |
| Z46629 | 3'UTR | 7 | 3398 | TG |
| Z46629 | 3'UTR | 18 | 3056 | T |
| Z46788 | CDS | 2.5 | 972 | AAGAAGGATGCA (SEQ ID NO:345) |
| Z46788 | 3'UTR | 25.5 | 1389 | AC |
| Z46788 | 3'UTR | 16 | 1603 | A |
| Z48051 | CDS | 7 | 448 | TCC |
| Z48051 | 3'UTR | 10.75 | 2250 | AAAT |
| Z48199 | 3'UTR | 16 | 1516 | T |
| Z48482 | 3'UTR | 3.6 | 2202 | TTTGT |
| Z48570 | 5'UTR | 14 | 703 | A |
| Z48614 | UNKNOWN | 7.5 | 1656 | TG |
| Z48950 | 3'UTR | 13 | 884 | A |
| Z49105 | UNKNOWN | 20.5 | 1097 | CA |
| Z49105 | UNKNOWN | 19 | 1290 | A |
| Z49148 | CDS | 4.66 | 392 | AAGGCC |
| Z49194 | 3'UTR | 16.75 | 2498 | TTCC |
| Z49825 | CDS | 5.66 | 1200 | GCT |
| Z49835 | 3'UTR | 12 | 1816 | T |
| Z49995 | UNKNOWN | 15 | 1499 | A |
| Z50022 | CDS | 6.33 | 437 | CTG |
| Z50194 | CDS | 4 | 1081 | CGCAGC |
| Z50194 | CDS | 6.66 | 741 | CAG |
| Z72499 | CDS | 7 | 208 | CAG |
| Z72499 | 5'UTR | 8.66 | 97 | CCG |
| Z72499 | 5'UTR | 5.66 | 75 | GGA |
| Z73903 | 5'UTR | 3.66 | 324 | GGGGTC |
| Z74615 | 3'UTR | 7 | 6195 | AC |
| Z74615 | 3'UTR | 22 | 4739 | A |
| Z74615 | 3'UTR | 15 | 5529 | T |
| Z75190 | CDS | 11.66 | 38 | GCT |
| Z78323 | UNKNOWN | 5.66 | 347 | TGC |
| Z78328 | UNKNOWN | 7 | 91 | CTG |
| Z78347 | UNKNOWN | 7.66 | 511 | TGC |
| Z78379 | UNKNOWN | 6 | 414 | TTG |
| Z78385 | UNKNOWN | 16 | 428 | A |
| Z82215 | CDS | 5.66 | 4034 | GGA |
| Z82216 | CDS | 6.33 | 1074 | GAT |
| Z82216 | 5'UTR | 3.16 | 52 | GCGGCGGCGGCA (SEQ ID NO:346) |
| Z82216 | 5'UTR | 8 | 39 | GGC |
| Z82248 | 5'UTR | 3.57 | 54 | GCCTGCA |
| Z82248 | 3'UTR | 14 | 1561 | T |
| Z83844 | CDS | 5.66 | 397 | AGG |
| Z83844 | 3'UTR | 17 | 898 | CA |
| Z83844 | 3'UTR | 17 | 1117 | A |
| Z84723 | CDS | 7.33 | 1266 | AGC |

TABLE 1-continued

| Genbank # | Region | # reps | Position | Unit sequence |
|---|---|---|---|---|
| Z93929 | CDS | 17 | 110 | T |
| Z97171 | 3'UTR | 13 | 2211 | GT |
| Z97200 | 5'UTR | 9.5 | 907 | CT |
| Z97200 | 5'UTR | 12 | 864 | T |
| Z97200 | 3'UTR | 4.5 | 2595 | CAAT |
| Z97200 | 3'UTR | 13.5 | 2205 | TA |
| Z97630 | 5'UTR | 4.5 | 101 | GAGGCA |
| Z97632 | 5'UTR | 3.8 | 110 | TTCTG |
| Z97989 | 3'UTR | 12 | 2081 | A |
| Z98046 | CDS | 3.5 | 1805 | CAGTGC |
| Z98449 | UNKNOWN | 18 | 0 | T |
| Z98484 | UNKNOWN | 66 | 0 | T |
| Z98497 | UNKNOWN | 6.66 | 299 | TTA |
| Z98519 | UNKNOWN | 59 | 0 | T |
| Z98519 | UNKNOWN | 13 | 203 | G |
| Z98521 | UNKNOWN | 39 | 0 | T |
| Z98527 | UNKNOWN | 71 | 7 | T |
| Z99358 | UNKNOWN | 13 | 224 | AC |
| Z99399 | UNKNOWN | 14 | 327 | A |
| Z99427 | UNKNOWN | 29 | 0 | T |
| Z99715 | CDS | 7.5 | 1181 | AC |
| Z99715 | 5'UTR | 10 | 732 | AAG |
| Z99716 | CDS | 7 | 114 | GCA |

What is claimed is:

1. A method for identifying a candidate polymorphic repeat within a coding sequence, the method comprising the steps of:

(a) detecting tandem repeats in a target coding sequence;
   (b) scoring the repeats for polymorphic probability; and
   (c) generating a dataset correlating the repeats with polymorphic probability to identify a candidate polymorphic repeat.

2. A method according to claim 1, wherein steps (a)–(c) are effected by a computer program.

3. A method according to claim 1, wherein the coding sequence is selected from the group consisting of a single coding sequence, a concatamerized coding sequence and a coding sequence library.

4. A method according to claim 1, wherein the coding sequence is determined physically from transcribed polynucleotides.

5. A method according to claim 1, wherein the coding sequence is determined in silico from genomic sequence.

6. A method according to claim 1, wherein the scoring step comprises determining the type and number of the repeats.

7. A method according to claim 1, further comprising the steps of:

(d) detecting the candidate polymorphic repeat in each of a population of different coding sequences, each from different individuals; and
   (e) determining whether the candidate polymorphic repeat is polymorphic in the population.. wherein polymorphism of the candidate polymorphic repeat within the population indicates a polymorphic repeat.

8. A method according to claim 7, further comprising the step of:

(f) correlating variance at the polymorphic repeat with phenotypic variation.

9. A method according to claim 7, further comprising the step of:

(f) detecting in a test coding region the presence or absence of variance at the polymorphic repeat.

10. A method according to claim 7, further comprising the step of:

(f) detecting in a test coding region the presence or absence of variance at the polymorphic repeat, wherein the polymorphic repeat is found in Table 1.

11. A method according to claim 7, further comprising the step of:

(f) detecting in a test coding region the presence or absence of variance at the polymorphic repeat, wherein the detecting step is effected by specific polynucleotide hybridization.

12. A method according to claim 7, further comprising the step of:

(f) detecting in a test coding region the presence or absence of variance at the polymorphic repeat, wherein the detecting step is effected inferentially by detecting the amino acid sequence of a polypeptide translate of the coding region.

13. A method according to claim 7, further comprising the step of:

(f) detecting in a test coding region the presence or absence of variance at the polymorphic repeat, wherein the polymorphic repeat is in a corresponding Table 1-referenced genbank entry having an unannotated start and stop site or a "/cds=UNKNOWN" indication or absence of a "/cds=" field.

14. A method according to claim 7, further comprising the step of:

(f) detecting in a test coding region the presence or absence of variance at the polymorphic repeat, wherein the polymorphic repeat is selected from the group consisting of:
    human Sperm Acrosomal Protein-1 repeat, consisting of eight TG repeats at position 875 of gb=AF047437;
    human Herpes Viral Entry Protein C repeat) consisting of eight GAG repeats at position 1464 of gb=AF060231; and
    human MEK kinase 1 (MEKK 1) repeat, consisting of eight AAC repeats at position 2290 of gb=AF042838.

* * * * *